(12) United States Patent
Jones et al.

(10) Patent No.: US 8,138,168 B1
(45) Date of Patent: Mar. 20, 2012

(54) RENIN INHIBITORS

(75) Inventors: Benjamin Jones, Cardiff-By-The-Sea, CA (US); Stephen W. Kaldor, Del Mar, CA (US); Walter Keung, Carlsbad, CA (US); Andre A. Kiryanov, San Diego, CA (US); Zhe Li, San Diego, CA (US); Jeffrey A. Stafford, San Diego, CA (US); John Tyhonas, Chula Vista, CA (US); Craig Behnke, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 656 days.

(21) Appl. No.: 12/239,538

(22) Filed: Sep. 26, 2008

Related U.S. Application Data

(60) Provisional application No. 60/975,490, filed on Sep. 26, 2007.

(51) Int. Cl.
*A61K 31/407* (2006.01)
*A61K 31/4745* (2006.01)
*A61K 31/4178* (2006.01)
*C07D 453/02* (2006.01)

(52) U.S. Cl. .......... 514/211.08; 514/316; 514/322; 546/187; 546/199; 548/306.1

(58) Field of Classification Search ............ 514/211.08, 514/316, 322; 546/187, 199; 548/306.1
See application file for complete search history.

(56) References Cited

U.S. PATENT DOCUMENTS

| 6,448,271 | B1 * | 9/2002 | Lubisch et al. | 514/322 |
| 6,476,050 | B2 * | 11/2002 | Aquila et al. | 514/318 |

FOREIGN PATENT DOCUMENTS

| WO | WO01/68604 A2 | 9/2001 |
| WO | WO02/068420 A1 | 9/2002 |
| WO | WO03/051840 A1 | 6/2003 |
| WO | WO03/075921 A2 | 9/2003 |
| WO | WO03/087304 A2 | 10/2003 |
| WO | WO2004/058264 A1 | 7/2004 |
| WO | WO2004/082638 A2 | 9/2004 |
| WO | WO2006/007540 A2 | 1/2006 |
| WO | WO2006/007998 A1 | 1/2006 |
| WO | WO2006/044509 A2 | 4/2006 |
| WO | WO2006/104280 A1 | 5/2006 |
| WO | WO2006/098519 A1 | 9/2006 |
| WO | WO2007/056170 A2 | 5/2007 |
| WO | WO2007/082554 A1 | 7/2007 |
| WO | WO2008/003736 A1 | 1/2008 |

* cited by examiner

*Primary Examiner* — Susannah Chung
(74) *Attorney, Agent, or Firm* — Matthew J. Russo; C. Amy Smith

(57) ABSTRACT

The invention relates to compounds having the formulae:

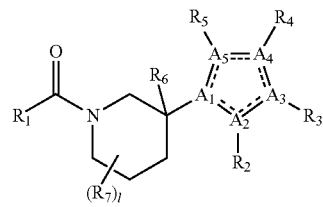

wherein the variables are as defined herein. The invention further relates to methods of making and using these compounds, and pharmaceutical compositions, kits and articles of manufacture comprise the compounds.

90 Claims, 1 Drawing Sheet

FIGURE 1

DNA Sequence Encoding First PCR Primer [SEQ ID NO: 1]

AAGCTTATGG ATGGATGGAG A

DNA Sequence Encoding Second PCR Primer [SEQ ID NO: 2]

GGATCCTCAG CGGGCCAAGG C

RENIN INHIBITORS

RELATED APPLICATIONS

This application claims the benefit of U.S. Provisional Application No. 60/975,490, filed Sep. 26, 2007 which is incorporated herein by reference.

FIELD OF THE INVENTION

The present invention relates to compounds that may be used to inhibit renin, as well as compositions of matter and kits comprising these compounds. The invention also relates to methods for inhibiting renin and treatment methods using compounds according to the present invention.

BACKGROUND OF THE INVENTION

The renin-angiotensin-aldosterone system ("RAAS") is one of the hormonal mechanisms involved in regulating pressure/volume homeostasis and also in the development of hypertension, a condition that can progress to more serious cardiovascular diseases such as congestive heart failure. Activation of RAAS begins with secretion of the enzyme renin from juxtaglomerular cells in the kidney.

Renin, a member of the aspartyl protease family, passes from the kidneys into the blood where it cleaves angiotensinogen to generate the decapeptide angiotensin I. Angiotensin I is then cleaved in the lungs, the kidneys and other organs by the angiotensin-converting enzyme (ACE) to form the octapeptide angiotensin II. Angiotensin II, which is known to work on at least two receptor subtypes ($AT_1$ and $AT_2$), increases blood pressure both directly by arterial vasoconstriction and indirectly by liberating from the adrenal glands the sodium-ion-retaining hormone aldosterone. Angiotensin II also produces other physiological effects such as promoting sodium and fluid retention, inhibiting renin secretion, increasing sympathetic nervous system activity, stimulating vasopressin secretion, causing a positive cardiac inotropic effect and modulating other hormonal systems.

Modulation of the RAAS represents a major advance in the treatment of cardiovascular diseases. In particular, the rationale to develop renin inhibitors lies in its specificity (Kleinert H. D., *Cardiovasc. Drugs*, 1995, 9, 645). The only substrate known for renin is angiotensinogen, which can only be processed (under physiological conditions) by renin. Inhibitors of the enzymatic activity of renin are therefore expected to bring about a reduction in the formation of angiotensin I and angiotensin II.

In view of the foregoing, renin is an attractive target for the discovery of new therapeutics for cardiovascular disease, hypertension, congestive heart failure, myocardial infarction, renal protection, inflammation, neurological diseases, cancer and other diseases. Accordingly, there is a need to find new renin inhibitors for use as therapeutic agents to treat human diseases.

SUMMARY OF THE INVENTION

The present invention relates to compounds that have activity for inhibiting renin. The present invention provides compounds, pharmaceutical compositions, articles of manufacture and kits comprising these compounds, and also methods of using and method of preparing these compounds.

In one aspect, the invention is directed to compounds having the formula:

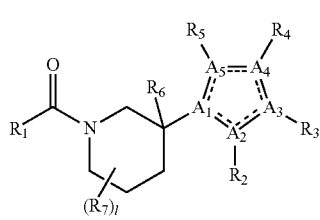

wherein l is 0, 1, 2, or 3;

$A_1$, $A_2$, $A_3$, $A_4$, and $A_5$ are each independently selected from the group consisting of C and N, provided that two of $A_1$, $A_1$, $A_3$, $A_4$, and $A_5$ are N;

$R_1$ is selected from the group consisting of ($C_{1-10}$)alkoxy, ($C_{4-12}$)aryloxy, hetero($C_{1-10}$)aryloxy, amino, ($C_{1-10}$)alkylamino, sulfonamido, ($C_{1-10}$)alkyl, halo($C_{1-10}$)alkyl, hydroxy ($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, amino($C_{1-10}$)alkyl, ($C_{3-12}$) cycloalkyl($C_{1-10}$)alkyl, hetero($C_{3-12}$)cycloalkyl($C_{1-10}$)alkyl, ($C_{4-12}$)aryl($C_{1-10}$)alkyl, hetero($C_{1-10}$)aryl($C_{1-10}$)alkyl, ($C_{9-12}$)bicycloaryl($C_{1-10}$)alkyl, hetero($C_{8-12}$)bicycloaryl ($C_{1-10}$)alkyl, hetero($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl. ($C_{9-12}$)bicycloaryl and hetero($C_{4-12}$)bicycloaryl, each unsubstituted or substituted;

$R_2$ is selected from the group consisting of hydrogen, halo, nitro, cyano, thio, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, sulfonyl, sulfinyl, ($C_{1-10}$)alkyl, halo($C_{1-10}$)alkyl, hydroxy($C_{1-10}$) alkyl, carbonyl($C_{1-4}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$) cycloalkyl($C_{1-10}$)alkyl, hetero($C_{3-12}$)cycloalkyl($C_{1-10}$)alkyl, ($C_{4-12}$)aryl($C_{3-10}$)alkyl, hetero($C_{1-10}$)aryl($C_{1-10}$)alkyl, ($C_{9-12}$)bicycloaryl($C_{1-10}$)alkyl, hetero($C_{8-12}$)bicycloaryl ($C_{1-10}$)alkyl, hetero($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted, provided that $R_2$ is absent when $A_2$ is a nitrogen that forms part of a double bond;

$R_3$ and $R_4$ are each independently selected from the group consisting of hydrogen, halo, nitro, cyano, thio, hydroxy, carbonyloxy, ($C_{1-10}$)alkoxy, ($C_{4-12}$)aryloxy, hetero($C_{1-10}$) aryloxy, carbonyl, oxycarbonyl, aminocarbonyl, amino, ($C_{1-10}$)alkylamino, sulfonamide, sulfonyl, sulfinyl, ($C_{1-10}$) alkyl, halo($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl ($C_{1-10}$)alkyl, ($C_{1-10}$)azaalkyl, ($C_{1-10}$)oxaalkyl, ($C_{1-10}$) oxoalkyl, imino($C_{1-10}$)alkyl, ($C_{3-12}$)cycloalkyl($C_{1-10}$)alkyl, hetero($C_{3-12}$)cycloalkyl($C_{1-10}$)alkyl, ($C_{4-12}$)aryl($C_{1-10}$)alkyl, hetero($C_{1-10}$)aryl($C_{1-10}$)alkyl, ($C_{9-12}$)bicycloaryl($C_{1-10}$) alkyl, hetero($C_{8-12}$)bicycloaryl($C_{1-10}$)alkyl, hetero($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)bicycloaryl and hetero($C_{4-12}$)bicycloaryl, each unsubstituted or substituted, and $R_2$ and $R_3$, and $R_3$ and $R_4$, may be taken together to form a 5, 6, 7, 8 membered saturated, unsaturated or aromatic ring, provided that $R_3$ and $R_4$ are each independently absent when $A_3$ and $A_4$, respectively, is a nitrogen that forms part of a double bond;

$R_5$ is selected from the group consisting of hydrogen, halo, nitro, cyano, thio, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, and $R_4$ and $R_5$ may be taken together to form a 5, 6, 7, 8 membered saturated, unsaturated or aromatic ring, provided that $R_5$ is absent when $A_5$ is a nitrogen that forms part of a double bond;

$R_6$ is selected from the group consisting of hydrogen, hydroxyl, unsubstituted and substituted $(C_{1-6})$alkyl, —COOR$_9$, and —CH$_2$OR$_9$, where $R_9$ is selected from the group consisting of hydrogen, $(C_{1-6})$alkyl, $(C_6)$aryl, $(C_{5-6})$heteroaryl, $(C_{3-6})$cycloalkyl, and hetero$(C_{2-5})$cycloalkyl, each unsubstituted or substituted; and $R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and provided that
when $A_2$ and $A_5$ are both N, $A_1$, $A_3$ and $A_4$ are C, $R_3$ and $R_4$ are taken together to form a substituted phenyl, and $R_2$ is a substituted alkyl, $R_1$ is not $(C_{1-10})$alkoxy, $(C_{4-12})$aryloxy, or hetero$(C_{1-10})$aryloxy,
when $A_2$ and $A_5$ are both N, $A_1$, $A_3$ and $A_4$ are C, $R_3$ and $R_4$ are taken together to form a substituted pyrimidinyl, and $R_2$ is a substituted alkyl, at least one of the substituents on R, contains one or more heteroatoms,
when $A_1$ and $A_3$ are each N, $A_2$, $A_4$ and $A_5$ are each C, and $R_4$ and $R_5$ are taken together to form an unstituted phenyl, $R_1$ is not a phenyl,
$R_2$ and $R_5$ are not both absent,
$R_2$ and $R_5$ are not both hydrogen, and
only one of $R_2$ and $R_3$, $R_3$ and $R_4$, and $R_4$ and $R_5$ are taken together to form a ring.

In another aspect, the invention relates to pharmaceutical compositions that comprise a renin inhibitor according to the present invention as an active ingredient and a pharmaceutical acceptable excipient. Pharmaceutical compositions according to the invention may optionally comprise 0.001%-100% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

In another aspect, the invention provides kits and other articles of manufacture for treating disease states associated with renin. In one embodiment, a kit is provided that comprises a composition comprising at least one renin inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another aspect, the invention provides an article of manufacture that comprises a composition comprising at least one renin inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The article of manufacture may also optionally comprise additional components, such as syringes for administration of the composition. The article of manufacture may comprise the composition in single or multiple dose forms.

In another aspect, the invention is related to methods for preparing the compounds, compositions and kits according to the present invention. For example, several synthetic schemes are provided herein for synthesizing compounds according to the present invention.

In another aspect, the invention is related to reagents that may be used in the preparation of the compounds according to the invention.

In another aspect, the invention is related to methods for using compounds, compositions, kits and articles of manufacture according to the present invention. In one embodiment, the compounds, compositions, kits and articles of manufacture are used to inhibit renin.

In one embodiment, the compounds, compositions, kits and articles of manufacture are used to treat a disease state for which renin possess activity that contributes to the pathology and/or symptomology of the disease state. In another embodiment, a compound is administered to a subject wherein renin activity within the subject is altered, preferably reduced.

In another embodiment, a prodrug of a compound is administered to a subject that is converted to the compound in vivo where it inhibits renin.

In another embodiment, a method of inhibiting renin is provided that comprises contacting a renin with a compound according to the present invention.

In another embodiment, a method of inhibiting renin is provided that comprises causing a compound according to the present invention to be present in a subject in order to inhibit renin in vivo.

In another embodiment, a method of inhibiting renin is provided that comprises administering a first compound to a subject that is converted in vivo to a second compound wherein the second compound inhibits renin in vivo. It is noted that the compounds of the present invention may be the first or second compounds.

In another embodiment, a therapeutic method is provided that comprises administering a compound according to the present invention.

In another embodiment, a method of treating a condition in a patient that is known to be mediated by renin, or which is known to be treated by renin inhibitors, comprising administering to the patient a therapeutically effective amount of a compound according to the present invention.

In another embodiment, a method is provided for treating a disease state for which renin possess activity that contributes to the pathology and/or symptomology of the disease state, the method comprising: causing a compound according to the present invention to be present in a subject in a therapeutically effective amount for the disease state.

In another embodiment, a method is provided for treating a disease state for which renin possess activity that contributes to the pathology and/or symptomology of the disease state, the method comprising: administering a first compound to a subject that is converted in viva to a second compound such that the second compound is present in the subject in a therapeutically effective amount for the disease state. It is noted that the compounds of the present invention may be the first or second compounds.

In another embodiment, a method is provided for treating a disease state for which renin possess activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by renin, or that is known to be treated by renin inhibitors.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound of or having the formula" is intended to encompass the compound and all pharmaceutically acceptable ionized forms and solvates, all possible stereoisomers, all possible resonance forms and tautomers, all pharmaceutically acceptable salts and their polymorphs, unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibit renin and thus may themselves be prodrugs for another compound. Such prodrugs of another compound may or may not themselves independently have renin inhibitory activity.

BRIEF DESCRIPTION OF THE FIGURE

FIG. 1 illustrates SEQ ID NO: 1 and SEQ ID NO: 2 referred to in this application.

DEFINITIONS

Unless otherwise stated, the following terms used in the specification and claims shall have the following meanings for the purposes of this Application.

"*" is used through out the Specification and in the Claims to indicate the point of attachment of a substituent to the remainder of the molecule on which the substituent is drawn.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_{3-8}$ rings such as cyclopropane, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkoxy" means the radical —O-alkyl; the alkyl group is as defined in this Application and can be optionally substituted.

"Alkyl" represented by itself means a straight or branched, saturated or unsaturated, aliphatic radical having a chain of carbon atoms, optionally with oxygen (See "oxaalkyl") or nitrogen atoms (See "azaalkyl") between the carbon atoms. $C_X$ alkyl and $C_{X-Y}$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, pentyl, hexyl, vinyl, allyl, 1-propenyl, isopropenyl, 1-butenyl, 2-butenyl, 3-butenyl, 2-methylallyl, ethynyl, 1-propynyl, 2-propynyl, ethyloxymethyl, (—$CH_2$—O—$CH_2CH_3$), ethylaminomethyl (—$CH_2$—NH—$CH_2CH_3$) and the like). Alkyl represented along with another radical (e.g., as in arylalkyl, heteroarylalkyl) means a straight or branched, saturated or unsaturated aliphatic divalent radical having the number of atoms indicated or when no atoms are indicated means a bond (e.g., ($C_{6-10}$)aryl($C_{1-3}$)alkyl includes, benzyl, phenylethyl, 1-phenylethyl, 3-phenylpropyl, 2-thienylmethyl, 2-pyridinylmethyl and the like).

"Alkenyl" means a straight or branched, carbon chain that contains at least one carbon-carbon double bond. Examples of alkenyl include vinyl, allyl, isopropenyl, pentenyl, hexenyl, heptenyl, 1-propenyl, 2-butenyl, 2-methyl-2-butenyl, and the like.

"Alkynyl" means a straight or branched, carbon chain that contains at least one carbon-carbon triple bond. Examples of alkynyl include ethynyl, propargyl, 3-methyl-1-pentynyl, 2-heptynyl and the like.

"Alkylene", unless indicated otherwise, means a straight or branched, saturated or unsaturated, aliphatic, divalent radical. $C_X$ alkylene and $C_{X-Y}$ alkylene are typically used where X and Y indicate the number of carbon atoms in the chain. For example, $C_{1-6}$alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-butenylene (—CH$_2$CH═CHCH$_2$—), 2-methyltetramethylene (—CH$_2$CH(CH$_3$)CH$_2$CH$_2$—), pentamethylene (—CH$_2$CH$_2$CH$_2$CH$_1$CH$_2$—) and the like.

"Alkenylene" means a straight or branched, divalent carbon chain having one or more carbon-carbon double bonds. Examples of alkenylene include ethene-1,2-diyl, propene-1,3-diyl, methylene-1,1-diyl, and the like.

"Alkynylene" means a straight or branched, divalent carbon chain having one or more carbon-carbon triple bonds. Examples of alkynylene include ethyne-1,2-diyl, propyne-1,3-diyl, and the like.

"Alkylidene" means a straight or branched saturated or unsaturated, aliphatic radical connected to the parent molecule by a double bond. $C_X$alkylidene and $C_{X-Y}$alkylidene are typically used where X and Y indicate the number of carbon atoms in the chain. For example, $C_{1-6}$alkylidene includes methylidene (═CH$_2$), ethylidene (═CHCH$_3$), isopropylidene (═C(CH$_3$)$_2$), propylidene (═CHCH$_2$CH$_3$), allylidene (═CH—CH═CH$_2$), and the like.

"Amino" means the radical —NR$_a$R$_b$, where R$_a$ and R$_b$ are each independently hydrogen or a non-hydrogen substituent. Representative amino groups include, without limits, —NH$_2$, —NHCH$_3$, —N(CH$_3$)$_2$, —NH(C$_{1-10}$)alkyl, —N((C$_{1-10}$)alkyl)$_2$, —NHaryl, —NHheteroaryl, —N(aryl)$_2$, —N(heteroaryl)$_2$, and the like. Optionally, R$_a$ and R$_b$ together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Amido" refers to the group —C(O)NR$_a$R$_b$, where R$_a$ and R$_b$ are each independently hydrogen or a non-hydrogen substituent. Representative amino groups include, without limits, —C(O)NH$_2$, —C(O)NHCH$_3$, —C(O)N(CH$_3$)$_2$, —C(O)NH(C$_{1-10}$)alkyl, —C(O)N((C$_{1-10}$)alkyl)$_2$, —C(O)NHaryl, —C(O)NHheteroaryl, —C(O)N(aryl)$_2$, —C(O)N(heteroaryl)$_2$, and the like.

"Animal" includes humans, non-human mammals (e.g., dogs, cats, rabbits, cattle, horses, sheep, goats, swine, deer, and the like) and non-mammals (e.g., birds, reptiles and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or polycyclic ring assembly where all the ring atoms are carbon atoms, and at least one of the rings comprising the ring assembly is an aromatic ring. If one or more ring atoms is not carbon (e.g., N, 5), the ring assembly is a heteroaryl. $C_X$aryl and $C_{X-Y}$aryl are typically used where X and Y indicate the number of carbon atoms in the ring.

"Azaalkyl" means an alkyl, as defined above, except where one or more substituted or unsubstituted nitrogen atoms (—N—) are positioned between carbon atoms of the alkyl. For example, an (C$_{2-6}$) azaalkyl refers to a chain comprising between 2 and 6 carbons and one or more nitrogen atoms positioned between the carbon atoms.

"Bicyclic" means a two-ringed ring assembly where the two rings are fused together, linked by a single bond or linked by two bridging atoms.

"Bicycloalkyl" means a saturated or partially unsaturated fused bicyclic or bridged polycyclic ring assembly.

"Bicycloaryl" means a ring assembly of two rings, wherein the rings are linked by a single bond or fused and at least one of the rings comprising the ring assembly is an aromatic ring. $C_X$-bicycloaryl and $C_{X-Y}$-bicycloaryl are typically used where X and Y indicate the number of carbon atoms in the bicyclic ring assembly and directly attached to the ring.

"Bridging ring" as used herein refers to a ring that is bonded to another ring to form a compound having a bicyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NR$_a$R$_b$, where R$_a$ and R$_b$ are each independently hydrogen or a non-hydrogen substituent.

"Carbocycle" means a ring consisting of carbon atoms.

"Carbocyclic ketone derivative" means a carbocyclic derivative wherein the ring contains a —C(═O)— moiety.

"Carbonyl" typically means a divalent radical —C(═O)—. It is noted that the term "carbonyl" when referring to a monovalent substituent can alternatively refer to a substituted carbonyl or acyl group, —C(═O)R$_a$, where R$_a$ is hydrogen or a non-hydrogen substituent on the carbonyl carbon, forming different carbonyl-containing groups including acids, acid halides, aldehydes, amides, esters, and ketones.

"Carboxy" typically means a divalent radical —C(O)O—. It is noted that the term "carboxy" when referring to a monovalent substituent means a substituted carboxy, —C(O)OR, where R$_a$ is hydrogen or a non-hydrogen substituent on the carboxyl group forming different carboxy containing groups including acids and esters. It is further noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a radical comprising a non-aromatic, saturated or partially unsaturated, monocyclic, fused or bridged polycyclic ring assembly. $C_X$ cycloalkyl and $C_{X-Y}$ cycloalkyl are typically used where X and Y indicate the number of carbon atoms in the ring assembly. For example, $C_{3-10}$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

"Cycloalkylene" means a divalent radical comprising a saturated or partially unsaturated, monocyclic or polycyclic ring assembly. $C_X$ cycloalkylene and $C_{X-Y}$ cycloalkylene are typically used where X and Y indicate the number of carbon atoms in the ring assembly.

"Cyclyl" means a mono- or polycyclic radical, typically a mono-, bi- or tricyclic, unsaturated, partially saturated or saturated ring system with typically 3 to 22, more typically 3 to 14, most typically 3-7, ring atoms and is unsubstituted or substituted by one or more substituents independently selected typically from the substituents as defined in this Application.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a multi-ring assembly wherein the rings comprising the ring assembly are so linked that the ring atoms that are common to two rings are directly bound to each other. The fused ring assemblies may be saturated, partially saturated, carbocyclics, heterocyclics, aromatics, heteroaromatics, and the like. Non-exclusive examples of common fused rings include decalin, naphthalene, anthracene, phenanthrene, indole, benzofuran, purine, quinoline, and the like.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g., halo-substituted $(C_{1-3})$alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroalkyl" means alkyl, as defined in this Application, provided that one or more of the atoms within the alkyl chain is a heteroatom.

"Heteroaryl" means a monocyclic or polycyclic ring assembly wherein at least one ring atom is a heteroatom and the remaining ring atoms are carbon, and at least one of the rings comprising the ring assembly is an aromatic ring. Monocyclic heteroaryl groups include, but are not limited to, cyclic aromatic groups having five or six ring atoms, wherein at least one ring atom is a heteroatom and the remaining ring atoms are carbon. The nitrogen atoms of such heteroaryl rings can be optionally quaternerized and the sulfur atoms of such heteroaryl rings can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, triazole, 1,3,4-thiadiazole, triazole and tetrazole. "Heteroaryl" also includes polycyclic ring assemblies, wherein a heteroaromatic ring is fused or linked by a bond to one or more rings independently selected from the group consisting of an aromatic ring, a cycloalkyl ring, a cycloalkenyl ring, a heterocycloalkyl ring and another heteroaromatic ring. Bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The polycylic heteroaryl ring assembly can be attached to the parent molecule through either the heteroaryl group itself or the aryl, cycloalkyl, cycloalkenyl or heterocycloalkyl group to which it is fused. The heteroaryl groups of this invention can be substituted or unsubstituted.

"Heterobicycloaryl" means bicycloaryl, as defined in this Application, provided that one or more of the atoms within the ring assembly is a heteroatom. For example, hetero $(C_{4-12})$bicycloaryl as used in this Application includes, but is not limited to, indoline, 2-amino-4-oxo-3,4-dihydropteridin-6-yl, tetrahydroisoquinolinyl, and the like.

"Heterocycloalkyl" means cycloalkyl, as defined in this Application, provided that one or more of the atoms forming the ring is a heteroatom. Non-exclusive examples of heterocycloalkyl include piperidyl, 4-morpholyl, 4-piperazinyl, pyrrolidinyl, perhydropyrrolizinyl, 1,3-dioxanyl, 1,4-dioxanyl and the like.

"Heteroatom" refers to an atom that is not a carbon atom. Particular examples of heteroatoms include, but are not limited to nitrogen, oxygen, and sulfur.

"Heteroatom moiety" includes a moiety where the atom by which the moiety is attached is not a carbon. Examples of heteroatom moieties include —NR=, —NR—, —N$^+$(O$^-$)=, —O—, —S— or —S(O)$_2$—, wherein R is hydrogen or a non-hydrogen substituent.

"Heterobicycloalkyl" means bicycloalkyl, as defined in this Application, provided that one or more of the atoms within the ring is a heteroatom. For example hetero$(C_{9-12})$bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like.

"Heterocyclyl" refers to a mono- or polycyclic radical, typically a mono-, bi- or tricyclic, unsaturated, partially saturated or saturated ring system with typically 3 to 22, more typically 3 to 14, most typically 3-7, ring atoms, and with one or more, preferably one to four, heteroatoms independently selected from nitrogen, oxygen, sulfur, S(=O)—, —S(=O)$_2$—, and is unsubstituted or substituted by one or more substituents independently selected typically from the substituents defined in this Application.

"Heterocycloalkylene" means cycloalkylene, as defined in this Application, provided that one or more of the ring member carbon atoms is replaced by a heteroatom.

"Hydroxy" means the radical —OH.

"IC$_{50}$" refers to the molar concentration of an inhibitor that produces 50% inhibition of the target enzyme.

"Iminoketone derivative" means a derivative comprising the moiety —C(=NR)—, wherein R is hydrogen or a non-hydrogen substituent attached to the nitrogen.

"Isomers" mean any compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four different substituents (where no two are the same) is termed a "chiral center." A compound with one chiral center has two enantiomeric forms of opposite chirality. A mixture of equal amounts of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-s sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Leaving group" means a moiety that can be displaced by another moiety, such as by nucleophilic attack, during a chemical reaction. Leaving groups are well known in the art and include, for example, halides and $OSO_2R'$ where R' is, for example, alkyl, haloalkyl, or aryl optionally substituted by halo, alkyl, alkoxy, amino, and the like. Non-limiting examples of leaving groups include chloro, bromo, iodo, mesylate, tosylate, and other similar groups.

"Moiety" means an interconnected group of atoms, generally referred to by its most characteristic structural component. For example, a "carbonyl moiety" refers to groups that contain a carbonyl group.

"Nitro" means the radical —$NO_2$.

"Oxaalkyl" means an alkyl, as defined above, except where one or more oxygen atoms (—O—) are positioned between carbon atoms of the alkyl. For example, an $(C_{2-6})$oxaalkyl refers to a chain comprising between 2 and 6 carbons wherein one or more oxygen atoms is positioned between two carbon atoms.

"Oxy" typically means the radical —O—. It is noted that the term "oxy" when referring to a monovalent radical can alternatively refer to a substituents oxy group, —OR—, where R is hydrogen or a non-hydrogen substituent on the'oxy radical forming oxy-containing groups including hydroxy, alkoxy, aryloxy, heteroaryloxy and carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have renin inhibitory activity. For example, an inhibitor comprising a hydroxy group may be administered as an ester that is converted by hydrolysis in viva to the hydroxy compound. Suitable esters that may be converted in viva into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide or as an N-alkyl (particularly N-methyl or N-ethyl) that is converted by hydrolysis or oxidation in viva to the amine compound.

"Protected derivatives" means derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, p-methoxybenzyl, methylthiomethyl ether, pivaloyl, silyl ether, carbobenzyloxy, benzyl, tert-butoxycarbonyl, p-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis,* 3rd edition, John Wiley & Sons, Inc. 1999.

"Ring" means a carbocyclic or a heterocyclic system.

"Substituent convertible to hydrogen in vivo" means any group that is convertible to a hydrogen atom by enzymological or chemical means including, but not limited to, hydrolysis, reduction and oxidation. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl (—(O)CO—$C(CH_3)_3$), benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; —C(O)CH ($NH_2$)$CH_3$), Arg (arginine), Asn (asparagine), Asp (aspartic acid), Cys (cysteine), Glu (glutamic acid), H is (histidine), Ile (isoleucine), Leu (leucine; —C(O)CH($NH_2$)$CH_2CH(CH_3)_2$), Lys (lysine), Met (methionine), Phe (phenylalanine), Pro (praline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups (—(O)CO—$C(CH_3)_3$), and the like. Suitable peptide residues include peptide residues comprising two to five, and optionally two to three, of the aforesaid amino acid residues. Examples of such peptide residues include, but are not limited to, residues of such peptides as Ala-Ala (—C(O)CH(NH)$CH_3$—C(O)CH($NH_2$)$CH_3$)), Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups (—(O)CO—C(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and halogenoethoxycarbonyl groups (such as β,β,β-trichloroethoxycarbonyl and β-iodoethoxycarbonyl). Further examples of substituents "convertible to hydrogen in vivo" include enzymatic oxidizable groups such as N-alkyls, particularly N-methyl and N-ethyl.

"Optionally substituted" refers to the optional replacement of hydrogen with a monovalent or divalent radical. "Unsubstituted" means that a given moiety consist of only hydrogen atoms bound at available valences. "Substituted" refers to the replacement of hydrogen with a monovalent or divalent radical. The substituents of an "optionally substituted" group may include, without limitation, one or more substituents independently selected from the group or designated subsets thereof, aldehyde, $(C_{1-10})$alkyl, alkylene, alkylidene, amide, amino, aminoalkyl, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted.

In one particular embodiment, examples of substituents include, but are not limited to, hydrogen, halo, nitro, cyano, thio, oxy, hydroxy, carbonyloxy, $(C_{1-10})$alkoxy, $(C_{4-14})$aryloxy, $(C_{1-13})$heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, $(C_{1-10})$haloalkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, $(C_{3-12})$heterocycloalkyl$(C_{1-10})$alkyl, aryl$(C_{1-10})$alkyl, $(C_{1-10})$heteroaryl$(C_{1-5})$alkyl, $(C_{9-12})$bicycloaryl$(C_{1-5})$alkyl, $(C_{8-12})$heterobicycloaryl$(C_{1-5})$alkyl, $(C_{3-12})$cycloalkyl, $(C_{3-12})$heterocycloalkyl, $(C_{9-12})$bicycloalkyl, $(C_{3-12})$heterobicycloalkyl, $(C_{4-12})$aryl, $(C_{1-10})$heteroaryl, $(C_{9-12})$bicycloaryl and $(C_{4-12})$heterobicycloaryl, the substituents are as defined herein. In addition, the substituent is itself optionally substituted by a further substituent. In one particular embodiment, examples of the further substituent include, but are not limited to, hydrogen, halo, nitro, cyano, thio, oxy, hydroxy, carbonyloxy, $(C_{1-10})$alkoxy, $(C_{4-12})$aryloxy, $(C_{1-10})$heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, $(C_{1-10})$haloalkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, $(C_{3-12})$heterocycloalkyl$(C_{1-10})$alkyl, aryl$(C_{1-10})$alkyl, $(C_{1-10})$heteroaryl$(C_{1-5})$alkyl, $(C_{9-12})$bicycloaryl$(C_{1-5})$alkyl, $(C_{8-12})$heterobicycloaryl$(C_{1-5})$alkyl, $(C_{3-12})$cycloalkyl, $(C_{3-12})$heterocycloalkyl, $(C_{9-12})$bicycloalkyl, $(C_{3-12})$heterobicycloalkyl, $(C_{4-12})$aryl, $(C_{1-10})$heteroaryl, $(C_{9-12})$bicycloaryl and $(C_{4-12})$heterobicycloaryl, the substituents are as defined herein.

"Sulfinyl" means the radical —S(O)—. It is noted that the term "sulfinyl" when referring to a monovalent substituent can alternatively refer to a substituted sulfinyl group, —S(═O)R, where R is hydrogen or a non-hydrogen substituent on the sulfur atom forming different sulfinyl groups including sulfinic acids, sulfinamides, sulfinyl esters, and sulfoxides.

"Sulfonyl" means the radical —S(O)$_2$—. It is noted that the term "sulfonyl" when referring to a monovalent substituent can alternatively refer to a substituted sulfonyl group, —S(═O)$_2$R, where R is hydrogen or a non-hydrogen substituent on the sulfur atom forming different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thiocarbonyl" means the radical —C(S)—. It is noted that the term thiocarbonyl when referring to a monovalent substituent can alternatively refer to a substituted thiocarbonyl group, —C(═S)$_2$R, where R is hydrogen or a non-hydrogen substituent on the carbon atom forming different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH$_3$) as well as —CR$_a$R$_b$R$_c$ where R$_a$, R$_b$, and R$_c$ may each independently be hydrogen or any other substituent where the atom attached to the carbon is not a hydrogen atom. Hence, —CF$_3$, —CH$_{10}$H and —CH$_2$CN, for example, are all $C_1$ alkyls.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH$_3$) as well as —CR$_a$R$_b$R$_c$ where R$_a$, R$_b$, and R$_c$ may each independently be hydrogen or any other substituent where the atom attached to the carbon is a heteroatom or cyano. Hence, $CF_3$, $CH_2OH$ and $CH_2CN$, for example, are all $C_1$ alkyls.

DETAILED DESCRIPTION OF THE INVENTION

The present invention relates to compounds, pharmaceutical compositions, kits and articles of manufacture that may be used to inhibit renin. The present invention also relates to methods for inhibiting renin and treatment methods using compounds according to the present invention. The present invention further relates to methods for the preparation of the renin inhibitors of the invention, and to compounds that are useful for the preparation of the renin inhibitors of the invention.

It is noted that the compounds of the present invention may also possess inhibitory activity for other aspartyl proteases (e.g., pepsin, gastricsin, napsin, BACE 1 & 2 and cathepsin D and E) and thus may be used to address disease states associated with these other family members. In addition, the compounds of the present invention may be useful as inhibitors of plasmepsins to treat malaria and as inhibitors of *Candida albicans* secreted aspartyl proteases to treat fungal infections.

In one aspect, the invention is directed to compounds that are active against renin.

In one embodiment, compounds of the present invention are of the formula:

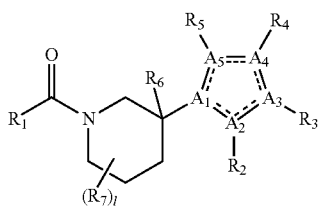

wherein l is 0, 1, 2, or 3;

$A_1$, $A_2$, $A_3$, $A_4$, and $A_5$ are each independently selected from the group consisting of C and N, provided that two of $A_1$, $A_2$, $A_3$, $A_4$, and $A_5$ are N;

$R_1$ is selected from the group consisting of $(C_{1-10})$alkoxy, $(C_{4-12})$aryloxy, hetero$(C_{1-10})$aryloxy, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, amino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_2$ is selected from the group consisting of hydrogen, halo, nitro, cyano, thio, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that $R_2$ is absent when $A_2$ is a nitrogen that forms part of a double bond;

$R_3$ and $R_4$ are each independently selected from the group consisting of hydrogen, halo, nitro, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamide, sulfonyl, sulfinyl, $(C_{1-10})$alkyl, halo$(C_{1-10})$hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, and $R_2$ and $R_3$, and $R_3$ and $R_4$, may be taken together to form a 5, 6, 7, 8 membered saturated, unsaturated or aromatic ring, provided that $R_3$ and $R_4$ are each independently absent when $A_3$ and $A_4$, respectively, is a nitrogen that forms part of a double bond;

$R_5$ is selected from the group consisting of hydrogen, halo, nitro, cyano, thio, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, and $R_4$ and $R_5$ may be taken together to form a 5, 6, 7, 8 membered saturated, unsaturated or aromatic ring, provided that $R_5$ is absent when $A_5$ is a nitrogen that forms part of a double bond;

$R_6$ is selected from the group consisting of hydrogen, hydroxyl, unsubstituted and substituted $(C_{1-6})$alkyl, —$COOR_9$, and —$CH_2OR_9$, where $R_9$ is selected from the group consisting of hydrogen, $(C_{1-6})$alkyl, $(C_6)$aryl, $(C_{5-6})$heteroaryl, $(C_{3-6})$cycloalkyl, and hetero$(C_{2-5})$cycloalkyl, each unsubstituted or substituted; and $R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and provided that
when $A_2$ and $A_5$ are both N, $A_1$, $A_3$ and $A_4$ are C, $R_3$ and $R_4$ are taken together to form a substituted phenyl, and $R_2$ is a substituted alkyl, $R_1$ is not $(C_{1-10})$alkoxy, $(C_{4-12})$aryloxy, or hetero$(C_{1-10})$aryloxy, when $A_2$ and $A_5$ are both N, $A_1$, $A_3$ and $A_4$ are C, $R_3$ and $R_4$ are taken together to form a substituted pyrimidinyl, and $R_2$ is a substituted alkyl, at least one of the substituents on $R_2$ contains one or more heteroatoms, when $A_1$ and $A_3$ are each N, $A_1$, $A_4$ and $A_5$ are each C, and $R_4$ and $R_5$ are taken together to form an unstituted phenyl, $R_2$ is not a phenyl, R, and $R_5$ are not both absent, $R_2$ and $R_5$ are not both hydrogen, and only one of $R_2$ and $R_3$, $R_3$ and $R_4$, and $R_4$ and $R_5$ are taken together to form a ring.

In another embodiment, the compounds of the invention are of the formula selected from the following group:

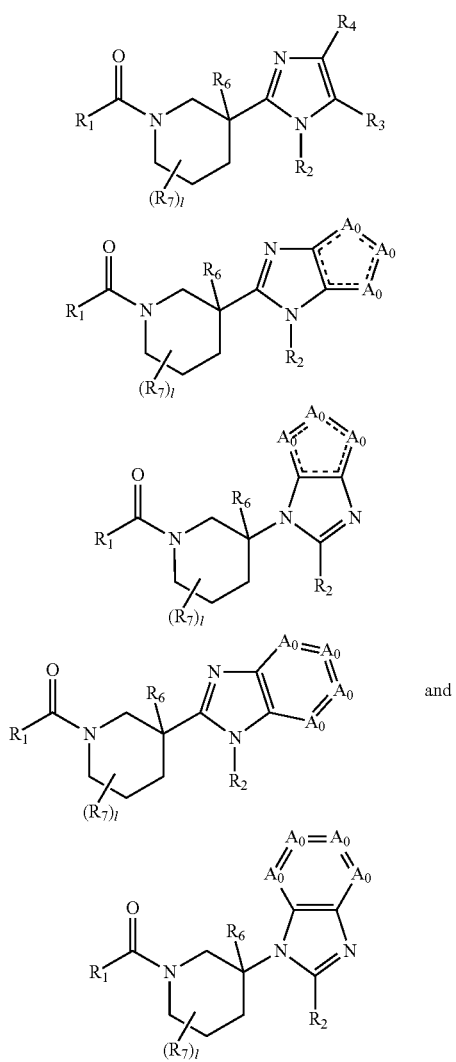

wherein
l is 0, 1, 2, or 3;
each $A_0$ is independently selected from the group consisting of $CR_{10}R_{10}'$, $NR_8$, O, and S;
$R_1$ is selected from the group consisting of $(C_{1-10})$alkoxy, $(C_{4-12})$aryloxy, hetero$(C_{1-10})$aryloxy, amino, $(C_{1-10})$ alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, amino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_2$ is selected from the group consisting of $(C_{1-10})$alkoxy, $(C_{4-12})$aryloxy, hetero$(C_{1-10})$aryloxy, carbonyloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that
when $R_1$ is a substituted alkyl and the fused ring to which $R_2$ is attached is a substituted benzimidazole, $R_1$ is not $(C_{1-10})$alkoxy, $(C_{4-12})$aryl, or hetero$(C_{1-10})$aryl,
when $R_2$ is a substituted alkyl, and the fused ring to which $R_2$ is attached is a substituted pyrimidinylimadazole, at least one of the substituents on $R_2$ contains one or more heteroatoms, and
when the fused ring to which $R_2$ is attached is an unsubstituted benzimidazole, is not phenyl;

$R_3$ and $R_4$ are each independently selected from the group consisting of hydrogen, halo, nitro, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_6$ is selected from the group consisting of hydrogen, hydroxyl, unsubstituted and substituted $(C_{1-6})$alkyl, —COOR$_9$, and —CH$_2$OR$_9$, where R$_9$ is selected from the group consisting of hydrogen, $(C_{1-6})$alkyl, $(C_6)$aryl, $(C_{5-6})$heteroaryl, $(C_{3-6})$cycloalkyl, and hetero$(C_{2-5})$cycloalkyl, each unsubstituted or substituted;

$R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl($C_{1-10}$)alkyl, ($C_{4-12}$)aryl($C_{1-10}$)alkyl, hetero($C_{1-10}$) aryl($C_{1-10}$)alkyl, ($C_{9-12}$)bicycloaryl($C_{1-10}$)alkyl, hetero ($C_{3-12}$)bicycloaryl($C_{1-10}$)alkyl, hetero($C_{1-10}$)alkyl, ($C_{3-12}$) cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

$R_8$ is selected from the group consisting of hydrogen, hydroxyl, ($C_{1-10}$)alkoxy, ($C_{4-12}$)aryloxy, hetero($C_{1-10}$)aryloxy, carbonyloxy, carbonyl, aminocarbonyl, oxycarbonyl, amino, ($C_{1-10}$)alkylamino, sulfonamido, sulfonyl, sulfinyl, ($C_{1-10}$)alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-10}$)alkyl, hetero($C_{3-12}$)cycloalkyl ($C_{1-10}$)alkyl, ($C_{4-12}$)aryl($C_{1-10}$)alkyl, hetero($C_{1-10}$)aryl ($C_{1-10}$)alkyl, ($C_{9-12}$)bicycloaryl($C_{1-10}$)alkyl, hetero($C_{8-12}$)bicycloaryl($C_{1-10}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted, or $R_8$ is absent when the nitrogen to which it is bound forms part of a double bond; and $R_{10}$ and $R_{10}$' are each independently selected from the group consisting of hydrogen, halo, nitro, cyano, thio, oxy, hydroxy, carbonyloxy, ($C_{1-10}$)alkoxy, ($C_{4-12}$)aryloxy, hetero ($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl ($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl ($C_{1-10}$)alkyl, hetero($C_{3-12}$)cycloalkyl($C_{1-10}$)alkyl, ($C_{4-12}$)aryl ($C_{1-10}$)alkyl, hetero($C_{1-10}$)aryl($C_{1-10}$)alkyl, ($C_{9-12}$) bicycloaryl($C_{1-10}$)alkyl, hetero($C_{8-12}$)bicycloaryl($C_{1-10}$) alkyl, hetero($C_{1-10}$)alkyl, ($C_{3-12}$)cycloalkyl, hetero($C_{3-12}$) cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero ($C_{4-12}$)bicycloaryl, each unsubstituted or substituted, or $R_{10}$ is absent when the carbon to which it is bound forms part of a double bond.

In another embodiment, the compounds of the invention are of the formula

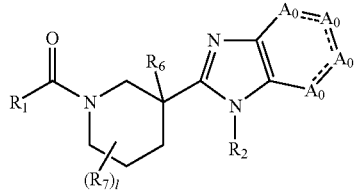

wherein
l is 0, 1, 2, or 3;
each $A_0$ is independently selected from the group consisting of $CR_{10}R_{10}$', $NR_8$, O, and S;
$R_1$ is selected from the group consisting of ($C_{1-10}$)alkoxy, ($C_{4-12}$)aryloxy, hetero($C_{1-10}$)aryloxy, amino, ($C_{1-10}$)alkylamino, sulfonamido, ($C_{1-10}$)alkyl, halo($C_{1-10}$)alkyl, hydroxy ($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, amino($C_{1-10}$)alkyl, ($C_{3-12}$) cycloalkyl($C_{1-10}$)alkyl, hetero($C_{3-12}$)cycloalkyl($C_{1-10}$)alkyl, ($C_{4-12}$)aryl($C_{1-10}$)alkyl, hetero($C_{1-10}$)aryl($C_{1-10}$)alkyl, ($C_{9-12}$)bicycloaryl($C_{1-10}$)alkyl, hetero($C_{8-12}$)bicycloaryl ($C_{1-10}$)alkyl, hetero($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

$R_2$ is selected from the group consisting of ($C_{1-10}$)alkoxy, ($C_{4-12}$)aryloxy, hetero($C_{1-10}$)aryloxy, carbonyloxy, carbonyl, oxycarbonyl, aminocarbonyl, amino, ($C_{1-10}$)alkylamino, sulfonamido, sulfonyl, sulfinyl, ($C_{1-10}$)alkyl, halo($C_{1-10}$)alkyl, hydroxy($C_{1-10}$)alkyl, carbonyl($C_{1-4}$)alkyl, thiocarbonyl ($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino ($C_{1-10}$)alkyl, ($C_{3-12}$)cycloalkyl($C_{1-10}$)alkyl, hetero($C_{3-12}$)cycloalkyl($C_{1-10}$)alkyl, ($C_{4-12}$)aryl($C_{1-10}$)alkyl, hetero($C_{1-10}$) aryl($C_{1-10}$)alkyl, ($C_{9-12}$)bicycloaryl($C_{1-10}$)alkyl, hetero ($C_{8-12}$)bicycloaryl($C_{1-10}$)alkyl, hetero($C_{1-10}$)alkyl, ($C_{3-12}$) cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted, provided that when $R_2$ is a substituted alkyl and the fused ring to which $R_2$ is attached is a substituted benzimidazole, $R_1$ is not ($C_{1-10}$)alkoxy, ($C_{4-12}$)aryl, or hetero($C_{1-10}$)aryl, when $R_2$ is a substituted alkyl and the fused ring to which $R_2$ is attached is a substituted pyrimidinylimadazole, at least one of the substituents on $R_2$ contains one or more heteroatoms;

$R_6$ is selected from the group consisting of hydrogen, hydroxyl, unsubstituted and substituted ($C_{1-6}$)alkyl, —COOR$_9$, and —CH$_2$OR$_9$, where $R_9$ is selected from the group consisting of hydrogen, ($C_{1-6}$)alkyl, ($C_6$)aryl, ($C_{5-6}$) heteroaryl, ($C_{3-6}$)cycloalkyl, and hetero($C_{2-5}$)cycloalkyl, each unsubstituted or substituted;

$R_7$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl ($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino ($C_{1-10}$)alkyl, ($C_{3-12}$)cycloalkyl($C_{1-10}$)alkyl, hetero($C_{3-12}$)cycloalkyl($C_{1-10}$)alkyl, ($C_{4-12}$)aryl($C_{1-10}$)alkyl, hetero($C_{1-10}$) aryl($C_{1-10}$)alkyl, ($C_{9-12}$)bicycloaryl($C_{1-10}$)alkyl, hetero ($C_{4-12}$)bicycloaryl($C_{1-10}$)alkyl, hetero($C_{1-10}$)alkyl, ($C_{3-12}$) cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl($C_{9-12}$) bicycloaryl and hetero($C_{4-12}$)bicycloaryl, each unsubstituted or substituted;

$R_8$ is selected from the group consisting of hydrogen, hydroxyl, ($C_{1-10}$)alkoxy, ($C_{4-12}$)aryloxy, hetero($C_{1-10}$)aryloxy, carbonyloxy, carbonyl, aminocarbonyl, oxycarbonyl, amino, ($C_{1-10}$)alkylamino, sulfonamido, sulfonyl, sulfinyl, ($C_{1-10}$)alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-10}$)alkyl, hetero($C_{3-12}$)cycloalkyl ($C_{1-10}$)alkyl, ($C_{4-12}$)aryl($C_{1-10}$)alkyl, hetero($C_{1-10}$)aryl ($C_{1-10}$)alkyl, ($C_{9-12}$)bicycloaryl($C_{1-10}$)alkyl, hetero($C_{8-12}$)bicycloaryl($C_{1-10}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted, or $R_8$ is absent when the nitrogen to which it is bound forms part of a double bond; and $R_{10}$ and $R_{10}$' are each independently selected from the group consisting of hydrogen, halo, nitro, cyano, thio, oxy, hydroxy, carbonyloxy, ($C_{1-10}$)alkoxy, ($C_{4-12}$)aryloxy, hetero ($C_{1-10}$)aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl $(C_{1-10})$alkyl, hetero$(C_{3-12})$cycloalkyl$(C_{1-10})$alkyl, $(C_{4-12})$aryl $(C_{1-10})$alkyl, hetero$(C_{1-10})$aryl$(C_{1-10})$alkyl, $(C_{9-12})$ bicycloaryl$(C_{1-10})$alkyl, hetero$(C_{8-12})$bicycloaryl$(C_{1-10})$ hetero$(C_{1-10})$alkyl, $(C_{3-12})$cycloalkyl, hetero$(C_{3-12})$ cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero $(C_{4-12})$bicycloaryl, each unsubstituted or substituted, or $R_{10}'$ is absent when the carbon to which it is bound forms part of a double bond.

In other embodiment, the compounds of the invention are of a formula selected from the following group:

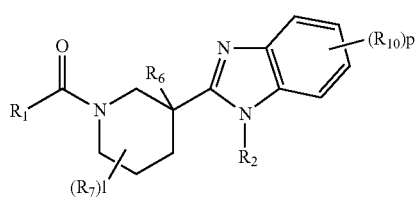

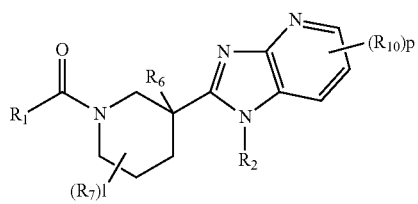

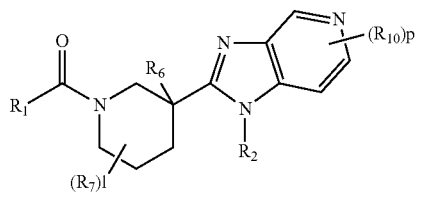

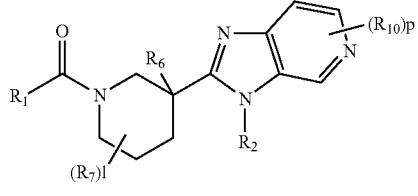

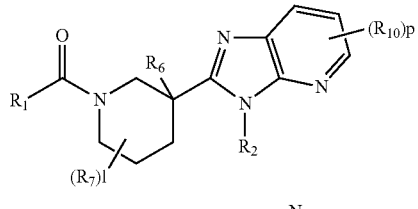

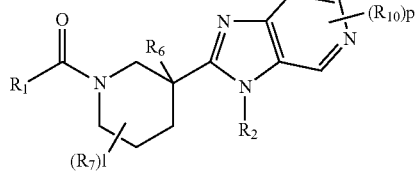

-continued

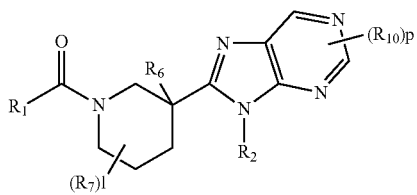

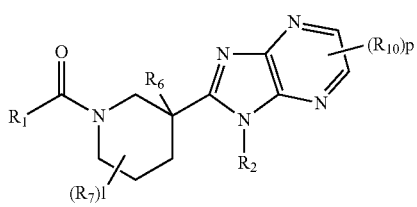

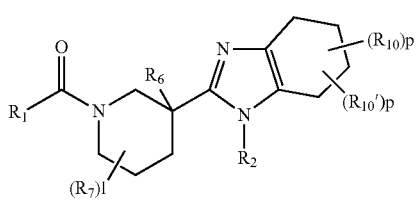

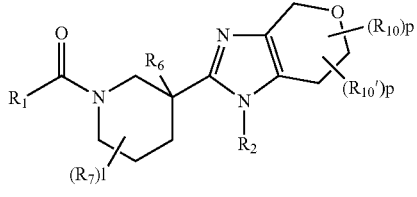

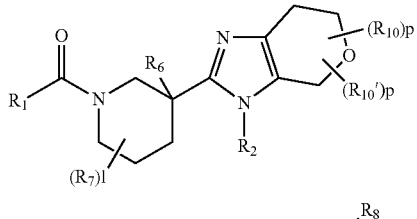

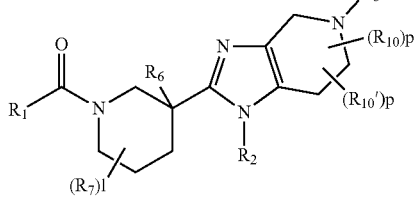

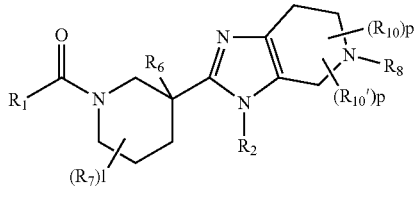

-continued

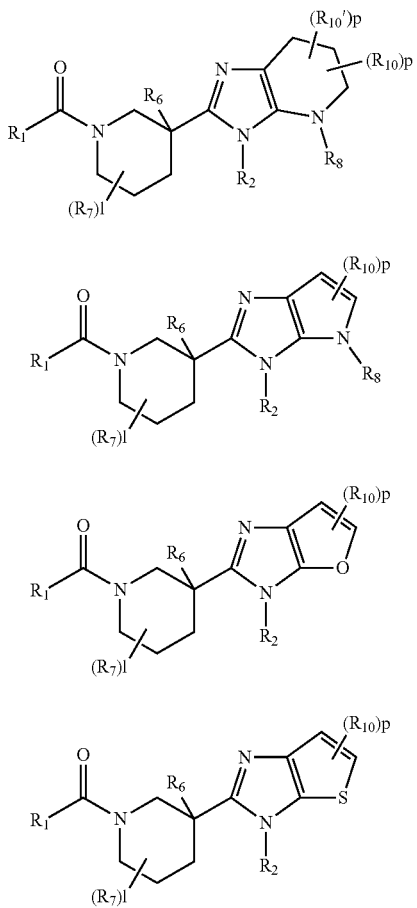

wherein l is 0, 1, 2, or 3;

p is 0, 1, 2, 3, or 4;

$R_1$ is selected from the group consisting of $(C_{1-10})$alkoxy, $(C_{4-12})$aryloxy, hetero$(C_{1-10})$aryloxy, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, amino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_2$ is selected from the group consisting of $(C_{1-10})$alkoxy, $(C_{4-12})$aryloxy, hetero$(C_{1-10})$aryloxy, carbonyloxy, carbonyl, oxycarbonyl, aminocarbonyl, amino, $(C_{1-10})$alkylamino, sulfonamido, sulfonyl, sulfinyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl$(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that when $R_2$ is a substituted alkyl and the fused ring to which $R_2$ is attached is a substituted benzimidazole, $R_1$ is not $(C_{1-10})$alkoxy, $(C_{4-12})$aryl, or hetero$(C_{1-10})$aryl, and when $R_2$ is a substituted alkyl and the fused ring to which $R_2$ is attached is a substituted pyrimidinylimadazole, at least one of the substituents on $R_2$ contains one or more heteroatoms;

$R_6$ is selected from the group consisting of hydrogen, hydroxyl, unsubstituted and substituted $(C_{1-6})$alkyl, —COOR$_9$, and —CH$_2$OR$_9$, where R$_9$ is selected from the group consisting of hydrogen, $(C_{1-6})$alkyl, $(C_6)$aryl, $(C_{5-6})$heteroaryl, $(C_{3-6})$cycloalkyl, and hetero$(C_{2-5})$cycloalkyl, each unsubstituted or substituted;

$R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-12})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_8$ is selected from the group consisting of hydrogen, hydroxyl, $(C_{1-10})$alkoxy, $(C_{4-12})$aryloxy, hetero$(C_{1-10})$aryloxy, carbonyloxy, carbonyl, aminocarbonyl, oxycarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and each $R_{10}$ or $R_{10}'$ is independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl, $(C_{1-10})$alkyl, $(C_{9-12})$bicycloaryl$(C_{1-10})$alkyl, hetero$(C_{8-12})$bioycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

In another embodiment, the compounds of the invention are of the formula

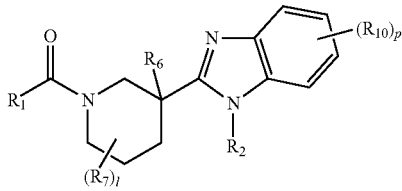

wherein l is 0, 1, 2, or 3;

p is 0, 1, 2, 3, or 4;

$R_1$ is selected from the group consisting of $(C_{1-10})$alkoxy, $(C_{4-12})$aryloxy, hetero$(C_{1-10})$aryloxy, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, amino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_2$ is selected from the group consisting of hydrogen, $(C_{1-10})$alkoxy, $(C_{4-12})$aryloxy, hetero$(C_{1-10})$aryloxy, carbonyloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that when $R_2$ is a substituted alkyl and the benzimidazole ring to which $R_2$ is attached is substituted, $R_1$ is not $(C_{1-10})$alkoxy, $(C_{4-12})$aryl or hetero$(C_{1-10})$aryl;

$R_6$ is selected from the group consisting of hydrogen, hydroxyl, unsubstituted and substituted $(C_{1-6})$alkyl, —COOR$_9$, and —CH$_2$OR$_9$, where R$_9$ is selected from the group consisting of hydrogen, $(C_{1-6})$alkyl, $(C_6)$aryl, $(C_{5-6})$heteroaryl, $(C_{3-6})$cycloalkyl, and hetero$(C_{2-5})$cycloalkyl, each unsubstituted or substituted;

$R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamide, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-14})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and each $R_{10}$ is independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{9-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

In still another embodiment, the compounds of the invention are of the formula:

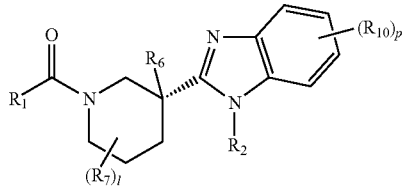

wherein l is 0, 1, 2, or 3;

p is 0, 1, 2, 3, or 4;

$R_1$ is selected from the group consisting of $(C_{1-10})$alkoxy, $(C_{4-12})$aryloxy, hetero$(C_{1-10})$aryloxy, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, amino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_2$ is selected from the group consisting of $(C_{1-10})$alkoxy, $(C_{4-12})$aryloxy, hetero$(C_{1-10})$aryloxy, carbonyloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-10})$cycloalkyl, hetero$(C_{3-12})$cycloalkyl, $(C_{9-12})$bicycloalkyl, hetero$(C_{3-12})$bicycloalkyl, hetero$(C_{1-10})$aryl, $(C_{9-12})$bicycloaryl and hetero$(C_{4-12})$bicycloaryl, each unsubstituted or substituted, provided that when $R_2$ is a substituted alkyl and the benzimidazole ring to which R2 is attached is substituted, $R_1$ is not $(C_{1-10})$alkoxy, $(C_{4-12})$aryl or hetero$(C_{1-10})$aryl;

$R_6$ is selected from the group consisting of hydrogen, hydroxyl, unsubstituted and substituted $(C_{1-6})$alkyl, —COOR$_9$, and —CH$_2$OR$_9$, where R$_9$ is selected from the group consisting of hydrogen, (C$_{1-6}$)alkyl, (C$_6$)aryl, (C$_{5-6}$)heteroaryl, (C$_{3-6}$)cycloalkyl, and hetero(C$_{2-5}$)cycloalkyl, each unsubstituted or substituted;

R$_7$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-10}$)alkyl, hetero(C$_{3-12}$)cycloalkyl(C$_{1-10}$)alkyl, (C$_{4-12}$)aryl(C$_{1-10}$)alkyl, hetero(C$_{1-10}$)aryl(C$_{1-10}$)alkyl, (C$_{9-12}$)bicycloaryl(C$_{1-10}$)alkyl, hetero(C$_{8-12}$)bicycloaryl(C$_{1-10}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted; and each R$_{10}$ is independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-10}$)alkyl, hetero(C$_{3-12}$)cycloalkyl(C$_{1-10}$)alkyl, (C$_{4-12}$)aryl(C$_{1-10}$)alkyl, hetero(C$_{1-10}$)aryl(C$_{1-10}$)alkyl, (C$_{9-12}$)bicycloaryl(C$_{1-10}$)alkyl, hetero(C$_{9-12}$)bicycloaryl(C$_{1-10}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted.

In yet another embodiment, the compounds of the invention are of the formula:

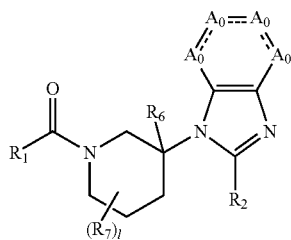

wherein l is 0, 1, 2, or 3;

each A$_0$ is independently selected from the group consisting of CR$_{10}$R$_{10}$', NR$_8$, O, and S;

R$_1$ is selected from the group consisting of (C$_{1-10}$)alkoxy, (C$_{4-12}$)aryloxy, hetero(C$_{1-10}$)aryloxy, amino, (C$_{1-10}$)alkylamino, sulfonamido, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, amino(C$_{1-10}$)alkyl, (C$_{3-12}$)cycloalkyl(C$_{1-10}$)alkyl, hetero(C$_{3-12}$)cycloalkyl(C$_{1-10}$)alkyl, (C$_{4-12}$)aryl(C$_{1-10}$)alkyl, hetero(C$_{1-10}$)aryl(C$_{1-10}$)alkyl, (C$_{1-12}$)bicycloaryl(C$_{1-10}$)alkyl, hetero(C$_{8-12}$)bicycloaryl(C$_{1-10}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted;

R$_2$ is selected from the group consisting of (C$_{1-10}$)alkoxy, (C$_{4-12}$)aryloxy, hetero(C$_{1-10}$)aryloxy, carbonyloxy, carbonyl, oxycarbonyl, aminocarbonyl, amino, (C$_{1-10}$)alkylamino, sulfonamido, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-10}$)alkyl, hetero(C$_{3-12}$)cycloalkyl(C$_{1-10}$)alkyl, (C$_{4-12}$)aryl(C$_{1-10}$)alkyl, hetero(C$_{1-10}$)aryl(C$_{1-10}$)alkyl, (C$_{4-12}$)bicycloaryl(C$_{1-10}$)alkyl, hetero(C$_{8-12}$)bicycloaryl(C$_{1-10}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted, provided that when the fused ring to which R$_2$ is attached is an unsubstituted benzimadazole, R$_1$ is not phenyl;

R$_6$ is selected from the group consisting of hydrogen, hydroxyl, unsubstituted and substituted (C$_{1-6}$)alkyl, —COOR$_9$, and —CH$_2$OR$_9$, where R$_9$ is selected from the group consisting of hydrogen, (C$_{1-6}$)alkyl, (C$_6$)aryl, (C$_{5-6}$)heteroaryl, (C$_{3-6}$)cycloalkyl, and hetero(C$_{2-5}$)cycloalkyl, each unsubstituted or substituted;

R$_7$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-10}$)alkyl, hetero(C$_{3-12}$)cycloalkyl(C$_{1-10}$)alkyl, (C$_{4-12}$)aryl(C$_{1-10}$)alkyl, hetero(C$_{1-10}$)aryl(C$_{1-10}$)alkyl, (C$_{9-12}$)bicycloaryl(C$_{1-10}$)alkyl, hetero(C$_{8-12}$)bicycloaryl(C$_{1-10}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted;

R$_8$ is selected from the group consisting of hydrogen, hydroxyl, (C$_{1-10}$)alkoxy, (C$_{4-12}$)aryloxy, hetero(C$_{1-10}$)aryloxy, carbonyloxy, carbonyl, aminocarbonyl, oxycarbonyl, amino, (C$_{1-10}$)alkylamino, sulfonamido, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-10}$)alkyl, hetero(C$_{3-12}$)cycloalkyl(C$_{1-10}$)alkyl, (C$_{4-12}$)aryl(C$_{1-10}$)alkyl, hetero(C$_{1-10}$)aryl(C$_{1-10}$)alkyl, (C$_{9-12}$)bicycloaryl(C$_{1-10}$)alkyl, hetero(C$_{8-12}$)bicycloaryl(C$_{1-10}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted, or R$_8$ is absent when the nitrogen to which it is bound forms part of a double bond; and R$_{10}$ and R$_{10}$' are each selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-10}$)alkyl, hetero($C_{3-12}$)cycloalkyl($C_{1-10}$)alkyl, ($C_{4-12}$)aryl($C_{1-10}$)alkyl, hetero($C_{1-10}$)aryl($C_{1-10}$)alkyl, ($C_{9-12}$)bicycloaryl($C_{1-10}$)alkyl, hetero($C_{8-12}$)bicycloaryl($C_{1-10}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted, or $R_{10}'$ is absent when the carbon to which it is bound forms part of a double bond.

In yet another embodiment, the compounds of the invention are of a formula selected from the following group:

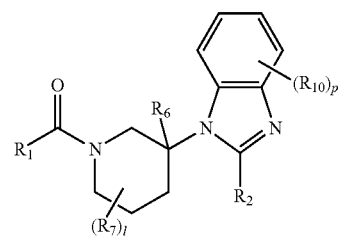

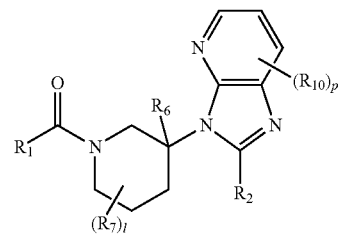

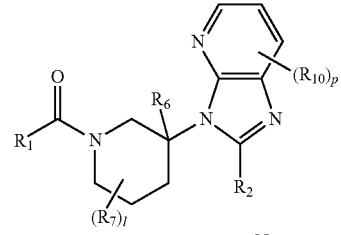

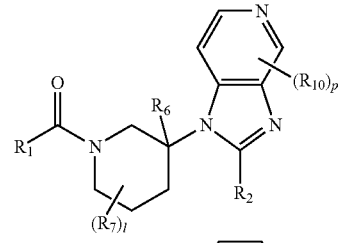

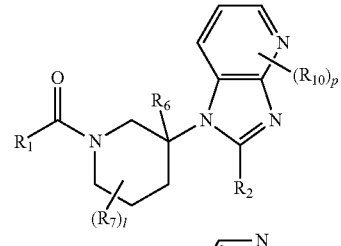

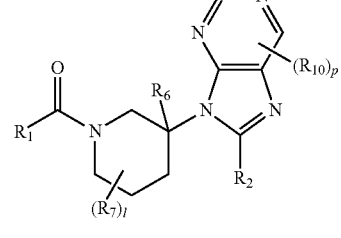

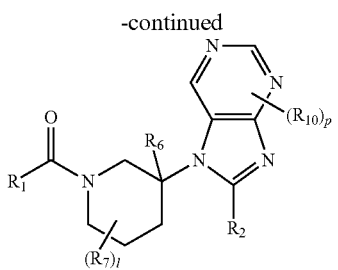

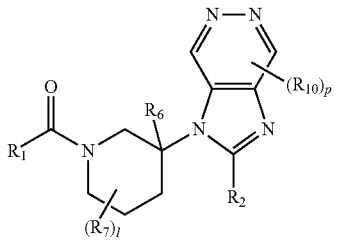

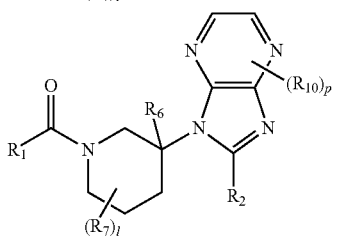

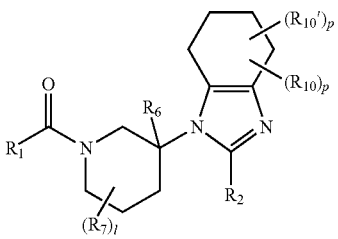

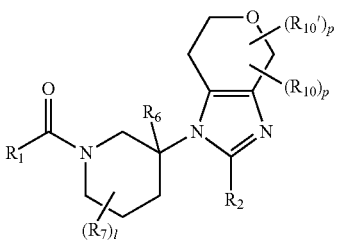

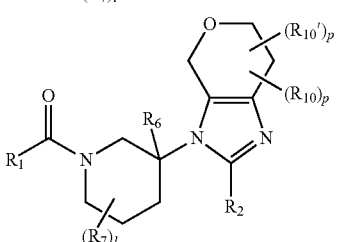

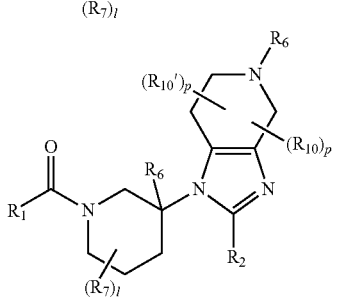

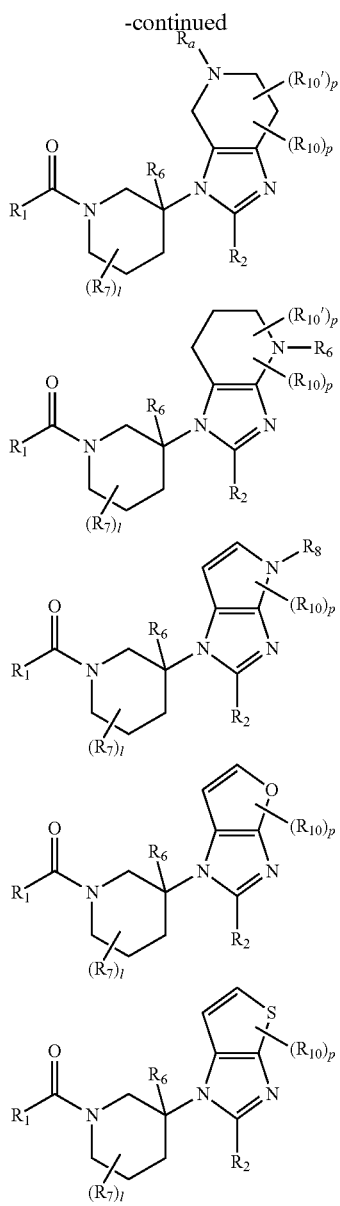

wherein l is 0, 1, 2, or 3;

p is 0, 1, 2, 3, or 4;

$R_1$ is selected from the group consisting of $(C_{1-10})$alkoxy, $(C_{4-12})$aryloxy, hetero$(C_{1-10})$aryloxy, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, amino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_2$ is selected from the group consisting of $(C_{1-10})$alkoxy, $(C_{4-12})$aryloxy, hetero$(C_{1-10})$aryloxy, carbonyloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that when the fused ring to which $R_2$ is attached is an unsubstituted benzimadazole, $R_2$ is not phenyl;

$R_6$ is selected from the group consisting of hydrogen, hydroxyl, unsubstituted and substituted $(C_{1-6})$alkyl, —COOR$_9$, and —CH$_2$OR$_9$, where $R_9$ is selected from the group consisting of hydrogen, $(C_{1-6})$alkyl, $(C_6)$aryl, $(C_{5-6})$heteroaryl, $(C_{3-6})$cycloalkyl, and hetero$(C_{7-5})$cycloalkyl, each unsubstituted or substituted;

$R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_8$ is selected from the group consisting of hydrogen, hydroxyl, $(C_{1-10})$alkoxy, $(C_{4-12})$aryloxy, hetero$(C_{1-10})$aryloxy, carbonyloxy, carbonyl, aminocarbonyl, oxycarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{3-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, or $R_8$ is absent when the nitrogen to which it is bound forms part of a double bond; and each $R_{10}$ and $R_{10}'$ is independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

In another embodiment, the compounds of the invention are of the formula:

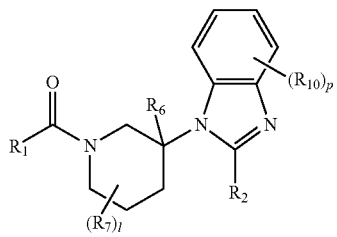

wherein l is 0, 1, 2, or 3;

p is 0, 1, 2, 3, or 4;

$R_1$ is selected from the group consisting of $(C_{1-10})$alkoxy, $(C_{4-12})$aryloxy, hetero$(C_{1-10})$aryloxy, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, amino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-16})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_2$ is selected from the group consisting of $(C_{1-10})$alkoxy, $(C_{4-12})$aryloxy, hetero$(C_{1-10})$aryloxy, carbonyloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that when the fused ring to which $R_2$ is attached is an unsubstituted benzimidazole, $R_2$ is not a phenyl;

$R_6$ is selected from the group consisting of hydrogen, hydroxyl, unsubstituted and substituted $(C_{1-6})$alkyl, —COOR$_9$, and —CH$_2$OR$_9$, where $R_9$ is selected from the group consisting of hydrogen, $(C_{1-6})$alkyl, $(C_6)$aryl, $(C_{5-6})$heteroaryl, $(C_{3-6})$cycloalkyl, and hetero$(C_{2-5})$cycloalkyl, each unsubstituted or substituted;

$R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and $R_{10}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl$(C_{4-12})$aryl, hetero$(C_{1-10})$aryl, $(C_{9-12})$bicycloaryl and hetero$(C_{4-12})$bicycloaryl, each unsubstituted or substituted.

In yet another embodiment, the compounds of the invention are of the formula:

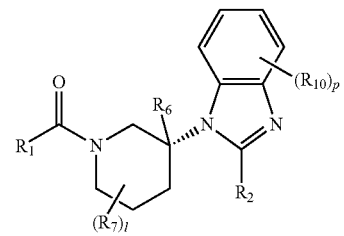

wherein l is 0, 1, 2, or 3;

p is 0, 1, 2, 3, or 4;

$R_1$ is selected from the group consisting of $(C_{1-10})$alkoxy, $(C_{4-12})$aryloxy, hetero$(C_{1-10})$aryloxy, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{4-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{1-10})$bicycloaryl, each unsubstituted or substituted;

$R_2$ is selected from the group consisting of $(C_{1-10})$alkoxy, $(C_{4-12})$aryloxy, hetero$(C_{1-10})$aryloxy, carbonyloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that when the benzimidazole ring to which $R_2$ is attached is unsubstituted, $R_2$ is not phenyl;

$R_6$ is selected from the group consisting of hydrogen, hydroxyl, unsubstituted and substituted $(C_{1-6})$alkyl, —$COOR_9$, and —$CH_2OR_9$, where $R_9$ is selected from the group consisting of hydrogen, $(C_{1-6})$alkyl, $(C_6)$aryl, $(C_{5-6})$heteroaryl, $(C_{3-6})$cycloalkyl, and hetero$(C_{2-5})$cycloalkyl, each unsubstituted or substituted;

$R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino $(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero $(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and $R_{10}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl, $(C_{1-10})$alkyl, hetero$(C_{1-10})$aryl$(C_{1-10})$alkyl, $(C_{9-12})$bicycloaryl $(C_{1-10})$alkyl, hetero$(C_{8-12})$bicycloaryl$(C_{1-10})$alkyl, hetero $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

$R_1$

In some variations of the above embodiments, $R_1$ is selected from the group consisting of amino, $(C_{1-10})$alkylamino, $(C_{1-10})$alkyl, hetero$(C_{1-10})$alkyl, amino$(C_{1-10})$alkyl, $(C_{3-12})$cycloalkyl, hetero$(C_{3-12})$cycloalkyl, $(C_{4-12})$aryl, hetero$(C_{1-10})$aryl, each unsubstituted or substituted. In some other variations, $R_1$ is selected from the group consisting of $(C_{1-6})$alkyl and amino, each unsubstituted or substituted. In some other variations, $R_1$ is unsubstituted or substituted $(C_{1-6})$alkyl. In yet other variations, $R_1$ is unsubstituted or substituted amino.

In particular variations of the above embodiments, $R_1$ is —$NHR_{11}$. In some variations of these particular variations, $R_{11}$ is selected from the group consisting of $(C_{1-10})$alkoxy, $(C_{4-12})$aryloxy, hetero$(C_{1-10})$aryloxy, carbonyl, oxycarbonyl, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero $(C_{3-12})$cycloalkyl$(C_{1-10})$alkyl, $(C_{4-12})$aryl$(C_{1-10})$alkyl, hetero $(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each unsubstituted or substituted with 1-3 substituents.

In other variations, $R_{11}$ is selected from the group consisting of $(C_{1-6})$alkyl, hydroxy$(C_{1-6})$alkyl, carbonyl$(C_{1-6})$alkyl, $(C_{3-12})$cycloalkyl$(C_{1-6})$alkyl, hetero$(C_{3-12})$cycloalkyl$(C_{1-6})$alkyl, aryl$(C_{1-6})$alkyl, hetero$(C_{1-10})$aryl$(C_{1-6})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero $(C_{4-12})$bicycloaryl, each unsubstituted or substituted with 1-3 substituents.

In still other variations, $R_{1i}$ is selected from the following group: methyl, ethyl, propyl,

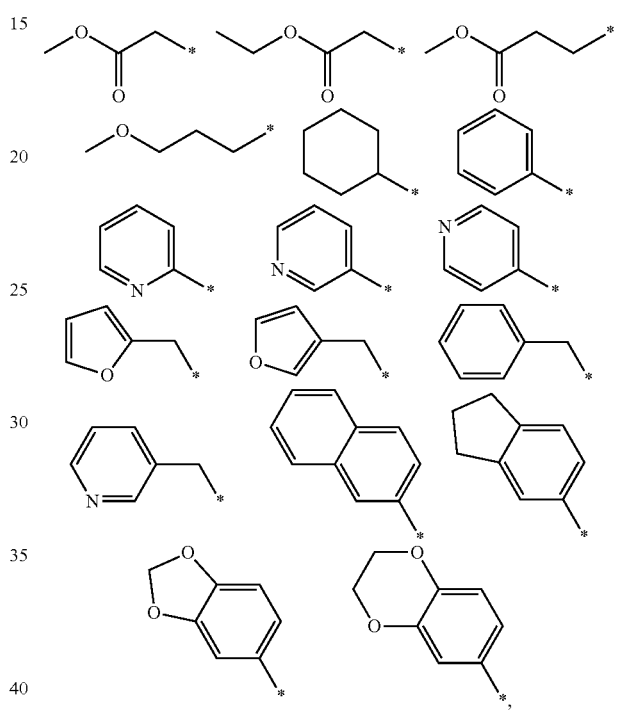

each unsubstituted or substituted with 1-3 substituents.

In some variations, the substituents on $R_{11}$, when present, are each independently selected from the group consisting of halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-10})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each unsubstituted or further substituted. In other variations, the substituents on $R_{11}$ are each independently selected from the group consisting of halo, perhalo$(C_{1-6})$alkyl, $(C_{1-6})$alkyl, aryl, aryl$(C_{1-6})$alkyl, heteroaryl$(C_{1-6})$alkyl, $(C_{1-6})$alkoxy, and $(C_{1-6})$alkylcarbonyl, each unsubstituted or further substituted. In still other variations, the substituents on $R_{11}$ are each independently selected from the group consisting of chloro, methyl, trifluoromethyl, isobutyl, phenyl, phenylmethyl, and methoxy. In other variation, one of the substituents on $R_{11}$ is chloro. In yet other variation, one of the substituents on $R_{11}$ is methyl.

In other particular variations of the above embodiments, $R_1$ is of the formula

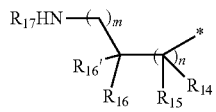

where m is 0, 1 or 2;

n is 0 or 1;

$R_{14}$ and $R_{15}$ are each individually selected from the group consisting of hydrogen, hydroxyl, $(C_{1-6})$alkyl, hydroxy$(C_{1-6})$alkyl, $(C_{1-6})$alkoxy, aryl$(C_{1-6})$alkyl, heteroaryl$(C_{1-6})$alkyl, cycloalkyl$(C_{1-6})$alkyl, and $(C_{1-6})$heteracycloalkyl$(C_{1-6})$alkyl, provided that only one of $R_{14}$ and $R_{15}$ is hydroxyl;

$R_{16}$ is selected from the group consisting of hydrogen, cyano, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl $(C_{1-10})$alkyl, hetero$(C_{3-12})$cycloalkyl$(C_{1-10})$alkyl, $(C_{4-12})$aryl $(C_{1-10})$alkyl, heteroaryl$(C_{1-10})$alkyl, $(C_{9-12})$bicycloaryl $(C_{1-10})$alkyl, hetero$(C_{8-12})$bicycloaryl$(C_{1-10})$alkyl, hetero $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, and any two substitutents bound to adjacent atoms of $R_{16}$ may be taken together to form a 5, 6, or 7 membered, unsubstituted or substituted, saturated, unsaturated or aromatic ring;

$R_{16}'$ is selected from the group consisting of hydrogen, unsubstituted $(C_{1-6})$alkyl and substituted $(C_{1-6})$alkyl; and $R_{17}$ is selected from the group consisting of hydrogen, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero$(C_{3-12})$cycloalkyl $(C_{1-10})$alkyl, $(C_{4-12})$aryl$(C_{1-10})$alkyl, hetero$(C_{1-10})$aryl $(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and provided that $R_{14}$ and $R_{15}$ may be taken together to form a 5, 6, or 7 membered, unsubstituted or substituted, saturated, unsaturated or aromatic ring, $R_{15}$ and $R_{16}$ may be taken together to form a 5, 6, or 7 membered, unsubstituted or substituted, saturated, unsaturated or aromatic ring, $R_{16}$ and $R_{16}'$ may be taken together to form a 3, 4, 5, or 6 membered, unsubstituted or substituted, saturated, unsaturated or aromatic ring, and $R_{16}$ and $R_{17}$ may be taken together to form a 5, 6, or 7 membered, unsubstituted or substituted, aryl or heteroaryl.

In yet another particular variations of the above embodiments, $R_1$ is of the formula

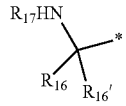

where $R_{16}$ is selected from the group consisting of $(C_{1-6})$alkyl, amino$(C_{1-6})$alkyl, alkoxy$(C_{1-6})$alkyl, aryl$(C_{1-6})$alkyl, heteroaryl$(C_{1-6})$alkyl, and aryloxy$(C_{1-6})$alkyl, aryl, heteroaryl, cycloalkyl$(C_{1-6})$alkyl and heterocycloalkyl$(C_{1-6})$alkyl, each unsubstituted or substituted;

$R_{16}'$ is selected from the group consisting of hydrogen, unsubstituted or substituted $(C_{1-6})$alkyl;

$R_{17}$ is selected from the group consisting of hydrogen, $(C_{1-6})$alkyl, hydroxyl$(C_{1-6})$alkyl, alkoxy$(C_{1-4})$alkyl, halo $(C_{1-6})$alkyl, amino$(C_{1-6})$alkyl, each unsubstituted or substituted; and provided that $R_{16}$ and $R_{16}'$ may be taken together to form a 3, 4, 5, or 6 membered, unsubstituted or substituted, saturated, unsaturated or aromatic ring, and $R_{16}$ and $R_{17}$ may be taken together to form a 5, 6, or 7 membered, unsubstituted or substituted, aryl or heteroaryl.

Of the immediately preceding particular variations, in some variations, $R_{16}$ is selected from the group consisting of methyl, ethyl, isopropyl, isobutyl, sec-butyl, tertbutyl, phenylmethyl, cyclohexyl, pyridylmethyl, 1-chloromethyl, each individually unsubstituted or substituted. In other variations, $R_{16}$ and $R_{17}$ are taken together to form a 5, 6, or 7 membered, unsubstituted or substituted cycloalkyl or heterocycloalkyl. In still other variations, $R_{16}$ and $R_{17}$ are taken together to form an unsubstituted or substituted pyrrolindyl. In yet still other variations, $R_{16}$ and $R_{16}'$ are taken together to form a 3, 4, 5, or 6 membered, unsubstituted or substituted cycloalkyl or heterocycloalkyl, each individually unsubstituted or substituted. In still further variations, $R_{16}$ and $R_{16}'$ are taken together to form a cyclobutyl or cyclopropyl ring, each individually unsubstituted or substituted.

In all these variations, the substituents on $R_{16}$, $R_{17}$, or the rings formed by taking together $R_{16}$ and $R_{16}'$ or $R_{16}$ and $R_{17}$, are each individually selected from the group consisting of halo, nitro, cyano, thio, oxy, hydroxy, carbonyloxy, $(C_{1-10})$ alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$ alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, $(C_{1-10})$azaalkyl, $(C_{1-10})$oxaalkyl, $(C_{1-10})$ oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$ alkyl, hetero$(C_{8-12})$bicycloaryl$(C_{1-10})$alkyl, hetero$(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or further substituted.

In another particular variations of the above embodiments, $R_1$ is a substituted alkyl of the formula

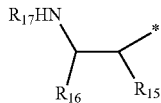

where $R_{15}$ is selected from the group consisting of hydrogen, hydroxyl, $(C_{1-6})$alkyl, hydroxy$(C_{1-6})$alkyl, $(C_{1-6})$alkoxy, aryl$(C_{1-6})$alkyl, heteroaryl$(C_{1-6})$alkyl, cycloalkyl$(C_{1-6})$alkyl, and $(C_{1-6})$heterocycloalkyl$(C_{1-6})$alkyl, provided that only one of $R_{14}$ and $R_{15}$ is hydroxyl; $R_{16}$ is a $(C_{1-10})$alkyl or a cyclic moiety selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, wherein said $(C_{1-10})$alkyl and cyclic moiety are each independently unsubstituted or substituted with 1-3 substituents, or $R_{15}$ and $R_{16}$ are taken together to form a 5, 6, or 7 membered, unsubstituted or substituted, saturated, unsaturated or aromatic ring, and the substituents bonded to $R_{16}$ or to the ring formed by taking together $R_{15}$ and $R_{16}$ are each independently selected from the group consisting of halo, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonyl, $(C_{1-10})$alkyl, halo$(C_{1-10})$alkyl, perhalo$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, each unsubstituted or substituted, and any two substituents bonded to adjacent atoms may be taken together to form a 5, 6, or 7 membered, unsubstituted or substituted, saturated, unsaturated or aromatic ring; and $R_{17}$ is selected from the group consisting of hydrogen, $(C_{1-10})$alkyl, halo$(C_{1-10})$alkyl, hydroxy$(C_{1-10})$alkyl, carbonyl$(C_{1-10})$alkyl, sulfonyl$(C_{1-10})$alkyl, sulfinyl$(C_{1-10})$alkyl, $(C_{1-10})$azaalkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

Of the immediately preceding particular variations, in some variations, $R_{15}$ and $R_{16}$ are taken together to form a ring selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

In some variations, the ring formed by taking $R_{15}$ and $R_{16}$ together is a pyrrolidinyl of the formula

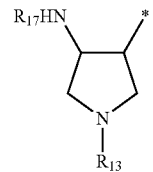

where $R_{13}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amido, carboxamido, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

In some variations, $R_{13}$ is selected from the group consisting of hydrogen, unsubstituted $(C_{1-6})$alkyl, $R_{18}$ substituted $(C_{1-6})$alkyl,

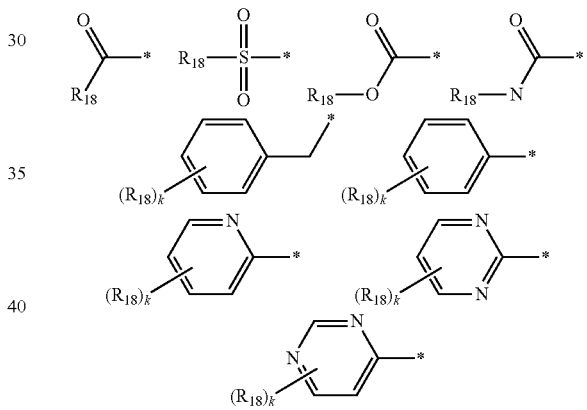

where
k is 0, 1, or 2;
each $R_{18}$ is independently selected from the group consisting of hydrogen, oxy, cyano, nitro, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$arYl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or is further substituted with 1-3 substituents,
where
the 1-3 substituents bonded to $R_{18}$ are each independently selected from the group consisting of halo, nitro, cyano, thio, oxy, hydroxy, oxo, carbonyloxy, $(C_{1-10})$alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-10}$)alkyl, hetero($C_{3-12}$)cycloalkyl($C_{1-10}$)alkyl, ($C_{4-12}$)aryl($C_{1-10}$)alkyl, hetero($C_{1-10}$)aryl($C_{1-10}$)alkyl, ($C_{9-12}$)bicycloaryl($C_{1-10}$)alkyl, hetero($C_{8-12}$)bicycloaryl($C_{1-10}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or further substituted.

Particularly, $R_{18}$ is selected from the group consisting of nitro, cyano, and

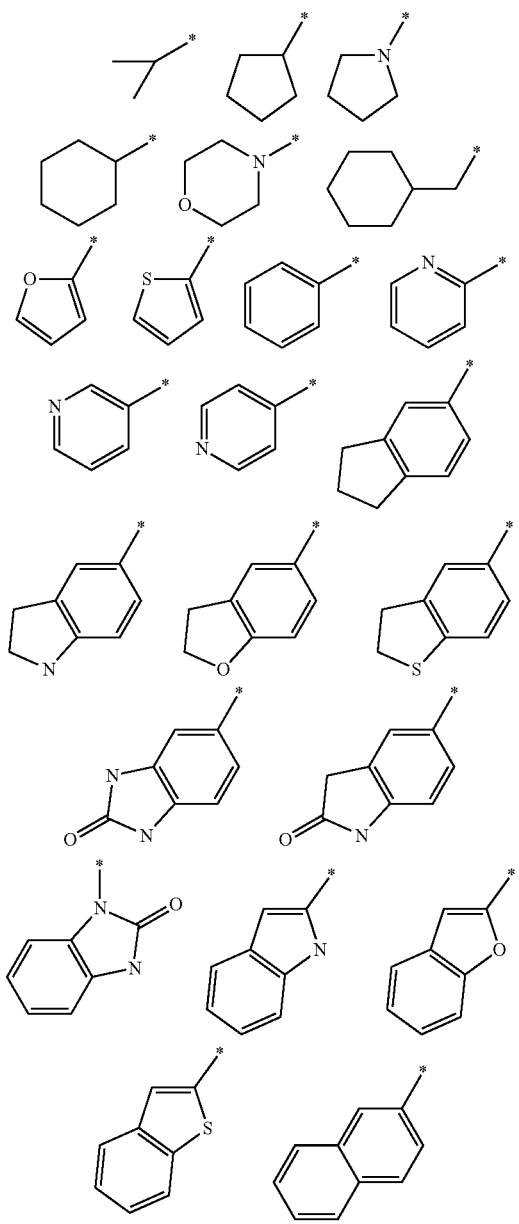

each unsubstituted or substituted with 1-3 substituents.

More particularly, $R_{18}$ is selected from the group consisting of

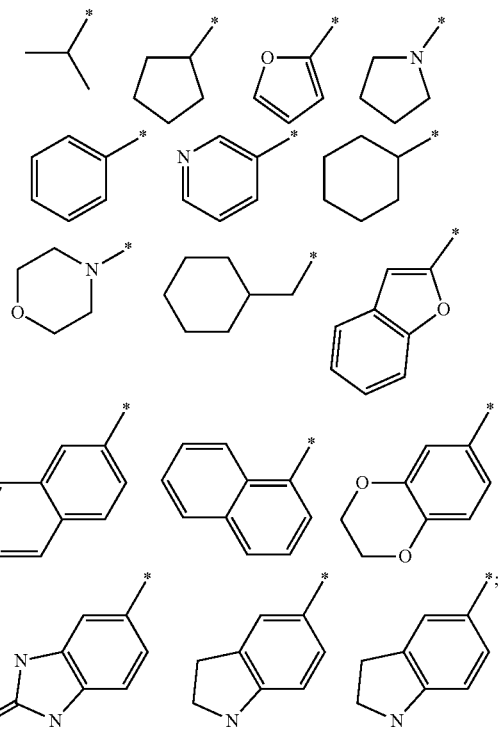

each unsubstituted or substituted with 1-3 substituents.

Most particularly, $R_{18}$ is selected from the group consisting of

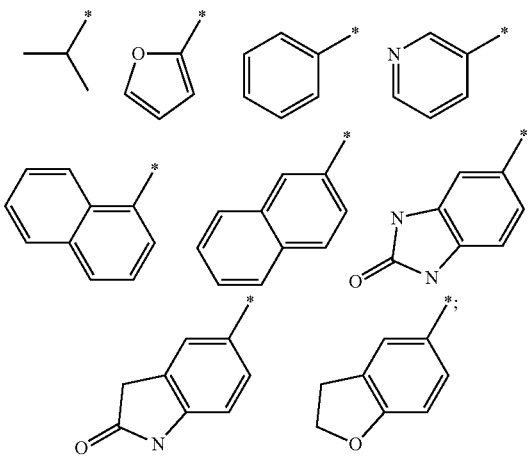

each unsubstituted or substituted with 1-3 substituents.

It is noted that when $R_{18}$ is substituted, in some variations, the 1-3 substituents bonded to $R_{18}$ are each independently selected from the group consisting of halo, nitro, cyano, thio, oxy, hydroxy, oxo, carbonyloxy, $(C_{1-10})$alkoxy, $(C_{1-10})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-10})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or further substituted.

In other variations, the 1-3 substituents bonded to $R_{18}$ are each independently selected from the group consisting of halo, cyano, oxo, $(C_{1-6})$alkyl, halo$(C_{1-6})$alkyl, perhalo$(C_{1-6})$alkyl, $(C_6)$aryl, $(C_{1-6})$heteroaryl, $(C_{1-6})$alkoxy, aryloxy, heteroaryloxy, and $(C_{1-6})$alkylthio, each unsubstituted or further substituted.

In still other variations, the substitutents on $R_{18}$ are each independently selected from the group consisting of methyl, ethyl, propyl, isopropyl, trifluoromethyl, butyl, isobutyl, t-butyl, oxo, phenyl, pyridinyl, methoxy, phenoxy, proylthio, methoxycarbonyl, difluoromethoxy, and

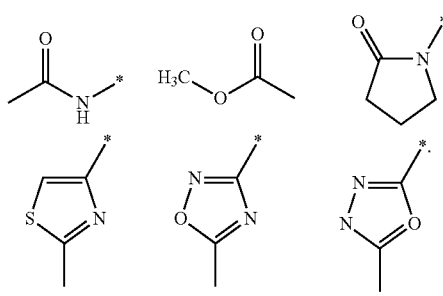

Compounds SYR145132U, 144392B and 144393B on the "160 benzimidazoles Apr. 11, 2007" List]

In yet other particular variations of the above embodiments, $R_1$ is of the formula

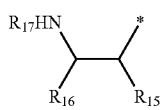

and $R_{16}$ is a cyclic moiety selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 substituents,
where
each said 1-3 substituents on $R_{16}$ is independently selected from the group consisting of halo, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonyl, $(C_{1-10})$alkyl, halo$(C_{1-10})$alkyl, perhalo$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, each unsubstituted or substituted, or any two substituents bonded to adjacent atoms of the cyclic moiety are taken together to form a 5, 6, or 7 membered, unsubstituted or substituted, saturated, unsaturated or aromatic ring.

In some variations, $R_{16}$ is selected from the group consisting of

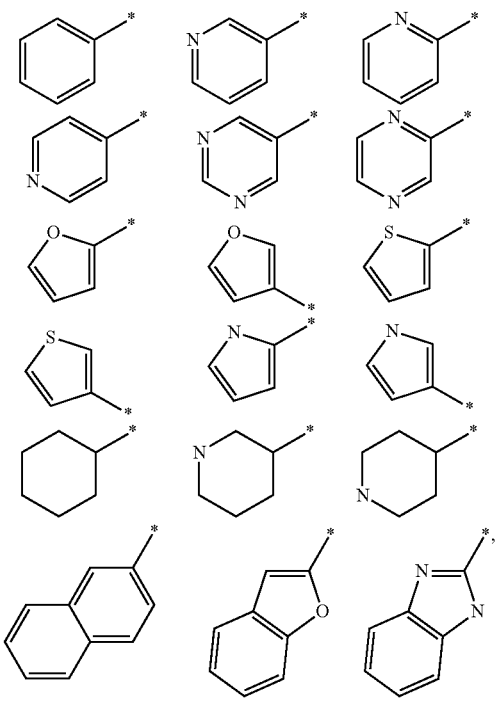

each unsubstituted or substituted with said 1-3 substituents.

In other variations, $R_{16}$ is selected from the group consisting of

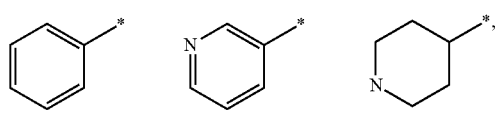

each unsubstituted or substituted with 1-3 substituents.

It is noted that when $R_{16}$ is substituted, the substituents bonded to $R_{16}$ are each independently selected from the group consisting of halo, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonyl, $(C_{1-10})$alkyl, halo$(C_{1-10})$alkyl, perhalo$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-10})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, each unsubstituted or further substituted with 1-3 substituents. Particularly, the substituents on $R_{16}$ are each independently selected from the group consisting of halo, hydroxy, $(C_{1-10})$alkoxy, $(C_{4-12})$aryloxy, $(C_{1-6})$alkyl, hydroxy$(C_{1-6})$alkyl, alkoxy$(C_{1-6})$alkyl, $(C_{4-12})$aryl, hetero$(C_{1-10})$aryl, $(C_{3-12})$cycloalkyl, hetero$(C_{3-12})$cycloalkyl, hydroxycyclo$(C_{3-6})$alkyl, alkoxycyclo$(C_{3-6})$alkyl, amido, carboxamido, sulfonamide, carbamate, urea, each unsubstituted or further substituted. More particularly, the substituents on $R_{16}$ are each independently selected from the group consisting of halo, hydroxyl, unsubstituted or substituted $(C_{1-6})$alkyl, and unsubstituted or substituted $(C_{1-10})$alkoxy. Further, any two substituents bonded to adjacent ring atoms of the $R_{16}$ cyclic moiety may be taken together to form a five, six or seven membered, unsubstituted or substituted, saturated, unsaturated or aromatic ring.

Subgenus Where R16 is Alkyamino: ZLP-1 and ZLP-4 Provisional Claim 40

In yet other particular variations of the above embodiments, $R_1$ is of the formula

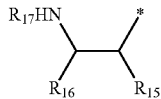

and $R_{16}$ is a substituted methyl of the formula

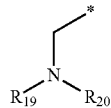

where $R_{19}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_{20}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{1-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; or $R_{19}$ and $R_{20}$ are taken together to form a 5, 6, or 7 membered, unsubstituted or substituted, saturated, unsaturated or aromatic ring.

(ZLP4) The compound according to provisional claim 40.

Of the immediately preceding variations, in some variations, $R_{19}$ is selected from the group consisting of hydrogen, unsubstituted $(C_{1-6})$alkyl, and substituted $(C_{1-6})$alkyl;

$R_{20}$ is selected from the group consisting of hydrogen, $(C_{1-6})$alkyl,

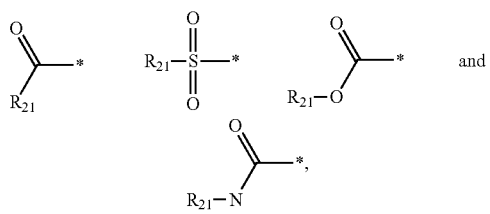

where each $R_{21}$ is independently selected from the group consisting of hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulftnyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 substituents, where the substituents on $R_{21}$ are each independently selected from the group consisting of halo, nitro, cyano, thio, oxy, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, or when $R_{11}$ is a ring selected from the group consisting of $(C_{3-12})$cycloalkyl, $(C_{4-12})$aryl, hetero$(C_{1-10})$aryl, hetero$(C_{3-12})$cycloalkyl, any two substituents bonded to adjacent ring atoms of $R_{21}$ may be taken to form a 5, 6, or 7 membered, unsubstituted or substituted, unsaturated, saturated or aromatic ring.

In other variations, $R_{21}$ are each independently selected from the group consisting of $(C_{1-6})$alkyl, isopropyl, and
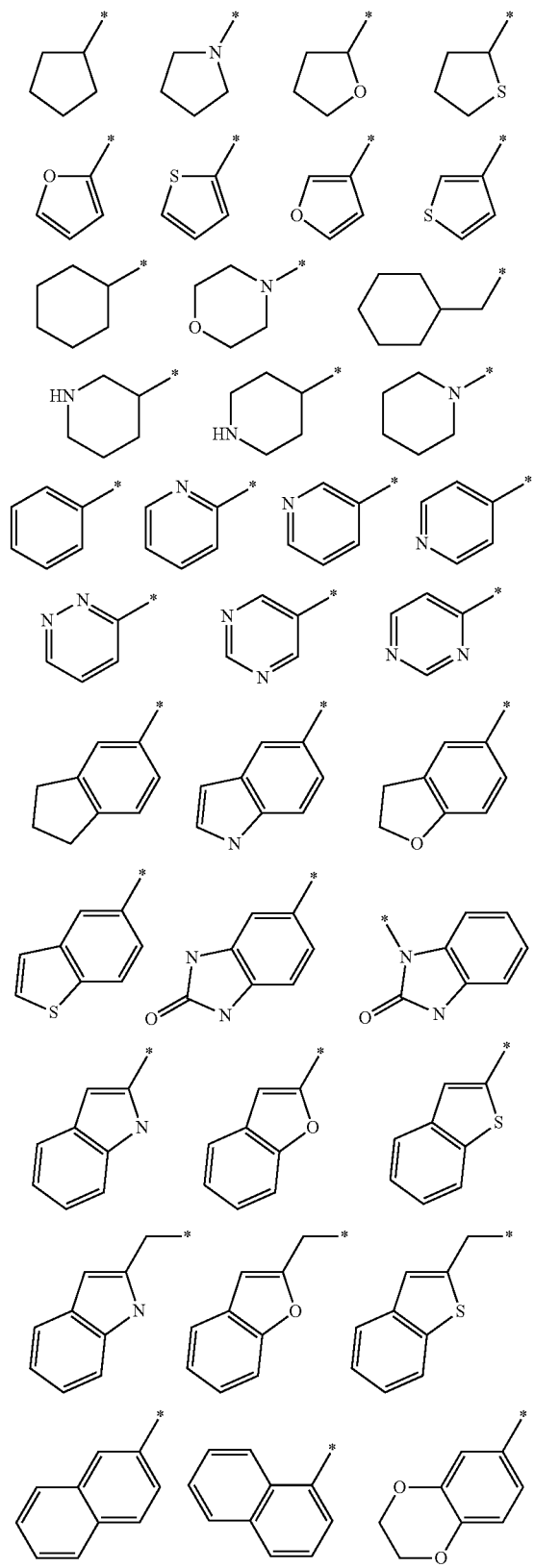
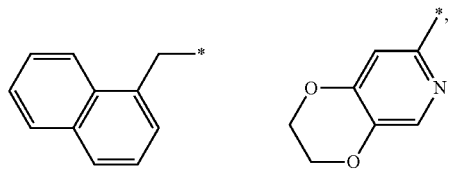
each unsubstituted or substituted with 1-3 substituents.
In other variations, $R_{21}$ are each independently selected from the group consisting of $(C_{1-6})$alkyl, isopropyl,
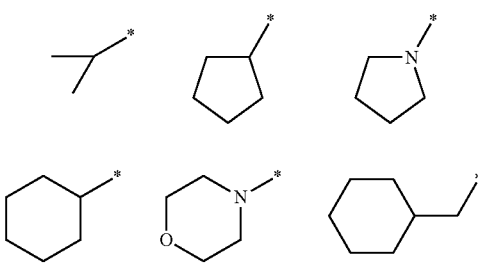
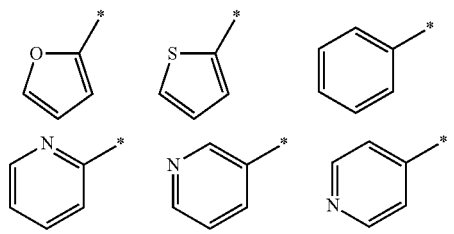
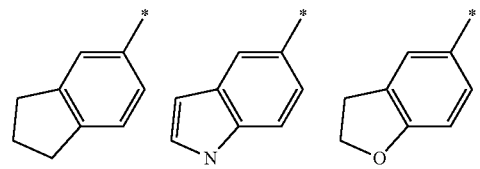
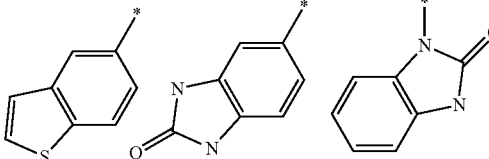
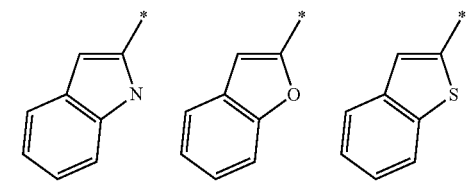
each unsubstituted or substituted with 1-3 substituents.

In still other variations, $R_{21}$ are each independently selected from the group consisting of

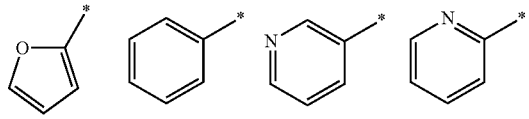

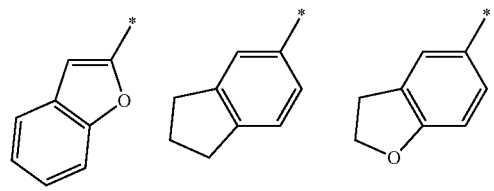

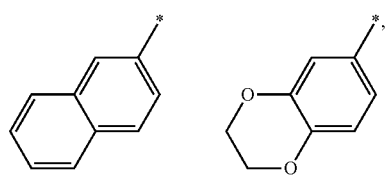

each unsubstituted or substituted with 1-3 substituents.

It is noted that when $R_{21}$ is substituted, the substituents on $R_{21}$ are each independently selected from the group consisting of halo, nitro, cyano, thio, oxy, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, $(C_{1-10})$azaalkyl, $(C_{1-10})$oxaalkyl, $(C_{1-10})$ oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$ alkyl, hetero$(C_{8-12})$bicycloaryl$(C_{1-10})$alkyl, hetero$(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each unsubstituted or substituted.

Particularly, the substitutents on $R_{21}$ are each independently selected from the group consisting of halo, nitro, cyano, oxo, $(C_{1-6})$alkyl, halo$(C_{1-6})$alkyl, perhalo$(C_{1-6})$alkyl, amido, alkoxycarbonyl, $(C_6)$aryl, $(C_{1-5})$heteroaryl, $(C_{1-6})$cycloalkyl, $(C_{1-6})$heterocycloalkyl, $(C_{1-6})$alkoxy, aryloxy, heteroaryloxy, and $(C_{1-6})$alkylthio, each unsubstituted or further substituted.

More particularly, the substitutents on $R_{21}$ are each independently selected from the group consisting of oxo, chloro, fluoro, cyano, nitro, methyl, ethyl, propyl, isopropyl, tertbutyl, phenyl, substituted phenyl, halo substituted phenyl, piperidinyl, thiophene, methoxy, difluoromethoxy, trifluoromethoxy, ethoxy, phenoxy, methoxycarbonyl, ethoxycarbonyl, $(C_{1-6})$alkylthio,

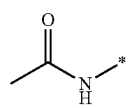 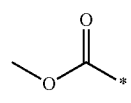 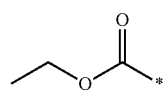

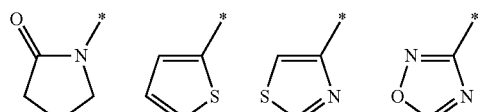

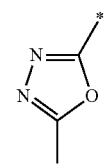

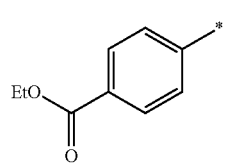

and

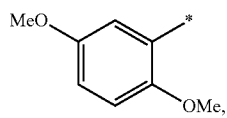

each unsubstituted or further substituted.

Most particularly, the substitutents on $R_{21}$ is selected from the group consisting of methoxy, phenyl, chloro, and

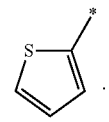

It is also noted that, in all of the above variations regarding the substituents on $R_{21}$, any two substituents bonded to adjacent ring atoms of $R_{21}$ may be taken to form a 5, 6, or 7 membered, unsubstituted or substituted, unsaturated, saturated or aromatic ring.

PROTHETIC EXAMPLES

In other particular variations of the above embodiments, $R_1$ is of the formula

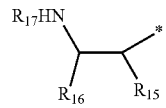

$R_{16}$ is a substituted methyl of the formula

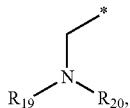

and $R_{19}$ and $R_{20}$ are taken together to form a ring of the formula

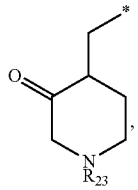

where
$R_{23}$ is selected from the group consisting of hydrogen, unsubstituted $(C_{1-6})$alkyl, $R_{14}$ substituted $(C_{1-6})$alkyl,

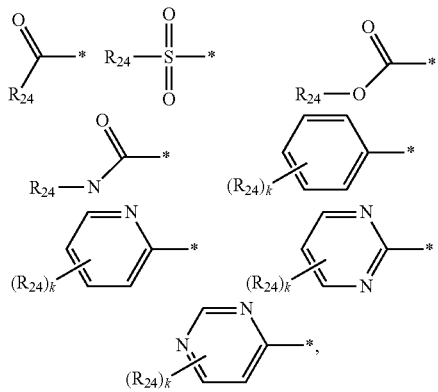

where
k is 0, 1, or 2;
each $R_{24}$ is independently selected from the group consisting of oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 substituents.
where
the substituents on $R_{24}$ are each independently selected from the group consisting of halo, nitro, cyano, thio, oxy, oxo, hydroxy, carbonyloxy, $(C_{1-10})$alkoxy, $(C_{4-12})$aryloxy, hetero$(C_{1-10})$aryloxy, carbonyl, oxy-carbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

In some variations, $R_{24}$ is selected from the group consisting of $(C_{1-6})$alkyl,

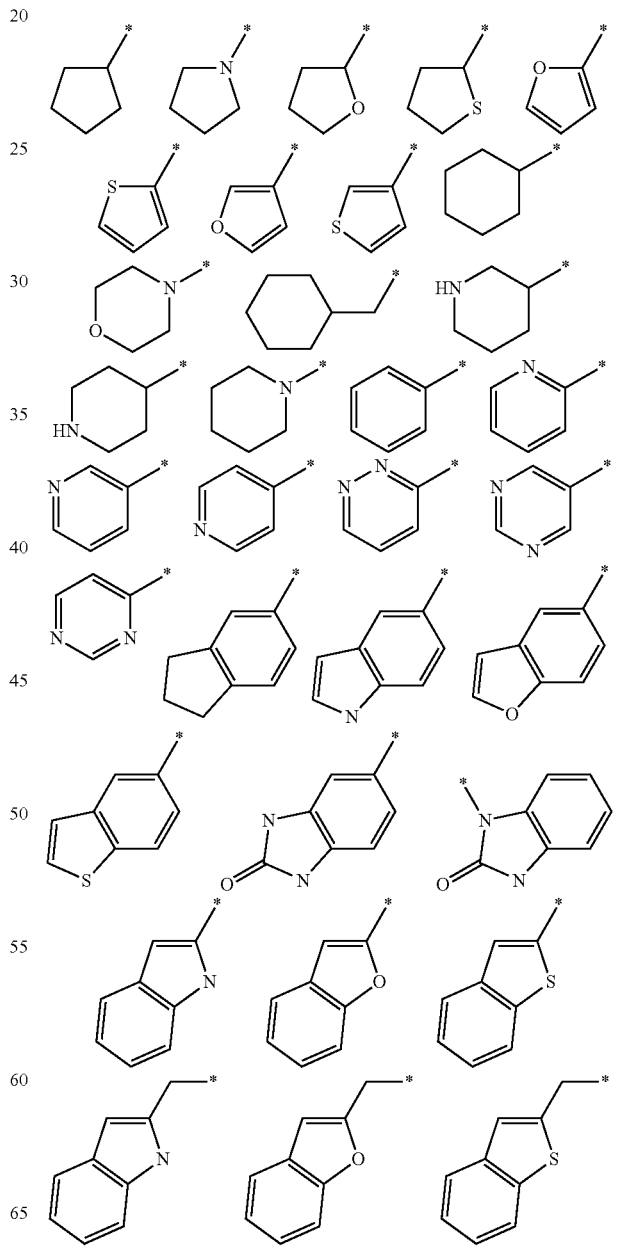

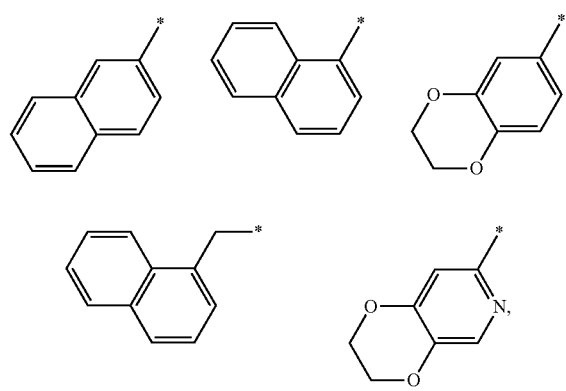

each unsubstituted or substituted with 1-3 substituents.

In other variations, R$_{24}$ is selected from the group consisting of (C$_{1-6}$)alkyl,

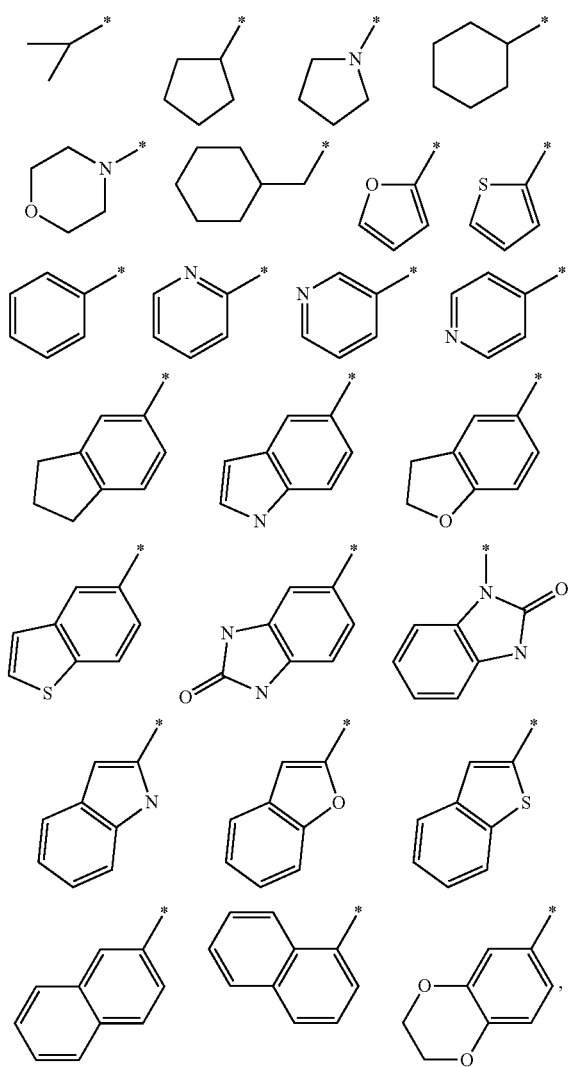

each unsubstituted or substituted with 1-3 substituents.

In still other variations, R$_{24}$ is selected from the group consisting of

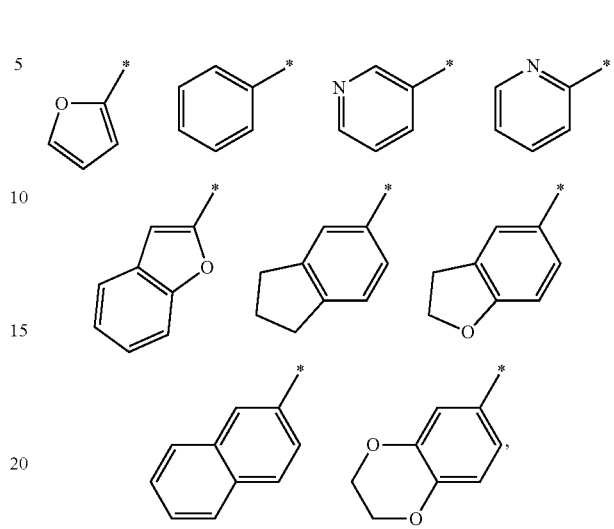

each unsubstituted or substituted with 1-3 substituents.

It is noted that when R24 is substituted, the substitutents on R$_{24}$ are each independently selected from the group consisting of halo, cyano, oxo, (C$_{1-6}$)alkyl, halo(C$_{1-6}$)alkyl, perhalo (C$_{1-6}$)alkyl, (C$_6$)aryl, (C$_{1-6}$)heteroaryl, (C$_{1-6}$)alkoxy, aryloxy, heteroaryloxy, and (C$_{1-6}$)alkylthio, each unsubstituted or further substituted. More particularly, the substitutents on R$_{24}$ are each independently selected from the group consisting of methyl, ethyl, propyl, isopropyl, tertbutyl, phenyl, substituted phenyl, halosubstituted phenyl, piperidinyl, thiophene, methoxy, difluoromethoxy, trifluoromethoxy, ethoxy, phenoxy, methoxycarbonyl, ethoxycarbonyl,

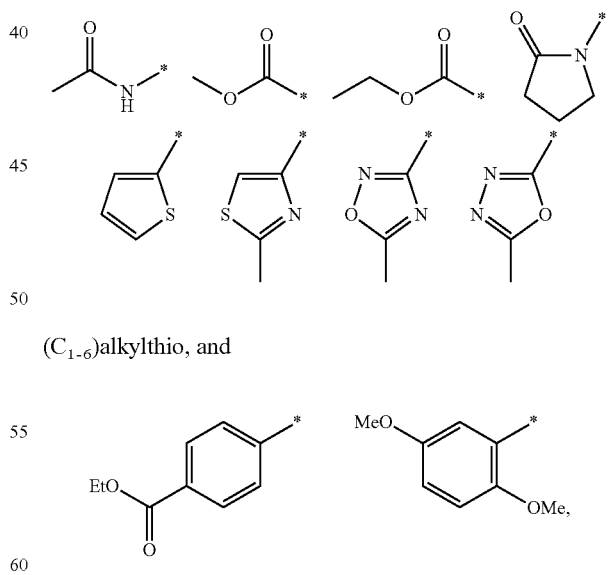

(C$_{1-6}$)alkylthio, and each unsubstituted or substituted.

(ZLP2 compounds from the "160 Benzimidazoles Apr. 11, 2007" List, Only 4 Examples)

In yet other particular variations of the above embodiments, R$_1$ is of the formula

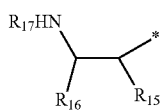

and $R_{16}$ is a substituted methyl of the formula

where $R_{26}$ is selected from the group consisting of hydrogen, carbonyl, oxycarbonyl, aminocarbonyl, sulfonyl, sulfinyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl ($C_{1-10}$)alkyl, aza($C_{1-10}$)alkyl, ($C_{1-10}$)oxaalkyl, ($C_{1-10}$) oxoalkyl, imino($C_{1-10}$)alkyl, ($C_{3-12}$)cycloalkyl($C_{1-10}$)alkyl, hetero($C_{3-12}$)cycloalkyl($C_{1-10}$)alkyl, ($C_{4-12}$)aryl($C_{1-10}$)alkyl, hetero($C_{1-10}$)aryl($C_{1-10}$)alkyl, ($C_{9-12}$)bicycloaryl($C_{1-10}$) alkyl, hetero($C_{8-12}$)bicycloaryl($C_{1-10}$)alkyl, hetero($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each unsubstituted or substituted with 1-3 substituents
where
the substituents on $R_{26}$ are each independently selected from the group consisting of hydrogen, halo, nitro, cyano, thio, oxy, hydroxy, oxo, carbonyloxy, ($C_{1-10}$)alkoxy, ($C_{4-12}$) aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy ($C_{1-10}$)alkyl, carbonyl($C_{1-10}$)alkyl, thiocarbonyl($C_{1-10}$)alkyl, sulfonyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-10}$) alkyl, hetero($C_{3-12}$)cycloalkyl($C_{1-10}$)alkyl, ($C_{4-12}$)aryl($C_{1-10}$) alkyl, hetero($C_{1-10}$)aryl($C_{1-10}$)alkyl, ($C_{9-12}$)bicycloaryl ($C_{1-10}$)alkyl, hetero($C_{9-12}$)bicycloaryl($C_{1-10}$)alkyl, hetero ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{3-12}$)aryl, ($C_{9-12}$)bicycloaryl and hetero($C_{4-12}$)bicycloaryl, each unsubstituted or further substituted, and any two substituents bonded to adjacent atoms of $R_{26}$ may be taken together to form a 5, 6, or 7 membered, unsubstituted or substituted, saturated, unsaturated or aromatic ring.

In some variations, $R_{26}$ is selected from the group consisting of hydrogen, ($C_{1-6}$)alkyl, ($C_{3-12}$)cycloalkyl, hetero($C_{3-12}$) cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$)bicycloaryl and hetero ($C_{4-12}$)bicycloaryl, each unsubstituted or substituted with said 1-3 substituents.

In other variations, $R_{26}$ is selected from the group consisting of hydrogen, ($C_{1-6}$)alkyl,

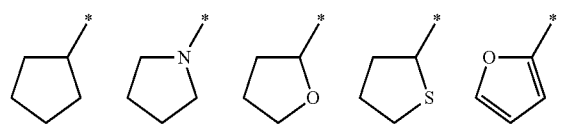

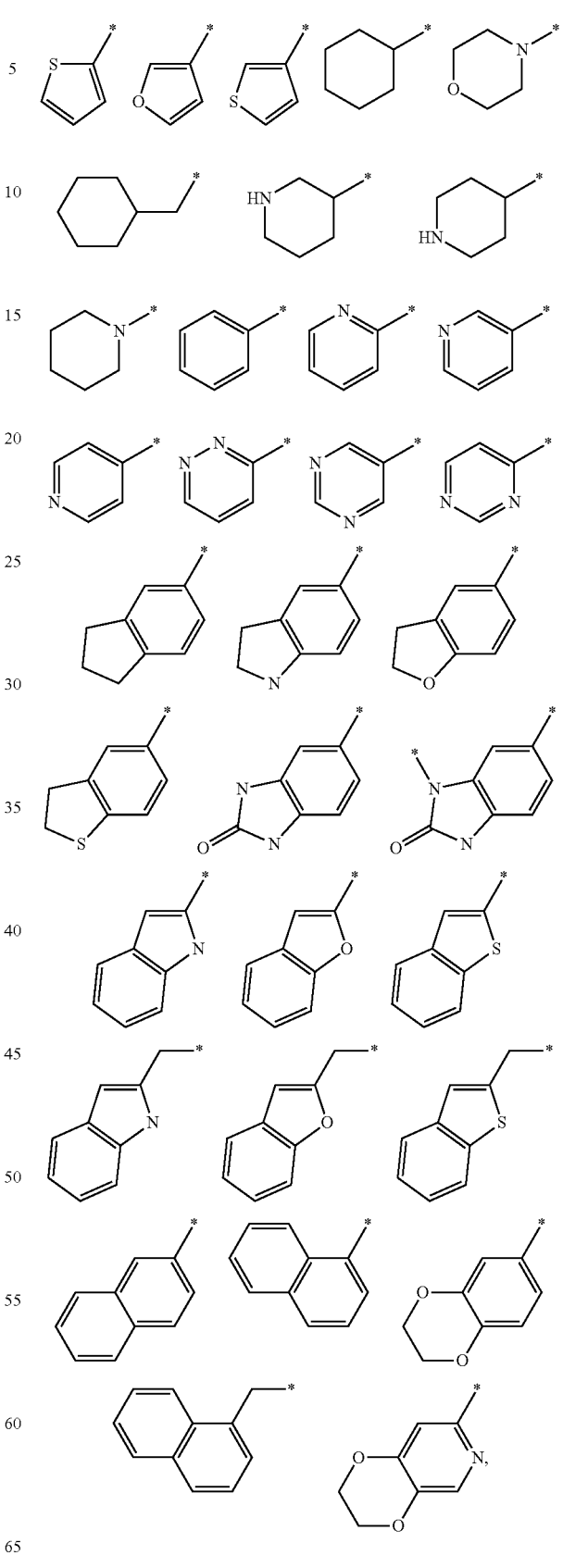

each unsubstituted or substituted with said 1-3 substituents.

In still other variations, $R_{26}$ is selected from the group consisting of

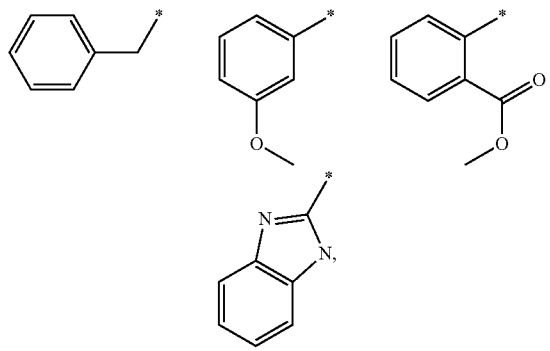

each unsubstituted or substituted with said 1-3 substituents.

It is further noted that when $R_{26}$ is substituted, the substituents on $R_{26}$ are each independently selected from the group consisting of hydrogen, halo, nitro, cyano, thio, oxy, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or further substituted.

In some variations, the substituents on $R_{26}$ are each independently selected from the group consisting of oxo, $(C_{1-6})$alkyl, alkylthio, $(C_{1-6})$alkoxy, haloalkyl, perhaloalkyl, $(C_{1-6})$alkoxy, aryloxy, $(C_{1-6})$alkoxycarbonyl, aryl, heteroaryl, cycloalkyl, and heterocycloalkyl, each unsubstituted or further substituted.

It is further noted that any two substituents bonded to adjacent atoms of $R_{26}$ may be taken together to form a 5, 6, or 7 membered, unsubstituted or substituted, saturated, unsaturated or aromatic ring.

Claiming the BenzimidazolesMay 312007_143 Samples and Prophetic Examples

In yet other particular variations of the above embodiments, $R_1$ is of the formula

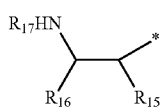

and $R_{16}$ is a substituted methyl of the formula

where $R_{28}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$ alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 substituents where the substituents on $R^{28}$ are each independently selected from the group consisting of halo, nitro, cyano, thio, oxy, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-30})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl $(C_{1-10})$alkyl, hetero$(C_{3-12})$cycloalkyl$(C_{1-10})$alkyl, $(C_{4-12})$aryl $(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero $(C_{4-12})$bicycloaryl, each unsubstituted or further substituted; and any two substituents bonded to adjacent atoms of $R_{28}$ may be taken together to form a five, six or seven membered saturated, unsaturated or aromatic ring, each unsubstituted or substituted.

In some variations, $R_{28}$ is selected from the group consisting of $(C_{1-6})$alkyl, aryl, heteroaryl, cycloalkyl and heterocycloalkyl, aryl$(C_{1-6})$alkyl, heteroaryl$(C_{1-6})$alkyl, cycloalkyl $(C_{1-6})$alkyl, and heterocycloalkyl$(C_{1-6})$alkyl, each unsubstituted or substituted with 1-3 substituents.

In some variations, $R^{28}$ is selected from the group consisting of aryl and heteroaryl, each unsubstituted or substituted with 1-3 substituents.

In still other variations, $R^{28}$ is selected from the group consisting of

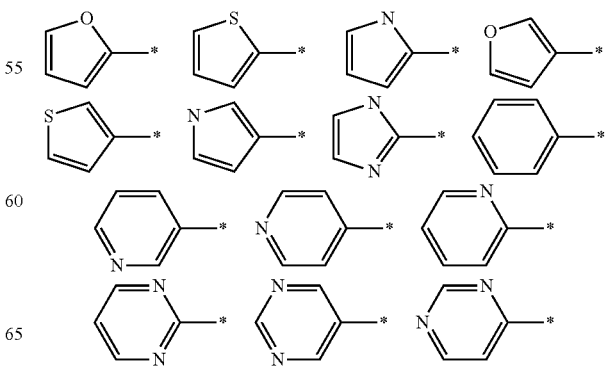

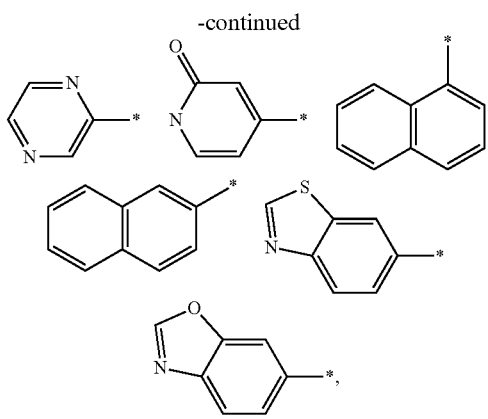

each unsubstituted or substituted with 1-3 substituents.

In yet other variations, $R_{28}$ is selected from the group consisting of

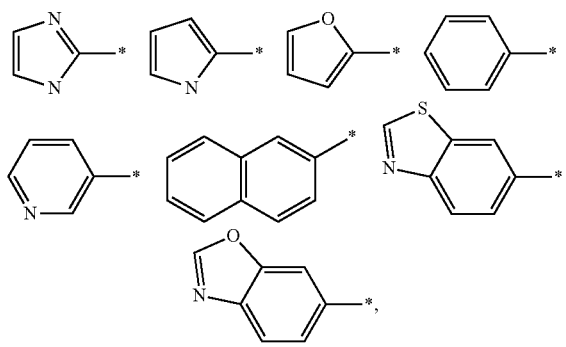

each unsubstituted or substituted with 1-3 substituents.

In other variations, $R_{28}$ is an unsubstituted or a substituted phenyl.

In other variations, $R_{28}$ is a unsubstituted or substituted naphthyl of the formula

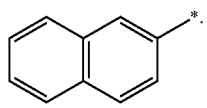

In still other variations, $R_{28}$ is selected from the group consisting of substituted six-membered aryls and heteroaryls, where the aryls and heteroaryls are substituted with 1-3 substituents, and one of said 1-3 substituents is bonded to the ring atom at the para-position relative to the point where $R_{28}$ is attached to the remainder of the molecular.

It is noted that in all the above variations of $R_{28}$, when it is substituted, the substituents are each independently selected from the group consisting of halo, nitro, cyano, thio, oxy, oxo, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$alkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{4-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{3-12})$bicycloaryl and hetero$(C_{4-12})$bicycloaryl, each unsubstituted or further substituted. It is further noted that any two substituents bonded to adjacent atoms of $R_{28}$ may be taken together to form a five, six or seven membered saturated, unsaturated or aromatic ring, each unsubstituted or further substituted.

In some variations, the substituents on $R_{28}$ are each independently selected from the group consisting of halo, oxo, alkoxy, aryloxy, $(C_{1-6})$alkyl, hydroxyalkyl, alkoxyalkyl, aryl, heteroaryl, cycloalkyl, heterocycloalkyl, hydroxycyclo$(C_{3-6})$alkyl, alkoxycyclo$(C_{3-6})$alkyl, amido, carboxamido, sulfonamide, carbamate, urea, each unsubstituted or further substituted, and any two substituents bonded to adjacent atoms of $R_{28}$ may be taken together to form a five, six or seven membered, saturated, unsaturated or aromatic ring, each unsubstituted or substituted.

In other variations, the substituents on $R_{28}$ are each independently selected from the group consisting of fluoro, chloro, bromo, tertbutyl, amino, oxo,

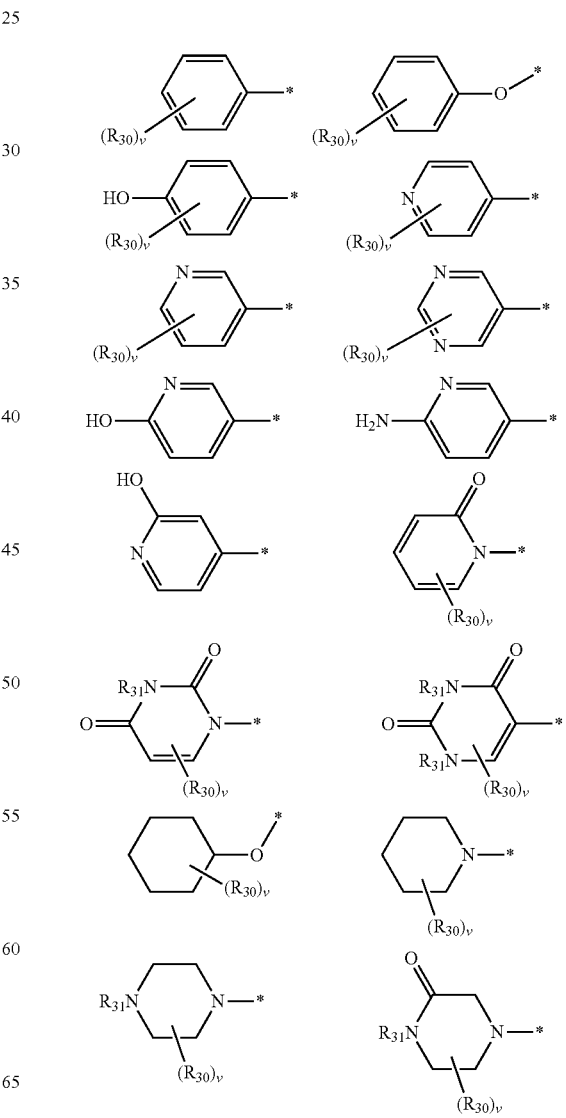

-continued
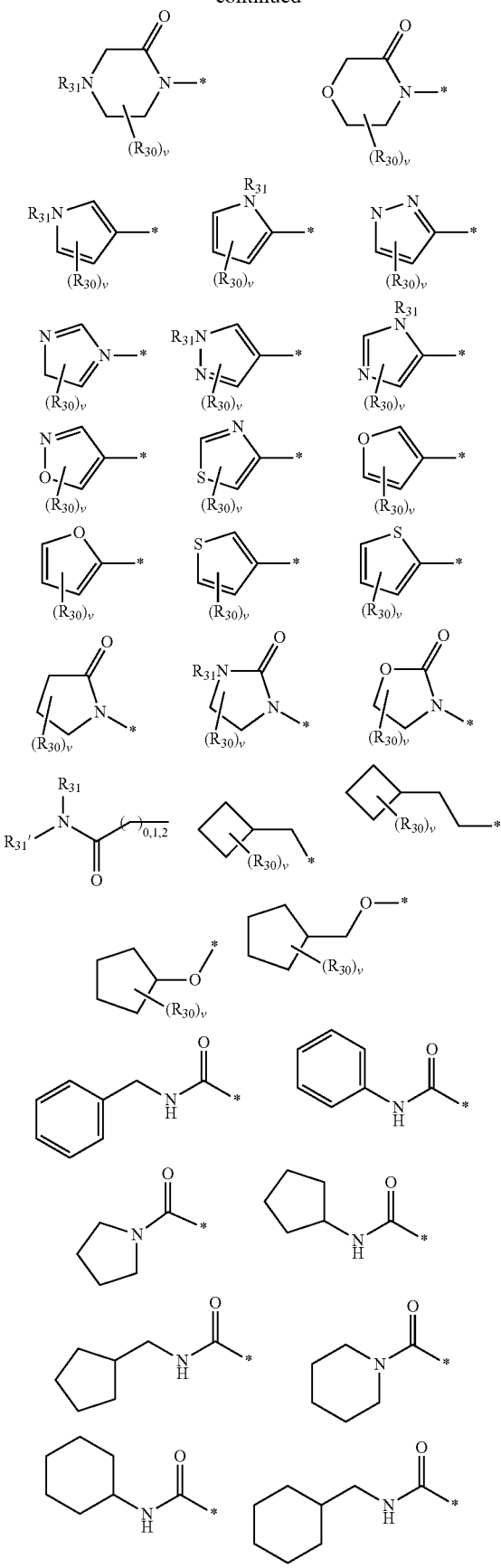
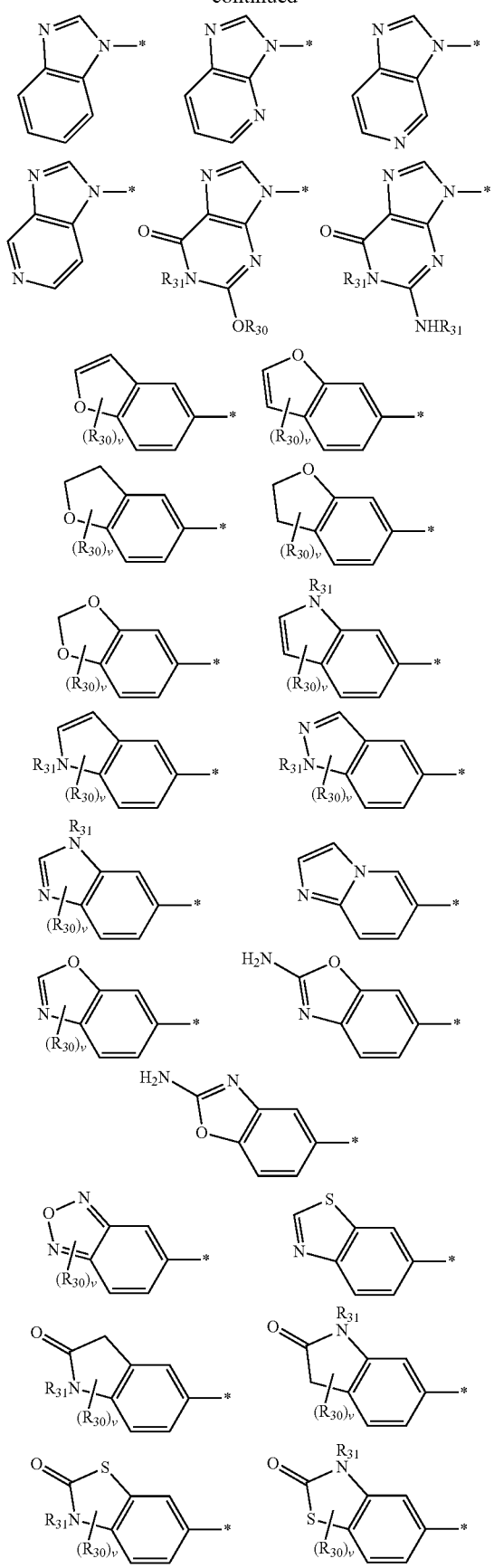

-continued

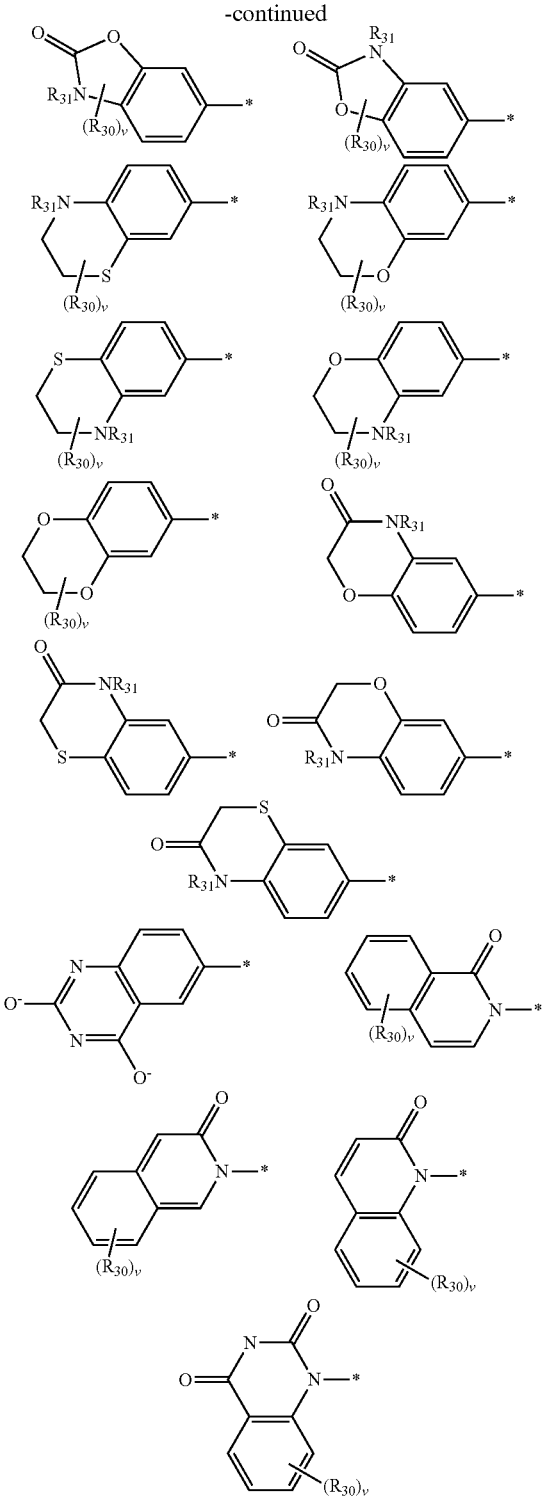

where
v is 0, 1, 2 or 3;
each $R_{30}$ is independently selected from the group consisting of hydrogen, halo, hydroxyl, cyano, amino, oxo, $(C_{1-6})$alkyl, alkylamino, alkylaminooxy, aminocarbonyl, alkoxycarbonyl, $(C_{1-6})$alkoxy, alkoxyalkyl, heterocycloalkyl, aryl, heteroaryl, alkylsulfonyl, amidosulfonyl, aminosulfonyl, sulfonyl, amino, amido, carboxamido, carbamate, and urea, each unsubstituted or substituted, and any two of $R_{30}$ bound to adjacent ring atoms may be taken together to form a 5 or 6 membered, unsubstituted or substituted, saturated, unsaturated or aromatic ring; and each $R_{31}$ or $R_{31}'$ is independently selected from the group consisting of hydrogen, $(C_{1-6})$alkyl, hydroxyalkyl, alkoxyalkyl, cycloalkyl, hydroxycyclo$(C_{3-6})$alkyl, alkoxycyclo $(C_{3-6})$alkyl, each unsubstituted or substituted, and any two of $R_{30}$ and $R_{31}$ bonded to adjacent atoms and any two of $R_{31}$ and $R_{31}'$ bonded to the same atom may be taken to form a 5, 6 or 7 membered, unsubstituted or substituted, saturated, unsaturated or aromatic ring.

In some other variations, the substituents on $R_{23}$ are each independently selected from the group consisting of tertbutyl,

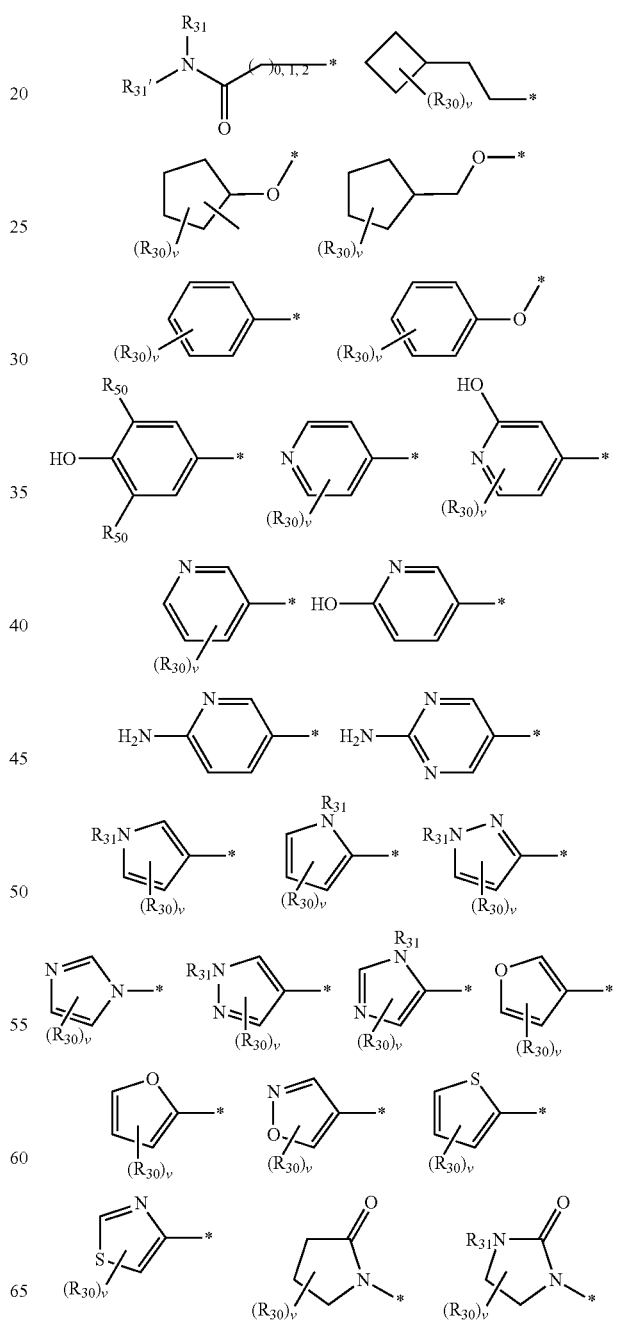

-continued

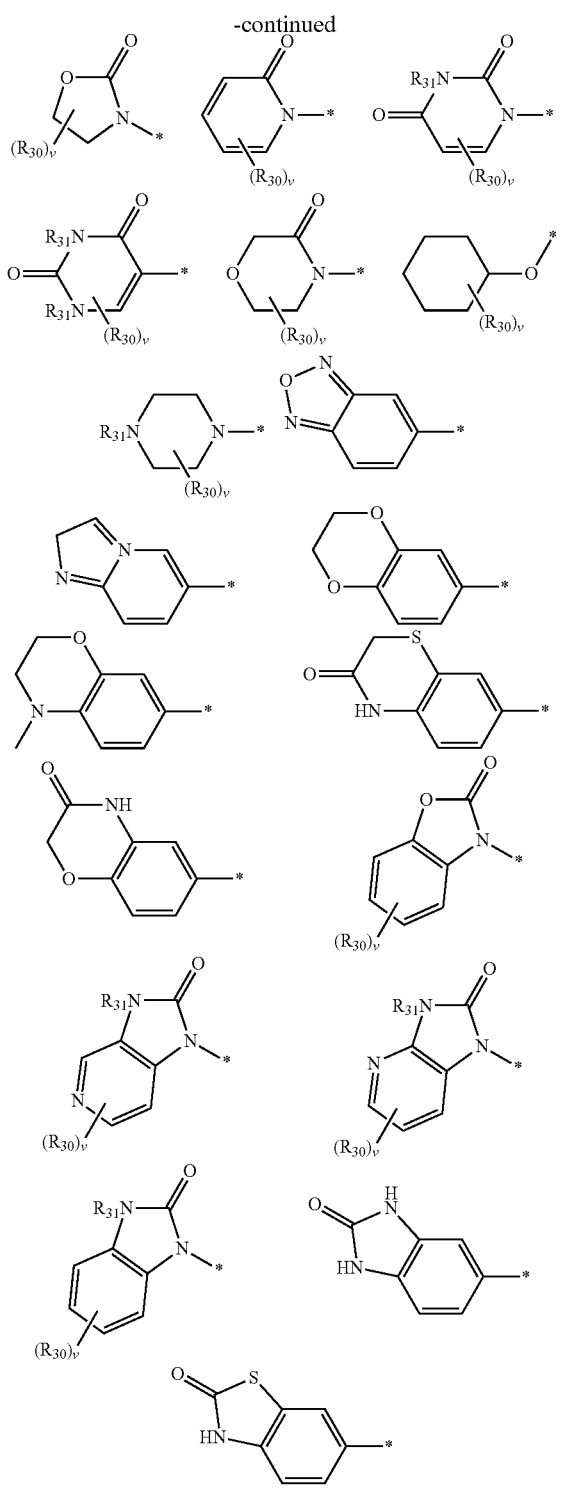
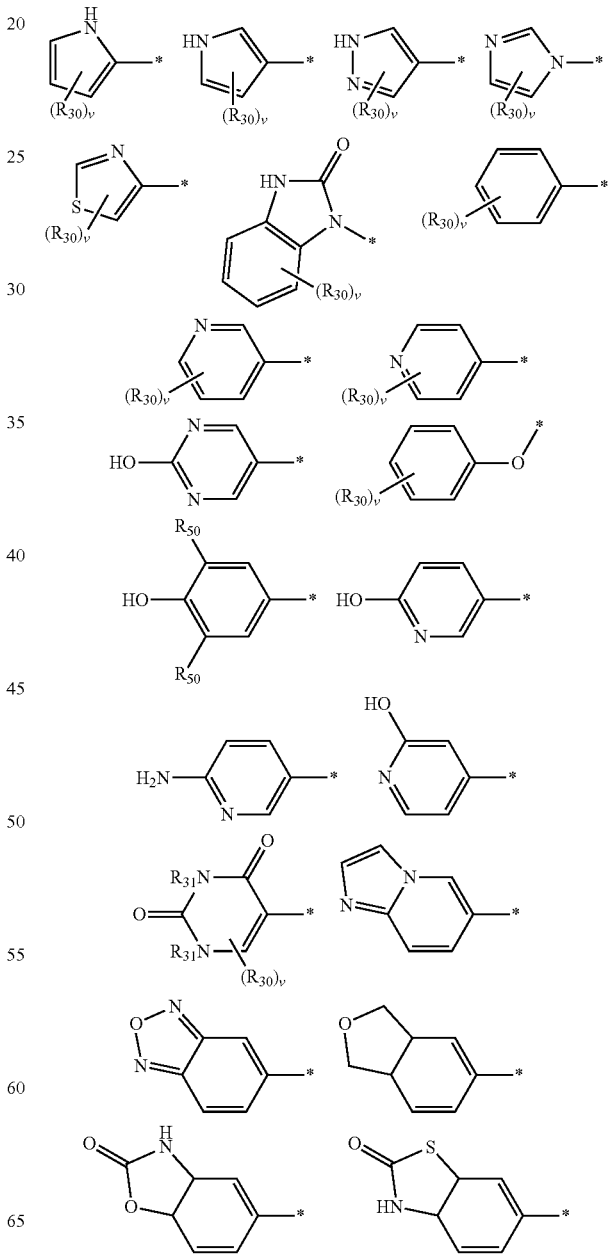

where

V is 0, 1, 2 or 3;

each $R_{30}$ is independently selected from the group consisting of hydrogen, halo, hydroxyl, cyano, amino, oxo, $(C_{1-6})$alkyl, alkylamino, alkylaminooxy, aminocarbonyl, alkoxycarbonyl, $(C_{1-6})$alkoxy, alkoxyalkyl, heterocycloalkyl, aryl, heteroaryl, alkylsulfonyl, amidosulfonyl, aminosulfonyl, sulfonyl, amino, amido, carboxamido, carbamate, and urea, each unsubstituted or substituted, and any two $R_{30}$ bonded to adjacent ring atoms may be taken together to form a 5 or 6 membered, unsubstituted or substituted, saturated, unsaturated or aromatic ring;

each $R_{31}$ or $R_{31}'$ is independently selected from the group consisting of hydrogen, $(C_{1-6})$alkyl, hydroxyalkyl, alkoxyalkyl, cycloalkyl, hydroxycyclo$(C_{3-6})$alkyl, alkoxycyclo$(C_{3-6})$alkyl, each unsubstituted or substituted, and any two of $R_{30}$ and $R_{31}$ bonded to adjacent atoms and any two of $R_{31}$ and $R_{31}'$ bonded to the same atom may be taken to form a 5, 6 or 7 membered, unsubstituted or substituted, saturated, unsaturated or aromatic ring; and each $R_{50}$ is independently selected from the group consisting of H, methyl, methoxy, chloro, and fluoro.

In other variations, the substituents on $R_{28}$ are each independently selected from the group consisting of tertbutyl,

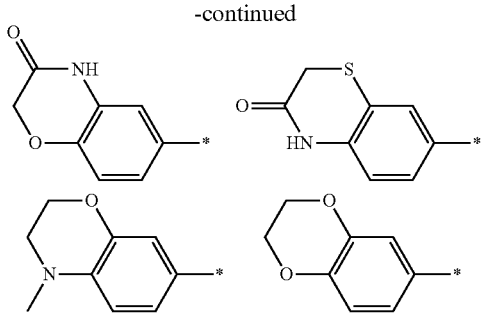

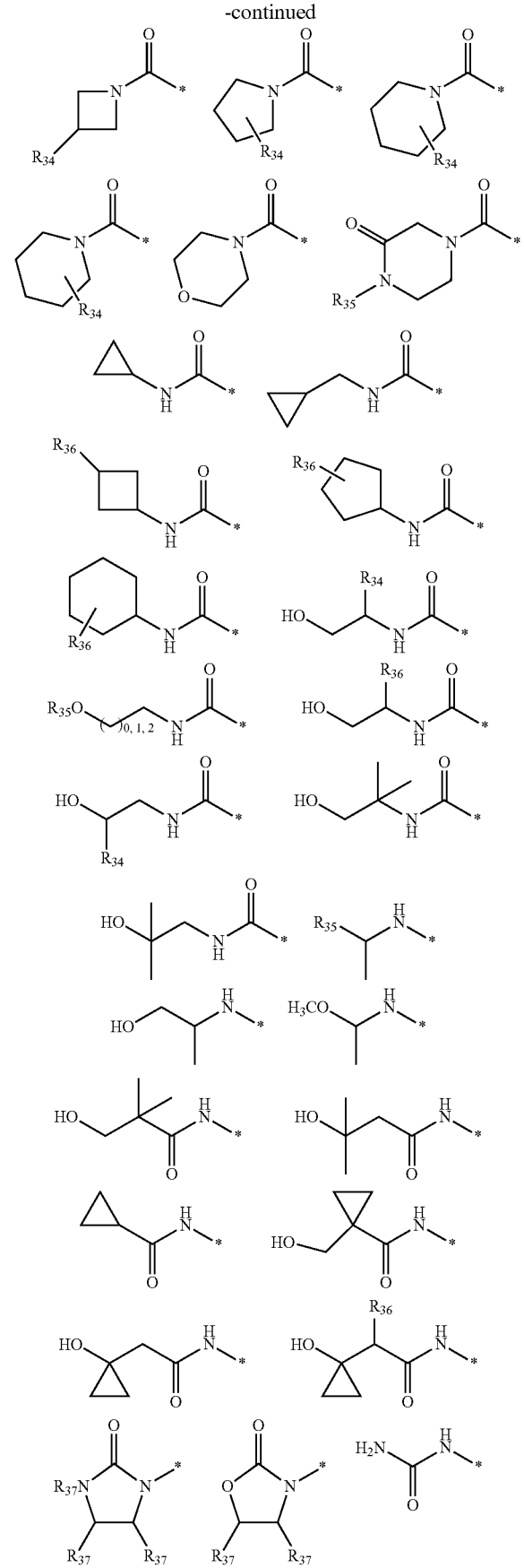

where v is 0, 1, 2 or 3;

each $R_{30}$ is independently selected from the group consisting of hydrogen, halo, cyano, amino, oxo, $(C_{1-6})$alkyl, alkylamino, alkylaminooxy, aminocarbonyl, alkoxycarbonyl, $(C_{1-6})$alkoxy, alkoxyalkyl, heterocycloalkyl, aryl, heteroaryl, alkylsulfonyl, amidosulfonyl, aminosulfonyl, sulfonyl, amino, amido, carboxamido, carbamate, and urea, each unsubstituted or substituted, and any two $R_{30}$ bonded to adjacent ring atoms may be taken together to form a 5 or 6 membered, unsubstituted or substituted, saturated, unsaturated or aromatic ring;

each $R_{31}$ is independently selected from the group consisting of hydrogen, $(C_{1-6})$alkyl, hydroxyalkyl, alkoxyalkyl, cycloalkyl, hydroxycyclo$(C_{3-6})$alkyl, alkoxycyclo$(C_{3-6})$alkyl, each unsubstituted or substituted, and any two of $R_{30}$ and $R_{31}$ bonded to adjacent ring atoms may be taken together to form a 5 or 6 membered, unsubstituted or substituted, saturated, unsaturated or aromatic ring; and each $R_{50}$ is independently selected from the group consisting of H, methyl, methoxy, chloro, and fluoro.

In yet other variations, $R_{30}$ is selected from the group consisting of hydrogen, halo, hydroxyl, cyano, oxo, $(C_{1-6})$alkyl, —NHC(O)CH$_3$, alkylsulfonyl, amino, —C(O)NH—$(C_{1-6})$alkyl, —C(O)NH—$(C_{1-6})$alkyl$(C_{1-6})$alkoxy, $(C_{1-6})$alkoxy, hydroxy$(C_{1-6})$alkylamino, $(C_{1-6})$alkoxy$(C_{1-6})$alkyl, and —NH—$(C_{1-6})$alkyl, heterocycloalkylacyl, amido, carboxamido, phenyl, and $(C_{1-4})$heteroaryl.

In still other variations, $R_{30}$ is selected from the group consisting of hydrogen, hydroxyl, halo, hydroxyl, cyano, oxo, $(C_{1-6})$alkyl, hydroxy$(C_{1-6})$alkyl, phenyl, $(C_{1-6})$alkoxy$(C_{1-6})$alkyl, amino, sulfonyl, $(C_{1-6})$alkoxy, $(C_{1-6})$alkylsulfonyl, morpholinyl,

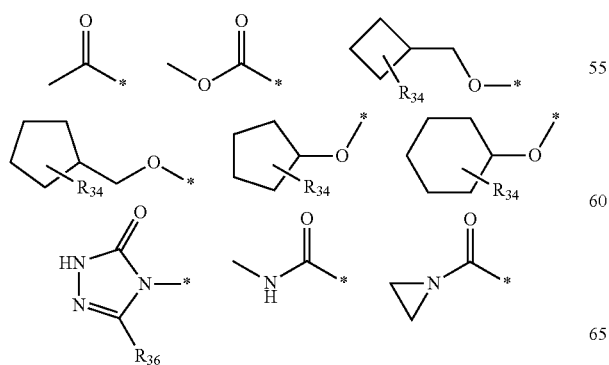

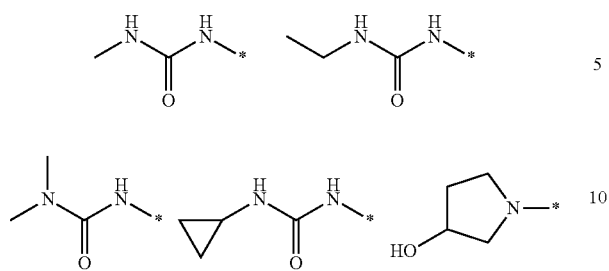

wherein

R$_{34}$ is selected from the group consisting of hydrogen, hydroxyl, halo, and hydroxymethyl;

R$_{35}$ is selected from the group consisting of hydrogen and unsubstituted or substituted (C$_{1-6}$)alkyl;

R$_{36}$ is selected from the group consisting of hydroxyl, unsubstituted or substituted (C$_{1-6}$)alkyl; and R$_{37}$ is selected from the group consisting of hydrogen, (C$_{1-6}$)alkyl, cycloalkyl, hydroxy(C$_{1-6}$)alkyl, alkoxy(C$_{1-6}$)alkyl, hydroxycyloalkyl, alkoxycycloalkyl, halo(C$_{1-6}$)alkyl, and halocycloalkyl, each unsubstituted or substituted.

In some further variations, R$_{30}$ is selected from the group consisting hydrogen, hydroxyl, fluoro, chloro, cyano, oxo, methyl, propyl, isopropyl, tertbutyl, phenyl, hydroxyethyl, methoxymethyl, methoxyethyl, ethoxypropyl, —NH$_2$, —N(CH$_3$)$_2$, —NH(CH$_3$), cyclopropylamino, methoxy, ethoxy, isopropyloxy, cyclopropylmethyloxy, methylsulfonyl, morpholinyl,

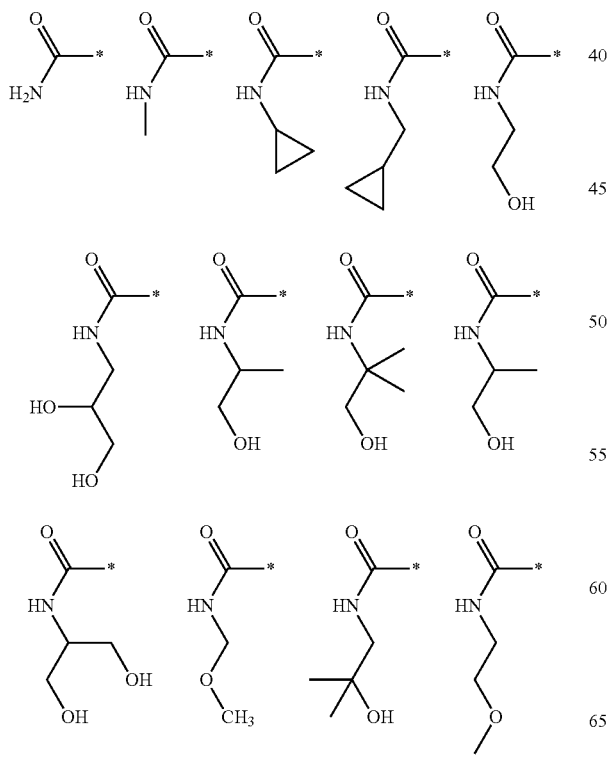

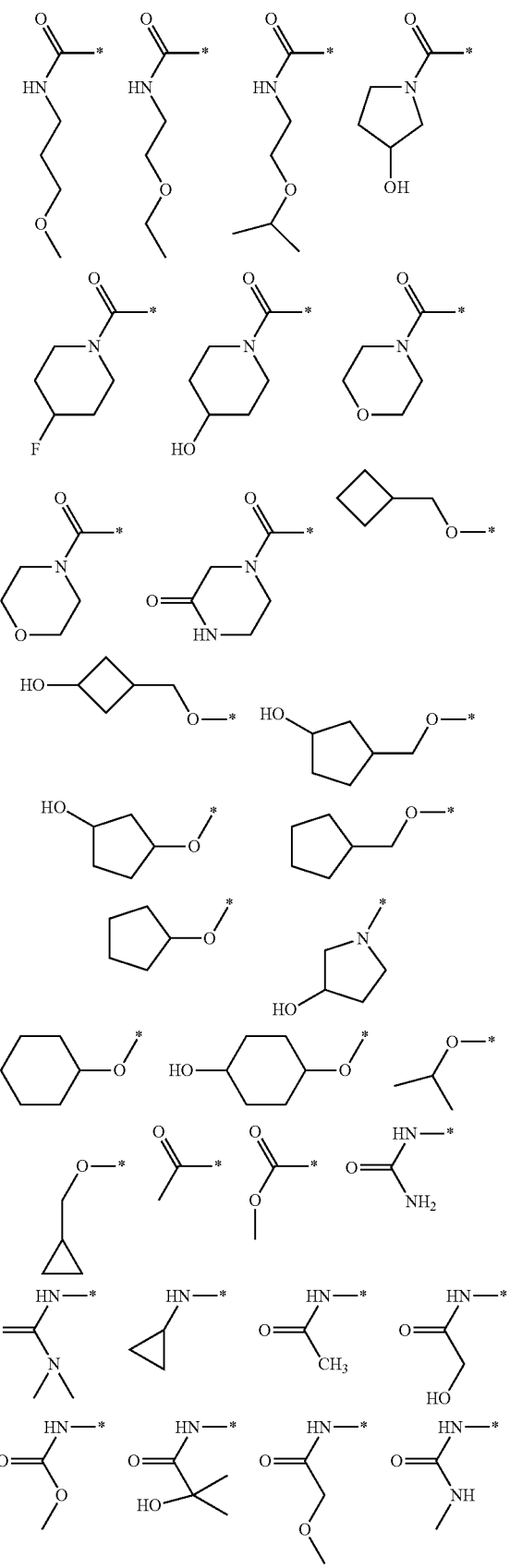

-continued

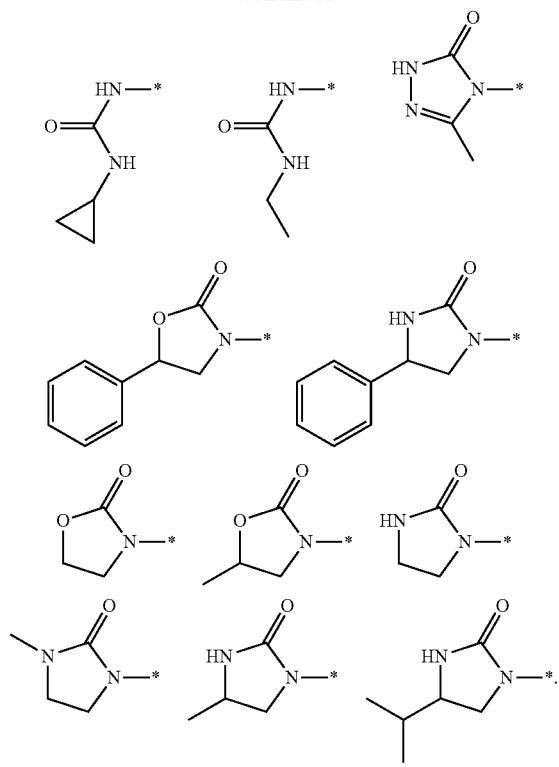

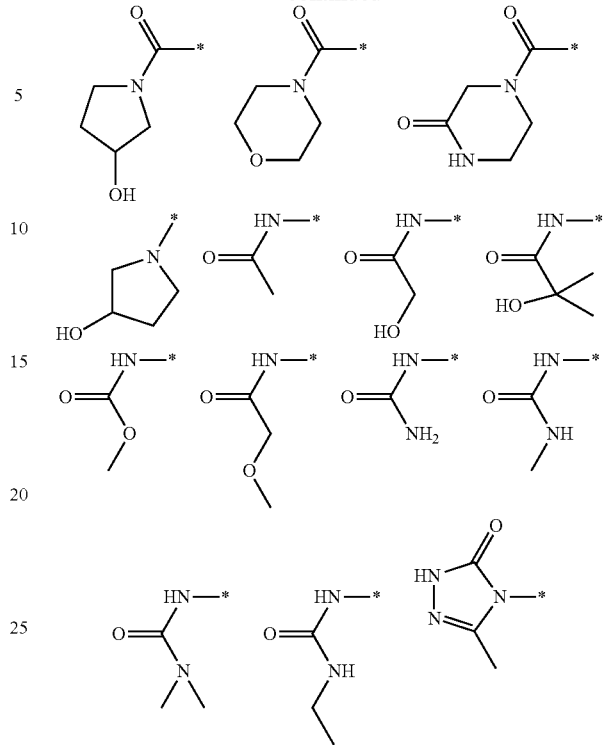

In still some further variations, $R_{30}$ is selected from the group consisting hydrogen, hydroxyl, fluoro, chloro, cyano, oxo, methyl, n-propyl, isopropyl, tertbutyl, hydroxyethyl, methoxymethyl, methoxyethyl, —$NH_2$, —$N(CH_3)_2$, methoxy, ethoxy, isopropyloxy, methylsulfonyl, morpholinyl,

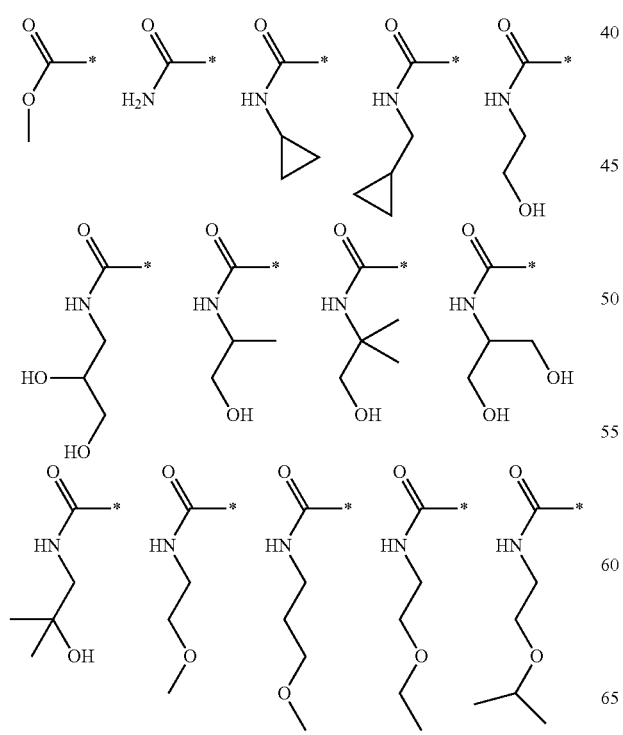

In some variations of the above embodiments and variations, $R^{31}$ is selected from the group consisting of hydrogen, hydroxyl, and unsubstituted or substituted $(C_{1-6})$alkyl.

In yet other particular variations of the above embodiments, $R_1$ is of the formula

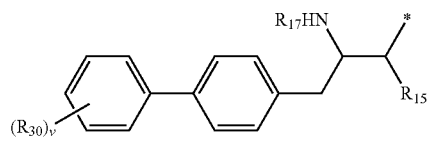

where v is 0, 1, 2, or 3; and $R_{30}$ is selected from the group consisting of hydroxyl, chloro,

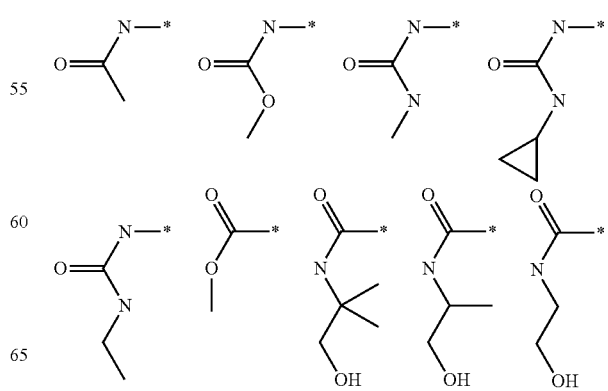

-continued

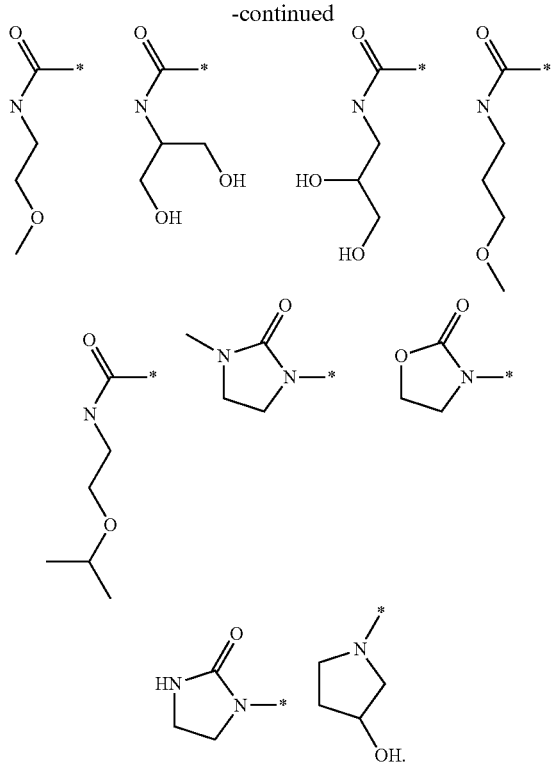

In still other particular variations of the above embodiments, $R_1$ is of the formula

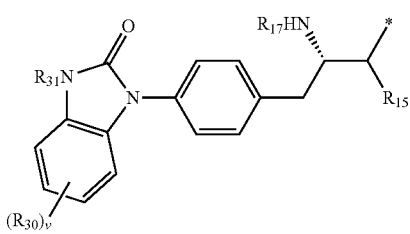

where
v is 0, 1, 2, or 3;
$R_{15}$ is selected from the group consisting of hydrogen, hydroxyl, $(C_{1-4})$alkyl, hydroxy$(C_{1-4})$alkyl, $(C_{1-4})$alkoxy, aryl $(C_{1-4})$alkyl, heteroaryl$(C_{1-4}$alkyl, cycloalkyl$(C_{1-4})$alkyl, and $(C_{1-4})$heterocycloalkyl$(C_{1-4})$alkyl;
$R_{17}$ is selected from the group consisting of hydrogen, $(C_{1-6})$alkyl, halo$(C_{1-6})$alkyl, hydroxy$(C_{1-6})$alkyl, carbonyl $(C_{1-6})$alkyl, sulfonyl$(C_{1-6})$alkyl, sulfinyl$(C_{1-6})$alkyl, $(C_{1-6})$ azaalkyl, $(C_{3-12})$cycloalkyl$(C_{1-6})$alkyl, hetero$(C_{3-2})$cycloalkyl$(C_{1-6})$alkyl, $(C_{4-12})$aryl$(C_{1-6})$alkyl, hetero$(C_{1-10})$aryl $(C_{1-6})$alkyl, $(C_{9-12})$bicycloaryl$(C_{1-6})$alkyl, hetero$(C_{8-12})$ bicycloaryl$(C_{1-6})$alkyl, hetero$(C_{1-6})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;
$R_{30}$ is selected from the group consisting of hydrogen, fluoro, methyl, propyl, hydroxyethyl, and methoxyethyl; and
$R_{31}$ is selected from the group consisting of hydrogen and $(C_{1-6})$alkyl.
In other particular variations of the above embodiments, $R_1$ is of the formula

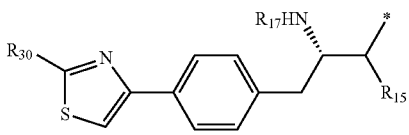

where
$R_{15}$ is selected from the group consisting of hydrogen, hydroxyl, $(C_{1-4})$alkyl, hydroxy$(C_{1-4})$alkyl, $(C_{1-4})$alkoxy, aryl $(C_{1-4})$alkyl, heteroaryl$(C_{1-4})$alkyl, cycloalkyl$(C_{1-4})$alkyl, and $(C_{1-4})$heterocycloalkyl$(C_{1-4})$alkyl;
$R_{17}$ is selected from the group consisting of hydrogen, $(C_{1-6})$alkyl, halo$(C_{1-6})$alkyl, hydroxy$(C_{1-6})$alkyl, carbonyl $(C_{1-6})$alkyl, sulfonyl$(C_{1-6})$alkyl, sulfinyl$(C_{1-6})$alkyl, $(C_{1-6})$ azaalkyl, $(C_{3-12})$cycloalkyl$(C_{1-6})$alkyl, hetero$(C_{3-12})$cycloalkyl$(C_{1-6})$alkyl, $(C_{4-12})$aryl$(C_{1-6})$alkyl, hetero$(C_{1-10})$aryl $(C_{1-6})$alkyl, $(C_{9-12})$bicycloaryl$(C_{1-6})$alkyl, hetero$(C_{8-12})$ bicycloaryl$(C_{1-6})$alkyl, hetero$(C_{1-6})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;
$R_{30}$ is selected from the group consisting of hydrogen, hydroxyl,

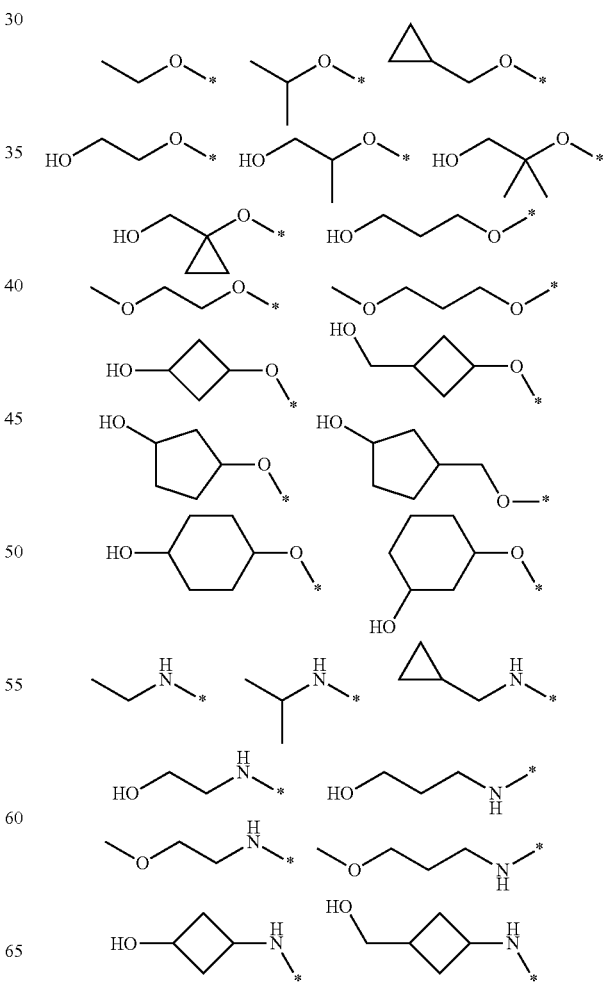

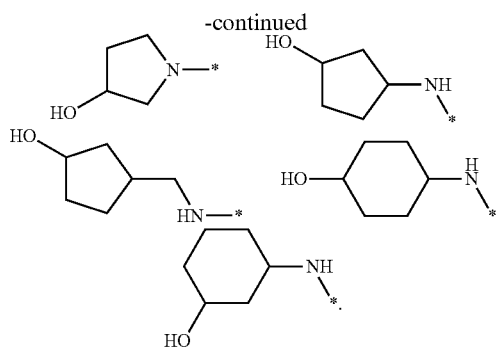

R15

In some further variations of the above embodiments and variations, when present, $R_{15}$ is selected from the group consisting of hydrogen, hydroxyl, $(C_{1-6})$alkyl, hydroxyl$(C_{1-6})$alkyl, aryl$(C_{1-6})$alkyl, heteroaryl$(C_{1-6})$alkyl. In other further variations, $R_{15}$ is selected from the group consisting of hydrogen, hydroxyl, and benzyl. In still other further variations, $R_{15}$ is hydrogen.

R17

In some further variations of the above embodiments and variations, when present, $R_{17}$ is selected from the group consisting of hydrogen, $(C_{1-6})$alkyl, hydroxyl$(C_{1-6})$alkyl, alkoxy$(C_{1-6})$alkyl, halo$(C_{1-6})$alkyl, amino$(C_{1-6})$alkyl, each unsubstituted or substituted. In other further variations, $R_{17}$ is hydrogen.

R2

In some further variations of the above embodiments and variations, when present, $R_2$ is $(C_{1-4})$alkyl, halo$(C_{1-10})$alkyl, hydroxy$(C_{1-10})$alkyl, $(C_{1-6})$alkoxy$(C_{1-10})$alkyl carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, each unsubstituted or substituted.

In particular variations, $R_2$ is -L-$R_{25}$, where

L is a linker providing 1, 2, 3, 4, 5 or 6 atom separation between the ring atom and $R^{25}$ to which L is attached, wherein the atoms of the linker providing the separation are selected from the group consisting of carbon, oxygen, nitrogen, and sulfur; and $R_{25}$ is selected from the group consisting of cyano, halo, hydroxyl, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, amido, carboxamido, sulfonamido, imino, sulfonyl, sulfinyl, $(C_{1-10})$alkyl, $(C_{1-10})$haloalkyl, $(C_{1-10})$perhaloalkyl, $(C_{1-10})$azaalkyl, $(C_{1-10})$oxaalkyl, $(C_{1-10})$oxoalkyl, imino$(C_{1-10})$alkyl, aryl, and heteroaryl, each unsubstituted or substituted.

In other variations, L is $(C_{1-4})$alkyl, unsubstituted or substituted. In yet other variations, L is —$(CH_2)_3$—. In still other variations, L is —$(CH_2)_2$—. In yet still other variations, L is —$(CH_2)$—.

In variations of the above embodiments and variations, $R_{25}$ is selected from the group consisting of cyano, halo, haloalkyl, perhaloalkyl, hydroxyl, carbonyloxy, $(C_{1-10})$alkoxy, $(C_{4-12})$aryloxy, hetero$(C_{1-10})$aryloxy, carbonyl, carboxamido, amido, oxycarbonyl, aminocarbonyl, amino, $(C_{1-10})$alkylamino, sulfonamido, imino, sulfonyl, sulfinyl, aryl and heteroaryl, each unsubstituted or substituted. In other variations, $R_{25}$ is selected from the group consisting of —F, —Cl, —CN, —$CF_3$, —$OR_{27}$, —$C(O)NR_{27}R_{27}'$, —$OC(O)$ $NR_{27}R_{27}'$, —$O(CH_2)_nOR_{27}$ $NR_{27}R_{27}'$, —$NHC(O)OR_{27}$, —$NHC(O)R_{27}$, —$NHS(O)_2R_{27}$, $(C_{4-14})$aryl, and $(C_{1-13})$heteroaryl, where n is 1 or 2, and $R_{27}$ and $R_{27}'$ are each independently selected from the group consisting of H, perhalo$(C_{1-7})$alkyl, $(C_{1-7})$alkyl, hydroxyl$(C_{1-7})$alkyl, $(C_6)$aryl and $(C_{1-5})$heteroaryl, each unsubstituted or substituted. In still other variations, $R_{25}$ is selected from the group consisting of —OH, —F, —$CF_3$, —CN, —$OCH_3$, —$OCH_2CH_3$, —$OCF_3$, —$OC(O)NHCH_3$, —$OC(O)NHCH_3$, —$(O)NHCH_3$, —$C(O)$ $NHCH_2CH_3$, —$NHS(O)_2CH_3$, —$NHC(O)CH_2OH$, —$NHC(O)CH_3$, —$OCH_2OCH_3$, —$OCH_2OCH_2CH_3$, —$O(CH_2)_2$ $OH$, —$O(CH_2)_2OCH_3$, —$O(CH_2)_2OCH_2CH_3$, —$OCH_2CH(OH)CH_2OCH_3$, —$OCH_2CH(OH)CH_2OH$, —$(C_{1-5})$heteroaryl, —$(CH_2)_2(C_{1-5})$heteroaryl, —$(CH_2)_2(C_{1-5})$heteroaryl,

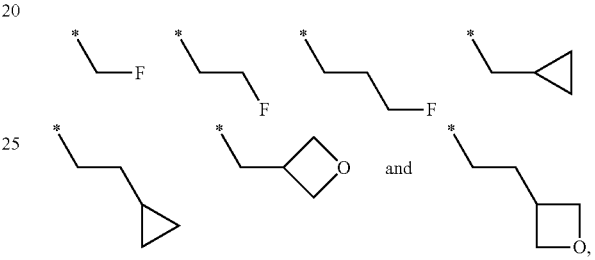

each unsubstituted or substituted. In some particular variations, $R_{25}$ is selected from the group consisting of —F, —$CF_3$, —CN, —OH, and —$OCH_3$, In some particular variations of the above embodiments and variations, $R_2$ is selected from the group consisting of —$(CH_2)_2F$, —$(CH_2)_3OCH_3$, $(CH_2)_3OH$, —$(CH_2)_3OEt$, —$(CH_2)_3OCF_3$, —$(CH_2)_3CF_3$, —$(CH_2)_3CN$, —$(CH_2)_3OC(O)NHCH_3$, —$(CH_2)_3NHC(O)OCH_3$, —$(CH_2)_2NHC(O)CH_3$, —$(CH_2)_2CN$, —$(CH_2)_2CF_3$, —$(CH_2)_3NHC(O)OCH_3$, —$(CH_2)_2OCONHCH_3$, —$(CH_2)_2C(O)NHCH_3$, —$(CH_2)_2OCF_3$, —$(CH_2)_2NHS(O)_2CH_3$, —$(CH_2)_2CONHCH_2CH_3$, —$(CH_2)_2C(O)NHCH_2OH$, —$(CH_2)_2(C_{1-4})$heteroaryl, —$CH_2CONHCH_3$, —$CH_2CONHCH_2CH_3$, and —$(CH_2)_2(C_{1-4})$heteroaryl, each unsubstituted or substituted.

In other particular variations, $R_2$ is selected from the group consisting of —$(CH_2)_2F$, —$(CH_2)_3CF_3$, —$(CH_2)_3OCH_3$, —$(CH_2)_3OH$, —$(CH_2)_3CN$,

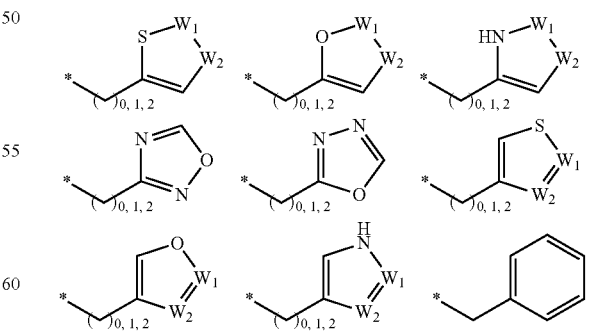

where $W_1$ and $W_2$ are each independently —CH— or —N—. In some variations, $W_1$ is —CH—. In other variations, $W_1$ is —N—. In still other variations, both $W_1$ and $W_2$ are —CH—.

In still other particular variations, $R_2$ is —$(CH_2)_3OCH_3$.

$R_6$

In some particular variations of the above embodiments and variations, $R_6$ is selected from the group consisting of hydrogen, hydroxyl, $(C_{1-3})$alkyl, $(C_{1-3})$alkoxy, $(C_{1-3})$alkoxy$(C_{1-3})$alkyl, and —COOR where R is alkyl, cycloalkyl, cycloheteroalkyl, aryl and heteroaryl, each unsubstituted or substituted. In other particular variations, $R_6$ is selected from the group consisting of hydrogen and hydroxyl.

$R_7$

In some particular variations of the above embodiments and variations, $R_7$ is selected from the group consisting of hydrogen, halo, cyano, thio, oxy, hydroxy, carbonyloxy, alkoxy, aryloxy, heteroaryloxy, carbonyl, aminocarbonyl, amino, $(C_{1-10})$alkylamino, $(C_{1-10})$alkyl, carbonyl$(C_{1-3})$alkyl, sulfonyl$(C_{1-3})$alkyl, amino$(C_{1-10})$alkyl, $(C_{3-4})$cycloalkyl$(C_{1-10})$alkyl, hetero$(C_{3-7})$cycloalkyl$(C_{1-10})$alkyl, $(C_{4-12})$aryl$(C_{1-10})$alkyl, heteroaryl$(C_{1-10})$alkyl, and aminocarbonyloxy, each unsubstituted or substituted. In other particular variations, $R_7$ is selected from the group consisting of hydrogen, methyl, ethyl, and methoxy.

$R_{10}$

In some variations of the above embodiments and variations, $R_{10}$ and $R_{10}'$ are each independently selected from the group consisting of hydrogen, cyano, nitro, oxo, halo, hydroxyl, carbonyloxy, $(C_{1-10})$alkoxy, carbonyl, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, sulfonyl$(C_{1-10})$alkyl, $(C_{1-10})$azaalkyl, $(C_{1-10})$oxaalkyl, $(C_{1-10})$oxoalkyl, hetero$(C_{1-10})$alkyl, each unsubstituted or substituted.

In other variations, $R_{10}$ and $R_{10}'$ are each independently selected from the group consisting of hydrogen, $(C_{1-6})$alkyl, cyano, oxo, and halo.

In still other variations, $R_{10}$ and $R_{10}'$ are each independently selected from the group consisting of hydrogen, methyl, isopropyl, chloro, fluoro, oxo, nitro, and methoxy.

In some particular variations when $R_{10}$ is bound to a benzimidazole of the formula

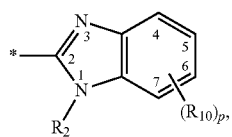

$R_{10}$ is selected from the group consisting of hydrogen, 4-methyl, 5-methyl, 6-methyl, 6-isopropyl, 4-fluoro, 5-fluoro, 6-fluoro, 7-fluoro, 4-chloro, 5-chloro, 6-chloro, 7-chloro, 4-cyano, 6-cyano, 7-cyano, 5-nitro, 6-nitro, 4-methoxy, 6-methoxy, and 7-methoxy.

In other particular variations, $R_{10}$ is selected from the group consisting of hydrogen, 4-methyl, 5-methyl, 6-methyl, 6-fluoro, 4-chloro, 6-chloro, and 7-chloro. In other particular variations, $R_{10}$ is selected from the group consisting of hydrogen and 4-chloro. In other particular variations, $R_{10}$ is selected from the group consisting of hydrogen and 4-methyl. In still other particular variations, $R_{10}$ is selected from the group consisting of hydrogen and 7-chloro.

Particular examples of compounds according to the present invention include, but are not limited to:

3-(1H-benzo[d]imidazol-2-yl)-N-(3-chloro-4-methylphenyl)piperidine-1-carboxamide;

3-(1H-benzo[d]imidazol-2-yl)-N-benzoylpiperidine-1-carboxamide;

3-(1H-benzo[d]imidazol-2-yl)-N-(naphthalen-2-yl)piperidine-1-carboxamide;

3-(1H-benzo[d]imidazol-2-yl)-N-benzoylpiperidine-1-carboxamide;

3-(1H-benzo[d]imidazol-2-yl)-N-(3,5-dimethylphenyl)piperidine-1-carboxamide;

3-(1H-benzo[d]imidazol-2-yl)-N-(4-chloro-3-(trifluoromethyl)phenyl)piperidine-1-carboxamide;

3-(1H-benzo[d]imidazol-2-yl)-N-phenylpiperidine-1-carboxamide;

3-(1H-benzo[d]imidazol-2-yl)-N-(2,3-dihydro-1H-inden-5-yl)piperidine-1-carboxamide;

3-(1H-benzo[d]imidazol-2-yl)-N-cyclohexylpiperidine-1-carboxamide;

N-(benzo[d][1,3]dioxol-5-yl)-3-(1H-benzo[d]imidazol-2-yl)piperidine-1-carboxamide;

(2S)-methyl 2-(3-(1H-benzo[d]imidazol-2-yl)piperidine-1-carboxamido)-3-phenylpropanoate;

(2R)-methyl 2-(3-(1H-benzo[d]imidazol-2-yl)piperidine-1-carboxamido)-3-phenylpropanoate;

ethyl 3-(3-(1H-benzo[d]imidazol-2-yl)piperidine-1-carboxamido)propanoate;

3-(1H-benzo[d]imidazol-2-yl)-N-(2,3-dihydrobenzo[b][1,4]dioxin-6-yl)piperidine-1-carboxamide;

3-(1H-benzo[d]imidazol-2-yl)-N-(biphenyl-2-yl)piperidine-1-carboxamide;

3-(1H-benzo[d]imidazol-2-yl)-N-propylpiperidine-1-carboxamide;

N-(benzo[c][1,2,5]thiadiazol-4-yl)-3-(1H-benzo[d]imidazol-2-yl)piperidine-1-carbothioamide;

(2S)-methyl 2-(3-(1H-benzo[d]imidazol-2-yl)piperidine-1-carboxamido)-4-methylpentanoate;

3-(1H-benzo[d]imidazol-2-yl)-N-(pyridin-3-yl)piperidine-1-carboxamide;

3-(1H-benzo[d]imidazol-2-yl)-N-(furan-2-ylmethyl)piperidine-1-carboxamide;

(S)-3-amino-1-((R)-3-(1-(3-methoxypropyl)-1H-benzo[d]imidazol-2-yl)-3-phenylpropan-1-one;

(3R)-1-(3-(1H-benzo[d]imidazol-2-yl)piperidin-1-yl)-3-amino-4-(4-chlorophenyl)butan-1-one;

(3R)-3-amino-4-(4-chlorophenyl)-1-(3-(1-(3-methoxypropyl)-1H-benzo[d]imidazol-2-yl)piperidin-1-yl)butan-1-one;

(3S)-1-(3-(1H-benzo[d]imidazol-2-yl)piperidin-1-yl)-3-amino-3-(4-(trifluoromethyl)phenyl)propan-1-one;

(3S)-1-(3-(1H-benzo[d]imidazol-2-yl)piperidin-1-yl)-3-amino-3-(2-nitrophenyl)propan-1-one;

(3R)-1-(3-(1H-benzo[d]imidazol-2-yl)piperidin-1-yl)-3-amino-4-(2-chlorophenyl)butan-1-one;

(3S)-1-(3-(1H-benzo[d]imidazol-2-yl)piperidin-1-yl)-3-amino-3-(2,3-dimethoxyphenyl)propan-1-one;

(3R)-1-(3-(1H-benzo[d]imidazol-2-yl)piperidin-1-yl)-3-amino-4-(benzo[b]thiophen-3-yl)butan-1-one;

(3S)-1-(3-(1H-benzo[d]imidazol-2-yl)piperidin-1-yl)-3-amino-3-(3-chlorophenyl)propan-1-one;

(3S)-1-(3-(1H-benzo[d]imidazol-2-yl)piperidin-1-yl)-3-amino-3-(3,5-dimethoxyphenyl)propan-1-one;

(3R)-1-(3-(1H-benzo[d]imidazol-2-yl)piperidin-1-yl)-3-amino-5-phenylpentan-1-one;

(3S)-1-(3-(1H-benzo[d]imidazol-2-yl)piperidin-1-yl)-3-amino-3-(4-nitrophenyl)propan-1-one;

(3R)-1-(3-(1H-benzo[d]imidazol-2-yl)piperidin-1-yl)-3-amino-4-(4-bromophenyl)butan-1-one;

(3S)-1-(3-(1H-benzo[d]imidazol-2-yl)piperidin-1-yl)-3-amino-3-(2,4-dichlorophenyl)propan-1-one;

(3R)-1-(3-(1H-benzo[d]imidazol-2-yl)piperidin-1-yl)-3-amino-4-(3,4-dichlorophenyl)butan-1-one;

(3S)-1-(3-(1H-benzo[d]imidazol-2-yl)piperidin-1-yl)-3-amino-3-(2,3-dichlorophenyl)propan-1-one;

(3R)-1-(3-(1H-benzo[d]imidazol-2-yl)piperidin-1-yl)-3-amino-4-(naphthalen-1-yl)butan-1-one;
(3R)-1-(3-(1H-benzo[d]imidazol-2-yl)piperidin-1-yl)-3-amino-4-(4-nitropentyl)butan-1-one;
(3S)-1-(3-(1H-benzo[d]imidazol-2-yl)piperidin-1-yl)-3-amino-3-(3-nitrophenyl)propan-1-one;
(3S)-1-(3-(1H-benzo[d]imidazol-2-yl)piperidin-1-yl)-3-amino-3-(3-bromophenyl)propan-1-one;
(3R)-1-(3-(1H-benzo[d]imidazol-2-yl)piperidin-1-yl)-3-amino-4-o-tolylbutan-1-one;
(3R)-1-(3-(1H-benzo[d]imidazol-2-yl)piperidin-1-yl)-3-amino-4-m-tolylbutan-1-one;
(3R)-1-(3-(1H-benzo[d]imidazol-2-yl)piperidin-1-yl-3-amino-4-(naphthalen-2-yl)butan-1-one;
(3-(1H-benzo[d]imidazol-2-yl)piperidin-1-yl)(pyrrolidin-2-yl)methanone
(2S)-1-(3-(1H-benzo[d]imidazol-2-yl)piperidin-1-yl)-2-amino-4-methylpentan-1-one;
(2S)-1-(3 (1H-benzo[d]imidazol-2-yl)piperidin-1-yl)-2-amino-3-methylbutan-1-one;
(2S,3S)-1-(3-(1H-benzo[d]imidazol-2-yl)piperidin-1-yl)-2-amino-3-methylpentan-1-one;
(3-(1H-benzo[d]imidazol-2-yl)piperidin-1-yl)((S)-1-(piperidin-4-yl)pyrrolidin-2-yl)methanone;
(2R)-1-(3-(1H-benzo[d]imidazol-2-yl)piperidin-1-yl)-2-aminopropan-1-one;
(2R)-1-(3-(1H-benzo[d]imidazol-2-yl)piperidin-1-yl)-2-aminobutan-1-one;
(3-(1H-benzo[d]imidazol-2-yl)piperidin-1-yl)(piperidin-3-yl)methanone;
(2S)-1-(3-(1H-benzo[d]imidazol-2-yl)piperidin-1-yl)-2-aminopropan-1-one;
(3-(1H-benzo[d]imidazol-2-yl)piperidin-1-yl)((R)-pyrrolidin-2-yl)methanone;
(3-(1H-benzo[d]imidazol-2-yl)piperidin-1-yl)(azetidin-3-yl)methanone;
(2S)-1-(3-(1H-benzo[d]imidazol-2-yl)piperidin-1-yl)-2-amino-3,3-dimethylbutan-1-one;
(3-(1H-benzo[d]imidazol-2-yl)piperidin-1-yl)(1S,2S)-2-aminocyclopentyl)methanone;
(2R)-1-(3-(1H-benzo[d]imidazol-2-yl)piperidin-1-yl)-2-amino-3-phenylpropan-1-one;
(3-(1H-benzo[d]imidazol-2-yl)piperidin-1-yl)(1-aminocyclobutyl)methanone;
(2R)-1-(3-(1H-benzo[d]imidazol-2-yl)piperidin-1-yl-2-amino-3-chloropropan-1-one;
(2S)-1-(3-(1H-benzo[d]imidazol-2-yl)piperidin-1-yl)-2-amino-2-cyclohexylethanone;
(2S)-1-(3-(1H-benzo[d]imidazol-2-yl)piperidin-1-yl-2-amino-3-(pyridin-2-yl)propan-1-one;
(3-(1H-benzo[d]imidazol-2-yl)piperidin-1-yl)(1-aminocyclopropyl)methanone;
1-(3-(1H-benzo[d]imidazol-2-yl)piperidin-1-yl)-2-(methylamino)-3-phenylpropan-1-one;
(3R)-3-amino-1-(3-(1-(3-methoxypropyl)-1H-benzo[d]imidazol-2-yl)piperidin-1-yl)-3-phenylpropan-1-one;
(3S)-3-amino-1-(3-(1-(3-methoxypropyl)-1H-benzo[d]imidazol-2-yl)piperidin-1-yl)-3-phenylpropan-1-one;
(3S)-3-amino-4-(4-chlorophenyl)-1-(3-(1-(3-methoxypropyl)-1H-benzo[d]imidazol-2-yl)piperidin-1-yl)butan-1-one;
(R)-3-amino-4-(4-chlorophenyl)-1-((R)-3-(1-(3-methoxypropyl)-1H-benzo[d]imidazol-2-yl)piperidin-1-yl)butan-1-one;
(S)-3-amino-4-(4-chlorophenyl)-1-((R)-3-(1-(3-methoxypropyl)-1H-benzo[d]imidazol-2-yl)piperidin-1-yl)butan-1-one;
(S)-3-amino-4-(4-chlorophenyl)-1-0)-3-(1-(3-methoxypropyl)-1H-benzo[d]imidazol-2-yl)piperidin-1-yl)butan-1-one;
(R)-1((R)-3-(1H-benzo[d]imidazol-2-yl)piperidin-1-yl)-3-amino-4-(biphenyl-4-yl)butan-1-one;
(R)-3-Amino-4-(biphenyl-4-yl)-1((R)-3-(1-(3-methoxypropyl)-1H-benzo[d]imidazol-2-yl)piperidin-1-yl)butan-1-one;
4-(biphenyl-4-yl)-3-hydroxy-1-((R)-3-(1-(3-methoxypropyl)-1H-benzo[d]imidazol-2-yl)piperidin-1-yl)butan-1-one;
(R)-3-amino-1((R)-3-(1-(3-methoxypropyl)-1H-benzo[d]imidazol-2-yl)piperidin-1-yl)-4-(naphthalen-2-yl)butan-1-one;
(R)-3-amino-4-(4-chlorophenyl)-1((R)-3-(1-(3-methoxypropyl)-1H-benzo[d]imidazol-2-yl)piperidin-1-yl)butan-1-one;
(R)-3-amino-4-(3,4-difluorophenyl)-1((R)-3-(1-(3-methoxypropyl)-1H-benzo[d]imidazol-2-yl)piperidin-1-yl)butan-1-one;
(R)-3-amino-4-(3,4-dichlorophenyl)-1-((R)-3-(1-(3-methoxypropyl)-1H-benzo[d]imidazol-2-yl)piperidin-1-yl)butan-1-one;
(R)-3-amino-1-((R)-3-(1-(3-methoxypropyl)-1H-benzo[d]imidazol-2-yl)piperidin-1-yl)-4-(pyridin-4-yl)butan-1-one;
(R)-3-amino-4-(3-chlorophenyl)-1-((R)-3-(1-(3-methoxypropyl)-1H-benzo[d]imidazol-2-yl)piperidin-1-yl)butan-1-one;
(S)-3-amino-3-(3-bromophenyl)-1((R)-3-(1-(3-methoxypropyl)-1H-benzo[d]imidazol-2-yl)piperidin-1-yl)propan-1-one;
(R)-3-amino-1((R)-3-(5,5-dichloro-1-(3-methoxypropyl)-1H-benzo[d]imidazol-2-yl)piperidin-1-yl)-4-(naphthalen-2-yl)butan-1-one;
(R)-3-amino-1((R)-3-(1-(3-methoxypropyl)-1H-benzo[d]imidazol-2-yl)piperidin-1-yl)-4-(pyridin-3-yl)butan-1-one;
(S)-3-amino-3-(3-chlorophenyl)-1((R)-3-(1-(3-methoxypropyl)-1H-benzo[d]imidazol-2-yl)piperidin-1-yl)propan-1-one;
(S)-3-amino-1((R)-3-(1-(3-methoxypropyl)-1H-benzo[d]imidazol-2-yl)piperidin-1-yl)-3-(3-(trifluoromethyl)phenyl)propan-1-one;
3-((S)-1-amino-3-((R)-3-(1-(3-methoxypropyl)-1H-benzo[d]imidazol-2-yl)piperidin-1-yl)-3-oxopropyl)benzonitrile;
(R)-3-amino-1((R)-3-(1-(3-methoxypropyl)-1H-benzo[d]imidazol-2-yl)piperidin-1-yl)-4-(2,4,5-trifluorophenyl)butan-1-one;
(R)-3-amino-1((R)-3-(1-(3-methoxypropyl)-1H-benzo[d]imidazol-2-yl)piperidin-1-yl)-4-phenylbutan-1-one;
(S)-3-amino-4-(benzyloxy)-1((R)-3-(1-(3-methoxypropyl)-1H-benzo[d]imidazol-2-yl)piperidin-1-yl)butan-1-one;
(S)-3-amino-1((R)-3-(1-(3-methoxypropyl)-1H-benzo[d]imidazol-2-yl)piperidin-1-yl)-3-phenylpropan-1-one;
(R)-3-amino-4-(4-tert-butylphenyl)-1((R)-3-(1-(3-methoxypropyl)-1H-benzo[d]imidazol-2-yl)piperidin-1-yl)butan-1-one;
(R)-3-amino-4-(4-bromophenyl)-1((R)-3-(1-(3-methoxypropyl)-1H-benzo[d]imidazol-2-yl)piperidin-1-yl)butan-1-one;
(2R,3R)-3-amino-2-hydroxy-1((R)-3-(1-(3-methoxypropyl)-1H-benzo[d]imidazol-2-yl)piperidin-1-yl)-3-phenylpropan-1-one;

4-amino-3-(4-chlorophenyl)-1((R)-3-(1-(3-methoxypropyl)-1H-benzo[d]imidazol-2-yl)piperidin-1-yl)butan-1-one;
3-amino-1-((R)-3-(1-(3-methoxypropyl)-1H-benzo[d]imidazol-2-yl)piperidin-1-yl)-3-(piperidin-4-yl)propan-1-one;
(R)-3-amino-1((R)-3-(6-fluoro-1-(3-methoxypropyl)-1H-benzo[d]imidazol-2-yl)piperidin-1-yl)-4-(naphthalen-2-yl)butan-1-one;
(R)-3-amino-1((R)-3-(5-fluoro-1-(3-methoxypropyl)-1H-benzo[d]imidazol-2-yl)piperidin-1-yl)-4-(naphthalen-2-yl)butan-1-one;
(R)-3-Amino-1-((R)-3-(7-chloro-1-(3-methoxypropyl)-1H-benzo[d]imidazol-2-yl)piperidin-1-yl)-4-(naphthalene-2-yl)butan-1-one;
(R)-3-amino-4-(biphenyl-4-yl)-1((R)-3-(7-chloro-1-(3-methoxypropyl)-1H-benzo[d]imidazol-2-yl)piperidin-1-yl)butan-1-one;
(R)-3-amino-1((R)-3-(6-chloro-1-(3-methoxypropyl)-1H-benzo[d]imidazol-2-yl)piperidin-1-yl)-4-(naphthalen-2-yl)butan-1-one;
(R)-3-amino-1-(3-(5-methoxy-3-(3-methoxypropyl)-3H-imidazo[4,5-b]pyridin-2-yl)piperidin-1-yl)-4-(naphthalen-2-yl)butan-1-one;
(R)-2-(1-(3-amino-4-(naphthalen-2-yl)butanoyl)piperidin-3-yl)-3-(3-methoxypropyl)-3H-imidazo[4,5-b]pyridin-5(4H)-one;
(R)-3-amino-1-(3-(5-chloro-3-(3-methoxypropyl)-3H-imidazo[4,5-b]pyridin-2-yl)piperidin-1-yl)-4-(naphthalen-2-yl)butan-1-one;
(R)-3-amino-4-(biphenyl-4-yl)-1-((R)-3-(3-(3-methoxypropyl)-3H-imidazo[4,5-c]pyridin-2-yl)piperidin-1-yl)butan-1-one;
(R)-3-amino-1((R)-3-(4-methoxy-1-(3-methoxypropyl)-1H-benzo[d]imidazol-2-yl)piperidin-1-yl)-4-(naphthalen-2-yl)butan-1-one;
(R)-3-amino-1-((R)-3-(1-(3-methoxypropyl)-5-methyl-1H-benzo[d]imidazol-2-yl)piperidin-1-yl)-4-(naphthalen-2-yl)butan-1-one;
(R)-3-amino-1-((R)-3-(1-(3-methoxypropyl)-4-methyl-1H-benzo[d]imidazol-2-yl)piperidin-1-yl)-4-(naphthalen-2-yl)butan-1-one;
(R)-3-amino-1-((R)-3-(4-methoxy-1-(3-methoxypropyl)-1H-benzo[d]imidazol-2-yl)piperidin-1-yl)-4-(naphthalen-2-yl)butan-1-one;
(R)-3-amino-1-((R)-3-(7-methoxy-1-(3-methoxypropyl)-1H-benzo[d]imidazol-2-yl)piperidin-1-yl)-4-(naphthalen-2-yl)butan-1-one;
2-((R)-1-((R)-3-amino-4-(naphthalen-2-yl)butanoyl)piperidin-3-yl)-1-(3-methoxypropyl)-1H-benzo[d]imidazole-6-carbonitrile;
(R)-3-amino-1-((R)-3-(6-methoxy-1-(3-methoxypropyl)-1H-benzo[d]imidazol-2-yl)piperidin-1-yl)-4-(naphthalen-2-yl)butan-1-one;
methyl 2-O-((R)-3-amino-4-(naphthalen-2-yl)butanoyl)piperidin-3-yl)-1-(3-methoxypropyl)-1H-benzo[d]imidazole-6-carboxylate;
methyl 2-O-((R)-3-amino-4-(naphthalen-2-yl)butanoyl)piperidin-3-yl)-1-(3-methoxypropyl)-1H-benzo[d]imidazole-7-carboxylate;
(3R)-3-amino-1-(3-(6-(hydroxymethyl)-1-(3-methoxypropyl)-1H-benzo[d]imidazol-2-yl)piperidin-1-yl)-4-(naphthalen-2-yl)butan-1-one;
(R)-3-amino-1((R)-3-(1-(3-methoxypropyl)-6-nitro-1H-benzo[d]imidazol-2-yl)piperidin-1-yl)-4-(naphthalen-2-yl)butan-1-one;
(R)-3-amino-1((R)-3-(1-(3-methoxypropyl)-7-nitro-1H-benzo[d]imidazol-2-yl)piperidin-1-yl)-4-(naphthalen-2-yl)butan-1-one;
(R)-3-amino-1((R)-3-(6-isopropyl-1-(3-methoxypropyl)-1H-benzo[d]imidazol-2-yl)piperidin-1-yl)-4-(naphthalen-2-yl)butan-1-one;
(R)-3-amino-1-((R)-3-(5-isopropyl-1-(3-methoxypropyl)-1H-benzo[d]imidazol-2-yl)piperidin-1-yl)-4-(naphthalen-2-yl)butan-1-one;
(R)-3-amino-4-(biphenyl-4-yl)-1((R)-3-(4-chloro-1-(3-methoxypropyl)-1H-benzo[d]imidazol-2-yl)piperidin-1-yl)butan-1-one;
(S)-3-amino-1((R)-3(1-(3-methoxypropyl)-1H-benzo[d]imidazol-2-yl)piperidin-1-yl)-3-(pyridin-3-yl)propan-1-one;
(S)-3-amino-1-((R)-3-(1-(3-methoxypropyl)-1H-benzo[d]imidazol-2-yl)piperidin-1-yl)-3-(4-methoxypyridin-3-yl)propan-1-one;
(S)-3-amino-3-(3-methoxyphenyl)-1-(R)-3-(1-(3-methoxypropyl)-1H-benzo[d]imidazol-2-yl)piperidine-1-yl)propan-1-one;
(R)-3-amino-4-(biphenyl-3-yl)-1-((R)-3-(1-(3-methoxypropyl)-1H-benzo[d]imidazol-2-yl)piperidin-1-yl)butan-1-one;
Methyl 4'-((R)-2-amino-4-((R)-3-(1-(3-methoxypropyl)-1H-benzo[d]imidazol-2-yl)piperidin-1-yl)-4-oxobutyl)biphenyl-4-carboxylate;
(R)-3-amino-4-(biphenyl-4-yl)-1((R)-3-(1-(3-methoxypropyl)-1H-benzo[d]imidazol-2-yl)piperidin-1-yl)butan-1-one;
(R)-3-amino-1((R)-3-(1-(3-methoxypropyl)-1H-benzo[d]imidazol-2-yl)piperidin-1-yl)-4-(4-(pyridin-3-yl)phenyl)butan-1-one;
(R)-3-amino-1((R)-3-(1-(3-methoxypropyl)-1H-benzo[d]imidazol-2-yl)piperidin-1-yl)-4-(4-(pyridin-4-yl)phenyl)butan-1-one;
(R)-3-amino-1((R)-3-(1-(3-methoxypropyl)-1H-benzo[d]imidazol-2-yl)piperidin-1-yl)-4-(4'-(morpholine-4-carbonyl)biphenyl-4-yl)butan-1-one;
(R)-3-amino-1-((R)-3-(1-(3-methoxypropyl)-1H-benzo[d]imidazol-2-yl)piperidin-1-yl)-4-(4'-morpholinobiphenyl-4-yl)butan-1-one;
N-(4'-((R)-2-amino-4-((R)-3-(1-(3-methoxypropyl)-1H-benzo[d]imidazol-2-yl)piperidin-1-yl)-4-oxobutyl)biphenyl-4-yl)acetamide;
(R)-3-amino-4-(2'-(methoxymethyl)biphenyl-4-yl)-1-((R)-3-(1-(3-methoxypropyl)-1H-benzo[d]imidazol-2-yl)piperidin-1-yl)butan-1-one;
(R)-3-amino-4-(4-(3-chloropyridin-4-yl)phenyl)-1-((R)-3-(1-(3-methoxypropyl)-1H-benzo[d]imidazol-2-yl)piperidin-1-yl)butan-1-one;
(R)-3-amino-4-(4-(2,6-dimethoxypyridin-3-yl)phenyl)-1((R)-3-(1-(3-methoxypropyl)-1H-benzo[d]imidazol-2-yl)piperidin-1-yl)butan-1-one;
(R)-3-amino-4-(4-(2-chloropyridin-4-yl)phenyl)-1-((R)-3-(1-(3-methoxypropyl)-1H-benzo[d]imidazol-2-yl)piperidin-1-yl)butan-1-one;
4'-((R)-2-amino-4-((R)-3-(1-(3-methoxypropyl)-1H-benzo[d]imidazol-2-yl)piperidin-1-yl)-4-oxobutyl)-N-cyclopropyl)biphenyl-4-carboxamide;
(R)-3-amino-1((R)-3-(1-(3-methoxypropyl)-1H-benzo[d]imidazol-2-yl)piperidin-1-yl)-4-(4-(6-morpholinopyridin-3-yl)phenyl)butan-1-one;
(R)-3-amino-4-(4-(6-aminopyridin-3-yl)phenyl)-1-((R)-3-(1-(3-methoxypropyl)-1H-benzo[c]imidazol-2-yl)piperidin-1-yl)butan-1-one;

(R)-3-amino-4-(4-(3,5-dimethyl-1H-pyrazol-4-yl)phenyl)-1-((R)-3-(1-(3-methoxypropyl)-1H-benzo[d]imidazol-2-yl)piperidin-1-yl)butan-1-one;

(R)-3-amino-4-(4-(6-ethoxypyridin-3-yl)phenyl)-1-((R)-3-(1-(3-methoxypropyl)-1H-benzo[d]imidazol-2-yl)piperidin-1-yl)butan-1-one;

(R)-3-amino-4-(4-(imidazo[1,2-a]pyridin-6-yl)phenyl)-1-((R)-3-(1-(3-methoxypropyl)-1H-benzo[d]imidazol-2-yl)piperidin-1-yl)butan-1-one;

(R)-3-amino-4-(4-(benzo[c][1,2,5]oxadiazol-5-yl)phenyl)-1-((R)-3-(1-(3-methoxypropyl)-1H-benzo[d]imidazol-2-yl)piperidin-1-yl)butan-1-one;

(R)-4-(4-(1H-pyrazol-5-yl)phenyl)-3-amino-1-((R)-3-(1-(3-methoxypropyl)-1H-benzo[d]imidazol-2-yl)piperidin-1-yl)butan-1-one;

(R)-3-amino-4-(4-(6-isopropoxypyridin-3-yl)phenyl)-1-((R)-3-(1-(3-methoxypropyl)-1H-benzo[d]imidazol-2-yl)piperidin-1-yl)butan-1-one;

(R)-3-amino-4-(4-(6-(cyclopropylmethoxy)pyridin-3-yl)phenyl)-1-((R)-3-(1-(3-methoxypropyl)-1H-benzo[d]imidazol-2-yl)piperidin-1-yl)butan-1-one;

(R)-3-amino-1((R)-3-(1-(3-methoxypropyl)-1H-benzo[d]imidazol-2-yl)piperidin-1-yl)-4-(4-(3-methoxypyridin-4-yl)phenyl)butan-1-one;

(R)-3-amino-4-(4-(furan-3-yl)phenyl)-1-((R)-3-(1-(3-methoxypropyl)-1H-benzo[d]imidazol-2-yl)piperidin-1-yl)butan-1-one;

(R)-3-amino-4-(4-(furan-2-yl)phenyl)-1-((R)-3-(1-(3-methoxypropyl)-1H-benzo[d]imidazol-2-yl)piperidin-1-yl)butan-1-one;

(R)-3-amino-4-(4-(6-(dimethylamino)pyridin-3-yl)phenyl)-1-((R)-3-(1-(3-methoxypropyl)-1H-benzo[d]imidazol-2-yl)piperidin-1-yl)butan-1-one;

(R)-3-amino-1-((R)-3-(1-(3-methoxypropyl)-1H-benzo[d]imidazol-2-yl)piperidin-1-yl)-4-(4-(2-methoxypyridin-4-yl)phenyl)butan-1-one;

(R)-3-amino-1-((R)-3-(1-(3-methoxypropyl)-1H-benzo[d]imidazol-2-yl)piperidin-1-yl)-4-(4-(pyrimidin-5-yl)phenyl)butan-1-one;

(R)-3-amino-4-(4-(2-fluoropyridin-4-yl)phenyl)-1-((R)-3-(1-(3-methoxypropyl)-1H-benzo[d]imidazol-2-yl)piperidin-1-yl)butan-1-one;

(R)-3-amino-4-(4-(2-fluoropyridin-3-yl)phenyl)-1-((R)-3-(1-(3-methoxypropyl)-1H-benzo[d]imidazol-2-yl)piperidin-1-yl)butan-1-one;

(R)-4-(4-(1H-pyrrol-3-yl)phenyl)-3-amino-1-((R)-3-(1-(3-methoxypropyl)-1H-benzo[d]imidazol-2-yl)piperidin-1-yl)butan-1-one;

(R)-4-(4-(1H-pyrrol-2-yl)phenyl)-3-amino-1-((R)-3-(1-(3-methoxypropyl)-1H-benzo[d]imidazol-2-yl)piperidin-1-yl)butan-1-one;

(R)-3-amino-4-(4-(2-aminopyrimidin-5-yl)phenyl)-1-((R)-3-(1-(3-methoxypropyl)-1H-benzo[d]imidazol-2-yl)piperidin-1-yl)butan-1-one;

(R)-3-amino-4-(2'-chlorobiphenyl-4-yl)-1-((R)-3-(1-(3-methoxypropyl)-1H-benzo[d]imidazol-2-yl)piperidin-1-yl)butan-1-one;

(R)-3-amino-4-(4'-methoxybiphenyl-4-yl)-1-((R)-3-(1-(3-methoxypropyl)-1H-benzo[d]imidazol-2-yl)piperidin-1-yl)butan-1-one;

(R)-3-amino-1-((R)-3-(1-(3-methoxypropyl)-1H-benzo[d]imidazol-2-yl)piperidin-1-yl)-4-(2'-methylbiphenyl-4-yl)butan-1-one;

(R)-3-amino-4-(3'-methoxybiphenyl-4-yl)-1-((R)-3-(1-(3-methoxypropyl)-1H-benzo[d]imidazol-2-yl)piperidin-1-yl)butan-1-one;

(R)-3-amino-4-(2'-methoxybiphenyl-4-yl)-1-((R)-3-(1-(3-methoxypropyl)-1H-benzo[d]imidazol-2-yl)piperidin-1-yl)butan-1-one;

(R)-3-amino-4-(2'-fluorobiphenyl-4-yl)-1-((R)-3-(1-(3-methoxypropyl)-1H-1-benzo[d]imidazol-2-yl)piperidin-1-yl)butan-1-one;

(R)-3-amino-4-(4'-(dimethylamino)biphenyl-4-yl)-1-((R)-3-(1-(3-methoxypropyl)-1H-benzo[d]imidazol-2-yl)piperidin-1-yl)butan-1-one;

(R)-3-amino-1-((R)-3-(1-(3-methoxypropyl)-1H-benzo[d]imidazol-2-yl)piperidin-1-yl)-4-(4-(4-methoxypyridin-3-yl)phenyl)butan-1-one;

(R)-3-amino-1-((R)-3-(1-(3-methoxypropyl)-1H-benzo[d]imidazol-2-yl)piperidin-1-yl)-4-(4-(2-methoxypyridin-3-yl)phenyl)butan-1-one;

4'-((R)-2-amino-4-((R)-3-(1-(3-methoxypropyl)-1H-benzo[d]imidazol-2-yl)piperidin-1-yl)-4-oxobutyl)biphenyl-4-carbonitrile;

(R)-3-amino-1-((R)-3-(1-(3-methoxypropyl)-1H-benzo[d]imidazol-2-yl)piperidin-1-yl)-4-(4'-(methylsulfonyl)biphenyl-4-yl)butan-1-one;

(R)-3-amino-4-(4-(3,5-dimethylisoxazol-4-yl)phenyl-1-((R)-3-(1-(3-methoxypropyl)-1H-benzo[d]imidazol-2-yl)piperidin-1-yl)butan-1-one;

(R)-3-amino-4-(4-(2-chloropyridin-3-yl)phenyl)-1-((R)-3-(1-(3-methoxypropyl)-1H-benzo[d]imidazol-2-yl)piperidin-1-yl)butan-1-one;

4'-((R)-2-amino-4-((R)-3-(1-(3-methoxypropyl)-1H-benzo[d]imidazol-2-yl)piperidin-1-yl)-4-oxobutyl)biphenyl-4-carboxamide;

5-(4-((R)-2-amino-4-((R)-3-(1-(3-methoxypropyl)-1H-benzo[d]imidazol-2-yl)piperidin-1-yl)-4-oxobutyl)phenyl)pyrimidine-2,4(1H,3H)-dione;

(R)-3-amino-4-(4'-aminobiphenyl-4-yl)-1-((R)-3-(1-(3-methoxypropyl)-1H-benzo[d]imidazol-2-yl)piperidin-1-yl)butan-1-one;

1-(4'-((R)-2-amino-4-((R)-3-(1-(3-methoxypropyl)-1H-benzo[d]imidazol-2-yl)piperidin-1-yl)-4-oxobutyl)biphenyl-4-yl)-3-cyclopropylurea;

1-(4'-((R)-2-amino-4-((R)-3-(1-(3-methoxypropyl)-1H-benzo[d]imidazol-2-yl)piperidin-1-yl)-4-oxobutyl)biphenyl-4-yl)urea;

1-(4'-((R)-2-amino-4-((R)-3-(1-(3-methoxypropyl)-1H-benzo[d]imidazol-2-yl)piperidin-1-yl)-4-oxobutyl)biphenyl-4-yl)-3-ethylurea;

3-(4'-((R)-2-amino-4-((R)-3-(1-(3-methoxypropyl)-1H-benzo[d]imidazol-2-yl)piperidin-1-yl)-4-oxobutyl)biphenyl-4-yl)-1,1-dimethylurea;

1-(4'-((R)-2-amino-4-((R)-3-(1-(3-methoxypropyl)-1H-benzo[d]imidazol-2-yl)piperidin-1-yl)-4-oxobutyl)biphenyl-4-yl)-3-methylurea;

methyl 4'-((R)-2-amino-4-((R)-3-(1-(3-methoxypropyl)-1H-benzo[d]imidazol-2-yl)piperidin-1-yl)-4-oxobutyl)biphenyl-4-ylcarbamate;

4'-((R)-2-amino-4-((R)-3-(1-(3-methoxypropyl)-1H-benzo[d]imidazol-2-yl)piperidin-1-yl)-4-oxobutyl)-N-(2-methoxyethyl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-N-(2-ethoxyethyl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-N-(2-isopropoxyethyl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-N-(3-methoxypropyl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-N-(2,3-dihydroxypropyl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-N-(2-hydroxyethyl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-N-(1-hydroxy-2-methylpropan-2-yl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-N-(1,3-dihydroxypropan-2-yl)biphenyl-4-carboxamide;

(R)-3-amino-4-(4'-((R)-3-hydroxypyrrolidine-1-carbonyl)biphenyl-4-yl)-1-((R)-3-(1-(3-methoxypropyl)-1H-benzo[d]imidazol-2-yl)piperidin-1-yl)butan-1-one;

4'-((R)-2-amino-4-((R)-3-(1-(3-methoxypropyl)-1H-benzo[d]imidazol-2-yl)piperidin-1-yl)-4-oxobutyl)-N—((R)-1-hydroxypropan-2-yl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-N—((S)-1-hydroxypropan-2-yl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-N-(2-hydroxy-2-methylpropyl)biphenyl-4-carboxamide;

4-(4'-((R)-2-amino-4-((R)-3-(1-(3-methoxypropyl)-1H-benzo[d]imidazol-2-yl)piperidin-1-yl)-4-oxobutyl)biphenylcarbonyl)piperazin-2-one;

4'-((R)-2-amino-4-((R)-3-(1-(3-methoxypropyl)-1H-benzo[d]imidazol-2-yl)piperidin-1-yl)-4-oxobutyl)-3-fluoro-N-(2-hydroxyethyl) biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-3-fluoro-N-(2-methoxyethyl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-2-chloro-N-(2-hydroxyethyl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-2-chloro-N-(2-methoxyethyl)biphenyl-4-carboxamide;

5-(4-((R)-2-amino-4-((R)-3-(1-(3-methoxypropyl)-1H-benzo[d]imidazol-2-yl)piperidin-1-yl)-4-oxobutyl)phenyl)-N-(2-hydroxyethyl)picolinamide;

5-(4-((R)-2-amino-4-((R)-3-(1-(3-methoxypropyl)-1H-benzo[d]imidazol-2-yl)piperidin-1-yl)-4-oxobutyl)phenyl)-N-(2-methoxyethyl)picolinamide;

5-(4-((R)-2-amino-4-((R)-3-(1-(3-methoxypropyl)-1H-benzo[d]imidazol-2-yl)piperidin-1-yl)-4-oxobutyl)phenyl)-N-(1-hydroxy-2-methylpropan-2-yl)thiophene-2-carboxamide;

N-(4'-((R)-2-amino-4-((R)-3-(1-(3-methoxypropyl)-1H-benzo[d]imidazol-2-yl)piperidin-1-yl)-4-oxobutyl)biphenyl-4-yl)-2-methoxyacetamide;

N-(4'-((R)-2-amino-4-((R)-3-(1-(3-methoxypropyl)-1H-benzo[d]imidazol-2-yl)piperidin-1-yl)-4-oxobutyl)biphenyl-4-yl)-2-hydroxy-2-methylpropanamide;

N-(4'-((R)-2-amino-4-((R)-3-(1-(3-methoxypropyl)-1H-benzo[d]imidazol-2-yl)piperidin-1-yl)-4-oxobutyl)biphenyl-4-yl)-2-hydroxyacetamide;

(R)-3-amino-4-(4-(2-ethoxythiazol-4-yl)phenyl)-1-((R)-3-(1-(3-methoxypropyl)-1H-benzo[d]imidazol-2-yl)piperidin-1-yl)butan-1-one;

(R)-3-amino-1-((R)-3-(1-(3-methoxypropyl)-1H-benzo[d]imidazol-2-yl)piperidin-1-yl)-4-(4-(2-methoxythiazol-4-yl)phenyl)butan-1-one;

(R)-3-amino-4-(4-(2-isopropylthiazol-4-yl)phenyl)-1-((R)-3-(1-(3-methoxypropyl)-1H-benzo[d]imidazol-2-yl)piperidin-1-yl)butan-1-one;

4-((R)-2-amino-4-((R)-3(1-(3-methoxypropyl)-1H-benzo[d]imidazol-2-yl)piperidin-1-yl)-4-oxobutyl)-N-cyclohexylbenzamide;

(R)-3-amino-4-(4-(1,2-dimethyl-1H-imidazol-5-yl)phenyl)-1-((R)-3-(1-(3-methoxypropyl)-1H-benzo[d]imidazol-2-yl)piperidin-1-yl)butan-1-one;

5-(4-((R)-2-amino-4-((R)-3-(1-(3-methoxypropyl)-1H-benzo[d]imidazol-2-yl)piperidin-1-yl)-4-oxobutyl)phenyl)-1,3-dimethylpyrimidine-2,4(1H,3H)-dione;

4-(4'-((R)-2-amino-4-((R)-3-(1-(3-methoxypropyl)-1H-benzo[d]imidazol-2-yl)piperidin-1-yl)-4-oxobutyl)biphenyl-4-yl)-3-methyl-1H-1,2,4-triazol-5(4H)-one;

1-(4-((R)-2-amino-4-((R)-3-(1-(3-methoxypropyl)-1H-benzo[d]imidazol-2-yl)piperidin-1-yl)-4-oxobutyl)phenyl)pyridin-2(1H)-one;

(R)-4-(4-(1H-imidazol-1-yl)phenyl)-3-amino-1-((R)-3-(1-(3-methoxypropyl)-1H-benzo[d]imidazol-2-yl)piperidin-1-yl)butan-1-one;

1-(4-((R)-2-amino-4-((R)-3-(1-(3-methoxypropyl)-1H-benzo[d]imidazol-2-yl)piperidin-1-yl)-4-oxobutyl)phenyl)pyrrolidin-2-one;

1-(4-((R)-2-amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione;

1-(4-((R)-2-amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione;

1-(4-((R)-2-amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione;

1-(4-((R)-2-Amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione;

1-(4-((R)-2-amino-4-((R)-3-(1-(3-methoxypropyl)-1H-benzo[d]imidazol-2-yl)piperidin-1-yl)-4-oxobutyl)phenyl)-3-(2-methoxyethyl)-1H-benzo[d]imidazol-2(3H)-one;

1-(4-((R)-2-amino-4-((R)-3-(1-(3-methoxypropyl)-1H-benzo[d]imidazol-2-yl)piperidin-1-yl-4-oxobutyl)phenyl)-5-methyl-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-6-methyl-1H-benzo[d]imidazol-2(31-1)-one;

1-(4-((R)-2-amino-4-((R)-3-(1-(3-methoxypropyl)-1H-benzo[d]imidazol-2-yl)piperidin-1-yl)-4-oxobutyl)phenyl)-4-fluoro-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-7-fluoro-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-5,6-dimethyl-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-3-methyl-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-3-propyl-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-3-(2-hydroxyethyl)-1H-benzo[d]imidazol-2(3H)-one;

1-(4-((R)-2-amino-4-((R)-3(1-(3-methoxypropyl)-1H-benzo[d]imidazol-2-yl)piperidin-1-yl)-4-oxobutyl)phenyl)-5-fluoro-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-6-fluoro-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-4-methyl-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-7-methyl-1H-benzo[d]imidazol-2(3H)-one;

1-(4-((R)-2-amino-4-((R)-3-(1-(3-methoxypropyl)-1H-benzo[d]imidazol-2-yl)piperidin-1-34)-4-oxobutyl)phenyl)-5-methoxy-1H-benzo[d]imidazol-2(3H)-one;

1-(4-((R)-2-amino-4-((R)-3-(1-(3-methoxypropyl)-1H-benzo[d]imidazol-2-yl)piperidin-1-yl)-4-oxobutyl)phenyl)-6-methoxy-1H-benzo[d]imidazol-2(3H)-one 2-(4-((R)-2-amino-4-((R)-3-(1-(3-methoxypropyl)-1H-benzo[d]imidazol-2-yl)piperidin-1-yl)-4-oxobutyl)phenyl)isoquinolin-1(2H)-one;

2-(4-((R)-2-amino-4-((R)-3-(1-(3-methoxypropyl)-1H-benzo[d]imidazol-2-yl)piperidin-1-yl)-4-oxobutyl)phenyl)isoquinolin-1(2H)-one;

(R)-3-amino-1((R)-3-(1-(3-methoxypropyl)-1H-benzo[d]imidazol-2-yl)piperidin-1-yl)-4-(4-(4-phenylpiperazin-1-yl)phenyl)butan-1-one;

(R)-4-(4-(4-acetylpiperazin-1-yl)phenyl)-3-amino-1((R)-3-(1-(3-methoxypropyl)-1H-benzo[d]imidazol-2-yl)piperidin-1-yl)butan-1-one;

4-(4-((R)-2-amino-4-((R)-3-(1-(3-methoxypropyl)-1H-benzo[d]imidazol-2-yl)piperidin-1-yl)-4-oxobutyl)phenyl)-1-phenylpiperazin-2-one;

(R)-3-amino-4-(4-(4-hydroxypiperidin-1-yl)phenyl)-1-((R)-3-(1-(3-methoxypropyl)-1H-benzo[d]imidazol-2-yl)piperidin-1-yl)butan-1-one;

(R)-3-amino-4-(4-(4-(hydroxymethyl)piperidin-1-yl)phenyl)-1-((R)-3-(1-(3-methoxypropyl)-1H-benzo[d]imidazol-2-yl)piperidin-1-yl)butan-1-one;

(R)-3-amino-4-(4-(4-(hydroxymethyl)piperidin-1-yl)phenyl)-1-((R)-3-(1-(3-methoxypropyl)-1H-benzo[d]imidazol-2-yl)piperidin-1-yl)butan-1-one;

methyl 1-(4-((R)-2-amino-4-((R)-3-(1-(3-methoxypropyl)-1H-benzo[d]imidazol-2-yl)piperidin-1-yl)-4-oxobutyl)phenyl)piperidine-4-carboxylate;

(R)-3-amino-1-((R)-3-(1-(3-methoxypropyl)-1H-benzo[d]imidazol-2-yl)piperidin-1-yl)-4-(4-phenoxyphenyl)butan-1-one;

N-(2-(2-((R)-1((R)-3-amino-4-(naphthalen-2-yl)butanoyl)piperidin-3-yl)-1H-benzo[d]imidazol-1-yl)ethyl)acetamide;

(R)-3-amino-2-benzyl-4-(4-chlorophenyl)-1-((R)-3-(1-(3-methoxypropyl)-1H-benzo[d]imidazol-2-yl)piperidin-1-yl)butan-1-one;

(R)-3-amino-1((R)-3-(1-(3-methoxypropyl)-4,5,6,7-tetrahydro-1H-benzo[d]imidazol-2-yl)piperidin-1-yl)-4-(naphthalen-2-yl)butan-1-one;

methyl 4'-((2R)-2-amino-4-(3-(5-tert-butyl-1-(3-methoxypropyl)-1H-imidazol-2-yl)-3-hydroxypiperidin-1-yl)-4-oxobutyl)biphenyl-4-carboxylate;

(R)-3-amino-1((R)-3-(2-(3-methoxypropyl)-1H-benzo[d]imidazol-1-yl)piperidin-1-yl)-4-(naphthalen-2-yl)butan-1-one;

(R)-3-amino-1-((S)-3-(2-methyl-1H-benzo[d]imidazol-1-yl)piperidin-1-yl)-4-(naphthalen-2-yl)butan-1-one;

(R)-3-amino-1((R)-3-(2-methyl-1H-benzo[d]imidazol-1-yl)piperidin-1-yl)-4-(naphthalen-2-yl)butan-1-one;

(3R)-3-amino-1-(3-(1-(3-methoxypropyl)-1H-benzo[d]imidazol-2-yl)-5-methylpiperidin-1-yl)-4-(naphthalen-2-yl)butan-1-one;

(R)-3-amino-4-(4-chlorophenyl)-14(S)-3-hydroxy-3-(1-(3-methoxypropyl)-1H-benzo[d]imidazol-2-yl)piperidin-1-yl)butan-1-one;

(R)-3-amino-4-(4-chlorophenyl)-1((R)-3-hydroxy-3-(1-(3-methoxypropyl)-1H-benzo[d]imidazol-2-yl)piperidin-1-yl)butan-1-one;

N—((S)-2-amino-4-((R)-3-(1-(3-methoxypropyl)-1H-benzo[d]imidazol-2-yl)piperidin-1-yl)-4-oxobutyl)-2-naphthamide;

1-((S)-2-amino-4-((R)-3-(1-(3-methoxypropyl)-1H-benzo[d]imidazol-2-yl)piperidin-1-yl)-4-oxobutyl)-3-(2-methoxyphenyl)urea;

N—((S)-2-amino-4-((R)-3-(1-(3-methoxypropyl)-1H-benzo[d]imidazol-2-yl)piperidin-1-yl)-4-oxobutyl)-5-phenylfuran-2-carboxamide;

N—((S)-2-amino-4-((R)-3-(1-(3-methoxypropyl)-1H-benzo[d]imidazol-2-yl)piperidin-1-yl)-4-oxobutyl)-5-phenylthiophene-2-carboxamide;

1-((S)-2-amino-4-((R)-3-(1-(3-methoxypropyl)-1H-benzo[d]imidazol-2-yl)piperidin-1-yl)-4-oxobutyl)-3-(4-methoxyphenyl)urea;

1-((S)-2-amino-4-((R)-3-(1-(3-methoxypropyl)-1H-benzo[d]imidazol-2-yl)piperidin-1-yl)-4-oxobutyl)-3-(3-methoxyphenyl)urea;

1-((S)-2-amino-44 (R)-3-(1-(3-methoxypropyl)-1H-benzo[d]imidazol-2-yl)piperidin-1-yl)-4-oxobutyl)-3-(3,4-dichlorophenyl)urea;

1-((S)-2-amino-4-((R)-3-(1-(3-methoxypropyl)-1H-benzo[d]imidazol-2-yl)piperidin-1-yl)-4-oxobutyl)-3-(3-chlorophenyl)urea;

1-((S)-2-amino-4-((R)-3-(1-(3-methoxypropyl)-1H-benzo[d]imidazol-2-yl)piperidin-1-yl)-4-oxobutyl)-3-(2-chlorophenyl)urea;

1-((S)-2-amino-4-((R)-3-(1-(3-methoxypropyl)-1H-benzo[d]imidazol-2-yl)piperidin-1-yl)-4-oxobutyl)-3-(2,3-dihydrobenzo[b][1,4]dioxin-6-yl)urea;

N—((S)-2-amino-4-((R)-3-(1-(3-methoxypropyl)-1H-benzo[d]imidazol-2-yl)piperidin-1-yl)-4-oxobutyl)-4-(thiophen-2-yl)benzamide;

N—((S)-2-amino-4-((R)-3-(1-(3-methoxypropyl)-1H-benzo[d]imidazol-2-yl)piperidin-1-yl)-4-oxobutyl)-5-(2-fluorophenyl)furan-2-carboxamide;

N—((S)-2-amino-4-((R)-3-(1-(3-methoxypropyl)-1H-benzo[d]imidazol-2-yl)piperidin-1-yl)-4-oxobutyl)-4-(thiophen-3-yl)benzamide;

N—((S)-2-amino-4-((R)-3-(1-(3-methoxypropyl)-1H-benzo[d]imidazol-2-yl)piperidin-1-yl)-4-oxobutyl)-3,4-dichlorobenzamide;

N—((S)-2-amino-4-((R)-3-(1-(3-methoxypropyl)-1H-benzo[d]imidazol-2-yl)piperidin-1-yl)-4-oxobutyl)benzofuran-2-carboxamide;

N—((S)-2-amino-4-((R)-3-(1-(3-methoxypropyl)-1H-benzo[d]imidazol-2-yl)piperidin-1-yl)-4-oxobutyl)biphenyl-4-carboxamide;

1-((S)-2-amino-4-((R)-3-(1-(3-methoxypropyl)-1H-benzo[d]imidazol-2-yl)piperidin-1-yl)-4-oxobutyl)-3-(2-(trifluoromethoxy)phenyl)urea;

1-((S)-2-amino-4-((R)-3-(1-(3-methoxypropyl)-1H-benzo[d]imidazol-2-yl)piperidin-1-yl)-4-oxobutyl)-3-(2,3-dihydro-1H-inden-5-yl)urea;

N—((S)-2-amino-4-((R)-3-(1-(3-methoxypropyl)-1H-benzo[d]imidazol-2-yl)piperidin-1-yl)-4-oxobutyl)-5-(2,4-dichlorophenyl)furan-2-carboxamide;

1-((S)-2-amino-4-((R)-3-(1-(3-methoxypropyl)-1H-benzo[d]imidazol-2-yl)piperidin-1-yl)-4-oxobutyl)-3-(5-tert-butyl-2-methoxyphenyl)urea;

1-((S)-2-amino-4-((R)-3-O-(3-methoxypropyl)-1H-benzo[d]imidazol-2-yl)piperidin-1-yl)-4-oxobutyl)-3-phenylurea;

N—((S)-2-amino-4-((R)-3-(1-(3-methoxypropyl)-1H-benzo[d]imidazol-2-yl)piperidin-1-yl)-4-oxobutyl)-3-phenoxybenzamide;

N—((S)-2-amino-4-((R)-3-(1-(3-methoxypropyl)-1H-benzo[d]imidazol-2-yl)piperidin-1-yl)-4-oxobutyl)-2,3-dihydrobenzofuran-5-carboxamide;

1-((S)-2-amino-4-((R)-3-(1-(3-methoxypropyl)-1H-benzo[d]imidazol-2-yl)piperidin-1-yl)-4-oxobutyl)-3-(2-phenoxyphenyl)urea;

1-((S)-2-amino-4-((R)-3-(1-(3-methoxypropyl)-1H-benzo[d]imidazol-2-yl)piperidin-1-yl)-4-oxobutyl)-3-(2,5-dimethoxyphenyl)urea;

1-((S)-2-amino-4-((R)-3-(1-(3-methoxypropyl)-1H-benzo[d]imidazol-2-yl)piperidin-1-yl-4-oxobutyl)-3-(2-(difluoromethoxy)phenyl)urea;

N—((S)-2-amino-4-((R)-3-(1-(3-methoxypropyl)-1H-benzo[d]imidazol-2-yl)piperidin-1-yl)-4-oxobutyl)-5-(2-nitrophenyl)furan-2-carboxamide;

N—((S)-2-amino-4-((R)-3-(1-(3-methoxypropyl)-1H-benzo[d]imidazol-2-yl)piperidin-1-yl)-4-oxobutyl)-5-(2,5-dichlorophenyl)furan-2-carboxamide;

N—((S)-2-amino-4-((R)-3-(1-(3-methoxypropyl)-1H-benzo[d]imidazol-2-yl)piperidin-1-yl)-4-oxobutyl)-5-(2,3-dichlorophenyl)furan-2-carboxamide;

N—((S)-2-amino-4-((R)-3-(1-(3-methoxypropyl)-1H-benzo[d]imidazol-2-yl)piperidin-1-yl)-4-oxobutyl)-4-phenoxybenzamide;

1-((S)-2-amino-4-((R)-3-(1-(3-methoxypropyl)-1H-benzo[d]imidazol-2-yl)piperidin-yl)-4-oxobutyl)-3-(2,4-dimethoxyphenyl)urea;

N—((S)-2-amino-4-((R)-3-(1-(3-methoxypropyl)-1H-benzo[d]imidazol-2-yl)piperidin-1-yl)-4-oxobutyl)-4-methoxybenzamide;

N—((S)-2-amino-4-((R)-3-(1-(3-methoxypropyl)-1H-benzo[d]imidazol-2-yl)piperidin-1-yl)-4-oxobutyl)-4-chlorobenzenesulfonamide;

methyl 3-((S)-2-amino-4-((R)-3-(1-(3-methoxypropyl)-1H-benzo[d]imidazol-2-yl)piperidin-1-yl)-4-oxobutylcarbamoyl)benzoate;

1-((S)-2-amino-4-((R)-3-(1-(3-methoxypropyl)-1H-benzo[d]imidazol-2-yl)piperidin-1-yl)-4-oxobutyl)-3-(4-chlorophenyl)urea;

1-((S)-2-amino-4-((R)-3-(1-(3-methoxypropyl)-1H-benzo[d]imidazol-2-yl)piperidin-1-yl)-4-oxobutyl)-3-(2-(methylthio)phenyl)urea;

1-((S)-2-amino-4-((R)-3-(1-(3-methoxypropyl)-1H-benzo[d]imidazol-2-yl)piperidin-1-yl)-4-oxobutyl)-3-(2-methoxyphenyl)urea;

1-((S)-2-amino-4-((R)-3-(1-(3-methoxypropyl)-1H-benzo[d]imidazol-2-yl)piperidin-1-yl)-4-oxobutyl)-3-(2-propylphenyl)urea;

1-((S)-2-amino-4-((R)-3-(1-(3-methoxypropyl)-1H-benzo[d]imidazol-2-yl)piperidin-1-yl)-4-oxobutyl)-3-(2-methoxy-5-methylphenyl)urea;

1-((S)-2-amino-4-((R)-3-(1-(3-methoxypropyl)-1H-benzo[d]imidazol-2-yl)piperidin-1-yl)-4-oxobutyl)-3-(3-phenoxyphenyl)urea;

N—((S)-2-amino-4-((R)-3-(1-(3-methoxypropyl)-1H-benzo[d]imidazol-2-yl)piperidin-1-yl)-4-oxobutyl)-2,6-dichlorobenzamide;

N—((S)-2-amino-4-((R)-3-(1-(3-methoxypropyl)-1H-benzo[d]imidazol-2-yl)piperidin-1-yl)-4-oxobutyl)-2,6-dichlorobenzenesulfonamide;

1-((S)-2-amino-4-((R)-3-(1-(3-methoxypropyl)-1H-benzo[d]imidazol-2-yl)piperidin-1-yl)-4-oxobutyl)-3-(biphenyl-2-yl)urea;

1-((S)-2-amino-4-((R)-3-(1-(3-methoxypropyl)-1H-benzo[d]imidazol-2-yl)piperidin-1-yl)-4-oxobutyl)-3-(4-methoxy-2-methylphenyl)urea;

N—((S)-2-amino-4-((R)-3-(1-(3-methoxypropyl)-1H-benzo[d]imidazol-2-yl)piperidin-1-yl)-4-oxobutyl)-3,4-dimethylbenzamide;

ethyl 4-(5-((S)-2-amino-4-((R)-3-(1-(3-methoxypropyl)-1H-benzo[d]imidazol-2-yl)piperidin-1-yl)-4-oxobutylcarbamoyl)furan-2-yl)benzoate;

N—((S)-2-amino-4-((R)-3-(1-(3-methoxypropyl)-1H-benzo[d]imidazol-2-yl)piperidin-1-yl)-4-oxobutyl)-5-(3,5-dichlorophenyl)furan-2-carboxamide;

N—((S)-2-amino-4-((R)-3-(1-(3-methoxypropyl)-1H-benzo[d]imidazol-2-yl)piperidin-1-yl)-4-oxobutyl)-5-(3-chlorophenyl)furan-2-carboxamide;

N—((S)-2-amino-4-((R)-3-(1-(3-methoxypropyl)-1H-benzo[c]imidazol-2-yl)piperidin-1-yl)-4-oxobutyl)-5-(3-nitrophenyl)furan-2-carboxamide;

N—((S)-2-amino-4-((R)-3-(1-(3-methoxypropyl)-1H-benzo[d]imidazol-2-yl)piperidin-1-yl)-4-oxobutyl)-3-chlorobenzamide;

N—((S)-2-amino-4-((R)-3-(1-(3-methoxypropyl)-1H-benzo[d]imidazol-2-yl)piperidin-1-yl)-4-oxobutyl)-2-phenoxynicotinamide;

N—((S)-2-amino-4-((R)-3-(1-(3-methoxypropyl)-1H-benzo[d]imidazol-2-yl)piperidin-1-yl)-4-oxobutyl)-3-chlorobenzenesulfonamide;

1-((S)-2-amino-4-((R)-3-(1-(3-methoxypropyl)-1H-benzo[d]imidazol-2-yl)piperidin-1-yl)-4-oxobutyl)-3-(2-isopropylphenyl)urea;

1-((S)-2-amino-4-((R)-3-(1-(3-methoxypropyl)-1H-benzo[d]imidazol-2-yl)piperidin-1-yl)-4-oxobutyl)-3-(2-tert-butylphenyl)urea;

N—((S)-2-amino-4-((R)-3-(1-(3-methoxypropyl)-1H-benzo[d]imidazol-2-yl)piperidin-1-yl)-4-oxobutyl)-3-(5-methyl-1,2,4-oxadiazol-3-yl)benzamide;

N—((S)-2-amino-4-((R)-3-(1-(3-methoxypropyl)-1H-benzo[d]imidazol-2-yl)piperidin-1-yl)-4-oxobutyl)-5-(4-fluorophenyl)furan-2-carboxamide;

N—((S)-2-amino-4-((R)-3-(1-(3-methoxypropyl)-1H-benzo[d]imidazol-2-yl)piperidin-1-yl)-4-oxobutyl)-3,4-dichlorobenzenesulfonamide;

N—((S)-2-amino-4-((R)-3-(1-(3-methoxypropyl)-1H-benzo[d]imidazol-2-yl)piperidin-1-yl)-4-oxobutyl)-2-chlorobenzenesulfonamide;

N—((S)-2-amino-4-((R)-3-(1-(3-methoxypropyl)-1H-benzo[d]imidazol-2-yl)piperidin-1-yl)-4-oxobutyl)-2-(propylthio)nicotinamide;

N—((S)-2-amino-4-((R)-3-(1-(3-methoxypropyl)-1H-benzo[d]imidazol-2-yl)piperidin-1-yl)-4-oxobutyl)-2,3-dihydrobenzo[b][1,4]dioxine-6-carboxamide;

N—((S)-2-amino-4-((R)-3-(1-(3-methoxypropyl)-1H-benzo[d]imidazol-2-yl)piperidin-1-yl)-4-oxobutyl)-4-chlorobenzamide;

N—((S)-2-amino-4-((R)-3-(1-(3-methoxypropyl)-1H-benzo[d]imidazol-2-yl)piperidin-1-yl)-4-oxobutyl)-3-methoxybenzamide;

N—((S)-2-amino-4-((R)-3-(1-(3-methoxypropyl)-1H-benzo[d]imidazol-2-yl)piperidin-1-yl)-4-oxobutyl)-1-naphthamide;

N—((S)-2-amino-4-((R)-3-(1-(3-methoxypropyl)-1H-benzo[d]imidazol-2-yl)piperidin-1-yl)-4-oxobutyl)propane-2-sulfonamide;

N—((S)-2-amino-4-((R)-3-(1-(3-methoxypropyl)-1H-benzo[d]imidazol-2-yl)piperidin-1-yl)-4-oxobutyl)-6-(piperidin-1-yl)picolinamide;

methyl 4-((S)-2-amino-4-((R)-3-(1-(3-methoxypropyl)-1H-benzo[d]imidazol-2-yl)piperidin-1-yl)-4-oxobutylcarbamoyl)benzoate;

N—((S)-2-amino-4-((R)-3-(1-(3-methoxypropyl-1H-benzo[d]imidazol-2-yl)piperidin-1-yl)-4-oxobutyl)-3-methoxybenzenesulfonamide;

N—((S)-2-amino-4-((R)-3-(1-(3-methoxypropyl)-1H-benzo[d]imidazol-2-yl)piperidin-1-yl)-4-oxobutyl)benzenesulfonamide;

N—((S)-2-amino-4-((R)-3-(1-(3-methoxypropyl)-1H-benzo[d]imidazol-2-yl)piperidin-1-yl)-4-oxobutyl)benzamide;

N—((S)-2-amino-4-((R)-3-(1-(3-methoxypropyl)-1H-benzo[d]imidazol-2-yl)piperidin-1-yl)-4-oxobutyl)-3-fluorobenzamide;

N—((S)-2-amino-4-((R)-3-(1-(3-methoxypropyl)-1H-benzo[d]imidazol-2-yl)piperidin-1-yl)-4-oxobutyl)-2-cyclohexylacetamide;

N—((S)-2-amino-4-((R)-3-(1-(3-methoxypropyl)-1H-benzo[d]imidazol-2-yl)piperidin-1-yl)-4-oxobutyl)-2-chlorobenzamide;

N—((S)-2-amino-4-((R)-3-(1-(3-methoxypropyl)-1H-benzo[d]imidazol-2-yl)piperidin-1-yl)-4-oxobutyl)-4-methoxybenzenesulfonamide;

1-((S)-2-amino-4-((R)-3-(1-(3-methoxypropyl)-1H-benzo[d]imidazol-2-yl)piperidin-1-yl)-4-oxobutyl)-3-(2,5-dimethoxyphenethyl)urea;

1-((S)-2-amino-4-((R)-3-(1-(3-methoxypropyl)-1H-benzo[d]imidazol-2-yl)piperidin-1-yl)-4-oxobutyl)-3-cyclohexylurea;

N—((S)-2-amino-4-((R)-3-(1-(3-methoxypropyl)-1H-benzo[d]imidazol-2-yl)piperidin-1-yl)-4-oxobutyl)-2-methoxybenzenesulfonamide;

N—((S)-2-amino-4-((R)-3-(1-(3-methoxypropyl)-1H-benzo[d]imidazol-2-yl)piperidin-1-yl)-4-oxobutyl)furan-2-carboxamide;

N—((S)-2-amino-4-((R)-3-(1-(3-methoxypropyl)-1H-benzo[d]imidazol-2-yl)piperidin-1-yl)-4-oxobutyl)cyclohexanecarboxamide;

N—((S)-2-amino-4-((R)-3-(1-(3-methoxypropyl)-1H-benzo[d]imidazol-2-yl)piperidin-1-yl)-4-oxobutyl)-2-methoxybenzamide;

N—((S)-2-amino-4-((R)-3-(1-(3-methoxypropyl)-1H-benzo[d]imidazol-2-yl)piperidin-1-yl)-4-oxobutyl)morpholine-4-carboxamide;

methyl 2-(3-((S)-2-amino-4-((R)-3-(1-(3-methoxypropyl)-1H-benzo[d]imidazol-2-yl)piperidin-1-yl)-4-oxobutyl)ureido)benzoate;

ethyl 2-(3-((S)-2-amino-4-((R)-3-(1-(3-methoxypropyl)-1H-benzo[d]imidazol-2-yl)piperidin-1-yl)-4-oxobutyl)ureido)benzoate;

N—((S)-2-amino-4-((R)-3-(1-(3-methoxypropyl)-1H-benzo[d]imidazol-2-yl)piperidin-1-yl)-4-oxobutyl)cyclopentanecarboxamide;

1-((S)-2-amino-4-((R)-3-(1-(3-methoxypropyl)-1H-benzo[d]imidazol-2-yl)piperidin-1-yl)-4-oxobutyl)-3-cyclopentylurea;

N—((S)-2-amino-4-((R)-3-(1-(3-methoxypropyl)-1H-benzo[d]imidazol-2-yl)piperidin-1-yl)-4-oxobutyl)isobutyramide;

N—((S)-2-amino-4-((R)-3-(1-(3-methoxypropyl)-1H-benzo[d]imidazol-2-yl)piperidin-1-yl)-4-oxobutyl)pyrrolidine-1-carboxamide;

N—((S)-2-amino-4-((R)-3-(1-(3-methoxypropyl)-1H-benzo[d]imidazol-2-yl)piperidin-1-yl)-4-oxobutyl)propane-2-sulfonamide;

1-((S)-2-amino-4-((R)-3-(1-(3-methoxypropyl)-1H-benzo[d]imidazol-2-yl)piperidin-1-yl)-4-oxobutyl)-3-(2-cyanophenyl)urea;

((3R,4S)-4-amino-1-(2,3-dihydrobenzo[b][1,4]dioxin-6-yl)sulfonyl)pyrrolidin-3-yl)((R)-3-(1-(3-methoxypropyl)-1H-benzo[d]imidazol-2-yl)piperidin-1-yl)methanone;

((3S,4R)-3-amino-4-((R)-3-(1-(3-methoxypropyl)-1H-benzo[d]imidazol-2-yl)piperidine-1-carbonyl)pyrrolidin-1-ylsulfonyl)-1H-benzo[d]imidazol-2(3H)-one;

((3R,4S)-4-amino-1-(4-bromo-2,6-dichlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,4,6-trichlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(naphthalen-2-ylsulfonyl)pyrrolidin-3-yl)((R)-3-(1-(3-methoxypropyl-1H-benzo[d]imidazol-2-yl)piperidin-1-yl)methanone;

((3R,4S)-4-amino-1-(4-bromo-2-chlorophenylsulfonyl)pyrrolidin-3-yl)((R)-3-(1-(3-methoxypropyl)-1H-benzo[d]imidazol-2-yl)piperidin-1-yl)methanone;

((3R,3S)-4-amino-1-(2,5-dichlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(4-chloro-2,5-dimethylphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,4,5-trichlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2-chlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,6-dichlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(biphenyl-4-ylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2-chloro-4-fluorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,4-dichlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-chlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(5-phenylfuran-2-carbonyl)pyrrolidin-3-yl)((R)-3-(1-(3-methoxypropyl)-1H-benzo[d]imidazol-2-yl)piperidin-1-yl)methanone;

((3R,4S)-4-amino-(3-chloro-2-methylphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(naphthalen-1-yl)sulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,3-dihydrobenzofuran-5-ylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2-chloro-5(trifluoromethyl)phenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-methoxyphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-phenoxybenzoyl)pyrrolidin-3-yl) ((R)-3-(1-(3-methoxypropyl)-1H-benzo[d]imidazol-2-yl) piperidin-1-yl)methanone;

((3R,4S)-4-amino-1-(2-chloro-6-methylphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(1-methyl-1H-indol-5-ylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3,4-dichlorophenylsulfonyl)pyrrolidin-3-yl)((R)-3-(1-(3-methoxypropyl)-1H-benzo[d]imidazol-2-yl)piperidin-1-yl)methanone;

((3R,4S)-1-(2-naphthoyl)-4-aminopyrrolidin-3-yl)((R)-3-(1-(3-methoxypropyl)-1H-benzo[b]imidazol-2-yl)piperidin-1-ylmethanone;

((3R,4S)-4-amino-1-(2,3-dichlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-(2-methylthiazol-4-yl)phenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3,4-dichlorobenzoyl)pyrrolidin-3-yl) ((R)-3-(1-(3-methoxypropyl)-1H-benzo[d]imidazol-2-yl) piperidin-1-yl)methanone;

((3R,4S)-4-amino-1-(2-phenoxynicotinoyl)pyrrolidin-3-yl) ((R)-3-(1-(3-methoxypropyl)-1H-benzo[d]imidazol-2-yl) piperidin-1-yl)methanone;

(3S,4R)-3-amino-N-(3-methoxyphenyl)-4-((R)-3-(1-(3-methoxypropyl)-1H-benzo[d]imidazol-2-yl)piperidine-1-carbonyl)pyrrolidine-1-carboxamide;

((3R,4S)-4-amino-1-(3-phenoxyphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(4-methoxyphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(4-chlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(isopropylsulfonyl)pyrrolidin-3-yl)-((R)-3-(1-(3-methoxypropyl)-1H-benzo[d]imidazol-2-yl) piperidin-1-yl)methanone;

((3R,4S)-4-amino-1-(3,4-dimethoxyphenylsulfonyl)pyrrolidin-3-yl)((R)-3-(1-(3-methoxypropyl)-1H-benzo[d]imidazol-2-yl)piperidin-1-yl)methanone;

methyl 2-((3S,4R)-3-amino-4((R)-3-(1-(3-methoxypropyl)-1H-benzo[d]imidazol-2-yl)piperidine-1-carbonyl)pyrrolidin-1-ylsulfonyl)benzoate;

((3R,4S)-4-amino-1-(4-tert-butylphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-chlorobenzoyl)pyrrolidin-3-yl)((R)-3-(1-(3-methoxypropyl)-1H-benzo[d]imidazol-2-yl)piperidin-1-yl)methanone;

((3R,4S)-1-(1-naphthoyl)-4-aminopyrrolidin-3-yl)((R)-3-(1-(3-methoxypropyl)-1H-benzo[d]imidazol-2-yl)piperidin-1-yl)methanone;

methyl 3-((3S,4R)-3-amino-4-((R)-3-(1-(3-methoxypropyl)-1H-benzo[d]imidazol-2-yl)piperidine-1-carbonyl)pyrrolidine-1-carbonyl)benzoate;

(3S,4R)-3-amino-N-(3-chlorophenyl)-4-((R)-3-(1-(3-methoxypropyl)-1H-benzo[d]imidazol-2-yl)piperidine-1-carbonyl)pyrrolidine-1-carboxamide;

((3R,4S)-4-amino-1-(2-methoxyphenylsulfonyl)pyrrolidin-3-yl)((R)-3-(1-(3-methoxypropyl)-1H-benzo[d]imidazol-2-yl)piperidin-1-yl)methanone;

N-(4-((3S,4R)-3-amino-4-((R)-3-(1-(3-methoxypropyl)-1H-benzo[d]imidazol-2-yl)piperidine-1-carbonyl)pyrrolidin-1-ylsulfonyl)phenyl)acetamide;

((3R,4S)-4-amino-1-(4-methoxy-2-nitrophenylsulfonyl)pyrrolidin-3-yl)((R)-3-(1-(3-methoxypropyl)-1H-benzo[d]imidazol-2-yl)piperidin-1-yl)methanone;

1-(4-((3S,4R)-3-amino-4-((R)-3-(1-(3-methoxypropyl)-1H-benzo[d]imidazol-2-yl)piperidine-1-carbonyl)pyrrolidin-1-ylsulfonyl)phenyl)pyrrolidin-2-one;

((3R,4S)-4-amino-1-(2,4-dimethylphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(phenylsulfonyl)pyrrolidin-3-yl)((R)-3-(1-(3-methoxypropyl)-1H-benzo[d]imidazol-2-yl)piperidin-1-yl)methanone;

((3R,4 S)-4-amino-1-benzoylpyrrolidin-3-yl)((R)-3-(1-(3-methoxypropyl)-1H-benzo[d]imidazol-2-yl)piperidin-1-yl)methanone;

(3S,4R)-3-amino-N-cyclohex yl-4-((R)-3-(1-(3-methoxypropyl)-1H-benzo[d]imidazol-2-yl)piperidine-1-carbonyl)pyrrolidine-1-carboxamide;

((3R,4S)-4-amino-1-(2-methoxybenzoyl)pyrrolidin-3-yl) ((R)-3(1-(3-methoxypropyl)-1H-benzo[d]imidazol-2-yl) piperidin-1-yl)methanone;

(3S,4R)-3-amino-N-(4-chlorophenyl)-4-((R)-3-(1-(3-methoxypropyl)-1H-benzo[d]imidazol-2-yl)piperidine-1-carbonyl)pyrrolidine-1-carboxamide;

3S,4R)-3-amino-N-(2-chlorophenyl)-4-((R)-3-(1-(3-methoxypropyl)-1H-benzo[d]imidazol-2-yl)piperidine-1-carbonyl)pyrrolidine-1-carboxamide;

(3S,4R)-2-chlorophenyl 3-amino-4-((R)-3-(1-(3-methoxypropyl)-1H-benzo[d]imidazol-2-yl)piperidine-1-carbonyl)pyrrolidine-1-carboxylate;

4-((3S,4R)-3-amino-4-((R)-3-(1-(3-methoxypropyl)-1H-benzo[d]imidazol-2-yl)piperidine-1-carbonyl)pyrrolidin-1-ylsulfonyl)-3-chlorobenzonitrile;

((3R,4S)-4-amino-1-(1-methyl-1H-indol-4-ylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-fluorobenzoyl)pyrrolidin-3-yl)((R)-3-(1-(3-methoxypropyl)-1H-benzo[d]imidazol-2-yl)piperidin-1-yl)methanone;

((3R,4S)-4-amino-1-(4-methoxybenzoyl)pyrrolidin-3-yl) ((R)-3-(1-(3-methoxypropyl)-1H-benzo[d]imidazol-2-yl) piperidin-1-yl)methanone;

((3R,4S)-4-amino-1-(cyclopentanecarbonyl)pyrrolidin-3-yl) ((R)-3-(1-(3-methoxypropyl)-1H-benzo[d]imidazol-2-yl) piperidin-1-yl)methanone;

1-(3S,4R)-3-amino-4-((R)-3-(1-(3-methoxypropyl)-1H-benzo[d]imidazol-2-yl)piperidine-1-carbonyl)pyrrolidin-1-yl)-2-methylpropan-1-one;

1-(3S,4R)-3-amino-4-((R)-3-(1-(3-methoxypropyl)-1H-benzo[d]imidazol-2-yl)piperidine-1-carbonyl)pyrrolidin-1-yl)-2-cyclohexylethanone;

((3R,4S)-4-amino-1-(2-chlorobenzoyl)pyrrolidin-3-yl)((R)-3-(1-(3-methoxypropyl)-1H-benzo[d]imidazol-2-yl)piperidin-1-yl)methanone;

(3S,4R)-3-amino-N-cyclopentyl-4-((R)-3-(1-(3-methoxypropyl)-1H-benzo[d]imidazol-2-yl)piperidine-1-carbonyl)pyrrolidine-1-carboxamide;

(3S,4R)-3-amino-N-(2-methoxyphenyl)-4-((R)-3-(1-(3-methoxypropyl)-1H-benzo[d]imidazol-2-yl)piperidine-1-carbonyl)pyrrolidine-1-carboxamide;

((3R,4S)-4-amino-1-(5-bromo-2-methoxyphenylsulfonyl) pyrrolidin-3-yl)((R)-3-(1-(3-methoxypropyl)-1H-benzo[d]imidazol-2-yl)piperidin-1-yl)methanone;

((3R,4S)-4-amino-1-(2-(trifluoromethyl)phenylsulfonyl) pyrrolidin-3-yl)((R)-3-(1-(3-methoxypropyl)-1H-benzo[d]imidazol-2-yl)piperidin-1-yl)methanone;

2-((3S,4R)-3-amino-4-((R)-3-(1-(3-methoxypropyl)-1H-benzo[d]imidazol-2-yl)piperidine-1-carbonyl)pyrrolidin-1-ylsulfonyl)-4-methylbenzonitrile;

(3S,4R)-3-amino-4-((R)-3-(1-(3-methoxypropyl)-1H-benzo[d]imidazol-2-yl)piperidine-1-carbonyl)-N-phenylpyrrolidine-1-carboxamide;

((3R,4S)-4-amino-1-(cyclohexanecarbonyl)pyrrolidin-3-yl)((R)-3-(1-(3-methoxypropyl)-1H-benzo[d]imidazol-2-yl)piperidin-1-yl)methanone;

((3R,4S)-4-amino-1-(benzofuran-2-carbonyl)pyrrolidin-3-yl)((R)-3-(1-(3-methoxypropyl)-1H-benzo[d]imidazol-2-yl)piperidin-1-yl)methanone;

(3S,4R)-4-chlorophenyl 3-amino-4-((R)-3-(1-(3-methoxypropyl)-1H-benzo[d]imidazol-2-yl)piperidine-1-carbonyl)pyrrolidine-1-carboxylate;

(3S,4R)-3-(trifluoromethyl)phenyl 3-amino-4-((R)-3-(1-(3-methoxypropyl)-1H-benzo[d]imidazol-2-yl)piperidine-1-carbonyl)pyrrolidine-1-carboxylate;

((3R,4S)-4-amino-1-(3-(5-methyl-1,2,4-oxadiazol-3-yl) phenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2-methoxy-5-methylphenylsulfonyl) pyrrolidin-3-yl)((R)-3-(1-(3-methoxypropyl)-1H-benzo[d]imidazol-2-yl)piperidin-1-yl)methanone;

((3R,4S)-4-amino-1-(2-methoxy-4-nitrophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(5-chloro-2-methoxyphenylsulfonyl) pyrrolidin-3-yl)((R)-3-(1-(3-methoxypropyl)-1H-benzo[d]imidazol-2-yl)piperidin-1-yl)methanone;

((3R,4S)-4-amino-1-(2,5-dimethoxyphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,6-dichlorobenzoyl)pyrrolidin-3-yl) ((R)-3-(1-(3-methoxypropyl)-1H-benzo[9]imidazol-2-yl) piperidin-1-yl)methanone;

((3S,4R)-3-amino-N-(4-methoxyphenyl)-4-((R)-3-(1-(3-methoxypropyl)-1H-benzo[d]imidazol-2-yl)piperidine-1-carbonyl)pyrrolidine-1-carboxamide;

((3R,4S)-4-amino-1-(4-chlorobenzoyl)pyrrolidin-3-yl)((R)-3-(1-(3-methoxypropyl)-1,1-benzo[d]imidazol-2-yl)piperidin-1-yl)methanone;

((3R,4S)-4-amino-1-(pyrrolidine-1-carbonyl)pyrrolidin-3-yl)((R)-3-(1-(3-methoxypropyl)-1H-benzo[d]imidazol-2-yl)piperidin-1-yl)methanone;

((3R,4S)-4-amino-1-(2-(propylthio)nicotinoyl)pyrrolidin-3-yl)((R)-3-(1-(3-methoxypropyl)-1H-benzo[d]imidazol-2-yl)piperidin-1-yl)methanone;

((3R,4S)-4-amino-1-(3-(difluoromethoxy)phenylsulfonyl) pyrrolidin-3-yl)((R)-3-(1-(3-methoxypropyl)-1H-benzo[d]imidazol-2-yl)piperidin-1-yl)methanone;

((3R,4S)-4-amino-1-(furan-2-carbonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-methoxybenzoyl)pyrrolidin-3-yl) ((R)-3-(1-(3-methoxypropyl)-1H-benzo[d]imidazol-2-yl)piperidin-1-yl)methanone;

methyl 4-((3S,4R)-3-amino-4-((R)-3-(1-(3-methoxypropyl)-1H-benzo[d]imidazol-2-yl)piperidine-1-carbonyl)pyrrolidine-1-carbonyl)benzoate;

((3R,4S)-4-amino-1-(morpholine-4-carbonyl)pyrrolidin-3-yl)((R)-3-(1-(3-methoxypropyl)-1H-benzo[d]imidazol-2-yl)piperidin-1-yl)methanone;

methyl 2-((3S,4R)-3-amino-4-((R)-3-(1-(3-methoxypropyl)-1H-benzo[d]imidazol-2-yl)piperidine-1-carbonyl)pyrrolidine-1-carbonyl)benzoate;

((3R,4S)-4-amino-1-(2,6-dichlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,6-difluorophenylsulfonyl)pyrrolidin-3-yl)((R)-3-(1-(3-methoxypropyl)-1H-benzo[d]imidazol-2-yl)piperidin-1-yl)methanone;

2-((3S,4R)-3-amino-4-((R)-3-(1-(3-methoxypropyl)-1H-benzo[d]imidazol-2-yl)piperidine-1-carbonyl)pyrrolidin-1-ylsulfonyl)benzonitrile;

((3R,4S)-4-amino-1-(3-fluorophenylsulfonyl)pyrrolidin-3-yl)((R)-3-(1-(3-methoxypropyl)-1H-benzo[d]imidazol-2-yl)piperidin-1-yl)methanone;

N-(3-((3S,4R)-3-amino-4-((R)-3-(1-(3-methoxypropyl)-1H-benzo[d]imidazol-2-yl)piperidine-1-carbonyl)pyrrolidin-1-ylsulfonyl)phenyl)acetamide;

((3R,4S)-4-amino-1-(3-(2-methylpyrimidin-4-yl)phenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-(5-methyl-1,3,4-oxadiazol-2-yl) phenylsulfonyl)pyrrolidin-3-yl)((R)-3-(1-(3-methoxypropyl)-1H-benzo[d]imidazol-2-yl)piperidin-1-yl)methanone;

methyl 2-((R)-2-amino-4-((R)-3-(1-(3-methoxypropyl)-1H-benzo[d]imidazol-2-yl)piperidin-1-yl)-4-oxobutoxy)benzoate;

(R)-3-amino-4-(3-methoxyphenoxy)-1-((R)-3-(1-(3-methoxypropyl)-1H-benzo[d]imidazol-2-yl)piperidin-1-yl)butan-1-one;

(R)-4-(1H-benzo[d]imidazol-2-yloxy)-3-amino-1((R)-3-(1-(3-methoxypropyl)-1H-benzo[d]imidazol-2-yl)piperidin-1-yl)butan-1-one;

(R)-3-amino-4-(4-(2-((S)-3-hydroxypyrrolidin-1-yl)thiazol-4-yl)phenyl)-1-((R)-3-(1-(3-methoxypropyl)-1H-benzo[d]imidazol-2-yl)piperidin-1-yl)butan-1-one;

1-(4'-((R)-2-amino-4-((R)-3-(1-(3-methoxypropyl)-1H-benzo[d]imidazol-2-yl)piperidin-1-yl)-4-oxobutyl)biphenyl-4-yl)imidazolidin-2-one;

(R)-3-amino-4-(4-(2-hydroxypyridin-4-yl)phenyl)-1-((R)-3-(1-(3-methoxypropyl)-1H-benzo[d]imidazol-2-yl)piperidin-1-yl)butan-1-one;

6-(4-((R)-2-amino-4-((R)-3-(1-(3-methoxypropyl)-1H-benzo[c]imidazol-2-yl)piperidin-1-yl)-4-oxobutyl)phenyl)-2H-benzo[b][1,4]oxazin-3(4H)-one;

6-(4-((R)-2-amino-4-((R)-3-(1-(3-methoxypropyl)-1H-benzo[d]imidazol-2-yl)piperidin-1-yl)-4-oxobutyl)phenyl)-2H-benzo[b][1,4]oxazin-3(4H)-one;

(R)-3-amino-1-((R)-3-(1-(3-methoxypropyl)-1H-benzo[d]imidazol-2-yl)piperidin-1-yl)-4-(4-(4-methyl-3,4-dihydro-2H-benzo[b][1,4]oxazin-7-yl)phenyl)butan-1-one;

1-(4-((R)-2-amino-4-((R)-3-(1-(3-methoxypropyl)-1H-benzo[d]imidazol-2-yl)piperidin-1-yl)-4-oxobutyl)phenyl)-6-fluoro-1H-benzo[d]imidazol-2(3H)-one;

1-(4'-((R)-2-amino-4-((R)-3-(4-fluoro-1-(3-methoxypropyl)-1H-benzo[d]imidazol-2-yl)piperidin-1-yl)-4-oxobutyl)biphenyl-4-yl)imidazolidin-2-one 7-(4-((R)-2-amino-4-((R)-3-(4-fluoro-1-(3-methoxypropyl)-1H-benzo[d]imidazol-2-yl)piperidin-1-yl)-4-oxobutyl)phenyl)-2H-benzo[b][1,4]thiazin-3(4H)-one 7-(4-((R)-2-amino-4-((R)-3-(4-fluoro-1-(3-methoxypropyl)-1H-benzo[d]imidazol-2-yl)piperidin-1-yl)-4-oxobutyl)phenyl)-2H-benzo[b][1,4]oxazin-3(4H)-one (R)-3-amino-1((R)-3-(4-fluoro-1-(3-methoxypropyl)-1H-benzo[d]imidazol-2-yl)piperidin-1-yl)-4-(4-(2-hydroxypyridin-4-yl)phenyl)butan-1-one N-(2-(2-((R)-1((R)-3-amino-4-(4-(6-hydroxypyridin-3-yl)phenyl)butanoyl)piperidin-3-yl)-1H-benzo[d]imidazol-1-yl)ethyl)acetamide N-(2-(2-((R)-1((R)-3-amino-4-(4-(6-aminopyridin-3-yl)phenyl)butanoyl)piperidin-3-yl)-1H-benzo[d]imidazol-1-yl)ethyl)acetamide 3-(2-((R)-1((R)-3-amino-4-(4-(4-methyl-3,4-dihydro-2H-benzo[b][1,4]oxazin-7-yl)phenyl)butanoyl)piperidin-3-yl)-1H-benzo[d]imidazol-1-yl)propanamide N-(2-(2-((R)-1-((R)-3-amino-4-(4-(2,2-difluorobenzo[d][1,3]dioxol-5-yl)phenyl)butanoyl)piperidin-3-yl)-1H-benzo[d]imidazol-1-yl)ethyl)acetamide N-(2-(2-((R)-1-((R)-3-amino-4-(4-(2,3-dihydrobenzo[b][1,4]dioxin-6-yl)phenyl)butanoyl)piperidin-3-yl)-1H-benzo[d]imidazol-1-yl)ethyl)acetamide N-(2-(2-((R)-1((R)-3-amino-4-(4-(2-aminopyrimidin-5-yl)phenyl)butanoyl)piperidin-3-yl)-1H-benzo[d]imidazol-1-yl)ethyl)acetamide (R)-3-amino-1-((R)-3-(4-fluoro-1-(3-methoxypropyl)-1H-benzo[d]imidazol-2-yl)piperidin-1-yl)-4-(4-(6-hydroxypyridin-3-yl)phenyl)butan-1-one (R)-3-amino-4-(4-(6-aminopyridin-3-yl)phenyl)-1-((R)-3-(4-fluoro-1-(3-methoxypropyl)-1H-benzo[d]imidazol-2-yl)piperidin-1-yl)butan-1-one (R)-3-amino-1-((R)-3-(4-fluoro-1-(3-methoxypropyl)-1H-benzo[d]imidazol-2-yl)piperidin-1-yl)-4-(4-(4-methyl-3,4-dihydro-2H-benzo[b][1,4]oxazin-7-yl)phenyl)butan-1-one (R)-3-amino-4-(4-(2,2-difluorobenzo[d][1,3]dioxol-5-yl)phenyl)-1-((R)-3-(4-fluoro-1-(3-methoxypropyl)-1H-benzo[d]imidazol-2-yl)piperidin-1-yl)butan-1-one (R)-3-amino-4-(4-(2,3-dihydrobenzo[b][1,4]dioxin-6-yl)phenyl)-1((R)-3-(4-fluoro-1-(3-methoxypropyl)-1H-benzo[d]imidazol-2-yl)piperidin-1-yl)butan-1-one (R)-3-amino-4-(4-(2-aminopyrimidin-5-yl)phenyl)-1-((R)-3-(4-fluoro-1-(3-methoxypropyl)-1H-benzo[d]imidazol-2-yl)piperidin-1-yl)butan-1-one methyl 4'-((R)-4-((R)-3-(1-(2-acetamidoethyl)-1H-benzo[d]imidazol-2-yl)piperidin-1-yl)-2-amino-4-oxobutyl)biphenyl-4-ylcarbamate 5-(4-((R)-2-amino-4-((R)-3-(4-fluoro-1-(3-methoxypropyl)-1H-benzo[d]imidazol-2-yl)piperidin-1-yl)-4-oxobutyl)phenyl)indolin-2-one 6-(4-((R)-2-amino-4-((R)-3-(4-fluoro-1-(3-methoxypropyl)-1H-benzo[d]imidazol-2-yl)piperidin-1-yl)-4-oxobutyl)phenyl)indolin-2-one 5-(4-((R)-2-amino-4-((R)-3-(4-fluoro-1-(3-methoxypropyl)-1H-benzo[d]imidazol-2-yl)piperidin-1-yl)-4-oxobutyl)phenyl)benzo[d]oxazol-2(3H)-one N-(2-(2-((R)-1((R)-3-amino-4-(4-(2-hydroxypyridin-4-yl)phenyl)butanoyl)piperidin-3-yl)-1H-benzo[d]imidazol-1-yl)ethyl)acetamide N-(2-(2-((R)-1((R)-3-amino-4-(4'-(2-oxoimidazolidin-1-yl)biphenyl-4-yl)butanoyl)piperidin-3-yl)-1H-benzo[d]imidazol-1-yl)ethyl)acetamide (R)-3-amino-4-(4-(2-aminobenzo[d]oxazol-5-yl)phenyl)-1((R)-3-(4-fluoro-1-(3-methoxypropyl)-1H-benzo[d]imidazol-2-yl)piperidin-1-yl)butan-1-one N-(2-(2-((R)-1((R)-3-amino-4-(4-(2-oxo-2,3-dihydrobenzo[b][1,4]oxathiin-6-yl)phenyl)butanoyl)piperidin-3-yl)-1H-benzo[d]imidazol-1-yl)ethyl)acetamide N-(2-(2-((R)-1((R)-3-amino-4-(4-(2-oxoindolin-5-yl)phenyl)butanoyl)piperidin-3-yl)-1H-benzo[d]imidazol-1-yl)ethyl)acetamide N-(2-(2-((R)-1((R)-3-amino-4-(4-(2-oxoindolin-6-yl)phenyl)butanoyl)piperidin-3-yl)-1H-benzo[d]imidazol-1-yl)ethyl)acetamide N-(2-(2-((R)-1-((R)-3-amino-4-(4-(2-oxo-2,3-dihydrobenzo[d]oxazol-5-yl)phenyl)butanoyl)piperidin-3-yl)-1H-benzo[d]imidazol-1-yl)ethyl)acetamide 5-(4-((R)-2-amino-4-((R)-3-(4-fluoro-1-(3-methoxypropyl)-1H-benzo[d]imidazol-2-yl)piperidin-1-yl)-4-oxobutyl)phenyl)benzo[d]oxazol-2(3H)-one (R)-3-amino-4-(4-(2-aminobenzo[d]oxazol-5-yl)phenyl)-1-((R)-3-(4-fluoro-1-(3-methoxypropyl)-1H-benzo[d]imidazol-2-yl)piperidin-1-yl)butan-1-one N-(2-(2-((R)-1-((R)-3-amino-4-(4-(2-aminopyrimidin-5-yl)phenyl)butanoyl)piperidin-3-yl)-4-chloro-1H-benzo[d]imidazol-1-yl)ethyl)acetamide N-(2-(2-((R)-1((R)-3-amino-4-(4-(6-aminopyridin-3-yl)phenyl)butanoyl)piperidin-3-yl)-4-methyl-1H-benzo[d]imidazol-1-yl)ethyl)acetamide N-(2-(2-((R)-1-((R)-3-amino-4-(4-(2-aminopyrimidin-5-yl)phenyl)butanoyl)piperidin-3-yl)-4-methyl-1H-benzo[d]imidazol-1-yl)ethyl)acetamide N-(2-(2-((R)-1((R)-3-amino-4-(4-(6-hydroxypyridin-3-yl)phenyl)butanoyl)piperidin-3-yl)-4-methyl-1H-benzo[d]imidazol-1-yl)ethyl)acetamide N-(2-(2-((R)-1((R)-3-amino-4-(4-(2,2-difluorobenzo[d][1,3]dioxol-5-yl)phenyl)butanoyl)piperidin-3-yl)-4-methyl-1H-benzo[d]imidazol-1-yl-ethyl)acetamide N-(2-(2-((R)-1((R)-3-amino-4-(4-(4-methyl-3,4-dihydro-2H-benzo[b][1,4]oxazin-7-yl)phenyl)butanoyl)piperidin-3-yl)-4-methyl-1H-benzo[d]imidazol-1-yl)ethyl)acetamide N-(2-(2-((R)-1-((R)-3-amino-4-(4-(6-hydroxypyridin-3-yl)phenyl)butanoyl)piperidin-3-yl)-1H-benzo[d]imidazol-1-yl)ethyl)acetamide N-(2-(2-((R)-1-((R)-3-amino-4-(4-(2,3-dihydrobenzo[b][1,4]dioxin-6-yl)phenyl)butanoyl)piperidin-3-yl)-4-methyl-1H-benzo[d]imidazol-1-yl)ethyl)acetamide N-(2-(2-((R)-1-((R)-3-amino-4-(4-(6-hydroxypyridin-3-yl)phenyl)butanoyl)piperidin-3-yl)-4-chloro-1H-benzo[d]imidazol-1-yl)ethyl)acetamide N-(2-(2-((R)— 1-((R)-3-amino-4-(4-(6-aminopyridin-3-yl)phenyl)butanoyl)piperidin-3-yl)-4-chloro-1H-benzo[d]imidazol-1-yl)ethyl)acetamide 3-(2-((R)-1-((R)-3-amino-4-(4-(6-aminopyridin-3-yl)phenyl)butanoyl)piperidin-3-yl)-1H-benzo[d]imidazol-1-yl)propanamide;

3-(2-((R)-1((R)-3-amino-4-(4-(2-aminopyrimidin-5-yl)phenyl)butanoyl)piperidin-3-yl)-1H-benzo[d]imidazol-1-yl)propanamide;

3-(2-((R)-1-((R)-3-amino-4-(4-(4-methyl-3,4-dihydro-2H-benzo[b][1,4]oxazin-7-yl)phenyl)butanoyl)piperidin-3-yl)-1H-benzo[d]imidazol-1-yl)propanamide;

3-(2-((R)-1((R)-3-amino-4-(4-(4-methyl-3,4-dihydro-2H-benzo[b][1,4]oxazin-7-yl)phenyl)butanoyl)piperidin-3-yl)-1H-benzo[d]imidazol-1-yl)propanamide;

3-(2-((R)-1((R)-3-amino-4-(4-(2,3-dihydrobenzo[b][1,4]dioxin-6-yl)phenyl)butanoyl)piperidin-3-yl)-1H-benzo[d]imidazol-1-yl)propanamide;

3-(2-((R)-1-((R)-3-amino-4-(biphenyl-4-yl)butanoyl)piperidin-3-yl)-1H-benzo[d]imidazol-1-yl)propanamide;

3-(2-((R)-1((R)-4-(4'-acetamidobiphenyl-4-yl)-3-aminobutanoyl)piperidin-3-yl)-1H-benzo[d]imidazol-1-yl)propanamide;

3-(2-((R)-1((R)-3-amino-4-(4'-methoxybiphenyl-4-yl)butanoyl)piperidin-3-yl)-1H-benzo[d]imidazol-1-yl)propanamide;

3-(2-((R)-1((R)-3-amino-4-(4-(pyridin-4-yl)phenyl)butanoyl)piperidin-3-yl)-1H-benzo[d]imidazol-1-yl)propanamide;

3-(2-((R)-1((R)-3-amino-4-(4'-chlorobiphenyl-4-yl)butanoyl)piperidin-3-yl)-1H-benzo[d]imidazol-1-yl)propanamide;

(R)-3-amino-4-(4-(2,3-dihydrobenzofuran-5-yl)phenyl)-1((R)-3-(4-fluoro-1-(3-methoxypropyl)-1H-benzo[d]imidazol-2-yl)piperidin-1-yl)butan-1-one;

N-(4'-((R)-2-amino-4-((R)-3-(4-fluoro-1-(3-methoxypropyl)-1H-benzo[d]imidazol-2-yl)piperidin-1-yl)-4-oxobutyl)biphenyl-4-yl)acetamide;

(R)-3-amino-1((R)-3-(4-fluoro-1-(3-methoxypropyl)-1H-benzo[d]imidazol-2-yl)piperidin-1-yl)-4-(4'-methoxybiphenyl-4-yl)butan-1-one;

(R)-3-amino-4-(4-(2,3-dihydrobenzofuran-5-yl)phenyl)-1-((Z)-3-(1-(3-methoxypropyl)-4-methyl-1H-benzo[d]imidazol-2-yl)piperidin-1-yl)butan-1-one (R)-3-amino-4-(4-(benzofuran-5-yl)phenyl)-1-((R)-3-(1-(3-methoxypropyl)-4-methyl-1H-benzo[d]imidazol-2-yl)piperidin-1-yl)butan-1-one 5-(4-((R)-2-amino-4-((R)-3-(1-(3-methoxypropyl)-4-methyl-1H-benzo[d]imidazol-2-yl)piperidin-1-yl)-4-oxobutyl)phenyl)indolin-2-one 7-(4-((R)-2-amino-4-((R)-3-(1-(3-methoxypropyl)-4-methyl-1H-benzo[d]imidazol-2-yl)piperidin-1-yl)-4-oxobutyl)phenyl)-2H-benzo[b][1,4]thiazin-3(4H)-one 7-(4-((R)-2-amino-4-((R)-3-(1-(3-methoxypropyl)-4-methyl-1H-benzo[d]imidazol-2-yl)piperidin-1-yl)-4-oxobutyl)phenyl)-2H-benzo[b][1,4]oxazin-3(4H)-one 5-(4-((R)-2-amino-4-((R)-3-(1-(3-methoxypropyl)-4-methyl-1H-benzo[d]imidazol-2-yl)piperidin-1-yl)-4-oxobutyl)phenyl)-1-methylindolin-2-one (R)-4-(4-(1H-indazol-5-yl)phenyl)-3-amino-1-((R)-3-(1-(3-methoxypropyl)-4-methyl-1H-benzo[d]imidazol-2-yl)piperidin-1-yl)butan-1-one (R)-3-amino-4-(4-(3-amino-1H-indazol-5-yl)phenyl)-1-((R)-3-(1-(3-methoxypropyl)-4-methyl-1H-benzo[d]imidazol-2-yl)piperidin-1-yl)butan-1-one 3-(2-((R)-1((R)-3-amino-4-(4-(2,3-dihydrobenzofuran-5-yl)phenyl)butanoyl)piperidin-3-yl)-4-methyl-1H-benzo[d]imidazol-1-yl)-N-methylpropanamide (3R)-3-amino-1-(3-(5-chloro-3-(3-methoxypropyl)-3H-imidazo[4,5-b]pyridin-2-yl)piperidin-1-yl)-4-(naphthalen-2-yl)butan-1-one;

(3R)-3-amino-1-(3-(5-methoxy-3-(3-methoxypropyl)-3H-imidazo[4,5-b]pyridin-2-yl)piperidin-1-yl)-4-(naphthalen-2-yl)butan-1-one;

(R)-3-amino-4-(4-(6-hydroxypyridin-3-yl)phenyl)-1-((R)-3-(3-(3-methoxypropyl)-7-methyl-3H-imidazo[4,5-b]pyridin-2-yl)piperidin-1-yl)butan-1-one;

(R)-3-amino-4-(biphenyl-4-yl)-1((R)-3-(3-(3-methoxypropyl)-7-methyl-3H-imidazo[4,5-b]pyridin-2-yl)piperidin-1-yl)butan-1-one;

3-((3S,4R)-3-amino-4-((R)-3-(1-(3-methoxypropyl)-1H-benzo[d]imidazol-2-yl)piperidine-1-carbonyl)pyrrolidin-1-yl)benzonitrile;

3-((3S,4R)-3-amino-4-((R)-3-(1-(3-methoxypropyl)-1H-benzo[d]imidazol-2-yl)piperidine-1-carbonyl)pyrrolidin-1-yl)benzonitrile;

((3R,4S)-4-amino-1-(4-nitrophenyl)pyrrolidin-3-yl)((R)-3-(1-(3-methoxypropyl)-1H-benzo[d]imidazol-2-yl)piperidin-1-yl)methanone; and (R)-3-amino-4-(4-(2-aminopyrimidin-5-yl)phenyl)-1((R)-3-(1-(2-fluoroethyl)-1H-benzo[d]imidazol-2-yl)piperidin-1-yl)butan-1-one.

It is noted that the compounds of the present invention may be in the form of a pharmaceutically acceptable salt. It is further note that the compounds of the present invention may be in a mixture of stereoisomers, or the compound may comprise a single stereoisomer.

In another aspect, the present invention is related to a pharmaceutical composition comprising as an active ingredient a compound according to any one of the above embodiments and variations. In one embodiment, the composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In another embodiment, the pharmaceutical composition comprises a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, the invention is related to a kit which comprises a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another aspect, the invention is related to an article of manufacture comprising a compound of any one of the above embodiments and variations and packaging materials. In one embodiment, the packaging material comprises a container for housing the compound. In another embodiment, the container comprises a label indicating one or more members of the group consisting of a disease state for which the compound is to be administered, storage information, dosing information and/or instructions regarding how to administer the compound. In another embodiment, the article of manufacture comprises the compound in a multiple dose form.

In a further aspect, the invention is related to a therapeutic method comprising administering a compound to a subject.

In one embodiment, the method comprises contacting renin with a compound of any one of the above embodiments and variations.

In yet another embodiment is a method of inhibiting renin which comprises causing a compound of any one of the above embodiments and variations to be present in a subject in order to inhibit renin in vivo.

A further embodiment is a method of inhibiting renin which comprises administering a first compound to a subject that is converted in vivo to a second compound wherein the second compound inhibits renin in vivo, the second compound being a compound according to any one of the above embodiments and variations.

Another further embodiment is a method of treating a disease state for which renin possesses activity contributes to the pathology and/or symptomology of the disease state. In one variation, the method comprises causing a compound of any one of the above embodiments and variations to be present in a subject in a therapeutically effective amount for the disease state. In another variation, the method comprises administering a compound of any one of the above embodiments and variations to a subject, wherein the compound is present in the subject in a therapeutically effective amount for the disease state. In a further variation, the method comprises administering a first compound to a subject that is converted in vivo to a second compound wherein the second compound inhibits renin in viva, the second compound being a compound according to any one of the above embodiments and variations.

In one variation of the above embodiments and variations, the disease state is selected from the group consisting of cardiovascular disease, hypertension, congestive heart failure, myocardial infarction, renal protection, inflammation, neurological disease and cancer.

Another aspect of the invention is directed to method of preparing the compounds of the invention.

In one embodiment, the method of preparing the compounds includes coupling a compound of the formula

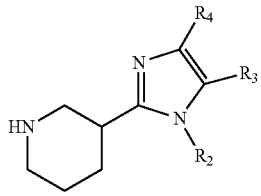

to a compound of the formula

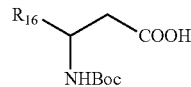

under conditions that form an intermediate of the formula

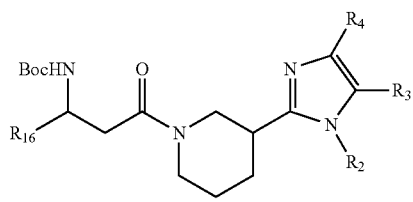

wherein $R_2$ is selected from the group consisting of $(C_{1-10})$alkoxy, $(C_{4-12})$aryloxy, hetero$(C_{1-10})$aryloxy, carbonyloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl $(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that $R_3$ and $R_4$ are each independently selected from the group consisting of hydrogen, halo, nitro, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamide, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, and $R_3$ and $R_4$ may be taken together to form a 5, 6, 7, 8 membered saturated, unsaturated or aromatic ring;

$R_{16}$ is a $(C_{1-10})$alkyl or a cyclic moiety selected from the group consisting of $(C_{3-14}$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, wherein said $(C_{1-10})$alkyl, and cyclic moiety are each independently unsubstituted or substituted with 1-3 substituents that are each independently selected from the group consisting of carbonyl, oxycarbonyl, aminocarbonyl, sulfonyl, $(C_{1-10})$alkyl, halo$(C_{1-10})$alkyl, perhalo$(C_{1-10})$alkyl, $(C_{3-12})$cycloalkyl$(C_{1-10})$alkyl, hetero$(C_{3-12})$cycloalkyl $(C_{1-10})$alkyl, $(C_{4-12})$aryl$(C_{1-10})$alkyl, hetero$(C_{1-10})$aryl $(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, each unsubstituted or substituted, and any two substituents bonded to adjacent atoms of $R_{16}$ may be taken together to form a 5, 6, or 7 membered, unsubstituted or substituted, saturated, unsaturated or aromatic ring; and provided that when $R_3$ and $R_4$ are taken together to form a substituted pyrimidinyl and $R_2$ is a substituted alkyl, at least one of the substituents on $R_2$ contains one or more heteroatoms.

In some variations of the preceding embodiment, the method of preparing the compounds of the invention further includes deprotecting the intermediate of the formula

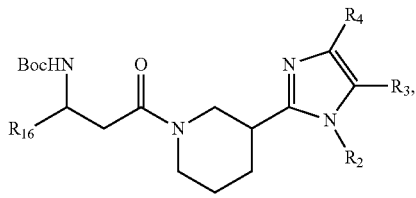

under conditions that form a compound of the formula

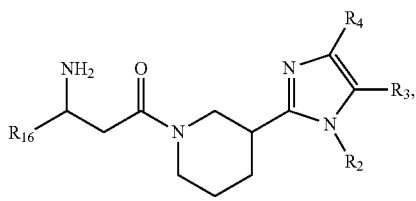

In other variations of the preceding embodiment, the method of preparing the compounds of the invention further includes:

coupling a compound of the formula

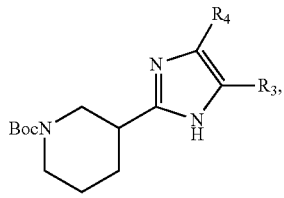

to a compound of the formula X—R₂, where X is a leaving group, under conditions that form a compound of the formula

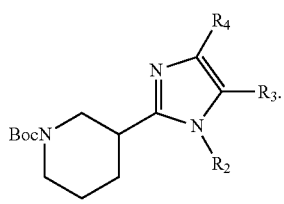

In other variations of the preceding embodiment, the method of preparing the compounds of the invention further includes coupling

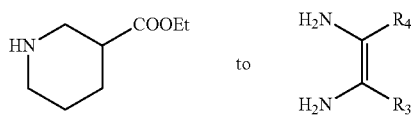

under conditions that form a compound of the formula

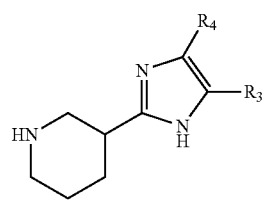

In other variations of the preceding embodiment of the method of preparing the compounds of the invention, $R_3$ and $R_4$ are taken together to form an unsubstituted or substituted phenyl.

In some particular variations of the method of preparing the compounds of the invention, $R_{16}$ is a substituted methyl selected from the group consisting of:

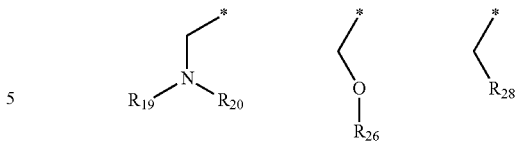

where $R_{19}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-10})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_{20}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, provided that $R_{19}$ and $R_{20}$ may be taken together to form a 5, 6, or 7 membered, unsubstituted or substituted, saturated, unsaturated or aromatic ring.

$R_{26}$ is selected from the group consisting of hydrogen, carbonyl, oxycarbonyl, aminocarbonyl, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 substituents that are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero ($C_{1-10}$)aryl, ($C_{9-12}$)bicycloaryl and hetero($C_{4-12}$)bicycloaryl, each unsubstituted or substituted with 1-3 substituents, and any two substituents bonded to adjacent atoms of $R_{26}$ may be taken together to form a 5, 6, or 7 membered, unsubstituted or substituted, saturated, unsaturated or aromatic ring;

$R_{28}$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$) alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl ($C_{1-10}$)alkyl, aza($C_{1-10}$)alkyl, ($C_{1-10}$)oxaalkyl, ($C_{1-10}$) oxoalkyl, imino($C_{1-10}$)alkyl, ($C_{3-12}$)cycloalkyl($C_{1-10}$)alkyl, hetero($C_{3-12}$)cycloalkyl($C_{1-10}$)alkyl, ($C_{4-12}$)aryl($C_{1-10}$)alkyl, hetero($C_{1-10}$)aryl($C_{1-10}$)alkyl, ($C_{9-12}$)bicycloaryl($C_{1-10}$) alkyl, hetero($C_{8-12}$)bicycloaryl($C_{1-10}$)alkyl, hetero($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each unsubstituted or substituted with 1-3 substituents.

In more particular variations of the method of preparing the compound of the invention, $R_{16}$ is a substituted methyl of the formula

where $R_{28}$ is selected from the group consisting of

each unsubstituted or substituted with 1-3 substituents that are each independently selected from the group consisting of halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$) alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl ($C_{1-10}$)alkyl, ($C_{1-10}$)azaalkyl, ($C_{1-10}$)oxaalkyl, ($C_{1-10}$) oxoalkyl, imino($C_{1-10}$)alkyl, ($C_{3-12}$)cycloalkyl($C_{1-10}$)alkyl, hetero($C_{3-12}$)cycloalkyl($C_{1-10}$)alkyl, ($C_{4-12}$)aryl($C_{1-10}$)alkyl, hetero($C_{1-10}$)aryl($C_{1-10}$)alkyl, ($C_{9-12}$)bicycloaryl($C_{1-10}$) alkyl, hetero($C_{8-17}$)bicycloaryl($C_{1-10}$)alkyl, hetero($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each unsubstituted or substituted, and any two substituents bonded to adjacent atoms of $R_{28}$ may be taken together to form a five, six or seven membered saturated, unsaturated or aromatic ring, each unsubstituted or substituted.

In some variations, $R_{28}$ is an unsubstituted or a substituted phenyl. In other variations, $R_{28}$ is a unsubstituted or substituted naphthyl of the formula

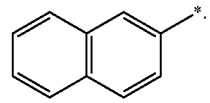

In still other variations, $R_{28}$ is selected from the group consisting of substituted six-membered aryls and heteroaryls, where the aryls and heteroaryls are substituted with 1-3 substituents, and one of said 1-3 substituents is bonded to the ring atom at the para-position relative to the point where $R^{28}$ is attached to the remainder of the molecular.

It is noted that for all the above variations, when $R_{28}$ is substituted, the substituents on $R_{28}$ are each independently selected from the group consisting of halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamide, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl ($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl ($C_{1-10}$)alkyl, hetero($C_{3-12}$)cycloalkyl($C_{1-10}$)alkyl, ($C_{4-12}$)aryl ($C_{1-10}$)alkyl, hetero($C_{1-10}$)aryl($C_{1-10}$)alkyl, ($C_{9-12}$) bicycloaryl($C_{1-10}$)alkyl, hetero($C_{8-12}$)bicycloaryl($C_{1-10}$) alkyl, hetero($C_{1-10}$)alkyl, ($C_{3-12}$)cycloalkyl, hetero($C_{3-12}$) cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero ($C_{4-12}$)bicycloaryl, each unsubstituted or further substituted, and any two substituents bonded to adjacent atoms of $R_{28}$ may be taken together to form a five, six or seven membered saturated, unsaturated or aromatic ring, each unsubstituted or substituted.

In some variation, the substituents on $R_{28}$ are each independently selected from the group consisting of halo, alkoxy, aryloxy, ($C_{1-6}$)alkyl, hydroxyalkyl, alkoxyalkyl, aryl, heteroaryl, cycloalkyl, heterocycloalkyl, hydroxycyclo($C_{3-6}$) alkyl, alkoxycyclo($C_{3-6}$)alkyl, amido, carboxamido, sulfonamide, carbamate, urea, each unsubstituted or further substituted, and any two substituents bonded to adjacent atoms of $R_{28}$ may be taken together to form a five, six or seven membered, saturated, unsaturated or aromatic ring, each unsubstituted or substituted.

In other variations, the substituents on $R_{28}$ are each independently selected from the group consisting of fluoro, chloro, bromo, tertbutyl, amino

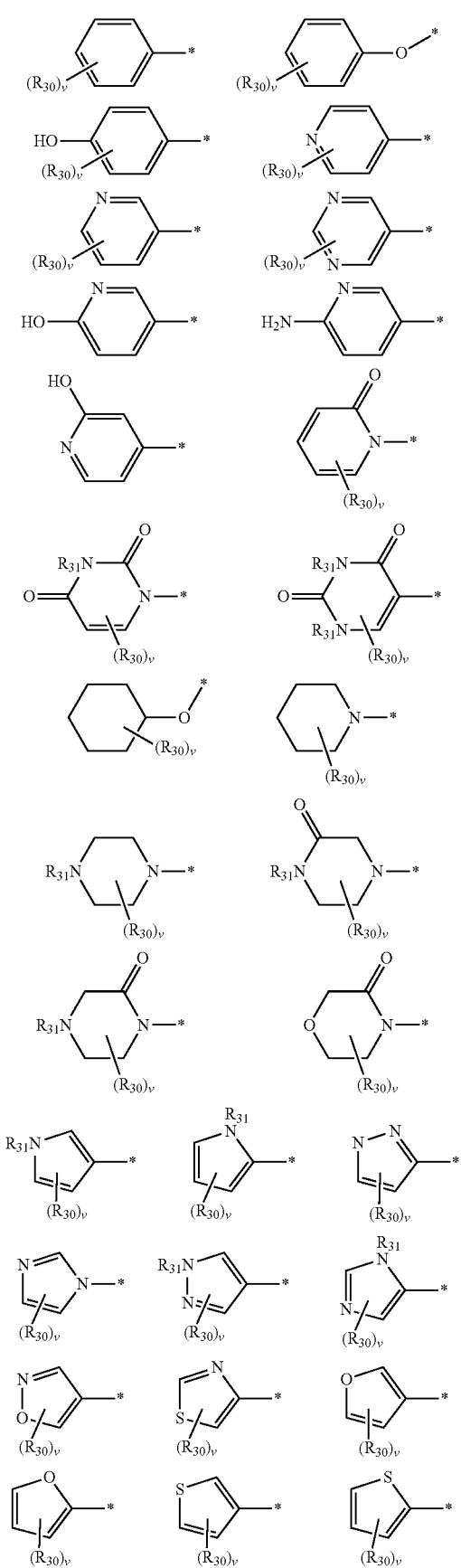
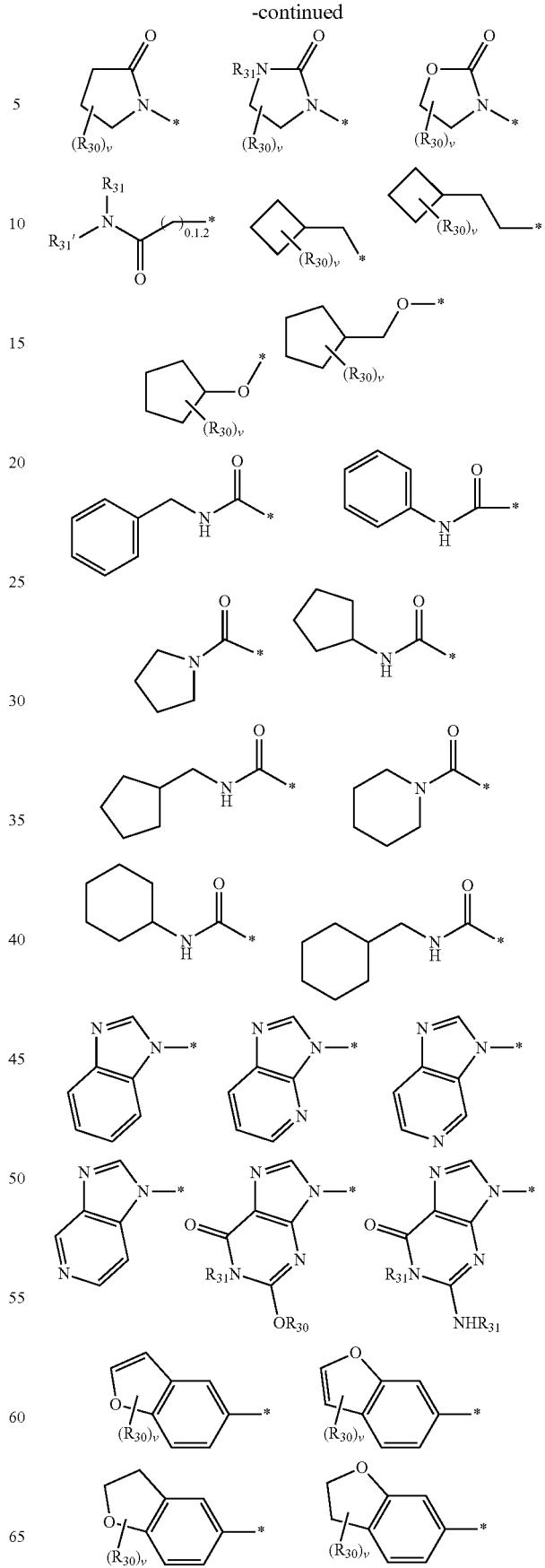

-continued

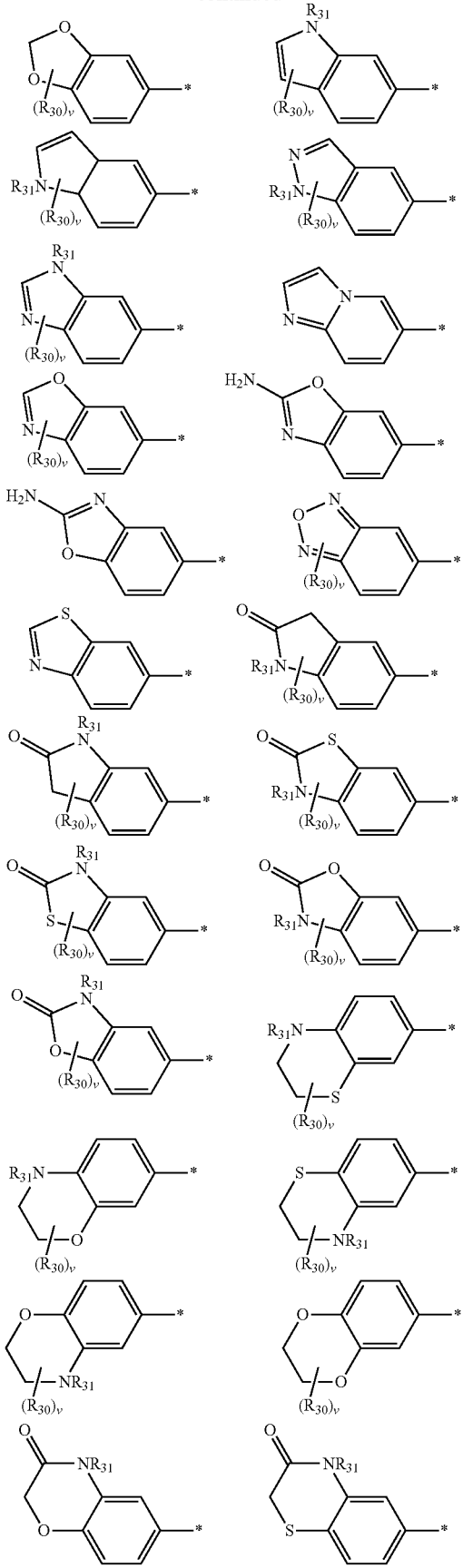
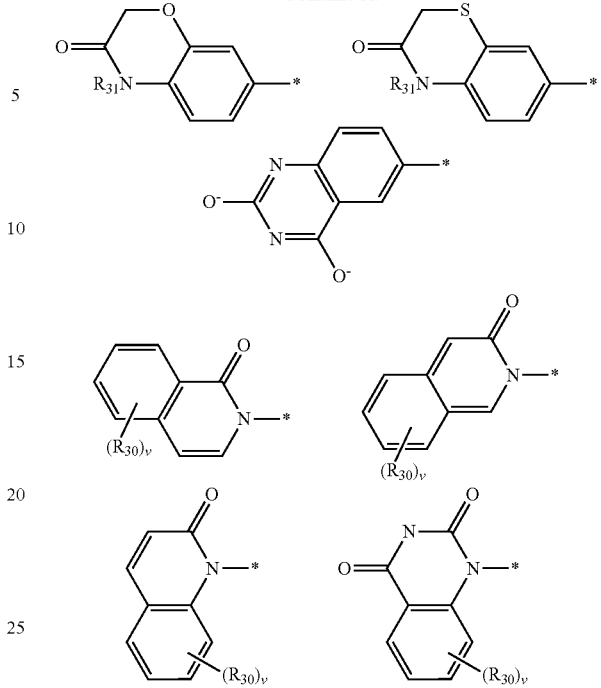

where v is 0, 1, 2 or 3;

each $R_{30}$ is independently selected from the group consisting of hydrogen, halo, hydroxyl, cyano, amino, oxo, ($C_{1-6}$) alkyl, alkylamino, alkylaminooxy, aminocarbonyl, alkoxycarbonyl, ($C_{1-6}$)alkoxy, alkoxyalkyl, heterocycloalkyl, aryl, heteroaryl, alkylsulfonyl, amidosulfonyl, aminosulfonyl, sulfonyl, amino, amido, carboxamido, carbamate, and urea, each unsubstituted or substituted, and any two of $R_{30}$ bound to adjacent ring atoms may be taken together to form a 5 or 6 membered, unsubstituted or substituted, saturated, unsaturated or aromatic ring; and each $R_{31}$ or $R_{31}'$ is independently selected from the group consisting of hydrogen, ($C_{1-6}$)alkyl, hydroxyalkyl, alkoxyalkyl, cycloalkyl, hydroxycyclo($C_{3-6}$)alkyl, alkoxycyclo ($C_{3-6}$)alkyl, each unsubstituted or substituted, and any two of $R_{30}$ and $R_{31}$ bonded to adjacent atoms and any two of $R_{31}$ and $R_{31}'$ bonded to the same atom may be taken to form a 5, 6 or 7 membered, unsubstituted or substituted, saturated, unsaturated or aromatic ring.

In still other variations, the substituents on $R_{28}$ are each independently selected from the group consisting of tertbutyl,

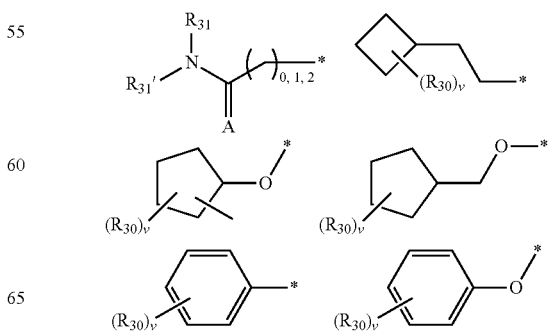

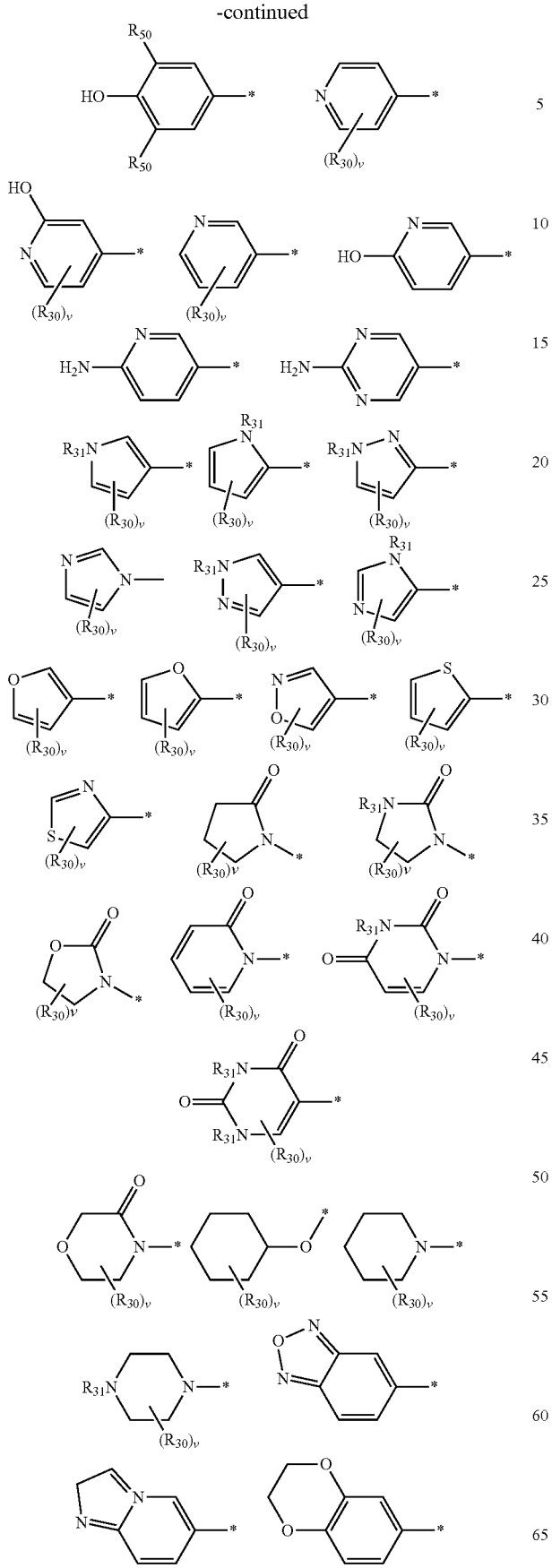
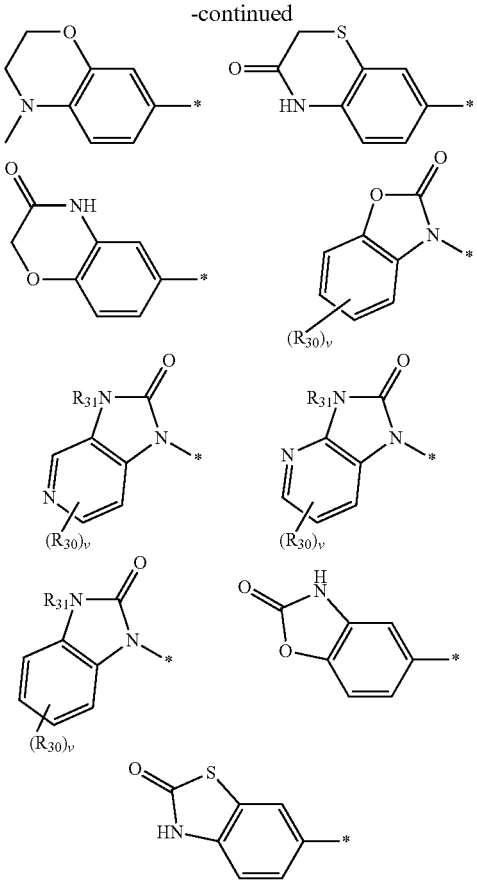

where
v is 0, 1, 2 or 3;

each $R_{30}$ is independently selected from the group consisting of hydrogen, halo, hydroxyl, cyano, amino, oxo, $(C_{1-6})$ alkyl, alkylamino, alkylaminooxy, aminocarbonyl, alkoxycarbonyl, $(C_{1-6})$alkoxy, alkoxyalkyl, heterocycloalkyl, aryl, heteroaryl, alkylsulfonyl, amidosulfonyl, aminosulfonyl, sulfonyl, amino, amino, carboxamido, carbamate, and urea, each unsubstituted or substituted, and any two $R_{30}$ bonded to adjacent ring atoms may be taken together to form a 5 or 6 membered, unsubstituted or substituted, saturated, unsaturated or aromatic ring;

each $R_{31}$ or $R_{31}'$ is independently selected from the group consisting of hydrogen, $(C_{1-6})$alkyl, hydroxyalkyl, alkoxyalkyl, cycloalkyl, hydroxycyclo$(C_{3-6})$alkyl, alkoxycyclo$(C_{3-6})$alkyl, each unsubstituted or substituted, and any two of $R_{30}$ and $R_{31}$ bonded to adjacent atoms and any two of $R_{31}$ and $R_{31}'$ bonded to the same atom may be taken to form a 5, 6 or 7 membered, unsubstituted or substituted, saturated, unsaturated or aromatic ring; and each $R_{50}$ is independently selected from the group consisting of H, methyl, methoxy, chloro, and fluoro.

In still other variations, the substituents on $R_{28}$ are each independently selected from the group consisting of tertbutyl,

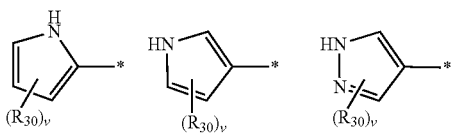

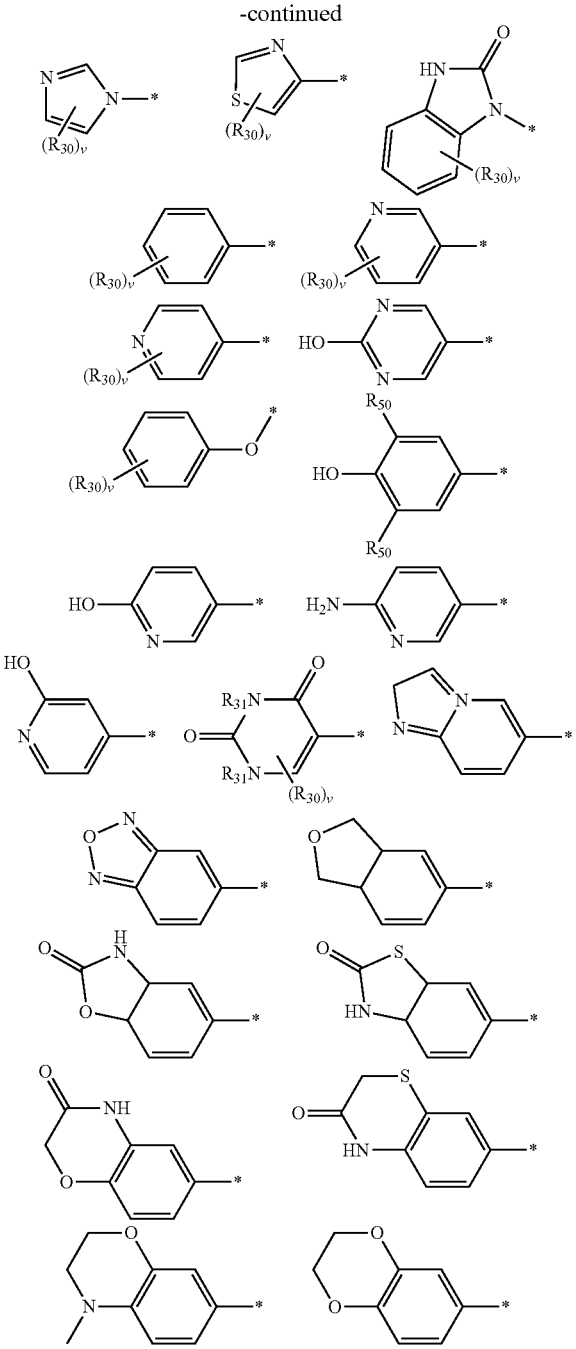

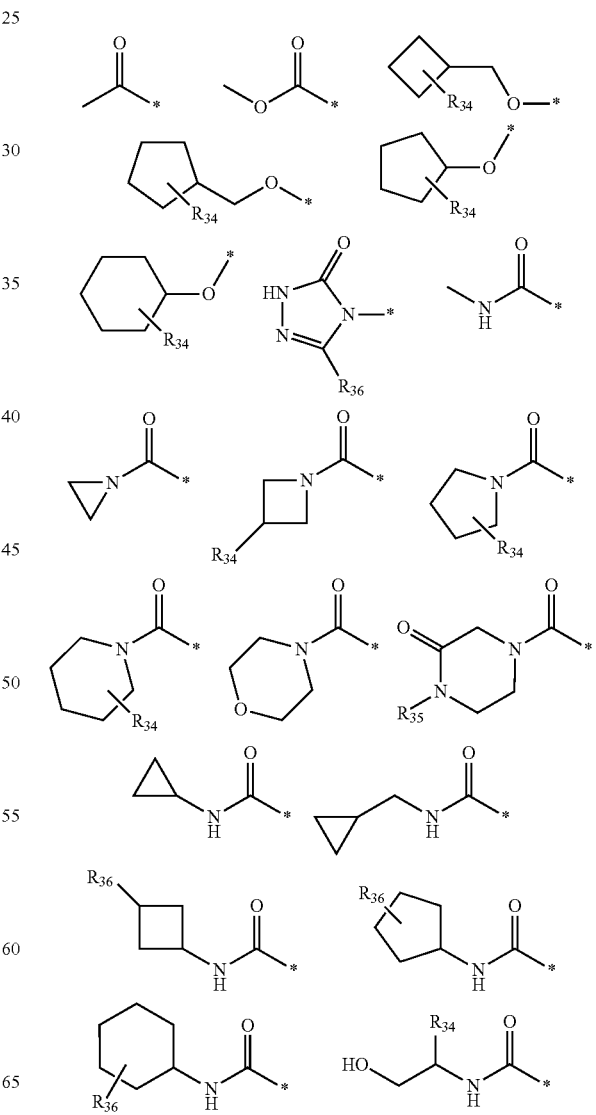

where v is 0, 1, 2 or 3;

each $R_{30}$ is independently selected from the group consisting of hydrogen, halo, cyano, amino, oxo, $(C_{1-6})$alkyl, alkylamino, alkylaminooxy, aminocarbonyl, alkoxycarbonyl, $(C_{1-6})$alkyl, alkoxyalkyl, heterocycloalkyl, aryl, heteroaryl, alkylsulfonyl, amidosulfonyl, aminosulfonyl, sulfonyl, amino, amido, carboxamido, carbamate, and urea, each unsubstituted or substituted, and any two $R_{30}$ bonded to adjacent ring atoms may be taken together to form a 5 or 6 membered, unsubstituted or substituted, saturated, unsaturated or aromatic ring;

each $R_{31}$ is independently selected from the group consisting of hydrogen, $(C_{1-6})$alkyl, hydroxyalkyl, alkoxyalkyl, cycloalkyl, hydroxycyclo$(C_{3-6})$alkyl, alkoxycyclo$(C_{3-6})$alkyl, each unsubstituted or substituted, and any two of $R_{30}$ and $R_{31}$ bonded to adjacent ring atoms may be taken together to form a 5 or 6 membered, unsubstituted or substituted, saturated, unsaturated or aromatic ring; and each $R_{50}$ is independently selected from the group consisting of H, methyl, methoxy, chloro, and fluoro.

In some variations of the preceding variations of the method of preparing compounds of the invention, $R_{30}$ is selected from the group consisting of hydrogen, halo, hydroxyl, cyano, oxo, $(C_{1-6})$alkyl, —NHC(O)CH$_3$, alkylsulfonyl, amino, —C(O)NH—$(C_{1-6})$alkyl, —C(O)NH—$(C_{1-6})$alkyl$(C_{1-6})$alkoxy, $(C_{1-6})$alkoxy, hydroxy$(C_{1-6})$alkylamino, $(C_{1-6})$alkoxy$(C_{1-6})$alkyl, and —NH—$(C_{1-6})$alkyl, heterocycloalkylacyl, amido, carboxamido, phenyl, and $(C_{1-4})$heteroaryl.

In other variations, $R_{30}$ is selected from the group consisting of hydrogen, hydroxyl, halo, hydroxyl, cyano, oxo, $(C_{1-6})$alkyl, hydroxy$(C_{1-6})$alkyl, phenyl, $(C_{1-6})$alkoxy$(C_{1-6})$alkyl, amino, sulfonyl, $(C_{1-6})$alkoxy, $(C_{1-6})$alkylsulfonyl, morpholinyl,

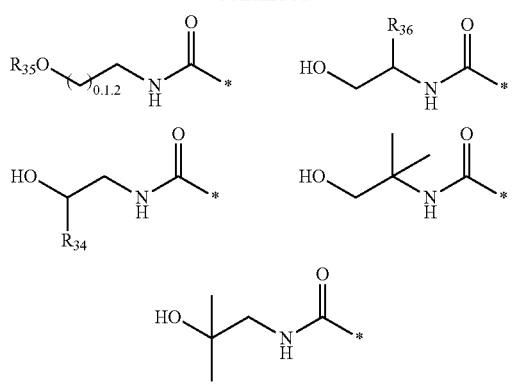

wherein

R$_{34}$ is selected from the group consisting of hydrogen, hydroxyl, halo, and hydroxymethyl;

R$_{35}$ is selected from the group consisting of hydrogen and unsubstituted or substituted (C$_{1-6}$)alkyl;

R$_{36}$ is selected from the group consisting of hydroxyl, unsubstituted or substituted (C$_{1-6}$)alkyl; and R$_{37}$ is selected from the group consisting of hydrogen, (C$_{1-6}$)alkyl, cycloalkyl, hydroxy(C$_{1-6}$)alkyl, alkoxy(C$_{1-6}$)alkyl, hydroxycyloalkyl, alkoxycycloalkyl, halo(C$_{1-6}$)alkyl, and halocycloalkyl, each unsubstituted or substituted.

In still other variations, R$_{30}$ is selected from the group consisting hydrogen, hydroxyl, fluoro, chloro, cyano, oxo, methyl, propyl, isopropyl, tertbutyl, phenyl, hydroxyethyl, methoxymethyl, methoxyethyl, ethoxypropyl, —NH$_2$, —N(CH$_3$)$_2$, —NH(CH$_3$), cyclopropylamino, methoxy, ethoxy, isopropyloxy, cyclopropylmethyloxy, methylsulfonyl, morpholinyl,

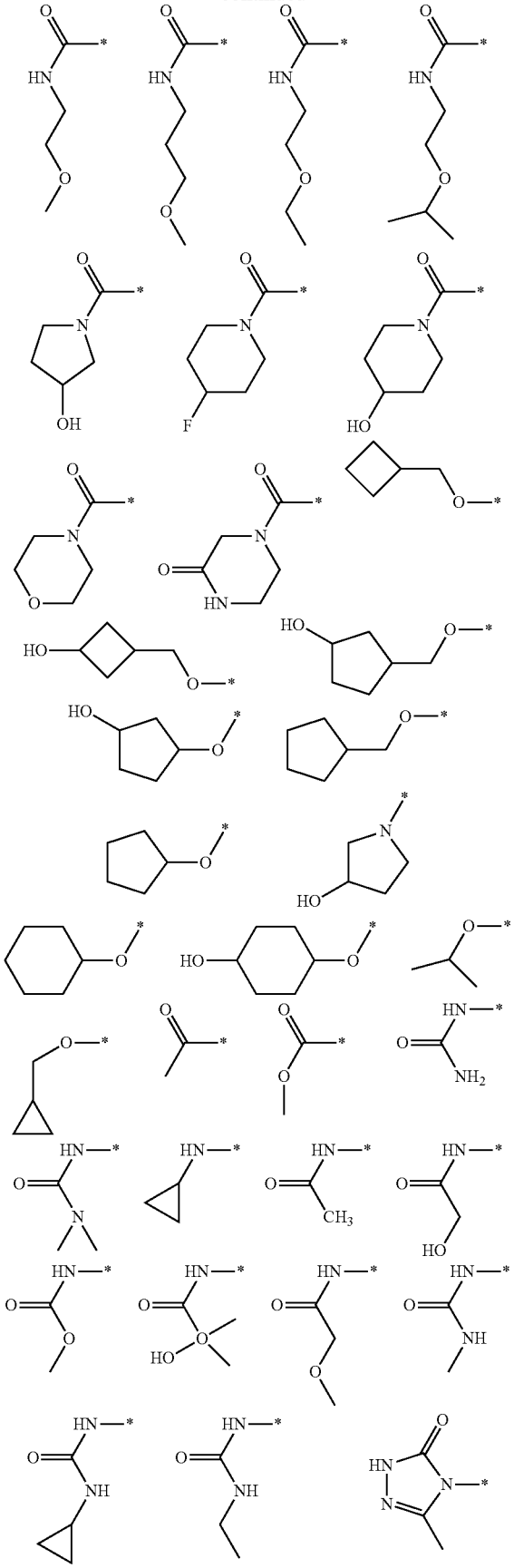

-continued

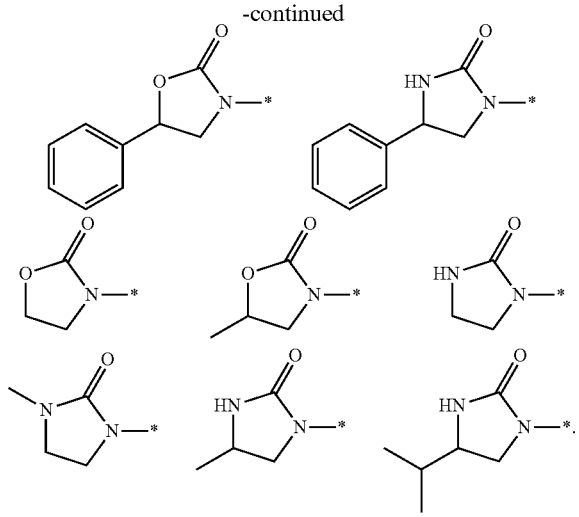

In still further variations, $R_{30}$ is selected from the group consisting hydrogen, hydroxyl, fluoro, chloro, cyano, oxo, methyl, n-propyl, isopropyl, tertbutyl, hydroxyethyl, methoxymethyl, methoxyethyl, —$NH_2$, —$N(CH_3)_2$, methoxy, ethoxy, isopropyloxy, methylsulfonyl, morpholinyl,

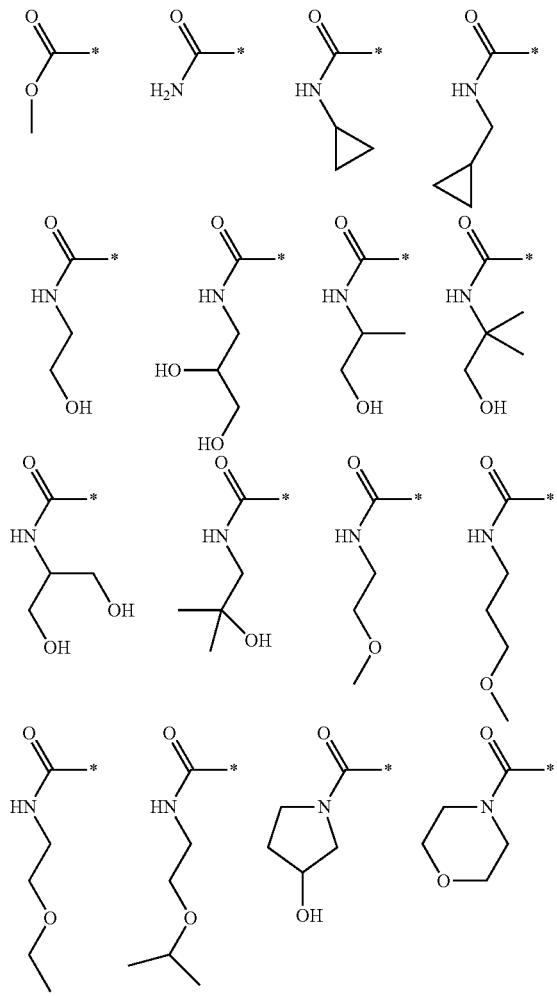

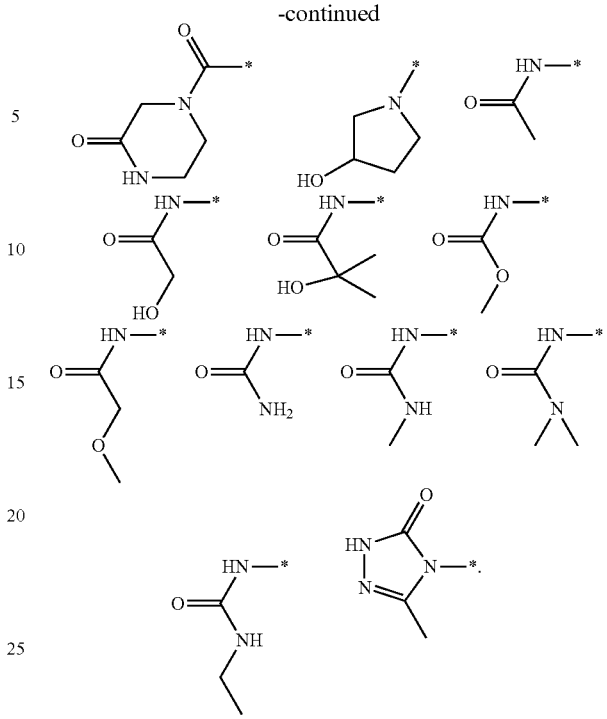

In some variations of the method of preparing the compounds of the invention, $R_{31}$ is selected from the group consisting of hydrogen, hydroxyl, and unsubstituted or substituted $(C_{1-6})$alkyl.

Salts, Hydrates, and Prodrugs of Renin Inhibitors

It should be recognized that the compounds of the present invention may be present and optionally administered in the form of salts, hydrates and prodrugs that are converted in vivo into the compounds of the present invention.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

It is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as $(C_{1-4})$ alkyl halides, e.g., methyl, ethyl, iso-propyl and tert-butyl chlorides, bromides and iodides; di$(C_{1-4})$ alkyl sulfates, e.g., dimethyl, diethyl and diamyl sulfates; $(C_{10-18})$ alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water-soluble and oil-soluble compounds of the present invention.

Compounds of the invention further include prodrug derivatives of the compounds. It is noted that in many instances, the prodrugs themselves also fall within the scope of the range of compounds according to the present invention.

Various forms of prodrugs are well known in the art. For examples of such prodrug derivatives, see, e.g., a) Design of Prodrugs, Bundgaard, A. Ed., Elsevier, 1985 and Method in Enzymology, Widder, K. et al., Ed.; Academic, 1985, vol. 42, p. 309-396;

b) Bundgaard, H. "Design and Application of Prodrugs" in A Textbook of Drug Design and Development, Krosgaard-Larsen and H. Bundgaard, Ed., 1991, Chapter 5, p. 113-191; and c) Bundgaard, H., Advanced Drug Delivery Review, 1992, 8, 1-38.

Each of which is incorporated herein by reference.

Pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Indications for Use of Renin Inhibitors

Renin inhibitors of the present invention may be used to treat and/or prevent high blood pressure, cardiovascular diseases, congestive heart failure, myocardial infarction, renal protection, inflammation, neurological disease and cancer.

Renin is a proteolytic enzyme synthesized and stored principally in the juxtaglomerular apparatus. When renin is released into the blood from the kidney, the renin-angiotensin-aldosterone system ("RAAS") is activated. Renin acts on the alpha-2 globulin angiotensinogen (synthesized in the liver) to generate angiotensin I. This non-pressor decapeptide is converted to angiotensin II by angiotensin-converting enzyme (ACE). The major pharmacological effects of angiotensin II are vasoconstriction and stimulation of the adrenal cortex to release aldosterone, a hormone which causes sodium retention. Vasoconstriction and conservation of sodium both contribute to increased blood pressure. Angiotensin II also produces other physiological effects such as inhibiting renin secretion, increasing sympathetic nervous system activity, stimulating vasopressin secretion, causing a positive cardiac inotropic effect and modulating other hormonal systems. Thus, the renin-angiotensin system plays an important role in normal cardiovascular homeostasis and in some forms of elevated blood pressure (hypertension).

The reduction of the activity of renin in a subject through inhibition may therefore be used to therapeutically address the diseases and conditions caused by the overactivation of RAAS.

Thus, renin inhibiting compounds of the present invention may be used as agents for control of hypertension, may also be used to treat and/or prevent congestive heart failure and hyperaldosteronism, vascular diseases related to diabetes, and renal diseases such as acute or chronic renal failure. In addition, the renin inhibiting compounds may also be used as diagnostic agents for identification of cases of hypertension due to renin excess.

It is noted that the compounds of the present invention may also possess inhibitory activity for other aspartyl proteases (e.g., pepsin, gastricsin, napsin, BACE 1 & 2 and cathepsin D and E) and thus may be used to address disease states associated with these other family members.

In addition, the compounds of the present invention may be useful as inhibitors of plasmepsins to treat malaria and as inhibitors of *Candida albicans* secreted aspartyl proteases to treat fungal infections.

It is further noted that additional diseases beyond those disclosed herein may also be identified as the biological roles that renin and the RAAS system play in various pathways become more fully understood.

Combination Therapy

A wide variety of therapeutic agents may have a therapeutic additive or synergistic effect when used in combination with renin inhibitors according to the present invention. Such therapeutic agents may additively or synergistically combine with the renin inhibitors to reduce or alleviate the effects and symptoms of cardiovascular disease.

The compounds according to the present invention may be used in combination with other therapeutic agents, wherein the cells are treated with a compound according to the present invention before, at the same time, and/or after the cells are treated with the one or more additional cardiovascular therapeutics; these treatments are referred to herein as combination therapy. It is noted that administration of one agent before another is referred to herein as sequential therapy, even if the agents are also administered together. It is noted that combination therapy is intended to cover methods where agents are administered before or after each other (sequential therapy) as well as when the agents are administered at the same time.

Representative classes of cardiovascular agents that may be used with the renin inhibitors of the present invention include, but are not limited to, diuretics, adrenergic blocking agents, vasodilators, calcium channel blockers, angiotensin converting enzyme (ACE) inhibitors, potassium channel activators, antiserotoninergic agents, thromboxane synthetase inhibitors, angiotensin II antagonists, angiotensin II receptor blockers, and other agents useful for treating (in a human or other mammal) hypertension, congestive heart failure, or vascular diseases related to diabetes, or for treating renal diseases such as acute or chronic renal failure.

Representative diuretics include hydrochlorothiazide, polythiazide, piretanide, torasemide, bumetanide, amiloride, chlorothiazide, indapamide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, albuterol, nadolol, propranolol, timolol, carteolol and the like or a pharmaceutically acceptable salt thereof.

Representative vasodilators include hydralazine, minoxidil, diazoxide, nitroprusside, flusequinan and the like or a pharmaceutically acceptable salt thereof.

Representative calcium channel blockers include aminone, bencyclane, diltiazem, fendiline, flunarizine, nicardipine, nimodipine, perhexylene, verapamil, gallopamil, nifedipine and the like or a pharmaceutically acceptable salt thereof.

Representative ACE inhibitors include ramipril, aptopril, enalapril, lisinopril, fosinopril, captopril and the like or a pharmaceutically acceptable salt thereof.

Representative potassium channel activators include pinacidil, glibenclamide, glimepiride, diaoxide, cromocalim, and the like or a pharmaceutically acceptable salt thereof.

Representative antiserotoninergic agents include ketanserin and the like or a pharmaceutically acceptable salt thereof.

Representative angiotensin II antagonists include DUP527 and the like or a pharmaceutically acceptable salt thereof.

Representative angiotensin II receptor blockers (angiotensin II receptor antagonists (ARBs)) include losartan, irbesartan, valsartan, omapatrilat, gemopatrilat and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

Dosage, Host and Safety

The compounds of the present invention are stable and can be used safely. In particular, the compounds of the present invention are useful as renin inhibitors for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Compositions Comprising Renin Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The renin inhibitors and compositions comprising them may be administered or coadministered in any conventional dosage form. Co-administration in the context of this invention is intended to mean the administration of more than one therapeutic agent, one of which includes a renin inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerin, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of an inhibitor of the present invention to reduce renin activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more renin inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

A. Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain variation of the above embodiments and variations, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, *lycopodium* and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

B. Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the renin inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The renin inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral Ph. Then, a renin inhibitor is added to the resulting mixture, preferably above room temperature, more preferably at about 30-35 Oc, and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

D. Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The renin inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a Lnicrofine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the renin inhibitor alone or in combination with other pharmaceutically acceptable excipients can also be administered.

E. Formulations for Other Routes of Administrations

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
| --- | --- |
| Compound of the Present Invention | 10-100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of the Present Invention | 1% |
| Microcrystalline Cellulose | 73% |
| Stearic Acid | 25% |
| Colloidal Silica | 1%. |

Kits Comprising Renin Inhibitors

The invention is also directed to kits and other articles of manufacture for treating diseases associated with renin. It is noted that diseases are intended to cover all conditions for which the renin possess activity that contributes to the pathology and/or symptomology of the condition.

In one variation of the above embodiments and variations, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another variation of the above embodiments and variations, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific variation of the above embodiments and variations of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Preparation and Assaying of Renin Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet and Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art. For example, appropriate prodrugs can be prepared by reacting a non-derivatized compound with a suitable carbamylating agent (e.g., 1,1-acyloxyalkylcarbonochloridate, para-nitrophenyl carbonate, or the like) or an acylating agent. Further examples of methods of making prodrugs are described in Saulnier et al. Bioorganic and Medicinal Chemistry Letters, 1994, Vol. 4, p. 1985. Those of ordinary skill in the art have the knowledge and means to accomplish this without undue experimentation.

Protected derivatives of the compounds can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

Compounds according to the present invention may be conveniently prepared or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet and Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or thee-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl)
atm (atmosphere)
ATP (adenosine triphphatase)
Boc (tert-butyloxycarbonyl)
BOP (bis(2-oxo-3-oxazolidinyl)phosphinic chloride)
Brij35 (polyoxyethyleneglycol dodecyl ether)
BSA (bovine serum albumin)
CBZ (benzyloxycarbonyl)
CDI (1,1-carbonyldiimidazole)
DCC (dicyclohexylcarbodiimide)
DCE (dichloroethane)
DCM (dichloromethane)
DIEA (di-isopropylethylamine)
DMAP (4-dimethylaminopyridine)
DME (1,2-dimethoxyethane)
DMF (N,N-dimethylformamide)
DMPU (N,N'-dimethylpropyleneurea)
DMSO (dimethylsulfoxide)
DTT (dithiothreitol)
EDCI (ethylcarbodiimide hydrochloride)
EDTA (ethylenediaminetetraacetic acid)
Et (ethyl)
$Et_2O$ (diethyl ether)
EtOAc (ethyl acetate)
FMOC (9-fluorenylmethoxycarbonyl)
g (grams)
hrs (hours)
HATU (2-(7-aza-1H-benzotriazole-1-yl)-1,1,3,3-tetramethyluronium hexafluorophosphate)
HOAc or AcOH (acetic acid)
HOBT (1-hydroxybenzotriazole)
HOSu (N-hydroxysuccinimide)
HPLC (high performance liquid chromatography)
Hz (hertz)
IBCF (isobutyl chloroformate)
i.v. (intravenous)
i-PrOH (isopropanol)
L (liters)
LAH (lithium aluminium hydride)
M (molar)
mCPBA (meta-chloroperbenzoic acid)
Me (methyl)
MeOH (methanol)
mg (milligrams)
MHz (megahertz)
µL (microliters)
mL (milliliters)
mM (millimolar)
min (minutes)
mmol (millimoles)
mol (moles)
MOMCl (methoxymethyl chloride)
MOPS (morpholinepropanesulfonic acid)
mp (melting point)
NaOAc (sodium acetate)
$NEt_3$ (triethylamine)
OMe (methoxy)

OTf (O-triflate)
OMs (O-mesylate)
Pd(dppf)Cl$_2$ (bis(diphenyl phosphino)ferrocene dichloro palladium (II)
psi (pounds per square inch)
RP (reverse phase)
rt (ambient temperature)
SPA (scintillation proximity assay)
TBAF (tetra-n-butylammonium fluoride)
TBDMS (tert-butyldimethylsilyl)
TBS (t-butyldimethylsilyl)
tBu (tert-butyl)
TEA (triethylamine)
TFA (trifluoroacetic acid)
TFAA (trifluoroacetic anhydride)
THF (tetrahydrofuran)
TIPS (triisopropylsilyl)
TLC (thin layer chromatography)
TMS (trimethylsilyl)
TMSE (2-(trimethylsilyl)ethyl)
TMSI (trimethylsilyliodide)
RT (retention time)

All references to ether or Et$_2$O are to diethyl ether; and brine refers to a saturated aqueous solution of NaCl. Unless otherwise indicated, all temperatures are expressed in ° C. (degrees Centigrade). All reactions are conducted under an inert atmosphere at rt unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad). When two rotomers are observed, the combined NMR spectra are presented.

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60° F.-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

The entire disclosures of all documents cited throughout this application are incorporated herein by reference.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991.

General synthetic routes for producing compounds of the present invention are shown in the schemes below. The various substituents may be selected from among the various substituents otherwise taught herein.

In each of the above reaction procedures or schemes, the various substituents may be selected from among the various substituents otherwise taught herein.

A. General Synthetic Route I

The imidazol-2-ylpiperidine analogs can be synthesized according to Scheme 1. Condensation of the piperidine-3-carboxylate (1a) with diamine compounds 1b (e.g., aromatic diamines and heterocyclic diamines, such as o-phenylenediamine) in acidic medium, e.g., aqueous HCl, at elevated temperature gives intermediate 1c. Protection of the free amine group of 1c with Boc anhydride (1d) yields the imidazole intermediate 1e, which can be alkylated with alkyl halide compound 1f in the presence of a base such as NaH to give 1g. Removal of N-Boc group in acid conditions such as TFA in DCM or HCl in dioxane affords key piperidine intermediate 1h. Deravitization of the amine group of 1h with reagent such as isocyanate 1n to give renin inhibitor 1r, or with acid or protected amino acid 1i to give, after proper deprotection if needed, the renin inhibitor 1m.

Scheme 1.

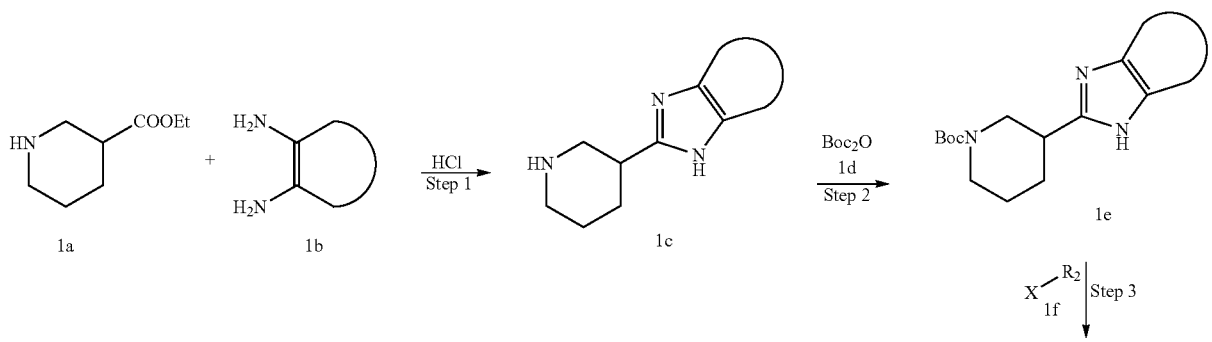

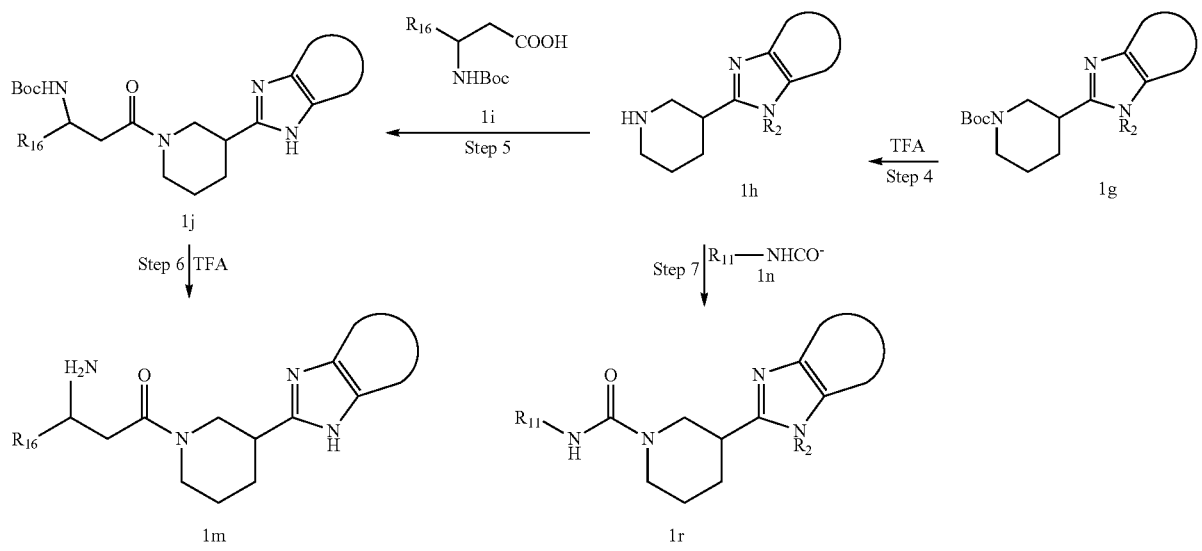

where X is a leaving group

B. General Synthetic Route II

Imidazol-2-ylpiperidine analogs 2m can also be synthesized according to the synthetic route shown in Scheme 2. Coupling of piperidine-3-carboxylic acid (2a) with diamine compounds 2b such as benzene-1,2-diamine with peptide coupling reagent such as EDCI in DCM or DMF gives intermediate 2c. Cyclization of 2c in the presence of acid such as acetic acid with heating (generally 40 to 120° C.) produces 2d, which can be alkylated with 2e in the presence of a base such as NaH to give 2f. Removal of N-Boc group in acid conditions such as TFA in DCM affords key piperidine intermediate 2h; Derivatization of the amine group of 2h with reagent such as isocyanate 2n to give renin inhibitor 2r, or with acid or protected amino acid 2i, after proper deprotection if needed, gives the final renin inhibitor 2m.

Scheme 2.

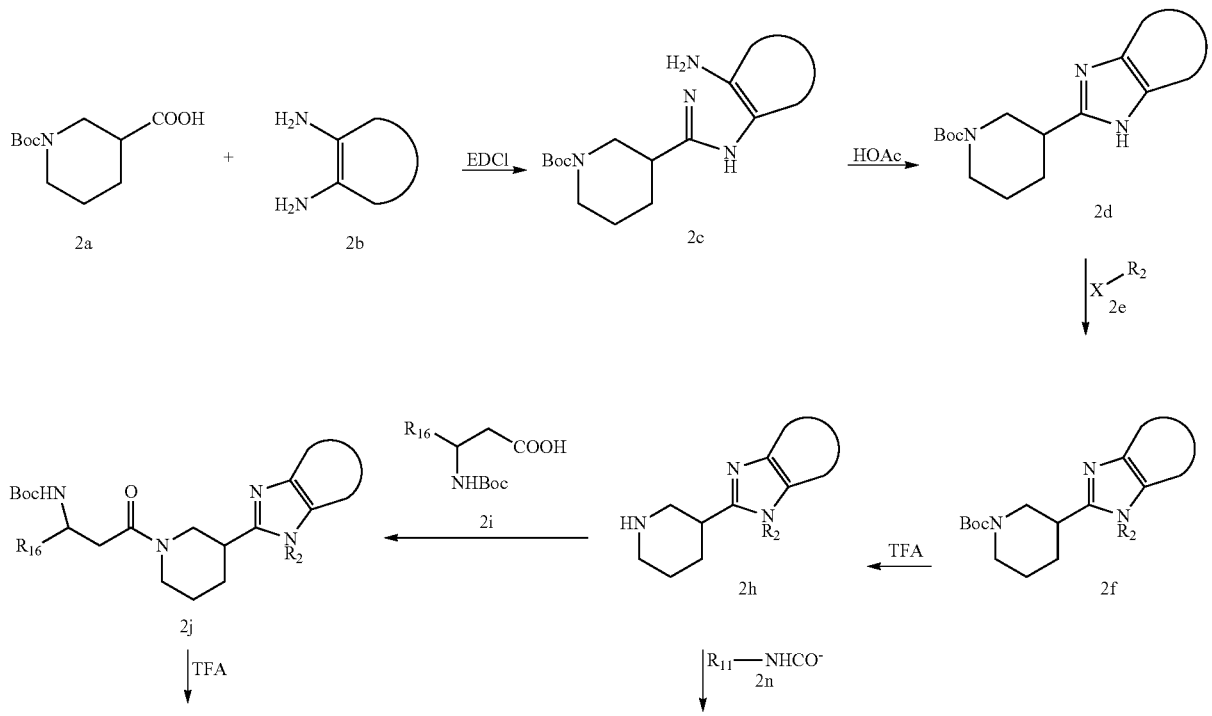

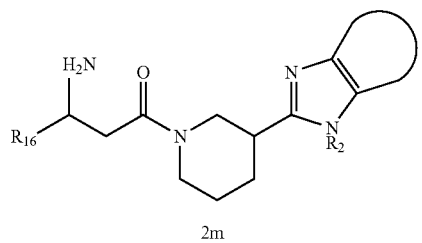

2m where X is a leaving group

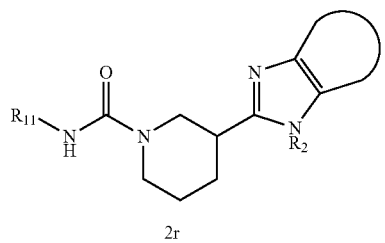

2r

C. General Synthetic Route III

Alternatively, the renin inhibitors 3m may be synthesized as shown in Scheme 3. Amine 3a may be reacted with ortho-halo-nitro compound 3b (such as 2-F or 2-Cl nitrobenzenes) via SNAr reaction to give intermediate 3c. Reduction of nitro to amine by palladium catalysized hydrogenation or metal reduction (such as by Tin(II) chloride), followed by amide coupling with 3d yields 3e. Upon heating 3e in the presence dehydrating agent such as acetic acid gives key intermediate 3f. Deprotection and then derivatization of the amine with the appropriate reagents such as isocyanate 3n, acid or protected amino acids 3l according to Scheme 1 yield product 3r or 3m, respectively.

D. General Synthetic Route IV

The inhibitors of the invention may be prepared in a synthetic route shown in Scheme 4. The N-protected piperidine-3-aldehyde (4a) may be prepared from its corresponding ester $4a^0$ through direct reduction with MAL in THF at low temperature (e.g. −78° C.). Alternately, 4a may be pprepared from the oxidation of alcohol $4a^1$ in pyridine sulfur trioxide. Reaction of aldehyde 4a with diamine 4b, in the presence of an oxidizing agent such as Oxone® 14 or air, gives 4c, which upon deprotection gives the piperidine intermediate 4d. Deprotection and then derivatization of the amine with the appropriate reagent 4i and 4n according to Scheme 1, Steps 4-7, yield products 4m and 4r, respectively.

Scheme 3.

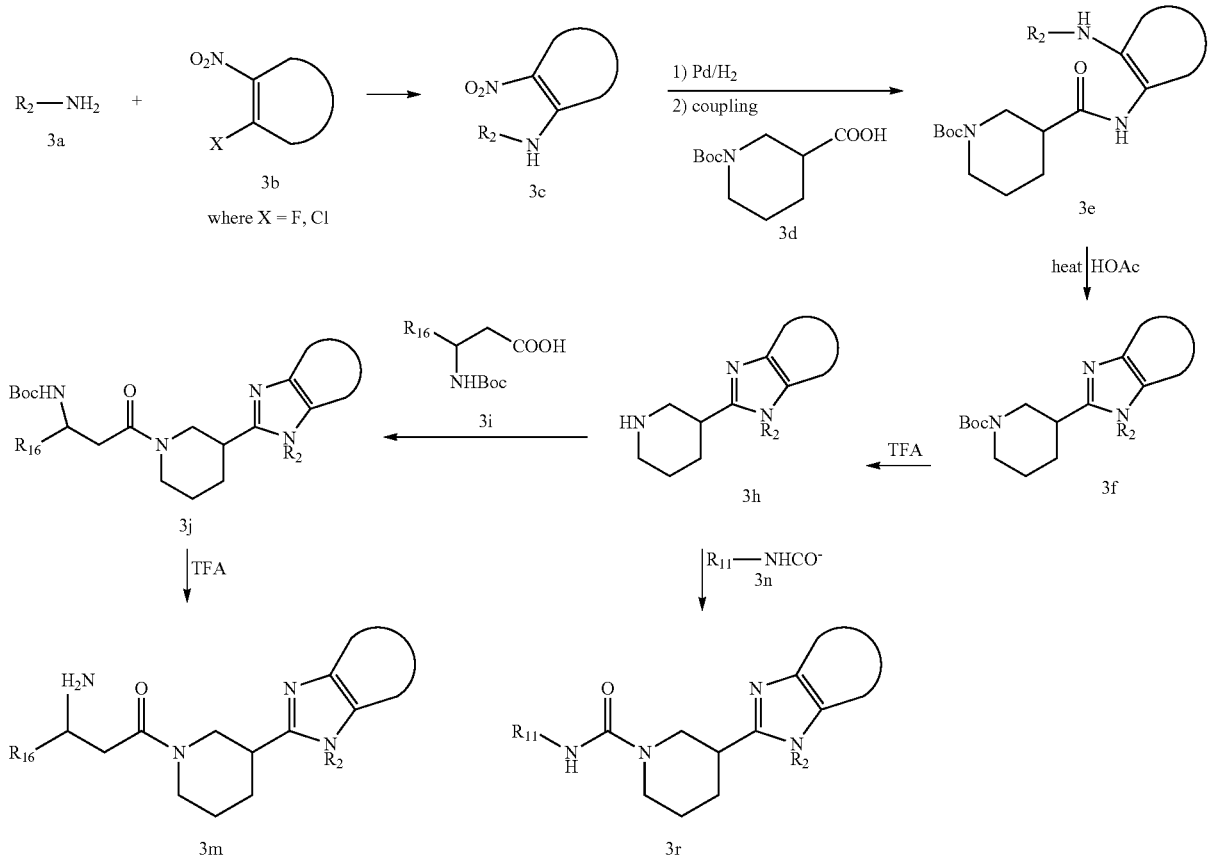

Scheme 4.

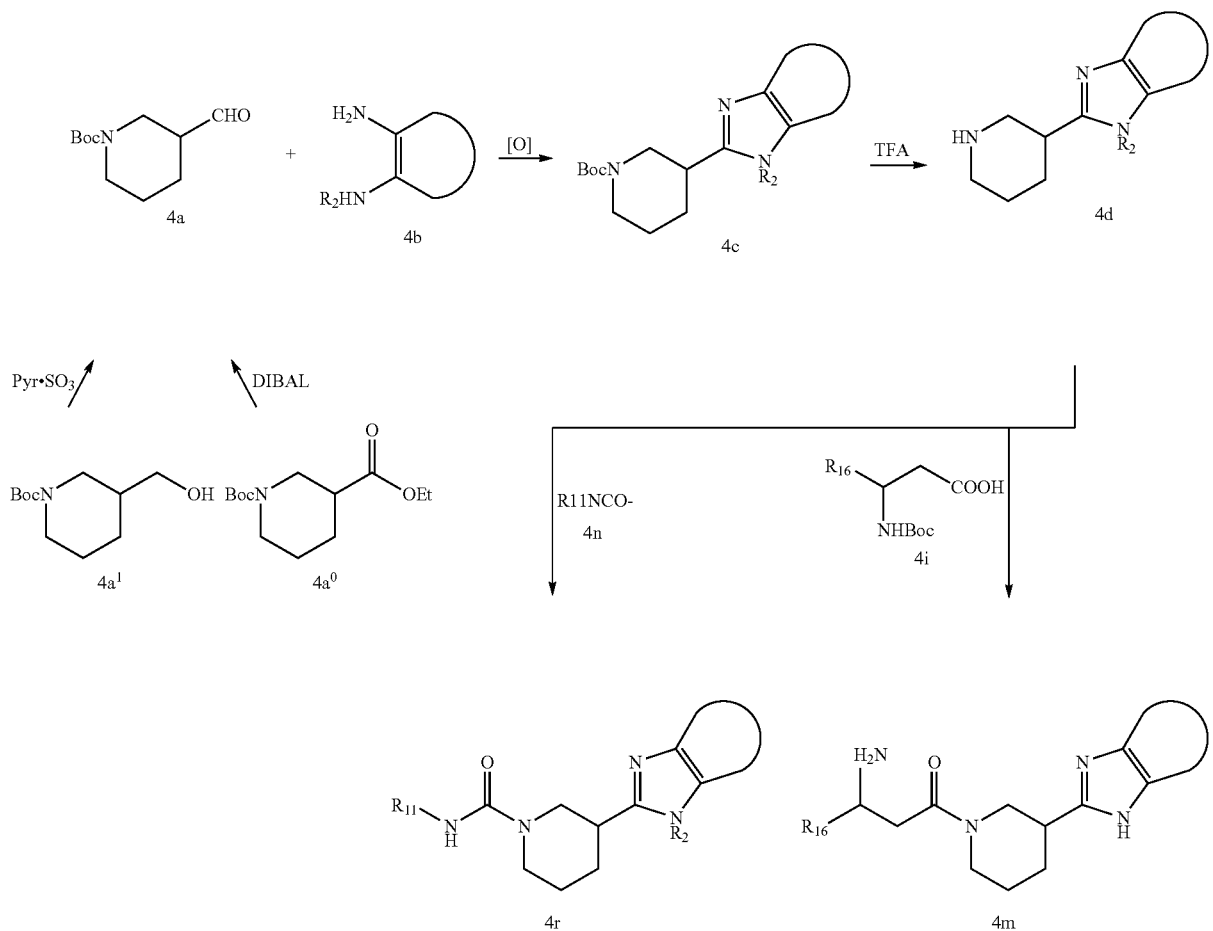

E. General Synthetic Route V

Renin inhibitors having an imidazole ring fused to a saturated or unsaturated cyclic or heterocyclic ring may be synthesized via Scheme 5. Coupling of the N-protected piperidine-3-carboxylic acid (5a) with a saturated or unsaturated cyclic or heterocyclic diamine 5b using EDCI or other amide/peptide coupling reagents gives 5c, which upon heating with acetic acid or other acids to give the dihydro-imidazole intermediate 5d. Alkylation with 5e followed with oxidation with oxygen (air) or other oxidation agents such Oxone®14, DDQ, etc. gives the aromatized N—$R_2$ cyclic imidazole 5f. Deprotection and then derivatization of the amine with 5l or 5n according to Scheme 1, Steps 4-7 yield products 5m or 5r, respectively, in good yields.

Scheme 5.

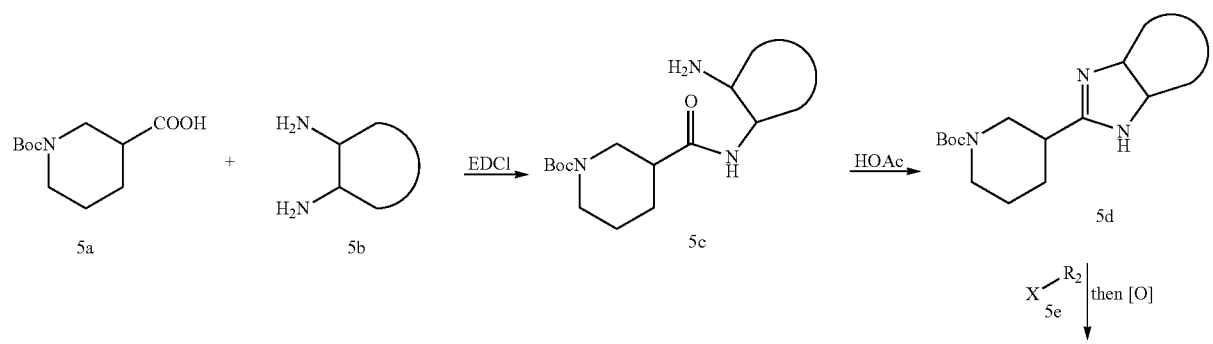

-continued

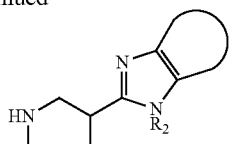
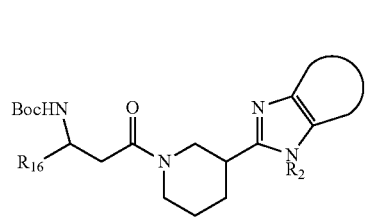
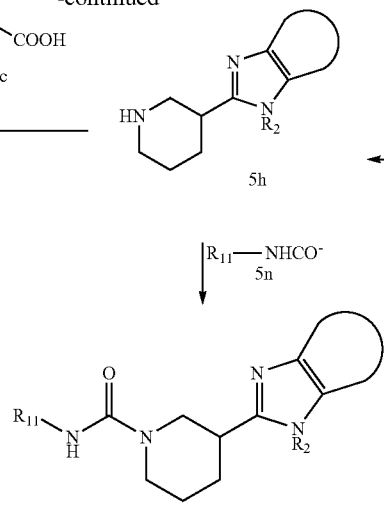
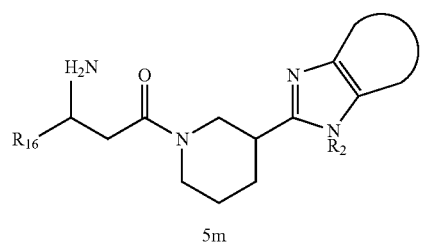

F. General Synthetic Route VI

Alpha-hydroxy imidazol-2-ylpiperidine analogs 61 may be synthesized according to Scheme 6. The n-alkylated imidazole 6c (a benzimidazole is shown) is deprotonated with a base such as BuLi in THF at low temperature (−78° C. to RT), and further reaction with N-protected piperidin-3-one (6d) affords the hydroxyl intermediate 6e. Deprotection of the N-Boc group in acid conditions such as TFA in DCM affords the piperidine intermediate 6f. The hydroxyl group may be protected with protecting groups such as trimethylsilyl; then the amine group may be derivatized with 6g and deprotected according to Scheme 1, Steps 5-6 to afford hydroxyl renin inhibitor 6i.

G. General Synthetic Route VII

Alpha carboxylate and alpha-hydroxymethyl renin inhibitors 7m and 7n respectively, can be synthesized according to Scheme 7. Palladium mediated reaction of N-protected piperidine-3-carboxylate (7a) with 2-halo or sulfonate analog 7b gives 7c. Reduction of carboxylate with LAH or DIBAL in THF at temperature ranging from −78° C. to 70° C. and protection with groups such as diphenylmethylsilyl chloride affords the hydroxymethyl analog 7d, 7c and 7d can be easily converted to final renin inhibitors 7m and 7n respectively, following procedures described in Scheme 1, Steps 4-6.

Scheme 6

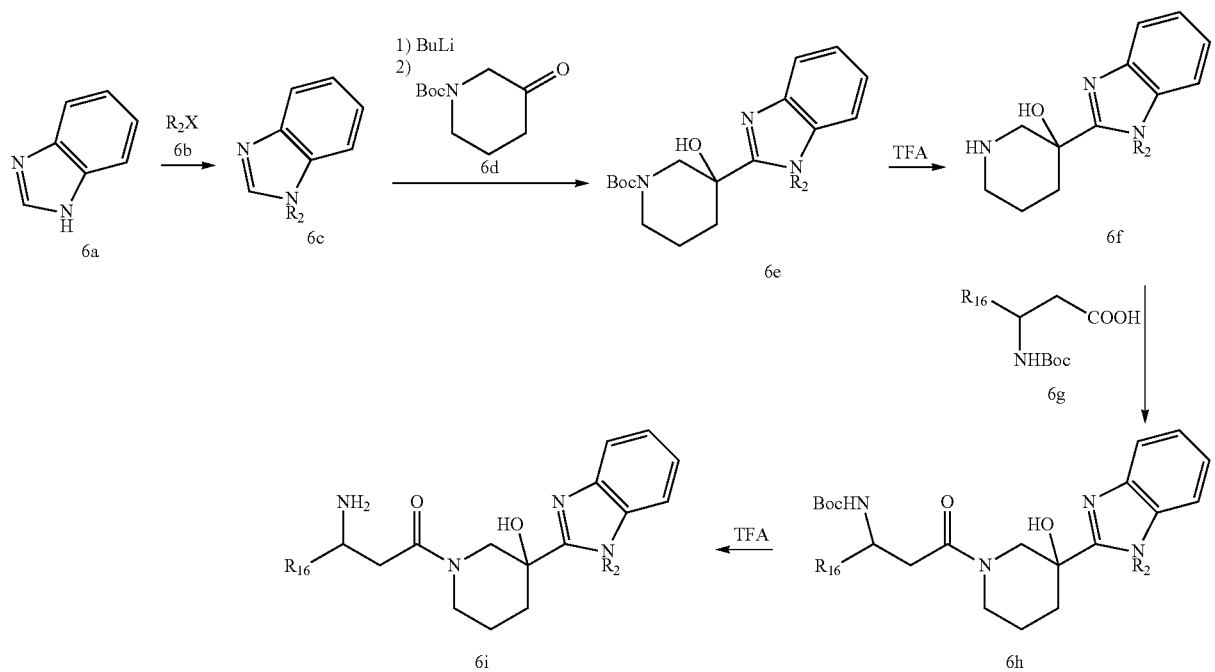

Scheme 7

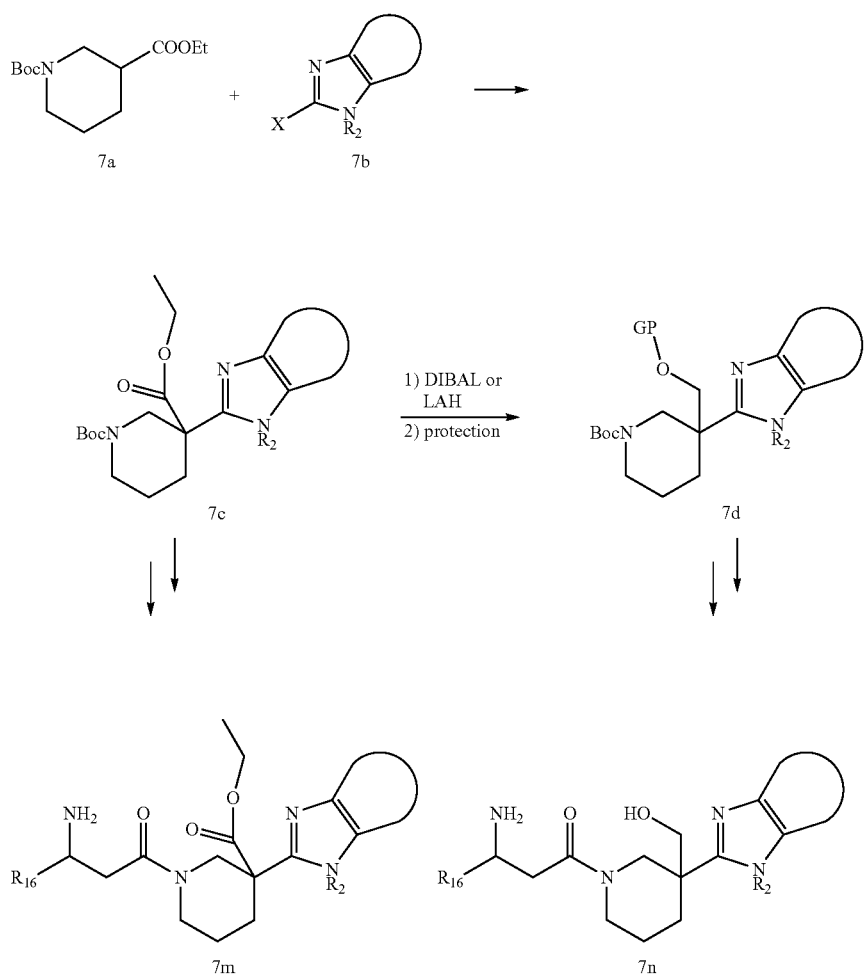

where
X = Br, Cl or OTf, etc
PG = protecting group

H. General Synthetic Route VIII

Renin inhibitors where the N—R, of the imidazole is an acylaminoalkyl group can be synthesized according to Scheme 8. N-alkylation of 8a with N-phthalimide alkylhalo 8b (bromide or iodide) gives Sc. Removal of the N-Boc group in acid conditions such as TFA in DCM affords the piperidine intermediate 8d, which is then coupled with acid 8e to afford 8f. The phthalyl protecting group is removed by reacting with hydrazine to the free amino derivative 8g. Acylation with acid chloride or acid 8h, e.g. acetyl chloride, followed Bac deprotection gives renin inhibitor 8j with acylaminoaklyl side chain. It is noted that alkylation could also occur at the other nitrogen.

Scheme 8.

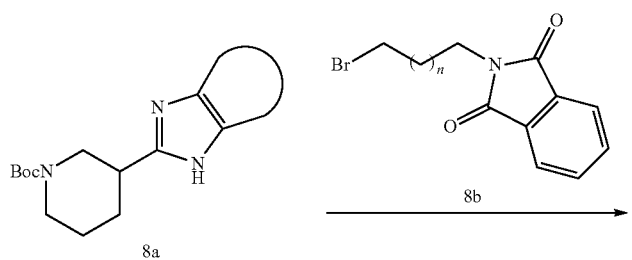

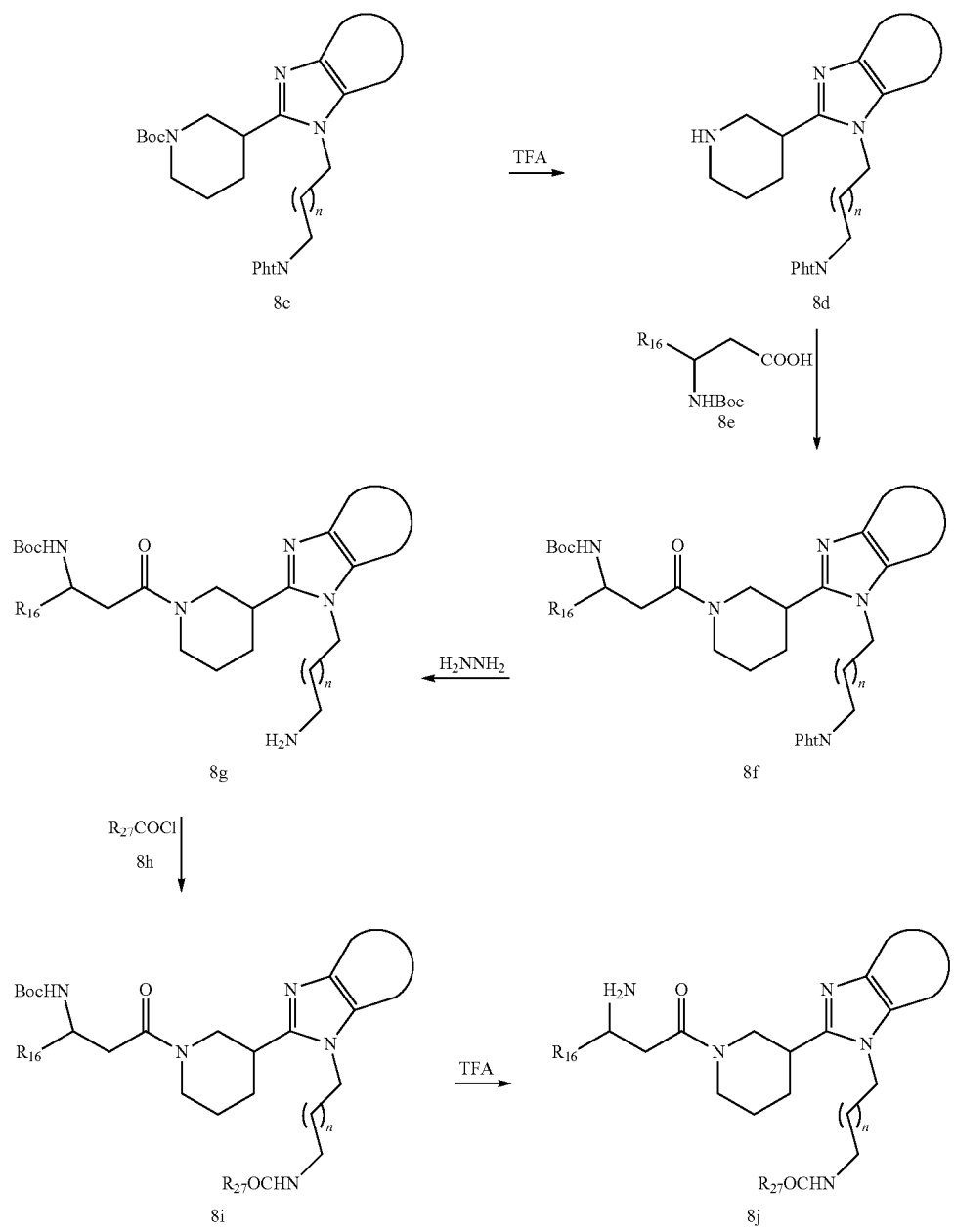

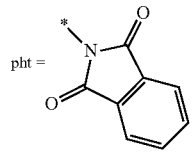

where
n = 0,1 pht =

I. General Synthetic Route IX

Renin inhibitors where the N—R, side chain of the imidazole is an acylaminoalkyl group may also be made according Scheme 9. N-alkylation of 9a with co-azido-alkyl iodide 9b gives 9c. Removal of the N-Boc group yields 9d, which is then coupled with acid 9e to afford 9f. The azido group is converted to the free amino derivative 9g by hydrogenation in the presence palladium carbon or by reaction with $Ph_3P$/water in THF. Acylation with acid chloride (such as acetyl chloride) or acid 9h, followed Boc deprotection, gives renin inhibitor 9j with an acylaminoalkyl side chain. It is noted that alkylation could also occur at the other nitrogen.

Scheme 9.

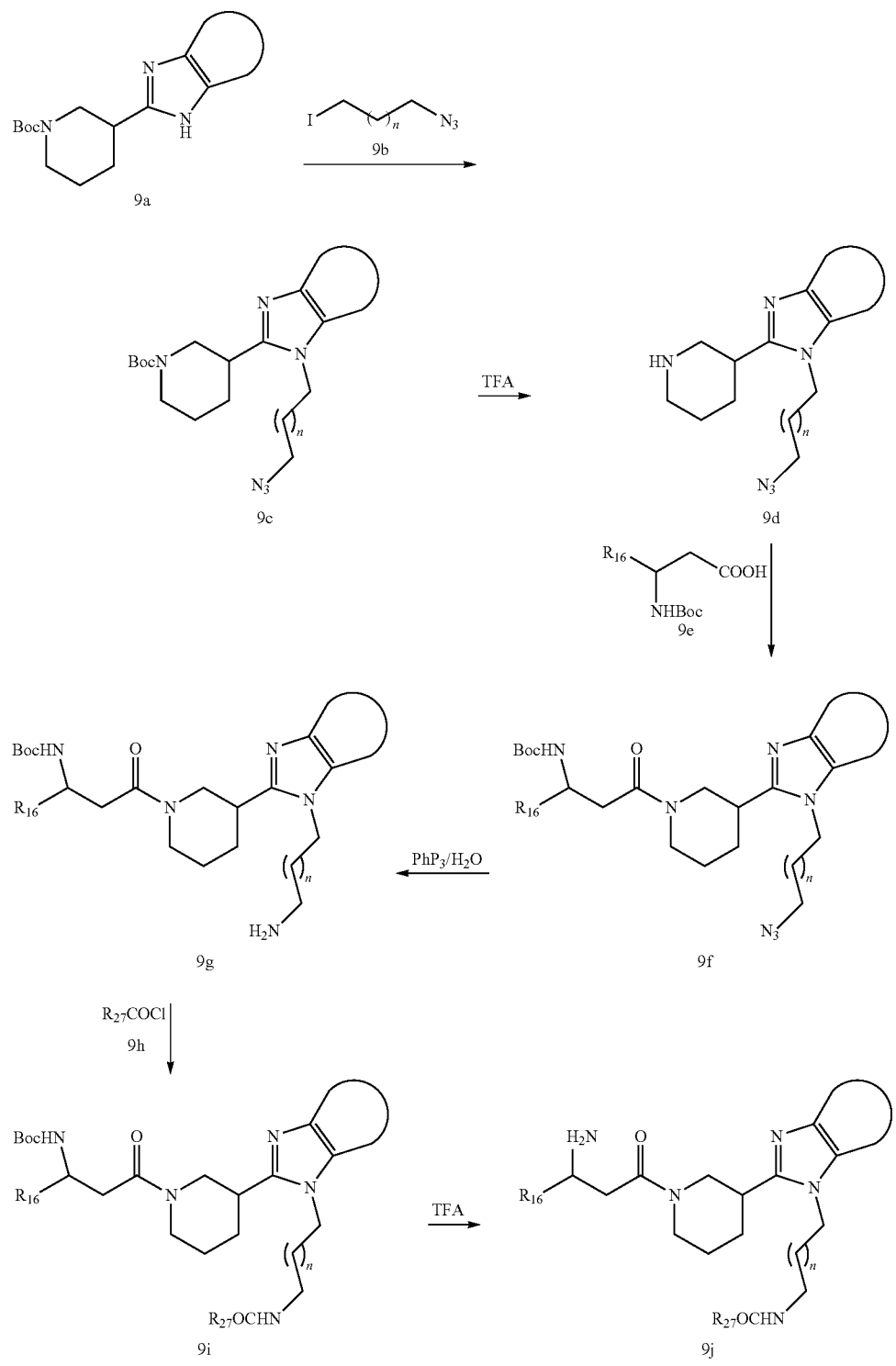

where n = 0,1

Alternatively, renin inhibitors with an acylaminoalkyl side chaim may be prepared according Scheme 10. N-alkylation of 10a with chloro or bromo acetonitrile (10b) gives 10c[1] (and the regioisomer 10c[2]). Reduction of the nitrile group to the amino group by hydrogenation in the presence a metal catalyst such as Raney nickel, amino protection with acetyl chloride (or other protecting group) and Boc-deprtoection with TFA yields 10d, which is then coupled with acid 10e to afford 10f. Finally, Boc deprotection gives renin inhibitor 10g with an acylaminoalkly side chain.

Scheme 10

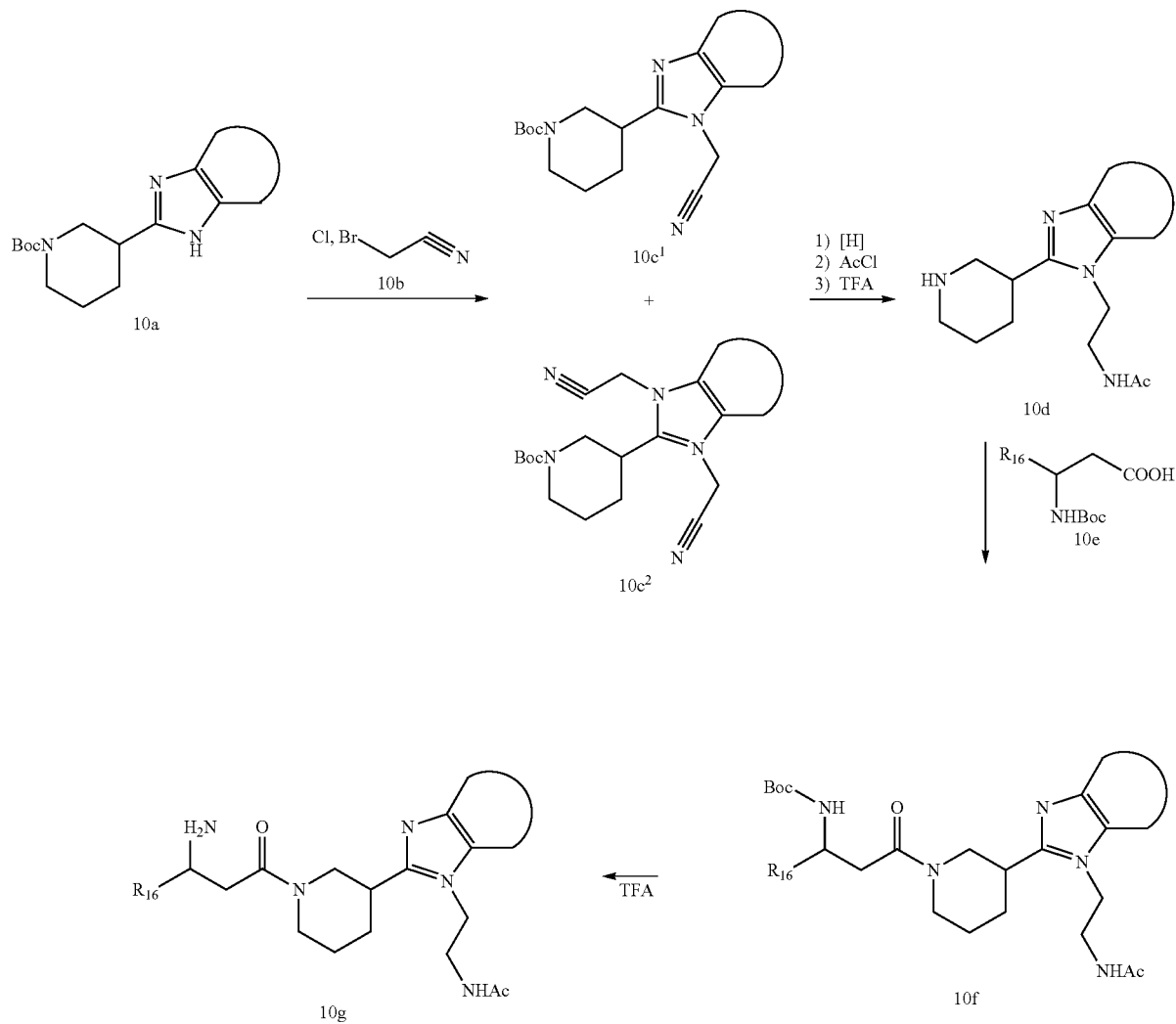

J. General Synthetic Route X

N-linked benzimidazole piperidine renin inhibitor 11j can be made according to the method shown in Scheme 11. Displacement of 2-halophenyl or pyridyl nitro compound 10a with 3-amino-1-Cbz(or Boc) piperidine (11b) gives the adduct 11c, reduction of nitro to amine yields 11d, which is cyclized to form the imidazole analog 11f by reacting with an acid, ester or aldehyde 11e under appropriate conditions such as heating in acetic acid to give 11f. The Cbz protecting group (or Boc) is then removed under standard conditions gives the free piperidine 11g, which can be coupled to 11h and deprotected, according to Scheme 1, Steps 5-6, to give renin inhibitor 11j.

Scheme 11.

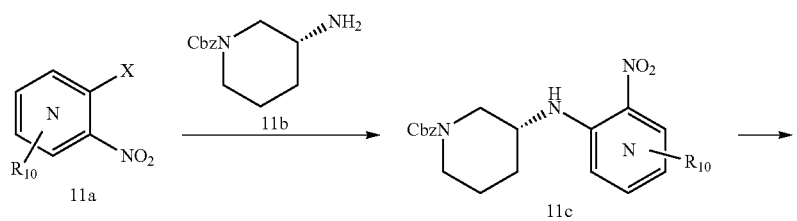

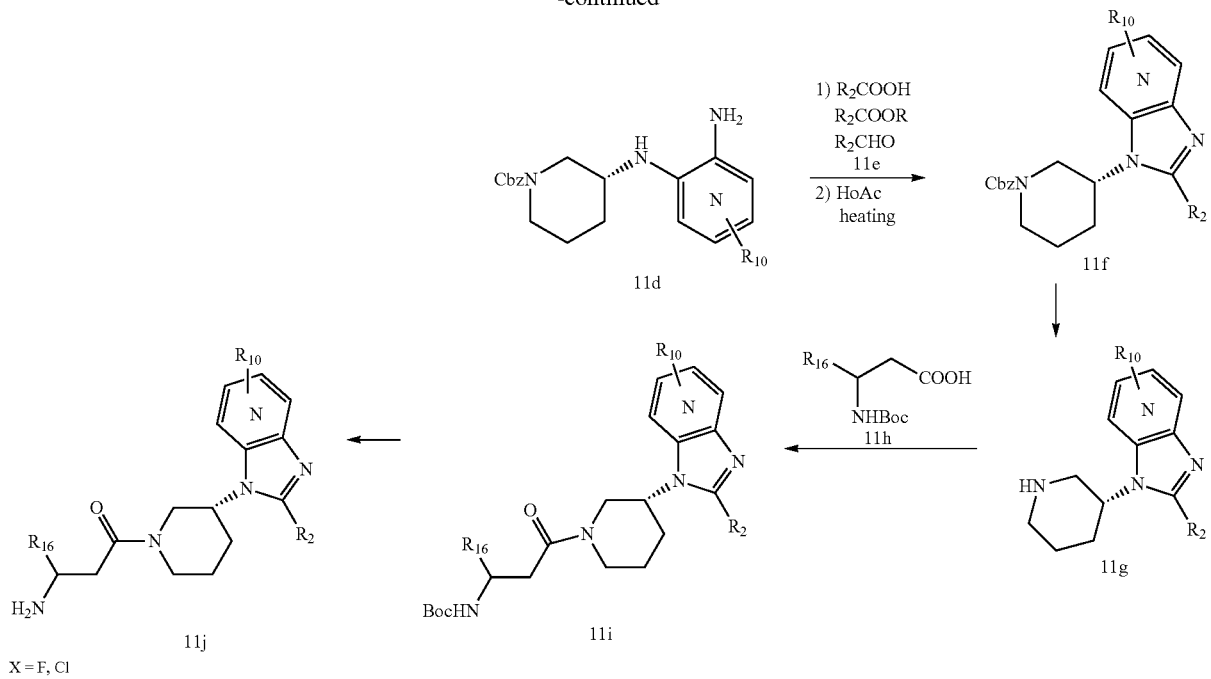

K. General Synthetic Route XI

Renin inhibitors of the invention may be synthesized according to Scheme 12. The imidazole analog 12a (where $R_3$ and $R_4$ may be taken together to form a ring) is N-alkylated with $R_2X$ 12b in the presence of a base to give 12c, which is treated with base such as BuLi or a Grignard reagent (such as isopropyl magnesium bromide) and reacted with n-protected piperidin-3-one (12d) following a similar reaction sequence shown in Scheme 6 to afford the hydroxyl analog 12e. The hydroxyl group can be reductively removed by platinum catalyst hydrogenation, Pd—C/hydrogen or other methods such as trialkylsilane/$SF_3$ or trialkylsilane/TFA ($TiCl_3$/$LiAlH_4$, Breslow, Ronald; Hunt, John T.; Smiley, Richard; Tarnowski, Thomas; JACSAT; J. Am. Chem. Soc.; EN; 105; 16; 1983; 5337-5342.) ($NaBH_4$fITA: Nutaitis, Charles F.; Obaza-Nutaitis, Judy; OPPIAK; Org. Prep. Proceed. Int.; EN; 29; 3; 1997; 315-321); (HI/glacial acetic acid: Gilman; Meals; JOCEAH; J. Org. Chem.; 8; 1943; 126, 139.).

Intermediates 12e and 12f can be transformed into the final renin inhibitors 12i by similar reactions as shown in Scheme 1, Steps 4-6.

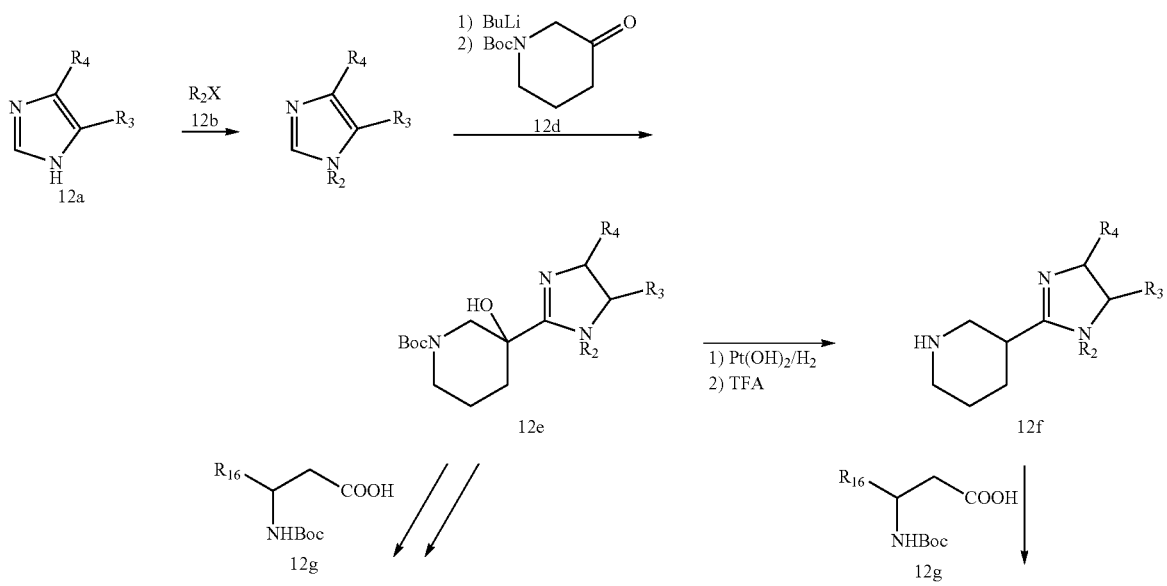

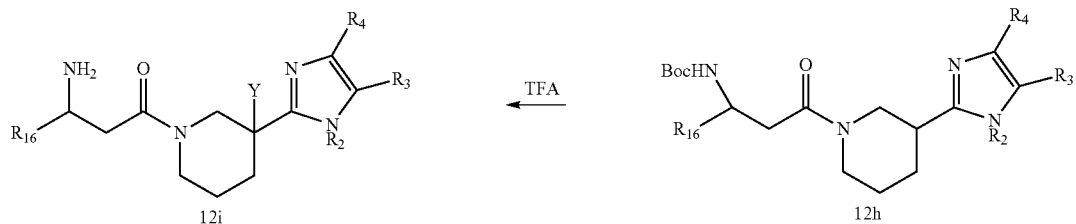

where
X is a leaving group
Y is H or OH

L. Synthesis of 3,4-Diaminobutyric Acid Analogs

Renin inhibitors that are 3,4-diaminobutyric acid analogs may be prepared by further derivatizing the amino group on the piperidine as shown in Scheme 13. Protected piperidine intermediate 13a may be coupled to protected 3,4-diaminobutanoic acid 13b. After removing 4-N-Boc group under acidic conditions, the free amine 13c is obtained. Reaction with an acid/acid chloride, sulfonyl chloride, isocyanate or chloroformate 13d following typical amine coupling conditions gives, after removing Fmoc protecting group with base (piperidine/DMF), renin inhibitors 13e.

Scheme 13.

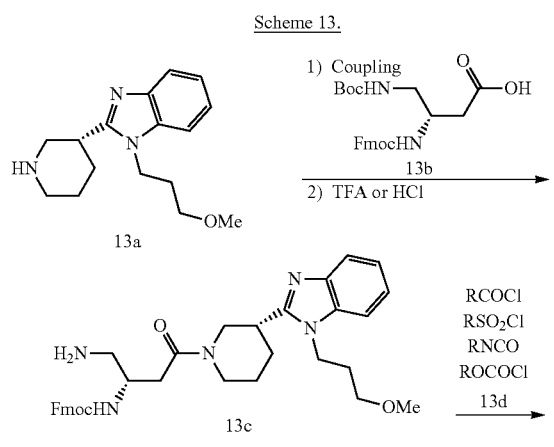

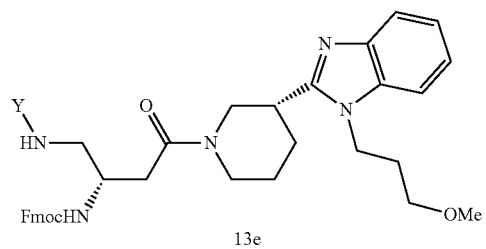

where
Y is RCO; RSO2-, RNCO-, or ROCO-
R is aryl, heteroaryl, alkyl, or heteroalkyl

M. Synthesis of 3-Amino-4-diaminobutyric Acid Analogs 3-amino-4-diaminobutyric acid analogs of the renin inhibitors of the invention may be prepared according to Scheme 14. The piperidine intermediate 14a may be coupled to protected 3-amino-4-hydroxybutanoic (14b). After removing 4-O-benzyl group under hydrogenation conditions, the free alcohol 14c is obtained. Reaction with 14d (phenols, heteroaryl, hydroxyl, or NH group of certain amide and cyclic amide (e.g., 14g)) by following typical Mitsunobu conditions gives, after removing Fmoc protecting group with base (piperidine/DMF), the aryl ether renin inhibitors 14e or the "amide" analog 14f.

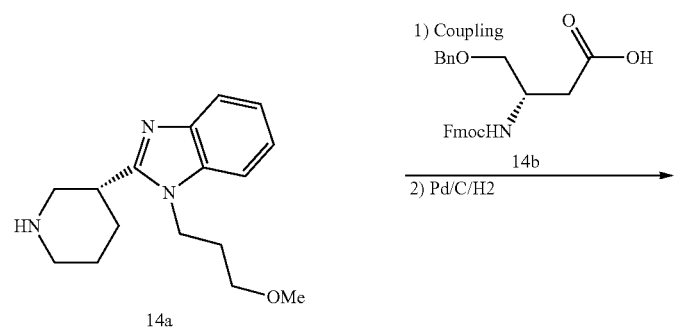

-continued

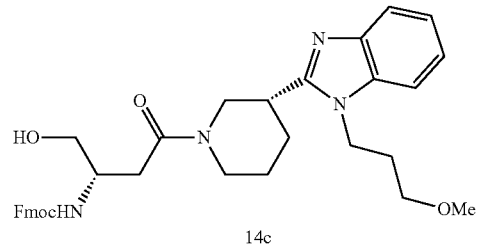
14c

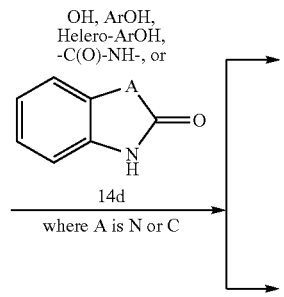
14d
where A is N or C

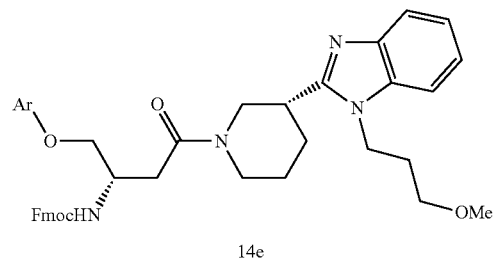
14e

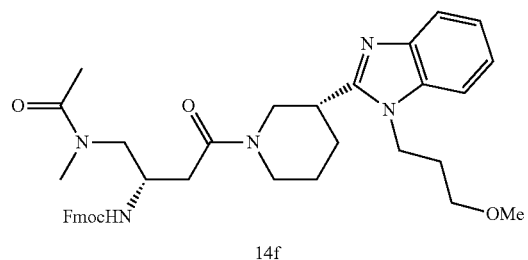
14f

N. Synthesis of Pyrrolidine Amino Acid Analogs Pyrrolidine amino acid analogs of renin inhibitors of the invention may be prepared by the route shown in Scheme 13. The piperidine intermediate 15a is coupled to a protected N-Boc-3-N-Fmoc pyrrolidine-4-carboxylic acid 15b (made from 15f). After removing 4-N-Boc group under acidic conditions, the free amine 15c is obtained. The free amine 15c may be further derivatized with acid/acid chloride, sulfonyl chloride, isocyanate or chloroformate, and after removing Fmoc protecting group with base (piperidine/DMF), to obtain an amide sulfonamide, urea, or carbamate analog, respectively, of the renin inhibitors 15d.

-continued

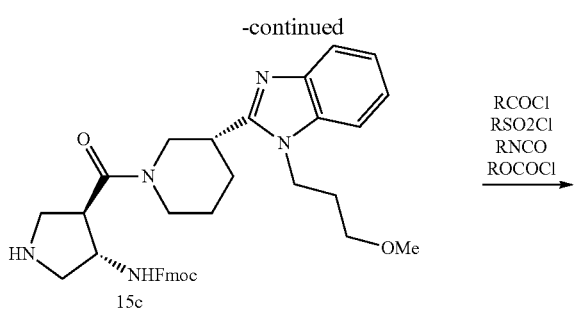
15c

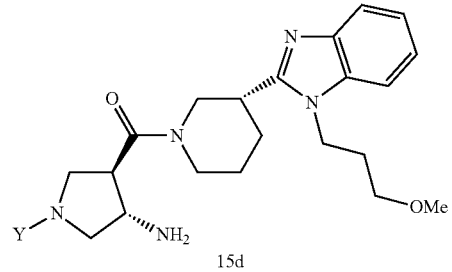
15d

Scheme 15.

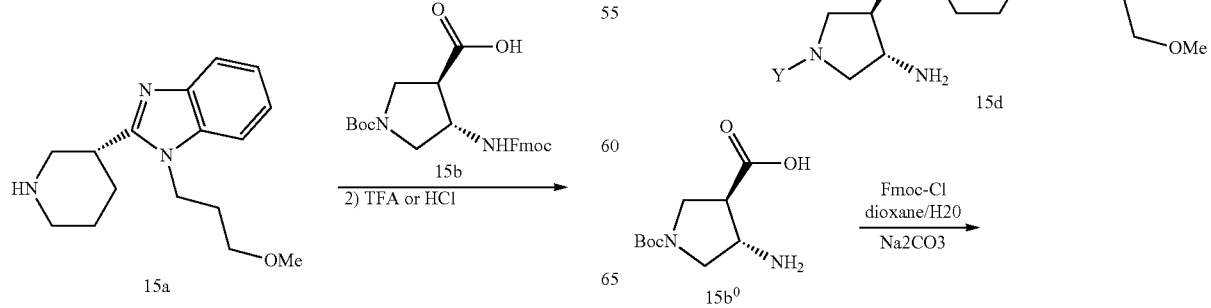

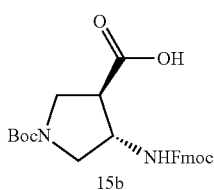
15b where
Y is RCO⁻, RSO2-, RNCO⁻, or ROCO⁻
R is aryl, heteroaryl, alkyl, or heteroalkyl O. Synthesis of Imidazole Reagents Imidazoles used in the synthesis of the renin inhibitors of the invention are purchased or may be synthesized through many known synthetic methods, e.g., the route shown in Scheme 16.

Aldehyde 16a may react with amine 16b in the presence of acid catalyst and/or dehydrating agent (such as molecular sieves, $TiCl_4$ etc.) to yields the imine 16c. The imine 16c may reacts with toluene p-sulfonylmethyl isocyanide (TOSMIC) (16d) in basic conditions (such as NaH in DME or $IC_2CO_3$ in MeOH) to give imidazole 16e. Deprotonation of 2-H of 16e with a strong base such as BuLi or a Grignard reagent followed by reaction with N-protected 3-piperidone (16f) and subsequent reduction of alpha-hydroxy group with $Pt(OH)_2$ hydrogentation or other reagents described earlier (e.g., Scheme 12), gives piperidine imidazole ananlog 16g, which is converted to the final renin inhibitor 16h using procedures shown in Scheme 1, Steps 5 and 6.

17b undergoes Wolff rearrangement catalyzed by silver salt, e.g., benzoic acid salt to give a reactive carbene which is reacted with MeOH to afford the methyl ester. After hydrolysis with base such as LiOH, the beta-amino acid 17c is obtained. Other methods such as Schollkopf method (Synthesis 1981, page 969) are also known to be useful in obtaining non-commercial beta amino acids.

Scheme 17.

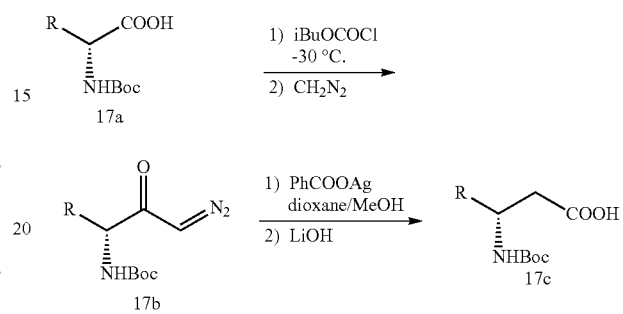

where R is alkyl, heteroalkyl, aryl or heteroaryl

Q. General Synthetic Route for α-hydroxy-β-Amino Acids

Alpha-hydroxy-beta-amino acids can be synthesized using the corresponding alpha-amino acids according to Scheme 18. N-protected α-amino acid 18a is first converted to its Weinreb amide 18c through coupling with N,O-dimethylhydroxyamine (18b). Reduction with LAH in THF gives alde- Scheme 16.

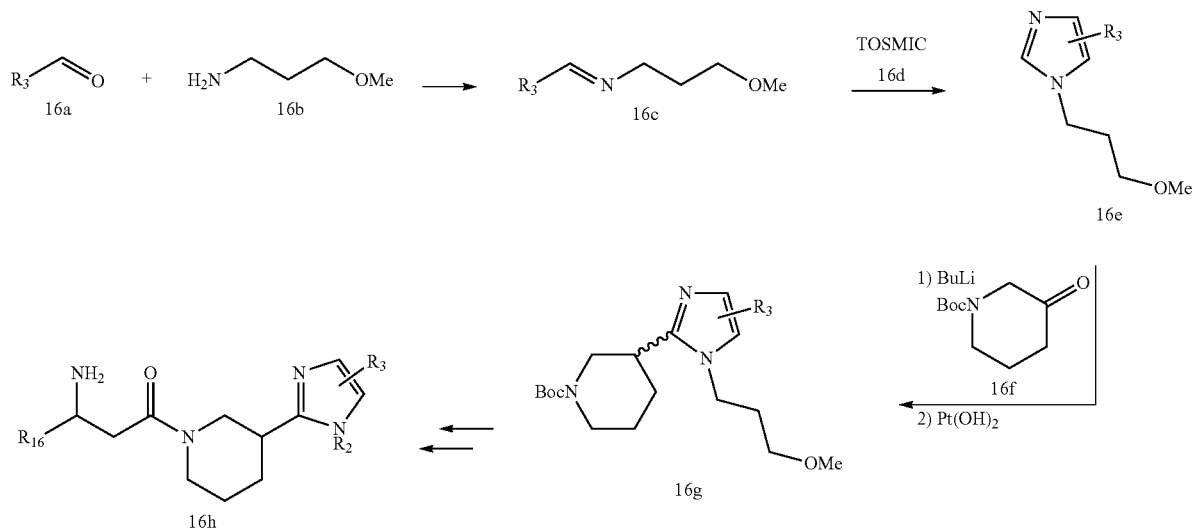

P. General Synthetic Route for O-Amino Acids

The beta-amino acids can be easily obtained from readily available α-amino acid acids through Arndt-Eistert Synthesis. N-protected amino acid 17a is transformed to alpha-diazoketone 17b by reaction with isobutyl chloroformate at low temperature and then with diazomethane. Intermediate hyde 18d, which reacts with potassium or sodium cyanide to afford, after hydrolysis with aqueous HCl, the 1-hydroxy-2-amino acid 18e. Fisher esterification followed by N,O-protection with CDI then ester hydrolysis gives the protected alpha-hydroxy-beta-amino acids 18g, which are ready for further coupling reactions.

Scheme 18.

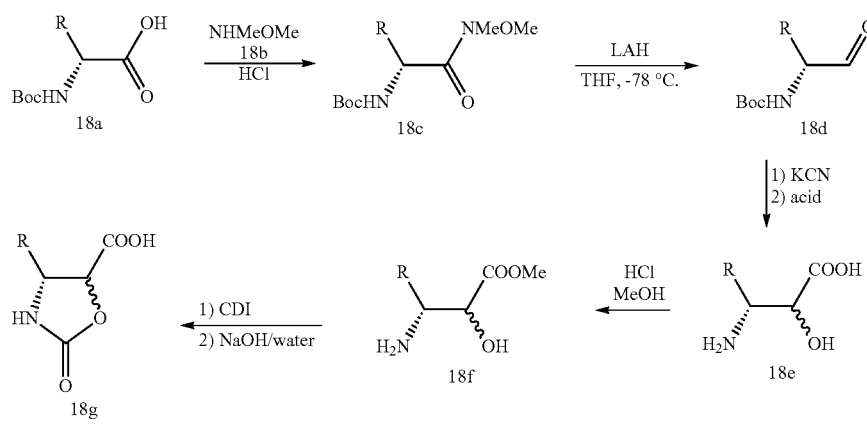

where R is alkyl, heteroalkyl, aryl or heteroaryl

R. General Synthetic Route for Alpha-Alkyl-Beta-Amino Acid

Alpha-alkyl-beta-amino acids can also be synthesized using the corresponding amino acid esters according to Scheme 19. N-protected amino acid ester 19a is treated with base such as NaH or a Phosphazene base such as $P_4$-t-Bu and alkyl halide 19b to give 19c and/or 19e depending on the amount of base and halide used. Ester hydrolysis with hydroxide gives the protected alpha-hydroxy-beta-amino acids $19d^1$ and/or $19d^2$. The amino group of 19a may need to be double protected with groups such as bis-Boc. If an ω-dihalide 19e is used, cyclic alkyl amino acid 19h may be obtained.

Scheme 19.

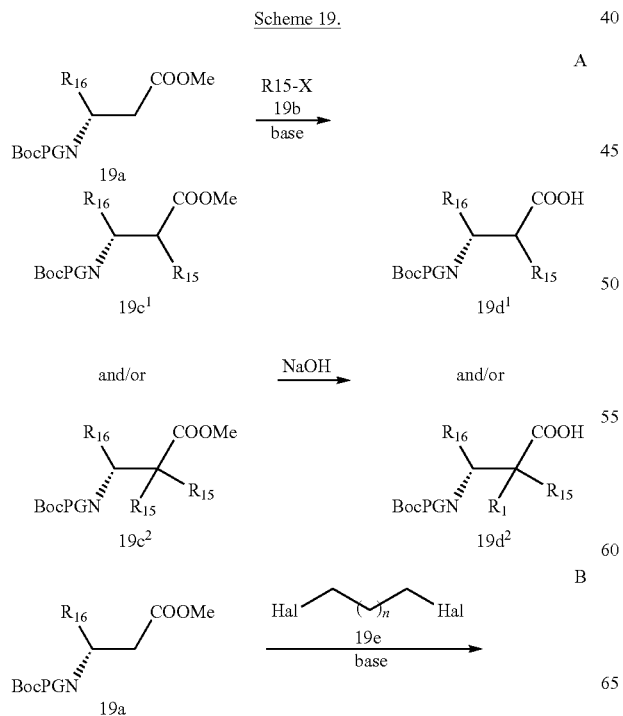

-continued

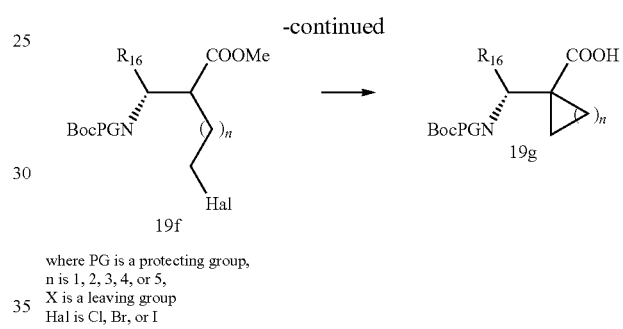

where PG is a protecting group,
n is 1, 2, 3, 4, or 5,
X is a leaving group
Hal is Cl, Br, or I

S. General Synthetic Route for Methylamino-Beta-Amino Acid

Beta-amino acid 19e may be synthesized according Scheme 20. Aldehyde 20a condenses with ethyl 2-cycnoacetate 20b to yield α,β-unsaturated ester 20c. Hydrogenolysis with palladium on carbon and hydrogen reduces both the cyano and the unsaturated bonds to produce 20d after Boc-N protection. Hydrolysis with hydroxide in a mixture of water and dioxane (or THF or EtOH) yields 20e.

Scheme 20.

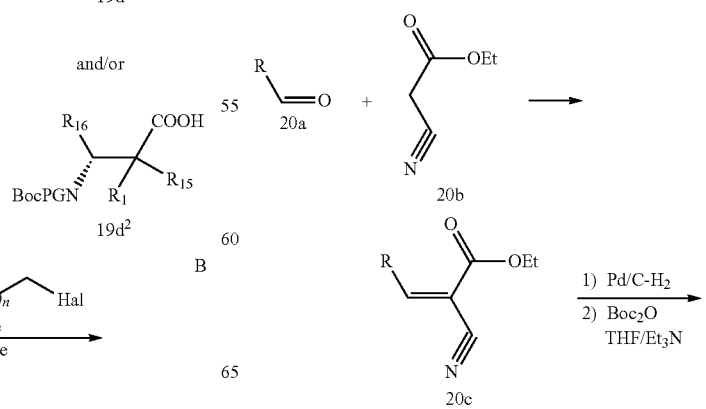

-continued

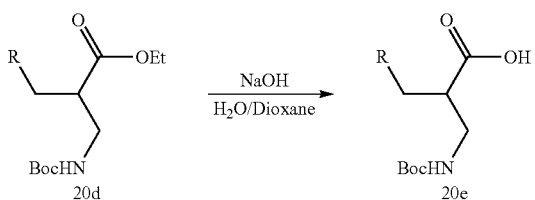

where R is alkyl, heteroalkyl, aryl or heteroaryl

T. General Synthetic Route for Beta-Amino Acid

Renin inhibitors of the invention having further substituents, e.g., biaryl or heterobiaryls, may be prepared from amino acids which have a reactive handle, such as OH (phenol) or halide, that can be further functionalized. Referring to Scheme 21, biaryl or heterobiaryl 21c can be obtained by coupling the bromide 21a to a halide 21b applying Suzuki conditions. Aryl ether 21e may be formed from coupling 21a to $R_aOH$ 21d employing palladium catalyst or Cu catalyst (Ullman reaction or similar conditions). This reaction is normally carried out at high temperature and may use base such as NaOtBu. Adduct 21g may be formed by coupling amines or anilines 21f to 21a under Buchwald or Hartwig conditions (palladium catalyst and base). Adduct 21g may also form by coupling certain amide and cyclic amide nitrogen to 21a in the presence of a copper salt (normally copper I salt such as CO) and base such as $K_3PO_4$ and diamino-ligand such as N,N'-dimethylethlyenediamine or N,N'-dimethylcyclhexyl-1,2-diamine at elevated temperature (such as refluxing dioxane or toluene). The halide 20a can also be converted to the corresponding pinacol borate 21i via the reaction with bis(pinacolato)diboron 21b in the presence of a palladium catalyst such as Pddpff. The borate 21i can undergo further Suzuki couplings with halide 21j to form the adduct 21k, which otherwise is hard to obtain from 21a.

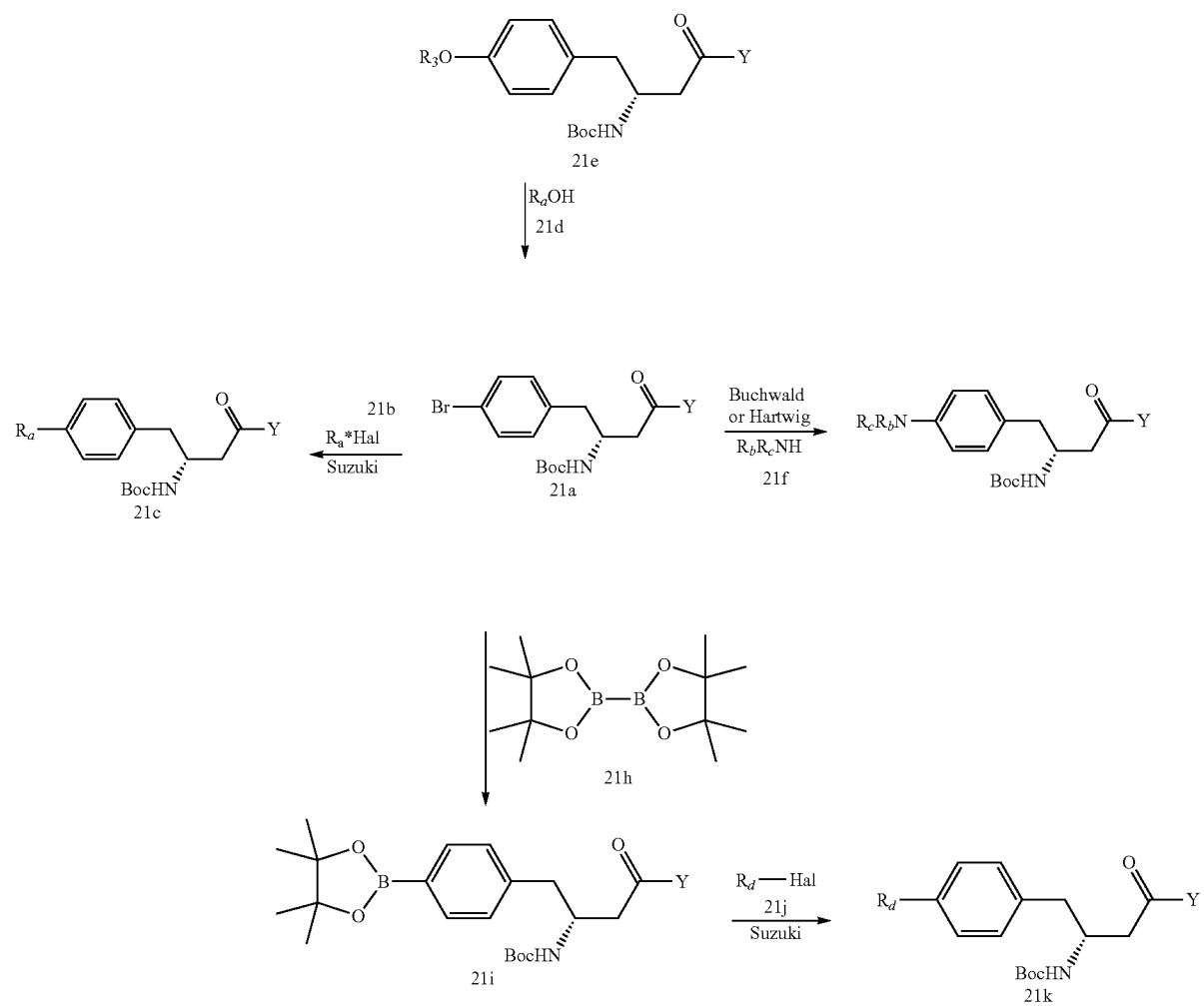

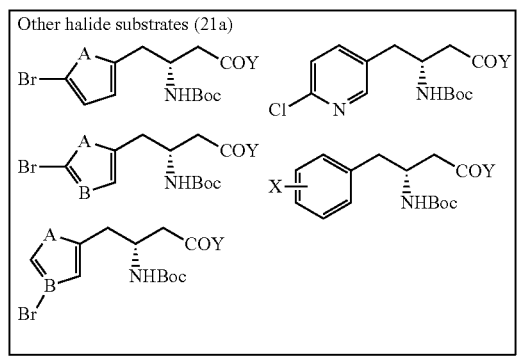

where
A = O, S, NR$_e$
B = N, CH
X = Br, I, Cl
Y represents the remainder of the molecule, which connects to the C(O) through the ring nitrogen of a substituted piperdine
R$_a$ = Ar, heteroAr
R$_b$, R$_c$, R$_d$ and R$_e$ are each independently Ar, heteroAr, alkyl and heteroalkyl U. General Synthetic Route for Biaryls Biaryls may be prepared from many halides such as aryl and hereroaryl bromides and iodides by the Suzuki and Buchwald reactions. A few examples that these routes are applicable are shown in Scheme 22. Substrate 22a, which can be made according to Scheme 13 from the coupling of free amine 13c and the corresponding heteroaryl acids 22c/22d/22e, may react with boronic acid (Suzuki) or nitrogen compounds (Buchwald) to give the desired bi-aryl analogs 22b after de-protection. These routes are also suitable for aryl or heteroaryl acids such as 22d and 22e.

Scheme 22.

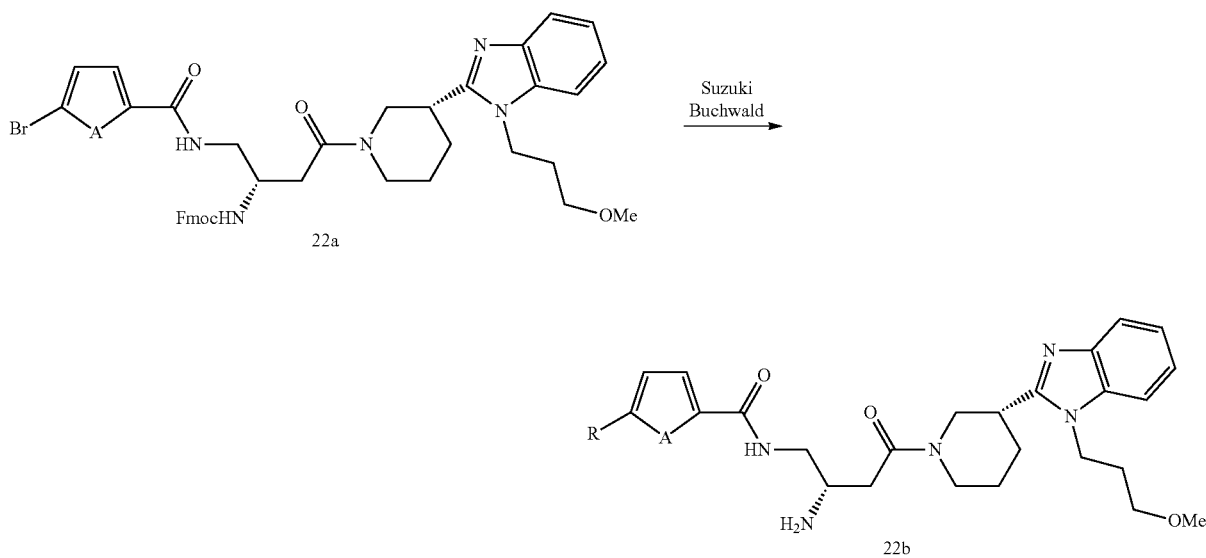

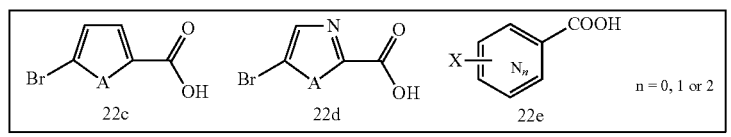

where
A = O, NMe, S
R = Ar, heteroAr, alkyl, or
X = Cl, Br or I

More examples for Suzuki and Buchwald reactions are shown in Scheme 23. The biaryls, 23b and 23d, where R=aryl or heteroaryl (Suzuki conditions) or where R=nitrogen containing analogs (Buchwald conditions) or R=ether type (Ullman conditions) compounds can be obtained as described previously.

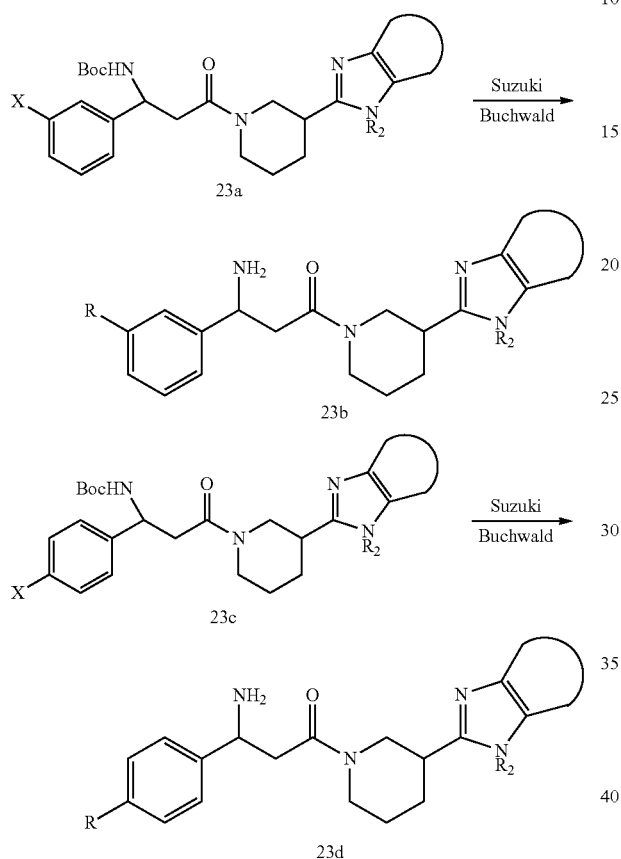

Scheme 23.

Scheme 24, 25 and 26 further show examples for the synthesis of heteroaryl β-amino acids. In Scheme 24, the aldehyde 24a or 24g is reacted with glycine Wittig reagent 24b in the presence of a base to give N-Boc imine 24c or 24h respectively. Reduction of the double with NaBH$_4$/NiCl, produces alpha-aminoester 24d or 24i. Ester hydrolysis followed by procedures shown in Scheme 17, converts the alpha-aminoacid to beta-aminoacid 24e or 24j. The chiral aminoacid 24f may be synthesized from asymmetric hydrogenation of 24c, using catalysts such as (R,R)—Pr-DuPHOS-Rh as described by Burk et. al. (*J. Am. Soc.* 1994, 116:10847-10848).

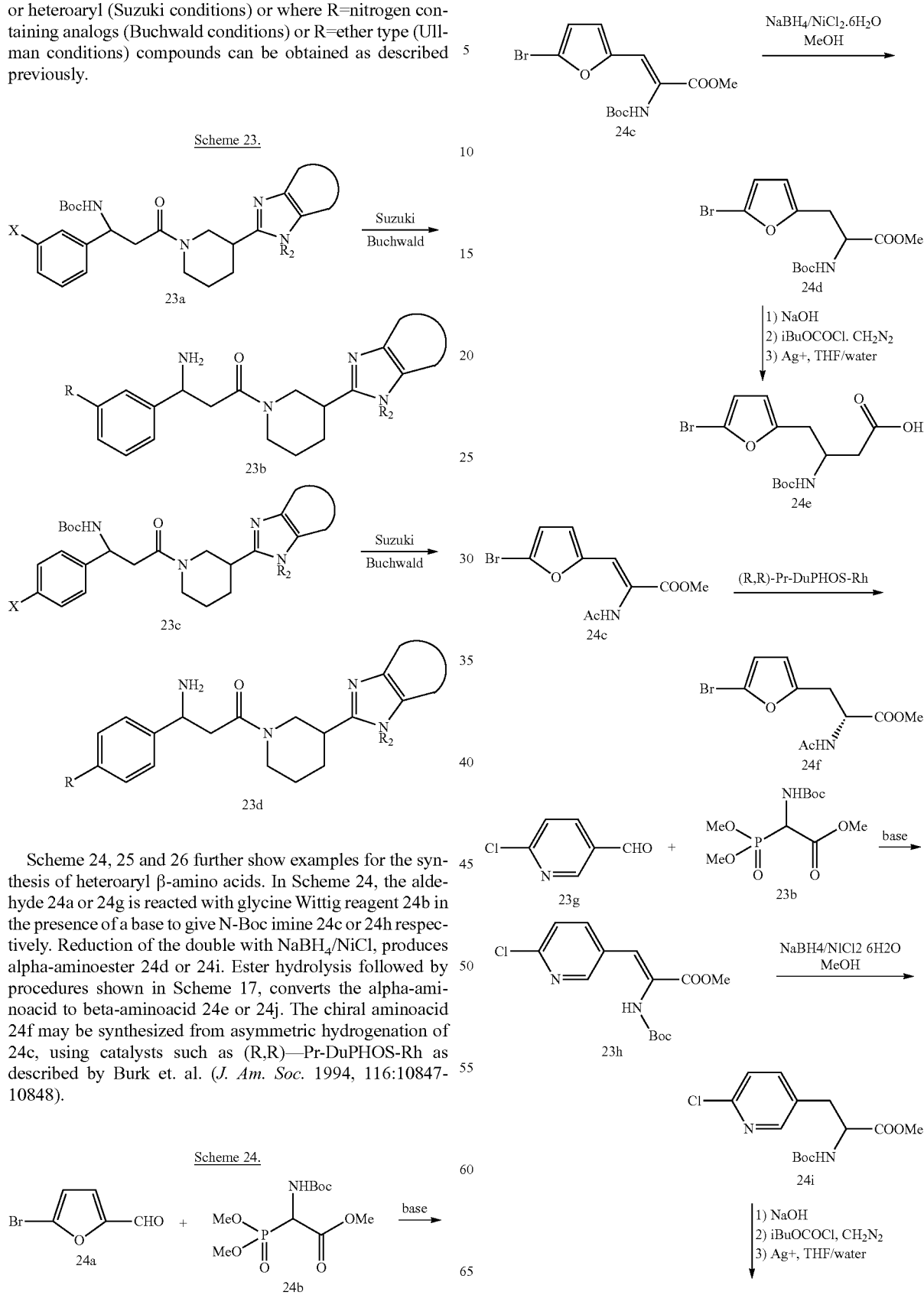

Scheme 24.

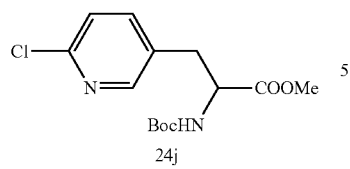

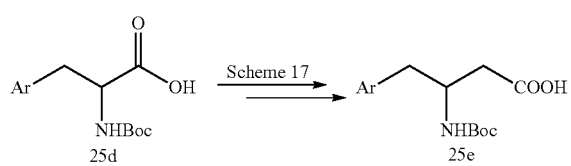

Alternatively, these beta-aminoacids can be made through the synthetic routes depicted in Scheme 25 and 26. Referring to Scheme 25, alkylation of arylmethyl halide 25a with diethyl acetamidomalonate 25h in basic conditions gives 25c. Hydrolysis of both esters and amide and N-Boc protection gives amino acid 25d, which is transformed to the beta amino acid 25e following similar procedures described in Scheme 17. Compound 25f can be made by this method.

Referring to Scheme 26, condensation of an aldehyde 26a with N-acetylglycine 26b in the presence of sodium acetate and acetic anhydride yields the oxazolone 26c. Treatment of 26c with base and then acid, gives the unsaturated amino acid 26d. Double bond reduction with zinc in HCl, followed by removal of N-acetyl group and protection with Boc anhydride, gives N-Boc amino acid 26f, which is converted to beta-aminoacid using procedures shown in Scheme 17. Specifically, the furan analog 26h may be further reacted with bromine and then converted according to Scheme 17, to 5-bromofuran beta amino acid 26j.

Scheme 25

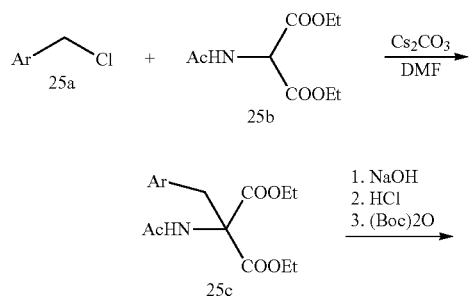

Scheme 26

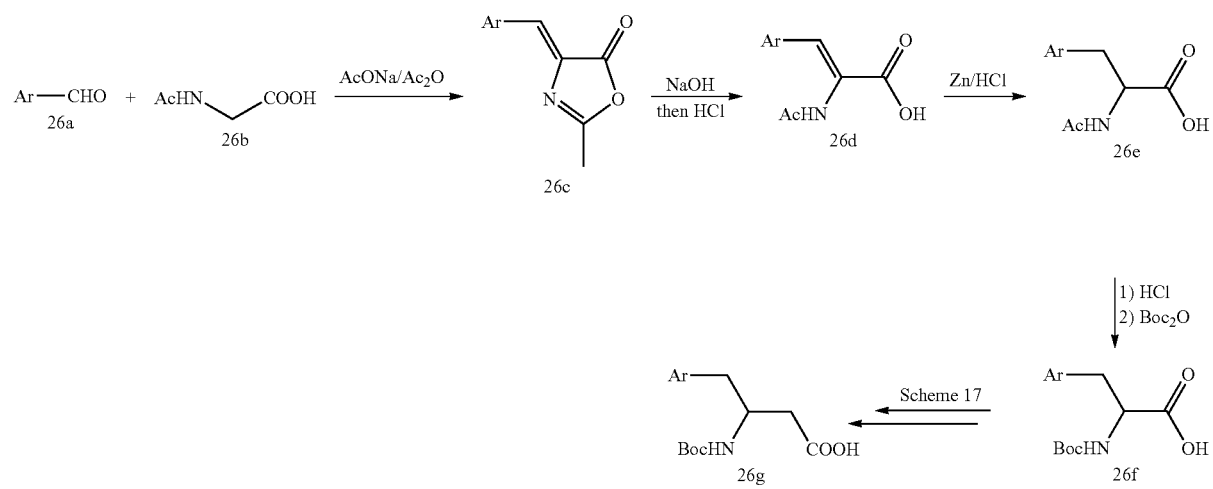

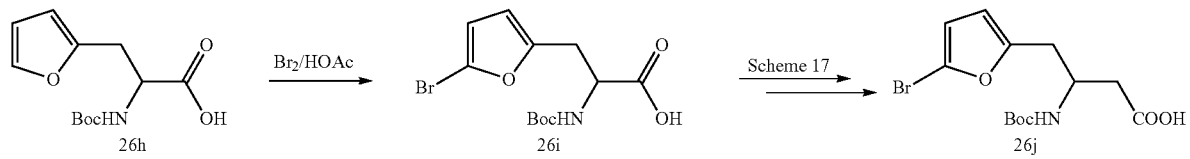

Scheme 27 shows the Buchwald amination reaction of the bromide 27a or other halides with imidazol-2-ones 27b to give products N-aryls, 27c, 27d or 27e. The reaction is normally carried at high temperature in dioxane or toluene in the presence of diamine ligand such as N,N'-dimethylethylenediamine and a cupper catalyst such as Cu(I) I.

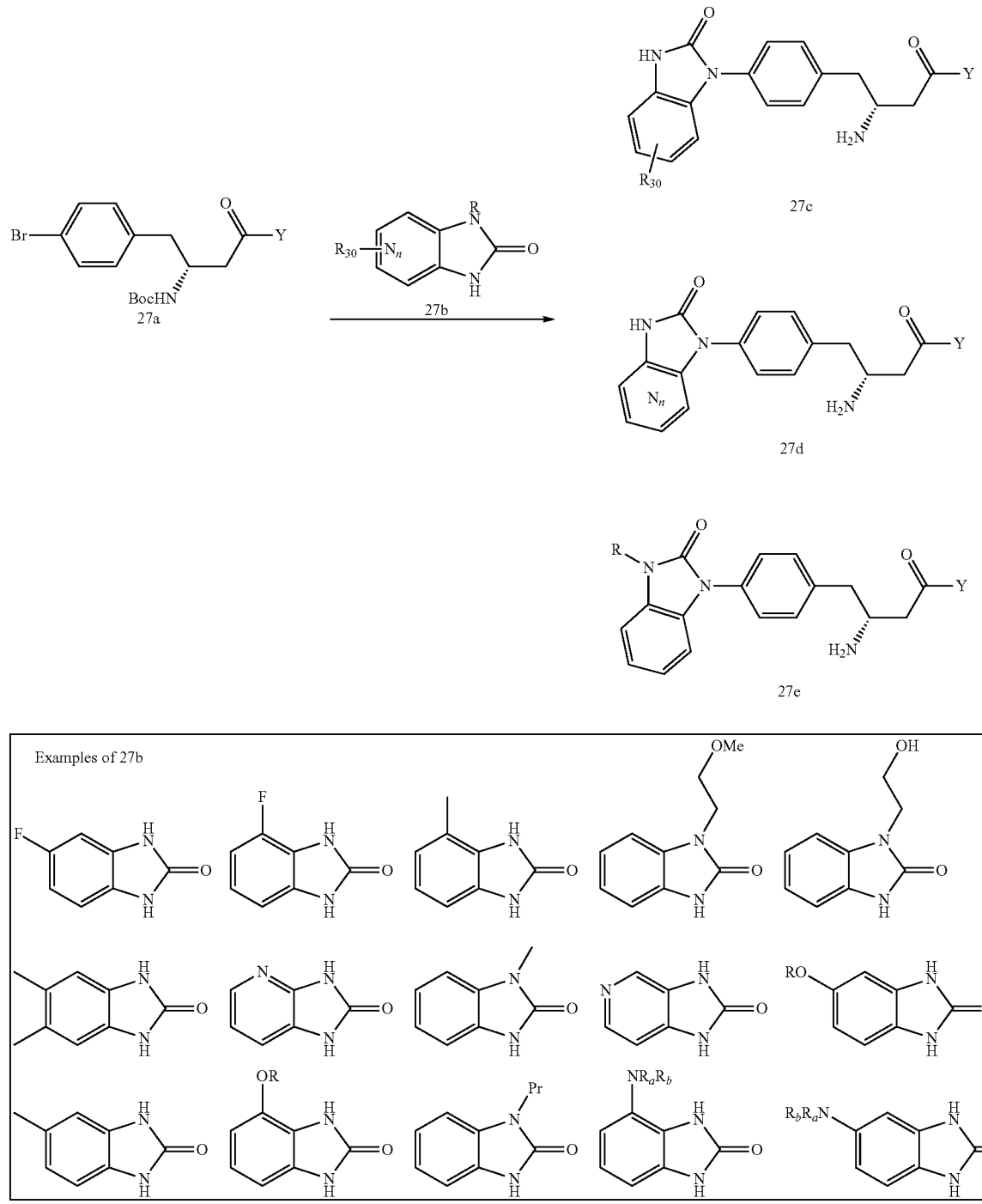

where
n is 0, 1, or 2
Y represents the remainder of the molecule, which connects to the C(O) through the ring nitrogen of a substituted piperidine
R, $R_a$, or $R_b$, is each independently alkyl, heteroalkyl, aryl or heteroaryl In some cases, the imidazolone analogs 27c can also be made by the route shown in Scheme 28. Reaction of aniline 28a with ortho-halo aryl nitro compound 28b gives 28c after reduction of the nitro group with reagent such as Pd/H$_2$, NaHS, Ti(II) Cl$_2$ etc. If Boc group was removed under some reaction conditions (acidic), it can be easily added on again with Boc$_2$O. 28c is converted to 28d using carbonyl reagent such as CDI, COCl$_2$. (See Scheme 29).

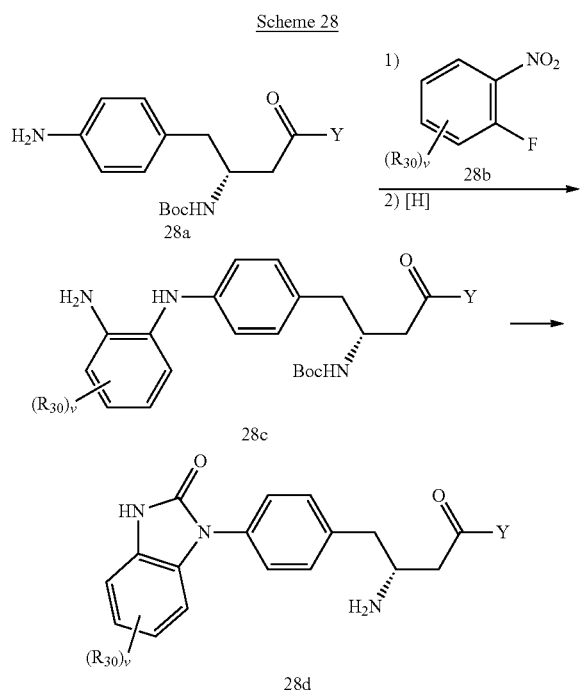

where
Y represents the remainder of the molecule, which connects to the C(O) through the ring nitrogen of a substituted piperidine

V. Synthesis of Reagents

The imidazol-2-ones 27b substrates for Buchwald amination reaction can be easily synthesized from 1,2-diamines 29a and a carbonyl sources such as CDI or 29b.

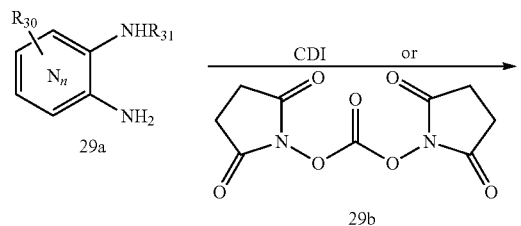

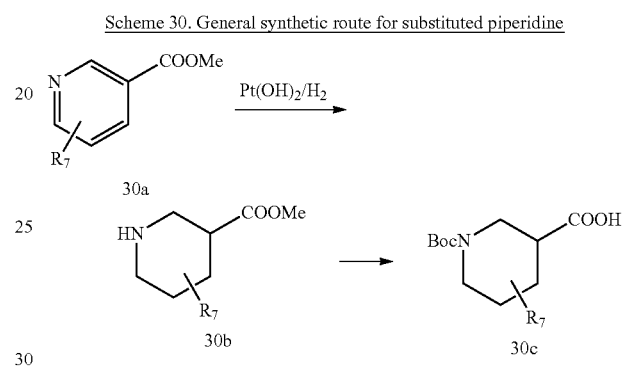

where n is 0, 1, or 2

One way to synthesize substituted piperidines 30c is shown in Scheme 30. Hydrogenation of substituted pyridines 30a catalyzed by platinum hydroxide gives piperidine 30b. N-protection with Bac group followed by hydrolysis of the methyl ester yields the desired 30c.

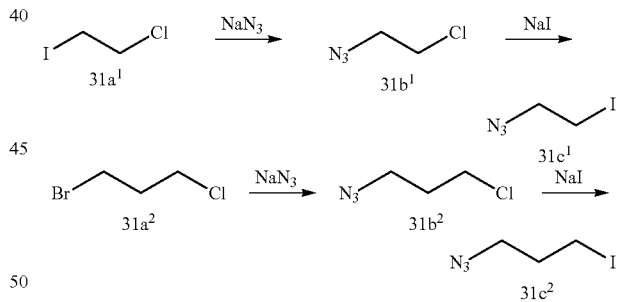

ω-azidoalkyl iodide reagent can be synthesized according to Scheme 31. Azide displacement of 1-chloro-ω-bromo(or iodo)alkane 31a gives the azido intermediate 31b. Conversion of the chloride 31b$^1$ to iodide 31c$^1$ is effected by Finkelstein reaction, i.e., heating with NaI in acetone.

W. General Synthetic Route for Pyridine Analogs

Pyridine analogs of structure 32j, 32h and 32i can be made by the synthetic routes shown in Scheme 32. 32g is synthesized by similar procedures described earlier in General Synthetic Route V (Scheme 5), deprotection of 32g gives 32h. Displacement of 32h with alkoxide or hydroxide gives 32j, after deprotection

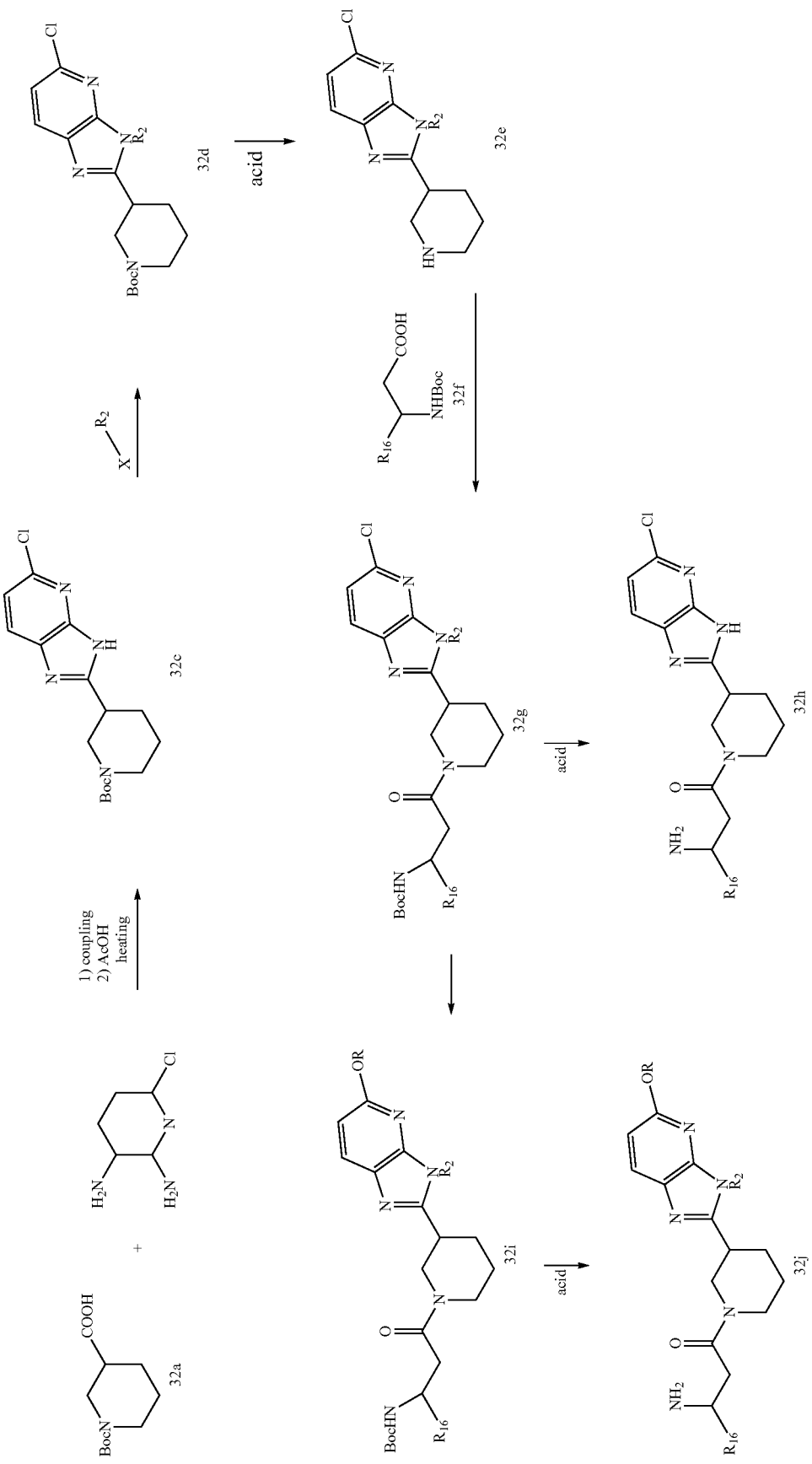
Scheme 32.
where
X is a leaving group
R is hydrogen, alkyl

Alternatively, the pyridine analogs can also be made through the route shown in Scheme 33. Amine 33b displacement of dichloropyridine 33a gives 33c which is treated with sodium methoxide (or other alkoxide) produces 33d. Following procedures shown earlier in General Synthetic Route IV (Scheme 4), compound 33j is obtained. De-methylation in pyridine-HCl at 150° C. gives the tautomers $33k^1$ and $33k^2$.

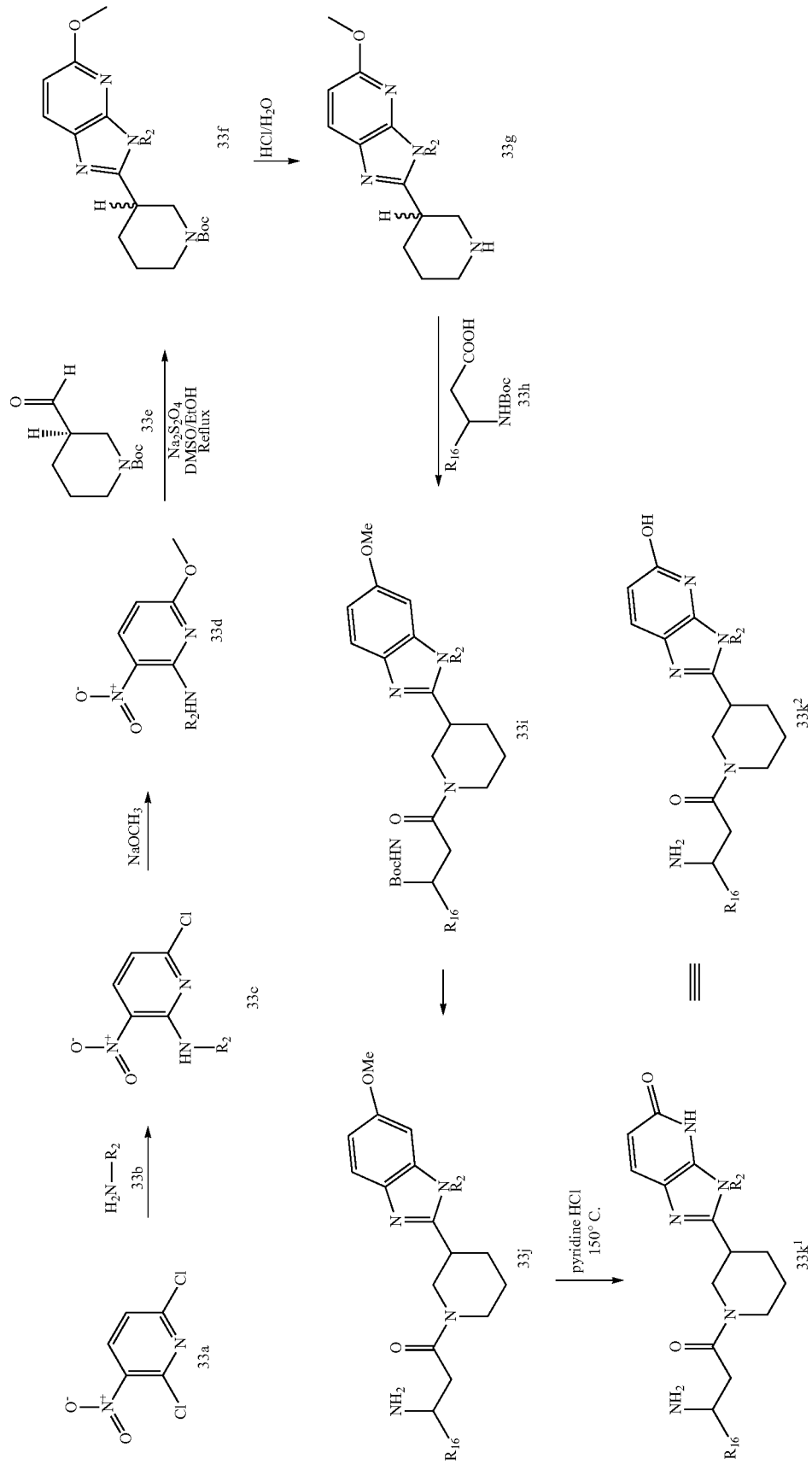
Scheme 33.

X. Synthetic Route for Benzothiazole and Benzoxazole Amino Acid Analogs.

Benzothiazole and benzoxazole amino acid analogs 34f can be synthesized by the route shown in Scheme 34. Protected amino acid nitro compound 34a is reduced to the aniline analog 34b by acid/metal or hydrogenation procedure. 34b is then reacted with bromine, followed by potassium thiocyanate (KSCN), normally in acetic acid or ethanol, to give Benzothiazole 34d (A=S) or cynogen bromide (BrCN) to give the benzoxazole analog 34d (A=O). 34c may or may not be isolated. If the free amino acid is used (X=H), the amino group of 34d is first protected with Boc group before the next reaction. The NW of the triazole/oxazole 34d can be derivatized with, for example, acid chloride, isocyanate or alkyl group (reductive amination). 34d is coupled with piperidine 34e to give 34f after deprotection.

Y. Synthetic Route for Selected Pyrrolidine Renin Inhibitors.

Pyrrolidine renin inhibitors with direct N—C bond can be synthesized according to Scheme 35. N-protected pyrrolidine 35a (eg, PG=Boc or Fmoc) reacts with aryl halide or heteroaryl halide 35b under appreciate conditions such as Buchwald conditions (e.g. $Cs_2CO_3$, $Cu_2O$ and Compound 35c in $CH_3CN$ reflusing) to give the N-aryl/heteroaryl pyrrolidine renin inhibitor 35d after removal the protection group PG. One example of 35d is $35d^1$ which is derived from 15c (Scheme 15). The aryl/heteroaryl can be further manipulated if a pendant group is present such as ester or $NO_1$ groups.

Scheme 34. Synthetic routes for benzothiazole and benzoxazole analogs

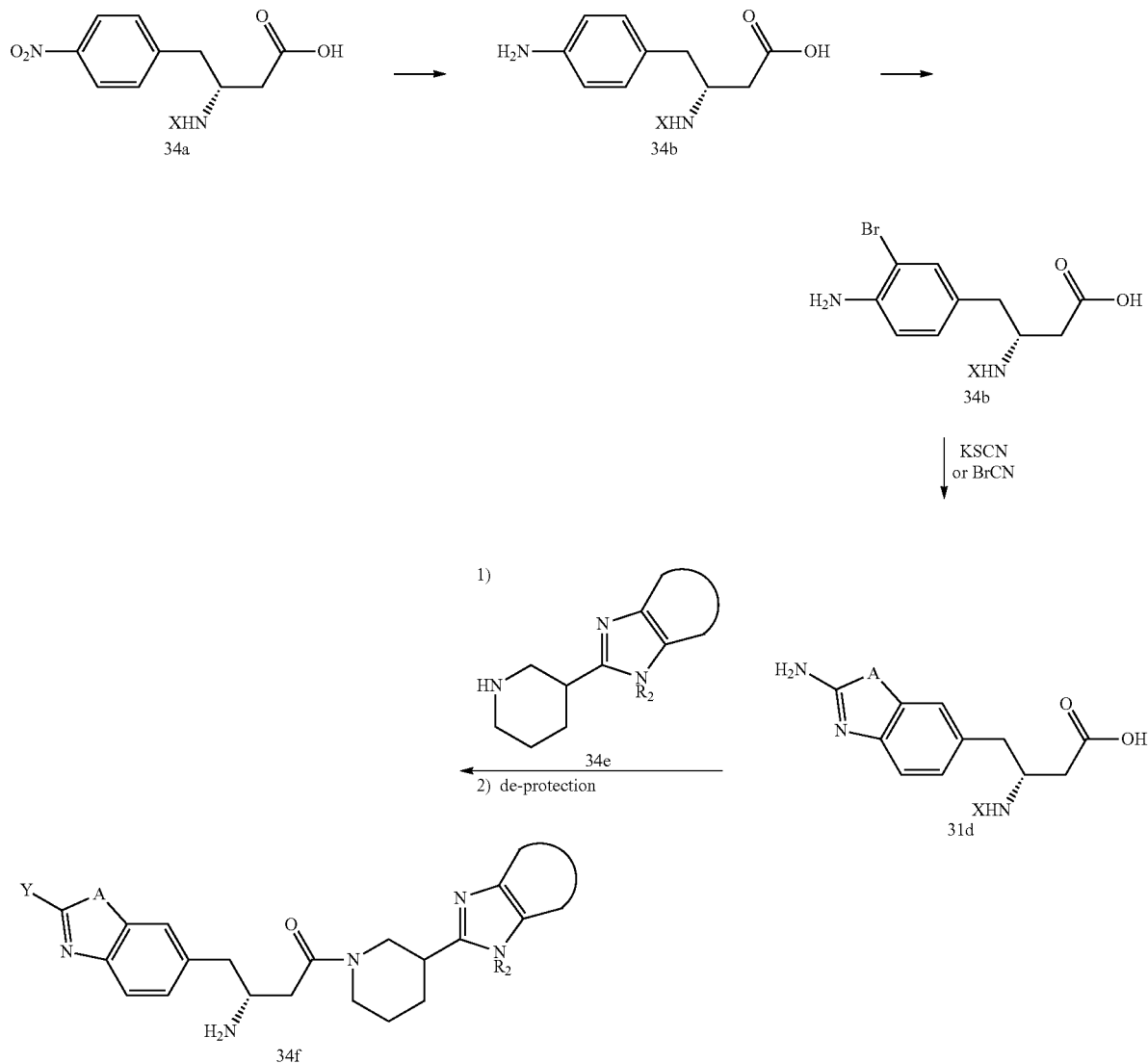

where
A = O or S
X = H or Fmoc
Y = $NH_2$ or NHR
R = alkyl, heteroalkyl, aryl, or heteroaryl

Scheme 35.

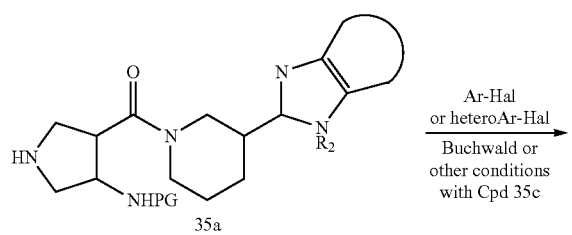

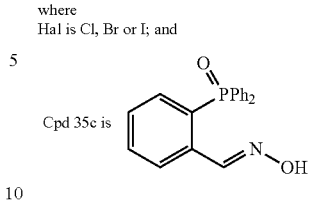

where
Hal is Cl, Br or I; and

Cpd 35c is

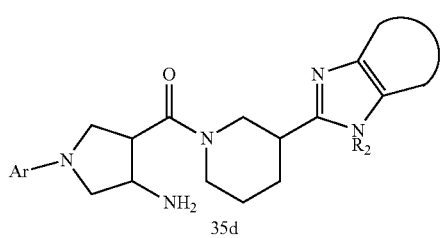

The pyrrolidine analog can be synthesized according Scheme 36, using procedures similar to literature reference. Treating the unsaturated acid with 36b in the presence catalytic TFA gives the pyrrolidine acid 36c. The acid is then converted to the acyl azide by reacting with DPPA, and rearrangement via Curtius reaction to give the N-Boc pyrrolydine acid 36d after hydrolysis of the ester. Acid-amine coupling followed by de-benzylation gives the required pyrrolidine intermediate 36f.

Scheme 36.

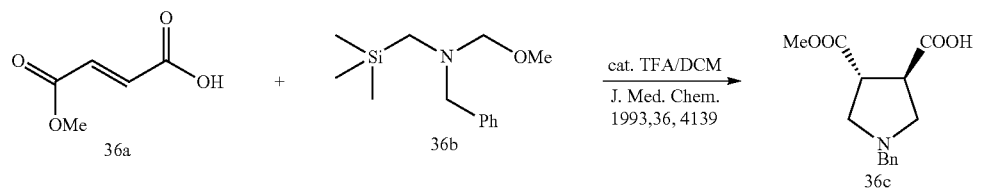

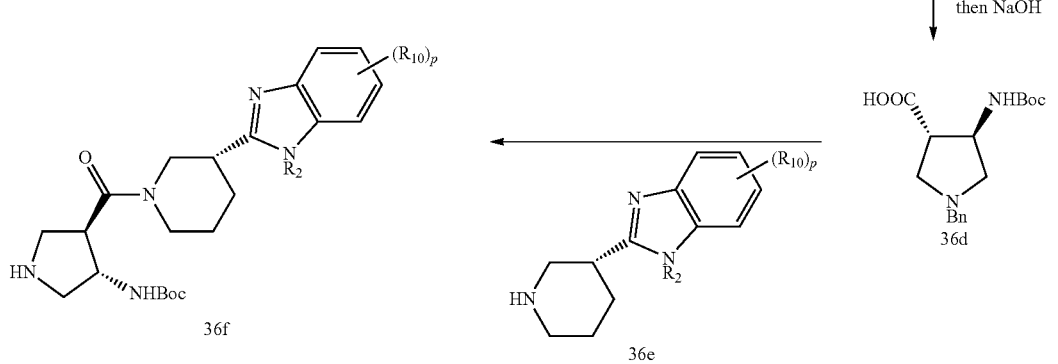

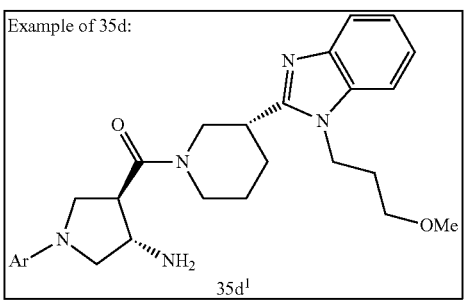

Z. Chiral Separation.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a Chiral-Pak AD-H, ChiralPak AS-H, ChiralCel OD-H, or ChiralCel OJ-H column (5μ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 μL in methanol at 0.1 mg/mL in concentration.

In another variation, preparative chiral separations are performed using a Berger MultiGram II SFC purification system. For example, samples can be loaded onto a ChiralPak AD column (21×250 mm, 10μ). In particular variations, the flow rate for separation can be 70 mL/min, the injection volume up to 2 mL, and the inlet pressure set at 130 bar. Stacked injections can be applied to increase the efficiency.

AA. General HPLC conditions:

Agilent LC/MSD System Configuration

AB. Biological Testing

The activity of compounds as renin inhibitors may be assayed in vitro, in vivo or in a cell line. Example D below provides an in vitro enzymatic activity assay for activity against renin.

Test compounds in varying concentrations may be reacted with recombinant human renin in the presence of substrate, e.g., QXL520-γ-Abu-Ile-His-Pro-Phe-His-Leu-Val-Ile-His-Thr-Lys (HiLyteFluo488)-Arg-OH (Anaspec, San Jose, Calif.). The reaction can be followed kinetically using fluorescence (excitation $\lambda=485$ nm; emission $\lambda=538$ nm). Inhibition constants ($IC_{50}$) may be calculated by non-linear curve fitting of the compound concentrations and fluorescence intensities to the standard $IC_{50}$ equation. $IC_{50}$ values for selected compounds of the present invention are given in Table XII.

Description of the syntheses of particular compounds according to the present invention based on the above reaction schemes as set forth herein.

The present invention is further exemplified, but not limited, by examples provided below that describe the synthesis of particular compounds according to the invention.

It will be apparent to those skilled in the art that various modifications and variations can be made in the compounds, compositions, kits, and methods of the present invention without departing from the spirit or scope of the invention. Thus, it is intended that the present invention cover the modi- 1. Agilent 1100 HPLC system
    Quaternary Pump
    Well-plate Sampler
    Multiple Wavelength Detectors
    Column Heater
2. MSD mass detector
3. Alltech ELSD 2000 detector
4. Columns
    FSTTFA (F)    Phenomenex Gemini 3u C18 4.6 × 30 mm
    STDTFA (S)    Phenomenex Luna 5u C18 4.6 × 50 mm
5. Gradient
    Solvent A    0.05% TFA in $H_2O$
    Solvent B    0.035% TFA in Acetonitrile

| Time (min) | Flow Rate (mL/min) | F-1 (B %) | F-2 (B %) | F-3 (B %) | F-4 (B %) | F-5 (B %) | F-6 (B %) | F-7 (B %) | F-8 (B %) | F-9 (B %) |
|---|---|---|---|---|---|---|---|---|---|---|
| 0.00 | 3.5 | 1 | 5 | 10 | 25 | 45 | 75 | 1 | 5 | 10 |
| 1.50 | 3.5 | 95 | 95 | 95 | 95 | 95 | 95 | 10 | 25 | 45 |
| 1.60 | 3.5 | 95 | 95 | 95 | 95 | 95 | 95 | 95 | 95 | 95 |
| 1.70 | 3.5 | 95 | 95 | 95 | 95 | 95 | 95 | 95 | 95 | 95 |
| 1.80 | 3.5 | 1 | 5 | 10 | 25 | 45 | 75 | 1 | 5 | 10 |
| 2.00 | 3.5 | 1 | 5 | 10 | 25 | 45 | 75 | 1 | 5 | 10 |

| Time (min) | Flow Rate (mL/min) | S-1 (B %) | S-2 (B %) | S-3 (B %) | S-4 (B %) | S-5 (B %) | S-6 (B %) | S-7 (B %) | S-8 (B %) | S-9 (B %) |
|---|---|---|---|---|---|---|---|---|---|---|
| 0.00 | 3.5 | 1 | 5 | 10 | 25 | 45 | 75 | 1 | 5 | 10 |
| 3.00 | 3.5 | 95 | 95 | 95 | 95 | 95 | 95 | 10 | 25 | 45 |
| 3.10 | 3.5 | 95 | 95 | 95 | 95 | 95 | 95 | 95 | 95 | 95 |
| 3.20 | 3.5 | 95 | 95 | 95 | 95 | 95 | 95 | 95 | 95 | 95 |
| 3.30 | 3.5 | 1 | 5 | 10 | 25 | 45 | 75 | 1 | 5 | 10 |
| 3.50 | 3.5 | 1 | 5 | 10 | 25 | 45 | 75 | 1 | 5 | 10 |

EXAMPLE

Example 1

Synthesis of 3-(1H-Benzo[d]imidazol-2-yl)-N-(3-chloro-4-methylphenyl)piperidine-1-carboxamide (1)

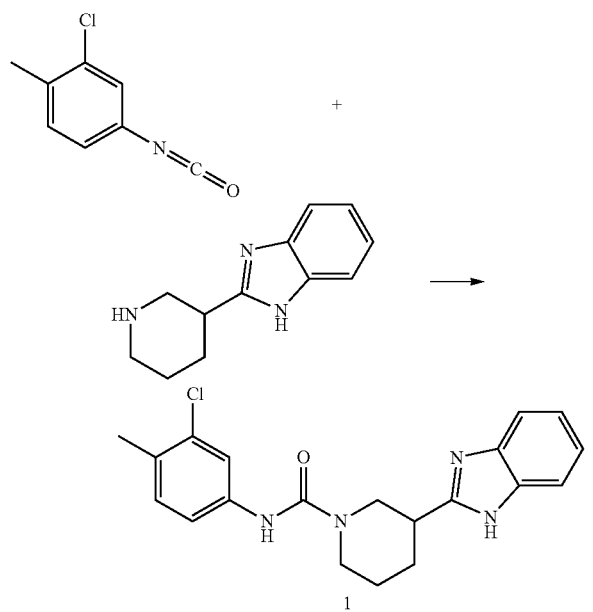

2-(piperidin-3-yl)-1H-benzo[d]imidazole (100.0 mg, 0.497 mmol) was dissolved in dichloromethane (3.0 mL). To the stirred suspension was added 2-chloro-4-isocyanato-1-methylbenzene (84.1 mg, 0.502 mmol). The reaction was stirred at ambient temperature for one hour. The crude mixture was then concentrated in vacuo and the residue was dissolved in minimal amounts of dimethylformamide and purified via preparative HPLC (10%-50% acetonitrile in water). The pure fractions were combines and lyophilized to yield the title compound 1 as a fluffy white solid (147.5 mg, 63.7%). $^1$H NMR (400 MHz, DMSO-$d_6$) δ ppm 1.55-1.65 (m, 1H), 1.83 (d, J=13.73 Hz, 1H), 1.97 (q, 0.1=18.28 Hz, 1H), 2.25 (s, 3H), 2.30 (s, 1H), 2.99 (t, J=11.44 Hz, 1H), 3.23 (t, J=13.34 Hz, 1H), 3.34-3.38 (m, 1H), 4.11 (d, J=13.35 Hz, 1H), 4.48 (d, J=13.35 Hz, 1H), 7.20 (d, J=8.4 Hz, 1H), 7.32 (d, J=8.5 Hz, 1H), 7.51-7.34 (m, 1H), 7.63 (s, 1H), 7.78-7.80 (m, 1H), 8.76 (s, 1H), ESI-MS: m/z 369.2 (M+H)$^+$.

Example 2

Synthesis of N-(3-chloro-4-methylphenyl)-3-(1-(3-methoxypropyl)-1H-benzo[d]imidazol-2-yl)piperidine-1-carboxamide (2)

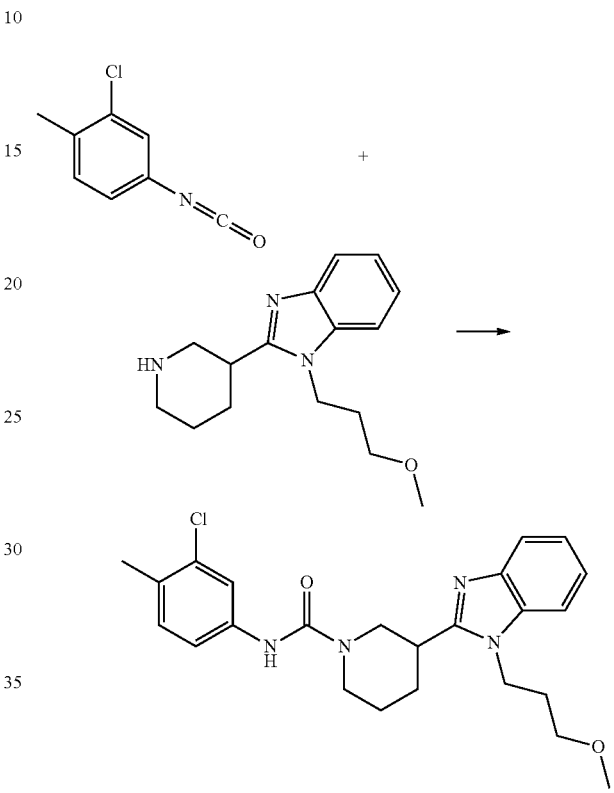

N-(3-chloro-4-methylphenyl)-3-(1-(3-methoxypropyl)-1H-benzo[d]imidazol-2-yl)piperidine-1-carboxamide may be prepared according to Example 1 by using the corresponding N-alkylated piperidinyl benzoimidazole.

Other compounds that were prepared according to the procedure outlined in Example 1-A using the corresponding isocyanato starting reagents are listed in Table I. As described in Example 2, N-alkylated analogs of these compounds may be prepared by using the corresponding N-alkylated piperidinyl benzoimidazole starting reagents.

TABLE I

| Compound No. | Structure/Name | ESI-MS: m/z (M + H$^+$) |
|---|---|---|
| 3 | ![structure] 3-(1H-benzo[d]imidazol-2-yl)-N-benzoylpiperidine-1-carboxamide | 335.4 |

TABLE I-continued
| Compound No. | Structure/Name | ESI-MS: m/z (M + H+) |
|---|---|---|
| 4 | 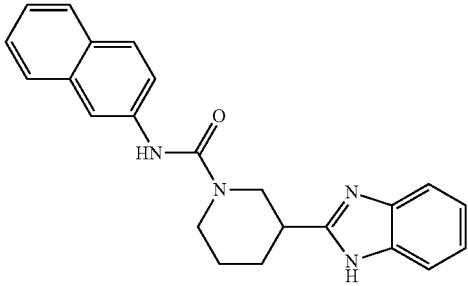  3-(1H-benzo[d]imidazol-2-yl)-N-(naphthalen-2-yl)piperidine-1-carboxamide | 371.4 |
| 5 | 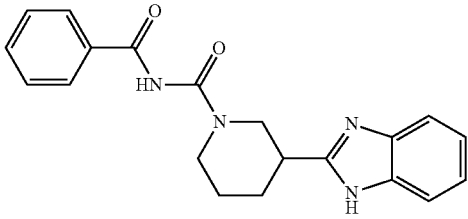  3-(1H-benzo[d]imidazol-2-yl)-N-benzoylpiperidine-1-carboxamide | 349.3 |
| 6 | 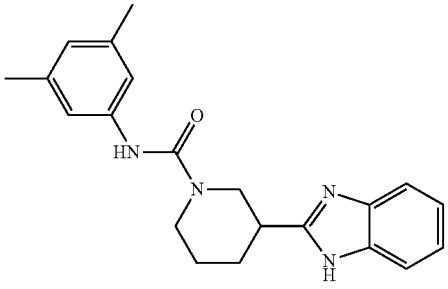  3-(1H-benzo[d]imidazol-2-yl)-N-(3,5-dimethylphenyl)piperidine-1-carboxamide | 349.4 |
| 7 | 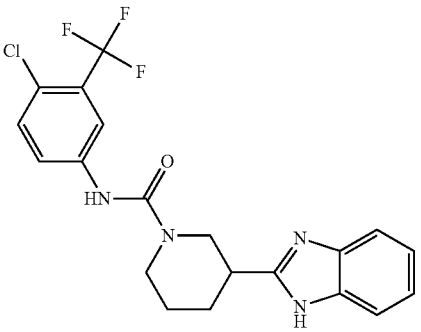  3-(1H-benzo[d]imidazol-2-yl)-N-(4-chloro-3-(trifluoromethyl)phenyl)piperidine-1-carboxamide | 423.3 |

TABLE I-continued

| Compound No. | Structure/Name | ESI-MS: m/z (M + H+) |
|---|---|---|
| 8 | 3-(1H-benzo[d]imidazol-2-yl)-N-phenylpiperidine-1-carboxamide | 321.3 |
| 9 | 3-(1H-benzo[d]imidazol-2-yl)-N-(2,3-dihydro-1H-inden-5-yl)piperidine-1-carboxamide | 361.4 |
| 10 | 3-(1H-benzo[d]imidazol-2-yl)-N-cyclohexylpiperidine-1-carboxamide | 327.4 |
| 11 | N-(benzo[d][1,3]dioxol-5-yl)-3-(1H-benzo[d]imidazol-2-yl)piperidine-1-carboxamide | 365.3 |

TABLE I-continued
| Compound No. | Structure/Name | ESI-MS: m/z (M + H+) |
|---|---|---|
| 12 | 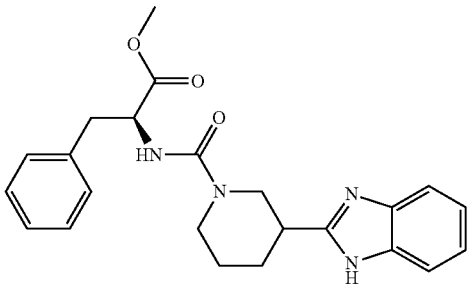<br>(2S)-methyl 2-(3-(1H-benzo[d]imidazol-2-yl)piperidine-1-carboxamido)-3-phenylpropanoate | 407.4 |
| 13 | 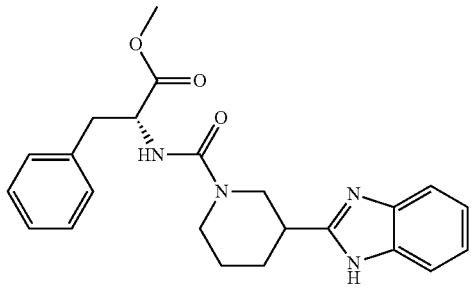<br>(2R)-methyl 2-(3-(1H-benzo[d]imidazol-2-yl)piperidine-1-carboxamido)-3-phenylpropanoate | 407.4 |
| 14 | 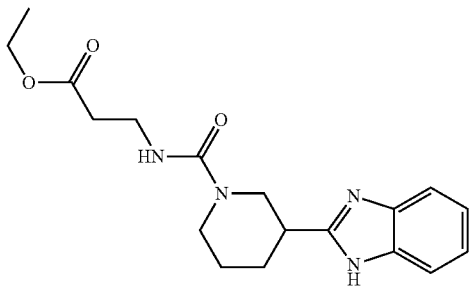<br>ethyl 3-(3-(1H-benzo[d]imidazol-2-yl)piperidine-1-carboxamido)propanoate | 345.4 |
| 15 | 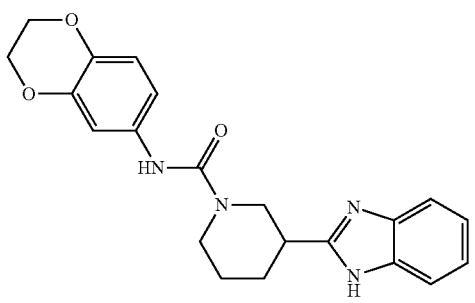<br>3-(1H-benzo[d]imidazol-2-yl)-N-(2,3-dihydrobenzo[b][1,4]dioxin-6-yl)piperidine-1-carboxamide | 379.3 |

TABLE I-continued

| Compound No. | Structure/Name | ESI-MS: m/z (M + H+) |
|---|---|---|
| 16 | 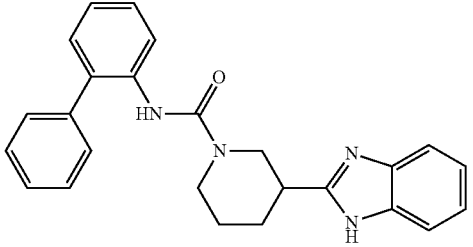<br>3-(1H-benzo[d]imidazol-2-yl)-N-(biphenyl-2-yl)piperidine-1-carboxamide | 397.4 |
| 17 | 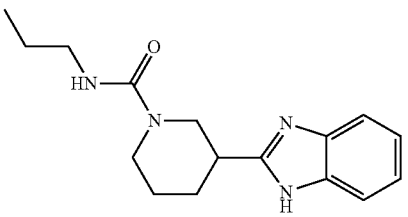<br>3-(1H-benzo[d]imidazol-2-yl)-N-propylpiperidine-1-carboxamide | 287.4 |
| 18 | 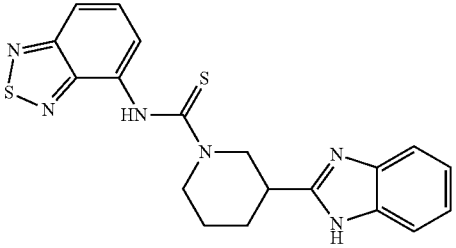<br>N-(benzo[c][1,2,5]thiadiazol-4-yl)-3-(1H-benzo[d]imidazol-2-yl)piperidine-1-carboxthioamide | 395.3 |
| 19 | 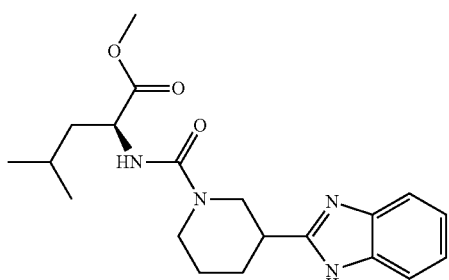<br>(2S)-methyl 2-(3-(1H-benzo[d]imidazol-2-yl)piperidine-1-carboxamido)-4-methylpentanoate | 373.4 |
| 20 | 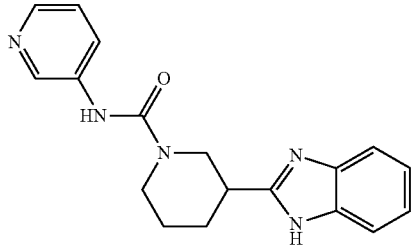<br>3-(1H-benzo[d]imidazol-2-yl)-N-(pyridin-3-yl)piperidine-1-carboxamide | 322.3 |

TABLE I-continued

| Compound No. | Structure/Name | ESI-MS: m/z (M + H+) |
|---|---|---|
| 21 | 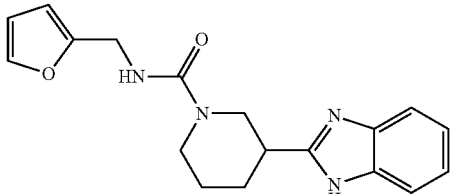<br>3-(1H-benzo[d]imidazol-2-yl)-N-(furan-2-ylmethyl)piperidine-1-carboxamide | 325.3 |
| 22 | 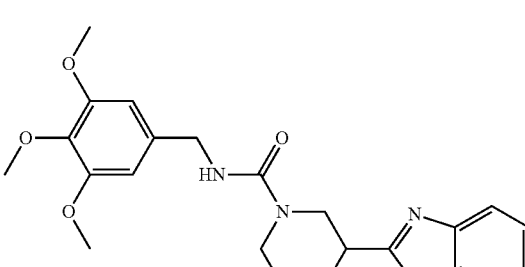<br>3-(1H-benzo[d]imidazol-2-yl)-N-(3,4,5-trimethoxybenzyl)piperidine-1-carboxamide | Not tested |

Example 3

Synthesis of (3R)-1-(3-(1H-Benzo[d]imidazol-2-yl)piperidin-1-yl)-3-amino-4-(4-chlorophenyl)butan-1-one (23)

Step A.

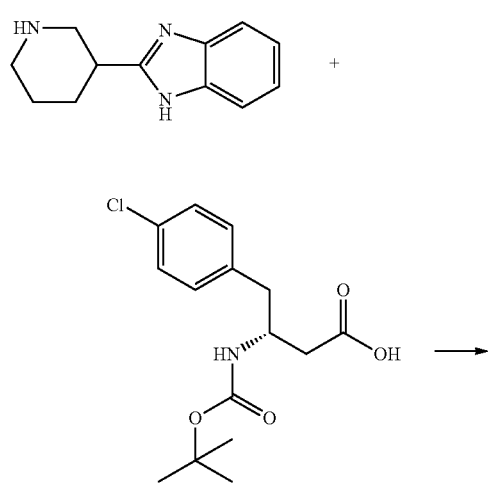

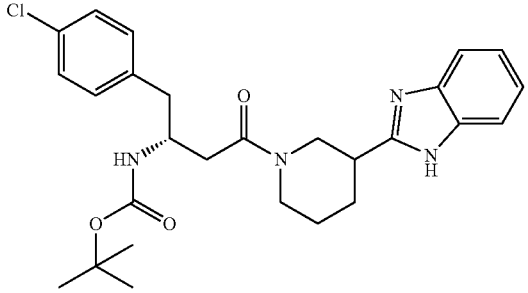

3A

To a flask containing 2-(piperidin-3-yl)-1H-benzo[d]imidazole hydrochloride (200.0 mg, 0.841 mmol) and (R)-3-(tert-butoxycarbonylamino)-4-(4-chlorophenyl) butanoic acid (282.5 mg, 0.900 mmol) was added dichloromethane (5 mL) and triethylamine (0.23 mL, 1.683 mmol); the reaction mixture was stirred at room temperature until all the components dissolved. To the solution was added 1-(3-dimethylaminopropyl)-3-ethylcarbodiimide hydrochloride (193.5 mg, 1.010 mmol) followed by N-hydroxybenzotriazole (142.1 mg, 1.052 mmol). The solution was stirred at ambient temperature for 12 hrs and diluted with excess DCM (5 mL). The solution was washed with water (2×8 mL) and brine (1x 5 mL), and then the organic layer was collected, dried with $Na_2SO_4$, and concentrated to yield tert-butyl (2R)-4-(3-(1H-benzo[d]imidazol-2-yl)piperidin-1-yl)-1-(4-chlorophenyl)-4-oxobutan-2-ylcarbamate (3A) as an amorphous solid (415.9 mg, 99.5% yield). ESI-MS: m/z 497.4 (M+H)+.

Step B.

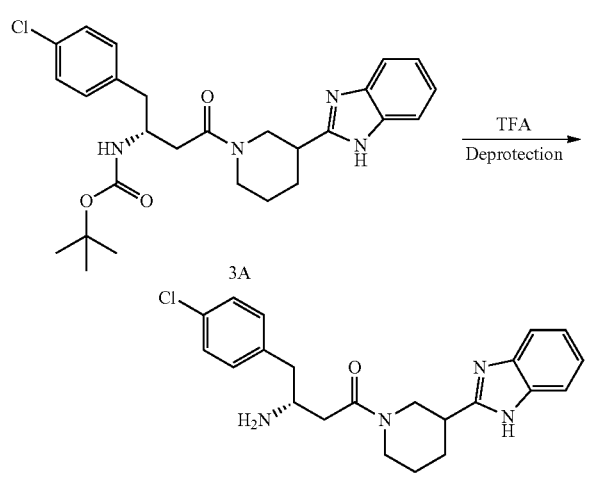

Compound 3A from Step A (60.0 mg, 0.121 mmol) was dissolved in dichloromethane (2 mL) and trifluoroacetic acid (1 mL) was added to the vigorously stirred solution at ambient temperature. The reaction was stirred for 2 hrs and then concentrated to an oil. The crude oil was purified via preparative HPLC to yield the title compound (3R)-1-(3-(1H-benzo[d] imidazol-2-yl)piperidin-1-yl)-3-amino-4-(4-chlorophenyl) butan-1-one (22) as the TFA salt (30.0 mg, 50.1%). $^1$H NMR (400 MHz, DMSO-$d_6$) δ ppm 1.42-1.49 (m, 1H), 1.72-1.99 (m, 2H), 2.60-3.29 (m, 7H), 3.40-3.56 (m, 1H), 3.65-3.84 (m, 2H), 4.07-4.17 (m, 1H), 4.35 (d, J=17.04 Hz, 0.5H), 4.73 (d, J=12.17 Hz, 0.5H), 7.29-7.43 (m, 6H), 7.66 (d, J=25.88 Hz, 2H), 7.87 (d, J=16.47 Hz, 3H). ESI-MS: m/z 397.2 (M+H)$^+$.

Example 4

Synthesis of (3R)-3-amino-4-(4-chlorophenyl)-1-(3-(1-(3-methoxypropyl)-1H-benzo[d]imidazol-2-yl) piperidin-1-yl)butan-1-one (24)

tert-Butyl (2R)-4-(3-(1H-benzo[d]imidazol-2-yl)piperidin-1-yl)-1-(4-chlorophenyl)-4-oxobutan-2-ylcarbamate (3A) (100.0 mg, 0.201 mmol), as prepared in Example 3, Step A, was dissolved in acetonitrile (1.2 mL) followed by the addition of 1-bromo-3-methoxypropane (307.9 mg, 20.1 mmol) and potassium carbonate (60 mg, 0.434 mmol). The reaction was stirred for 16 hrs at 65° C. The mixture was then cooled to ambient temperature and filtered through Celite. The filtrate was concentrated to tert-butyl (2R)-1-(4-chlorophenyl)-4-(3-(1-(3-methoxypropyl)-1H-benzo[d]imidazol-2-yl)piperidin-1-yl)-4-oxobutan-2-ylcarbamate (4A) an amorphous solid and used without further purification. ESI-MS: m/z 569.4 (M+H)$^+$.

Step B.

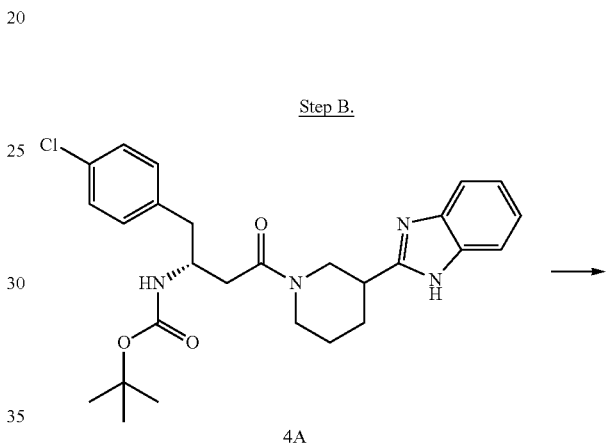

Step A.

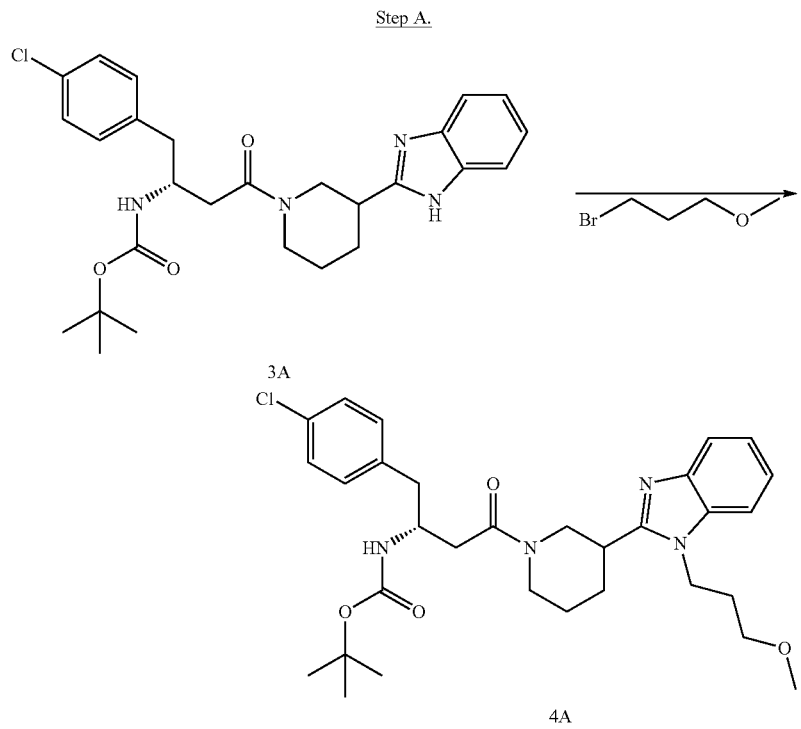

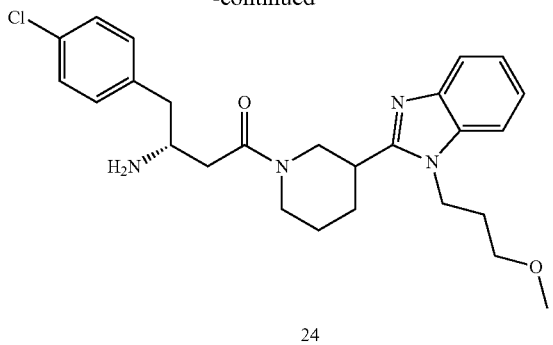

24

Deprotection of Compound 4A as described in Example 3, Step B yielded the title compound (3R)-3-Amino-4-(4-chlorophenyl)-1-(3-(1-(3-methoxypropyl)-1H-benzo[d]imidazol-2-yl)piperidin-1-yl)butan-1-one (24). ESI-MS: m/z 469.3 (M+H)+.

Other compounds that were prepared according to the procedure outlined in Example 3 using the corresponding butanoic acid starting reagents are listed in Table II. N-Alkylated analogs of these compounds may be prepared by the procedure outlined in Example 4, Step A, followed by deprotection according to the procedure in Example 3, Step B.

TABLE II

| Compound No. | Structure/Name | ESI-MS: m/z (M + H+) |
|---|---|---|
| 25 | (3S)-1-(3-(1H-benzo[d]imidazol-2-yl)piperidin-1-yl)-3-amino-3-(4-(trifluoromethyl)phenyl)propan-1-one | 417.1 |
| 26 | (3S)-1-(3-(1H-benzo[d]imidazol-2-yl)piperidin-1-yl)-3-amino-3-(2-nitrophenyl)propan-1-one | 394.1 |
| 27 | (3R)-1-(3-(1H-benzo[d]imidazol-2-yl)piperidin-1-yl)-3-amino-4-(2-chlorophenyl)butan-1-one | 397.1 |
| 28 | (3S)-1-(3-(1H-benzo[d]imidazol-2-yl)piperidin-1-yl)-3-amino-3-(2,3-dimethoxyphenyl)propan-1-one | 409.1 |

TABLE II-continued

| Compound No. | Structure/Name | ESI-MS: m/z (M + H⁺) |
|---|---|---|
| 29 | 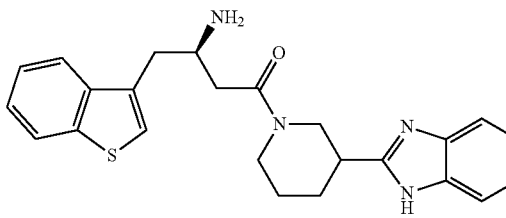<br>(3R)-1-(3-(1H-benzo[d]imidazol-2-yl)piperidin-1-yl)-3-amino-4-(benzo[b]thiophen-3-yl)butan-1-one | 419.1 |
| 30 | 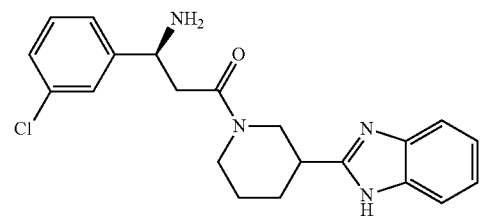<br>(3S)-1-(3-(1H-benzo[d]imidazol-2-yl)piperidin-1-yl)-3-amino-3-(3-chlorophenyl)propan-1-one | 383.2 |
| 31 | 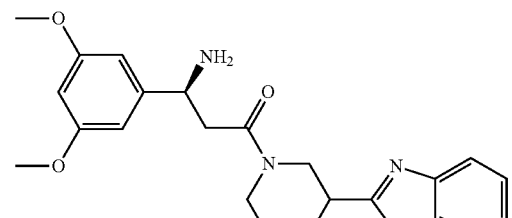<br>(3S)-1-(3-(1H-benzo[d]imidazol-2-yl)piperidin-1-yl)-3-amino-3-(3,5-dimethoxyphenyl)propan-1-one | 409.2 |
| 32 | 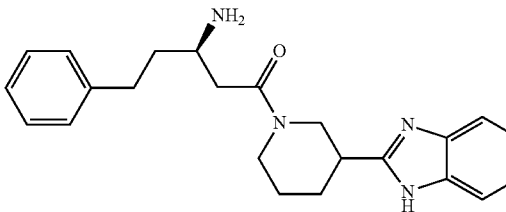<br>(3R)-1-(3-(1H-benzo[d]imidazol-2-yl)piperidin-1-yl)-3-amino-5-phenylpentan-1-one | 377.2 |
| 33 | 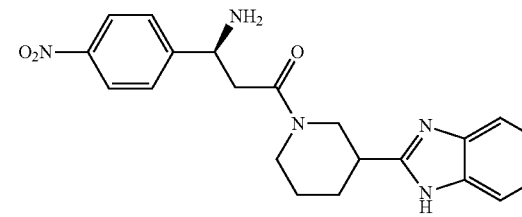<br>(3S)-1-(3-(1H-benzo[d]imidazol-2-yl)piperidin-1-yl)-3-amino-3-(4-nitrophenyl)propan-1-one | 394.2 |

TABLE II-continued

| Compound No. | Structure/Name | ESI-MS: m/z (M + H⁺) |
|---|---|---|
| 34 | 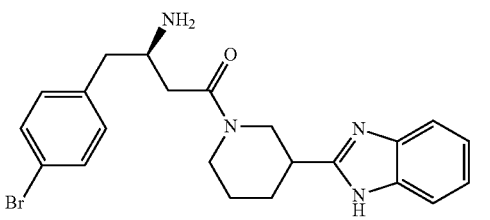<br>(3R)-1-(3-(1H-benzo[d]imidazol-2-yl)piperidin-1-yl)-3-amino-4-(4-bromophenyl)butan-1-one | 441.2 |
| 35 | 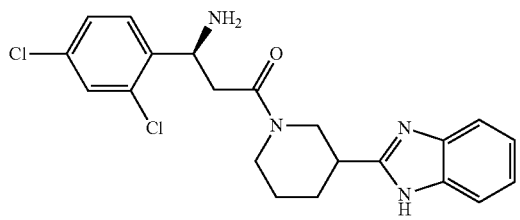<br>(3S)-1-(3-(1H-benzo[d]imidazol-2-yl)piperidin-1-yl)-3-amino-3-(2,4-dichlorophenyl)propan-1-one | 417.1 |
| 36 | 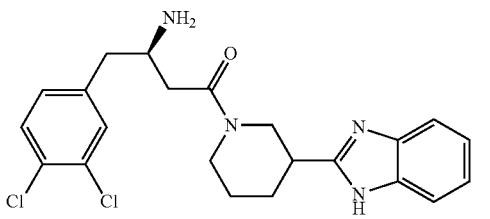<br>(3R)-1-(3-(1H-benzo[d]imidazol-2-yl)piperidin-1-yl)-3-amino-4-(3,4-dichlorophenyl)butan-1-one | 431.1 |
| 37 | 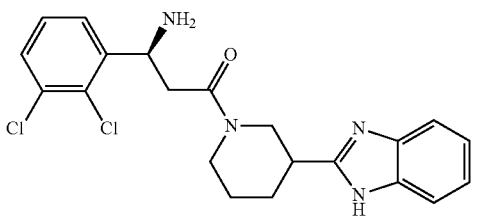<br>(3S)-1-(3-(1H-benzo[d]imidazol-2-yl)piperidin-1-yl)-3-amino-3-(2,3-dichlorophenyl)propan-1-one | 417.1 |
| 38 | 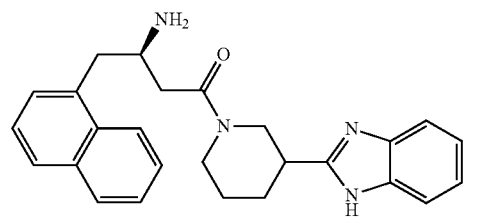<br>(3R)-1-(3-(1H-benzo[d]imidazol-2-yl)piperidin-1-yl)-3-amino-4-(naphthalen-1-yl)butan-1-one | 413.2 |

TABLE II-continued

| Compound No. | Structure/Name | ESI-MS: m/z (M + H+) |
|---|---|---|
| 39 | 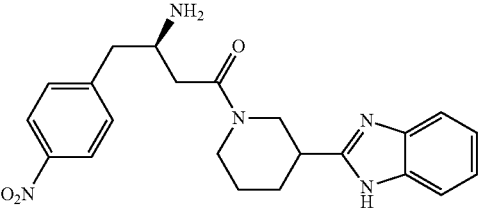<br>(3R)-1-(3-(1H-benzo[d]imidazol-2-yl)piperidin-1-yl)-3-amino-4-(4-nitrophenyl)butan-1-one | 408.2 |
| 40 | 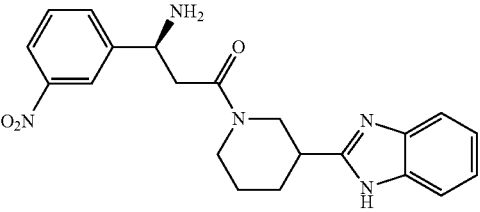<br>(3S)-1-(3-(1H-benzo[d]imidazol-2-yl)piperidin-1-yl)-3-amino-3-(3-nitrophenyl)propan-1-one | 394.2 |
| 41 | 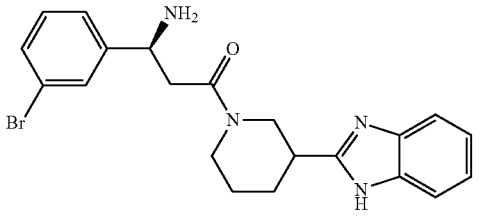<br>(3S)-1-(3-(1H-benzo[d]imidazol-2-yl)piperidin-1-yl)-3-amino-3-(3-bromophenyl)propan-1-one | 427.1 |
| 42 | 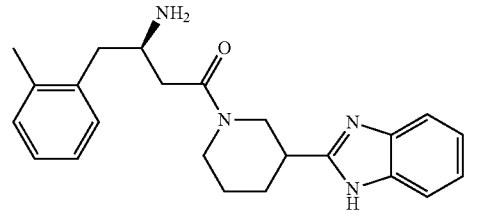<br>(3R)-1-(3-(1H-benzo[d]imidazol-2-yl)piperidin-1-yl)-3-amino-4-o-tolylbutan-1-one | 377.2 |
| 43 | 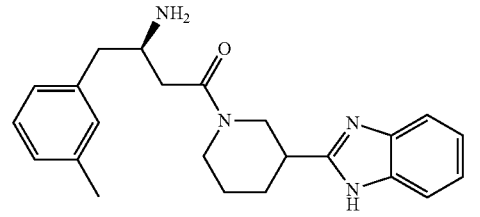<br>(3R)-1-(3-(1H-benzo[d]imidazol-2-yl)piperidin-1-yl)-3-amino-4-m-tolylbutan-1-one | 377.2 |

TABLE II-continued

| Compound No. | Structure/Name | ESI-MS: m/z (M + H⁺) |
|---|---|---|
| 44 | 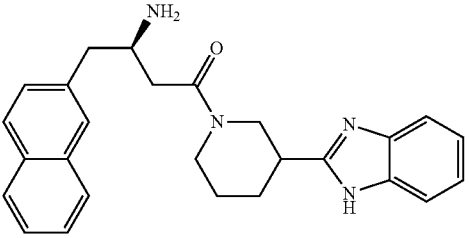<br>(3R)-1-(3-(1H-benzo[d]imidazol-2-yl)piperidin-1-yl)-3-amino-4-(naphthalen-2-yl)butan-1-one | 413.2 |
| 45 | 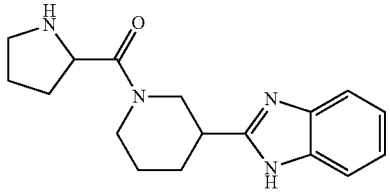<br>(3-(1H-benzo[d]imidazol-2-yl)piperidin-1-yl)(pyrrolidin-2-yl)methanone | 299.2 |
| 46 | 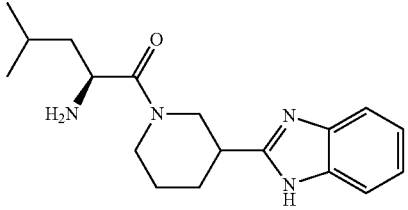<br>(2S)-1-(3-(1H-benzo[d]imidazol-2-yl)piperidin-1-yl)-2-amino-4-methylpentan-1-one | 315.2 |
| 47 | 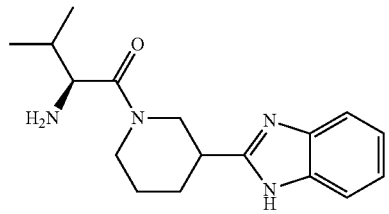<br>(2S)-1-(3-(1H-benzo[d]imidazol-2-yl)piperidin-1-yl)-2-amino-3-methylbutan-1-one | 301.2 |
| 48 | 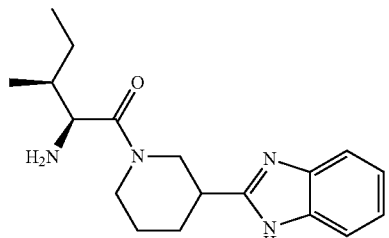<br>(2S,3S)-1-(3-(1H-benzo[d]imidazol-2-yl)piperidin-1-yl)-2-amino-3-methylpentan-1-one | 315.2 |

TABLE II-continued

| Compound No. | Structure/Name | ESI-MS: m/z (M + H⁺) |
|---|---|---|
| 49 | 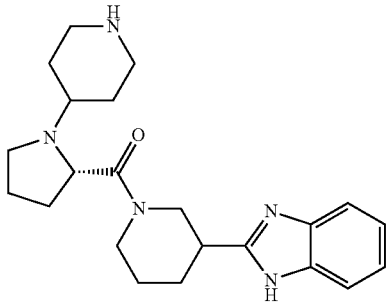 (3-(1H-benzo[d]imidazol-2-yl)piperidin-1-yl)((S)-1-(piperidin-4-yl)pyrrolidin-2-yl)methanone | 382.2 |
| 50 | 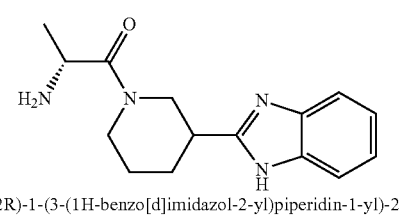 (2R)-1-(3-(1H-benzo[d]imidazol-2-yl)piperidin-1-yl)-2-aminopropan-1-one | 273.2 |
| 51 | 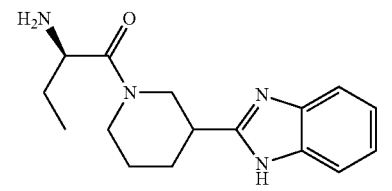 (2R)-1-(3-(1H-benzo[d]imidazol-2-yl)piperidin-1-yl)-2-aminobutan-1-one | 287.2 |
| 52 | 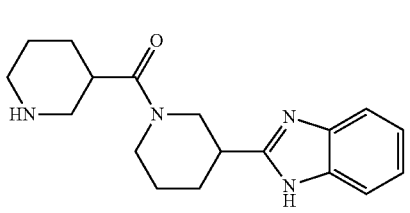 (3-(1H-benzo[d]imidazol-2-yl)piperidin-1-yl)(piperidin-3-yl)methanone | 313.2 |
| 53 | 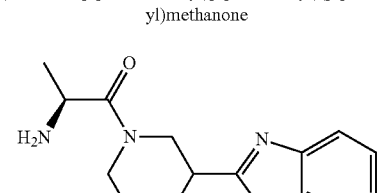 (2S)-1-(3-(1H-benzo[d]imidazol-2-yl)piperidin-1-yl)-2-aminopropan-1-one | 273.2 |
| 54 | 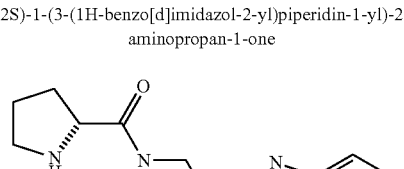 (3-(1H-benzo[d]imidazol-2-yl)piperidin-1-yl)((R)-pyrrolidin-2-yl)methanone | 299.2 |

TABLE II-continued

| Compound No. | Structure/Name | ESI-MS: m/z (M + H⁺) |
|---|---|---|
| 55 | 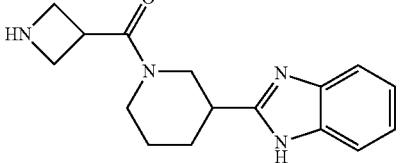<br>(3-(1H-benzo[d]imidazol-2-yl)piperidin-1-yl)(azetidin-3-yl)methanone | 285.2 |
| 56 | 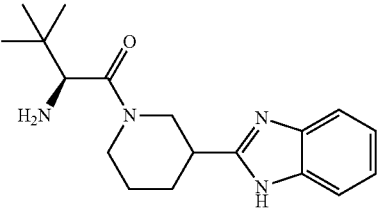<br>(2S)-1-(3-(1H-benzo[d]imidazol-2-yl)piperidin-1-yl)-2-amino-3,3-dimethylbutan-1-one | 315.2 |
| 57 | 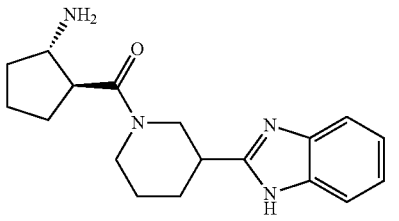<br>(3-(1H-benzo[d]imidazol-2-yl)piperidin-1-yl)((1S,2S)-2-aminocyclopentyl)methanone | 313.2 |
| 58 | 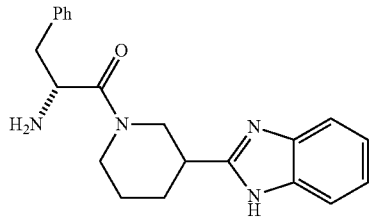<br>(2R)-1-(3-(1H-benzo[d]imidazol-2-yl)piperidin-1-yl)-2-amino-3-phenylpropan-1-one | 349.2 |
| 59 | 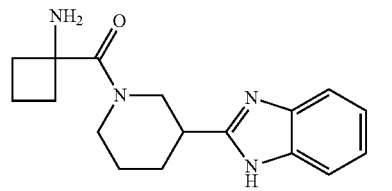<br>(3-(1H-benzo[d]imidazol-2-yl)piperidin-1-yl)(1-aminocyclobutyl)methanone | 299.2 |
| 60 | 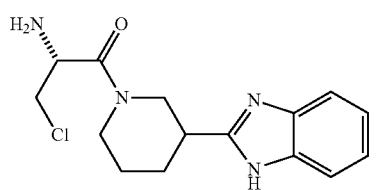<br>(2R)-1-(3-(1H-benzo[d]imidazol-2-yl)piperidin-1-yl)-2-amino-3-chloropropan-1-one | 307.1 |

TABLE II-continued

| Compound No. | Structure/Name | ESI-MS: m/z (M + H+) |
|---|---|---|
| 61 | 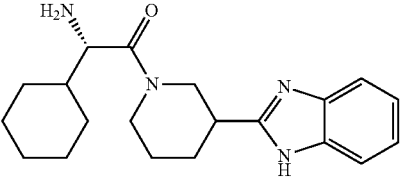<br>(2S)-1-(3-(1H-benzo[d]imidazol-2-yl)piperidin-1-yl)-2-amino-2-cyclohexylethanone | 341.2 |
| 62 | 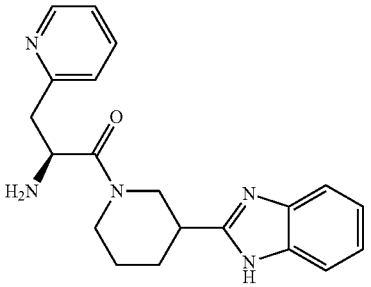<br>(2S)-1-(3-(1H-benzo[d]imidazol-2-yl)piperidin-1-yl)-2-amino-3-(pyridin-2-yl)propan-1-one | 350.2 |
| 63 | 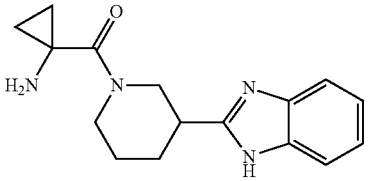<br>(3-(1H-benzo[d]imidazol-2-yl)piperidin-1-yl)(1-aminocyclopropyl)methanone | 285.2 |
| 64 | 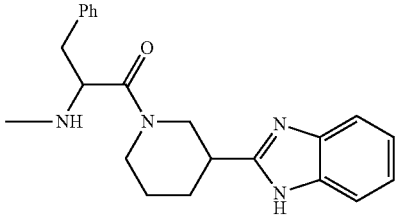<br>1-(3-(1H-benzo[d]imidazol-2-yl)piperidin-1-yl)-2-(methylamino)-3-phenylpropan-1-one | 363.2 |
| 65 | 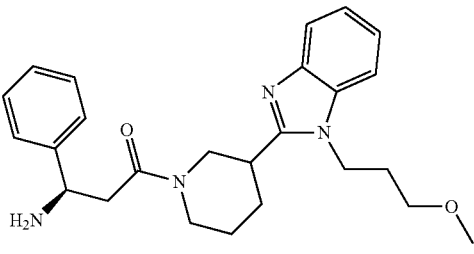<br>(3R)-3-amino-1-(3-(1-(3-methoxypropyl)-1H-benzo[d]imidazol-2-yl)piperidin-1-yl)-3-phenylpropan-1-one | 421.4 |

TABLE II-continued

| Compound No. | Structure/Name | ESI-MS: m/z (M + H+) |
|---|---|---|
| 66 | 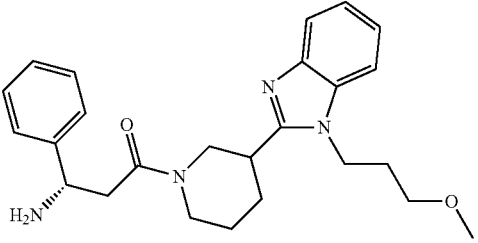<br>(3S)-3-amino-1-(3-(1-(3-methoxypropyl)-1H-benzo[d]imidazol-2-yl)piperidin-1-yl)-3-phenylpropan-1-one | 421.2 |
| 67 | 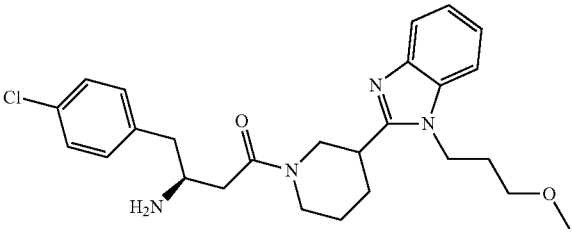<br>(3S)-3-amino-4-(4-chlorophenyl)-1-(3-(1-(3-methoxypropyl)-1H-benzo[d]imidazol-2-yl)piperidin-1-yl)butan-1-one | 469.3 |
| 68 | 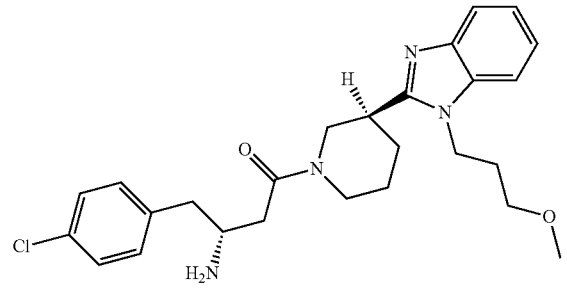<br>(R)-3-amino-4-(4-chlorophenyl)-1-((S)-3-(1-(3-methoxypropyl)-1H-benzo[d]imidazol-2-yl)piperidin-1-yl)butan-1-one | 469.3 |
| 69 | 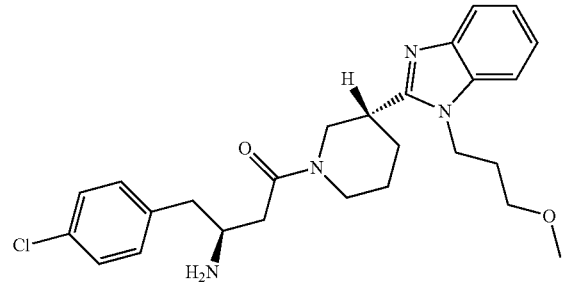<br>(S)-3-amino-4-(4-chlorophenyl)-1-((R)-3-(1-(3-methoxypropyl)-1H-benzo[d]imidazol-2-yl)piperidin-1-yl)butan-1-one | 469.3 |

TABLE II-continued

| Compound No. | Structure/Name | ESI-MS: m/z (M + H+) |
|---|---|---|
| 70 | 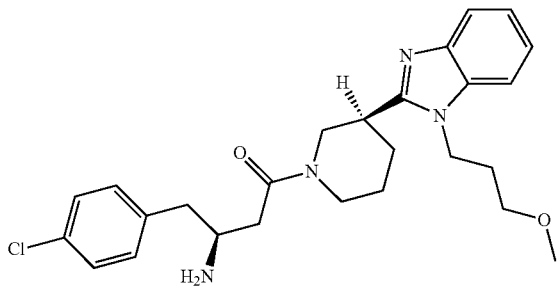<br>(S)-3-amino-4-(4-chlorophenyl)-1-((S)-3-(1-(3-methoxypropyl)-1H-benzo[d]imidazol-2-yl)piperidin-1-yl)butan-1-one | 469.3 |

Example 5

Synthesis of (R)-1((R)-3-(1H-benzo[d]imidazol-2-yl)piperidin-1-yl)-3-amino-4-(biphenyl-4-yl)butan-1-one (71)

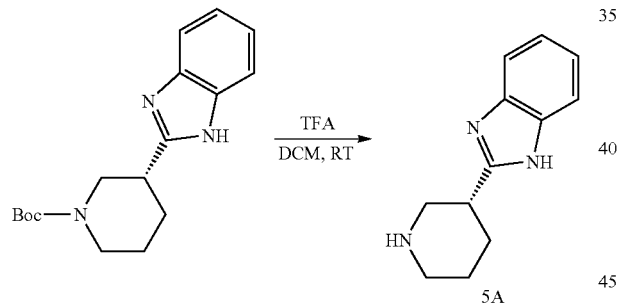

(R)-tert-butyl 3-(1H-benzo[d]imidazol-2-yl)piperidine-1-carboxylate (0.29 mmol, 88 mg) in $CH_2Cl_2$ (10 mL) was added TFA (1 mL). The reaction solution was stirred at rt for 1 h and then concentrated in vacuo. The residue containing (R)-2-(piperidin-3-yl)-1H-benzo[d]imidazole (5A) was carried directly on to the next step without further purification. ESI-MS: m/z 202.4 $(M+H)^+$.

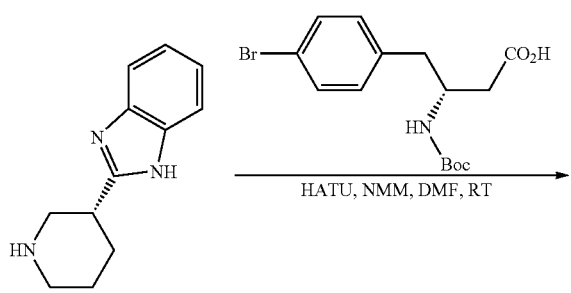

-continued

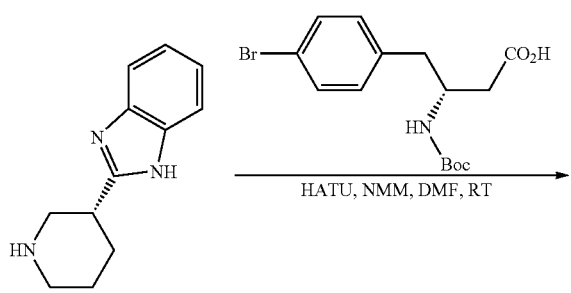

(R)-2-(Piperidin-3-yl)-1H-benzo[d]imidazole (5A) (0.29 mmol, 58 mg) in DMF (15 mL) was added (R)-4-(4-bromophenyl)-3-(tert-butoxycarbonylamino)butanoic acid (0.32 mmol, 115 mg) and N-methylmorphine (1.16 mmol, 0.13 mL). The reaction mixture was stirred at rt for 5 min and then added HATU (0.32 mmol, 122 mg) and kept stirring at rt overnight. The reaction mixture was poured into $H_2O$, extracted with EtOAc. The extract was washed with $H_2O$, brine, dried over $MgSO_4$ and filtered. The filtrate was concentrated in vacuo and purified by preparative LC/MS (35-60% $CH_3CN$ in $H_2O$) to afford tert-butyl (R)-4-((R)-3-(1H-benzo[d]imidazol-2-yl)piperidin-1-yl)-1-(4-bromophenyl)-4-oxobutan-2-ylcarbamate (5B) (0.22 mmol, 120 mg, two-step yield: 75.9%). ESI-MS: m/z 542.3 $(M+H)^+$.

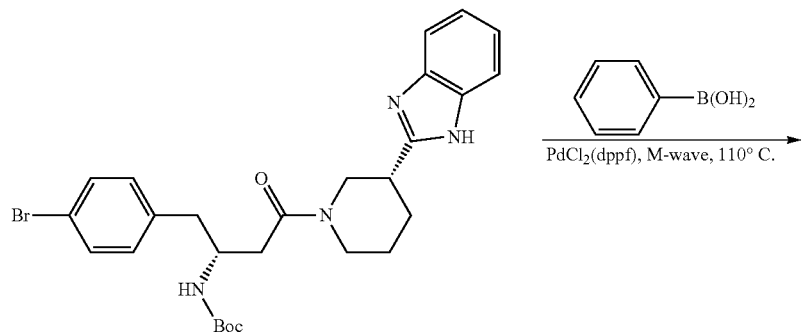

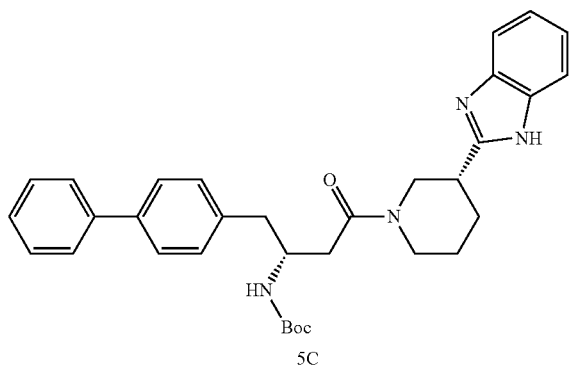
5C tert-Butyl (R)-4-((R)-3-(1H-benzo[d]imidazol-2-yl)piperidin-1-yl)-1-(4-bromophenyl)-4-oxobutan-2-ylcarbamate (5B) (0.22 mmol, 120 mg) in dioxane (2 mL) was added phenylboronic acid (0.29 mmol, 35 mg), 1,1'-bis(diphenylphosphino)ferrocene (0.011 mmol, 8 mg) and sat'd NaHCO$_3$ (1 mL). The reaction mixture was heated to 110° C. in microwave for 15 min and then poured into H$_2$O, extracted with EtOAc. The extract was washed with brine, dried over MgSO$_4$ and filtered. The filtrate was concentrated in vacuo. The residue containing tert-butyl (R)-4-((R)-3-(1H-benzo[d]imidazol-2-yl)piperidin-1-yl)-1-(biphenyl-4-yl)-4-oxobutan-2-ylcarbamate (5C) was carried directly on to the next step without further purification. ESI-MS: m/z 539.5 (M+H)$^+$.

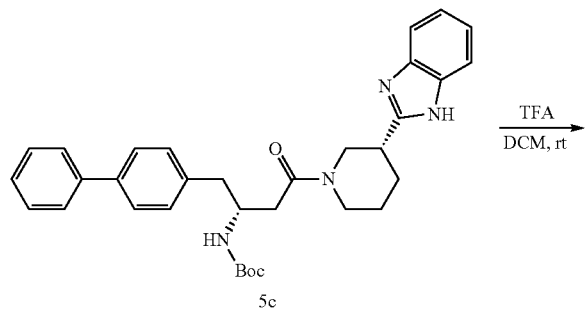
5c

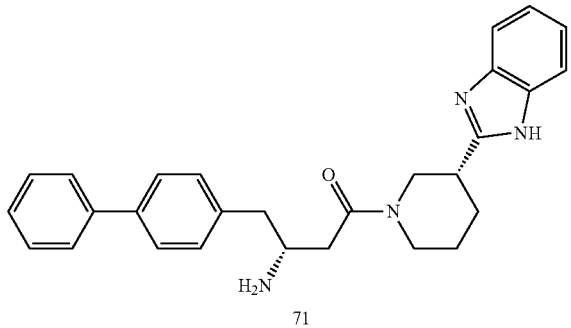
71 tert-Butyl (R)-4-((R)-3-(1H-benzo[d]imidazol-2-yl)piperidin-1-yl)-1-(biphenyl-4-yl)-4-oxobutan-2-ylcarbamate (5C) (0.22 mmol, 120 mg) in DCM (5 mL) was added TEA (1 mL). The reaction solution was stirred at rt for 1 h and then concentrated in vacuo. The residue was purified by preparative LC/MS (20-50% CH$_3$CN in H$_2$O) to afford the title compound (R)-1-((R)-3-(1H-benzo[d]imidazol-2-yl)piperidin-1-yl)-3-amino-4-(biphenyl-4-yl)butan-1-one (71) (0.14 mmol, 63 mg, two-step yield: 63.6%). ESI-MS: m/z 439.4 (M+H)$^+$. 1H NMR (400 MHz, MeOD) δ ppm 1.56-1.75 (m, 1H) 1.92 (ddd, J=13.77, 7.29, 3.51Hz, 1H) 2.06 (dd, J=13.01, 3.66 Hz, 1H) 2.38 (dd, J=9.09, 3.73 Hz, 1H) 2.69-2.89 (m, 2H) 3.00-3.16 (m, 2H) 3.16-3.26 (m, 1H) 3.39-3.49 (m, 1H) 3.88 (ddd, J=10.80, 7.33, 3.79 Hz, 1H) 4.32 (d, J=9.54 Hz, 1H) 4.64 (d, J=13.14 Hz, 1H) 4.83 (dd, J=12.92, 3.44 Hz, 1H) 7.29-7.46 (m, 5H) 7.54-7.66 (m, 6H) 7.77 (dd, J=6.16, 3.13 Hz, 2H).

Example 6

Synthesis of (R)-3-Amino-4-(biphenyl-4-yl)-1((R)-3-(1-(3-methoxypropyl)-1H-benzo[d]imidazol-2-yl)piperidin-1-yl)butan-1-one (72) and (R)-4-(biphenyl-4-yl)-3-hydroxy-1-(3-(1-(3-methoxypropyl)-1H-benzo[d]imidazol-2-yl)piperidin-1-yl)butan-1-one (73)

Step A.

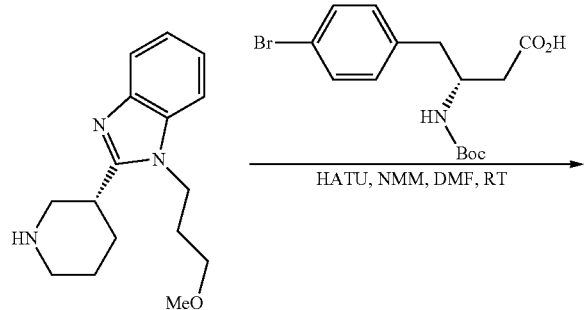

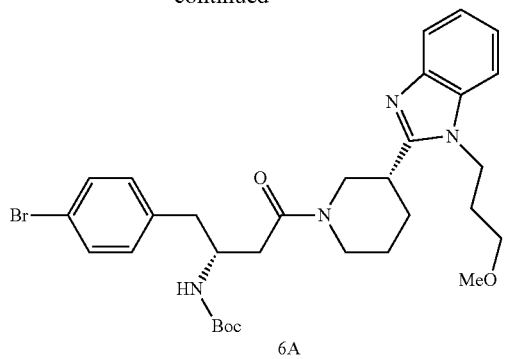

(R)-1-(3-Methoxypropyl)-2-(piperidin-3-yl)-1H-benzo[d]imidazole (0.29 mmol, 79 mg) in DMF (15 mL) was added to (R)-4-(4-bromophenyl)-3-(tert-butoxycarbonylamino)butanoic acid (0.32 mmol, 115 mg) and N-methylmorphine (1.16 mmol, 0.13 mL). The reaction mixture was stirred at rt for 5 min and then added HATU (0.32 mmol, 122 mg) and kept stifling at rt overnight. The reaction mixture was poured into $H_2O$, extracted with EtOAc. The extract was washed with $H_2O$, brine, dried over $MgSO_4$ and filtered. The filtrate was concentrated in vacuo and purified by preparative LC/MS (35-60% $CH_3CN$ in $H_2O$) to afford tert-butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (6A) (0.26 mmol, 160 mg, yield: 89.7%). ESI-MS: m/z 614.4 (M+H)⁺.

Step B.

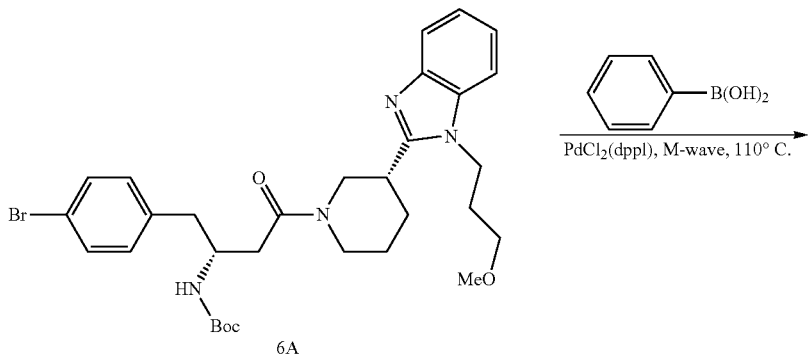

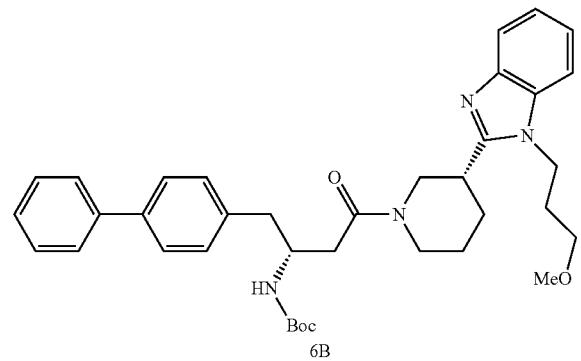

6A (0.26 mmol, 160 mg) in dioxane (2 mL) was added phenylboronic acid (0.34 mmol, 41 mg), 1,1'-bis(diphenylphosphino)ferrocene (0.013 mmol, 10 mg) and sat'd NaHCO$_3$ (1 mL). The reaction mixture was heated to 110° C. in microwave for 15 min and then poured into H$_2$O, extracted with EtOAc. The extract was washed with brine, dried over MgSO$_4$ and filtered. The filtrate was concentrated in vacuo. The residue containing tert-Butyl (R)-1-(biphenyl-4-yl)-4-((R)-3-(1-(3-methoxypropyl)-1H-benzo[d]imidazol-2-yl)piperidin-1-yl)-4-oxobutan-2-ylcarbamate (6B) was carried directly on to the next step without further purification. ESI-MS: m/z 611.5 (M+H)$^+$.

Step C.

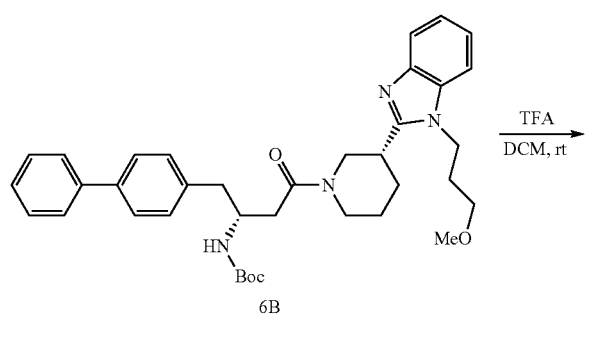

6B

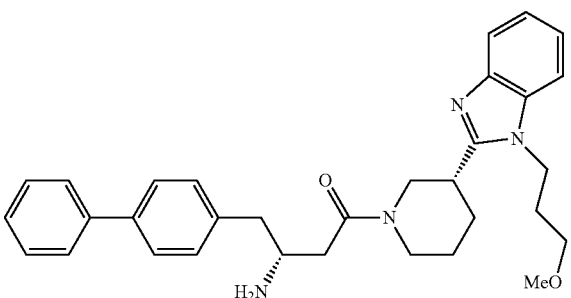

72

6B (0.26 mmol, 160 mg) in DCM (5 mL) was added TEA (1 mL). The reaction solution was stirred at rt for 1 h and then concentrated in vacuo. The residue was purified by preparative LC/MS (20-50% CH$_3$CN in H$_2$O) to afford (R)-3-Amino-4-(biphenyl-4-yl)-1-((R)-3-(1-(3-methoxypropyl)-1H-benzo[d]imidazol-2-yl)piperidin-1-yl)butan-1-one (72) (0.26 mmol, 132 mg, two-step yield: 99.4%). ESI-MS: m/z 511.5 (M+H)$^+$.

Step D.

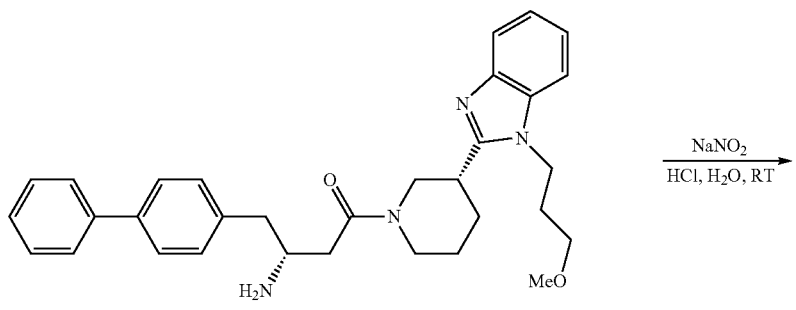

72

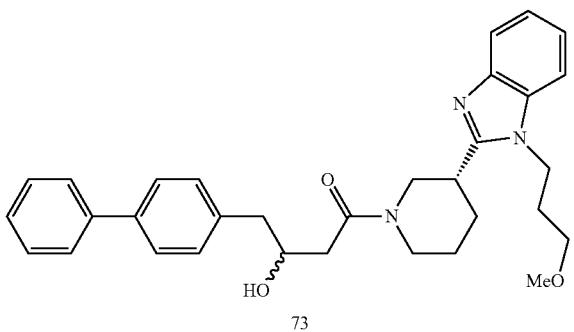

73

(R)-3-Amino-4-(biphenyl-4-yl)-1-((R)-3-(1-(3-methoxypropyl)-1,1-benzo[d]imidazol-2-yl)piperidin-1-yl)butan-1-one (0.26 mmol, 132 mg) in MeOH (1 mL) was added HCl (0.5 M, 2 mL) and NaNO₂ (179 mg in 9 mL H₂O). The reaction solution was stirred at rt overnight and then adjusted to pH9, extracted with EtOAc. The extract was washed with brine, dried over MgSO₄, and concentrated in vacuo. The residue was purified by preparative LC/MS (30-50% CH₃CN in H₂O) to afford (R)-4-(Biphenyl-4-yl)-3-hydroxy-1-(3-(1-(3-methoxypropyl)-1H-benzo[d]imidazol-2-yl)piperidin-1-yl)butan-1-one (73) (0.012 mmol, 6 mg, yield: 4.6%). ESI-MS: m/z 512.5 (M+H)⁺. 1H NMR (400 MHz, MeOD) δ ppm 1.53-1.87 (m, 1H) 1.88-2.40 (m, 4H) 2.53-2.83 (m, 2H) 2.85-3.20 (m, 2H) 3.28 (m, 3H) 3.34-3.46 (m, 3H) 3.47-3.59 (m, 1H) 3.62-3.72 (m, 1H) 4.12 (t, 1H) 4.29-4.39 (m, 1H) 4.55 (t, J=7.17 Hz, 1H) 4.58-4.66 (m, 1H) 4.66-4.77 (m, 1H) 4.80 (br.s, 1H) 7.28-7.45 (m, 5H) 7.50-7.65 (m, 6H) 7.73-7.92 (m, 2H).

Example 7

Synthesis of (R)-3-amino-1((R)-3-(1-(3-methoxypropyl)-1H-benzo[d]imidazol-2-yl)piperidin-1-yl)-4-(naphthalen-2-yl)butan-1-one (74)

Step A.

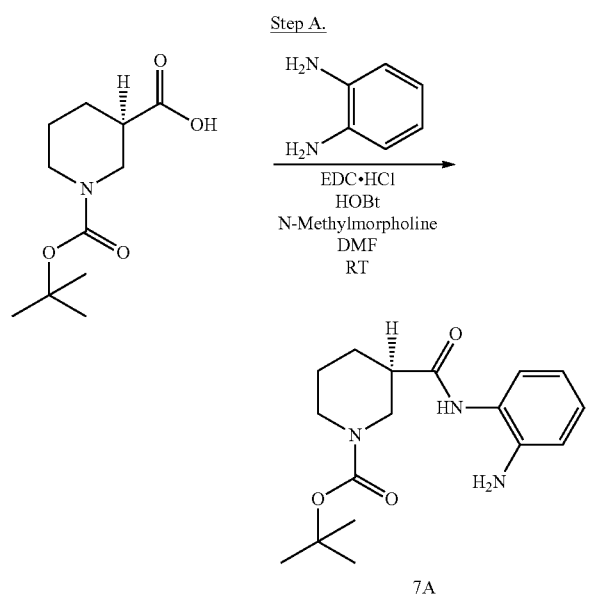

(R)-1-(tert-Butoxycarbonyl)piperidine-3-carboxylic acid (17.45 mmol, 4.0 g) and benzene-1,2-diamine (17.45 mmol, 1.87 g) were added to a 100 mL round-bottomed flask equipped for stirring under nitrogen. DMF (30 mL) and 4-methylmorpholine (52.35 mmol, 5.76 mL) were added and the resultant solution was allowed to stir for 5 min at room temperature. N1-((ethylimino)methylene)-N3,N3-dimethylpropane-1,3-diamine hydrochloride (20.94 mmol, 4.01 g) and 1H-benzo[d][1,2,3]triazol-1-ol (20.94 mmol, 2.83 g) were then added and the reaction was allowed to stir at room temperature for 16 hr. The reaction solution was poured into water and extracted with ethyl acetate. The organic layer was washed three times with water, two times with saturated aqueous sodium bicarbonate, and once with saturated aqueous sodium chloride. The organic layer was collected and dried with Na₂SO₄. This mixture was then filtered, the filtrate was collected and concentrated and dried in-vacuo affording (R)-tert-Butyl 3-(2-aminophenylcarbamoyl)piperidine-1-carboxylate (7A) as a brownish foam that was carried directly on to the next step without further purification. ESI-MS: m/z 320.4 (M+H)⁺.

Step B.

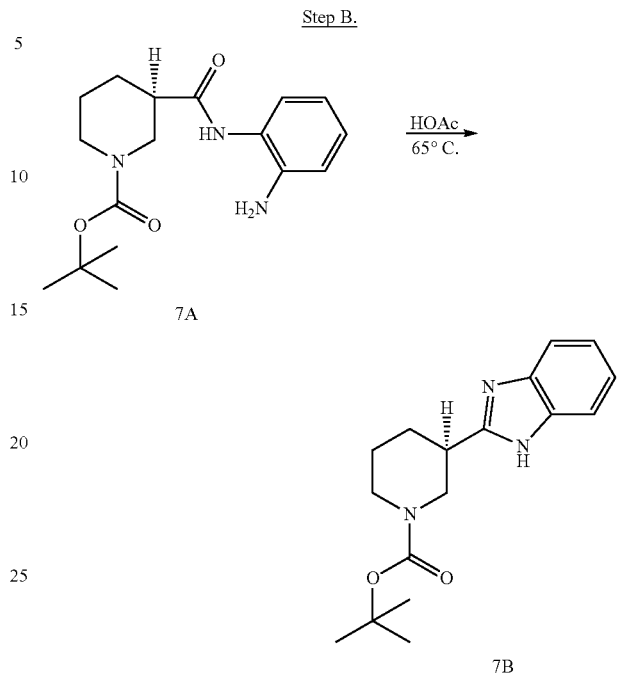

(R)-tert-Butyl 3-(2-aminophenylcarbamoyl)piperidine-1-carboxylate (7A) (2.80 g, 8.77 mmol) was added to a 100 mL round-bottomed flask equipped for stirring under nitrogen. Glacial acetic acid (20 mL) was then added and the resultant solution was stirred at 65° C. under nitrogen for 2 hr. Analysis of the reaction mixture at this time by LC/MS indicated that the reaction was complete. The reaction solution was then concentrated in-vacuo to give a brownish oil. Toluene (30 mL) was added and the subsequent solution was concentrated in vacuo. This was repeated three times to remove any trace quantities of acetic acid affording (R)-tert-Butyl 3-(1H-benzo[d]imidazol-2-yl)piperidine-1-carboxylate (7B) as a tannish-white solid. (13.94 mmol, 4.2 g, 80% over 2-steps). ¹H NMR (400 MHz, DMSO-d₆) δ ppm 1.34-1.52 (m, 10H) 1.73-1.83 (m, 2H) 2.10-2.17 (br. s. 1H) 2.79-2.96 (m, 2H) 3.89-3.96 (br. s., 1H) 4.08-4.33 (br.s., 1H) 4.33-4.43 (br.s, 1H) 7.09-7.18 (dd, 2H, 8.97 Hz, 6.19 Hz) 7.39-7.48 (d, 1H, 6.82 Hz) 7.49-7.57 (d, 1H, 7.07 Hz) 12.27 (s, 1H) ESI-MS: adz 302.4 (M+H)⁺.

Step C.

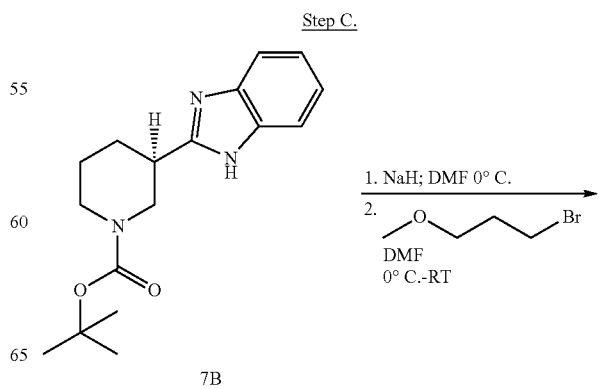

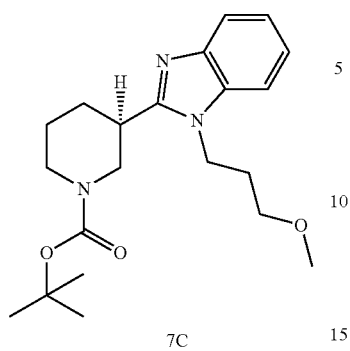

7C (R)-tert-Butyl 3-(1H-benzo[d]imidazol-2-yl)piperidine-1-carboxylate (7B) (9.95 mmol, 3.0 g) was added to a 200 mL round-bottomed flask equipped for stirring under nitrogen. DMF (50 mL) was added and the resultant solution was cooled to 0° C. with an ice bath. NaH (60% in mineral oil, 11.95 mmol, 0.478 g) was then added and the subsequent solution was allowed to stir under nitrogen for 0.5 hr. At this time 1-bromo-3-methoxypropane (12.44 mmol, 1.90 g) was added, the ice bath was removed and the reaction solution was allowed to warm to room temperature and stir for 1 hr. The reaction solution was then poured into ice-water, extracted with ethyl acetate, and washed once with saturated aqueous sodium chloride. The organic layer was collected and subsequently dried with anhydrous Na₂SO₄ and filtered. This filtrate was collected, concentrated, and dried in-vacuo affording a brown oil. This material was then purified by chromatography on silica gel (3-10% CH₃OH in CH₂Cl₂) to afford (R)-tert-butyl 3-(1-(3-methoxypropyl)-1H-benzo[d]imidazol-2-yl)piperidine-1-carboxylate (7C) as a brown oil (9.63 mmol, 3.6 g, 96% yield). $^{1}$H NMR (400 MHz, DMSO-d₆) δ ppm 1.55-1.71 (br.s., 1H) 1.79-1.88 (br.s., 1H) 2.04-2.13 (m, 4H) 2.74-2.88 (br.s., 1H) 2.98-3.38 (m, 7H) 4.21-4.39 (m, 3H) 7.22-7.28 (m, 2H) 7.34-7.40 (dd, 1H, 6.57 Hz, 2.02 Hz) 7.72-7.77 (dd, 1H, 6.57 Hz, 2.02 Hz). ESI-MS: m/z 374.4 (M+H)⁺.

Step D.

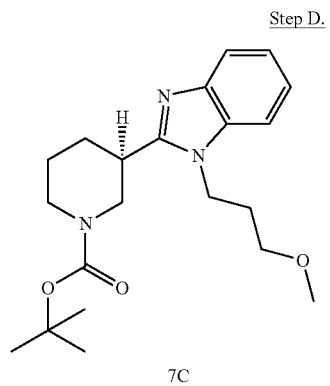

7C

HCl/H₂O
―――――
EtOH
reflux

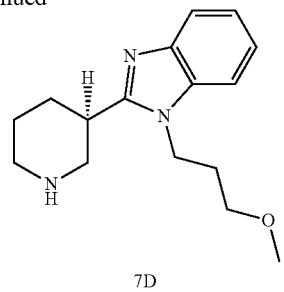

7D (R)-tert-Butyl 3-(1-(3-methoxypropyl)-1H-benzo[d]imidazol-2-yl)piperidine-1-carboxylate (4.82 mmol; 1.8 g) was added to a 100 mL round-bottomed flask equipped with a reflux condenser and stirring under nitrogen. EtOH (15 mL) and HCl (8 M in H₂O; 4 mL) were then added and the solution was heated to reflux for 10 min. Analysis of the reaction mixture by LC/MS indicated that the reaction was complete. The solvent was then removed in-vacuo. The resultant oil was then extracted with EtOAc and a 10% aqueous K₂CO₃ solution. The organic layer was collected and dried with Na₂SO₄, and was then filtered. The filtrate was concentrated and dried in-vacuo affording (R)-1-(3-methoxypropyl)-2-(piperidin-3-yl)-1H-benzo[d]imidazole (7D) as a brown oil (4.76 mmol, 1.3 g, 99% yield). ESI-MS: m/z 274.4 (M+H)⁺.

Step E.

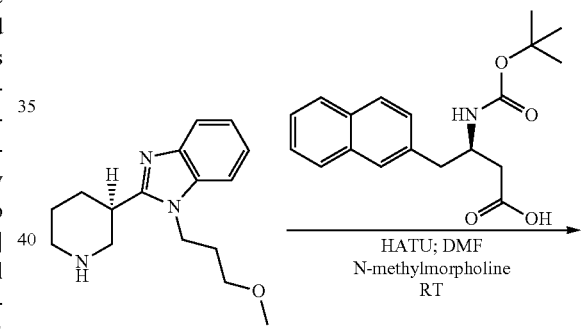

HATU; DMF
N-methylmorpholine
RT

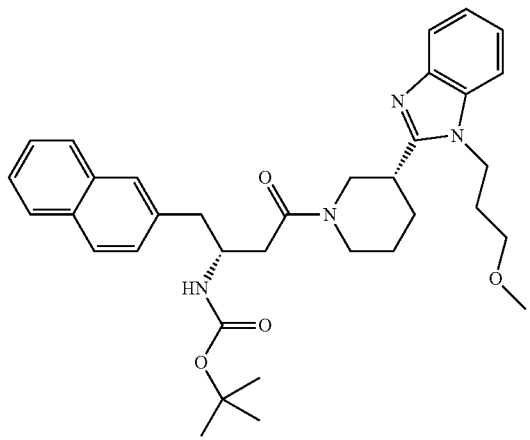

7E (R)-1-(3-methoxypropyl)-2-(piperidin-3-yl)-1H-benzo[d]imidazole (7D) (0.387 mmol, 0.120 g) was added to a 10 mL round-bottomed flask equipped for stirring under nitrogen.

DMF (3 mL), (R)-3-(tert-butoxycarbonylamino)-4-(naphthalen-2-yl)butanoic acid (0.387 mmol, 0.127 g) and N-methylmorpholine (1.55 mmol, 0.170 mL) were then added and the solution was allowed to stir at rt for 5 min. HATU (0.426 mmol, 0.162 g) was added and the resultant solution was stirred at room temperature for 3 hr. The reaction solution was then directly purified by preparative LC/MS (25-95% CH$_3$CN in H$_2$O). The resultant fractions were collected and the solvent was removed in-vacuo affording tert-butyl (R)-4-((R)-3-(1-(3-methoxypropyl)-1H-benzo[d]imidazol-2-yl)piperidin-1-yl)-1-(naphthalen-2-yl)-4-oxobutan-2-ylcarbamate (7E) as a clear oil (0.359 mmol, 0.210 g, 93% yield). ESI-MS: m/z 585.5 (M+Hr.

Step F.

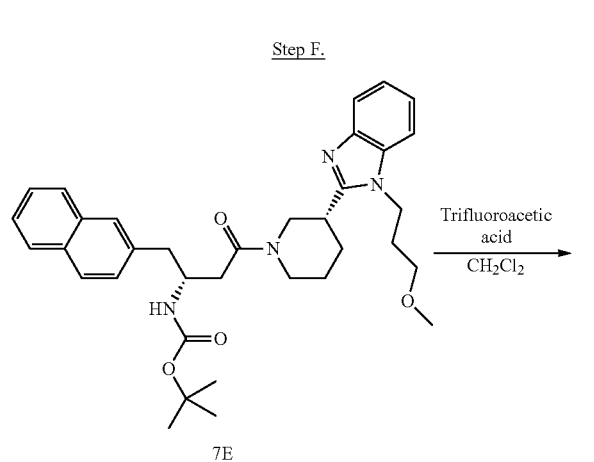

7E

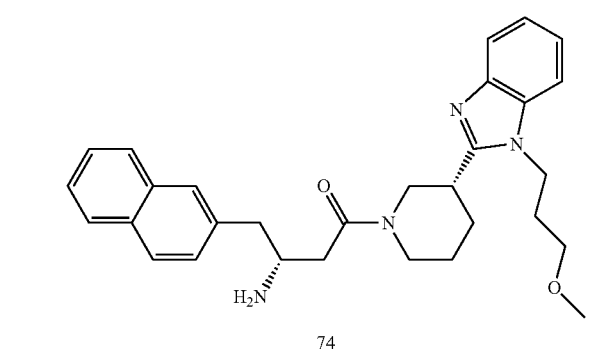

74 tert-Butyl (R)-4-((R)-3-(1-(3-methoxypropyl)-1H-benzo[d]imidazol-2-yl)piperidin-1-yl)-1-(naphthalen-2-yl)-4-oxobutan-2-ylcarbamate (7E) (0.257 mmol, 0.150 g) was added to a 10 mL round-bottomed flask equipped for stirring under nitrogen and dissolved in CH$_2$Cl$_2$ (2 mL). Trifluoroacetic acid (2 mL) was then added and the solution was stirred at room temperature for 2 hr. The solvent was removed in-vacuo affording a clear colored oil. This oil was re-dissolved in methanol (3 mL), filtered, and then purified by preparative CH$_3$CN in H$_2$O (25-95%). The resultant fractions were collected and the solvent was removed in-vacuo affording a clear colored oil. This oil was re-dissolved in CH$_3$CN (1 mL) and water (2 mL). The resultant solution was frozen and lyophilized to afford (R)-3-amino-1((R)-3-(1-(3-methoxypropyl)-1H-benzo[d]imidazol-2-yl)piperidin-1-yl)-4-(naphthalen-2-yl)butan-1-one (74) as its trifluoroacetic acid salt and as a white flocculent solid (0.152 mmol, 0.091 g, yield 59%) $^1$H NMR (400 MHz, DMSO-d$_6$) δ ppm 1.42-1.56 (m, 1H) 1.75-2.00 (m, 3H) 2.03-2.18 (m, 2H) 2.62-2.75 (m, 3H) 2.90-3.00 (m, 1H) 3.03-3.29 (m, 8H) 3.34-3.45 (m, 2H) 3.77-3.87 (m, 2H) 4.09-4.68 (m, 3H) 7.42-7.55 (m, 5H) 7.72-8.02 (m, 6H) ESI-MS: 485.5 m/z (M+H)$^+$.

Example 8

Synthesis of (R)-3-amino-4-(4-chlorophenyl)-1((R)-3-(1-(3-methoxypropyl)-1H-benzo[d]imidazol-2-yl)piperidin-1-yl)butan-1-one (75)

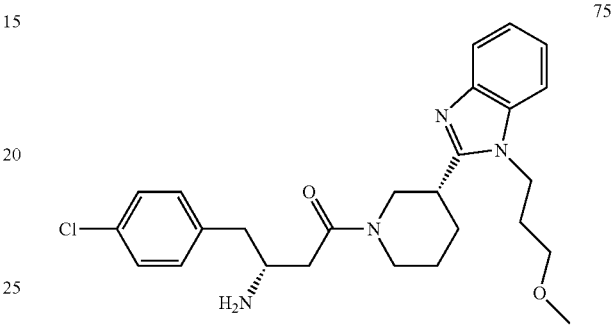

75

The title compound was prepared according to the procedure outlined in Example 7, Steps A-F, using reagent (R)-3-(tert-butoxycarbonylamino)-4-(4-chlorophenyl)butanoic acid in Step E. ESI-MS: m/z 470.4 (M+H)$^+$. 1H NMR (400 MHz, DMSO-d$_6$, 65° C.) δ ppm 1.50-1.62 (m, 1H) 1.83-2.16 (m, 5H) 2.64-2.77 (m, 2H) 2.85-3.06 (m, 3H) 3.10-3.27 (m, 5H) 3.32-3.41 (m, 2H) 3.70-3.87 (br. s., 1H) 4.26-4.59 (m, 2H) 5.01-5.36 (m, 4H) 7.27-7.42 (m, 6H) 7.59-7.66 (m, 2H).

Example 9

Synthesis of (R)-3-amino-4-(3,4-difluorophenyl)-1((R)-3-(1-(3-methoxypropyl)-1H-benzo[d]imidazol-2-yl)piperidin-1-yl)butan-1-one (76)

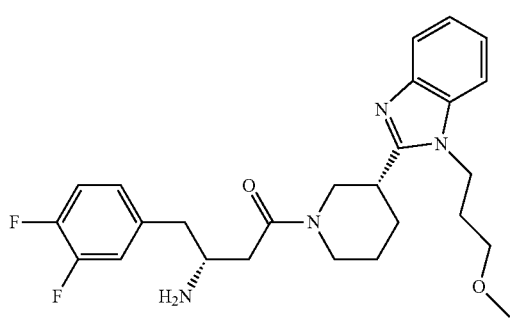

76

The title compound was prepared according to the procedure outlined in Example 7, Steps A-F, using reagent (R)-3-(tert-butoxycarbonylamino)-4-(3,4-difluorophenyl)butanoic acid in Step E. ESI-MS: m/z 471.1 (M+H)$^+$. $^1$H NMR (400 MHz, DMSO-d$_6$) δ ppm 1.45-2.14 (m, 6H) 2.52-2.79 (m, 3H) 2.85-3.01 (m, 3H) 3.16-3.20 (m, 4H) 3.28-3.48 (m, 3H) 3.67-

4.12 (m, 2H) 4.33-4.64 (m, 4H) 7.11-7.16 (br. s, 1H) 7.37-7.47 (m, 4H) 7.71-7.80 (m, 2H).

Example 10

Synthesis of (R)-3-amino-4-(3,4-dichlorophenyl)-1 ((R)-3-(1-(3-methoxypropyl)-1H-benzo[d]imidazol-2-yl)piperidin-1-yl)butan-1-one (77)

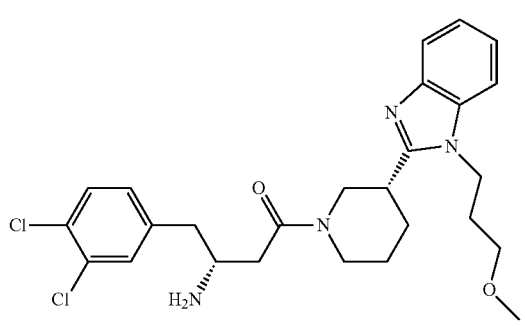

The title compound was prepared according to the procedure outlined in Example 7, Steps A-F, using reagent (R)-3-(tert-butoxycarbonylamino)-4-(3,4-dichlorophenyl)butanoic acid in Step E. ESI-MS: m/z 504.3 (M+H)$^+$. 1H NMR (400 MHz, DMSO-d$_6$) δ ppm 1.45-1.62 (m, 1H) 1.76-2.20 (m, 5H) 2.59-2.82 (m, 3H) 2.91-3.09 (m, 2H) 3.09-3.21 (m, 5H) 3.26-3.54 (m, 4H) 3.67-4.21 (m, 2H) 4.35-4.70 (m, 3H) 7.30 (ddd, J=8.21, 5.94, 2.02 Hz, 1H) 7.43-7.56 (m, 2H) 7.56-7.66 (m, 2H) 7.73-7.88 (m, 2H).

Example 11

Synthesis of (R)-3-amino-1-((R)-3-(1-(3-methoxypropyl)-1H-benzo[d]imidazol-2-yl)piperidin-1-yl)-4-(pyridin-4-yl)butan-1-one (78)

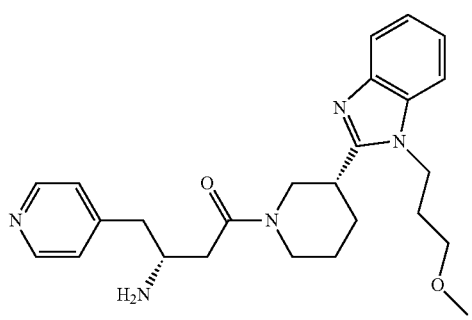

The title compound was prepared according to the procedure outlined in Example 7, Steps A-F, using starting material (R)-3-(tert-butoxycarbonylamino)-4-(pyridin-4-yl)butanoic acid in Step E. ESI-MS: 436.5 m/z (M+H)$^+$. 1H NMR (400 MHz, DMSO-d$_6$) δ ppm 1.45-1.55 (m, 1H) 1.78-2.19 (m, 4H) 2.64-2.76 (m, 3H) 2.92-3.21 (m, 7H) 3.28-3.44 (m, 4H) 3.79-3.89 (m, 2H) 4.08-4.65 (m, 4H) 7.41-7.49 (m, 2H) 7.66-7.81 (m, 4H) 8.72-8.77 (m, 2H).

Example 12

Synthesis of (R)-3-amino-4-(3-chlorophenyl)-1((R)-3-(1-(3-methoxypropyl)-1H-benzo[d]imidazol-2-yl) piperidin-1-yl)butan-1-one (79)

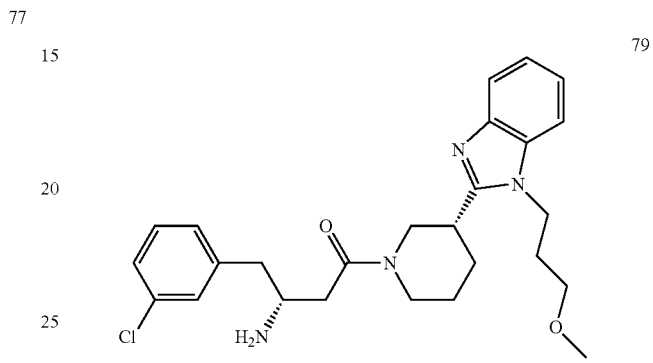

The title compound was prepared according to the procedure outlined in Example D1, Steps A-F, using reagent (R)-3-(tert-butoxycarbonylamino)-4-(3-chlorophenyl)butanoic acid in Step E. ESI-MS: m/z 470.1 (M+H)*. 1H NMR (400 MHz, DMSO-d$_6$) δ ppm 1.46-1.59 (m, 1H) 1.79-2.22 (m, 5H) 2.52-2.80 (m, 2H) 2.87-3.21 (m, 5H) 3.27-3.55 (m, 3H) 3.66-4.20 (m, 2H) 4.34-4.71 (m, 3H) 7.23-7.41 (m, 4H) 7.48-7.57 (m, 2H) 7.77-7.88 (m, 2H).

Example 13

Synthesis of (S)-3-amino-3-(3-bromophenyl)-1((R)-3-(1-(3-methoxypropyl)-1H-benzo[d]imidazol-2-yl) piperidin-1-yl)propan-1-one (80)

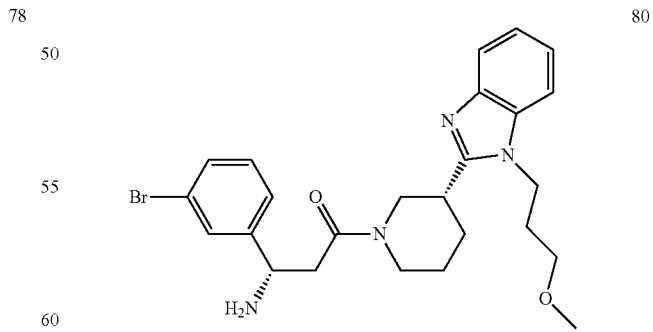

The title compound was prepared according to the procedure outlined in Example 7, Steps A-F, using starting material (S)-3-(3-bromophenyl)-3-(tert-butoxycarbonylamino)propanoic acid in Step E. ESI-MS: m/z 501.3 (M+H)$^+$. 1H NMR (400 MHz, DMSO-d$_6$) δ ppm 1.45-1.57 (m, 1H) 1.82-2.18

(m, 5H) 2.65-3.22 (m, 7H) 3.26-3.48 (m, 3H) 3.92-4.71 (m, 5H) 7.36-7.62 (m, 5H) 7.73-7.83 (m, 3H).

Example 14

Synthesis of (R)-3-amino-1((R)-3-(5,6-dichloro-1-(3-methoxypropyl)-1H-benzo[d]imidazol-2-yl)piperidin-1-yl)-4-(naphthalen-2-yl)butan-1-one (81)

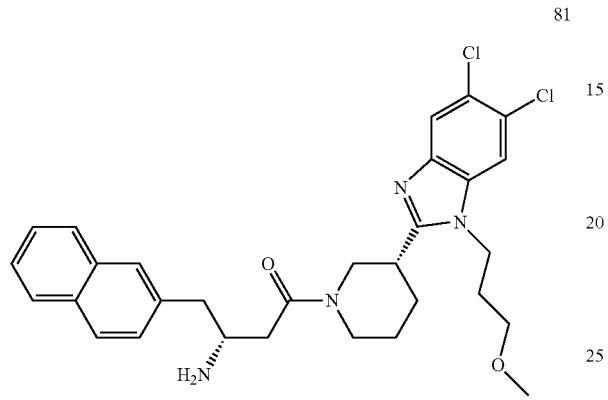

The title compound was prepared according to the procedure outlined in Example DI, Steps A-F, using reagents (R)-3-(tert-butoxycarbonylamino)-4-(naphthalen-2-yl)butanoic acid and (R)-5,6-dichloro-1-(3-methoxypropyl)-2-(piperidin-3-yl)-1H-benzo[d]imidazole in Step E. ESI-MS: m/z 553.4 (M+H)$^+$. 1H NMR (400 MHz, DMSO-d$_6$) δ ppm 1.35-1.52 (m, 1H) 1.65-1.89 (m, 3H) 1.91-2.10 (m, 2H) 2.60-2.82 (m, 2H) 2.89-3.18 (m, 7H) 3.18-3.44 (m, 3H) 3.69-3.99 (m, 2H) 4.07-4.21 (m, 1H) 4.23-4.53 (m, 2H) 7.40-7.57 (m, 3H) 7.75-8.00 (m, 6H).

Example 15

Synthesis of (R)-3-amino-1((R)-3-(1-(3-methoxypropyl)-1H-benzo[d]imidazol-2-yl)piperidin-1-yl)-4-(pyridin-3-yl)butan-1-one (82)

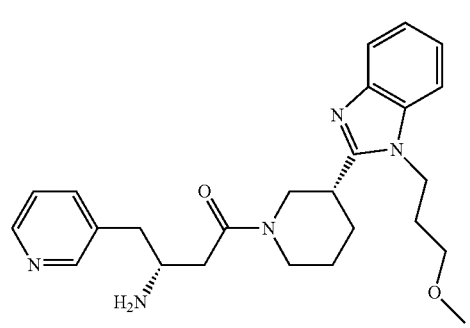

The title compound was prepared according to the procedure outlined in Example 7, Steps A-F, using starting material (R)-3-(tert-butoxycarbonylamino)-4-(pyridin-3-yl)butanoic acid in Step E. ESI-MS: m/z 436.4 (M+H)$^+$. 1H NMR (400 MHz, DMSO-d$_6$) δ ppm 1.41-1.65 (m, 1H) 1.75-2.23 (m, 5H) 2.57-2.85 (m, 3H) 3.18 (d, J=7.33 Hz, 6H) 3.23-3.50 (m, 4H) 3.72-4.22 (m, 2H) 4.30-4.70 (m, 3H) 7.43-7.57 (m, 2H) 7.70-7.88 (m, 3H) 8.16 (d, J=7.83 Hz, 1H) 8.21 (d, J=8.08 Hz, 1H) 8.67-8.77 (m, 2H).

Example 16

Synthesis of (S)-3-amino-3-(3-chlorophenyl)-1((R)-3-(1-(3-methoxypropyl)-1H-benzo[d]imidazol-2-yl)piperidin-1-yl)propan-1-one (83)

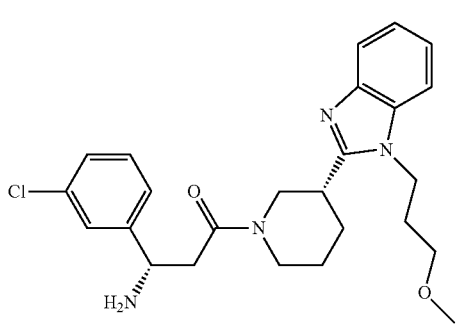

The title compound was prepared according to the procedure outlined in Example 7, Steps A-F, using starting material (S)-3-(tert-butoxycarbonylamino)-3-(3-chlorophenyl)propanoic acid in Step E. ESI-MS: m/z 455.1 (M+H)$^+$. 1H NMR (400 MHz, DMSO-d$_6$) δ ppm 1.41-1.65 (m, 1H) 1.76-2.22 (m, 5H) 2.62-3.55 (m, 10H) 3.90-4.75 (m, 5H) 7.41-7.54 (m, 5H) 7.63 (d, J=15.16 Hz, 1H) 7.71-7.86 (m, 2H).

Example 17

Synthesis of (S)-3-amino-1-((R)-3-(1-(3-methoxypropyl)-1H-benzo[d]imidazol-2-yl)piperidin-1-yl)-3-(3-(trifluoromethyl)phenyl)propan-1-one (84)

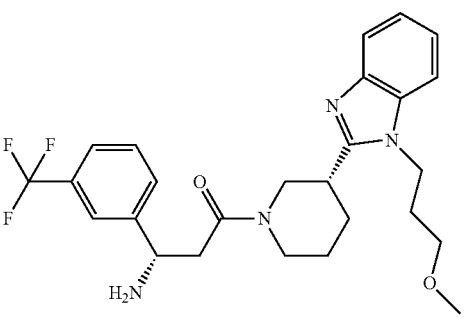

The title compound was prepared according to the procedure outlined in Example 7, Steps A-F, using starting material (S)-3-(tert-butoxyamino)-3-(3-(trifluoromethyl)phenyl)propanoic acid in Step E. ESI-MS: m/z 489.1 (M+H)$^+$. $^1$H NMR (400 MHz, DMSO-d$_6$) δ ppm 1.41-1.67 (m, 1H) 1.77-2.23 (m, 5H) 2.62-3.20 (m, 6H) 3.21-3.59 (m, 4H) 3.89-4.27 (m, 1H) 4.33-4.87 (m, 4H) 7.41-7.56 (m, 2H) 7.62-7.72 (m, 1H) 7.72-7.88 (m, 4H) 7.94 (d, J=11.37 Hz, 1H).

Example 18

Synthesis of 3-((S)-1-amino-3-((R)-3-(1-(3-methoxypropyl)-1H-benzo[d]imidazol-2-yl)piperidin-1-yl)-3-oxopropyl)benzonitrile (85)

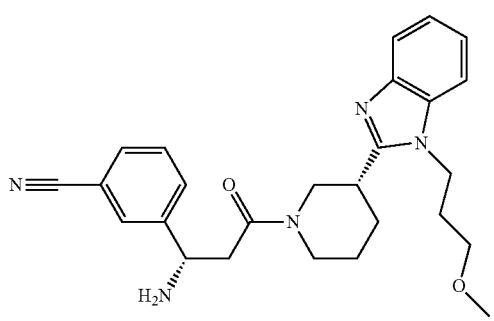

85

The title compound was prepared according to the procedure outlined in Example 7, Steps A-F, using starting material (S)-3-(tert-butoxyamino)-3-(3-cyanophenyl)propanoic acid in Step E. ESI-MS: m/z 446.2 (M+H)+. 1H NMR (400 MHz, DMSO-d$_6$) δ ppm 1.45-1.66 (m, 1 H) 1.79-2.22 (m, 5H) 2.62-3.21 (m, 6H) 3.22-3.54 (m, 4H) 3.92-4.26 (m, 1H) 4.33-4.68 (m, 3H) 4.75 (br. s., 1H) 7.40-7.54 (m, 2H) 7.60-7.70 (m, 1H) 7.73-7.90 (m, 4H) 8.02 (d, J=19.45 Hz, 1H).

Example 19

Synthesis of (R)-3-amino-1((R)-3-(1-(3-methoxypropyl)-1H-benzo[d]imidazol-2-yl)piperidin-1-yl)-4-(2,4,5-trifluorophenyl)butan-1-one (86)

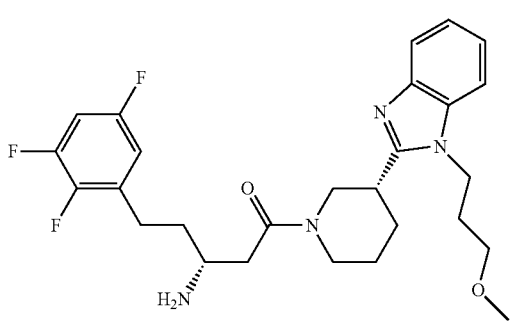

86

The title compound was prepared according to the procedure outlined in Example 7, Steps A-F, using starting material (R)-3-(tert-butoxycarbonylamino)-4-(2,4,5-trifluorophenyl)butanoic acid in Step E. ESI-MS: m/z 489.4 (M+H)+. 1H NMR (400 MHz, DMSO-d$_6$) δ ppm 1.41-1.61 (m, 1H) 1.74-2.18 (m, 5H) 2.57-2.85 (m, 3H) 2.85-3.22 (m, 6 H) 3.25-3.46 (m, 3H) 3.70 (br. s., 1H) 3.79-4.07 (m, 1H) 4.22-4.65 (m, 3H) 7.28-7.45 (m, 2H) 7.46-7.64 (m, 2H) 7.64-7.75 (m, 2H).

Example 20

Synthesis of (R)-3-amino-1((R)-3-(1-(3-methoxypropyl)-1H-benzo[d]imidazol-2-yl)piperidin-yl)-4-phenylbutan-1-one (87)

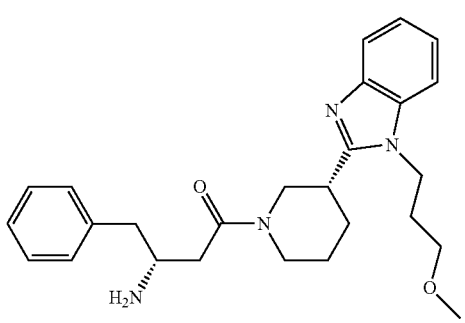

87

The title compound was prepared according to the procedure outlined in Example 7, Steps A-F, using starting material (R)-3-(tert-butoxycarbonylamino)-4-phenylbutanoic acid in Step E. ESI-MS: m/z 435.1 (M+H)+. 1H NMR (400 MHz, DMSO-d$_6$) δ ppm 1.40-1.60 (m, 1 H) 1.72-2.22 (m, 5H) 2.56-2.79 (m, 3H) 2.82-3.22 (m, 5H) 3.23-3.53 (m, 4H) 3.70 (br. s., 1H) 3.77-4.19 (m, 1H) 4.29-4.71 (m, 3H) 7.23-7.41 (m, 5H) 7.45-7.57 (m, 2H) 7.74-7.90 (m, 2H).

Example 21

Synthesis of (S)-3-amino-4-(benzyloxy)-1-((R)-3-(1-(3-methoxypropyl)-1H-benzo[d]imidazol-2-yl)piperidin-1-yl)butan-1-one (88)

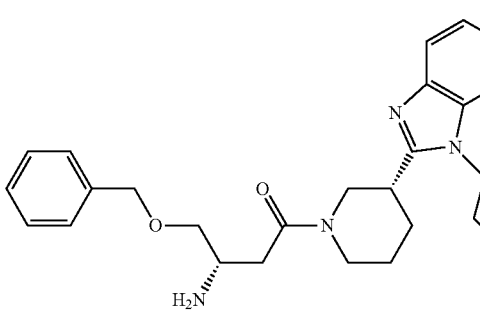

88

The title compound was prepared according to the procedure outlined in Example 7, Steps A-F, using starting material (S)-4-(benzyloxy)-3-(tert-butoxycarbonylamino)butanoic acid in Step E. ESI-MS: m/z 465.2 (M+H)+. 1H NMR (400 MHz, DMSO-d$_6$) δ ppm 1.44-1.70 (m, 1H) 1.76-2.23 (m, 5H) 2.63-2.89 (m, 3H) 2.95-3.20 (m, 4H) 3.28-3.39 (m, 3H) 3.42-

3.75 (m, 4H) 3.88-4.22 (m, 1H) 4.41-4.76 (m, 6H) 7.24-7.44 (m, 5H) 7.48-7.59 (m, 2H) 7.80 (d, J=8.08 Hz, 1H) 7.88 (t, 0.7=7.33 Hz, 1H).

Example 22

Synthesis of (S)-3-amino-1((R)-3-(1-(3-methoxypropyl)-1H-benzo[d]imidazol-2-yl)piperidin-1-yl)-3-phenylpropan-1-one (89)

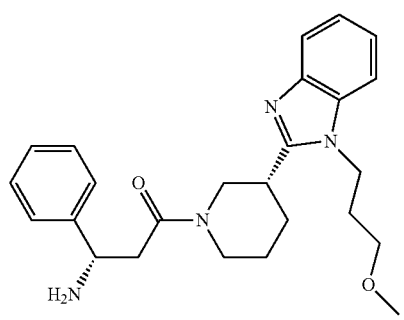

89

The title compound was prepared according to the procedure outlined in Example 7, Steps A-F, using starting material (S)-3-(tert-butoxycarbonylamino)-3-phenylpropanoic acid in Step E. ESI-MS: m/z 421.2 (M+H)$^+$. 1H NMR (400 MHz, DMSO-d$_6$) δ ppm 1.43-1.64 (m, 1H) 1.78-2.19 (m, 5H) 2.64-3.25 (m, 8H) 3.25-3.55 (m, 3H) 3.88-4.71 (m, 6H) 7.33-7.57 (m, 7H) 7.70-7.82 (m, 2H).

Example 23

Synthesis of (R)-3-amino-4-(4-tert-butylphenyl)-1 ((R)-3-(1-(3-methoxypropyl)-1H-benzo[d]imidazol-2-yl)piperidin-1-yl)butan-1-one (90)

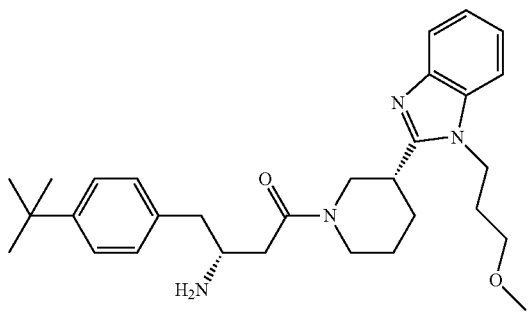

90

The title compound was prepared according to the procedure outlined in Example 7, Steps A-F, using starting material (R)-3-(tert-butoxycarbonylamino)-4-(4-tert-butylphenyl)butanoic acid in Step E. ESI-MS: m/z 491.2 (M+H)$^+$. 1H NMR (400 MHz, DMSO-d$_6$) δ ppm 1.27 (d, J=4.04 Hz, 9H) 1.39-1.58 (m, 1H) 1.74-2.21 (m, 5H) 2.56-2.78 (m, 3H) 2.80-3.23 (m, 6H) 3.23-3.49 (m, 4H) 3.68 (br. s., 1H) 3.78-4.18 (m, 1H) 4.32-4.69 (m, 4H) 7.20 (dd, J=9.85, 8.34 Hz, 2H) 7.37 (dd, J=13.26, 8.21Hz, 2H) 7.41-7.52 (m, J=13.86, 6.85, 6.69, 6.69 Hz, 2H) 7.70-7.84 (m, 2H).

Example 24

Synthesis of (R)-3-amino-4-(4-bromophenyl)-1((R)-3-(1-(3-methoxypropyl)-1H-benzo[d]imidazol-2-yl) piperidin-1-yl)butan-1-one (91)

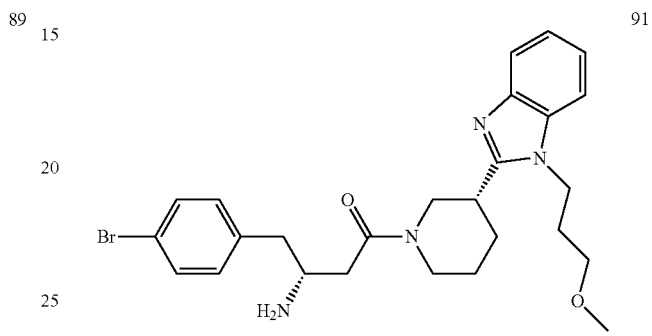

91

The title compound was prepared according to the procedure outlined in Example 7, Steps A-F, using starting material (R)-4-(4-bromophenyl)-3-(Cert-butoxycarbonylamino)butanoic acid in Step E. ESI-MS: m/z 514.1 (M+H)$^+$. 1H NMR (400 MHz, DMSO-d$_6$) δ ppm 1.40-1.62 (m, 1H) 1.71-2.21 (m, 5H) 2.57-2.80 (m, 3H) 2.83-3.14 (m, 3H) 3.19 (d, J=13.64 Hz, 3H) 3.26-3.47 (m, 3H) 3.68 (br. s., 1H) 3.78-4.13 (m, 1H) 4.21-4.67 (m, 5H) 7.25 (dd, J=8.34, 6.82 Hz, 2H) 7.33-7.49 (m, 2H) 7.55 (dd, J=12.13, 8.34 Hz, 2H) 7.66-7.80 (m, 2H).

Example 25

Synthesis of (2R,3R)-3-amino-2-hydroxy-1-((R)-3-(1-(3-methoxypropyl)-1H-benzo[d]imidazol-2-yl) piperidin-1-yl)-3-phenylpropan-1-one (92)

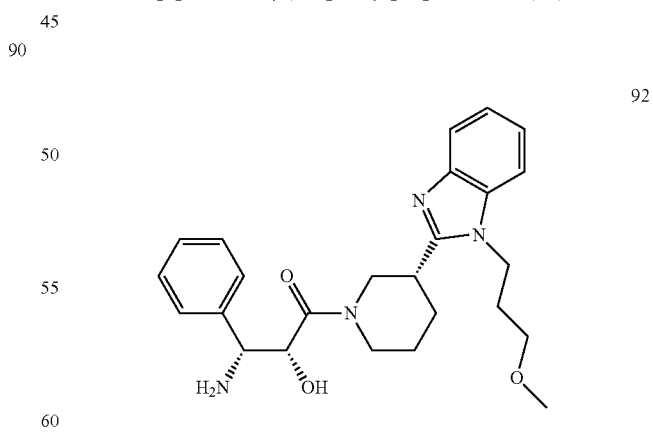

92

The title compound was prepared according to the procedure outlined in Example D1, Steps A-F, using starting material (2R,3R)-3-(tert-butoxycarbonylamino)-2-hydroxy-4-phenylbutanoic acid in Step E. ESI-MS: m/z 437.2 (M+H)$^+$. 1H NMR (400 MHz, DMSO-d$_6$) δ ppm 1.45-1.62 (m, 1H) 1.74-2.21 (m, 5H) 2.63-3.09 (m, 2H) 3.18 (d, J=2.27 Hz, 3H)

3.23-3.58 (m, 4H) 4.00-4.59 (m, 7H) 4.74-4.94 (m, 1H) 7.31-7.54 (m, 7H) 7.67-7.82 (m, 2H).

Example 26

Synthesis of 4-amino-3-(4-chlorophenyl)-1-((R)-3-(1-(3-methoxypropyl)-1H-benzo[d]imidazol-2-yl)piperidin-1-yl)butan-1-one (93)

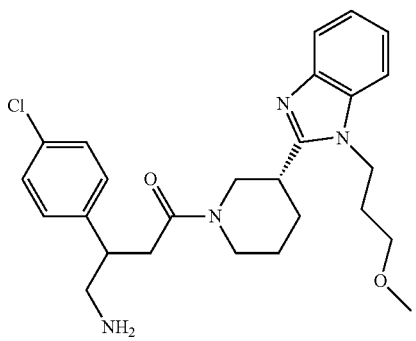

The title compound was prepared according to the procedure outlined in Example 7, Steps A-F, using starting material (2R)-4-(tert-butoxycarbonylamino)-3-(4-chlorobenzyl)-2-hydroxybutanoic acid in Step E. ESI-MS: m/z 470.1 (M+H)⁺. ¹H NMR (400 MHz, DMSO-d₆) δ ppm 1.28-1.65 (m, 1H) 1.72-2.17 (m, 5H) 2.55-3.51 (m, 13H) 3.91-4.20 (m, 1H) 4.31-4.64 (m, 4H) 7.26-7.49 (m, 5H) 7.64-7.82 (m, 3H).

Example 27

Synthesis of Intermediates: (R)-tert-butyl 3-(4-chloro-1-(3-methoxypropyl)-1H-benzo[d]imidazol-2-yl)piperidine-1-carboxylate (27D¹) and (R)-tert-butyl 3-(7-chloro-1-(3-methoxypropyl)-1H-benzo[d]imidazol-2-yl)piperidine-1-carboxylate (27D²)

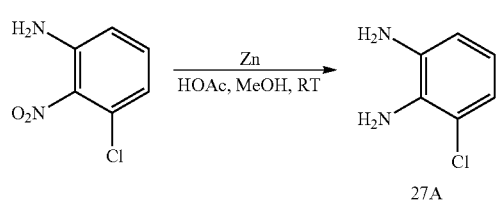

3-Chloro-2-nitroaniline (27.35 mmole, 4.72 g) in MeOH (120 mL) in HOAc (Glacial, 12 mL) was cooled in ice-water bath and added Zn (dust, 162.5 mmole, 8.95 g) in 3 portions. The ice-water bath was removed and let slowly warm up to RT. The reaction mixture was stirred at rt overnight, filtered over Celite 500 and then concentrated in vacuo. The residue was dissolved in EtOAc (100 mL) and H₂O (50 mL). The aqueous layer was adjusted to pH 8-9 by using sat'd NaHCO₃, washed with brine, dried over MgSO₄ and filtered. The organic layers containing 3-chlorobenzene-1,2-diamine (27A) were combined, concentrated in vacuo and carried directly on to the next step without further purification. ESI-MS: m/z 143.3 (M₊H)⁺.

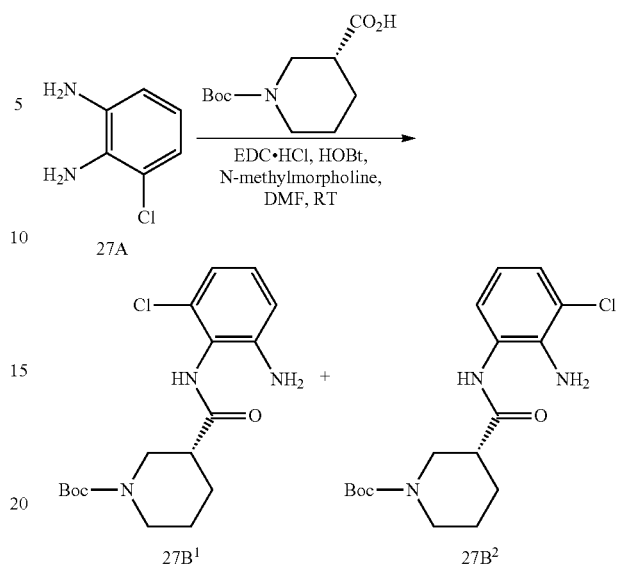

3-Chlorobenzene-1,2-diamine (27A) (27.35 mmole, 3.90 g) in DMF (60 mL) was added (R)-(−)-N-Boc-Nipecotic acid (32.82 mmole, 7.52 g) and N-methylmorpholine (82.05 mmole, 9.02 mL). The reaction mixture was stirred at rt for 5 min and then added EDC.HCl (35.56 mmole, 6.82 g) and HOBt (35.56 mmole, 4.81 g). The reaction mixture was kept stirring at rt overnight and then poured into H₂O, extracted with EtOAc. The extract was washed with H₂O, brine, dried over MgSO₄ and filtered. The filtrate was concentrated in vacuo and purified by flash chromatography (Silica gel EtOAc-hexane: 1:3) to afford a mixture of (R)-tert-Butyl 3-(2-amino-6-chlorophenylcarbamoyl)piperidine-1-carboxylate (27B¹) and (R)-tert-butyl 3-(2-amino-3-chlorophenylcarbamoyl)piperidine-1-carboxylate (27B²) (26.90 mmole, 9.52 g, two-step yield: 98.4%). ESI-MS: m/z 354.3 (M+H)⁺.

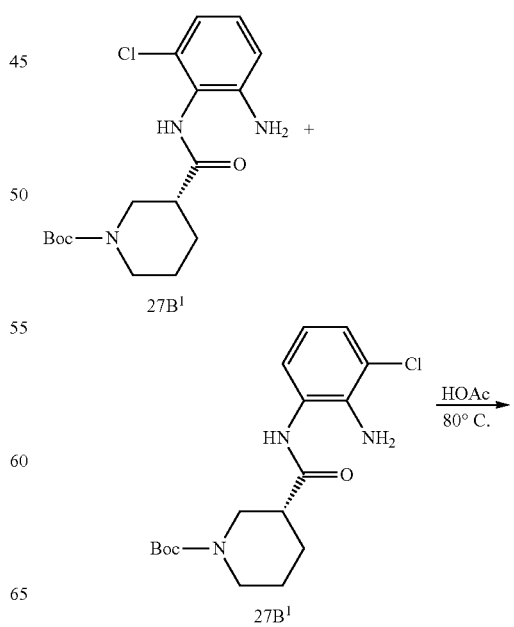

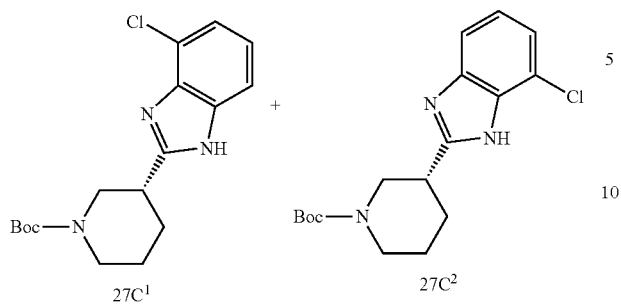

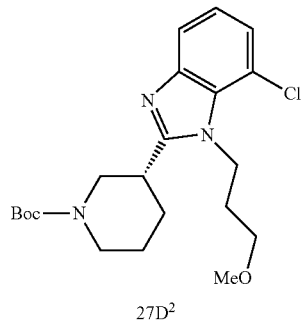

A mixture of (R)-tert-butyl 3-(2-amino-6-chlorophenylcarbamoyl)piperidine-1-carboxylate (27B¹) and (R)-tert-butyl 3-(2-amino-3-chlorophenylcarbamoyl)piperidine-1-carboxylate (27B¹) (26.90 mmole, 9.52 g) was added HOAc (Glacial, 20 mL). The reaction mixture was heated to 80° C. and stirred for 3 hr. HOAc was removed by evaporation and the residue was purified by flash chromatography (Silica gel EtOAc-hexane: 1:1) to afford a mixture of (R)-tert-Butyl 3-(4-chloro-1H-benzo[d]imidazol-2-yl)piperidine-1-carboxylate (27C¹) and (R)-tert-butyl 3-(7-chloro-1H-benzo[d]imidazol-2-yl)piperidine-1-carboxylate (27C²) (23.67 mmole, 8.02 g, yield: 88.0%). ESI-MS: m/z 336.4 (M+H)⁺.

A mixture of (R)-tert-butyl 3-(4-chloro-1-(3-methoxypropyl)-1H-benzo[d]imidazol-2-yl)piperidine-1-carboxylate (27C¹) and (R)-tert-butyl 3-(7-chloro-1-(3-methoxypropyl)-1H-benzo[d]imidazol-2-yl)piperidine-1-carboxylate (27C²) (23.82 mmole, 8.00 g) in DMF (150 mL) was cooled in ice-water bath and NaH (28.58 mmole, 1.14 g) in 3 portions. The reaction solution was stirred at 0° C. for 30 min and then added 1-bromo-3-methoxypropane. The cooling bath was removed and the reaction solution was heated to 80° C. for 3 hr. The reaction solution was poured into H₂O, extracted with EtOAc. The extract was washed with brine, dried over MgSO₄ and filtered. bThe filtrate was concentrated in vacuo and purified by flash chromatography (Silica gel, EtOAc-hexane: 1:3) to afford a mixture of (R)-tert-butyl 3-(4-chloro-1-(3-methoxypropyl)-1H-benzo[d]imidazol-2-yl)piperidine-1-carboxylate (27D¹) and (R)-tert-butyl 3-(7-chloro-1-(3-methoxypropyl)-1H-benzo[d]imidazol-2-yl)piperidine-1-carboxylate (27D²) (18.39 mmole, 7.50 g, yield: 77.2%). ESI-MS: m/z 408.4 (M+H)⁺.

Example 28

Synthesis of 3-amino-1-((R)-3-(1-(3-methoxypropyl)-1H-benzo[d]imidazol-2-yl)piperidin-1-yl)-3-(piperidin-4-yl)propan-1-one (94)

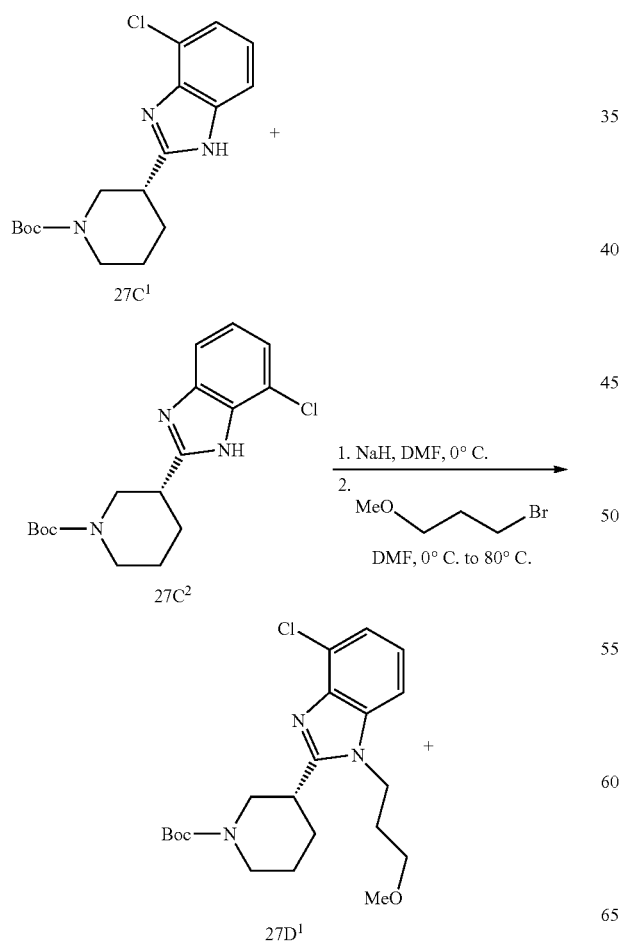

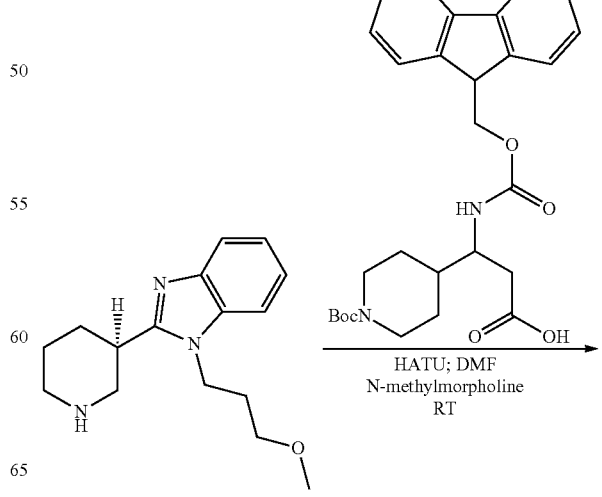

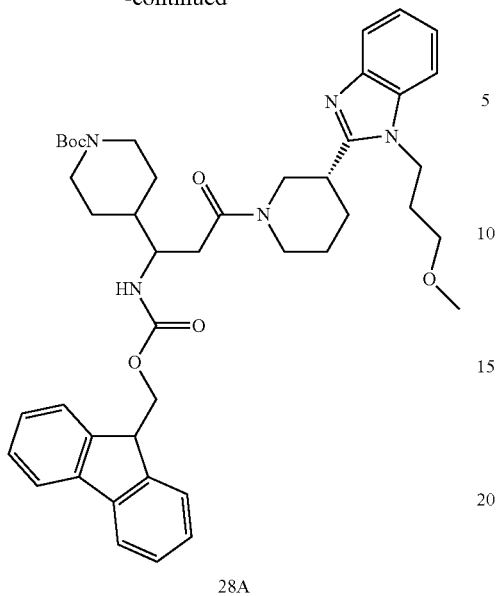

28A (R)-1-(3-Methoxypropyl)-2-(piperidin-3-yl)-1H-benzo[d]imidazole (0.293 mmol, 0.080 g) was added to a 10 mL round-bottomed flask equipped for stirring under nitrogen. DMF (3 mL), 3-((9H-fluoren-9-yl)methoxy)carbonylamino)-3-(1-(tert-butoxycarbonyl)piperidin-4-yl)propanoic acid (0.293 mmol, 0.145 g) and N-methylmorpholine (0.879 mmol, 0.097 mL) were then added and the solution was allowed to stir at rt for 5 min. HATU (0.322 mmol, 0.122 g) was added and the resultant solution was stirred at room temperature for 3 hr. The reaction solution was then directly purified by preparative LC/MS (35-95% $CH_3CN$ in $H_2O$). The resultant fractions were collected and the solvent was removed in-vacuo affording tert-butyl 4-(1-(((9H-fluoren-9-yl)methoxy)carbonylamino)-3-((R)-3-(1-(3-methoxypropyl)-1H-benzo[d]imidazol-2-yl)piperidin-1-yl)-3-oxopropyl)piperidine-1-carboxylate (28A) as a clear oil which was used without further purification. ESI-MS: m/z 750.6 $(M+H)^+$.

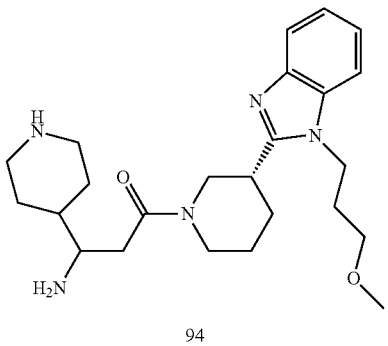

94

Compound 28A (0.293 mmol max, crude oil) was added to a 10 mL round-bottomed flask equipped for stirring under nitrogen and dissolved in $CH_2Cl_2$ (2 mL). Trifluoroacetic acid (2 mL) was then added and the solution was stirred at room temperature for 2 hr. The solvent was removed in-vacuo affording a clear colored oil. This oil was re-dissolved in DMF (3 mL) and piperidine (0.500 mL) and allowed to stir at room temperature for 3 hr. This reaction solution was then directly purified by preparative LC/MS (5-50% $CH_3CN$ in $H_2O$). The resultant fractions were collected and the solvent was removed in-vacuo affording a clear colored oil. This oil was re-dissolved in $CH_3CN$ (1 mL) and water (2 mL). The resultant solution was frozen and lyophilized to afford 3-amino-1-((R)-3-(1-(3-methoxypropyl)-1H-benzo[d]imidazol-2-yl)piperidin-1-yl)-3-(piperidin-4-yl)propan-1-one (94) as its bis-trifluoroacetic acid salt and as a clear oil (0.176 mmol, 0.118 g, 60% yield over 3-steps). ESI-MS: m/z 428.5 $(M+H)^+$.

Example 29

Synthesis of (R)-3-amino-1((R)-3-(6-fluoro-1-(3-methoxypropyl)-1,1-benzo[d]imidazol-2-yl)piperidin-1-yl)-4-(naphthalen-2-yl)butan-1-one (95) and (R)-3-amino-1-((R)-3-(5-fluoro-1-(3-methoxypropyl)-1H-benzo[d]imidazol-2-yl)piperidin-1-yl)-4-(naphthalen-2-yl)butan-1-one (96)

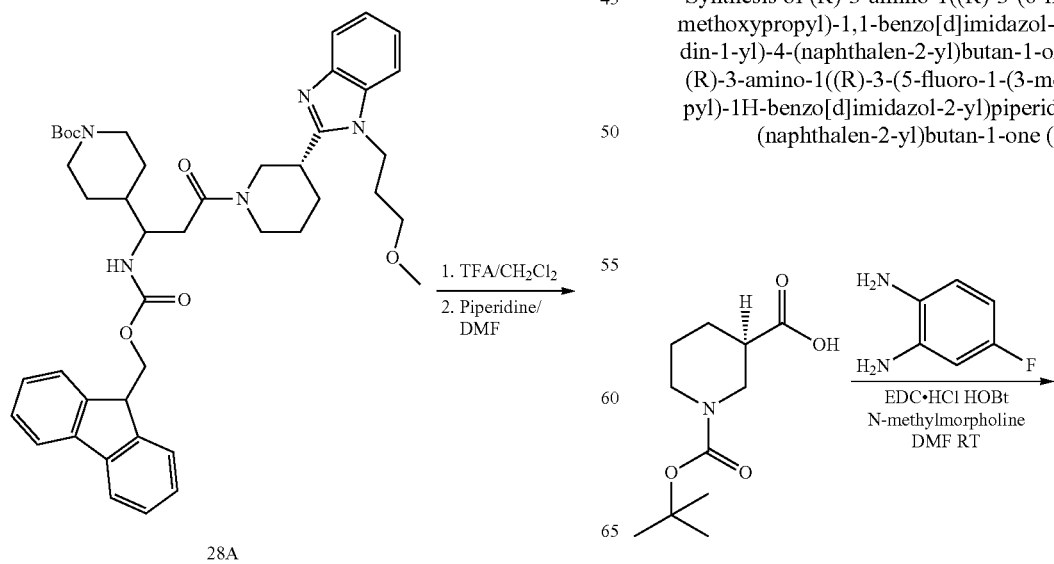

28A

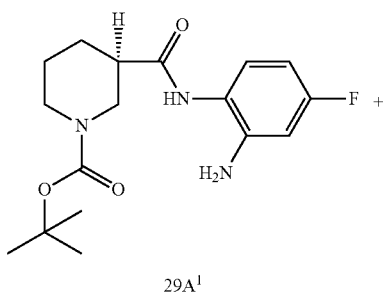

29A¹

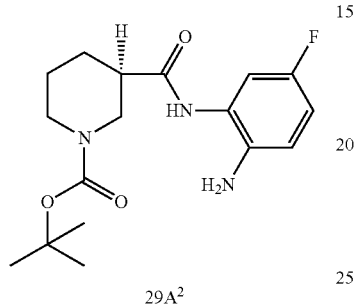

29A²

(R)-1-(tert-Butoxycarbonyl)piperidine-3-carboxylic acid (8.72 mmol, 2.0 g) and 4-fluorobenzene-1,2-diamine (8.72 mmol, 1.1 g) were added to a 50 mL round-bottomed flask equipped for stirring under nitrogen. DMF (10 mL) and 4-methylmorpholine (26.2 mmol, 2.9 mL) were added and the resultant solution was allowed to stir for 5 min at room temperature. N1-((ethylimino)methylene)-N3,N3-dimethylpropane-1,3-diamine hydrochloride (10.5 mmol, 2.0 g) and 1H-benzo[d][1,2,3]triazol-1-ol (10.5 mmol, 1.42 g) were then added and the reaction was allowed to stir at room temperature for 16 hr. The reaction solution was poured into water and extracted with ethyl acetate. The organic layer was washed three times with water, two times with saturated aqueous sodium bicarbonate, and once with saturated aqueous sodium chloride. The organic layer was collected and NaiSO₄ was added to remove residual water. The mixture was then filtered; the filtrate was collected, concentrated, and dried in-vacuo affording a mixture of (R)-tert-Butyl 3-(2-amino-4-fluorophenylcarbamoyl)piperidine-1-carboxylate (29A¹) and (R)-tert-butyl 3-(2-amino-5-fluorophenylcarbamoyl)piperidine-1-carboxylate (29A²) as a brownish foam that was carried directly on to the next step without further purification. ESI-MS: m/z 338.3 (M+H)⁺.

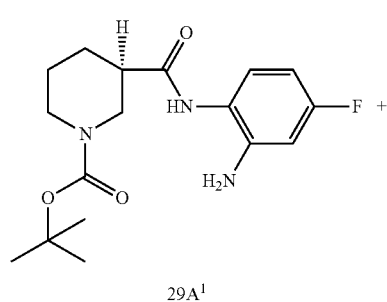

29A¹

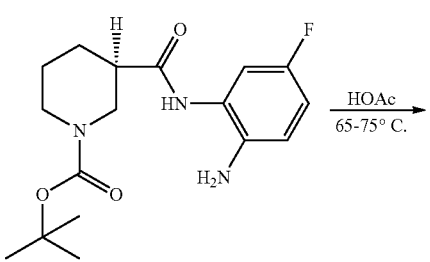

29A²

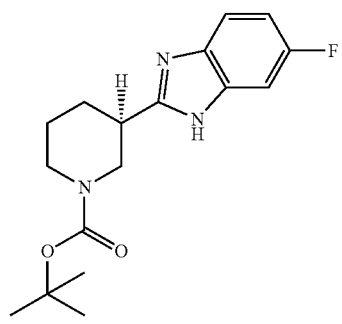

29B

Mixture of 29A¹ and 29A² (8.72 mmol, crude oil) were added to a 100 mL round-bottomed flask equipped for stirring under nitrogen. Glacial acetic acid (20 mL) was then added and the resultant solution was stirred at 65° C. under nitrogen for 2 hrs and at 75° C. for 2 hr. Analysis of the reaction mixture by LC/MS indicated that the reaction was complete. The reaction solution was then concentrated in-vacuo and gave a brownish oil. Toluene (30 mL) was added and the subsequent solution was concentrated in vacuo. The dissolution in toluene and re-concentration were repeated three times to remove any trace quantities of acetic acid affording (R)-tert-Butyl 3-(6-fluoro-1H-benzo[d]imidazol-2-yl)piperidine-1-carboxylate (29B) as a brown oil which was used without further purification. ESI-MS: m/z 320.4 (M+H)⁺.

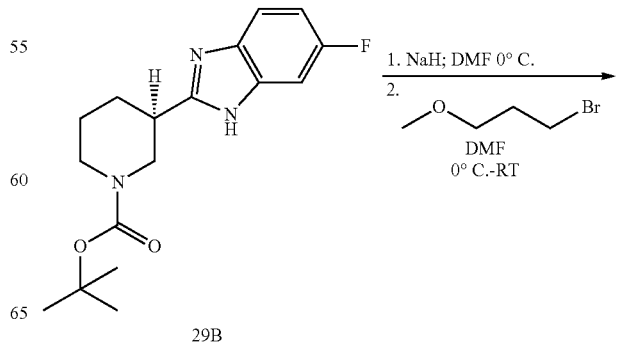

29B

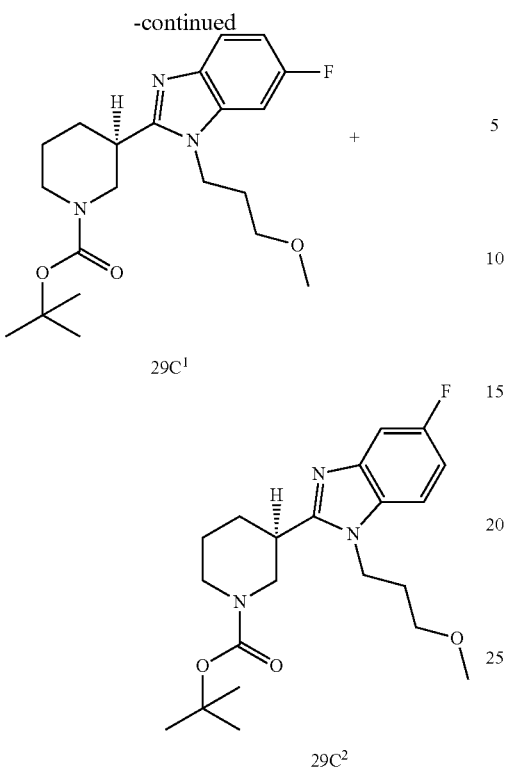

29C¹

29C²

29B (1.85 mmol max, 0.590 g of crude oil) was added to a 100 mL round-bottomed flask equipped for stirring under nitrogen. DMF (10 mL) was added and the resultant solution was cooled to 0° C. with an ice bath. NaH (60% in mineral oil, 2.04 mmol, 0.081 g) was then added and the subsequent solution was allowed to stir under nitrogen for 0.5 hr. At this time 1-bromo-3-methoxypropane (2.13 mmol, 0.326 g) was added, the ice bath was removed and the reaction solution was allowed to warm to room temperature and stir for 1 hr. The reaction solution was then poured into ice-water, extracted with ethyl acetate, and washed once with saturated aqueous sodium chloride. The organic layer was collected and anhydrous Na$_2$SO$_4$ was added to remove water. The suspension was then filtered. This filtrate was collected, concentrated, and dried in-vacuo affording a brown oil. This material was then purified by chromatography on silica gel (5-10% CH$_3$OH/CH$_2$Cl$_2$) to afford a mixture of (R)-tert-Butyl 3-(6-fluoro-1-(3-methoxypropyl)-1H-benzo[d]imidazol-2-yl)piperidine-1-carboxylate (29C¹ and (R)-tert-butyl 3-(5-fluoro-1-(3-methoxypropyl)-1H-benzo[d]imidazol-2-yl)piperidine-1-carboxylate (29C²) as a clear oil which was carried on without further purification. ESI-MS: m/z 392.4 (M+H)⁺.

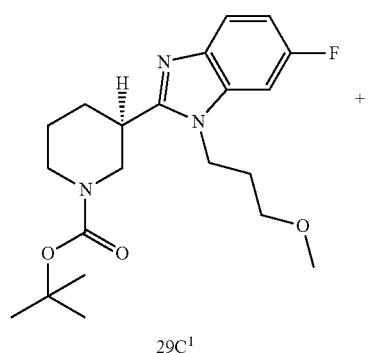

29C¹

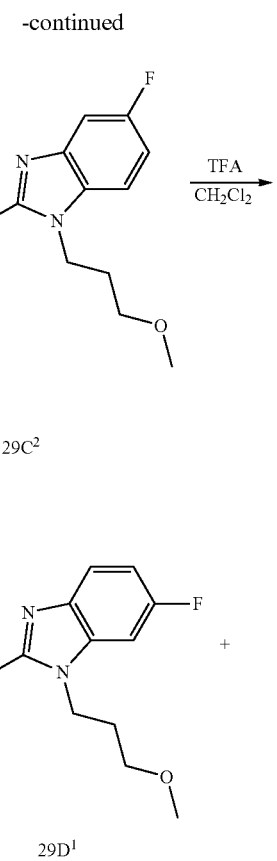

29C²

29D¹

29D²

A mixture of 29C¹ and 29C² (0.38 mmol, 0.150 g) was added to a 10 mL round-bottomed flask equipped for stirring under nitrogen. Dichloromethane (1 mL) and trifluoroacetic acid (1 mL) were then added and the resultant solution was allowed to stir under nitrogen for 4 hr. The reaction was then concentrated and dried in-vacuo affording a mixture of (R)-6-fluoro-1-(3-methoxypropyl)-2-(piperidin-3-yl)-1H-benzo[d]imidazole (29D¹) and (R)-5-fluoro-1-(3-methoxypropyl)-2-(piperidin-3-yl)-1H-benzo[d]imidazole (29D²) as a brown oil that was used without further purification. ESI-MS: m/z 292.4 (M+H)⁺,

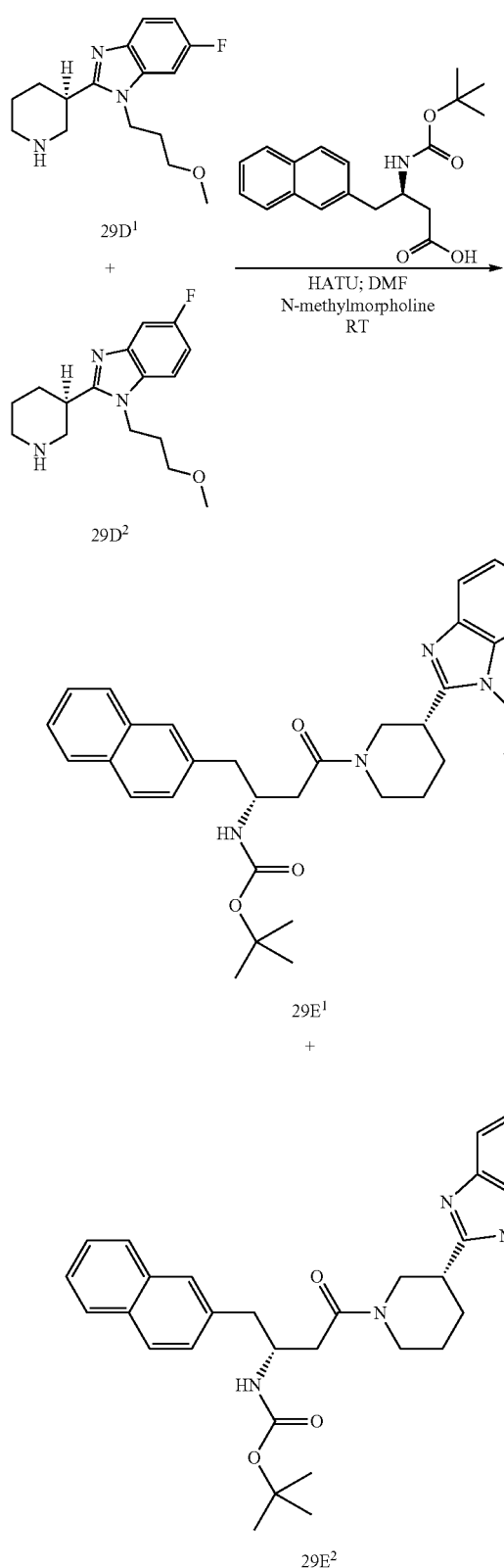

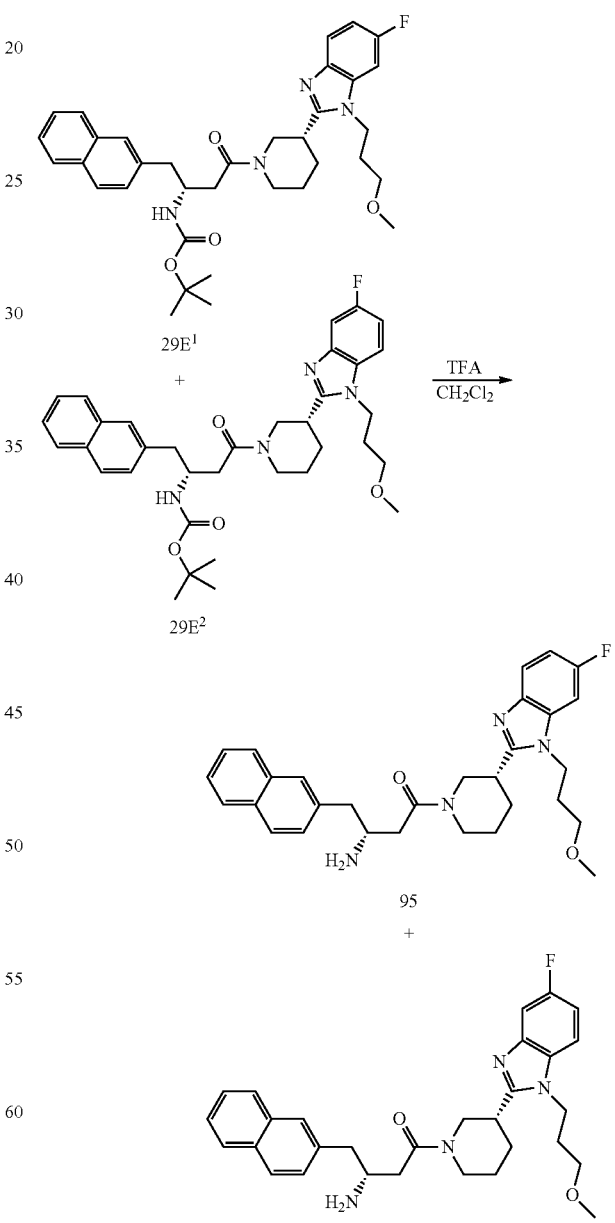

0.108 g) and N-methylmorpholine (1.52 mmol, 0.167 mL) were then added and the solution was allowed to stir at rt for 5 min. HATU (0.410 mmol, 0.156 g) was added and the resultant solution was stirred at room temperature for 3 hR. The reaction solution was then directly purified by preparative LC/MS (35-95% CH$_3$CN in H$_2$O). The resultant fractions were collected and the solvent was removed in-vacuo affording tert-Butyl (R)-4-((R)-3-(6-fluoro-1-(3-methoxypropyl)-1H-benzo[d]imidazol-2-yl)piperidin-1-yl)-1-(naphthalen-2-yl)-4-oxobutan-2-ylcarbamate (29E$^1$) and tert-butyl (R)-4-((R)-3-(5-fluoro-1-(3-methoxypropyl)-1H-benzo[d]imidazol-2-yl)piperidin-1-yl)-1-(naphthalen-2-yl)-4-oxobutan-2-ylcarbamate (29E$^2$) as a clear oil (0.153 mmol, 0.093 g, 40% yield over 4-steps). ESI-MS: m/z 603.5 (M+H)$^+$.

A mixture of 29D$^1$ and 29D$^2$ (0.380 mmol max, crude oil) were added to a 10 mL round-bottomed flask equipped for stirring under nitrogen. DMF (2 mL), (R)-3-(tert-butoxycarbonylamino)-4-(naphthalen-2-yl)butanoic acid (0.400 mmol, A mixture of 29E¹ and 29E² (0.153 mmol, 0.093 g)) was added to a 10 mL round-bottomed flask equipped for stirring under nitrogen and dissolved in CH₂Cl₂ (2 mL). Trifluoroacetic acid (2 mL) was then added and the solution was stirred at room temperature for 2 hr. The solvent was removed in-vacuo affording a clear colored oil. The enantiomers were further separated by Berger Prep/SFC under the following conditions: column: ChiralPak AD-H (5 um, 21.2×250 mm); mobile phase:A: liquid CO₂, B: 10 mM NH₄OAc in EtOH, flow rate: 50 mL/min, gradient: 17% B, run time: 52 min (half-stack-injection method applied), prep injection volume: 500 uL, yielding separated positional isomers (total 83% yield):

Compound 95. (R)-3-amino-1((R)-3-(6-fluoro-1-(3-methoxypropyl)-1H-benzo[d]imidazol-2-yl)piperidin-1-yl)-4-(naphthalen-2-yl)butan-1-one (0.066 mmol, 0.033 g). ESI-MS: m/z 503.4 (M+H)⁺.

Compound 96. (R)-3-amino-1((R)-3-(5-fluoro-1-(3-methoxypropyl)-1H-benzo[d]imidazol-2-yl)piperidin-1-yl)-4-(naphthalen-2-yl)butan-1-one (0.062 mmol, 0.031 g). ESI-MS: m/z 503.4 (M+H)⁺.

Example 30

Synthesis of (R)-3-Amino-1((R)-3-(7-chloro-1-(3-methoxypropyl)-1H-benzo[d]imidazol-2-yl)piperidin-1-yl)-4-(naphthalen-2-yl)butan-1-one (97)

Step A.

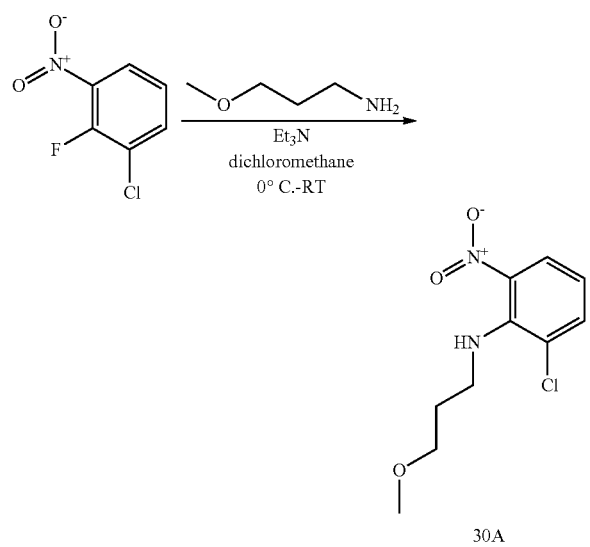

1-Chloro-2-fluoro-3-nitrobenzene (2.85 mmol, 0.500 g) was added to an oven dried 50 mL round-bottomed flask equipped for stifling under nitrogen. Dichlormethane (10 mL) and triethylamine (3.13 mmol, 0.437 mL) were added and the resultant solution was cooled to 0° C. with an ice-bath. 3-Methoxypropan-1-amine (2.85 mmol, 0.292 mL) was then added drop-wise via syringe and the resultant solution was stirred at 0° C. for 1 hr. The ice-bath was removed and the reaction was allowed to warm to room temperature and stirred for 16 hr. The reaction solution was poured into water and extracted twice with dichloromethane (50 mL). The organic layer was collected and water was subsequently removed with anhydrous Na₂SO₄ and the suspension was filtered. The filtrate was collected, concentrated, and dried in-vacuo affording an orange oil, which was then purified by chromatography on slica gel (10-70% ethyl aetate/hexanes) to afford 2-chloro-N-(3-methoxypropyl)-6-nitroaniline (30A) as a yellow solid (2.23 mmol, 0.542 g, 78% yield). ESI-MS: m/z 245.3 (M+H)⁺.

Step B.

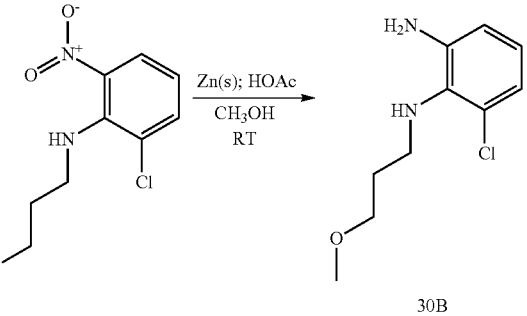

2-Chloro-N-(3-methoxypropyl)-6-nitroaniline (30A) (2.23 mmol, 0.542 g) was added to an oven dried 50 mL round-bottomed flask equipped for stirring under nitrogen. Methanol (10 mL) and acetic acid (1 mL, glacial) were then added. Zinc (11.17 mmol, 0.730 g, 20-30 mesh) was then added and the resultant mixture was allowed to stir at room temperature for 16 hr. Analysis of the reaction by LC/MS indicated a complete conversion to product at this time. This resultant mixture was then filtered over Celite®, concentrated in-vacuo, and transferred to a 250 mL seperatory funnel with ethyl acetate (2×20 mL) and water (2×10 mL). The layers were separated and the organic layer was washed once with saturated aqueous sodium chloride (40 mL). The organic layer was collected and water was subsequently removed with anhydrous Na₂SO₄, and the suspension filtered. This filtrate was collected, concentrated, and dried in-vacuo affording 6-Chloro-N-1-(3-methoxypropyl)benzene-1,2-diamine (30B) a brown oil which was used without further purification. ESI-MS: m/z 215.3 (M+H)⁺.

Step C.

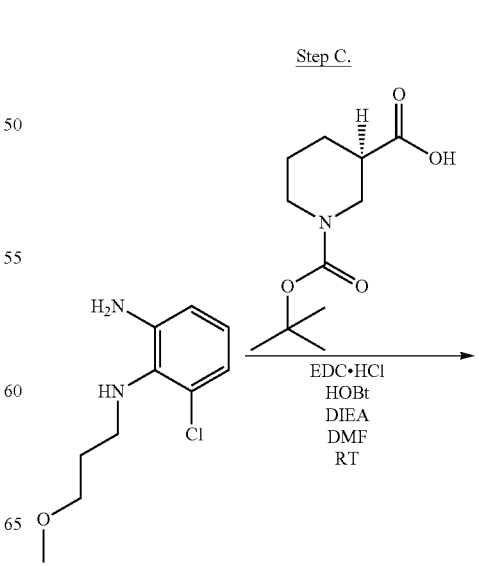

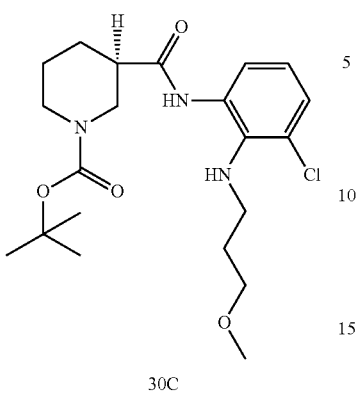

30C (R)-1-(tert-Butoxycarbonyl)piperidine-3-carboxylic acid (30B) (2.23 mmol, 0.511 g) and 6-chloro-N-1-(3-methoxypropyl)benzene-1,2-diamine (2.23 mmol, crude oil) were added to a 25 mL round-bottomed flask equipped for stirring under nitrogen. DMF (5 mL) and diisopropylethylamine (6.69 mmol, 1.2 mL) were added and the resultant solution was allowed to stir for 5 min at room temperature. N1-((ethylimino)methylene)-N3,N3-dimethylpropane-1,3-diamine hydrochloride (2.45 mmol, 0.470 g) and 1H-benzo[d][1,2,3]triazol-1-ol (2.45 mmol, 0.331 g) were then added and the reaction was allowed to stir at room temperature for 16 hr. Analysis of the reaction solution by LC/MS indicated multiple products along with a small quantity of the desired title compound. The reaction solution was poured into water and extracted with ethyl acetate. The organic layer was washed three times with water, two times with saturated aqueous sodium bicarbonate, and once with saturated aqueous sodium chloride. The organic layer was collected and Na₂SO4 was added to remove residual water. This mixture was then filtered; the filtrate was collected, concentrated, and dried in-vacuo affording (R)-tert-Butyl 3-(3-chloro-2-(3-methoxypropylamino)phen ylcarbamoyl)piperidine-1-carboxylate (30C) a brownish foam that was carried directly on to the next step without further purification. ESI-MS: m/z 426.4 (M+H)⁺.

Step D.

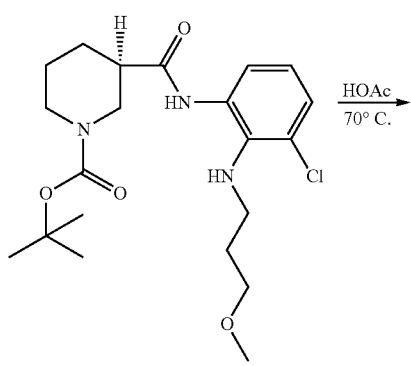

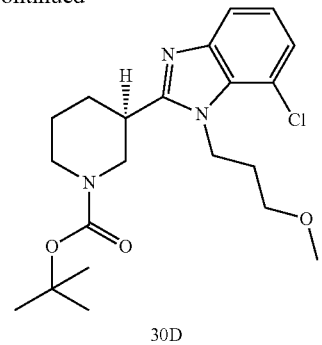

30D (R)-tert-Butyl 3-(3-chloro-2-(3-methoxypropylamino) phenylcarbamoyl)piperidine-1-carboxylate (30C) (crude material, 2.23 mmol max) was added to a 50 mL round-bottomed flask equipped for stirring under nitrogen. Glacial acetic acid (10 mL) was then added and the resultant solution was stirred at 70° C. under nitrogen for 16 hr. Analysis of the reaction mixture at this time by LC/MS indicated that the reaction was complete. The reaction solution was then concentrated in-vacuo to give a brownish oil. Toluene (30 mL) was added and the subsequent solution was concentrated in vacuo. This dissolution in toluene and re-concentration was repeated three times to remove any trace quantities of acetic acid affording (R)-tert-butyl 3-(7-chloro-1-(3-methoxypropyl)-1H-benzo[d]imidazol-2-yl)piperidine-1-carboxylate (30D) as a brown oil. This oil was then purified by preparative LC/MS (25-85% CH₃CN in H₂O) to afford the title compound 30D as a tan oil (0.233 mmol, 0.095 g, 10% yield over 3-steps). 1H NMR (400 MHz, DMSO-d₆) δ ppm 1.39 (s, 9H) 1.46-1.60 (m, 1H) 1.72-1.96 (m, 2H) 1.97-2.12 (m, 3H) 2.77-2.92 (m, 1H) 3.02-3.15 (m, 2H) 3.24 (s, 3H) 3.29-3.40 (m, 2H) 3.93-4.02 (m, 1H) 4.12 (br. s., 1H) 4.51-4.59 (m, 2H) 7.20 (t, J=7.83 Hz, 1H) 7.28 (d, J=7.83 Hz, 1H) 7.58 (d, J=7.83 Hz, 1H) ESI-MS: m/z 408.2 (M+H)⁺.

Step E.

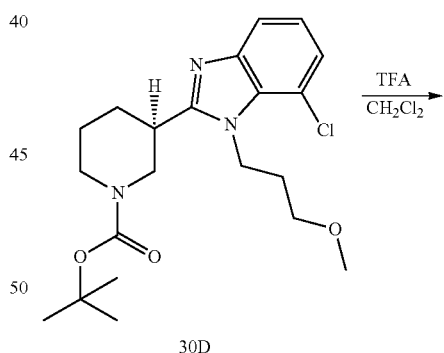

30D

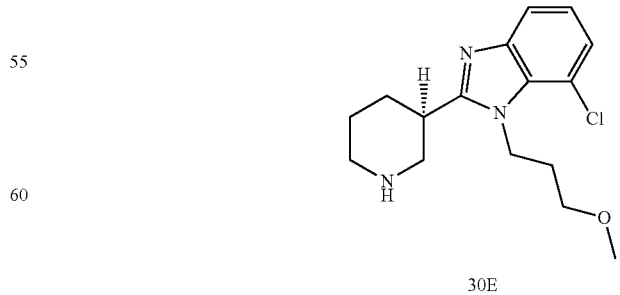

30E (R)-tert-Butyl 3-(7-chloro-1-(3-methoxypropyl)-1H-benzo[d]imidazol-2-yl)piperidine-1-carboxylate (0.222 mmol, 0.090 g) was added to a 10 mL round-bottomed flask equipped for stirring under nitrogen. Dichloromethane (1 mL) and trifluoroacetic acid (1 mL) were then added and the resultant solution was allowed to stir under nitrogen for 4 hr. The reaction was then concentrated and dried in-vacuo affording (R)-7-Chloro-1-(3-methoxypropyl)-2-(piperidin-3-yl)-1H-benzo[d]imidazole (30E) a brown oil and used without further purification. ESI-MS: m/z 308.2 (M+H)⁺.

Step F.

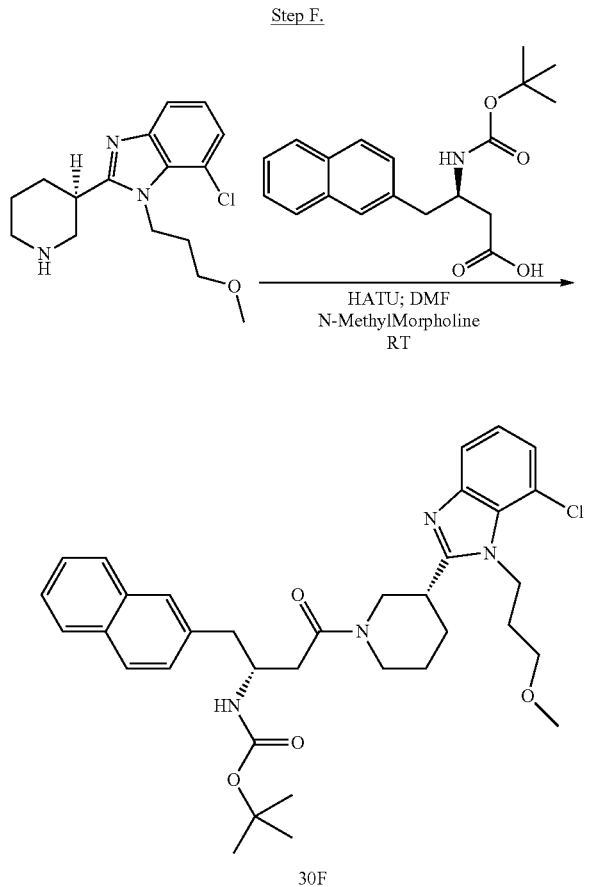

30F ((R)-7-chloro-1-(3-methoxypropyl)-2-(piperidin-3-yl)-1H-benzo[d]imidazole (0.111 mmol max, about half of crude oil from Step E) was added to a 15 mL round-bottomed flask equipped for stirring under nitrogen. DMF (2 mL), (R)-3-(tert-butoxycarbonylamino)-4-(naphthalen-2-yl)butanoic acid (0.122 mmol, 0.040 g) and N-methylmorpholine (0.555 mmol, 0.061 mL) were then added and the solution was allowed to stir at rt for 5 min. HATU (0.122 mmol, 0.046 g) was added and the resultant solution was stirred at room temperature for 3 hr. The reaction solution was then directly purified by preparative LC/MS (20-85% CH₃CN in H₂O). The resultant fractions were collected and the solvent was removed in-vacuo affording tert-butyl (R)-4-((R)-3-(1-(3-methoxypropyl)-1H-benzo[d]imidazol-2-yl)piperidin-1-yl)-1-(naphthalen-2-yl)-4-oxobutan-2-ylcarbamate (30F) as a clear oil that was used directly onto the next step. ESI-ESI-MS: m/z 619.5 (M+H)⁺.

Step G.

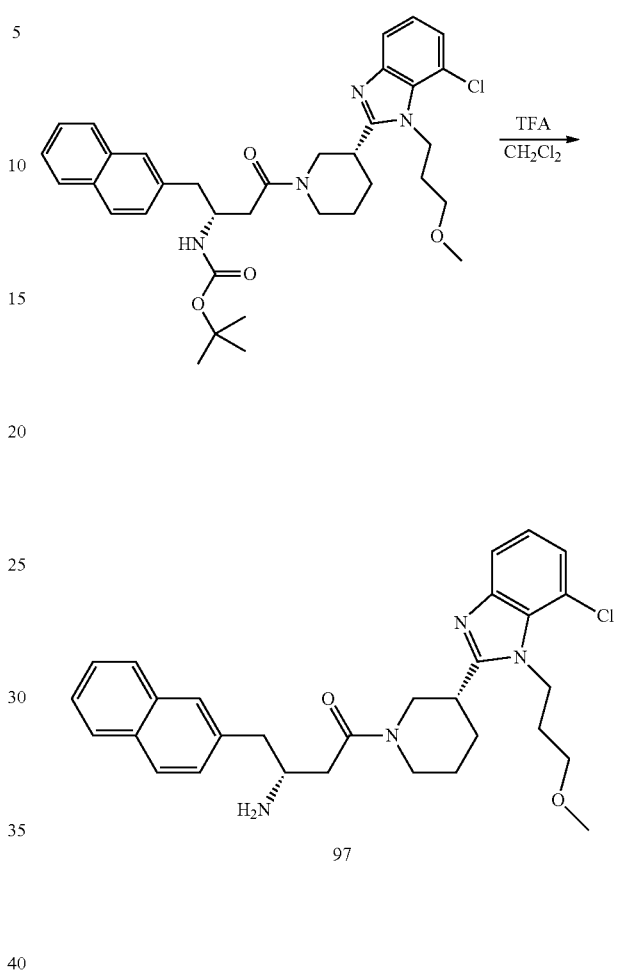

97 tert-Butyl (R)-4-((R)-3-(7-chloro-1-(3-methoxypropyl)-1H-benzo[d]imidazol-2-yl)piperidin-1-yl)-1-(naphthalen-2-yl)-4-oxobutan-2-ylcarbamate (0.111 mmol max, crude oil from Step F) was added to a 10 mL round-bottomed flask equipped for stirring under nitrogen. Dichloromethane (1 mL) and trifluoroacetic acid (1 mL) were then added and the resultant solution was allowed to stir under nitrogen for 4 HR. The solvent was removed in-vacuo affording a clear colored oil. This oil was re-dissolved in methanol (3 mL), filtered, and then purified by preparative LC/MS (25-65% CH₃CN in H₂O). The resultant fractions were collected and the solvent was removed in-vacuo affording a clear colored oil. This oil was re-dissolved in CH₃CN (1 mL) and water (2 mL). The resultant solution was frozen and lyophilized to afford (R)-3-amino-1-((R)-3-(7-chloro-1-(3-methoxypropyl)-1H-benzo[d]imidazol-2-yl)piperidin-1-yl)-4-(naphthalen-2-yl)butan-1-one (97) as its trifluoroacetic acid salt as a white flocculent solid (0.052 mmol, 0.033 g, 47% over 3-steps) ¹H NMR (400 MHz, DMSO-d₆) δ ppm 1.35-1.56 (m, 1H) 1.63-2.14 (m, 5H) 2.60-2.78 (m, 2H) 2.88-3.42 (m, 9H) 3.69-4.01 (m, 3H) 4.00-4.61 (m, 5H) 7.10-7.30 (m, 2H) 7.42-7.60 (m, 4H) 7.73-7.99 (m, 4H) ESI-MS: m/z 519.2 (M+H)⁺.

Example 31

Synthesis of (R)-3-amino-4-(biphenyl-4-yl)-1-((R)-3-(7-chloro-1-(3-methoxypropyl)-1H-benzo[d]imidazol-2-yl)piperidin-1-yl)butan-1-one (98)

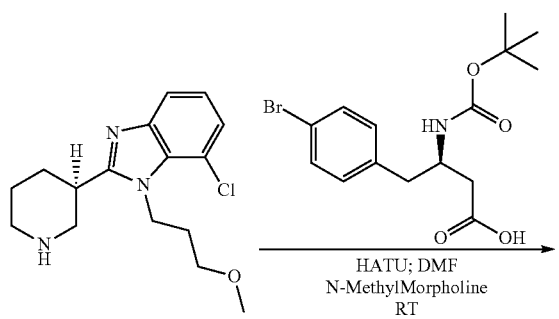

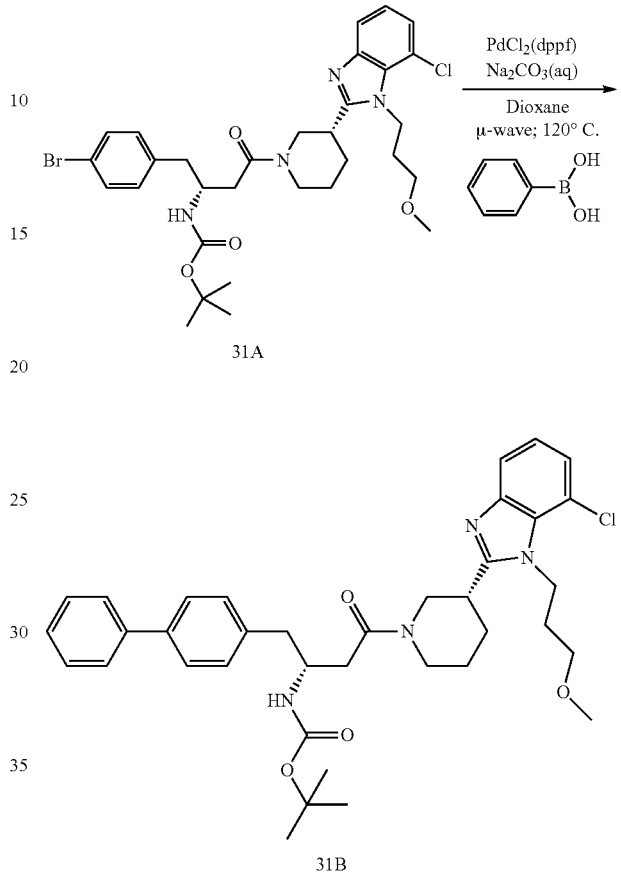

((R)-7-Chloro-1-(3-methoxypropyl)-2-(piperidin-3-yl)-1H-benzo[d]imidazole (30E) (0.111 mmol, crude oil) prepared according to the procedure described in Example 30, Steps A-E was added to a 15 mL round-bottomed flask equipped for stirring under nitrogen. DMF (2 mL), (R)-4-(4-bromophenyl)-3-(tert-butoxycarbonylamino)butanoic acid (0.122 mmol, 0.032 g) and N-methylmorpholine (0.555 mmol, 0.061 mL) were then added and the solution was allowed to stir at rt for 5 min. HATU (0.122 mmol, 0.046 g) was added and the resultant solution was stirred at room temperature for 3 hrs. The reaction solution was then directly purified by preparative LC/MS (20-85% CH₃CN in H₂O). The resultant fractions were collected and the solvent was removed in-vacuo affording tert-butyl (R)-1-(4-bromophenyl)-4-((R)-3-(7-chloro-1-(3-methoxypropyl)-1H-benzo[d]imidazol-2-yl)piperidin-1-yl)-4-oxobutan-2-ylcarbamate (31A) as a clear oil that was used directly onto the next step. ESI-MS: m/z 647.3 (M+H)⁺.

tert-Butyl (R)-1-(4-bromophenyl)-4-((R)-3-(7-chloro-1-(3-methoxypropyl)-1H-benzo[d]imidazol-2-yl)piperidin-1-yl)-4-oxobutan-2-ylcarbamate (31A) (0.111 mmol max, crude oil) and phenylboronic acid (0.144 mmol, 0.018 g) were added to a 5 mL microwave vessel equipped with a magnetic stir bar. Dioxane (2 mL) and Na₂CO₃ (1 mL of a 2 M in aqueous solution) were then added and the reaction vessel was flushed with nitrogen gas. PdCl₂(dppf) (0.006 mmol, 0.004 g) was added, the reaction vessel was sealed and placed in a microwave reactor and heated to 120° C. for 15 minutes. The reaction solution was then poured into water, extracted with ethyl acetate, and washed once with saturated aqueous sodium chloride. The organic layer was collected and subsequently dried with anhydrous Na₂SO₄ and filtered. This filtrate was collected, concentrated, and dried in-vacuo. This crude material was directly purified by preparative LC/MS (gradient 25-85% CH₃CN in H₂O). The resultant fractions were collected and the solvent was removed in-vacuo affording tert-butyl (R)-1-(biphenyl-4-yl)-4-((R)-3-(7-chloro-1-(3-methoxypropyl)-1H-benzo[d]imidazol-2-yl)piperidin-1-yl)-4-oxobutan-2-ylcarbamate (31B) as a clear oil. ESI-MS: m/z 645.5 (M+H)⁺.

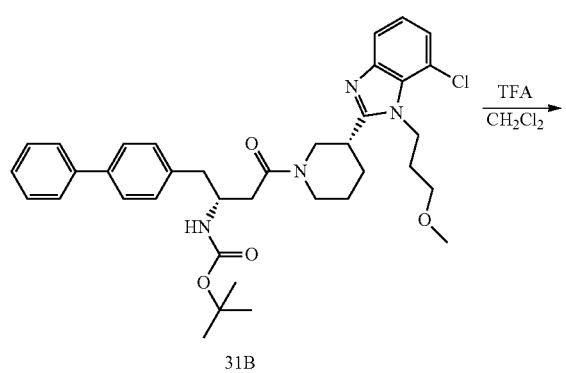

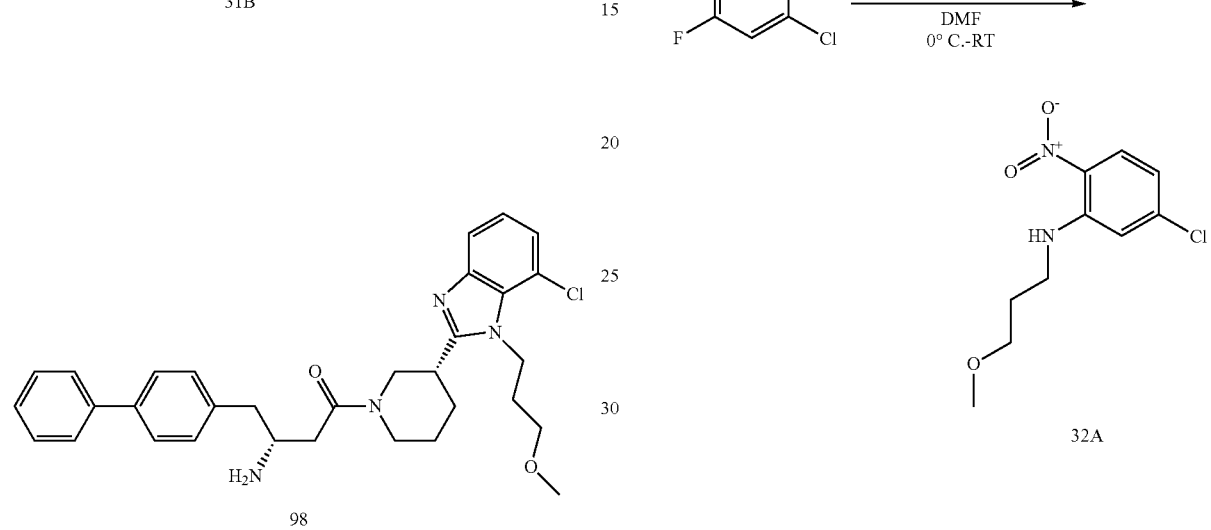

tert-Butyl (R)-1-(biphenyl-4-yl)-4-((R)-3-(7-chloro-1-(3-methoxypropyl)-1H-benzo[d]imidazol-2-yl)piperidin-1-yl)-4-oxobutan-2-ylcarbamate (31B) (0.111 mmol max, crude oil) was added to a 10 mL round-bottomed flask equipped for stirring under nitrogen. Dichloromethane (1 mL) and trifluoroacetic acid (1 mL) were then added and the resultant solution was allowed to stir under nitrogen for 4 hr. The solvent was removed in-vacuo affording a clear colored oil. This oil was re-dissolved in methanol (3 mL), filtered, and then purified by preparative LC/MS (20-45% $CH_3CN$ in $H_2O$). The resultant fractions were collected and the solvent was removed in-vacuo affording a clear colored oil. This oil was re-dissolved in $CH_3CN$ (1 mL) and water (2 mL). The resultant solution was frozen and lyophilized to afford(R)-3-amino-4-(biphenyl-4-yl)-1-((R)-3-(7-chloro-1-(3-methoxypropyl)-1H-benzo[d]imidazol-2-yl)piperidin-1-yl)butan-1-one (98) as its trifluoroacetic acid salt as a white flocculent solid (0.067 mmol, 0.044 g, 60% over 4-steps). $^1H$ NMR (400 MHz, DMSO-$d_6$) δ ppm 1.40-1.59 (m, 1H) 1.71-2.16 (m, 5H) 2.58-3.49 (m, 12H) 3.67-4.04 (m, 2H) 4.37-4.62 (m, 3H) 7.13-7.23 (m, 1H) 7.23-7.30 (m, 1H) 7.30-7.41 (m, 3H) 7.47 (td, J=7.58, 3.54 Hz, 2H) 7.50-7.71 (m, 5H) ESI-MS: m/z 545.2 (M+H)$^+$.

Example 32

Synthesis of (R)-3-amino-1-((R)-3-(6-chloro-1-(3-methoxypropyl)-1H-benzo[d]imidazol-2-yl)piperidin-1-yl)-4-(naphthalen-2-yl)butan-1-one (99)

4-Chloro-2-fluoro-1-nitrobenzene (2.85 mmol, 0.500 g) was added to an oven dried 25 mL round-bottomed flask equipped for stirring under nitrogen. DMF (5 mL) was added and the resultant solution was cooled to 0° C. with an ice-bath. 3-Methoxypropan-1-amine (2.99 mmol, 0.306 mL) was then added drop-wise via syringe and the resultant solution was stirred at 0° C. for 1 hr. The ice-bath was removed and the reaction was allowed to warm to room temperature and stir for 16 hr. The reaction solution was then poured into water, extracted with ethyl acetate, and washed once with saturated aqueous sodium chloride. The organic layer was collected and subsequently dried with anhydrous $Na_2SO_4$ and filtered; filtrate was collected, concentrated, and dried in-vacuo affording 5-chloro-N-(3-methoxypropyl)-2-nitroaniline (32A) as an orange oil. This material was used directly in the next step without further purification. ESI-MS: m/z 245.3 (M+H)$^+$.

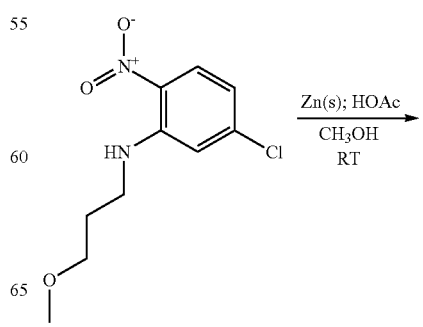

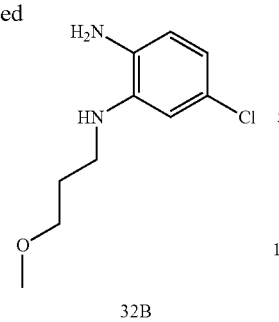

32B

5-Chloro-N-(3-methoxypropyl)-2-nitroaniline (32A) (2.85 mmol max, crude oil) was added to an oven dried 100 mL round-bottomed flask equipped for stirring under nitrogen. Methanol (20 mL) and acetic acid (1.5 mL, glacial) were then added. Zinc (15.29 mmol, 1.0 g, 20-30 mesh) was then added and the resultant mixture was allowed to stir at room temperature for 16 hr. Analysis of the reaction by LC/MS indicated a complete conversion to product at this time. This resultant mixture was then filtered over Celite®, concentrated in-vacuo, and transferred to a 250 mL seperatory funnel with ethyl acetate (2×30 mL) and water (2×20 mL). The layers were separated and the organic layer was washed once with saturated aqueous sodium chloride (40 mL). The organic layer was collected and subsequently dried with anhydrous Na$_2$SO$_4$ and filtered. This filtrate was collected, concentrated, and dried in-vacuo affording 5-chloro-N-1-(3-methoxypropyl)benzene-1,2-diamine (32B) a brown oil which was used directly in the next step without further purification. ESI-MS: m/z 215.3 (M+H)$^+$.

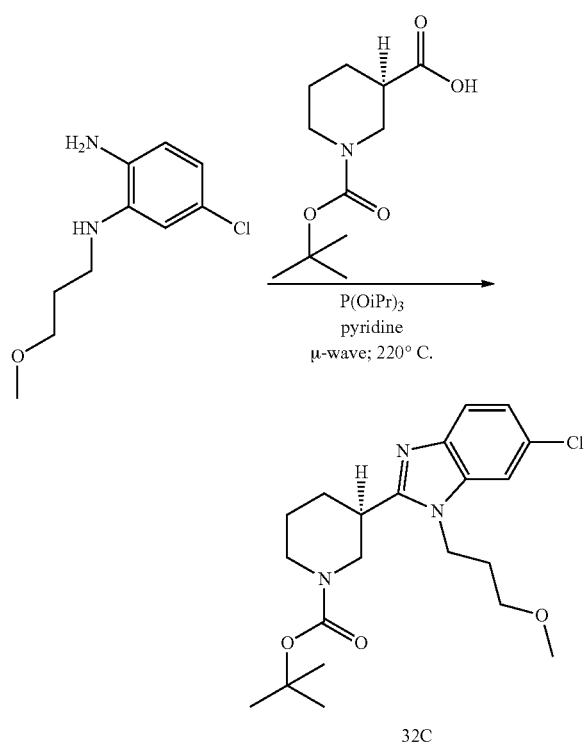

5-Chloro-N-1-(3-methoxypropyl)benzene-1,2-diamine (32B) (0.932 mmol; 0.200 g) and (R)-1-(tert-butoxycarbonyl)piperidine-3-carboxylic acid (0.932 mmol; 0.214 g) were added to a 5 mL microwave vessel equipped with a magnetic stir bar. Pyridine (2 mL) and triisopropylphosphite (1.03 mmol; 0.270 mL) were then added and the reaction vessel was flushed with nitrogen gas. The reaction vessel was sealed and placed in a microwave reactor and heated to 220° C. for 15 minutes. The reaction solution was then poured into water, extracted with ethyl acetate, and washed once with saturated aqueous sodium chloride. The organic layer was collected and subsequently dried with anhydrous Na$_2$SO$_4$ and filtered. This filtrate was collected, concentrated, and dried in-vacuo. This crude material was purified by silica gel chromatography (20% CH$_3$CN/CH$_2$Cl$_2$). The resultant fractions were collected and the solvent was removed in-vacuo affording (R)-tert-butyl 3-(6-chloro-1-(3-methoxypropyl)-1H-benzo[d]imidazol-2-yl)piperidine-1-carboxylate (32C) as a tan oil (0.135 mmol, 0.055 g, 14% yield over 3-steps). ESI-MS: m/z 408.4 (M+H)$^+$.

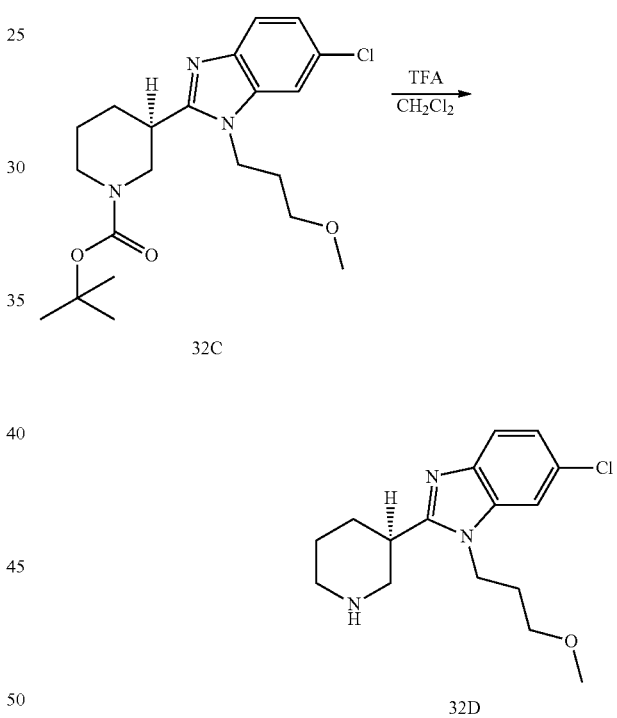

((R)-tert-Butyl 3-(6-chloro-1-(3-methoxypropyl)-1H-benzo[d]imidazol-2-yl)piperidine-1-carboxylate (32C) (0.135 mmol, 0.055 g) was added to a 10 mL round-bottomed flask equipped for stirring under nitrogen. Dichloromethane (1 mL) and trifluoroacetic acid (1 mL) were then added and the resultant solution was allowed to stir under nitrogen for 4 hr. The reaction was then concentrated and dried in-vacuo affording (R)-6-chloro-1-(3-methoxypropyl)-2-(piperidin-3-yl)-1H-benzo[d]imidazole (32D) as a tan oil that was used directly in the next step without further purification. ESI-MS: m/z 308.3 (M+H)$^+$.

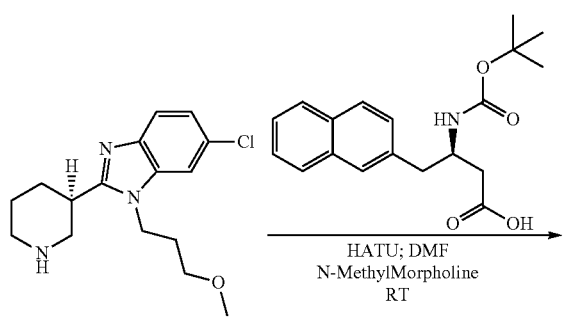

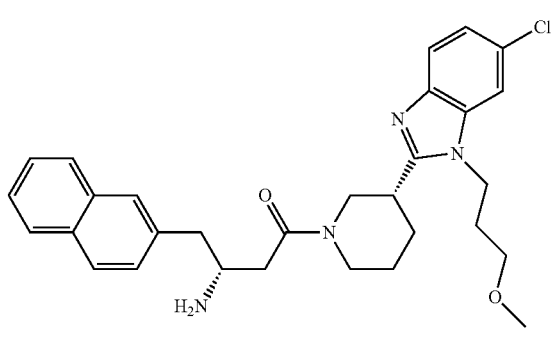

(R)-6-Chloro-1-(3-methoxypropyl)-2-(piperidin-3-yl)-1H-benzo[d]imidazole (32D) (0.135 mmol, 0.055 g) was added to a 15 mL round-bottomed flask equipped for stirring under nitrogen. DMF (2 mL), (R)-3-(tert-butoxycarbonylamino)-4-(naphthalen-2-yl)butanoic acid (0.197 mmol, 0.053 g) and N-methylmorpholine (0.706 mmol, 0.079 mL) were then added and the solution was allowed to stir at rt for 5 min. HATU (0.197 mmol, 0.075 g) was added and the resultant solution was stirred at room temperature for 3 hr. The reaction solution was then directly purified by preparative LC/MS (25-85% CH$_3$CN in H$_2$O). The resultant fractions were collected and the solvent was removed in-vacuo affording tert-Butyl (R)-4-((R)-3-(6-chloro-1-(3-methoxypropyl)-1H-benz o[d]imidazol-2-yl)piperidine-1-yl)-1-(naphthalen-2-yl)-4-oxobutan-2-ylcarbamate (32E) as a clear oil that was used directly onto the next step. ESI-MS: m/z 619.5 (M+H)$^+$, tert-Butyl (R)-4-((R)-3-(6-chloro-1-(3-methoxypropyl)-1H-benzo[d]imidazol-2-yl)piperidin-1-yl)-1-(naphthalen-2-yl)-4-oxobutan-2-ylcarbamate (32E) (0.135 mmol max, crude oil) was added to a 10 mL round-bottomed flask equipped for stirring under nitrogen. Dichloromethane (1 mL) and trifluoroacetic acid (1 mL) were then added and the resultant solution was allowed to stir under nitrogen for 4 hr. The solvent was removed in-vacuo affording a clear colored oil. This oil was re-dissolved in methanol (3 mL), filtered, and then purified by preparative LC/MS (15-55% CH$_3$CN in H$_2$O). The resultant fractions were collected and the solvent was removed in-vacuo affording a clear colored oil. This oil was re-dissolved in CH$_3$CN (1 mL) and water (2 mL). The resultant solution was frozen and lyophilized to afford (R)-3-amino-1-((R)-3-(6-chloro-1-(3-methoxypropyl)-1H-benzo[d]imidazol-2-yl)piperidin-1-yl)-4-(naphthalen-2-yl)butan-1-one (99) as its trifluoroacetic acid salt and as a white flocculent solid (0.074 mmol, 0.047 g, 55% yield over 3-steps). $^1$H NMR (400 MHz, DMSO-d$_6$) δ ppm 1.33-1.54 (m, 1H) 1.68-2.11 (m, 5H) 2.61-2.77 (m, 3H) 2.88-3.44 (m, 9H) 3.71-4.04 (m, 2H) 4.07-4.23 (m, 1H) 4.25-4.39 (m, 1H) 4.49 (dd, J=36.51, 13.26 Hz, 1H) 7.21-7.31 (m, 1H) 7.44 (ddd, J=8.40, 4.61, 1.64 Hz, 1H) 7.47-7.56 (m, 2H) 7.61 (dd, J=17.43, 8.59 Hz, 1H) 7.71-8.06 (m, 5H). ESI-MS: m/z 519.4 (M+H)$^+$, Example 33

Synthesis of (R)-3-amino-1-(3-(5-methoxy-3-(3-methoxypropyl)-3H-imidazo[4,5-b]pyridin-2-yl)piperidin-1-yl)-4-(naphthalen-2-yl)butan-1-one (100)

Step A.

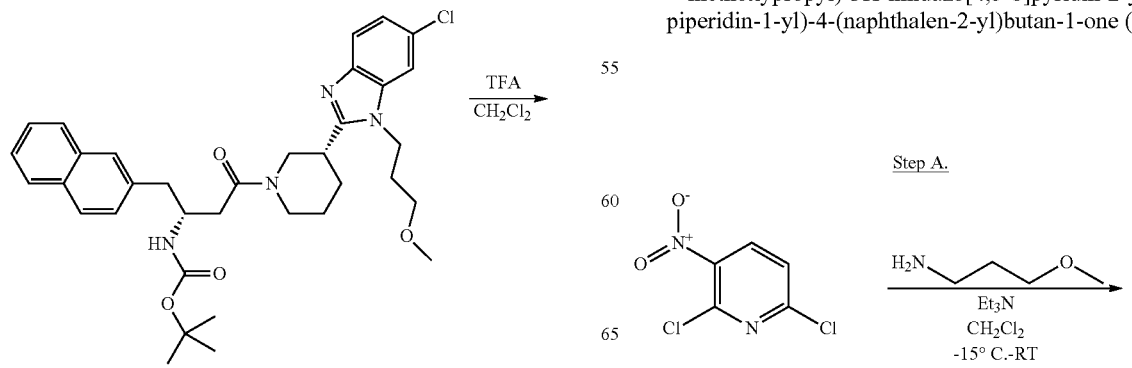

-continued

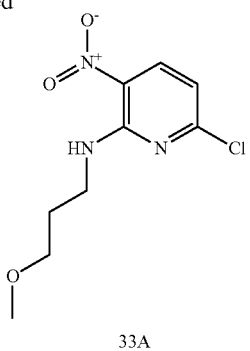

33A 2,6-Dichloro-3-nitropyridine (3.29 mmol, 0.635 g) was added to an oven dried 50 mL round-bottomed flask equipped for stirring under nitrogen. Dichlormethane (12 mL) and triethylamine (3.62 mmol, 0.504 mL) were added and the resultant solution was cooled to −15° C. with an acetone/ice bath. 3-methoxypropan-1-amine (3.29 mmol, 0.337 mL) was then added drop-wise via syringe and the resultant solution was stirred at −15° C. for 0.5 hr. The acetone/ice bath was removed and the reaction was allowed to warm to room temperature and stir for 0.5 hr. The reaction solution was poured into water and extracted twice with dichloromethane (50 mL). The organic layer was collected and subsequently dried with anhydrous $Na_2SO_4$ and filtered. This filtrate was collected, concentrated, and dried in-vacuo affording an orange oil. This material was then purified by chromatography on silica gel (20% ethyl acetate/hexanes) to afford 6-chloro-N-(3-methoxypropyl)-3-nitropyridin-2-amine (33A) as a yellow solid (3.01 mmol, 0.740 g, 92% yield). $^1$H NMR (400 MHz, DMSO-$d_6$) δ ppm 1.79-1.89 (m, 2H) 3.00 (s, 3H) 3.43 (t, J=6.06 Hz, 2H) 3.53-3.61 (m, 2H) 6.77 (d, J=8.59 Hz, 1H) 8.42 (d, J=8.08 Hz, 1H). ESI-MS: m/z 246.2 $(M+H)^+$.

Step B.

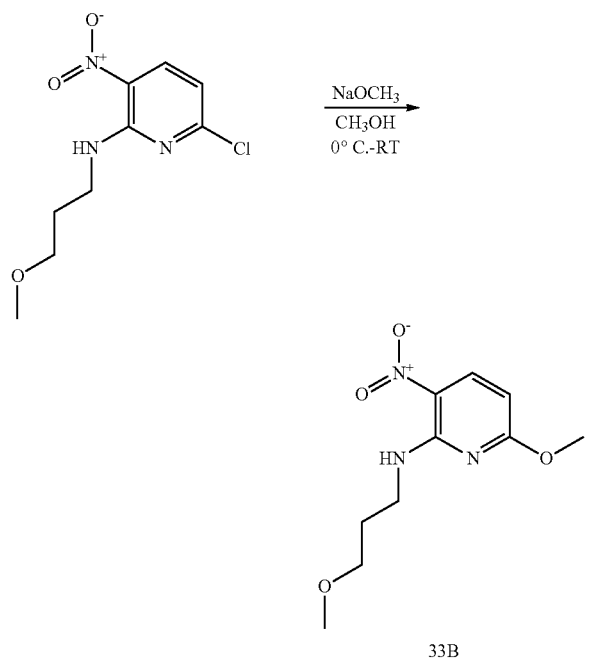

33B

6-Chloro-N-(3-methoxypropyl)-3-nitropyridin-2-amine (33A) (1.56 mmol, 0.383 g)) was added to an oven dried 50 mL round-bottomed flask equipped for stirring under nitrogen. Methanol (10 mL) was then added and the solution was cooled to 0° C. with an ice-bath. Sodium methoxide (6.93 mmol, 1.3 mL of a 30 wt % soln. in $CH_3OH$) was then added dropwise via syringe at 0° C. The ice bath was removed and the solution was allowed to warm to room temperature and stir for 2 hr. The reaction solution was then poured into water (150 mL) and the pH was adjusted to pH=7 with 1N HCl. The resultant solution was extracted with ethyl acetate, and washed once with saturated aqueous sodium chloride. The organic layer was collected and subsequently dried with anhydrous $Na_2SO_4$ and filtered. This filtrate was collected, concentrated, and dried in-vacuo affording 6-methoxy-N-(3-methoxypropyl)-3-nitropyridin-2-amine (33B) as a brown oil. This crude material was used directly in the next step without further purification. ESI-MS: m/z 242.3 $(M+H)^+$.

Step C.

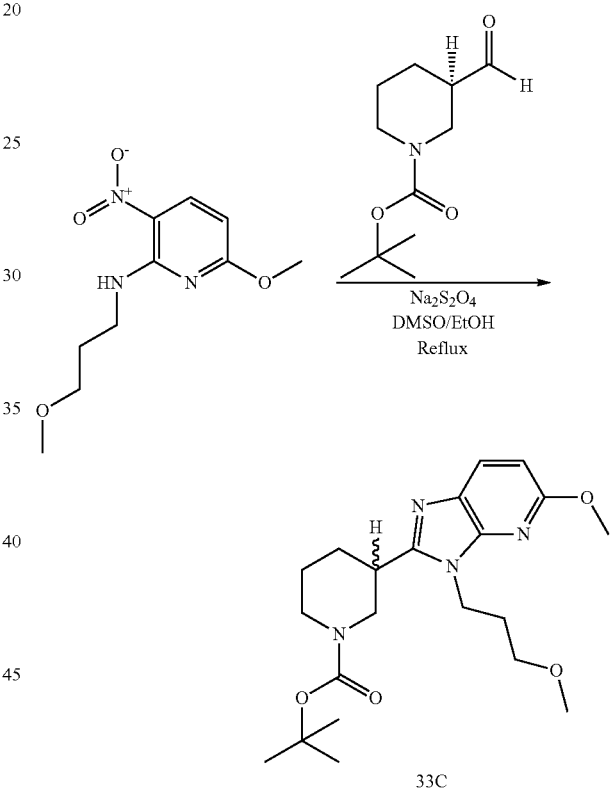

33C

6-Methoxy-N-(3-methoxypropyl)-3-nitropyridin-2-amine (33B) (1.56 mmol max, crude oil) and (R)-tert-butyl 3-formylpiperidine-1-carboxylate (1.56 mmol, 0.332 g) were added to an oven dried 50 mL round-bottomed flask equipped with a reflux condenser and for stirring under nitrogen. Ethanol (4 mL) and dimethyl sulfoxide (2 mL) were added and the solution was allowed to stir at room temperature for 5 min. Sodium hydrosulfite (4.68 mmol; 0.959 g of 85%) was then added and the resultant mixture was heated to reflux and allowed to stir for 16 hr. The reaction solution was then concentrated in-vacuo, poured into water (100 mL), extracted with ethyl acetate, and washed once with saturated aqueous sodium chloride. The organic layer was collected and subsequently dried with anhydrous $Na_2SO_4$ and filtered. This filtrate was collected, concentrated, and dried in-vacuo affording a brown oil that was further purified by silica gel chromatography (20% $CH_3CN/CH_2Cl_2$) to afford tert-butyl 3-(5-methoxy-3-(3-methoxypropyl)-3H-imidazo[4,5-b]pyridin-2-yl)piperidine-1-carboxylate (33C) as a clear oil (1.19 mmol, 0.481 g, 76% yield over 2-steps). $^1$H NMR (400 MHz, CHLOROFORM-d) δ ppm 1.48 (s, 9H) 1.54-1.70 (m, 1H) 1.84 (dt, J=13.83, 2.81Hz, 1H) 2.02-2.21 (m, 4H) 2.73-2.88 (m, 1H) 2.96-3.18 (m, 2H) 3.29-3.41 (m, 5H) 3.98 (s, 3H) 4.08-4.44 (m, 4H) 6.65 (d, J=8.59 Hz, 1H) 7.86 (d, J=8.59 Hz, 1H). ESI-MS: m/z 405.5 (M+H)$^+$.

Step D.

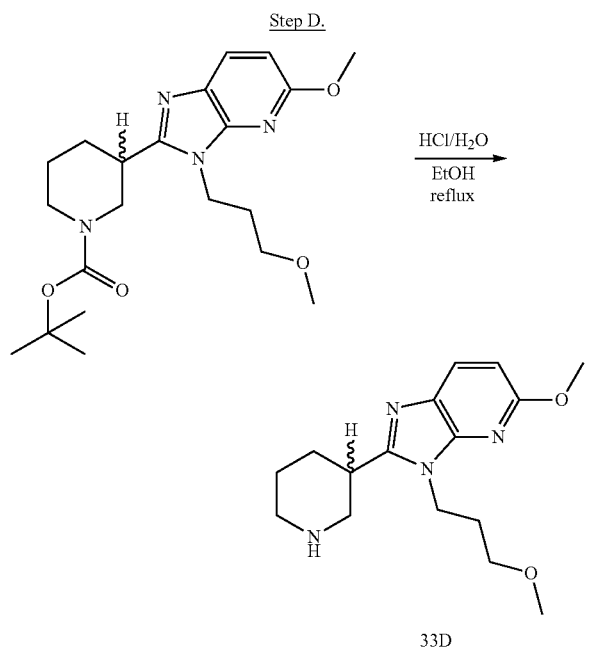

33D tert-Butyl 3-(5-methoxy-3-(3-methoxypropyl)-3H-imidazo[4, 5-13]pyridin-2-yl)piperidine-1-carboxylate (33C) (1.19 mmol; 0.481 g) was added to a 100 mL round-bottomed flask equipped with a reflux condenser and stirring under nitrogen. EtOH (15 mL) and HCl (8M in H$_2$O; 4 mL) were then added and the solution was heated to reflux for 15 min. Analysis of the reaction mixture by LC/MS indicated that the reaction was complete at this time. The ethanol was then removed in-vacuo. The resultant solution was extracted with EtOAc and a 10% aqueous K$_2$CO$_3$ solution. The organic layer was collected and dried with Na$_2$SO$_4$. This was then filtered and concentrated and dried in-vacuo affording 5-Methoxy-3-(3-methoxypropyl)-2-(piperidin-3-yl)-3H-imidazo[4,5-b]pyridine (330) as a brown oil. (1.15 mmol, 0.351 g, 97% yield). ESI-MS: m/z 305.1 (M+H)$^+$.

Step E.

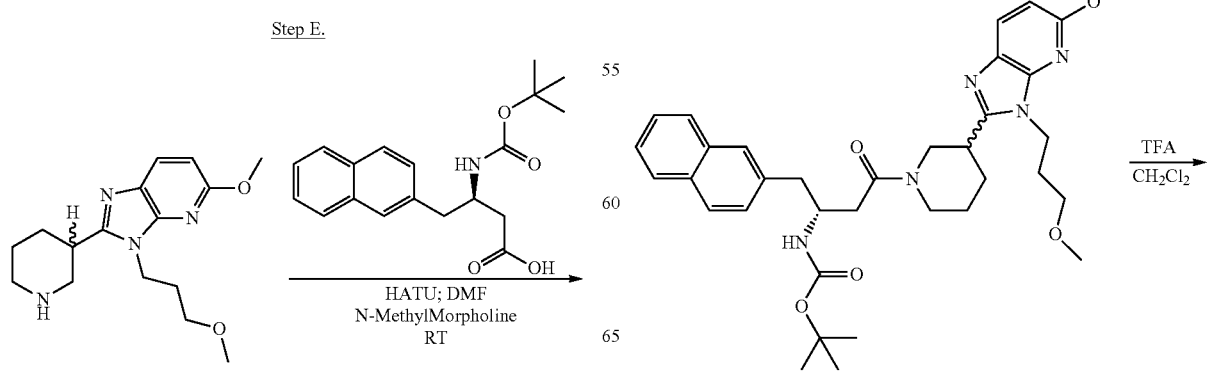

-continued

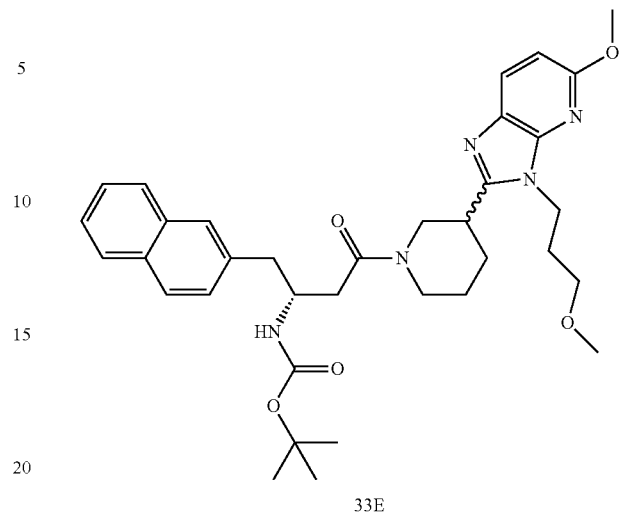

33E

5-Methoxy-3-(3-methoxypropyl)-2-(piperidin-3-yl)-3H-imidazo[4,5-b]pyridine (33D) (0.600 mmol, 0.182 g) was added to a 15 mL round-bottomed flask equipped for stirring under nitrogen. DMF (2 mL), (R)-3-(tert-butoxycarbonylamino)-4-(naphthalen-2-yl)butanoic acid (0.455 mmol, 0.150 g) and N-methylmorpholine (1.8 mmol, 0.198 mL) were then added and the solution was allowed to stir at rt for 5 min. HATU (0.660 mmol, 0.251 g) was added and the resultant solution was stirred at room temperature for 3 hr. The reaction solution was then directly purified by preparative LC/MS (35-80% CH$_3$CN in H$_2$O). The resultant fractions were collected and the solvent was removed in-vacuo affording (R)-tert-butyl 4-(3-(5-methoxy-3-(3-methoxypropyl)-3H-imidazo[4,5-b]pyridin-2-yl)piperidin-1-yl)-1-(naphthalen-2-yl)-4-oxobutan-2-ylcarbamate (33E) as a clear oil. (0.333 mmol, 0.205 g, 73% yield). ESI-MS: m/z 616.5 (M+H)$^+$.

Step F.

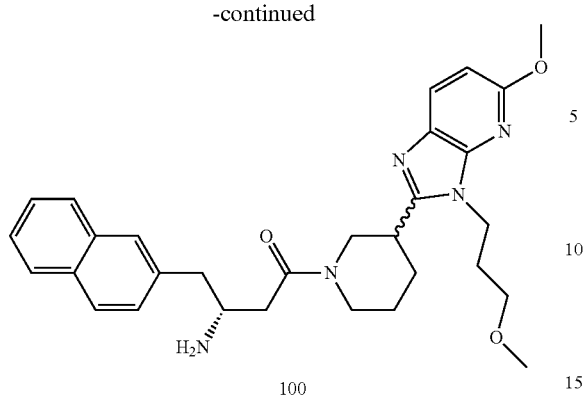

100

(R)-tert-Butyl 4-(3-(5-methoxy-3-(3-methoxypropyl)-3H-imidazo[4,5-b]pyridin-2-yl)piperidin-1-yl)-1-(naphthalen-2-yl)-4-oxobutan-2-ylcarbamate (33E) (0.069 mmol, 0.042 g) was added to a 10 mL round-bottomed flask equipped for stirring under nitrogen. Dichloromethane (1 mL) and trifluoroacetic acid (1 mL) were then added and the resultant solution was allowed to stir under nitrogen for 4 hr. The solvent was removed in-vacuo affording a clear colored oil. This oil was re-dissolved in methanol (3 mL), filtered, and then purified by preparative LC/MS (5-55% $CH_3CN$ in $H_2O$). The resultant fractions were collected and the solvent was removed in-vacuo affording a clear colored oil. This oil was re-dissolved in $CH_3CN$ (1 mL) and water (2 mL). The resultant solution was frozen and lyophilized to afford (R)-3-amino-1-(3-(5-methoxy-3-(3-methoxypropyl)-3H-imidazo[4,5-b]pyridin-2-yl)piperidin-1-yl)-4-(naphthalen-2-yl)butan-1-one (100) as its trifluoroacetic acid salt and as a white flocculent solid (0.067 mmol, 0.035 g, 98% yield) $^1$H NMR (400 MHz, DMSO-$d_6$) δ ppm 1.37-1.58 (m, 1 H) 1.68-2.14 (m, 5H) 2.57-2.89 (m, 2H) 2.89-3.23 (m, 8H) 3.24-3.48 (m, 2H) 3.92 (d, J=2.53 Hz, 5H) 4.02-4.35 (m, 2H) 4.36-4.62 (m, 1H) 6.63-6.76 (m, 1 FI) 7.35-7.59 (m, 3 H) 7.72-8.02 (m, 5H). ESI-MS: m/z 516.2 (M+H)⁺.

Example 34

Synthesis of (R)-2-(1-(3-amino-4-(naphthalen-2-yl)butanoyl)piperidin-3-yl)-3-(3-methoxypropyl)-3H-imidazo[4,5-b]pyridin-5(4H)-one (101)

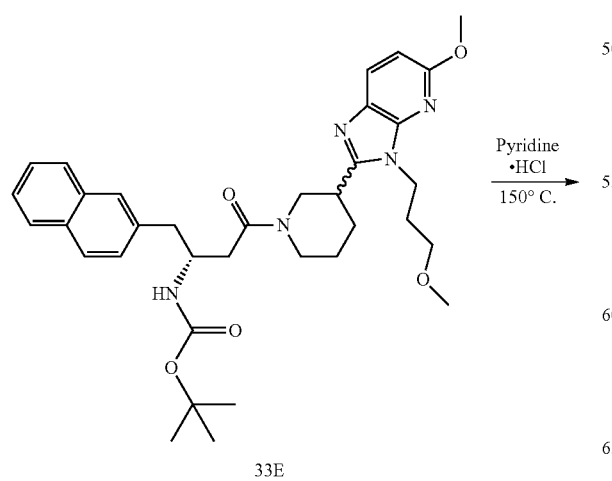

33E

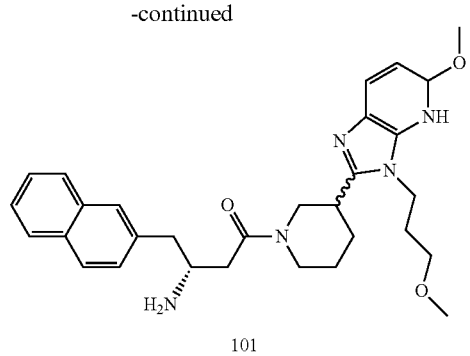

101

(R)-tert-Butyl 4-(3-(5-methoxy-3-(3-methoxypropyl)-3H-imidazo[4,5-b]pyridin-2-yl)piperidin-1-yl)-1-(naphthalen-2-yl)-4-oxobutan-2-ylcarbamate (33E) (0.114 mmol, 0.070 g) prepared according to Example 33, Steps A-E and pyridine hydrochloride (8.65 mmol, 1.00 g) were added to a 15 mL round bottomed flask equipped for stirring under nitrogen. The reaction was subsequently heated to 150° C. and stirred for 15 min. The reaction was cooled to room temperature and water (2 mL) was added. The solution was stirred for 30 minutes at room temperature to allow the solid to completely dissolve. This solution was then filtered and directly purified by preparative LC/MS (10-50% $CH_3CN$ in $H_2O$). The resultant fractions were collected and the solvent was removed in-vacuo affording the title compound as a clear colored oil (0.004 mmol, 0.002 g, 3% yield). ESI-MS: m/z 502.2 (M+H)⁺.

Example 35

Synthesis of (R)-3-amino-1-(3-(5-chloro-3-(3-methoxypropyl)-3H-imidazo[4,5-b]pyridin-2-yl)piperidin-1-yl)-4-(naphthalen-2-yl)butan-1-one (102)

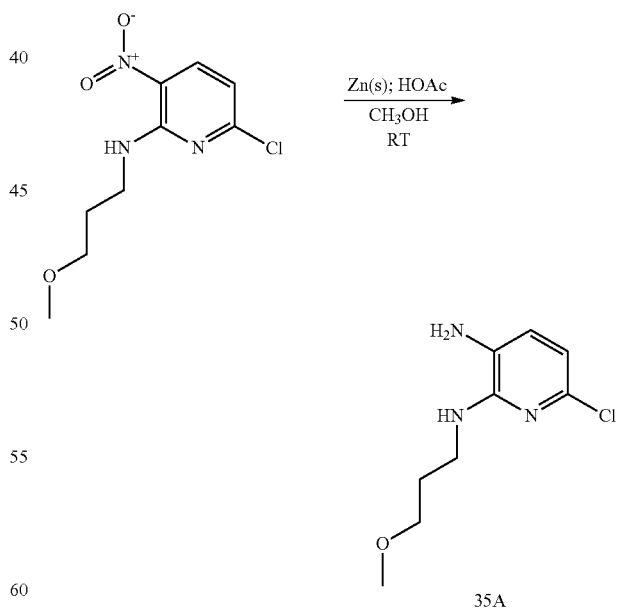

35A

6-Chloro-N-(3-methoxypropyl)-3-nitropyridin-2-amine (2.84 mmol, 0.698 g) was added to an oven dried 50 mL round-bottomed flask equipped for stirring under nitrogen. Methanol (15 mL) and acetic acid (1.5 mL, glacial) were then added. Zinc (15.29 mmol, 1.0 g, 20-30 mesh) was then added and the resultant mixture was allowed to stir at room temperature for 16 hr. Analysis of the reaction by LC/MS indicated a complete conversion to product at this time. This resultant mixture was then filtered over Celite®, concentrated in-vacuo, and transferred to a 250 mL seperatory funnel with ethyl acetate (2×30 mL) and water (2×20 mL). The layers were separated and the organic layer was washed once with saturated aqueous sodium chloride (40 mL). The organic layer was collected and subsequently dried with anhydrous Na₂SO₄ and filtered. This filtrate was collected, concentrated, and dried in-vacuo affording 6-chloro-N2-(3-methoxypropyl)pyridine-2,3-diamine (35A) as a brown oil which was used directly in the next step without further purification. ESI-MS: mix 216.3 (M+H)⁺.

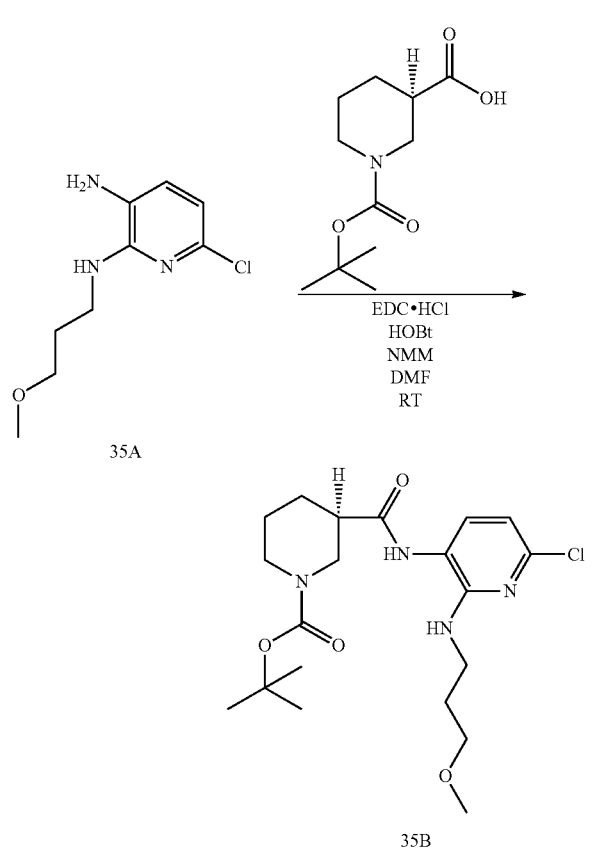

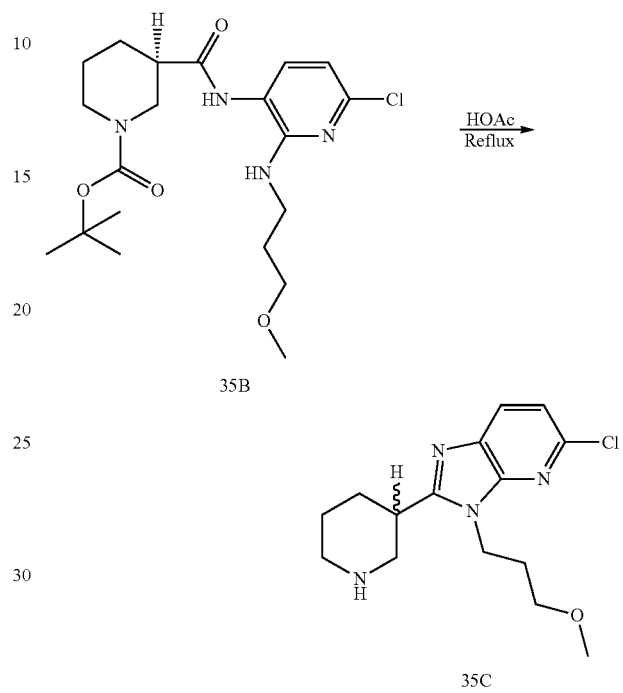

(R)-1-(cert-Butoxycaxbonyl)piperidine-3-carboxylic acid (2.84 mmol, 0.651 g) and 6-chloro-N2-(3-methoxypropyl)pyridine-2,3-diamine (35A) (2.84 mmol, crude oil) was added to a 50 mL round-bottomed flask equipped for stirring under nitrogen. DMF (10 mL) and N-methylmorpholine (11.36 mmol, 1.25 mL) were added and the resultant solution was allowed to stir for 5 min at room temperature. N1-((ethylimino)methylene)-N3,N³-dimethylpropane-1,3-diamine hydrochloride (3.12 mmol, 0.598 g) and 1H-benzo[d][1,2,3]triazol-1-ol (3.12 mmol, 0.422 g) were then added and the reaction was allowed to stir at room temperature for 16 hr. Analysis of the reaction solution by LC/MS indicated multiple products along with a small quantity of the desired title compound. The reaction solution was poured into water and extracted with ethyl acetate. The organic layer was washed three times with water, two times with saturated aqueous sodium bicarbonate, and once with saturated aqueous sodium chloride. The organic layer was collected and dried with Na₂SO₄ and then filtered. The filtrate was collected, concentrated, and dried in-vacuo affording (R)-tert-butyl 3-(6-chloro-2-(3-methoxypropylamino)pyridin-3-ylcarbamoyl)piperidine-1-carboxylate (35B) as a brownish foam that was carried directly on to the next step without further purification. ESI-MS: m/z 427.4 (M+H)⁺.

Compound 35B (crude material, 2.84 mmol max) prepared in Step 13 was added to a 50 trLL round-bottomed flask equipped for stirring under nitrogen. Glacial acetic acid (10 mL) was then added and the resultant solution was stirred at reflux under nitrogen for 16 hr. The reaction solution was concentrated in-vacuo to give a brownish oil. Toluene (30 mL) was added and the subsequent solution was concentrated in vacuo; this was repeated three times to remove any trace quantities of acetic acid affording the title compound as a brown oil. This oil was then purified by preparative LC/MS (5-50% CH₃CN in H₂O) to afford 5-chloro-3-(3-methoxypropyl)-2-(piperidin-3-yl)-3H-imidazo[4,5-b]pyridine (35C) as a tan oil. (088 mmol, 0.122 g, 10% yield over 3-steps). Subsequent analysis of a later derivative of this compound revealed that the chiral center had been epimerized during this reaction sequence. ESI-MS: m/z 309.4 (M+H)⁺.

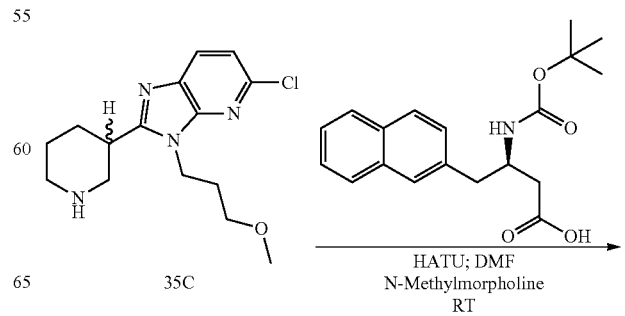

-continued

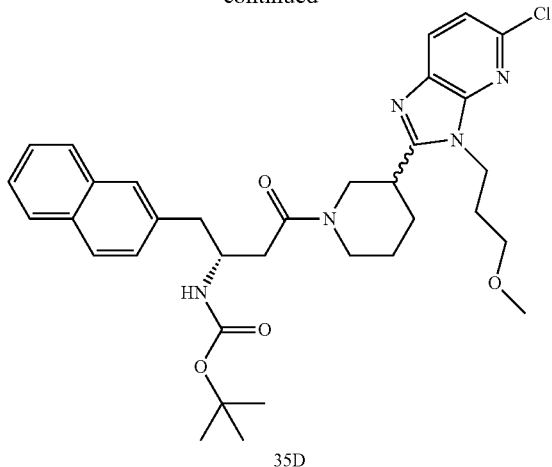

35D

Compound 35C (0.288 mmol, 0.122 g) was added to a 10 mL round-bottomed flask equipped for stirring under nitrogen. DMF (2 mL), (R)-3-(tert-butoxycarbonylamino)-4-(naphthalen-2-yl)butanoic acid (0.455 mmol, 0.150 g) and N-methylmorpholine (1.15 mmol, 0.127 mL) were then added and the solution was allowed to stir at it for 5 min. HATU (0.317 mmol, 0.120 g) was added and the resultant solution was stirred at room temperature for 3 hr. The reaction solution was then directly purified by preparative LC/MS (40-95% $CH_3CN$ in $H_2O$). The resultant fractions were collected and the solvent was removed in-vacuo affording (R)-tert-Butyl 4-(3-(5-chloro-3-(3-methoxypropyl)-3H-imidazo[4,5-b]pyridin-2-yl)piperidin-1-yl)-1-(naphthalen-2-yl)-4-oxobutan-2-ylcarbamate (35D) as a clear oil (0.177 mmol, 0.110 g, 62% yield). ESI-MS: m/z 620.4 $(M+H)^+$.

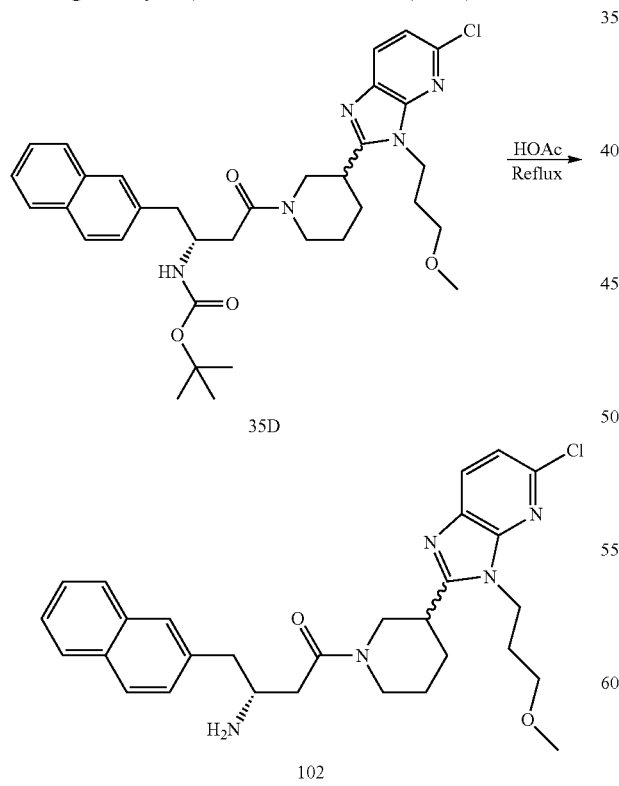

35D

HOAc / Reflux

102

(R)-4-(4-bromobenzyl)-2-oxoxazolidine-5-carboxylic acid-(R)-tert-Butyl 4-(3-(5-chloro-3-(3-methoxypropyl)-3H-imidazo[4,5-b]pyridin-2-yl)piperidin-1-yl)-1-(naphthalen-2-yl)-4-oxobutan-2-ylcarbamate (35D) (0.045 mmol, 0.028 g) was added to a 10 mL round-bottomed flask equipped for stirring under nitrogen. Acetic acid (3 mL) was added and the resultant solution was allowed to stir at reflux under nitrogen for 4 hr. The solvent was removed in-vacuo affording a clear colored oil. This oil was re-dissolved in methanol (3 mL), filtered, and then purified by preparative LC/MS (25-50% $CH_3CN$ in $H_2O$). The resultant fractions were collected and the solvent was removed in-vacuo affording a clear oil. This oil was re-dissolved in $CH_3CN$ (1 mL) and water (2 mL). The resultant solution was frozen and lyophilized to afford (R)-3-amino-1-(3-(5-chloro-3-(3-methoxypropyl)-3H-imidazo[4,5-b]pyridin-2-yl)piperidin-1-yl)-4-(naphthalen-2-yl)butan-1-one (102) as its trifluoroacetic acid salt and as a white flocculent solid. (0.008 mmol, 0.0043 g, 18% yield) ESI-MS: m/z 520.4 $(M+H)^+$.

Example 36

Synthesis of (R)-3-amino-4-(biphenyl-4-yl)-1((R)-3-(3-(3-methoxypropyl)-3H-imidazo[4,5-c]pyridin-2-yl)piperidin-1-yl)butan-1-one (103)

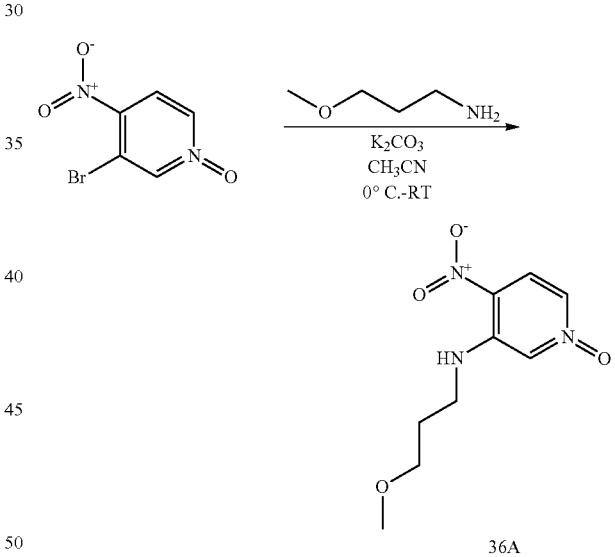

36A

3-Bromo-4-nitropyridine 1-oxide (4.57 mmol, 1.0 g) was added to an oven dried 200 mL round-bottomed flask equipped for stirring under nitrogen. Acetonitrile (30 mL) and $K_2CO_3$ (11.42 mmol, 1.60 g) were added and the resultant solution was cooled to 0° C. with an ice bath.

3-Methoxypropan-1-amine (5.02 mmol, 0.514 mL) was then added drop-wise via syringe and the resultant solution was stirred at 0° C. for 0.5 hr. The ice bath was removed and the reaction was allowed to warm to room temperature and stir for 16 hr. The reaction solution was filtered over Celite®. The filtrate was collected, concentrated, and dried in-vacuo affording 3-(3-methoxypropylamino)-4-nitropyridine 1-oxide (36A) as dark brown oil which was used without further purification. ESI-MS: mh 228.3 $(M+H)^+$.

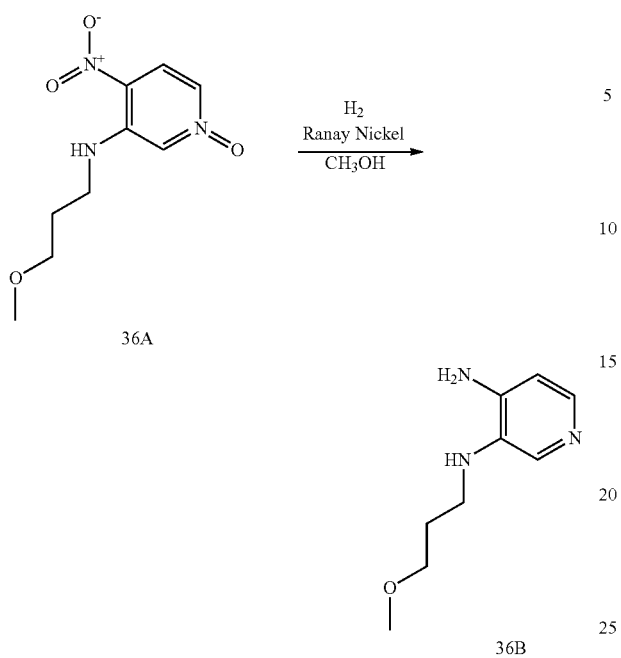

3-(3-Methoxypropylamino)-4-nitropyridine 1-oxide (3.69 mmol, 0.842 g) was added to an oven dried 50 mL round-bottomed flask equipped for stirring. Methanol (15 mL) was then added and the solution was vacuum degassed with nitrogen three times. Ranay nickel (0.5 mL of a 50% slurry in H$_2$O) was then added and the solution was degassed an additional three times with nitrogen. The reaction was then evacuoted under vacuum and hydrogen gas was added via balloon pressure and the reaction was stirred under hydrogen for 16 hr. At this time, the hydrogen balloon was removed and the solution was vacuum de-gassed with nitrogen twice. The reaction solution was then filtered over Celite®. The filtrate was collected, concentrated, and dried in-vacuo affording N3-(3-Methoxypropyl)pyridine-3,4-diamine (36B) as dark brown oil which was used without further purification. ESI-MS: m/z 182.3 (M+H)$^+$.

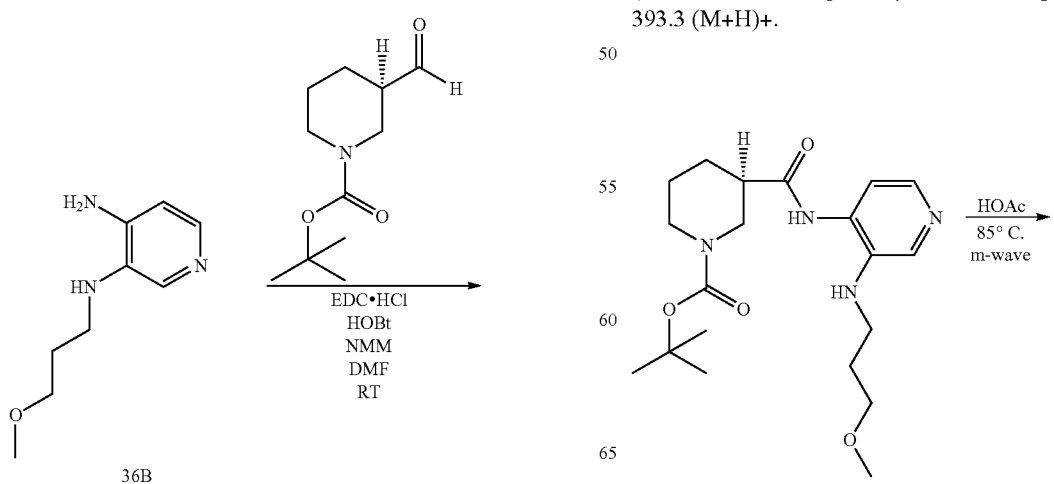

(R)-1-(tert-Butoxycarbonyl)piperidine-3-carboxylic acid (2.15 mmol, 0.493 g) and N3-(3-methoxypropyl)pyridine-3,4-diamine (36B) (2.15 mmol, 0.493 g) were added to a 25 mL round-bottomed flask equipped for stirring under nitrogen. DMF (7 mL) and 4-methylmorpholine (6.45 mmol, 0.709 mL) were added and the resultant solution was allowed to stir for 5 min at room temperature. N1-((ethylimino)methylene)-N3,N3-dimethylpropane-1,3-diamine hydrochloride (2.37 mmol, 0.453 g) and 1H-benzo[d][1,2,3]triazol-1-ol (2.37 mmol, 0.320 g) were then added and the reaction was allowed to stir at room temperature for 16 hr. Analysis of the reaction solution by LC/MS indicated multiple products along with a small quantity of the desired title compound. The reaction solution was poured into water and extracted with ethyl acetate. The organic layer was washed three times with water, two times with saturated aqueous sodium bicarbonate, and once with saturated aqueous sodium chloride. The organic layer was collected and dried with Na$_2$SO$_4$. This mixture was then filtered, the filtrate was collected and concentrated and dried in-vacuo affording a brown oil. This oil was directly purified by preparative LC/MS (10-80% CH$_3$CN in H$_2$O) to afford (R)-tert-butyl 3-(3-(3-methoxypropylamino)pyridin-4-ylcarbamoyl)piperidine-1-carboxylate (36C) as a clear oil (0.614 mmol, 0.241 g, 29% yield over 3-steps). ESI-MS: m/z 393.3 (M+H)+.

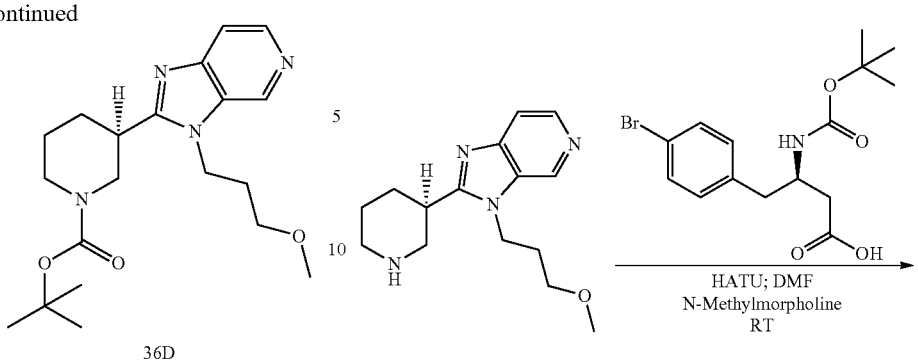

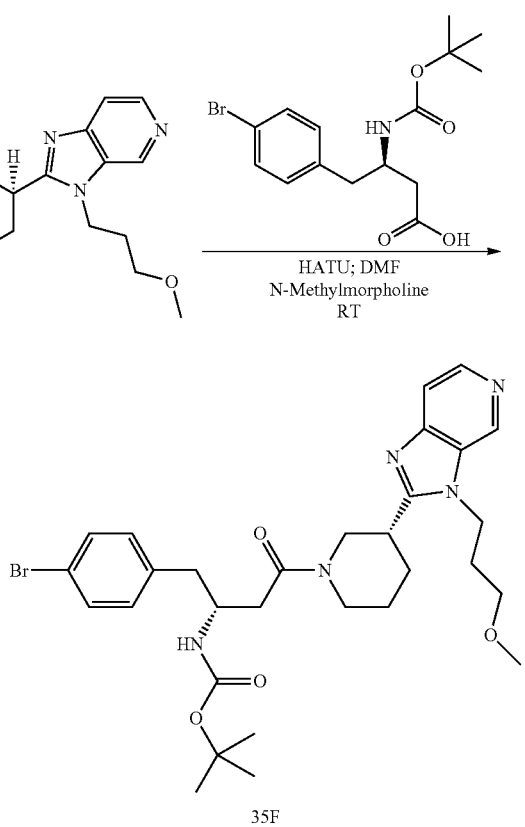

(R)-tert-Butyl 3-(3-(3-methoxypropylamino)pyridin-4-yl-carbamoyl)piperidine-1-carboxylate (36C) (0.614 mmol, 0.241 g) was added to a 5 mL microwave reactor. Glacial acetic acid (2 mL) was then added and the resultant solution heated at 85° C. in the microwave for 1.5 hr. The reaction solution was then transferred to a 50 mL round bottomed flask and concentrated in-vacuo to give a brownish oil. Toluene (30 mL) was added and the subsequent solution was concentrated in vacuo. This was repeated three times to remove any trace quantities of acetic acid affording the title compound as a brown oil. This oil was then purified by silica gel chromatography (5-15% CH$_3$OH/CH$_2$Cl$_2$) to afford (R)-tert-butyl 3-(3-(3-methoxypropyl)-3,1-imidazo[4,5-c]pyridin-2-yl)piperidine-1-carboxylate (36D) as a clear oil (0.279 mmol, 0.105 g, 45% yield). ESI-MS: m/z 375.3 (M+H)+.

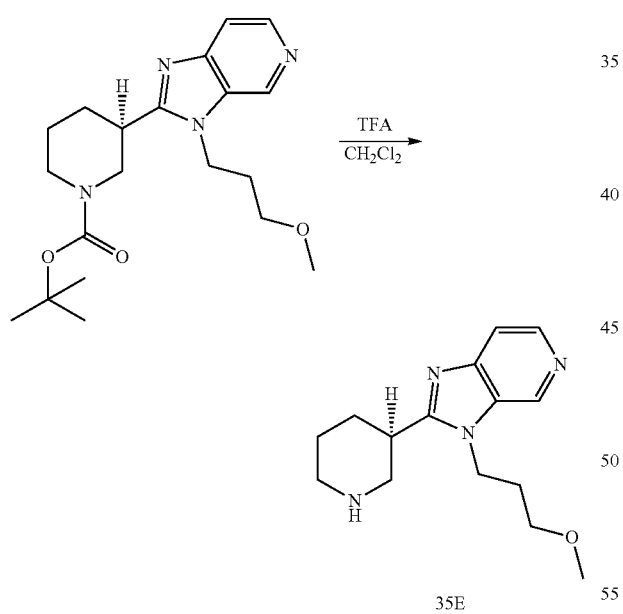

(R)-tert-Butyl 3-(3-(3-methoxypropyl)-3H-imidazo[4,5-c]pyridin-2-yl)piperidine-1-carboxylate (36D) (0.279 mmol, 0.105 g) was added to a 10 mL round-bottomed flask equipped for stirring under nitrogen. Dichloromethane (1 mL) and trifluoroacetic acid (1 mL) were then added and the resultant solution was allowed to stir under nitrogen for 4 hr. The reaction was then concentrated and dried in-vacuo affording (R)-3-(3-Methoxypropyl)-2-(piperidin-3-yl)-3H-imidazo[4,5-c]pyridine (35E) as a clear oil that was used without further purification. ESI-MS: m/z 275.1 (M+H)+.

(R)-3-(3-Methoxypropyl)-2-(piperidin-3-yl)-3H-imidazo[4,5-c]pyridine (35E) (0.279 mmol, crude oil) was added to a 15 mL round-bottomed flask equipped for stirring under nitrogen. DMF (2 mL), (R)-4-(4-bromophenyl)-3-(tert-butoxycarbonylamino)butanoic acid (0.335 mmol, 0.086 g) and N-methylmorpholine (1.95 mmol, 0.214 mL) were then added and the solution was allowed to stir at rt for 5 min. HATU (0.335 mmol, 0.127 g) was added and the resultant solution was stirred at room temperature for 3 hr. The reaction solution was then directly purified by preparative LC/MS (25-85% CH$_3$CN in H$_2$O). The resultant fractions were collected and the solvent was removed in-vacuo affording tert-butyl (R)-1-(4-bromophenyl)-4-((R)-3-(3-(3-methoxypropyl)-3H-imidazo[4,5-c]pyridin-2-yl)piperidin-1-yl)-4-oxobutan-2-ylcarbamate (35F) as a clear oil (0.238 mmol, 0.146 g, 85% yield). ESI-ESI-MS: adz 614.3 (M+H)+.

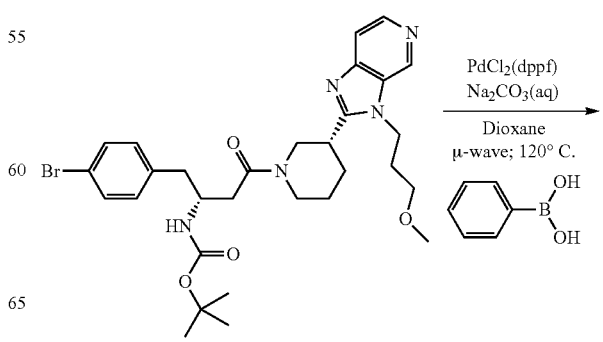

-continued

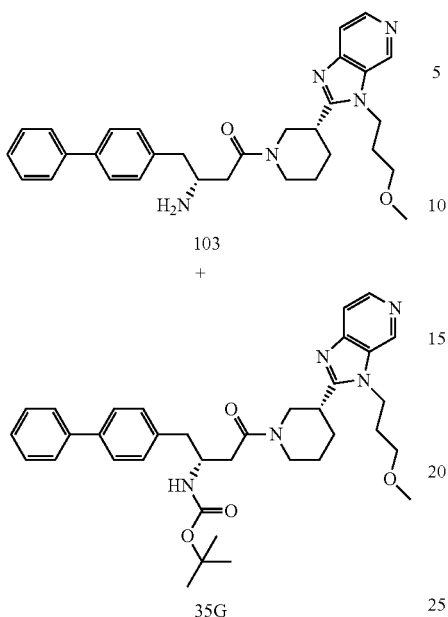

35G tert-Butyl (R)-1-(4-bromophenyl)-4-((R)-3-(3-(3-methoxypropyl)-3H-imidazo[4,5-c]pyridin-2-yl)piperidin-1-yl)-4-oxobutan-2-ylcarbamate (35F) (0.229 mmol, 0.141 g) and phenylboronic acid (0.298 mmol, 0.036 g) were added to a 5 mL microwave vessel equipped with a magnetic stir bar. Dioxane (2 mL) and $Na_2CO_3$ (1 mL of a 2M in $H_2O$ soln.) were then added and the reaction vessel was flushed with nitrogen gas. $PdCl_2$(dppf) (0.011 mmol, 0.008 g) was added, the reaction vessel was sealed and placed in a microwave reactor and heated to 120° C. for 25 minutes. The reaction solution was then poured into water, extracted with ethyl acetate, and washed once with saturated aqueous sodium chloride. The organic layer was collected and subsequently dried with anhydrous $Na_2SO_4$ and filtered. This filtrate was collected, concentrated, and dried in-vacuo. This crude material was directly purified by preparative LC/MS (25-85% $CH_3CN$ in $H_2O$). The resultant fractions were collected and the solvent was removed in-vacuo.

tert-Butyl (R)-1-(biphenyl-4-yl)-4-((R)-3-(3-(3-methoxypropyl)-3H-imidazo[4,5-c]pyridin-2-yl)piperidin-1-yl)-4-oxobutan-2-ylcarbamate (39G) was recovered as a clear oil (0.09 mmol, 0.055 g, 39% yield). (ESI-MS: m/z 612.4 $(M+H)^+$. (R)-3-amino-4-(biphenyl-4-yl)-1-((R)-3-(3-(3-methoxypropyl)-3H-imidazo[4,5-c]pyridin-2-yl)piperidin-1-yl)butan-1-one (103) was isolated as a clear oil (0.035 mmol, 0.022 g, 15% yield). This oil was re-dissolved in $CH_3CN$ (1 mL) and water (2 mL). The resultant solution was frozen and lyophilized to afford Compound 103 as its trifluoroacetic acid salt and as a white flocculent solid. 1H NMR (400 MHz, DMSO-$d_6$) δ ppm 1.41-1.61 (m, 1H) 1.70-2.20 (m, 5H) 2.60-2.86 (m, 3H) 2.88-3.38 (m, 10H) 3.76-4.09 (m, 2H) 4.34-4.65 (m, 2H) 7.29-7.41 (m, 3H) 7.42-7.51 (m, 2H) 7.56-7.71 (m, 4H) 8.09 (t, J=6.06 Hz, 1H) 8.57 (t, J=6.19 Hz, 1H) 9.38 (d, J=10.61Hz, 1H). ESI-MS: m/z 512.3 $(M+H)^+$.

Example 37

Synthesis of (R)-3-amino-1((R)-3-(4-methoxy-1-(3-methoxypropyl)-1H-benzo[d]imidazol-2-yl)piperidin-1-yl-4-(naphthalen-2-yl)butan-1-one (104)

Step A.

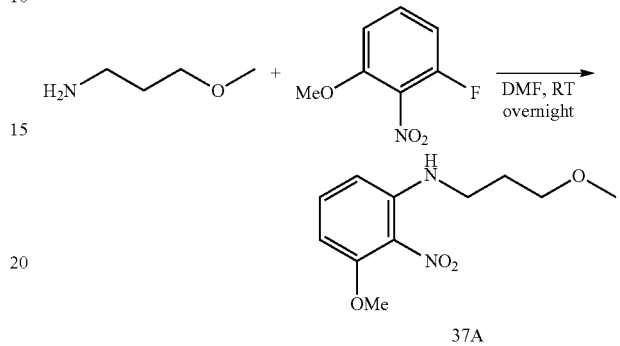

37A

Into a 25 mL round bottomed was added 1-fluoro-3-methoxy-2-nitrobenzene (500 mg, 2.92 mmol) and N,N-dimethylforamide (5.8 mL). The flask was cooled to −15° C. and 3-methoxypropylamine (313 mg, 3.5 mmol) in N,N-dimethylforamide (2.2 mL) was slowly added. The reaction was allowed to warm to room temperature overnight. Solvent was removed under vacuum and the residue was purified by column chromatography (20% ethylacetate:hexanes) to give 3-methoxy-N-(3-methoxypropyl)-2-nitroaniline (37A) as a yellow oil (560 mg, 80% yield). ESI-MS:m/z 241.3 $(M+H)^+$.

Step B.

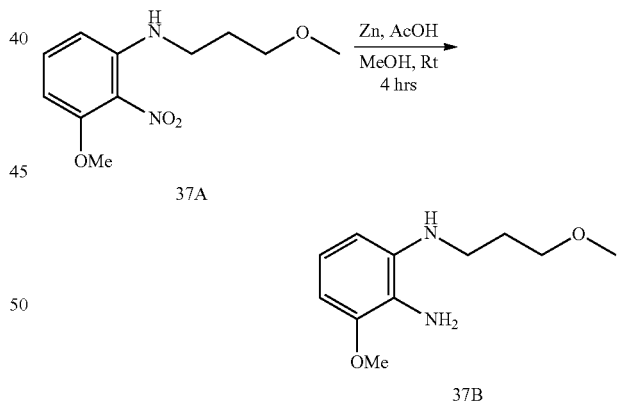

37B

Into a 100 mL round bottomed flask was added 3-methoxy-N-(3-methoxypropyl)-2-nitroaniline (36A) (560 mg, 2.33 mmol) and methanol (46 mL). Zinc metal (2.11 g, 32.4 mmol) and acetic acid (2.0 mL) was added and the mixture was stirred at room temperature for 5 hr. The mixture was filtered through a fritted Buchner funnel and the solvent was removed under vacuum. Ethyl acetate (100 mL) was added and the precipitate was filtered through a Buchner funnel with a pad of Celite. The filtrate was concentrated under vacuum to leave 3-methoxy-$N^1$-(3-methoxypropyl)benzene-1,2-diamine (37B) as a yellow oil which was used without further purification. ESI-MS:mlz 211.4 $(M-F1-1)^+$.

Step C.

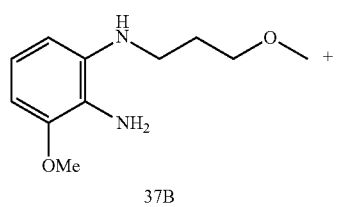

37B

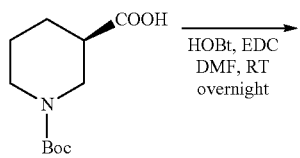

HOBt, EDC
DMF, RT
overnight

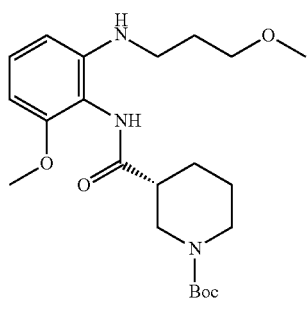

37C

The residue 37B was dissolved in N,N-dimethylforamide (12 mL). HOSt (241 mg, 1.78 mmol), EDC (341 mg, 1.78 mmol), and (R)-1-(tert-butoxycarbonyl)piperidine-3-carboxylic acid (409 mg, 1.78 mmol) were added and stirred overnight at room temperature. The solvent was removed under vacuum and the residue was partitioned between water (25 mL) and ethyl acetate (25 mL). The organic layer was separated and the aqueous was extracted with ethyl acetate (2×25 mL). The organics were combined and washed with 1N NaOH (25 mL). The organics were dried over sodium sulfate and filtered. Solvent was removed under vacuum and the residue (R)-tert-butyl 3-(2-methoxy-6-(3-methoxypropylamino)phenylcarbamoyl)piperidine-1-carboxylate (37C) was taken into the next step without further purification. ESI-MS:m/z 422.5 (M+H)$^+$.

Step D.

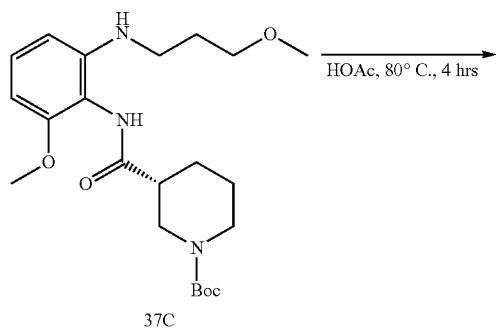

HOAc, 80° C., 4 hrs

37C

-continued

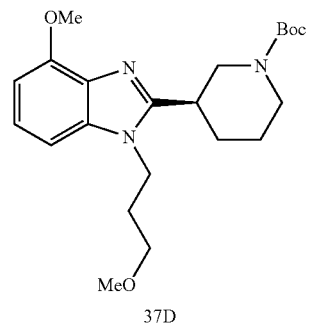

37D

The residue (37C) was dissolved with acetic acid (15 mL) and heated to 80° C. for 4 hr. Solvent was removed under vacuum. The residue containing (R)-ter(R)-tert-butyl 3-(4-methoxy-1-(3-methoxypropyl)-1H-benzo[d]imidazol-2-yl)piperidine-1-carboxylate (37D) was used in the next step without further purification. ESI-MS:m/z 404.5 (M+H)$^+$.

Step E.

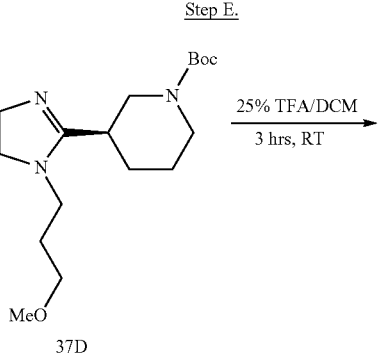

37D

25% TFA/DCM
3 hrs, RT

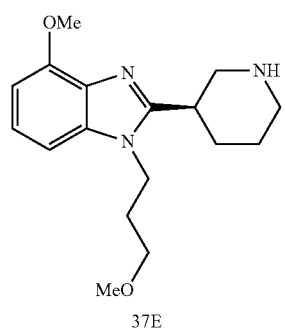

37E

Into a 10 mL round bottomed was added (R)-ter(R)-tert-butyl 3-(4-methoxy-1-(3-methoxypropyl)-1H-benzo[d]imidazol-2-yl)piperidine-1-carboxylate (36D), 25% trifluoroacetic acid in dichloromethane (5 mL) was added and stirred at room temperature for 3 hrs. The solvent was removed under vacuum. The residue containing (R)-4-methoxy-1-(3-methoxypropyl)-2-(piperidin-3-yl)-1H-benzo[d]imidazole (37E) was used in the next step without purification. ESI-MS:m/z 303.2 (M+H)$^+$.

Step F.

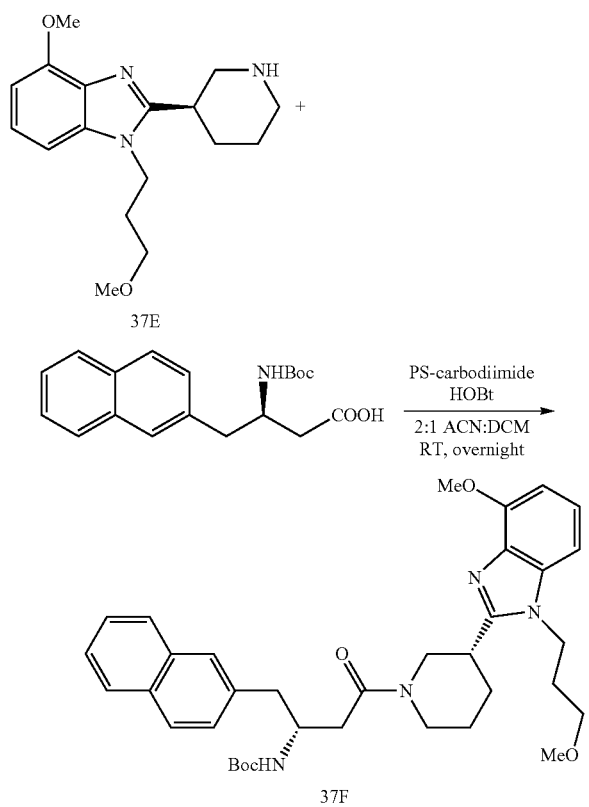

(R)-4-methoxy-1-(3-methoxypropyl)-2-(piperidin-3-yl)-1H-benzo[d]imidazole (37E) (133 mg, 438 µmol) was dissolved with 2:1 acetonitrile:dichloromethane (2.2 mL). (R)-3-(tert-butoxycarbonylamino)-4-(naphthalen-2-yl)butanoic acid (159 mg, 482 µmol) in 2:1 acetonitrile:dichloromethane (2.3 mL) was added. HOBt (65 mg, 482 µmol) in DMF (2.3 mL) was added. Into a fritted syringe was added PS-carbodiimide resin (1.31 mmol/g, 669 mg). The amine, acid and HOBt solutions were taken up in the syringe and capped. The mixture was shaken overnight at room temperature. The solution was expelled into a round bottomed and the solvent was removed under vacuum. The residue containing tert-butyl (R)-4-((R)-3-(4-methoxy-1-(3-methoxypropyl)-1H-benzo[d]imidazol-2-yl)piperidin-1-yl)-1-(naphthalen-2-yl)-4-oxobutan-2-ylcarbamate. (37F) was taken into the next step without further purification. ESI-MS:m/z 615.5 (M+H)$^+$.

Step G.

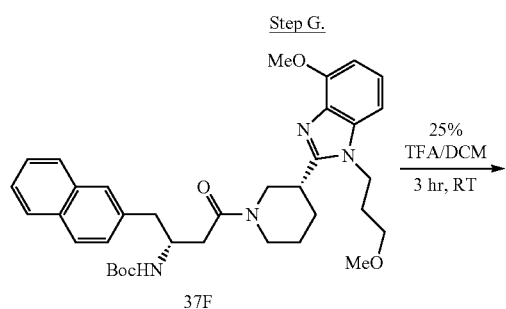

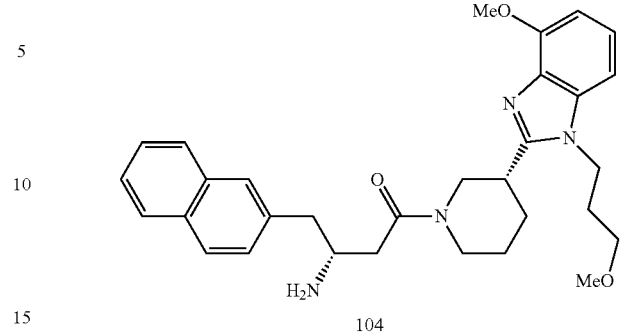

tert-Butyl (R)-4-((R)-3-(4-methoxy-1-(3-methoxypropyl)-1H-benzo[d]imidazol-2-yl)piperidin-1-yl)-1-(naphthalen-2-yl)-4-oxobutan-2-ylcarbamate (37F) was dissolved in 25% trifluoroacetic acid and stirred at room temperature for 3 hr. Solvent was removed under vacuum and purified by preparatory LC/MS (25-30% CH$_3$CN in H$_2$O) to give (R)-3-amino-1((R)-3-(4-methoxy-1-(3-methoxypropyl)-1H-ben-zokflimidazol-2-yl)piperidin-1-yl)-4-(naphthalen-2-yl) butari-1-one (104) as a TFA salt (35 mg, 13%). 1H NMR (400 MHz, DMSO-d$_6$) δ ppm 1.45 (br. s., 1H) 1.78 (m, 2H) 1.88-2.18 (m, 3H) 2.53-2.79 (m, 3H) 2.86-3.50 (m, 9H) 3.82 (br. s., 2H) 4.00 (m, 3H) 4.05-4.70 (m, 3H) 7.07 (m, 1H) 7.34-7.58 (m, 5H) 7.76-7.95 (m, 4 H). ESI-MS:m/z 515.4 (M+H)$^+$.

Example 38

Synthesis of (R)-3-amino-1((R)-3-(1-(3-methoxypropyl)-5-methyl-1H-benzo[d]imidazol-2-yl)piperidin-1-yl)-4-(naphthalen-2-yl)butan-1-one (105)

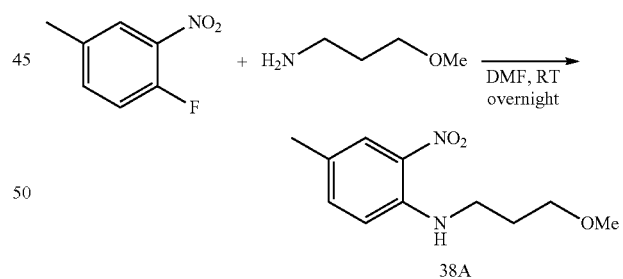

N-(3-Methoxypropyl)-4-methyl-2-nitroaniline (38A) was prepared as described in Example 37, Step A. ESI-MS:m/z 225.4 (M+H)$^+$.

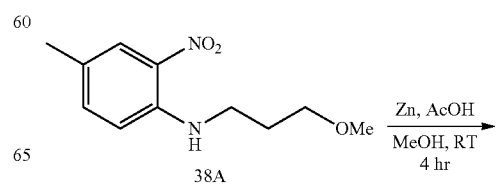

287
-continued

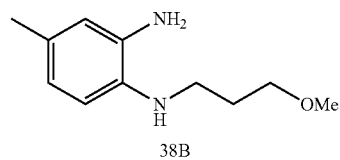

N1-(3-Methoxypropyl)-4-methylbenzene-1,2-diamine (38B) was prepared as described in Example 37, Step B. ESI-MS:m/z 195.4 (M+H)+.

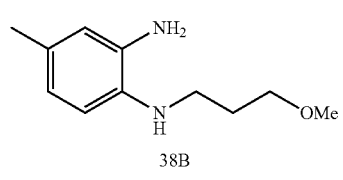

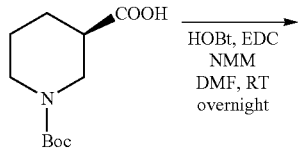

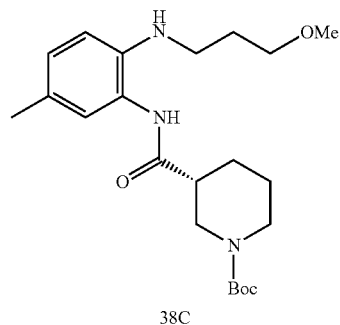

(R)-tert-Butyl 3-(2-(3-methoxypropylamino)-5-methylphenylcarbamoyl)piperidine-1-carboxylate (38C) was prepared as described in Example 37, Step C. ESI-MS:m/z 406.5 (M+H)+.

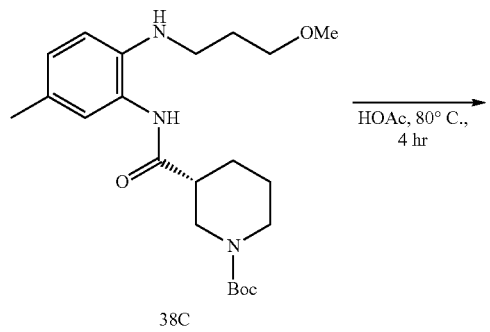

288
-continued

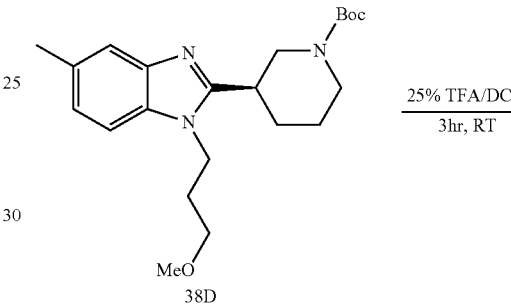

(R)-tert-Butyl 3-(1-(3-methoxypropyl)-5-methyl-1H-benzo[d]imidazol-2-yl)piperidine-1-carboxylate (38D) was prepared as described in Example 37, Step D. ESI-MS:m/z 288.4 (M+H)+.

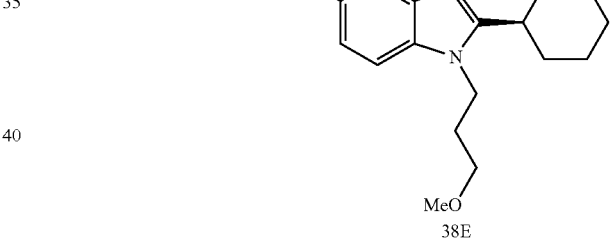

(R)-1-(3-Methoxypropyl)-5-methyl-2-(piperidin-3-yl)-1H-benzo[d]imidazole (38E) was prepared as described in Example 37, Step E. ESI-MS:mlz 288.4 (M+H)+.

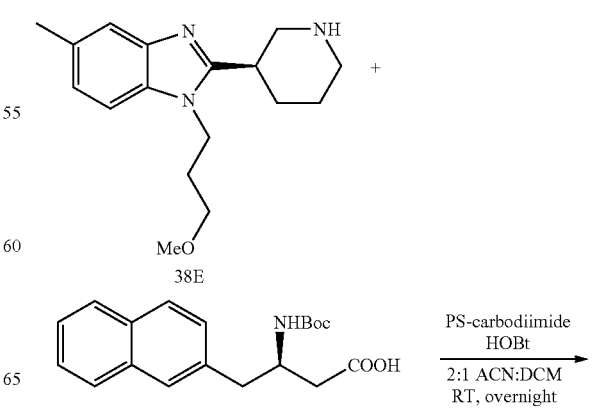

Example 39

Synthesis of (R)-3-amino-1((R)-3-(1-(3-methoxypropyl)-4-methyl-1H-benzo[d]imidazol-2-yl)piperidin-1-yl)-4-(naphthalen-2-yl)butan-1-one (106) and (R)-3-amino-1((R)-3-(1-(3-methoxypropyl)-7-methyl-1H-benzo[c]imidazol-2-yl)piperidin-1-yl)-4-(naphthalen-2-yl)butan-1-one (107)

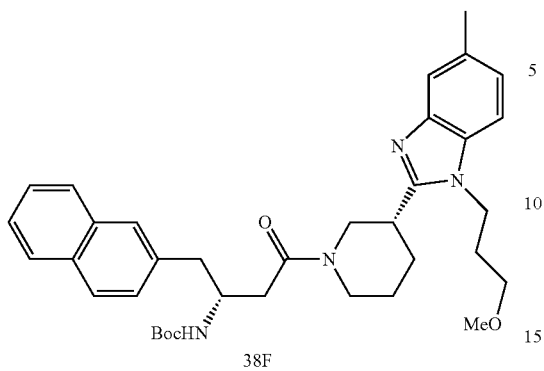

tert-Butyl (R)-4-((R)-3-(1-(3-methoxypropyl)-5-methyl-1H-benzoldlimidazol-2-yl)piperidin-1-yl)-1-(naphthalen-2-yl)-4-oxobutan-2-ylcarbamate (38F) was prepared as described in Example 37, Step F. ESI-MS:m/z 599.5 (M+H)⁺.

Step A.

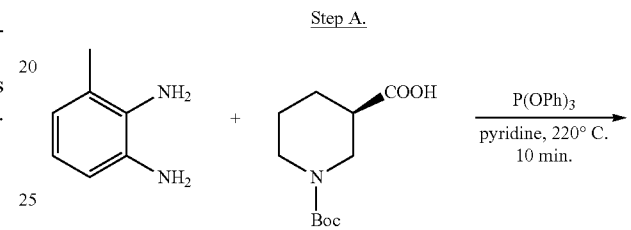

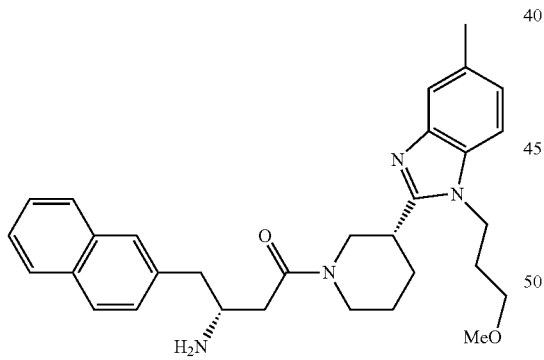

Compound 105 was prepared as described in Example 37, Step G. Purified by preparatory LC/MS (25-25% CH₃CN in H₂O) gave (R)-3-amino-1((R)-3-(1-(3-methoxypropyl)-5-methyl-1H-benzo[d]imidazol-2-yl)piperidin-1-yl)-4-(naphthalen-2-yl)butan-1-one (105) as a TFA salt (131 mg, 36% yield). 1H NMR (400 MHz, DMSO-d₆) δ ppm 1.38-1.62 (m, 1H) 1.71-2.22 (m, 5H) 2.47-2.49 (m, 2H) 2.57-2.77 (m, 2H) 2.87-3.47 (m, 9H) 3.78 (m, 2H) 3.97 (s, 2H) 4.08-4.69 (m, 3H) 7.30-7.59 (m, 5H) 7.69-7.95 (m, 5H). ESI-MS:m/z 499.5 (M+H)⁺.

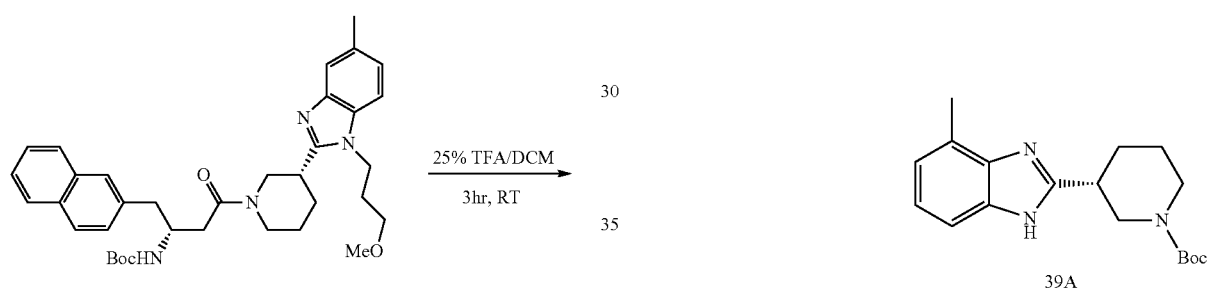

Into a microwave vial was added 3-methylbenzene-1,2-diamine (150 mg, 1.23 mmol) and (R)-1-(tert-butoxycarbonyl)piperidine-3-carboxylic acid (281 mg, 1.23 mmol). The mixture was dissolved with pyridine (6.2 mL). Triphenylphosphite (469 mg, 1.51 mmol) was added and the vial was capped. The reaction was microwaved at 220° C. for 10 minutes. Solvent was removed under vacuum and the residue was purified by preparatory LC/MS (20-30% CH₃CN in H₂O) to give (R)-tert-butyl 3-(4-methyl-1H-benzo[d]imidazol-2-yl)piperidine-1-carboxylate (39A) (80 mg, 21% yield). ESI-MS:m/z 316.4 (M+H)⁺.

Step B.

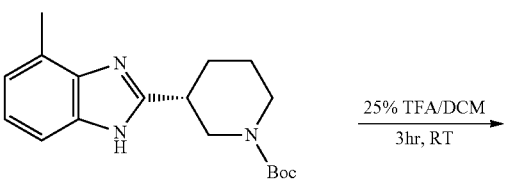

-continued

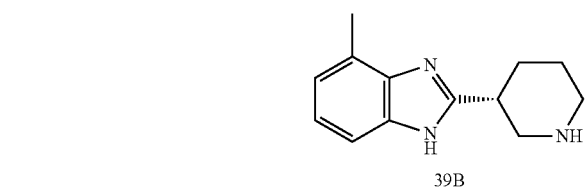
39B

Into a 10 mL round bottomed was added (R)-tert-butyl 3-(4-methyl-1H-benzo[d]imidazol-2-yl)piperidine-1-carboxylate (39A). 25% trifluoroacetic acid in dichloromethane (5 mL) was added and stirred at room temperature for 3 hr. The solvent was removed under vacuum and the residue containing (R)-4-methyl-2-(piperidin-3-yl)-1H-benzo[d]imidazole (39B) was used in the next step without purification. ESI-MS:m/z 215.1 (M+H)$^+$.

Step C.

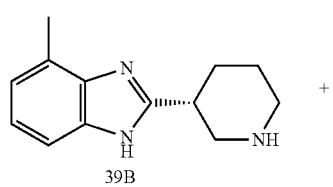
39B

+

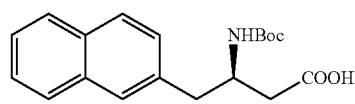

→ PS-carbodiimide HOBt
2:1 ACN:DCM
RT, overnight

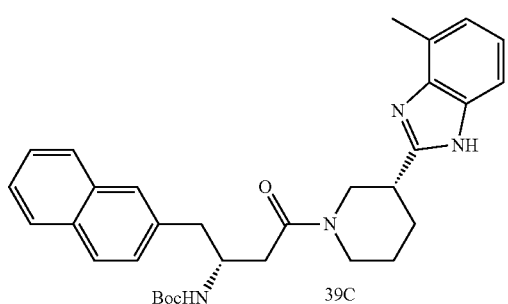
BocHN  39C (R)-4-Methyl-2-(piperidin-3-yl)-1H-benzo[d]imidazole (80 mg, 372 µmol) was dissolved in 2:1 acetonitrile:dichloromethane (1.9 mL). (R)-3-(tert-butoxycarbonylamino)-4-(naphthalen-2-yl)butanoic acid (135 mg, 409 µmol) in 2:1 acetonitrile:dichloromethane (2.0 mL) was added. HOBt (55 mg, 409 µmol in DMF (4.1 mL) was added. Into a fritted syringe was added PS-carbodiimide resin (975 mg, 1.34 mmol. The amine, acid and HOBt solutions were taken up in the syringe and capped. The mixture was shaken overnight at room temperature. The solution was expelled into a round bottomed and the solvent was removed under vacuum. The residue containing tert-butyl (R)-4-((R)-3-(4-methyl-1H-benzo[d]imidazol-2-yl)piperidin-1-yl)-1-(naphthalen-2-yl)-4-oxobutan-2-ylcarbamate (39C) was taken into the next step without further purification. ESI-MS:m/z 527.5 (M+H)$^+$.

Step D.

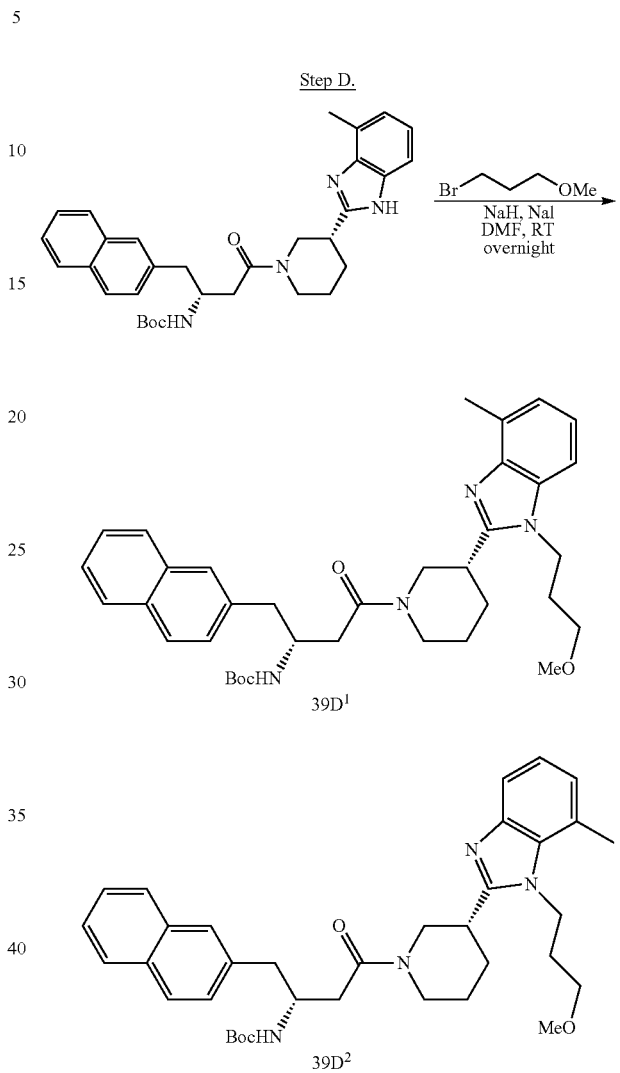

Into a 10 mL round bottomed flask was added tert-butyl (R)-4-((R)-3-(4-methyl-1H-benzo[d]imidazol-2-yl)piperidin-1-yl)-1-(naphthalen-2-yl)-4-oxobutan-2-ylcarbamate (39C) (68 mg, 129 µmol) and N,N-dimethylforamide (0.5 mL). NaI (25 mg, 168 µmol) and NaH (7 mg, 168 µmol, 60% disp.) were added in sequence. The mixture was stirred for 30 minutes at room temperature. 3-Methoxypropyl bromide (26 mg, 168 µmol) was added at once and stirred overnight at room temperature. Solvent was removed under vacuum and the residue containing tert-butyl (R)-4-((R)-3-(1-(3-methoxypropyl)-4-methyl-1H-benzo[d]imidazol-2-yl)piperidin-1-yl)-1-(naphthalen-2-yl)-4-oxobutan-2-ylcarbamate (39D$^1$) and tert-butyl (R)-4-((R)-3-(1-(3-methoxypropyl)-7-methyl-1H-benzo[d]imidazol-2-yl)piperidin-1-yl)-1-(naphthalen-2-yl)-4-oxobutan-2-ylcarbamate (39D$^2$) used without further purification. ESI-MS:m/z 599.5 (M+H)$^+$.

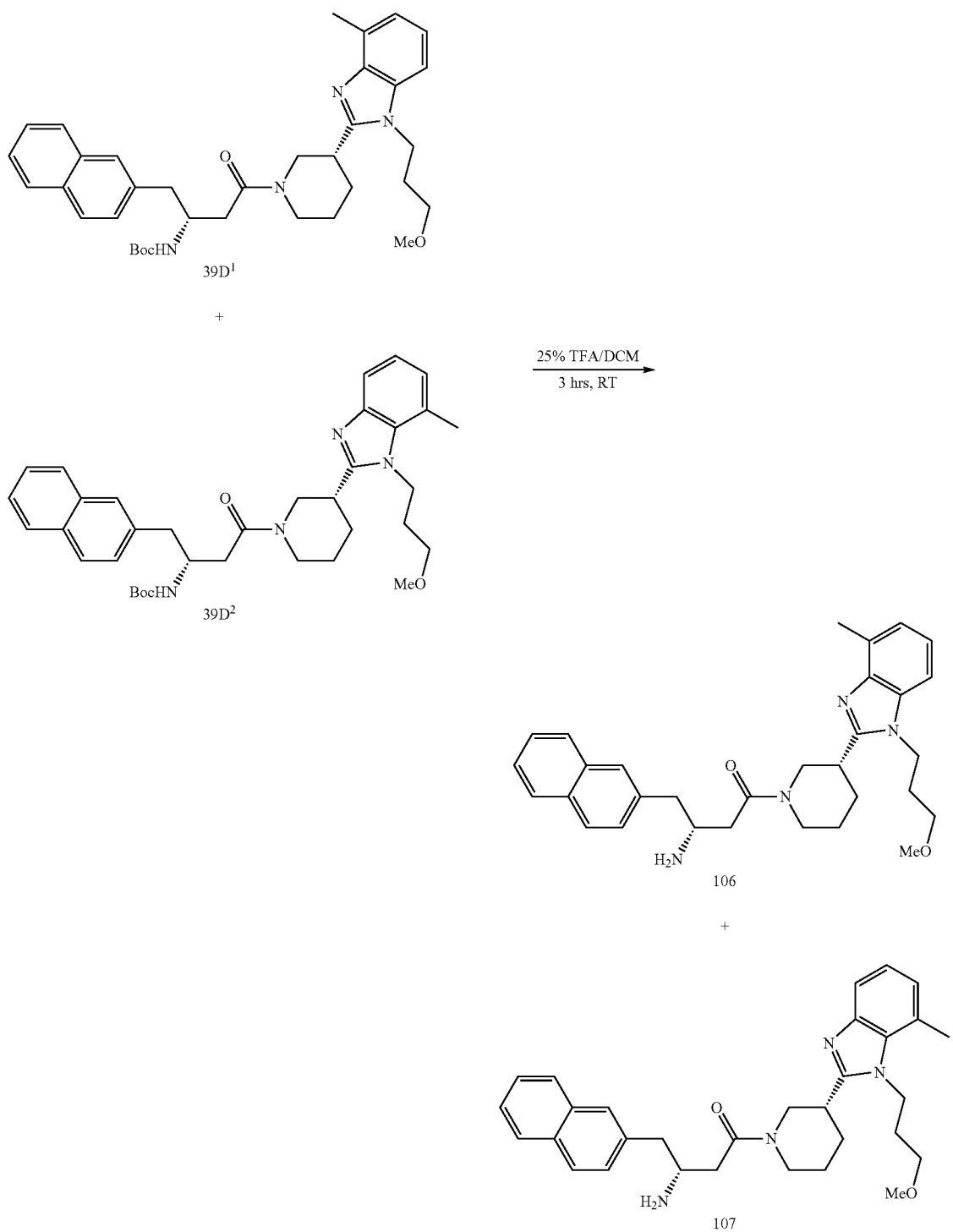

The residue from Step D above was dissolved in 25% trifluoroacetic acid and stirred at room temperature for 3 hrs. The solvent was removed in-vacuo affording a clear colored oil that the regioisomers were further separated by Berger Prep/SFC under the conditions: column: ChiralPak AD-H (5 µm, 21.2×250 mm); mobile phases: A is liquid $CO_2$, B is 10 mM $NH_4OAc$ in EtOH; flow rate: 50 mL/min; gradient: 17% B; run time: 52 min (half-stack-injection method applied); and Prep injection volume: 500 µL. The resultant regioisomers:

Compound 106: (R)-3-Amino-1-((R)-3-(1-(3-methoxypropyl)-4-methyl-1H-benzo[d]imidazol-2-yl)piperidin-1-yl)-4-(naphthalen-2-yl)butan-1-one (15 mg, 23% yield). ESI-MS: m/z 498.3 (M+H)$^+$.

Compound 107: (R)-3-Amino-1-((R)-3-(1-(3-methoxypropyl)-7-methyl-1H-benzo[d]imidazol-2-yl)piperidin-1-yl)-4-(naphthalen-2-yl)butan-1-one (8 mg, 13% yield). ESI-MS:mlz 498.3 (M+H)⁺.

Example 40

Synthesis of (R)-3-amino-1((R)-3-(4-methoxy-1-(3-methoxypropyl)-1H-benzo[d]imidazol-2-yl)piperidin-1-yl)-4-(naphthalen-2-yl)butan-1-one (104) and (R)-3-amino-1-((R)-3-(7-methoxy-1-(3-methoxypropyl)-1H-benzo[d]imidazol-2-yl)piperidin-1-yl)-4-(naphthalen-2-yl)butan-1-one (108)

Step A.

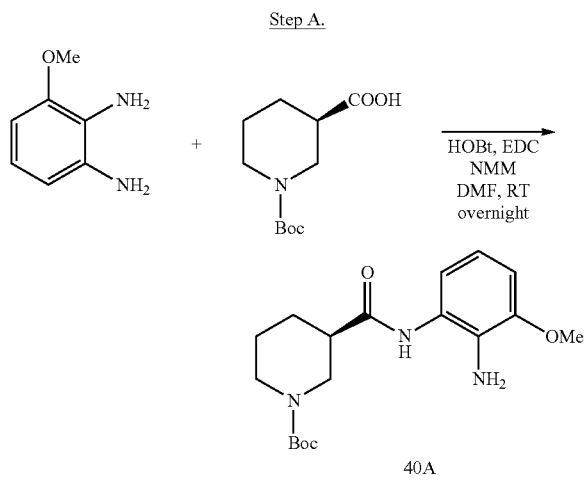

3-Methoxybenzene-1,2-diamine (920 mg, 6.66 mmol) was dissolved in N,N-dimethylforamide (6.7 mL). HOBt (1.08 g, 7.99 mmol), EDC (1.53 g, 7.99 mmol), and ®-1-(tert-butoxycarbonyl)piperidine-3-carboxylic acid (1.83 g, 7.99 mmol) were added and stirred overnight at room temperature. The solvent was removed under vacuum and the residue was partitioned between water (25 mL) and ethyl acetate (25 mL). The organic layer was separated and the aqueous was extracted with ethyl acetate (2×25 mL). The organics were combined and washed with 1N NaOH (25 mL). The organics were dried over sodium sulfate and filtered. Solvent was removed under vacuum and the residue containing ®-tert-butyl 3-(2-Amino-3-methoxyphenylcarbamoyl)piperidine-1-carboxylate (40A) was taken into the next step without further purification. ESI-MS:m/z 350.4 (M+H)⁺.

Step B.

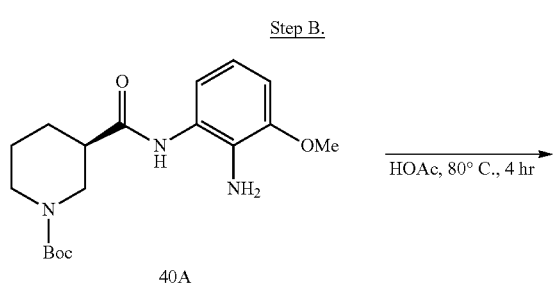

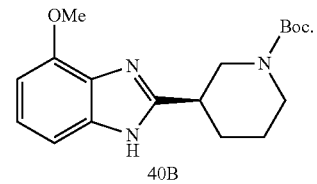

The residue from Step A was dissolved with acetic acid (15 mL) and heated to 80° C. for 4 hr. Solvent was removed under vacuum. The residue containing (R)-tert-butyl 3-(4-methoxy-1H-benzo[d]imidazol-2-yl)piperidine-1-carboxylate (40B) was used in the next step without further purification. ESI-MS:m/z 332.5 (M+H)⁺.

Step C.

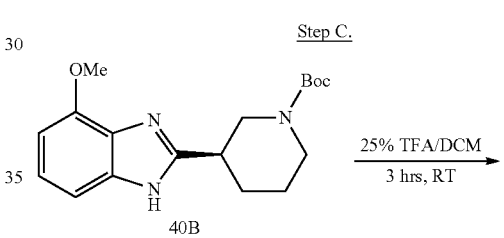

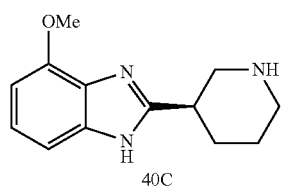

Into a 10 mL round bottomed was added (R)-tert-butyl 3-(4-methoxy-1H-benzo[d]imidazol-2-yl)piperidine-1-carboxylate (40B). 25% trifluoroacetic acid in dichloromethane (5 mL) was added and stirred at room temperature for 3 hr. The solvent was removed under vacuum. The residue containing (R)-4-Methoxy-2-(piperidin-3-yl)-1H-benzo[d]imidazole (40B) was used in the next step without purification. ESI-MS:m/z 232.4 (M+H)⁺.

Step D.

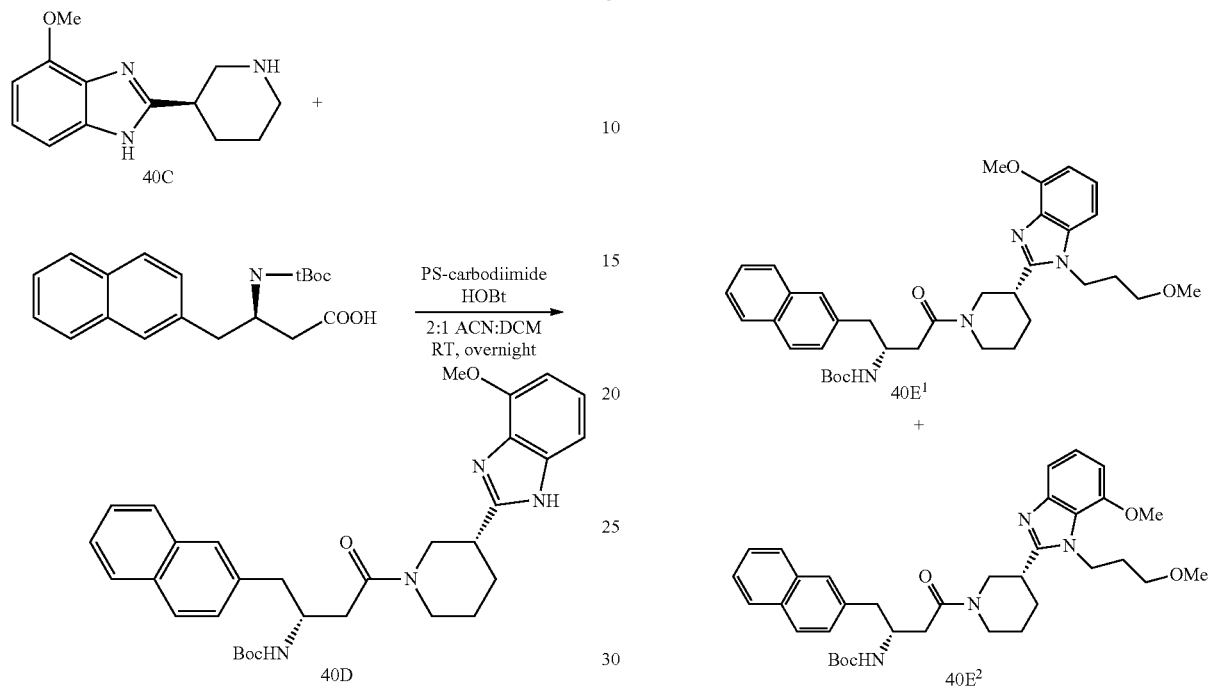

(R)-4-Methoxy-2-(piperidin-3-yl)-1H-benzo[d]imidazole (140 mg, 603 vmol) was dissolved with 2:1 acetonitrile:dichloromethane (3.0 mL). (R)-3-(tert-butoxycarbonylamino)-4-(naphthalen-2-yl)butanoic acid (218 mg, 663 µmol) in 2:1 acetonitrile:dichloromethane (3.3 mL) was added. HOBt (90 mg, 663 µmol) in DMF (3.3 mL) was added. Into a fritted syringe was added PS-carbodiimide resin (1.31 mmol/g, 921 mg). The amine, acid and HOBt solutions were taken up in the syringe and capped. The mixture was shaken overnight at room temperature. The solution was expelled into a round bottomed and the solvent was removed under vacuum. The residue containing tert-butyl (R)-4-((R)-3-(4-methoxy-1H-benzo[d]imidazol-2-yl)piperidin-1-yl)-1-(naphthalen-2-yl)-4-oxobutan-2-ylcarbamate (40D) was taken into the next step without further purification. ESI-MS: m/z 542.3 (M+H)$^+$.

Step E.

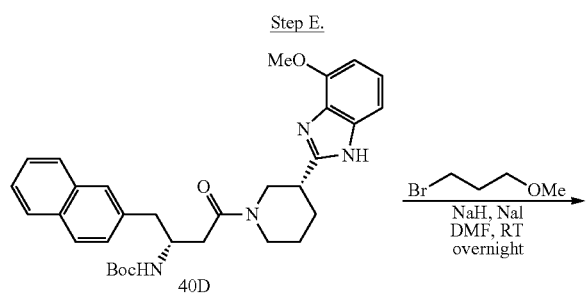

Into a 10 mL round bottomed was added the residue containing 40D from Step D (180 mg, 332 µmol) and N,N-dimethylforamide (1.7 mL). NaI (75 mg, 497 µmol) and NaH (20 mg, 497 µmol, 60% disp.) were added in sequence. The mixture was stirred for 30 minutes at room temperature. 3-Methoxy propyl bromide (76 mg, 497 µmol) was added at once and stirred overnight at room temperature. Solvent was removed under vacuum and the residue containing the mixture of tert-butyl (R)-4-((R)-3-(4-methoxy-1-(3-methoxypropyl)-1H-benzo[d]imidazol-2-yl)piperidin-1-yl)-1-(naphthalen-2-yl)-4-oxobutan-2-ylcarbamate (40E$^1$) and tert-butyl (R)-4-((R)-3-(7-methoxy-1-(3-methoxypropyl)-1H-benzo[d]imidazol-2-yl)piperidin-1-yl)-1-(naphthalen-2-yl)-4-oxobutan-2-ylcarbamate (40E$^2$) used without further purification. ESI-MS:m/z 615.5 (M+H)$^+$.

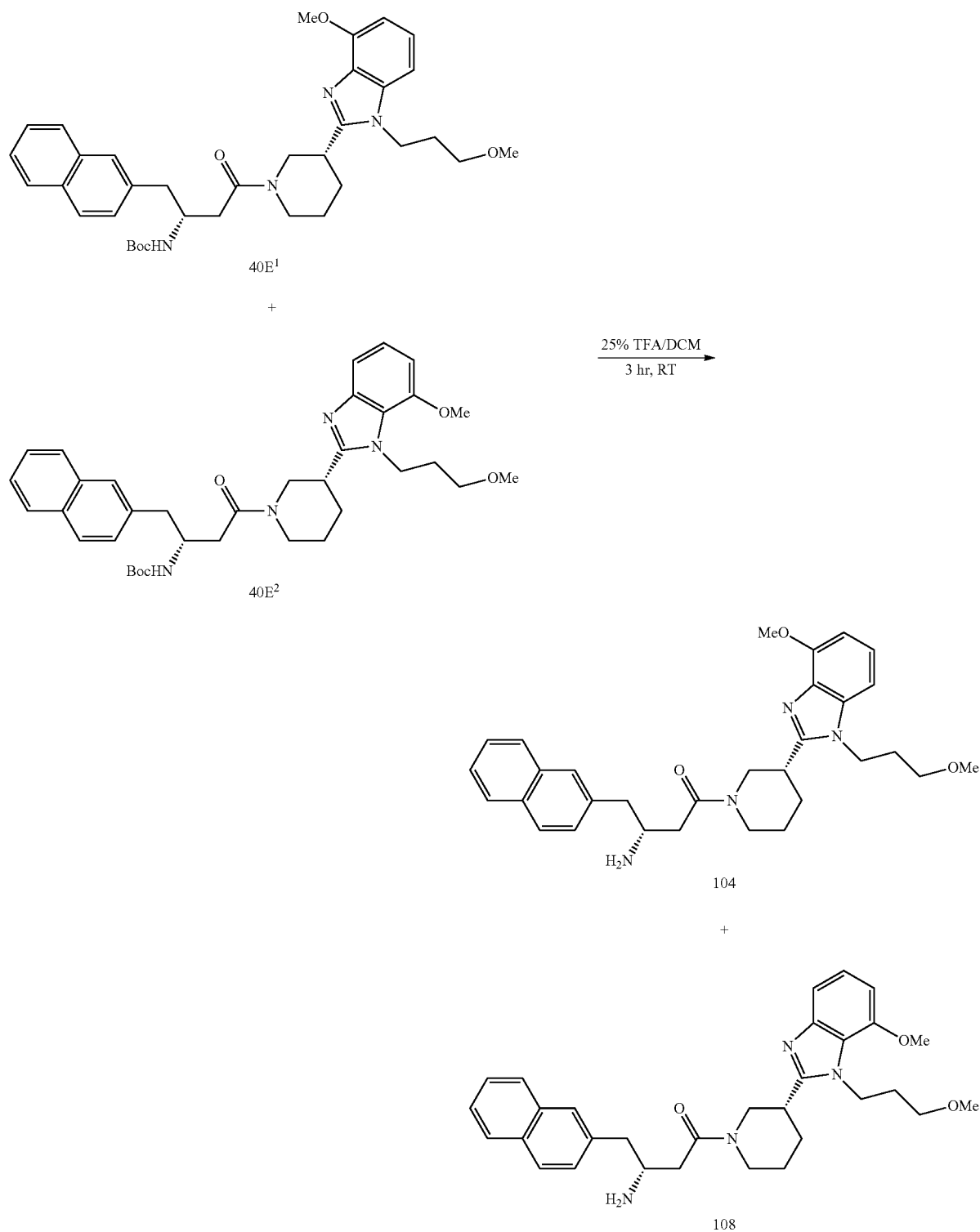

Residue from Step E was dissolved in 25% trifluoroacetic acid and stirred at room temperature for 3 hr. Solvent was removed under vacuum and purified by preparatory LC/MS (25-30% CH$_3$CN in H$_2$O) to give (R)-3-amino-1-((R)-3-(4-methoxy-1-(3-methoxypropyl)-1H-benzo[d]imidazol-2-yl)piperidin-1-yl)-4-(naphthalen-2-yl)butan-1-one (104) and (R)-3-amino-1-((R)-3-(7-methoxy-1-(3-methoxypropyl)-1H-benzo[c]imidazol-2-yl)piperidin-1-yl)-4-(naphthalen-2-yl)butan-1-one (108) as a mixture of TFA salts (11 mg, 5% yield). ESI-MS:m/z 515.4 (M+H)$^+$.

Example 41

Synthesis of 24(R)-1((R)-3-amino-4-(naphthalen-2-yl)butanoyl)piperidin-3-yl)-1-(3-methoxypropyl)-1H-benzo[d]imidazole-6-carbonitrile (109)

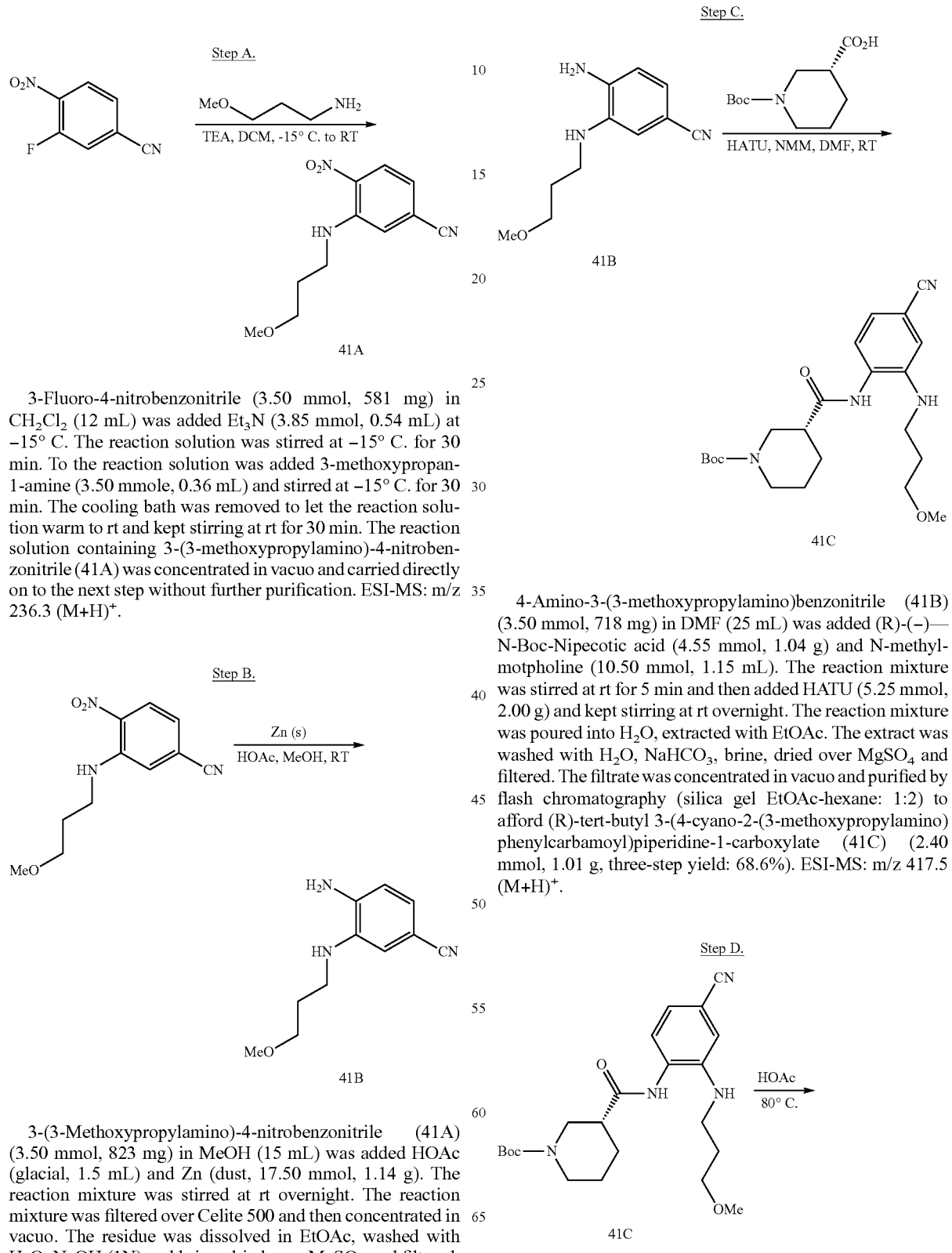

3-Fluoro-4-nitrobenzonitrile (3.50 mmol, 581 mg) in CH$_2$Cl$_2$ (12 mL) was added Et$_3$N (3.85 mmol, 0.54 mL) at −15° C. The reaction solution was stirred at −15° C. for 30 min. To the reaction solution was added 3-methoxypropan-1-amine (3.50 mmole, 0.36 mL) and stirred at −15° C. for 30 min. The cooling bath was removed to let the reaction solution warm to rt and kept stirring at rt for 30 min. The reaction solution containing 3-(3-methoxypropylamino)-4-nitrobenzonitrile (41A) was concentrated in vacuo and carried directly on to the next step without further purification. ESI-MS: m/z 236.3 (M+H)$^+$.

3-(3-Methoxypropylamino)-4-nitrobenzonitrile (41A) (3.50 mmol, 823 mg) in MeOH (15 mL) was added HOAc (glacial, 1.5 mL) and Zn (dust, 17.50 mmol, 1.14 g). The reaction mixture was stirred at rt overnight. The reaction mixture was filtered over Celite 500 and then concentrated in vacuo. The residue was dissolved in EtOAc, washed with H$_2$O, NaOH (1N) and brine, dried over MgSO$_4$ and filtered. The filtrate containing 4-amino-3-(3-methoxypropylamino) benzonitrile (41B) was concentrated in vacuo and carried directly on to the next step without further purification. ESI-MS: m/z 206.4 (M+H)$^+$.

4-Amino-3-(3-methoxypropylamino)benzonitrile (41B) (3.50 mmol, 718 mg) in DMF (25 mL) was added (R)-(−)—N-Boc-Nipecotic acid (4.55 mmol, 1.04 g) and N-methyl-motpholine (10.50 mmol, 1.15 mL). The reaction mixture was stirred at rt for 5 min and then added HATU (5.25 mmol, 2.00 g) and kept stirring at rt overnight. The reaction mixture was poured into H$_2$O, extracted with EtOAc. The extract was washed with H$_2$O, NaHCO$_3$, brine, dried over MgSO$_4$ and filtered. The filtrate was concentrated in vacuo and purified by flash chromatography (silica gel EtOAc-hexane: 1:2) to afford (R)-tert-butyl 3-(4-cyano-2-(3-methoxypropylamino) phenylcarbamoyl)piperidine-1-carboxylate (41C) (2.40 mmol, 1.01 g, three-step yield: 68.6%). ESI-MS: m/z 417.5 (M+H)$^+$.

-continued

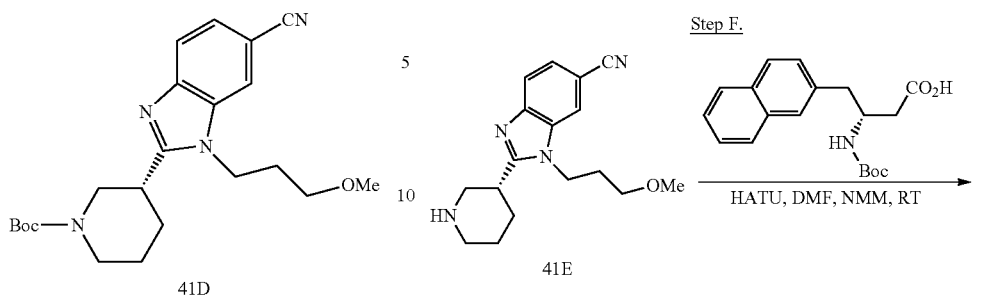

(R)-tert-Butyl 3-(4-cyano-2-(3-methoxypropylamino) phenylcarbamoyl)piperidine-1-carboxylate (41C) (2.40 mmol, 1.00 g) was added HOAc (glacial, 3 mL). The reaction mixture was heated to 80° C. and stirred for 7 hr. HOAc was removed by evaporation and the residue was purified by flash chromatography (silica gel EtOAc-hexane: 1:4) to afford (R)-tert-butyl 3-(6-cyano-1-(3-methoxypropyl)-1H-benzo[d] iimidazol-2-yl)piperidine-1-carboxylate (41D) (0.20 mmol, 80 mg, yield: 8.3%). ESI-MS: m/z 399.4 (M+H)$^+$.

Step E.

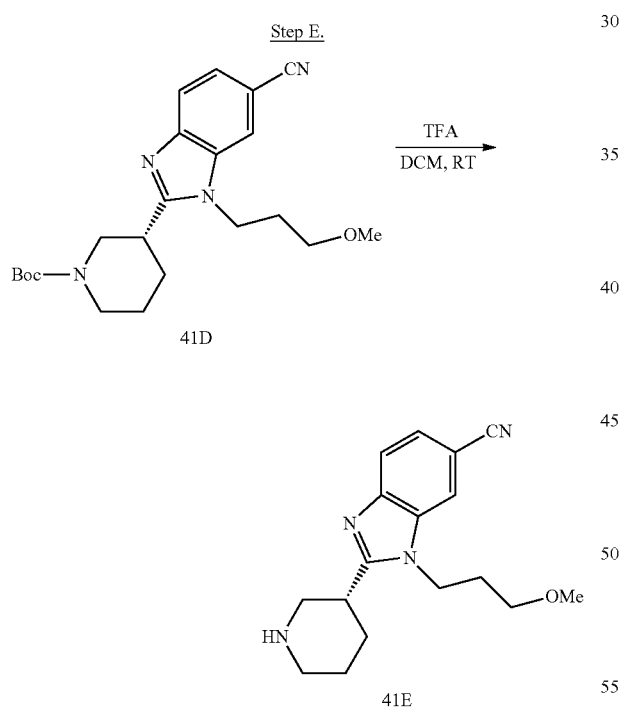

(R)-tert-Butyl 3-(6-cyano-1-(3-methoxypropyl)-1H-benzo[d]imidazol-2-yl)piperidine-1-carboxylate (41D) (0.20 mmol, 80 mg) in DCM (10 mL) was added TFA (2 mL). The reaction solution was stirred at rt for 1 hr and then concentrated in vacuo. The residue containing (R)-1-(3-Methoxypropyl)-2-(piperidin-3-yl)-1H-benzo[d]imidazole-6-carbonitrile (41E) was carried directly on to the next step without further purification. ESI-MS: m/z 236.3 (M+H)$^+$.

Step F.

(R)-1-(3-Methoxypropyl)-2-(piperidin-3-yl)-1H-benzo[d]imidazole-6-carbonitrile (41E) (0.20 mmol, 80 mg) in DMF (6 mL) was added (R)-3-(tert-butoxycarbonylamino)-4-(naphthalen-2-yl)butanoic acid (0.22 mmol, 72 mg) and N-methylmorpholine (0.80 mmol, 0.09 mL). The reaction mixture was stirred at it for 5 min and then added HATU (0.22 mmol, 84 mg) and kept stirring at it overnight. The reaction mixture was poured into H$_2$O, extracted with EtOAc. The extract was washed with H$_2$O, NaHCO$_3$, brine, dried over MgSO$_4$ and filtered. The filtrate was concentrated in vacuo and purified by preparative LC/MS (40-90% CH$_3$CN in H$_2$O) to afford tert-Butyl (R)-4-((R)-3-(6-cyano-1-(3-methoxypropyl)-1H-benzo[d]imidazol-2-yl)piperidin-1-yl)-1-(naphthalen-2-yl)-4-oxobutan-2-ylcarbamate (41F) (0.16 mmol, 100 mg, yield: 80%). ESI-MS: m/z 610.5 (M+H)$^+$.

Step G.

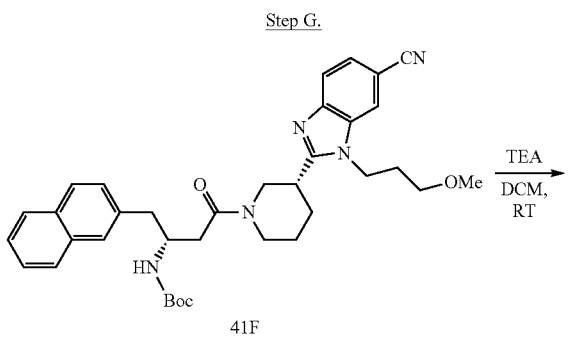

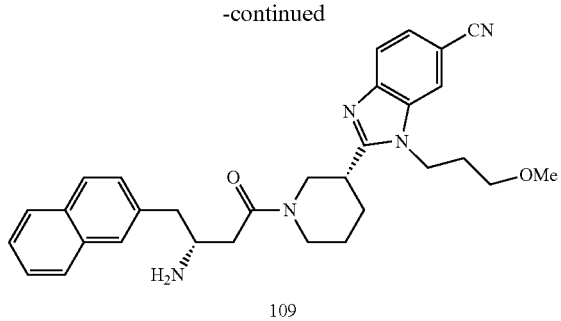

109 tert-Butyl(R)-4-((R)-3-(6-cyano-1-(3-methoxypropyl)-1H-benzo[d]imidazol-2-yl)piperidin-1-yl)-1-(naphthalen-2-yl)-4-oxobutan-2-ylcarbamate (41F) (0.16 mmol, 98 mg) in DCM (2 mL) was added TEA (2 mL). The reaction solution was stirred at rt for 1 hr and then concentrated in vacuo. The residue was purified by preparative LC/MS (20-50% $CH_3CN$ in $H_2O$) to afford 2-((R)-1-((R)-3-amino-4-(naphthalen-2-yl)butanoyl)piperidin-3-yl)-1-(3-methoxypropyl)-1H-benzo[d]imidazole-6-carbonitrite (109) (0.14 mmol, 71 mg, yield: 87.5%). ESI-MS: m/z 510.5 (M+H)$^+$. 1H NMR (400 MHz, DMSO-$d_6$) δ ppm 1.28 (none, 1H) 1.68-2.05 (m, 3H) 2.33 (m, 2H) 2.64-2.77 (m, 2H) 2.89-3.23 (m, 7H) 3.29 (t, J=5.81Hz, 1H) 3.42 (dd, J=14.15, 11.18 Hz, 3H) 3.71-3.98 (m, 2H) 4.14-4.24 (m, 2H) 4.31-4.53 (m, 2H) 7.41-7.47 (m, 1H) 7.49-7.55 (m, 2H) 7.55-7.61 (m, 1H) 7.67-7.77 (m, 1H) 7.80 (d, J=4.67 Hz, 1 H) 7.82-7.96 (m, 3H) 8.17 (d, J=5.75 Hz, 1H).

Example 42

Synthesis of (R)-3-amino-1((R)-3-(6-methoxy-1-(3-methoxypropyl)-1H-benzo[d]imidazol-2-yl)piperidin-1-yl)-4-(naphthalen-2-yl)butan-1-one (110)

Step A.

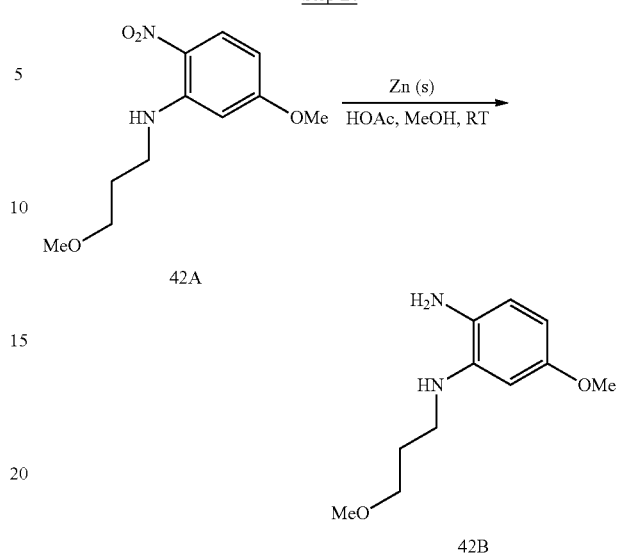

3-Fluoro-4-nitroanisole (3.50 mmol, 599 mg) in $CH_2Cl_2$ (12 mL) was added $Et_3N$ (3.85 mmol, 0.54 mL) at −15° C. The reaction solution was stirred at −15° C. for 30 min. To the reaction solution was added 3-methoxypropan-1-amine (3.50 mmole, 0.36 mL) and stirred at −15° C. for 30 min. The cooling bath was removed to let the reaction solution warm to it and kept stirring at it for 30 min. The reaction solution containing 5-methoxy-N-(3-methoxypropyl)-2-nitroaniline (42A) was concentrated in vacuo and carried directly on to the next step without further purification. ESI-MS: m/z 241.3 (M+H)$^+$.

Step B.

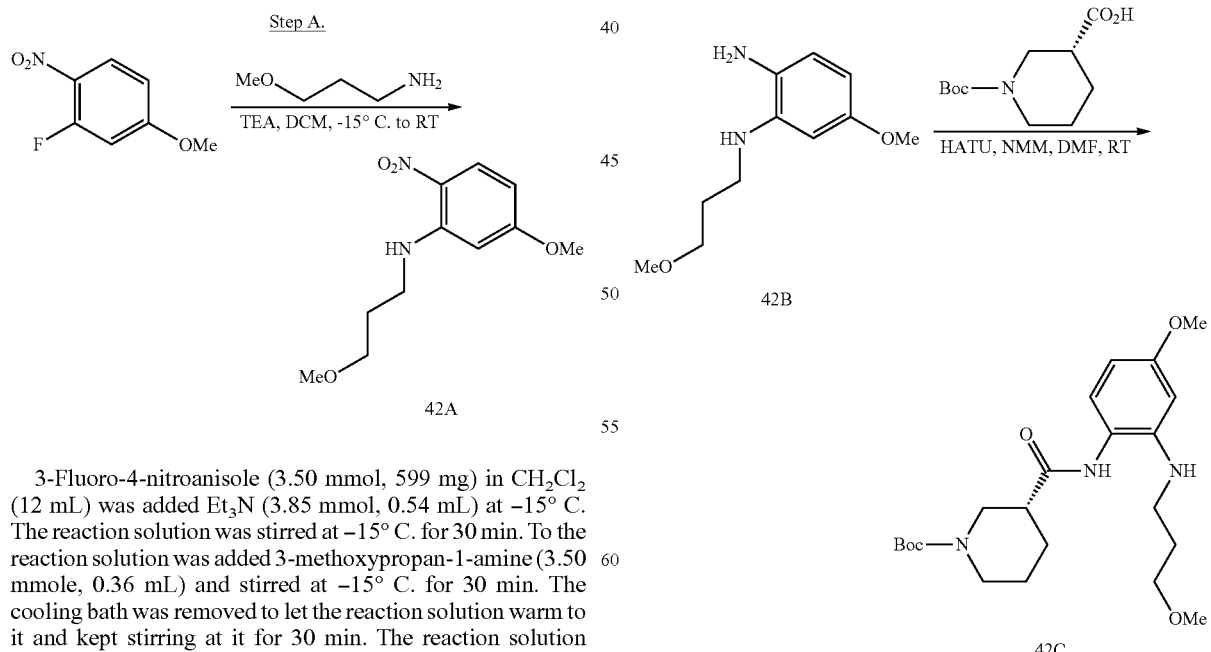

5-Methoxy-N-(3-methoxypropyl)-2-nitroaniline (42A) (3.50 mmol, 841 mg) in MeOH (15 mL) was added HOAc (glacial, 1.5 mL) and Zn (dust, 17.50 mmol, 1.14 g). The reaction mixture was stirred at it overnight. The reaction mixture was filtered over Celite 500 and then concentrated in vacuo. The residue was dissolved in EtOAc, washed with HAD, NaOH (1N) and brine, dried over $MgSO_4$ and filtered. The filtrate containing 5-methoxy-N$^t$-(3-methoxypropyl)benzene-1,2-diamine (41B) was concentrated in vacuo and carried directly on to the next step without further purification. ESI-MS: m/z 211.4 (M+H)$^+$.

Step C.

5-Methoxy-N$^1$-(3-methoxypropyl)benzene-1,2-diamine (42B) (1.81 mmol, 380 mg) in DMF (20 mL) was added (R)-(−)-N-Boc-nipecotic acid (2.35 mmol, 541 mg) and N-methylmorpholine (5.43 mmol, 0.60 mL). The reaction mixture was stirred at rt for 5 min and then added HATU (2.72 mmol, 1.03 g) and kept stirring at rt overnight. The reaction mixture was poured into H₂O, extracted with EtOAc. The extract was washed with H₂O, NaHCO₃, brine, dried over MgSO₄ and filtered. The filtrate was concentrated in vacuo and purified by flash chromatography (silica gel, EtOAc-hexane: 1:2) to afford (R)-tert-butyl 3-(4-methoxy-2-(3-methoxypropylamino)phenylcarbarnoyl)piperidine-1-carboxylate (42C) (2.82 mmol, 1.19 g, three-step yield: 80.6%). ESI-MS: m/z 422.5 (M+H)⁺.

Step D.

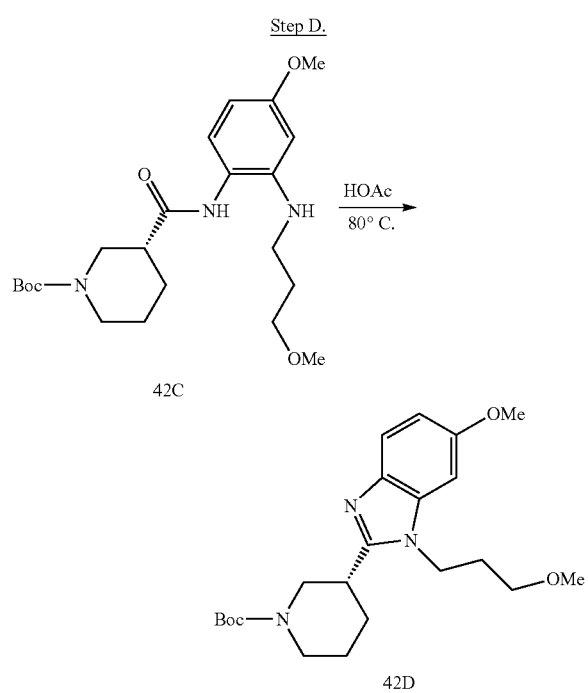

42C

42D (R)-tert-Butyl 3-(4-methoxy-2-(3-methoxypropylamino)phenylcarbamoyl)piperidine-1-carboxylate (42C) (2.82 mmol, 1.19 g) was added HOAc (glacial, 4.0 mL). The reaction mixture was heated to 80° C. and stirred for 7 hr. The reaction solution containing (R)-tert-butyl 3-(6-methoxy-1-(3-methoxypropyl)-1H-benzo[d]imidazol-2-yl)piperidine-1-carboxylate (420) was concentrated in vacuo and carried directly on to the next step without further purification. ESI-MS: m/z 404.5 (M+H)⁺.

Step E.

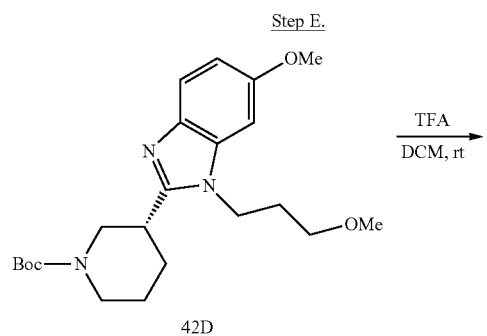

42D

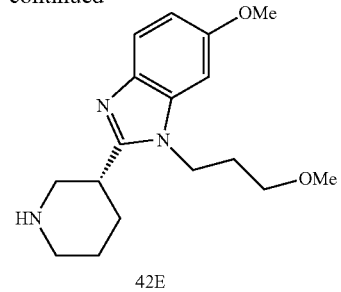

42E (R)-tert-Butyl 3-(6-methoxy-1-(3-methoxypropyl)-1H-benzo[d]imidazol-2-yl)piperidine-1-carboxylate (42D) (2.82 mmol, 1.14 g) in DCM (10 mL) was added TFA (3 mL). The reaction solution was stirred at rt for 1 hr and then concentrated in vacuo. The residue containing (R)-6-methoxy-1-(3-methoxypropyl)-2-(piperidin-3-yl)-1H-benzo[d]imidazole (42E) was carried directly on to the next step without further purification. ESI-MS: m/z 304.4 (M+H)⁺.

Step F.

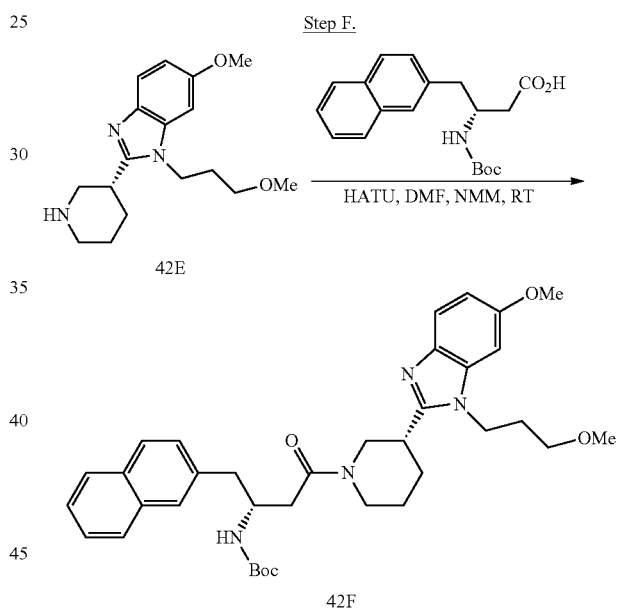

42F (R)-6-Methoxy-1-(3-methoxypropyl)-2-(piperidin-3-yl)-1H-benzo[d]imidazole (41E) (2.82 mmol, 0.86 g) in DMF (16 mL) was added (R)-3-(tert-butoxycarbonylamino)-4-(naphthalen-2-yl)butanoic acid (3.10 mmol, 1.02 g) and N-methylmorpholine (11.28 mmol, 1.24 mL). The reaction mixture was stirred at rt for 5 min and then added HATU (3.10 mmol, 1.18 g) and kept stirring at rt overnight. The reaction mixture was poured into H₂O, extracted with EtOAc. The extract was washed with H₂O, NaHCO₃, brine, dried over MgSO₄ and filtered. The filtrate was concentrated in vacuo and purified by preparative LC/MS (40-90% CH₃CN in H₂O) to afford tert-butyl (R)-4-((R)-3-(6-methoxy-1-(3-methoxypropyl)-1H-benzo[d]imidazol-2-yl)piperidin-1-yl)-1-(naphthalen-2-yl)-4-oxobutan-2-ylcarbamate (42F) (0.63 mmol, 0.387 g, three-step yield: 22.3%). ESI-MS: m/z 616.5 (M+H)⁺.

Step G.

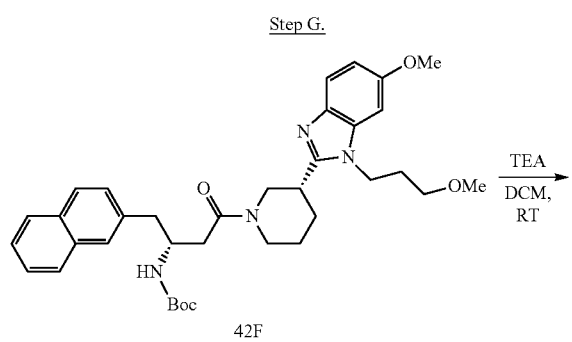

42F

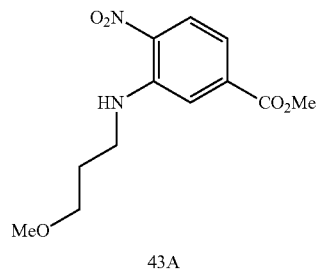

43A

Methyl 3-fluoro-4-nitrobenzoate (10.14 mmol, 2.02 g) in CH$_2$Cl$_2$ (12 mL) was added Et$_3$N (11.15 mmol, 1.57 mL) at −15° C. The reaction solution was stirred at −15° C. for 30 min, To the reaction solution was added 3-methoxypropan-1-amine (11.2 mmole, 1.15 mL) and stirred at −15° C. for 30 min. The cooling bath was removed to let the reaction solution warm to rt and kept stirring at rt for 30 min. The reaction solution containing methyl 3-(3-methoxypropylamino)-4-nitrobenzoate (43B) was concentrated in vacuo and carried directly on to the next step without further purification. ESI-MS: m/z 269.3 (M+H)$^+$.

110 tert-Butyl (R)-4-((R)-3-(6-methoxy-1-(3-methoxypropyl)-1H-benzo[d]imidazol-2-yl)piperidin-1-yl)-1-(naphthalen-2-yl)-4-oxobutan-2-ylcarbamate (42F) (0.63 mmol, 387 mg) in DCM (15 mL) was added TEA (3 mL). The reaction solution was stirred at rt for 1 hr and then concentrated in vacuo. The residue was purified by preparative LC/MS (20-50% CH$_3$CN in H$_2$O) to afford (R)-3-amino-1-((R)-3-(6-methoxy-1-(3-methoxypropyl)-1H-benzo[d]imidazol-2-yl)piperidin-1-yl)-4-(naphthalen-2-yl)butan-1-one (110) (0.05 mmol, 27 mg, yield: 7.9%). ESI-MS: m/z 515.5 (M+H)$^+$. 1H NMR (400 MHz, DMSO-d$_6$) δ ppm 1.38-1.56 (m, 1H) 1.72-1.99 (m, 4H) 2.01-2.21 (m, 2H) 2.58-2.77 (m, 3H) 2.87-2.98 (m, 1H) 3.01-3.25 (m, 7H) 3.37 (t, J=5.75 Hz, 2H) 3.82 (d, 0.1=10.23 Hz, 2H) 3.88 (d, J=7.07 Hz, 3H) 4.05-4.69 (m, 3H) 7.04-7.12 (m, 1H) 7.35 (d, J=13.07 Hz, 1H) 7.45 (dd, J=8.46, 2.72 Hz, 1H) 7.48-7.55 (m, 2H) 7.64 (t, J=9.69 Hz, 1H) 7.80 (d, J=6.06 Hz, 1H) 7.83-8.03 (m, 3H).

Step B.

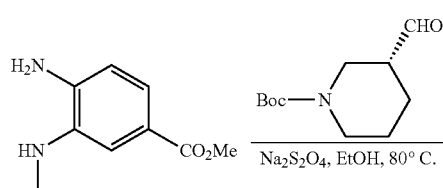

43A

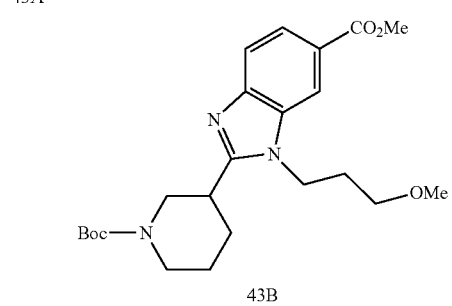

43B

Methyl 3-(3-methoxypropylamino)-4-nitrobenzoate (43A) (4.00 mmol, 1.07 g) in EtOH (30 mL) was added tert-butyl 3-formylpiperidine-1-carboxylate (4.00 mmol, 0.85 g) and Na$_2$S$_2$O$_4$ solution (12.0 mmol, 2.09 g in 12 mL H$_2$O). The reaction mixture was heated at 80° C. for 5 hrs and then poured into H$_2$O, extracted with EtOAc. The extract was washed with H$_2$O, brine, dried over MgSO$_4$ and filtered. The filtrate containing methyl 2-(1-(tert-butoxycarbonyl)piperidin-3-yl)-1-(3-methoxypropyl)-1H-benzo[d]imidazole-6-carboxylate (43B) was concentrated in vacuo and carried directly on to the next step without further purification. ESI-MS: m/z 432.4 (M+H)$^+$.

Example 43

Synthesis of methyl 2-(1-((R)-3-amino-4-(naphthalen-2-yl)butanoyl)piperidin-3-yl)-1-(3-methoxypropyl)-1H-benzo[d]imidazole-6-carboxylate (111)

Step A.

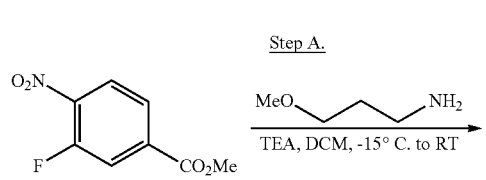

Step C.

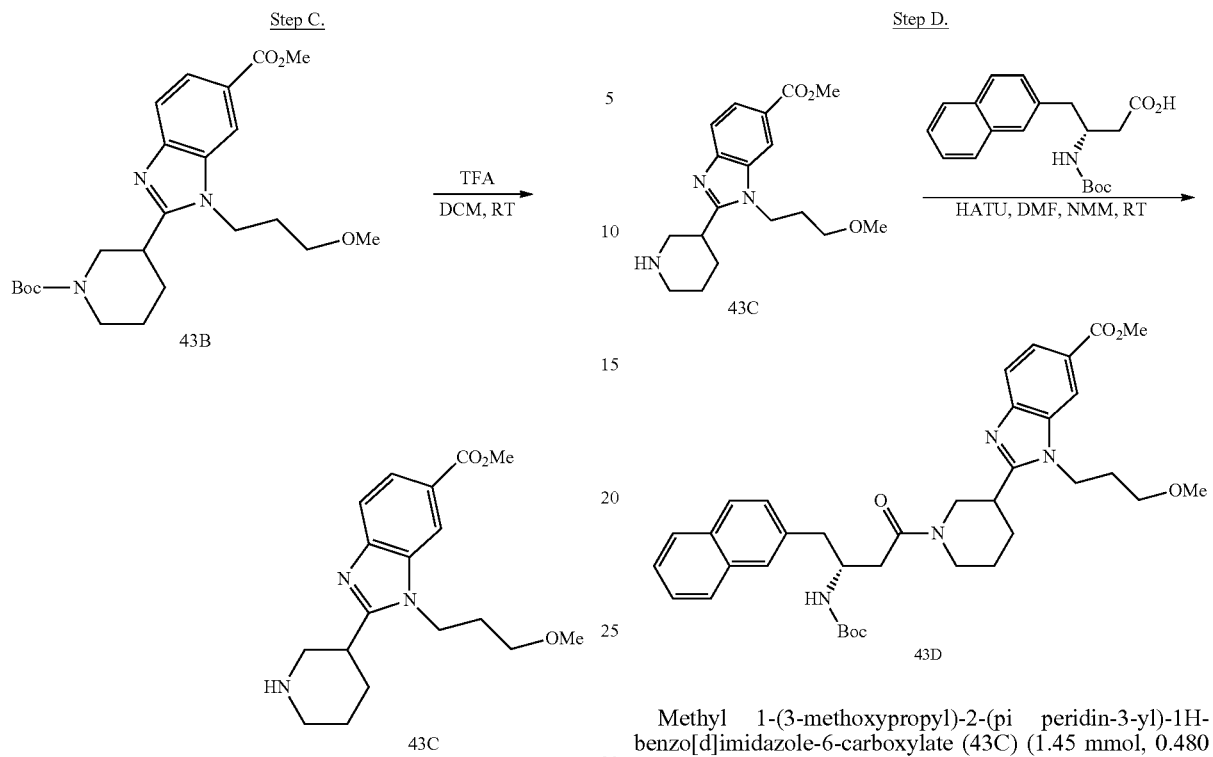

Methyl 2-(1-(tert-bu toxycarbonyl)piperidin-3-yl)-1-(3-methoxypropyl)-1H-benzo[d]imidazole-6-carboxylate (43B) (3.10 mmol, 1.25 g) in DCM (10 mL) was added TFA (2 mL). The reaction solution was stirred at rt for 1 hr and then concentrated in vacuo. The residue was purified by preparative LC/MS (15-40% $CH_3CN$ in $H_2O$) to afford methyl 1-(3-methoxypropyl)-2-(piperidin-3-yl)-1H-benzo[d]imidazole-6-carboxylate (43C) (1.48 mmol, 490 mg, yield: 47.7%). ESI-MS: m/z 332.4 $(M+H)^+$.

Step D.

Methyl 1-(3-methoxypropyl)-2-(pi peridin-3-yl)-1H-benzo[d]imidazole-6-carboxylate (43C) (1.45 mmol, 0.480 g) in DMF (20 mL) was added (R)-3-(tert-butoxycarbonylamino)-4-(naphthalene-2-yl)butanoic acid (1.60 mmol, 0.527 g) and N-methylmorpholine (5.80 mmol, 0.64 mL). The reaction mixture was stirred at rt for 5 min and then added HATU (1.60 mmol, 0.608 g) and kept stirring at rt overnight. The reaction mixture was poured into $H_2O$, extracted with EtOAc. The extract was washed with $H_2O$, $NaHCO_3$, brine, dried over $MgSO_4$ and filtered. The filtrate was concentrated in vacuo and purified by preparative LC/MS (50-80% $CH_3CN$ in $H_2O$) to afford methyl 2-(1-((R)-3-(tert-butoxycarbonylamino)-4-(naphthalene-2-yl)butan oyl)butano yl)piperidine-3-yl)-1-(3-methoxypropyl)-1H-benzo[d]imidazole-6-carboxylate (43D) (1.09 mmol, 0.70 g, yield: 75.2%). ESI-MS: m/z 643.5 $(M+H)^+$.

Step E.

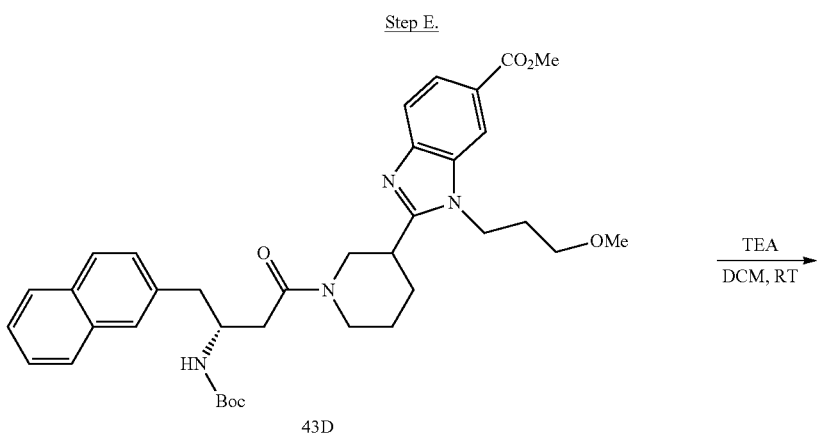

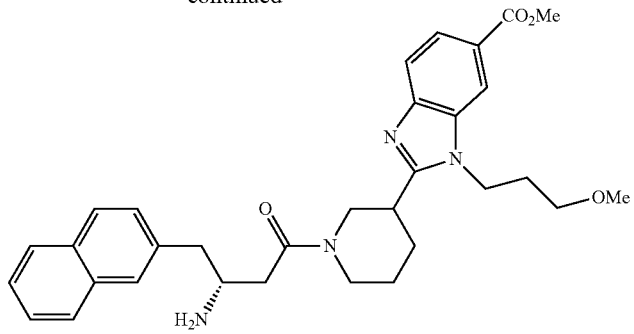

111

Methyl 2-(1-((R)-3-(tert-butoxycarbonylamino)-4-(naphthalen-2-yl)butanoyl)piperidin-3-yl)-1-(3-methoxypropyl)-1H-benzo[d]imidazole-6-carboxylate (43D) (0.22 mmol, 140 mg) in DCM (10 mL) was added TEA (2 mL). The reaction solution was stirred at rt for 1 hr and then concentrated in vacuo. The residue was purified by preparative LC/MS (20-50% $CH_3CN$ in $H_2O$) to afford methyl 2-(14(R)-3-amino-4-(naphthalen-2-yl)butanoyl)piperidin-3-yl)-1-(3-methoxypropyl)-1H-benzo[d]imidazole-6-carboxylate (111) (0.05 mmol, 26 mg, yield: 22.7%). ESI-MS: m/z 543.5 $(M+H)^+$. 1H NMR (400 MHz, DMSO-$d_6$) δ ppm 1.70-2.12 (m, 6H) 2.70 (d, J=6.51Hz, 3H) 2.87-3.06 (m, 2H) 3.06-3.19 (m, 4H) 3.19-3.25 (m, 2H) 3.30 (t, J=5.62 Hz, 1H) 3.27-3.32 (m, 1H) 3.74-3.85 (m, 2H) 3.89 (d, J=6.88 Hz, 3H) 3.96 (s, 1H) 4.18-4.60 (m, 3H) 7.44 (dd, J=9.03, 6.13 Hz, 1H) 7.48-7.56 (m, 2H) 7.63-7.72 (m, 1H) 7.80 (d, J=7.39 Hz, 1H) 7.84 (dd, J=8.91, 2.08 Hz, 2H) 7.87-7.95 (m, 3H).

Example 44

Synthesis of methyl 2-(1-((R)-3-amino-4-(naphthalen-2-yl)butanoyl)piperidin-3-yl)-1-(3-methoxypropyl)-1H-benzo[d]imidazole-7-carboxylate (112)

Step A.

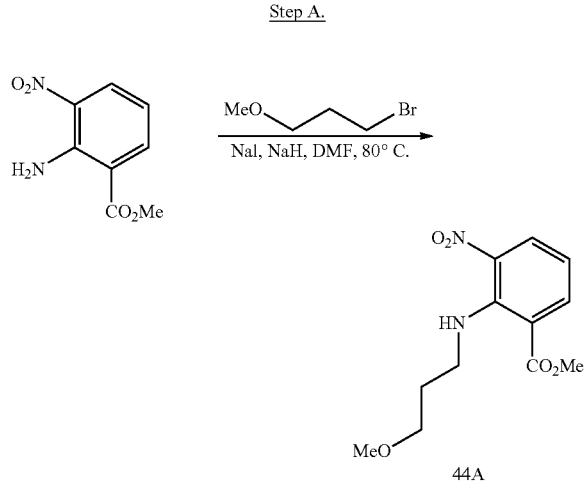

Methyl 2-amino-3-nitrobenzoate (3.82 mmol, 0.75 g) in DMF (20 mL) was added NaI (8.40 mmol, 1.26 g). The reaction solution was stirred at 0° C. for 5 min and then added NaH (5.00 mmol, 0.20 g) at 0° C. The reaction solution was stirred at 0° C. for 30 min and then added 1-bromo-3-methoxypropane (5.00 mmol, 0.77 g). The reaction solution was heated to 80° C. and kept stirring at 80° C. for 6 hr. After cooling down the reaction solution was poured into $H_2O$, extracted with EtOAc. The extract was washed with $H_2O$, brine dried over $MgSO_4$ and filtered. The filtrate was concentrated in vacuo and purified by flash chromatography (silica gel, EtOAc-hexane: 5:95) to afford methyl 2-(3-methoxypropylamino)-3-nitrobenzoate (44A) (1.49 mmol, 800 mg, yield: 78.1%). ESI-MS: m/z 269.3 $(M+H)^+$.

Step B.

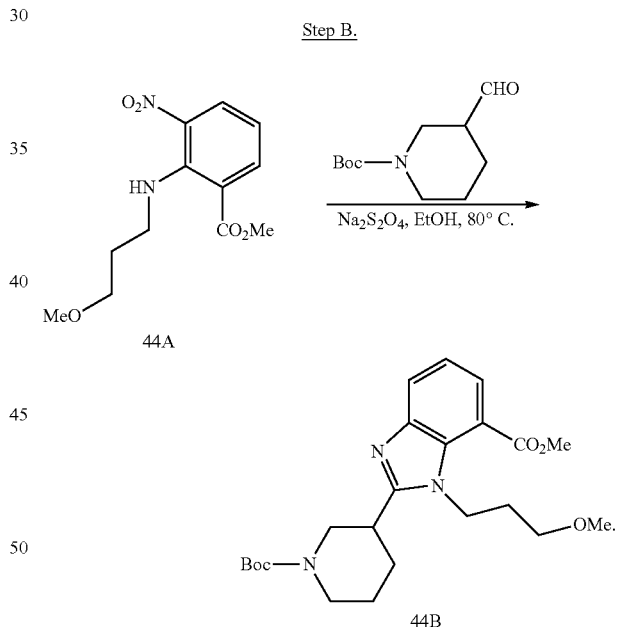

Methyl 2-(3-methoxypropylamino)-3-nitrobenzoate (3.82 mmol, 1.02 g) (44A) in EtOH (30 mL) was added tert-butyl 3-formylpiperidine-1-carboxylate (3.82 mmol, 0.82 g) and $Na_2S_2O_4$ solution (11.46 mmol, 2.00 g in 12 mL $H_2O$). The reaction mixture was heated at 80° C. for 5 hrs and then poured into $H_2O$, extracted with EtOAc. The extract was washed with $H_2O$, brine, dried over $MgSO_4$ and filtered. The filtrate containing methyl 2-(1-(tert-butoxycarbonyl)piperidin-3-yl)-1-(3-methoxypropyl)-1H-benzo[d]imidazole-7-carboxylate (44B) was concentrated in vacuo and carried directly on to the next step without further purification. ESI-MS: m/z 432.4 $(M+H)^+$.

Step C.

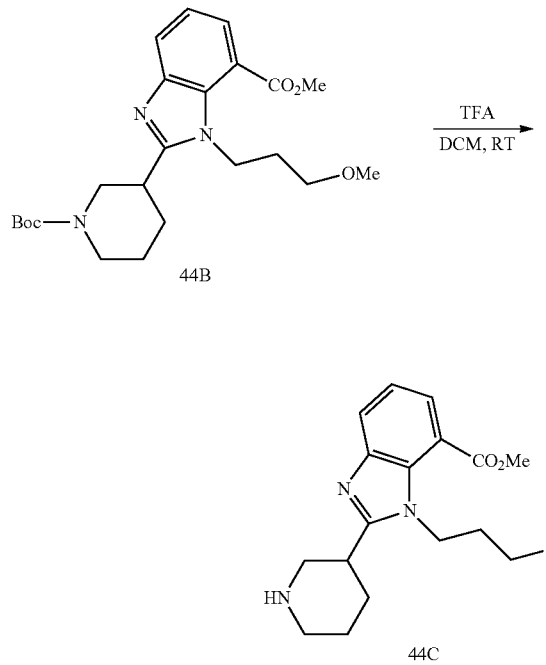

Methyl 2-(1-(tert-butoxycarbonyl)piperidin-3-yl)-1-(3-methoxypropyl)-1H-benzo[d]imidazole-7-carboxylate (44B) (1.91 mmol, 400 mg) in DCM (10 mL) was added TFA (2 mL). The reaction solution was stirred at rt for 1 hr and then concentrated in vacuo. The residue was purified by preparative LC/MS (15-40% $CH_3CN$ in $H_2O$) to afford methyl 1-(3-methoxypropyl)-2-(piperidin-3-yl)-1H-benzo[d]imidazole-7-carboxylate (44C) (0.36 mmol, 120 mg, yield: 18.8%). EST-MS: m/z 332.4 (M+H)⁺.

Step D.

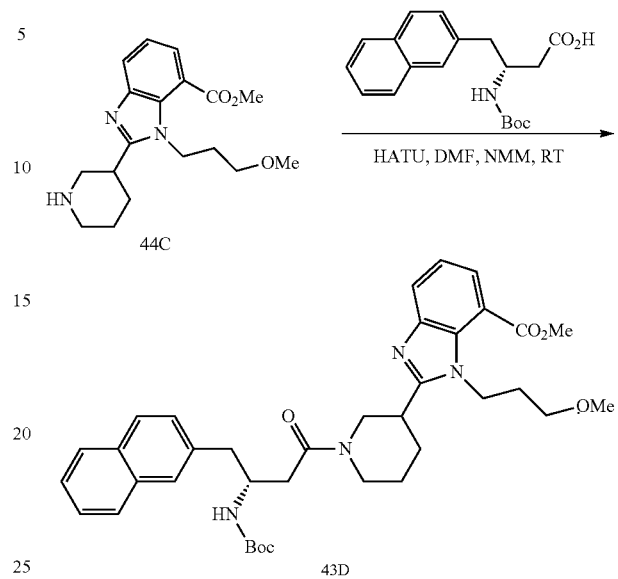

Methyl 1-(3-methoxypropyl)-2-(piperidin-3-yl)-1H-benzo[d]imidazole-7-carboxylate (42C) (0.36 mmol, 120 mg) in DMF (10 mL) was added (R)-3-(tert-butoxycarbonylamino)-4-(naphthalen-2-yl)butanoic acid (0.40 mmol, 132 mg) and N-methylmorpholine (1.44 mmol, 0.16 mL). The reaction mixture was stirred at rt for 5 min and then added HATU (0.40 mmol, 152 mg) and kept stirring at rt overnight. The reaction mixture was poured into $H_2O$, extracted with EtOAc. The extract was washed with $H_2O$, $NaHCO_3$, brine, dried over $MgSO_4$ and filtered. The filtrate was concentrated in vacuo and purified by preparative LC/MS (40-70% $CH_3CN$ in $H_2O$) to afford methyl 2-(1-((R)-3-(tert-butoxycarbonylamino)-4-(naphthalen-2-yl)butanoyl)piperidin-3-yl)-1-(3-methoxypropyl)-1H-benzo[d]imidazole-7-carboxylate (44D) (0.06 mmol, 40 mg, yield: 16.7%). ESI-MS: m/z 643.5 (M+H)⁺.

Step E.

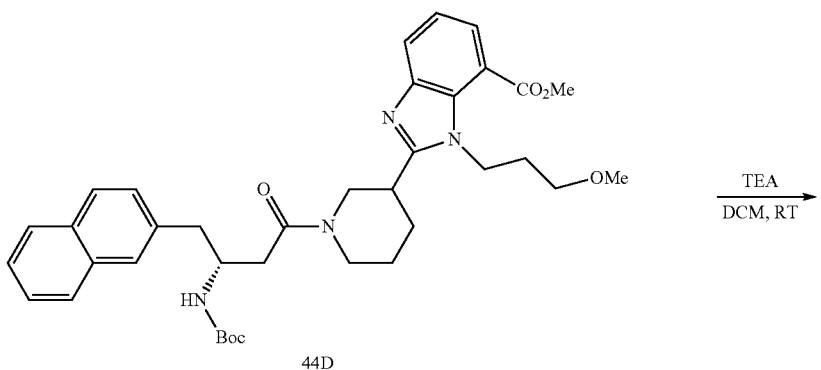

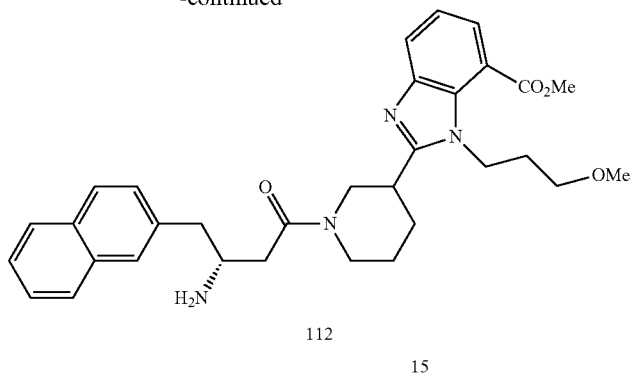

112

Methyl 2-(1-((R)-3-(tert-butoxycarbonylamino)-4-(naphthalen-2-yl)butanoyl)piperidin-3-yl)-1-(3-methoxypropyl)-1H-benzo[d]imidazole-7-carboxylate (440) (0.04 mmol, 25 mg) in DCM (5 mL) was added TEA (1 mL). The reaction solution was stirred at rt for 1 hr and then concentrated in vacuo. The residue was purified by preparative LC/MS (20-50% a $CH_3CN$ in $H_2O$) to afford methyl 2-(1-((R)-3-amino-4-(naphthalen-2-yl)butanoyl)piperidin-3-yl)-1-(3-methoxypropyl)-1H-benzo[d]imidazole-7-carboxylate (112) (0.018 mmol, 10 mg, yield: 45.0%). ESI-MS: 543.5 m/z (M+H)$^+$. $^1$H NMR (400 MHz, MeOD) δ ppm 1.52-1.74 (m, 2H) 1.85-2.11 (m, 4H) 2.15-2.32 (m, 2H) 2.65 (s, 2H) 2.69-2.89 (m, 4H) 2.90-3.09 (m, 4H) 3.23 (s, 1H) 3.35 (t, J=5.53 Hz, 1H) 3.40-3.50 (m, 1H) 3.89 (d, J=13.83 Hz, 1H) 4.34-4.44 (m, 2H) 4.57 (dd, 2H) 4.66 (d, 0.1=13.07 Hz, 2H) 7.43 (t, J=8.12 Hz, 1H) 7.47-7.53 (m, 2H) 7.56 (t, J=8.72 Hz, 1H) 7.76-7.93 (m, 4H) 7.93-7.98 (m, 2H).

Example 45

Synthesis of (3R)-3-amino-1-(3-(6-(hydroxymethyl)-1-(3-methoxypropyl)-1,1-benzo[d]imidazol-2-yl)piperidin-1-yl)-4-(naphthalen-2-yl)butan-1-one (113)

Step A.

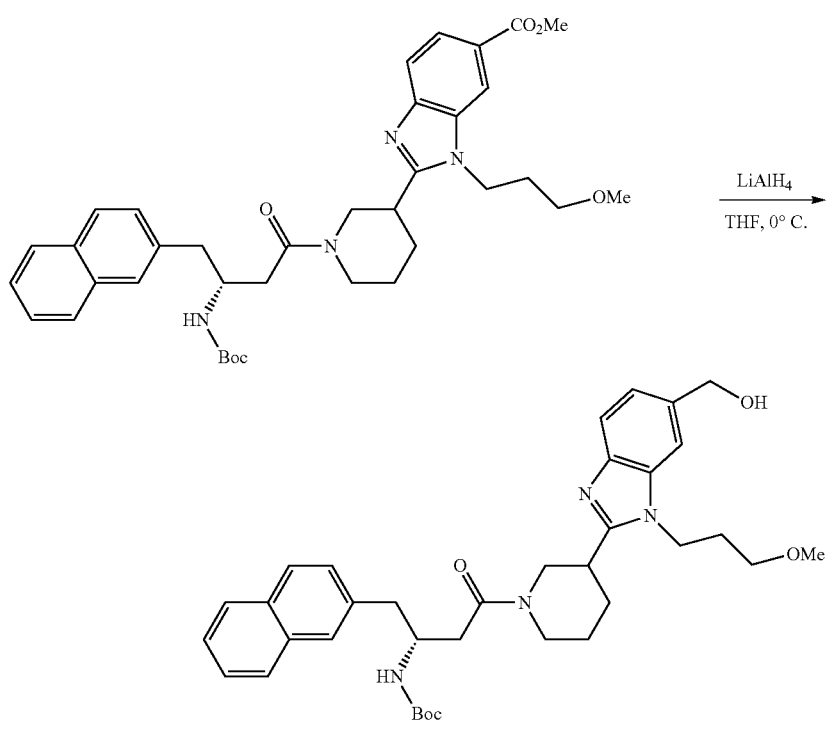

45A

Methyl 2-(1-((R)-3-(tert-butoxycarbonylamino)-4-(naphthalen-2-yl)butanoyl)piperidin-3-yl)-1-(3-methoxypropyl)-1H-benzo[d]imidazole-6-carboxylate (0.12 mmol, 75 mg) in THF (10 mL) was added LiAlH₄ (0.13 mmol, 4.9 mg) at 0° C. The reaction mixture was stirred at 0° C. for 30 min and then poured into sat. NaHCO₃, extracted with EtOAc. The extract was washed with brine, dried over MgSO₄ and filtered. The filtrate containing tert-butyl (2R)-4-(3-(6-(hydroxymethyl)-1-(3-methoxypropyl)-1H-benzo[d]imidazol-2-yl)piperidin-1-yl)-1-(naphthalen-2-yl)-4-oxobutan-2-ylcarbamate (45A) was concentrated in vacuo and carried directly on to the next step without further purification. ESI-MS: m/z 615.5 (M+H)⁺.

imidazol-2-yl)piperidin-1-yl)-4-(naphthalen-2-yl)butan-1-one (113) (0.016 mmol, 8 mg, two-step yield: 13.3%). ESI-MS: m/z 515.5 (M+H)⁺. 1H NMR (400 MHz, MeOD) δ ppm 1.56-1.70 (m, 1H) 1.77-2.09 (m, 2H) 1.85-1.86 (m, 3H) 2.12-2.34 (m, 3H) 2.63-3.02 (m, 4H) 3.03-3.11 (m, 2H) 3.13 (d, J=7.26 Hz, 2H) 3.15-3.27 (m, 3H) 3.29 (s, 1H) 3.36-3.51 (m, 3H) 3.67-4.29 (m, 4H) 4.50-4.72 (m, 1H) 7.39-7.44 (m, 2H) 7.49 (ddd, J=9.32, 6.06, 2.81Hz, 3H) 7.56 (d, 0.7=8.65 Hz, 1H) 7.69-7.74 (m, 1H) 7.79-7.94 (m, 3H).

Step B.

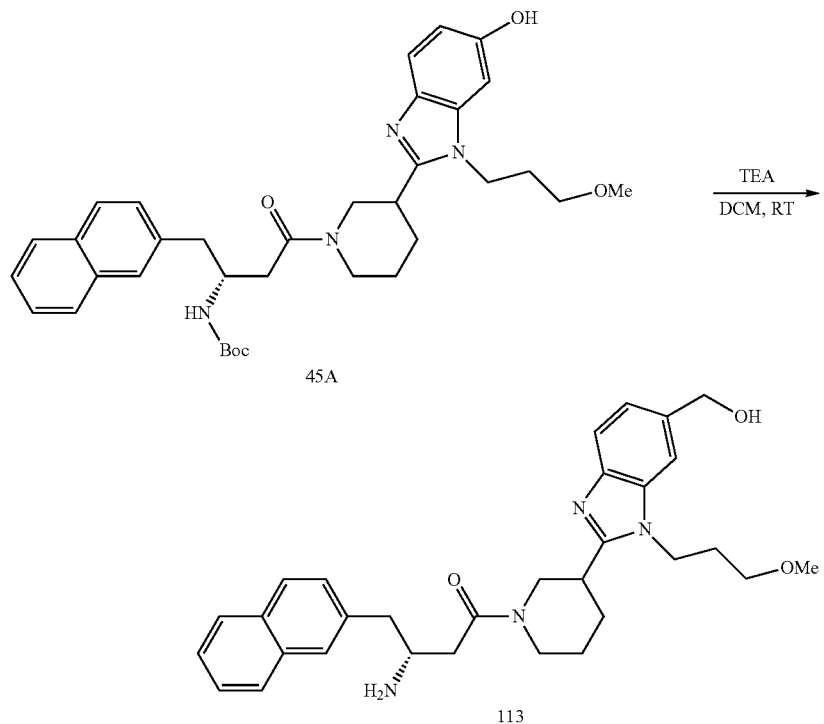

tert-Butyl (2R)-4-(3-(6-(hydroxymethyl)-1-(3-methoxypropyl)-1H-benzo[d]imidazol-2-yl)piperidin-1-yl)-1-(naphthalen-2-yl)-4-oxobutan-2-ylcarbamate (45A) (0.20 mmol, 120 mg) in DCM (10 mL) was added TEA (2 mL). The reaction solution was stirred at rt for 1 hr and then concentrated in vacuo. The residue was purified by preparative LC/MS (5-45% CH₃CN in H₂O) to afford (3R)-3-amino-1-(3-(6-(hydroxymethyl)-1-(3-methoxypropyl)-1H-benzo[d]

Example 46

Synthesis of (R)-3-amino-1-((R)-3-(1-(3-methoxypropyl)-6-nitro-1H-benzo[d]imidazol-2-yl)piperidin-1-yl)-4-(naphthalen-2-yl)butan-1-one (114) and (R)-3-amino-1-((R)-3-(1-(3-methoxypropyl)-7-nitro-1H-benzo[d]imidazol-2-yl)piperidin-1-yl)-4-(naphthalen-2-yl)butan-1-one (115)

Step A.

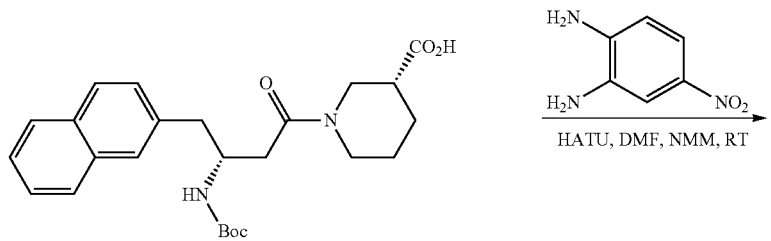

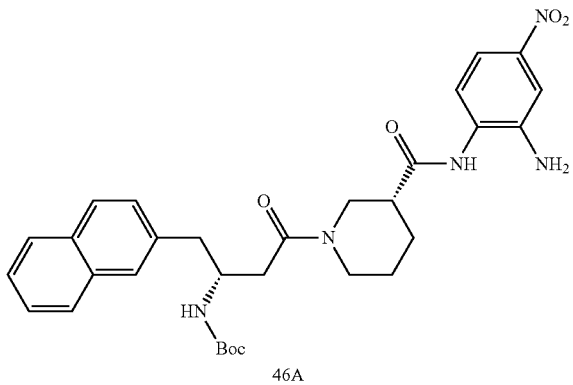

46A (R)-1-((R)-3-(tert-Butoxycarbonylamino)-4-(naphthalen-2-yl)butanoyl)piperidine-3-carboxylic acid (0.454 mmol, 200 mg) in DMF (15 mL) was added 4-nitrobenzene-1,2-diamine (0.454 mmol, 77 mg) and N-methylmorpholine (1.36 mmol, 0.15 mL). The reaction mixture was stirred at rt for 5 min and then added HATU (0.50 mmol, 190 mg) and kept stirred at rt overnight. The reaction mixture was poured into $H_2O$, extracted with EtOAc. The extract was washed with $H_2O$, $NaHCO_3$, brine, dried over $MgSO_4$ and filtered. The filtrate containing tert-Butyl (R)-4-((R)-3-(2-amino-4-nitrophenylcarbamoyl)piperidin-1-yl)-1-(naphthalen-2-yl)-4-oxobutan-2-ylcarbamate (46A) was concentrated in vacuo and carried directly on to the next step without further purification. ESI-MS: m/z 576.4 $(M+H)^+$.

Step B.

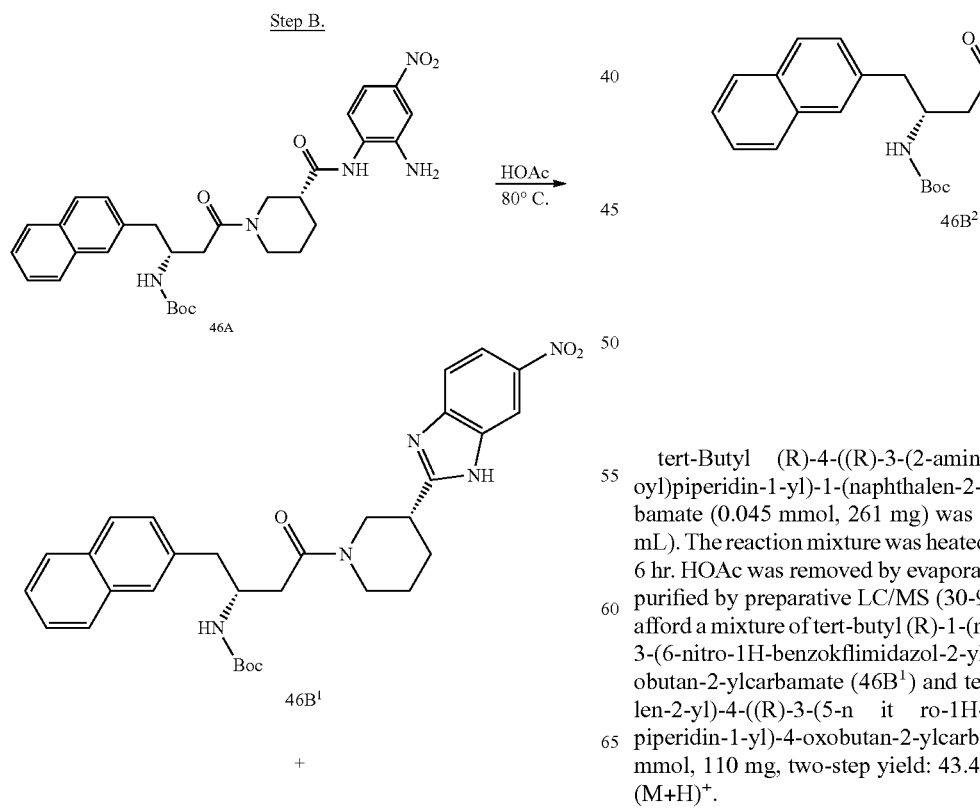

tert-Butyl (R)-4-((R)-3-(2-amino-4-nitrophenylcarbamoyl)piperidin-1-yl)-1-(naphthalen-2-yl)-4-oxobutan-2-ylcarbamate (0.045 mmol, 261 mg) was added HOAc (glacial, 4 mL). The reaction mixture was heated to 80° C. and stirred for 6 hr. HOAc was removed by evaporation and the residue was purified by preparative LC/MS (30-90% $CH_3CN$ in $H_2O$) to afford a mixture of tert-butyl (R)-1-(naphthalen-2-yl)-4-((R)-3-(6-nitro-1H-benzo[d]imidazol-2-yl)piperidin-1-yl)-4-oxobutan-2-ylcarbamate ($46B^1$) and ten-butyl (R)-1-(naphthalen-2-yl)-4-((R)-3-(5-nitro-1H-benzo[d]imidazol-2-yl)piperidin-1-yl)-4-oxobutan-2-ylcarbamate ($46B^2$) (0.197 mmol, 110 mg, two-step yield: 43.4%). ESI-MS: m/z 558.5 $(M+H)^+$.

Step C.
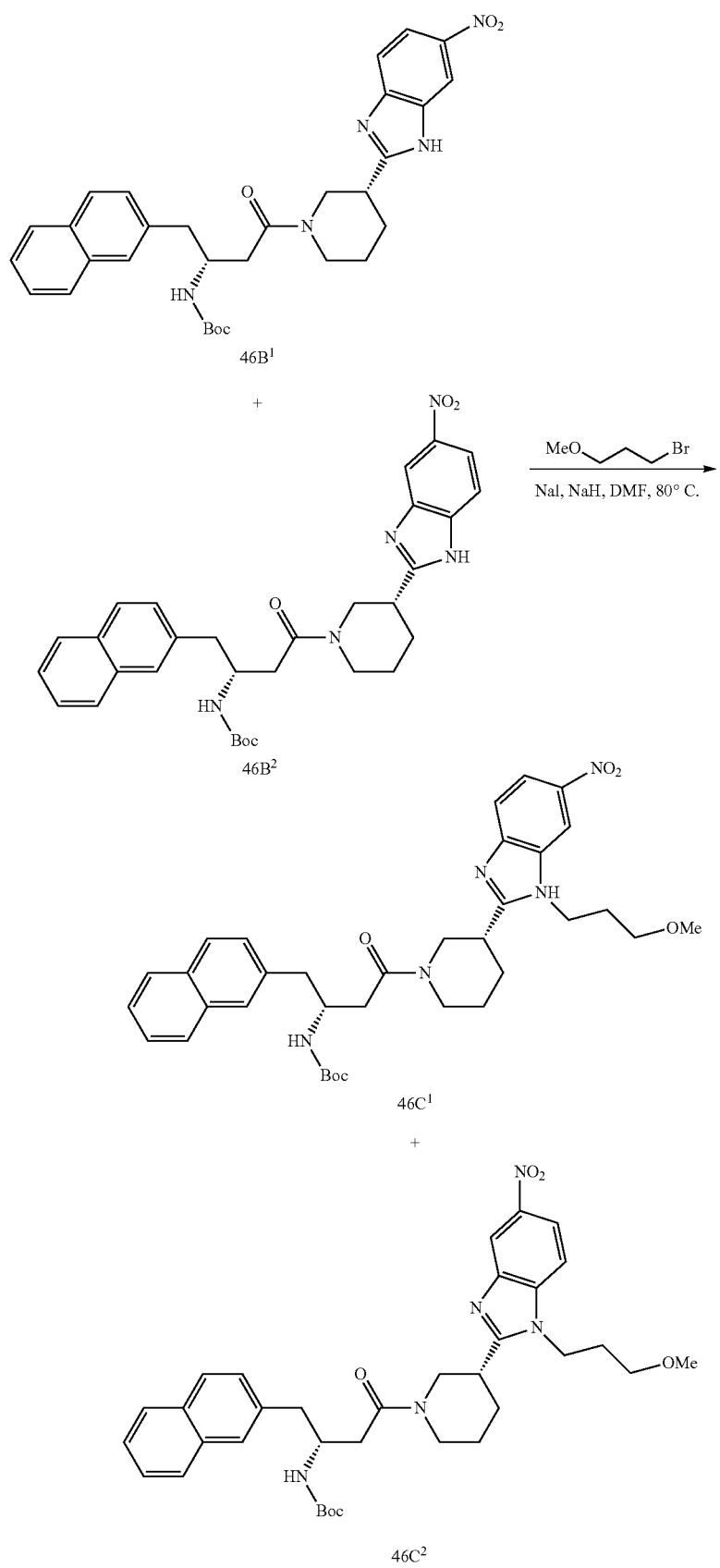

The mixture of tert-butyl (R)-1-(naphthalen-2-yl)-4-((R)-3-(6-nitro-1H-benzo[d]imidazol-2-yl)piperidin-1-yl)-4-oxobutan-2-ylcarbamate (46B¹) and tert-butyl (R)-1-(naphthalen-2-yl)-4-((R)-3-(5-nitro-1H-benzo[d]imidazol-2-yl)piperidin-1-yl)-4-oxobutan-2-ylcarbamate (46B²) (0.20 mmol, 110 mg) in DMF (15 mL) was added NaI (0.22 mmol, 33 mg). The reaction solution was stirred at 0° C. for 5 min and then added NaH (0.26 mmol, 10 mg) at 0° C. The reaction solution was stirred at 0° C. for 30 min and then added 1-bromo-3-methoxypropane (0.26 mmol, 39 mg). The reaction solution was heated to 80° C. and kept stirring at 80° C. for 4 hrs. After cooling down the reaction solution was poured into 1120, extracted with EtOAc. The extract was washed with H₂O, brine dried over MgSO₄ and filtered. The filtrate containing tert-butyl (R)-4-((R)-3-(1-(3-methoxypropyl)-6-nitro-1H-benzo[d]imidazol-2-yl)piperidin-1-yl)-1-(naphthalen-2-yl)-4-oxobutan-2-ylcarbamate (46C¹) and tart-butyl (R)-4-((R)-3-(1-(3-methoxypropyl)-5-nitro-1H-benzo[d]imidazol-2-yl)piperidin-1-yl)-1-(naphthalen-2-yl)-4-oxobutan-2-ylcarbamate (46C²) was concentrated in vacuo and carried directly on to the next step without further purification. EST-MS: m/z 630.5 (M+H)⁺.

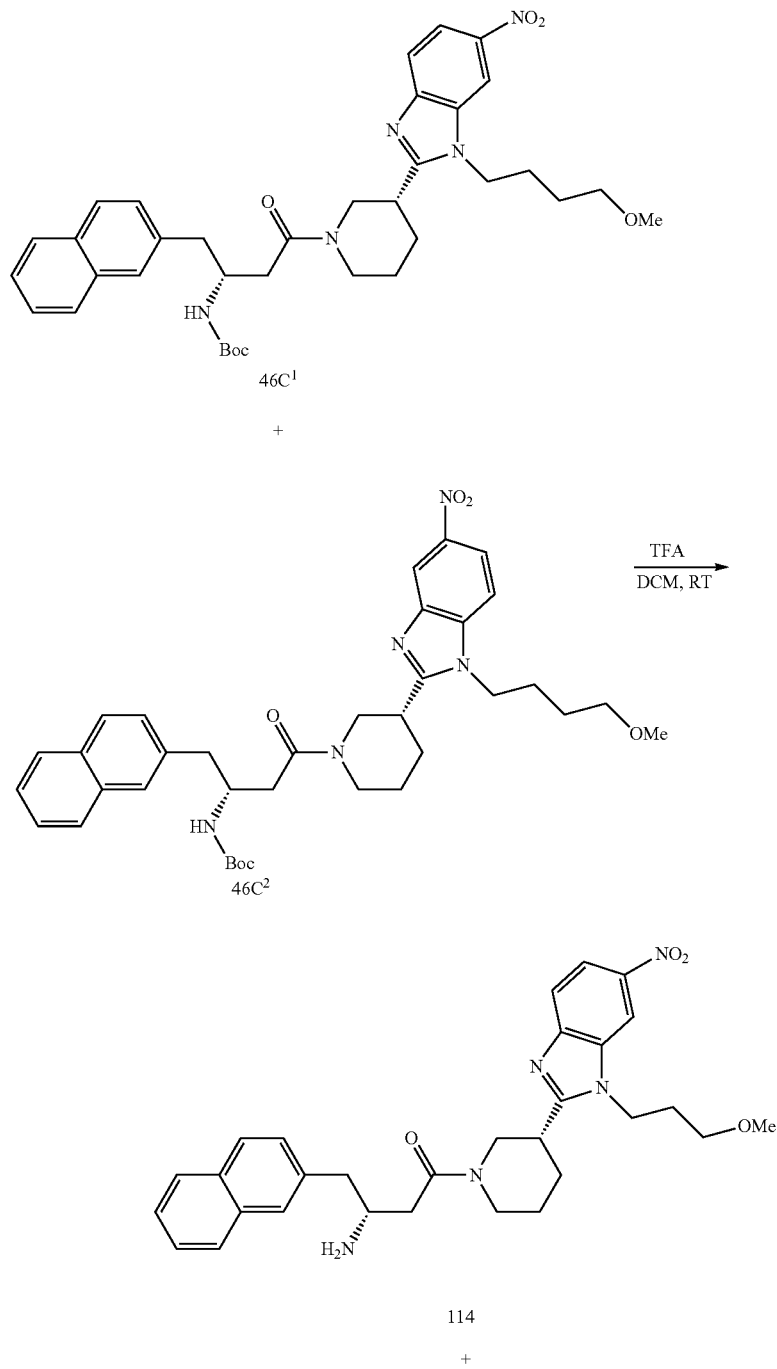

Step D.

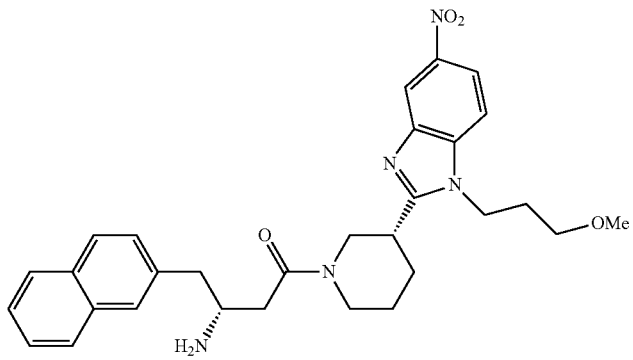

115

A mixture of tert-butyl (R)-4-((R)-3-(1-(3-methoxypropyl)-6-nitro-1H-benzo[d]imidazol-2-yl)piperidin-1-yl)-1-(naphthalen-2-yl)-4-oxobutan-2-ylcarbamate (46C) and tert-butyl (R)-4-((R)-3-(1-(3-methoxypropyl)-5-nitro-1H-benzoicijimidazol-2-yl)piperidin-1-yl)-1-(naphthalen-2-yl)-4-oxobutan-2-ylcarbamate (46C²) (0.20 mmol, 124 mg) in DCM (10 mL) was added TEA (2 mL). The reaction solution was stirred at rt for 1 hr and then concentrated in vacuo.

The residue was separated by preparative LC/MS (35-60% CH₃CN in H₂O) to afford the two regioisomers:

Compound 114: (R)-3-amino-1-((R)-3-(1-(3-methoxypropyl)-6-nitro-1H-benzo[d]imidazol-2-yl)piperidin-1-yl)-4-(naphthalen-2-yl)butan-1-one (0.028 mmol, 15 mg, yield: 14.0%). ESI-MS: m/z 530.5 (M+H)⁺. 1H NMR (400 MHz, MeOD) δ ppm 1.35-1.70 (m, 1H) 1.71-1.90 (m, 1H) 1.91-2.08 (m, 4H) 2.19-2.32 (m, 2H) 2.66-3.08 (m, 4H) 3.08-3.20 (m, 4H) 3.20-3.28 (m, 4H) 3.33-3.46-3.51 (m, 3H) 3.62-4.07 (m, 2H) 4.11-4.36 (m, 1H) 7.34-7.45 (m, 2H) 7.46-7.56 (m, 1H) 7.64-7.74 (m, 1H) 7.78 (t, J=6.51Hz, 2H) 7.83-7.93 (m, 2H) 8.08-8.25 (m, 1H) 8.33-8.53 (m, 1H).

Compound 115: (R)-3-arni no-1-((R)-3-(1-(3-methoxypropyl)-5-nitro-1H-benzo[d]imidazol-2-yl)piperidin-1-yl)-4-(naphthalen-2-yl)butan-1-one (115) (0.043 mmol, 23 mg, yield: 21.5%). ESI-MS: m/z 530.5 (M+H)⁺. 1H NMR (400 MHz, MeOD) δ ppm 1.50-1.69 (m, 1H) 1.72-2.29 (m, 4H) 2.55-2.95 (m, 4H) 2.95-3.13 (m, 4H) 3.14-3.27 (m, 4H) 3.34-3.67 (m, 3H) 3.77-4.07 (m, 2H) 4.09-4.32 (m, 1H) 4.36-4.76 (m, 2H) 7.30-7.60 (m, 2H) 7.63-7.82 (m, 3H) 7.82-7.94 (m, 3H) 7.95-8.33 (m, 1H) 8.42-8.62 (m, 1H).

Example 47

Synthesis of (R)-3-amino-1((R)-3-(6-isopropyl-1-(3-methoxypropyl)-1H-benzo[d]imidazol-2-yl)piperidin-yl)-4-(naphthalen-2-yl)butan-1-one (116) and (R)-3-amino-1((R)-3-(5-isopropyl-1-(3-methoxypropyl)-1H-benzo[d]imidazol-2-yl)piperidin-1-yl)-4-(naphthalen-2-yl)butan-1-one (117)

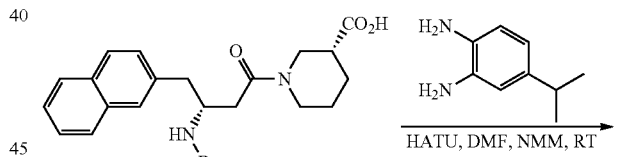

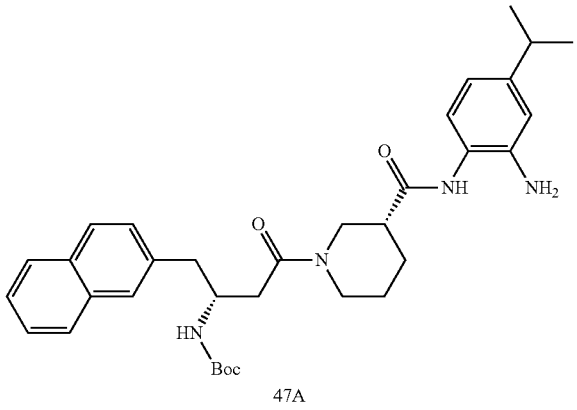

47A (R)-1((R)-3-(tert-butoxycarbonylamino)-4-(naphthalen-2-yl)butanoyl)piperidine-3-carboxylic acid (0.454 mmol, 200 mg) in DMF (15 mL) was added 4-isopropylbenzene-1,2-diamine (0.454 mmol, 68 mg) and N-methylmorpholine (1.36 mmol, 0.15 mL). The reaction mixture was stirred at rt for 5 min and then added HATU (0.50 mmol, 190 mg) and kept stirring at rt overnight. The reaction mixture was poured into H₂O, extracted with EtOAc. The extract was washed with H₂O, NaHCO₃, brine, dried over MgSO₄ and filtered. The filtrate containing Cert-butyl (R)-4-((R)-3-(2-amino-4-isopropylphenylcarbamoyl)piperidin-1-yl)-1-(naphthalen-2-yl)-4-oxobutan-2-ylcarbamate (47A) was concentrated in vacuo and carried directly on to the next step without further purification. ESI-MS: m/z 573.5 (M+H)⁺.

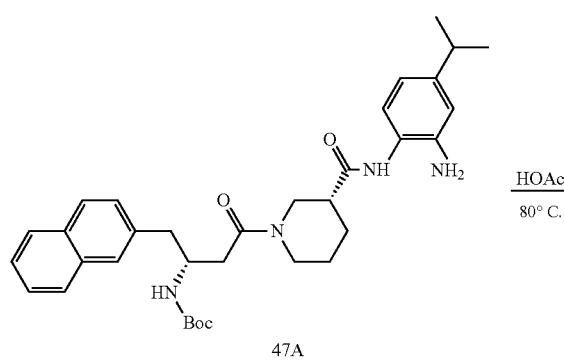

47A

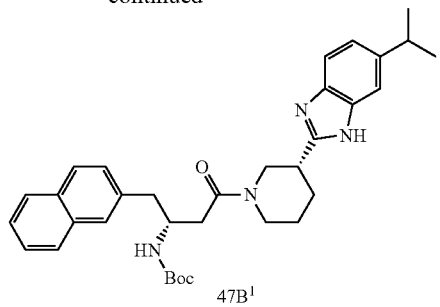

47B¹

+

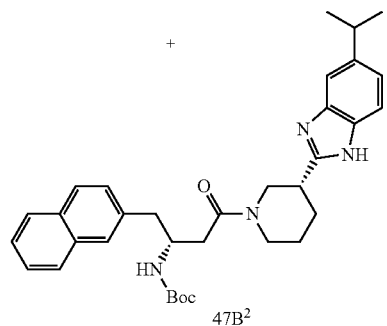

47B²

47A (0.454 mmol, 260 mg) was added HOAc (glacial, 4 mL). The reaction mixture was heated to 80° C. and stirred for 6 hr. HOAc was removed by evaporation and the residue was purified by preparative LC/MS (40-90% CH₃CN in H₂O) to afford a mixture of tert-butyl (R)-4-((R)-3-(6-isopropyl-1H-benzo[d]imidazol-2-yl)piperidin-1-yl)-1-(naphthalen-2-yl)-4-oxobutan-2-ylcarbamate (47B¹) and tert-butyl (R)-4-((R)-3-(5-isopropyl-1H-benzo[d]imidazol-2-yl)piperidin-1-yl-1-(naphthalen-2-yl-4-oxobutan-2-ylcarbamate (47B²) (0.09 mmol, 50 mg, two-step yield: 19.8%). EST-MS: nilz 555.5 (M+H)⁺.

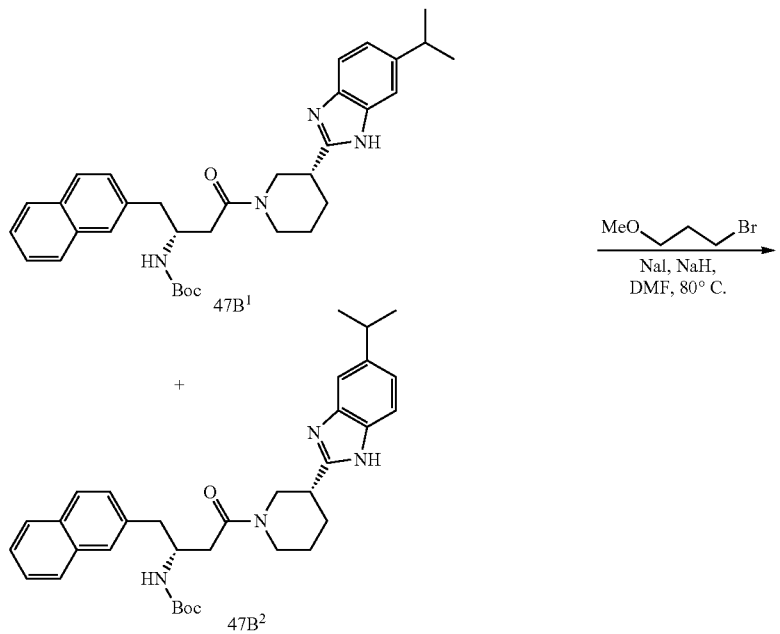

-continued

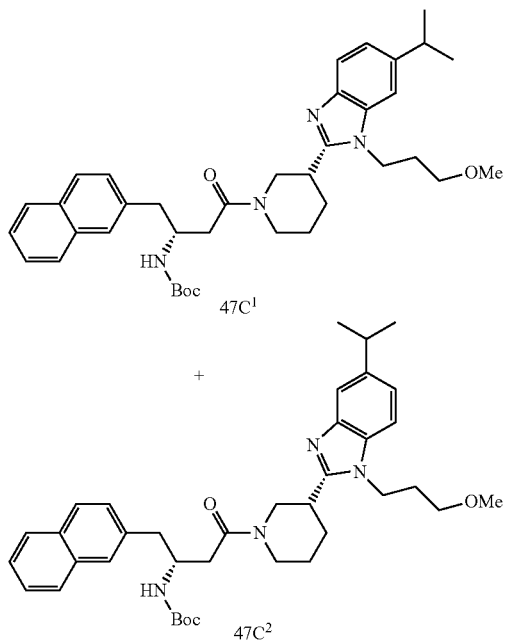

To a mixture of 478¹ and 47B² (0.09 mmol, 50 mg) in DMF (10 mL) was added NaI (0.10 mmol, 15 mg). The reaction solution was stirred at 0° C. for 5 min and then added NaH (0.12 mmol, 3 mg) at 0° C. The reaction solution was stirred at 0° C. for 30 min and then added 1-bromo-3-methoxypropane (0.12 mmol, 18 mg). The reaction solution was heated to 80° C. and kept stirring at 80° C. for 4 hrs. After cooling down the reaction solution was poured into H$_2$O, extracted with EtOAc. The extract was washed with H$_2$O, brine dried over MgSO$_4$ and filtered. The filtrate containing Step C. tert-butyl (R)-4-((R)-3-(6-isopropyl-1-(3-methoxypropyl)-1H-benzo[d]imidazol-2-yl)piperidin-1-yl)-1-(naphthalen-2-yl)-4-oxobutan-2-ylcarbamate (47C¹) and tert-butyl (R)-4-((R)-3-(5-isopropyl-1-(3-methoxypropyl)-1,1-benzo[d]imidazol-2-yl)piperidin-1-yl)-1-(naphthalen-2-yl)-4-oxobutan-2-ylcarbamate (47C²) was concentrated in vacuo and carried directly on to the next step without further purification. ESI-MS: m/z 627.6 (M+H)$^+$.

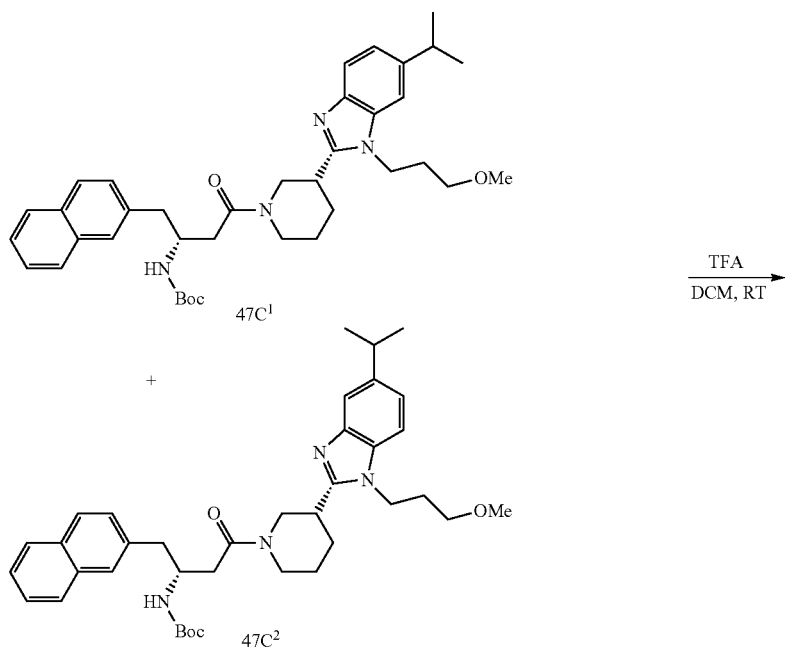

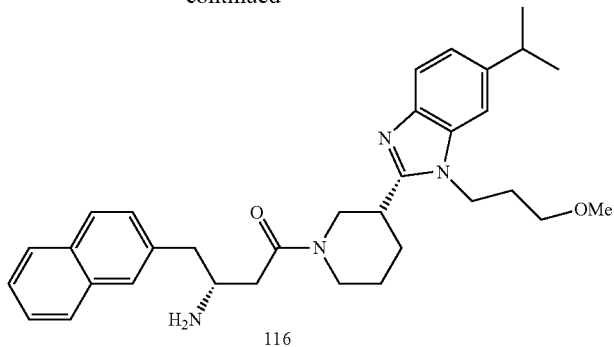

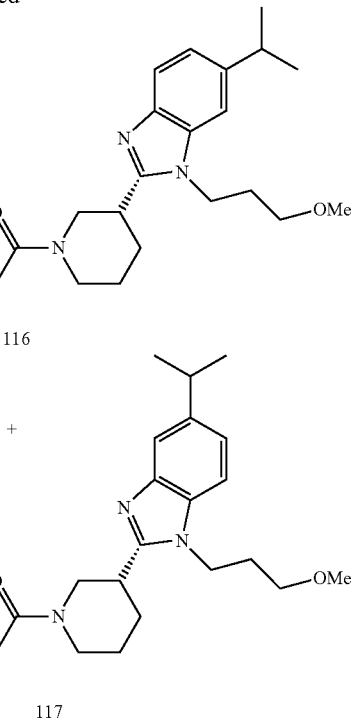

A mixture of 47C¹ and 47C² (0.09 mmol, 56 mg) in DCM (10 mL) was added TEA (2 mL). The reaction solution was stirred at rt for 1 hr and then concentrated in vacuo. The residue was purified by preparative LC/MS (35-60% $CH_3CN$ in $H_2O$) to afford a mixture of (R)-3-amino-1-((R)-3-(6-isopropyl-1-(3-methoxypropyl)-1H-benzo[d]imidazol-2-yl)piperidin-1-yl)-4-(naphthalen-2-yl)butan-1-one (116) and (R)-3-amino-1-((R)-3-(5-isopropyl-1-(3-methoxypropyl)-1H-benz olagimidazol-2-yl)piperidin-1-yl)-4-(naphthalen-2-yl) butan-1-one (117) (0.059 mmol, 31 mg, two-step: 65.6%). ESI-MS: m/z 527.6 (M+H)⁺.

Example 48

Synthesis of (R)-3-amino-4-(biphenyl-4-yl)-1-((R)-3-(4-chloro-1-(3-methoxypropyl)-1H-benzo[d]imidazol-2-yl)piperidin-1-yl)butan-1-one (118)

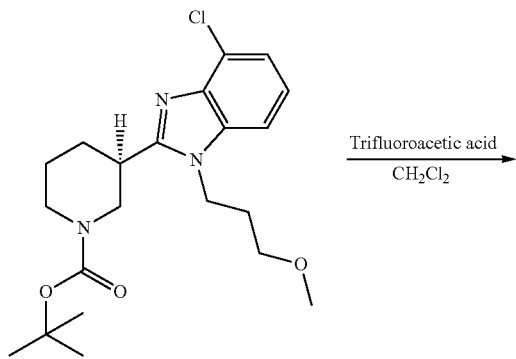 → Trifluoroacetic acid / $CH_2Cl_2$

-continued

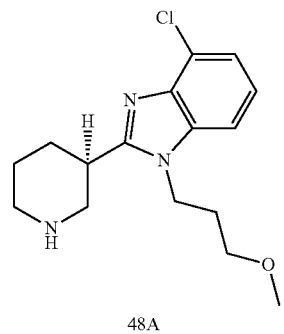

48A (R)-tert-Butyl3-(4-chloro-1-(3-methoxypropyl)-1H-benzo[d]imidazol-2-yl)piperidine-1-carboxylate (0.245 mmol, 0.100 g) was added to a 10 mL round-bottomed flask equipped for stirring under nitrogen. Dichloromethane (1 mL) and trifluoroacetic acid (1 mL) were then added and the resultant solution was allowed to stir under nitrogen for 4 hr. The reaction was then concentrated and dried in-vacuo affording (R)-4-chloro-1-(3-methoxypropyl)-2-(piperidin-3-yl)-1H-benzo[d]imidazole (48A) as a light brown oil that was used without further purification. ESI-MS: m/z 308.2 (M+H)⁺.

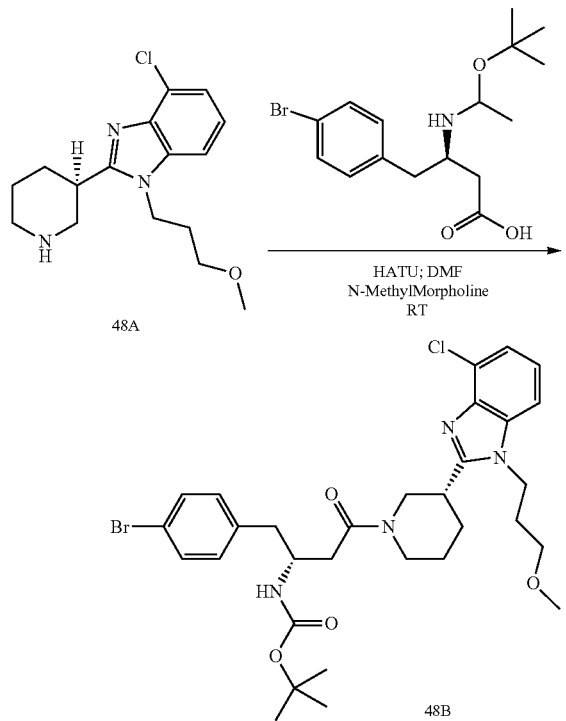

(R)-4-chloro-1-(3-methoxypropyl)-2-(piperidin-3-yl)-1H-benzo[d]imidazole (0.245 mmol, crude oil) (48A) was added to a 15 mL round-bottomed flask equipped for stirring under nitrogen. DMF (2 mL), (R)-4-(4-bromophenyl)-3-(tert-butoxycarbonylamino)butanoic acid (0.319 mmol, 0.082 g) and N-methylmorpholine (1.47 mmol, 0.162 mL) were then added and the solution was allowed to stir at rt for 5 min. HATU (0.319 mmol, 0.121 g) was added and the resultant solution was stirred at room temperature for 3 hr. The reaction solution was then directly purified by preparative LC/MS (25-85% CH$_3$CN in H$_2$O). The resultant fractions were collected and the solvent was removed in-vacuo affording tert-Butyl (R)-1-(4-bromophenyl)-4-((R)-3-(4-chloro-1-(3-methoxypropyl)-1H-benzo[d]imidazol-2-yl)piperidin-1-yl)-4-oxobutan-2-ylcarbamate (48B) as a clear oil which was used without further quantification. ESI-ESI-MS: m/z 647.3 (M+H)$^+$.

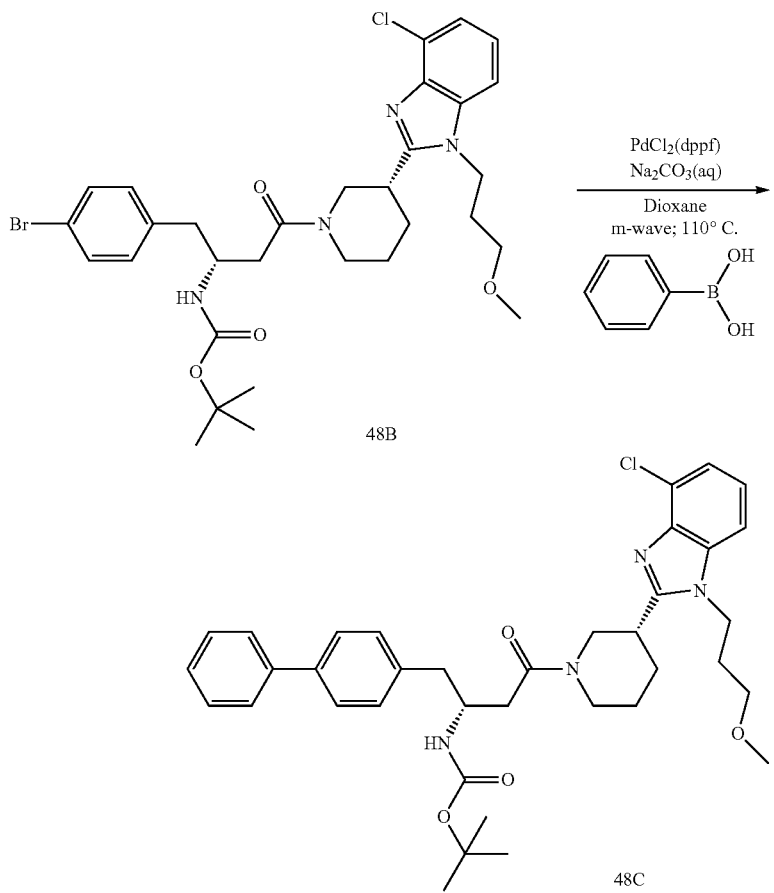

tert-Butyl (R)-1-(4-bromophenyl)-4-((R)-3-(4-chloro-1-(3-methoxypropyl)-1H-benzo[d]imidazol-2-yl)piperidin-1-yl)-4-oxobutan-2-ylcarbamate (48B) (0.245 mmol, crude oil) and phenylboronic acid (0.294 mmol, 0.036 g) were added to a 5 mL microwave vessel equipped with a magnetic stir bar. Dioxane (2 mL) and $Na_2CO_3$ (1 mL of a 2M in aq. soln.) were then added and the reaction vessel was flushed with nitrogen gas. $PdCl_2$(dppf) (0.025 mmol, 0.018 g) was added, the reaction vessel was sealed and placed in a microwave reactor and heated to 110° C. for 15 minutes. The reaction solution was then poured into water, extracted with ethyl acetate, and washed once with saturated aqueous sodium chloride. The organic layer was collected and subsequently dried with anhydrous $Na_2SO_4$ and filtered. This filtrate was collected, concentrated, and dried in-vacuo. This crude material was directly purified by preparative LC/MS (25-85% $CH_3CN$ in $H_2O$). The resultant fractions were collected and the solvent was removed in-vacuo affording tert-butyl (R)-1-(biphenyl-4-yl)-4-((R)-3-(4-chloro-1-(3-methoxypropyl)-1H-benzo[d]imidazol-2-yl)piperidin-1-yl)-4-oxobutan-2-ylcarbamate (48C) as a clear oil. ESI-MS: m/z 645.3 $(M+H)^+$.

tert-Butyl (R)-1-(biphenyl-4-yl)-4-((R)-3-(4-chloro-1-(3-methoxypropyl)-1H-benzo[d]imidazol-2-yl)piperidin-1-yl)-4-oxobutan-2-ylcarbamate (48C) (0.245 mmol, crude oil) was added to a 10 mL round-bottomed flask equipped for stirring under nitrogen. Dichloromethane (2 mL) and trifluoroacetic acid (2 mL) were then added and the solution was stirred at room temperature for 2 hr. The solvent was removed in-vacuo affording a clear colored oil. This oil was re-dissolved in methanol (3 mL), filtered, and then purified by preparative LC/MS (15-65% $CH_3CN$ in $H_2O$). The resultant fractions were collected and the solvent was removed in-vacuo affording a clear colored oil. This oil was re-dissolved in $CH_3CN$ (1 mL) and water (2 mL). The resultant solution was frozen and lyophilized to afford (R)-3-amino-4-(biphenyl-4-yl)-1-((R)-3-(4-chloro-1-(3-methoxypropyl)-1H-benzo[d]imidazol-2-yl)piperidin-1-yl)butan-1-one (118) as its trifluoroacetic acid salt and as a white flocculent solid (0.134 mmol, 0.088 g, 55% yield over 4-steps). ESI-MS: 545.2 m/z $(M+H)^+$. $^1H$ NMR (400 MHz, DMSO-$d_6$) δ ppm 1.40-1.55 (m, 1H) 1.70-2.14 (m, 5H) 2.61-2.87 (m, 3H) 2.87-3.09 (m, 4H) 3.09-3.31 (m, 5H) 3.40-3.85 (m, 2H) 3.95-4.62 (m, 5H) 7.17-7.30 (m, 2H) 7.33-7.42 (m, 3H) 7.42-7.56 (m, 3H) 7.58-7.72 (m, 4H).

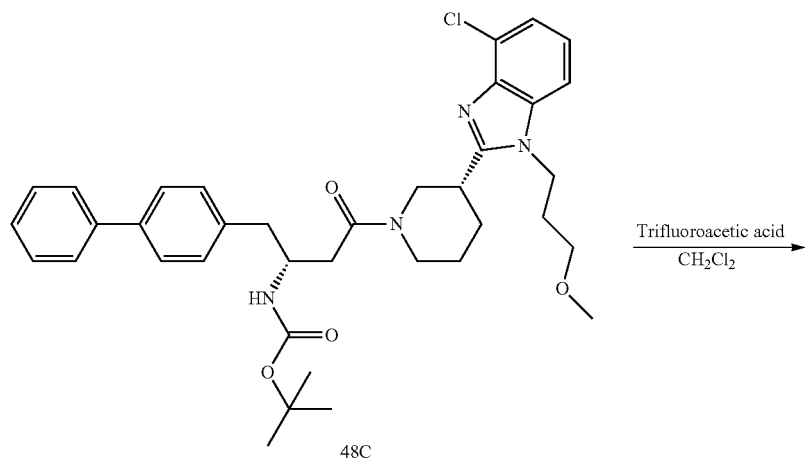

48C

Trifluoroacetic acid / $CH_2Cl_2$

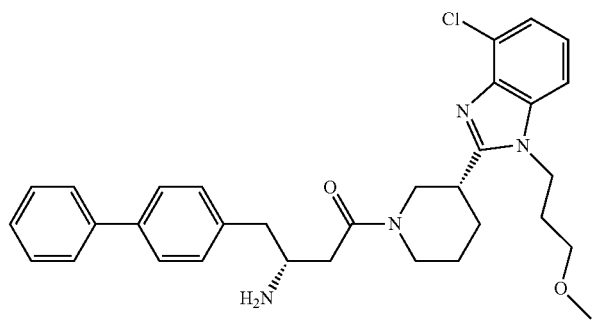

118

Example 49

Synthesis of (S)-3-amino-1((R)-3-(1-(3-methoxypropyl)-1H-benzo[d]imidazol-2-yl)piperidin-1-yl)-3-(pyridin-3-yppropan-1-one (119)

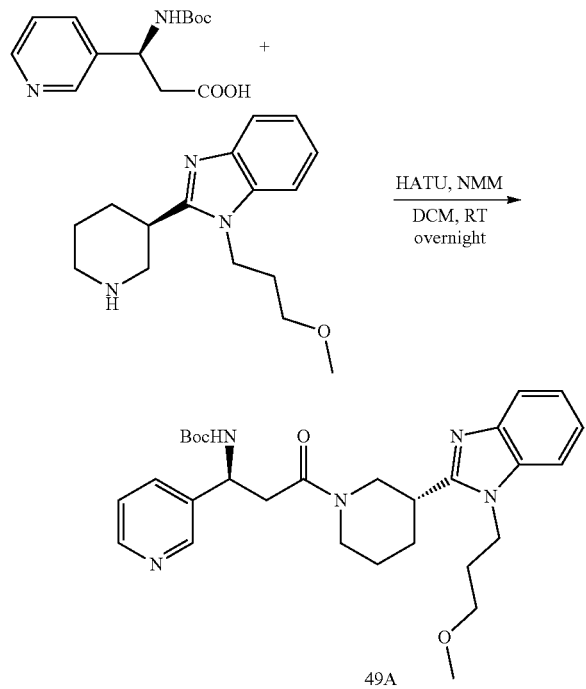

49A

Into a 10 mL round bottomed flask was added (S)-3-(tert-butoxycarbonylamino)-3-(pyridin-3-yl)propanoic acid (63 mg, 238 µmol) and (R)-1-(3-methoxypropyl)-2-(piperidin-3-yl)-1H-benzo[d]imidazole (65 mg, 238 µmol). The mixture was dissolved with dichloromethane (2.5 mL) and N-methylmorpholine (96 mg, 952 µmol) and HATU (160 mg, 262 µmol) were added. The mixture was stirred overnight at room temperature. Solvent was removed under vacuum. The residue containing tert-Butyl(S)-34(R)-3-(1-(3-methoxypropyl)-1,1-benzo[d]imidazol-2-yl)piperidin-1-yl)-3-oxo-1-(pyridin-3-yl)propylcarbamate (49A) was used in the next step without further purification. ESI-MS:mlz 522.5 (M+H)+.

Step B.

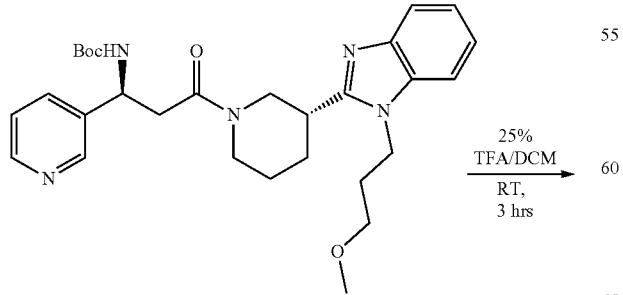

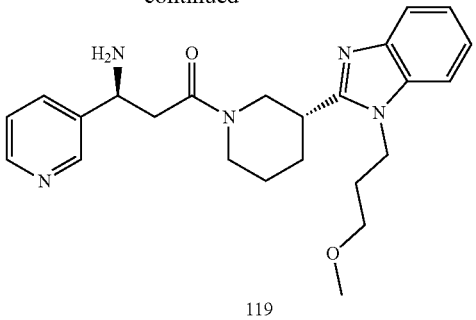

119 tert-Butyl(S)-3-((R)-3-(1-(3-methoxypropyl)-1H-benzo[d]imidazol-2-yl)piperidin-1-yl)-3-oxo-1-(pyridin-3-yepropylcarbamate (49A) was dissolved in 25% trifluoroacetic acid and stirred at room temperature for 3 hr. Solvent was removed under vacuum and purified by preparatory LC/MS (5-25% $CH_3CN$ in $H_2O$) to give (S)-3-amino-1((R)-3-(1-(3-methoxypropyl)-1H-benzo[d]imidazol-2-yl)piperidin-1-yl)-3-(pyridin-3-yl)propan-1-one (119) as a TFA salt (119 mg, 94% yield). 1H NMR (400 MHz, DMSO-$d_6$) δ ppm 1.39-1.67 (m, 1 H) 1.77-2.22 (m, 5H) 2.69 (s, 1H) 2.87-3.57 (m, 8H) 3.96 (s, 1H) 4.16-4.67 (m, 4H) 4.77 (br. s., 1H) 7.43-7.65 (m, 3H) 7.74-7.89 (m, 2H) 7.97-8.12 (m, 1H) 8.56-8.91 (m, 2H). ESI-MS:m/z 422.4 (M+H)+.

Example 50

Synthesis of (S)-3-amino-1((R)-3-(1-(3-methoxypropyl)-1H-benzo[d]imidazol-2-yl)piperidin-1-yl)-3-(4-methoxypyridin-3-yppropan-1-one (120)

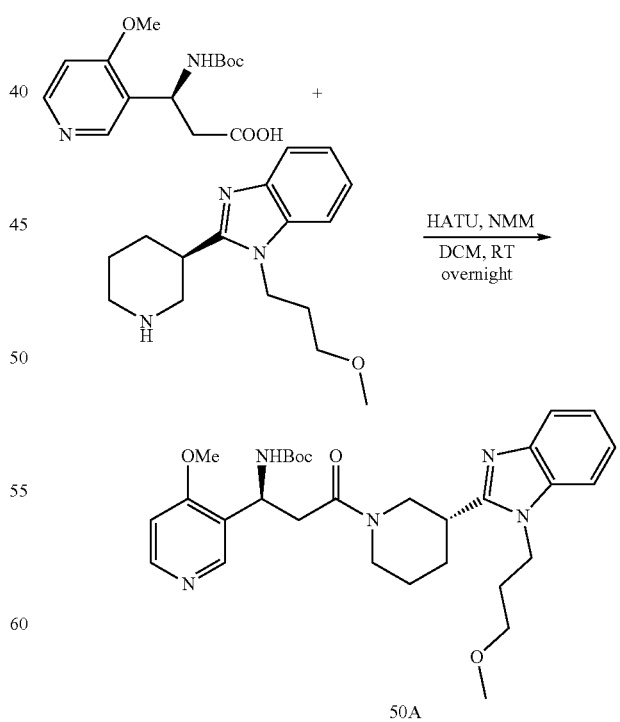

50A tert-Butyl(S)-3-((R)-3-(1-(3-methoxypropyl)-1H-benzo[d]imidazol-2-yl)piperidin-1-yl)-1-(4-methoxypyridin-3- yl)-3-oxopropylcarbamate (50A) was prepared as described for Example 49, Step A. ESI-MS:m/z 552.5 (M+H)⁺.

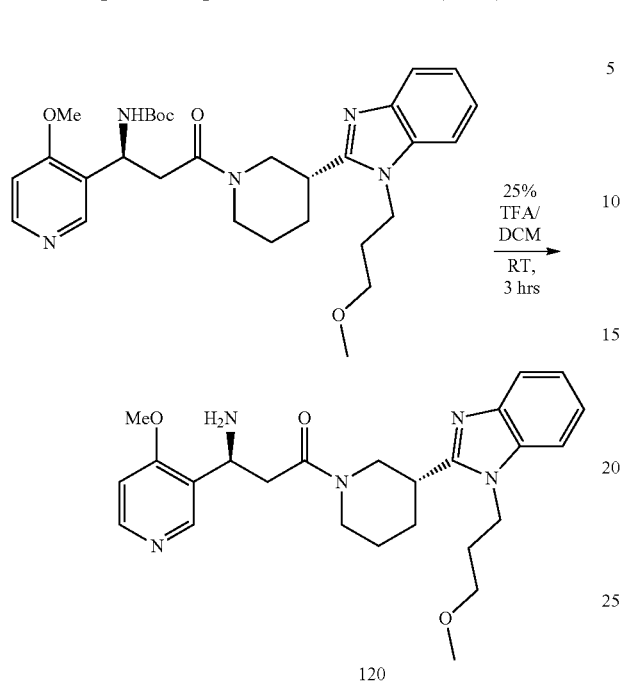

120

(S)-3-Amino-1((R)-3-(1-(3-methoxypropyl)-1H-benzo[d]imidazol-2-yl)piperidin-1-yl)-3-(4-methoxypyridin-3-yl)propan-1-one (120) was prepared as described for Example 49, Step B and was purified by preparatory LC/MS (10-25% CH₃CN in H₂O) to give the product as a TFA salt (108 mg, 80% yield). 1H NMR (400 MHz, DMSO-$d_6$) δ ppm 1.42-1.67 (m, 1H) 1.78-2.23 (m, 5H) 2.62-3.20 (m, 7H) 3.22-3.38 (m, 2H) 3.48 (m, 1H) 3.84 (m, 3H) 3.96 (s, 1H) 4.19-4.73 (m, 4H) 6.88 (m, 1H) 7.49 (m, 2H) 7.74-7.92 (m, 3H) 8.28-8.32 (m, 1H). ESI-MS:m/z 452.4 (M+H)⁺.

Example 51

Synthesis of (S)-3-amino-3-(3-methoxyphenyl)-1-(R)-3-(1-(3-methoxypropyl)-1H-benzo[d]imidazol-2-yl)piperidine-1-yppropan-1-one (121)

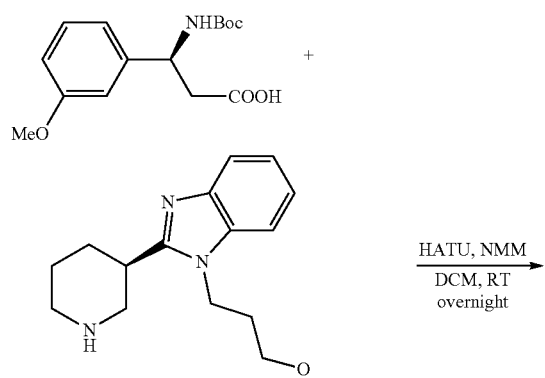

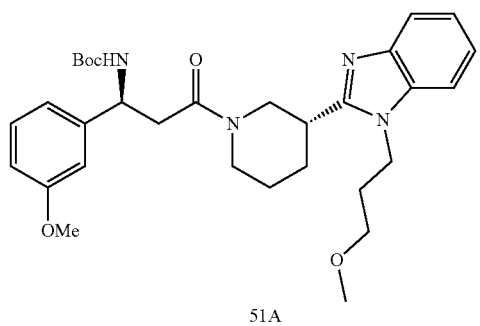

51A tert-Butyl(S)-1-(3-methoxyphenyl)-3-((R)-3-(1-(3-methoxypropyl)-1H-benzo[d]imidazol-2-yl)piperidin-1-yl)-3-oxopropylcarbamate (51A) was prepared as described for Example 49, Step A. ESI-MS:m/z 551.5 (M+H)⁺.

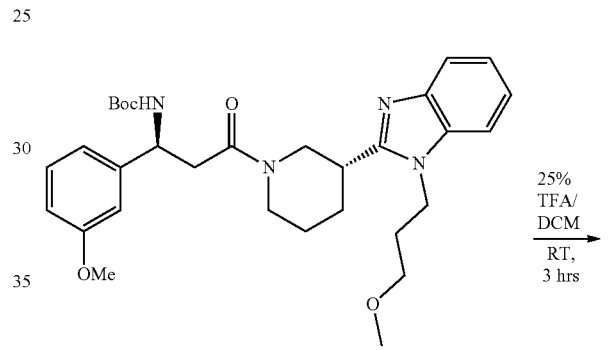

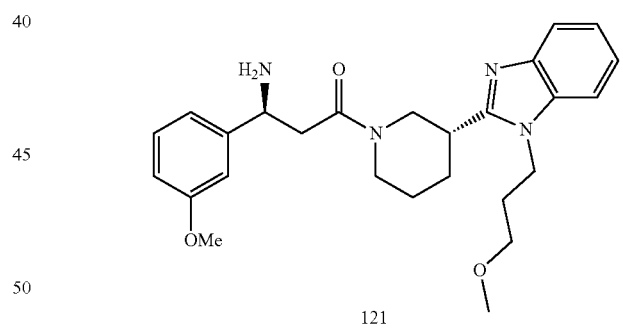

121

(S)-3-Amino-3-(3-methoxyphenyl)-1-((R)-3-(1-(3-methoxypropyl)-1H-benzo[d]imidazol-2-yl)piperidin-1-yppropan-1-one (121) was prepared as described for Example 49, Step B and was purified by preparatory LC/MS (15-25% CH₃CN in H₂O) to give the product as a TFA salt (111 mg, 83% yield). 1H NMR (400 MHz, DMSO-$d_6$) δ ppm 1.42-1.64 (m, 1 H) 1.79-2.20 (m, 5H) 2.62-3.25 (m, 7H) 3.25-3.37 (m, 2H) 3.49 (m, 1H) 3.72-3.80 (m, 3H) 3.89-4.25 (m, 1H) 4.34-4.69 (m, 4H) 6.95 (m, 1H) 7.02-7.16 (m, 2H) 7.28-7.37 (m, 1H) 7.42-7.52 (m, 2H) 7.73-7.84 (m, 2H). ESI-MS:m/z 451.4 (M+H)⁺.

Example 52

Synthesis of (R)-3-amino-4-(biphenyl-3-yl)-1-((R)-3-(1-(3-methoxypropyl)-1H-benzo[d]imidazol-2-yl)piperidin-1-yl)butan-1-one (122)

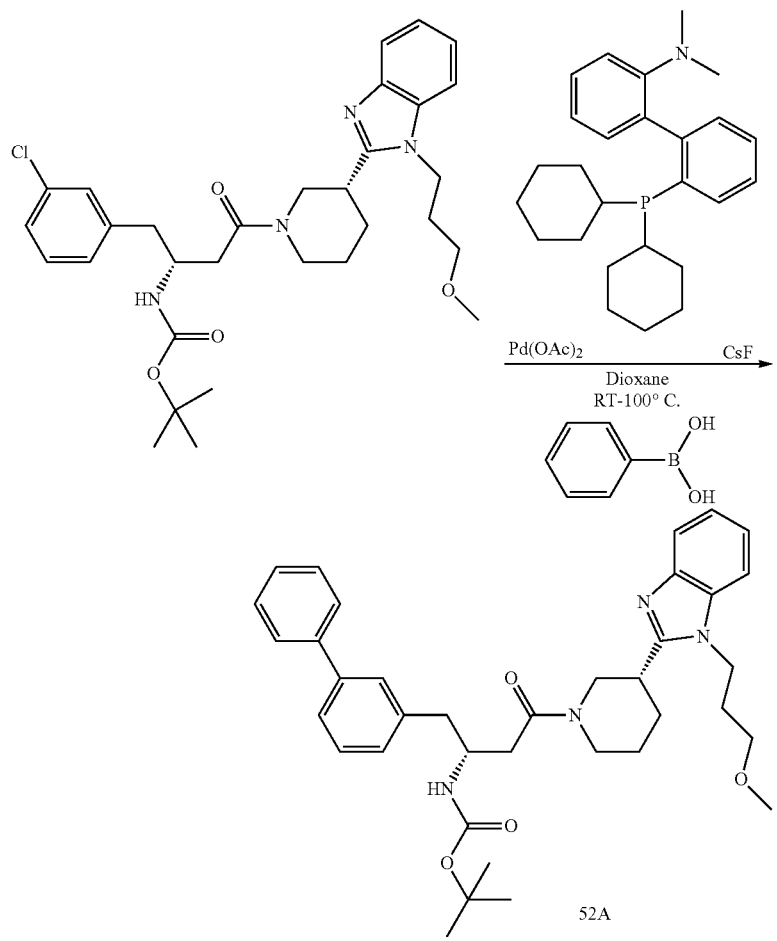

tert-Butyl (R)-1-(3-chlorophenyl)-4-((R)-3-(1-(3-methoxypropyl)-1,1-benzo[d]imidazol-2-yl)piperidin-1-yl)-4-oxobutan-2-ylcarbamate (0.105 mmol, 0.060 g), phenylboronic acid (0.158 mmol, 0.019 g), cesium fluoride (0.315 mmol, 0.048 g), 2'-(dicyclohexylphosphino)-N,N-dimethylbiphenyl-2-amine (0.016 mmol, 0.006 g), and dioxane (3 mL) were added to an oven-dried 25 mL Schlenk flask equipped for stirring under nitrogen and under vacuum. Vacuum degassed the solution three times with nitrogen. Added diacetoxypalladium (0.010 mmol, 0.002 g) and vacuum degassed the reaction solution three times with nitrogen and allowed to stir at room temperature under nitrogen for 16 hrs. Heated the reaction to 100° C. and allowed to heat under nitrogen for 72 hrs. The reaction solution was then poured into water, extracted with ethyl acetate, and washed once with saturated aqueous sodium chloride. The organic layer was collected and subsequently dried with anhydrous $Na_2SO_4$ and filtered. This filtrate was collected, concentrated, and dried in-vacuo. This crude material was directly purified by preparative LC/MS (30-80% $CH_3CN$ in $H_2O$). The resultant fractions were collected and the solvent was removed in-vacuo affording tert-butyl (R)-1-(biphenyl-3-yl)-4-((R)-3-(1-(3-methoxypropyl)-1H-benzo[d]imidazol-2-yl)piperidin-1-yl)-4-oxobutan-2-ylcarbamate (52A) as a clear oil. (0.05 mmol, 0.030 g, 47% yield). ESI-MS: m/z 611.3 $(M+H)^+$.

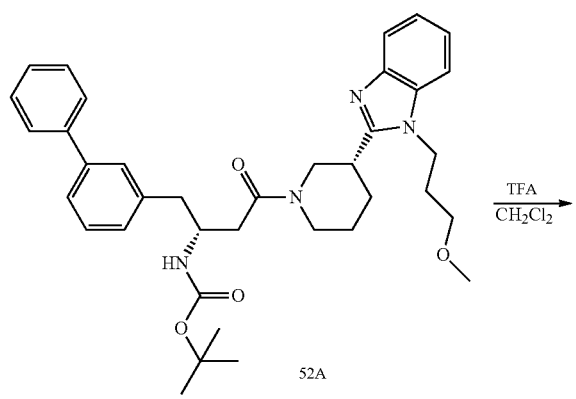

-continued

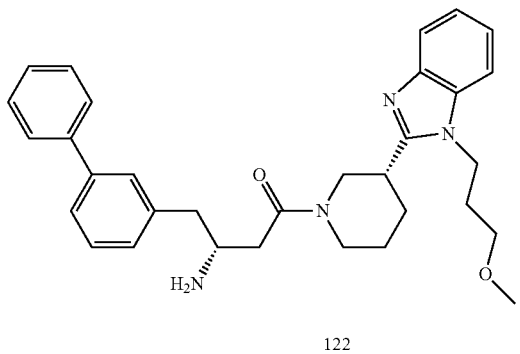

122 tert-Butyl(R)-1-(biphenyl-3-yl)-4-((R)-3-(1-(3-methoxypropyl)-1H-benzo[d]imidazol-2-yl)piperidin-1-yl)-4-oxobutan-2-ylcarbamate (52A) (0.05 mmol, 0.030 g) was weighed into a 20 mL round-bottomed flask equipped for stirring under nitrogen. $CH_2Cl_2$ (1 mL) and trifluoroacetic acid (1 mL) were then added and the solution was stirred at room temperature for 2 hrs. The solvent was removed in-vacuo affording a clear colored oil. This oil was re-dissolved in methanol (3 mL), filtered, and then purified by preparative LC/MS (20-55% $CH_3CN$ in $H_2O$). The resultant fractions were collected and the solvent was removed in-vacuo affording a clear colored oil. This oil was re-dissolved in $CH_3CN$ (1 mL) and water (2 mL). The resultant solution was frozen and lyophilized to afford (R)-3-amino-4-(biphenyl-3-yl)-1-((R)-3-(1-(3-methoxypropyl)-1H-benzo[d]imidazol-2-yl)piperidin-1-yl)butan-1-one (122) as its trifluoroacetic acid salt and as a white flocculent solid (0.021 mmol, 0.013 g, 42% yield). $^1$H NMR (400 MHz, DMSO-$d_5$) δ ppm 1.39-1.58 (m, 1H) 1.73-2.15 (m, 5H) 2.60-2.88 (m, 4H) 2.90-3.13 (m, 4H) 3.15-3.25 (m, 3H) 3.30-3.51 (m, 3H) 4.07-4.32 (m, 2H) 4.34-4.68 (m, 3H) 7.23-7.32 (m, 1H) 7.33-7.52 (m, 6H) 7.54-7.61 (m, 2H) 7.62-7.80 (m, 4H). ESI-MS: m/z 511.2 (M+H)$^+$.

Example 53

Synthesis of Methyl 4'-((R)-2-amino-4-((R)-3-(1-(3-methoxypropyl)-1H-benzo[d]imidazol-2-yl)piperidin-1-yl-4-oxobutyl)biphenyl-4-carboxylate (123)

Step A.

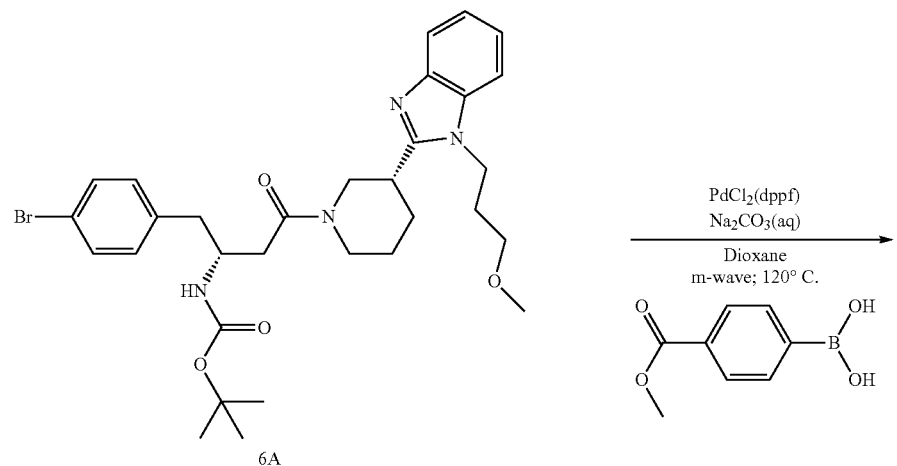

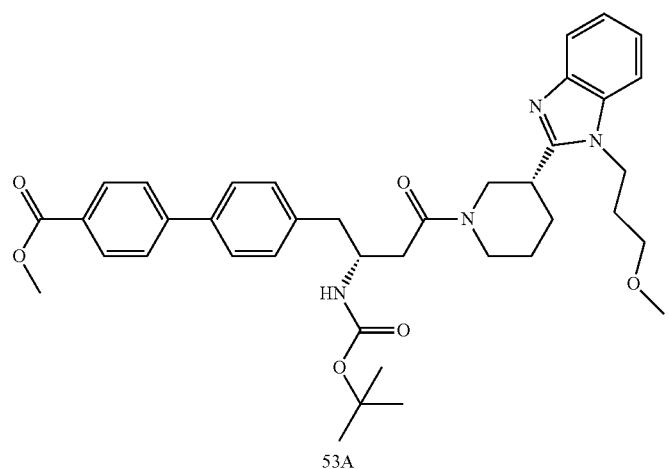

53A tert-Butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (6A) (as prepared in Example 6, Step A) (0.114 mmol, 0.070 g) and 4-(methoxycarbonyl)phenylboronic acid (0.148 mmol, 0.027 g) were added to a 5 mL microwave vessel equipped with a magnetic stir bar. Dioxane (2 mL) and Na₂CO₃ (1 mL of a 2 M aq. soln.) were then added and the reaction vessel was flushed with nitrogen gas. PdCl₂(dppf) (0.006 mmol, 0.004 g) was added, the reaction vessel was sealed and placed in a microwave reactor and heated to 120° C. for 15 minutes. The reaction solution was then poured into water, extracted with ethyl acetate, and washed once with saturated aqueous sodium chloride. The organic layer was collected and subsequently dried with anhydrous Na₂SO₄ and filtered. This filtrate was collected, concentrated, and dried in-vacuo. This crude material was directly purified by preparative LC/MS (25-85% CH₃CN in H₂O). The resultant fractions were collected and the solvent was removed in-vacuo affording methyl 4'-((R)-2-(tert-butoxycarbonylamino)-4-((R)-3-(1-(3-methoxypropyl)-1H-benzo[d]imidazol-2-yl)piperidin-1-yl)-4-oxobutyl)biphenyl-4-carboxylate (53A) as a clear oil. (0.08 mmol, 0.054 g, 70% yield). ESI-MS: m/z 669.4 (M+H)⁺.

Methyl 4'-((R)-2-(tert-butoxycarbonylamino)-4-((R)-3-(1-(3-methoxypropyl)-1H-benzo[d]imidazol-2-yl)piperidin-1-yl)-4-oxobutyl)biphenyl-4-carboxylate (53A) (0.08 mmol, 0.054 g) was weighed into a 20 mL scintillation vial and dissolved in CH₂Cl₂ (2 mL). Trifluoroacetic acid (2 mL) was then added and the solution was stirred at room temperature for 2 hrs. The solvent was removed in-vacuo affording a clear colored oil. This oil was re-dissolved in methanol (3 mL), filtered, and then purified by preparative LC/MS (20-55% CH₃CN in H₂O). The resultant fractions were collected and the solvent was removed in-vacuo affording a clear colored oil. This oil was re-dissolved in CH₃CN (1 mL) and water (2 mL). The resultant solution was frozen and lyophilized to afford methyl 4'-((R)-2-amino-4-((R)-3-(1-(3-methoxypropyl)-1H-benzo[d]imidazol-2-yl)piperidin-1-yl)-4-oxobutyl)biphenyl-4-carboxylate (123) as its trifluoroacetic acid salt and as a white flocculent solid. (0.07 mmol, 0.040 g, 88% yield). 1H NMR (400 MHz, DMSO-d₆) δ ppm 1.40-1.63 (m, 1H) 1.73-2.21 (m, 5H) 2.56-2.87 (m, 3H) 2.91-3.15 (m, 3H) 3.16-3.52 (m, 5H) 3.68-3.92 (m, 4H) 4.05-4.70 (m, 5H) 7.37-7.53 (m, 4H) 7.68-7.87 (m, 6H) 8.02-8.07 (m, 2H). ESI-MS: 569.3 m/z (M+H)⁺.

Other compounds that were prepared according to the general procedure described for Examples 52 or 53 are listed in Table III.

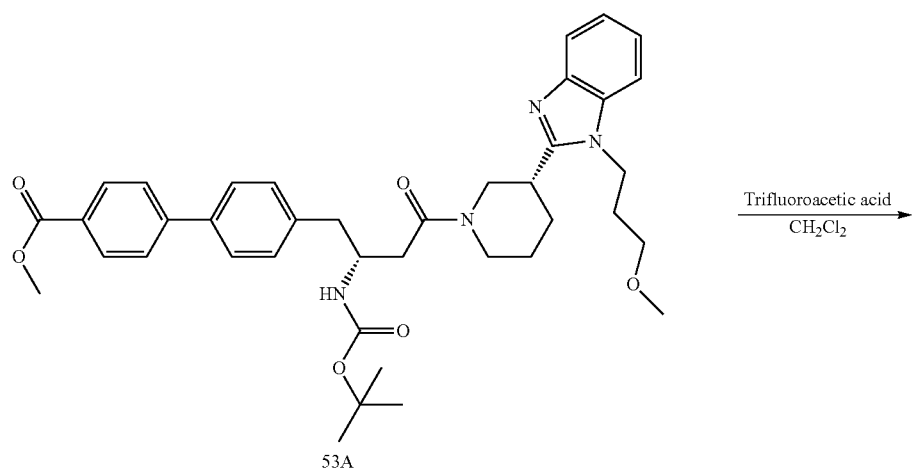

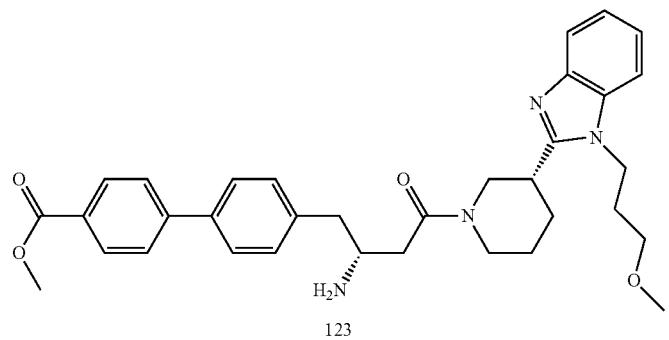

TABLE III

| Compound No. | Structure/Name | Physical Property |
|---|---|---|
| 124 | 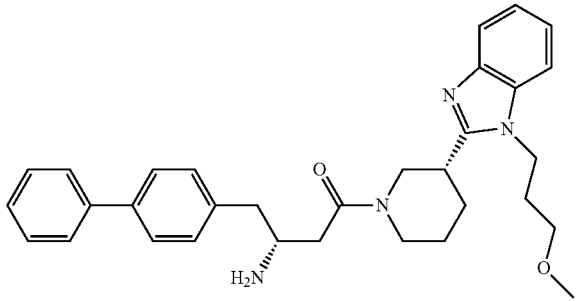<br>(R)-3-amino-4-(biphenyl-4-yl)-1-((R)-3-(1-(3-methoxypropyl)-1H-benzo[d]imidazol-2-yl)piperidin-1-yl)butan-1-one | ESI-MS: m/z 511.4 (M + H)$^+$.<br>1H NMR (400 MHz, DMSO-d$_6$) δ ppm 1.41-1.59 (m, 1 H) 1.72-2.17 (m, 6 H) 2.62-2.86 (m, 3 H) 2.90-3.54 (m, 10 H) 3.66-4.09 (m, 2 H) 4.21-4.63 (m, 3 H) 7.26-7.42 (m, 5 H) 7.42-7.51 (m, 2 H) 7.57-7.71 (m, 6 H) |
| 125 | 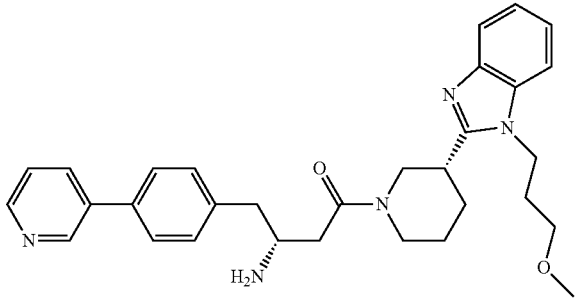<br>(R)-3-amino-1-((R)-3-(1-(3-methoxypropyl)-1H-benzo[d]imidazol-2-yl)piperidin-1-yl)-4-(4-(pyridin-3-yl)phenyl)butan-1-one. | ESI-MS: m/z 512.2 (M + H)$^+$.<br>1H NMR (400 MHz, DMSO-d$_6$) δ ppm 1.42-1.62 (m, 1 H) 1.73-2.22 (m, 5 H) 2.59-2.88 (m, 3 H) 2.92-3.16 (m, 4 H) 3.16-3.48 (m, 5 H) 3.76 (br. s., 1 H) 3.82-4.70 (m, 4 H) 7.40-7.53 (m, 4 H) 7.66 (dt, J = 7.83, 5.56 Hz, 1 H) 7.72-7.84 (m, 4 H) 8.27 (ddd, J = 16.74, 9.92, 1.64 Hz, 1 H) 8.67 (d, J = 5.05 Hz, 1 H) 9.00 (dd, J = 6.19, 2.15 Hz, 1 H). |
| 126 | 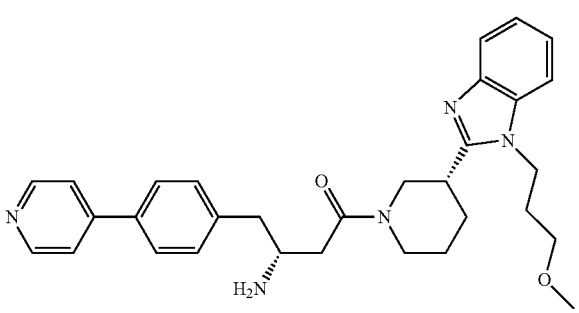<br>(R)-3-amino-1-((R)-3-(1-(3-methoxypropyl)-1H-benzo[d]imidazol-2-yl)piperidin-1-yl)-4-(4-(pyridin-4-yl)phenyl)butan-1-one | ESI-MS: m/z 512.2 (M + H)$^+$.<br>1H NMR (400 MHz, DMSO-d$_6$) δ ppm 1.41-1.63 (m, 1 H) 1.74-2.22 (m, 5 H) 2.61-2.76 (m, 2 H) 2.81-3.47 (m, 9 H) 3.83-4.69 (m, 6 H) 7.42-7.55 (m, 4 H) 7.72-7.84 (m, 2 H) 7.95 (dd, J = 13.26, 8.21 Hz, 2 H) 8.12 (dd, J = 15.66, 6.32 Hz, 2 H) 8.84 (d, J = 5.56 Hz, 2 H) |
| 127 | 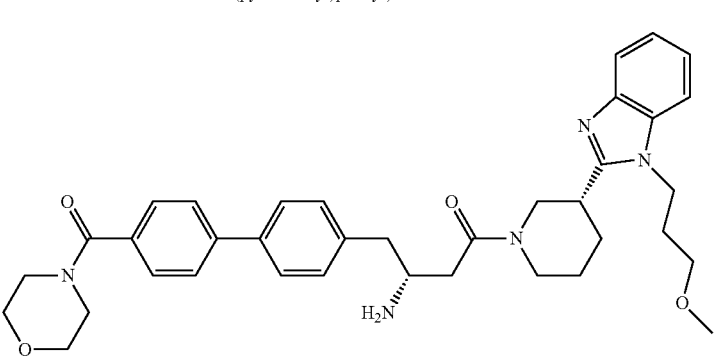<br>(R)-3-amino-1-((R)-3-(1-(3-methoxypropyl)-1H-benzo[d]imidazol-2-yl)piperidin-1-yl)-4-(4'-(morpholine-4-carbonyl)biphenyl-4-yl)butan-1-one | ESI-MS: m/z 624.3 (M + H)$^+$.<br>1H NMR (400 MHz, DMSO-d$_6$) δ ppm 1.41-1.64 (m, 1 H) 1.73-2.24 (m, 5 H) 2.57-2.85 (m, 3 H) 2.88-3.15 (m, 4 H) 3.16-3.91 (m, 16 H) 4.10-4.72 (m, 4 H) 7.36-7.44 (m, 2 H) 7.45-7.57 (m, 4 H) 7.65-7.88 (m, 6 H) |

TABLE III-continued

| Compound No. | Structure/Name | Physical Property |
|---|---|---|
| 128 | 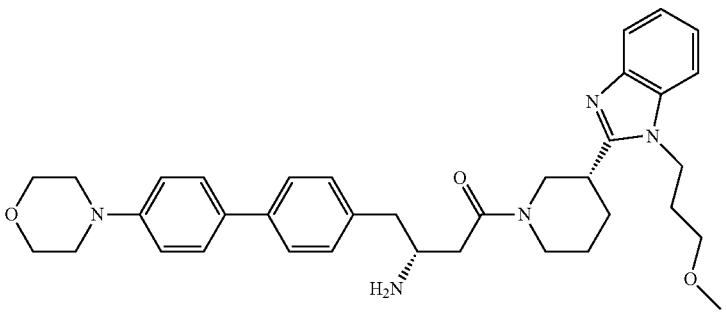<br>(R)-3-amino-1-((R)-3-(1-(3-methoxypropyl)-1H-benzo[d]imidazol-2-yl)piperidin-1-yl)-4-(4'-morpholinobiphenyl-4-yl)butan-1-one | ESI-MS: m/z 596.3 (M + H)$^+$.<br>1H NMR (400 MHz, DMSO-d$_6$) δ ppm 1.40-1.62 (m, 1 H) 1.72-2.21 (m, 5 H) 2.58-2.81 (m, 4 H) 2.86-3.10 (m, 4 H) 3.10-3.51 (m, 10 H) 3.63-4.18 (m, 6 H) 4.27-4.70 (m, 3 H) 6.99-7.06 (m, 2 H) 7.27-7.37 (m, 2 H) 7.40-7.52 (m, 2 H) 7.52-7.64 (m, 4 H) 7.70-7.85 (m, 2 H) |
| 129 | 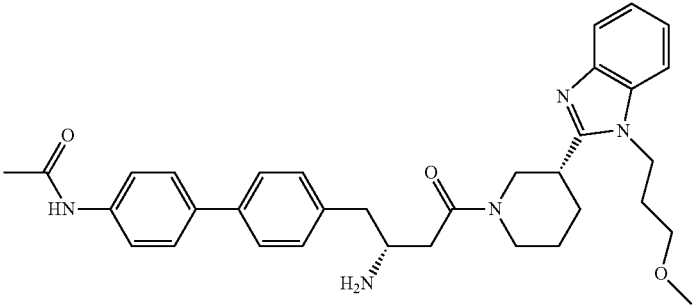<br>N-(4'-((R)-2-amino-4-((R)-3-(1-(3-methoxypropyl)-1H-benzo[d]imidazol-2-yl)piperidin-1-yl)-4-oxobutyl)biphenyl-4-yl)acetamide | ESI-MS: m/z 568.2 (M + H)$^+$.<br>1H NMR (400 MHz, DMSO-d$_6$) δ ppm 1.42-1.63 (m, 1 H) 1.74-2.24 (m, 8 H) 2.57-2.82 (m, 3 H) 2.87-3.14 (m, 4 H) 3.16-3.56 (m, 5 H) 3.65-3.80 (m, 1 H) 3.81-4.73 (m, 4 H) 7.35 (t, J = 8.84 Hz, 2 H) 7.45-7.72 (m, 8 H) 7.75-7.89 (m, 2 H) 10.07 (s, 1 H) |
| 130 | 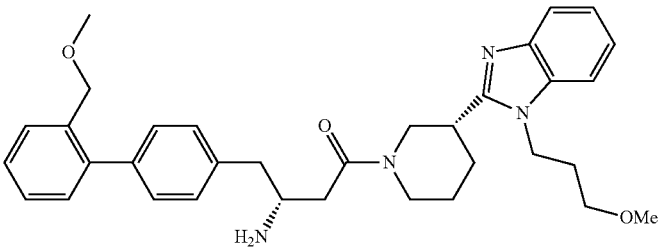<br>(R)-3-amino-4-(2'-(methoxymethyl)biphenyl-4-yl)-1-((R)-3-(1-(3-methoxypropyl)-1H-benzo[d]imidazol-2-yl)piperidin-1-yl)butan-1-one | ESI-MS: 555.25 m/z (M + H)$^+$. |
| 131 | 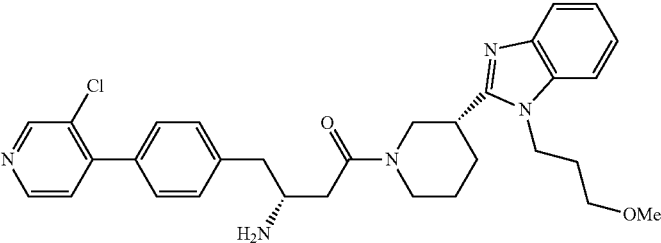<br>(R)-3-amino-4-(4-(3-chloropyridin-4-yl)phenyl)-1-((R)-3-(1-(3-methoxypropyl)-1H-benzo[d]imidazol-2-yl)piperidin-1-yl)butan-1-one | ESI-MS: 546.21 m/z (M + H)$^+$. |

TABLE III-continued

| Compound No. | Structure/Name | Physical Property |
|---|---|---|
| 132 | 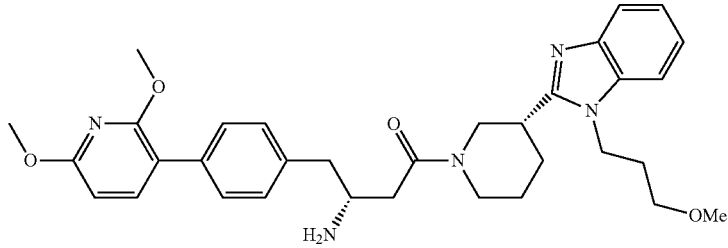<br>(R)-3-amino-4-(4-(2,6-dimethoxypyridin-3-yl)phenyl)-1-((R)-3-(1-(3-methoxypropyl)-1H-benzo[d]imidazol-2-yl)piperidin-1-yl)butan-1-one | ESI-MS: 572.27 m/z (M + H)+. |
| 133 | 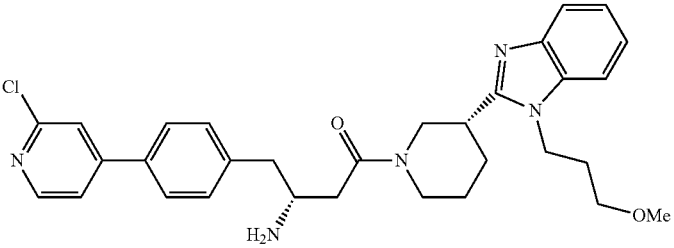<br>(R)-3-amino-4-(4-(2-chloropyridin-4-yl)phenyl)-1-((R)-3-(1-(3-methoxypropyl)-1H-benzo[d]imidazol-2-yl)piperidin-1-yl)butan-1-one | ESI-MS: 546.21 m/z (M + H)+. |
| 134 | 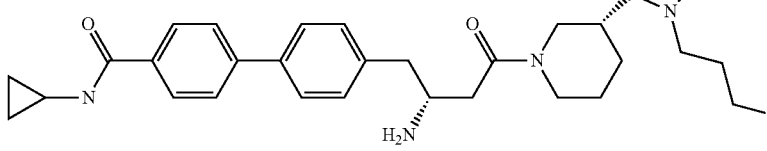<br>4'-((R)-2-amino-4-((R)-3-(1-(3-methoxypropyl)-1H-benzo[d]imidazol-2-yl)piperidin-1-yl)-4-oxobutyl)-N-cyclopropylbiphenyl-4-carboxamide | ESI-MS: 594.27 m/z (M + H)+.<br>1H NMR (400 MHz, DMSO-d$_6$) δ ppm 0.59 (d, J = 3.28 Hz, 2 H) 0.66-0.74 (m, 2 H) 1.51 (br. s., 1 H) 1.74-2.18 (m, 5 H) 2.63-3.49 (m, 13 H) 3.75 (br. s., 1 H) 4.06-4.67 (m, 4 H) 7.40 (t, J = 8.72 Hz, 4 H) 7.73 (dd, J = 17.56, 8.21 Hz, 6 H) 7.88-7.94 (m, 2 H) 8.46 (br. s., 1 H). |
| 135 | 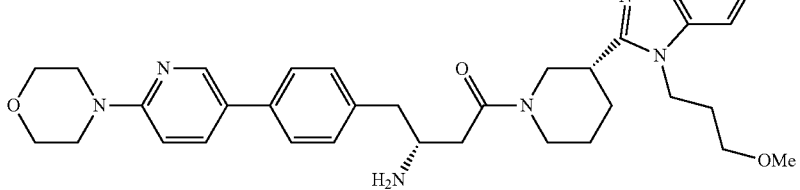<br>(R)-3-amino-1-((R)-3-(1-(3-methoxypropyl)-1H-benzo[d]imidazol-2-yl)piperidin-1-yl)-4-(4-(6-morpholinopyridin-3-yl)phenyl)butan-1-one | ESI-MS: 597.3 m/z (M + H)+. |

TABLE III-continued

| Compound No. | Structure/Name | Physical Property |
|---|---|---|
| 136 | 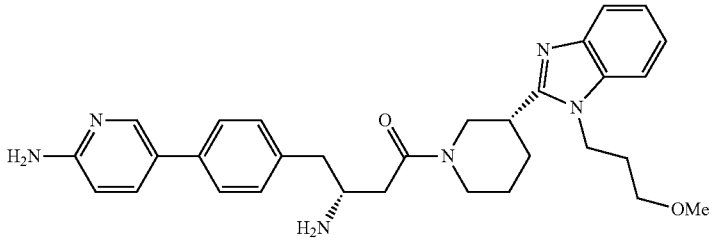<br>(R)-3-amino-4-(4-(6-aminopyridin-3-yl)phenyl)-1-((R)-3-(1-(3-methoxypropyl)-1H-benzo[d]imidazol-2-yl)piperidin-1-yl)butan-1-one | ESI-MS: 527.22 m/z (M + H)$^+$.<br>$^1$H NMR (400 MHz, DMSO-d$_6$) δ ppm 1.40-1.62 (m, 1 H) 1.73-2.20 (m, 5 H) 2.61-2.85 (m, 3H) 2.87-3.48 (m, 11 H) 3.66-4.09 (m, 2 H) 4.23-4.64 (m, 3 H) 7.08 (d, J = 9.85 Hz, 1 H) 7.33-7.46 (m, 4 H) 7.59-7.76 (m, 4 H) 8.03-8.32 (m, 4 H). |
| 137 | 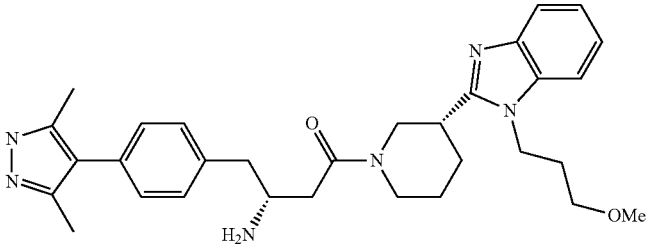<br>(R)-3-amino-4-(4-(3,5-dimethyl-1H-pyrazol-4-yl)phenyl)-1-((R)-3-(1-(3-methoxypropyl)-1H-benzo[d]imidazol-2-yl)piperidin-1-yl)butan-1-one | ESI-MS: 529.25 m/z (M + H)$^+$. |
| 138 | 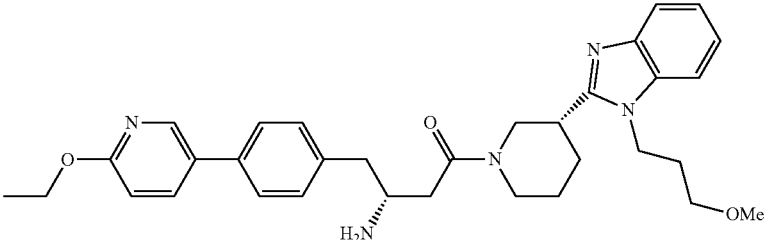<br>(R)-3-amino-4-(4-(6-ethoxypyridin-3-yl)phenyl)-1-((R)-3-(1-(3-methoxypropyl)-1H-benzo[d]imidazol-2-yl)piperidin-1-yl)butan-1-one | ESI-MS: 556.24 m/z (M + H)$^+$.<br>$^1$H NMR (400 MHz, DMSO-d$_6$) δ ppm 1.34 (t, J = 7.07 Hz, 3 H) 1.40-1.62 (m, 1 H) 1.71-2.22 (m, 5 H) 2.59-2.85 (m, 3 H) 2.88-3.13 (m, 4 H) 3.15-3.48 (m, 6 H) 3.74 (br. s., 1 H) 3.80-4.68 (m, 7 H) 6.89 (dd, J = 8.72, 1.89 Hz, 1 H) 7.31-7.52 (m, 4 H) 7.65 (dd, J = 11.37, 8.08 Hz, 2 H) 7.70-7.82 (m, 2 H) 7.97-8.04 (m, 1 H) 8.47 (d, J = 2.02 Hz, 1 H). |
| 139 | 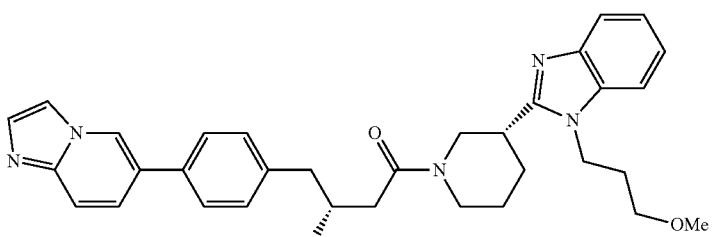<br>(R)-3-amino-4-(4-(imidazo[1,2-a]pyridin-6-yl)phenyl)-1-((R)-3-(1-(3-methoxypropyl)-1H-benzo[d]imidazol-2-yl)piperidin-1-yl)butan-1-one | ESI-MS: 551.23 m/z (M + H)$^+$.<br>$^1$H NMR (400 MHz, DMSO-d$_6$) δ ppm 1.43-1.65 (m, 1 H) 1.72-2.22 (m, 5 H) 2.6-2.76 (m, 3 H) 2.81-3.52 (m, 11 H) 3.73-4.12 (m, 2 H) 4.26-4.65 (m, 3 H) 7.31-7.56 (m, 4 H) 7.67-7.85 (m, 4 H) 8.07 (d, J = 9.60 Hz, 1 H) 8.19-8.35 (m, 3 H) 9.28 (d, J = 6.57 Hz, 1 H). |

TABLE III-continued

| Compound No. | Structure/Name | Physical Property |
|---|---|---|
| 140 | 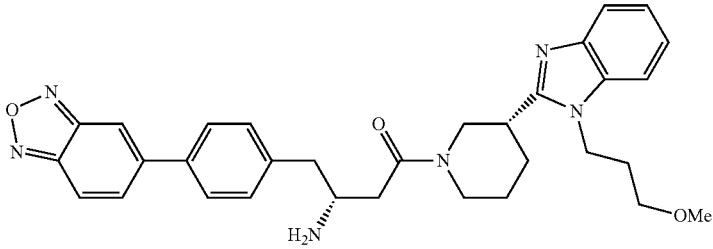<br>(R)-3-amino-4-(4-(benzo[c][1,2,5]oxadiazol-5-yl)phenyl)-1-((R)-3-(1-(3-methoxypropyl)-1H-benzo[d]imidazol-2-yl)piperidin-1-yl)butan-1-one | ESI-MS: 553.2 m/z (M + H)$^+$.<br>$^1$H NMR (400 MHz, DMSO-d$_6$) δ ppm 1.40-1.63 (m, 1 H) 1.73-2.20 (m, 5 H) 2.63-2.90 (m, 3 H) 2.93-3.48 (m, 9 H) 3.72-4.12 (m, 2 H) 4.21- 4.68 (m, 3 H) 7.33-7.52 (m, 4 H) 7.64-7.76 (m, 2 H) 7.84-8.05 (m, 3 H) 8.13-8.21 (m, 1 H) 8.31 (d, J = 6.06 Hz, 1 H). |
| 141 | 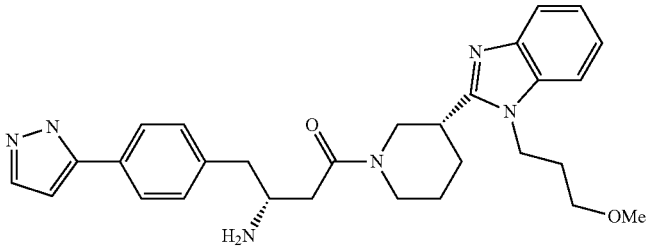<br>(R)-4-(4-(1H-pyrazol-5-yl)phenyl)-3-amino-1-((R)-3-(1-(3-methoxypropyl)-1H-benzo[d]imidazol-2-yl)piperidin-1-yl)butan-1-one | ESI-MS: 501.2 m/z (M + H)$^+$. |
| 142 | 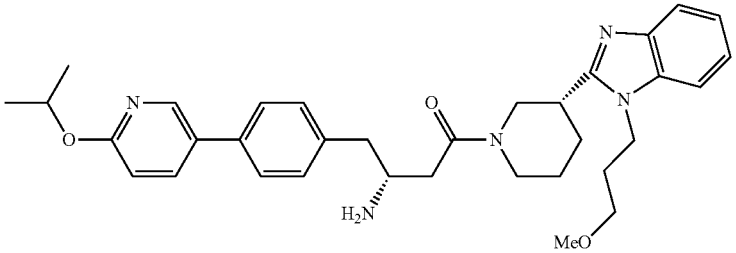<br>(R)-3-amino-4-(4-(6-isopropoxypyridin-3-yl)phenyl)-1-((R)-3-(1-(3-methoxypropyl)-1H-benzo[d]imidazol-2-yl)piperidin-1-yl)butan-1-one | ESI-MS: 570.3 m/z (M + H)$^+$.<br>$^1$H NMR (400 MHz, DMSO-d$_6$) δ ppm 1.32 (dd, J = 6.19, 1.39 Hz, 6 H) 1.44-1.61 (m, 1 H) 1.73-2.21 (m, 5 H) 2.58-2.85 (m, 3 H) 2.86-3.48 (m, 9 H) 3.67-4.15 (m, 2 H) 4.25-4.69 (m, 3 H) 5.29 (dq, J = 12.35, 6.09, 5.94, 1.64 Hz, 1 H) 7.32-7.51 (m, 4 H) 7.65 (dd, J = 11.49, 8.21 Hz, 2 H) 7.69-7.81 (m, 2 H) 7.95-8.01 (m, 2 H) 8.47 (d, J = 2.53 Hz, 1 H). |
| 143 | 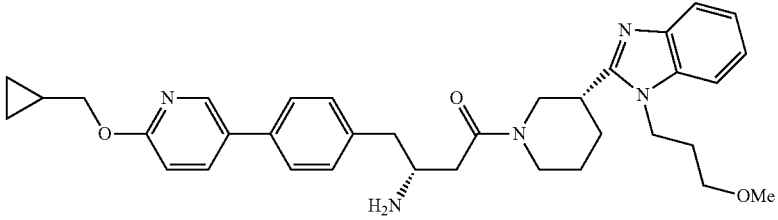<br>(R)-3-amino-4-(4-(6-(cyclopropylmethoxy)pyridin-3-yl)phenyl)-1-((R)-3-(1-(3-methoxypropyl)-1H-benzo[d]imidazol-2-yl)piperidin-1-yl)butan-1-one | ESI-MS: 582.26 m/z (M + H)$^+$.<br>$^1$H NMR (400 MHz, DMSO-d$_6$) δ ppm 0.28-0.38 (m, 2 H) 0.50-0.62 (m, 2 H) 1.17-1.34 (m, 1 H) 1.41-1.62 (m, 1 H) 1.73-2.22 (m, 5 H) 2.58-2.84 (m, 3 H) 2.88-3.48 (m, 9 H) 3.73 (br. s., 1 H) 3.80-4.17 (m, 3 H) 4.25-4.68 (m, 3 H) 6.91 (dd, J = 8.59, 1.52 Hz, 1 H) 7.32-7.51 (m, 4 H) 7.59-7.80 (m, 4 H) 7.99 (ddd, J = 8.72, 6.57, 2.65 Hz, 1 H) 8.41-8.50 (m, 1 H). |

TABLE III-continued

| Compound No. | Structure/Name | Physical Property |
|---|---|---|
| 144 | 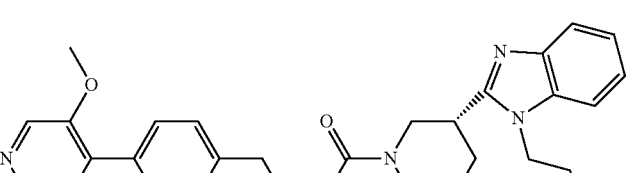<br>(R)-3-amino-1-((R)-3-(1-(3-methoxypropyl)-1H-benzo[d]imidazol-2-yl)piperidin-1-yl)-4-(4-(3-methoxypyridin-4-yl)phenyl)butan-1-one | ESI-MS: 542.25 m/z (M + H)+. |

Example 54

Synthesis of (R)-3-amino-4-(4-(furan-3-yl)phenyl)-1-((R)-3-(1-(3-methoxypropyl)-1H-benzo[d]imidazol-2-yl)piperidin-1-yl)butan-1-one (145)

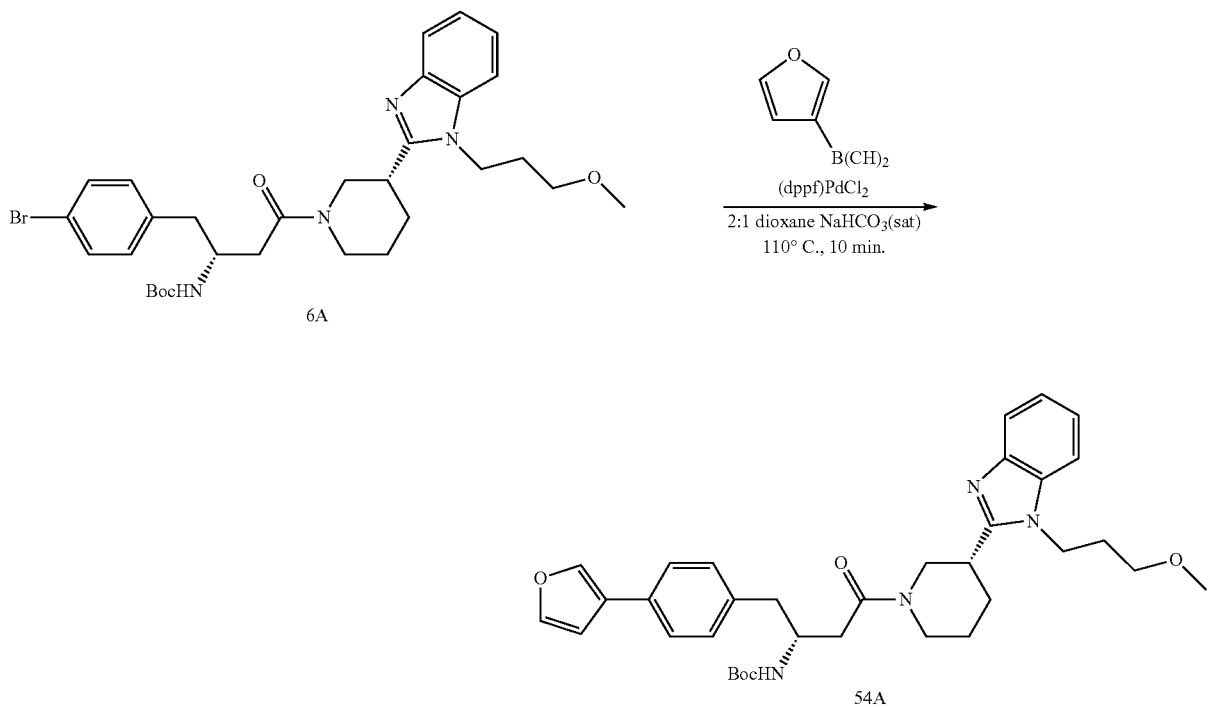

tert-Butyl(R)-1-(4-(furan-3-yl)phenyl)-4-((R)-3-(1-(3-methoxypropyl)-1H-benzo[d]imidazol-2-yl)piperidin-1-yl)-4-oxobutan-2-ylcarbamate (54A) was prepared from 6A (Example 6, Step A) as described for Example 53, Step A. ESI-MS:m/z 601.5 (M+H)+.

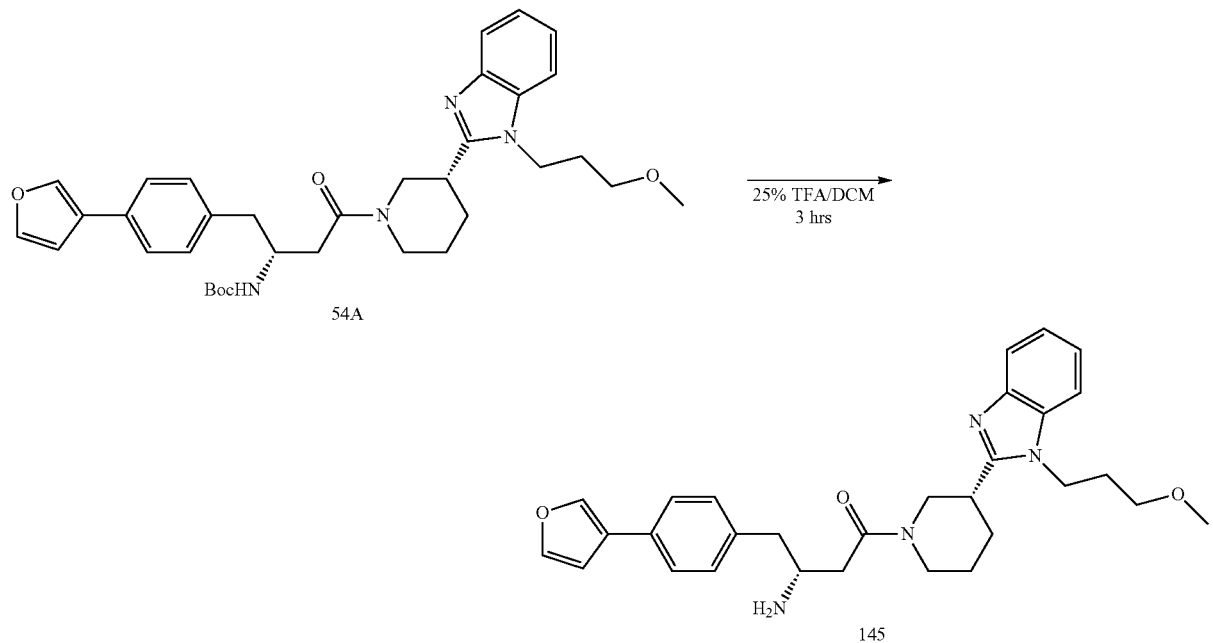

tert-Butyl(R)-1-(4-(furan-3-yl)phenyl)-4-((R)-3-(1-(3-methoxypropyl)-1,1-benzo[d]imidazol-2-yl)piperidin-1-yl)-4-oxobutan-2-ylcarbamate (54A) was dissolved in 25% trifluoroacetic acid and stirred at room temperature for 3 hrs. Solvent was removed under vacuum and purified by preparatory LC/MS (20-50% $CH_3CN$ in $H_2O$) to give product (R)-3-amino-4-(4-(furan-3-yl)phenyl)-1-((R)-3-(1-(3-methoxypropyl)-1H-benzo[d]imidazol-2-yl)piperidin-1-yl)butan-1-one (145) as a TFA salt (32 mg, 64% yield). 1H NMR (400 MHz, DMSO-$d_6$) δ ppm 1.51 (br. s., 1H) 1.72-2.22 (m, 5H) 2.57-3.51 (m, 1H) 3.71 (br. s., 1H) 3.77-4.73 (m, 5H) 6.96 (br. s., 1H) 7.30 (m, 2H) 7.37-7.50 (m, 2H) 7.59 (m, 2H) 7.75 (br. s., 3H) 8.17 (s, 1H). ESI-MS:mlz 501.2 $(M+H)^+$.

Example 55

Synthesis of (R)-3-amino-4-(4-(furan-2-yl)phenyl)-1-((R)-3-(1-(3-methoxypropyl)-1H-benzo[c]iimidazol-2-yl)piperidin-1-yl)butan-1-one (146)

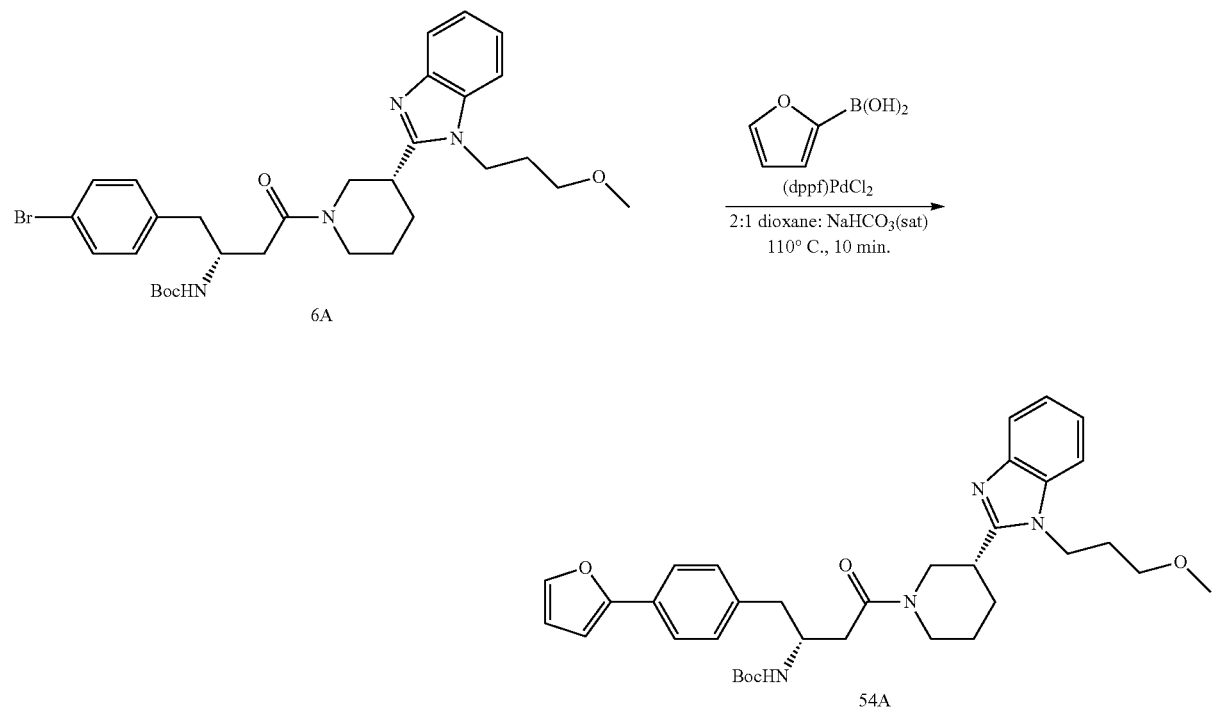

363 tert-Butyl(R)-1-(4-(furan-2-yl)phenyl)-4-((R)-3-(1-(3-methoxypropyl)-1H-benzo[d]imidazol-2-yl)piperidin-1-yl)-4-oxobutan-2-ylcarbamate (54A) was prepared as described in Example 54, Step A. ESI-MS:m/z 601.5 (M+H)+.

364 ppm 1.53 (br. s., 1H) 1.74-2.18 (m, 5H) 2.72 (br. s., 2H) 2.86-3.50 (m, 6H) 3.65 (m, 3H) 3.73-3.91 (m, 2H) 4.35 (s, 4H) 7.38 (m, 2H) 7.43-7.57 (m, 5H) 7.64-7.76 (m, 4H). ESI-MS:m/z 501.2 (M+H)+.

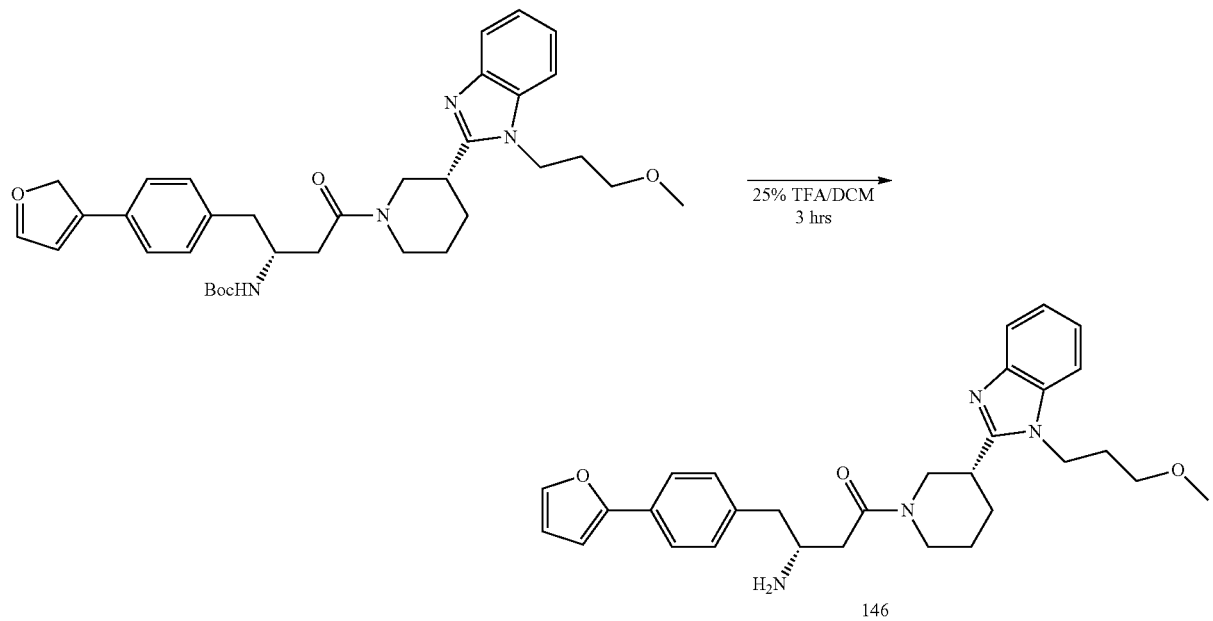

(R)-3-Amino-4-(4-(furan-2-yl)phenyl)-1-((R)-3-(1-(3-methoxypropyl)-1H-benzo[d]imidazol-2-yl)piperidin-1-yl)butan-1-one (146) was prepared as described above for Example 54, Step B and was purified by preparatory LC/MS (20-50% CH₃CN in H₂O) to give the product 146 as a TFA salt (13 mg, 26% yield). ¹H NMR (400 MHz, DMSO-d₆) δ

Example 56

Synthesis of (R)-3-amino-4-(4-(6-(dimethylamino)pyridin-3-yl)phenyl)-1-((R)-3-(1-(3-methoxypropyl)-1H-benzo[d]imidazol-2-yl)piperidin-1-yl)butan-1-one (147)

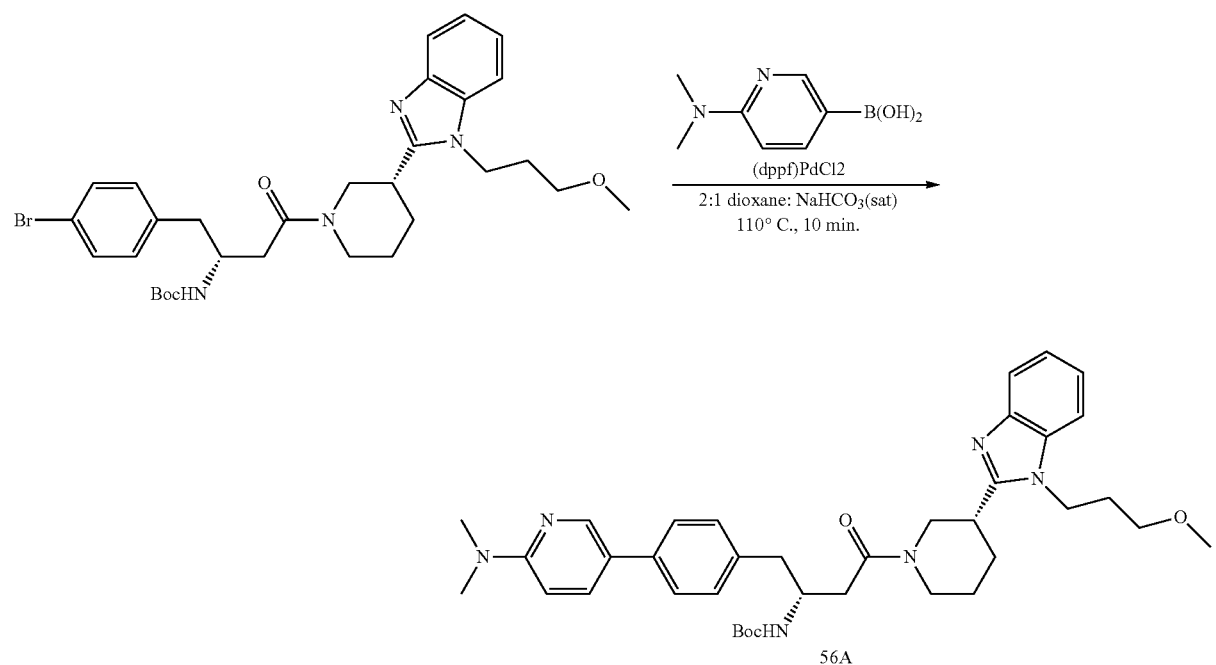

tert-Butyl(R)-1-(4-(6-(dimethylamino)pyridin-3-yl)phenyl)-4-((R)-3-(1-(3-methoxypropyl)-1H-benzo[d]imidazol-2-yl)piperidin-1-yl)-4-oxobutan-2-ylcarbamate (56A) was prepared as described for Example 54, Step A. ESI-MS:m/z 655.5 (M+H)⁺.

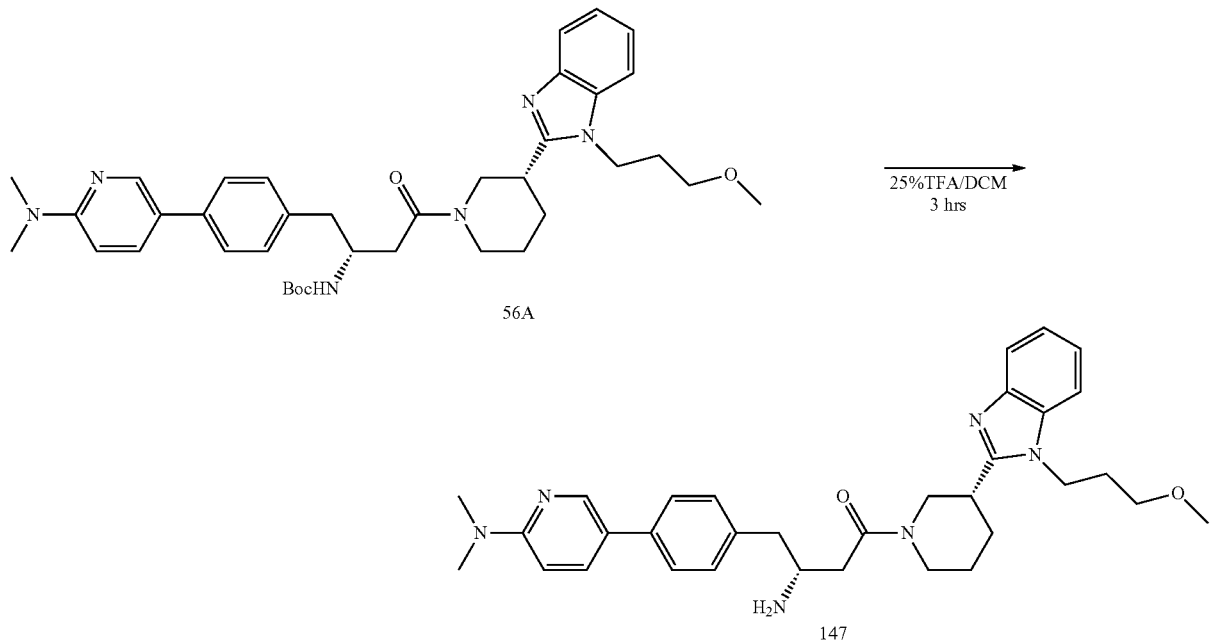

(R)-3-amino-4-(4-(6-(dimethylamino)pyridin-3-yl)phenyl)-1-((R)-3-(1-(3-methoxypropyl)-1H-benzo[d]imidazol-2-yl)piperidin-1-yl)butan-1-one (147) was prepared as described above for Example 54, Step B and was purified by preparatory LC/MS (10-40% CH$_3$CN in H$_2$O) to give the product 147 as a TFA salt (47 mg, 95% yield). 1H NMR (400 MHz, DMSO-d$_6$) δ ppm 1.51 (br. s., 1H) 1.76-2.21 (m, 5H) 2.59-3.49 (m, 1H) 3.74 (br. s., 2H) 4.06-4.70 (m, 4H) 7.10 (m, 1H) 7.38 (m, 2H) 7.48 (m, 2H) 7.66 (m, 2H) 7.79 (m, 2H) 8.09-8.19 (m, 1H) 8.34 (m, 1H). ESI-MS:m/z 555.3 (M+H)⁺.

Example 57

Synthesis of (R)-3-amino-1-((R)-3-(1-(3-methoxypropyl)-1H-benzo[d]imidazol-2-yl)piperidin-1-yl)-4-(4-(2-methoxypyridin-4-yl)phenyl)butan-1-one (148)

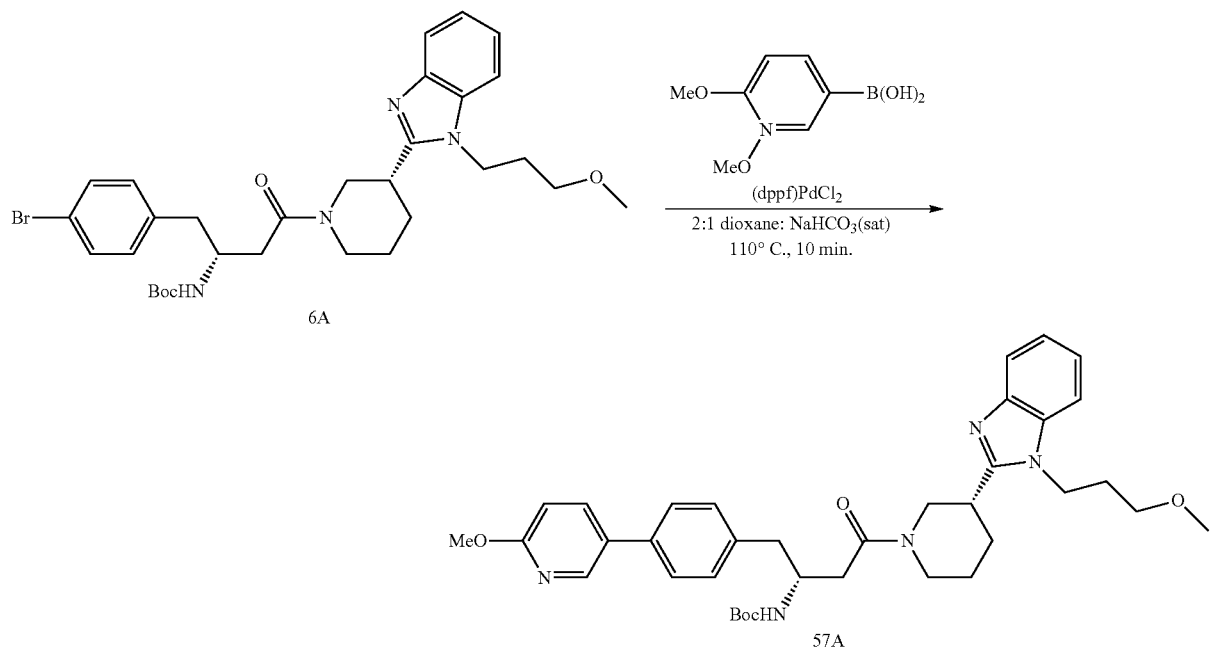

(tert-Butyl(R)-4-((R)-3-(1-(3-methoxypropyl)-1H-benzo[d]imidazol-2-yl)piperidin-1-yl)-1-(4-(2-methoxypyridin-4-yl)phenyl)-4-oxobutan-2-ylcarbamate (57A) was prepared as described for Example 54, Step A. ESI-MS:m/z 642.5 (M+H)+.

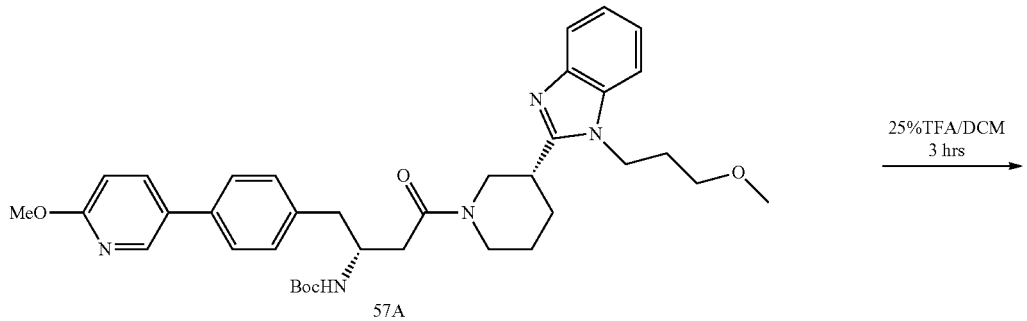

(R)-3-amino-1-((R)-3-(1-(3-methoxypropyl)-1H-benzo[d]inaidazol-2-yl)piperidin-1-yl)-4-(4-(6-methoxypyridin-3-yl)phenyl)butan-1-one (148) was prepared as described above for Example 54, Step B and was purified by preparatory LC/MS (20-55% CH$_3$CN in H$_2$O) to give product as a TFA salt (39 mg, 92% yield). 1H NMR (400 MHz, DMSO-d$_6$) δ ppm 1.51 (br. s., 1H) 1.75-2.22 (m, 5H) 2.60-2.85 (m, 3H) 2.88-3.50 (m, 9H) 3.67-3.88 (m, 1H) 3.90 (m, 3H) 4.10-4.72 (m, 4H) 6.92 (m, 1H) 7.38 (m, 2H) 7.42-7.52 (m, 2H) 7.65 (m, 2H) 7.80 (m, 2H) 8.01 (m, 1H) 8.49 (m, 1H). ESI-MS:m/z 542.2 (M+H)+.

Example 58

Synthesis of (R)-3-amino-1-((R)-3-(1-(3-methoxypropyl)-1H-benzo[d]imidazol-2-yl)piperidin-1-yl)-4-(4-(pyrimidin-5-yl)phenyl)butan-1-one (149)

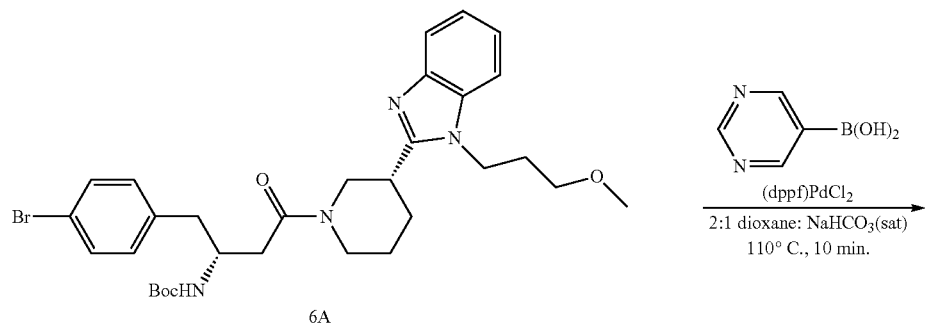

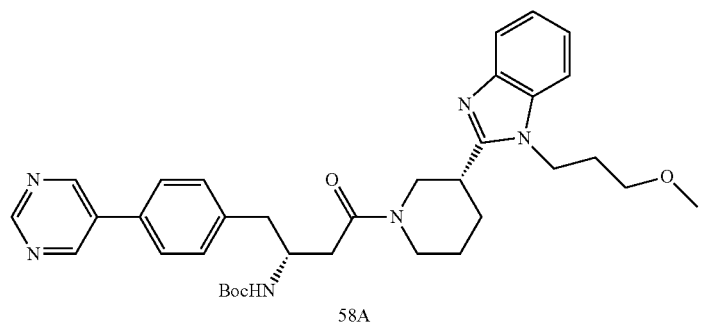

tert-Butyl(R)-4-((R)-3-(1-(3-methoxypropyl)-1H-benzo[d]imidazol-2-yl)piperidin-1-yl)-4-oxo-1-(4-(pyrimidin-5-yl)phenyl)butan-2-ylcarbamate (58A) was prepared as described in Example 54, Step A. ESI-MS:m/z 613.5 (M+H)$^+$.

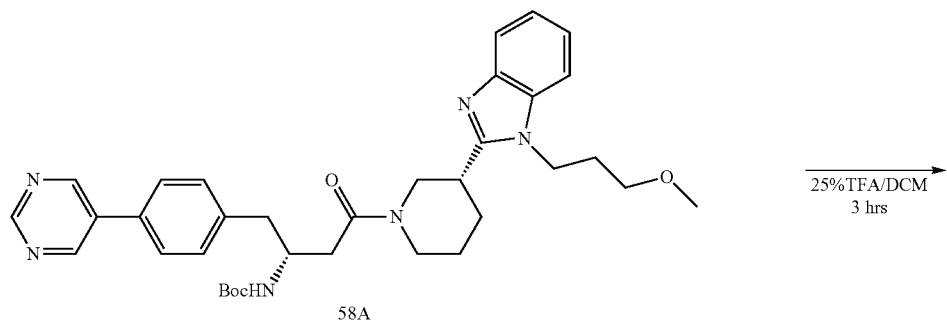

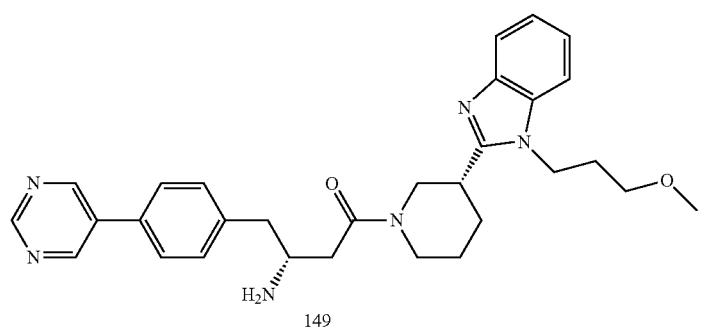

(R)-3-Amino-1-((R)-3-(1-(3-methoxypropyl)-1H-benzo[d]imidazol-2-yl)piperidin-1-yl)-4-(4-(pyrimidin-5-yl)phenyl)butan-1-one (149) was prepared as described above for Example 54, Step B and was purified by preparatory LC/MS (15-50% $CH_3CN$ in $H_2O$) to give the product as a TFA salt (35 mg, 83% yield). 1H NMR (400 MHz, DMSO-$d_6$) δ ppm 1.51 (br. s., 1H) 1.90 (m, 5H) 2.61-3.50 (m, 12H) 3.77 (br. s., 1H) 4.06-4.70 (m, 4H) 7.46 (m, 4H) 7.69-7.79 (m, 2H) 7.82 (m, 2H) 9.15 (m, 3H). ESI-MS:m/z 513.2 (M+H)$^+$.

Example 59

Synthesis of (R)-3-amino-4-(4-(2-fluoropyridin-4-yl)phenyl)-1-((R)-3-(1-(3-methoxypropyl)-1H-benzo[d]imidazol-2-yl)piperidin-1-yl)butan-1-one (150)

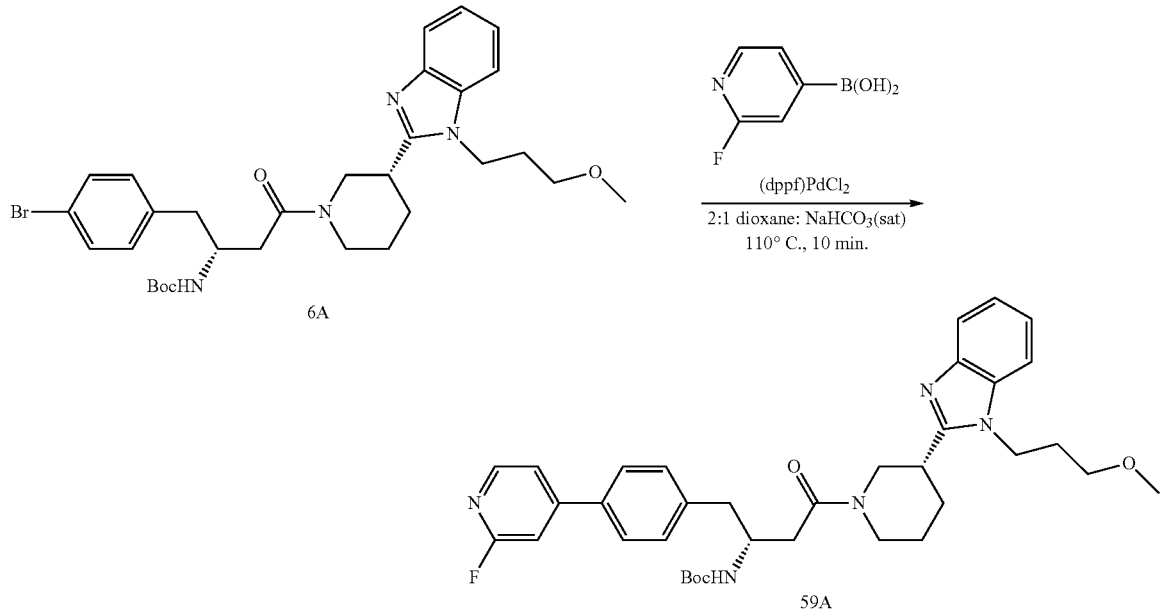

tert-Butyl(R)-1-(4-(2-fluoropyridin-4-yl)phe n yl)-4-((R)-3-(1-(3-methoxypropyl)-1H-benzo[d]imidazol-2-yl)piperidin-1-yl)-4-oxobutan-2-ylcarbamate (59A) was prepared as described for Example 54, Step A. ESI-MS:m/z 630.5 (M+H)$^+$.

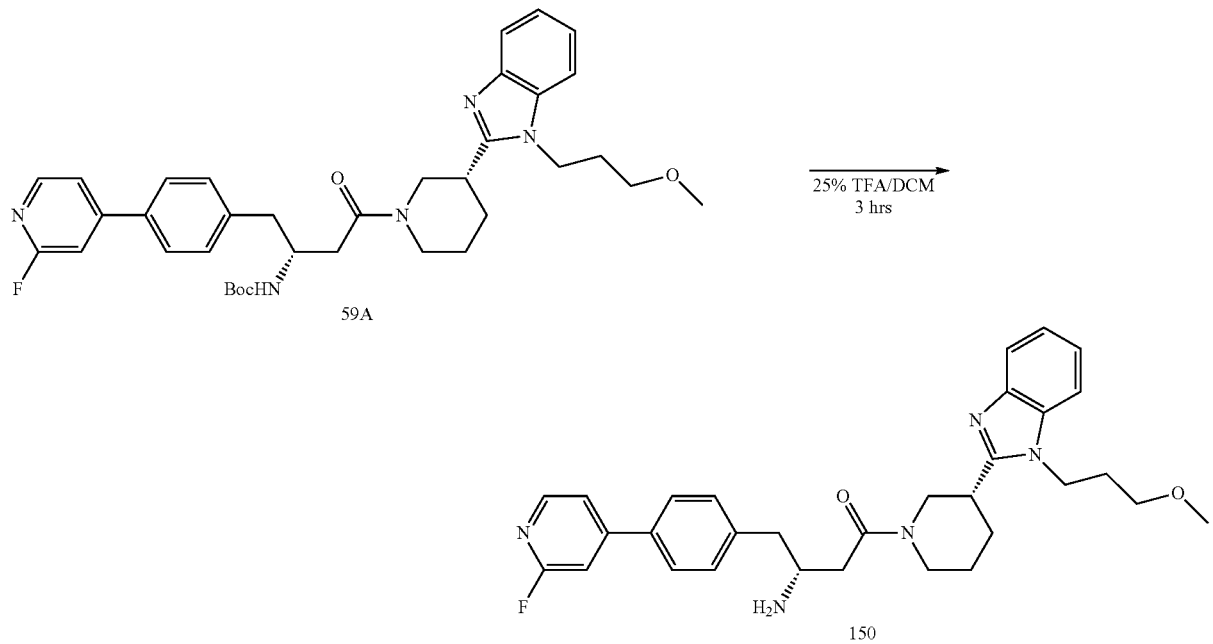

(R)-3-amino-4-(4-(2-fluoropyridin-4-yl)phenyl)-1-((R)-3-(1-(3-methoxypropyl)-1H-benzo[d]imidazol-2-yl)piperidin-1-yl)butan-1-one (150) was prepared as described above for Example 53, Step B and was purified by preparatory LC/MS (20-40% CH$_3$CN in H$_2$O) to give the product as a TFA salt (37 mg, 86% yield). 1H NMR (400 MHz, DMSO-d$_6$) δ ppm 1.50 (br. s., 1H) 1.74-2.20 (m, 5H) 2.63-3.02 (m, 4H) 3.03-3.25 (m, 6H) 3.34 (m, 2H) 3.70-3.90 (m, 1H) 4.04-4.68 (m, 4H) 7.46 (m, 4H) 7.53 (m, 1H) 7.71 (m, 3H) 7.87 (m, 2H) 8.31 (m, 1 H). ESI-MS:m/z 530.2 (M+H)$^+$.

Example 60
Synthesis of (R)-3-amino-4-(4-(2-fluoropyridin-3-yl)phenyl)-1-((R)-3-(1-(3-methoxypropyl)-1H-benzo[d]imidazol-2-yl)piperidin-1-yl)butan-1-one (151)
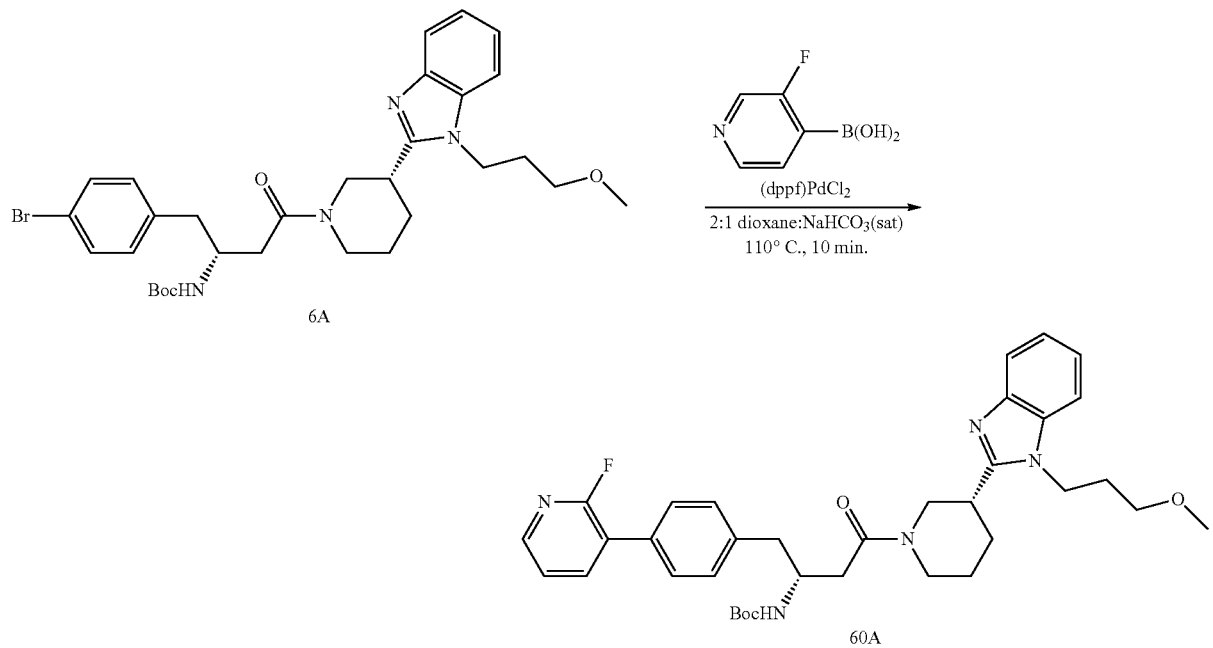
tert-Butyl(R)-1-(4-(2-fluoropyridin-3-yl)phenyl)-4-((R)-3-(1-(3-methoxypropyl)-1H-benzo[d]imidazol-2-yl)piperidin-1-yl)-4-oxobutan-2-ylcarbamate (60A) was prepared as described in Example 54, Step A. ESI-MS:m/z 630.5 (M+H)$^+$.
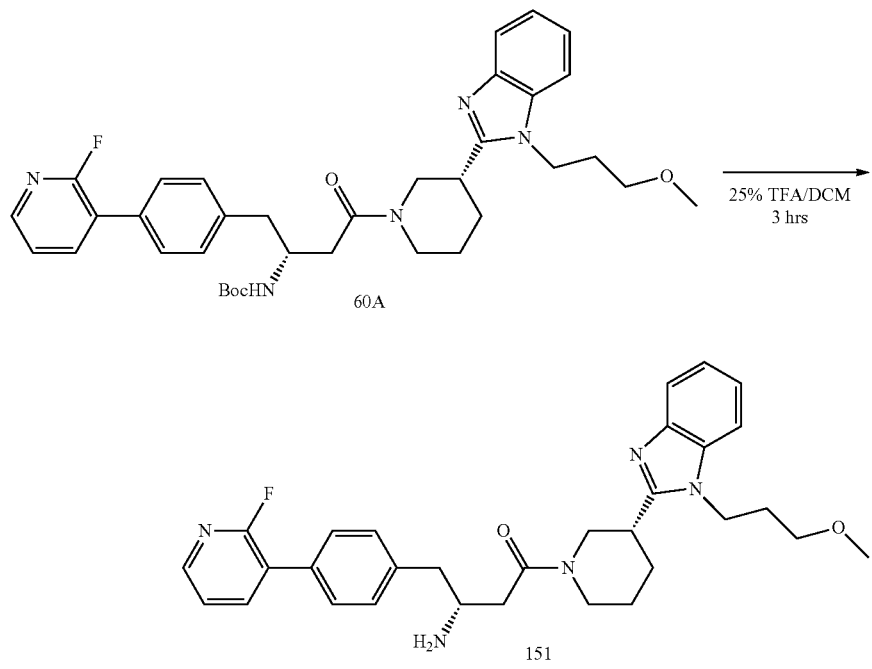

(R)-3-Amino-4-(4-(2-fluoropyridin-3-yl)phenyl)-1-((R)-3-(1-(3-methoxypropyl)-1H-benzo[d]imidazol-2-yl)piperidin-1-yl)butan-1-one (151) was prepared as described above for Example 54, Step B and was purified by preparatory LC/MS (20-40% CH$_3$CN in H$_2$O) to give the product as a TFA salt (40 mg, 93% yield). 1H NMR (400 MHz, DMSO-d$_6$) δ ppm 1.52 (br. s., 1H) 1.76-2.21 (m, 5H) 2.62-3.02 (m, 4H) 3.03-3.49 (m, 8H) 3.78 (m, 1H) 4.11-4.69 (m, 4H) 7.40-7.51 (m, 5H) 7.62 (m, 2H) 7.78 (m, 2H) 8.06-8.14 (m, 1H) 8.25 (m, 1H). ESI-MS:m/z 530.2 (M+H)$^+$.

Example 61

Synthesis of (R)-4-(4-(1H-pyrrol-3-yl)phenyl)-3-amino-1-((R)-3-(1-(3-methoxypropyl)-1H-benzo[d]imidazol-2-yl)piperidin-1-yl)butan-1-one (152)

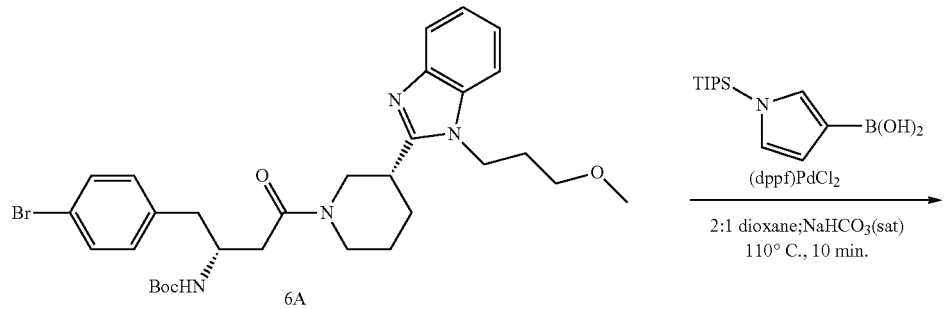

tert-Butyl(R)-4-((R)-3-(1-(3-methoxypropyl)-1H-benzofdlimidazol-2-yl)piperidin-1-yl)-4-oxo-1-(4-(1-(triisopropylsilyl)-1H-pyrrol-3-yl)phenyl)butan-2-ylcarbamate (61A) was prepared as described in Example 54, Step A. ESI-MS: m/z 756.6 (M+H)$^+$.

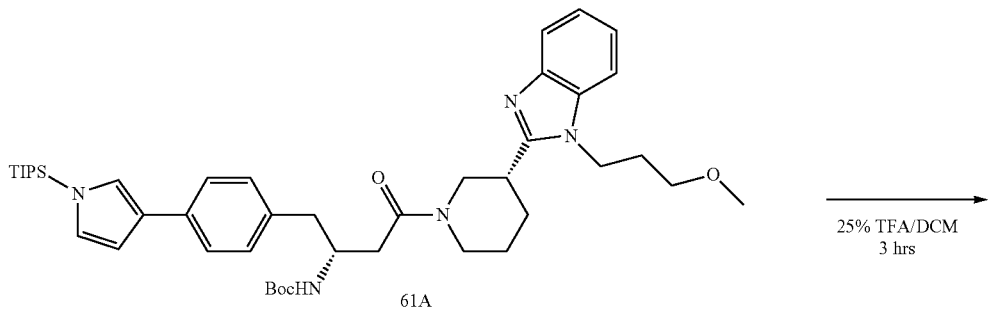

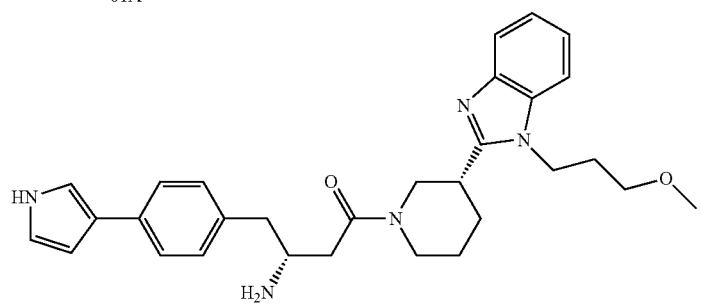

(R)-4-(4-(1H-Pyrrol-3-yl)phenyl)-3-amino-1-((R)-3-(1-(3-methoxypropyl)-1H-benzo[d]imidazol-2-yl)piperidin-1-yl)butan-1-one (152) was prepared as described above for Example 54, Step B and was purified by preparatory LC/MS (20-30% CH₃CN in H₂O) to give product as a TFA salt (12 mg, 24% yield). ESI-MS:m/z 500.2 (M+H)⁺.

Example 62

Synthesis of (R)-4-(4-(1H-pyrrol-2-yl)phenyl)-3-amino-1-((R)-3-(1-(3-methoxypropyl)-1H-benzo[d]imidazol-2-yl)piperidin-1-yl)butan-1-one (153)

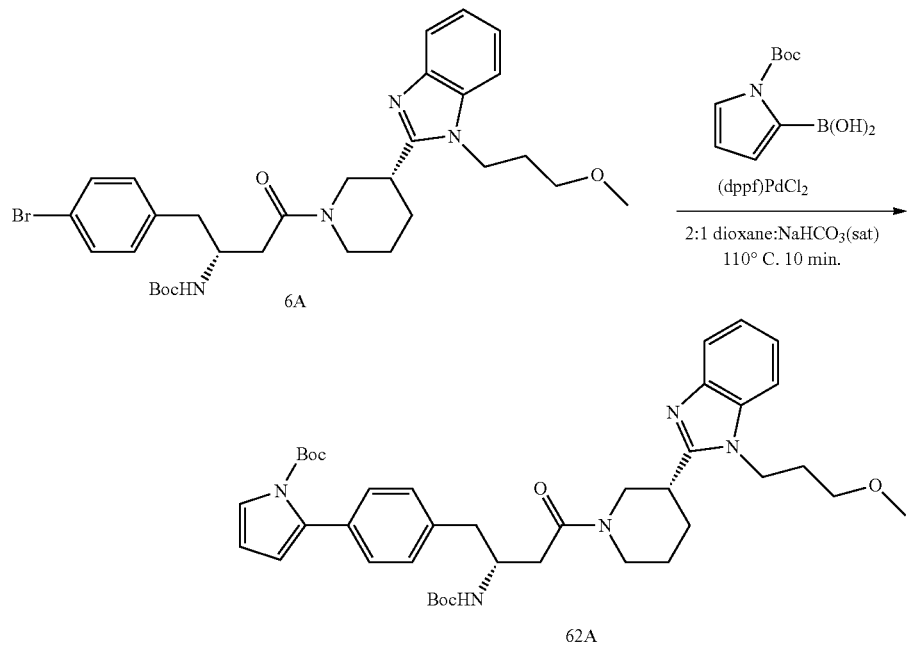

tert-Butyl 2-(4-((R)-2-(tert-butoxycarbonylamino)-4-((R)-3-(1-(3-methoxypropyl)-1H-benzo[d]imidazol-2-yl)piperidin-1-yl)-4-oxobutyl)phenyl)-1H-pyrrole-1-carboxylate (62A) was prepared as described in Example 54, Step A. ESI-MS:mh 600.5 (M+H)⁺.

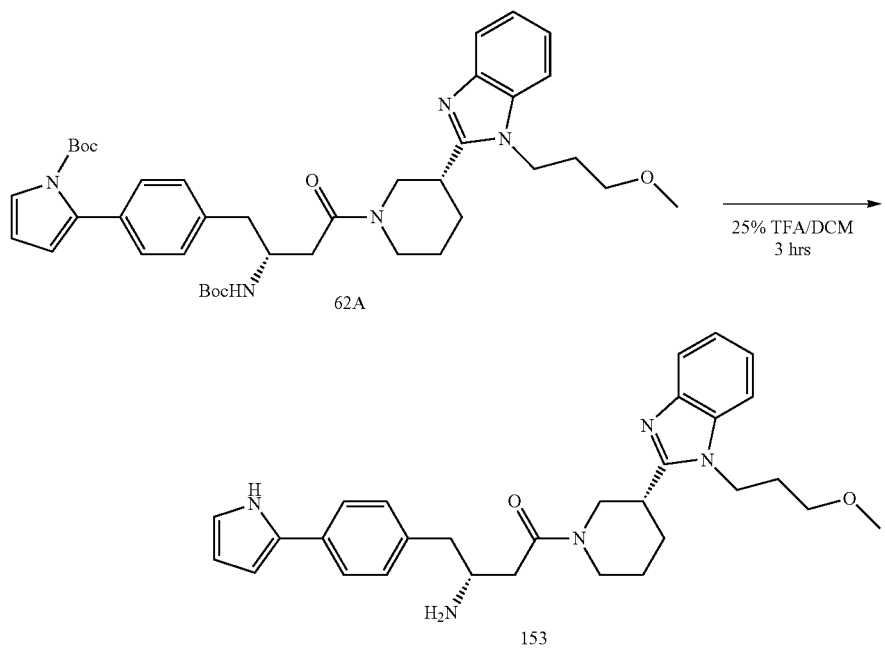

(R)-4-(4-(1H-pyrrol-2-yl)phenyl)-3-amino-1-((R)-3-(1-(3-methoxypropyl)-1H-benzo[d]imidazol-2-yl)piperidin-1-yl)butan-1-one (153) was prepared as described above for Example 54, Step B and was purified by preparatory LC/MS (20-30% CH$_3$CN in H$_2$O) to give product as a TFA salt (11 mg, 22% yield). ESI-MS:m/z 500.2 (M+H)$^+$.

Example 63

Synthesis of (R)-3-amino-4-(4-(2-aminopyrimidin-5-yl)phenyl)-1-((R)-3-(1-(3-methoxypropyl)-1H-benzo[d]imidazol-2-yl)piperidin-1-yl)buthn-1-one (154)

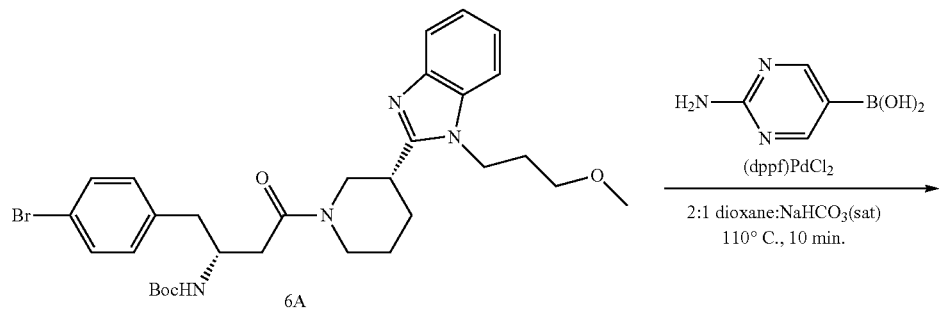

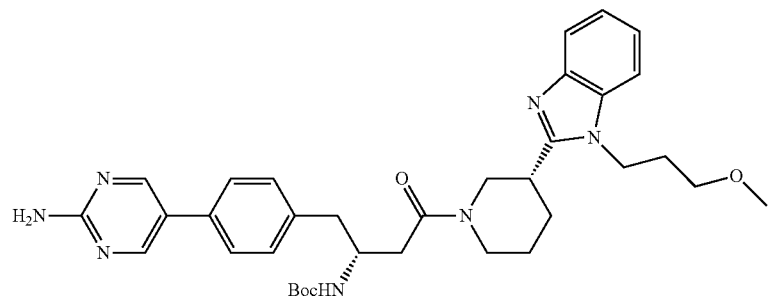

tert-Butyl(R)-1-(4-(2-aminopyrimidin-5-yl)phenyl)-4-((R)-3-(1-(3-methoxypropyl)-1H-benzo[d]imidazol-2-ylpiperidin-1-yl)-4-oxobutan-2-ylcarbamate (63A) was prepared as described in Example 54, Step A. ESI-MS:m/z 628.5 (M+H)$^+$.

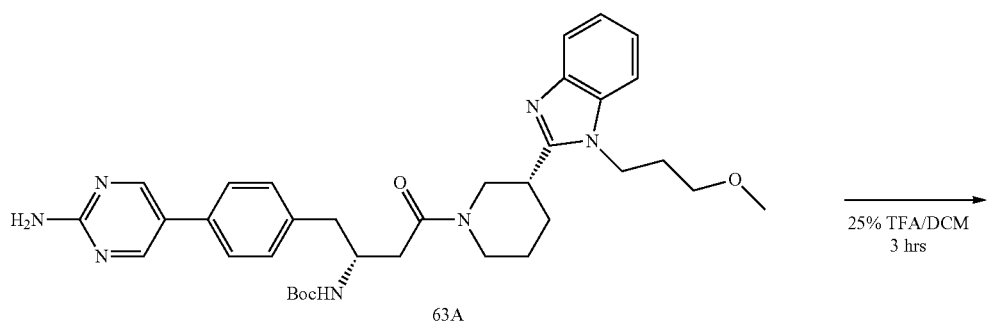

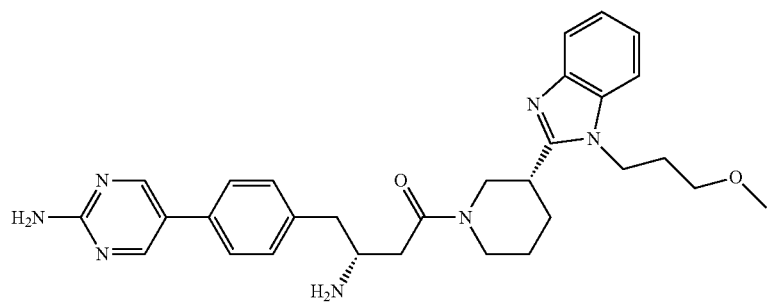

(R)-3-amino-4-(4-(2-aminopyrimidin-5-yl)phenyl)-1-((R)-3-(1-(3-methoxypropyl)-1H-benzo[d]imidazol-2-yl)piperidin-1-yl)butan-1-one (154) was prepared as described above for Example 54, Step B and was purified by preparatory LC/MS (10-35% CH$_3$CN in H$_2$O) to give product as a TFA salt (42 mg, 81% yield). 1H NMR (400 MHz, DMSO-d$_6$) δ ppm 1.51 (br. s., 1H) 1.75-2.22 (m, 5H) 2.58-2.81 (m, 3H) 2.88-3.52 (m, 9H) 3.71 (br. s., 1H) 4.11-4.72 (m, 4H) 7.35 (m, 2H) 7.45-7.55 (m, 2H) 7.63 (m, 2H) 7.78 (m, 1H) 7.83 (m, 1H) 8.65 (m, 2H). ESI-MS:m/z 528.2 (M+H)$^+$.

Example 64

Synthesis of (R)-3-amino-4-(2'-chlorobiphenyl-4-yl)-1((R)-3-(1-(3-methoxypropyl)-1H-benzo[d]imidazol-2-yl)piperidin-1-yl)butan-1-one (155)

Step A.

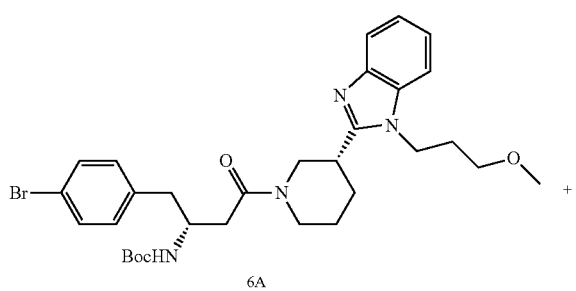

6A

+

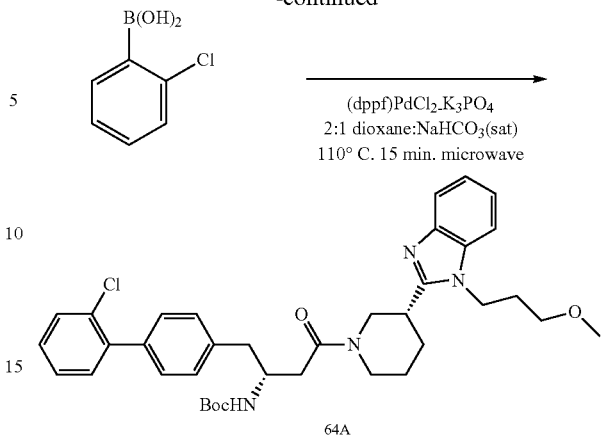

Into a microwave reaction vessel was added 2-chlorophenylboronic acid (22 mg, 137 μmol) and tert-butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (56 mg, 92 μmol). (dppf)PdCl$_2$ (3 mg, 45 μmol) was added and the mixture was dissolved with dioxane (0.6 mL) and saturated sodium bicarbonate (0.3 mL). The vessel was capped and microwaved for 10 minutes at 110° C. The mixture was filtered and the solvent removed under vacuum. The residue containing tert-butyl(R)-1-(2'-chlorobiphenyl-4-yl)-4-((R)-3-(1-(3-methoxypropyl-1H-benzo[d]imidazal-2-yl)piperidin-1-yl)-4-oxobutan-2-ylcarbamate (64A) was carried to the next step without further purification. ESI-MS:m/z 644.3 (M+H)$^+$.

Step B.

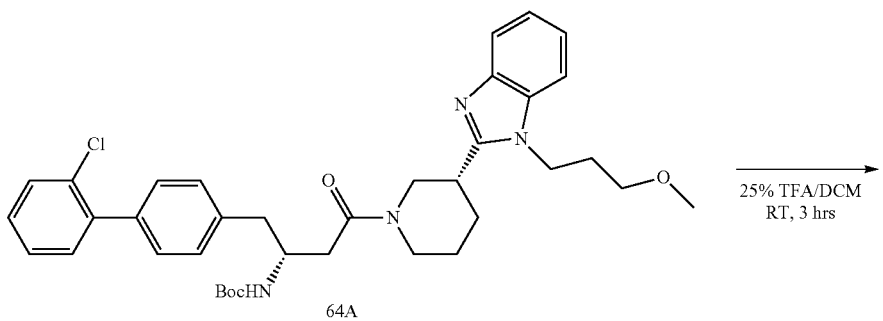

64A

25% TFA/DCM
RT, 3 hrs

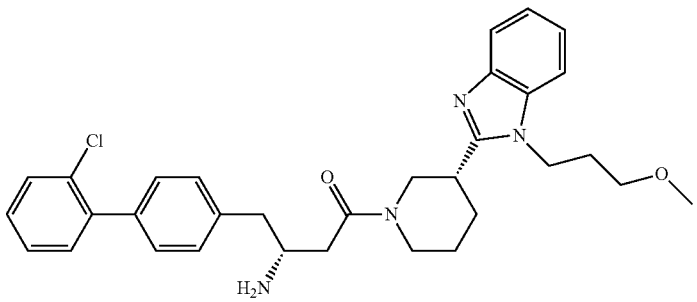

155

The solvent was removed and the residue containing (R)-3-amino-4-(2'-chlorobiphenyl-4-yl)-1-((R)-3-(1-(3-methoxypropyl)-1H-benzo[d]imidazol-2-yl)piperidin-1-yl)butan-1-one (155) was purified by preparatory LC/MS (20-40% $CH_3CN$ in $H_2O$) to give the product as a TFA salt (53 mg, 86% yield over two steps). ESI-MS:m/z 545.2 $(M+H)^+$.

Example 65

Synthesis of (R)-3-amino-4-(4'-methoxybiphenyl-4-yl)-1-((R)-3-(1-(3-methoxypropyl)-1H-benzo[d]imidazol-2-yl)piperidin-1-yl)butan-1-one (156)

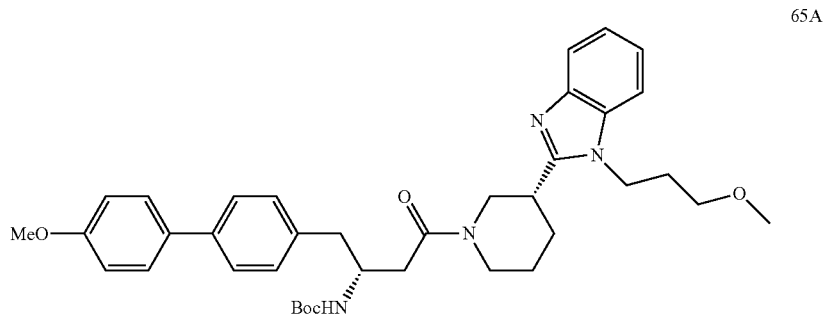

65A tert-Butyl(R)-1-(4'-methoxybiphenyl-4-yl)-4-((R)-3-(1-(3-methoxypropyl)-1H-benzo[d]imidazol-2-yl)piperidin-1-yl)-4-oxobutan-2-ylcarbamate (65A) was prepared as described for Example 64, Step A. ESI-MS:m/z 640.4 $(M+H)^+$.

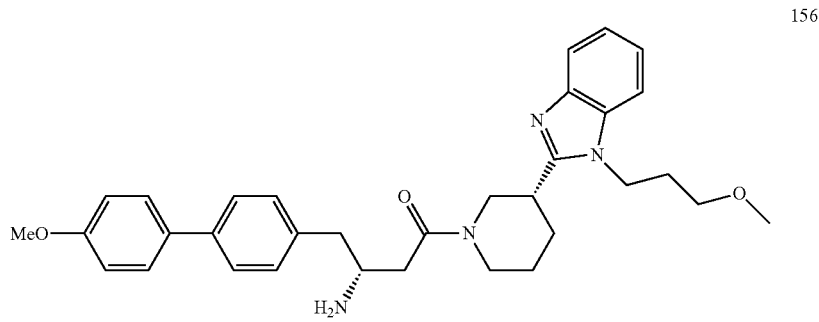

156

(R)-3-Amino-4-(4'-methoxybiphenyl-4-yl)-1-((R)-3-(1-(3-methoxypropyl)-1,1-benzo[d]imidazol-2-yl)piperidin-1-yl)butan-1-one (156) was prepared as described for Example 64, Step B and was purified by preparatory LC/MS (20-40% $CH_3CN$ in $H_2O$) to give the product as a TFA salt (46 mg, 76% yield over two steps). ESI-MS:m/z 541.3 $(M+H)^+$.

Example 66

Synthesis of (R)-3-amino-1((R)-3-(1-(3-methoxypropyl)-1H-benzo[d]imidazol-2-yl)piperidin-1-yl-4-(2'-methylbiphenyl-4-yl)butan-1-one (157)

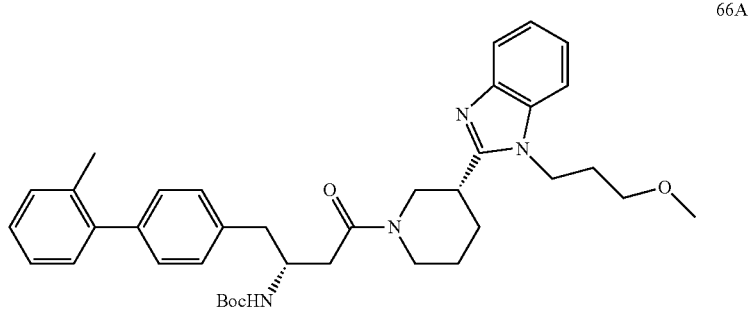

66A tert-Butyl(R)-4-((R)-3-(1-(3-methoxypropyl)-1H-benzo[d]imidazol-2-yl)ppiperidin-1-yl)-1-(2'-methylbiphenyl-4-yl)-4-oxobutan-2-ylcarbamate (66A) was prepared as described for Example 64, Step A. ESI-MS:m/z 624.4 (M+H)$^+$.

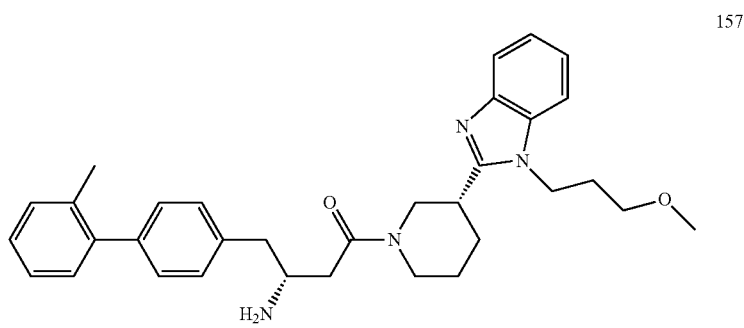

157

(R)-3-amino-1-((R)-3-(1-(3-methoxypropyl)-1H-benzo[d]imidazol-2-yl)piperidin-1-yl)-4-(2'-methylbiphenyl-4-yl)butan-1-one (66A) was prepared as described for Example 64, Step B and was purified by preparatory LC/MS (20-40% CH$_3$CN in H$_2$O) to give the product as a TFA salt (44 mg, 74% yield over two steps). ESI-MS:m/z 525.2 (M+H)$^+$.

Example 67

Synthesis of (R)-3-amino-4-(3'-methoxybiphenyl-4-yl-1((R)-3-(1-(3-methoxypropyl)-1H-benzo[d]imidazol-2-yl)piperidin-1-yl)butan-1-one (158)

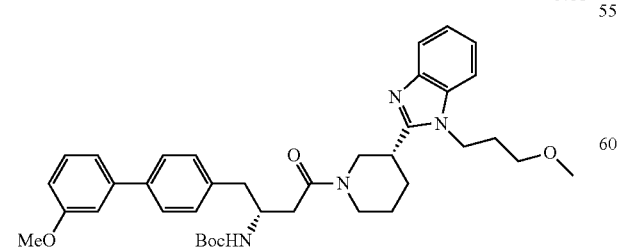

67A tert-Butyl(R)-1-(3'-methoxybiphenyl-4-yl)-4-((R)-3-(1-(3-methoxypropyl)-1H-benzo[d]imidazol-2-yl)piperidin-1-yl)-4-oxobutan-2-ylcarbamate (67A) was prepared as described for Example 64, Step A. ESI-MS:m/z 640.4 (M+H)$^+$.

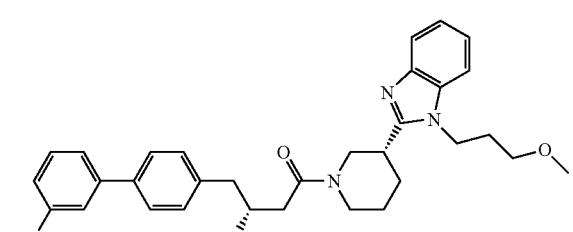

158

(R)-3-Amino-4-(3'-methoxybiphenyl-4-yl)-1-((R)-3-(1-(3-methoxypropyl)-1H-benzo[d]imidazol-2-yl)piperidin-1-yl)butan-1-one (158) prepared as described for Example 64, Step B and was purified by preparatory LC/MS (20-40% CH$_3$CN in H$_2$O) to give the product as a TFA salt (40 mg, 66% yield over two steps). ESI-MS:m/z 541.3 (M+H)$^+$.

Example 68

Synthesis of (R)-3-amino-4-(2'-methoxybiphenyl-4-yl-1-((R)-3-(1-(3-methoxypropyl)-1H-benzo[d]imidazol-2-yl)piperidin-1-yl)butan-1-one (159)

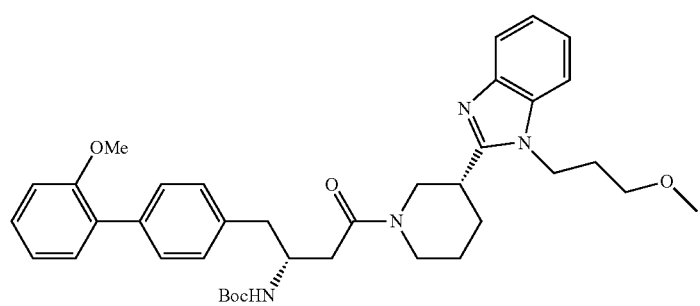

68A tert-Butyl(R)-1-(2'-methoxybiphen yl-4-yl)-4-((R)-3-(1-(3-methoxypropyl)-1H-benzo[d]imidazol-2-yl)piperidin-1-yl)-4-oxobutan-2-ylcarbamate (68A) was prepared as described for Example 64, Step A. ESI-MS:m/z 640.4 (M+H)$^+$.

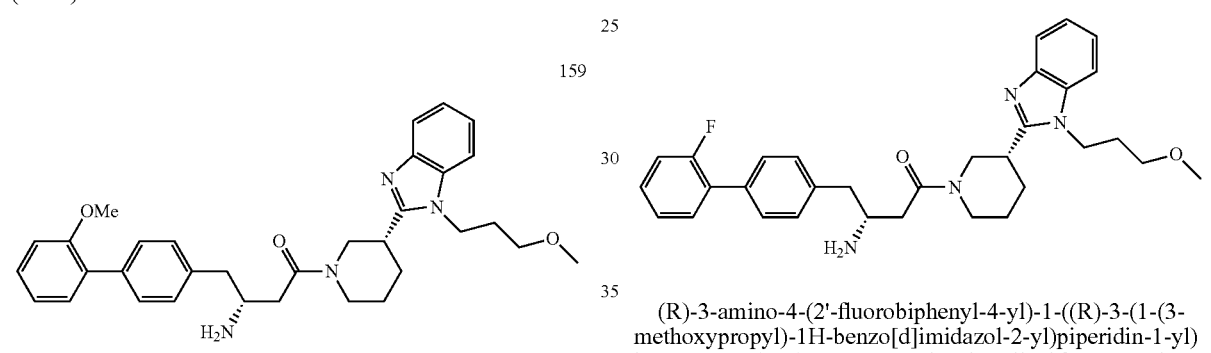

159

(R)-3-amino-4-(T-methoxybiphenyl-4-yl)-1((R)-3-(1-(3-methoxypropyl)-1H-benzo[d]imidazol-2-yl)piperidin-1-yl) butan-1-one (159) was prepared as described for Example 64, Step 13 and was purified by preparatory LC/MS (20-40% CH$_3$CN in H$_2$O) to give the product as a TFA salt (39 mg, 65% yield over two steps). ESI-MS:m/z 541.3 (M+H)$^+$.

Example 69

Synthesis of (R)-3-amino-4-(2'-fluorobiphenyl-4-yl)-1-((R)-3-(1-(3-methoxypropyl)-1H-benzo[d]imidazol-2-yl)piperidin-1-yl)butan-1-one (160)

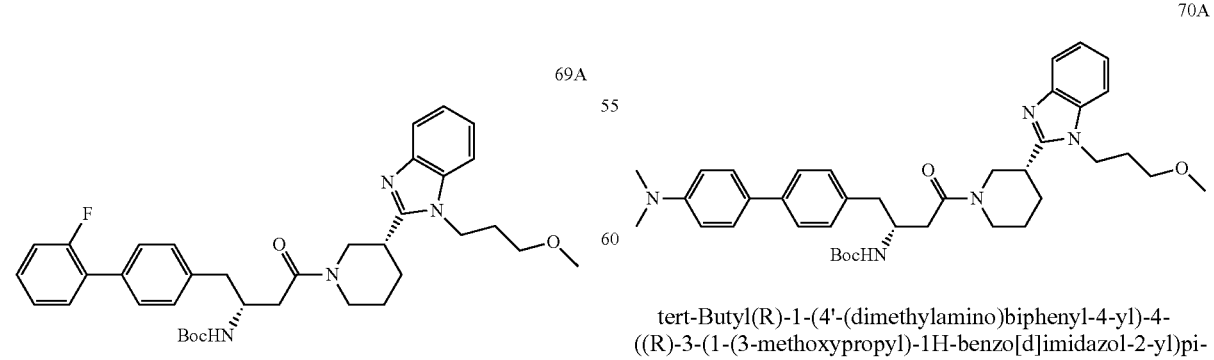

69A tert-Butyl(R)-1-(2'-fluorobiphenyl-4-yl)-4-((R)-3-(1-(3-methoxypropyl)-1,1-benzo[d]imidazol-2-yl)piperidin-1-yl)-4-oxobutan-2-yl carbamate (69A) was prepared as described for Example 64, Step A. ESI-MS:m/z 628.3 (M+H)$^+$.

160

(R)-3-amino-4-(2'-fluorobiphenyl-4-yl)-1-((R)-3-(1-(3-methoxypropyl)-1H-benzo[d]imidazol-2-yl)piperidin-1-yl) butan-1-one (160) was prepared as described for Example 64, Step B and was purified by preparatory LC/MS (20-40% CH$_3$CN in H$_2$O) to give the product as a TFA salt (37 mg, 61% yield over two steps). ESI-MS:m/z 529.2 (M+H)$^+$.

Example 70

Synthesis of (R)-3-amino-4-(4'-(dimethylamino) biphenyl-4-yl)-1-((R)-3-(1-(3-methoxypropyl)-1H-benzo[d]imidazol-2-yl)piperidin-1-yl)butan-1-one (161)

70A tert-Butyl(R)-1-(4'-(dimethylamino)biphenyl-4-yl)-4-((R)-3-(1-(3-methoxypropyl)-1H-benzo[d]imidazol-2-yl)piperidin-1-yl)-4-oxobutan-2-ylcarbamate (70A) was prepared as described for Example 64, Step A. ESI-MS:m/z 653.4 (M+H)$^+$.

161

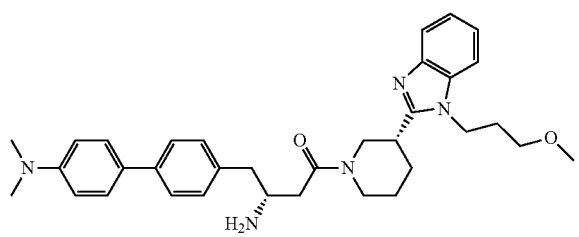

(R)-3-Amino-4-(4'-(dimethylamino)biphenyl-4-yl)-1-((R)-3-(1-(3-methoxypropyl)-1H-benzo[d]imidazol-2-yl)piperidin-1-yl)butan-1-one (161) was prepared as described for Example 64, Step B and was purified by preparatory LC/MS (20-40% CH$_3$CN in H$_2$O) to give the product as a TFA salt (41 mg, 66% yield over two steps). ESI-MS:m/z 554.3 (M+H)$^+$.

Example 71

Synthesis of (R)-3-amino-1((R)-3-(1-(3-methoxypropyl)-1H-benzo[d]imidazol-2-yl)piperidin-1-yl-4-(4-(4-methoxypyridin-3-yl)phenyl)butan-1-one (162)

71A

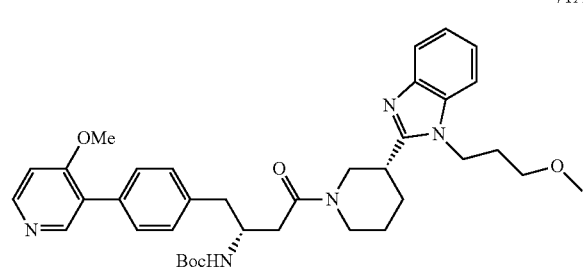

tert-Butyl(R)-4-((R)-3-(1-(3-methoxypropyl)-1H-benzo[d]imidazol-2-ylpperidin-1-yl)-1-(4-(4-methoxypyridin-3-yl)phenyl)-4-oxobutan-2-ylcarbamate (71A) was prepared as described for Example 64, Step A. ESI-MS:mh 641.4 (M+H)$^+$.

162

(R)-3-Amino-1-((R)-3-(1-(3-methoxypropyl)-1H-benzo[d]imidazol-2-yl)piperidin-1-yl)-4-(4-(4-methoxypyridin-3-yl)phenyl)butan-1-one (162) was prepared as described for Example 64, Step B and was purified by preparatory LC/MS (20-40% CH$_3$CN in H$_2$O) to give the product 162 as a TFA salt (31 mg, 50% yield over two steps). 1H NMR (400 MHz, DMSO-d$_6$) δ ppm 1.54 (br. s., 1H) 1.76-2.20 (m, 5H) 2.65-3.50 (m, 3H) 3.77 (br. s., 1H) 4.06 (m, 3H) 4.31-4.67 (m, 4H) 7.43 (m, 4H) 7.59 (m, 2H) 7.69 (m, 3H) 8.67 (m, 1H) 8.81 (m, 1H). ESI-MS:m/z 542.3 (M+H)$^+$.

Example 72

Synthesis of (R)-3-amino-1((R)-3-(1-(3-methoxypropyl)-1H-benzo[d]imidazol-2-yl)piperidin-1-yl)-4-(4-(2-methoxypyridin-3-yl)phenyl)butan-1-one (163)

72A

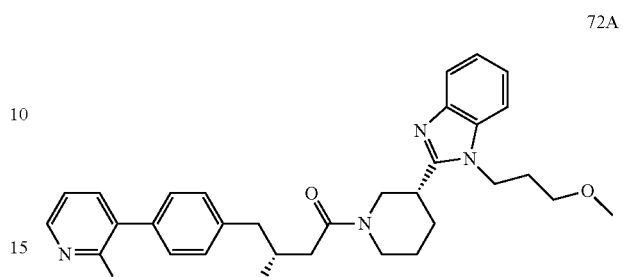

tert-Butyl(R)-4-((R)-3-(1-(3-methoxypropyl)-1H-benzo[d]imidazol-2-yl)piperidin-1-yl)-1-(4-(2-methoxypyridin-3-yl)phenyl)-4-oxobutan-2-ylcarbamate (72A) was prepared as described for Example 64, Step A. ESI-MS:m/z 641.4 (M+H)$^+$.

163

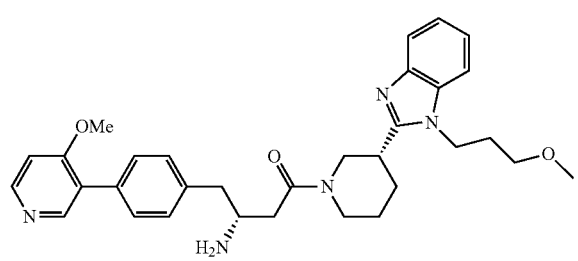

(R)-3-amino-1-((R)-3-(1-(3-methoxypropyl)-1H-benzo[d]imidazol-2-yl)piperidin-1-yl)-4-(4-(2-methoxypyridin-3-yl)phenyl)butan-1-one (163) was prepared as described for Example 63, Step B and was purified by preparatory LC/MS (20-40% CH$_3$CN in H$_2$O) to give the product 163 as a TFA salt (41 mg, 67% yield over two steps). 1H NMR (400 MHz, DMSO-d$_6$) δ ppm 1.52 (br. s., 1H) 2.06 (m, 4H) 2.64-3.48 (m, 12H) 3.75 (br. s., 1H) 3.88 (m, 3H) 4.07-4.67 (m, 4H) 7.10 (m, 1H) 7.35 (m, 4H) 7.56 (m, 2H) 7.72 (m, 3H) 8.18 (m, 1H). ESI-MS:m/z 542.3 (M+H)$^+$.

Example 73

Synthesis of 4'-((R)-2-amino-4-((R)-3-(1-(3-methoxypropyl)-1H-benzo[d]imidazol-2-yl)piperidin-1-yl)-4-oxobutyphiphenyl-4-carbonitrile (164)

73A

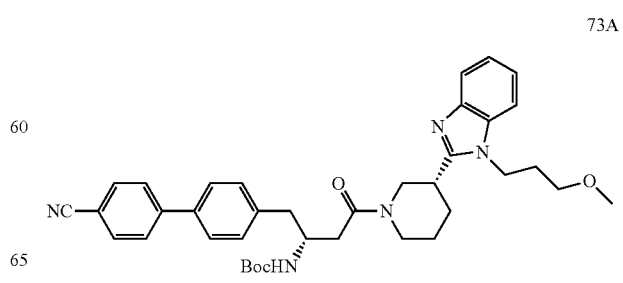

tert-Butyl(R)-1-(4'-cyanobiphenyl-4-yl)-4-((R)-3-(1-(3-methoxypropyl)-1H-benzo[d]imidazol-2-yl)piperidin-1-yl)-4-oxobutan-2-ylcarbamate (73A) was prepared as described for Example 64, Step A. ESI-MS:m/z 635.4 (M+H)+.

164

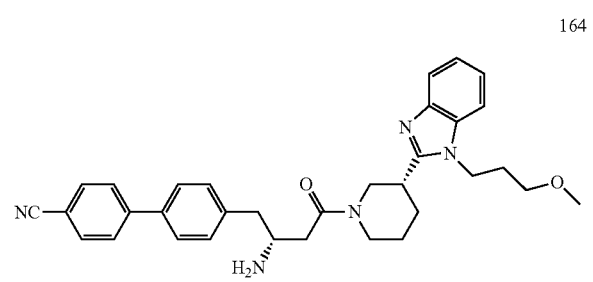

4'-((R)-2-amino-4-((R)-3-(1-(3-methoxypropyl)-1H-benzo[d]imidazol-2-yl)piperidin-1-yl)-4-oxobutyl)biphenyl-4-carbonitrile (164) was prepared as described for Example 64, Step B and was purified by preparatory LC/MS (20-40% CH$_3$CN in H$_2$O) to give the product 164 as a TFA salt (44 mg, 72% yield over two steps). 1H NMR (400 MHz, DMSO-d$_6$) δ ppm 1.50 (br. s., 1H) 1.73-2.18 (m, 5H) 2.64-3.48 (m, 12H) 3.76 (br. s., 1H) 4.03-4.66 (m, 4H) 7.43 (m, 4H) 7.67-7.80 (m, 5H) 7.86-7.95 (m, 3H). ESI-MS:m/z 536.2 (M+H)+.

Example 74

Synthesis of (R)-3-amino-1-((R)-3-(1-(3-methoxypropyl)-1H-benzo[d]imidazol-2-yl)piperidin-1-yl)-4-(4'-(methylsulfonyl)biphenyl-4-yl)butan-1-one (165)

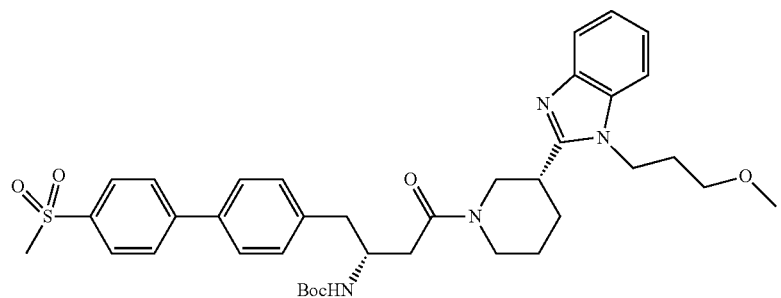

74A tert-Butyl(R)-4-((R)-3-(1-(3-methoxypropyl)-1H-benzo[d]imidazol-2-yl)piperidin-1-yl)-1-(4'-(methylsulfonyl)biphenyl-4-yl)-4-oxobutan-2-ylcarbamate (74A) was prepared as described for Example 64, Step A. ESI-MS:m/z 688.3 (M+H)+.

(R)-3-Amino-1((R)-3-(1-(3-methoxypropyl)-1H-benzo[d]imidazol-2-yl)piperidin-1-yl)-4-(4'-(methylsulfonyebiphenyl-4-yl)butan-1-one (165) was prepared as described for Example 64, Step B and was purified by preparatory LC/MS (20-40% CH$_3$CN in H$_2$O) to give the product 165 as a TFA salt (41 mg, 63% yield over two steps). 1H NMR (400 MHz, DMSO-d$_6$) δ ppm 1.51 (br. s., 1H) 1.75-2.19 (m, 5H) 2.63-3.48 (m, 15H) 3.76 (br. s., 1H) 4.06-4.67 (m, 4H) 7.44 (m, 4H) 7.69-7.80 (m, 4H) 7.94 (m, 4H). ESI-MS:m/z 589.2 (M+H)+.

Example 75

Synthesis of (R)-3-amino-4-(4-(3,5-dimethylisoxazol-4-yl)phenyl)-1-((R)-3-(1-(3-methoxypropyl)-1H-benzo[d]imidazol-2-yl)piperidin-1-yl)butan-1-one (166)

75A

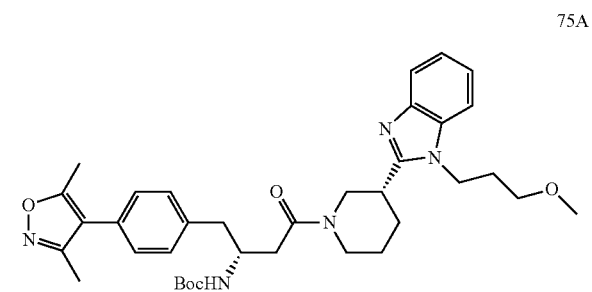

74A tert-Butyl(R)-1-(4-(3,5-dimethylisoxazol-4-yl)phenyl)-4-((R)-3-(1-(3-methoxypropyl)-1H-benzo[d]imidazol-2-yl)piperidin-1-yl)-4-oxobutan-2-ylcarbamate (75A) was prepared as described for Example 64, Step A. ESI-MS:m/z 629.4 (M+H)+.

165

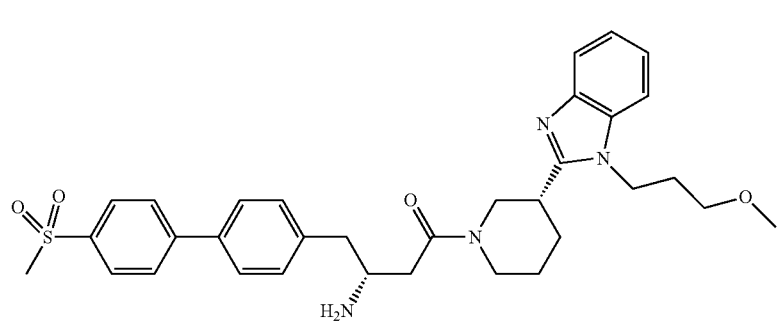

166

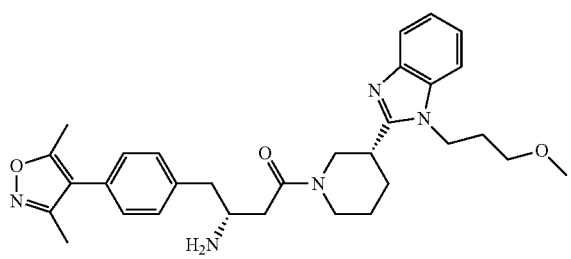

(R)-3-Amino-4-(4-(3,5-dimethylisoxazol-4-yl)phenyl)-1-aR)-3-(1-(3-methoxypropyl)-1H-benzo[d]imidazol-2-yl)piperidin-1-yl)butan-1-one (166) was prepared as described for Example 64, Step B and was purified by preparatory LC/MS (20-40% CH₃CN in H₂O) to give the product 166 as a TFA salt (35 mg, 58% yield over two steps). ESI-MS:m/z 530.2 (M+H)⁺.

Example 76

Synthesis of (R)-3-amino-4-(4-(2-chloropyridin-3-yl)phenyl)-1-((R)-3-(1-(3-methoxypropyl)-1H-benzo[d]imidazol-2-yl)piperidin-1-yl)butan-1-one (167)

76A

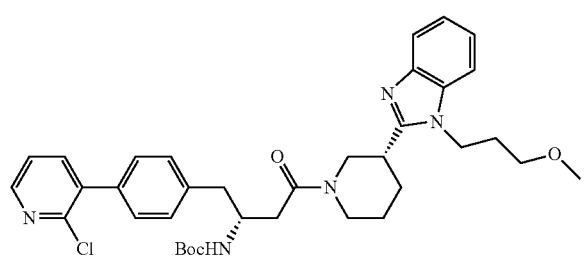

tert-Butyl(R)-1-(4-(2-chloropyridin-3-yl)phenyl)-4-((R)-3-(1-(3-methoxypropyl)-1H-benzo[d]imidazol-2-yl)piperidin-1-yl)-4-oxobutan-2-ylcarbamate (76A) was prepared as described for Example 64, Step A. ESI-MS:m/z 645.3 (M+H)⁺.

167

(R)-3-Amino-4-(4-(2-chloropyridin-3-yl)phenyl)-1((R)-3-(1-(3-methoxypropyl)-1H-benzo[d]imidazol-2-yl)piperidin-1-yl)butan-1-one (167) was prepared as described for Example 64, Step B and was purified 167 by preparatory LC/MS (20-40% CH₃CN in H₂O) to give the product as a TFA salt (34 mg, 56% yield over two steps). ESI-MS:m/z 546.2 (M+H)⁺.

Example 77

Synthesis of 4% ((R)-2-amino-4-((R)-3-(1-(3-methoxypropyl)-1H-benzo[d]imidazol-2-yl)piperidin-1-yl)-4-oxobutyl)biphenyl-4-carboxamide (168)

77A

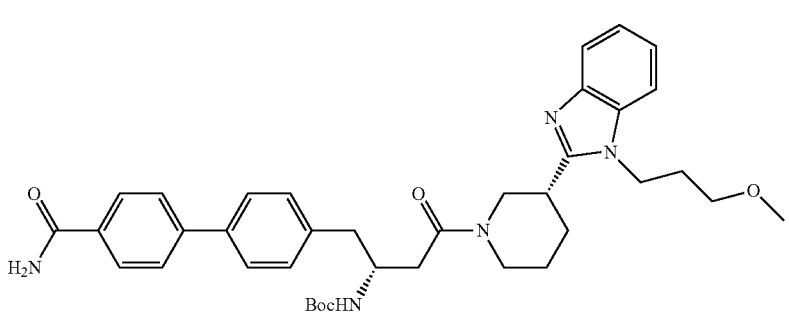

tert-Butyl(R)-1-(4'-carbamoylbiphenyl-4-yl)-4-((R)-3-(1-(3-mettioxypropyl)-1H-benzo[d]imidazol-2-yl)piperidin-1-yl)-4-oxobutan-2-ylcarbamate (77A) was prepared as described for Example 64, Step A. ESI-MS:m/z 653.4 (M+H)⁺.

168

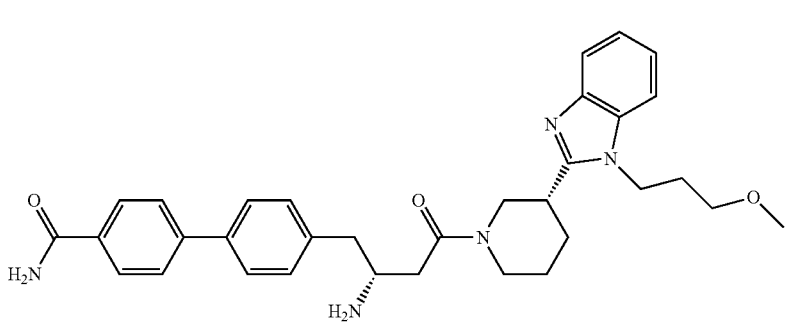

4'-((R)-2-Amino-4-((R)-3-(1-(3-methoxypropyl)-1H-benzo[d]imidazol-2-yl)piperidin-1-yl)-4-oxobutyl)biphenyl-4-carboxamide (168) was prepared as described for Example 64, Step B and was purified by preparatory LC/MS (20-40% CH$_3$CN in H$_2$O) to give the product 168 as a TFA salt (37 mg, 60% yield over two steps). 1H NMR (400 MHz, DMSO-d$_6$) δ ppm 1.51 (br. s., 1H) 1.75-2.19 (m, 5H) 2.61-3.47 (m, 12H) 3.75 (br. s., 1H) 4.07-4.67 (m, 4H) 7.34-7.48 (m, 5H) 7.74 (m, 6H) 7.97 (m, 3H). ESI-MS:mh 554.3 (M+H)$^+$.

Example 78

Synthesis of 5-(4-((R)-2-amino-4-((R)-3-(1-(3-methoxypropyl)-1H-benzo[d]imidazol-2-yl)piperidin-1-yl)-4-oxobutyl)phenyl)pyrimidine-2,4(1H,3H)-dione (169)

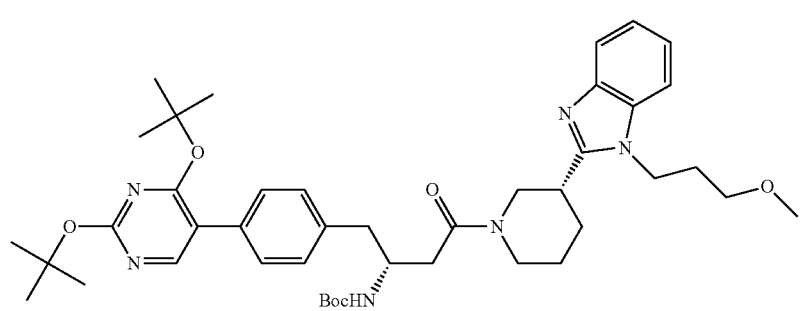

78A tert-Butyl(R)-1-(4-(2,4-di-tert-butoxypyrimidin-5-yl)phenyl)-4-((R)-3-(1-(3-methoxypropyl)-1H-benzo[d]imidazol-2-yl)piperidin-1-yl)-4-oxobutan-2-ylcarbamate (78A) was prepared as described for Example 64, Step A. ESI-MS:m/z 757.7 (M+H)$^+$.

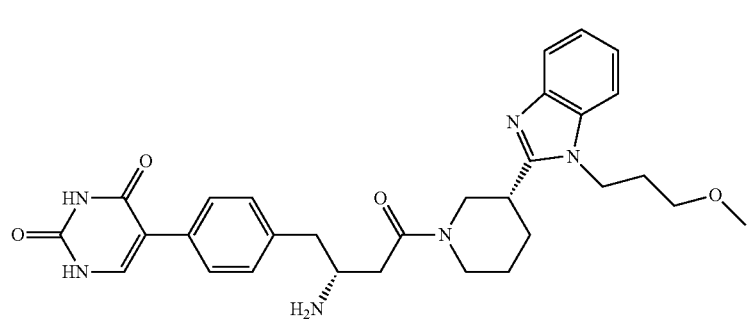

169

5-(4-((R)-2-amino-4-((R)-3-(1-(3-methoxypropyl)-1H-benzo[d]imidazol-2-yl)piperidin-1-yl)-4-oxobutyl)phenyl)pyrimidine-2,4(1H,3H)-dione (169) was prepared as described for Example 64, Step B and was purified by preparatory LC/MS (10-35% CH$_3$CN in H$_2$O) to give the product 169 as a TFA salt (36 mg, 68% yield over two steps). 1H NMR (400 MHz, DMSO-d$_6$) δ ppm 1.50 (br. s., 1H) 2.06 (d, J=115.92 Hz, 5H) 2.61-3.45 (m, 12H) 3.70 (br. s., 1H) 4.39 (d, J=15.41Hz, 4H) 7.26 (m, 2H) 7.43 (m, 2H) 7.55 (m, 2H) 7.61 (m, 1H) 7.74 (m, 2H) 11.17-11.23 (m, 1H) 11.28 (m, 1H). ESI-MS:m/z 545.2 (M+H)$^+$.

Example 79

Synthesis of (R)-3-amino-4-(4'-aminobiphenyl-4-yl)-1-((R)-3-(1-(3-methoxypropyl)-1H-benzo[d]imidazol-2-yl)piperidin-1-yl)butan-1-one (170)

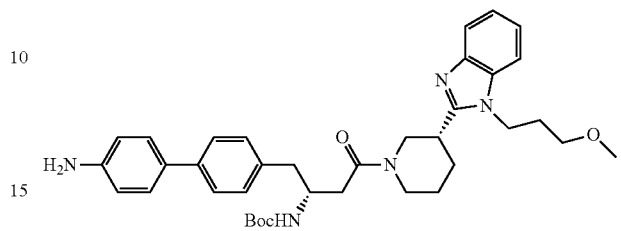

79A tert-Butyl (R)-1-(4'-aminobiphenyl-4-yl)-4-((R)-3-(1-(3-methoxypropyl)-1H-benzo[d]imidazol-2-yl)piperidin-1-yl)-4-oxobutan-2-ylcarbamate (79A) was prepared as described for Example 64, Step A. ESI-MS:m/z 626.5 (M+H)$^+$.

170

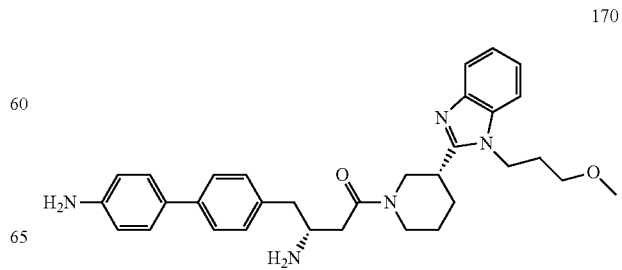

(R)-3-Amino-4-(4'-aminobiphenyl-4-yl)-1-((R)-3-(1-(3-methoxypropyl)-1H-benzo[d]imidazol-2-yl)piperidin-1-yl)butan-1-one (170) was prepared as described for Example 64, Step B and was purified by preparatory LC/MS (10-40% $CH_3CN$ in $H_2O$) to give the product 170 as a TFA salt (34 mg, 65% yield over two steps). 1H NMR (400 MHz, DMSO-$d_6$) δ ppm 1.52 (m, 1H) 1.74-2.20 (m, 5H) 2.59-3.47 (m, 12H) 3.72 (br. s., 1H) 4.08-4.68 (m, 4H) 6.96 (m, 2H) 7.32 (m, 2H) 7.40-7.62 (m, 6H) 7.71-7.81 (m, 2H). ESI-MS:m/z 526.2 $(M+H)^+$.

Example 80

Synthesis of 1-(4'-((R)-2-amino-4-((R)-3-(1-(3-methoxypropyl)-1H-benzo[d]imidazol-2-yl)piperidin-1-yl)-4-oxobutyphiphenyl-4-yl)-3-cyclopropylurea (171)

1-(4'-((R)-2-Amino-4-((R)-3-(1-(3-methoxypropyl)-1H-benzo[d]imidazol-2-yl)piperidin-1-yl)-4-oxobutyl)biphenyl-4-yl)-3-cyclopropylurea (171) was prepared as described for Example 64, Step B and was purified by preparatory LC/MS (20-40% $CH_3CN$ in $H_2O$) to give the product 171 as a TFA salt (29 mg, 49% yield over two steps). $^1$H NMR (400 MHz, DMSO-$d_6$) δ ppm 0.37-0.44 (m, 2H) 0.60-0.68 (m, 2H) 1.50 (br. s., 1H) 1.74-2.18 (m, 5H) 2.52-3.47 (m, 12H) 3.72 (br. s., 1H) 4.06-4.66 (m, 5H) 6.56 (br. s., 1H) 7.33 (m, 2H) 7.37 7.47 (m, 2H) 7.48-7.57 (m, 4H) 7.61 (m, 2H) 7.70 (m, 2H) 8.54 (m, 1H). ESI-MS:m/z 609.3 $(M+H)^+$.

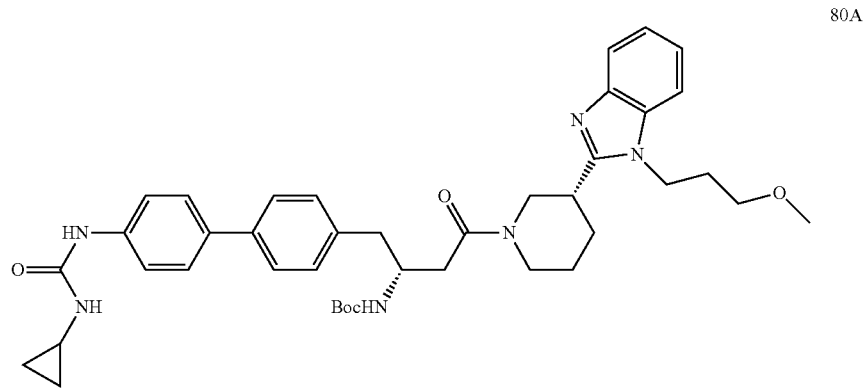

80A tert-Butyl(R)-1-(4'-(3-cyclopropylureido)biphenyl-4-yl)-4-((R)-3-(1-(3-methoxypropyl)-1H-benzo[d]imidazol-2-yl)piperidin-1-yl)-4-oxobutan-2-ylcarbamate (80A) was prepared as described for Example 64, Step A. ESI-MS:m/z 709.6 $(M+H)^+$.

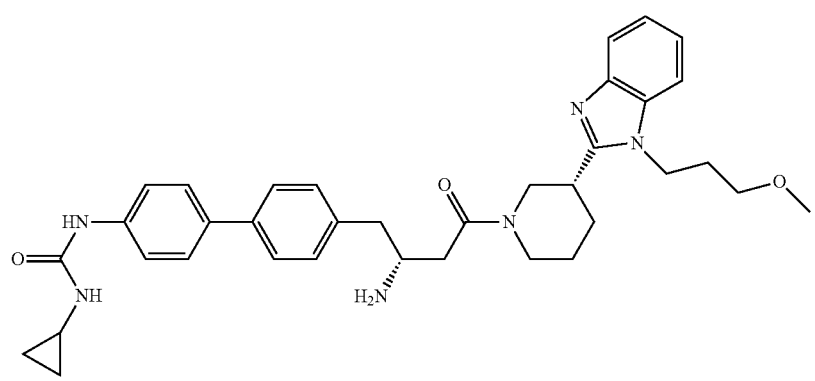

171

Example 81

Synthesis of 1-(4'-((R)-2-amino-4-((R)-3-(1-(3-methoxypropyl)-1H-benzo[d]imidazol-2-yl)piperidin-1-yl)-4-oxobutyl)biphenyl-4-yl)urea (172)

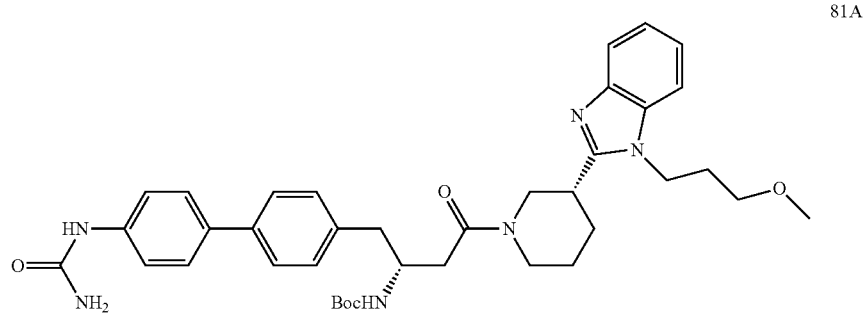

81A tert-Butyl(R)-4-((R)-3-(1-(3-methoxypropyl)-1H-benzo[d]imidazol-2-yl)piperidin-1-yl)-4-oxo-1-(4'-ureidobiphenyl-4-yl)butan-2-ylcarbamate (81A) was prepared as described for Example 64, Step A. ESI-MS:m/z 669.6 (M+H)$^+$.

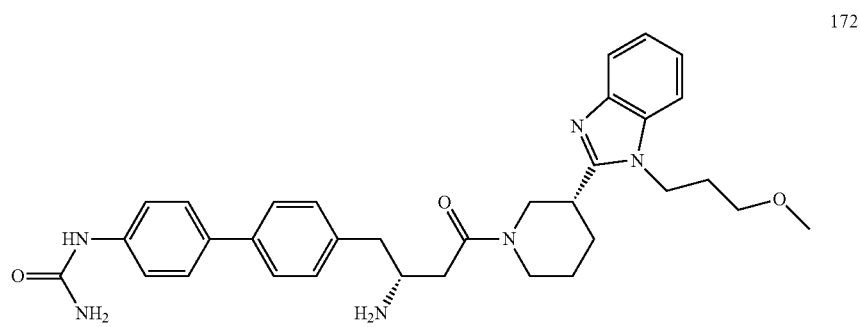

172

1-(4'-((R)-2-amino-4-((R)-3-(1-(3-methoxypropyl)-1H-benzo[d]imidazol-2-yl)piperidin-1-yl)-4-oxobutyl)biphenyl-4-yl)urea (172) was prepared as described for Example 64, Step B and was purified by preparatory LC/MS (15-35% CH$_3$CN in H$_2$O) to give the product 172 as a TFA salt (27 mg, 49% yield over two steps). 1H NMR (400 MHz, DMSO-d$_6$) δ ppm 1.52 (m, 1H) 1.74-2.19 (m, 5H) 2.59-3.46 (m, 10H) 3.66-3.88 (m, 1H) 4.36 (m, 6H) 5.92 (br. s., 2H) 7.33 (t, J=8.84 Hz, 2H) 7.44 (d,1=8.84 Hz, 2H) 7.47-7.56 (m, 4H) 7.60 (m, 2H) 7.73 (m, 2H) 8.71 (m, 1H). ESI-MS:m/z 569.2 (M+H)$^+$.

Example 82

Synthesis of 1-(4'-((R)-2-amino-4-((R)-3-(1-(3-methoxypropyl)-1H-benzo[d]imidazol-2-yl)piperidin-1-yl)-4-oxobutyl)biphenyl-4-yl)-3-ethylurea (173)

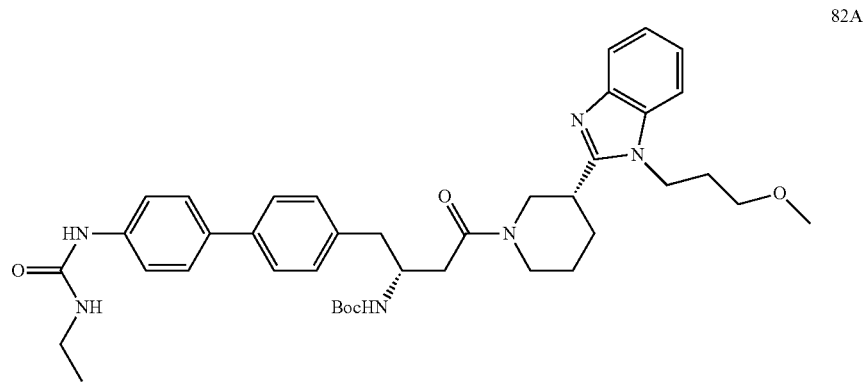

82A tert-Butyl(R)-1-(4'-(3-ethylureido)biphenyl-4-yl)-4-((R)-3-(1-(3-methoxypropyl)-1H-benzo[d]imidazol-2-yl)piperidin-1-yl)-4-oxobutan-2-ylcarbamate (82A) was prepared as described for Example 64, Step A. ESI-MS:m/z 697.6 (M+H)+.

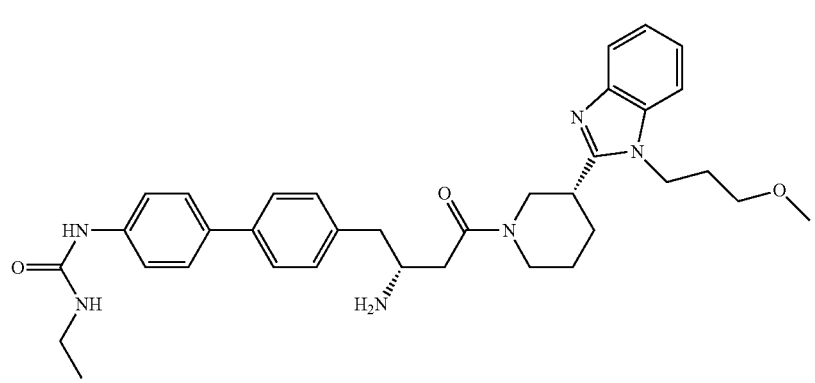

173

(1-(4'-((R)-2-Amino-4-((R)-3-(1-(3-methoxypropyl)-1H-benzo[d]imidazol-2-yl)piperidin-1-yl)-4-oxobutyl)biphenyl-4-yl)-3-ethylurea (173) was prepared as described for Example 64, Step B and was purified by preparatory LC/MS (20-35% CH3CN in H2O) to give the product 173 as a TFA salt (30 mg, 52% yield over two steps). 1H NMR (400 MHz, DMSO-d6) δ ppm 1.06 (m, 3H) 1.50 (br. s., 1H) 1.73-2.21 (m, 5H) 2.60-3.47 (m, 12H) 3.72 (br. s., 1H) 4.05-4.68 (m, 6H) 6.24 (br. s., 1H) 7.33 (m, 2H) 7.37-7.46 (m, 2H) 7.47-7.56 (m, 4H) 7.60 (m, 2H) 7.72 (m, 2H) 8.62 (m, 1H). ESI-MS:m/z 597.3 (M+H)+.

Example 83

Synthesis of 3-(4'-((R)-2-amino-4-((R)-3-(1-(3-methoxypropyl)-1H-benzo[d]imidazol-2-yl)piperidin-1-yl)-4-oxobutyl)biphenyl-4-yl)-1,1-dimethylurea (174)

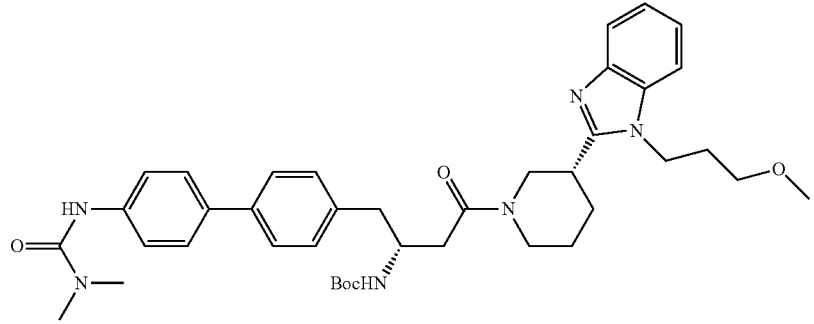

83A tert-Butyl(R)-1-(4'-(3,3-dimethylureido)biphenyl-4-yl)-4-((R)-3-(1-(3-methoxypropyl)-1H-benzo[d]hnidazol-2-yl)piperidin-1-yl)-4-oxobutan-2-ylcarbamate (83A) was prepared as described for Example 64, Step A. ESI-MS:m/z 697.6 (M+H)+.

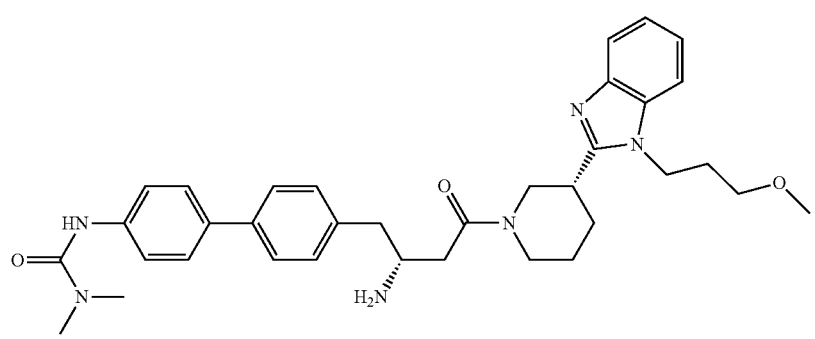

174

3-(4'-((R)-2-amino-4-((R)-3-(1-(3-methoxypropyl)-1H-benzo[d]imidazol-2-yl)piperidin-1-yl)-4-oxobutyphiphenyl-4-yl)-1,1-dimethylurea (174) was prepared as described for Example 64, Step B and was purified by preparatory LC/MS (20-40% $CH_3CN$ in $H_2O$) to give the product 174 as a TFA salt (26 mg, 45% yield over two steps). 1H NMR (400 MHz, DMSO-$d_6$) δ ppm 1.50 (br. s., 1H) 1.74-2.19 (m, 5H) 2.61-3.48 (m, 16H) 3.71 (br. s., 1H) 4.06-4.69 (m, 6H) 7.33 (m, 4H) 7.52-7.66 (m, 6H) 7.72 (m, 2H) 8.39 (s, 1H). ESI-MS:m/z 597.3 $(M+H)^+$.

1-(4'-((R)-2-Amino-4-((R)-3-(1-(3-methoxypropyl)-1H-benzo[d]imidazol-2-yl)piperidin-1-yl)-4-oxobutyl)biphenyl-4-yl)-3-methylurea (175) was prepared as described for Example 64, Step B and was purified by preparatory LC/MS (20-30% $CH_3CN$ in $H_2O$) to give the product 175 as a TFA salt (29 mg, 52% yield over two steps). 1H NMR (400 MHz, DMSO-$d_6$) δ ppm 1.42-1.59 (m, 1H) 1.73-2.20 (m, 5H) 2.58-3.48 (m, 14H) 3.65-3.89 (m, 1H) 4.07-4.68 (m, 5H) 6.12-6.21 (m, 1H) 7.33 (m, 2H) 7.36-7.56 (m, 6H) 7.59 (m, 2H) 7.69-7.80 (m, 2H) 8.72 (s, 1H). ESI-MS:m/z 583.2 $(M+H)^+$.

Example 84

Synthesis of 1-(4'-((R)-2-amino-4-((R)-3-(1-(3-methoxypropyl)-1H-benzo[d]imidazol-2-yl)piperidin-1-yl)-4-oxobutyl)biphenyl-4-yl)-3-methylurea (175)

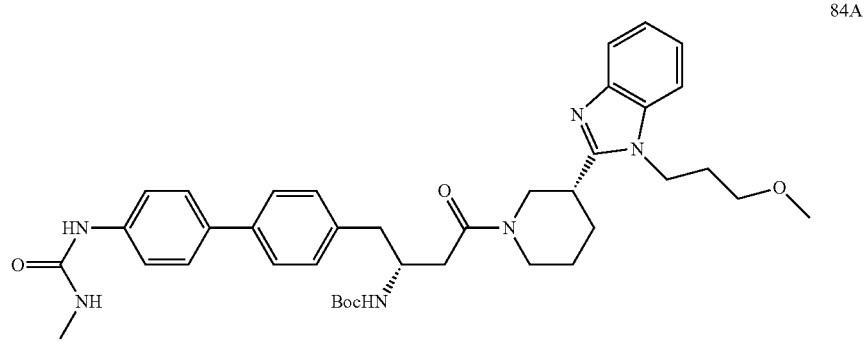

84A tert-Butyl(R)-4-((R)-3-(1-(3-methoxypropyl)-1H-benzo[d]imidazol-2-yl)piperidin-1-yl)-1-(4'-(3-methylureido)biphenyl-4-yl)-4-oxobutan-2-ylcarbamate (84A) was prepared as described for Example 64, Step A. ESI-MS:m/z 683.5 $(M+H)^+$.

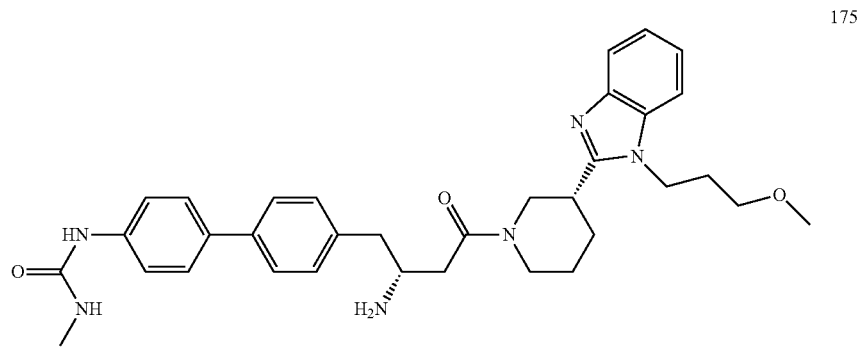

175

Example 85

Synthesis of methyl 4'-((R)-2-amino-4-((R)-3-(1-(3-methoxypropyl)-1H-benzo[d]imidazol-2-yl)piperidin-1-yl)-4-oxobutyl)biphenyl-4-ylcarbamate (176)

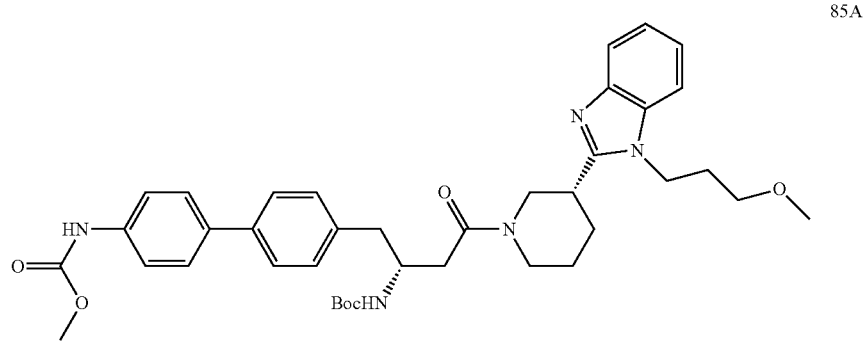

85A

[4'-((R)-2-tert-Butoxylcarbonylamino-4-{(R)-3-[1-(3-methoxy-propyl)-1H-benzoimidazol-2-yl]-piperidin-1-yl}-4-oxo-butyl)-biphenyl-4-yl]-carbamic acid methyl ester (85A) was prepared as described for Example 64, Step A. ESI-MS:m/z 684.6 (M+H)+.

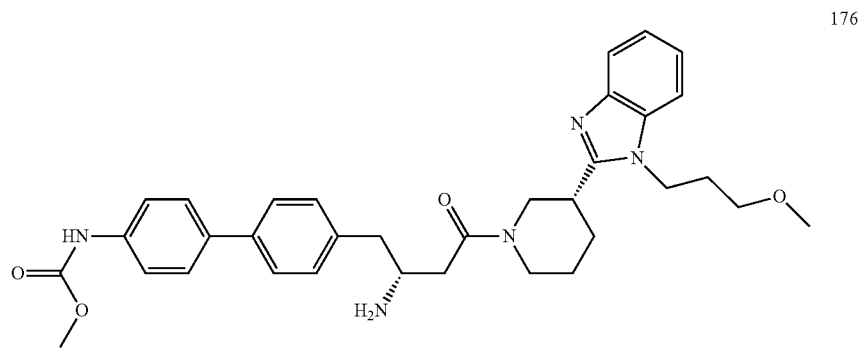

176

Methyl 4'-((R)-2-amino-4-((R)-3-(1-(3-methoxypropyl)-1H-benzo[d]imidazol-2-yl)piperidin-1-yl)-4-oxobutyl)biphenyl-4-ylcarbamate (176) was prepared as described for Example 64, Step B and was purified by preparatory LC/MS (20-35% CH₃CN in H₂O) to give the product 176 as a TFA salt (41 mg, 72% yield over two steps). 1H NMR (400 MHz, DMSO-d₆) δ ppm 1.50 (br. s., 1H) 1.90 (m, 5H) 2.59-3.47 (m, 11H) 3.68 (s, 4H) 4.34 (m, 5H) 7.34 (m, 2H) 7.38-7.48 (m, 2H) 7.53-7.66 (m, 6H) 7.73 (dm, 2H) 9.77 (s, 1H). ESI-MS: m/z 584.2 (M+H)+.

Example 86

Synthesis of 4'-((R)-2-amino-4-((R)-3-(1-(3-methoxypropyl)-1H-benzo[d]imidazol-2-yl)piperidin-1-yl)-4-oxobutyl)-N-(2-methoxyethyl)biphenyl-4-carboxamide (177)

Step A.

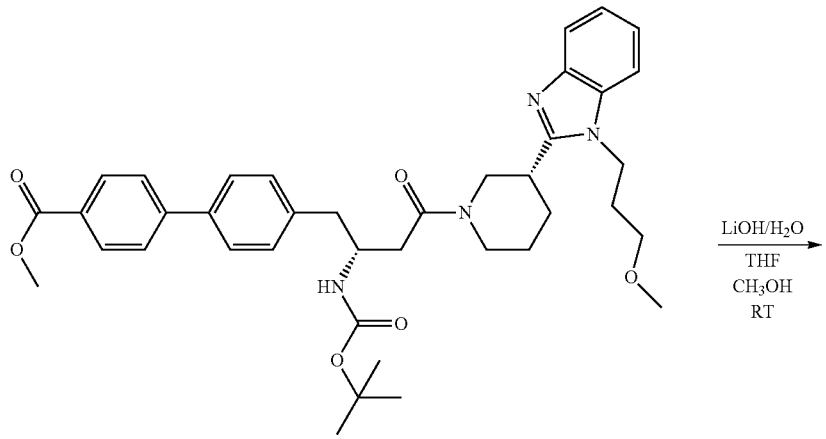

53A

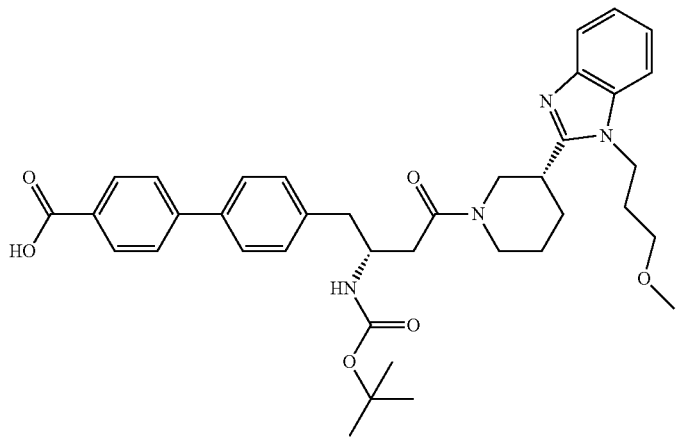

86A

Methyl 4'-((R)-2-(tert-butoxycarbonylamino)-4-((R)-3-(1-(3-methoxypropyl)-1H-benzo[d]imidazol-2-yl)piperidin-1-yl)-4-oxobutyl)biphenyl-4-carboxylate (53A) (prepared by the procedure for Example 53, Step A) (0.815 mmoles, 0.545 g) was added to a 25 mL round-bottomed flask equipped for stirring under nitrogen. Tetrahydrofuran (2 mL), methanol (1 mL), and LiOH (2.0 mmoles, 1.0 mL of 2N in $H_2O$) were then added and the resultant solution was allowed to stir at room temperature for 16 hrs. Citric acid (2.09 mmoles, 0.403 g) in $H_2O$ (1 mL) was then added and the resultant solution was concentrated in-vacuo, filtered, and then purified by preparative LC/MS. The resultant fractions were collected and the solvent was removed in-vacuo affording a brown colored oil. This oil was re-dissolved in $CH_3CN$ (1 mL) and water (2 mL). The resultant solution was frozen and lyophilized to afford 4'-((R)-2-(tert-butoxycarbonylamino)-4-((R)-3-(1-(3-methoxypropyl)-1H-benzo[d]imidazol-2-yl)piperidin-1-yl)-4-oxobutyl)biphenyl-4-carboxylic acid (86A) as a tan flocculent solid (0.637 mmoles, 0.417 g, 78% yield). ESI-MS: m/z 655.5 (M+H)$^+$.

Step B.

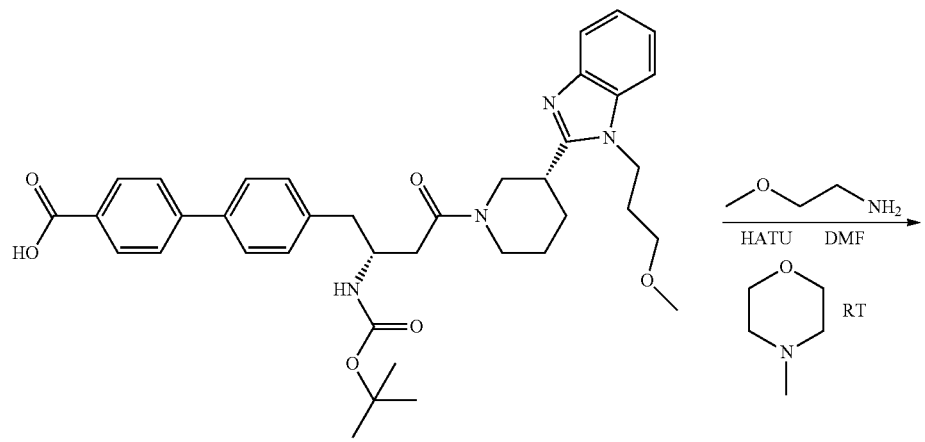

86A

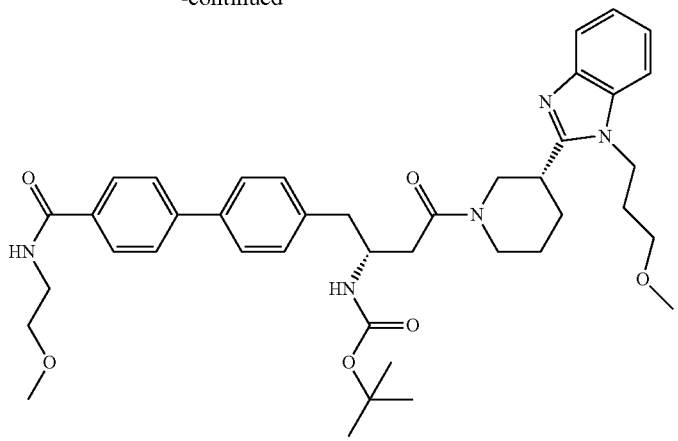

86B

4'-((R)-2-(tert-butoxycarbonylamino)-4-((R)-3-(1-(3-methoxypropyl)-1H-benzo[d]imidazol-2-yl)piperidin-1-yl)-4-oxobutyl)biphenyl-4-carboxylic acid (86A) (0.061 mmoles, 0.040 g) was added to a 5 mL round-bottomed flask equipped for stirring under nitrogen. DMF (1.0 mL), 2-methoxyethanamine (0.079 mmoles, 0.007 mL) and N-methylmorpholine (0.183 mmoles, 0.020 mL) were then added and the solution was allowed to stir at it for 5 min. HATU (0.079 mmoles, 0.030 g) was added and the resultant solution was stirred at room temperature for 3 hrs. The reaction solution was then directly purified by preparative LC/MS (20-65% $CH_3CN$ in $H_2O$). The resultant fractions were collected and the solvent was removed in-vacuo affording tert-butyl (R)-1-(4'-(2-methoxyethylcarbamoyl)biphenyl-4-yl)-4-((R)-3-(1-(3-methoxypropyl)-1H-benzo[d]imidazol-2-34)piperidin-1-yl)-4-oxobutan-2-ylcarbamate (86B) as a clear oil. (0.053 mmoles, 0.038 g, 86% yield). ESI-MS: m/z 712.4 (M+H)$^+$.

Step C.

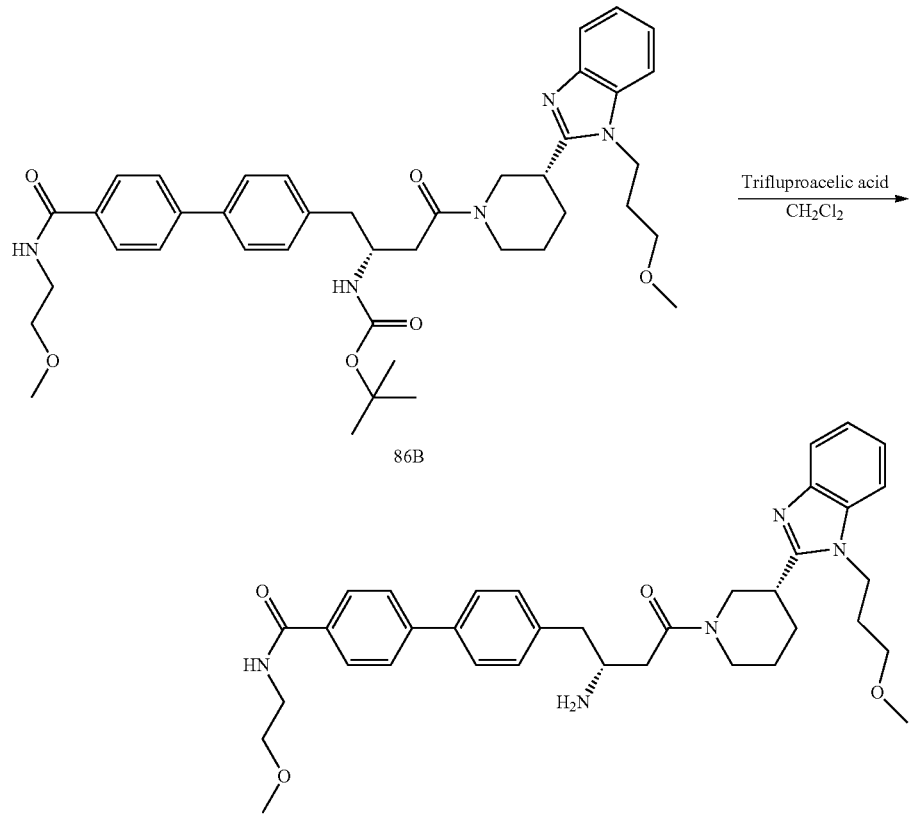

86B

177 tert-butyl (R)-1-(4'-(2-methoxyethylcarbamoyl)biphenyl-4-yl)-4-((R)-3-(1-(3-methoxypropyl)-1H-benzo[d]imidazol-2-yl)piperidin-1-yl)-4-oxobutan-2-ylcarbamate (86B) (0.053 mmoles, 0.038 g) was added to a 10 mL round-bottomed flask equipped for stirring under nitrogen. Dichloromethane (1 mL) and trifluoroacetic acid (1 mL) were then added and the resultant solution was allowed to stir under nitrogen for 4 hrs. The solvent was removed in-vacuo affording a clear colored oil. This oil was re-dissolved in Methanol (3 mL), filtered, and then purified by preparative LC/MS (0.5-50% $CH_3CN$ in $H_2O$). The resultant fractions were collected and the solvent was removed in-vacuo affording a clear colored oil. This oil was re-dissolved in $CH_3CN$ (1 mL) and water (2 mL). The resultant solution was frozen and lyophilized to afford 4'-((R)-2-amino-4-((R)-3-(1-(3-methoxypropyl)-1H-benzo[d]imidazol-2-yl)piperidin-1-yl)-4-oxobutyl)-N-(2-methoxyethyl)biphenyl-4-carboxamide (177) as its trifluoroacetic acid salt and as a white flocculent solid (0.033 mmoles, 0.024 g, 62% yield). ESI-MS: m/z 612.3 $(M+H)^+$. $^1$H NMR (400 MHz, DMSO-$d_6$) δ ppm 1.40-1.62 (m, 1H) 1.74-2.21 (m, 5H) 2.58-2.86 (m, 3H) 2.90-3.16 (m, 4H) 3.16-3.25 (m, 3H) 3.28 (s, 3H) 3.30-3.51 (m, 7H) 3.64-4.19 (m, 2H) 4.27-4.70 (m, 4H) 7.36-7.50 (m, 4H) 7.68-7.82 (m, 6H) 7.95 (dd, J=8.46, 2.40 Hz, 2H) 8.54-8.63 (m, 1H).

Other compounds that were prepared by the procedure of Example 86 are listed in Table IV.

TABLE IV

| Compound No. | Structure/Name | Physical Properties |
|---|---|---|
| 178 | 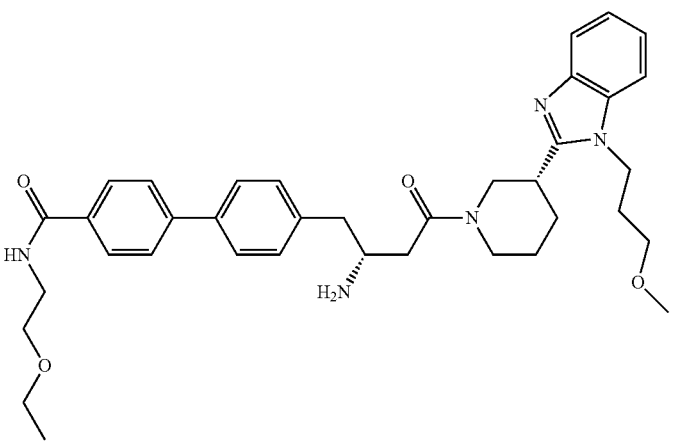<br>4'-((R)-2-amino-4-((R)-3-(1-(3-methoxypropyl)-1H-benzo[d]imidazol-2-yl)piperidin-1-yl)-4-oxobutyl)-N-(2-ethoxyethyl)biphenyl-4-carboxamide | ESI-MS: m/z 626.3 $(M + H)^+$<br>$^1$H NMR (400 MHz, DMSO-$d_6$) δ ppm 1.12 (t, J = 6.95 Hz, 3 H) 1.40-1.60 (m, 1 H) 1.72-2.18 (m, 5 H) 2.61-2.86 (m, 3 H) 2.89-3.23 (m, 8 H) 3.23-3.90 (m, 11 H) 4.01-4.65 (m, 3 H) 7.27-7.46 (m, 4 H) 7.62-7.81 (m, 6 H) 7.92-8.00 (m, 2 H) 8.59 (t, J = 5.68 Hz, 1 H) |
| 179 | 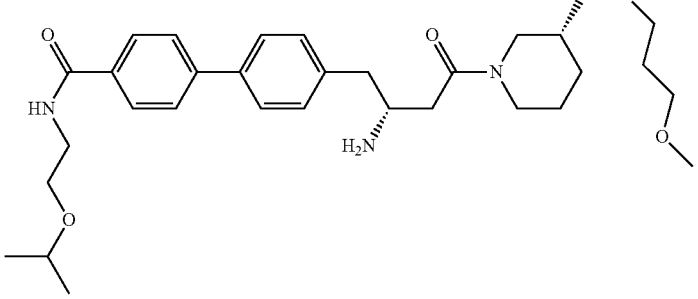<br>4'-((R)-2-amino-4-((R)-3-(1-(3-methoxypropyl)-1H-benzo[d]imidazol-2-yl)piperidin-1-yl)-4-oxobutyl)-N-(2-isopropoxyethyl)biphenyl-4-carboxamide | ESI-MS: m/z 640.4 $(M + H)^+$.<br>$^1$H NMR (400 MHz, DMSO-$d_6$) δ ppm 1.09 (d, J = 6.06 Hz, 6 H) 1.41-1.61 (m, 1 H) 1.73-2.19 (m, 6 H) 2.60-2.85 (m, 3H) 2.90-3.15 (m, 4 H) 3.15-3.27 (m, 3 H) 3.29-3.46 (m, 4 H) 3.47-3.62 (m, 4 H) 3.69-4.14 (m, 2 H) 4.25-4.68 (m, 3 H) 7.35-7.49 (m, 4 H) 7.68-7.81 (m, 6 H) 7.92-8.00 (m, 2 H) 8.53-8.60 (m, 1 H) |

TABLE IV-continued

| Compound No. | Structure/Name | Physical Properties |
| --- | --- | --- |
| 180 | 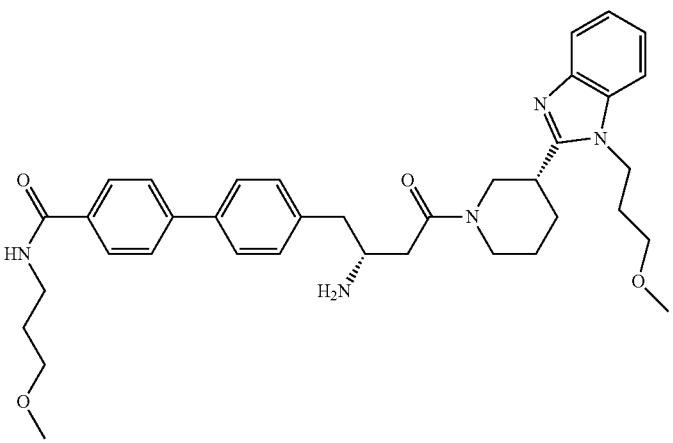

4'-((R)-2-amino-4-((R)-3-(1-(3-methoxypropyl)-1H-benzo[d]imidazol-2-yl)piperidin-1-yl)-4-oxobutyl)-N-(3-methoxypropyl)biphenyl-4-carboxamide | ESI-MS: m/z 626.4 (M + H)$^+$.<br>$^1$H NMR (400 MHz, DMSO-d$_6$) δ ppm 1.37-1.63 (m, 1 H) 1.70-2.23 (m, 7 H) 2.59-2.86 (m, 3 H) 2.89-3.16 (m, 4 H) 3.16-3.27 (m, 6 H) 3.27-3.47 (m, 7 H) 3.67-4.15 (m, 2 H) 4.26-4.70 (m, 4 H) 7.33-7.52 (m, 4 H) 7.64-7.81 (m, 6 H) 7.86-7.97 (m, 2 H) 8.48-8.57 (m, 1 H) |
| 181 | 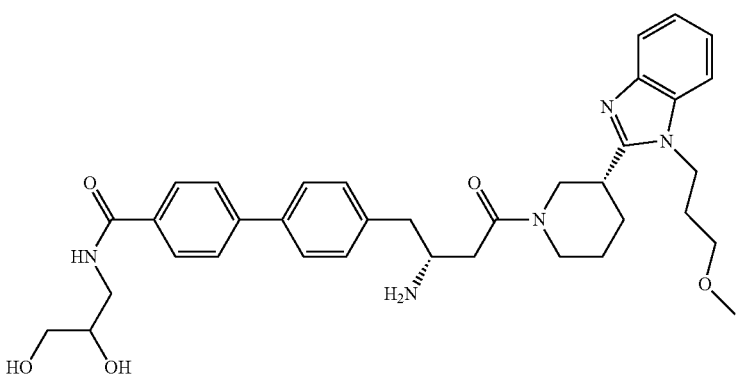

4'-((R)-2-amino-4-((R)-3-(1-(3-methoxypropyl)-1H-benzo[d]imidazol-2-yl)piperidin-1-yl)-4-oxobutyl)-N-(2,3-dihydroxypropyl)biphenyl-4-carboxamide | ESI-MS: m/z 628.3 (M + H)$^+$. |
| 182 | 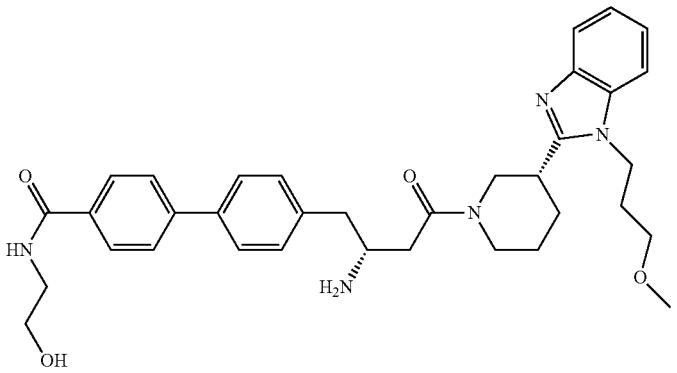

4'-((R)-2-amino-4-((R)-3-(1-(3-methoxypropyl)-1H-benzo[d]imidazol-2-yl)piperidin-1-yl)-4-oxobutyl)-N-(2-hydroxyethyl)biphenyl-4-carboxamide | ESI-MS: m/z 598.3 (M + H)$^+$. |

TABLE IV-continued

| Compound No. | Structure/Name | Physical Properties |
|---|---|---|
| 183 | 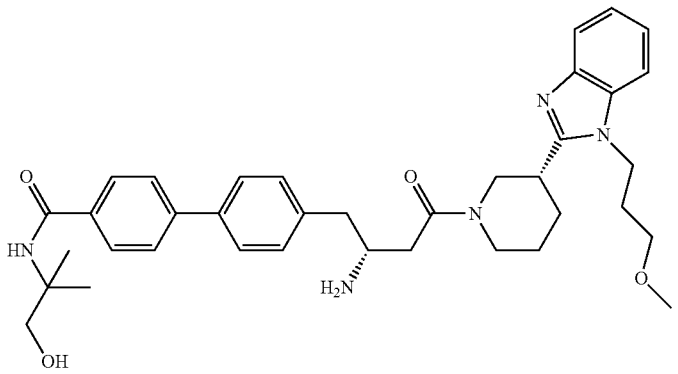

4'-((R)-2-amino-4-((R)-3-(1-(3-methoxypropyl)-1H-benzo[d]imidazol-2-yl)piperidin-1-yl)-4-oxobutyl)-N-(1-hydroxy-2-methylpropan-2-yl)biphenyl-4-carboxamide | ESI-MS: 626.3 m/z (M + H)⁺. 1H NMR (400 MHz, DMSO-d$_6$) δ ppm 1.33 (s, 6 H) 1.38-1.60 (m, 1 H) 1.71-2.18 (m, 5 H) 2.61-2.86 (m, 4 H) 2.87-3.23 (m, 7 H) 3.24-3.47 (m, 4 H) 3.65-4.08 (m, 2 H) 4.22-4.63 (m, 3 H) 7.27-7.46 (m, 4 H) 7.58 (s, 1 H) 7.63-7.80 (m, 6 H) 7.87-7.92 (m, 2 H) |
| 184 | 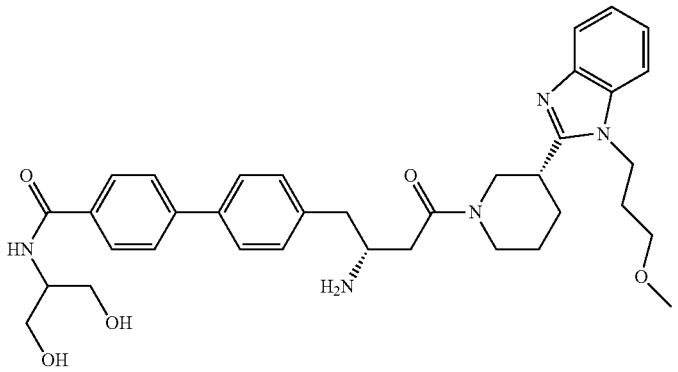

4'-((R)-2-amino-4-((R)-3-(1-(3-methoxypropyl)-1H-benzo[d]imidazol-2-yl)piperidin-1-yl)-4-oxobutyl)-N-(1,3-dihydroxypropan-2-yl)biphenyl-4-carboxamide | ESI-MS: 626.3 m/z (M + H)⁺. ¹H NMR (400 MHz, DMSO-d$_6$) δ ppm 1.40-1.58 (m, 1 H) 1.72-2.17 (m, 5 H) 2.61-2.86 (m, 3 H) 2.89-3.24 (m, 7 H) 3.24-3.47 (m, 3 H) 3.50-3.55 (m, 4 H) 3.67-4.08 (m, 4 H) 4.22-4.63 (m, 5 H) 7.26-7.47 (m, 4 H) 7.60-7.80 (m, 6 H) 7.94-8.04 (m, 3 H) |
| 185 | 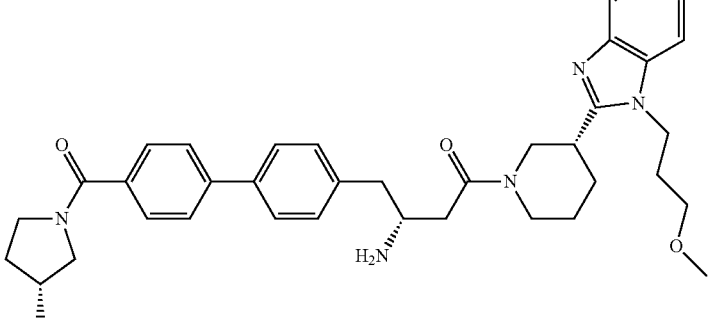

(R)-3-amino-4-(4'-((R)-3-hydroxypyrrolidine-1-carbonyl)biphenyl-4-yl)-1-((R)-3-(1-(3-methoxypropyl)-1H-benzo[d]imidazol-2-yl)piperidin-1-yl)butan-1-one | ESI-MS: 624.3 m/z (M + H)⁺. ¹H NMR (400 MHz, DMSO-d$_6$) δ ppm 1.40-1.60 (m, 1 H) 1.73-2.21 (m, 7 H) 2.58-2.85 (m, 3 H) 2.89-3.28 (m, 8 H) 3.28-3.68 (m, 8 H) 3.74 (br. s., 1 H) 3.80-4.66 (m, 5 H) 7.32-7.49 (m, 4H) 7.57-7.64 (m, 2 H) 7.66-7.77 (m, 6 H). |

TABLE IV-continued

| Compound No. | Structure/Name | Physical Properties |
|---|---|---|
| 186 | 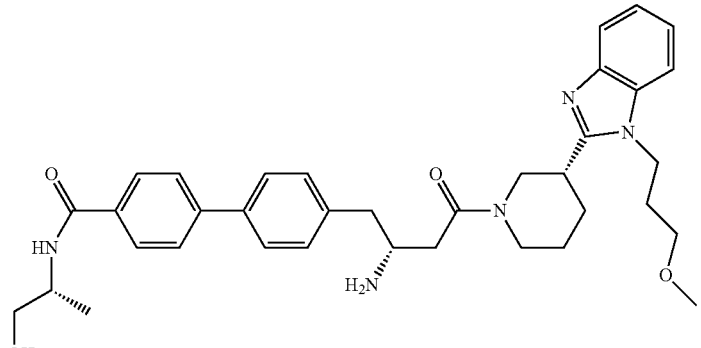<br>4'-((R)-2-amino-4-((R)-3-(1-(3-methoxypropyl)-1H-benzo[d]imidazol-2-yl)piperidin-1-yl)-4-oxobutyl)-N-((R)-1-hydroxypropan-2-yl)biphenyl-4-carboxamide | ESI-MS: 612.3 m/z (M + H)$^+$.<br>$^1$H NMR (400 MHz, DMSO-d$_6$) δ ppm 1.14 (d, J = 6.82 Hz, 3 H) 1.37-1.63 (m, 1 H) 1.72-2.21 (m, 5 H) 2.62-2.86 (m, 3 H) 2.90-3.25 (m, 7 H) 3.29-3.52 (m, 4 H) 3.74 (br. s., 1 H) 3.80-4.14 (m, 3 H) 4.25-4.66 (m, 5 H) 7.33-7.48 (m, 4 H) 7.65-7.83 (m, 6 H) 7.93-7.98 (m, 2 H) 8.10-8.19 (m, 1 H). |
| 187 | 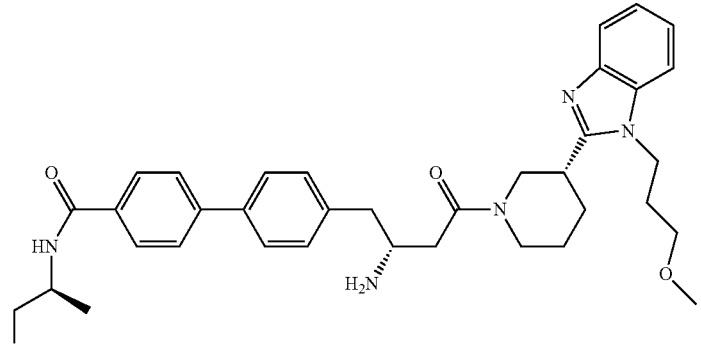<br>4'-((R)-2-amino-4-((R)-3-(1-(3-methoxypropyl)-1H-benzo[d]imidazol-2-yl)piperidin-1-yl)-4-oxobutyl)-N-((S)-1-hydroxypropan-2-yl)biphenyl-4-carboxamide | ESI-MS: 612.3 m/z (M + H)$^+$.<br>$^1$H NMR (400 MHz, DMSO-d$_6$) δ ppm 1.15 (d, J = 6.82 Hz, 3 H) 1.40-1.60 (m, 1 H) 1.72-2.21 (m, 5 H) 2.59-2.86 (m, 3 H) 2.90-3.25 (m, 7 H) 3.29-3.51 (m, 4 H) 3.74 (br. s., 1 H) 3.81-4.15 (m, 3 H) 4.27-4.68 (m, 5 H) 7.36-7.51 (m, 4 H) 7.67-7.81 (m, 6 H) 7.93-7.98 (m, 2 H) 8.16 (d, J = 8.08 Hz, 1 H). |
| 188 | 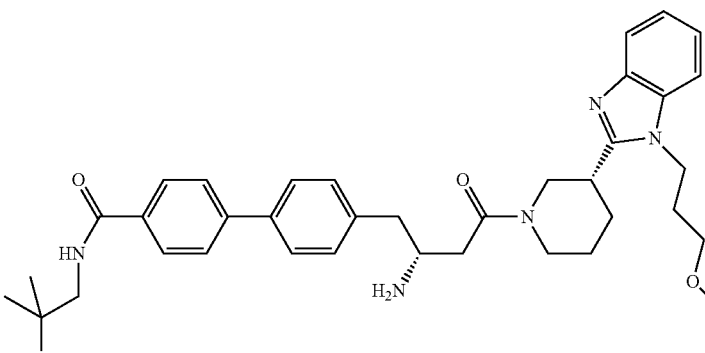<br>4'-((R)-2-amino-4-((R)-3-(1-(3-methoxypropyl)-1H-benzo[d]imidazol-2-yl)piperidin-1-yl)-4-oxobutyl)-N-(2-hydroxy-2-methylpropyl)biphenyl-4-carboxamide | ESI-MS: 612.3 m/z (M + H)$^+$.<br>$^1$H NMR (400 MHz, DMSO-d$_6$) δ ppm 1.14 (d, J = 6.82 Hz, 3 H) 1.37-1.63 (m, 1 H) 1.72-2.21 (m, 5 H) 2.62-2.86 (m, 3 H) 2.90-3.25 (m, 7 H) 3.29-3.52 (m, 4 H) 3.74 (br. s., 1 H) 3.80-4.14 (m, 3 H) 4.25-4.66 (m, 5 H) 7.33-7.48 (m, 4 H) 7.65-7.83 (m, 6 H) 7.93-7.98 (m, 2 H) 8.10-8.19 (m, 1 H). |

TABLE IV-continued

| Compound No. | Structure/Name | Physical Properties |
|---|---|---|
| 189 | 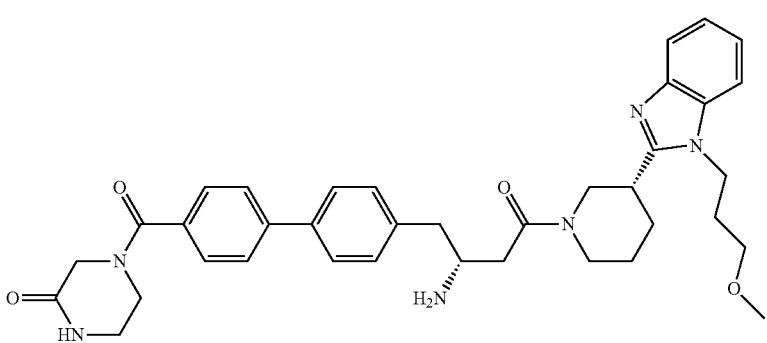

4-(4'-((R)-2-amino-4-((R)-3-(1-(3-methoxypropyl)-1H-benzo[d]imidazol-2-yl)piperidin-1-yl)-4-oxobutyl)biphenylcarbonyl)piperazin-2-one | ESI-MS: 637.4 m/z (M + H)$^+$.<br>$^1$H NMR (400 MHz, DMSO-d$_6$) δ ppm 1.39-1.61 (m, 1 H) 1.71-2.18 (m, 5 H) 2.60-2.86 (m, 3 H) 2.90-3.11 (m, 4 H) 3.12-3.47 (m, 8 H) 3.67-4.15 (m, 6 H) 4.23-4.66 (m, 4 H) 7.06-7.14 (m, 1 H) 7.30-7.58 (m, 6 H) 7.64-7.80 (m, 5 H) 8.16 (br. s., 1 H). |

Example 87

Synthesis of 4'-((R)-2-amino-4-((R)-3-(1-(3-methoxypropyl)-1H-benzo[d]imidazol-2-yl)piperidin-1-yl)-4-oxobutyl)-3-fluoro-N-(2-hydroxyethyl) biphenyl-4-carboxamide (190)

Step A.

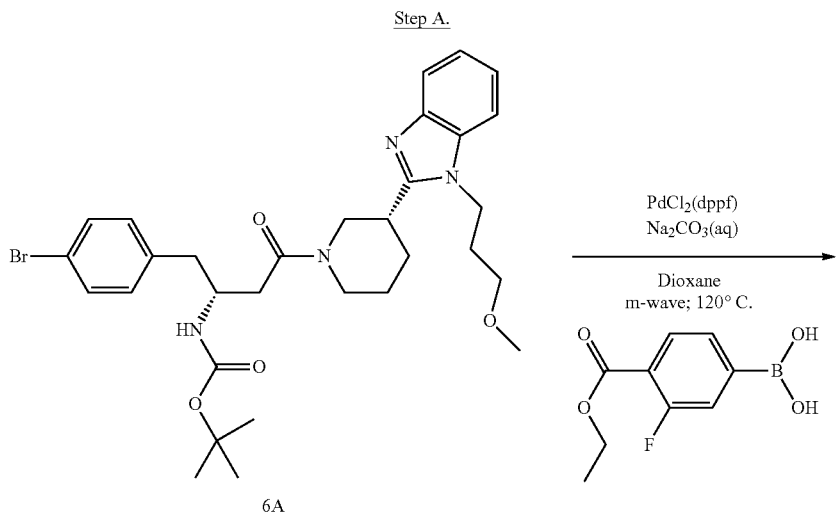

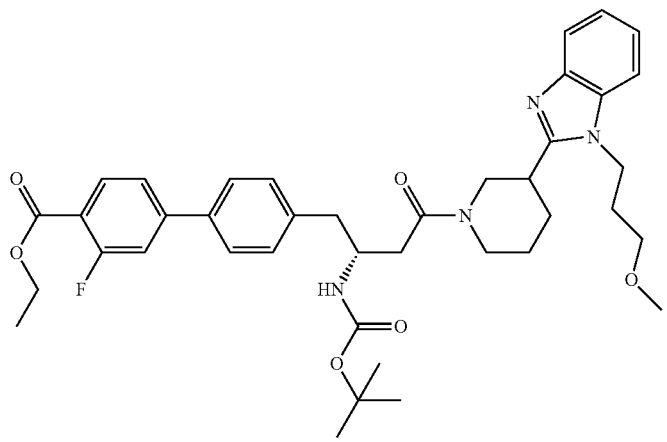

87A

Ethyl 4'-((R)-2-(tert-butoxycarbonylamino)-4-((R)-3-(1-(3-methoxypropyl)-1H-benzo[d]imidazol-2-yl)piperidin-1-yl)-4-oxobutyl)-3-fluorobiphenyl-4-carboxylate (87A) was prepared by the procedure of Example 53, Step A. ESI-MS: m/z 700.5 (M+H)$^+$.

Step B.

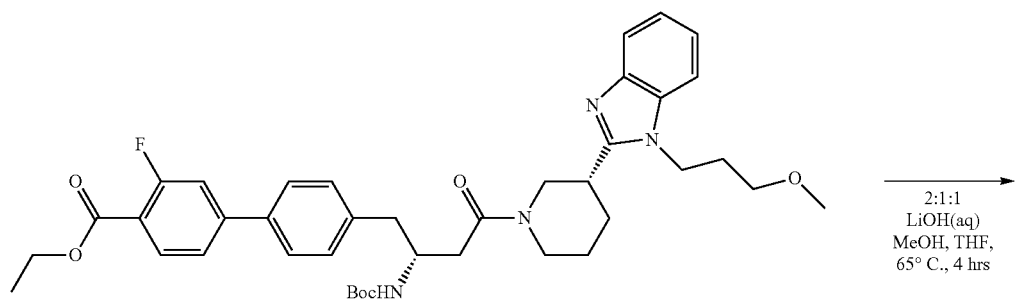

87A

2:1:1
LiOH(aq)
MeOH, THF,
65° C., 4 hrs

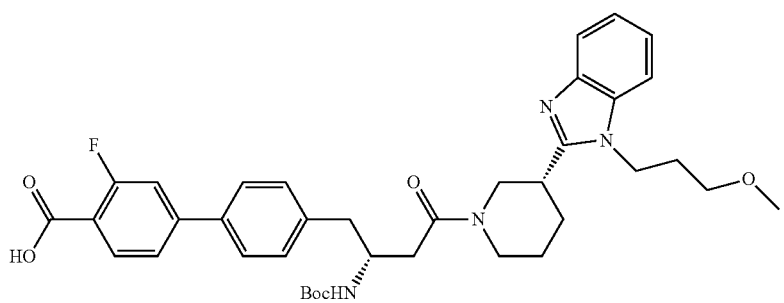

87B

4'-((R)-2-(tert-Butoxycarbonylamino)-4-((R)-3-(1-(3-methoxypropyl)-1,1-benzo[d]imidazol-2-yl)piperidin-1-yl)-4-oxobutyl)-3-fluorobiphenyl-4-carboxylic acid (87B) was prepared according to Example 86, Step A. The solvent was removed and the residue was purified by preparatory LC/MS (35-55% CH$_3$CN in H$_2$O) to give the product 87B (130 mg, 79% yield over two steps). ESI-MS:m/z 672.3 (M+H)$^+$.

Step C.

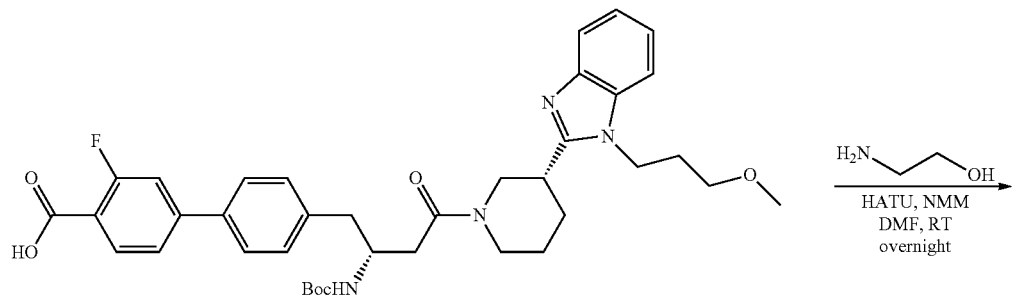

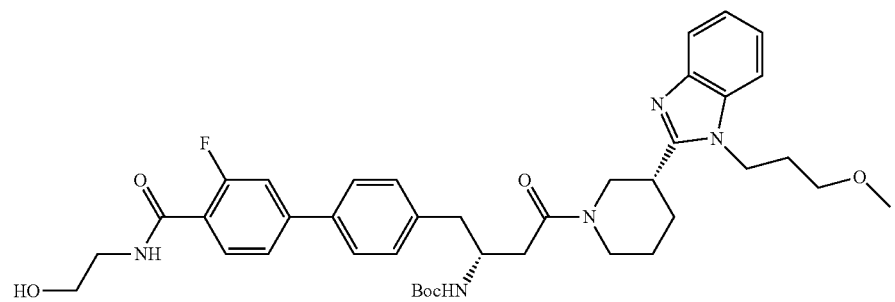

87C tert-Butyl (R)-1-(3'-fluoro-4'-(2-hydroxyethylcarbamoyl)biphenyl-4-yl)-4-((R)-3-(1-(3-methoxypropyl)-1H-benzo[d]imidazol-2-yl)piperidin-1-yl)-4-oxobutan-2-ylcarbamate (87C) was prepared according to Example 86, Step B. The solvent was removed and the residue was purified by preparatory LC/MS (25-50% CH$_3$CN in H$_2$O). ESI-MS:m/z 716.3 (M+H)$^+$.

Step D.

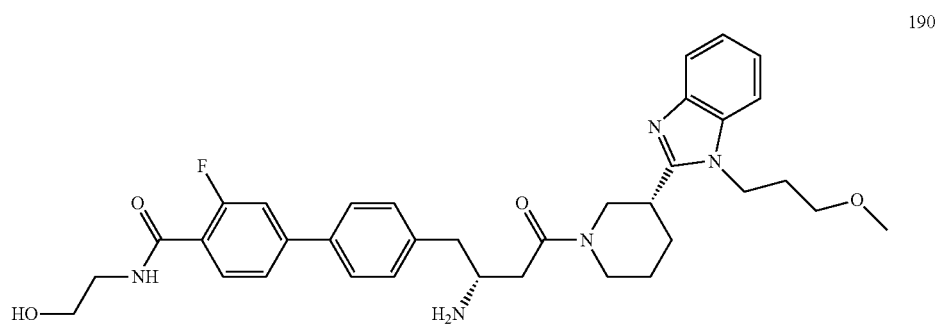

190

4'-((R)-2-amino-4-((R)-3-(1-(3-methoxypropyl)-1H-benzo[d]imidazol-2-yl)piperidin-1-yl)-4-oxobutyl)-3-fluoro-N-(2-hydroxyethyl)biphenyl-4-carboxamide (190) was prepared according to Example 86, Step C. The solvent was removed and the residue was purified by preparatory LC/MS (20-30% CH$_3$CN in H$_2$O) to give the product 190 as a TFA salt (15 mg, 21% yield over two steps). ESI-MS:m/z 616.3 (M+H)$^+$.

Example 88

Synthesis of 4'-((R)-2-amino-4-((R)-3-(1-(3-methoxypropyl)-1H-benzo[d]imidazol-2-yl)piperidin-1-yl)-4-oxobutyl)-3-fluoro-N-(2-methoxyethyphiphenyl-4-carboxamide (191)

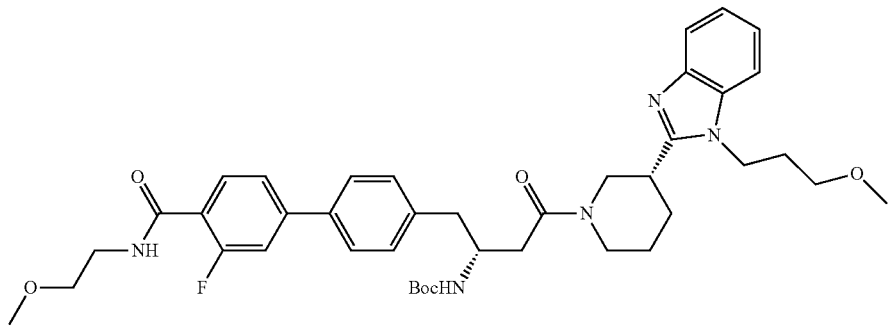

88A tert-Butyl (R)-1-(3'-fluoro-4'-(2-methoxyethylcarbamoyl)biphenyl-4-yl)-4-((R)-3-(1-(3-methoxypropyl)-1H-benzo[d]imidazol-2-yl)piperidin-1-yl)-4-oxobutan-2-ylcarbamate (88A) was prepared from 87B (Example 87) according to the procedure of Example 87, Step C. The solvent was removed and the residue was purified by preparatory LC/MS (35-55% $CH_3CN$ in $H_2O$). ESI-MS:m/z 730.5 (M+H)$^+$.

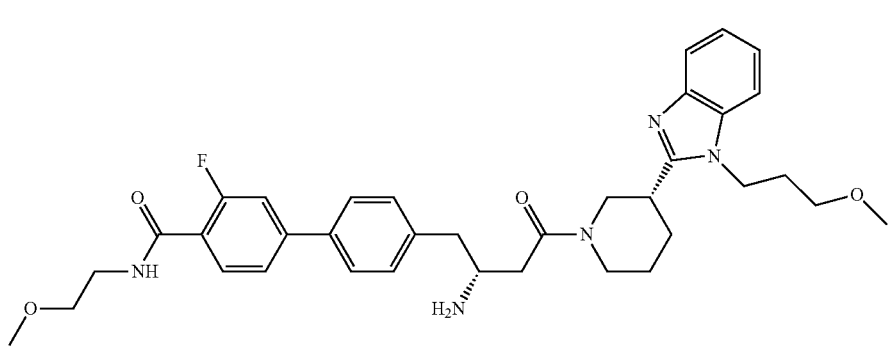

191

4'-((R)-2-Amino-4-((R)-3-(1-(3-methoxypropyl)-1H-benzoldlimidazol-2-yl)piperidin-1-yl)-4-oxobutyl)-3-fluoro-N-(2-methoxyethyl)biphenyl-4-carboxamide (191) was prepared from 88A according to the procedure of Example 87, Step D. The solvent was removed and the residue was purified by preparatory LC/MS (20-40% $CH_3CN$ in $H_2O$) to give the product 191 as a TFA salt (33 mg, 46% yield over two steps). 1H NMR (400 MHz, DMSO-$d_6$) δ ppm 1.41-1.62 (m, 1H) 1.74-2.20 (m, 5H) 2.61-3.50 (m, 19H) 3.70-3.90 (m, 1H) 4.09-4.68 (m, 4H) 7.41 (m, 4H) 7.62 (m, 2H) 7.68-7.81 (m, 5H) 8.29-8.35 (m, 1H). ESI-MS:m/z 630.3 (M+H)$^+$.

Example 89

Synthesis of 4'-((R)-2-amino-4-((R)-3-(1-(3-methoxypropyl)-1H-benzo[d]imidazol-2-yl)piperidin-1-yl)-4-oxobutyl)-2-chloro-N-(2-hydroxyethyl)biphenyl-4-carboxamide (192)

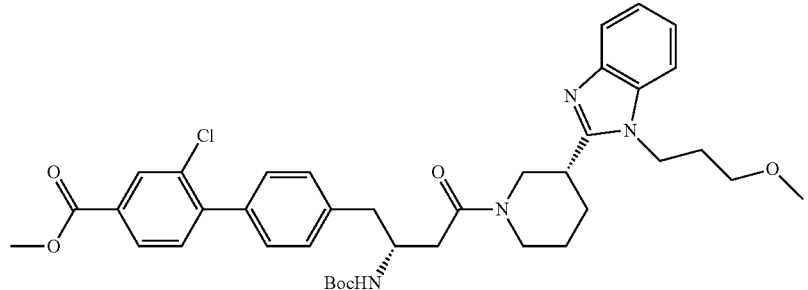

Methyl 4'-((R)-2-(tert-butoxycarbonylamino)-4-((R)-3-(1-(3-methoxypropyl)-1H-benzo[d]imidazol-2-yl)piperidin-1-yl)-4-oxobutyl)-2-chlorobiphenyl-4-carboxylate (89A) was prepared according to the procedure of Example 87, Step A. ESI-MS:m/z 702.3 (M+H)$^+$.

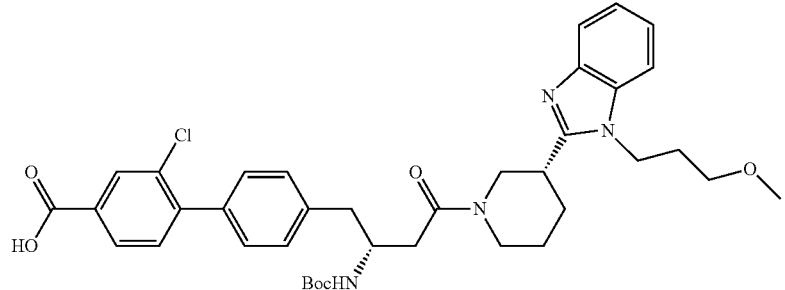

4'-((R)-2-(tert-Butoxycarbonylamino)-4-((R)-3-(1-(3-methoxypropyl)-1H-benzo[d]imidazol-2-yl)piperidin-1-yl)-4-oxobutyl)-2-chlorobiphenyl-4-carboxylic acid (89B) was prepared from 89A according to the procedure described in Example 87, Step B. The solvent was removed and the residue was purified by preparatory LC/MS (35-45% $CH_3CN$ in $H_2O$) to give the product (116 mg, 69% yield over two steps). ESI-MS:m/z 688.3 (M+H)$^+$.

tert-Butyl(R)-1-(2'-chloro-4'-(2-hydroxyethylcarbamoyl)biphenyl-4-yl)-4-((R)-3-(1-(3-methoxypropyl)-1H-benzo[d]imidazol-2-yl)piperidin-1-yl)-4-oxobutan-2-ylcarbamate (89C) was prepared from 89B according to the procedure described in Example 87, Step C. The solvent was removed

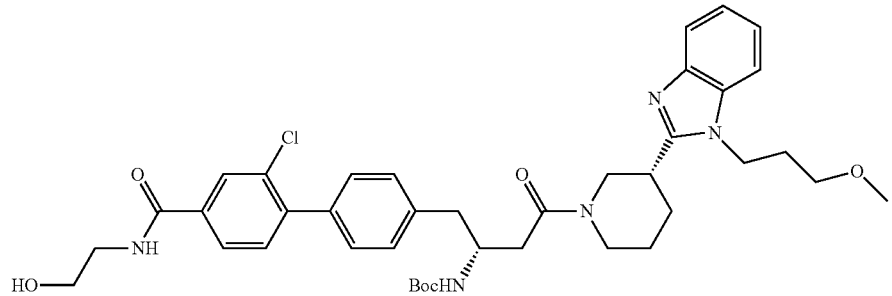

and the residue was purified by preparatory LC/MS (25-45% CH$_3$CN in H$_2$O). ESI-MS:m/z 732.3 (M+H)$^+$.

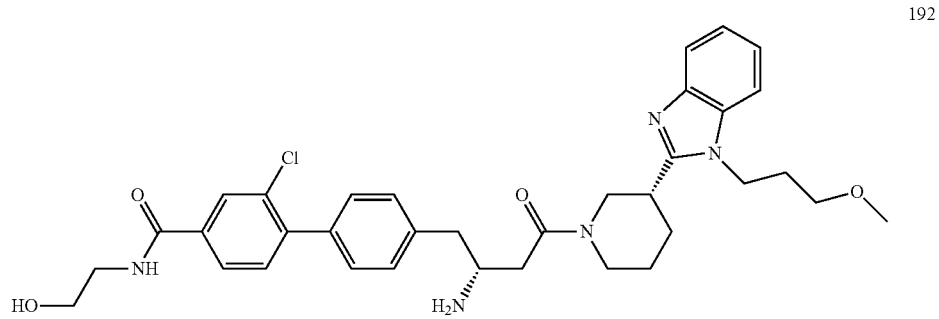

192

4'-((R)-2-amino-4-((R)-3-(1-(3-methoxypropyl)-1H-benzo[d]iimidazol-2-yl)piperidin-1-yl)-4-oxobutyl)-2-chloro-N-(2-hydroxyethyl)biphenyl-4-carboxamide (192) was prepared from 89C according to the procedure of Example 87, Step D. The solvent was removed and the residue was purified by preparatory LC/MS (20-35% CH$_3$CN in H$_2$O) to give the product 192 as a TFA salt (24 mg, 38% yield over two steps). ESI-MS:m/z 632.3 (M+H)$^+$.

Example 90

4'-((R)-2-amino-4-((R)-3-(1-(3-methoxypropyl)-1H-benzo[d]imidazol-2-yl)piperidin-1-yl)-4-oxobutyl)-2-chloro-N-(2-methoxyethyl)biphenyl-4-carboxamide (193)

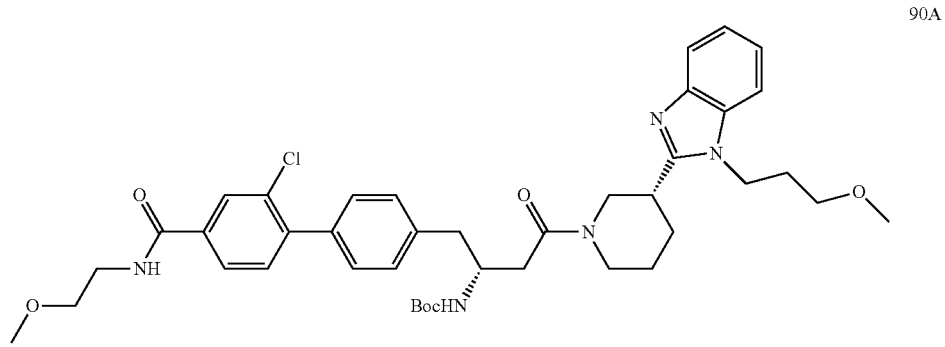

90A tert-Butyl(R)-1-(2'-chloro-4'-(2-methoxyethylcarbamoyl)biphenyl-4-yl)-4-((R)-3-(1-(3-methoxypropyl)-1H-benzo[d]imidazol-2-yl)piperidin-1-yl)-4-oxobutan-2-ylcarbamate (90A) was prepared from 89B (Example 89) according to the procedure described in Example 87, Step C. The solvent was removed and the residue was purified by preparatory LC/MS (35-50% CH$_3$CN in H$_2$O). ESI-MS:m/z 746.5 (M+H)$^+$.

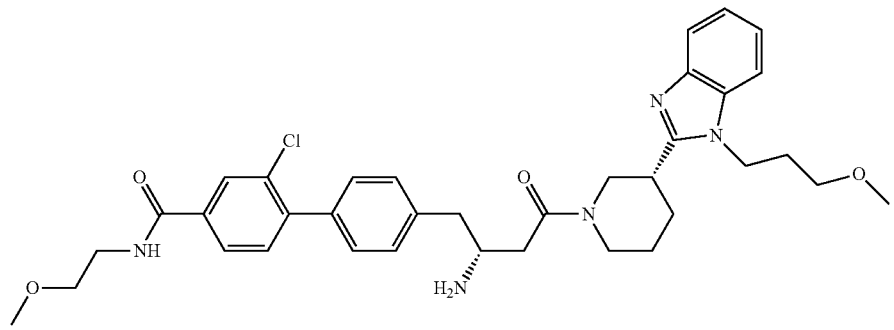

193

4'-((R)-2-Amino-4-((R)-3-(1-(3-methoxypropyl)-1H-benzo[d]imidazol-2-yl)piperidin-1-yl)-4-oxobutyl)-2-chloro-N-(2-methoxyethyl)biphenyl-4-carboxamide (193) was prepared from 90A according to the procedure of Example 87, Step D. The solvent was removed and the residue was purified by preparatory LC/MS (20-35% $CH_3CN$ in $H_2O$) to give the product 193 as a TFA salt (29 mg, 45% yield over two steps). 1H NMR (400 MHz, DMSO-$d_6$) δ ppm 1.50 (br. s., 1H) 1.93 (br. s., 5H) 2.63-3.51 (m, 19H) 3.77 (br. s., 1H) 4.07-4.66 (m, 4H) 7.36-7.52 (m, 7H) 7.72 (m, 2H) 7.92 (m, 1H) 8.04 (s, 1H) 8.74 (br. s., 1H). ESI-MS:m/z 646.3 $(M+H)^+$.

Example 91

Synthesis of 5-(4-((R)-2-amino-4-((R)-3-(1-(3-methoxypropyl)-1H-benzo[d]imidazol-2-yl)piperidin-1-yl)-4-oxobutyl)phenyl)-N-(2-hydroxyethyl)picolinamide (194)

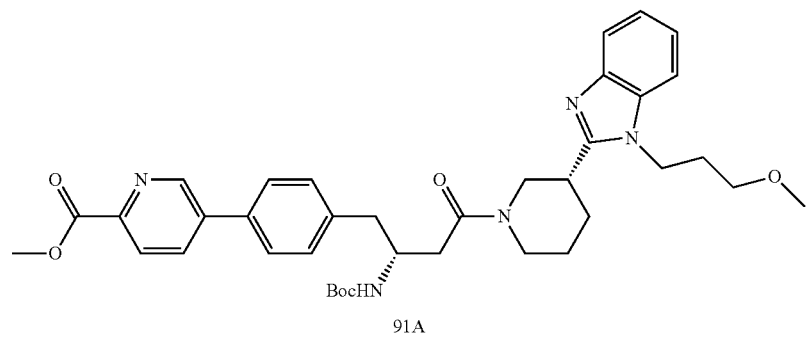

91A

Methyl 5-(4-((R)-2-(tert-butoxycarbonylamino)-4-((R)-3-(1-(3-methoxypropyl)-1H-benzo[d]imidazol-2-yl)piperidin-1-yl)-4-oxobutyl)phenyl)picolinate (91A) was prepared according to the procedure of Example 87, Step A. ESI-MS: m/z 670.5 $(M+H)^+$.

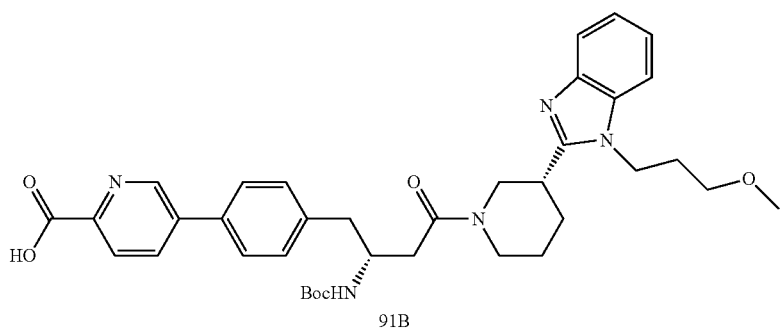

91B 5-(4-((R)-2-(tert-Butoxylcarbonylamino)-4-((R)-3-(1-(3-methoxypropyl)-1H-benzo[d]imidazol-2-yl)piperidin-1-yl)-4-oxobutyl)phenyl)picolinic acid (91B) was prepared from 91A according to the procedure described in Example 87, Step B. The solvent was removed and the residue was purified by preparatory LC/MS (25-45% CH$_3$CN in H$_2$O) to give the product (150 mg, 94% yield over two steps). ESI-MS:m/z 656.3 (M+H)$^+$.

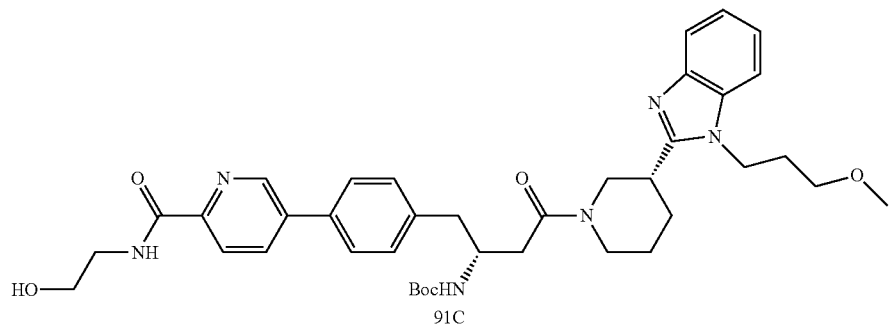

91C tert-Butyl (R)-1-(4-(6-(2-hydroxyethylcarbamoyl)pyridin-3-yl)phenyl)-4-((R)-3-(1-(3-methoxypropyl)-1H-benzo[d]imidazol-2-yl)piperidin-1-yl)-4-oxobutan-2-ylcaxbamate (91C) was prepared from 91B according to the procedure of Example 87, Step C. The solvent was removed and the residue was purified by preparatory LC/MS (25-45% CH$_3$CN in H$_2$O). ESI-MS:m/z 699.6 (M+H)$^+$.

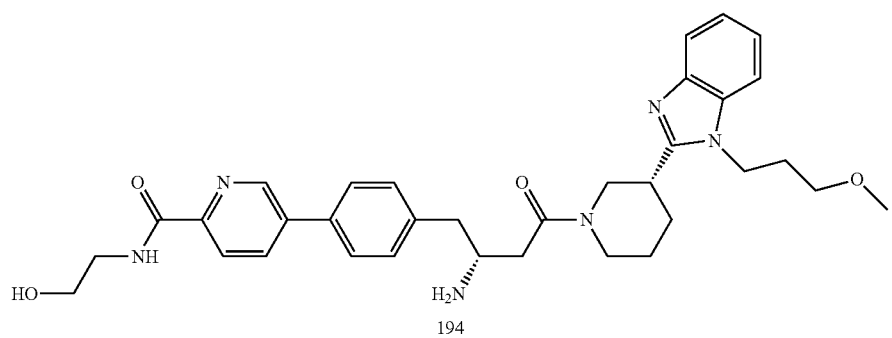

194

5-(4-((R)-2-Amino-4-((R)-3-(1-(3-methoxypropyl)-1H-benzo[d]imidazol-2-yl)piperidin-1-yl)-4-oxobutyl)phenyl)-N-(2-hydroxyethyl)picolinamide (194) was prepared according to the procedure of Example 87, Step D. The solvent was removed and the residue was purified by preparatory LC/MS (15-30% CH$_3$CN in H$_2$O) to give the product 194 as a TFA salt (25 mg, 31% yield over two steps). 1H NMR (400 MHz, DMSO-d$_6$) δ ppm 1.50 (br. s., 1H) 2.07 (m, 5H) 2.60-3.57 (m, 15H) 3.76 (br. s., 2H) 4.08-4.68 (m, 5H) 7.46 (m, 4H) 7.82 (m, 4H) 8.12 (m, 1H) 8.28 (m, 1H) 8.69 (m, 1H) 8.94-8.97 (m, 1H). ESI-MS:m/z 599.3 (M+H)$^+$.

Example 92

Synthesis of 5-(4-((R)-2-amino-4-((R)-3-(1-(3-methoxypropyl)-1H-benzo[d]imidazol-2-yl)piperidin-yl)-4-oxobutyl)phenyl)-N-(2-methoxyethyl)picolinamide (195)

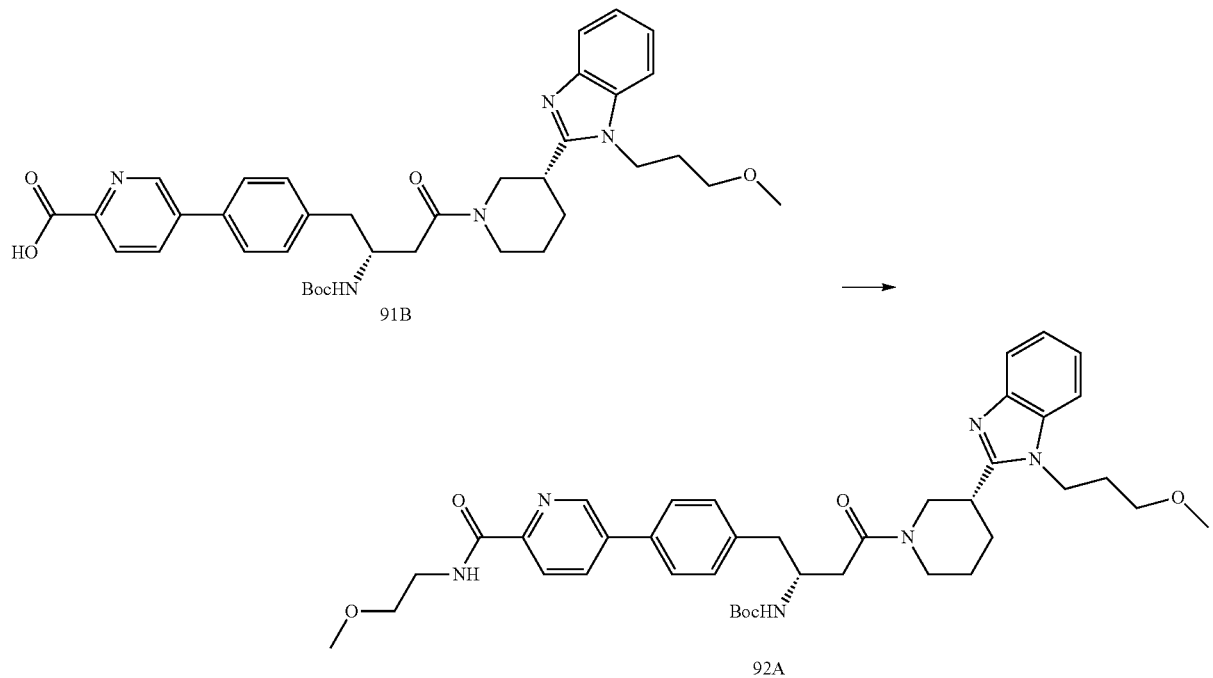

tert-Butyl (R)-1-(4-(6-(2-methoxyethylcarbamoyppyridin-3-yl)phenyl)-4-((R)-3-(1-(3-methoxypropyl)-1H-benzo[d]imidazol-2-yl)piperidin-1-yl)-4-oxobutan-2-ylcarbamate (92A) was prepared from 91B (prepared in Example 91) according to the procedure described for Example 87, Steps A-C. The solvent was removed and the residue was purified by preparatory LC/MS (35-45% CH$_3$CN in H$_2$O). ESI-MS: m/z 713.6 (M+H)$^+$.

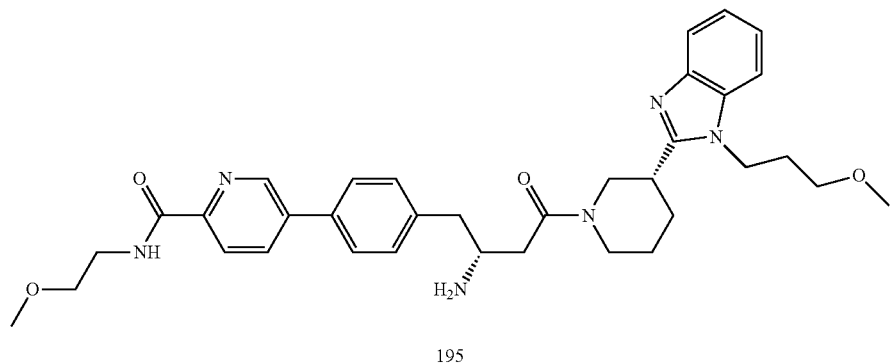

Compound 195 was prepared from 92A according to the procedure of Example 87, Step D. The solvent was removed and the residue was purified by preparatory LC/MS (15-40% CH$_3$CN in H$_2$O) to give the product 195 as a TFA salt (24 mg, 29% yield over two steps). 1H NMR (400 MHz, DMSO-d$_6$) δ ppm 1.74 (br. s., 1H) 1.92-2.36 (m, 5H) 2.69-3.28 (m, 9H) 3.39-3.67 (m, 10H) 3.98 (s, 2H) 4.65 (m, 3H) 7.44-7.52 (m, 2H) 7.63 (m, 2H) 7.78 (m, 3H) 7.85-7.95 (m, 1H) 8.14-8.24 (m, 2H) 8.91 (br. s., 1H). ESI-MS:m/z 613.3 (M+H)+.

Example 93

Synthesis of 5-(4-((R)-2-amino-4-((R)-3-(1-(3-methoxypropyl)-1H-benzo[d]imidazol-2-yl)piperidin-1-yl)-4-oxobutyphenye-N-(1-hydroxy-2-methylpropan-2-yl)thiophene-2-carboxamide (196)

5-(4-((R)-2-Amino-4-((R)-3-(1-(3-methoxypropyl)-1H-benzo[d]imidazol-2-yl)piperidin-1-yl)-4-oxobutyl)phenyl)-N-(1-hydroxy-2-methylpropan-2-yOthiophene-2-carboxamide (196) was prepared according to the procedure of Example 87, Step D. The solvent was removed and the residue was purified by preparatory LC/MS (15-35% $CH_3CN$ in $H_2O$) to give the product 196 as a TFA salt (18 mg, 26% yield over two steps). 1H NMR (400 MHz, DMSO-$d_6$) δ ppm 1.30 (s, 6H) 1.49 (br. s., 1H) 1.74-2.18 (m, 5H) 2.62-3.53 (m, 12H) 3.67-3.88 (m, 1H) 4.04-4.67 (m, 7H) 7.35 (m, 4H) 7.51 (m, 1H) 7.58 (s, 1H) 7.69 (m, 4H) 7.82 (m, 1H). ESI-MS:m/z 632.3 (M+H)+.

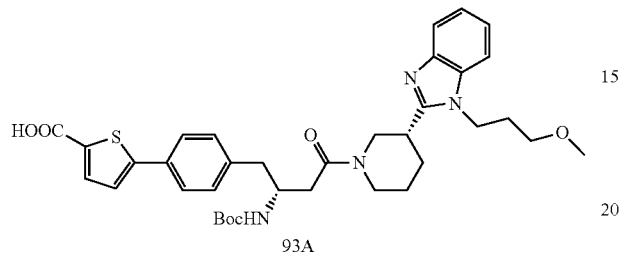

93A 5-(4-((R)-2-(tert-Butoxycarbonylamino)-4-((R)-3-(1-(3-methoxypropyl)-1H-benzo[d]imidazol-2-yl)piperidin-1-yl)-4-oxobutyl)phenyl)thiophene-2-carboxylic acid (93A) was prepared according to the procedure of Example 87, Step B.

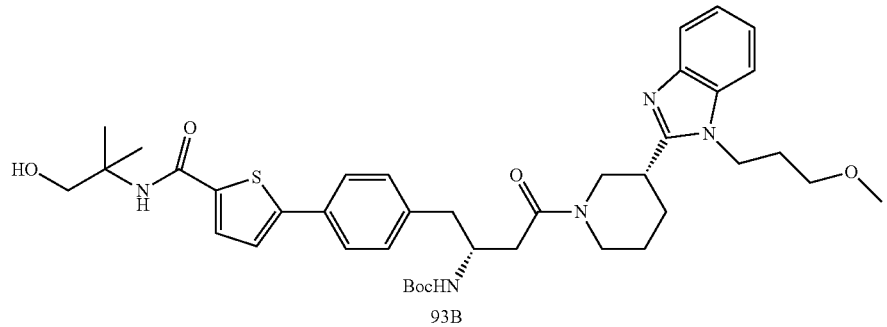

93B tert-Butyl (R)-1-(4-(5-(1-hydroxy-2-methylpropan-2-ylcarbamoyl)thiophen-2-yl)phenyl)-4-((R)-3-(1-(3-methoxypropyl)-1H-benzo[d]imidazol-2-yl)piperidin-1-yl)-4-oxobutan-2-ylcarbamate (93B) was prepared from 93A according to the procedure of Example 87, Step C. The solvent was removed and the residue was purified by preparatory LC/MS (30-50% $CH_3CN$ in $H_2O$). ESI-MS:m/z 732.4 (M+H)+.

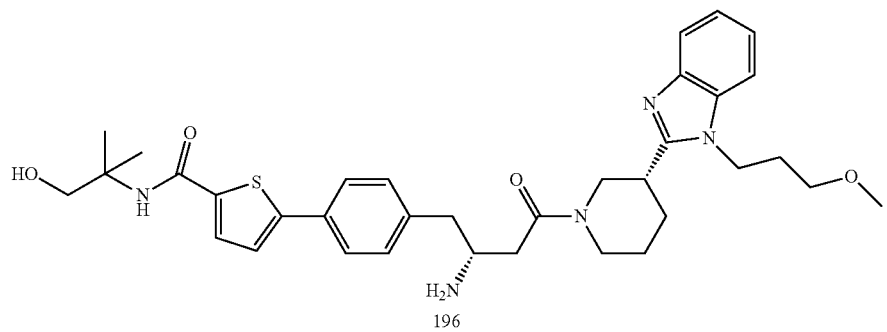

196

Example 94

Synthesis of N-(4'-((R)-2-amino-4-((R)-3-(1-(3-methoxypropyl)-1H-benzo[d]imidazol-2-yl)piperidin-1-yl)-4-oxobutyl)biphenyl-4-yl)-2-methoxyacetamide (197)

N-(4'-((R)-2-Amino-4-((R)-3-(1-(3-methoxypropyl)-1H-benzo[d]imidazol-2-yl)piperidin-1-yl)-4-oxobutyl)biphenyl-4-yl)-2-methoxyacetamide (197) was prepared according to the procedure of Example 86, Step C. The solvent was removed and the residue was purified by preparatory LC/MS (15-40% $CH_3CN$ in $H_2$) to give the product 197 as its TFA salt

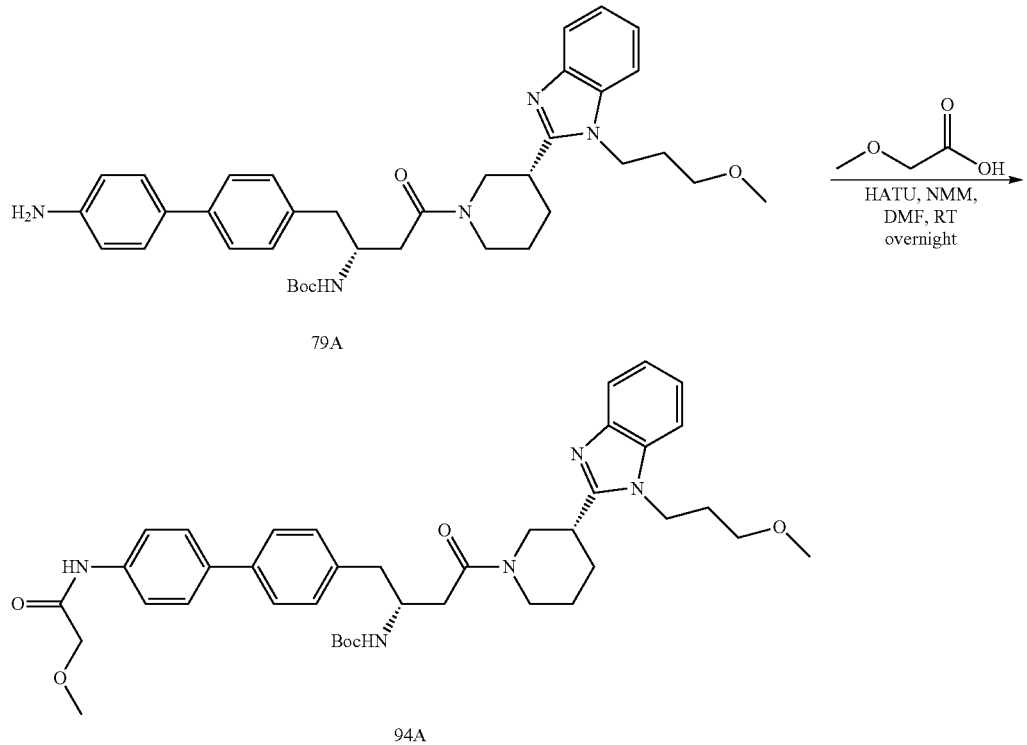

tert-Butyl (R)-1-(4'-(2-methoxyacetamido)biphenyl-4-yl)-4-((R)-3-(1-(3-methoxypropyl)-1H-benzo[d]imidazol-2-yl)piperidin-1-yl)-4-oxobutan-2-ylcarbamate (94A) was prepared from 79A (Example 79) according to the procedure of Example 86, Step B. The solvent was removed and the residue was purified by preparatory LC/MS (30-50% $CH_3CN$ in $H_2O$). ESI-MS:m/z 698.4 $(M+H)^+$.

(56 mg, 62% yield over two steps). 1H NMR (400 MHz, DMSO-$d_6$) δ ppm 1.50 (br. s., 1H) 1.73-2.20 (m, 5H) 2.58-3.46 (m, 14H) 3.73 (br. s., 1H) 4.02 (s, 2H) 4.35 (m, 5H) 7.35 (m, 2H) 7.39-7.50 (m, 2H) 7.63 (m, 4H) 7.77 (m, 4H) 9.88 (m, 1H). ESI-MS:m/z 598.3 $(M+H)^+$.

Step B.

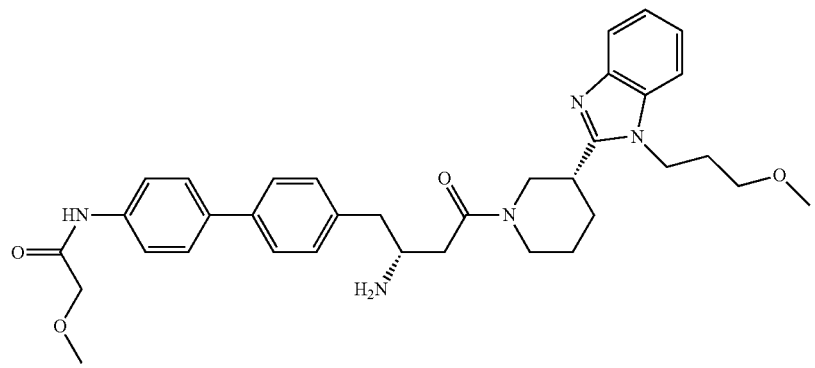

Example 95

Synthesis of N-(4'-((R)-2-amino-4-((R)-3-(1-(3-methoxypropyl)-1H-benzo[d]imidazol-2-yl)piperidin-1-yl)-4-oxobutyl)biphenyl-4-yl-2-hydroxyacetamide (198)

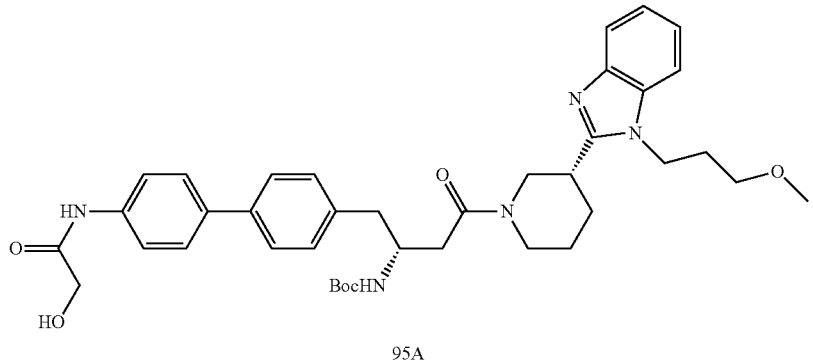

95A tert-Butyl (R)-1-(4'-(2-hydroxyacetamido)biphenyl-4-yl)-4-((R)-3-(1-(3-methoxypropyl)-1H-benzo[d]imidazol-2-yl)piperidin-1-yl)-4-oxobutan-2-ylcarbamate (95A) was prepared according to the procedure described in Example 94, Step A. The solvent was removed and the residue was purified by preparatory LC/MS (30-50% CH$_3$CN in H$_2$O). ESI-MS: m/z 684.4 (M+H)$^+$.

to the procedure of Example 94, Step B. The solvent was removed and the residue was purified by preparatory LC/MS (15-30% CH$_3$CN in H$_2$O) to give the product 198 as its TFA salt (21 mg, 24% yield over two steps). 1H NMR (400 MHz, DMSO-d$_6$) δ ppm 1.36 (s, 6H) 1.50 (br. s., 1 H) 1.73-2.19 (m, 5H) 2.59-3.46 (m, 13H) 3.73 (br. s., 1H) 4.08-4.68 (m, 4H) 7.35 (m, 2H) 7.44 (m, 2H) 7.64 (m, 4H) 7.74 (m, 2H) 7.84 (m, 2H) 9.67 (m, 1H). ESI-MS:m/z 584.2 (M+H)$^+$.

Example 96

Synthesis of N-(4'-((R)-2-amino-4-((R)-3-(1-(3-methoxypropyl)-1H-benzo[d]imidazol-2-yl)piperidin-1-yl)-4-oxobutyl)biphenyl-4-yl)-2-hydroxy-2-methylpropanamide (199)

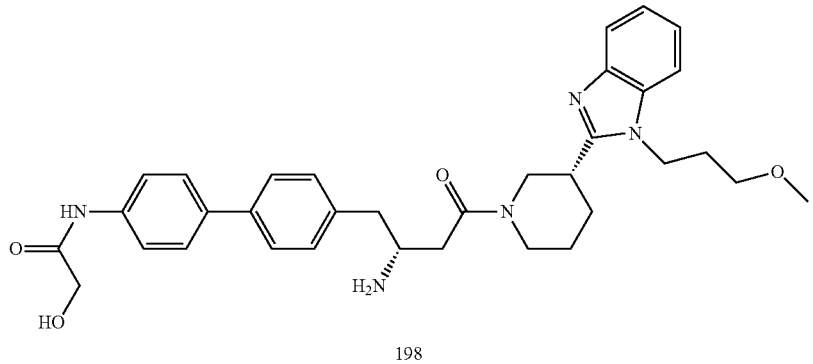

198

N-(4'-((R)-2-Amino-4-((R)-3-(1-(3-methoxypropyl)-1H-benzo[d]imidazol-2-yl)piperidin-1-yl)-4-oxobutyl)biphenyl-4-yl)-2-hydroxyacetamide (198) was prepared according

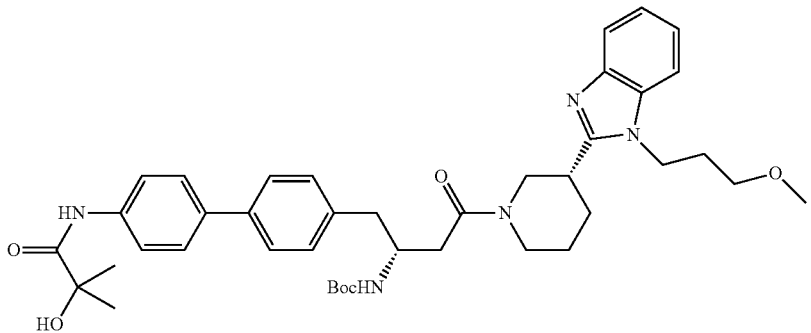

96A tert-Butyl (R)-1-(4'-(2-hydroxy-2-methylpropanamido)biphenyl-4-yl)-4-((R)-3-(1-(3-methoxypropyl)-1H-benzo[d]imidazol-2-yl)piperidin-1-yl)-4-oxobutan-2-ylcarbamate (96A) was prepared as described in Example 94, Step A. The solvent was removed and the residue was purified by preparatory LC/MS (35-50% CH$_3$CN in H$_2$O). ESI-MS:m/z 712.4 (M+H)$^+$.

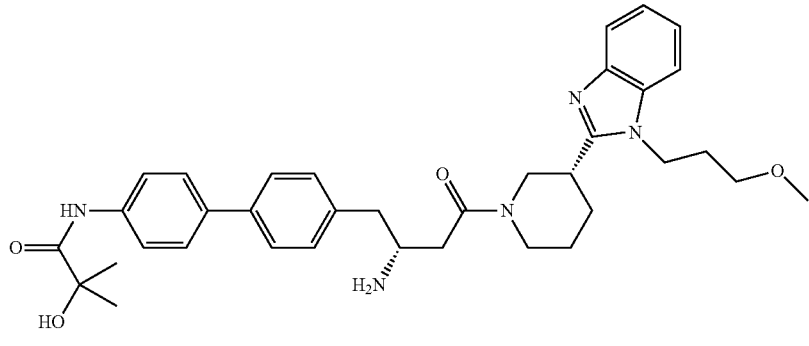

199

N-(4'-((R)-2-Amino-4-((R)-3-(1-(3-methoxypropyl)-1H-benzo[d]imidazol-2-yl)piperidin-1-yl)-4-oxobutyl)biphenyl-4-yl)-2-hydroxy-2-methylpropanamide (199) was prepared according to the procedure described in Example 94, Step B. The solvent was removed and the residue was purified by preparatory LC/MS (15-40% CH$_3$CN in H$_2$O) to give the product 199 as its TFA salt (36 mg, 39% yield over two steps). 1H NMR (400 MHz, DMSO-d$_6$) δ ppm 1.51 (br. s., 1H) 1.74-2.20 (m, 5H) 2.60-3.47 (m, 12H) 3.73 (br. s., 1H) 4.01 (s, 2H) 4.36 (br. s., 4H) 7.35 (m, 2H) 7.44 (br. s., 2H) 7.63 (m, 4H) 7.81 (m, 4H) 9.78 (s, 1H). ESI-MS:m/z 612.3 (M+H)$^+$.

Example 97

Synthesis of (R)-3-amino-4-(4-(2-ethoxythiazol-4-yl)phenyl)-1-((R)-3-(1-(3-methoxypropyl)-1H-benzo[d]imidazol-2-yl)piperidin-1-yl)butan-1-one (200)

Step A.

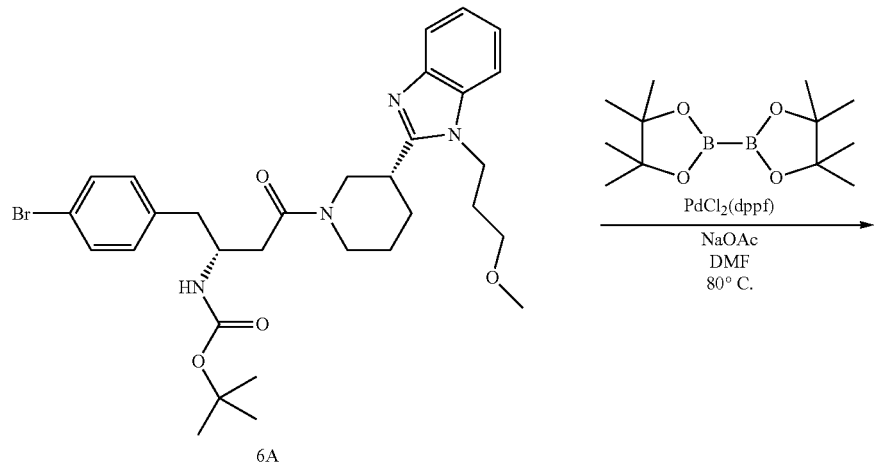

6A

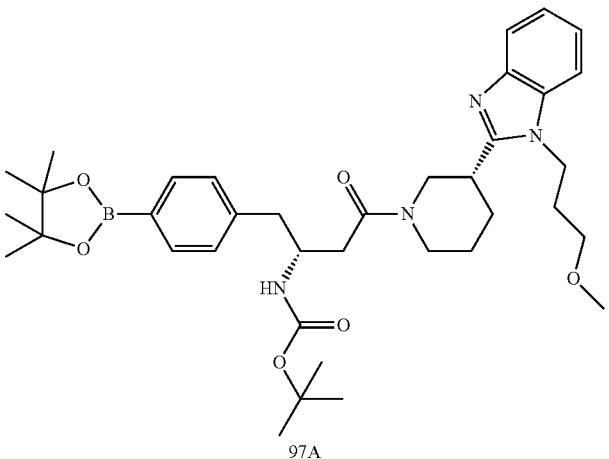

97A tert-Butyl(R)-1-(4-bromophenyl)-4-((R)-3-(1-(3-methoxypropyl)-1H-benzo[d]imidazol-2-yl)piperidin-1-yl)-4-oxobutan-2-ylcarbamate (6A) (prepared according to Example 6, Step A) (0.815 mmol, 0.500 g), bis(pinacolato)diboron (2.45 mmol, 0.623 g), Pd(dppf)Cl$_2$, and sodium acetate (2.45 mmol, 0.201 g) were then added to a reaction vessel. The reaction vessel was flushed with nitrogen, sealed, and heated to 80° C. for 48 hrs. The reaction solution was then poured into water, extracted with ethyl acetate, and washed once with saturated aqueous sodium chloride. The organic layer was collected and subsequently dried with anhydrous Na$_2$SO$_4$ and filtered. This filtrate was collected, concentrated, and dried in-vacuo. This crude material was directly purified by preparative LC/MS (15-85% CH$_3$CN in H$_2$O). The resultant fractions were collected and the solvent was removed in-vacuo affording the title compound as a brown oil. This oil was re-dissolved in CH$_3$CN (1 mL) and water (2 mL). The resultant solution was frozen and lyophilized to afford tert-butyl (R)-4-((R)-3-(1-(3-methoxypropyl)-1H-benzo[d]imidazol-2-yl)piperidin-1-yl)-4-oxo-1-(4-(4,4,5,5-tetramethyl-1,3,2-dioxaborolan-2-yl)phenyl)butan-2-ylcarbamate (97A) as a brown flocculent solid (0.646 mmol, 0.427 g, 79% yield). ESI-MS: m/z 661.6 (M+H)$^+$.

tert-Butyl (R)-4-((R)-3-O-(3-methoxypropyl)-1H-benzo[d]imidazol-2-yl)piperidin-1-yl)-4-oxo-1-(4-(4,4,5,5-tetramethyl-1,3,2-dioxaborolan-2-yl)phenyl)butan-2-ylcarbamate (97A) (0.091 mmol, 0.060 g) and 4-bromo-2-ethoxythiazole (0.10 mmol, 0.021 g) were added to a 5 mL microwave vessel equipped with a magnetic stir bar. Dioxane (2 mL) and Na$_2$CO$_3$ (1 mL of a 2 M aqueous solution) were then added and the reaction vessel was flushed with nitrogen gas. PdCl$_2$(dppf) (0.009 mmol, 0.007 g) was added, the reaction vessel was sealed and placed in a microwave reactor and heated to 110° C. for 15 minutes. The reaction solution was then poured into water, extracted with ethyl acetate, and washed once with saturated aqueous sodium chloride. The organic layer was collected and subsequently dried with anhydrous Na$_2$SO$_4$ and filtered. This filtrate was collected, concentrated, and dried in-vacuo. This crude material was directly purified by preparative LC/MS (25-85% CH$_3$CN in H$_2$O). The resultant fractions were collected and the solvent was removed in-vacuo affording tert-butyl (R)-4-(R)-3-(1-(3-methoxypropyl)-1H-benzo[d]imidazol-2-yl)piperidine-1-yl)-1-(4-(2-methoxythiazol-4-yl)phenyl)-4-oxobutan-2-ylcarbamate (97B) as a clear oil which was used directly in the next step without further quantification. ESI-MS: m/z 662.4 (M+H)$^+$.

Step B.

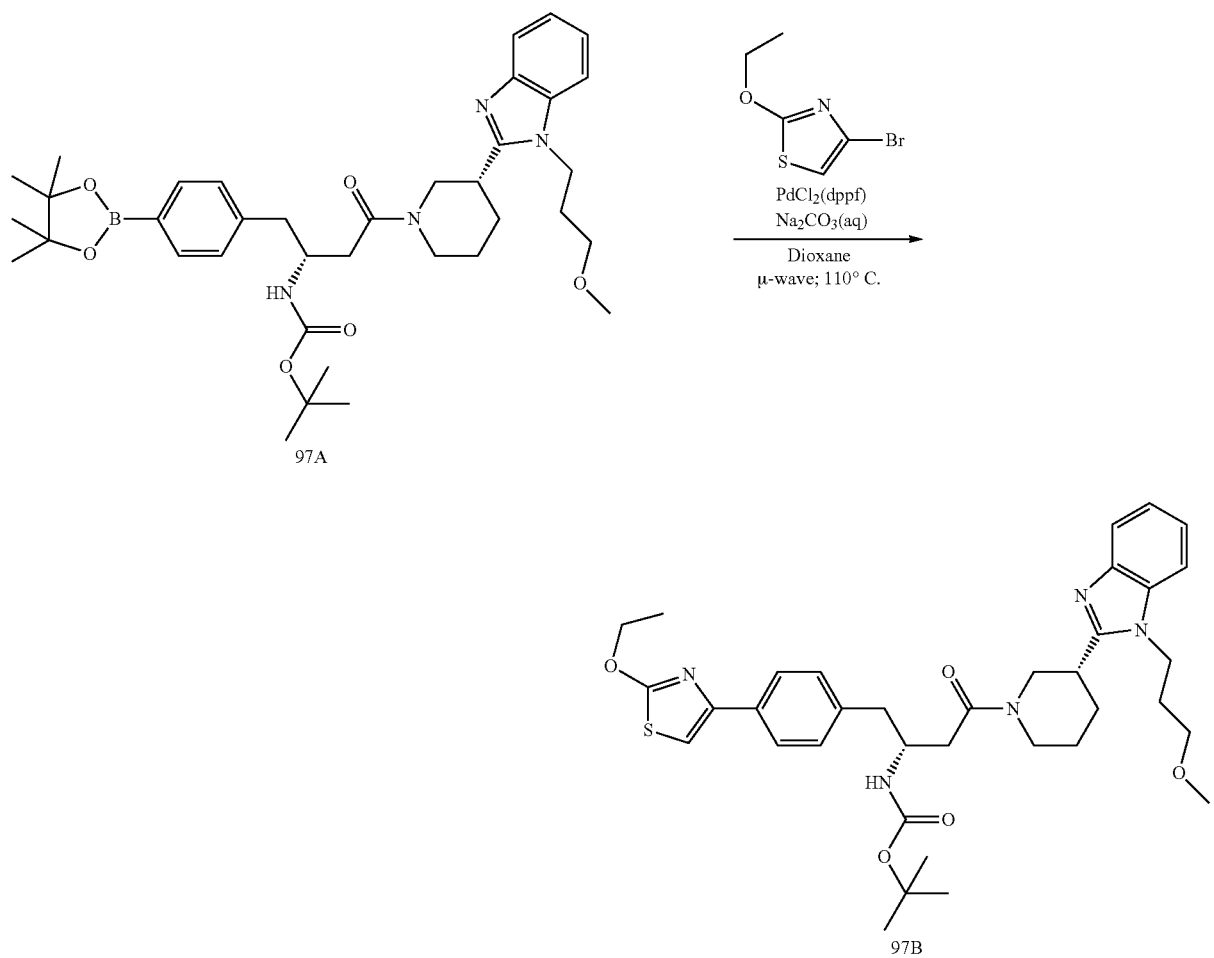

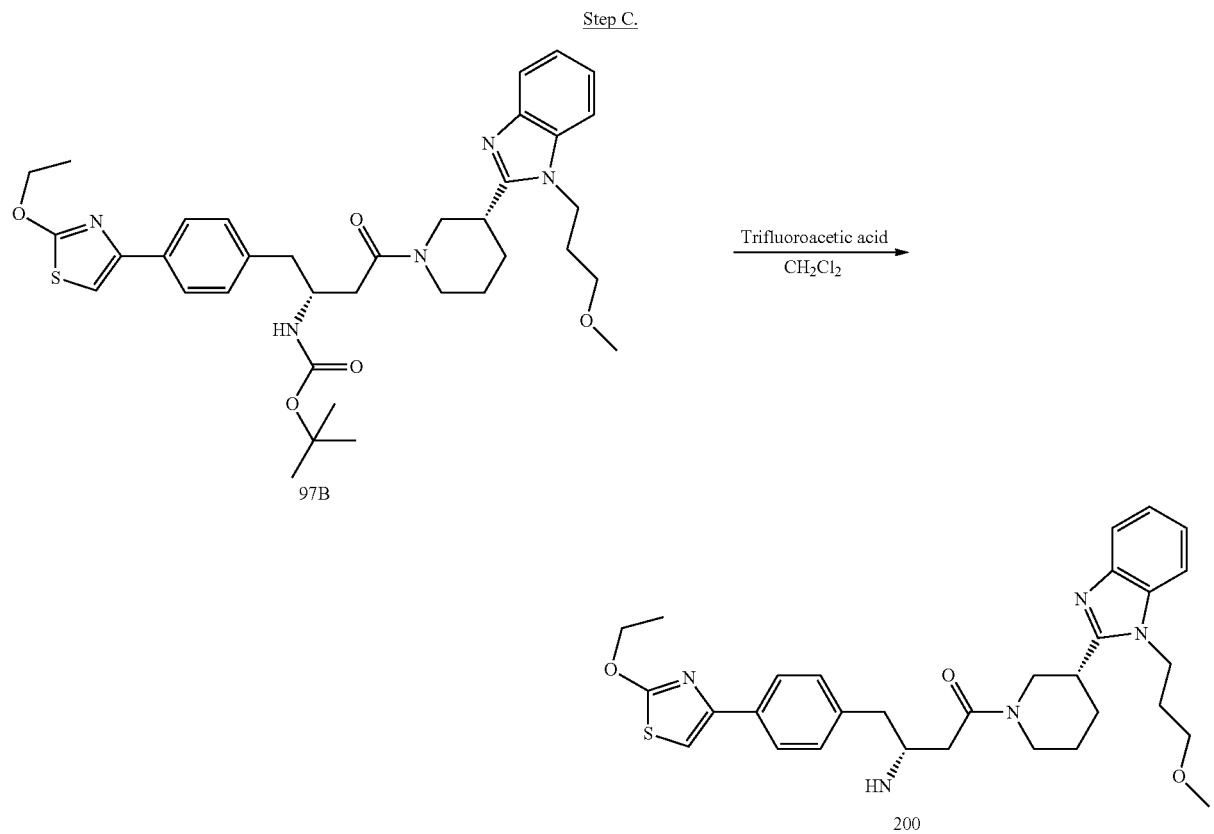

tert-Butyl (R)-1-(4-(2-ethoxythiazol-4-yl)phenyl)-4-((R)-3-(1-(3-methoxypropyl)-1H-benzo[d]imidazol-2-yl)piperidin-1-yl)-4-oxobutan-2-ylcarbamate (97B) (0.091 mmol max, crude oil) was added to a 10 mL round-bottomed flask equipped for stirring under nitrogen. Dichloromethane (2 mL) and trifluoroacetic acid (2 mL) were then added and the solution was stirred at room temperature for 2 hrs. The solvent was removed in-vacuo affording a clear colored oil. This oil was re-dissolved in methanol (3 mL), filtered, and then purified by preparative LC/MS (10-55% $CH_3CN$ in $H_2O$). The resultant fractions were collected and the solvent was removed in-vacuo affording a clear colored oil. This oil was re-dissolved in $CH_3CN$ (1 mL) and water (2 mL). The resultant solution was frozen and lyophilized to afford (R)-3-amino-4-(4-(2-ethoxythiazol-4-yl)phenyl)-1-((R)-3-(1-(3-methoxypropyl)-1H-benzo[d]imidazol-2-yl)piperidin-1-yl)butan-1-one (200) as its trifluoroacetic acid salt as a white flocculent solid (0.061 mmol, 0.041 g, 67% yield over 2-steps). ESI-MS: 562.2 m/z $(M+H)^+$. $^1H$ NMR (400 MHz, DMSO-$d_6$) δ ppm 1.39-1.66 (m, 1H) 1.67-2.12 (m, 5H) 2.28-2.44 (m, 2H) 2.56-2.95 (m, 4H) 2.94-3.28 (m, 7H) 3.84-4.05 (m, 1H) 4.09 (d, J=1.77 Hz, 5H) 4.44-4.61 (m, 1 H) 7.09-7.60 (m, 7H) 7.70-7.93 (m, 2H).

Other compounds that were prepared by the procedure of Example 97 are listed in Table V.

TABLE V

| Compound No. | Structure/Name | Physical Properties |
|---|---|---|
| 201 | ![structure]<br><br>201<br>(R)-3-amino-1-((R)-3-(1-(3-methoxypropyl)-1H-benzo[d]imidazol-2-yl)piperidin-1-yl)-4-(4-(2-methoxythiazol-4-yl)phenyl)butan-1-one | ESI-MS: 548.3 m/z $(M + H)^+$.<br>$^1H$ NMR (400 MHz, DMSO-$d_6$) δ ppm 1.39-1.66 (m, 1 H) 1.67-2.12 (m, 5 H) 2.28-2.44 (m, 2 H) 2.56-2.95 (m, 4 H) 2.94-3.28 (m, 7 H) 3.84-4.05 (m, 1 H) 4.09 (d, J = 1.77 Hz, 5 H) 4.44-4.61 (m, 1 H) 7.09-7.60 (m, 7 H) 7.70-7.93 (m, 2 H). |

| Compound No. | Structure/Name | Physical Properties |
| --- | --- | --- |
| 202 | 202<br>(R)-3-amino-4-(4-(2-isopropylthiazol-4-yl)phenyl)-1-((R)-3-(1-(3-methoxypropyl)-1H-benzo[d]imidazol-2-yl)piperidin-1-yl)butan-1-one | ESI-MS: 548.3 m/z $(M + H)^+$.<br>$^1$H NMR (400 MHz, DMSO-$d_6$) δ ppm 1.39-1.66 (m, 1 H) 1.67-2.12 (m, 5 H) 2.28-2.44 (m, 2 H) 2.56-2.95 (m, 4 H) 2.94-3.28 (m, 7 H) 3.84-4.05 (m, 1 H) 4.09 (d, J = 1.77 Hz, 5 H) 4.44-4.61 (m, 1 H) 7.09-7.60 (m, 7 H) 7.70-7.93 (m, 2 H) |

Example 98

Synthesis of 4-((R)-2-amino-4-((R)-3-(1-(3-methoxypropyl)-1H-benzo[d]imidazol-2-yl)piperidin-1-yl)-4-oxobutyl)-N-cyclohexylbenzamide (203)

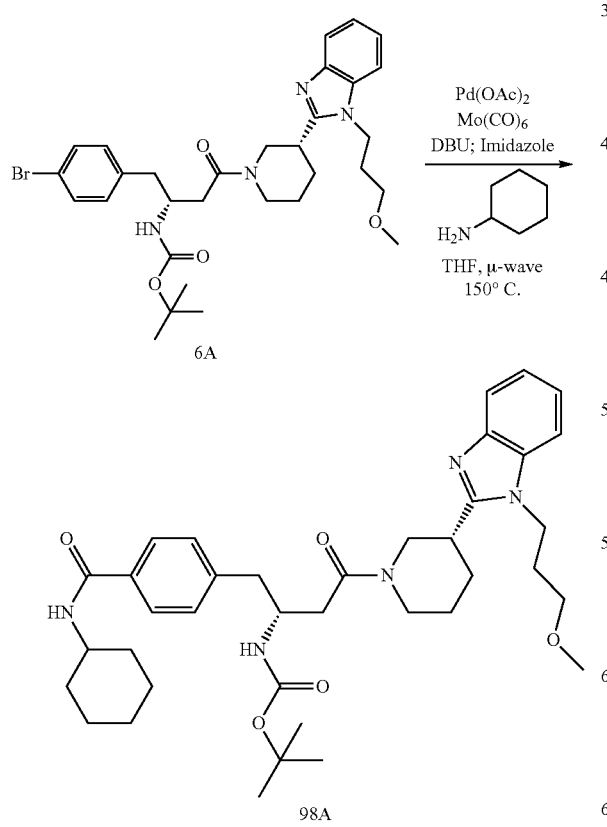

tert-Butyl (R)-1-(4-bromophenyl)-4-((R)-3-(1-(3-methoxypropyl)-11$^{-1}$-benzo[d]imidazol-2-yl)piperidin-1-yl)-4-oxobutan-2-ylcarbamate (6A) (as prepared in Example 6, Step A) (0.098 mmol, 0.060 g) was added to a 5 mL microwave vessel equipped for stirring. Cyclohexanamine (0.293 moles, 0.034 mL), palladium(II) acetate (0.01 mmol, 0.002 g), Mo(CO)$_6$ (0.098 mmol, 0.026 g), 1,8 diazabicyclo[5.4.0]undec-7-ene (0.293 mmol, 0.044 mL), imidazole (0.049 mmol, 0.003 g), and THF (2 mL) were then added. The flask was sealed and heated to 150° C. for 15 min in the microwave. The reaction mixture was filtered over celite and the solid rinsed with THF (20 mL). The filtrate was collected and concentrated in-vacuo. This crude oil was re-dissolved in methanol (3 mL), filtered, and then purified by preparative LC/MS (20-80% CH$_3$CN in H$_2$O). The resultant fractions were collected and the solvent was removed in-vacuo affording tert-butyl (R)-1-(4-(cyclohexylcarbamoyl)phenyl)-4-((R)-3-(1-(3-methoxypropyl)-1H-benzo[d]imidazol-2-yl)piperidin-1-yl)-4-oxobutan-2-ylcarbamate (98A) as a clear colored oil (0.039 mmol, 0.025 g, 39% yield). ESI-MS: 660.4 m/z $(M+H)^+$.

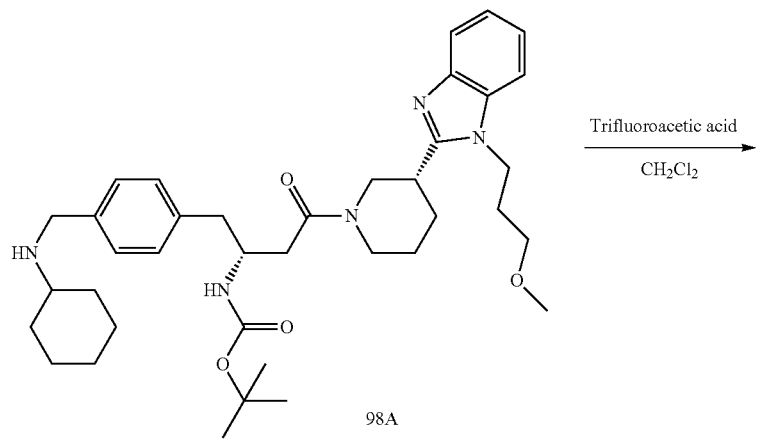

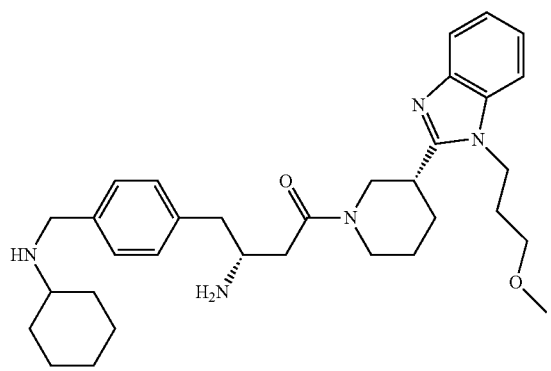

98A (0.039 mmol, 0.025 g) was added to a 10 mL round-bottomed flask equipped for stirring under nitrogen. Dichloromethane (2 mL) and trifluoroacetic acid (2 mL) were then added and the solution was stirred at room temperature for 2 hrs. The solvent was removed in-vacuo affording a clear colored oil. This oil was re-dissolved in methanol (3 mL), filtered, and then purified by preparative LC/MS (0.5-50% $CH_3CN$ in $H_2O$). The resultant fractions were collected and the solvent was removed in-vacuo affording a clear colored oil. This oil was re-dissolved in $CH_3CN$ (1 mL) and water (2 mL). The resultant solution was frozen and lyophilized to afford 4-((R)-2-amino-4-((R)-3-(1-(3-methoxypropyl)-1H-benzo[d]imidazol-2-yl)piperidin-1-yl)-4-oxobutyl)-N-cyclohexylbenzamide (203) as its trifluoroacetic acid salt and as a white flocculent solid. (0.009 mmol, 0.006 g, 24% yield). ESI-MS: 560.3 m/z $(M+H)^+$.

Example 99

Synthesis of (R)-3-amino-4-(4-(1,2-dimethyl-1H-imidazol-5-yl)phenyl)-1-((R)-3-(1-(3-methoxypropyl)-1H-benzo[d]imidazol-2-yl)piperidin-1-yl)butan-1-one (204)

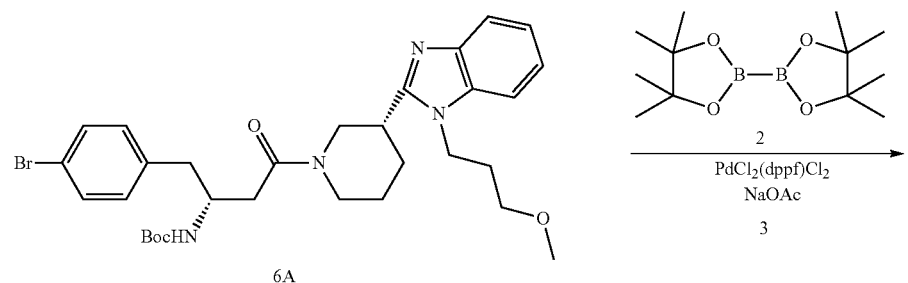

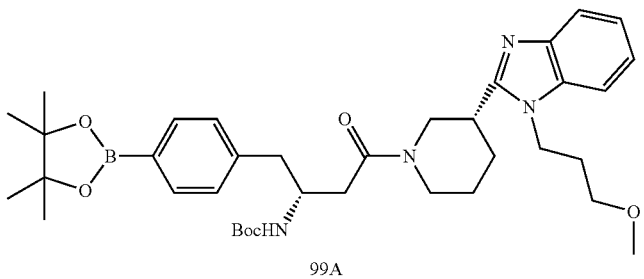

The mixture of aryl bromide, (R)-3-amino-4-(4-(2-ethoxythiazol-4-yl)phenyl)-1-((R)-3-(1-(3-methoxypropyl)-1H-benzo[d]imidazol-2-yl)piperidin-1-yl)butan-1-one (6A) (as prepared in Example 6, Step A) (614 mg, 1.00 mmol), bis(pinacolato)diboron (305 mg, 1.2 mmol, 1.2 eq), sodium acetate (246 mg, 3.0 mmol, 3 eq), Pd(dppf)Cl$_2$ (36.6 mg, 5% mol) in DMF (4 mL) was heated at 90° C. for 30 min in a microwave reactor. More pinocoldiboron (150 mg) was added, the reaction was heated at 90° C. for 105 min. Solvent was removed in vacuo, the black-brown residue was suspended in DCM and passed through a pad of SiO$_2$, washed with DCM, then 50% DCM/50% EtOAd2% MeOH. After removing solvents, the crude product tert-butyl (R)-4-((R)-3-(1-(3-methoxypropyl)-1H-benzoldjimidazol-2-yl)piperidin-1-yl)-4-oxo-1-(4-(4,4,5,5-tetramethyl-1,3,2-dioxaborolan-2-yl)phenyl)butan-2-ylcarbamate (99A) was obtained as a yellow oil (720 mg, 100% yield). ESI-MS: m/z 661.6 (M+H)$^+$. $^1$H NMR (400 MHz, MeOH-d$_4$) δ ppm 3.31 (s, 3H) 3.66-3.70 (m, 2H) 4.21-4.25 (m, 2H) 7.1-7.6 (m, 8H); HPLC rentation time: T. 1.070 min, FSTFA-2 method and T. 1.764 min, STDTFA-2 method.

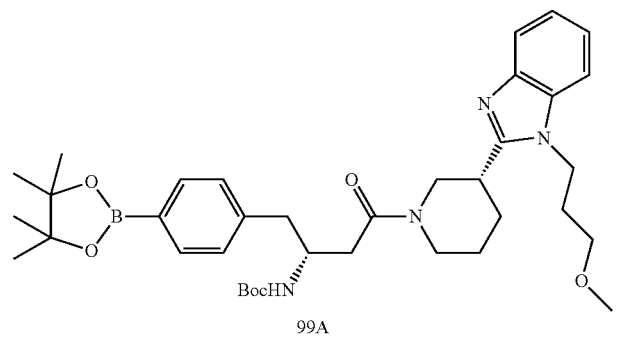 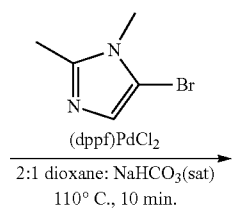

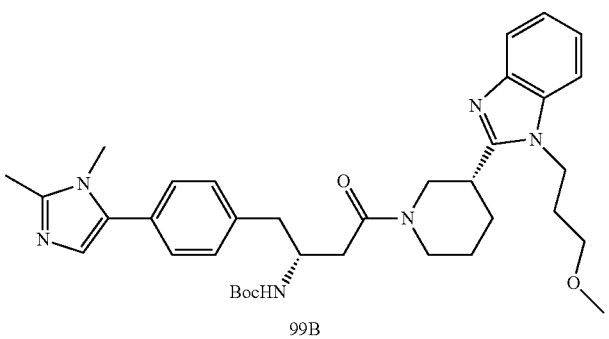

tert-Butyl (R)-1-(4-(1,2-dimethyl-1H-imidazol-5-yl)phenyl)-4-((R)-3-(1-(3-methoxypropyl)-1H-benzo[d]imidazol-2-yl)piperidin-1-yl)-4-oxobutan-2-ylcarbamate (99B) was prepared according to the procedure outlined in Example 97, Step B. ESI-MS:m/z 629.6 (M+H)$^+$.

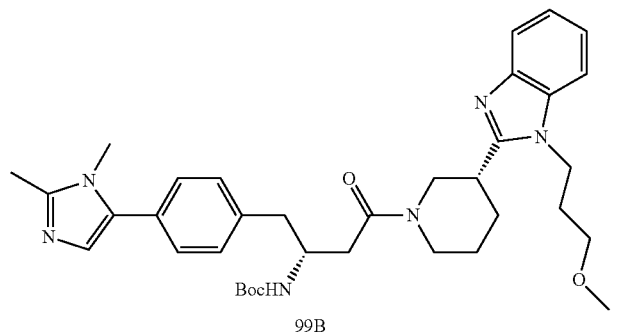

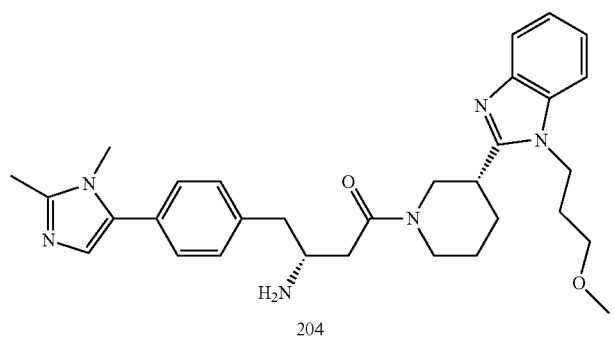

Crude product (R)-3-amino-4-(4-(1,2-dimethyl-1H-imidazol-5-yl)phenyl)-1-((R)-3-(1-(3-methoxypropyl)-1H-benzo[d]imidazol-2-yl)piperidin-1-yl)butan-1-one (204) was prepared as described above for Example 97, Sep C. Purification by preparatory LC/MS (10-30% CH$_3$CN in H$_2$O) gave the product 204 as its TFA salt (25 mg, 47% yield). 1H NMR (400 MHz, DMSO-d$_6$) δ ppm 1.53 (br. s., 1H) 1.95 (m, 5H) 2.66 (s, 5H) 2.84-3.51 (m, 9H) 3.65 (m, 3H) 3.72-3.90 (m, 1H) 4.35 (s, 5H) 7.38 (m, 2H) 7.44-7.56 (m, 4H) 7.65-7.74 (m, 3H). ESI-MS:m/z 529.2 (M+H)$^+$.

Example 100

Synthesis of 5-(4-((R)-2-amino-4-((R)-3-(1-(3-methoxypropyl)-1H-benzo[d]imidazol-2-yl)piperidin-1-yl)-4-oxobutyl)phenyl)-1,3-dimethylpyrimidine-2,4(1H,3H)-dione (205)

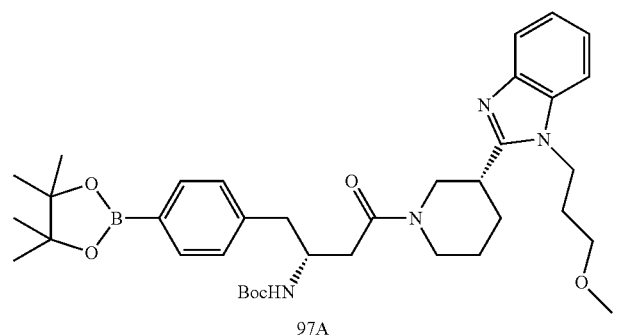 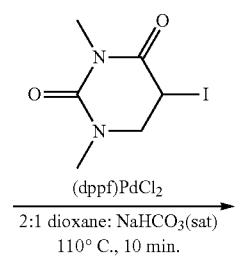

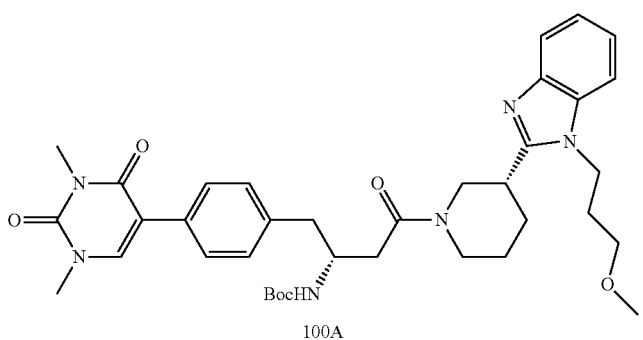

tert-Butyl (R)-1-(4-(1,3-dimethyl-2,4-dioxo-1,2,3,4-tetrahydropyrimidin-5-yl)phenyl)-4-((R)-3-(1-(3-methoxypropyl)-1H-benzo[d]imidazol-2-yl)piperidin-1-yl)-4-oxobutan-2-ylcarbamate (100A) was prepared according to the procedures outlined in Example 97, Step B. ESI-MS:m/z 673.5 (M+H)+.

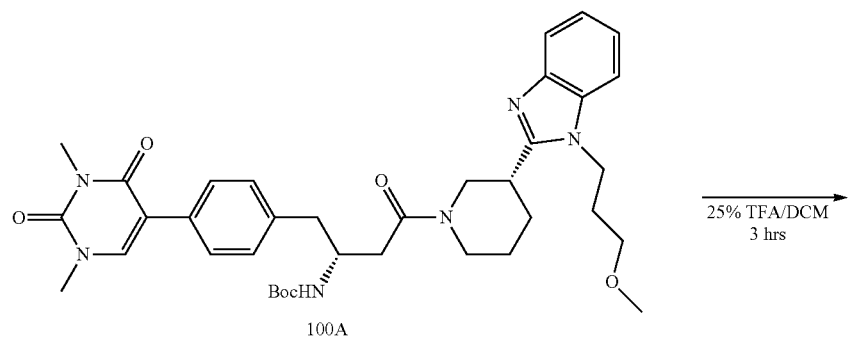

Crude product of 5-(4-((R)-2-amino-4-((R)-3-(1-(3-methoxypropyl)-1H-benzo[d]imidazol-2-yl)piperidin-1-yl)-4-oxobutyl)phenyl)-1,3-dimethylpyrimidine-2,4(1H,3H)-dione (205) was prepared as described above for Example 97, Step C. Purification by preparatory LC/MS (15-30% CH₃CN in H₂O) gave the product (205) as its TFA salt (31 mg, 42% yield). 1H NMR (400 MHz, DMSO-$d_6$) δ ppm 1.52 (br. s., 1H) 1.75-2.22 (m, 5H) 2.59-2.81 (m, 3H) 2.85-3.47 (m, 15H) 3.73 (br. s., 1H) 4.04-4.68 (m, 4H) 7.30 (m, 2H) 7.39-7.51 (m, 2H) 7.58 (t, Ham, 2H) 7.74 (m, 2H) 7.97 (m, 1H). ESI-MS: m/z 573.2 (M+H)+.

Example 101

Synthesis of 4-(4'-((R)-2-amino-4-((R)-3-(1-(3-methoxypropyl)-1H-benzo[d]imidazol-2-yl)piperidin-1-yl)-4-oxobutyl)biphenyl-4-yl)-3-methyl-1H-1,2,4-triazol-5(4H)-one (206)

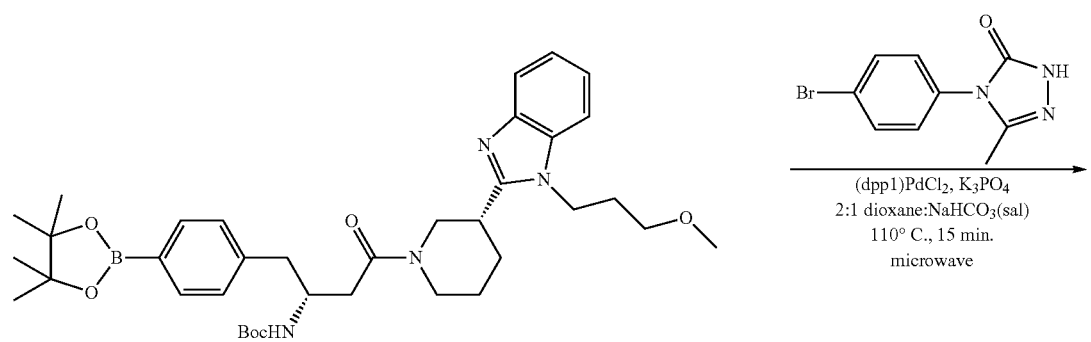

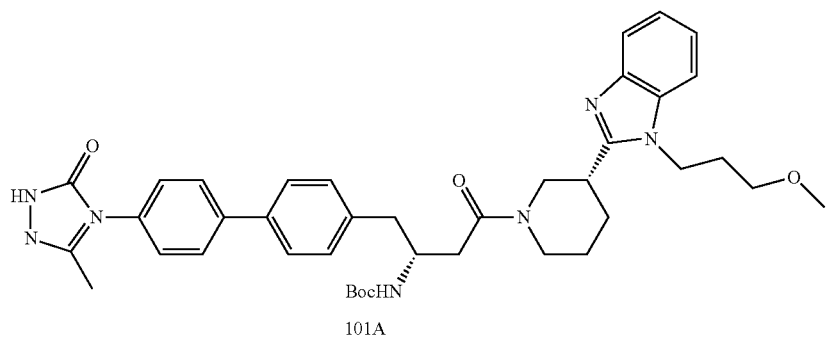

101A tert-butyl(R)-4-((R)-3-(1-(3-methoxypropyl)-1H-benzo[d]imidazol-2-yl)piperidin-1-yl)-1-(4'-(3-methyl-5-oxo-1H-1,2,4-triazol-4(5H)-yl)biphenyl-4-yl)-4-oxobutan-2-ylcarbamate (101A) was prepared according to the procedures outlined in Example 97, Step B. ESI-MS:m/z 708.6 (M+H)$^+$.

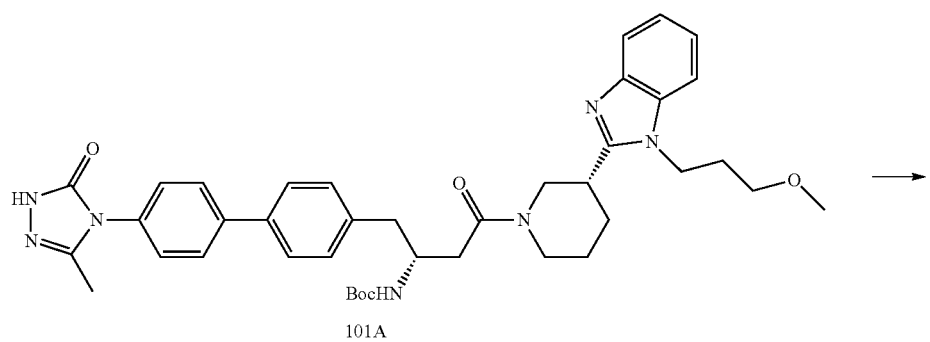

101A

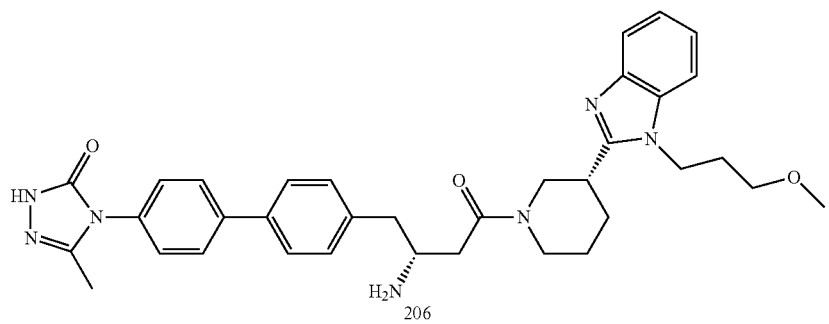

206

Crude product of 4-(4'-((R)-2-amino-4-((R)-3-(1-(3-methoxypropyl)-1H-benzo[d]imidazol-2-yl)piperidin-1-yl)-4-oxobutyl)biphenyl-4-yl)-3-methyl-1H-1,2,4-triazol-5(4H)-one (206) was prepared as described above for Example 97, Step C. Purification by preparatory LC/MS (20-40% CH$_3$CN in H$_2$O) gave the title compound as a TFA salt (20 mg, 14% yield over two steps). 1H NMR (400 MHz, DMSO-d$_6$) δ ppm 1.51 (br. s., 1H) 2.11 (s, 8H) 2.62-3.48 (m, 10H) 3.75 (br. s., 1H) 4.06-4.66 (m, 6H) 7.41 (m, 4H) 7.51 (m, 2H) 7.68-7.76 (m, 4H) 7.81 (m, 2H) 11.66 (s, 1H). ESI-MS:m/z 608.3 (M+H)$^+$.

Example 102

Synthesis of 1-(4-((R)-2-amino-4-((R)-3-(1-(3-methoxypropyl)-1H-benzo[d]imidazol-2-yl)piperidin-1-yl)-4-oxobutyl)phenyl)pyridin-2(1H)-one (207)

Step A.

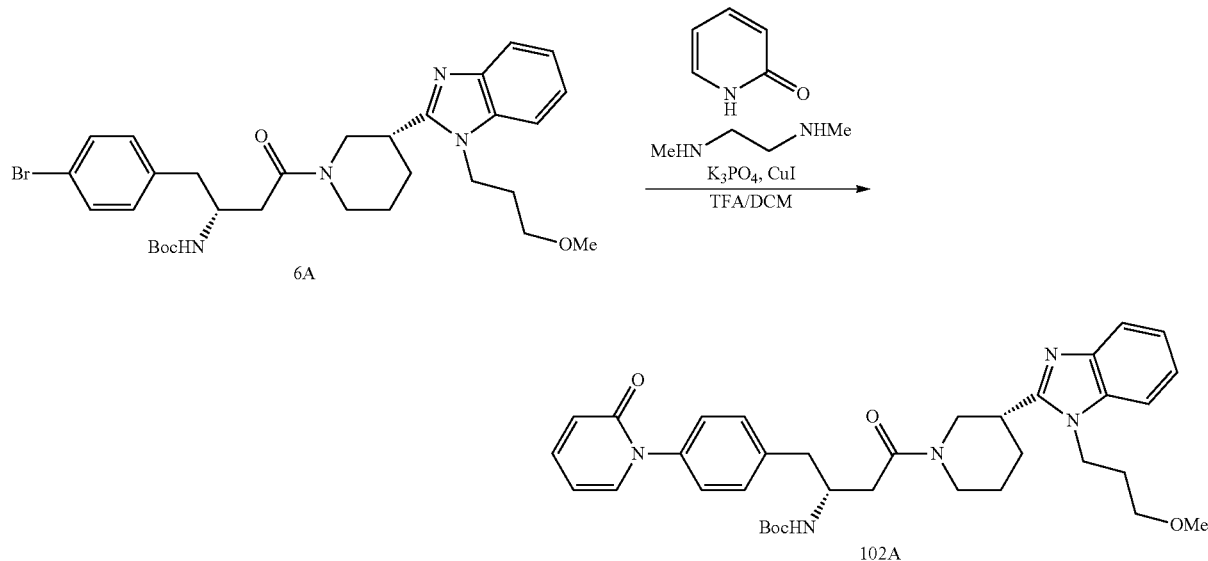

A suspension of bromide, tert-butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (6A) (prepared as described in Example 6, Step A) (45 mg, 0.088 mmol), 2-pyridone (16.7 mg, 2 eq), CuI (3.3 mg, 20% mol), N,N'-dimethylethylenediamine (3.1 mg, 40% mol), potassium phosphate ($K_3PO_4$) (37.4 mg, 2 eq) in 2 mL dioxane was heated at 110° C. for 19 hrs. The mixture was filtered; the filtrate was washed with EtOAc and concentrated to give a greenish oil which was used without further purification.

Step B.

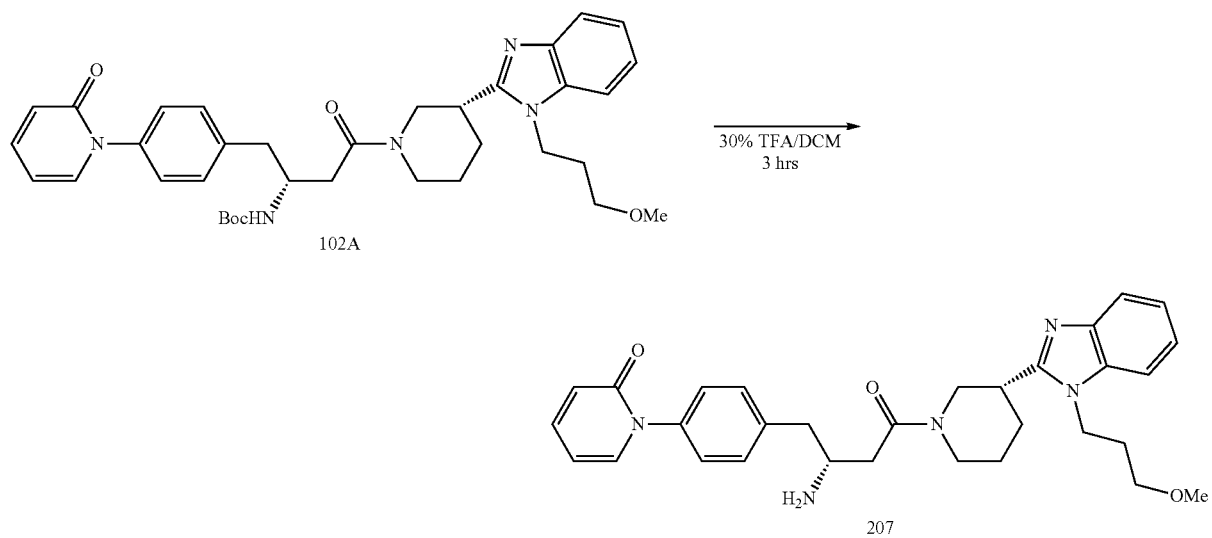

The residue was dissolved in 4 mL 30% TFA/DCM. After 10 mins, solvents removed in vacuo, the residue was dissolved in MeOH (2 mL) and filtered. The filtrate loaded on prep-HPLC for purification to give the product as a white powder (30.3 mg, 71% yield). ESI-MS: m/z 528.5 (M+H)$^+$. $^1$H NMR (400 MHz, MeOH-d$_4$) δ ppm 3.31 (s, 3H) 3.66-3.70 (m, 2H) 4.21-4.25 (m, 2H) 7.1-7.6 (m, 8H); HPLC retention time T=0.855 min, STDTFA-2 method.

Example 103

Synthesis of (R)-4-(4-(1H-imidazol-1-yl)phenyl)-3-amino-1-((R)-3-(1-(3-methoxypropyl)-1H-benzo[d]imidazol-2-yl)piperidin-1-yl)butan-1-one (208)

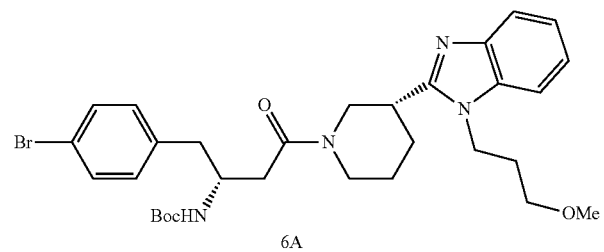
6A

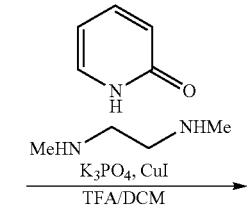

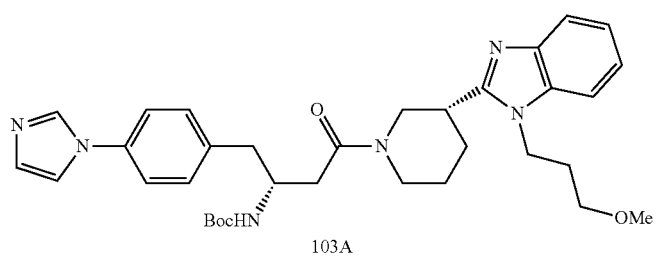
103A

A suspension of bromide, tert-butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (prepared from the procedure of Example 6, Step A) (45 mg, 0.088 mmol), imidazole (11 mg, 2 eq), CuI (3.3 mg, 20% mol), N,N'-dimethylethylenediamine (3.1 mg, 40% mol), potassium phosphate (K$_3$PO$_4$) (37.4 mg, 2 eq) in 2 mL dioxane was heated at 110° C. for 27 hrs. The mixture was filtered; the filtrate was washed with EtOAc and concentrated to give a greenish oil.

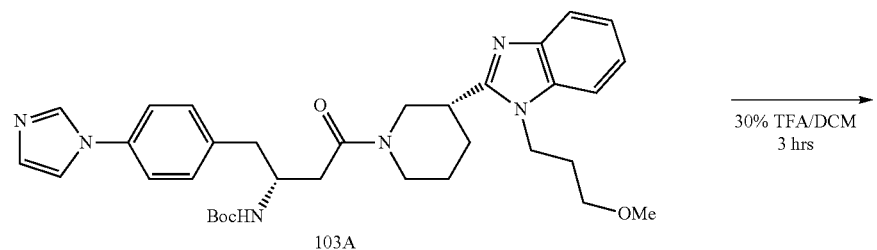
103A

30% TFA/DCM
3 hrs

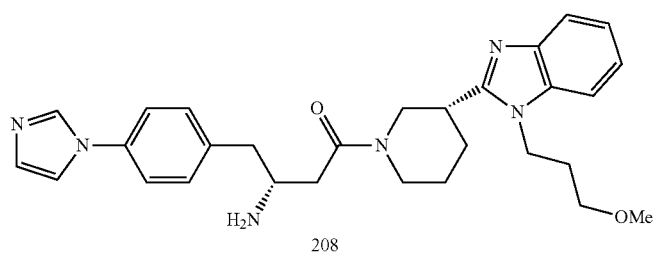
208

The residue was dissolved in 4 mL 30% TFA/DCM. After 20 mins, solvents removed in vacuo, the grey residue was dissolved in MeOH (2 mL) and filtered. The filtrate loaded on prep-HPLC for purification to give the product as a white sticky solid 8.4 mg (21% yield). ESI-MS: m/z 501.5 (M+H)$^+$. $^1$H NMR (400 MHz, MeOH-d$_4$) δ ppm 1.66 (m, 1H) 1.7-2.3 (m, 5H) 4.21-4.25 (m, 2H) 7.1-7.6 (m, 8H). HPLC retention time T=0.781 min, STDTFA-2 method.

Example 104

Synthesis of 1-(4-((R)-2-amino-4-((R)-3-(1-(3-methoxypropyl)-1H-benzo[d]imidazol-2-yl)piperidin-1-yl)-4-oxobutyl)phenyl)pyrrolidin-2-one (209)

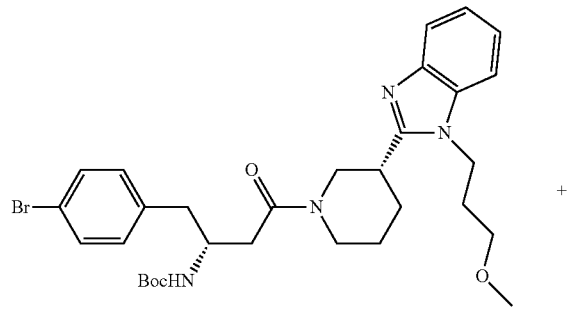
+
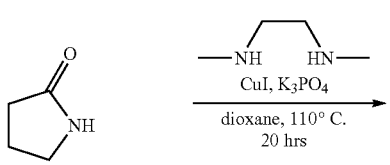

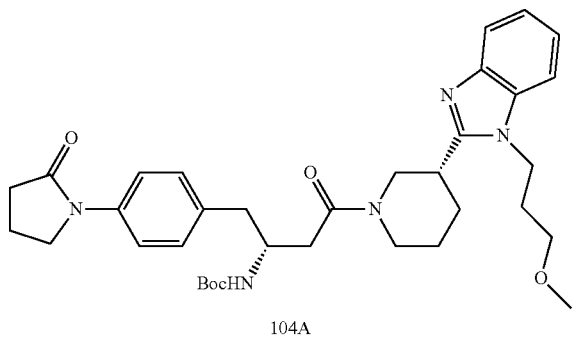

104A (tert-Butyl(R)-4-((R)-3-(1-(3-methoxypropyl)-1H-benzo[d]imidazol-2-yl)piperidin-1-yl)-4-oxo-1-(4-(2-oxopyrrolidin-1-yl)phenyl)butan-2-ylcarbamate (104A) was prepared as described in Example 102, Step A. ESI-MS:m/z 618.5 (M+H)$^+$.

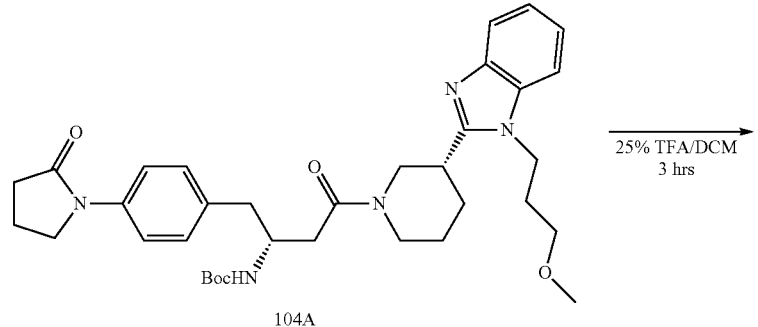

104A

→ 25% TFA/DCM
3 hrs

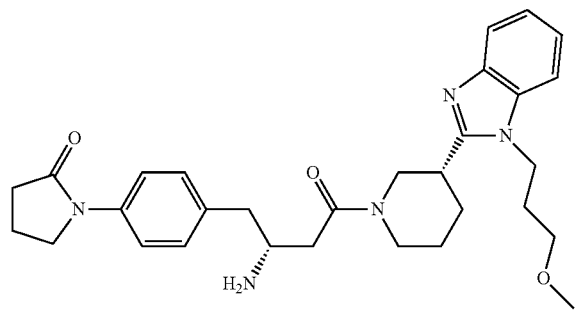

209

(tert-Butyl (R)-4-((R)-3-(1-(3-methoxypropyl)-1H-benzo[d]imidazol-2-yl)piperidin-1-yl)-4-oxo-1-(4-(2-oxopyrrolidin-1-yl)phenyl)butan-2-ylcarbamate (104A) was dissolved in 25% trifluoroacetic acid and stirred at room temperature for 3 hrs. Solvent was removed under vacuum and the residue was purified by preparatory LC/MS (15-40% CH₃CN in H₂O) to give the product 1-(4-((R)-2-amino-4-((R)-3-(1-(3-methoxypropyl)-1H-benzo[d]imidazol-2-yl)piperidin-1-yl)-4-oxobutyl)phenyl)pyrrolidin-2-one (209) as a TFA salt (8 mg, 17% yield). ESI-MS:m/z 518.2 (M+H)⁺.

Example 105

Synthesis of 1-(4-((R)-2-amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione (210)

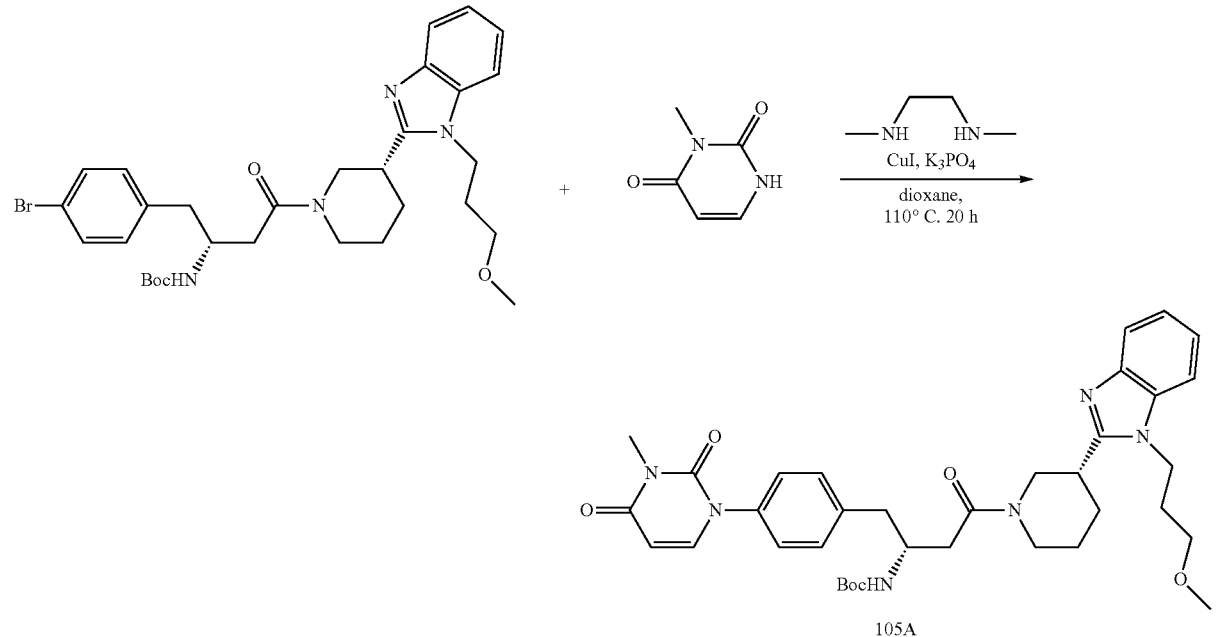

tert-Butyl(R)-4-((R)-3-(1-(3-methoxypropyl)-1H-benzo[d]imidazol-2-yl)piperidin-1-yl)-4-oxo-1-(4-(2-oxopyrrolidin-1-yl)phenyl)butan-2-ylcarbamate (105A) was prepared as described in Example 102, Step A. ESI-MS:m/z 659.5 (M+H)⁺.

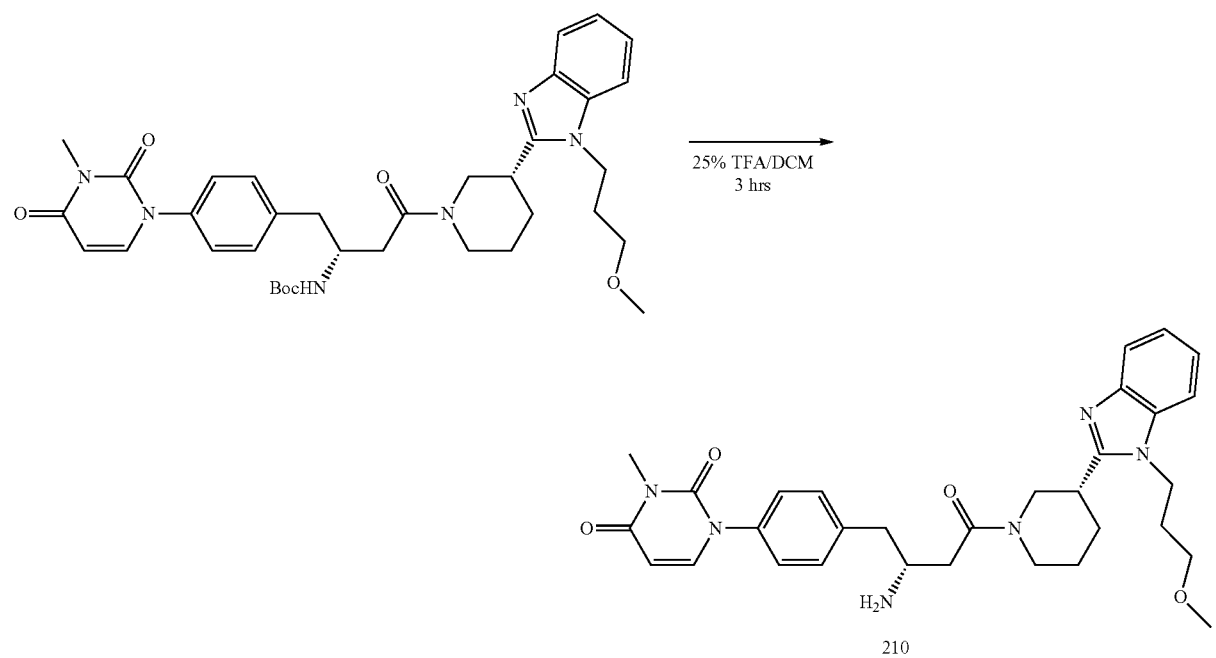

1-(4-((R)-2-amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione (210) was prepared as described in Example 104, Step B and was purified by preparatory LC/MS (10-40% CH$_3$CN in H$_2$O) to give the product (210) as a TFA salt (7 mg, 14% yield). ESI-MS:m/z 559.3 (M+H)$^+$.

Example 106

Synthesis of 1-(4-((R)-2-amino-4-((R)-3-(1-(3-methoxypropyl)-1H-benzo[d]imidazol-2-yl)piperidin-1-yl-4-oxobutyl)phenyl)-3-methylpyrimidine-2,4(1H,3H)-dione (211)

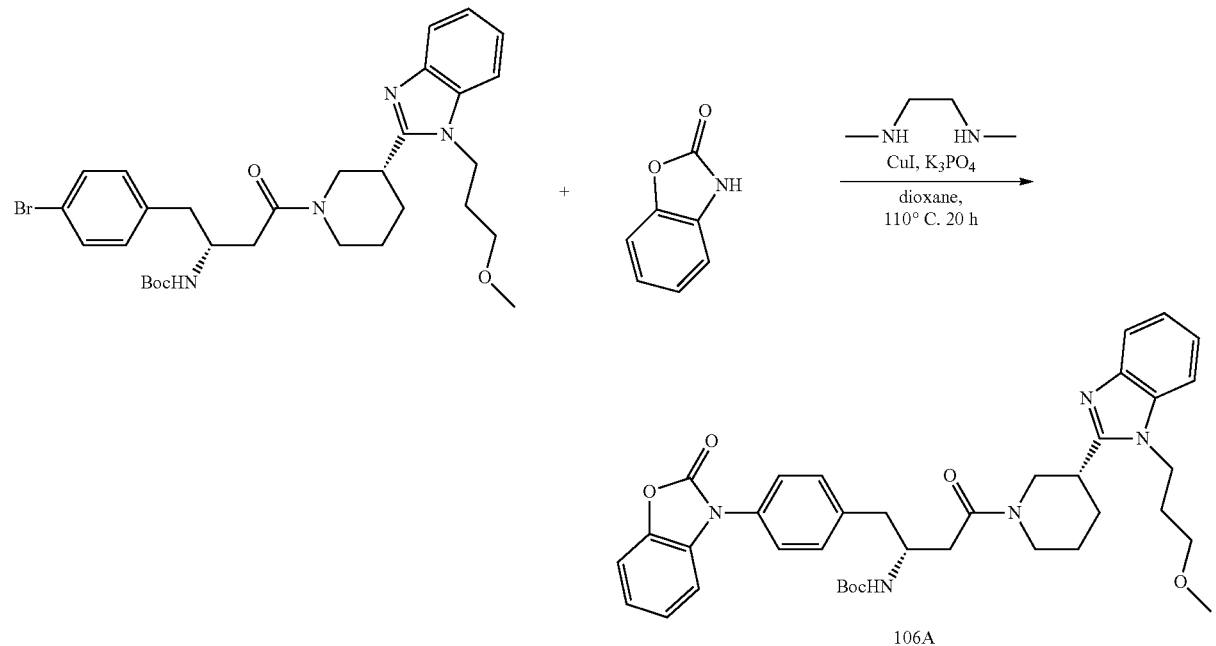

1-(4-((R)-2-Amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione (106A) was prepared as described in Example 102, Step A. ESI-MS:m/z 667.3 (M+H)$^+$.

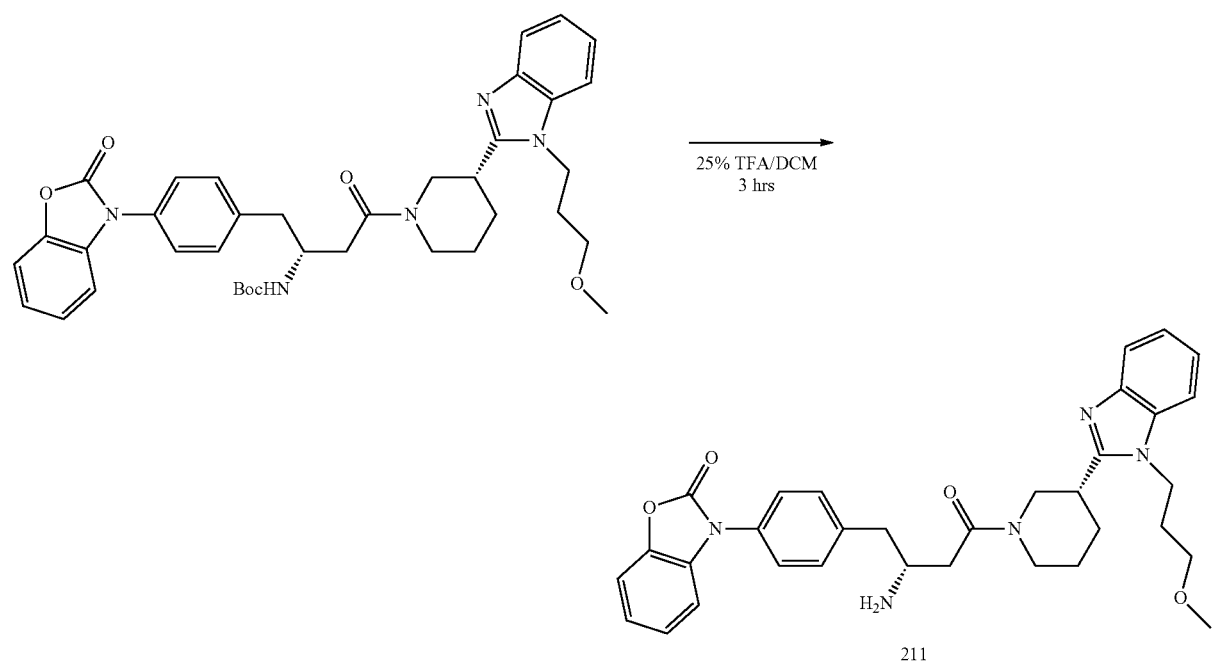

1-(4-((R)-2-amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione (211) was prepared as described in Example 104, Step B and was purified by preparatory LC/MS (25-30% CH₃CN in H₂O) to give the product (211) as a TFA salt (22 mg, 44% yield). ESI-MS:m/z 568.2 (M+H)⁺.

Example 107

Synthesis of 1-(4-((R)-2-amino-4-((R)-3-(1-(3-methoxypropyl)-1H-benzo[d]imidazol-2-yl)piperidin-1-yl)-4-oxobutyl)phenyl)-3-methylpyrimidine-2,4(1H, 3H)-dione (212)

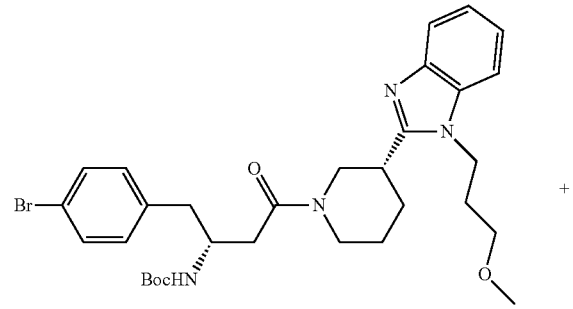
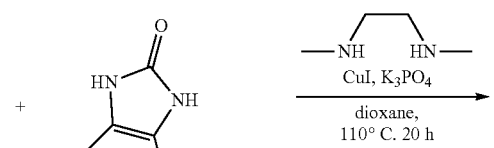
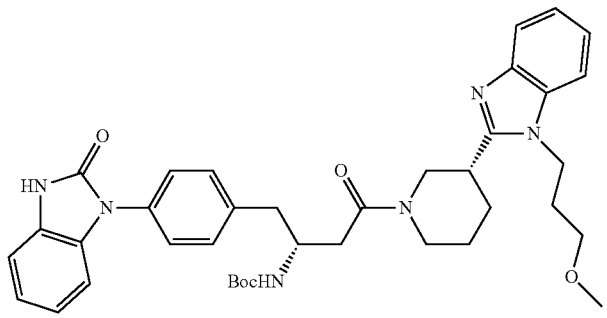

107A 1-(4-((R)-2-Amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione (107A) was prepared as described in Example 102, Step A. ESI-MS:m/z 667.5 (M+H)⁺.

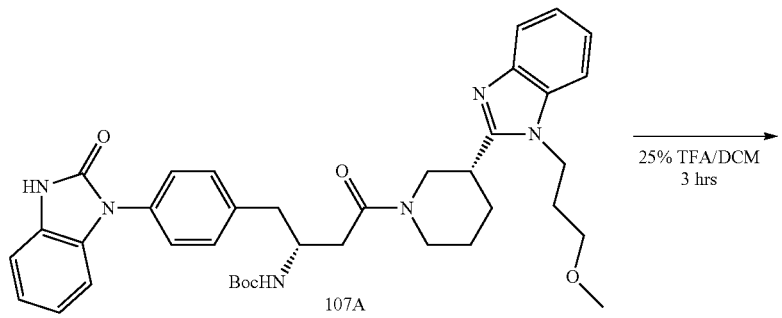

107A

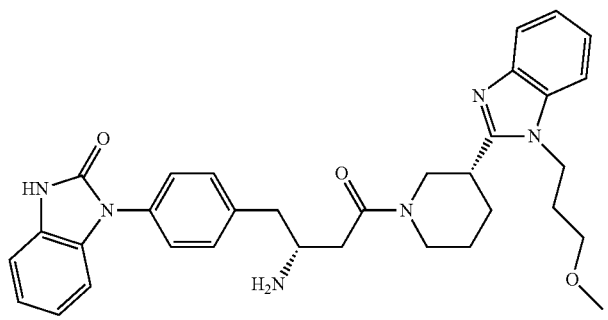

212

Crude product of 1-(4-((R)-2-amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione (212) was prepared as described in Example 104, Step B and was purified by preparatory LC/MS (25-30% CH$_3$CN in WO) to give the product (212) as a TFA salt (26 mg, 52% yield). 1H NMR (400 MHz, DMSO-d$_6$) δ ppm 1.52 (br. s., 1H) 1.74-2.19 (m, 5H) 2.73 (m, 3H) 2.80-3.48 (m, 8H) 3.77 (br. s., 1H) 4.08-4.69 (m, 5H) 6.96-7.10 (m, 4H) 7.35-7.56 (m, 6H) 7.73 (m, 2H). ESI-MS:m/z 567.2 (M+H)$^+$.

Example 108

1-(4-((R)-2-Amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione (213)

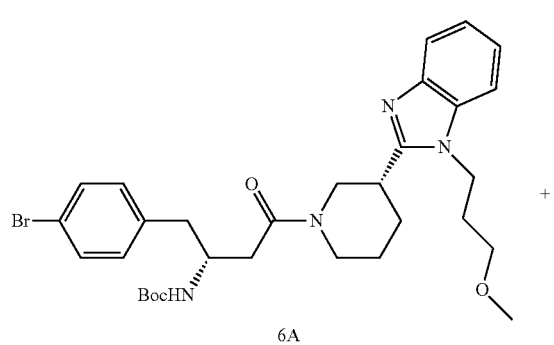

6A

+

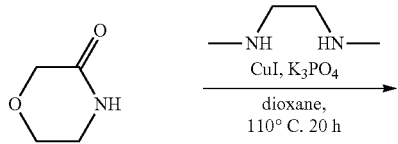

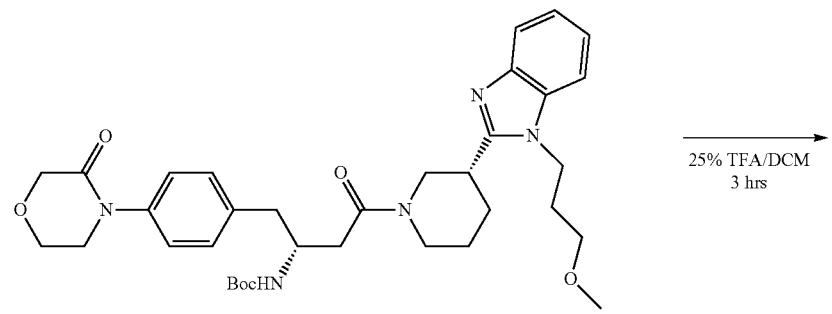

108A 1-(4-((R)-2-Amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione (108A) was prepared as described in Example 102, Step A. ESI-MS:m/z 634.5 (M+H)$^+$.

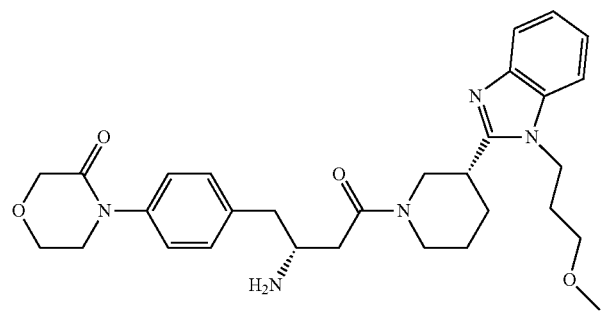

213

1-(4-((R)-2-Amino-4-((R)-3-(1-(3-methoxypropyl)-1H-benzo[d]imidazol-2-yl)piperidin-1-yl)-4-oxobutyl)phenyl)-3-methylpyrimidine-2,4(1H,3H)-dione (213) was prepared as described in Example 104, Step B and was purified by preparatory LC/MS (10-30% CH$_3$CN in H$_2$O) to give the product (213) as a TFA salt (7 mg, 15% yield). ESI-MS:m/z 534.4 (M+H)$^+$.

Example 109

Synthesis of 1-(4-((R)-2-amino-4-((R)-3-(1-(3-methoxypropyl)-1H-benzo[d]imidazol-2-yl)piperidin-1-yl)-4-oxobutyl)phenyl)-3-(2-methoxyethyl)-1H-benzo[d]imidazol-2(3H)-one (214)

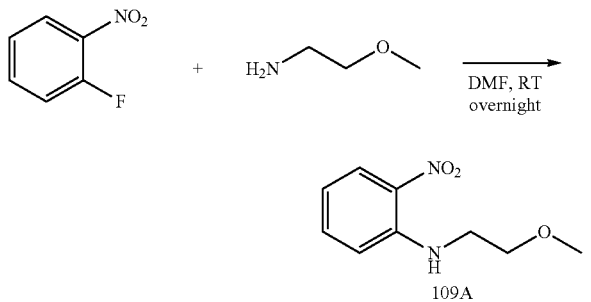

Into a 25 mL round bottomedwas added 2-fluoronitrobenzene (500 mg, 3.54 mmol) and DMF (7 mL), and 2-methoxyethylamine (346 mg, 4.60 mmol) in DMF (2.39 mL) was added slowly via syringe. The mixture was stirred at room temperature overnight. Solvent was removed under vacuum and the residue containing N-(2-methoxyethyl)-2-nitroaniline (109A) was taken to the next step without further purification. ESI-MS:m/z 197.3 (M+H)$^+$.

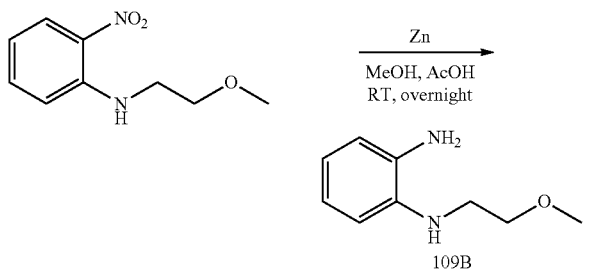

The residue 109A was dissolved in methanol (60 mL) and acetic acid (4 mL). Zinc metal (3.24 g, 49.6 mmol) was added and the mixture was stirred overnight at room temperature. The reaction was decanted off from unreacted zinc metal. The solvent was removed under vacuum and resuspended in ethyl acetate (30 mL). The precipitate was removed by filtration on a Buchner funnel with Celite. Solvent was removed from the filtrate and the residue was purified by column chromatography (2% MeOH/DCM) to give the product N1-(2-methoxyethyl)benzene-1,2-diamine (109B) as a red oil (422 mg, 72% yield over two steps). ESI-MS:m/z 167.4 (M+H)$^+$.

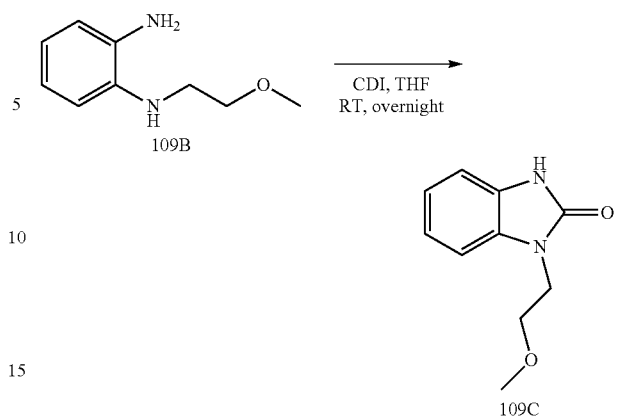

The residue 109B (422 mg, 2.54 mmol) was dissolved in THF (7.5 mL). CDI (494 mg, 3.05 mmol) in THF (7.6 mL) was added slowly via addition funnel. After addition the mixture was stirred overnight at room temperature, solvent was removed under vacuum. The residue was purified by column chromatography (5% MeOH/DCM) to give the product 1-(2-methoxyethyl)-1H-benzo[d]imidazol-2(3H)-one (109C) as an orange solid (449 mg, 92%). ESI-MS:m/z 193.3 (M+H)$^+$.

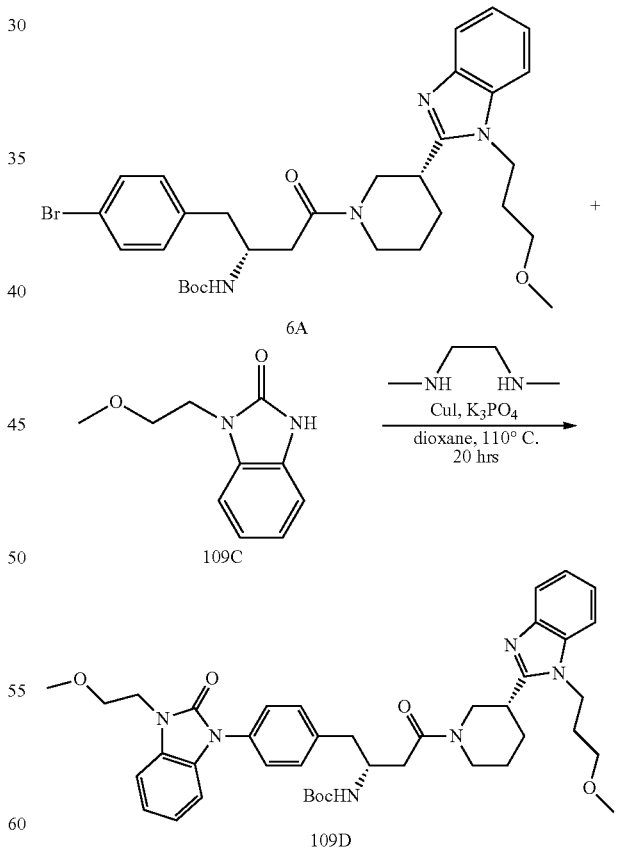

tert-Butyl (R)-1-(4-(3-(2-methoxyethyl)-2-oxo-2,3-dihydro-1H-benzo[d]imidazol-1-yl)phenyl)-4-((R)-3-(1-(3-methoxypropyl)-1H-benzo[d]imidazol-2-yl)piperidin-1-yl)-4-oxobutan-2-ylcarbamate (109D) was prepared as described in Example 102, Step A. ESI-MS:m/z 724.4 (M+H)$^+$.

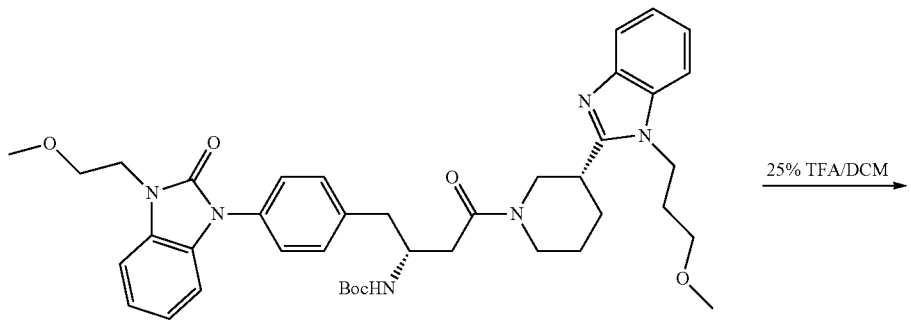

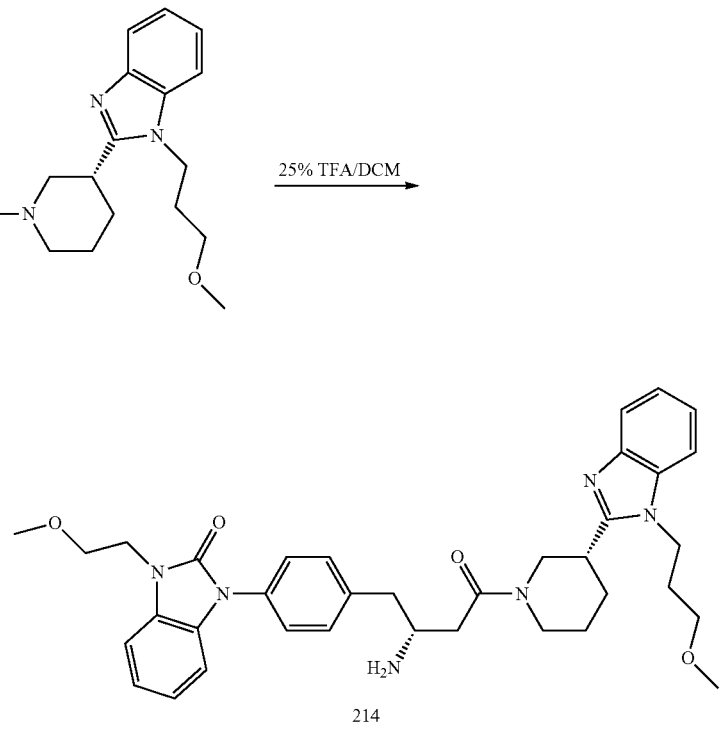

1-(4-((R)-2-Amino-4-((R)-3-(1-(3-methoxypropyl)-1H-benzo[d]imidazol-2-yl)piperidin-1-yl)-4-oxobutyl)phenyl)-3-(2-methoxyethyl)-1H-benzo[d]imidazol-2(3H)-one (214) was prepared as described in Example 104, Step B and was purified by preparatory LC/MS (20-45% $CH_3CN$ in $H_2O$) to give the product as a TFA salt (49 mg, 45% yield over two steps). 1H NMR (400 MHz, DMSO-$d_6$) δ ppm 1.53 (br. s., 1H) 1.93 (m, 5H) 2.63-3.48 (m, 15H) 3.65 (m, 2H) 3.79 (br. s., 1H) 4.08 (m, 2H) 4.38 (m, 4H) 7.04 (m, 2H) 7.13 (m 1H) 7.32 (m, 1H) 7.41-7.57 (m, 6H) 7.72-7.82 (m, 2H). ESI-MS:m/z 625.3 $(M+H)^+$.

Example 110

Synthesis of the mixture of 1-(4-((R)-2-amino-4-((R)-3-(1-(3-methoxypropyl)-1H-benzo[d]imidazol-2-yl)piperidin-1-yl)-4-oxobutyl)phenyl)-5-methyl-1H-benzo[d]imidazol-2(3H)-one (215) and 1-(4-((R)-2-amino-4-((R)-3-(1-(3-methoxypropyl)-1H-benzo[d]imidazol-2-yl)piperidin-1-yl)-4-oxobutyl)phenyl)-6-methyl-1H-benzo[d]imidazol-2(3H)-one (216)

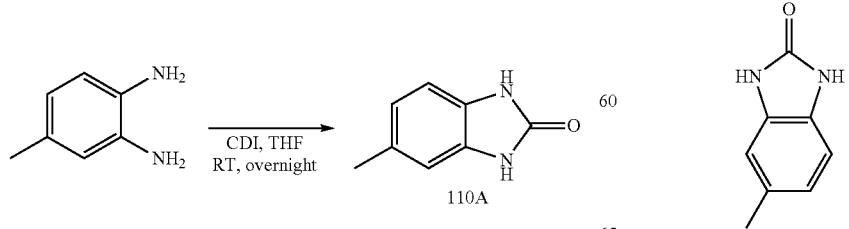

Into a 100 mL round bottomed flask, 3,4-diaminotoluene (1.00 g, 8.2 mmol) was dissolved in THF (8.2 mL). CDT (1.59 g, 9.8 mmol) in THF (25 mL) was added slowly via addition funnel. After addition the mixture was stirred overnight at room temperature. Solvent was removed under vacuum and the residue was purified by column chromatography (5% MeOH/DCM) to give the product 5-methyl-1H-benzo[d]imidazol-2(3H)-one (110A) as a brown-tan solid (990 mg, 82% yield). ESI-MS:m/z 149.4 $(M+H)^+$.

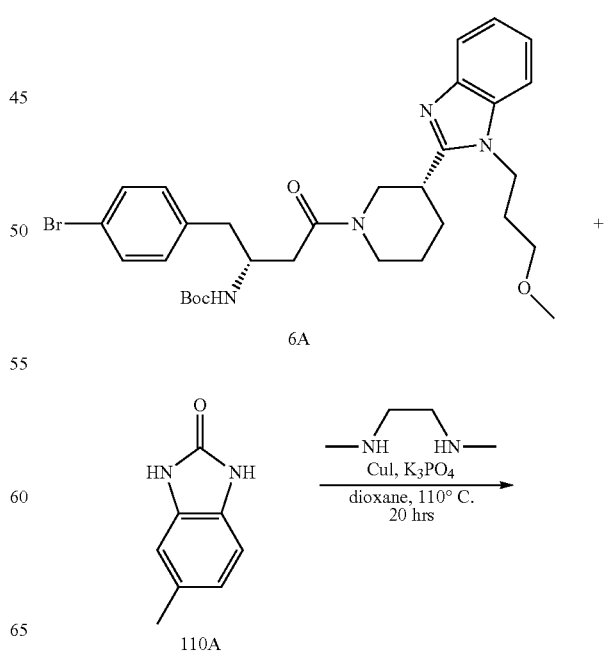

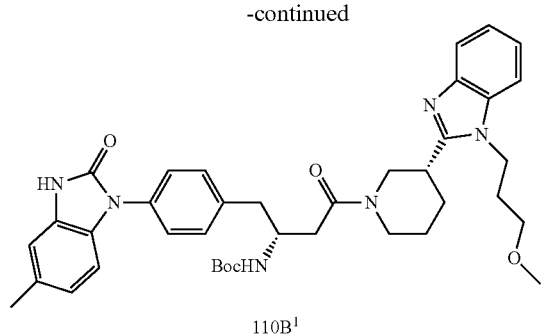

110B¹

+

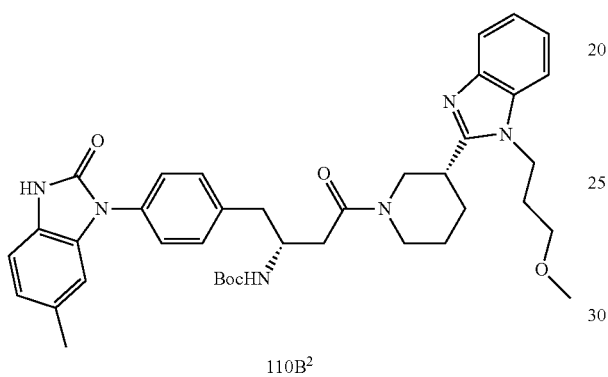

110B²

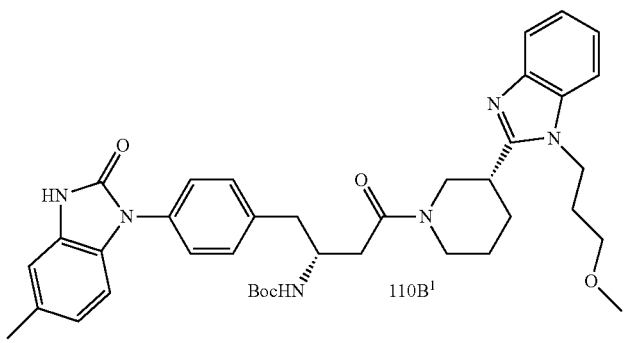

110B¹

25% TFA/DCM →

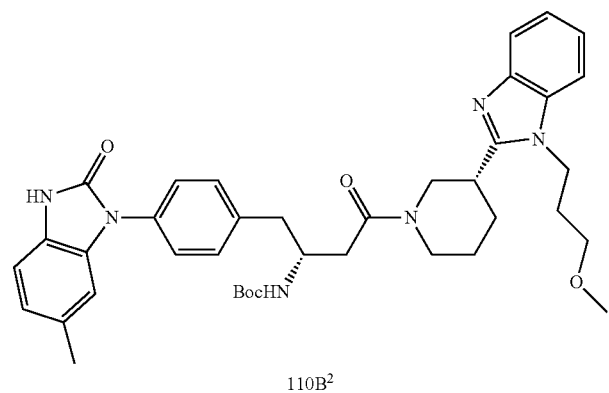

110B²

The mixture of tert-Butyl (R)-4-((R)-3-(1-(3-methoxypropyl)-1H-benzo[d]imidazol-2-yl)piperidin-1-yl)-1-(4-(5-methyl-2-oxo-2,3-dihydro-1H-benzo[d]imidazol-1-yl)phenyl)-4-oxobutan-2-ylcarbamate (110B¹) and tert-butyl (R)-4-((R)-3-(1-(3-methoxypropyl)-1H-benzo[d]imidazol-2-yl)piperidin-1-yl)-1-(4-(6-methyl-2-oxo-2,3-dihydro-1H-benzo[d]imidazol-1-yl)phenyl)-4-oxobutan-2-ylcarbamate (110B²) was prepared as described in Example 102, Step A and was purified by preparatory LC/MS (35-45% $CH_3CN$ in $H_2O$). ESI-MS:m/z 680.4 $(M+H)^+$.

-continued

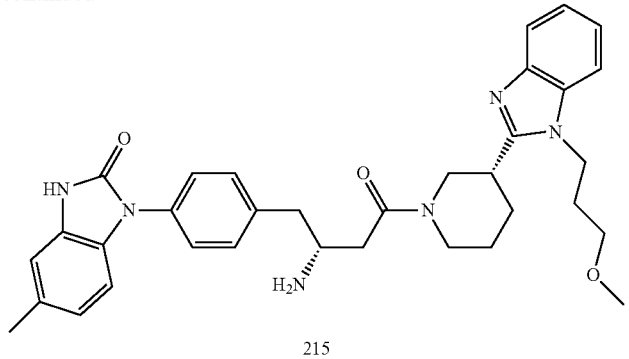
215

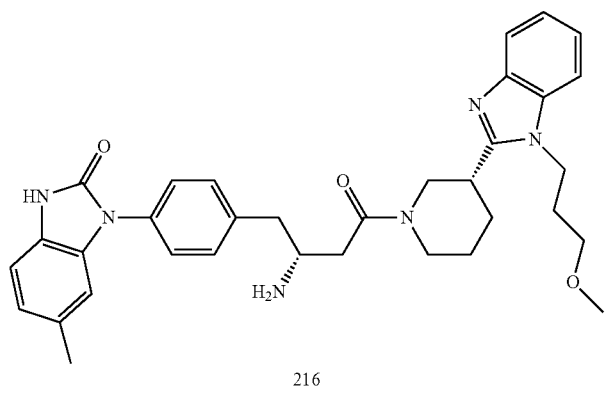
216

The mixture of 1-(4-((R)-2-amino-4-((R)-3-(1-(3-methoxypropyl)-1,1-benzo[d]imidazol-2-yl)piperidin-1-yl)-4-oxobutyl)phenyl)-5-methyl-1H-benzo[d]imidazol-2(3H)-one (215) and 1-(4-((R)-2-amino-4-((R)-3-(1-(3-methoxypropyl)-1H-benzo[d]imidazol-2-yl)piperidin-1-yl)-4-oxobutyl)phenyl)-6-methyl-1H-benzo[d]imidazol-2(3H)-one (216) was prepared as described in Example 104, Step 13 and was purified by preparatory LC/MS (20-45% CH₃CN in H₂O) to give the product as a TFA salt (8 mg, 8% yield over two steps). ESI-MS:m/z 581.3 (M+H)⁺.

Example 111

Synthesis of the mixture of 1-(4-((R)-2-amino-4-((R)-3-(1-(3-methoxypropyl)-1H-benzo[d]imidazol-2-yl)piperidin-1-yl)-4-oxobutyl)phenyl)-4-fluoro-1H-benzo[d]imidazol-2(3H)-one (217) and 1-(4-((R)-2-amino-4-((R)-3-(1-(3-methoxypropyl)-1H-benzo[d]imidazol-2-yl)piperidin-1-yl)-4-oxobutyl)phenyl)-7-fluoro-1H-benzo[d]imidazol-2(3H)-one (218)

(386 mg, 2.38 mmol) in THF (6 mL) was added slowly via addition funnel. The reaction was stirred at room temperature overnight. The resultant precipitate was isolated by filtration on a Buchner funnel and washed with cold THF to give 4-fluoro-1H-benzo[d]imidazol-2(3H)-one (111A) as a white solid (200 mg, 66%). ESI-MS:m/z 153.3 (M+H)⁺.

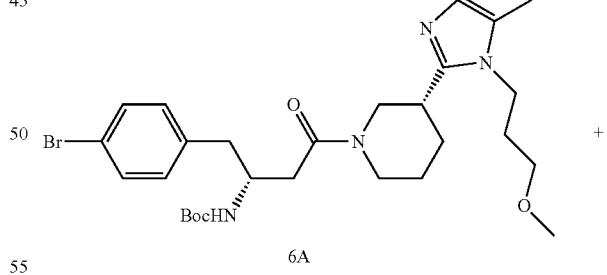
6A

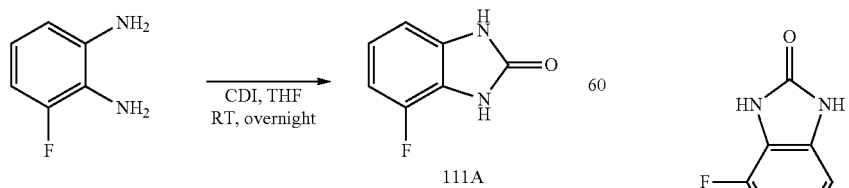
111A

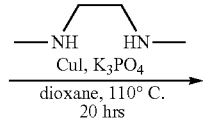

Into a 25 mL round bottomed flask was added 2,3-diaminofluorobenzene (250 mg, 1.98 mmol) and THF (2 mL). CDI -continued

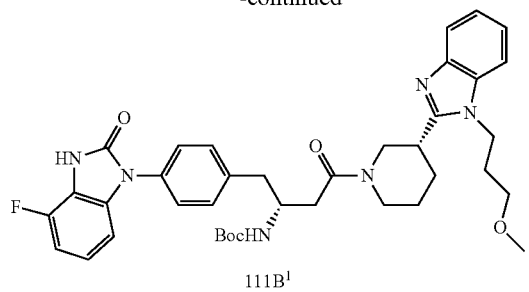
111B¹

+

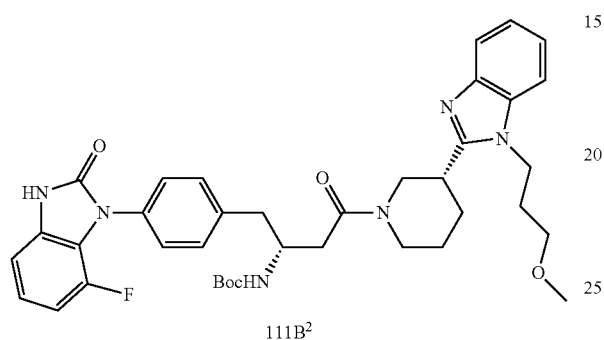
111B²

Crude product of the mixture of tert-butyl (R)-1-(4-(4-fluoro-2-oxo-2,3-dihydro-1H-benzo[d]imidazol-1-yl)phenyl)-4-((R)-3-(1-(3-methoxypropyl)-1H-benzo[d]imidazol-2-yl)piperidin-1-yl)-4-oxobutan-2-ylcarbamate (111B¹) and tert-butyl (R)-1-(4-(7-fluoro-2-oxo-2,3-dihydro-1H-benzo[d]imidazol-1-yl)phenyl)-4-((R)-3-(1-(3-methoxypropyl)-1H-benzoidlimidazol-2-yl)piperidin-1-yl)-4-oxobutan-2-ylcarbamate (111B²) was prepared as described in Example 102, Step A. The residue was purified by preparatory LC/MS (30-45% CH₃CN in H₂O). ESI-MS:m/z 684.3 (M+H)⁺.

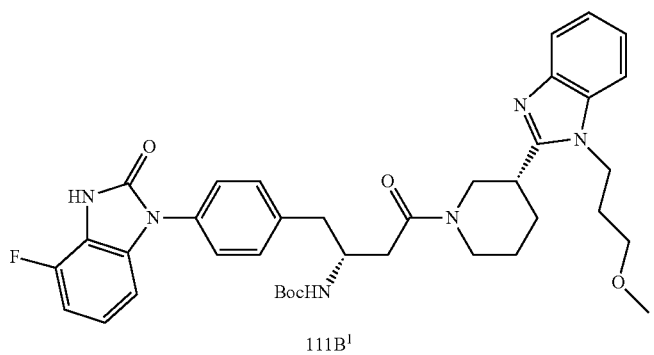
111B¹

+

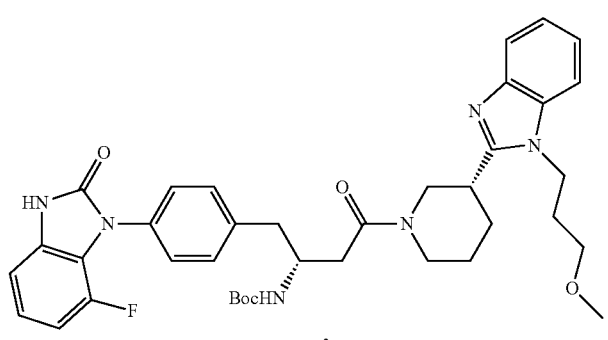
111B²

25% TFA/DCM →

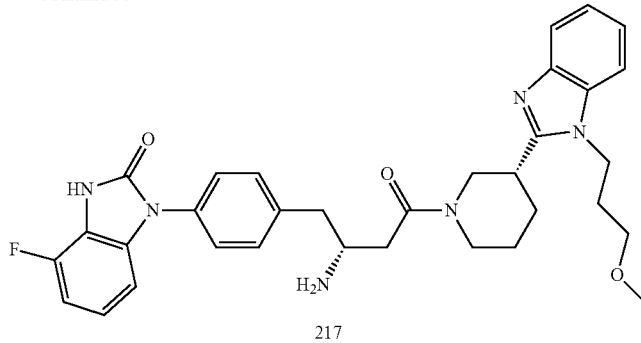

217

+

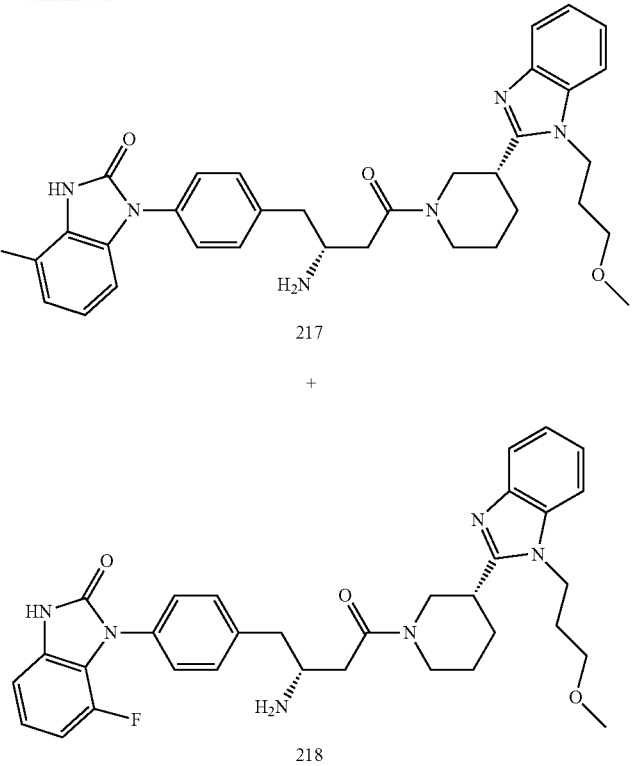

218

The mixture of 1-(4-((R)-2-amino-4-((R)-3-(1-(3-methoxypropyl)-1H-benzo[d]imidazol-2-yl)piperidin-1-yl)-4-oxobutyl)phenyl)-4-fluoro-1H-benzo[d]imidazol-2(3H)-one (217) and 1-(4-((R)-2-amino-4-((R)-3-(1-(3-methoxypropyl)-1H-benzo[d]imidazol-2-yl)piperidin-1-yl)-4-oxobutyl)phenyl)-7-fluoro-1H-benzo[d]imidazol-2(3H)-one (218) was prepared as described in Example 104, Step B and was purified by preparatory LC/MS (20-40% CH$_3$CN in H$_2$O) to give the product as a TFA salt (18 mg, 17% yield over two steps). 1H NMR (400 MHz, DMSO-d$_6$) δ ppm 1.53 (br. s., 1H) 1.76-2.19 (m, 5H) 2.62-3.46 (m, 12H) 3.78 (br. s., 1H) 4.10-4.68 (m, 4H) 6.82 (m, 1H) 6.99 (m, 2H) 7.37-7.56 (m, 6H) 7.74 (m, 2H) 11.74 (m, 1H). ESI-MS:m/z 585.3 (M+H)$^+$.

Example 112

Synthesis of 1-(4-((R)-2-amino-4-((R)-3-(1-(3-methoxypropyl)-1H-benzoldjimidazol-2-yl)piperidin-1-yl)-4-oxobutyl)phenyl)-5,6-dimethyl-1H-benzo[d]imidazol-2(3H)-one (219)

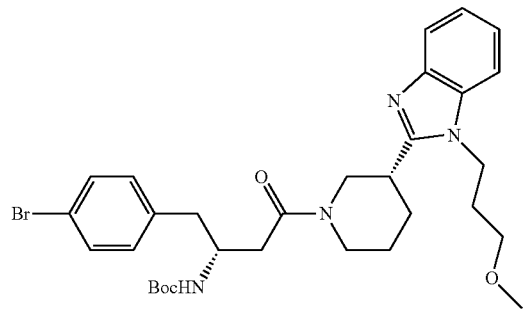

+

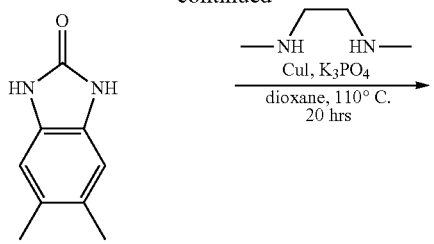

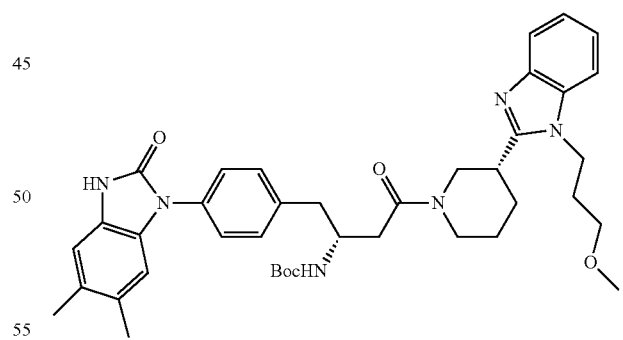

112A

Crude product of tert-butyl (R)-1-(4-(5,6-dimethyl-2-oxo-2,3-dihydro-1H-benzo[d]imidazol-1-yl)phenyl)-4-((R)-3-(1-(3-methoxypropyl)-1H-benzo[d]imidazol-2-yl)piperidin-1-yl)-4-oxobutan-2-ylcarbamate (112A) was prepared as described above for Example 102, Step A. The residue was purified by preparatory LC/MS (35-55% CH$_3$CN in H$_2$O). ESI-MS:m/z 695.5 (M+H)$^+$.

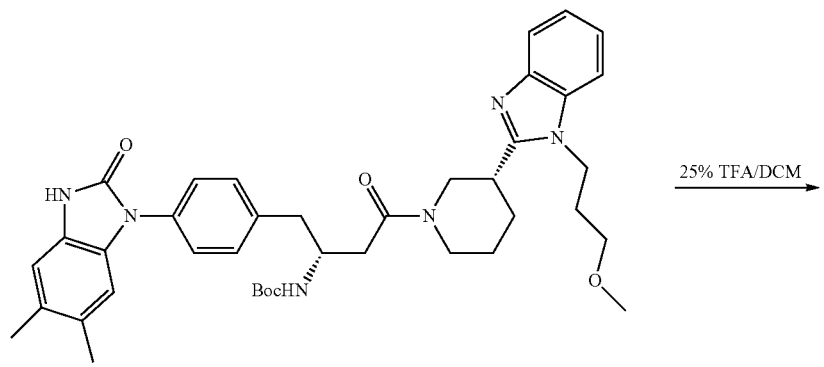

→ 25% TFA/DCM

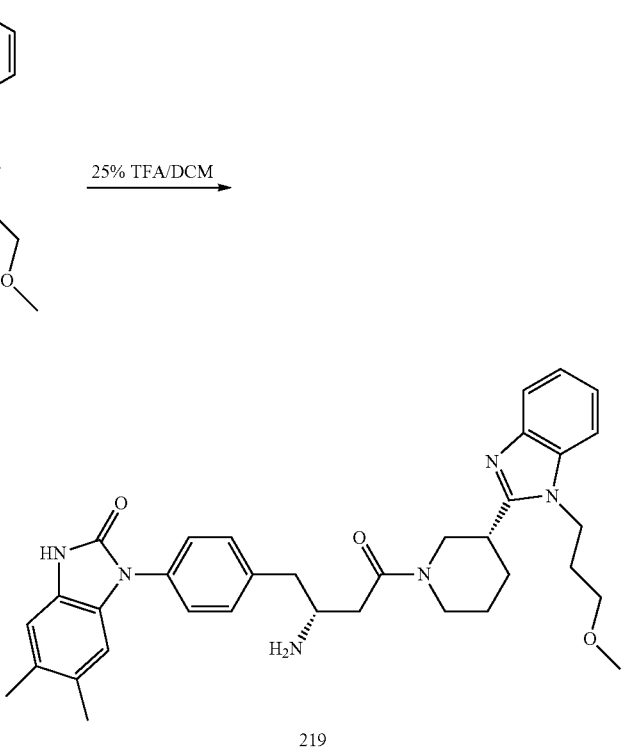

219

Crude product of 1-(4-((R)-2-amino-4-((R)-3-(1-(3-methoxypropyl)-1H-benzo[d]imidazol-2-yl)piperidin-1-yl)-4-oxobutyl)phenyl)-5,6-dimethyl-1H-benzo[d]imidazol-2(3H)-one (219) was prepared as described in Example 104, Step B and was purified by preparatory LC/MS (20-45% $CH_3CN$ in $H_2O$) to give the product as a TFA salt (20 mg, 19% yield over two steps). 1H NMR (400 MHz, DMSO-$d_5$) δ ppm 1.53 (br. s., 1H) 1.74-2.14 (m, 5H) 2.14-2.24 (m, 6H) 2.62-3.49 (m, 12H) 3.77 (br. s., 1H) 4.08-4.68 (m, 4H) 6.80 (m, 1H) 6.87 (m, 1H) 7.34-7.54 (m, 6H) 7.67-7.77 (m, 2H) 10.96 (m, 1H). ESI-MS:m/z 595.3 (M+H)$^+$.

Example 113

Synthesis of 1-(4-((R)-2-amino-4-((R)-3-(1-(3-methoxypropyl)-1H-benzo[d]imidazol-2-yl)piperidin-1-yl)-4-oxobutyl)phenyl)-3-methyl-1H-benzo[d]imidazol-2(3H)-one (220)

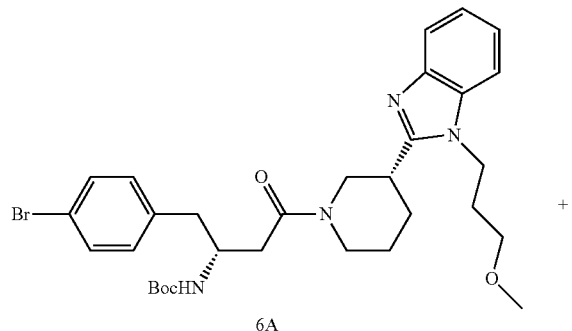

6A

+

-continued

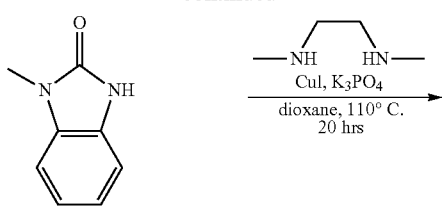

$\xrightarrow{\text{CuI, K}_3\text{PO}_4}{\text{dioxane, 110° C.}\\ \text{20 hrs}}$

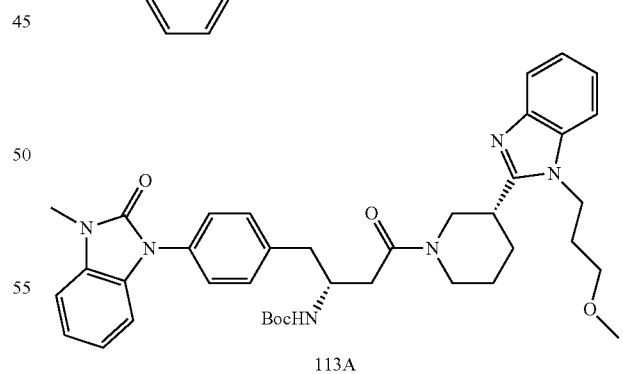

113A

Crude product of tert-butyl (R)-4-((R)-3-(1-(3-methoxypropyl)-1H-benzo[d]imidazol-2-yl)piperidin-1-yl)-1-(4-(3-methyl-2-oxo-2,3-dihydro-1H-benzo[d]imidazol-1-yl)phenyl)-4-oxobutan-2-ylcarbamate (113A) was prepared as described for Example 102, Step A and was purified by preparatory LC/MS (35-50% $CH_3CN$ in $H_2O$). ESI-MS:m/z 680.4 (M+H)$^+$.

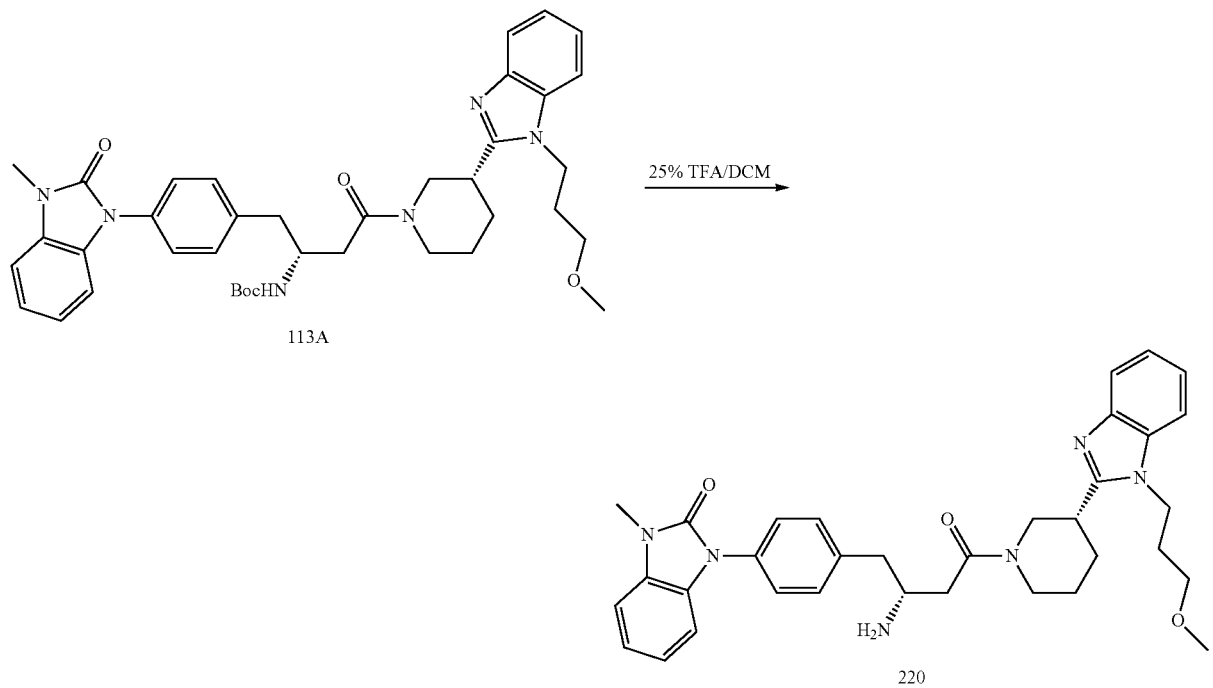

113A

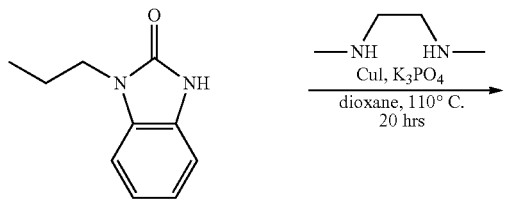

220

Crude product of 1-(4-((R)-2-amino-4-((R)-3-(1-(3-methoxypropyl)-1H-benzo[d]imidazol-2-yl)piperidin-1-yl)-4-oxobutyl)phenyl)-3-methyl-1H-benzo[d]imidazol-2(3H)-one (220) was prepared as described in Example 104, Step B and was purified by preparatory LC/MS (20-40% CH$_3$CN in H$_2$O) to give the product as a TFA salt (20 mg, 19% yield over two steps). 1H NMR (400 MHz, DMSO-d$_6$) δ ppm 1.53 (br. s., 1H) 1.93 (br. s., 5H) 2.61-3.46 (m, 15H) 3.79 (br. s., 1H) 4.10-4.69 (m, 4H) 7.00-7.09 (m, 2H) 7.16 (m, 1H) 7.26 (m, 1H) 7.38-7.57 (m, 6H) 7.70-7.81 (m, 2H). ESI-MS:m/z 581.3 (M+H)$^+$.

-continued

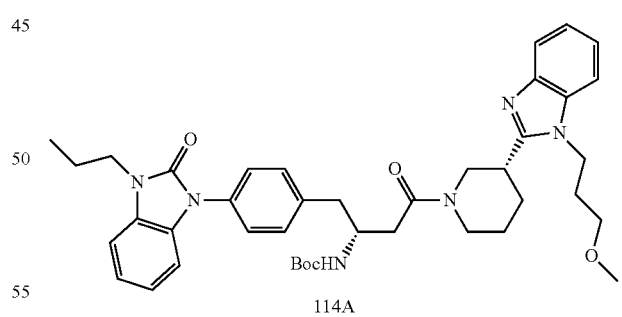

Example 114

Synthesis of 1-(4-((R)-2-amino-4-((R)-3-(1-(3-methoxypropyl)-1H-benzo[d]imidazol-2-yl)piperidin-1-yl)-4-oxobutyl)phenyl)-3-propyl-1H-benzo[d]imidazol-2(3H)-one (221)

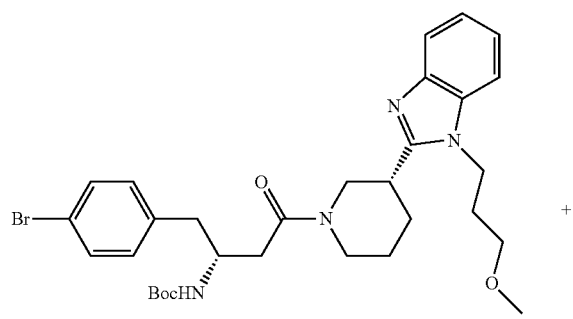

+

114A

Crude product of tert-butyl (R)-4-((R)-3-(1-(3-methoxypropyl)-1H-benzo[d]imidazol-2-yl)piperidin-1-yl)-4-oxo-1-(4-(2-oxo-3-propyl-2,3-dihydro-1H-benzo[d]imidazol-1-yl)phenyl)butan-2-ylcarbamate (114A) was prepared as described for Example 102, Step A and was purified by preparatory LC/MS (35-45% CH$_3$CN in H$_2$O). ESI-MS:m/z 708.4 (M+H)$^+$.

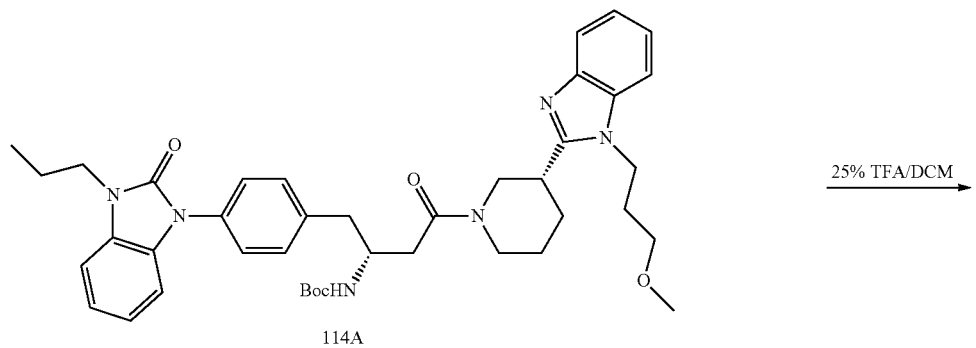

Crude product of 1-(4-((R)-2-amino-4-((R)-3-(1-(3-methoxypropyl)-1H-benzo[d]imidazol-2-yl)piperidin-1-yl)-4-oxobutyl)phenyl)-3-propyl-1H-benzo[d]imidazol-2(3H)-one (221) was prepared as described in Example 104, Step B and was purified by preparatory LC/MS (20-40% CH$_3$CN in H$_2$O) to give the product as a TFA salt (46 mg, 43% yield over two steps). 1H NMR (400 MHz, DMSO-d$_6$) δ ppm 0.92 (m, 3H) 1.53 (br. s., 1H) 1.66-1.76 (m, 2H) 1.93 (m, 5H) 2.63-3.46 (m, 12H) 3.72-3.83 (m, 1H) 3.87 (m, 2H) 4.11-4.68 (m, 4H) 7.01-7.08 (m, 2H) 7.14 (m, 1H) 7.32 (m, 1H) 7.39-7.57 (m, 6H) 7.70-7.80 (m, 2H). ESI-MS:m/z 609.3 (M+H)$^+$.

Example 115

Synthesis of 1-(4-((R)-2-amino-4-((R)-3-(1-(3-methoxypropyl)-1H-benzo[d]imidazol-2-yl)piperidin-1-yl)-4-oxobutyl)phenyl)-3-(2-hydroxyethyl)-1H-benzo[d]imidazol-2(3H)-one (222)

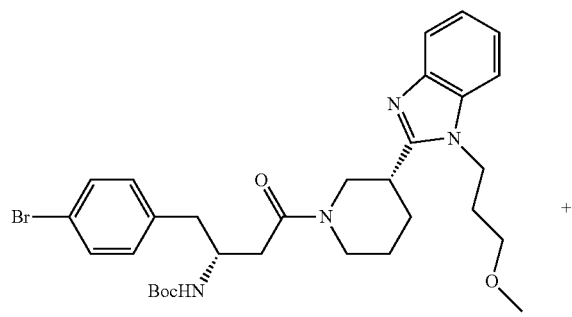

+

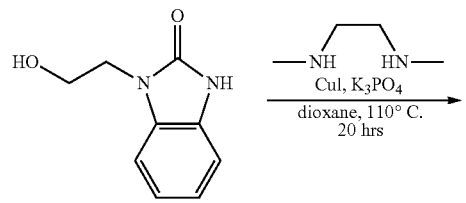

→

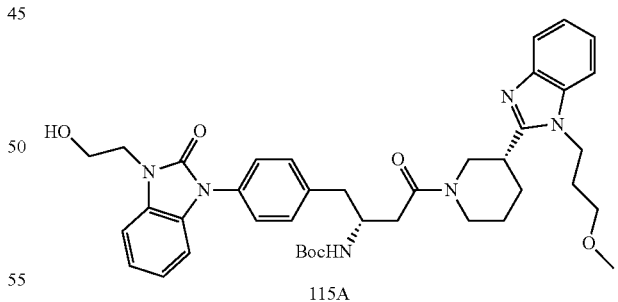

Crude product of tert-butyl (R)-1-(4-(3-(2-hydroxyethyl)-2-oxo-2,3-dihydro-1,1-benzotdjimidazol-1-yl)phenyl)-4-((R)-3-(1-(3-methoxypropyl)-1H-benzo[d]imidazol-2-yl)piperidin-1-yl)-4-oxobutan-2-ylcarbamate (115A) was prepared as described in Example 102, Step A. The residue was purified by preparatory LC/MS (30-40% CH$_3$CN in H$_2$O). ESI-MS:m/z 711.5 (M+H)$^+$.

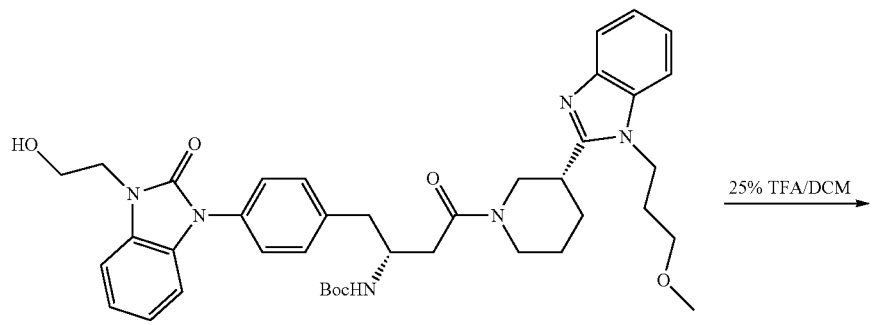

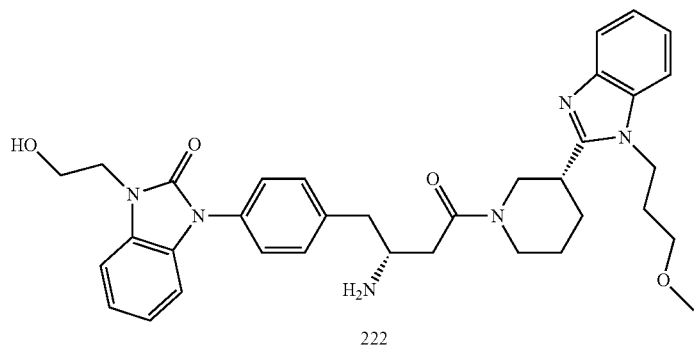

Crude product of 1-(4-((R)-2-amino-4-((R)-3-(1-(3-methoxypropyl)-1H-benzo[d]imidazol-2-yl)piperidin-1-yl)-4-oxobutyl)phenyl)-3-(2-hydroxyethyl)-1H-benzo[d]imidazol-2(3H)-one (222) was prepared as described for Example 104, Step B. The solvent was removed and the residue was purified by preparatory LC/MS (20-30% CH$_3$CN in H$_2$O) to give the product as a TFA salt (31 mg, 58% yield over two steps). 1H NMR (400 MHz, DMSO-d$_6$) δ ppm 1.53 (br. s., 1H) 1.93 (d, J=6.32 Hz, 5H) 2.63-3.47 (m, 12H) 3.67-3.73 (m, 2H) 3.82 (br. s., 1H) 3.92-3.99 (m, 2H) 4.10-4.68 (m, 4H) 7.01-7.06 (m, 2H) 7.10-7.17 (m, 1H) 7.31 (m, 1H) 7.38-7.57 (m, 6H) 7.74 (d, J=6.57 Hz, 2H). ESI-MS:m/z 611.3 (M−H)+.

Example 116

Synthesis of the mixture of 1-(4-((R)-2-amino-4-((R)-3-(1-(3-methoxypropyl)-1H-benzo[d]imidazol-2-yl)piperidin-1-yl)-4-oxobutyl)phenyl)-5-fluoro-1H-benzo[d]imidazol-2(3H)-one (223) and 1-(4-((R)-2-amino-4-((R)-3-(1-(3-methoxypropyl)-1H-benzo[d]imidazol-2-yl)piperidin-1-yl)-4-oxobutyl)phenyl)-6-fluoro-1H-benzo[d]imidazol-2(3H)-one (224)

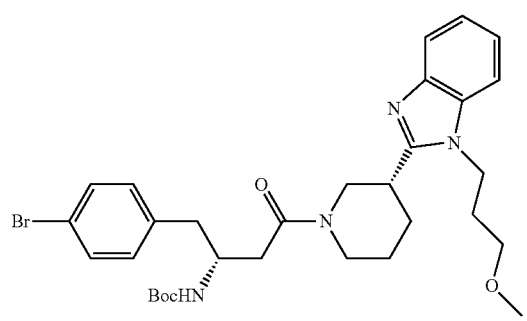

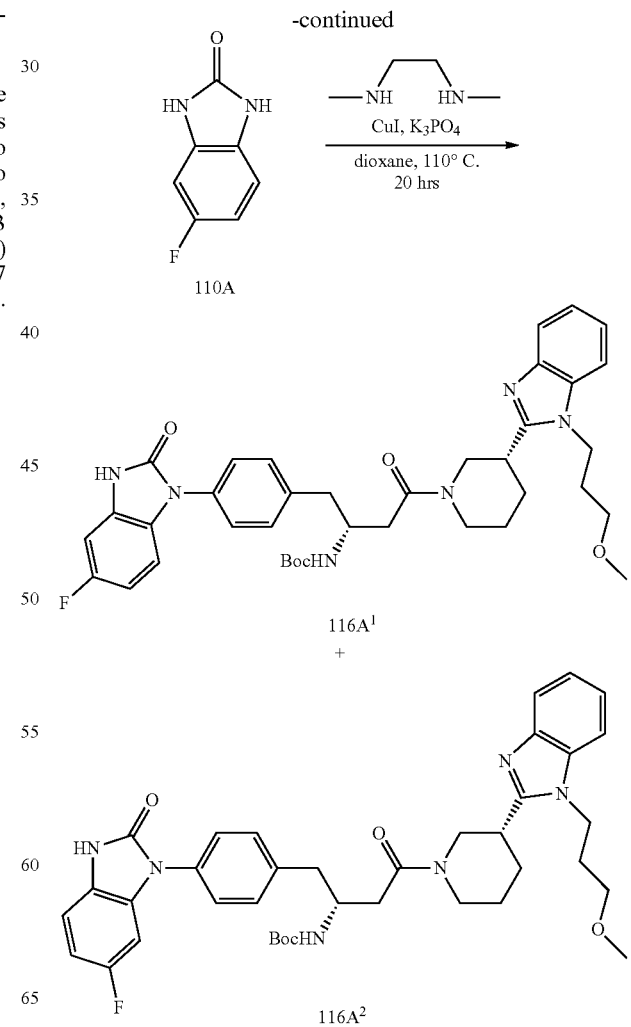

Into a 8 mL vial was added tert-butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (6A) (as prepared in Example 6, Step A) (90 mg, 147 µmol), 5-fluoro-1H-benzo[d]imidazol-2(3H)-one (110A) (45 mg, 293 µmol), potassium phosphate (62 mg, 293 µmol), copper(I) iodide (6 mg, 29 µmol) and $N^1,N^2$-dimethylethane-1,2-diamine (5 mg, 56 µmol). The mixture was suspended in dioxane (4 mL). The vial was capped with a high temperature Teflon cap and heated at 110° C. for 18 hrs. The reaction was filtered through a Buchner funnel with Celite. The solvent was removed from the filtrate under vacuum. The residue containing a mixture of tert-butyl (R)-1-(4-(5-fluoro-2-oxo-2,3-dihydro-1H-benzo[d]imidazol-1-yl)phenyl)-4-((R)-3-(1-(3-methoxypropyl)-1H-benzo[d]imidazol-2-yl)piperidin-1-yl)-4-oxobutan-2-ylcarbamate (116A') and tert-butyl (R)-1-(4-(6-fluoro-2-oxo-2,3-dihydro-1H-benzo[d]imidazol-1-yl)phenyl)-4-((R)-3-(1-(3-methoxypropyl)-1H-benzo[d]imidazol-2-yl)piperidin-1-yl)-4-oxobutan-2-ylcarbamate ($116A^2$) was purified by preparatory LC/MS (30-50% $CH_3CN$ in $H_2O$). ESI-MS:m/z 685.5 $(M+H)^+$.

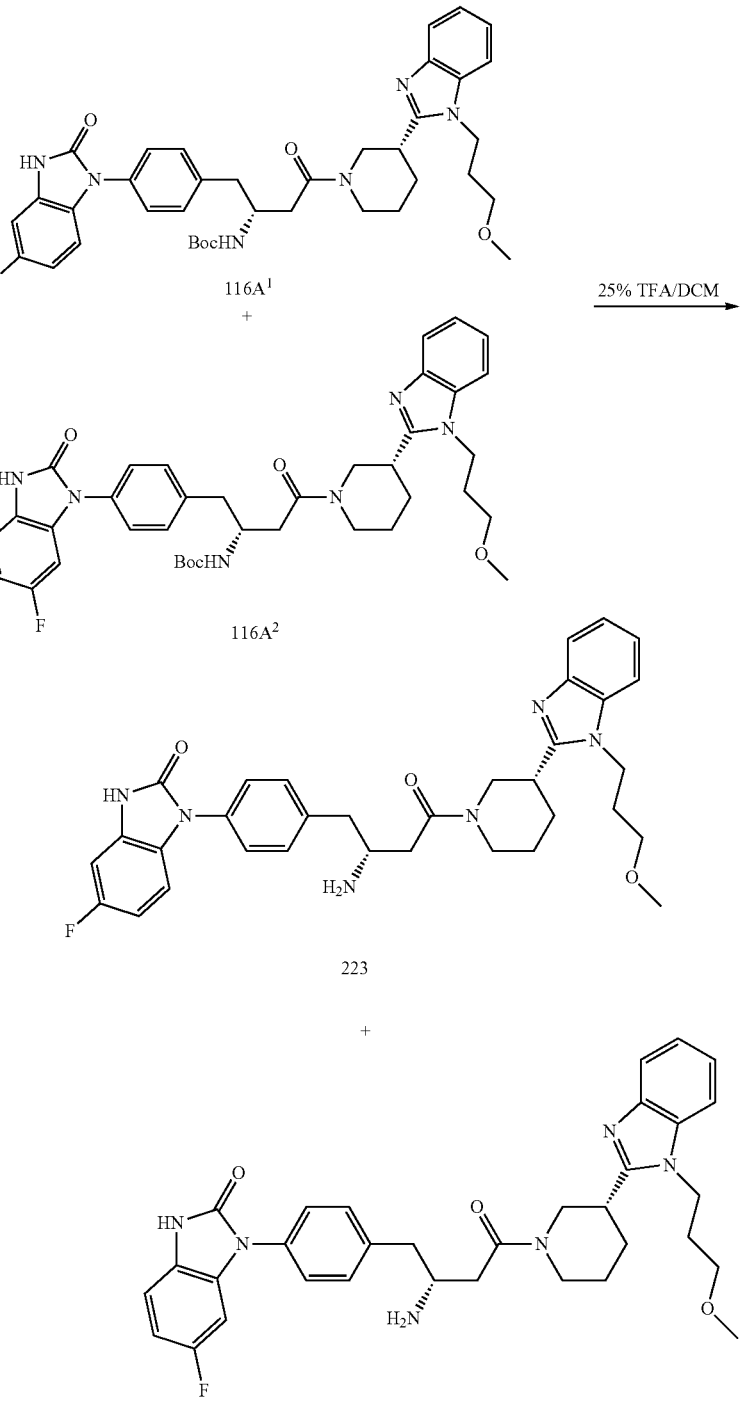

The product from the previous step was dissolved in 25% trifluoroacetic acid in dichloromethane (5 mL). The mixture was stirred at room temperature for 3 hrs. The solvent was removed and the residue was purified by preparatory LC/MS (20-40% CH$_3$CN in H$_2$O) to give the mixed product of 1-(4-((R)-2-amino-4-((R)-3-(1-(3-methoxypropyl)-1H-benzo[d]imidazol-2-yl)piperidin–1-yl)-4-oxobutyl)phenyl)-5-fluoro-1H-benzo[d]imidazol-2(3H)-one (223) and 1-(4-((R)-2-amino-4-((R)-3-(1-(3-methoxypropyl)-1H-benzo[d]imidazol-2-yl)piperidin-1-yl)-4-oxobutyl)phenyl)-6-fluoro-1H-henzo[d]imidazol-2(3H)-one (224) as a TFA salt (31 mg, 30% yield over two steps). 1H NMR (400 MHz, DMSO-d$_6$) δ ppm 1.53 (br. s., 1H) 1.75-2.19 (m, 5H) 2.62-3.48 (m, 12H) 3.77 (br. s., 1H) 4.07-4.68 (m, 4H) 6.77-7.10 (m, 3 H) 7.36-7.57 (m, 6H) 7.73 (m, 2H) 11.20-11.39 (m, 1H). ESI-MS:m/z 585.2 (M+H)$^+$.

Example 117

Synthesis of a mixture of 1-(4-((R)-2-amino-4-((R)-3-(1-(3-methoxypropyl)-1H-benzo[d]imidazol-2-yl)piperidin-1-yl)-4-oxobutyl)phenyl)-4-methyl-1H-benzo[d]imidazol-2(3H)-one (225) and 1-(4-((R)-2-amino-4-((R)-3-(1-(3-methoxypropyl)-1,1-benzo[d]imidazol-2-yl)piperidin-1-yl)-4-oxobutyl)phenyl)-7-methyl-1H-benzo[d]imidazol-2(3H)-one(226)

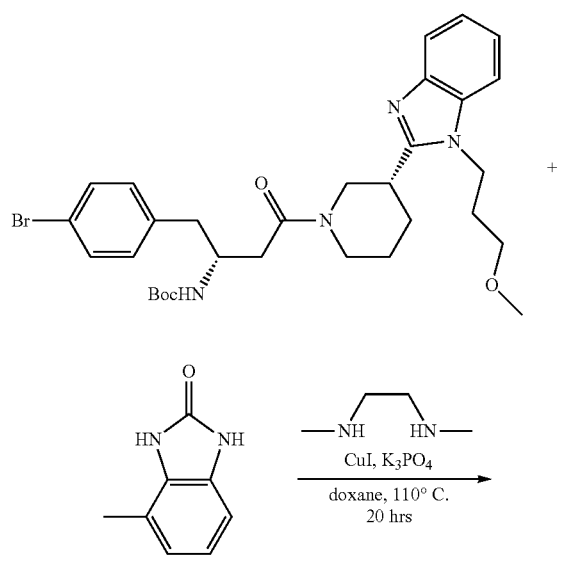

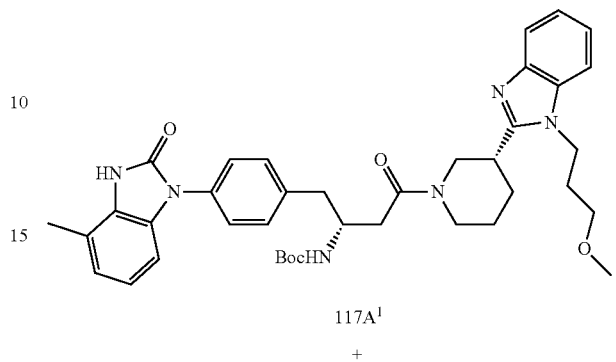

117A$^1$

+

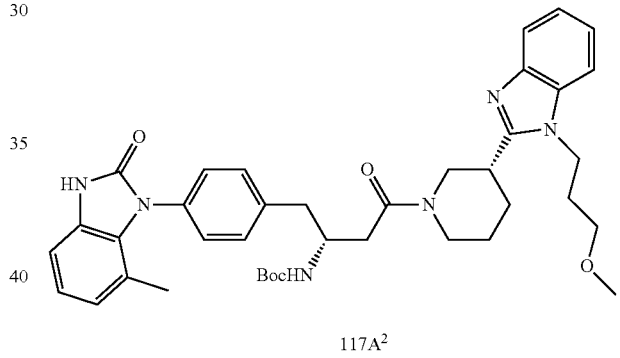

117A$^2$

Crude product of the mixture of tert-butyl (R)-4-((R)-3-(1-(3-methoxypropyl)-1H-benzo[d]imidazol-2-yl)piperidin-1-yl)-1-(4-(4-methyl-2-oxo-2,3-dihydro-1H-benzo[d]imidazol-1-yl)phenyl)-4-oxobutan-2-ylcarbamate (117A$^1$) and tert-butyl (R)-4-((R)-3-(1-(3-methoxypropyl)-1H-benzo[d]imidazol-2-yl)piperidin-1-yl)-1-(4-(7-methyl-2-oxo-2,3-dihydro-1H-benzo[d]imidazol-1-yl)phenyl)-4-oxobutan-2-ylcarbamate (117A$^2$) was prepared by the procedure dexcribed in Example 102, Step A. The residue was purified by preparatory LC/MS (30-50% CH$_3$CN in H$_2$O). ESI-MS:m/z 681.6 (M+H)$^+$.

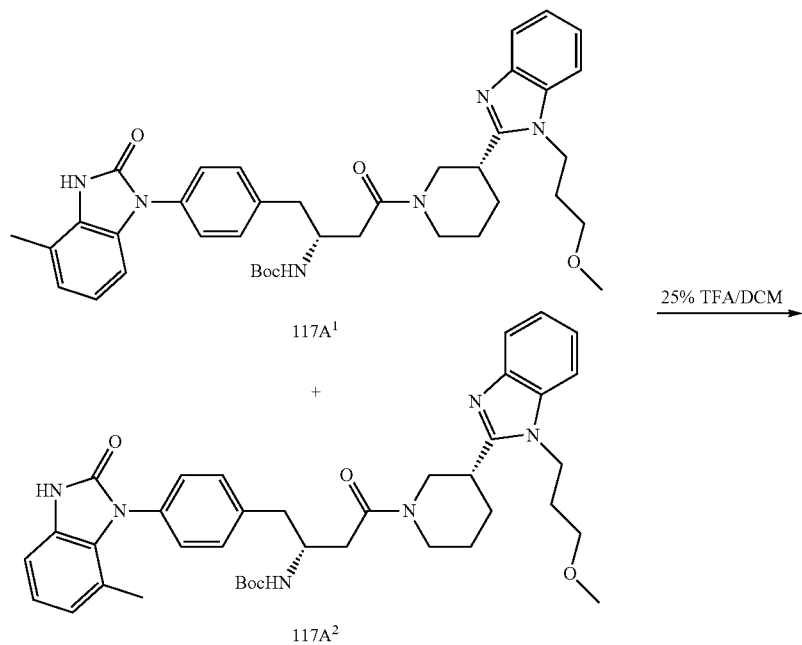
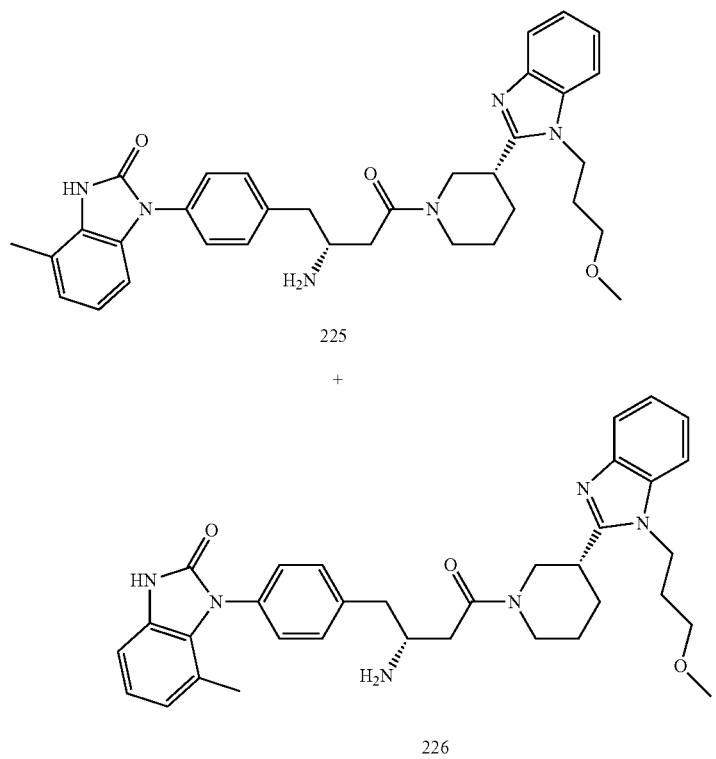

Mixture of crude product 1-(4-((R)-2-amino-4-((R)-3-(1-(3-methoxypropyl)-1H-benzo[d]imidazol-2-yl)piperidin-1-yl)-4-oxobutyl)phenyl)-4-methyl-1H-benzo[d]imidazol-2(3H)-one (225) and 1-(4-((R)-2-amino-4-((R)-3-(1-(3-methoxypropyl)-1H-benzo[d]imidazol-2-yl)piperidin-1-yl)-4-oxobutyl)phenyl)-7-methyl-1H-benzo[d]imidazol-2(3H)-one (226) was prepared according to the procedure described for Example 104, Step B. The solvent was removed and the residue was purified by preparatory LC/MS (20-40% CH₃CN in H₂O) to give the product as a TFA salt (37 mg, 36% yield over two steps). 1H NMR (400 MHz, DMSO-d₆) δ ppm 1.53 (br. s., 1H) 1.75-2.21 (m, 5H) 2.33 (s, 3H) 2.63-3.47 (m, 12H) 3.77 (br. s., 1H) 4.10-4.68 (m, 4H) 6.82 (m, 1H) 6.86-6.93 (m, 2H) 7.38-7.56 (m, 6H) 7.74 (m, 2H) 11.24 (m, 1H). ESI-MS: m/z 581.3 (M+H)⁺.

Example 118

Synthesis of the mixture of 1-(4-((R)-2-amino-4-((R)-3-(1-(3-methoxypropyl)-1H-benzo[d]imidazol-2-yl)piperidin-1-yl)-4-oxobutyl)phenyl)-5-methoxy-1H-benzo[d]imidazol-2(3H)-one (227) and 1-(4-((R)-2-amino-4-((R)-3-(1-(3-methoxyp ropyl)-1H-benzo[d]imidazol-2-yl)piperidin-1-yl)-4-oxobutyl) phenyl)-6-methoxy-1H-benzo[d]imidazol-2(3H)-one (228)

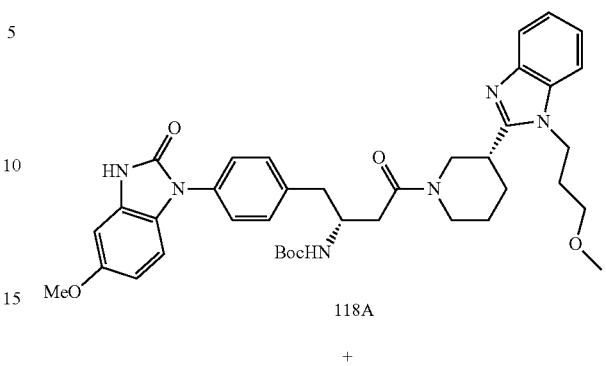

118A

+

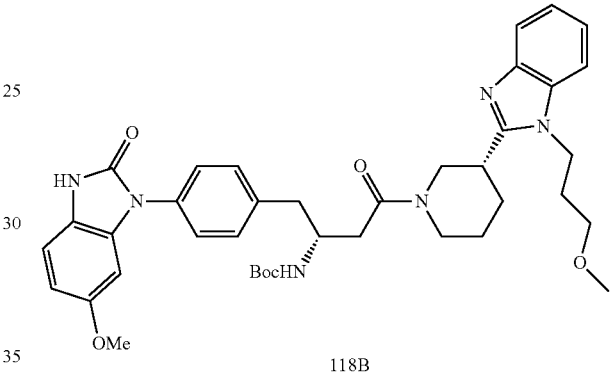

118B

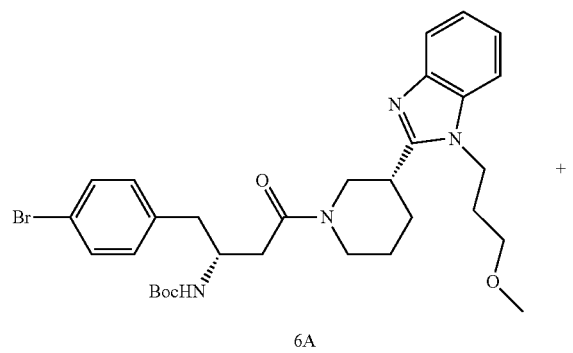

6A

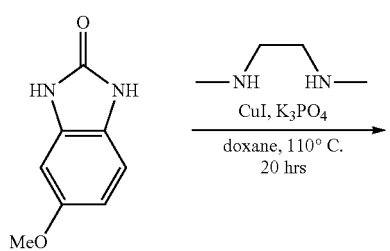

Into a 8 mL vial was added tert-butyl-(R)-1-(4-bromophenyl)-4-((R)-3-(1-(3-methoxypropyl)-1H-benzo[d]imidazol-2-yl)piperidin-1-yl)-4-oxobutan-2-ylcarbamate (90 mg, 147 μmol), 5-methoxy-1,4-benzo[d]imidazol-2(3H)-one (48 mg, 293 μmol), potassium phosphate (62 mg, 293 μmol), copper (I) iodide (6 mg, 29 μmol) and N¹,N²-dimethylethane-1,2-diamine (5 mg, 56 gmol). The mixture was suspended in dioxane (4 mL). The vial was capped with a high temperature Teflon cap and heated at 110° C. for 18 hrs. The reaction was filtered through a Buchner funnel with Celite. The solvent was removed from the filtrate under vacuum. The residue containing the mixture of tert-butyl (R)-1-(4-(5-methoxy-2-oxo-2,3-dihydro-1H-benzo[d]imidazol-1-yDphenyl)-4-((R)-3-(1-(3-methoxypropyl)-1H-benzo[d]imidazol-2-yl)piperidin-1-yl)-4-oxobutan-2-ylcarbamate (118A) and tert-butyl (R)-1-(4-(6-methoxy-2-oxo-2,3-dihydro-1H-benzo[d]imidazol-1-yl)phenyl)-4-((R)-3-(1-(3-methoxypropyl)-1,1-benzo[d]imidazol-2-yl)piperidin-1-yl)-4-oxobutan-2-ylcarbamate (118B) was purified by preparatory LC/MS (30-45% CH₃CN in H₂O). ESI-MS:m/z 697.5 (M+H)⁺.

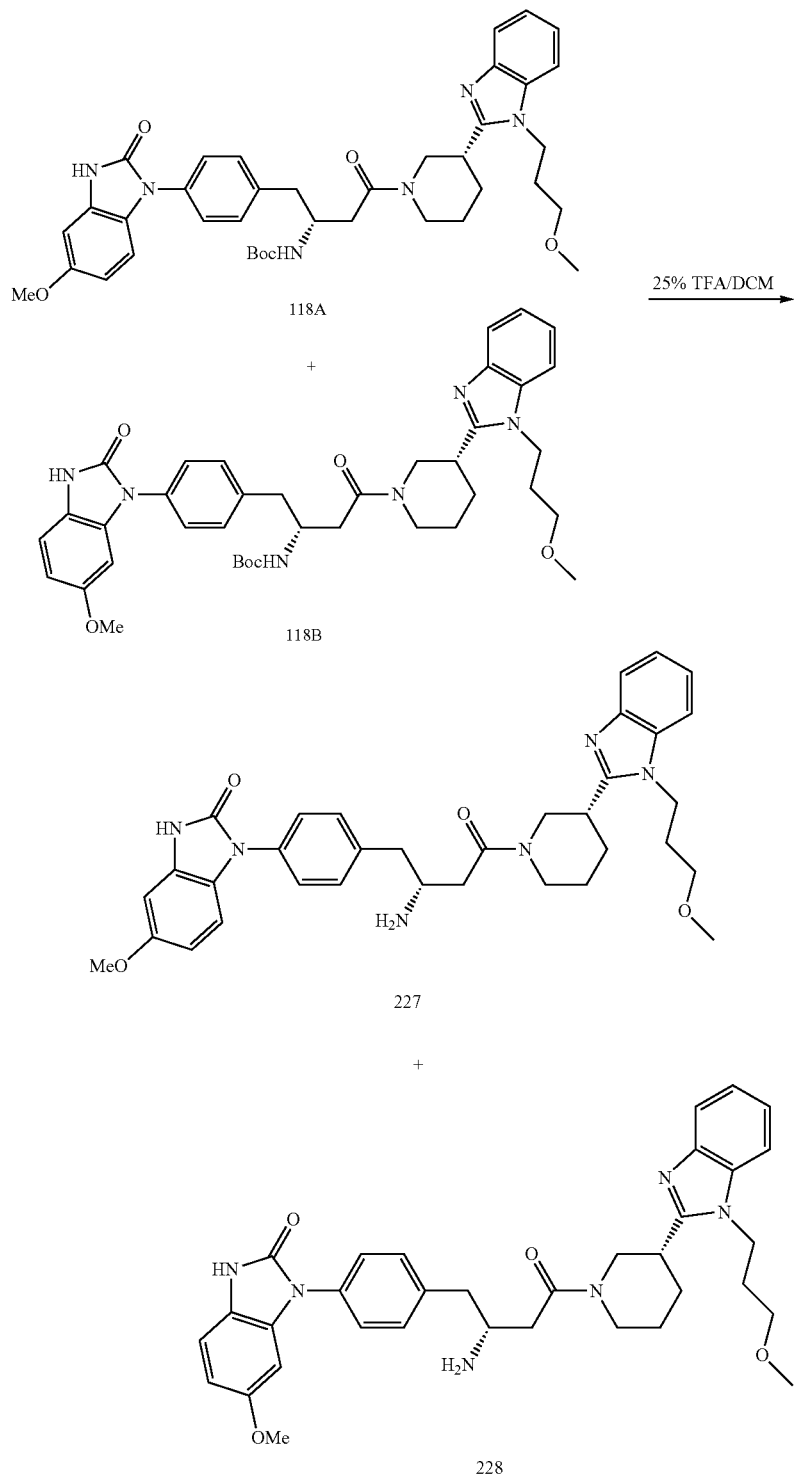

The product from the previous step was dissolved in 25% trifluoroacetic acid in dichloromethane (5 mL). The mixture was stirred at room temperature for 3 hrs. The solvent was removed and the residue containing the mixture of 1-(4-((R)-2-amino-4-((R)-3-(1-(3-methoxypropyl)-1H-benzo[d]imidazol-2-yl)piperidin-1-yl)-4-oxobutyl)phenyl)-5-methoxy-1H-benzo[d]imidazol-2(3H)-one (227) and 1-(4-((R)-2-amino-4-((R)-3-(1-(3-methoxypropyl)-1H-benzo[d]imidazol-2-yl)piperidin-1-yl)-4-oxobutyl)phenyl)-6-methoxy-1H-benzo[d]imidazol-2(3H)-one (228) was purified by preparatory LC/MS (15-35% $CH_3CN$ in $H_2O$) to give the product as a TFA salt (22 mg, 21% yield over two steps). 1H NMR (400 MHz, DMSO-$d_6$) δ ppm 1.53 (br. s., 1H) 1.74-2.19 (m, 5H) 2.62-3.47 (m, 12H) 3.66-3.91 (m, 4H) 4.10-4.68 (m, 4 H) 6.53-6.70 (m, 2H) 6.98 (m, 1H) 7.38-7.56 (m, 6H) 7.74 (m, 2H) 10.95-11.13 (m, 1H). ESI-MS:m/z 597.3 $(M+H)^+$.

Example 119

Synthesis of 2-(4-((R)-2-amino-4-((R)-3-(1-(3-methoxypropyl)-1H-benzo[d]imidazol-2-yl)piperidin-1-yl)-4-oxobutyl)phenyl)isoquinolin-1(2H)-one (229)

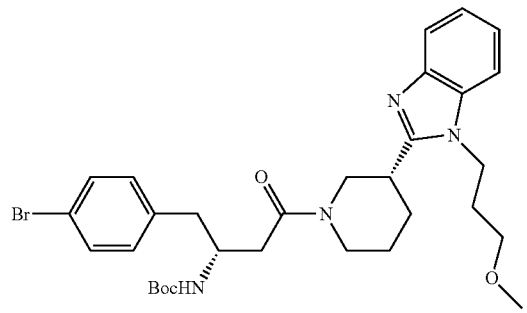

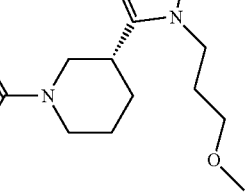

Crude product tert-butyl (R)-4-((R)-3-(1-(3-methoxypropyl)-1H-benzo[d]imidazol-2-yl)piperidin-1-yl)-4-oxo-1-(4-(1-oxoisoquinolin-2(1H)-yl)phenyl)butan-2-ylcarbamate (119A) was prepared according to the procedure described in Example 102, Step A. The residue was purified by preparatory LC/MS (30-60% CH₃CN in H₂O). ESI-MS:m/z 678.4 (M+H)⁺.

2-(4-((R)-2-Amino-4-((R)-3-(1-(3-methoxypropyl)-1H-benzo[d]imidazol-2-yl)piperidin-1-yl)-4-oxobutyl)phenyeisoquinolin-1(2H)-one (229) was prepared as described for Example 104, Step B. The solvent was removed and the residue was purified by preparatory LC/MS (20-45% CH₃CN in H₂O) to give the product as a TFA salt (41 mg, 40% yield over two steps). 1H NMR (400 MHz, DMSO-d₆) δ ppm 1.53 (br. s., 1H) 1.75-2.21 (m, 5H) 2.63-3.48 (m, 12H) 3.78

(br. s., 1H) 4.11-4.69 (m, 4H) 6.74 (m, 1H) 7.36-7.51 (m, 7H) 7.52-7.60 (m, 1H) 7.71-7.82 (m, 4H) 8.24 (m, 1H). ESI-MS: m/z 578.3 (M+H)⁺.

Example 120

Synthesis of 2-(4-((R)-2-amino-4-((R)-3-(1-(3-methoxypropyl)-1H-benzo[d]imidazol-2-yl)piperidin-1-yl)-4-oxobutyl)phenyl)isoquinolin-1(2H)-one (230)

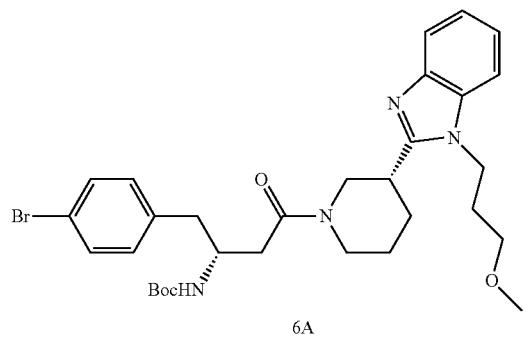

6A

+

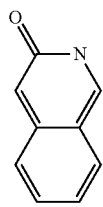

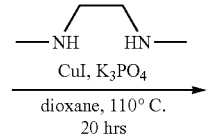

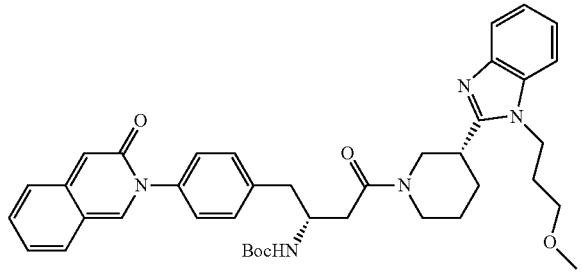

120A tert-Butyl (R)-4-((R)-3-(1-(3-methoxypropyl)-1H-benzo[d]imidazol-2-yl)piperidin-1-yl)-4-oxo-1-(4-(3-oxoisoquinolin-2(3H)-yl)phenyl)butan-2-ylcarbamate (120A) was prepared as described for Example 102, Step A. ESI-MS:m/z 678.5 (M+H)⁺.

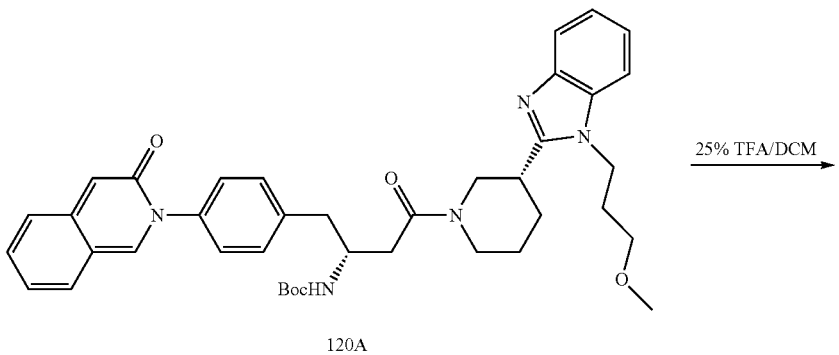

120A

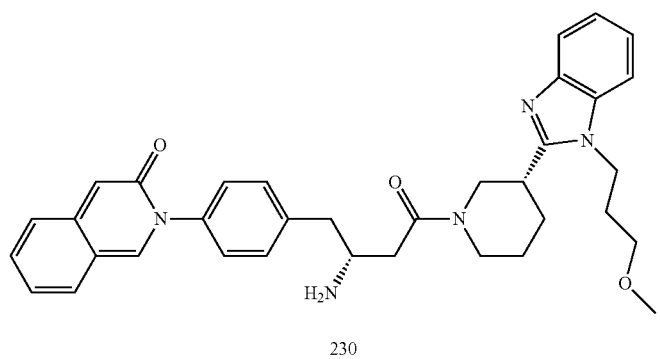

230

2-(4-((R)-2-Amino-4-((R)-3-(1-(3-methoxypropyl)-1H-benzo[d]imidazol-2-yl)piperidin-1-yl)-4-oxobutyl)phenyp-isoquinolin-3(2H)-one (230) was prepared as described for Example 104, Step B.

Example 121

Synthesis of (R)-3-amino-1-((R)-3-(1-(3-methoxypropyl)-1H-benzo[d]imidazol-2-yl)piperidin-1-yl)-4-(4-(4-phenylpiperazin-1-yl)phenyl)butan-1-one (231)

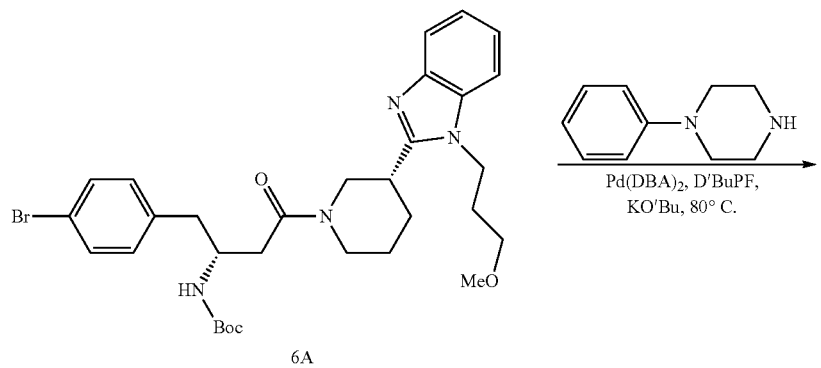

tert-Butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (6A) (prepared as described in Example 6, Step A) (0.29 mmole, 180 mg) in toluene (1 mL) was added bis(dibenzylideneacetone)palladium (0.015 mmole, 9 mg), 1,1'-bis(di-tert-butylphosphino)ferrocene (0.022 mmole, 10 mg), KOtBu (0.35 mmole, 39 mg) and 1-phenylpiperazine (0.32 mmole, 52 mg). The reaction mixture was heated to 80° C. for 6 hrs and then poured into H$_2$O, extracted with EtOAc. The extract was washed with brine, dried over MgSO$_4$ and filtered. The filtrate was concentrated in vacuo. The residue containing tert-Butyl (R)-4-((R)-3-(1-(3-methoxypropyl)-1H-benzo[d]imidazol-2-yl)piperidin–1-yl)-4-oxo-1-(4-(4-phenylpiperazin-1-yl)phenyl)butan-2-ylcarbamate (121A) was carried directly on to the next step without further purification. ESI-MS: m/z 695.7 (M+H)$^+$.

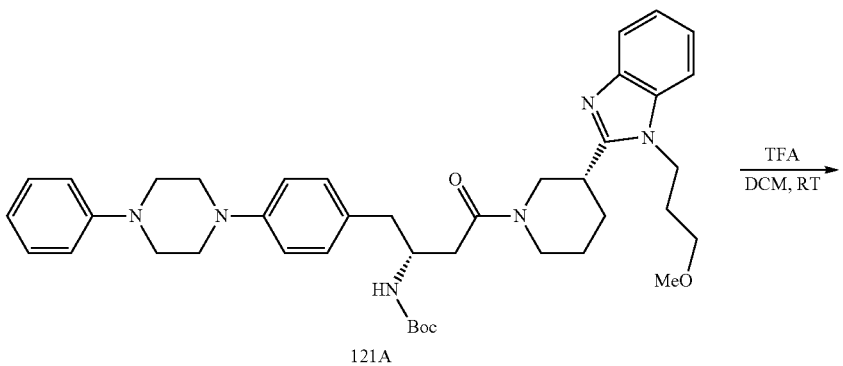

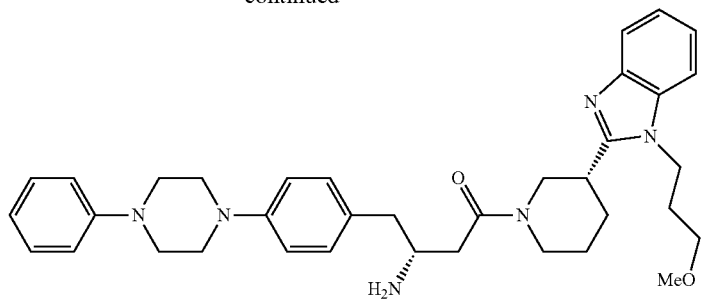

231

Residue from the last step (0.29 mmole, 202 mg) in DCM (10 mL) was added TEA (2 mL). The reaction solution was stirred at rt for 1 hr and then concentrated in vacuo. The residue was purified by preparative LC/MS (20-50% CH₃CN in H₂O) to afford (R)-3-amino-1((R)-3-(1-(3-methoxypropyl)-1H-benzo[d]imidazol-2-yl)piperidin-1-yl)-4-(4-(4-phenylpiperazin-1-yl)phenyl)butan-1-one (231) (0.11 mmole, 66 mg, two-step yield: 38.3%). ESI-MS: m/z 595.5 (M+H)⁺. 1H NMR (400 MHz, MeOD) δ ppm 1.59-1.79 (m, 1H) 1.89-2.15 (m, 3H) 2.18-2.27 (m, 2H) 2.28-2.37 (m, 1H) 2.63-2.81 (m, 2H) 2.82-2.94 (m, 1H) 2.94-3.09 (m, 2H) 3.19 (d, J=3.98 Hz, 1H) 3.27 (s, 3H) 3.39 (q, J=5.35 Hz, 1H) 3.43-3.61 (m, 5H) 3.78-3.90 (m, 2H) 3.95 (d, J=13.26 Hz, 1H) 4.15-4.24 (m, 1H) 4.49-4.62 (m, 1H) 4.65 (t, J=6.95 Hz, 2 H) 4.72 (d, J=13.39 Hz, 1H) 4.85 (d, J=12.69 Hz, 1H) 7.11-7.17 (m, 1H) 7.17-7.22 (m, 1H) 7.22-7.27 (m, 1H) 7.28-7.34 (m, 2H) 7.38-7.44 (m, 1H) 7.54 (t, J=8.05 Hz, 2H) 7.60-7.68 (m, 3H) 7.78-7.84 (m, 1H) 7.89-7.96 (m, 1H).

Example 122

Synthesis of (R)-4-(4-(4-acetylpiperazin-1-yl)phenyl)-3-amino-1-((R)-3-(1-(3-methoxypropyl)-1H-benzo[d]imidazol-2-yl)piperidin-1-yl)butan-1-one (232)

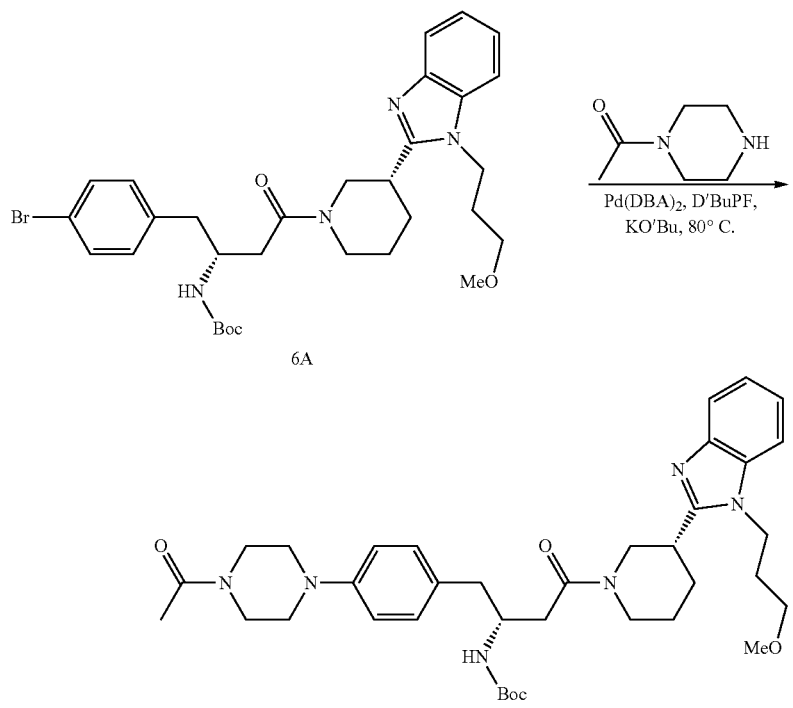

tert-Butyl (R)-1-(4-bromophenyl)-4-((R)-3(1-(3-methoxypropyl)-1H-benzo[d]imidazol-2-yl)piperidin-1-yl)-4-oxobutan-2-ylcarbamate (6A) (prepared as described in Example 6, Step A) (0.29 mmole, 180 mg) in toluene (1 mL) was added bis(dibenzylideneacetone)palladium (0.015 mmole, 9 mg), 1,1'-bis(di-tert-butylphosphino)ferrocene (0.022 mmole, 10 mg), KOtBu (0.35 mmole, 39 mg) and 1-acetylpiperazine (0.32 mmole, 41 mg). The reaction mixture was heated to 80° C. for 6 hrs and then poured into H₂O, extracted with EtOAc. The extract was washed with brine, dried over MgSO₄ and filtered. The filtrate was concentrated in vacuo. The residue containing tert-butyl (R)-1-(4-(4-acetylpiperazin-1-yl)phenyl)-4-((R)-3-(1-(3-methoxypropyl)-1H-benzo[d]imidazol-2-yl)piperidin-1-yl)-4-oxobutan-2-ylcarbamate (122A) was carried directly on to the next step without further purification. ESI-MS: m/z 661.6 (M+H)⁺.

0.9%). ESI-MS: m/z 561.5 (M+H)+. 1H NMR (400 MHz, MeOD) δ ppm 1.90-2.12 (m, 3H) 2.15 (s, 3H) 2.18-2.37 (m, 3H) 2.58-3.04 (m, 2H) 3.11-3.24 (m, 6H) 3.27 (s, 3H) 3.39-3.60 (m, 4H) 3.65-3.76 (m, 4H) 3.79 (dd, J=9.13, 4.58 Hz, 1H) 3.94 (d, J=14.21Hz, 1H) 4.14 (d, J=15.03 Hz, 1H) 4.42-4.60 (m, 1H) 4.64 (t, J=6.92 Hz, 1H) 4.72 (d, J=14.15 Hz, 1H)

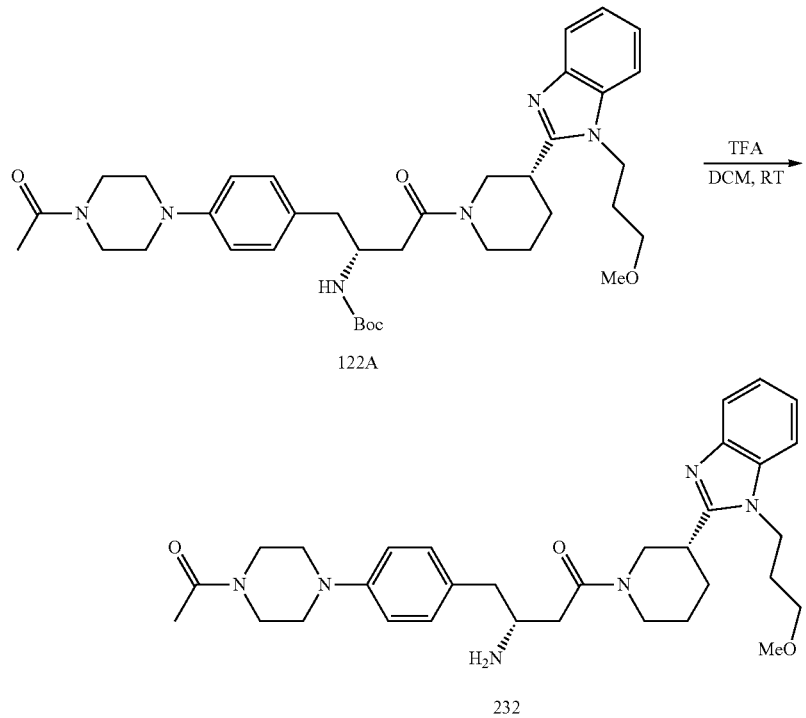

tert-Butyl (R)-1-(4-(4-acetylpiperazin-1-yl)phenyl)-4-((R)-3-(1-(3-methoxypropyl)-1H-benzo[d]imidazol-2-yl)piperidin-1-yl)-4-oxobutan-2-ylcarbamate (122A) (0.29 mmole, 202 mg) in DCM (10 mL) was added TEA (2 mL). The reaction solution was stirred at rt for 1 hr and then concentrated in vacuo. The residue was purified by preparative LC/MS (10-25% CH₃CN in H₂O) to afford (R)-4-(4-(4-Acetylpiperazin-1-yl)phenyl)-3-amino-1-((R)-3-(1-(3-methoxypropyl)-1H-benzo[d]imidazol-2-yl)piperidin-1-yl)butan-1-one (232) (0.0018 mmole, 1.5 mg, two-step yield:

6.96-7.05 (m, 2H) 7.14-7.24 (m, 2H) 7.56-7.66 (m, 2H) 7.75-7.82 (m, 1H) 7.86-7.93 (m, 1H).

Example 123

Synthesis of 4-(4-((R)-2-amino-4-((R)-3-(1-(3-methoxypropyl)-1H-benzo[d]imidazol-2-yl)piperidin-1-yl)-4-oxobutyl)phenyl)-1-phenylpiperazin-2-one (233)

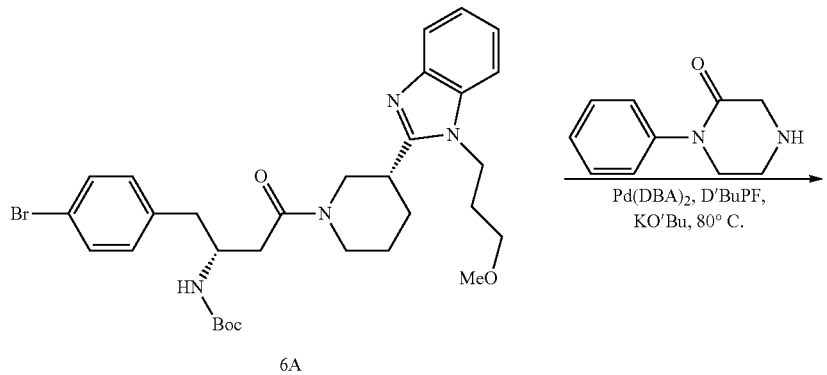

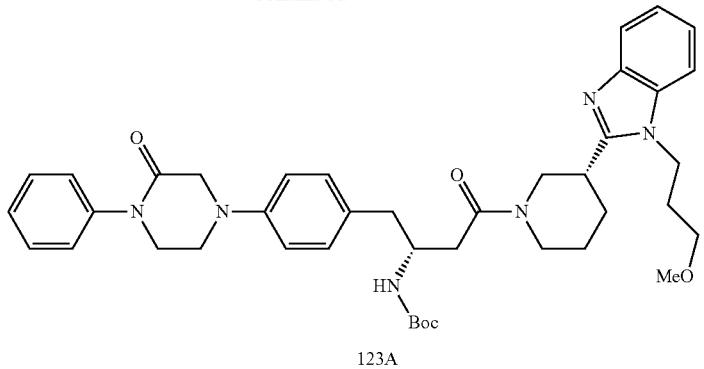

123A tert-Butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (6A) (prepared as described in Example 6, Step A) (0.29 mmole, 180 mg) in toluene (1 mL) was added bis(dibenzylideneacetone)palladium (0.015 mmole, 9 mg), 1,1'-bis(di-tert-butylphosphino)ferrocene (0.022 mmole, 10 mg), KOtBu (0.35 mmole, 39 mg) and 1-phenylpiperazin-2-one (1.13 TFA salt form) (0.32 mmole, 98 mg). The reaction mixture was heated to 80° C. for 6 hrs and then poured into $H_2O$, extracted with EtOAc. The extract was washed with brine, dried over $MgSO_4$ and filtered. The filtrate was concentrated in vacuo. The residue containing tert-butyl (R)-4-((R)-3-(1-(3-methoxypropyl)-1H-benzo[d]imidazol-2-yl)piperidin-1-yl)-4-oxo-1-(4-(3-oxo-4-phenylpiperazin-1-yl)phenyl)butan-2-ylcarbamate (123A) was carried directly on to the next step without further purification. ESI-MS: m/z 709.5 (M+H)$^+$.

tert-Butyl (R)-4-((R)-3-(1-(3-methoxypropyl)-1H-benzo[d]imidazol-2-yl)piperidin-1-yl)-4-oxo-1-(4-(3-oxo-4-phenylpiperazin-1-yl)phenyl)butan-2-ylcarbamate (123A) (0.29 mmole, 206 mg) in DCM (10 mL) was added TEA (2 mL). The reaction solution was stirred at rt for 1 hr and then concentrated in vacuo. The residue was purified by preparative LC/MS (45-55% $CH_3CN$ in $H_2O$) to afford 4-(4-((R)-2-Amino-4-((R)-3-(1-(3-methoxypropyl)-1H-benzo[d]imidazol-2-yl)piperidin-1-yl)-4-oxobutyl)phenyl)-1-phenylpiperazin-2-one (233) (0.11 mmole, 14 mg, two-step yield: 7.9%). ESI-MS: m/z 609.5 (M+H)$^+$. 1H NMR (400 MHz, MeOD) δ ppm 1.54-1.83 (m, 1H) 1.87-2.15 (m, 3H) 2.18-2.38 (m, 3H) 2.61-2.80 (m, 1H) 2.80-2.91 (m, 1H) 2.93-3.05 (m, 2H) 3.10-3.24 (m, 2H) 3.26 (s, 3H) 3.33-3.59 (m, 4H) 3.68 (t, J=5.43 Hz, 1H) 3.74-4.09 (m, 4H) 4.49-4.78 (m, 3H) 4.84 (br. s., 1H) 6.94-7.08 (m, 1H) 7.15-7.30 (m, 2H) 7.30-7.39 (m, 2H) 7.40-7.55 (m, 3H) 7.55-7.70 (m, 3H) 7.76-7.86 (m, 1H) 7.88-7.99 (m, 1H).

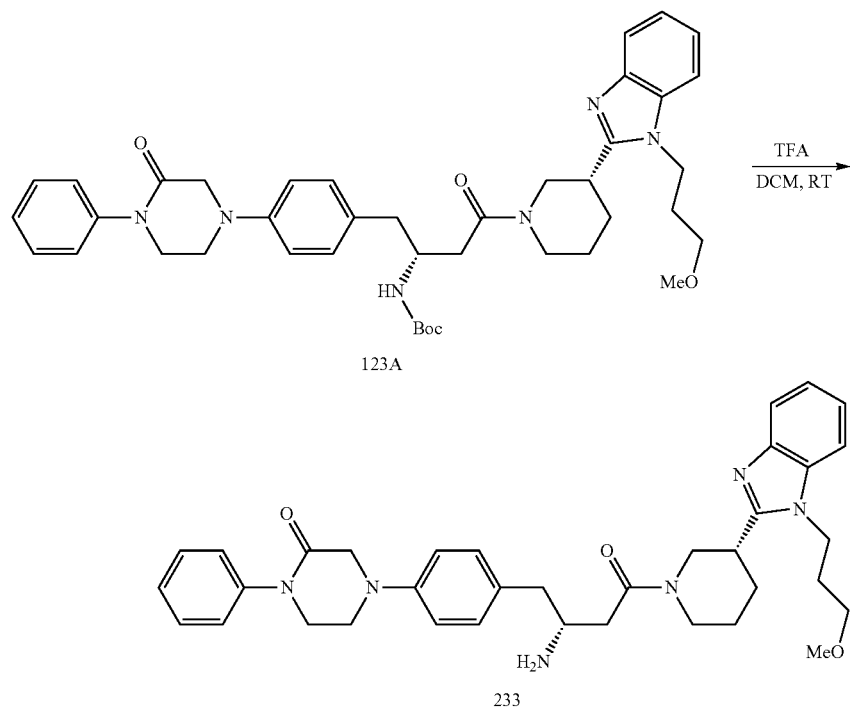

123A

→ TFA / DCM, RT

233

Example 124

Synthesis of (R)-3-amino-4-(4-(4-hydroxypiperidin-1-yl)phenyl)-1-((R)-3-(1-(3-methoxypropyl)-1H-benzo[d]imidazol-2-yl)piperidin-1-yl)butan-1-one (234)

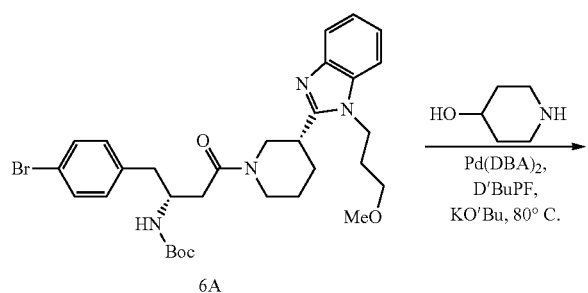

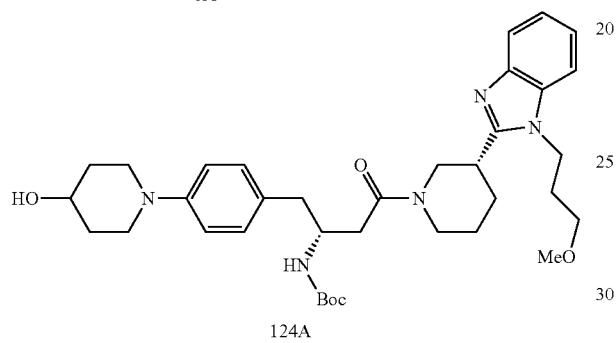

tert-Butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (6A) (prepared as described in Example 6, Step A) (0.325 mmole, 199 mg) in toluene (2 mL) was added bis(dibenzylideneacetone)palladium (0.016 mmole, 9 mg), 1,1'-bis(di-tert-butylphosphino)ferrocene (0.049 mmole, 23 mg), KOtBu (0.39 mmole, 44 mg) and 4-hydroxypiperidine (0.39 mmole, 39 mg). The reaction mixture was heated to 80° C. for 6 hrs and then poured into H$_2$O, extracted with EtOAc. The extract was washed with brine, dried over MgSO$_4$ and filtered. The filtrate was concentrated in vacuo. The residue containing tert-butyl (R)-1-(4-(4-hydroxypiperidin-1-yl)phenyl)-4-((R)-3-(1-(3-methoxypropyl)-1H-benzo[d]imidazol-2-yl)piperidin-1-yl)-4-oxobutan-2-ylcarbamate (124A) was carried directly on to the next step without further purification. ESI-MS: mh 634.5 (M+H)$^+$.

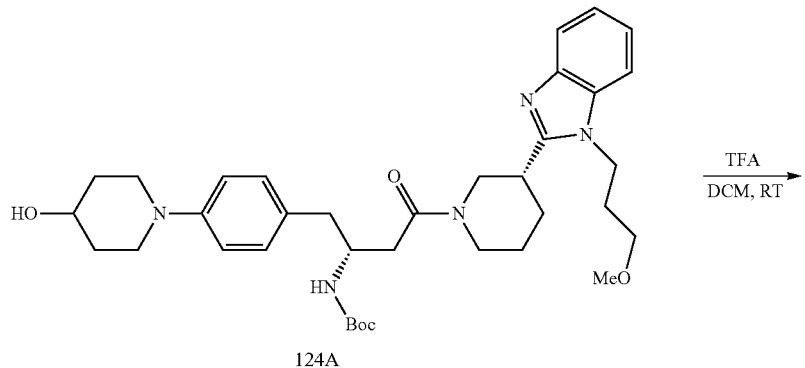

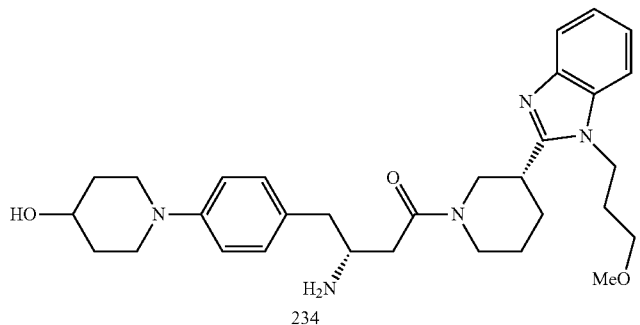

tert-Butyl (R)-1-(4-(4-hydroxypiperidin-1-yl)phenyl)-4-((R)-3-(1-(3-methoxypropyl)-1H-benzo[d]imidazol-2-yl)piperidin-1-yl)-4-oxobutan-2-ylcarbamate (0.325 mmole, 206 mg) in DCM (10 mL) was added TEA (2 mL). The reaction solution was stirred at rt for 1 hr and then concentrated in vacuo. The residue was purified by preparative LC/MS (10-15% $CH_3CN$ in $H_2O$) to afford (R)-3-Amino-4-(4-(4-hydroxypiperidin-1-yl)phenyl)-1-((R)-3-(1-(3-methoxypropyl)-1H-benzo[d]imidazol-2-yl)piperidin-1-yl)butan-1-one (234) (0.024 mmole, 13 mg, two-step yield: 7.5%). ESI-MS: m/z 534.7 (M+H)+. 1H NMR (400 MHz, MeOD) δ ppm 1.20-1.43 (m, 5H) 1.78-2.39 (m, 4H) 2.69-3.11 (m, 4H) 3.10-3.17 (m, 1H) 3.15-3.24 (m, 3H) 3.27 (s, 3H) 3.35-3.55 (m, 2H) 3.66-3.78 (m, 2H) 3.80-3.89 (m, 1H) 3.90-4.00 (m, 2 H) 4.37-4.46 (m, 1H) 4.48-4.58 (m, 1H) 4.59-4.67 (m, 2H) 4.67-4.76 (m, 1H) 7.30-7.35 (m, 1H) 7.38-7.46 (m, 3H) 7.55-7.67 (m, 2H) 7.73-7.82 (m, 1H) 7.83-7.93 (m, 1H).

Example 125

Synthesis of (R)-3-amino-4-(4-(4-(hydroxymethyl)piperidin-1-yl)phenyl)-1-((R)-3-(1-(3-methoxypropyl)-1H-benzo[d]imidazol-2-yl)piperidin-1-yl)butan-1-one (235)

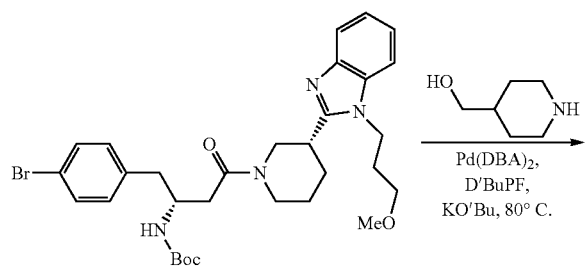

tert-Butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (0.325 mmole, 199 mg) in toluene (2 mL) was added bis(dibenzylideneacetone)palladium (0.016 mmole, 9 mg), 1,1'-bis(di-tert-butylphosphino)ferrocene (0.049 mmole, 23 mg), KOtBu (0.39 mmole, 44 mg) and 4-piperidine-methanol (0.39 mmole, 45 mg). The reaction mixture was heated to 80° C. for 6 hrs and then poured into $H_2O$, extracted with EtOAc. The extract was washed with brine, dried over $MgSO_4$ and filtered. The filtrate was concentrated in vacuo. The residue containing tert-butyl (R)-1-(4-(4-(hydroxymethyl)piperidin-1-yl)phenyl)-4-((R)-3-(1-(3-methoxypropyl)-1H-benzo[d]imidazol-2-yl)piperidin-1-yl)-4-oxobutan-2-ylcarbamate (125A) was carried directly on to the next step without further purification. ESI-MS: m/z 648.6 $(M+H)^+$.

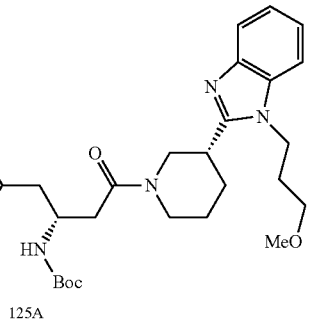

125A

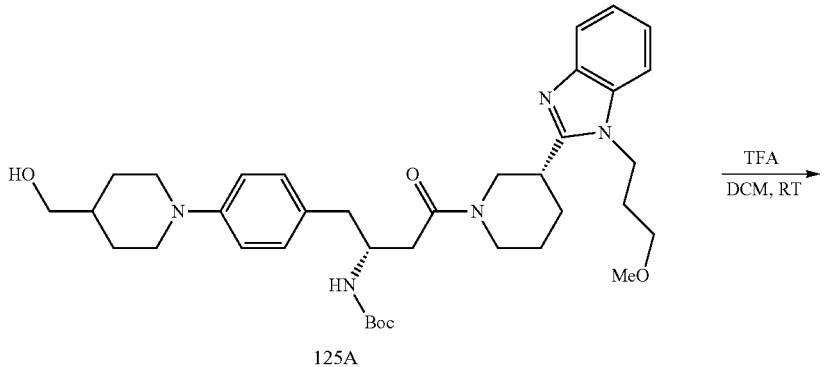

125A

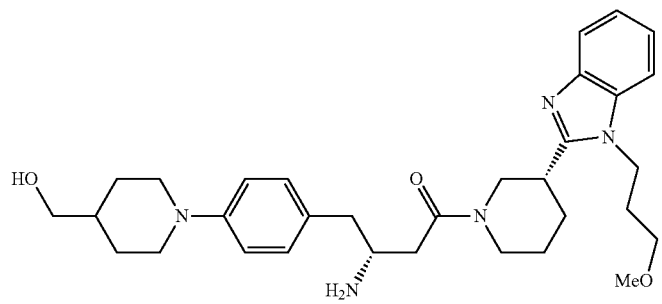

235 tert-Butyl (R)-1-(4-(4-(hydroxymethyl)piperidin-1-yl)phenyl)-4-((R)-3-(1-(3-methoxypropyl)-1H-benzo[d]irridazol-1-yl)piperidin-1-yl)-4-oxobutan-2-ylcarbamate (0.325 mmole, 211 mg) in DCM (10 mL) was added TEA (2 mL). The reaction solution was stirred at it for 1 hr and then concentrated in vacuo. The residue was purified by preparative LC/MS (10-15% CH₃CN in H₂O) to afford (R)-3-Amino-4-(4-(4-(hydroxymethyl)piperidin-1-yl)phenyl)-1-((R)-3-(1-(3-methoxypropyl)-1H-benzo[d]imidazol-2-yl)piperidin-1-yl)butan-1-one (235) (0.0055 mmole, 3 mg, two-step yield: 1.7%). ESI-MS: m/z 548.5 (M+H)⁺. 1H NMR (400 MHz, MeOD) δ ppm 1.43-1.54 (m, 2H) 1.62-1.76 (m, 2H) 1.91-2.16 (m, 4H) 2.21 (t, J=5.40 Hz, 2H) 2.25-2.37 (m, 1H) 2.54-3.11 (m, 3H) 3.12-3.15 (m, 1H) 3.16-3.25 (m, 2H) 3.27 (s, 3H) 3.36-3.55 (m, 4H) 3.61-3.77 (m, 3H) 3.83-3.92 (m, 1H) 3.93-4.02 (m, 1H) 4.32-4.42 (m, 1H) 4.50-4.60 (m, 1H) 4.63 (t, J=6.92 Hz, 2H) 4.67-4.84 (m, 1H) 7.20-7.39 (m, 1H) 7.40-7.51 (m, 2H) 7.52-7.57 (m, 1H) 7.58-7.65 (m, 2H) 7.75-7.81 (m, 1H) 7.85-7.92 (m, 1H).

Example 126

Synthesis of (R)-3-amino-4-(4-(4-(hydroxyethyl)piperidin-1-yl)phenyl)-1-((R)-3-(1-(3-methoxypropyl)-1H-benzo[d]imidazol-2-yl)piperidin-1-yl)butan-1-one (236)

tert-Butyl(R)-1-(4-bromophenyl)-4-((R)-3-(1-(3-methoxypropyl)-1H-benzo[d]imidazol-2-yl)piperidin-1-yl)-4-oxobutan-2-ylcarbamate (0.325 mmole, 199 mg) in toluene (2 mL) was added bis(dibenzylideneacetone)palladium (0.016 mmole, 9 mg), 1,1'-bis(di-tert-butylphosphino)ferrocene (0.049 mmole, 23 mg), KOtBu (0.39 mmole, 44 mg) and 4-piperidineethanol (0.39 mmole, 50 mg). The reaction mixture was heated to 80° C. for 6 hrs and then poured into H₂O, extracted with EtOAc. The extract was washed with brine, dried over MgSO₄ and filtered. The filtrate was concentrated in vacuo. The residue containing tert-butyl (R)-1-(4-(4-(2-hydroxyethyl)piperidin-1-yl)phenyl)-4-((R)-3-(1-(3-methoxypropyl)-1,1-benzo[d]imidazol-2-yl)piperidin-1-yl)-4-oxobutan-2-ylcarbamate (126A) was carried directly on to the next step without further purification. ESI-MS: m/z 662.6 (M+H)⁺.

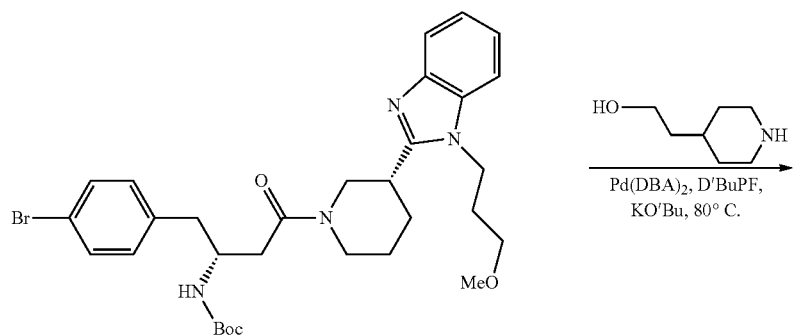

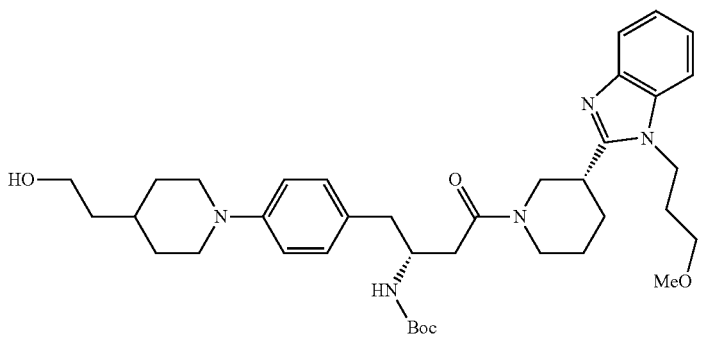

126A

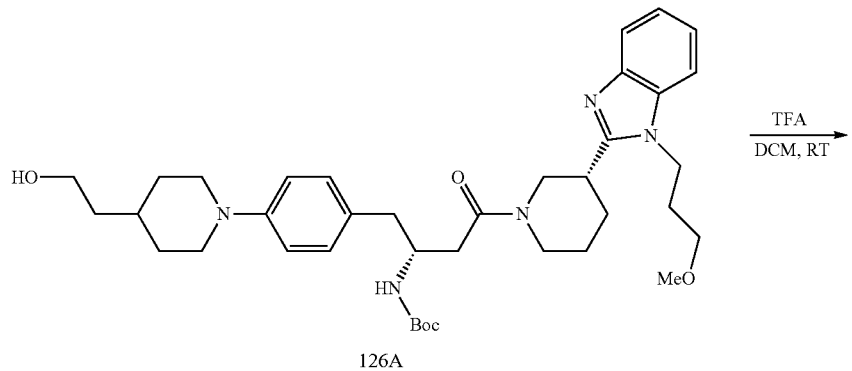

126A

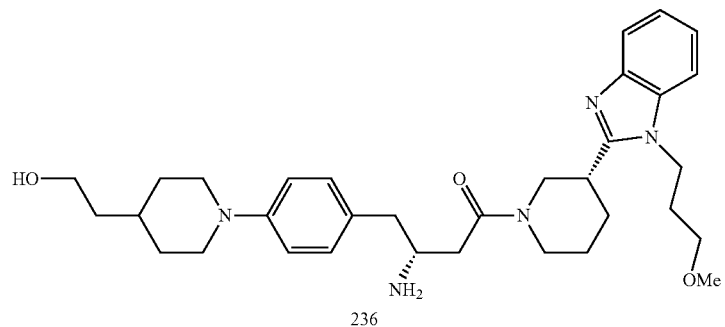

236

Residue 126A from the previous step (0.325 mmole, 215 mg) in DCM (10 mL) was added TEA (2 mL). The reaction solution was stirred at it for 1 hr and then concentrated in vacuo. The residue was purified by preparative LC/MS (10-15% CH₃CN in H₂O) to afford (R)-3-amino-4-(4-(4-(2-hydroxyethyl)piperidin-1-yl)phenyl)-1-((R)-3-(1-(3-methoxypropyl)-1H-benzo[d]imidazol-2-yl)piperidin-1-yl)butan-1-one (236) (0.007 mmole, 4 mg, two-step yield: 2.2%). ESI-MS: m/z 562.7 (M+H)⁺. 1H NMR (400 MHz, MeOD) δ ppm 1.24-1.35 (m, 1H) 1.54-1.78 (m, 3H) 1.80-1.99 (m, 2H) 1.99-2.16 (m, 3H) 2.16-2.24 (m, J=6.09, 5.87, 5.76, 5.76 Hz, 1H) 2.25-2.34 (m, 1H) 2.65-3.15 (m, 4H) 3.16-3.25 (m, 2H) 3.27 (s, 3H) 3.35-3.59 (m, 4H) 3.60-3.72 (m, 3H) 3.82-3.92 (m, 2H) 3.97 (d, J=15.28 Hz, 2H) 4.18 (d, J=12.19 Hz, 1H) 4.48-4.59 (m, 1H) 4.62 (t, J=7.01 Hz, 2H) 4.71 (d, J=14.84 Hz, 1H) 4.81 (br. s., 1H) 7.35-7.52 (m, 2H) 7.52-7.64 (m, 3H) 7.74-7.81 (m, 1H) 7.83-7.90 (m, 1H).

Example 127

Synthesis of methyl 1-(4-((R)-2-amino-4-((R)-3-(1-(3-methoxypropyl)-1H-benzo[d]imidazol-2-yl)piperidin-1-yl)-4-oxobutyl)phenyl)piperidine-4-carboxylate (237)

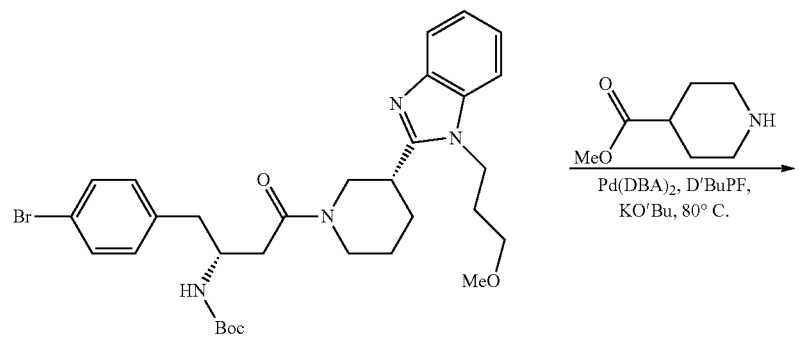

-continued

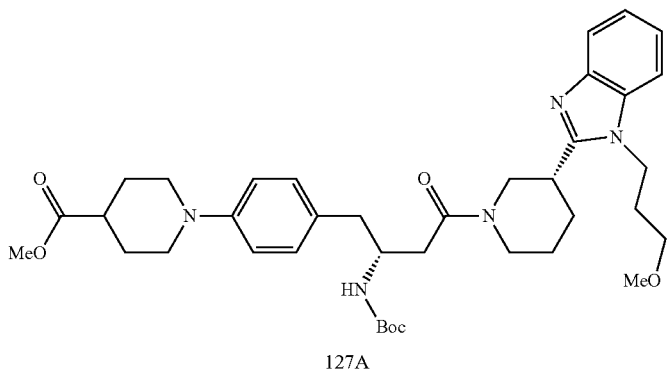

127A tert-Butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (0.325 mmole, 199 mg) in toluene (2 mL) was added bis(dibenzylideneacetone)palladium (0.016 mmole, 9 mg), 1,1'-bis(di-tert-butylphosphino)ferrocene (0.049 mmole, 23 mg), KOtBu (0.39 mmole, 44 mg) and methyl isonipecotate (0.39 mmole, 56 mg). The reaction mixture was heated to 80° C. for 6 hrs and then poured into H₂O, extracted with EtOAc. The extract was washed with brine, dried over MgSO₄ and filtered. The filtrate was concentrated in vacuo. The residue containing methyl 1-(4-((R)-2-(tert-butoxycarbonylamino)-4-((R)-3-(1-(3-methoxypropyl)-1H-benzo[d]imidazol-2-yl)piperidin-1-yl)-4-oxobutyl)phenyl)piperidine-4-carboxylate (127A) was carried directly on to the next step without further purification. ESI-MS: m/z 676.5 (M+H)⁺.

Residue 127A from the previous step (0.325 mmole, 220 mg) in DCM (10 mL) was added TEA (2 mL). The reaction solution was stirred at rt for 1 h and then concentrated in vacuo. The residue was purified by preparative LC/MS (10-15% CH₃CN in H₂O) to afford methyl 1-(4-((R)-2-amino-4-((R)-3-(1-(3-methoxypropyl)-1H-benzo[d]imidazol-2-yl) ppiperidin-1-yl)-4-oxobutyl)phenyl)piperidine-4-carboxylate (237) (0.010 mmole, 6 mg, two-step yield: 3.2%). ESI-MS: adz 576.5 (M+H)⁺. 1H NMR (400 MHz, MeOD) δ ppm 1.22-1.42 (m, 1H) 1.45-1.57 (m, 1H) 1.61-1.80 (m, 1H) 1.91-2.26 (m, 6H) 2.26-2.37 (m, 1H) 2.64-2.82 (m, 2H) 2.83-3.15 (m, 3H) 3.15-3.25 (m, 2H) 3.27 (s, 3H) 3.34-3.61 (m, 4H) 3.63-3.76 (m, 3H) 3.80-3.91 (m, 1H) 3.96 (d, J=14.65 Hz, 1H) 4.20 (d, J=12.25 Hz, 1H) 4.58 (q, J=7.33 Hz, 1H) 4.64 (t, J=6.95 Hz, 2H) 4.72 (d, J=13.20 Hz, 1H) 4.83 (br. s., 1H) 7.33 (d, J=3.54 Hz, 1H) 7.41 (s, 3H) 7.59-7.67 (m, J=5.84, 5.62, 5.51, 5.51Hz, 2H) 7.76-7.83 (m, 1H) 7.88-7.94 (m, 1H).

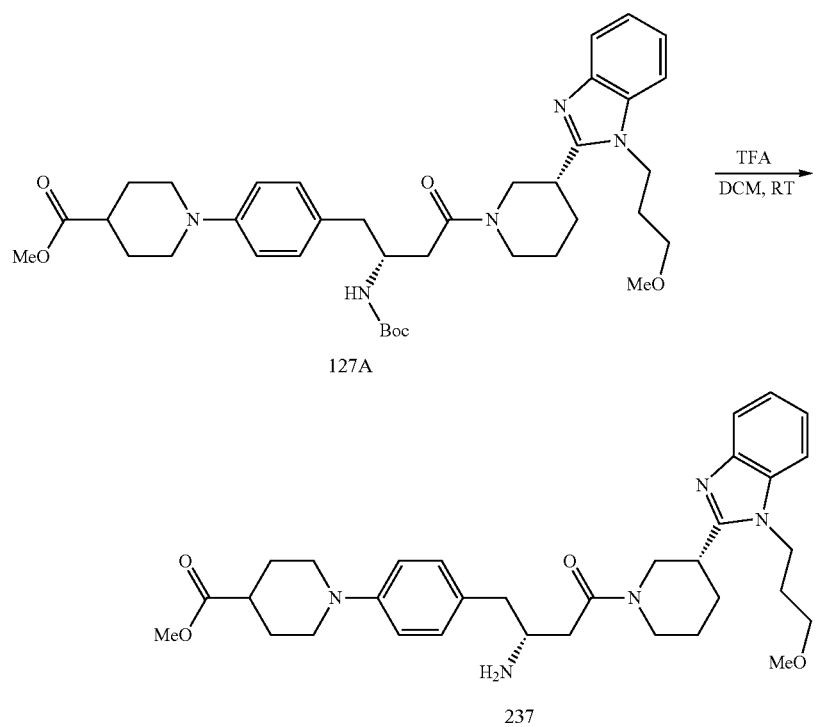

Example 128

Synthesis of (R)-3-amino-1-((R)-3-(1-(3-methoxypropyl)-1H-benzo[d]imidazol-2-yl)piperidin-1-yl)-4-(4-phenoxyphenyl)butan-1-one (238)

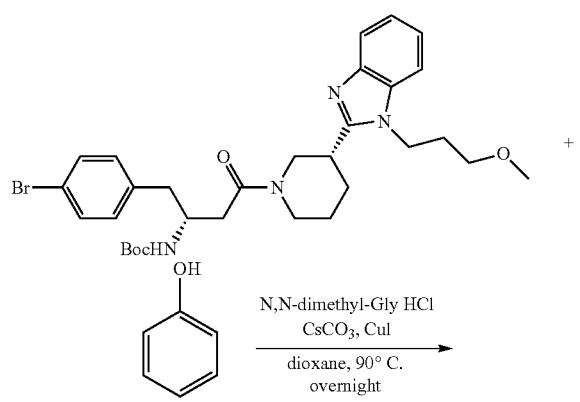

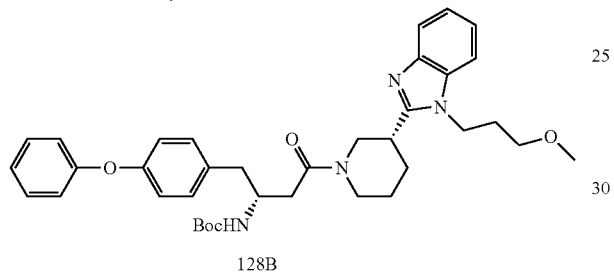

Into a 15 mL sealed tube vessel was added tert-butyl (R)-1-(4-bromophenyl)-4-((R)-3-(1-(3-methoxypropyl)-1H-benzo[d]imidazol-2-yl)piperidin-1-yl)-4-oxobutan-2-ylcarbamate (100 mg, 163 μmol), copper(I) iodide (3 mg, 16 μmol), N,N-dimethylglycine hydrochloride (7 mg, 49 μmol), cesium carbonate (106 mg, 326 μmol) and phenol (23 mg, 245 μmol). Dioxane (400 μL) was added and heated at 90° C. for 20 hrs. The reaction was cooled and filtered through a Buchner funnel with Celite. The solvent was removed from the filtrate and the residue was purified by preparatory LC/MS (40-50% $CH_3CN$ in $H_2O$) to give tert-butyl (R)-4-((R)-3-(1-(3-methoxypropyl)-1H-benzo[d]imidazol-2-yl)piperidin-1-yl)-4-oxo-1-(4-phenoxyphenyl)butan-2-ylcarbanlate (128B) as a TFA salt (55 mg, 50% yield). ESI-MS:m/z 627.3 $(M+H)^+$.

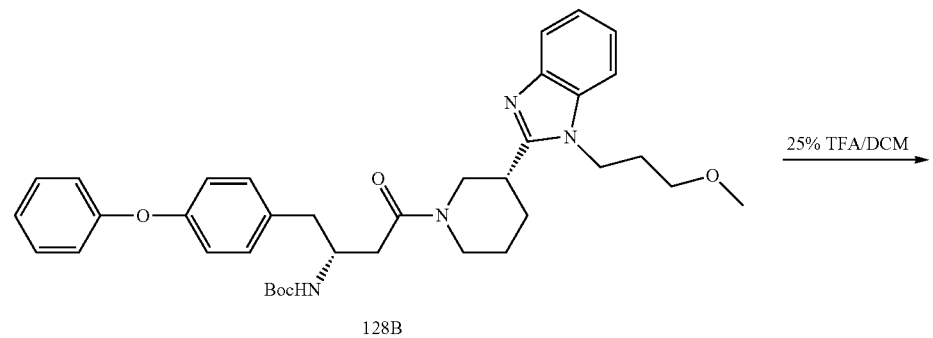

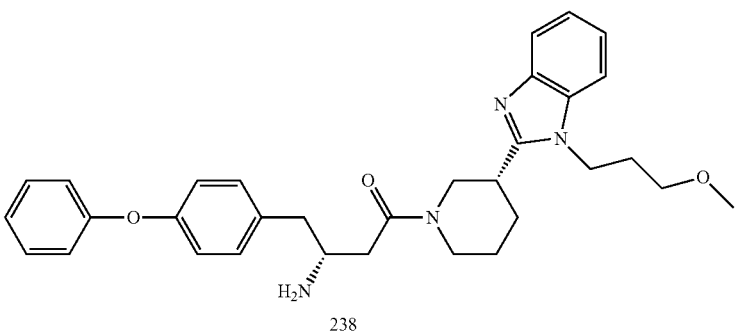

The solvent was removed and the residue was purified by preparatory LC/MS (20-50% CH$_3$CN in H$_2$O) to give (R)-3-amino-1((R)-3-(1-(3-methoxypropyl)-1H-benzo[d]imidazol-2-yl)piperidin-1-yl)-4-(4-phenoxyphenyl)butan-1-one (239) as TFA salt (47 mg, 45% yield over two steps). 1H NMR (400 MHz, DMSO-d6) δ ppm 1.52 (br. s., 1H) 1.76-2.21 (m, 5H) 2.58-3.48 (m, 12H) 3.62-3.89 (m, 1H) 4.08-4.67 (m, 4H) 6.94-7.04 (m, 4H) 7.14 (m, 1H) 7.29 (m, 2H) 7.34-7.49 (m, 4H) 7.73 (m, 2H). ESI-MS:m/z 527.2 (M+H)$^+$.

Example 129

Synthesis of N-(2-(2-((R)-1((R)-3-amino-4-(naphthalen-2-yl)butanoyl)piperidin-3-yl)-1H-benzo[d]imidazol-1-yl)ethyl)acetamide (239)

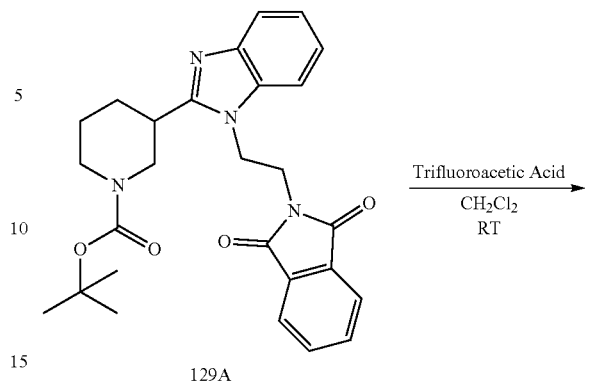

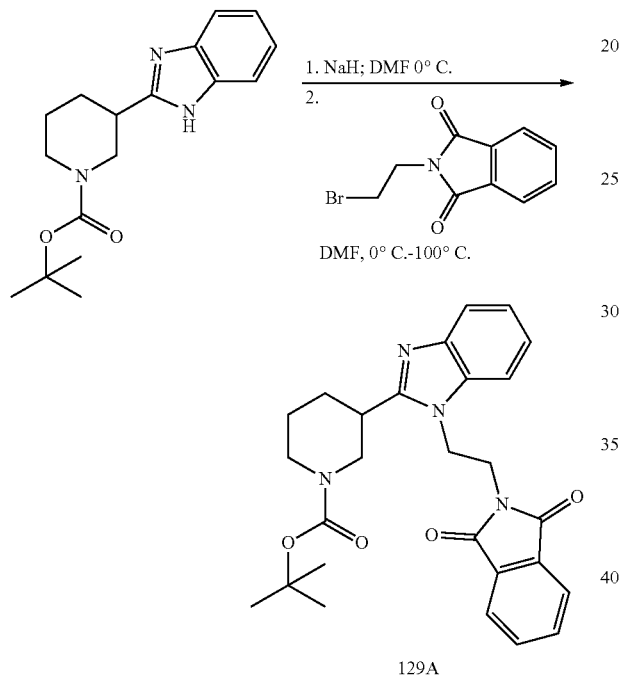

Tert-butyl 3-(1H-benzo[d]imidazol-2-yl)piperidine-1-carboxylate (4.36 mmol, 1.3 g) was added to a 50 mL oven-dried round-bottomed flask equipped for stirring under nitrogen. DMF (15 mL) was added and the solution was cooled to 0° C. NaH (4.80 mmol, 192 mg) was then added in one portion and the resultant solution was stirred at 0° C. for 0.5 hr. At this time 2-(2-bromoethyl)isoindoline-1,3-dione (5.01 mmoles, 1.27 g) was added; the ice bath was removed and the reaction solution was allowed to warm to room temperature and stirred for 16 hrs. The reaction was then heated to 100° C. and allowed to stir for an additional 16 hrs. Analysis of the reaction solution by LC/MS indicated about an approx. 10% conversion to the desired title compound (129A). The reaction was cooled to rt and then poured into ice-water, extracted with ethyl acetate, and washed once with saturated aqueous sodium chloride. The organic layer was collected and subsequently dried with anhydrous Na$_2$SO$_4$ and filtered. This filtrate was collected, concentrated, and dried in-vacuo affording tert-butyl 3-(1-(2-(1,3-dioxoisoindolin-2-yl)ethyl)-1H-benzo[d]imidazol-2-yl)piperidine-1-carboxylate (129A) as a mixture of products that was carried onto the next step without further purification. ESI-MS: m/z 475.3 (M+H)$^+$.

tert-Butyl 3-(1-(2-(1,3-dioxoisoindolin-2-yl)ethyl)-1H-benzo[d]imidazol-2-yl)piperidine-1-carboxylate (129A) (4.36 mmoles max, crude mixture) was added to a 20 mL scintillation vial equipped for stirring. CH$_2$Cl$_2$ (3 mL) and trifluoroacetic acid (1 mL) were then added and the resultant solution was allowed to stir at room temperature for 72 hrs. The reaction was concentrated and dried in-vacuo affording 2-(2-(2-(piperidin-3-yl)-1H-benzo[d]imidazol-1-yl)ethyl)isoindoline-1,3-dione (129B) as a mixture that was used without further purification. ESI-MS: m/z 375.3 (M+H)$^+$.

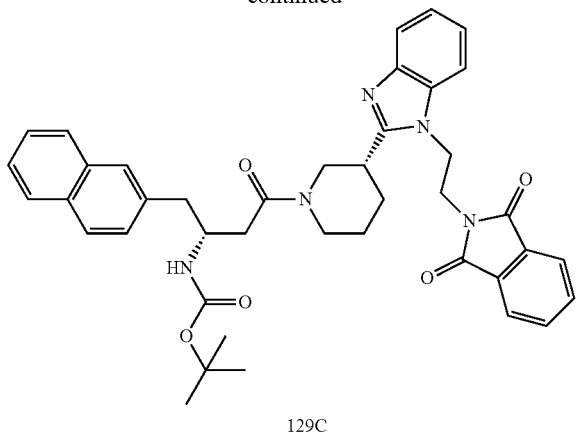

129C (R)-2-(2-(2-(piperidin-3-yl)-1H-benzo[d]imidazol-1-yl)-ethyl)isoindoline-1,3-dione (129B) (500 mg of mixture) from previous step, was weighed into a 25 mL round-bottomed flask equipped for stirring under nitrogen. DMF (3 mL), (R)-3-(tert-butoxycarbonylamino)-4-(naphthalen-2-yl)butanoic acid (2.48 mmoles, 0.817 g) and N-methylmorpholine (7.44 mmoles, 0.818 mL) were then added and the solution was allowed to stir at rt for 5 min. HATU (2.73 mmoles, 1.04 g) was added and the resultant solution was stirred at room temperature for 3 hrs. The reaction solution was then directly purified by preparative LC/MS (35-95% $CH_3CN$ in $H_2O$). The resultant fractions were collected and the solvent was removed in-vacuo affording tert-butyl (R)-4-((R)-3-(1-(2-(1,3-dioxoisoindolin-2-yl)ethyl)-1H-benzo[d]imidazol-2-yl)piperidin-1-yl)-1-(naphthalen-2-yl)-4-oxobutan-2-ylcarbamate (129C) as a clear oil. (0.105 mmoles, 0.072 g, 4% yield over 2-steps). ESI-MS: m/z 686.5 $(M+H)^+$.

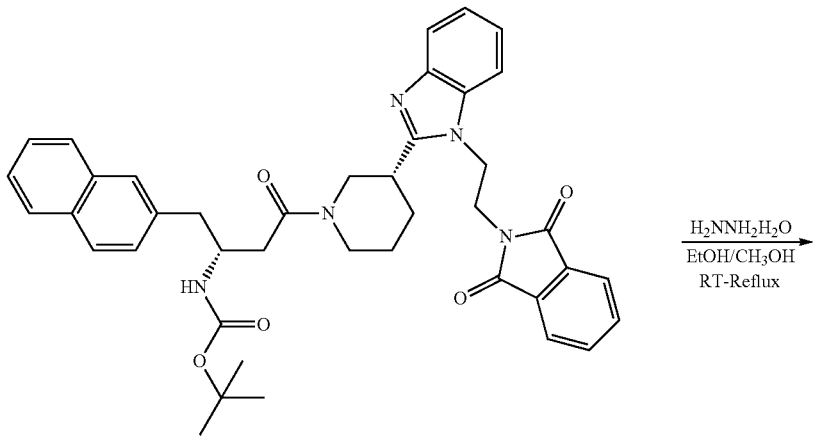

129C

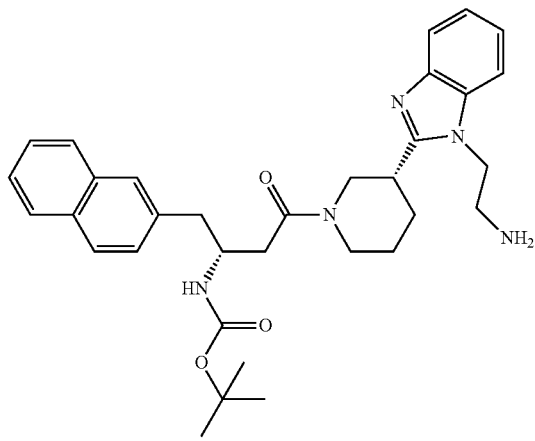

129D tert-Butyl (R)-4-((R)-3-(1-(2-(1,3-dioxoisoindolin-2-yl)ethyl)-1H-benzo[d]imidazol-2-yl)piperidin-1-yl)-1-(naphthalen-2-yl)-4-oxobutan-2-ylcarbamate (0.105 mmoles, 0.072 g) was added to a 25 mL round-bottomed flask equipped with a reflux condenser and for stirring under nitrogen. Ethanol (6 mL), methanol (6 mL), and hydrazine hydrate (0.84 mmoles, 0.041 mL) were then added and the solution was heated to reflux temperature for 2 hrs. The reaction solution was then concentrated and dried in-vacuo to give tert-butyl (R)-4-((R)-3-(1-(2-aminoethyl)-1H-benzo[d]imidazol-2-yl)piperidin-1-yl-1-(naphthalen-2-yl)-4-oxobutan-2-ylcarbamate (129D) as a brownish oil that was used without further purification. ESI-MS: m/z 556.5 (M+H)$^+$.

tert-Butyl (R)-4-((R)-3-(1-(2-aminoethyl)-1H-benzo[d]imidazol-2-yl)piperidin-1-yl)-1-(naphthalen-2-yl)-4-oxobutan-2-ylcarbamate (129D) was added to a 25 mL round-bottomed flask equipped for stirring under nitrogen. Dichloromethane (5 mL) was added and the solution was cooled to 0° C. with an ice/water bath. Acetyl chloride (0.703 mmoles; 0.050 mL) and pyridine (2.47 mmoles, 0.200 mL) were then added and the resultant solution was stirred at 0° C. for 10 min. Solution was allowed to warm to it and stirred for 1 hr. The reaction solution was subsequently concentrated in-vacuo, re-dissolved in methanol (3 mL), and then directly purified by preparative LC/MS (20-90% CH$_3$CN in H$_2$O) to afford tert-butyl (R)-4-((R)-3-(1-(2-acetamidoethyl)-1H-benzo[d]imidazol-2-yl)piperidin-1-yl)-1-(naphthalen-2-yl)-4-oxobutan-2-ylcarbamate (129E) as a clear oil (0.038 mmoles, 0.023 g, 36% yield over 2-steps). ESI-MS: m/z 598.5 (M+H)$^+$.

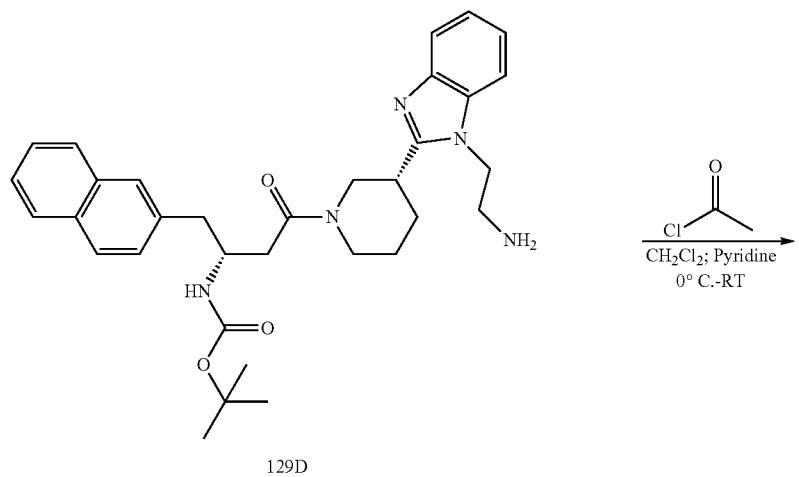

129D

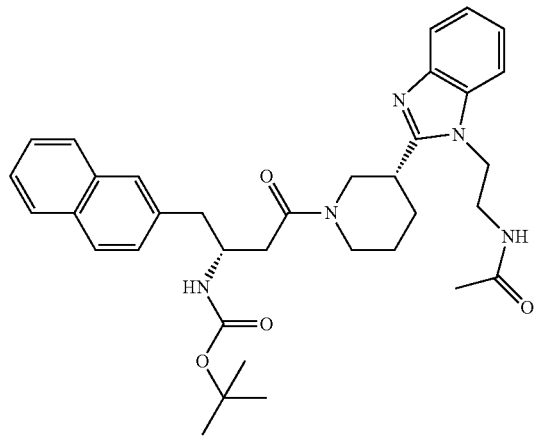

129E

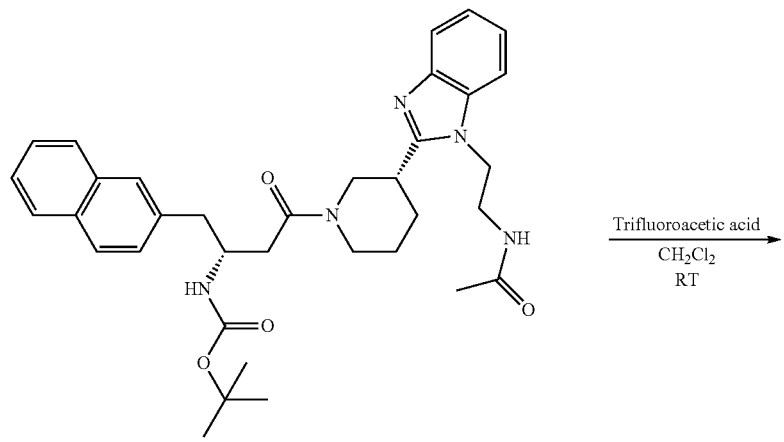

129E

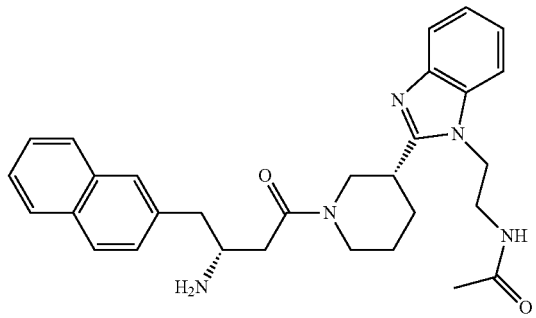

239

Residue from previous step tert-butyl (R)-4-((R)-3-(1-(2-acetamidoethyl)-1E-benzo[d]imidazol-2-yl)piperidin-1-yl)-1-(naphthalen-2-yl)-4-oxobutan-2-ylcarbamate (0.038 mmoles, 0.023 g) was weighed into a 20 mL scintillation vial and dissolved in $CH_2Cl_2$ (2 mL). Trifluoroacetic acid (2 mL) was then added and the solution was stirred at room temperature for 2 hrs. The solvent was removed in-vacuo affording a clear colored oil. This oil was re-dissolved in methanol (3 mL), filtered, and then purified by preparative LC/MS (5-55% $CH_3CN$ in $H_2O$). The resultant fractions were collected and the solvent was removed in-vacuo affording a clear colored oil. This oil was re-dissolved in $CH_3CN$ (1 mL) and water (2 mL). The resultant solution was frozen and lyophilized to afford N-(2-(2-((R)-1((R)-3-amino-4-(naphthalen-2-yl)butanoyl)piperidin-3-yl)-1H-benzo[d]imidazol-1-3`1)ethyl)acetamide (239) as its trifluoroacetic acid salt as a white flocculent solid. (0.029 mmoles, 0.018 g, 77% yield). $^1$H NMR (400 MHz, DMSO-$d_6$) δ ppm 1.14-1.31 (m, 0H) 1.35-1.73 (m, 4H) 1.73-2.01 (m, 2 H) 2.04-2.24 (m, 1H) 2.59-2.79 (m, 2H) 2.84-3.00 (m, 1H) 3.00-3.25 (m, 2H) 3.25-3.54 (m, 2H) 3.67-4.11 (m, 3H) 4.13-4.76 (m, 4H) 7.34-7.61 (m, 4H) 7.63-7.80 (m, 2H) 7.81-8.15 (m, 5H) ESI-MS: m/z 498.4 (M+H)$^+$.

Example 130

Synthesis of (R)-4-(4-bromobenzyl)-2-oxooxazolidine-5-carboxylic acid (130F)

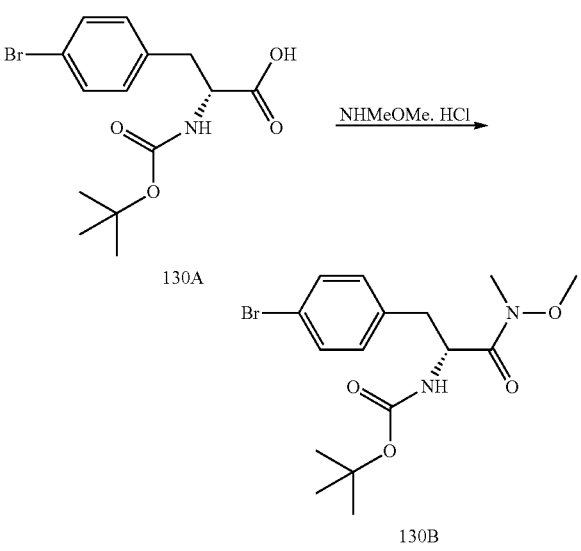

To a 0° C. solution of 130A (8 g), TEA (3.5 mL) and HATU (9.7 g) in dry CH₂Cl₂ (50 mL) was added N,O-dimethylhydroxylamine hydrochloride (2.75 g) and TEA (3.9 mL). The reaction was allowed to warm to RT, and stirred overnight. The reaction was partitioned between CH₂Cl₂ and 1N HCl. The organic layer was separate and washed with saturated NaHCO₃ and brine, dried over anhydrous Na₂SO₄, filtered and concentrated to give 9 g of (R)-tert-butyl 3-(4-bromophenyl)-1-(methoxy(methyl)amino)-1-oxopropan-2-ylcarbamate (130B). 1H NMR (300 MHz, CDCl₃) δ=7.40-7.29 (q, 2H), 7.04-7.01 (m, 2H), 5.19-5.14 (t, 1H), 4.92 (m, 1H) 3.67 (s, 3H), 3.18 (s, 3H), 3.03-2.98 (m, 1H), 1.39 (s, 9H).

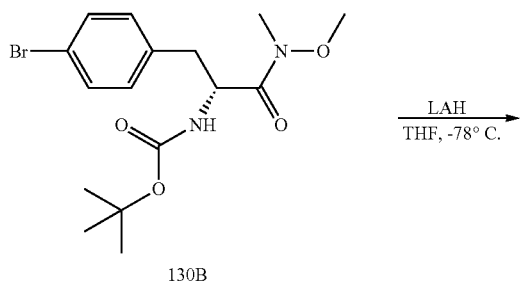

130B

LiAlH₄ (1 g) was added to 20 mL Et₂O in a round-bottom flask equipped with a pressure-equalizing dropping funnel, placed under N₂. Then a solution of compound 130B (9 g) in 50 mL Et₂O was added to the LiAlH₄ suspension at a rate in which the temperature was not allowed to exceed 5° C. After all amide was added, the reaction mixture was stirred for 30 min, then EtOAc was added, and 100 mL. KHSO₄ solution was added drop-wise to quench the reaction. The temperature of the mixture was maintained at less than 5° C. Then the mixture was washed with 1N HCl, saturated NaCO₃ and brine, and dried over anhydrous Na₂SO₄, concentrated to afford 7 g of crude (R)-tert-butyl 3-(4-bromophenyl)-1-(methoxy(methyl)amino)-1-oxopropan-2-ylcarbamate (130C). 1H NMR (300 MHz, CDCl₃) δ=9.61 (s, 1H), 7.44-7.40 (q, 2H), 7.06-7.01 (m, 2H), 5.01-5.00 (t, 1H), 4.40-4.38 (t, 1H) 3.08-3.04 (m, 2H), 1.49 (s, 9H).

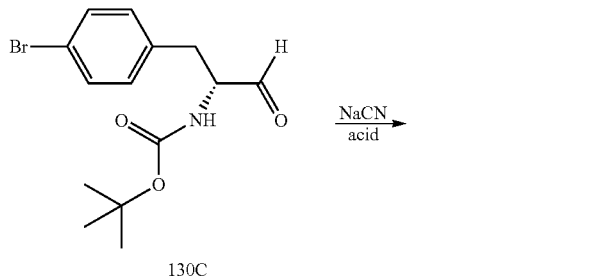

130C 130C (7 g) was dissolved in MeOH and chilled to 5° C. NaHSO₃ (2.22 g) was dissolved in de-ionized water and chilled to 5° C. before addition. Then the mixture was stirred at 5° C. for 2 hrs; then NaCN (1.25 g) was added and the mixture was stirred at it overnight. The organic layer was collected, dried with Na₂SO₄, filtered, and concentrated to yield a crude product. The crude product was dissolved in 1,4-dioxane, concentrated HCl and anisole. The solution was heated to reflux overnight, then cooled to RT, and concentrated in vacuo. Acetone was added and the suspension was filtered to product 2.9 g of crude (R)-3-amino-4-(4-bromophenyl)-2-hydroxybutanoic acid (130D). 1H NMR (300 MHz, CD₃OD) δ=7.53-7.50 (q, 2H), 7.26-7.23 (m, 2H), 4.09-4.06 (m, 1H), 3.82-3.80 (m, 1H), 3.09-2.98 (m, 2H).

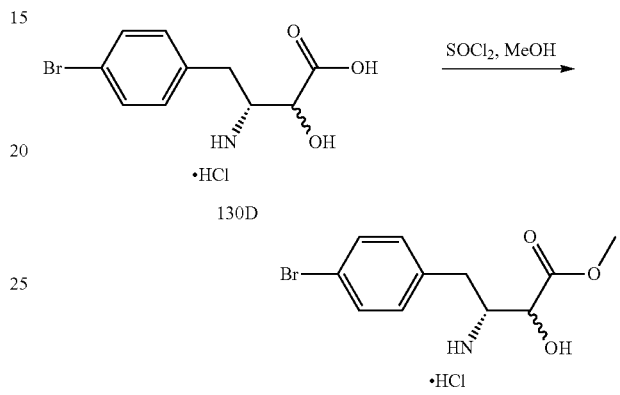

130D

A solution of MeOH was cooled to 0° C., SOCl₂ (5.2 g) was added drop-wise, and then compound 130D (2.9 g) in 10 mL MeOH was added to the above solution. The solution was allowed to warm to rt and stirred for 6 hrs. MeOH was removed under reduce pressure to afford 3 g of compound (R)-methyl 3-amino-4-(4-bromophenyl)-2-hydroxybutanoate (130E). 1H NMR (300 MHz, CD₃OD) δ=7.53-7.50 (q, 2H), 7.26-7.23 (m, 2H), 4.12-4.10 (m, 1H), 3.80 (m, 111), 3.74-3.70 (m, 3H), 3.09-2.98 (m, 2H).

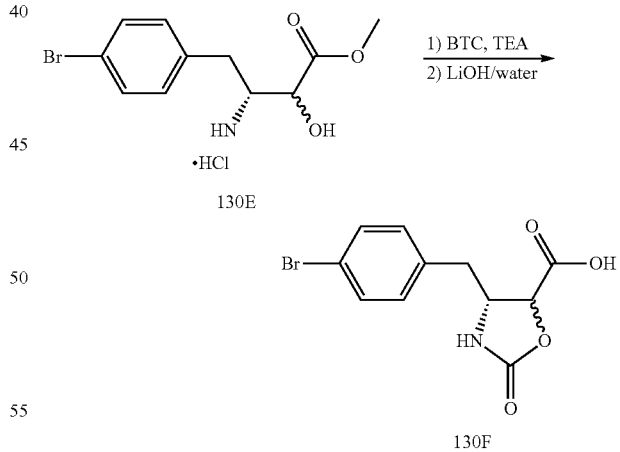

130E

130F

Compound 130E (2.9 g) was dissolved in 20 mL THF, and cooled to about 0° C. TEA was then added to the mixture and the mixture was stirred for 10 min. A solution of BTC (3 g) in THF was added drop-wise for 4 hrs while the temperature of the solution was maintained at below 5° C. THF was removed under reduce pressure, and the resulting mixture was partitioned between EtOAc and 1N NaHSO₃. The organic layer was dried with NaSO₄, filtered and concentrated, purified by chromatography (ethyl acetate:hexanes, 1:4) to afford the ester product (0.4 g).

To a solution of above ester product (0.4 g) in THF was added a solution of LiOH (0.16 g) in water; the mixture was stirred at rt for 4 hrs. The mixture was adjusted to pH 3 by 10% HCl. EtOAc was added, and the organic layer was washed with brine and dried with NaSO$_4$, and then concentrated to afford the product, which is pure (R)-4-(4-bromobenzyl)-2-oxooxazolidine-5-carboxylic acid (130F) (0.35 g). 1H NMR (300 MHz, DMSO-d$_6$) δ=7.49-7.45 (q, 2H), 7.22-7.18 (m, 2H), 4.75-4.70 (m, 1H), 4.16-4.10 (m, 1H), 3.00-2.88 (m, 2H).

Example 131

Synthesis of (R)-3-amino-2-benzyl-4-(4-chlorophenyl)-1-((R)-3-(1-(3-methoxypropyl)-1H-benzo[d]imidazol-2-yl)piperidin-1-yl)butan-1-one (ID: SYR147702B:001) (240)

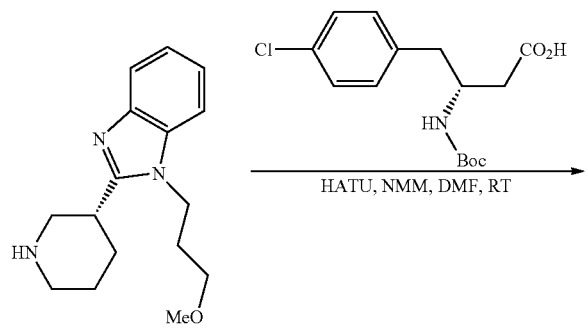

(R)-1-(3-Methoxypropyl)-2-(piperidin-3-yl)-1H-benzo[d]imidazole (0.25 mmole, 68 mg) in DMF (10 mL) was added (R)-4-(4-chlorophenyl)-3-(tert-butoxycarbonylamino)butanoic acid (0.28 mmole, 88 mg) and N-methylmorphine (1.00 mmole, 0.11 mL). The reaction mixture was stirred at it for 5 min and then added HATU (0.28 mmole, 107 mg) and kept stirring at it overnight. The reaction mixture was poured into H$_2$O, extracted with EtOAc. The extract was washed with H$_2$O, brine, dried over MgSO$_4$ and filtered. The filtrate was concentrated in vacuo. The residue containing tert-Butyl (R)-1-(4-chlorophenyl)-4-((R)-3-(1-(3-methoxypropyl)-1H-benzoldlimidazol-2-yl)piperidin-1-yl)-4-oxobutan-2-ylcarbamate (131A) was carried directly on to the next step without further purification. ESI-MS: mh 570.5 (M+H)$^+$.

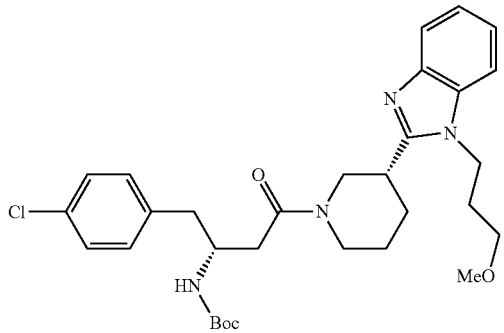

131A

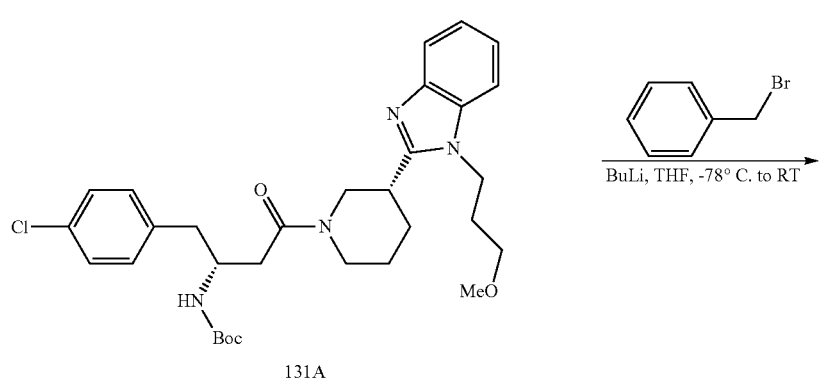

131A

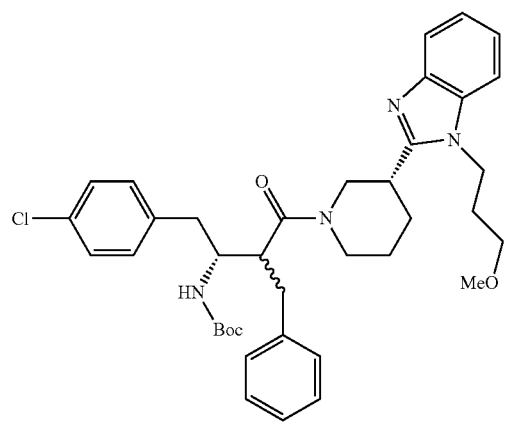

131B tert-Butyl (R)-1-(4-chlorophenyl)-4-((R)-3-(1-(3-methoxypropyl)-1H-benzo[d]imidazol-2-yl)piperidin-1-yl)-4-oxobutan-2-ylcarbamate (131A) (0.25 mmole, 142 mg) in THF (5 mL) was cooled to –78° C., added butyl lithium (0.375 mmole, 1.6 M in hexane, 0.23 mL) and stirred for 30 min. The reaction solution was added benzyl bromide (1.25 mmole, 0.15 mL) and stirred at rt overnight. The reaction mixture was poured into H₂O, extracted with EtOAc. The extract was washed with brine, dried over MgSO₄ and filtered. The filtrate was concentrated in vacuo. The residue containing tert-Butyl (R)-3-benzyl-1-(4-chlorophenyl)-4-((R)-3-(1-(3-methoxypropyl)-1H-benzo[d]imidazol-2-yl)piperidin-1-yl)-4-oxobutan-2-ylcarbamate (131B) was carried directly on to the next step without further purification. EST-MS: m/z 659.5 (M+H)⁺.

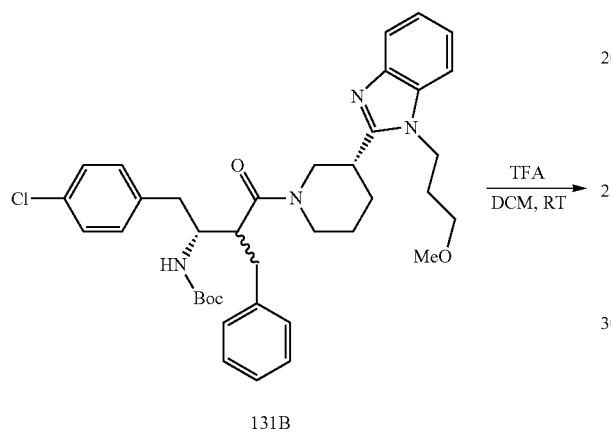

tert-Butyl (R)-3-benzyl-1-(4-chlorophenyl)-4-((R)-3-(1-(3-methoxypropyl)-1H-benzo[d]imidazol-2-yl)piperidin-1-yl)-4-oxobutan-2-ylcarbamate (131B) (0.25 mmole, 165 mg) in DCM (10 mL) was added TEA (2 mL). The reaction solution was stirred at rt for 1 hr and then concentrated in vacuo. The residue was purified by preparative LC/MS (25-30% CH₃CN in H₂O) to afford (R)-3-amino-2-benzyl-4-(4-chlorophenyl)-1-((R)-3-(1-(3-methoxypropyl)-1H-benzo[d]imidazol-2-yl)piperidin-1-yl)butan-1-one (240) (0.016 mmole, 9 mg, two-step yield: 6.4%). ESI-MS: m/z 560.4 (M+H)⁺. ESI-MS: m/z 560.4 (M+H)⁺. 1H NMR (400 MHz, MeOD) δ ppm 1.49-1.74 (m, 1H) 1.82-1.95 (m, 1H) 2.01-2.33 (m, 3H) 2.50-2.74 (m, 3H) 2.95-3.09 (m, 2H) 3.11-3.23 (m, 1H) 3.24 (s, 3H) 3.44-3.59 (m, 2H) 3.62-3.95 (m, 2H) 4.62-4.86 (m, 4H) 5.88-6.10 (m, 2H) 7.18 (d, 0.1=6.25 Hz, 2H) 7.23-7.32 (m, 2H) 7.38 (d, J=2.40 Hz, 5H) 7.57-7.76 (m, 3H) 7.99-8.07 (m, 1H).

Example 132

Synthesis of (R)-3-amino-1((R)-3-(1-(3-methoxypropyl)-4,5,6,7-tetrahydro-1H-benzo[d]imidazol-2-yl)piperidin-1-yl)-4-(naphthalen-2-yl)butan-1-one (241)

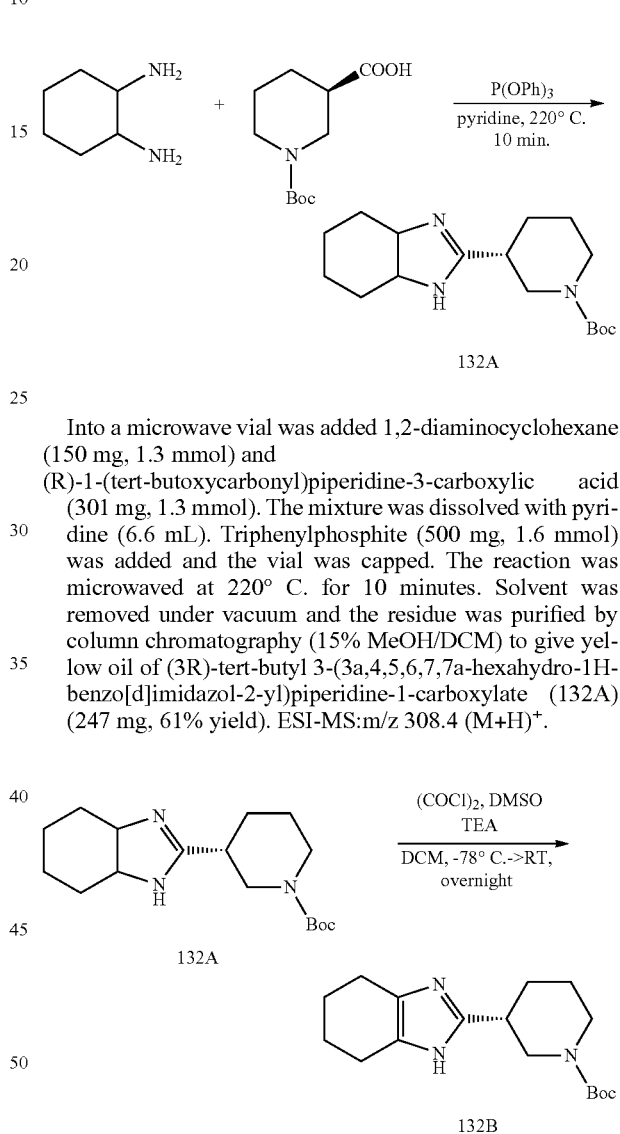

Into a microwave vial was added 1,2-diaminocyclohexane (150 mg, 1.3 mmol) and (R)-1-(tert-butoxycarbonyl)piperidine-3-carboxylic acid (301 mg, 1.3 mmol). The mixture was dissolved with pyridine (6.6 mL). Triphenylphosphite (500 mg, 1.6 mmol) was added and the vial was capped. The reaction was microwaved at 220° C. for 10 minutes. Solvent was removed under vacuum and the residue was purified by column chromatography (15% MeOH/DCM) to give yellow oil of (3R)-tert-butyl 3-(3a,4,5,6,7,7a-hexahydro-1H-benzo[d]imidazol-2-yl)piperidine-1-carboxylate (132A) (247 mg, 61% yield). ESI-MS:m/z 308.4 (M+H)⁺.

Oxalyl chloride (112 mg, 0.89 mmol) was added to a 10 mL round bottomed flask with dichloromethane (0.9 mL) and cooled to –78° C. DMSO (138 mg, 1.77 mmol) was added via syringe over 10 minutes. The reaction was stirred at –78° C. for an additional 10 min. before (132A) (247 mg, 0.81 mmol) in dichloromethane (0.2 mL) was added over 10 min. Triethylamine (407 mg, 4.0 mmol) was added over 10 min. at –78° C. The reaction was allowed to stir and warm to room temperature overnight. Solvent was removed under vacuum. The residue was purified by preparatory LC/MS (35-40% CH₃CN in H₂O) to give (R)-tert-butyl 3-(4,5,6,7-tetrahydro-1H-benzo[d]hnidazol-2-yl)piperidine-1-carboxylate (132B) as an oil (195 mg, 79% yield). ESI-MS:m/z 306.4 (M+H)⁺.

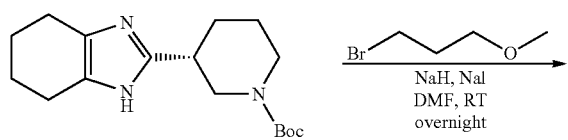

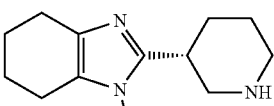

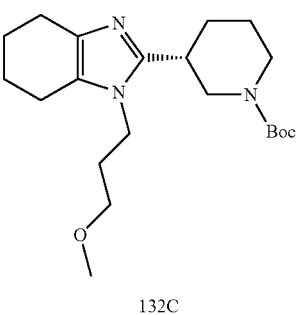

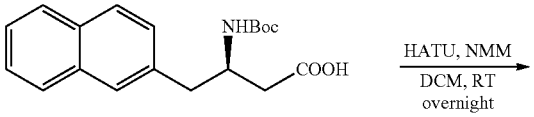

Into a 10 mL round bottomed was added (132B) (195 mg, 638 µmol) and N,N-dimethylforamide (2.1 mL). NaI (105 mg, 702 µmol) and NaH (33 mg, 830 µmol, 60% disp.) were added in sequence. The mixture was stirred for 30 minutes at room temperature. 3-methoxy propyl bromide (127 mg, 830 µmol) was added at once and stirred overnight at room temperature. Solvent was removed under vacuum and the residue was purified by preparatory LC/MS (30-35% $CH_3CN$ in $H_2O$) to give (R)-tert-butyl 3-(1-(3-methoxypropyl)-4,5,6,7-tetrahydro-1H-benzo[d]imidazol-2-yl)piperidine-1-carboxylate (132C) as an oil (40 mg, 17% yield). ESI-MS:m/z 376.4 $(M+H)^+$.

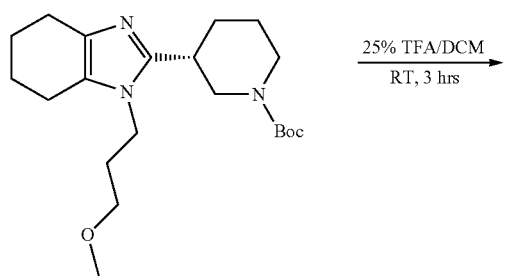

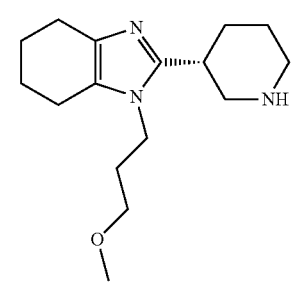

Into a 10 mL round bottomed flask was added (132C) (40 mg, 106 µmol). 25% trifluoroacetic acid in dichloromethane (5 mL) was added and stirred at room temperature for 3 hrs. The solvent was removed under vacuum. The residue (R)-1-(3-methoxypropyl)-2-(piperidin-3-yl)-4,5,6,7-tetrahydro-1H-benzo[d]imidazole (132D) was used in the next step without purification. ESI-MS:m/z 278.4 $(M+H)^+$.

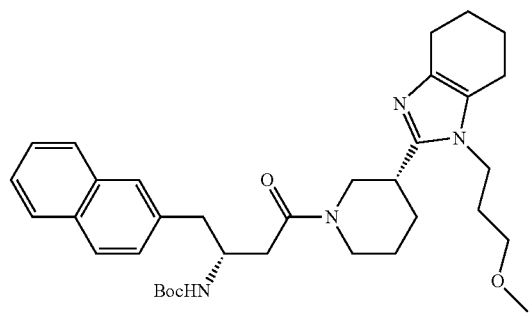

The residue (132D) from the previous step was added dichloromethane (1 mL). HATU (44 mg, 117 µmol, N-methyl-morpholine (43 mg, 424 µmol) and (R)-3-(tert-butoxy-carbonylamino)-4-(naphthalen-2-yl)butanoic acid (35 mg, 106 µmol). The reaction was stirred overnight at room temperature. Solvent was removed under vacuum and the residue containing tert-butyl (R)-4-((R)-3-(1-(3-methoxypropyl)-4,5,6,7-tetrahydro-1H benzo[d]imidazol-2-yl)piperidin-1-yl)-1-(naphthalen-2-yl)-4-oxobutan-2-ylcarbamate (132E) was carried on to the next step without further purification. ESI-MS:m/z 589.5 $(M+H)^+$.

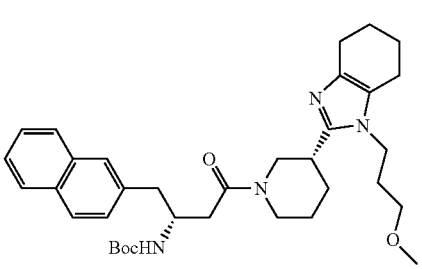

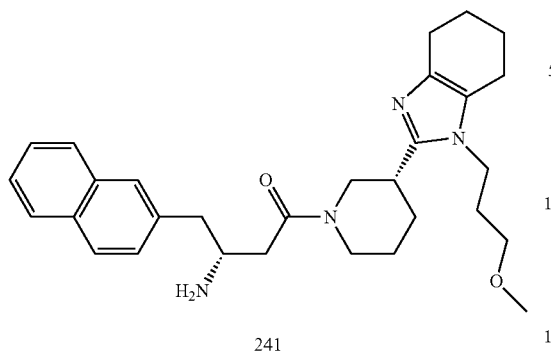

241

The residue 132E from the previous step was treated with 25% trifluoroacetic acid in dichloromethane (5 mL). The mixture was stirred at room temperature for 3 hrs. The solvent was removed under vacuum and the residue was purified by preparatory LC/MS (30-35% CH$_3$CN in H$_2$O) to give (R)-3-amino-1((R)-3-(1-(3-methoxypropyl)-4,5,6,7-tetrahydro-1H-benzo[d]imidazol-2-yl)piperidin-1-yl)-4-(naphthalen-2-yl)butan-1-one (241) as a TFA salt (30 mg, 47% yield from 132C). 1H NMR (400 MHz, DMSO-d$_6$)δ ppm 1.46 (br. s., 1H) 1.61-2.09 (m, 8H) 2.53-2.63 (m, 4H) 2.63-2.85 (m, 3H) 2.87-3.38 (m, 9H) 3.70-4.22 (m, 4H) 4.51 (br. s., 2H) 7.52 (m, 3H) 7.75-7.94 (m, 4H). ESI-MS:m/z 489.4 (M+H)$^+$.

Example 133

Synthesis of methyl 4'-((2R)-2-amino-4-(3-(5-tert-butyl-1-(3-methoxypropyl)-1,1-imidazol-2-yl)-3-hydroxypiperidin-1-yl)-4-oxobutyl)biphenyl-4-carboxylate (242)

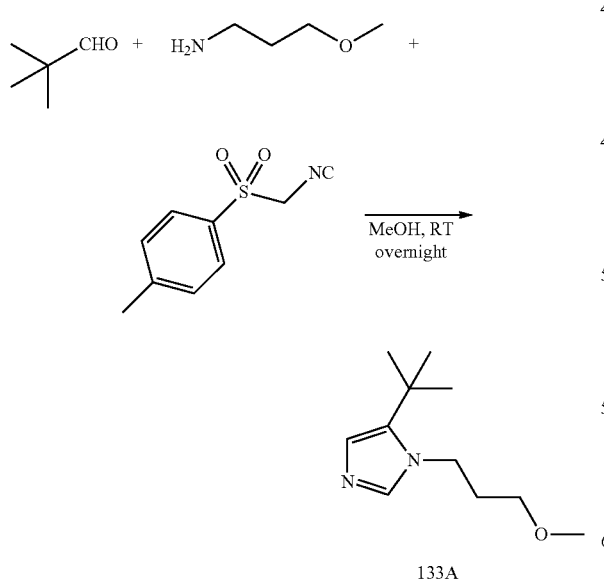

Into a 50 mL round bottomed flask was added pivaldehyde (500 mg, 5.8 mmol), 3-methoxypropylamine (569 mg, 6.4 mmol) and magnesium sulfate. Dichloromethane (20 mL) was added and the mixture was stirred overnight under nitrogen. The mixture was filtered through a pad of Celite and the solvent was removed form the filtrate under vacuum. The residue was dissolved in methanol (10 mL); 3-methoxypropylamine (466 mg, 5.2 mmol) and TOSMIC (942 mg, 4.8 mmol) was added and the mixture was again stirred overnight. Solvent was removed under vacuum, and the residue was purified by preparatory LC/MS (10-25% CH$_3$CN in H$_2$O) to give 5-tert-butyl-1-(3-methoxypropyl)-1H-imidazole (133A) as a yellow oil (376 mg, 40% yield). ESI-MS:m/z 197.4 (M+H)$^+$.

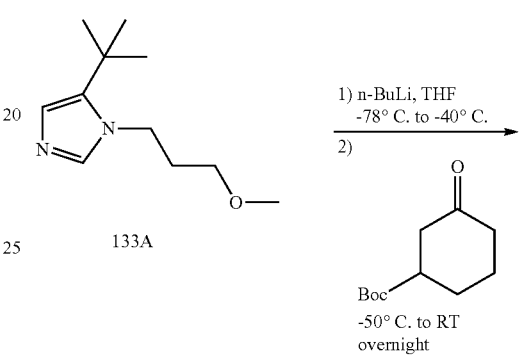

Into a 50 mL round bottomed flask was added 5-tert-butyl-1-(3-methoxypropyl)-1H-imidazole (133A) (376 mg, 1.9 mmol) and THF (9.6 mL). The solution was cooled to −78° C. and n-BuLi (843 µL, 2.5 M/hexanes, 2.1 mmol) was added slowly via syringe. The mixture was stirred for 20 minutes and slowly warmed to −30° C. The solution was cooled to −78° C. and N-Boc-3-piperidone (418 mg, 2.1 mmol) in THF (5 mL) was added slowly via syringe; the mixture was allowed to warm to room temperature overnight. Solvent was removed under vacuum and the residue was partitioned between water (25 mL) and ethyl acetate (25 mL). The organic layer was separated and discarded. The aqueous layer extracted with ethyl acetate (2×25 mL). The organic portions were combined and washed with brine (50 mL) and dried over sodium sulfate and filtered. The solvent was removed in vacuo and the residue was purified by preparatory LC/MS (10-45% CH$_3$CN in H$_2$O) to give tert-butyl 3-(5-tert-butyl-1-(3-methoxypropyl)-1H-imidazol-2-yl)-3-hydroxypiperidine-1-carboxylate (133B) as a yellow oil (160 mg, 21% yield). ESI-MS:m/z 396.5 (M+H)$^+$.

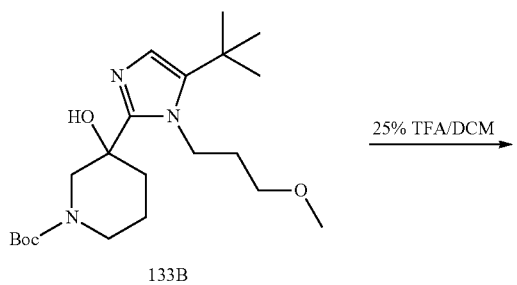

133B

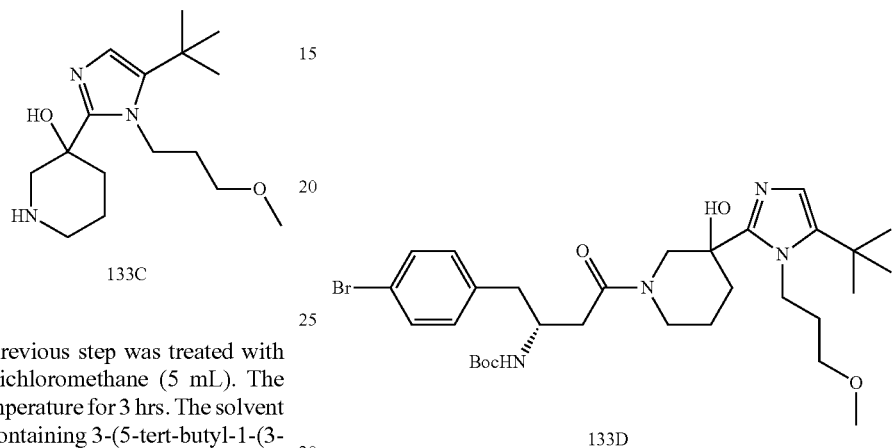

133C

The residue 133 from the previous step was treated with 25% trifluoroacetic acid in dichloromethane (5 mL). The mixture was stirred at room temperature for 3 hrs. The solvent was removed and the residue containing 3-(5-tert-butyl-1-(3-methoxypropyl)-1H-imidazol-2-yl)piperidin-3-ol (133C) was purified by preparatory LC/MS (10-45% $CH_3CN$ in $H_2O$). ESI-MS:m/z 296.2 $(M+H)^+$.

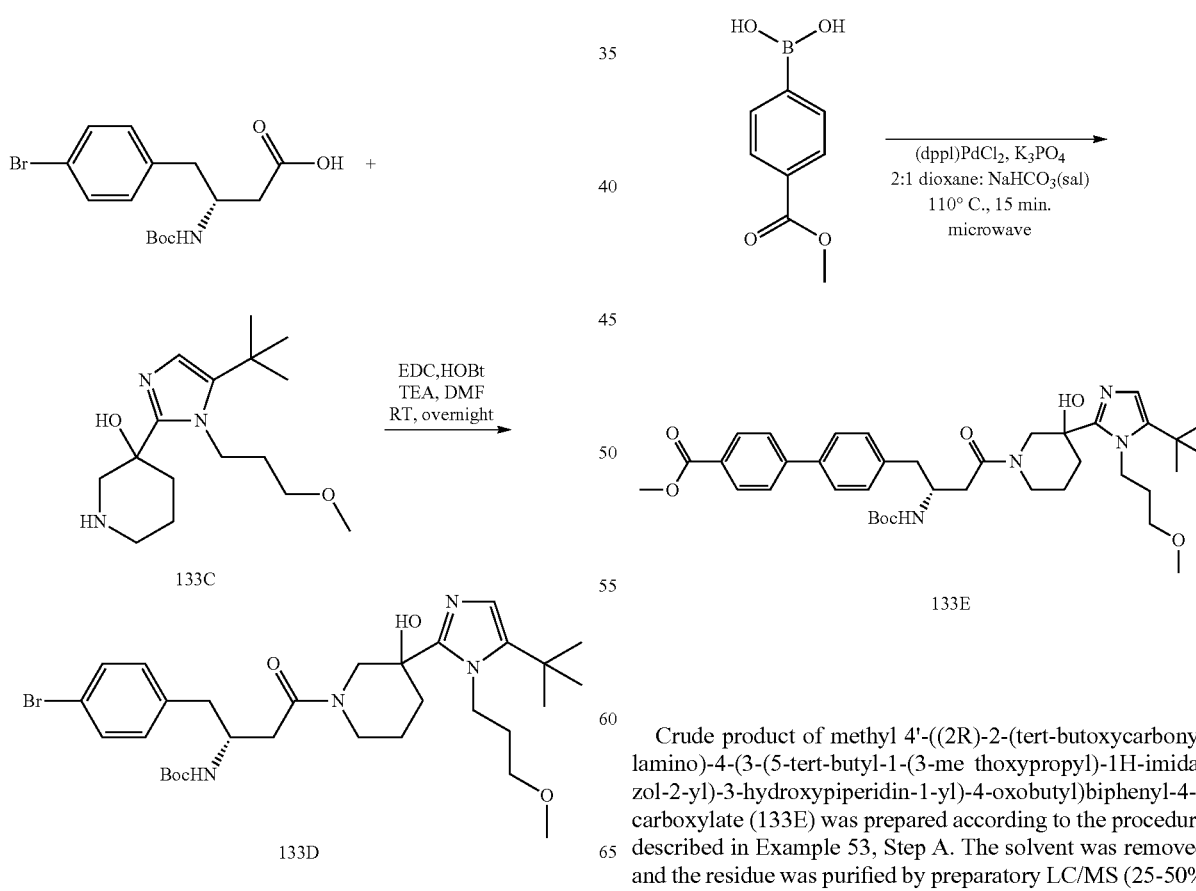

133D (R)-4-(4-bromophenyl)-3-(tert-butoxycarbonylamino)butanoic acid (45 mg, 81 gmol), EDC (24 mg, 125 μmol), HOBt (17 mg, 125 μmol) and 3-(5-tert-butyl-1-(3-methoxypropyl)-1H-imidazol-2-yl)piperidin-3-ol TFA salt (133C) (34 mg, 83 μmol) were added to a 10 mL round bottomed flask. DMF (420 μL) was added and the reaction was stirred overnight at room temperature. The solvent was removed and the residue was purified by preparatory LC/MS (35-50% $CH_3CN$ in $H_2O$) to give the product tert-butyl (2R)-1-(4-bromophenyl)-4-(3-(5-tert-butyl-1-(3-methoxypropyl)-1H-imidazol-2-yl)-3-hydroxypiperidin-1-yl)-4-oxobutan-2-ylcarbamate (133D) (29 mg, 55% yield). ESI-MS:m/z 635.4 $(M+H)^+$.

Crude product of methyl 4'-((2R)-2-(tert-butoxycarbonylamino)-4-(3-(5-tert-butyl-1-(3-me thoxypropyl)-1H-imidazol-2-yl)-3-hydroxypiperidin-1-yl)-4-oxobutyl)biphenyl-4-carboxylate (133E) was prepared according to the procedure described in Example 53, Step A. The solvent was removed and the residue was purified by preparatory LC/MS (25-50% $CH_3CN$ in $H_2O$). ESI-MS:m/z 691.6 $(M+H)^+$.

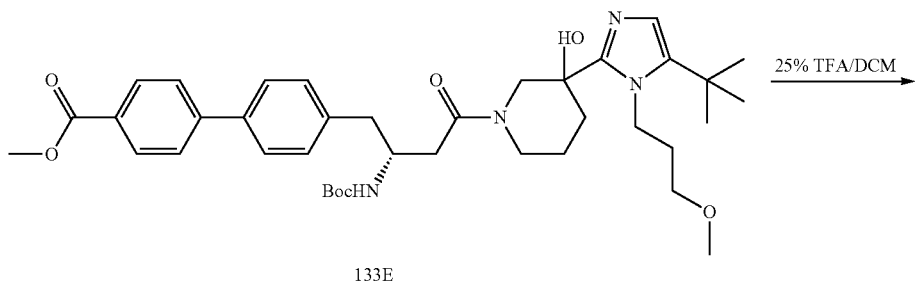

133E

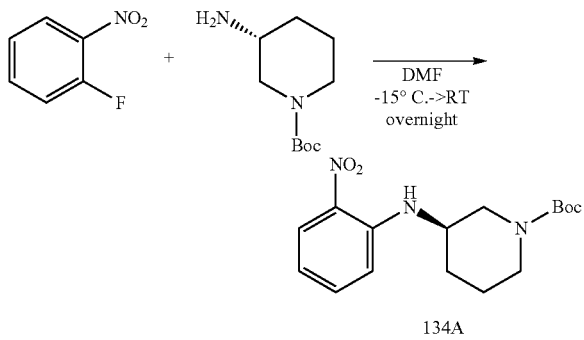

242

Product 133E from the previous step was treated with 25% trifluoroacetic acid in dichloromethane (5 mL). The mixture was stirred at room temperature for 3 hrs. The solvent was removed and the residue was purified by preparatory LC/MS (20-40% $CH_3CN$ in $H_2O$) to give the product methyl 4'-((2R)-2-amino-4-(3-(5-tert-butyl-1-(3-methoxypropyl)-1H-imidazol-2-yl)-3-hydroxypiperidin-1-yl)-4-oxobutyl)biphenyl-4-carboxylate (242) (19 mg, 59% yield over two steps). 1H NMR (400 MHz, DMSO-$d_6$) δ ppm 1.38 (m, 9H) 1.51-2.24 (m, 6H) 2.58-3.55 (m, 12H) 3.66-4.01 (m, 5H) 4.43 (br. s., 3H) 7.37-7.45 (m, 2H) 7.74 (m, 2H) 7.84 (m, 2H) 8.02-8.07 (m, 2H). ESI-MS:m/z 591.5 $(M+H)^+$.

Example 134

Synthesis of (R)-3-amino-1-((R)-3-(2-(3-methoxypropyl)-1H-benzo[d]imidazol-1-yl)piperidin-1-yl)-4-(naphthalen-2-yl)butan-1-one (243)

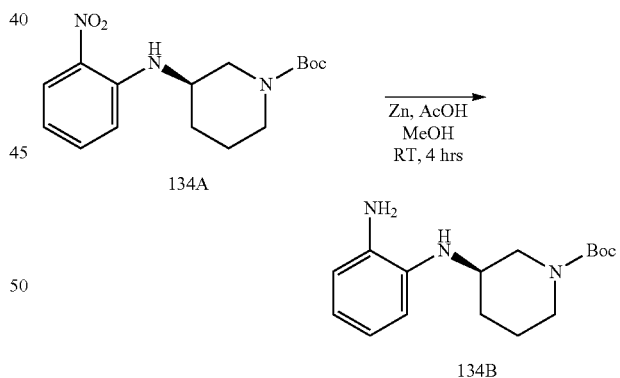

134A

Into a 25 mL round bottomed flask was added 1-fluoro-2-nitrobenzene (638 mg, 4.5 mmol) and N,N-dimethylformamide (9 mL). The flask was cooled to −15° C. and (R)-tert-butyl 3-aminopiperidine-1-carboxylate (950 mg, 4.7 mmol) in N,N-dimethylformamide (3 mL) was slowly added. The reaction was allowed to warm to room temperature overnight. Solvent was removed under vacuum and the residue was purified by column chromatography (15% ethylacetate:hexanes) to give (R)-cert-butyl 3-(2-nitrophenylamino)piperidine-1-carboxylate (134A) as a yellow oil (808 mg, 56% yield). ESI-MS:m/z 344.4 $(M+Na)^+$.

Into a 100 mL round bottomed flask was added 1334A and methanol (46 mL). Zinc metal (2.28 g, 34.9 mmol) and acetic acid (1.7 mL) was added and the mixture was stirred at room temperature for 5 hr. The mixture was filtered through a fritted Buchner funnel and the solvent was removed under vacuum. Ethyl acetate (100 mL) was added and the precipitate was filtered through a Buchner funnel with a pad of Celite. The filtrate was concentrated under vacuum to leave red oil (R)-tert-butyl 3-(2-aminophenylamino)piperidine-1-carboxylate (134B) which was used without further purification. ESI-MS: m/z 292.4 $(M+H)^+$.

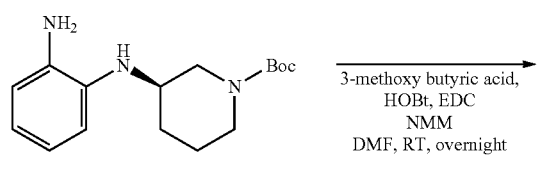

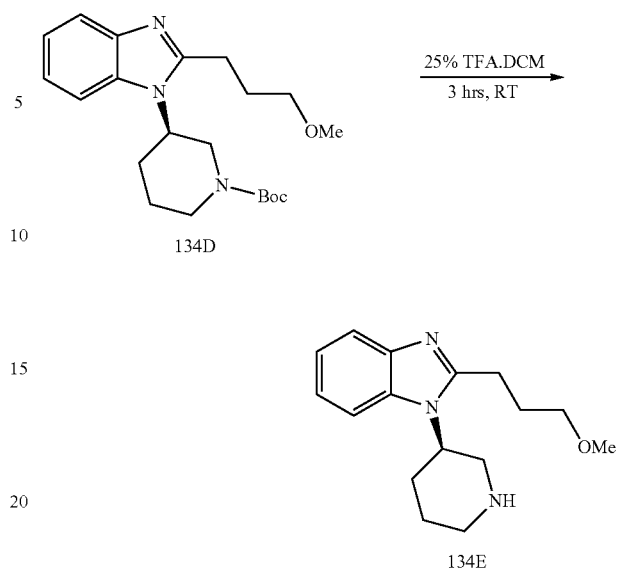

The residue 134B was dissolved in N,N-dimethylforamide (6.9 mL). HOBt (139 mg, 1.03 mmol), EDC (197 mg, 1.03 mmol), N-methylmorpholine (208 mg, 2.06 mmol) and 3-methoxybutyric acid (122 mg, 1.03 mmol) were added and stirred overnight at room temperature. The solvent was removed under vacuum and the residue was partitioned between water (10 mL) and ethyl acetate (10 mL). The organic layer was discarded, and the aqueous layer was extracted with ethyl acetate (2×10 mL). The organics were combined and washed with 1N NaOH (25 mL), dried over sodium sulfate and filtered. The solvent was removed under vacuum and the residue containing (R)-tert-butyl 3-(2-(4-methoxybutanamido)phenylamino)piperidine-1-carboxylate (134C) was taken into the next step without further purification. ESI-MS:m/z 392.5 (M+H)$^+$.

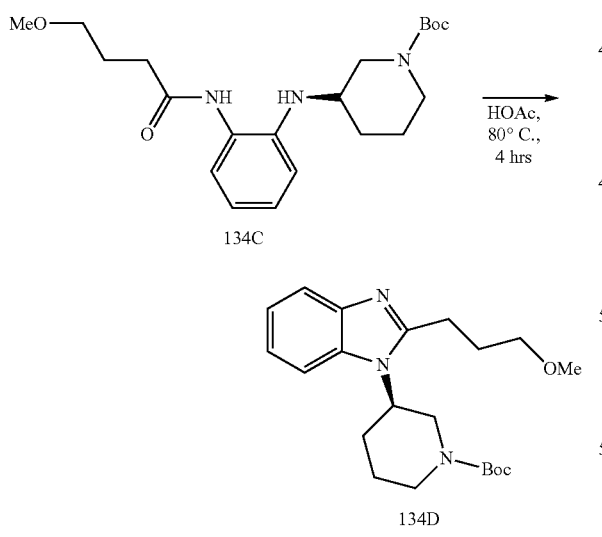

The residue 134C was dissolved with acetic acid (15 mL) and heated to 100° C. for 4 hr. Solvent was removed under vacuum. The residue containing (R)-tert-butyl 3-(2-(3-methoxypropyl)-1H-benzo[d]imidazol-1-yl)piperidine-1-carboxylate (134D) was used in the next step with out further purification. ESI-MS:m/z 374.4 (M+H)$^+$.

134D was dissolved in 25% trifluoroacetic acid and stirred at room temperature for 3 hr. Solvent was removed under vacuum and the residue containing (R)-2-(3-methoxypropyl)-1-(piperidin-3-yl)-1H-benzo[d]imidazole (134E) was used in the next step without further purification. ESI-MS: m/z 274.4 (M+H)$^+$.

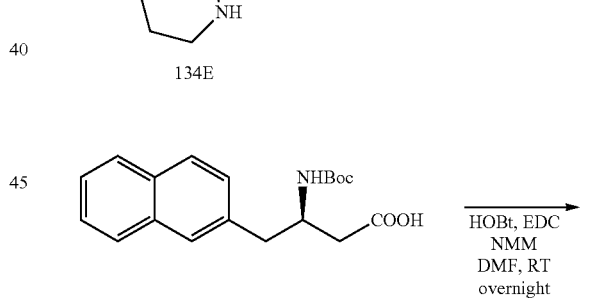

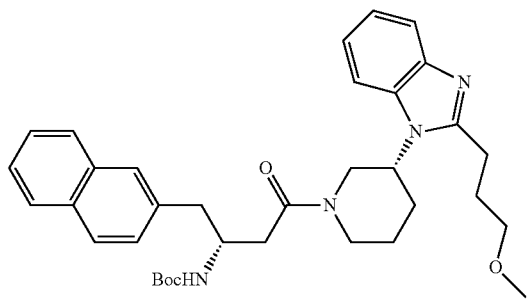

The residue 133E was dissolved in N,N-dimethylforamide (6.9 mL). HOBt (111 mg, 823 µmol), EDC (158 mg, 823

μmol), N-methylmorpholine (278 mg, 2.74 mmol) and (R)-3-(tert-butoxycarbonylamino)-4-(naphthalen-2-yl)butanoic acid (271 mg, 823 μmol) were added and stirred overnight at room temperature. The solvent was removed under vacuum and the residue was partitioned between water (10 mL) and ethyl acetate (10 mL). The organic layer was discarded and the aqueous layer was extracted with ethyl acetate (2×10 mL). The organics were combined, washed with 1N NaOH (25 mL), dried over sodium sulfate, and filtered. Solvent was removed under vacuum and the residue containing tert-butyl (R)-4-((R)-3-(2-(3-methoxypropyl)-1H-benzo[d]imidazol-1-yl)piperidin-1-yl)-1-(naphthalen-2-yl)-4-oxobutan-2-ylcarbamate 134F was taken into the next step without further purification. ESI-MS:m/z 585.5 (M+H)$^+$.

2H) 7.50 (m, 5H) 7.72-7.96 (m, 5H) 8.21 (m, 1H). ESI-MS: m/z 485.5 (M+H)$^+$.

Example 135

Synthesis of (R)-3-amino-1-((S)-3-(2-methyl-1H-benzo[d]imidazol-1-yl)piperidin-1-yl)-4-(naphthalen-2-yl)butan-1-one (244) and (R)-3-amino-1((R)-3-(2-methyl-1H-benzo[d]imidazol-1-yl)piperidin-1-yl)-4-(naphthalen-2-yl)butan-1-one (245)

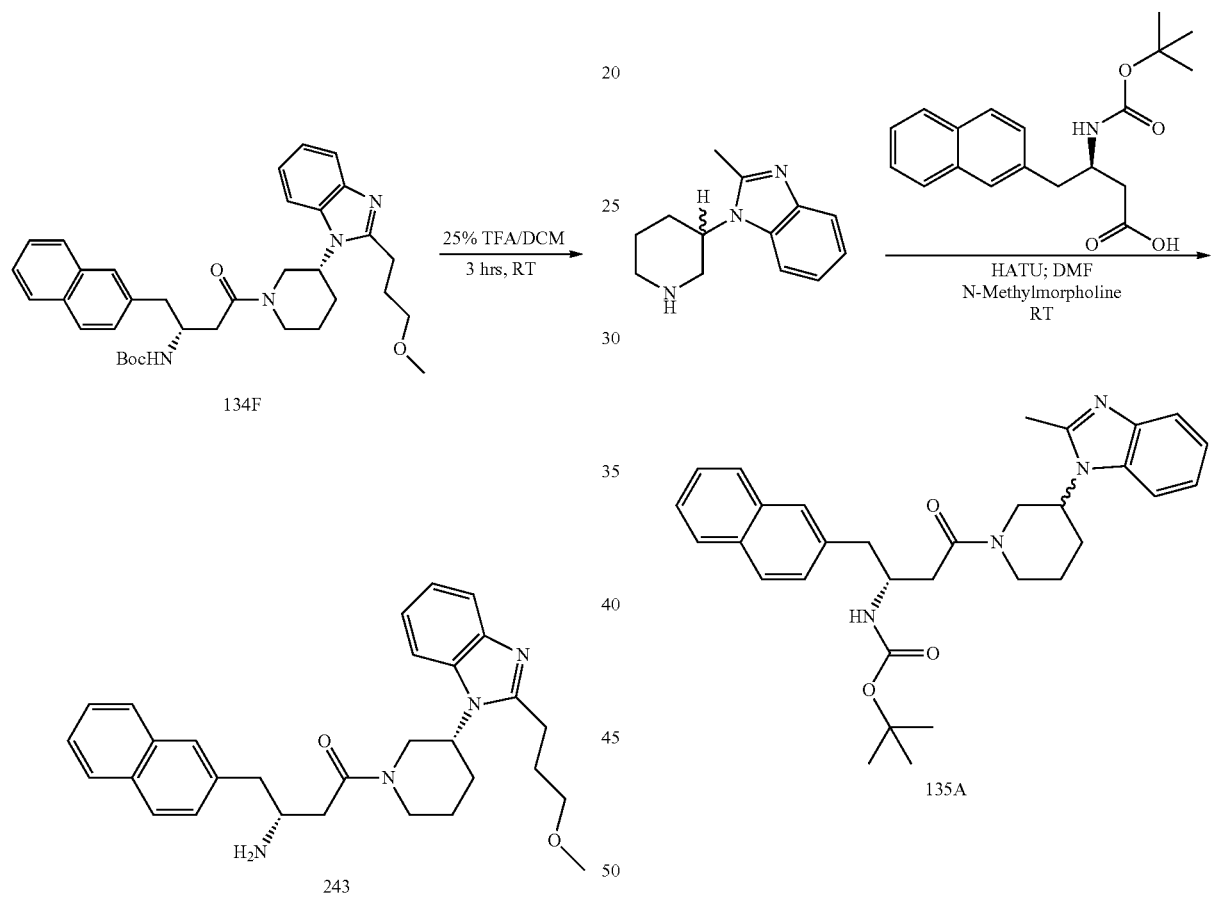

134F was dissolved in 25% trifluoroacetic acid and stirred at room temperature for 3 hr. Solvent was removed under vacuum and purified by preparatory LC/MS (20-25% CH$_3$CN in H$_2$O) to give (R)-3-amino-1((R)-3-(2-(3-methoxypropyl)-1H-benzo[d]imidazol-1-yl)piperidin-1-yl)-4-(naphthalen-2-yl)butan-1-one (243) as a TFA salt (97 mg, 24%). 1H NMR (400 MHz, DMSO-d$_6$) δ ppm 1.62 (m, 1H) 1.86 (br. s., 1H) 1.97-2.15 (m, 3H) 2.53-2.91 (m, 3H) 2.94-3.26 (m, 7H) 3.40 (m, 3H) 3.75-4.10 (m, 3H) 4.42-4.71 (m, (2-methyl-1-(piperidin-3-yl)-1H-benzo[d]imidazole (0.486 mmoles, 0.160 g) was added to a 10 mL round-bottomed flask equipped for stirring under nitrogen. DMF (4 mL), (R)-3-(tert-butoxycarbonylamino)-4-(naphthalen-2-yl)butanoic acid (0.486 mmoles, 0.140 g) and N-methylmorpholine (1.94 mmoles, 0.214 mL) were then added and the solution was allowed to stir at rt for 5 min. HATU (0.534 mmoles, 0.204 g) was added and the resultant solution was stirred at room temperature for 3 hr. The reaction solution was then directly purified by preparative LC/MS (35-95% CH3CN in H2O). The resultant fractions were collected and the solvent was removed in-vacuo affording (R)-tert-butyl 4-(3-(2-methyl-1H-benzo[d]imidazol-1-yl)piperidin-1-yl)-1-(naphthalen-2-yl)-4-oxobutan-2-ylcarbamate (1354) as a clear oil. ESI-MS: raiz 527.5 (M+H)$^+$.

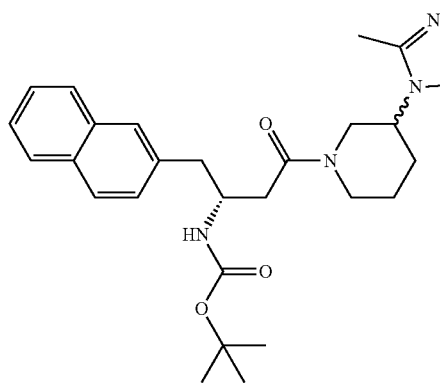

135A

1. TFA/CH$_2$Cl$_2$
2. Chiral SFC Chromatography

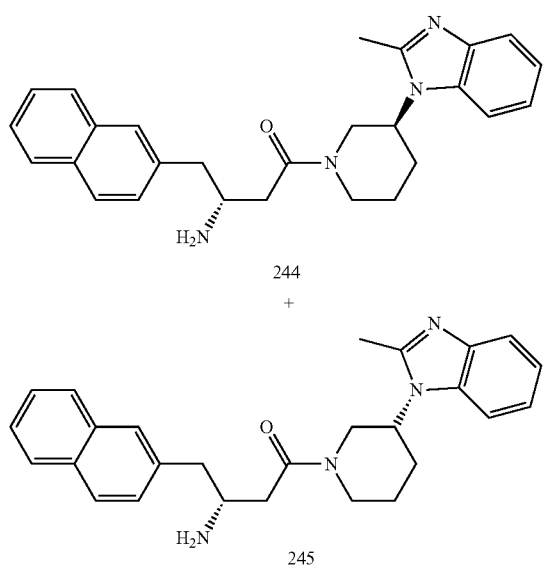

244

+

245

135A (0.486 mmoles max, crude oil) was added to a 10 mL round-bottomed flask equipped for stirring under nitrogen and dissolved in CH$_2$Cl$_2$ (2 mL). Trifluoroacetic acid (2 mL) was then added and the solution was stirred at room temperature for 2 hr. The solvent was removed in-vacuo affording a clear colored oil which was further separated by Berger PrepSFC Conditions: column: ChiralPak AD-H (5 μm, 21.2× 250 mm), mobile phase: A: liquid CO$_2$, B: 10 mM NH$_4$OAc in IPOH, flow rate: 50 mL/min, gradient: 30% B, run time: 35 min (stack-injection method applied), prep injection volume: 400 μL, yielding the separated enantiomers:

Eutomer: (R)-3-amino-1-((S)-3-(2-methyl-1H-benzo[d]imidazol-1-yl)piperidin-1-yl)-4-(naphthalen-2-yl)butan-1-one (244) (0.077 mmoles, 0.033 g). ESI-MS: m/z 427.4 (M+H)$^+$.

Distomer: (R)-3-amino-1-((R)-3-(2-methyl-1H-benzo[d]imidazol-1-yl)piperidin-1-yl)-4-(naphthalen-2-yl)butan-1-one (245) (0.061 mmoles, 0.026 g). ESI-MS: m/z 427.4 (M+H)$^+$.

Example 136

Synthesis of (3R)-3-amino-1-(3-(1-(3-methoxypropyl)-1H-benzo[d]imidazol-2-yl)-5-methylpiperidin-1-yl)-4-(nanhthalen-2-yl)butan-1-one (246)

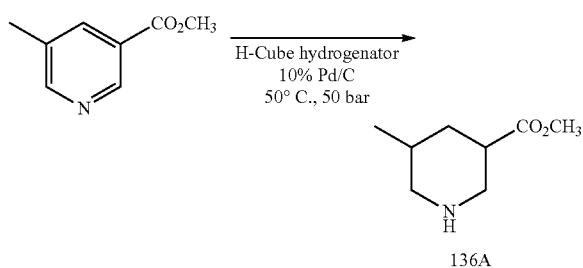

136A

Into a 100 mL round bottomed flask was added methyl-5-methylnicotinate (1.00 g, 6.6 mmol) and methanol (66 mL). The sample was hydrogenated using an H-Cube hydrogenator at 50° C. and 60 bar of hydrogen pressure. Solvent was removed under vacuum and the residue containing methyl 5-methylpiperidine-3-carboxylate (136A) was used in the next step without further purification. ESI-MS:m/z 158.4 (M+H)⁺.

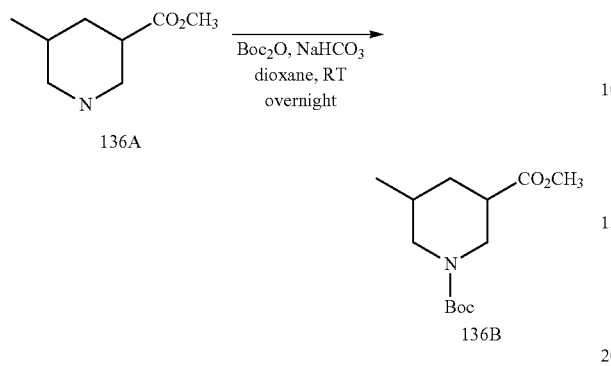

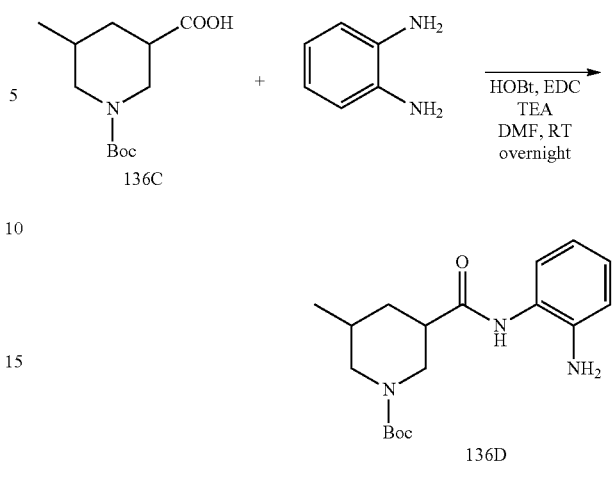

136A was dissolved in dioxane (15 mL). Di-tert-butyl dicarbonate (2.16 g, 9.9 mmol) and sodium bicarbonate (1.11 g, 13.2 mmol) was added and the mixture was stirred at room temperature overnight. Solvent was removed under vacuum and the residue was partitioned between water (50 mL) and ethyl acetate (50 mL). The mixture was transferred to a separatory funnel. The organic layer was separated and the aqueous was extracted with ethyl acetate (2×50 mL). The organics were combined and washed with brine (50 mL). The organics were dried over sodium sulfate and filtered. Solvent was removed under vacuum to leave a clear oil of 1-tert-butyl 3-methyl 5-methylpiperidine-1,3-dicarboxylate (136B) which was used in the next step without further purification. ESI-MS:m/z 280.4 (M+Na)⁺.

Enzene-1,2-diamine (928 mg, 8.58 mmol) was dissolved in N,N-dimethylforamide (6.6 mL). HOBt (1.16 g, 8.58 mmol), EDC (1.64 g, 8.58 mmol), and 1-(tert-butoxycarbonyl)-5-methylpiperidine-3-carboxylic acid (136C) (1.61 g, 6.6 mmol) were added and stirred overnight at room temperature. The solvent was removed under vacuum and the residue was partitioned between water (25 mL) and ethyl acetate (25 mL). The organic layer was separated and the aqueous solution was extracted with ethyl acetate (2×25 mL). The organics were combined and washed with 1N NaOH (25 mL). The organics were dried over sodium sulfate and filtered. Solvent was removed under vacuum and the residue containing tert-butyl 3-(2-aminophenylcarbamoyl)-5-methylpiperidine-1-carboxylate (136D) was taken into the next step without further purification. ESI-MS:m/z 334.4 (M+H)⁺.

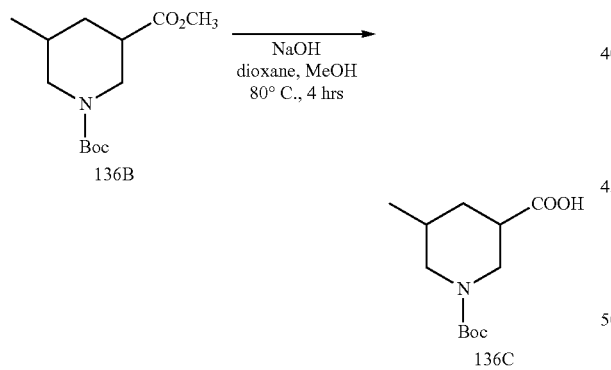

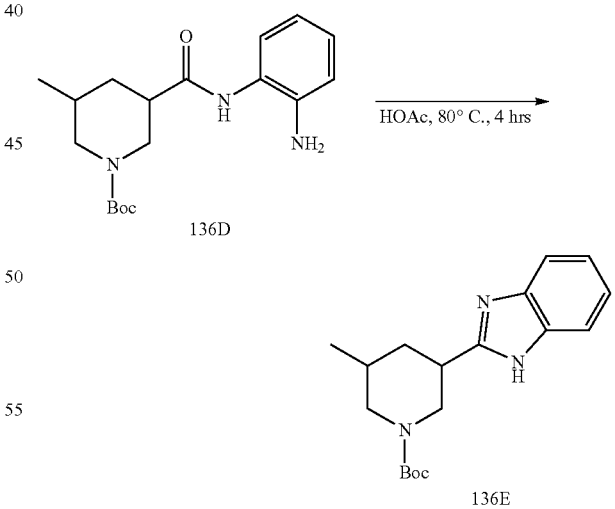

136B was dissolved with dioxane (14 mL) and methanol (7 mL). Sodium hydroxide (1.32 g, 33 mmol) in water (2 mL) was added and the mixture was heated to 80° C. for 5 hrs. Solvent was removed under vacuum and the residue was partitioned between 2N HCl (50 mL) and ethyl acetate (50 mL). The mixture was transferred to a separatory funnel and the organics were separated. The aqueous layer was extracted with ethyl acetate (2×25 mL), and the organics were combined and dried over sodium sulfate and filtered. Solvent was removed under vacuum to leave 1-(tert-butoxycarbonyl)-5-methylpiperidine-3-carboxylic acid (136C) as a white solid which was used without further purification. ESI-MS:m/z 266.4 (M+H)⁺.

The residue (136D) was dissolved with acetic acid (15 mL) and heated to 80° C. for 4 hr. Solvent was removed under vacuum. The residue containing tert-butyl 3-(1H-benzo[d]imidazol-2-yl)-5-methylpiperidine-1-carboxylate (135E) was used in the next step with out further purification. ESI-MS:m/z 316.4 (M+H)⁺.

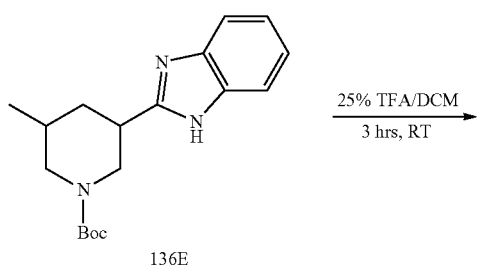

136E

Into a 10 mL round bottomed 136E and 25% trifluoroacetic acid in dichloromethane (5 mL) was added, and the mixture was stirred at room temperature for 3 hr. The solvent was removed under vacuum. The residue containing 2-(5-methylpiperidin-3-yl)-1H-benzo[d]imidazole (136F) was used in the next step without purification. ESI-MS:mh 216.4 (M+H)$^+$.

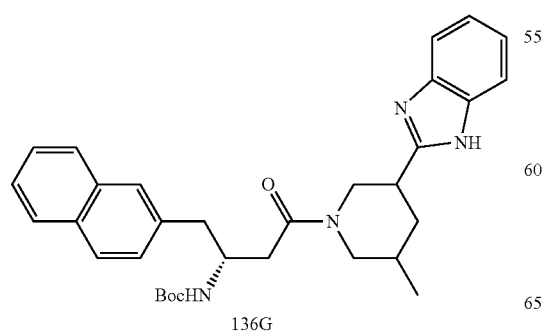

136F (137 mg, 634 μmol) was dissolved with 2:1 acetonitrile:dichloromethane (3.2 mL). (R)-3-(tert-butoxycarbonylamino)-4-(naphthalen-2-yl)butanoic acid (230 mg, 697 μmol) in 2:1 acetonitrile:dichloromethane (3.5 mL) was added. HOBt (94 mg, 697 umol) in DMF (3.5 mL) was added. Into a fritted syringe was added PS-carbodiimide resin (1.31 mmol/g, 968 mg). The amine, acid and HOBt solutions were taken up in the syringe and capped. The mixture was shaken overnight at room temperature. The solution was expelled into a round bottomed flask and the solvent was removed under vacuum. The residue containing tert-butyl (2R)-4-(3-(1H-benzo[d]imidazol-2-yl)-5-methylpiperidin-1-yl)-1-(naphthalen-2-yl)-4-oxobutan-2-ylcarbamate (136G) was taken into the next step without further purification. ESI-MS: m/z 527.4 (M+H)$^+$.

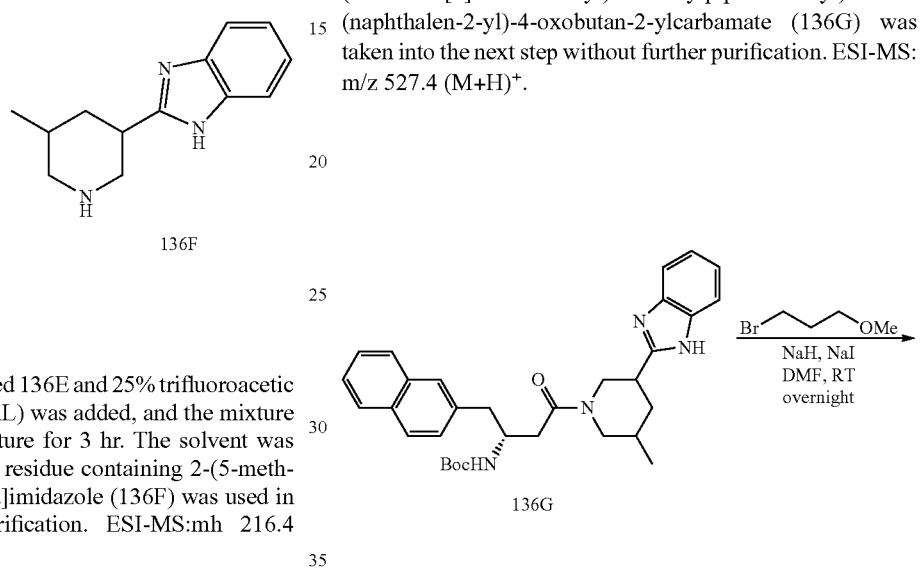

Into a 10 mL round bottomed flask was added 136G (158 mg, 298 μmol) and N,N-dimethylforamide (1.5 mL). NaI (67 mg, 447 μmol) and NaH (18 mg, 447 μmol, 60% disp.) were added in sequence. The mixture was stirred for 30 minutes at room temperature. 3-methoxy propyl bromide (68 mg, 447 μmol) was added at once and stirred overnight at room temperature. Solvent was removed under vacuum and the residue containing tert-butyl (2R)-4-(3-(1-(3-methoxypropyl)-1H-benzo[d]imidazol-2-yl)-5-methylpiperidin-1-yl)-1-(naphthalen-2-yl)-4-oxobutan-2-ylcarbamate (136H) was taken into the next step without further purification. ESI-MS:m/z 599.6 (M+H)$^+$.

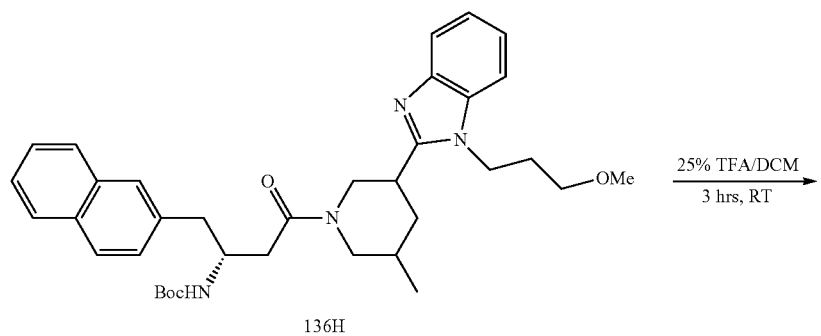

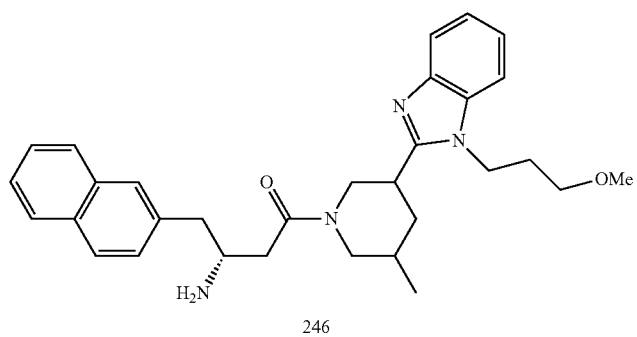

The residue 136H was dissolved in 25% trifluoroacetic acid and stirred at room temperature for 3 hr. Solvent was removed under vacuum and purified by preparatory LC/MS (25-35% $CH_3CN$ in $H_2O$) to give (3R)-3-amino-1-(3-(1-(3-methoxypropyl)-1H-benzo[d]imidazol-2-yl)-5-methylpiperidin-1-yl)-4-(naphthalen-2-yl)butan-1-one (246) as a TFA salt (13 mg, 9%). ESI-MS:m/z 499.5 $(M+H)^+$.

Example 137

Synthesis of (R)-3-amino-4-(4-chlorophenyl)-1-((S)-3-hydroxy-3-(1-(3-methoxypropyl)-1H-benzo[d]imidazol-2-yl)piperidin-1-yl)butan-1-one (247) and (R)-3-amino-4-(4-chlorophenyl)-1((R)-3-hydroxy-3-(1-(3-methoxypropyl)-1H-benzo[d]imidazol-2-yl)piperidin-1-yl)butan-1-one (248)

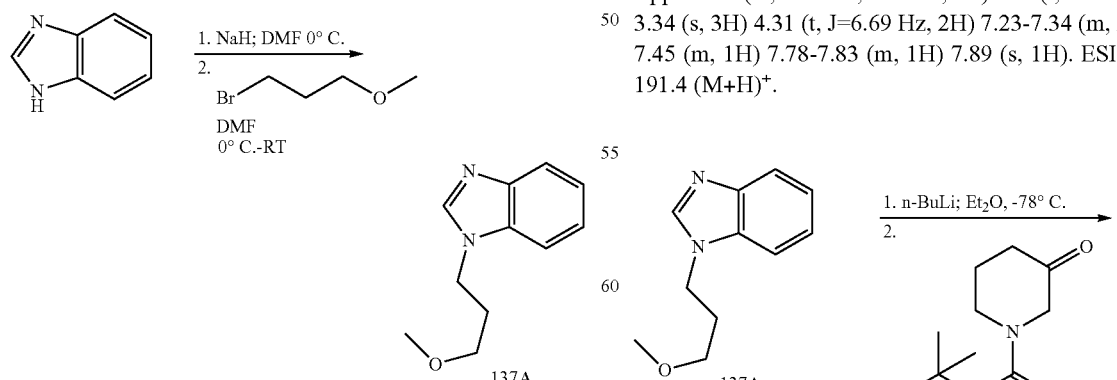

1H-benzo[d]imidazole (12.7 mmoles, 1.5 g) was added to an oven dried 200 mL round-bottomed flask equipped for stirring under nitrogen. DMF (20 mL) was added and the solution was cooled to 0° C. with an ice bath. To this cooled solution was added NaH (60% in mineral oil, 13.3 mmoles, 533 mg) in two portions. The resultant solution was allowed to stir at 0° C. for 30 minutes under nitrogen. 1-bromo-3-methoxypropane (14.0 mmoles, 2.14 g) was added and the solution was allowed to warm to room temperature and stirred for 1 hr. The reaction solution was then poured into ice-water, extracted with ethyl acetate, and washed once with saturated aqueous sodium chloride. The organic layer was collected and subsequently dried with anhydrous $Na_2SO_4$ and filtered. This filtrate was collected, concentrated, and dried in-vacuo. This material was then purified by chromatography on silica gel (5-15% $CH_3OH/CH_2Cl_2$) to afford 1-(3-methoxypropyl)-1H-benzo[d]imidazole (137A) as a clear oil (9.62 mmoles, 1.83 g, 76% yield). 1H NMR (400 MHz, CHLOROFORM-d) δ ppm 2.10 (dt, J=12.57, 6.22 Hz, 2H) 3.29 (t, J=5.68 Hz, 2H) 3.34 (s, 3H) 4.31 (t, J=6.69 Hz, 2H) 7.23-7.34 (m, 2H) 7.37-7.45 (m, 1H) 7.78-7.83 (m, 1H) 7.89 (s, 1H). ESI-MS: m/z 191.4 $(M+H)^+$.

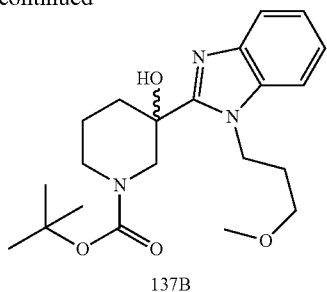

137B 1-(3-methoxypropyl)-1H-benzo[d]imidazole (137A) (9.62 mmoles; 1.83 g) was added to an oven dried 250 mL round-bottomed flask equipped with an addition funnel and for stirring under nitrogen. Et$_2$O (75 mL) was added and the solution was cooled to −78° C. with an acetone/CO$_2$(s) bath. N-BuLi (2.5M in hexanes, 10.1 mmoles, 4.0 mL) was added drop-wise via syringe and the resultant solution was allowed to stir at −78° C. for 45 minutes. Tert-butyl 3-oxopiperidine-1-carboxylate (10.1 mmoles, 2.01 g) in END (25 mL) was then added drop-wise to the reaction solution at −78° C. via addition funnel and allowed to stir for 1 hr. The reaction solution was then allowed to warm to rt and stir for ihr. The reaction solution was then poured into ice-water, extracted with ethyl acetate, and washed once with saturated aqueous sodium chloride. The organic layer was collected and subsequently dried with anhydrous Na.2SO$_4$ and filtered. The filtrate was collected, concentrated, and dried in-vacuo. The residue was then partially purified by chromatography on silica gel (5-15% CH$_3$OH/CH$_2$Cl$_2$) to afford tert-butyl 3-hydroxy-3-(1-(3-methoxypropyl)-1H-benzo[d]imidazol-2-yl)piperidine-1-carboxylate (137E) as a mixture of products that was carried onto the next step without further purification. ESI-MS: m/z 390.4 (M+H)$^+$.

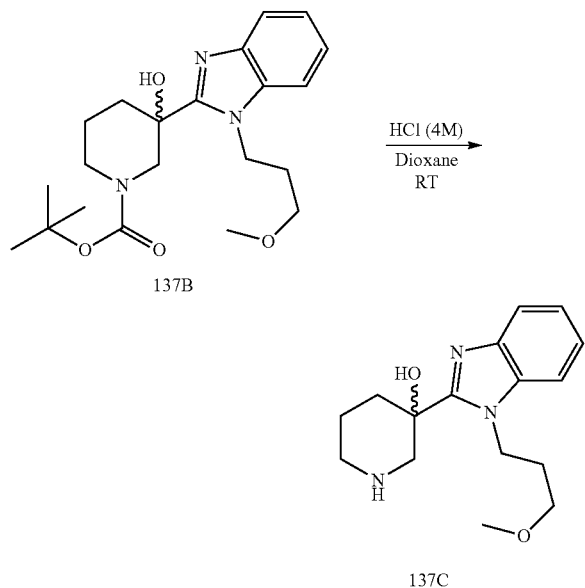

137B (9.62 mmoles, mixture from previous step) was added to a 25 mL round-bottomed flask equipped for stirring under nitrogen. HCl (4 M in dioxane, 10 mL) was then added and the solution was stirred at room temperature for 1 hr. The resultant solution was then extracted with Et(Mc and a 10% aqueous K$_2$CO$_3$ solution. The organic layer was collected and dried with Na$_2$SO$_4$. This was then filtered, concentrated, and dried in-vacuo affording as an approximate 1/1 mixture of 3-(1-(3-methoxypropyl)-1H-benzo[d]imidazol-2-yl)piperidin-3-ol (137C) and 1-(3-methoxypropyl)-1H-benzo[d]imidazole that was used without further purification. ESI-MS: m/z 290.4 (M+H)$^+$.

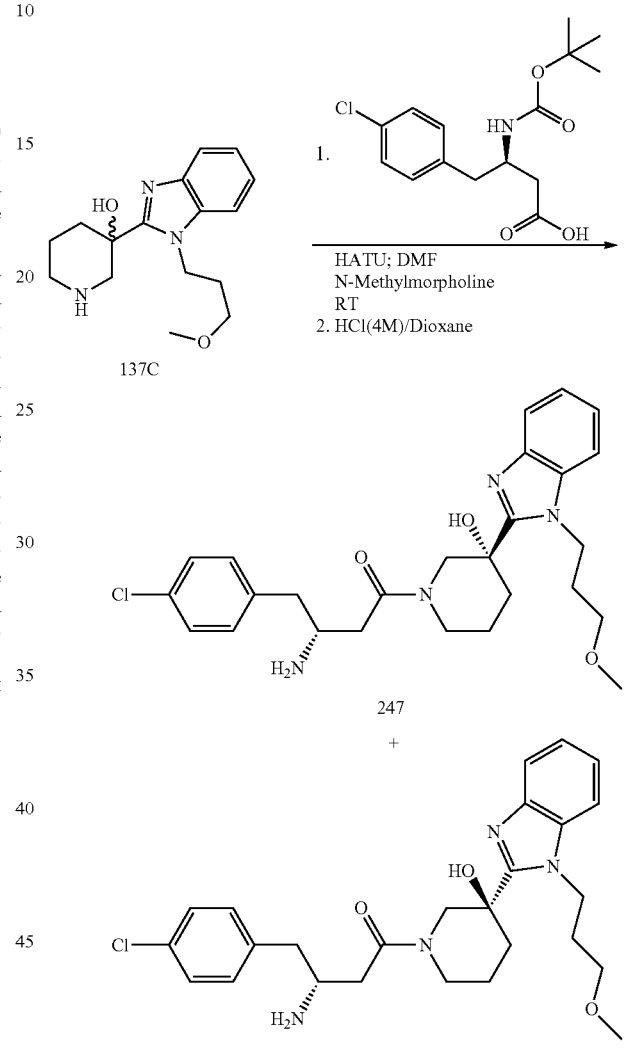

The mixture containing (3-(1-(3-methoxypropyl)-1H-benzo[d]imidazol-2-yl)piperidin-3-ol (137C) (0.200 g of mixture) was weighed into a 20 mL vial. DMF (5 mL), (R)-3-(tert-butoxycarbonylamino)-4-(4-chlorophenyl)butanoic acid (0.381 mmoles, 0.120 g) and N-methylmorpholine (1.038 mmoles, 0.114 mL) were then added and the solution was allowed to stir at it for 5 min. HATU (0.415 mmoles, 0.158 g) was added and the resultant solution was stirred at room temperature for 3 hr. The reaction solution was then directly purified by preparative LC/MS. ESI-MS: m/z 585.4 (M+H)$^+$. The resultant fractions were collected and the solvent was removed in-vacuo affording a clear oil. HCl (4 M in dioxane, 4 mL) was added and the solution was allowed to stir at room temperature for 3 hr. The solvent was removed in vacuo affording a mixture of the title diastereomers 247 and 248 as their HCl salts (0.324 mmoles, 169 mg, 94% yield).

These diastereomers were then separated by Berger PrepSFC Chromatography according to the following conditions: column: ChiralPak AD-H (5 μm, 10×250 mm), mobile phase: A: liquid $CO_2$ B: 10 mM NH4OAc in EtOH; flow rate: 15 mL/min, gradient: 25% B, run time: 15 min., prep injection volume: 500 μL, total injections: 11, QC-anal injection volume: 500 μL affording the separated enantiomers.

Distomer: (R)-3-amino-4-(4-chlorophenyl)-14(8)-3-hydroxy-3-(1-(3-methoxypropyl)-1H-benzo[d]imidazol-2-yl)piperidin-1-yl)butan-1-one (247) (61 mg, 34%). 1H NMR (400 MHz, DMSO-$d_6$) δ ppm 1.96-2.21 (m, 5H) 2.29-2.45 (m, 1H) 2.52-2.77 (m, 4H) 3.07-3.49 (m, 7H) 3.66-4.04 (m, 3H) 4.30-4.60 (m, 3H) 7.10-7.38 (m, 6H) 7.46-7.63 (m, 2H). ESI-MS: m/z 485.3 (M+H)$^+$.

Eutomer: (R)-3-amino-4-(4-chlorophenyl)-1-((R)-3-hydroxy-3-(1-(3-methoxypropyl)-1H-benzo[d]imidazol-2-yl)piperidin-1-yl)butan-1-one (247) (66.6 mg, 37%). 1H NMR (400 MHz, DMSO-$d_6$) δ ppm 1.91-2.43 (m, 5H) 2.52-2.79 (m, 4H) 3.11-3.31 (m, 6H) 3.36-3.48 (m, 2H) 3.67-4.08 (m, 2H) 4.23-4.58 (m, 4H) 7.12-7.28 (m, 4H) 7.29-7.37 (m, 2H) 7.46-7.60 (m, 2H) ESI-MS: m/z 485.3 (M+H)$^+$.

Example 138

General Procedure for the Synthesis of N-Substituted Derivatives of (S)-3,4-diamino-1((R)-3-(1-(3-methoxypropyl)-1H-benzo[d]imidazol-2-yl)piperidin-1-yl)butan-1-one (138F and 138G)

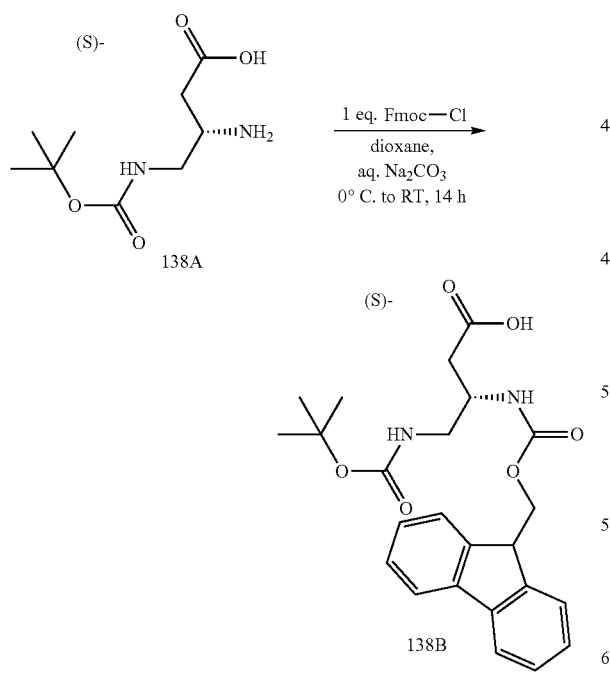

The amine group of (S)-3-amino-4-(tert-butoxycarbonylamino)hutanoic acid (138A) was protected with an Fmoc group according to standard Schotten-Baumen procedure yielding (S)-3-(((9H-fluoren-9-yl)methoxy)carbonylamino)-4-(tert-butoxycarbonylamino)butanoic acid (138B).

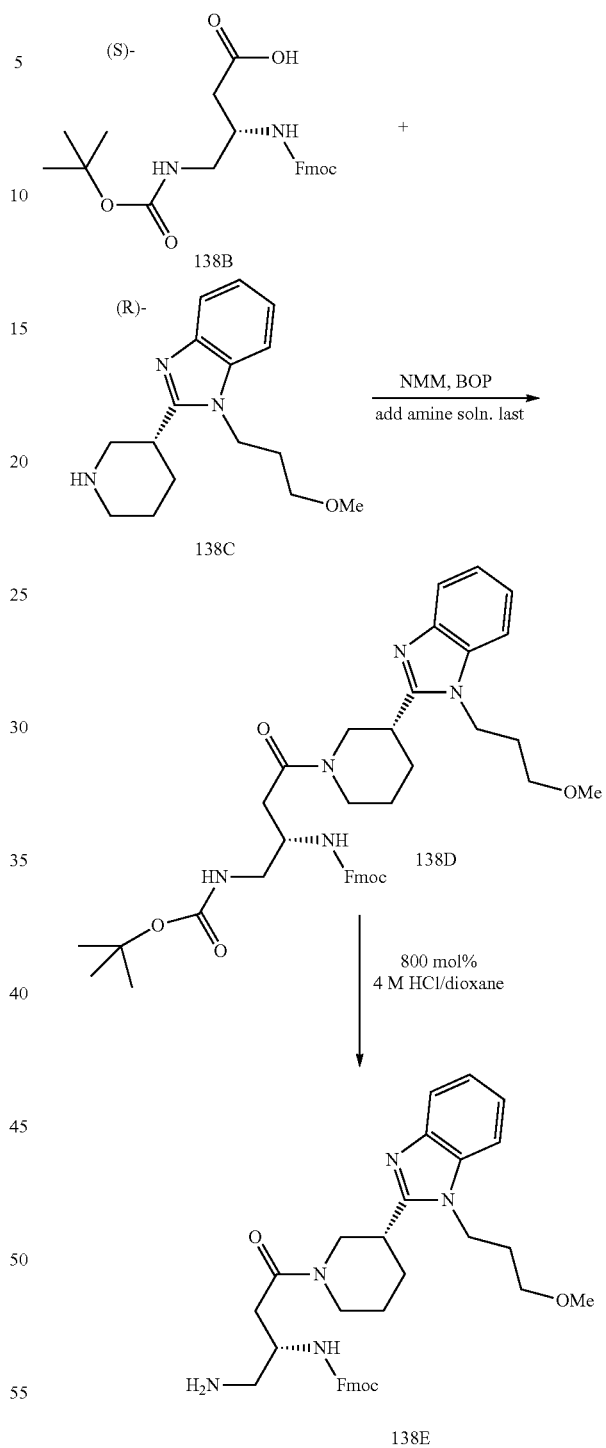

Piperidine (R)-1-(3-methoxypropyl)-2-(piperidin-3-yl)-1H-benzo[d]imidazole (138C) (3.19 g, 11.3 mmol) was acylated with the protected butanoic acid 138B (5 g, 11.4 mmol) in N-methylmorpholine using the standard BOP coupling reaction similar to HATU procedure of Example 7, Step E yielding tert-butyl (S)-2-(9H-fluoren-9-ylamino)-4-((R)-3-(1-(3-methoxypropyl)-1H-benzo[d]imidazol-2-yl)piperidin-1-yl)-4-oxobutylcarbamate (1380) (7.9 g, 11.4 mmol). ESI-MS: m/z 696.6 (MH$^+$).

Removal of the Bac group was accomplished by standard procedures (dioxane, 4 M Ha/dioxane, 20° C., 20 min; evapn.) yielding (S)-3-(9H-fluoren-9-ylamino)-4-amino-1-((R)-3-(1-(3-methoxypropyl)-1H-benzo[d]imidazol-2-yl)piperidin-1-yl)butan-1-one dihydrochloride salt (138E) (10.4 mmol, 90% yield). ESI-MS: m/z 597.5 (MH+). $^1$H NMR (400 MHz, MeOH-$d_4$) δ ppm 1.10-1.29 (m, 1H) 1.54-2.38 (m, 6H) 2.67-3.10 (m, 4H) 3.17-3.30 (m, 4H) 3.36-3.59 (m, 4H) 3.98-4.78 (m, 7H) 7.26-7.48 (m, 4H), 7.59-7.87 (m, 7H), 7.90-7.99 (m, 1 H). HPLC retention time, T=0.777 min, STDTFA-2 method.

Step C.

The preparation of the N-derivatization of (9H-fluoren-9-yl)methyl (S)-1-amino-4-((R)-3-(1-(3-methoxypropyl)-1H-benzo[d]imidazol-2-yl)piperidin-1-yl)-4-oxobutan-2-ylcarbamate (138E) were accomplished using one of the two procedures listed below:

In a 4 mL vial was placed acid chloride or chloroformate or isocyanate or sulfonyl chloride (0.2 mmol, 1.6 eq), followed by a stock solution of amine 137E (67 mg, 0.112 mmol, 1 eq) in 0.8 mL of amylene stabilized chloroform. Then DIEA (0.05 mL, 0.31 mmol, 2.5 eq) was added to the vial, and the reaction mixture was stirred at ambient temperature for 1 hour. Reaction progress was monitored by LC/MS. Chloroform was then removed under vacuum (Savant at low temperature) and 0.6 mL of 10% solution of piperidine in DMF was added to the mixture. After reacting for 1 hr, the solvents were removed under vacuum (Savant at medium temperature). The residue was dissolved in 0.8 mL of DMSO, transferred to 96 well plate and purified using LC-MS based purification (50 mm×10 mm Phenomenex Gemini Column using a 10-100% acetonitrile-water gradient) to yield the desired analog (137F).

Procedure A:

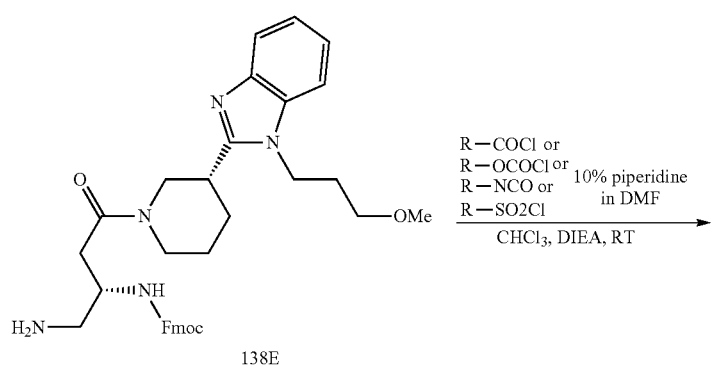

138E

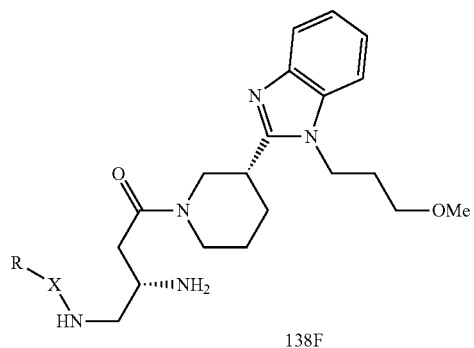

138F where
X is C(O), OC(O), NC(O), or S(O)$_2$, and
R is alkyl, heteroalkyl, aryl, or heteroaryl Procedure B:

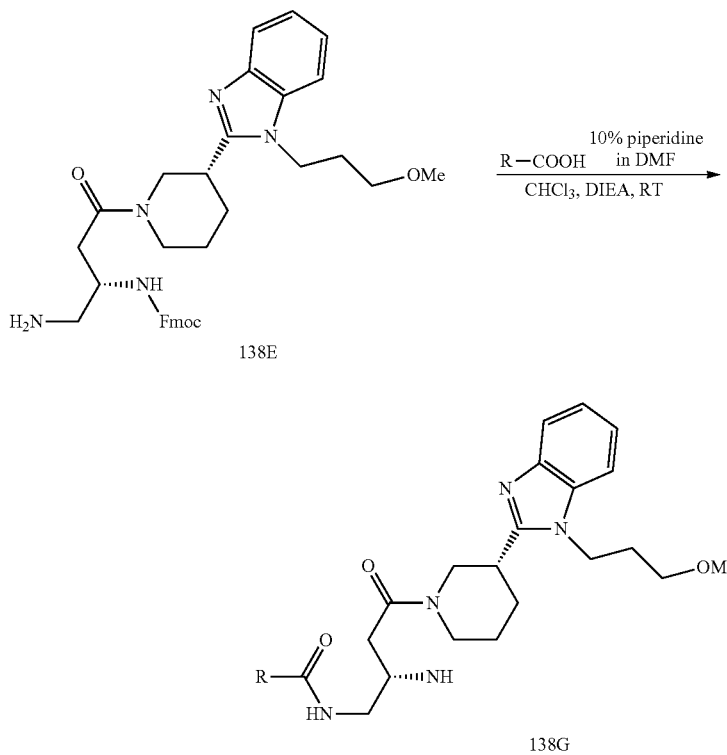

where
R is alkyl, heteroalkyl, aryl, or heteroaryl

In a 4 mL vial was added acid (0.2 mmol, 1.6 eq) and a stock solution of amine 137E (67 mg, 0.112 mmol, 1 eq) in 0.5 mL of amylene stabilized chloroform, followed by stock solution of (benzotriazol-1-yloxy)-tris(dimethylamino)-phosphonium hexafluorophosphate (BOP) (66 mg, 0.15 mmol, 1.2 eq) in 0.3 mL of amylene stabilized chloroform. Then DIEA (0.05 mL, 0.31 mmol, 2.5 eq) was added to the vial, and the reaction mixture was stirred at ambient temperature for 1 hr. Reaction progress was monitored by LC/MS.

Chloroform was then removed under vacuum (Savant at low temperature) and 0.6 mL of solution of 10% piperidine in DMF was added to the mixture. After 1 hour, solvents were removed under vacuum (Savant at medium temperature). The residue was dissolved in 0.8 mL of DMSO, transferred to 96 well plate and purified using LC-MS based purification (50 mm×10 mm Phenomenex Gemini Column using a 10-100% acetonitrile-water gradient) to yield the desired analog (138G).

Compounds that were prepared according to the general procedure outlined in Example 138 are listed in Table VI.

TABLE VI

| Compound No. | Structure/Name | ESI-MS: m/z (M + H$^+$) |
|---|---|---|
| 249 | ![structure] N-((S)-2-amino-4-((R)-3-(1-(3-methoxypropyl)-1H-benzo[d]imidazol-2-yl)piperidin-1-yl)-4-oxobutyl)-2-naphthamide | 528.3 |

TABLE VI-continued

| Compound No. | Structure/Name | ESI-MS: m/z (M + H⁺) |
|---|---|---|
| 250 | 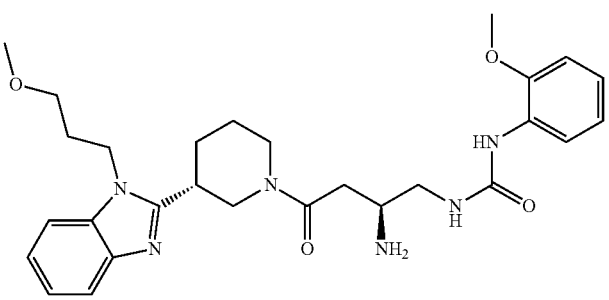<br>1-((S)-2-amino-4-((R)-3-(1-(3-methoxypropyl)-1H-benzo[d]imidazol-2-yl)piperidin-1-yl)-4-oxobutyl)-3-(2-methoxyphenyl)urea | 523.6 |
| 251 | 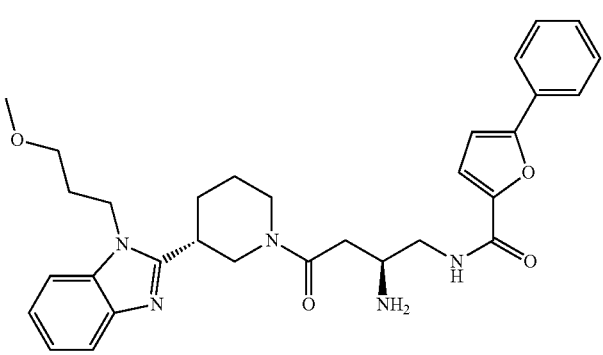<br>N-((S)-2-amino-4-((R)-3-(1-(3-methoxypropyl)-1H-benzo[d]imidazol-2-yl)piperidin-1-yl)-4-oxobutyl)-5-phenylfuran-2-carboxamide | 544.3 |
| 252 | 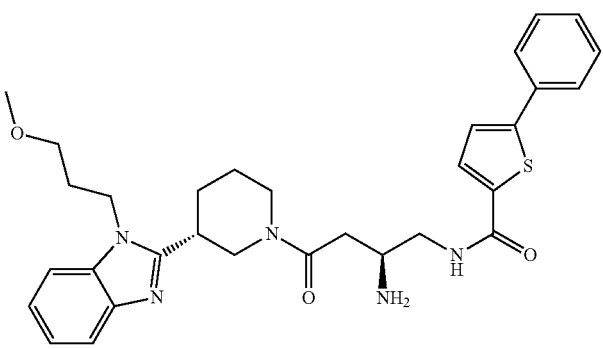<br>N-((S)-2-amino-4-((R)-3-(1-(3-methoxypropyl)-1H-benzo[d]imidazol-2-yl)piperidin-1-yl)-4-oxobutyl)-5-phenylthiophene-2-carboxamide | 560.4 |
| 253 | 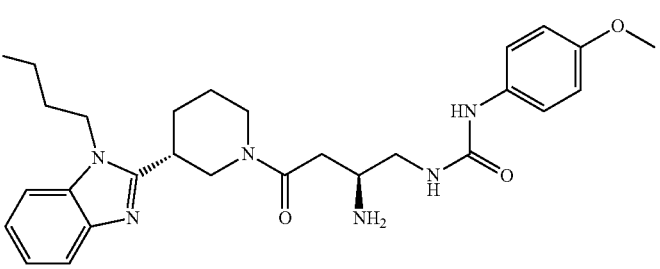<br>1-((S)-2-amino-4-((R)-3-(1-(3-methoxypropyl)-1H-benzo[d]imidazol-2-yl)piperidin-1-yl)-4-oxobutyl)-3-(4-methoxyphenyl)urea | 523.5 |

TABLE VI-continued

| Compound No. | Structure/Name | ESI-MS: m/z (M + H+) |
|---|---|---|
| 254 | 1-((S)-2-amino-4-((R)-3-(1-(3-methoxypropyl)-1H-benzo[d]imidazol-2-yl)piperidin-1-yl)-4-oxobutyl)-3-(3-methoxyphenyl)urea | 523.5 |
| 255 | 1-((S)-2-amino-4-((R)-3-(1-(3-methoxypropyl)-1H-benzo[d]imidazol-2-yl)piperidin-1-yl)-4-oxobutyl)-3-(3,4-dichlorophenyl)urea | 561.2 |
| 256 | 1-((S)-2-ainino-4-((R)-3-(1-(3-methoxypropyl)-1H-benzo[d]imidazol-2-yl)piperidin-1-yl)-4-oxobutyl)-3-(3-chlorophenyl)urea | 527.2 |
| 257 | 1-((S)-2-amino-4-((R)-3-(1-(3-methoxypropyl)-1H-benzo[d]imidazol-2-yl)piperidin-1-yl)-4-oxobutyl)-3-(2-chlorophenyl)urea | 527.1 |

TABLE VI-continued

| Compound No. | Structure/Name | ESI-MS: m/z (M + H+) |
|---|---|---|
| 258 | 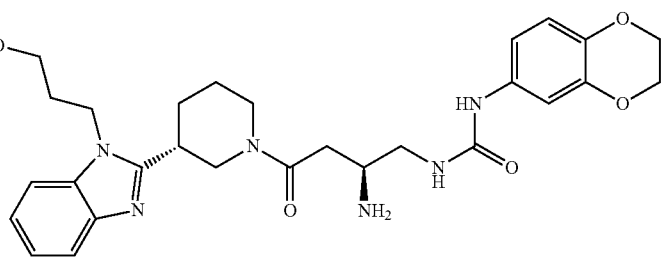  1-((S)-2-amino-4-((R)-3-(1-(3-methoxypropyl)-1H-benzo[d]imidazol-2-yl)piperidin-1-yl)-4-oxobutyl)-3-(2,3-dihydrobenzo[b][1,4]dioxin-6-yl)urea | 551.5 |
| 259 | 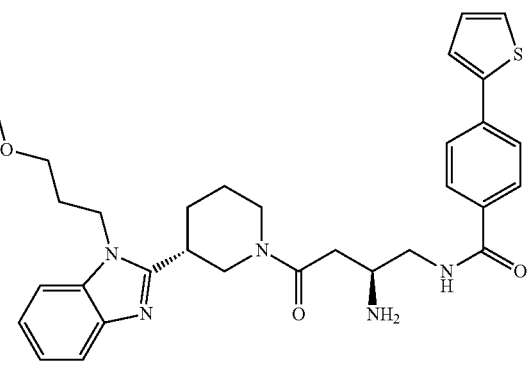  N-((S)-2-amino-4-((R)-3-(1-(3-methoxypropyl)-1H-benzo[d]imidazol-2-yl)piperidin-1-yl)-4-oxobutyl)-4-(thiophen-2-yl)benzamide | 560.0 |
| 260 | 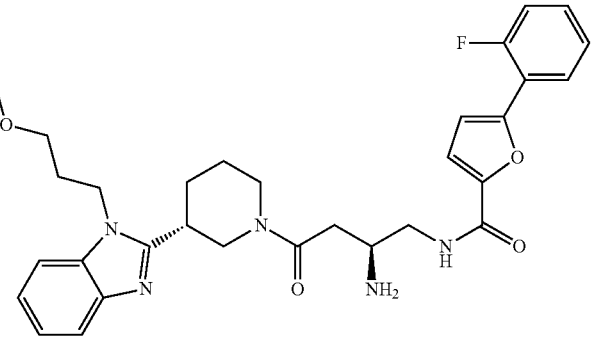  N-((S)-2-amino-4-((R)-3-(1-(3-methoxypropyl)-1H-benzo[d]imidazol-2-yl)piperidin-1-yl)-4-oxobutyl)-5-(2-fluorophenyl)furan-2-carboxamide | 562.0 |
| 261 | 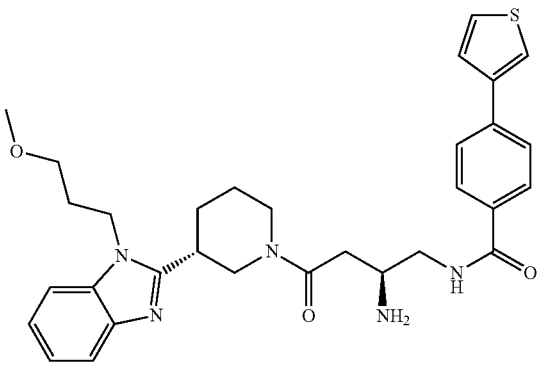  N-((S)-2-amino-4-((R)-3-(1-(3-methoxypropyl)-1H-benzo[d]imidazol-2-yl)piperidin-1-yl)-4-oxobutyl)-4-(thiophen-3-yl)benzamide | 560.0 |

| Compound No. | Structure/Name | ESI-MS: m/z (M + H+) |
|---|---|---|
| 262 | 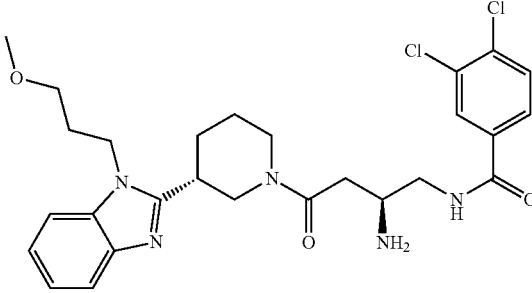<br>N-((S)-2-amino-4-((R)-3-(1-(3-methoxypropyl)-1H-benzo[d]imidazol-2-yl)piperidin-1-yl)-4-oxobutyl)-3,4-dichlorobenzamide | 546.3 |
| 263 | 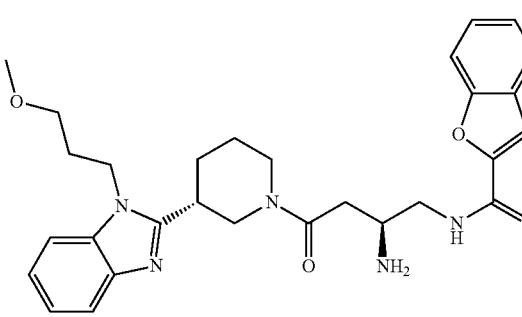<br>N-((S)-2-amino-4-((R)-3-(1-(3-methoxypropyl)-1H-benzo[d]imidazol-2-yl)piperidin-1-yl)-4-oxobutyl)benzofuran-2-carboxamide | 518.3 |
| 264 | 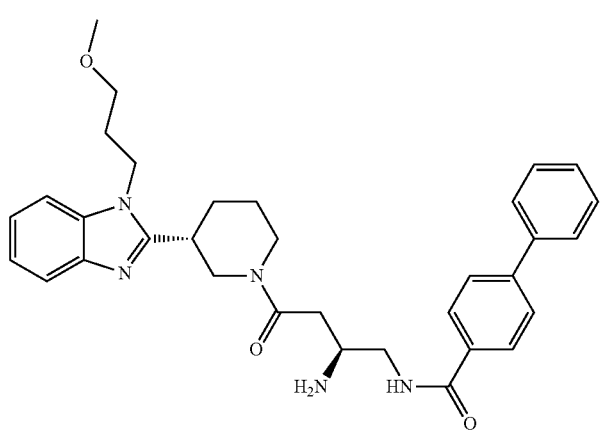<br>N-((S)-2-amino-4-((R)-3-(1-(3-methoxypropyl)-1H-benzo[d]imidazol-2-yl)piperidin-1-yl)-4-oxobutyl)biphenyl-4-carboxamide | 554.4 |

TABLE VI-continued

| Compound No. | Structure/Name | ESI-MS: m/z (M + H⁺) |
|---|---|---|
| 265 | 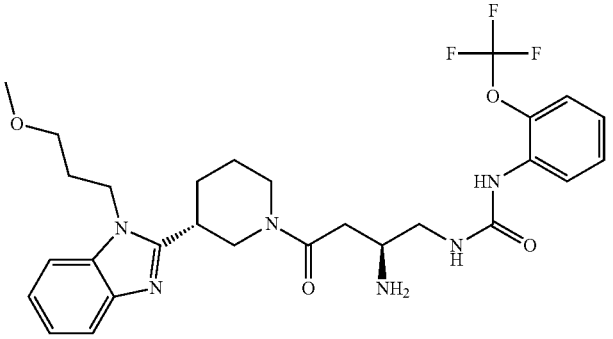 1-((S)-2-amino-4-((R)-3-(1-(3-methoxypropyl)-1H-benzo[d]imidazol-2-yl)piperidin-1-yl)-4-oxobutyl)-3-(2-(trifluoromethoxy)phenyl)urea | 577.2 |
| 266 | 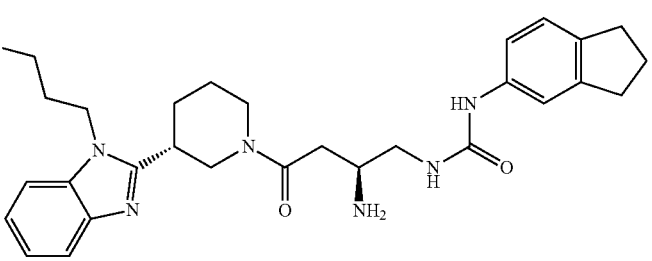 1-((S)-2-amino-4-((R)-3-(1-(3-methoxypropyl)-1H-benzo[d]imidazol-2-yl)piperidin-1-yl)-4-oxobutyl)-3-(2,3-dihydro-1H-inden-5-yl)urea | 533.1 |
| 267 | 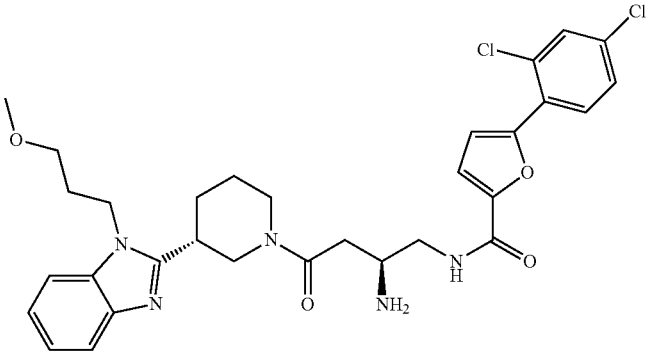 N-((S)-2-amino-4-((R)-3-(1-(3-methoxypropyl)-1H-benzo[d]imidazol-2-yl)piperidin-1-yl)-4-oxobutyl)-5-(2,4-dichlorophenyl)furan-2-carboxamide | 612.0 |
| 268 | 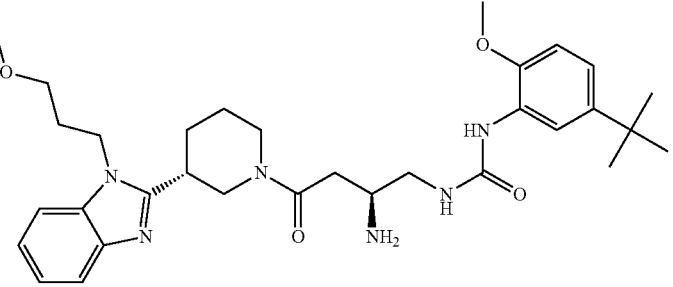 1-((S)-2-amino-4-((R)-3-(1-(3-methoxypropyl)-1H-benzo[d]imidazol-2-yl)piperidin-1-yl)-4-oxobutyl)-3-(5-tert-butyl-2-methoxyphenyl)urea | 579.6 |

TABLE VI-continued

| Compound No. | Structure/Name | ESI-MS: m/z (M + H+) |
|---|---|---|
| 269 | 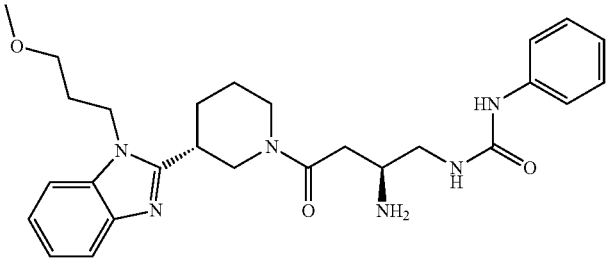   1-((S)-2-amino-4-((R)-3-(1-(3-methoxypropyl)-1H-benzo[d]imidazol-2-yl)piperidin-1-yl)-4-oxobutyl)-3-phenylurea | 493.5 |
| 270 | 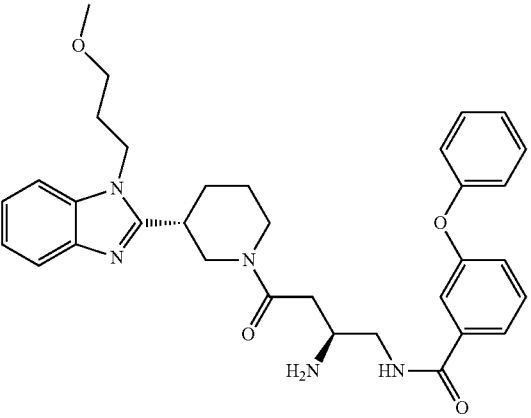   N-((S)-2-amino-4-((R)-3-(1-(3-methoxypropyl)-1H-benzo[d]imidazol-2-yl)piperidin-1-yl)-4-oxobutyl)-3-phenoxybenzamide | 570.4 |
| 271 | 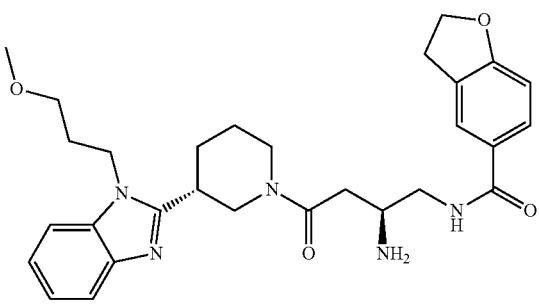   N-((S)-2-amino-4-((R)-3-(1-(3-methoxypropyl)-1H-benzo[d]imidazol-2-yl)piperidin-1-yl)-4-oxobutyl)-2,3-dihydrobenzofuran-5-carboxamide | 520.3 |
| 272 | 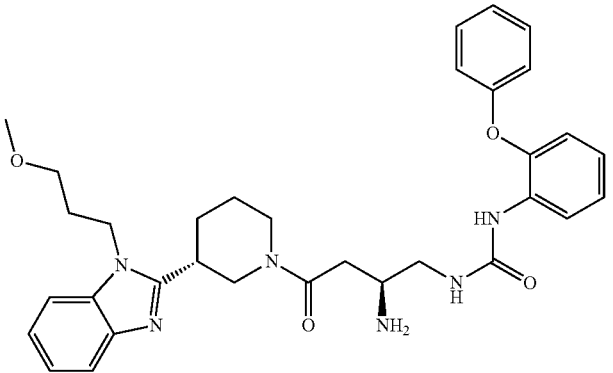   1-((S)-2-amino-4-((R)-3-(1-(3-methoxypropyl)-1H-benzo[d]imidazol-2-yl)piperidin-1-yl)-4-oxobutyl)-3-(2-phenoxyphenyl)urea | 585.2 |

TABLE VI-continued

| Compound No. | Structure/Name | ESI-MS: m/z (M + H+) |
|---|---|---|
| 273 | 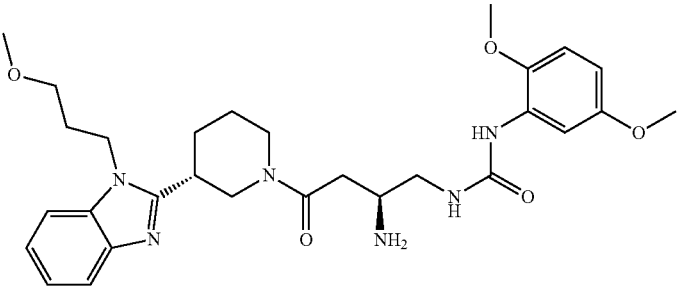<br>1-((S)-2-amino-4-((R)-3-(1-(3-methoxypropyl)-1H-benzo[d]imidazol-2-yl)piperidin-1-yl)-4-oxobutyl)-3-(2,5-dimethoxyphenyl)urea | 553.2 |
| 274 | 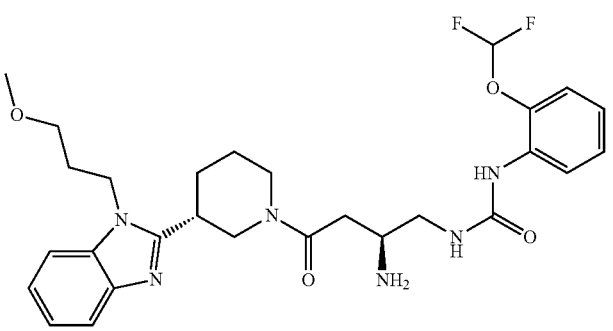<br>1-((S)-2-amino-4-((R)-3-(1-(3-methoxypropyl)-1H-benzo[d]imidazol-2-yl)piperidin-1-yl)-4-oxobutyl)-3-(2-(difluoromethoxy)phenyl)urea | 559.2 |
| 275 | 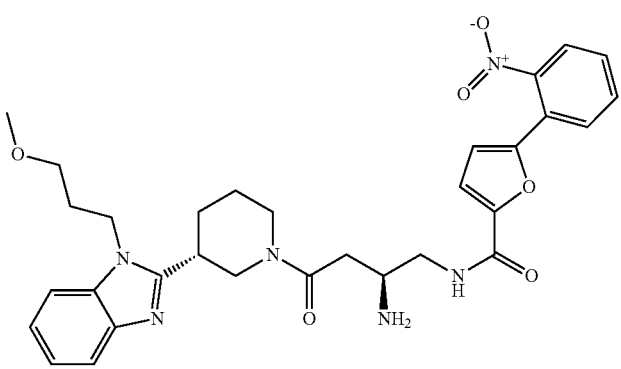<br>N-((S)-2-amino-4-((R)-3-(1-(3-methoxypropyl)-1H-benzo[d]imidazol-2-yl)piperidin-1-yl)-4-oxobutyl)-5-(2-nitrophenyl)furan-2-carboxamide | 589.2 |
| 276 | 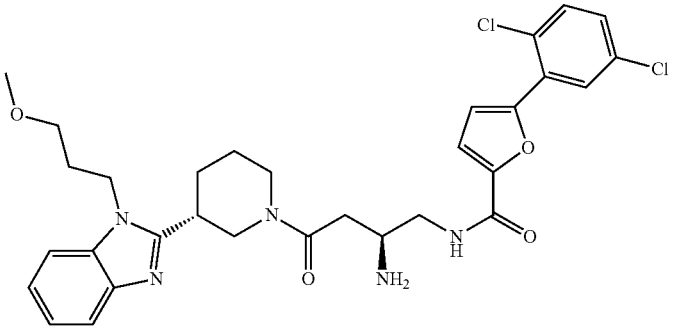<br>N-((S)-2-amino-4-((R)-3-(1-(3-methoxypropyl)-1H-benzo[d]imidazol-2-yl)piperidin-1-yl)-4-oxobutyl)-5-(2,5-dichlorophenyl)furan-2-carboxamide | 612.0 |

TABLE VI-continued
| Compound No. | Structure/Name | ESI-MS: m/z (M + H⁺) |
|---|---|---|
| 277 | 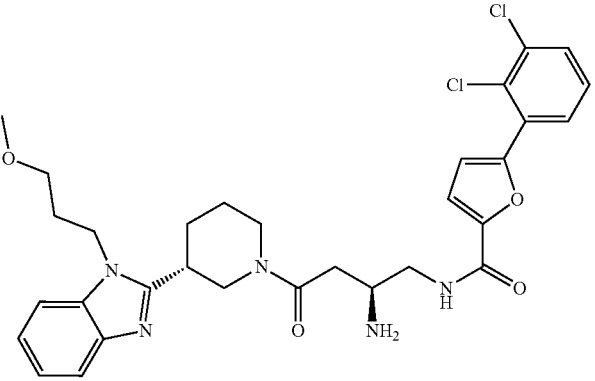<br>N-((S)-2-amino-4-((R)-3-(1-(3-methoxypropyl)-1H-benzo[d]imidazol-2-yl)piperidin-1-yl)-4-oxobutyl)-5-(2,3-dichlorophenyl)furan-2-carboxamide | 612.0 |
| 278 | 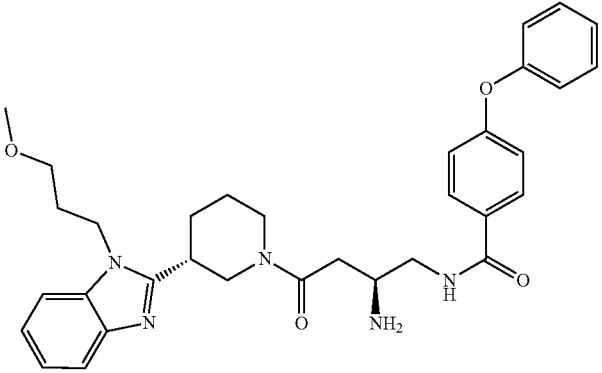<br>N-((S)-2-amino-4-((R)-3-(1-(3-methoxypropyl)-1H-benzo[d]imidazol-2-yl)piperidin-1-yl)-4-oxobutyl)-4-phenoxybenzamide | 570.4 |
| 279 | 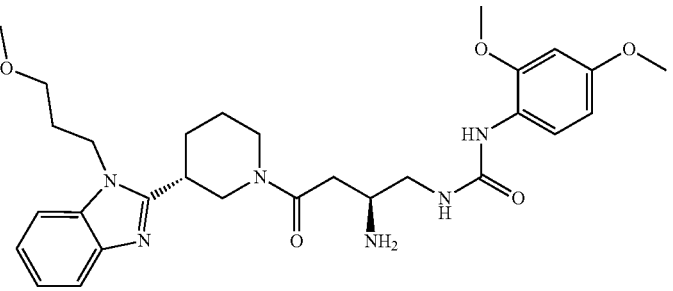<br>1-((S)-2-amino-4-((R)-3-(1-(3-methoxypropyl)-1H-benzo[d]imidazol-2-yl)piperidin-1-yl)-4-oxobutyl)-3-(2,4-dimethoxyphenyl)urea | 553.2 |

TABLE VI-continued

| Compound No. | Structure/Name | ESI-MS: m/z (M + H⁺) |
|---|---|---|
| 280 | 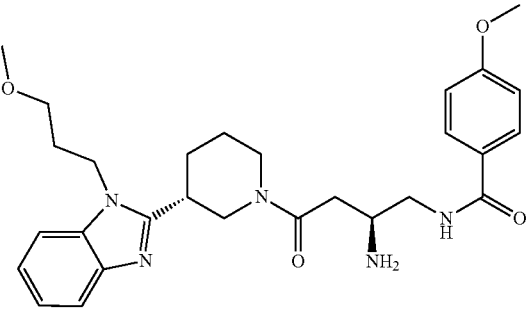<br>N-((S)-2-amino-4-((R)-3-(1-(3-methoxypropyl)-1H-benzo[d]imidazol-2-yl)piperidin-1-yl)-4-oxobutyl)-4-methoxybenzamide | 508.3 |
| 281 | 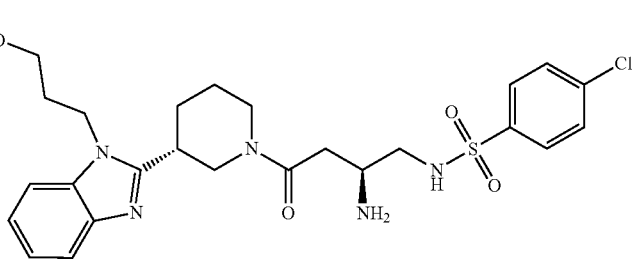<br>N-((S)-2-amino-4-((R)-3-(1-(3-methoxypropyl)-1H-benzo[d]imidazol-2-yl)piperidin-1-yl)-4-oxobutyl)-4-chlorobenzenesulfonamide | 548.3 |
| 282 | 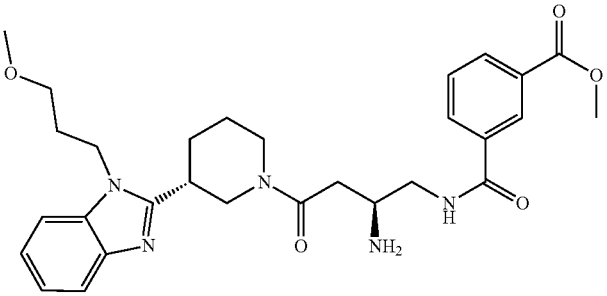<br>methyl 3-((S)-2-amino-4-((R)-3-(1-(3-methoxypropyl)-1H-benzo[d]imidazol-2-yl)piperidin-1-yl)-4-oxobutylcarbamoyl)benzoate | 536.4 |
| 283 | 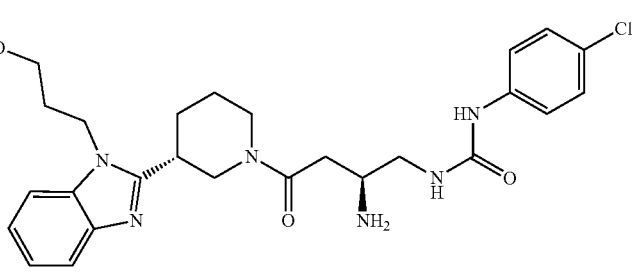<br>1-((S)-2-amino-4-((R)-3-(1-(3-methoxypropyl)-1H-benzo[d]imidazol-2-yl)piperidin-1-yl)-4-oxobutyl)-3-(4-chlorophenyl)urea | 527.2 |

TABLE VI-continued

| Compound No. | Structure/Name | ESI-MS: m/z (M + H⁺) |
|---|---|---|
| 284 | 1-((S)-2-amino-4-((R)-3-(1-(3-methoxypropyl)-1H-benzo[d]imidazol-2-yl)piperidin-1-yl)-4-oxobutyl)-3-(2-(methylthio)phenyl)urea | 539.1 |
| 285 | 1-((S)-2-amino-4-((R)-3-(1-(3-methoxypropyl)-1H-benzo[d]imidazol-2-yl)piperidin-1-yl)-4-oxobutyl)-3-(2-ethoxyphenyl)urea | 537.5 |
| 286 | 1-((S)-2-amino-4-((R)-3-(1-(3-methoxypropyl)-1H-benzo[d]imidazol-2-yl)piperidin-1-yl)-4-oxobutyl)-3-(2-propylphenyl)urea | 535.1 |
| 287 | 1-((S)-2-amino-4-((R)-3-(1-(3-methoxypropyl)-1H-benzo[d]imidazol-2-yl)piperidin-1-yl)-4-oxobutyl)-3-(2-methoxy-5-methylphenyl)urea | 537.1 |

TABLE VI-continued
| Compound No. | Structure/Name | ESI-MS: m/z (M + H⁺) |
|---|---|---|
| 288 | 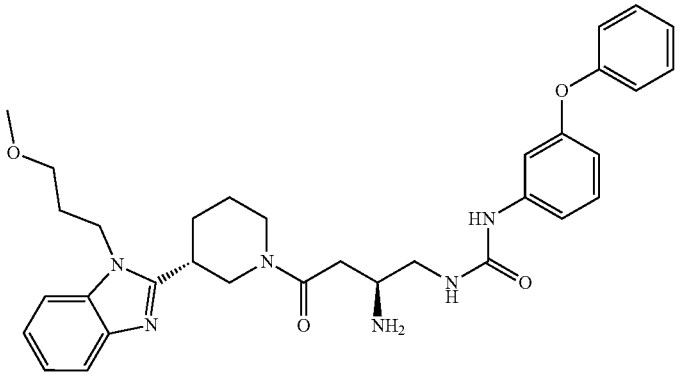<br>1-((S)-2-amino-4-((R)-3-(1-(3-methoxypropyl)-1H-benzo[d]imidazol-2-yl)piperidin-1-yl)-4-oxobutyl)-3-(3-phenoxyphenyl)urea | 585.2 |
| 289 | 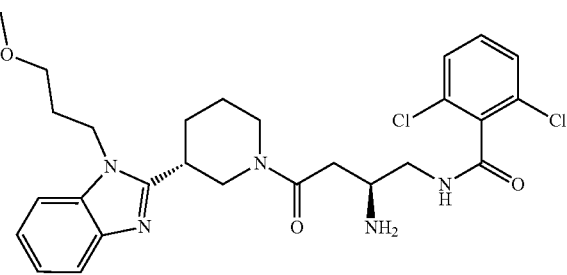<br>N-((S)-2-amino-4-((R)-3-(1-(3-methoxypropyl)-1H-benzo[d]imidazol-2-yl)piperidin-1-yl)-4-oxobutyl)-2,6-dichlorobenzamide | 546.3 |
| 290 | 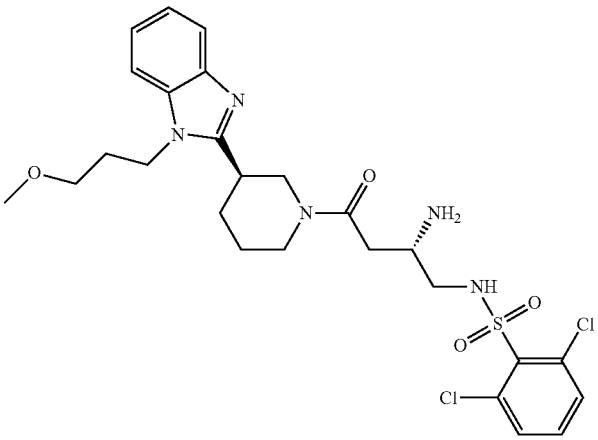<br>N-((S)-2-amino-4-((R)-3-(1-(3-methoxypropyl)-1H-benzo[d]imidazol-2-yl)piperidin-1-yl)-4-oxobutyl)-2,6-dichlorobenzenesulfonamide | 582.0 |

TABLE VI-continued

| Compound No. | Structure/Name | ESI-MS: m/z (M + H⁺) |
|---|---|---|
| 291 | 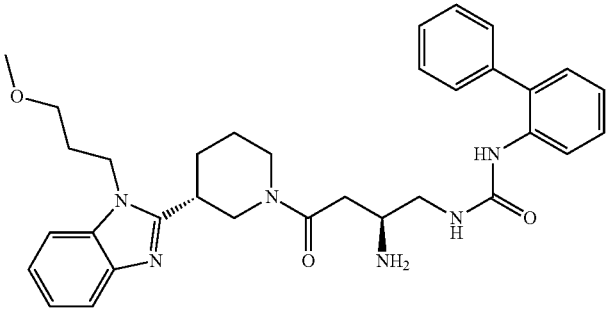<br>1-((S)-2-amino-4-((R)-3-(1-(3-methoxypropyl)-1H-benzo[d]imidazol-2-yl)piperidin-1-yl)-4-oxobutyl)-3-(biphenyl-2-yl)urea | 569.2 |
| 292 | 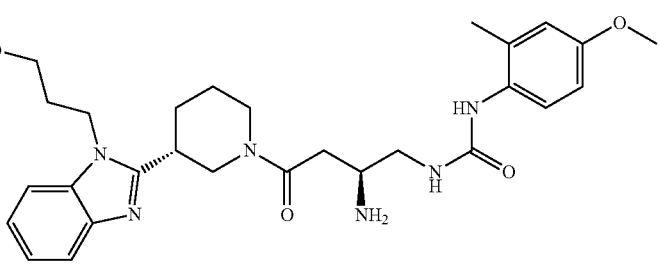<br>1-((S)-2-amino-4-((R)-3-(1-(3-methoxypropyl)-1H-benzo[d]imidazol-2-yl)piperidin-1-yl)-4-oxobutyl)-3-(4-methoxy-2-methylphenyl)urea | 537.5 |
| 293 | 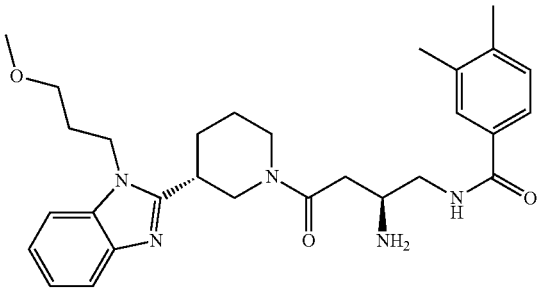<br>N-((S)-2-amino-4-((R)-3-(1-(3-methoxypropyl)-1H-benzo[d]imidazol-2-yl)piperidin-1-yl)-4-oxobutyl)-3,4-dimethylbenzamide | 506.3 |
| 294 | 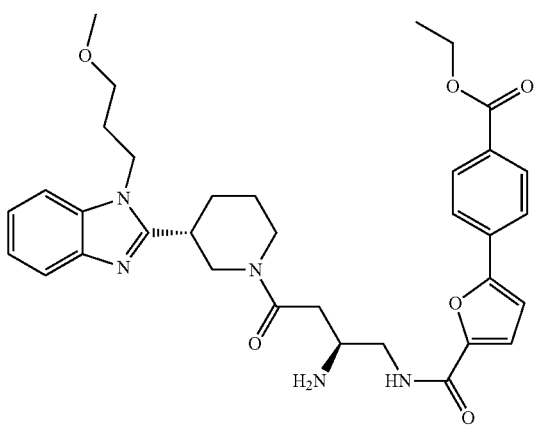<br>ethyl 4-(5-((S)-2-amino-4-((R)-3-(1-(3-methoxypropyl)-1H-benzo[d]imidazol-2-yl)piperidin-1-yl)-4-oxobutylcarbamoyl)furan-2-yl)benzoate | 616.4 |

TABLE VI-continued

| Compound No. | Structure/Name | ESI-MS: m/z (M + H⁺) |
|---|---|---|
| 295 | 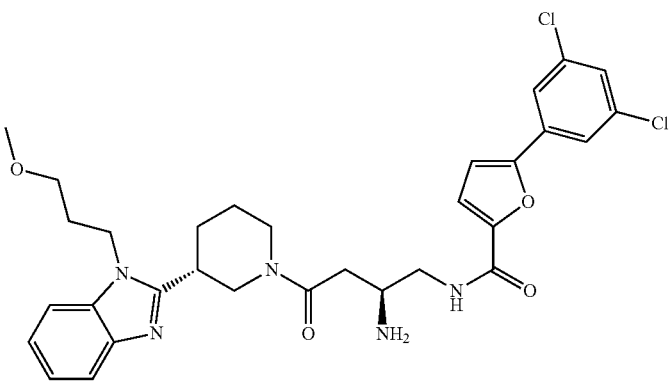 N-((S)-2-amino-4-((R)-3-(1-(3-methoxypropyl)-1H-benzo[d]imidazol-2-yl)piperidin-1-yl)-4-oxobutyl)-5-(3,5-dichlorophenyl)furan-2-carboxamide | 612.0 |
| 296 | 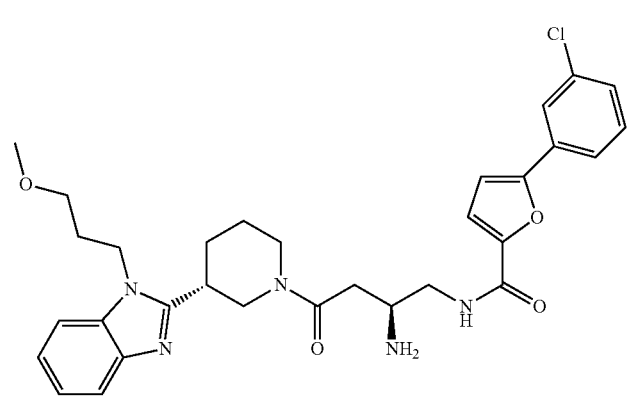 N-((S)-2-amino-4-((R)-3-(1-(3-methoxypropyl)-1H-benzo[d]imidazol-2-yl)piperidin-1-yl)-4-oxobutyl)-5-(3-chlorophenyl)furan-2-carboxamide | 578.4 |
| 297 | 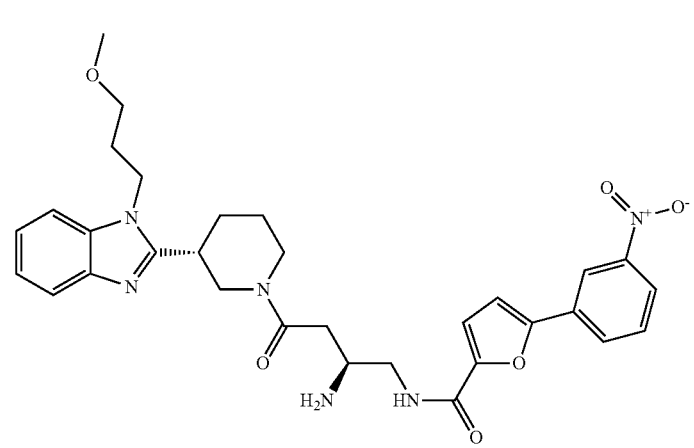 N-((S)-2-amino-4-((R)-3-(1-(3-methoxypropyl)-1H-benzo[d]imidazol-2-yl)piperidin-1-yl)-4-oxobutyl)-5-(3-nitrophenyl)furan-2-carboxamide | 589.2 |

TABLE VI-continued

| Compound No. | Structure/Name | ESI-MS: m/z (M + H⁺) |
|---|---|---|
| 298 | 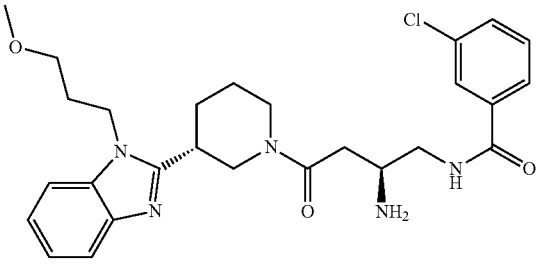  N-((S)-2-amino-4-((R)-3-(1-(3-methoxypropyl)-1H-benzo[d]imidazol-2-yl)piperidin-1-yl)-4-oxobutyl)-3-chlorobenzamide | 512.3 |
| 299 | 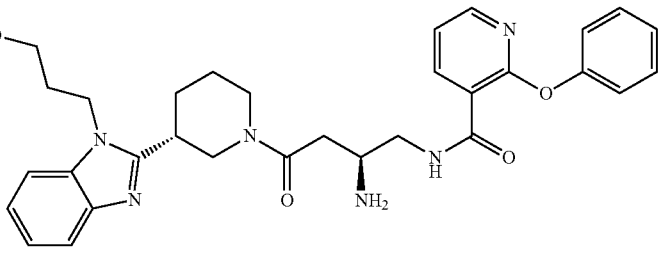  N-((S)-2-amino-4-((R)-3-(1-(3-methoxypropyl)-1H-benzo[d]imidazol-2-yl)piperidin-1-yl)-4-oxobutyl)-2-phenoxynicotinamide | 571.2 |
| 300 | 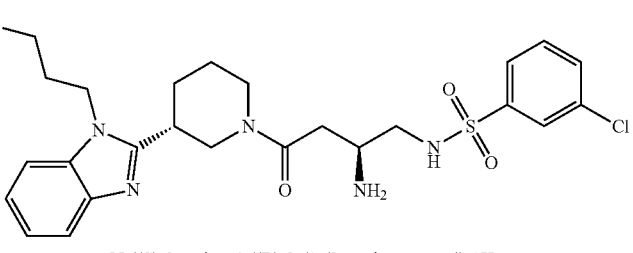  N-((S)-2-amino-4-((R)-3-(1-(3-methoxypropyl)-1H-benzo[d]imidazol-2-yl)piperidin-1-yl)-4-oxobutyl)-3-chlorobenzenesulfonamide | 548.3 |
| 301 | 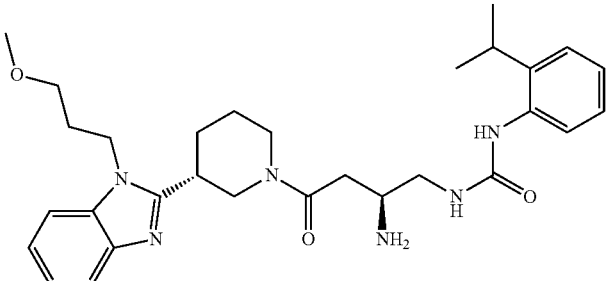  1-((S)-2-amino-4-((R)-3-(1-(3-methoxypropyl)-1H-benzo[d]imidazol-2-yl)piperidin-1-yl)-4-oxobutyl)-3-(2-isopropylphenyl)urea | 535.1 |

| Compound No. | Structure/Name | ESI-MS: m/z (M + H+) |
|---|---|---|
| 302 | 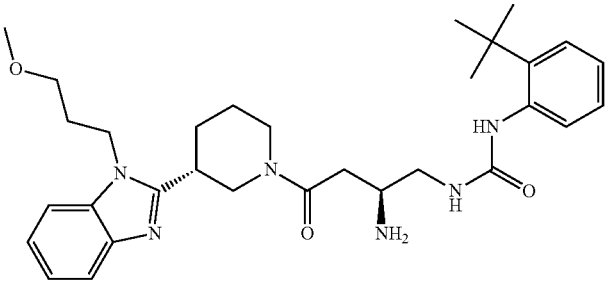1-((S)-2-amino-4-((R)-3-(1-(3-methoxypropyl)-1H-benzo[d]imidazol-2-yl)piperidin-1-yl)-4-oxobutyl)-3-(2-tert-butylphenyl)urea | 549.5 |
| 303 | 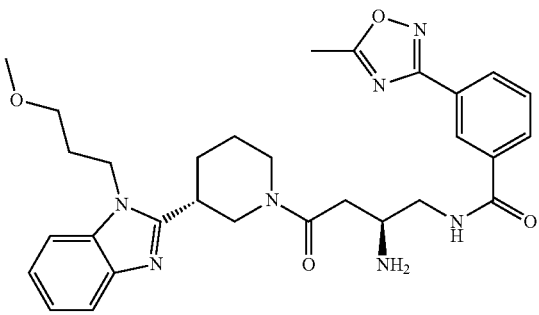N-((S)-2-amino-4-((R)-3-(1-(3-methoxypropyl)-1H-benzo[d]imidazol-2-yl)piperidin-1-yl)-4-oxobuty)-3-(5-methyl-1,2,4-oxadiazol-3-yl)benzamide | 560.0 |
| 304 | 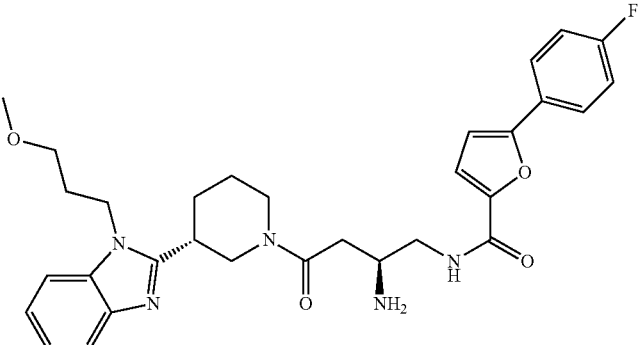N-((S)-2-amino-4-((R)-3-(1-(3-methoxypropyl)-1H-benzo[d]imidazol-2-yl)piperidin-1-yl)-4-oxobutyl)-5-(4-fluorophenyl)furan-2-carboxamide | 562.0 |

TABLE VI-continued

| Compound No. | Structure/Name | ESI-MS: m/z (M + H+) |
|---|---|---|
| 305 | N-((S)-2-amino-4-((R)-3-(1-(3-methoxypropyl)-1H-benzo[d]imidazol-2-yl)piperidin-1-yl)-4-oxobutyl)-3,4-dichlorobenzenesulfonamide | 582.0 |
| 306 | N-((S)-2-amino-4-((R)-3-(1-(3-methoxypropyl)-1H-benzo[d]imidazol-2-yl)piperidin-1-yl)-4-oxobutyl)-2-chlorobenzenesulfonamide | 548.3 |
| 307 | N-((S)-2-amino-4-((R)-3-(1-(3-methoxypropyl)-1H-benzo[d]imidazol-2-yl)piperidin-1-yl)-4-oxobutyl)-2-(propylthio)nicotinamide | 553.2 |
| 308 | N-((S)-2-amino-4-((R)-3-(1-(3-methoxypropyl)-1H-benzo[d]imidazol-2-yl)piperidin-1-yl)-4-oxobutyl)-2,3-dihydrobenzo[b][1,4]dioxine-6-carboxamide | 536.3 |

TABLE VI-continued

| Compound No. | Structure/Name | ESI-MS: m/z (M + H⁺) |
|---|---|---|
| 309 | N-((S)-2-amino-4-((R)-3-(1-(3-methoxypropyl)-1H-benzo[d]imidazol-2-yl)piperidin-1-yl)-4-oxobutyl)-4-chlorobenzamide | 512.3 |
| 310 | N-((S)-2-amino-4-((R)-3-(1-(3-methoxypropyl)-1H-benzo[d]imidazol-2-yl)piperidin-1-yl)-4-oxobutyl)-3-methoxybenzamide | 508.3 |
| 311 | N-((S)-2-amino-4-((R)-3-(1-(3-methoxypropyl)-1H-benzo[d]imidazol-2-yl)piperidin-1-yl)-4-oxobutyl)-1-naphthamide | 528.3 |
| 312 | N-((S)-2-amino-4-((R)-3-(1-(3-methoxypropyl)-1H-benzo[d]imidazol-2-yl)piperidin-1-yl)-4-oxobutyl)propane-2-sulfonamide | 480.2 |

TABLE VI-continued

| Compound No. | Structure/Name | ESI-MS: m/z (M + H+) |
|---|---|---|
| 313 | N-((S)-2-amino-4-((R)-3-(1-(3-methoxypropyl)-1H-benzo[d]imidazol-2-yl)piperidin-1-yl)-4-oxobutyl)-6-(piperidin-1-yl)picolinamide | 562.4 |
| 314 | methyl 4-((S)-2-amino-4-((R)-3-(1-(3-methoxypropyl)-1H-benzo[d]imidazol-2-yl)piperidin-1-yl)-4-oxobutylcarbamoyl)benzoate | 536.3 |
| 315 | N-((S)-2-amino-4-((R)-3-(1-(3-methoxypropyl)-1H-benzo[d]imidazol-2-yl)piperidin-1-yl)-4-oxobutyl)-3-methoxybenzenesulfonamide | 544.2 |
| 316 | N-((S)-2-amino-4-((R)-3-(1-(3-methoxypropyl)-1H-benzo[d]imidazol-2-yl)piperidin-1-yl)-4-oxobutyl)benzenesulfonamide | 514.3 |

TABLE VI-continued

| Compound No. | Structure/Name | ESI-MS: m/z (M + H⁺) |
|---|---|---|
| 317 | 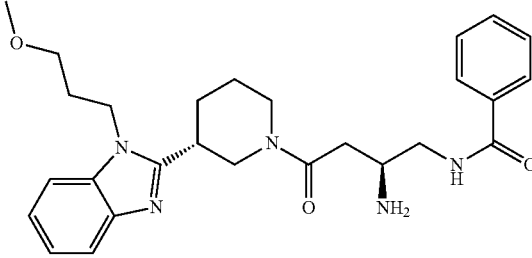<br>N-((S)-2-amino-4-((R)-3-(1-(3-methoxypropyl)-1H-benzo[d]imidazol-2-yl)piperidin-1-yl)-4-oxobutyl)benzamide | 478.3 |
| 318 | 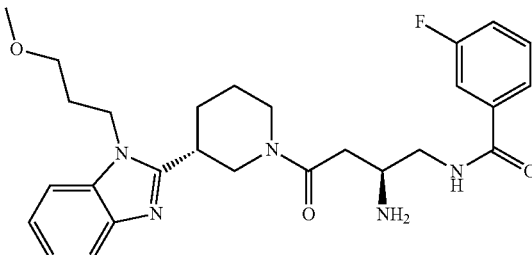<br>N-((S)-2-amino-4-((R)-3-(1-(3-methoxypropyl)-1H-benzo[d]imidazol-2-yl)piperidin-1-yl)-4-oxobutyl)-3-fluorobenzamide | 496.3 |
| 319 | 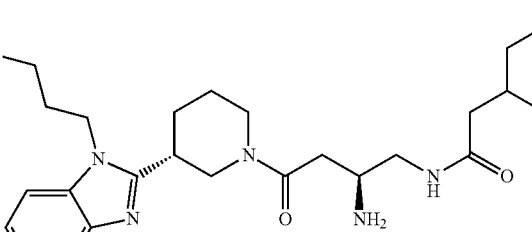<br>N-((S)-2-amino-4-((R)-3-(1-(3-methoxypropyl)-1H-benzo[d]imidazol-2-yl)piperidin-1-yl)-4-oxobutyl)-2-cyclohexylacetamide | 498.4 |
| 320 | 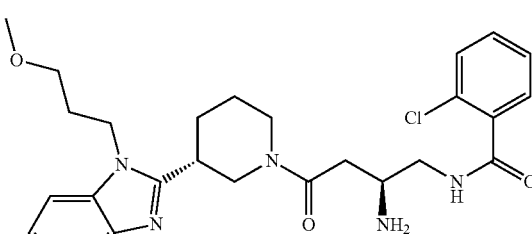<br>N-((S)-2-amino-4-((R)-3-(1-(3-methoxypropyl)-1H-benzo[d]imidazol-2-yl)piperidin-1-yl)-4-oxobutyl)-2-chlorobenzamide | 512.3 |
| 321 | 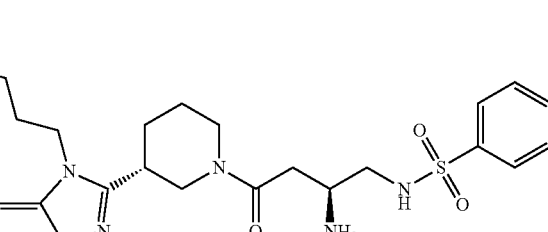<br>N-((S)-2-amino-4-((R)-3-(1-(3-methoxypropyl)-1H-benzo[d]imidazol-2-yl)piperidin-1-yl)-4-oxobutyl)-4-methoxybenzenesulfonamide | 544.3 |

TABLE VI-continued

| Compound No. | Structure/Name | ESI-MS: m/z (M + H⁺) |
|---|---|---|
| 322 | 1-((S)-2-amino-4-((R)-3-(1-(3-methoxypropyl)-1H-benzo[d]imidazol-2-yl)piperidin-1-yl)-4-oxobutyl)-3-(2,5-dimethoxyphenethyl)urea | 581.2 |
| 323 | 1-((S)-2-amino-4-((R)-3-(1-(3-methoxypropyl)-1H-benzo[d]imidazol-2-yl)piperidin-1-yl)-4-oxobutyl)-3-cyclohexylurea | 499.1 |
| 324 | N-((S)-2-amino-4-((R)-3-(1-(3-methoxypropyl)-1H-benzo[d]imidazol-2-yl)piperidin-1-yl)-4-oxobutyl)-2-methoxybenzenesulfonamide | 544.3 |
| 325 | N-((S)-2-amino-4-((R)-3-(1-(3-methoxypropyl)-1H-benzo[d]imidazol-2-yl)piperidin-1-yl)-4-oxobutyl)furan-2-carboxamide | 468.3 |

TABLE VI-continued

| Compound No. | Structure/Name | ESI-MS: m/z (M + H+) |
|---|---|---|
| 326 | 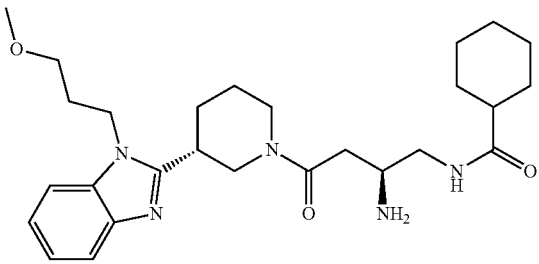<br>N-((S)-2-amino-4-((R)-3-(1-(3-methoxypropyl)-1H-benzo[d]imidazol-2-yl)piperidin-1-yl)-4-oxobutyl)cyclohexanecarboxamide | 484.3 |
| 327 | 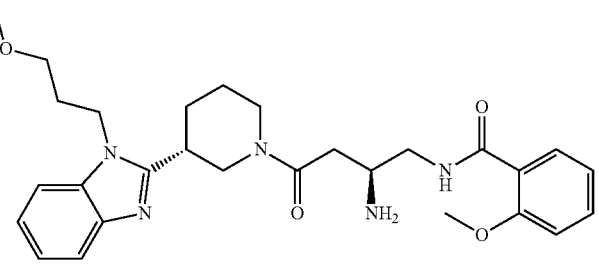<br>N-((S)-2-amino-4-((R)-3-(1-(3-methoxypropyl)-1H-benzo[d]imidazol-2-yl)piperidin-1-yl)-4-oxobutyl)-2-methoxybenzamide | 508.3 |
| 328 | 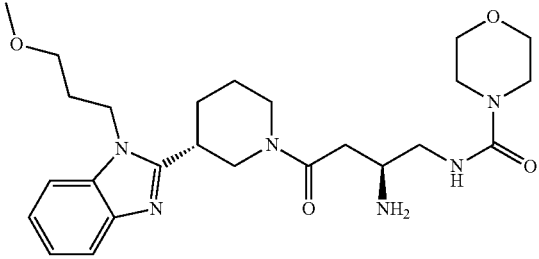<br>N-((S)-2-amino-4-((R)-3-(1-(3-methoxypropyl)-1H-benzo[d]imidazol-2-yl)piperidin-1-yl)-4-oxobutyl)morpholine-4-carboxamide | 487.1 |
| 329 | 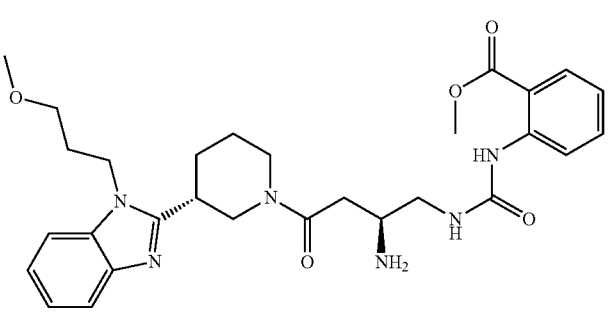<br>methyl 2-(3-((S)-2-amino-4-((R)-3-(1-(3-methoxypropyl)-1H-benzo[d]imidazol-2-yl)piperidin-1-yl)-4-oxobutyl)ureido)benzoate | 551.5 |

TABLE VI-continued

| Compound No. | Structure/Name | ESI-MS: m/z (M + H+) |
|---|---|---|
| 330 | 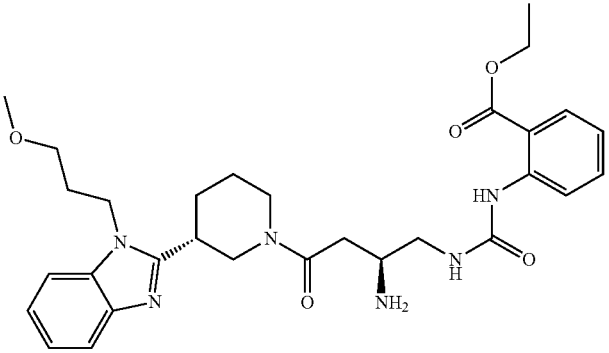<br>ethyl 2-(3-((S)-2-amino-4-((R)-3-(1-(3-methoxypropyl)-1H-benzo[d]imidazol-2-yl)piperidin-1-yl)-4-oxobutyl)ureido)benzoate | 565.2 |
| 331 | 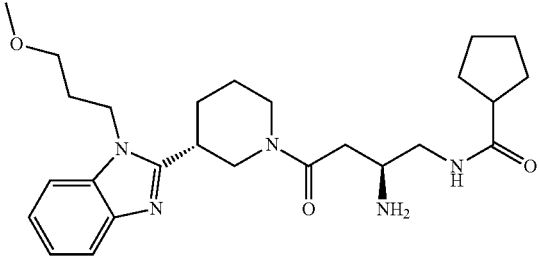<br>N-((S)-2-amino-4-((R)-3-(1-(3-methoxypropyl)-1H-benzo[d]imidazol-2-yl)piperidin-1-yl)-4-oxobutyl)cyclopentanecarboxamide | 470.4 |
| 332 | 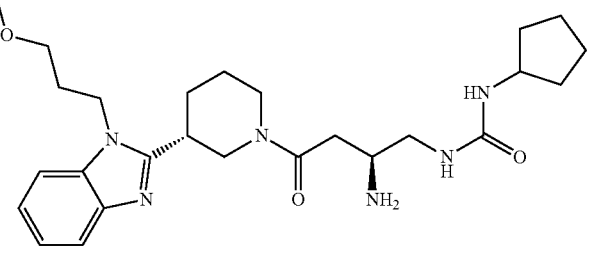<br>1-((S)-2-amino-4-((R)-3-(1-(3-methoxypropyl)-1H-benzo[d]imidazol-2-yl)piperidin-1-yl)-4-oxobutyl)-3-cyclopentylurea | 485.6 |
| 333 | 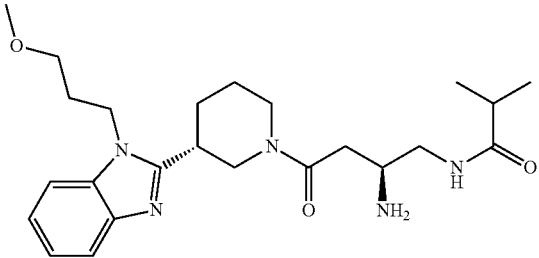<br>N-((S)-2-amino-4-((R)-3-(1-(3-methoxypropyl)-1H-benzo[d]imidazol-2-yl)piperidin-1-yl)-4-oxobutyl)isobutyramide | 444.4 |

| Compound No. | Structure/Name | ESI-MS: m/z (M + H+) |
|---|---|---|
| 334 | 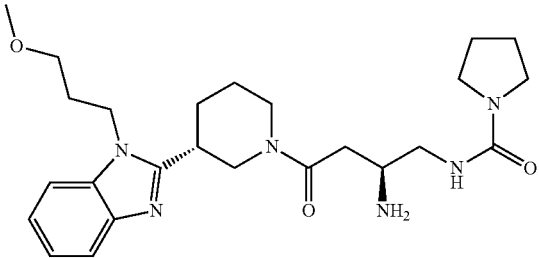<br>N-((S)-2-amino-4-((R)-3-(1-(3-methoxypropyl)-1H-benzo[d]imidazol-2-yl)piperidin-1-yl)-4-oxobutyl)pyrrolidine-1-carboxamide | 471.5 |
| 335 | 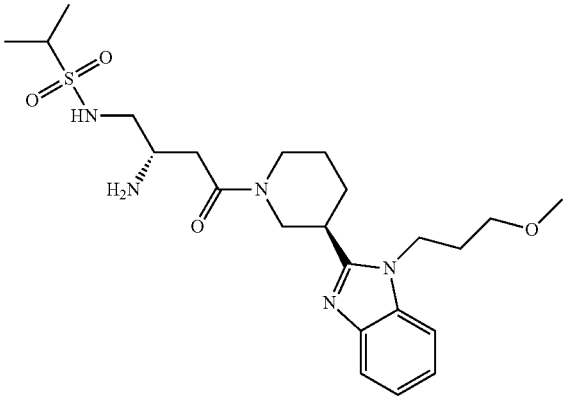<br>N-((S)-2-amino-4-((R)-3-(1-(3-methoxypropyl)-1H-benzo[d]imidazol-2-yl)piperidin-1-yl)-4-oxobutyl)propane-2-sulfonamide | 480.5 |
| 336 | 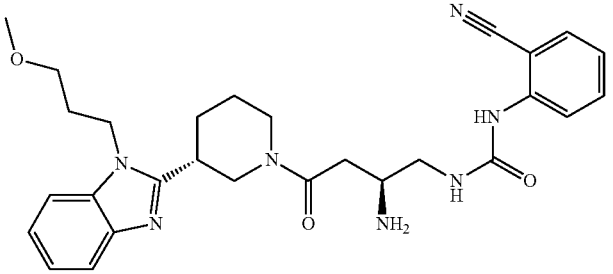<br>1-((S)-2-amino-4-((R)-3-(1-(3-methoxypropyl)-1H-benzo[d]imidazol-2-yl)piperidin-1-yl)-4-oxobutyl)-3-(2-cyanophenyl)urea | 518.3 |

Example 139

General Procedure for the Synthesis of N-Substituted Derivatives of (9H-fluoren-9-yl)methyl (3S,4R)-4-((R)-3-(1-(3-methoxypropyl)-1H-benzo[d]imidazol-2-yl)piperidine-1-carhonyppyrrolidin-3-ylcarbamate (139F and 139G)

Step A.

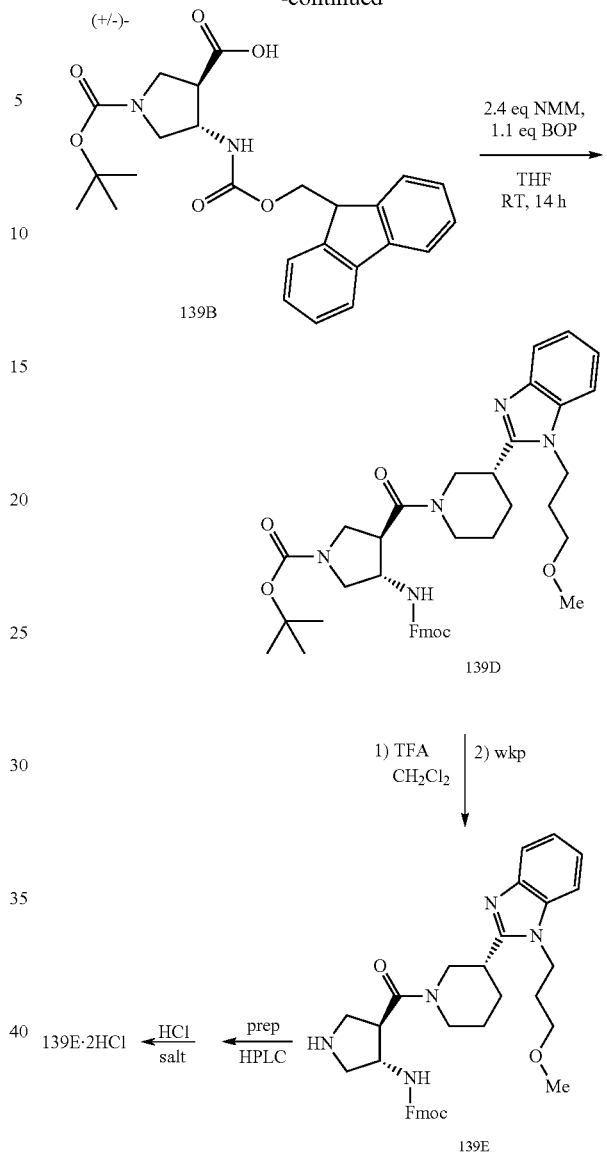

The amine group of Boc-pyrrolidine-amino acid, (3R,4S)-4-amino-1-(tert-butoxycarbonyl)pyrrolidine-3-carboxylic acid (139A), was protected with an Fmoc group according to standard Schotten-Baumen procedure yielding (3R,48)-4-(((9H-fluoren-9-yl)methoxy)carbonylamino)-1-(tert-butoxycarbonyl)pyrrolidine-3-carboxylic acid (139B). ESI-MS: m/z 453.3 (MH)+.

Step B.

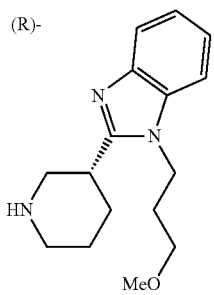

(R)-1-(3-methoxypropyl)-2-(piperidin-3-yl)-1H-benzo[d]imidazole (138C) (3.02 g) was coupled to (3R,4S)-4-(((9H-fluoren-9-yl)methoxy)carbonylamino)-1-(tert-butoxycarbonyl)pyrrolidine-3-carboxylic acid (5 g) (138B) using the standard BOP coupling procedure from Example 138, Step C, Procedure B. The deprotection was performed according to standard procedures (TFA/CH$_2$Cl$_2$; evapn; EtOAc/satd NaHCO$_3$; dry; evapn.) to yield the free amine, (9H-fluoren-9-yl)methyl (3S,4R)-4-((R)-3-(1-(3-methoxypropyl)-1H-benzo[d]imidazol-2-yl)piperidine-1-carbonyl)pyrrolidin-3-ylcarbamate (139E): ESI-MS: m/z 608.6 (MH+). $^1$H NMR (400 MHz, MeOH-d$_4$) δ ppm 1.66 (m, 1H) 1.7-2.3 (m, 5H) 4.21-4.25 (m, 2H) 7.1-7.6 (m, 8H). HPLC retention time, T=0.817 min, STDTFA-2 method.

Step C.

N-Derivatives of the free amine (9H-fluoren-9-yl)methyl (3S,4R)-4-((R)-3-(1-(3-methoxypropyl)-1H-benzo[d]imidazol-2-yl)piperidine-1-carbonyl)pyrrolidin-3-ylcarbamate (138E) were prepared using either Procedure A or B listed below:

Procedure A.

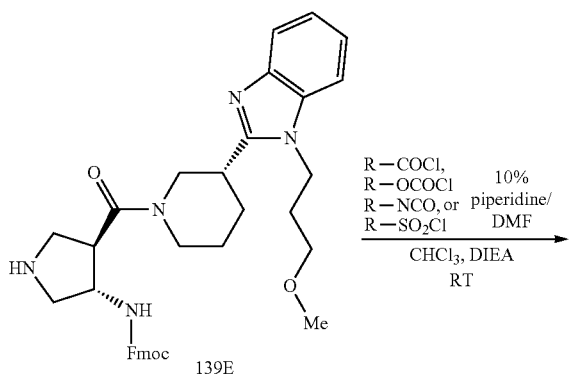

139E

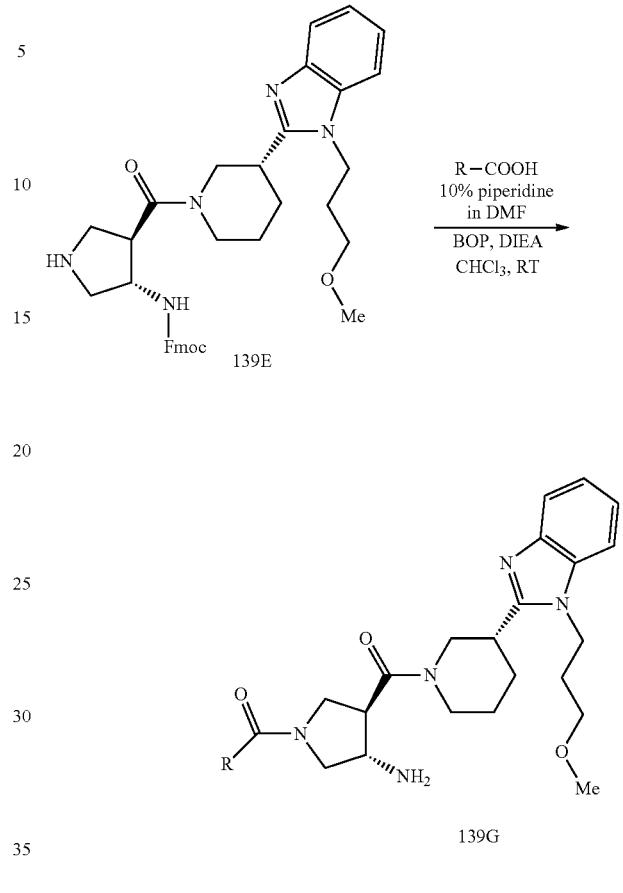

139F where
X is C(O), OC(O), NC(O), or S(O)$_2$, and
R is alkyl, heteroalkyl, aryl, or heteroaryl Procedure A: In a 4 mL vial was placed acid chloride or chloroformate or isocyanate or sulfonyl chloride (0.2 mmol, 1.6 eq), followed by a stock solution of (9H-fluoren-9-yl)methyl (3S,4R)-4-((R)-3-(1-(3-methoxypropyl)-1H-benzo[d]imidazol-2-yl)piperidine-1-carbonyl)pyrrolidin-3-ylcarbamate (139E) (75 mg, 0.124 mmol, 1 eq) in 0.8 mL of amylene stabilized chloroform. Then DIEA (0.05 mL, 0.31 mmol, 2.5 eq) was added to the vial, and the reaction mixture was stirred at ambient temperature for 1 hr. Reaction progress was monitored by LC/MS. Chloroform was then removed under vacuum (Savant at low temperature) and 0.6 mL of 10% solution of piperidine in DMF was added to the mixture. After 1 hr solvents were removed under vacuum (Savant at medium temperature). The residue was dissolved in 0.8 mL of DMSO, transferred to 96 well plate and purified using LC-MS based purification (50 mm×10 mm Phenomenex Gemini Column using a 10-100% acetonitrile-water gradient).

Procedure B.

139E

139G where
R is alkyl, heteroalkyl, aryl, or heteroaryl

In a 4 mL vial was added acid (0.2 mmol, 1.6 eq) and a stock solution of (9H-fluoren-9-yl)methyl (3S,4R)-4-((R)-3-(1-(3-methoxypropyl)-1H-benzo[d]imidazol-2-yl)piperidine-1-carbonyl)pyrrolidin-3-ylcarbamate (139E) (75 mg, 0.124 mmol, 1 eq) in 0.5 mL of amylene stabilized chloroform, followed by stock solution of (benzotriazol-1-yloxy)-tris(dimethylamino)-phosphonium hexafluorophosphate (BOP) (66 mg, 0.15 mmol, 1.2 eq) in 0.3 mL of amylene stabilized chloroform. Then DIEA (0.05 mL, 0.31 mmol, 2.5 eq) was added to the vial, and the reaction mixture was stirred at ambient temperature for 1 hour. Reaction progress was monitored by LC/MS. Chloroform was then removed under vacuum (Savant at low temperature) and 0.6 mL of solution of 10% piperidine in DMF was added to the mixture. After 1 hour solvents were removed under vacuum (Savant at medium temperature). The residue was dissolved in 0.8 mL of DMSO, transferred to 96 well plate and purified using LC-MS based purification (50 mm×10 mm Phenomenex Gemini Column using a 10-100% acetonitrile-water gradient).

Compounds that were prepared according to the General Procedure outlined in Example 138 are listed in Table VII.

TABLE VII

| Compound No. | Structure/Name | ESI-MS: m/z (M + H⁺) |
|---|---|---|
| 337 | 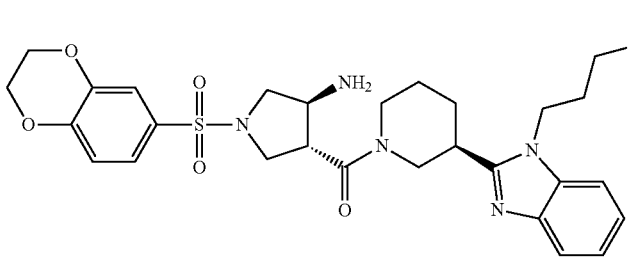<br>((3R,4S)-4-amino-1-(2,3-dihydrobenzo[b][1,4]dioxin-6-ylsulfony)pyrrolidin-3-yl)((R)-3-(1-(3-methoxypropyl)-1H-benzo[d]imidazol-2-yl)piperidin-1-yl)methanone | 584 |
| 338 | 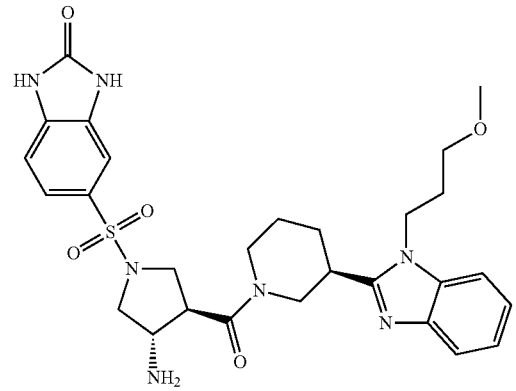<br>5((3S,4R)-3-amino-4((R)-3-(1-3-methoxypropyl)-1H-benzo[d]imidazol-2-yl)piperidine-1-carbonyl)pyrrolidin-1-ylsulfonyl)-1H-benzo[d]imidazol-2(3H)-one | 582 |
| 339 | 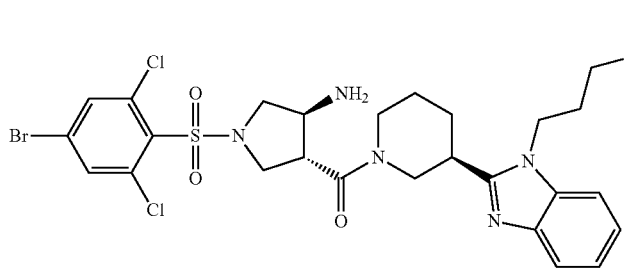<br>((3R,4S)-4-amino-1-(4-bromo-2,6-dichlorophenylsulfonyl)pyrrolidin-3-yl)((R)-3-(1-3-methoxypropyl)-1H-benzo[d]imidazol-2-yl)piperidin-1-yl)methanone | 672 |
| 340 | 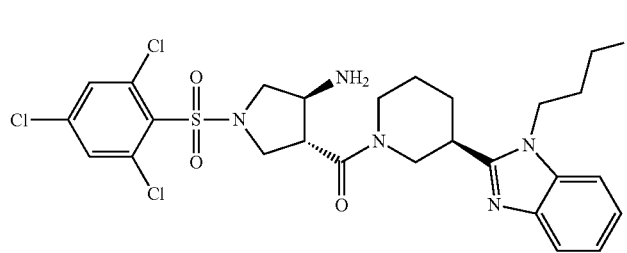<br>((3R,4S)-4-amino-1-(2,4,6-trichlorophenylsulfonyl)pyrrolidin-3-yl)((R)-3-(1(3-methoxypropyl)-1H-benzo[d]imidazol-2-yl)piperidin-1-yl)methanone | 628 |

TABLE VII-continued

| Compound No. | Structure/Name | ESI-MS: m/z (M + H⁺) |
|---|---|---|
| 341 | 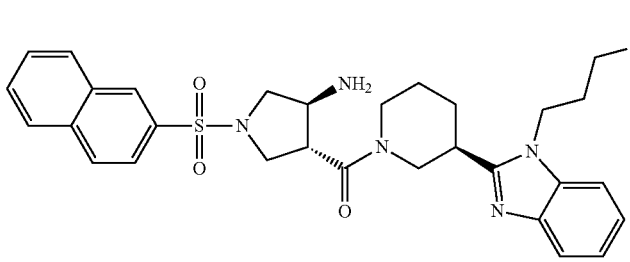<br>((3R,4S)-4-amino-1-(naphthalen-2-ylsulfonyl)pyrrolidin-3-yl)((R)-3-(1-(3-methoxypropyl)-1H-benzo[d]imidazol-2-yl)piperidin-1-yl)methanone | 576 |
| 342 | 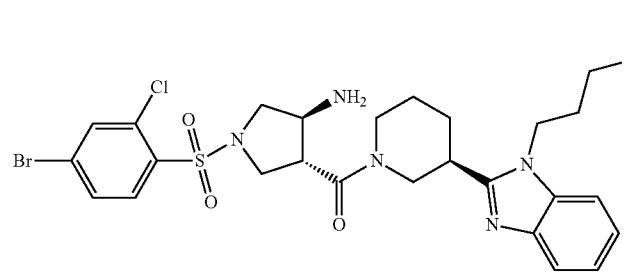<br>((3R,4S)-4-amino-1-(4-bromo-2-chlorophenylsulfonyl)pyrrolidin-3-yl)((R)-3-(1-(3-methoxypropyl)-1H-benzo[d]imidazol-2-yl)piperidin-1-yl)methanone | 638 |
| 343 | 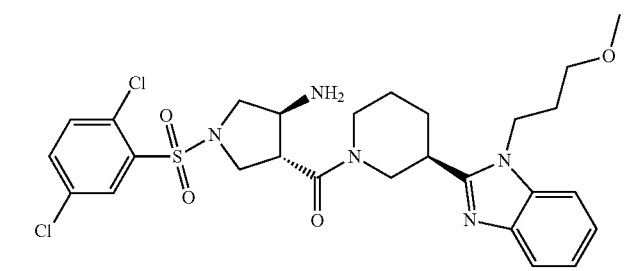<br>((3R,4S)-4-amino-1-(2,5-dichlorophenylsulfonyl)pyrrolidin-3-yl)((R)-3-(1-(3-methoxypropyl)-1H-benzo[d]imidazol-2-yl)piperidin-1-yl)methanone | 594 |
| 344 | 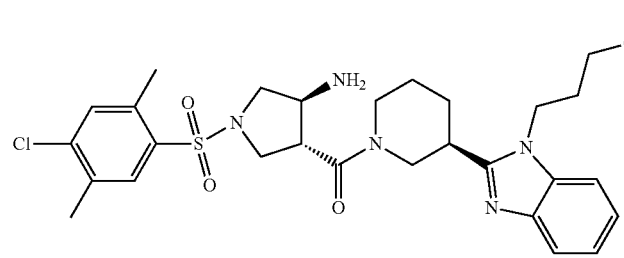<br>((3R,4S)-4-amino-1-(4-chloro-2,5-dimethylphenylsulfonyl)pyrrolidin-3-yl)((R)-3-(1-(3-methoxypropyl)-1H-benzo[d]imidazol-2-yl)piperidin-1-yl)methanone | 588 |

TABLE VII-continued

| Compound No. | Structure/Name | ESI-MS: m/z (M + H⁺) |
|---|---|---|
| 345 | 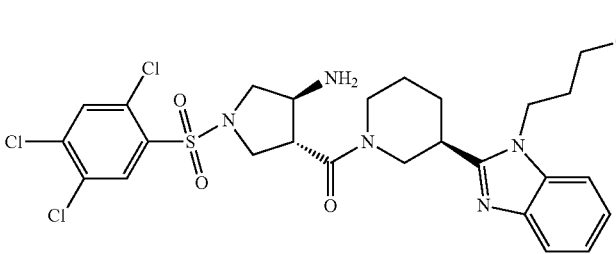<br>((3R,4S)-4-amino-1-(2,4,5-trichlorophenylsulfonyl)pyrrolidin-3-yl)((R)-3-(1-(3-methoxypropyl)-1H-benzo[d]imidazol-2-yl)piperidin-1-yl)methanone | 628 |
| 346 | 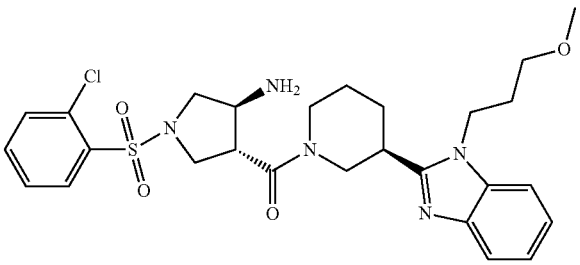<br>((3R,4S)-4-amino-1-(2-chlorophenylsulfonyl)pyrrolidin-3-yl)((R)-3-(1-(3-methoxypropyl)-1H-benzo[d]imidazol-2-yl)piperidin-1-yl)methanone | 560.0 |
| 347 | 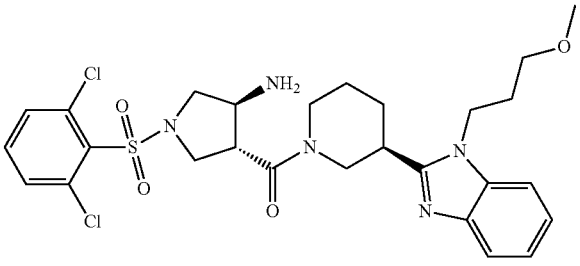<br>((3R,4S)-4-amino-1-(2,6-dichlorophenylsulfonyl)pyrrolidin-3-yl)((R)-3-(1-(3-methoxypropyl)-1H-benzo[d]imidazol-2-yl)piperidin-1-yl)methanone | 594 |
| 348 | 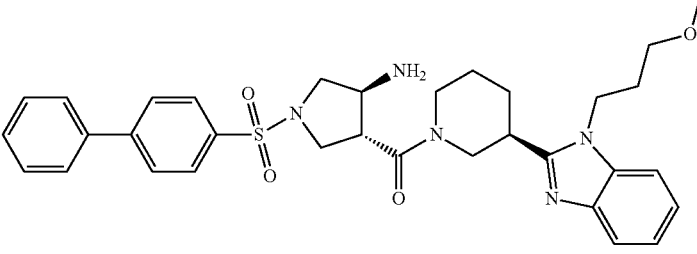<br>((3R,4S)-4-amino-1-(biphenyl-4-ylsulfonyl)pyrrolidin-3-yl)((R)-3-(1-(3-methoxypropyl)-1H-benzo[d]imidazol-2-yl)piperidin-1-yl)methanone | 602 |

| Compound No. | Structure/Name | ESI-MS: m/z (M + H+) |
|---|---|---|
| 349 | ((3R,4S)-4-amino-1-(2-chloro-4-fluorophenylsulfonyl)pyrrolidin-3-yl)((R)-3-(1-(3-methoxypropyl)-1H-benzo[d]imidazol-2-yl)piperidin-1-yl)methanone | 578 |
| 350 | ((3R,4S)-4-amino-1-(2,4-dichlorophenylsulfonyl)pyrrolidin-3-yl)((R)-3-(1-(3-methoxypropyl)-1H-benzo[d]imidazol-2-yl)piperidin-1-yl)methanone | 594 |
| 351 | ((3R,4S)-4-amino-1-(3-chlorophenylsulfonyl)pyrrolidin-3-yl)((R)-3-(1-(3-methoxypropyl)-1H-benzo[d]imidazol-2-yl)piperidin-1-yl)methanone | 560 |
| 352 | ((3R,4S)-4-amino-1-(5-phenylfuran-2-carbonyl)pyrrolidin-3-yl)((R)-3-(1-(3-methoxypropyl)-1H-benzo[d]imidazol-2-yl)piperidin-1-yl)methanone | 556 |

TABLE VII-continued

| Compound No. | Structure/Name | ESI-MS: m/z (M + H⁺) |
|---|---|---|
| 353 | 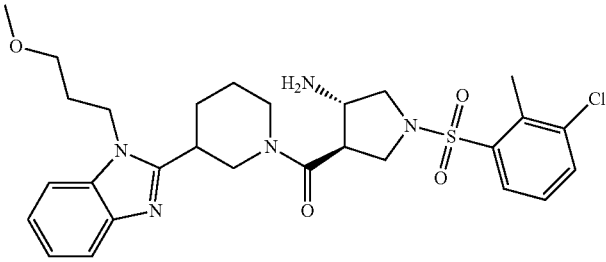<br>((3R,4S)-4-amino-1-(3-chloro-2-methylphenylsulfonyl)pyrrolidin-3-yl)((R)-3-(1-(3-methoxypropyl)-1H-benzo[d]imidazol-2-yl)piperidin-1-yl)methanone | 574 |
| 354 | 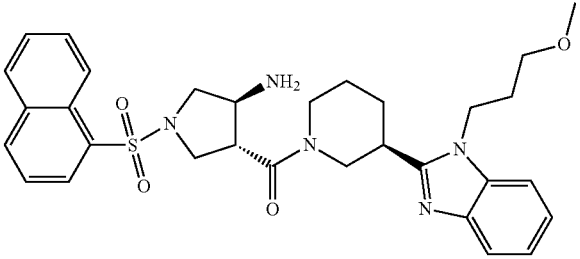<br>((3R,4S)-4-amino-1-(naphthalen-1-ylsulfonyl)pyrrolidin-3-yl)((R)-3-(1-(3-methoxypropyl)-1H-benzo[d]imidazol-2-yl)piperidin-1-yl)methanone | 576 |
| 355 | 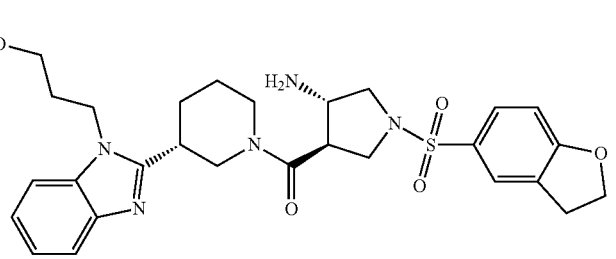<br>((3R,4S)-4-amino-1-(2,3-dihydrobenzofuran-5-ylsulfonyl)pyrrolidin-3-yl)((R)-3-(1-(3-methoxypropyl)-1H-benzo[d]imidazol-2-yl)piperidin-1-yl)methanone | 568 |
| 356 | 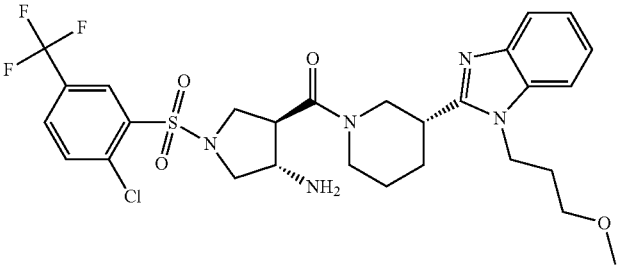<br>((3R,4S)-4-amino-1-(2-chloro-5-(trifluoromethyl)phenylsulfonyl)pyrrolidin-3-yl)((R)-3-(1-(3-methoxypropyl)-1H-benzo[d]imidazol-2-yl)piperidin-1-yl)methanone | 628 |

TABLE VII-continued

| Compound No. | Structure/Name | ESI-MS: m/z (M + H+) |
|---|---|---|
| 357 | ((3R,4S)-4-amino-1-(3-methoxyphenylsulfonyl)pyrrolidin-3-yl)((R)-3-(1-(3-methoxypropyl)-1H-benzo[d]imidazol-2-yl)piperidin-1-yl)methanone | 556.0 |
| 358 | ((3R,4S)-4-amino-1-(3-phenoxybenzoyl)pyrrolidin-3-yl)((R)-3-(1-(3-methoxypropyl)-1H-benzo[d]imidazol-2-yl)piperidin-1-yl)methanone | 582.4 |
| 359 | ((3R,4S)-4-amino-1-(2-chloro-6-methylphenylsulfonyl)pyrrolidin-3-yl)((R)-3-(1-(3-methoxypropyl)-1H-benzo[d]imidazol-2-yl)piperidin-1-yl)methanone | 574 |
| 360 | ((3R,4S)-4-amino-1-(1-methyl-1H-indol-5-ylsulfonyl)pyrrolidin-3-yl)((R)-3-(1-(3-methoxypropyl)-1H-benzo[d]imidazol-2-yl)piperidin-1-yl)methanone | 579 |

TABLE VII-continued

| Compound No. | Structure/Name | ESI-MS: m/z (M + H+) |
|---|---|---|
| 361 | ((3R,4S)-4-amino-1-(3,4-dichlorophenylsulfonyl)pyrrolidin-3-yl)((R)-3-(1-(3-methoxypropyl)-1H-benzo[d]imidazol-2-yl)piperidin-1-yl)methanone | 594.4 |
| 362 | ((3R,4S)-1-(2-naphthoyl)-4-aminopyrrolidin-3-yl)((R)-3-(1-(3-methoxypropyl)-1H-benzo[d]imidazol-2-yl)piperidin-1-yl)methanone | 540.3 |
| 363 | ((3R,4S)-4-amino-1-(2,3-dichlorophenyisulfonyl)pyrrolidin-3-yl)((R)-3-(1-(3-methoxypropyl)-1H-benzo[d]imidazol-2-yl)piperidin-1-yl)methanone | 594 |
| 364 | ((3R,4S)-4-amino-1-(3-(2-methylthiazol-4-yl)phenylsulfonyl)pyrrolidin-3-yl)((R)-3-(1-(3-methoxypropyl)-1H-benzo[d]imidazol-2-yl)piperidin-1-yl)methanone | 623 |

TABLE VII-continued

| Compound No. | Structure/Name | ESI-MS: m/z (M + H⁺) |
|---|---|---|
| 365 | 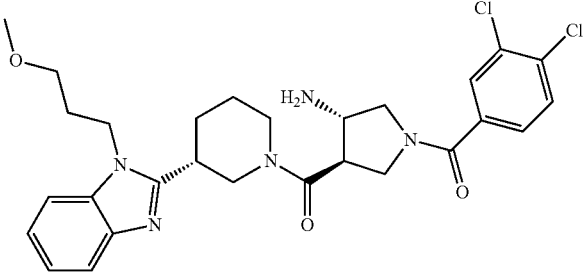<br>((3R,4S)-4-amino-1-(3,4-dichlorobenzoyl)pyrrolidin-3-yl)((R)-3-(1-(3-methoxypropyl)-1H-benzo[d]imidazol-2-yl)piperidin-1-yl)methanone | 558.0 |
| 366 | 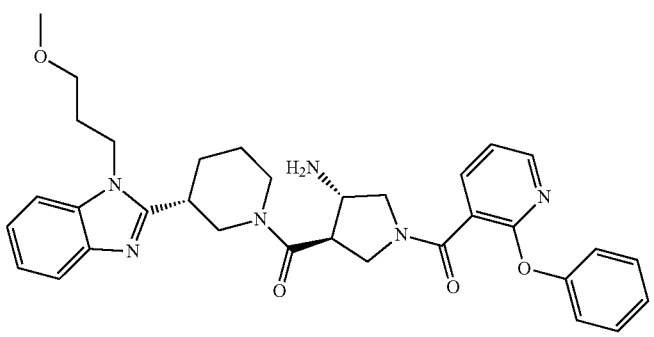<br>((3R,4S)-4-amino-1-(2-phenoxynicotinoyl)pyrrolidin-3-yl)((R)-3-(1-(3-methoxypropyl)-1H-benzo[d]imidazol-2-yl)piperidin-1-yl)methanone | 583.2 |
| 367 | 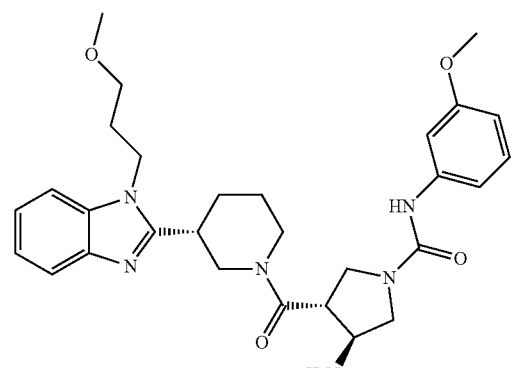<br>(3S,4R)-3-amino-N-(3-methoxyphenyl)-4-((R)-3-(1-(3-methoxypropyl)-1H-benzo[d]imidazol-2-yl)piperidine-1-carbonyl)pyrrolidine-1-carboxamide | 535.3 |
| 368 | 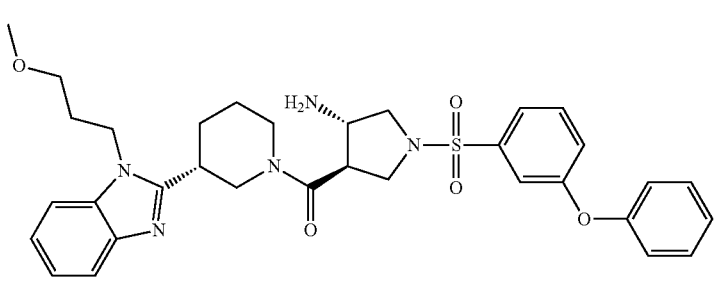<br>((3R,4S)-4-amino-1-(3-phenoxyphenylsulfonyl)pyrrolidin-3-yl)((R)-3-(1-(3-methoxypropyl)-1H-benzo[d]imidazol-2-yl)piperidin-1-yl)methanone | 618 |

| Compound No. | Structure/Name | ESI-MS: m/z (M + H⁺) |
|---|---|---|
| 369 | 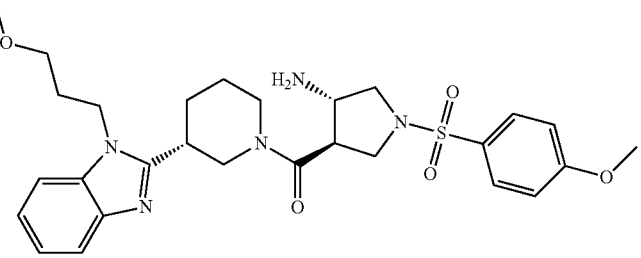<br>((3R,4S)-4-amino-1-(4-methoxyphenylsulfonyl)pyrrolidin-3-yl)((R)-3-(1-(3-methoxypropyl)-1H-benzo[d]imidazol-2-yl)piperidin-1-yl)methanone | 556.0 |
| 370 | 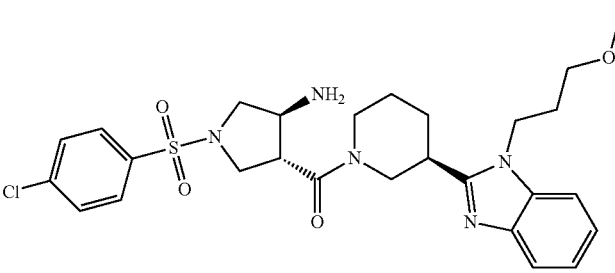<br>((3R,4S)-4-amino-1-(4-chlorophenylsulfonyl)pyrrolidin-3-yl)((R)-3-(1-(3-methoxypropyl)-1H-benzo[d]imidazol-2-yl)piperidin-1-yl)methanone | 560.0 |
| 371 | 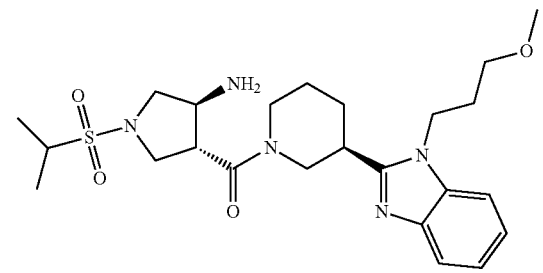<br>((3R,4S)-4-amino-1-(isopropylsulfonyl)pyrrolidin-3-yl)((R)-3-(1-(3-methoxypropyl)-1H-benzo[d]imidazol-2-yl)piperidin-1-yl)methanone | 492.3 |
| 372 | 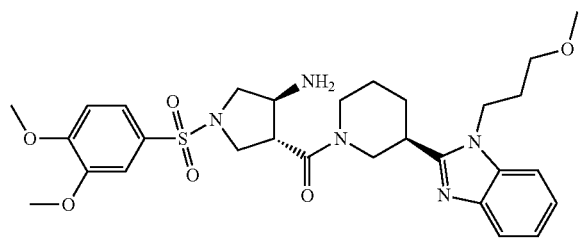<br>((3R,4S)-4-amino-1-(3,4-dimethoxyphenylsulfonyl)pyrrolidin-3-yl)((R)-3-(1-(3-methoxypropyl)-1H-benzo[d]imidazol-2-yl)piperidin-1-yl)methanone | 586 |

TABLE VII-continued

| Compound No. | Structure/Name | ESI-MS: m/z (M + H+) |
|---|---|---|
| 373 | 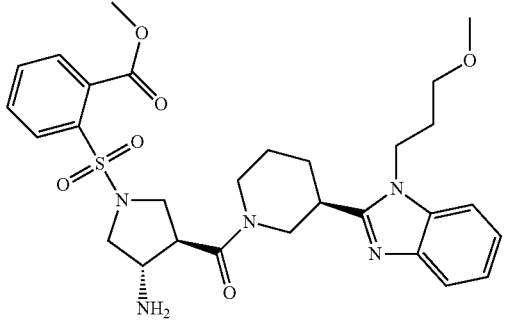 methyl 2-((3S,4R)-3-amino-4-((R)-3-(1-(3-methoxypropyl)-1H-benzo[d]imidazol-2-yl)piperidine-1-carbonyl)pyrrolidin-1-ylsulfonyl)benzoate | 584 |
| 374 | 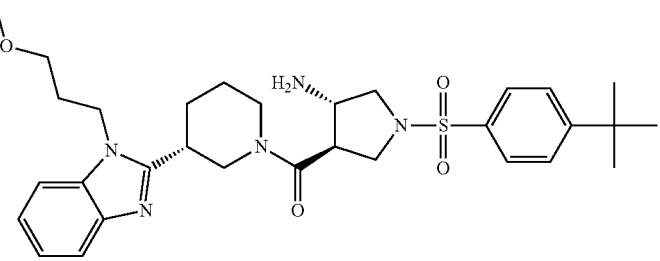 ((3R,4S)-4-amino-1-(4-tert-butylphenylsulfonyl)pyrrolidin-3-yl)((R)-3-(1-(3-methoxypropyl)-1H-benzo[d]imidazol-2-yl)piperidin-1-yl)methanone | 582 |
| 375 | 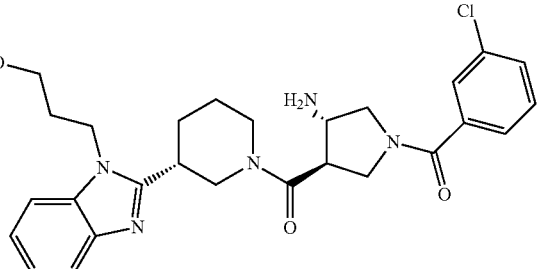 ((3R,4S)-4-amino-1-(3-chlorobenzoyl)pyrrolidin-3-yl)((R)-3-(1-(3-methoxypropyl)-1H-benzo[d]imidazol-2-yl)piperidin-1-yl)methanone | 524.3 |
| 376 | 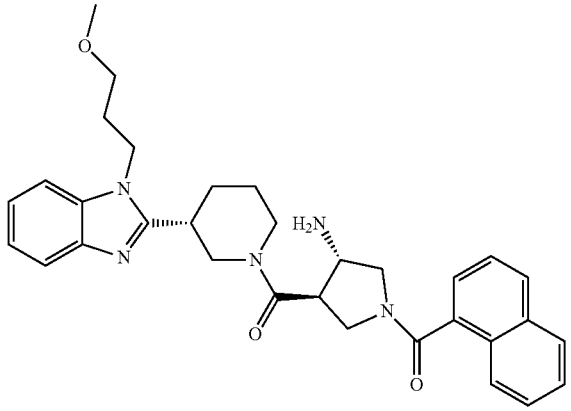 ((3R,4S)-1-(1-naphthoyl)-4-aminopyrrolidin-3-yl)((R)-3-(1-(3-methoxypropyl)-1H-benzo[d]imidazol-2-yl)piperidin-1-yl)methanone | 540.3 |

| Compound No. | Structure/Name | ESI-MS: m/z (M + H⁺) |
|---|---|---|
| 377 | 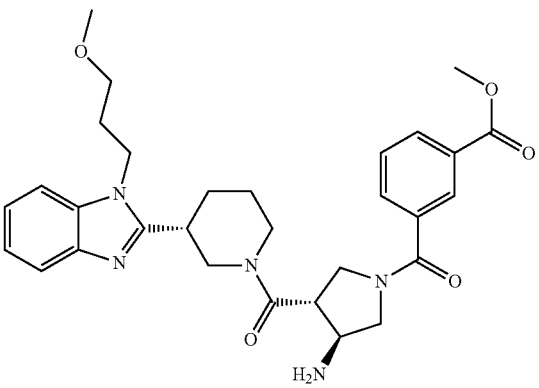

methyl 3-((3S,4R)-3-amino-4-((R)-3-(1-(3-methoxypropyl)-1H-benzo[d]imidazol-2-yl)piperidine-1-carbonyl)pyrrolidine-1-carbonyl)benzoate | 548.3 |
| 378 | 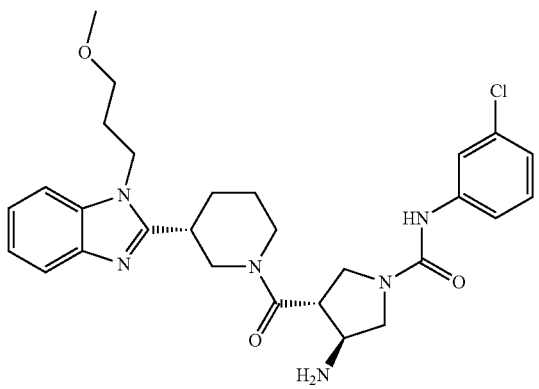

(3S,4R)3-amino-N-(3-chlorophenyl)-4-((R)-3-(1-(3-methoxypropyl)-1H-benzo[d]imidazol-2-yl)piperidine-1-carbonyl)pyrrolidine-1-carboxamide | 539.1 |
| 379 | 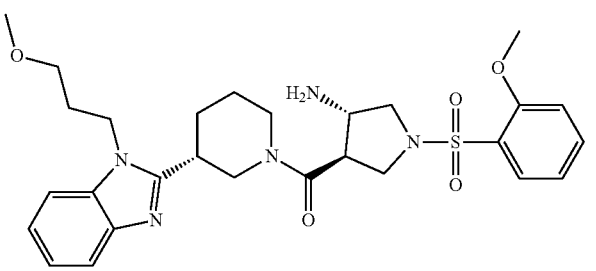

((3R,4S)-4-amino-1-(2-methoxyphenylsulfonyl)pyrrolidin-3-yl)((R)-3-(1-(3-methoxypropyl)-1H-benzo[d]imidazol-2-yl)piperidin-1-yl)methanone | 556.0 |

TABLE VII-continued

| Compound No. | Structure/Name | ESI-MS: m/z (M + H⁺) |
|---|---|---|
| 380 | N-(4-((3S,4R)-3-amino-4-((R)-3-(1-(3-methoxypropyl)-1H-benzo[d]imidazol-2-yl)piperidine-1-carbonyl)pyrrolidin-1-ylsulfonyl)phenyl)acetamide | 583 |
| 381 | ((3R,4S)-4-amino-1-(4-methoxy-2-nitrophenylsulfonyl)pyrrolidin-3-yl)((R)-3-(1-(3-methoxypropyl)-1H-benzo[d]imidazol-2-yl)piperidin-1-yl)methanone | 601 |
| 382 | 1-(4-((3S,4R)-3-amino-4-((R)-3-(1-(3-methoxypropyl)-1H-benzo[d]imidazol-2-yl)piperidine-1-carbonyl)pyrrolidin-1-ylsulfonyl)phenyl)pyrrolidin-2-one | 609 |
| 383 | ((3R,4S)-4-amino-1-(2,4-dimethylphenylsulfonyl)pyrrolidin-3-yl)((R)-3-(1-(3-methoxypropyl)-1H-benzo[d]imidazol-2-yl)piperidin-1-yl)methanone | 554 |

| Compound No. | Structure/Name | ESI-MS: m/z (M + H+) |
|---|---|---|
| 384 | ((3R,4S)-4-amino-1-(phenylsulfonyl)pyrrolidin-3-yl)((R)-3-(1-(3-methoxypropyl)-1H-benzo[d]imidazol-2-yl)piperidin-1-yl)methanone | 526.3 |
| 385 | ((3R,4S)-4-amino-1-benzoylpyrrolidin-3-yl)((R)-3-(1-(3-methoxypropyl)-1H-benzo[d]imidazol-2-yl)piperidin-1-yl)methanone | 490.3 |
| 386 | (3S,4R)-3-amino-N-cyclohexyl-4-((R)-3-(1-(3-methoxypropyl)-1H-benzo[d]imidazol-2-yl)piperidine-1-carbonyl)pyrrolidine-1-carboxamide | 511.5 |
| 387 | ((3R,4S)-4-amino-1-(2-methoxybenzoyl)pyrrolidin-3-yl)((R)-3-(1-(3-methoxypropyl)-1H-benzo[d]imidazol-2-yl)piperidin-1-yl)methanone | 520.3 |

TABLE VII-continued

| Compound No. | Structure/Name | ESI-MS: m/z (M + H+) |
|---|---|---|
| 388 | 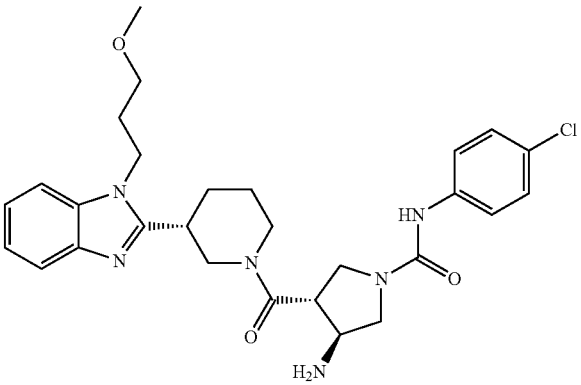 (3S,4R)-3-amino-N-(4-chlorophenyl)-4-((R)-3-(1-(3-methoxypropyl)-1H-benzo[d]imidazol-2-yl)piperidine-1-carbonyl)pyrrolidine-1-carboxamide | 539.1 |
| 389 | 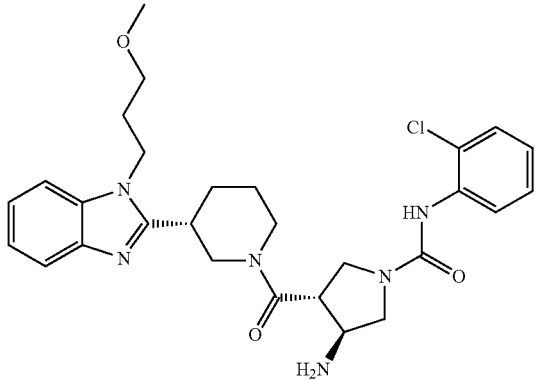 (3S,4R)-3-amino-N-(2-chlorophenyl)-4-((R)-3-(1-(3-methoxypropyl)-1H-benzo[d]imidazol-2-yl)piperidine-1-carbonyl)pyrrolidine-1-carboxamide | 539.1 |
| 390 | 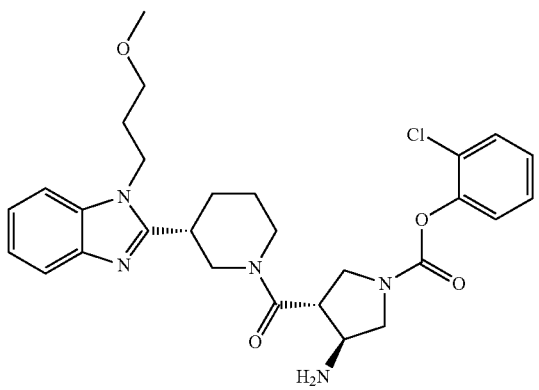 (3S,4R)-2-chlorophenyl 3-amino-4-((R)-3-(1-(3-methoxypropyl)-1H-benzo[d]imidazol-2-yl)piperidine-1-carbonyl)pyrrolidine-1-carboxylate | ND |

TABLE VII-continued

| Compound No. | Structure/Name | ESI-MS: m/z (M + H⁺) |
|---|---|---|
| 391 | 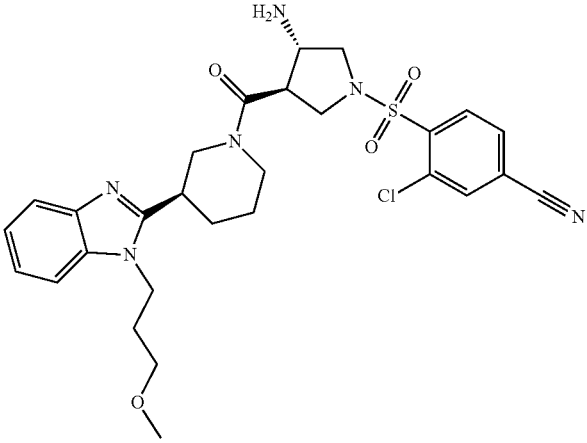
4-((3S,4R)-3-amino-4-((R)-3-(1-(3-methoxypropyl)-1H-benzo[d]imidazol-2-yl)piperidine-1-carbonyl)pyrrolidin-1-ylsulfonyl)-3-chlorobenzonitrile | 585 |
| 392 | 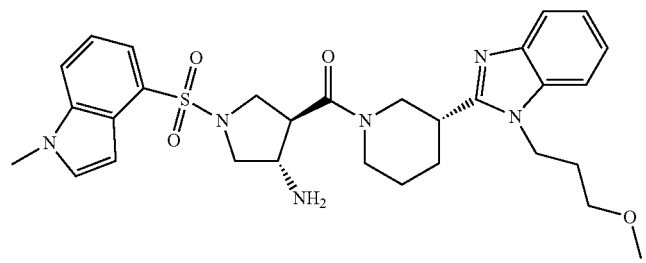
((3R,4S)-4-amino-1-(1-methyl-1H-indol-4-ylsulfonyl)pyrrolidin-3-yl)((R)-3-(1-(3-methoxypropyl)-1H-benzo[d]imidazol-2-yl)piperidin-1-yl)methanone | 579 |
| 393 | 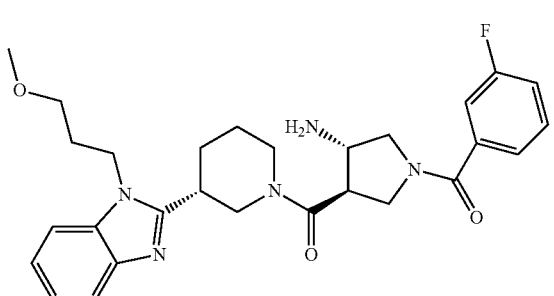
((3R,4S)-4-amino-1-(3-fluorobenzoyl)pyrrolidin-3-yl)((R)-3-(1-(3-methoxypropyl)-1H-benzo[d]imidazol-2-yl)piperidin-1-yl)methanone | 508.3 |
| 394 | 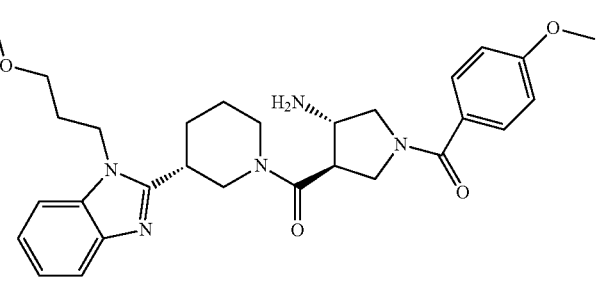
((3R,4S)-4-amino-1-(4-methoxybenzoyl)pyrrolidin-3-yl)((R)-3-(1-(3-methoxypropyl)-1H-benzo[d]imidazol-2-yl)piperidin-1-yl)methanone | 520.3 |

TABLE VII-continued

| Compound No. | Structure/Name | ESI-MS: m/z (M + H⁺) |
|---|---|---|
| 395 | 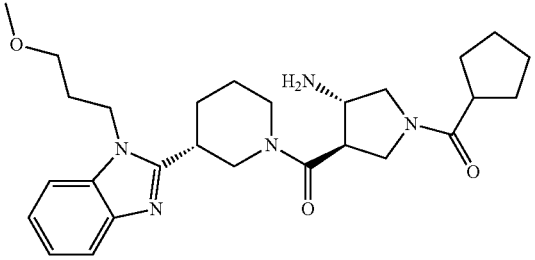 ((3R,4S)-4-amino-1-(cyclopentanecarbonyl)pyrrolidin-3-yl)((R)-3-(1-(3-methoxypropyl)-1H-benzo[d]imidazol-2-yl)piperidin-1-yl)methanone | 482.3 |
| 396 | 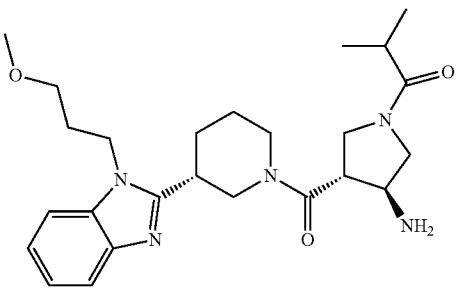 1-((3S,4R)-3-amino-4-((R)-3-(1-(3-methoxypropyl)-1H-benzo[d]imidazol-2-yl)piperidine-1-carbonyl)pyrrolidin-1-yl)-2-methylpropan-1-one | 456.3 |
| 397 | 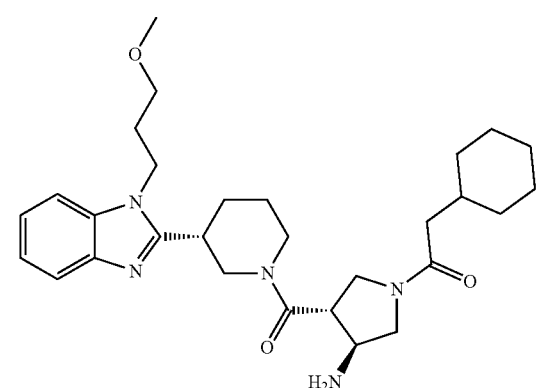 1-((3S,4R)-3-amino-4-((R)-3-(1-(3-methoxypropyl)-1H-benzo[d]imidazol-2-yl)piperidine-1-carbonyl)pyrrolidin-1-yl)-2-cyclohexylethanone | 510.3 |
| 398 | 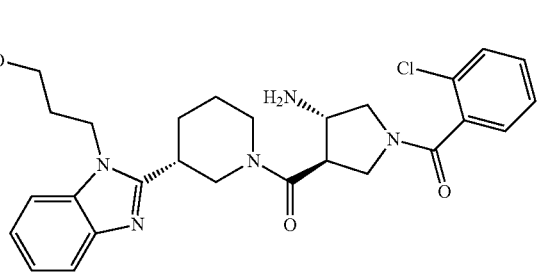 ((3R,4S)-4-amino-1-(2-chlorobenzoyl)pyrrolidin-3-yl)((R)-3-(1-(3-methoxypropyl)-1H-benzo[d]imidazol-2-yl)piperidin-1-yl)methanone | 524.3 |

| Compound No. | Structure/Name | ESI-MS: m/z (M + H⁺) |
|---|---|---|
| 399 | 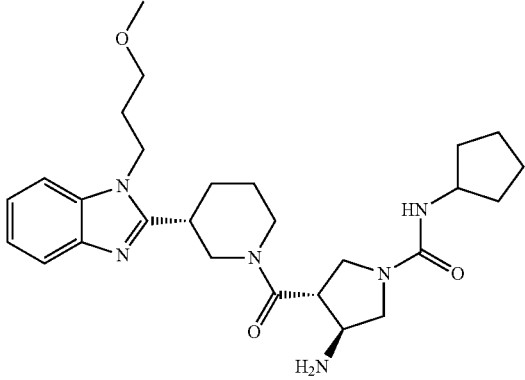<br>(3S,4R)-3-amino-N-cyclopentyl-4-((R)-3-(1-(3-methoxypropyl)-1H-benzo[d]imidazol-2-yl)piperidine-1-carbonyl)pyrrolidine-1-carboxamide | 497.5 |
| 400 | 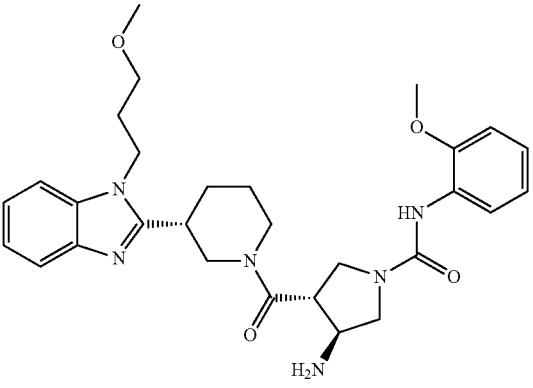<br>(3S,4R)-3-amino-N-(2-methoxyphenyl)-4-((R)-3-(1-(3-methoxypropyl)-1H-benzo[d]imidazol-2-yl)piperidine-1-carbonyl)pyrrolidine-1-carboxamide | 535.1 |
| 401 | 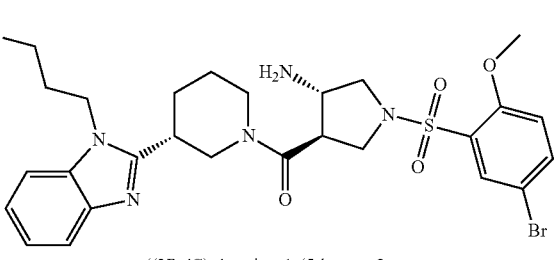<br>((3R,4S)-4-amino-1-(5-bromo-2-methoxyphenylsulfonyl)pyrrolidin-3-yl)((R)-3-(1-(3-methoxypropyl)-1H-benzo[d]imidazol-2-yl)piperidin-1-yl)methanone | 634 |

TABLE VII-continued

| Compound No. | Structure/Name | ESI-MS: m/z (M + H+) |
|---|---|---|
| 402 | ((3R,4S)-4-amino-1-(2-(trifluoromethyl)phenylsulfonyl)pyrrolidin-3-yl)((R)-3-(1-(3-methoxypropyl)-1H-benzo[d]imidazol-2-yl)piperidin-1-yl)methanone | 594 |
| 403 | 2-((3S,4R)-3-amino-4-((R)-3-(1-(3-methoxypropyl)-1H-benzo[d]imidazol-2-yl)piperidine-1-carbonyl)pyrrolidin-1-ylsulfonyl)-4-methylbenzonitrile | 565 |
| 404 | (3S,4R)-3-amino-4-((R)-3-(1-(3-methoxypropyl)-1H-benzo[d]imidazol-2-yl)piperidine-1-carbonyl)-N-phenylpyrrolidine-1-carboxamide | 505.1 |
| 405 | ((3R,4S)-4-amino-1-(cyclohexanecarbonyl)pyrrolidin-3-yl)((R)-3-(1-(3-methoxypropyl)-1H-benzo[d]imidazol-2-yl)piperidin-1-yl)methanone | 496.3 |

TABLE VII-continued

| Compound No. | Structure/Name | ESI-MS: m/z (M + H+) |
|---|---|---|
| 406 | 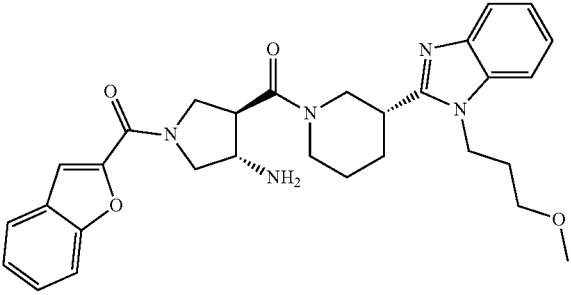((3R,4S)-4-amino-1-(benzofuran-2-carbonyl)pyrrolidin-3-yl)((R)-3-(1-(3-methoxypropyl)-1H-benzo[d]imidazol-2-yl)piperidin-1-yl)methanone | 530.3 |
| 407 | 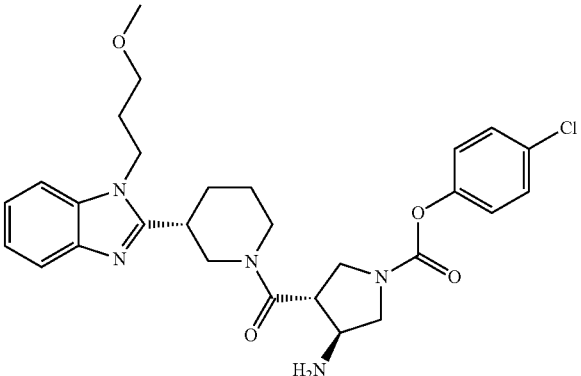(3S,4R)-4-chlorophenyl 3-amino-4-((R)-3-(1-(3-methoxypropyl)-1H-benzo[d]imidazol-2-yl)piperidine-1-carbonyl)pyrrolidine-1-carboxylate | 540.3 |
| 408 | 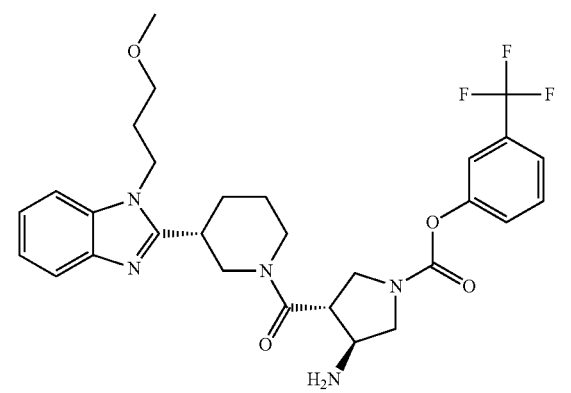(3S,4R)-3-(trifluoromethyl)phenyl 3-amino-4-((R)-3-(1-(3-methoxypropyl)-1H-benzo[d]imidazol-2-yl)piperidine-1-carbonyl)pyrrolidine-1-carboxylate | 574.4 |

| Compound No. | Structure/Name | ESI-MS: m/z (M + H⁺) |
|---|---|---|
| 409 | ((3R,4S)-4-amino-1-(3-(5-methyl-1,2,4-oxadiazol-3-yl)phenylsulfonyl)pyrrolidin-3-yl)((R)-3-(1-(3-methoxypropyl)-1H-benzo[d]imidazol-2-yl)piperidin-1-yl)methanone | 608 |
| 410 | ((3R,4S)-4-amino-1-(2-methoxy-5-methylphenylsulfonyl)pyrrolidin-3-yl)((R)-3-(1-(3-methoxypropyl)-1H-benzo[d]imidazol-2-yl)piperidin-1-yl)methanone | 570 |
| 411 | ((3R,4S)-4-amino-1-(2-methoxy-4-nitrophenylsulfonyl)pyrrolidin-3-yl)((R)-3-(1-(3-methoxypropyl)-1H-benzo[d]imidazol-2-yl)piperidin-1-yl)methanone | 601 |
| 412 | ((3R,4S)-4-amino-1-(5-chloro-2-methoxyphenylsulfonyl)pyrrolidin-3-yl)((R)-3-(1-(3-methoxypropyl)-1H-benzo[d]imidazol-2-yl)piperidin-1-yl)methanone | 590 |

TABLE VII-continued

| Compound No. | Structure/Name | ESI-MS: m/z (M + H+) |
|---|---|---|
| 413 | 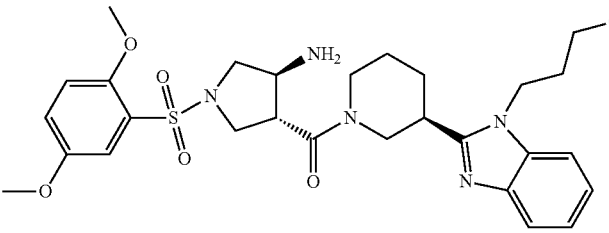((3R,4S)-4-amino-1-(2,5-dimethoxyphenylsulfonyl)pyrrolidin-3-yl)((R)-3-(1-(3-methoxypropyl)-1H-benzo[d]imidazol-2-yl)piperidin-1-yl)methanone | 586 |
| 414 | 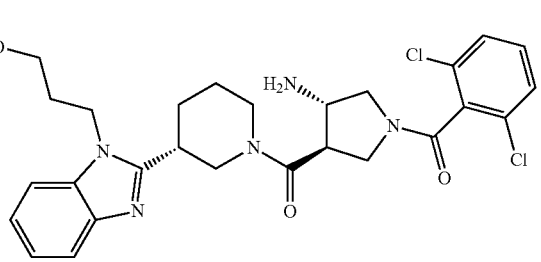((3R,4S)-4-amino-1-(2,6-dichlorobenzoyl)pyrrolidin-3-yl)((R)-3-(1-(3-methoxypropyl)-1H-benzo[d]imidazol-2-yl)piperidin-1-yl)methanone | 558.0 |
| 415 | 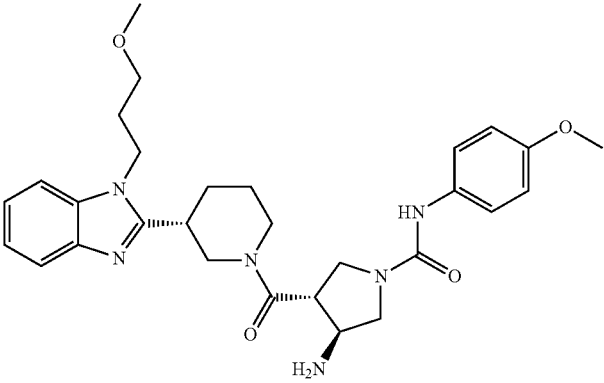(3S,4R)-3-amino-N-(4-methoxyphenyl)-4-((R)-3-(1-(3-methoxypropyl)-1H-benzo[d]imidazol-2-yl)piperidine-1-carbonyl)pyrrolidine-1-carboxamide | 535.1 |
| 416 | 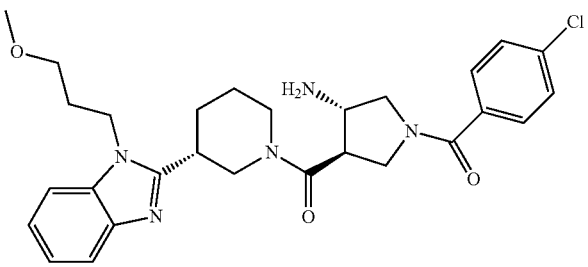((3R,4S)-4-amino-1-(4-chlorobenzoyl)pyrrolidin-3-yl)((R)-3-(1-(3-methoxypropyl)-1H-benzo[d]imidazol-2-yl)piperidin-1-yl)methanone | 524.3 |

TABLE VII-continued

| Compound No. | Structure/Name | ESI-MS: m/z (M + H+) |
|---|---|---|
| 417 | 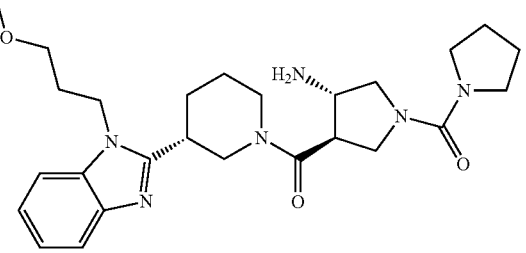((3R,4S)-4-amino-1-(pyrrolidine-1-carbonyl)pyrrolidin-3-yl)((R)-3-(1-(3-methoxypropyl)-1H-benzo[d]imidazol-2-yl)piperidin-1-yl)methanone | 483.5 |
| 418 | 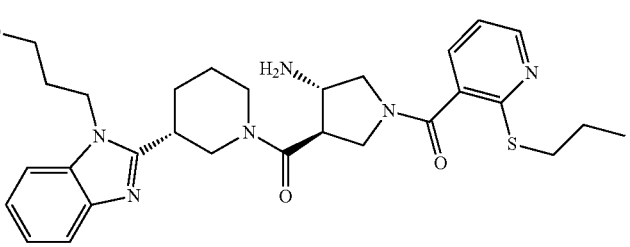((3R,4S)-4-amino-1-(2-(propylthio)nicotinoyl)pyrrolidin-3-yl)((R)-3-(1-(3-methoxypropyl)-1H-benzo[d]imidazo]-2-yl)piperidin-1-yl)methanone | 565.6 |
| 419 | 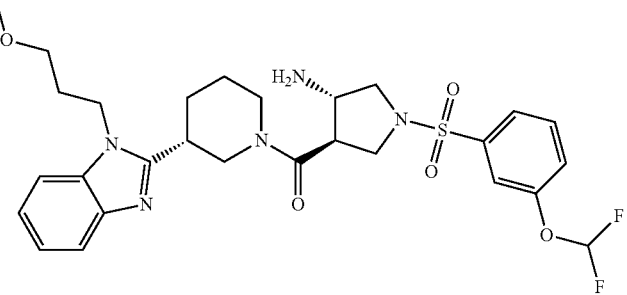((3R,4S)-4-amino-1-(3-(difluoromethoxy)phenylsulfonyl)pyrrolidin-3-yl)((R)-3-(1-(3-methoxypropyl)-1H-benzo[d]imidazol-2-yl)piperidin-1-yl)methanone | 592 |
| 420 | 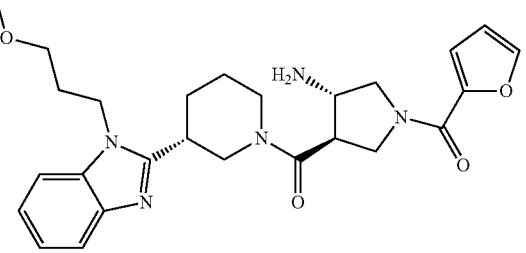((3R,4S)-4-amino-1-(furan-2-carbonyl)pyrrolidin-3-yl)((R)-3-(1-(3-methoxypropyl)-1H-benzo[d]imidazol-2-yl)piperidin-1-yl)methanone | 480.3 |

TABLE VII-continued

| Compound No. | Structure/Name | ESI-MS: m/z (M + H⁺) |
|---|---|---|
| 421 | 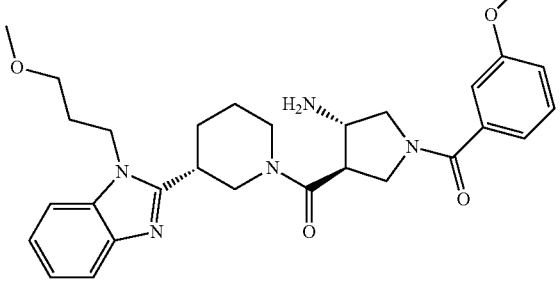<br>((3R,4S)-4-amino-1-(3-methoxybenzoyl)pyrrolidin-3-yl)((R)-3-(1-(3-methoxypropyl)-1H-benzo[d]imidazol-2-yl)piperidin-1-yl)methanone | 520.3 |
| 422 | 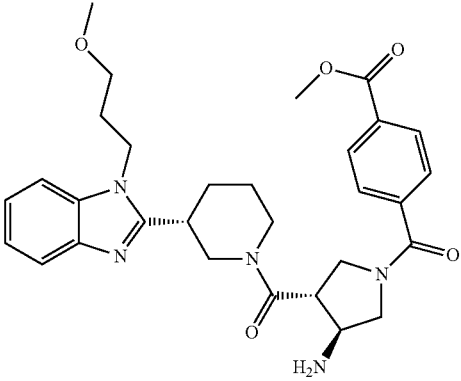<br>methyl 4-((3S,4R)-3-amino-4-((R)-3-(1-(3-methoxypropyl)-1H-benzo[d]imidazol-2-yl)piperidine-1-carbonyl)pyrrolidine-1-carbonyl)benzoate | 548.3 |
| 423 | 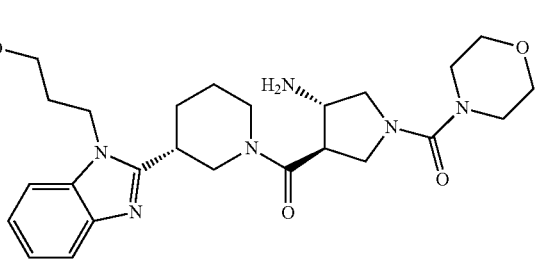<br>((3R,4S)-4-amino-1-(morpholine-4-carbonyl)pyrrolidin-3-yl)((R)-3-(1-(3-methoxypropyl)-1H-benzo[d]imidazol-2-yl)piperidin-1-yl)methanone | 499.1 |
| 424 | 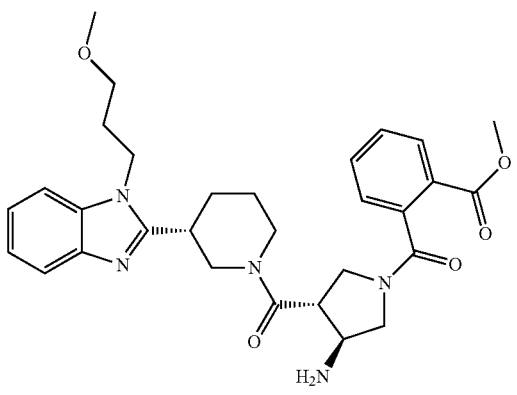<br>methyl 2-((3S,4R)-3-amino-4-((R)-3-(1-(3-methoxypropyl)-1H-benzo[d]imidazol-2-yl)piperidine-1-carbonyl)pyrrolidine-1-carbonyl)benzoate | 548.3 |

TABLE VII-continued

| Compound No. | Structure/Name | ESI-MS: m/z (M + H⁺) |
|---|---|---|
| 425 | ((3R,4S)-4-amino-1-(2,6-dichlorophenylsulfonyl)pyrrolidin-3-yl)((R)-3-(1-(3-methoxypropyl)-1H-benzo[d]imidazol-2-yl)piperidin-1-yl)methanone | 594 |
| 426 | ((3R,4S)-4-amino-1-(2,6-difluorophenylsulfonyl)pyrrolidin-3-yl)((R)-3-(1-(3-methoxypropyl)-1H-benzo[d]imidazol-2-yl)piperidin-1-yl)methanone | 562 |
| 427 | 2-((3S,4R)-3-amino-4-((R)-3-(1-(3-methoxypropyl)-1H-benzo[d]imidazol-2-yl)piperidine-1-carbonyl)pyrrolidin-1-ylsulfonyl)benzonitrile | 551 |
| 428 | ((3R,4S)-4-amino-1-(3-fluorophenylsulfonyl)pyrrolidin-3-yl)((R)-3-(1-(3-methoxypropyl)-1H-benzo[d]imidazol-2-yl)piperidin-1-yl)methanone | 544 |

TABLE VII-continued

| Compound No. | Structure/Name | ESI-MS: m/z (M + H⁺) |
|---|---|---|
| 429 | 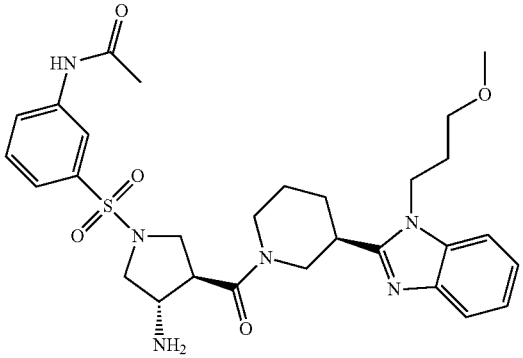<br>N-(3-((3S,4R)-3-amino-4-((R)-3-(1-(3-methoxypropyl)-1H-benzo[d]imidazol-2-yl)piperidine-1-carbonyl)pyrrolidin-1-ylsulfonyl)phenyl)acetamide | 583 |
| 430 | 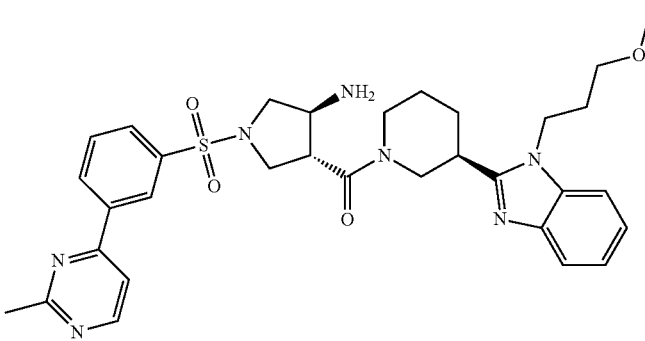<br>((3R,4S)-4-amino-1-(3-(2-methylpyrimidin-4-yl)phenylsulfonyl)pyrrolidin-3-yl)((R)-3-(1-(3-methoxypropyl)-1H-benzo[d]imidazol-2-yl)piperidin-1-yl)methanone | 618 |
| 431 | 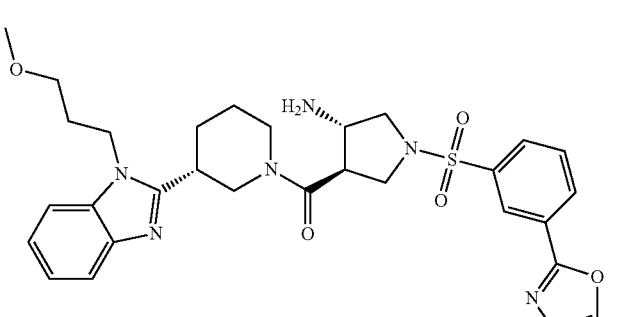<br>((3R,4S)-4-amino-1-(3-(5-methyl-1,3,4-oxadiazol-2-yl)phenylsulfonyl)pyrrolidin-3-yl)((R)-3-(1-(3-methoxypropyl)-1H-benzo[d]imidazol-2-yl)piperidin-1-yl)methanone | 608 |

Example 140
General Procedure for the Synthesis of Derivatives of (S)-3-amino-4-hydroxy-1-((R)-3-(1-(3-methoxypropyl)-1H-benzo[d]imidazol-2-yl)piperidin-1-yl)butan-1-one (140E)
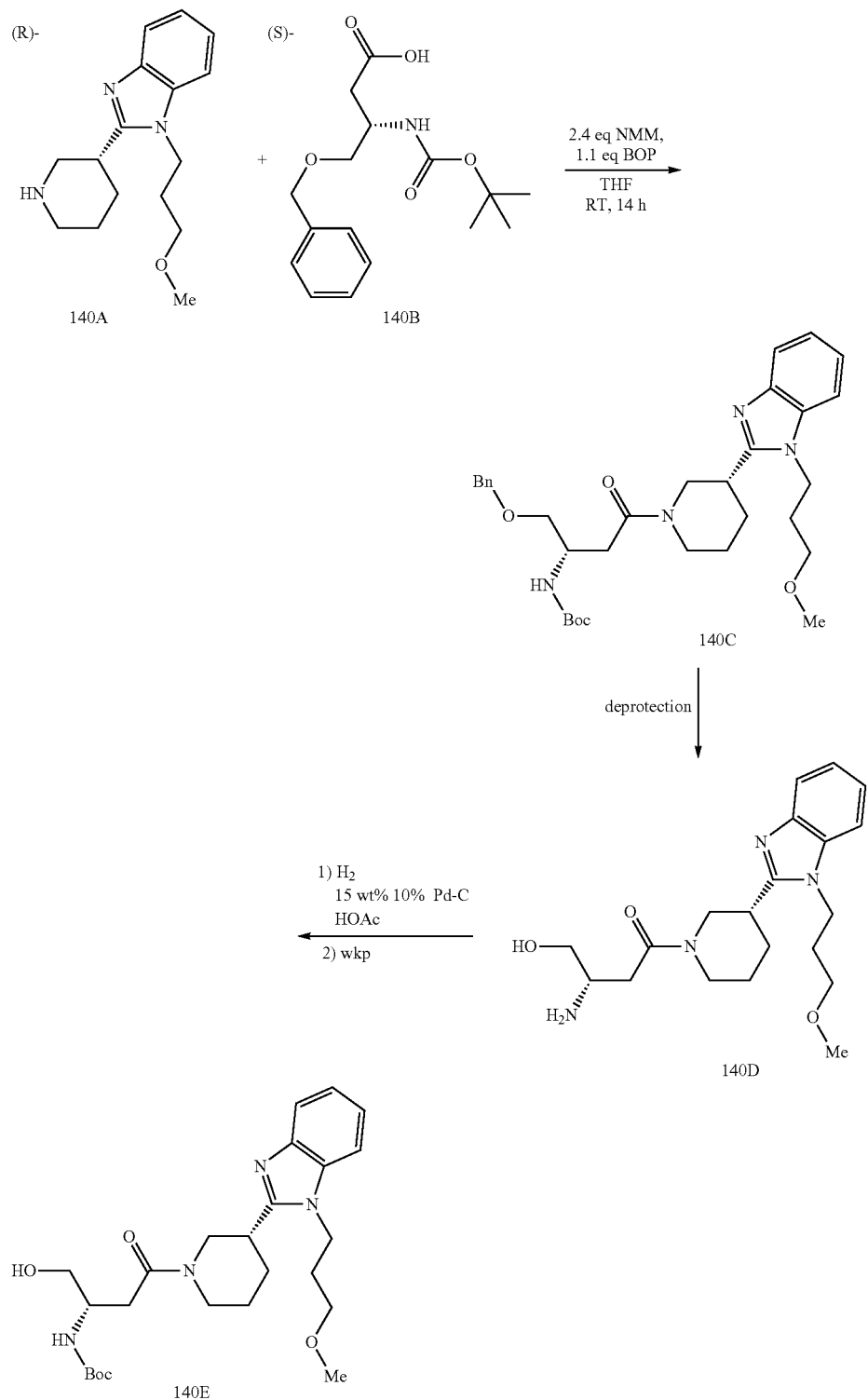

The piperidine, ((R)-1-(3-methoxypropyl)-2-(piperidin-3-yl)-1H-benzo[d]imidazole) (140A), was acylated with the homoserine acid, ((S)-4-(benzyloxy)-3-(tert-butoxycarbonylamino)butanoic acid) (140B) (3.4 g), using the standard BOP coupling procedure of Example 139, Step C, Procedure B. The deprotection of O-benzyl group 140C was performed according to standard hydrogenation procedure (20 wt % of 10% Pd—C, HOAc, H₂ (1 atm), 20° C., 18-36 hrs) to yield the free alcohol tert-butyl (S)-1-hydroxy-4-((R)-3-(1-(3-methoxypropyl)-1H-benzo[d]imidazol-2-yl)piperidin-1-yl)-4-oxobutan-2-ylcarbamate (140D). ESI-MS: m/z 475.5.

The benzyl ether amide material 140O (3.16 g, 5.6 mmol) was dissolved in AcOH (10% soln; 32 mL) under nitrogen, and then 10% palladium on activated carbon (1.26 g, 20 wt %) was added. The reaction mixture was stirred vigorously under a balloon of hydrogen (kept full) at room temperature overnight. Reaction progress was monitored by LC/MS. Once completed (18-36 h), the black mixture was filtered through Celite with additional MeOH washing, and the solvents were evaporated to dryness. This residue was taken up in EtOAc (~100 mL), washed with saturated NaHCO₃ (3×30 mL), and saturated NaCl (2×15 mL), and dried (Na₂SO₄). The organic phase was filtered and then evaporated (up to 45° C.) and placed on full vacuum to yield tert-butyl (S)-1-hydroxy-4-((R)-3-(1-(3-methoxypropyl)-1H-benzo[d]imidazol-2-yl)piperidin-1-yl)-4-oxobutan-2-ylcarbamate 140E (1.3 g) as a clear foaming glass. ESI-MS: m/z 475.5 (MH+). ¹H NMR (400 MHz, MeOH-d₄) δ ppm 1.66 (m, 1H) 1.7-2.3 (m, 5H) 4.21-4.25 (m, 2H) 7.1-7.6 (m, 8H). HPLC retention time, T=0.725 min, STDTFA-2 method.

Step B.

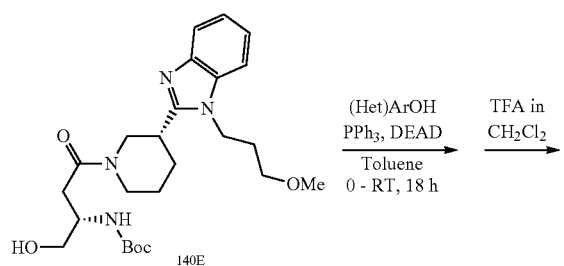

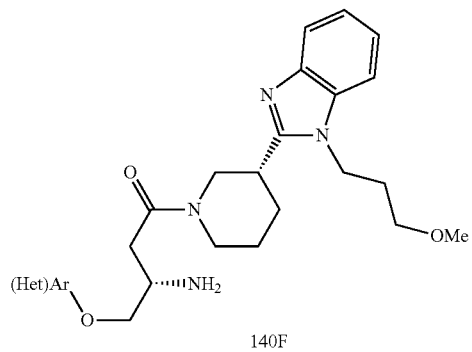

140F

Derivatives 140F were prepared using Mitsunobu conditions in a 0.115 mmol scale of 140E, followed by Boc-deprotection with mixture of TFA/CH₂Cl₂ (1:1).

In a 4 mL vial was added the phenol (0.23 mmol, 2 eq), triphenylphosphine (60 mg, 0.23 mmol, 2 eq) and a stock solution of tert-butyl (S)-1-hydroxy-4-((R)-3-(1-(3-methoxypropyl)-1H-benzo[d]imidazol-2-yl)piperidin-1-yl)-4-oxobutan-2-ylcarbamate (140E) (55 mg, 0.115 mmol, 1 eq) in 0.5 mL of toluene. To this solution at 0° C. was quickly added under nitrogen the diethylazodicarboxylate (40 mg, 0.23 mmol, 2.0 eq). The reaction mixture was stirred at ambient temperature overnight. Reaction progress was monitored by LC/MS. The reaction was diluted with EtOAc (2 mL) and washed with saturated NaHCO₃ (2×1 mL), dried with (Na₂SO₄), filtered and evaporated yielding the N-protected compound.

To this residue was added 0.6 mL of solution of TFA/CH₂Cl₂ (1:1). After 1 hour solvents were removed under vacuum (Savant at low temperature). The residue was dissolved in 0.8 mL of DMSO, transferred to 96 well plate and purified using LC-MS based purification (50 mm×10 mm Phenomenex Gemini Column using a 10-100% acetonitrile-water gradient) to yield 140F.

Compounds prepared according to the synthesis procedure outlined in Example 140 are listed in Table VIII.

TABLE VIII

| Compound No. | Structure/Name | ESI-MS: m/z (M + H⁺) |
|---|---|---|
| 432 | methyl 2-((R)-2-amino-4-((R)-3-(1-(3-methoxypropyl)-1H-benzo[d]imidazol-2-yl)piperidin-1-yl)-4-oxobutoxy)benzoate | 509 |

TABLE VIII-continued

| Compound No. | Structure/Name | ESI-MS: m/z (M + H+) |
|---|---|---|
| 433 | (R)-3-amino-4-(3-methoxyphenoxy)-1-((R)-3-(1-(3-methoxypropyl)-1H-benzo[d]imidazol-2-yl)piperidin-1-yl)butan-1-one | 481 |
| 434 | (R)-4-(1H-benzo[d]imidazol-2-yloxy)-3-amino-1-((R)-3-(1-(3-methoxypropyl)-1H-benzo[d]imidazol-2-yl)piperidin-1-yl)butan-1-one | 491 |

Table IX below lists other benzimidazole compounds prepared according to the schemes described above.

TABLE IX

| Compound No. | Structure/Name | ESI-MS: m/z (M + H+) |
|---|---|---|
| 435 | (R)-3-amino-4-(4-(2-((S)-3-hydroxypyrrolidin-1-yl)thiazol-4-yl)phenyl)-1-((R)-3-(1-(3-methoxypropyl)-1H-benzo[d]imidazol-2-yl)piperidin-1-yl)butan-1-one | 602.8 |

TABLE IX-continued

| Compound No. | Structure/Name | ESI-MS: m/z (M + H⁺) |
|---|---|---|
| 436 | 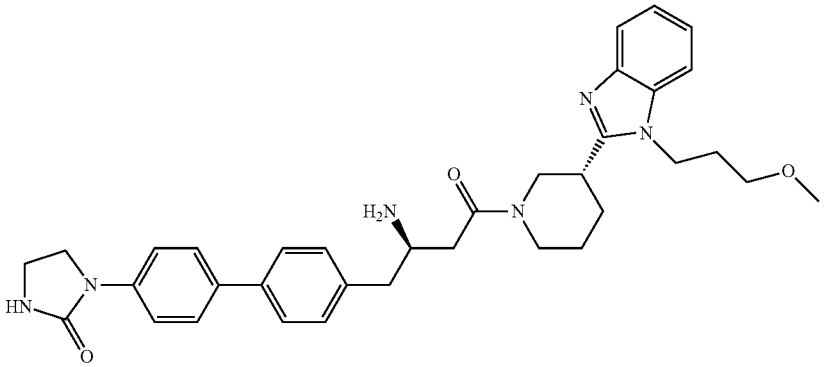<br>1-(4'-((R)-2-amino-4-((R)-3-(1-(3-methoxypropyl)-1H-benzo[d]imidazol-2-yl)piperidin-1-yl)-4-oxobutyl)biphenyl-4-yl)imidazolidin-2-one | 594.8 |
| 437 | 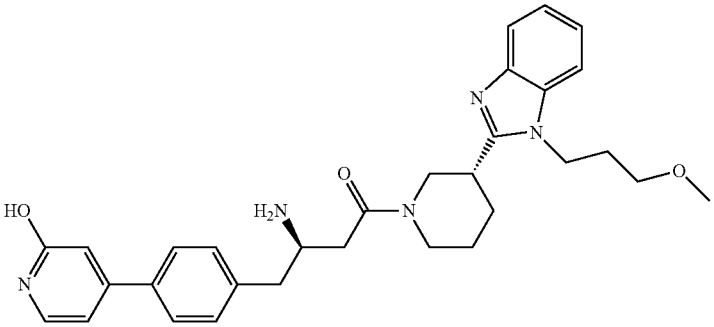<br>(R)-3-amino-4-(4-(2-hydroxypyridin-4-yl)phenyl)-1-((R)-3-(1-(3-methoxypropyl)-1H-benzo[d]imidazol-2-yl)piperidin-1-yl)butan-1-one | 527.7 |
| 438 | 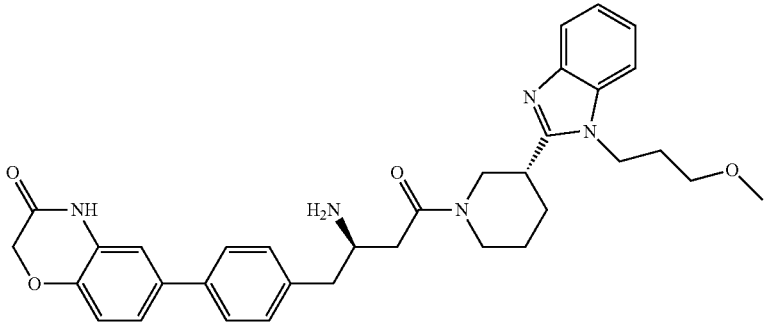<br>6-(4-((R)-2-amino-4-((R)-3-(1-(3-methoxypropyl)-1H-benzo[d]imidazol-2-yl)piperidin-1-yl)-4-oxobutyl)phenyl)-2H-benzo[b][1,4]oxazin-3(4H)-one | 581.7 |

TABLE IX-continued

| Compound No. | Structure/Name | ESI-MS: m/z (M + H⁺) |
|---|---|---|
| 439 | 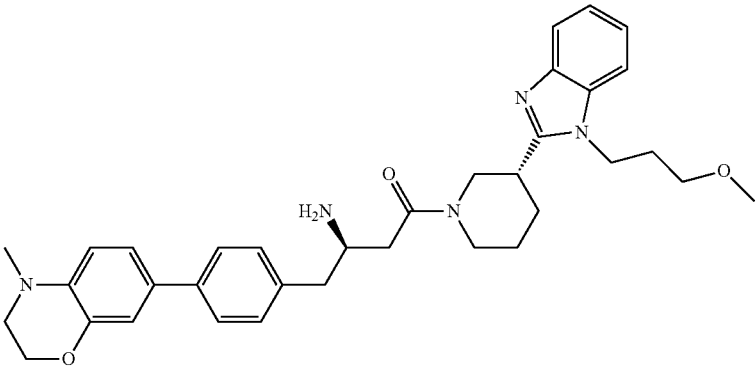<br>(R)-3-amino-1-((R)-3-(1-(3-methoxypropyl)-1H-benzo[d]imidazol-2-yl)piperidin-1-yl)-4-(4-(4-methyl-3,4-dihydro-2H-benzo[b][1,4]oxazin-7-yl)phenyl)butan-1-one | 581.8 |
| 440 | 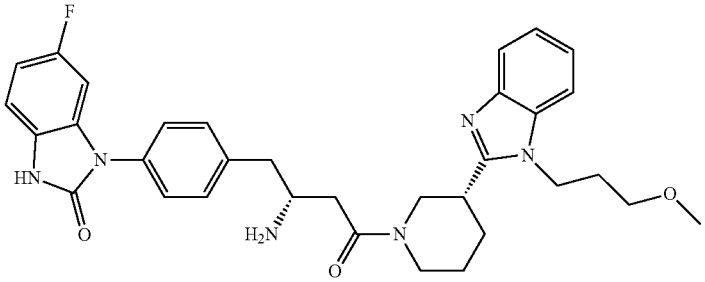<br>1-(4-((R)-2-amino-4-((R)-3-(1-(3-methoxypropyl)-1H-benzo[d]imidazol-2-yl)piperidin-1-yl)-4-oxobutyl)phenyl)-6-fluoro-1H-benzo[d]imidazol-2(3H)-one | 584.7 |
| 441 | 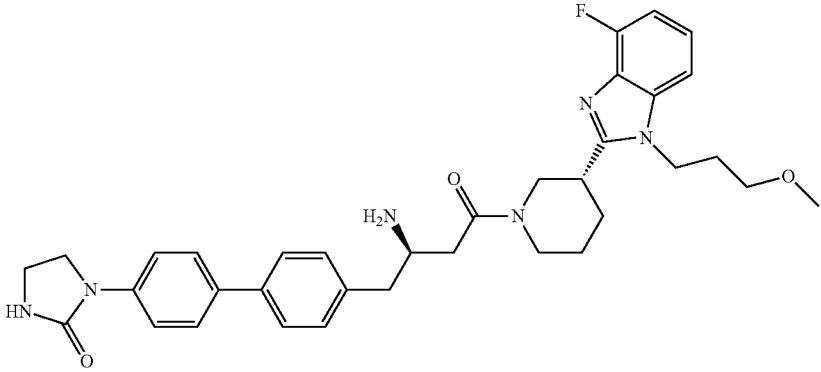<br>1-(4'-((R)-2-amino-4-((R)-3-(4-fluoro-1-(3-methoxypropyl)-1H-benzo[d]imidazol-2-yl)piperidin-1-yl)-4-oxobutyl)biphenyl-4-yl)imidazolidin-2-one | 612.7 |

TABLE IX-continued

| Compound No. | Structure/Name | ESI-MS: m/z (M + H+) |
|---|---|---|
| 442 | 7-(4-((R)-2-amino-4-((R)-3-(4-fluoro-1-(3-methoxypropyl)-1H-benzo[d]imidazol-2-yl)piperidin-1-yl)-4-oxobutyl)phenyl)-2H-benzo[b][1,4]thiazin-3(4H)-one | 615.8 |
| 443 | 7-(4-((R)-2-amino-4-((R)-3-(4-fluoro-1-(3-methoxypropyl)-1H-benzo[d]imidazol-2-yl)piperidin-1-yl)-4-oxobutyl )phenyl)-2H-benzo[b][1,4]oxazin-3(4H)-one | 599.7 |
| 444 | (R)-3-amino-1-((R)-3-(4-fluoro-1-(3-methoxypropyl)-1H-benzo[d]imidazol-2-yl)piperidin-1-yl)-4-(4-(2-hydroxypyridin-4-yl)phenyl)butan-1-one | 545.7 |

TABLE IX-continued

| Compound No. | Structure/Name | ESI-MS: m/z (M + H⁺) |
|---|---|---|
| 445 | 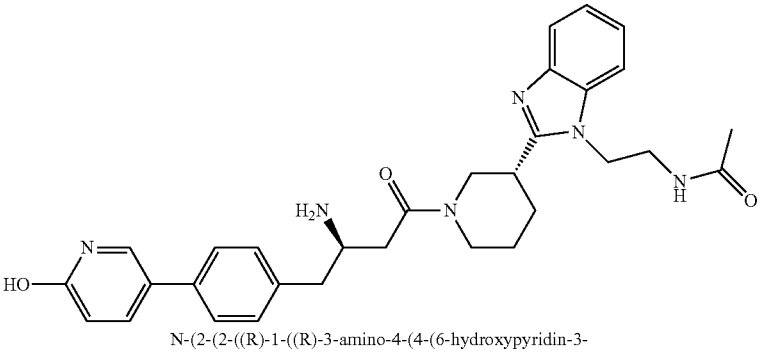<br>N-(2-(2-((R)-1-((R)-3-amino-4-(4-(6-hydroxypyridin-3-yl)phenyl)butanoyl)piperidin-3-yl)-1H-benzo[d]imidazol-1-yl)ethyl)acetamide | 540.7 |
| 446 | 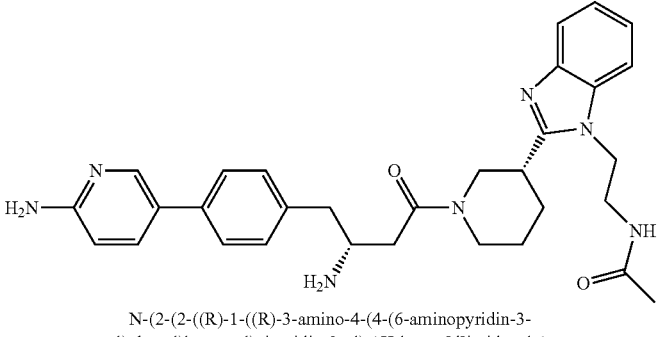<br>N-(2-(2-((R)-1-((R)-3-amino-4-(4-(6-aminopyridin-3-yl)phenyl)butanoyl)piperidin-3-yl)-1H-benzo[d]imidazol-1-yl)ethyl)acetamide | 539.7 |
| 447 | 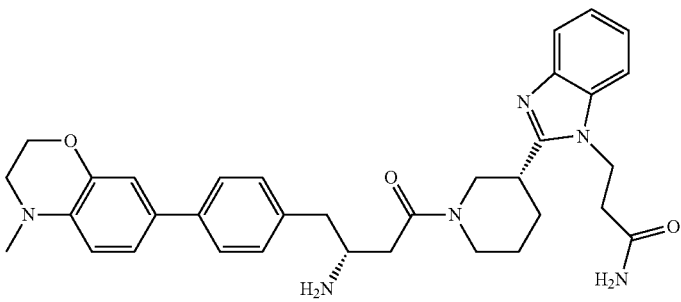<br>3-(2-((R)-1-((R)-3-amino-4-(4-(4-methyl-3,4-dihydro-2H-benzo[b][1,4]oxazin-7-yl)phenyl)butanoyl)piperidin-3-yl)-1H-benzo[d]imidazol-1-yl)propanamide | 594.8 |
| 448 | 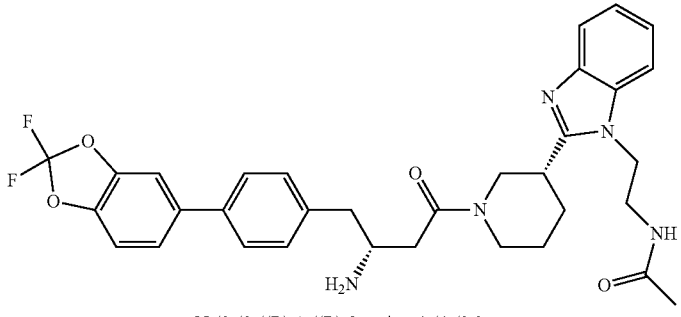<br>N-(2-(2-((R)-1-((R)-3-amino-4-(4-(2,2-difluorobenzo[d][1,3]dioxol-5-yl)phenyl)butanoyl)piperidin-3-yl)-1H-benzo[d]imidazol-1-yl)ethyl)acetamide | 603.7 |

TABLE IX-continued

| Compound No. | Structure/Name | ESI-MS: m/z (M + H+) |
|---|---|---|
| 449 | 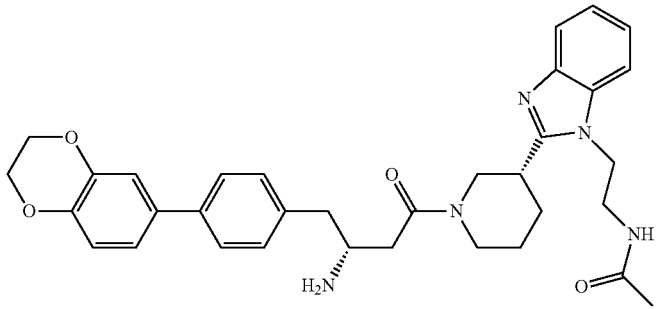<br>N-(2-(2-((R)-1-((R)-3-amino-4-(4-(2,3-dihydrobenzo[b][1,4]dioxin-6-yl)phenyl)butanoyl)piperidin-3-yl)-1H-benzo[d]imidazol-1-yl)ethyl)acetamide | 581.7 |
| 450 | 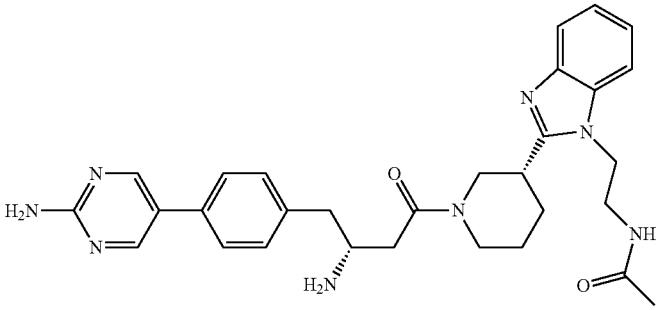<br>N-(2-(2-((R)-1-((R)-3-amino-4-(4-(2-aminopyrimidin-5-yl)phenyl)butanoyl)piperidin-3-yl)-1H-benzo[d]imidazol-1-yl)ethyl)acetamide | 540.7 |
| 451 | 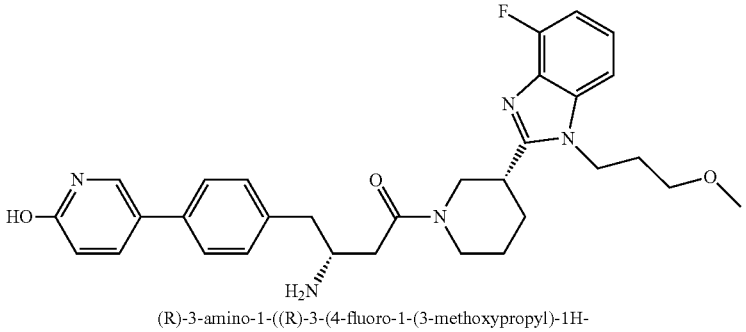<br>(R)-3-amino-1-((R)-3-(4-fluoro-1-(3-methoxypropyl)-1H-benzo[d]imidazol-2-yl)piperidin-1-yl)-4-(4-(6-hydroxypyridin-3-yl)phenyl)butan-1-one | 545.7 |
| 452 | 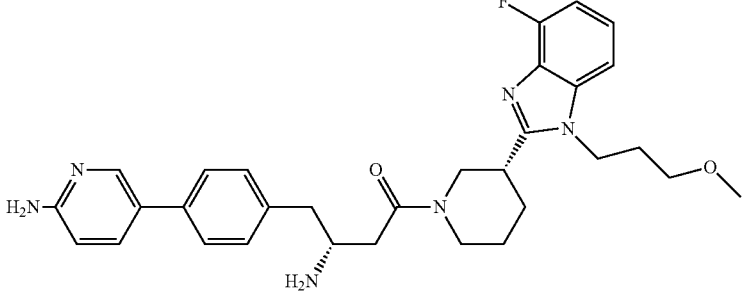<br>(R)-3-amino-4-(4-(6-aminopyridin-3-yl)phenyl)-1-((R)-3-(4-fluoro-1-(3-methoxypropyl)-1H-benzo[d]imidazol-2-yl)piperidin-1-yl)butan-1-one | 544.7 |

TABLE IX-continued

| Compound No. | Structure/Name | ESI-MS: m/z (M + H+) |
|---|---|---|
| 453 | 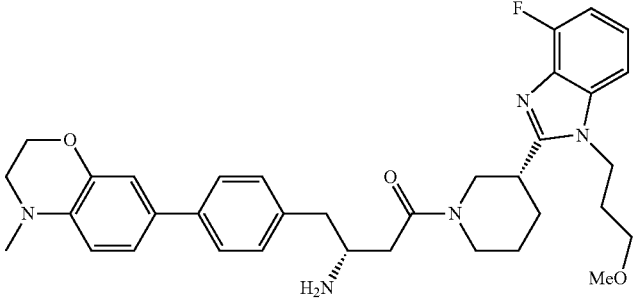<br>(R)-3-amino-1-((R)-3-(4-fluoro-1-(3-methoxypropyl)-1H-benzo[d]imidazol-2-yl)piperidin-1-yl)-4-(4-(4-methyl-3,4-dihydro-2H-benzo[b][1,4]oxazin-7-yl)phenyl)butan-1-one | 599.7 |
| 454 | 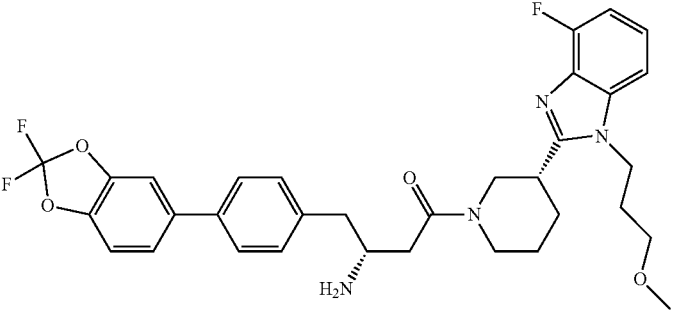<br>(R)-3-amino-4-(4-(2,2-difluorobenzo[d][1,3]dioxol-5-yl)phenyl)-1-((R)-3-(4-fluoro-1-(3-methoxypropyl)-1H-benzo[d]imidazol-2-yl)piperidin-1-yl)butan-1-one | 608.7 |
| 455 | 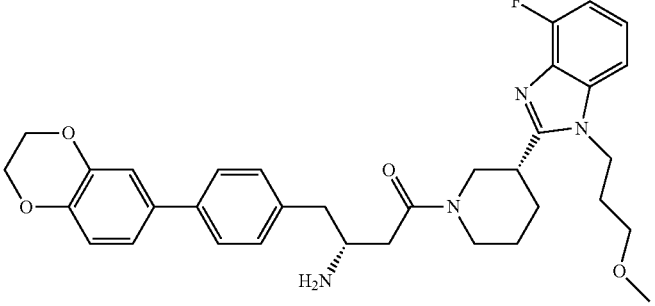<br>(R)-3-amino-4-(4-(2,3-dihydrobenzo[b][1,4]dioxin-6-yl)phenyl)-1-((R)-3-(4-fluoro-1-(3-methoxypropyl)-1H-benzo[d]imidazol-2-yl)piperidin-1-yl)butan-1-one | 586.7 |
| 456 | 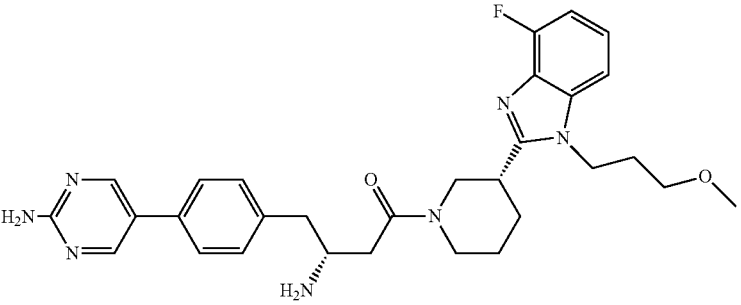<br>(R)-3-amino-4-(4-(2-aminopyrimidin-5-yl)phenyl)-1-((R)-3-(4-fluoro-1-(3-methoxypropyl)-1H-benzo[d]imidazol-2-yl)piperidin-1-yl)butan-1-one | 545.7 |

TABLE IX-continued

| Compound No. | Structure/Name | ESI-MS: m/z (M + H⁺) |
|---|---|---|
| 457 | 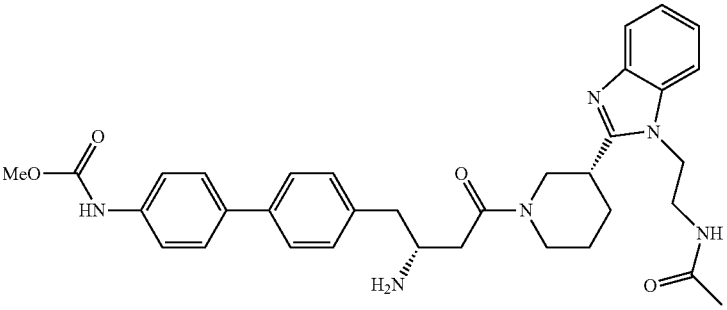methyl 4'-((R)-4-((R)-3-(1-(2-acetamidoethyl)-1H-benzo[d]imidazol-2-yl)piperidin-1-yl)-2-amino-4-oxobutyl)biphenyl-4-ylcarbamate | 596.7 |
| 458 | 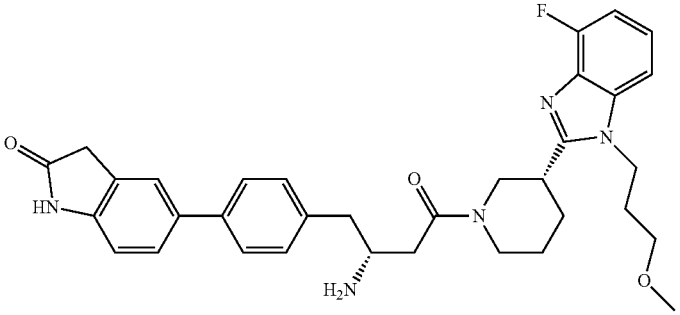5-(4-((R)-2-amino-4-((R)-3-(4-fluoro-1-(3-methoxypropyl)-1H-benzo[d]imidazol-2-yl)piperidin-1-yl)-4-oxobutyl)phenyl)indolin-2-one | 583.7 |
| 459 | 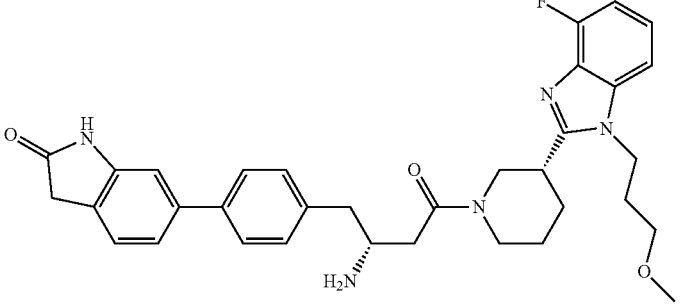6-(4-((R)-2-amino-4-((R)-3-(4-fluoro-1-(3-methoxypropyl)-1H-benzo[d]imidazol-2-yl)piperidin-1-yl)-4-oxobutyl)phenyl)indolin-2-one | 585.7 |
| 460 | 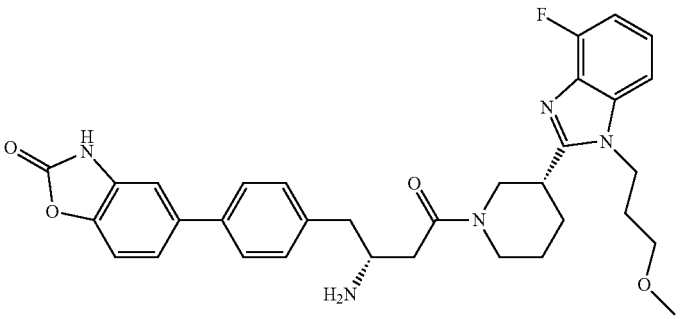5-(4-((R)-2-amino-4-((R)-3-(4-fluoro-1-(3-methoxypropyl)-1H-benzo[d]imidazol-2-yl)piperidin-1-yl)-4-oxobutyl)phenyl)benzo[d]oxazol-2(3H)-one | 585.7 |

TABLE IX-continued

| Compound No. | Structure/Name | ESI-MS: m/z (M + H⁺) |
|---|---|---|
| 461 | 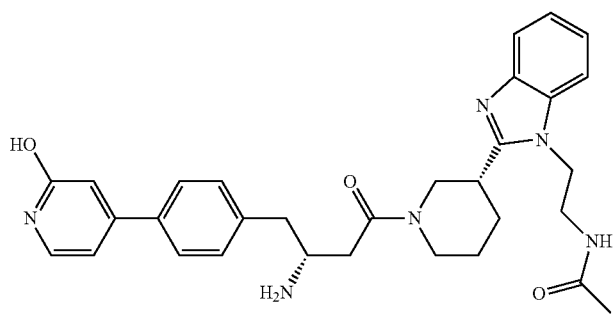<br>N-(2-(2-((R)-1-((R)-3-amino-4-(4-(2-hydroxypyridin-4-yl)phenyl)butanoyl)piperidin-3-yl)-1H-benzo[d]imidazol-1-yl)ethyl)acetamide | 540.7 |
| 462 | 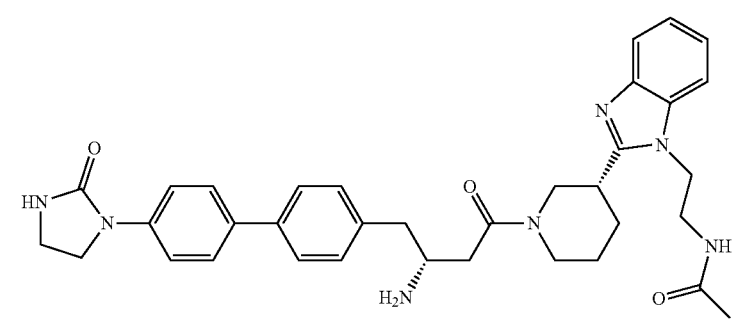<br>N-(2-(2-((R)-1-((R)-3-amino-4-(4'-(2-oxoimidazolidin-1-yl)biphenyl-4-yl)butanoyl)piperidin-3-yl)-1H-benzo[d]imidazol-1-yl)ethyl)acetamide | 607.8 |
| 463 | 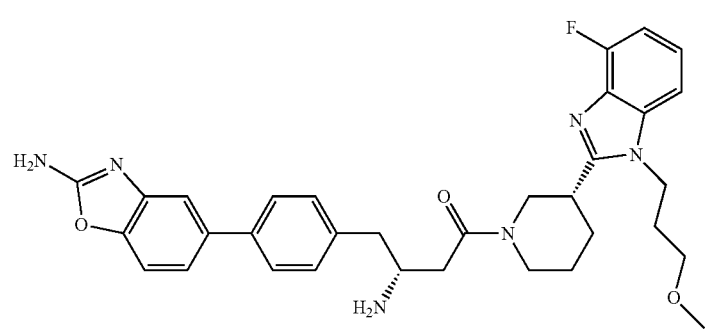<br>(R)-3-amino-4-(4-(2-aminobenzo[d]oxazol-5-yl)phenyl)-1-((R)-3-(4-fluoro-1-(3-methoxypropyl)-1H-benzo[d]imidazol-2-yl)piperidin-1-yl)butan-1-one | 584.7 |
| 464 | 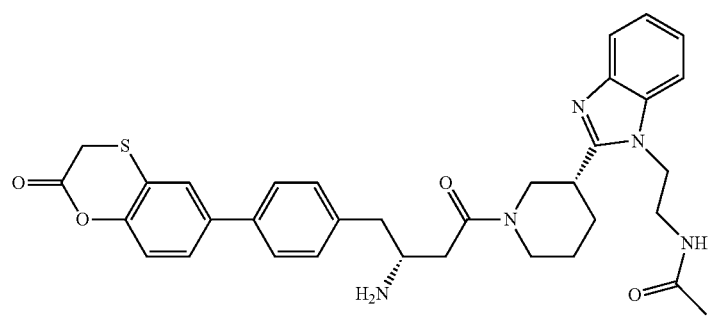<br>N-(2-(2-((R)-1-((R)-3-amino-4-(4-(2-oxo-2,3-dihydrobenzo[b][1,4]oxathiin-6-yl)phenyl)butanoyl)piperidin-3-yl)-1H-benzo[d]imidazol-1-yl)ethyl)acetamide | 610.8 |

TABLE IX-continued

| Compound No. | Structure/Name | ESI-MS: m/z (M + H+) |
|---|---|---|
| 465 | 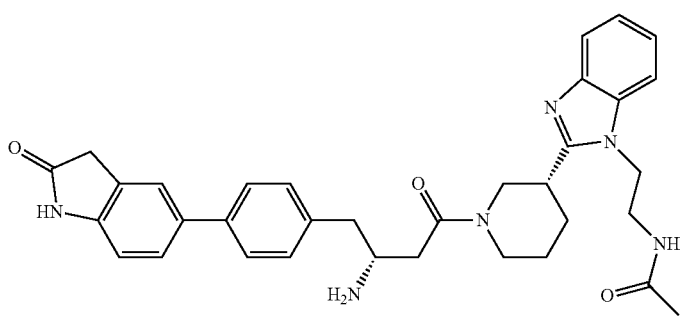<br>N-(2-(2-((R)-1-((R)-3-amino-4-(4-(2-oxoindolin-5-yl)phenyl)butanoyl)piperidin-3-yl)-1H-benzo[d]imidazol-1-yl)ethyl)acetamide | 578.7 |
| 466 | 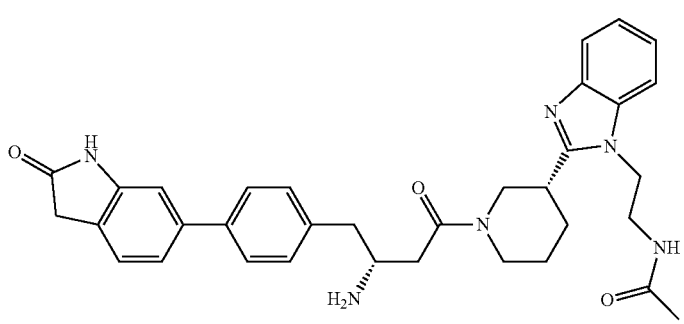<br>N-(2-(2-((R)-1-((R)-3-amino-4-(4-(2-oxoindolin-6-yl)phenyl)butanoyl)piperidin-3-yl)-1H-benzo[d]imidazol-1-yl)ethyl)acetamide | 578.7 |
| 467 | 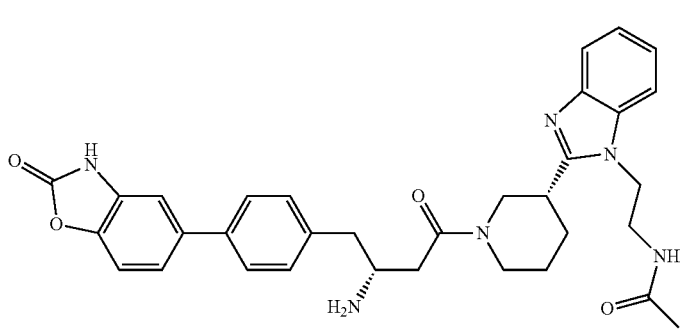<br>N-(2-(2-((R)-1-((R)-3-amino-4-(4-(2-oxo-2,3-dihydrobenzo[d]oxazol-5-yl)phenyl)butanoyl)piperidin-3-yl)-1H-benzo[d]imidazol-1-yl)ethyl)acetamide | 580.7 |
| 468 | 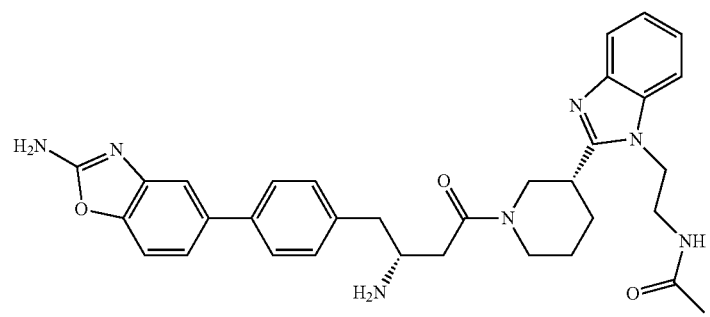<br>5-(4-((R)-2-amino-4-((R)-3-(4-fluoro-1-(3-methoxypropyl)-1H-benzo[d]imidazol-2-yl)piperidin-1-yl)-4-oxobutyl)phenyl)benzo[d]oxazol-2(3H)-one | 579.7 |

TABLE IX-continued

| Compound No. | Structure/Name | ESI-MS: m/z (M + H+) |
|---|---|---|
| 469 | 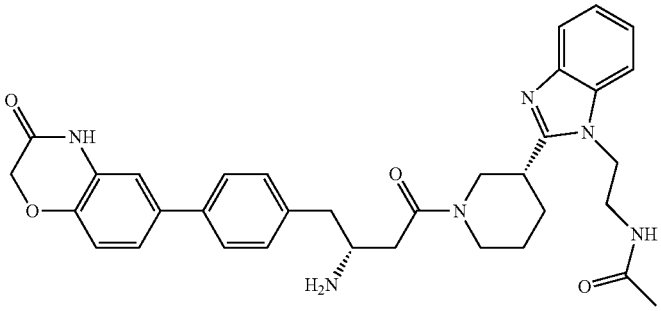<br>(R)-3-amino-4-(4-(2-aminobenzo[d]oxazol-5-yl)phenyl)-1-((R)-3-(4-fluoro-1-(3-methoxypropyl)-1H-benzo[d]imidazol-2-yl(piperidin-1-yl)butan-1-one | 594.7 |
| 470 | 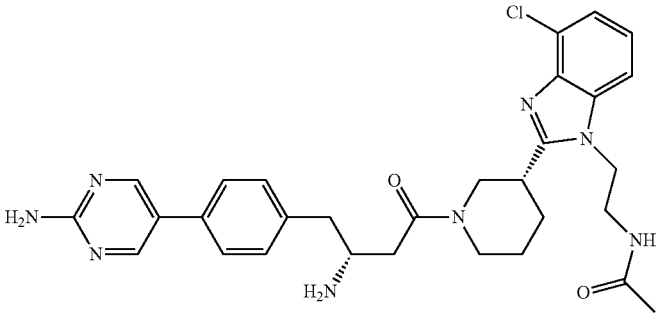<br>N-(2-(2-((R)-1-((R)-3-amino-4-(4-(2-aminopyrimidin-5-yl)phenyl)butanoyl)piperidin-3-yl)-4-chloro-1H-benzo[d]imidazol-1-yl)ethyl)acetamide | 575.1 |
| 471 | 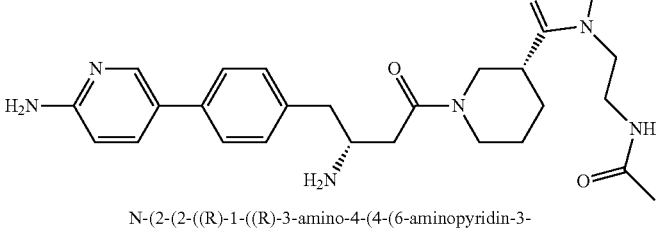<br>N-(2-(2-((R)-1-((R)-3-amino-4-(4-(6-aminopyridin-3-yl)phenyl)butanoyl)piperidin-3-yl)-4-methyl-1H-benzo[d]imidazol-1-yl)ethyl)acetamide | 553.7 |
| 472 | 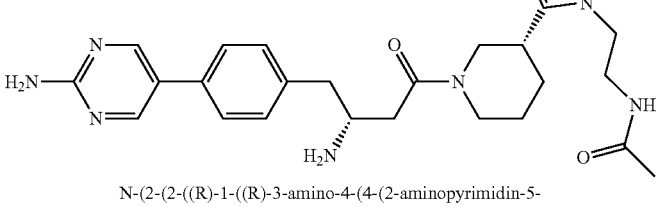<br>N-(2-(2-((R)-1-((R)-3-amino-4-(4-(2-aminopyrimidin-5-yl)phenyl)butanoyl)piperidin-3-yl)-4-methyl-1H-benzo[d]imidazol-1-yl)ethyl)acetamide | 554.7 |

TABLE IX-continued

| Compound No. | Structure/Name | ESI-MS: m/z (M + H+) |
|---|---|---|
| 473 | 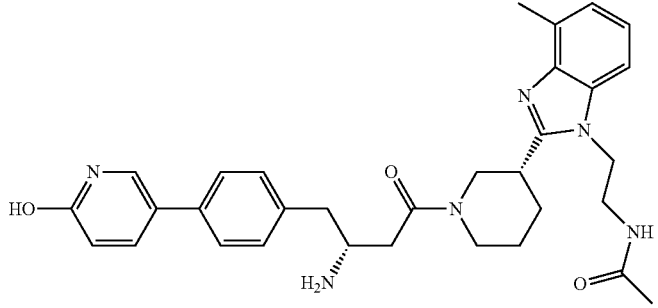<br>N-(2-(2-((R)-1-((R)-3-amino-4-(4-(6-hydroxypyridin-3-yl)phenyl)butanoyl)piperidin-3-yl)-4-methyl-1H-benzo[d]imidazol-1-yl)ethyl)acetamide | 554.7 |
| 474 | 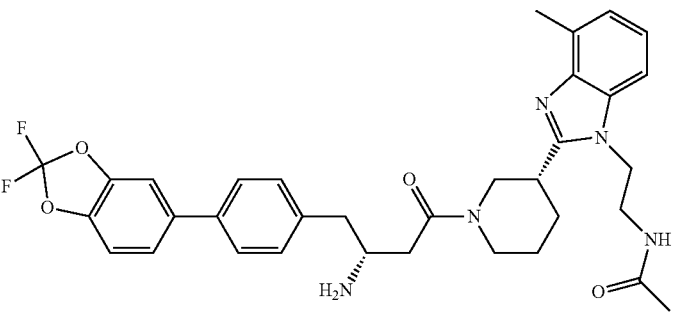<br>N-(2-(2-((R)-1-((R)-3-amino-4-(4-(2,2-difluorobenzo[d][1,3]dioxol-5-yl)phenyl)butanoyl)piperidin-3-yl)-4-methyl-1H-benzo[d]imidazol-1-yl)ethyl)acetamide | 617.7 |
| 475 | 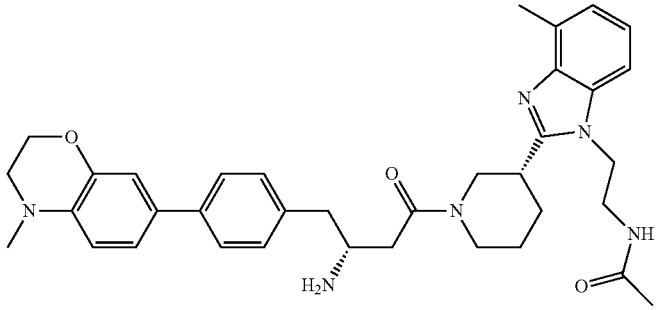<br>N-(2-(2-((R)-1-((R)-3-amino-4-(4-(4-methyl-3,4-dihydro-2H-benzo[b][1,4]oxazin-7-yl)phenyl)butanoyl)piperidin-3-yl)-4-methyl-1H-benzo[d]imidazol-1-yl)ethyl)acetamide | 608.8 |
| 476 | 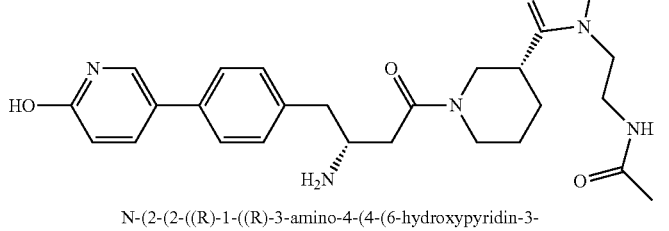<br>N-(2-(2-((R)-1-((R)-3-amino-4-(4-(6-hydroxypyridin-3-yl)phenyl)butanoyl)piperidin-3-yl)-1H-benzo[d]imidazol-1-yl)ethyl)acetamide | 526.6 |

TABLE IX-continued

| Compound No. | Structure/Name | ESI-MS: m/z (M + H+) |
|---|---|---|
| 477 | N-(2-(2-((R)-1-((R)-3-amino-4-(4-(2,3-dihydrobenzo[b][1,4]dioxin-6-yl)phenyl)butanoyl)piperidin-3-yl)-4-methyl-1H-benzo[d]imidazol-1-yl)ethyl)acetamide | 595.7 |
| 478 | N-(2-(2-((R)-1-((R)-3-amino-4-(4-(6-hydroxypyridin-3-yl)phenyl)butanoyl)piperidin-3-yl)-4-chloro-1H-benzo[d]imidazol-1-yl)ethyl)acetamide | 575.1 |
| 479 | N-(2-(2-((R)-1-((R)-3-amino-4-(4-(6-aminopyridin-3-yl)phenyl)butanoyl)piperidin-3-yl)-4-chloro-1H-benzo[d]imidazol-1-yl)ethyl)acetamide | 574.1 |
| 480 | 3-(2-((R)-1-((R)-3-amino-4-(4-(6-aminopyridin-3-yl)phenyl)butanoyl)piperidin-3-yl)-1H-benzo[d]imidazol-1-yl)propanamide | 525.7 |

TABLE IX-continued

| Compound No. | Structure/Name | ESI-MS: m/z (M + H+) |
|---|---|---|
| 481 | 3-(2-((R)-1-((R)-3-amino-4-(4-(2-aminopyrimidin-5-yl)phenyl)butanoyl)piperidin-3-yl)-1H-benzo[d]imidazol-1-yl)propanamide | 526.6 |
| 482 | 3-(2-((R)-1-((R)-3-amino-4-(4-(4-methyl-3,4-dihydro-2H-benzo[b][1,4]oxazin-7-yl)phenyl)butanoyl)piperidin-3-yl)-1H-benzo[d]imidazol-1-yl)propanamide | 580.7 |
| 483 | 3-(2-((R)-1-((R)-3-amino-4-(4-(2,2-difluorobenzo[d][1,3]dioxol-5-yl)phenyl)butanoyl)piperidin-3-yl)-1H-benzo[d]imidazol-1-yl)propanamide | 589.6 |
| 484 | 3-(2-((R)-1-((R)-3-amino-4-(4-(2,3-dihydrobenzo[b][1,4]dioxin-6-yl)phenyl)butanoyl)piperidin-3-yl)-1H-benzo[d]imidazol-1-yl)propanamide | 567.7 |

TABLE IX-continued

| Compound No. | Structure/Name | ESI-MS: m/z (M + H+) |
|---|---|---|
| 485 | 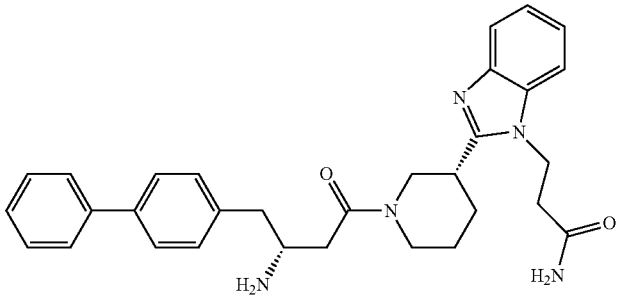<br>3-(2-((R)-1-((R)-3-amino-4-(biphenyl-4-yl)butanoyl)piperidin-3-yl)-1H-benzo[d]imidazol-1-yl)propanamide | 509.7 |
| 486 | 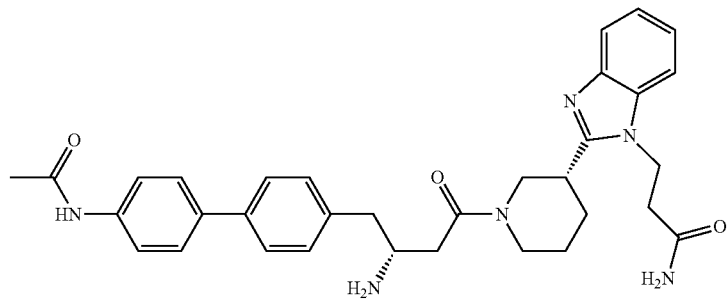<br>3-(2-((R)-1-((R)-4-(4'-acetamidobiphenyl-4-yl)-3-aminobutanoyl)piperidin-3-yl)-1H-benzo[d]imidazol-1-yl)propanamide | 566.7 |
| 487 | 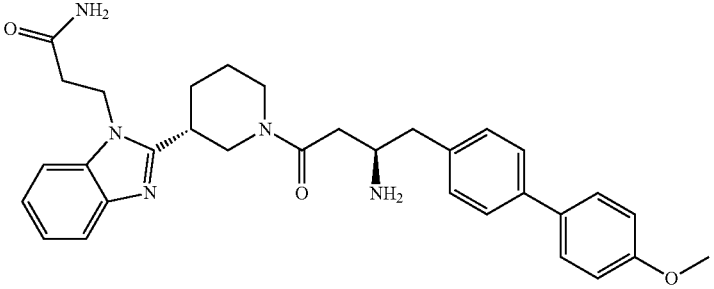<br>3-(2-((R)-1-((R)-3-amino-4-(4'-methoxybiphenyl-4-yl)butanoyl)piperidin-3-yl)-1H-benzo[d]imidazol-1-yl)propanamide | 539.7 |
| 488 | 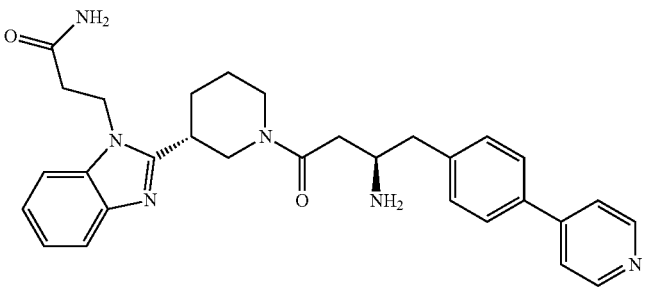<br>3-(2-((R)-1-((R)-3-amino-4-(4-(pyridin-4-yl)phenyl)butanoyl)piperidin-3-yl)-1H-benzo[d]imidazol-1-yl)propanamide | 510.6 |

TABLE IX-continued

| Compound No. | Structure/Name | ESI-MS: m/z (M + H+) |
|---|---|---|
| 489 | 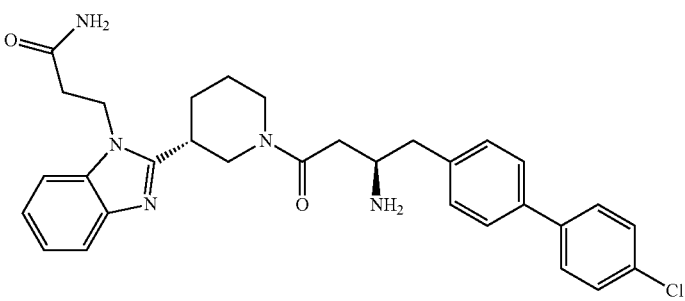3-(2-((R)-1-((R)-3-amino-4-(4'-chlorobiphenyl-4-yl)butanoyl)piperidin-3-yl)-1H-benzo[d]imidazol-1-yl)propanamide | 544.1 |
| 490 | 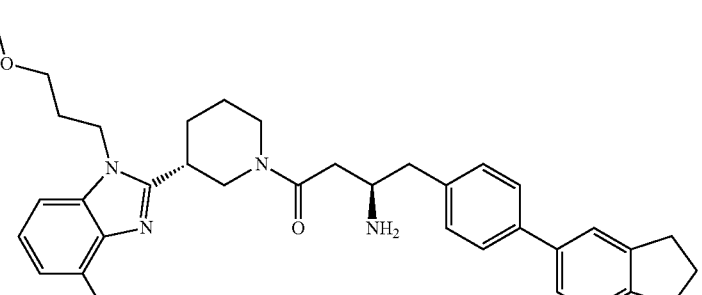(R)-3-amino-4-(4-(2,3-dihydrobenzofuran-5-yl)phenyl)-1-((R)-3-(4-fluoro-1-(3-methoxypropyl)-1H-benzo[d]imidazol-2-yl)piperidin-1-yl)butan-1-one | 570.7 |
| 491 | 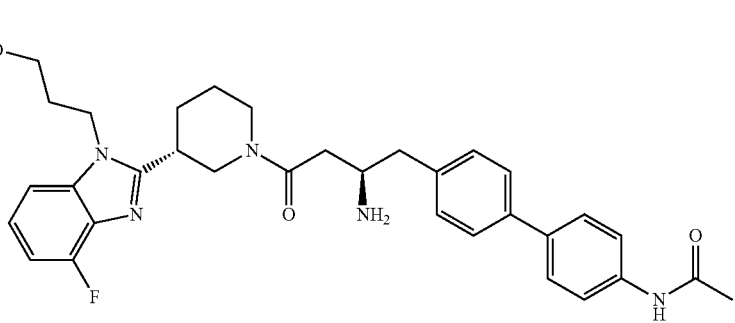N-(4'-((R)-2-amino-4-((R)-3-(4-fluoro-1-(3-methoxypropyl)-1H-benzo[d]imidazol-2-yl)piperidin-1-yl)-4-oxobutyl)biphenyl-4-yl)acetamide | 585.7 |
| 492 | 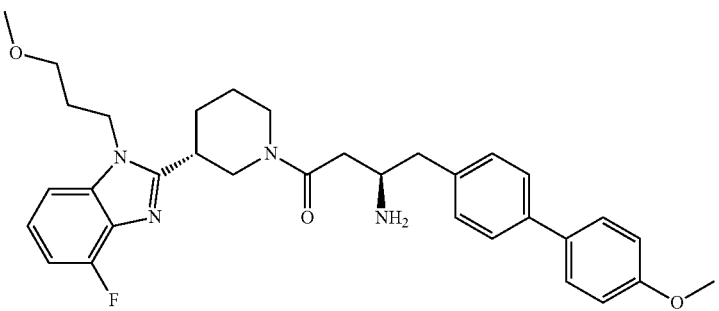(R)-3-amino-1-((R)-3-(4-fluoro-1-(3-methoxypropyl)-1H-benzo[d]imidazol-2-yl)piperidin-1-yl)-4-(4'-methoxybiphenyl-4-yl)butan-1-one | 558.7 |

TABLE IX-continued

| Compound No. | Structure/Name | ESI-MS: m/z (M + H⁺) |
|---|---|---|
| 493 | 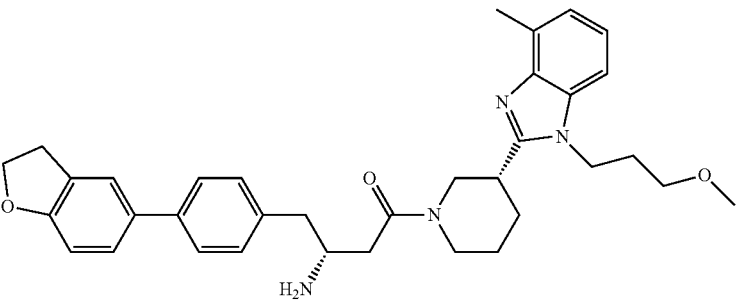<br>(R)-3-amino-4-(4-(2,3-dihydrobenzofuran-5-yl)phenyl)-1-((R)-3-(1-(3-methoxypropyl)-4-methyl-1H-benzo[d]imidazol-2-yl)piperidin-1-yl)butan-1-one | 566.74 |
| 494 | 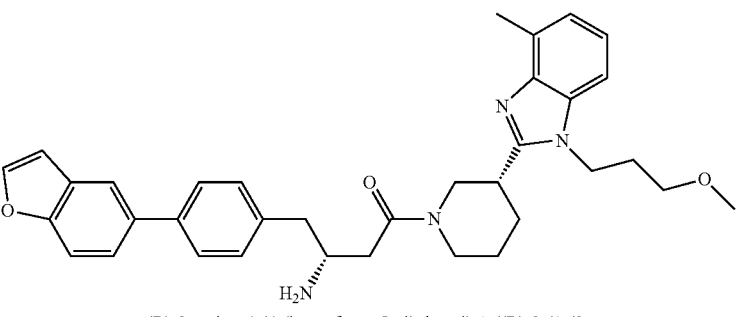<br>(R)-3-amino-4-(4-(benzofuran-5-yl)phenyl)-1-((R)-3-(1-(3-methoxypropyl)-4-methyl-1H-benzo[d]imidazol-2-yl)piperidin-1-yl)butan-1-one | 564.73 |
| 495 | 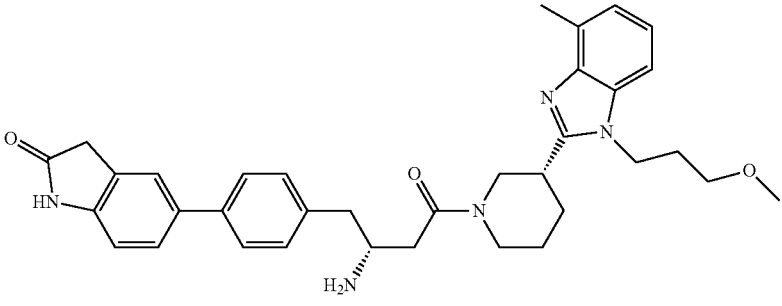<br>5-(4-((R)-2-amino-4-((R)-3-(1-(3-methoxypropyl)-4-methyl-1H-benzo[d]imidazol-2-yl)piperidin-1-yl)-4-oxobutyl)phenyl)indolin-2-one | 579.74 |
| 496 | 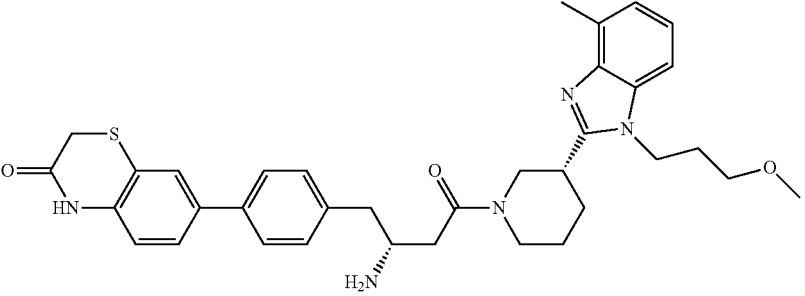<br>7-(4-((R)-2-amino-4-((R)-3-(1-(3-methoxypropyl)-4-methyl-1H-benzo[d]imidazol-2-yl)piperidin-1-yl)-4-oxobutyl)phenyl)-2H-benzo[b][1,4]thiazin-3(4H)-one | 611.81 |

TABLE IX-continued

| Compound No. | Structure/Name | ESI-MS: m/z (M + H+) |
|---|---|---|
| 497 | 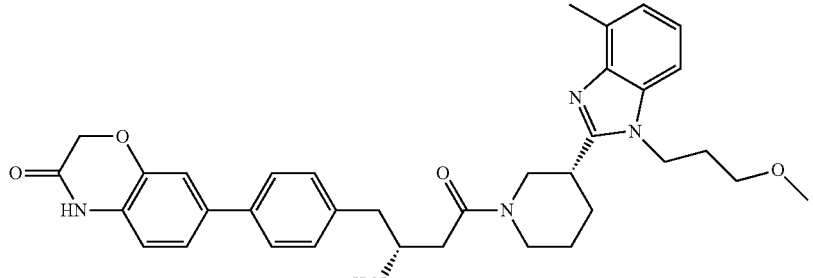  7-(4-((R)-2-amino-4-((R)-3-(1-(3-methoxypropyl)-4-methyl-1H-benzo[d]imidazol-2-yl)piperidin-1-yl)-4-oxobutyl)phenyl)-2H-benzo[b][1,4]oxazin-3(4H)-one | 595.74 |
| 498 | 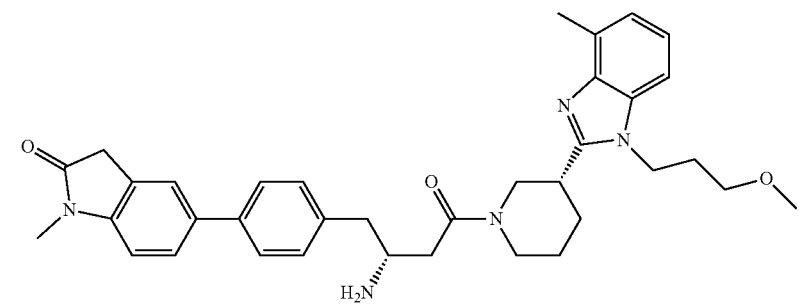  5-(4-((R)-2-amino-4-((R)-3-(1-(3-methoxypropyl)-4-methyl-1H-benzo[d]imidazol-2-yl)piperidin-1-yl)-4-oxobutyl)phenyl)-1-methylindolin-2-one | 593.77 |
| 499 | 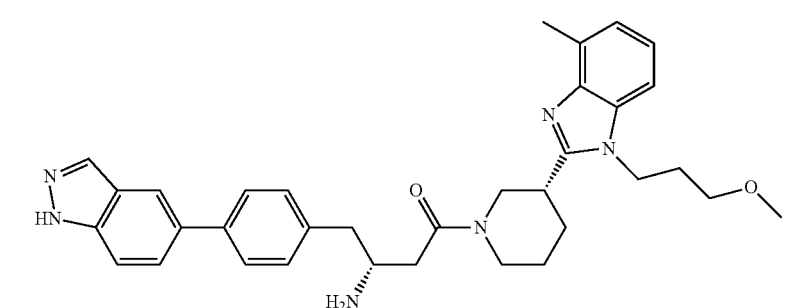  (R)-4-(4-(1H-indazol-5-yl)phenyl)-3-amino-1-((R)-3-(1-(3-methoxypropyl)-4-methyl-1H-benzo[d]imidazol-2-yl)piperidin-1-yl)butan-1-one | 564.73 |
| 500 | 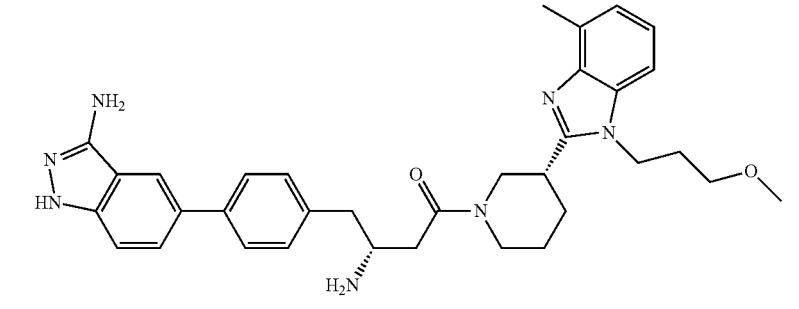  (R)-3-amino-4-(4-(3-amino-1H-indazol-5-yl)phenyl)-1-((R)-3-(1-(3-methoxypropyl)-4-methyl-1H-benzo[d]imidazol-2-yl)piperidin-1-yl)butan-1-one | 579.75 |

TABLE IX-continued

| Compound No. | Structure/Name | ESI-MS: m/z (M + H+) |
|---|---|---|
| 501 | 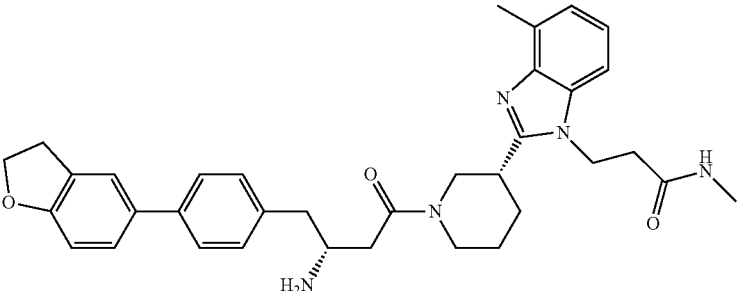{width=0} 3-(2-((R)-1-((R)-3-amino-4-(4-(2,3-dihydrobenzofuran-5-yl)phenyl)butanoyl)piperidin-3-yl)-4-methyl-1H-benzo[d]imidazol-1-yl)-N-methylpropanamide | 565.7 |

Table X below lists azabenzimidazole compounds prepared according to the schemes described above.

TABLE X

| Compound | Structure/Name | ESI-MS: m/z (M + H+) |
|---|---|---|
| 502 | 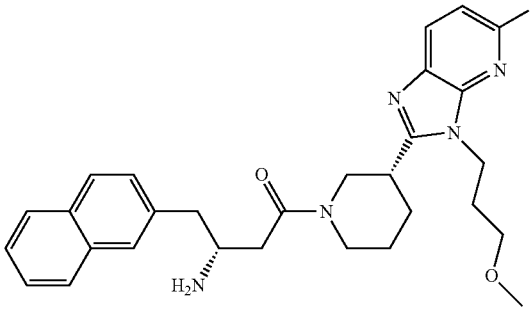 (3R)-3-amino-1-(3-(5-chloro-3-(3-methoxypropyl)-3H-imidazo[4,5-b]pyridin-2-yl)piperidin-1-yl)-4-(naphthalen-2-yl)butan-1-one | 520.07 |
| 503 | 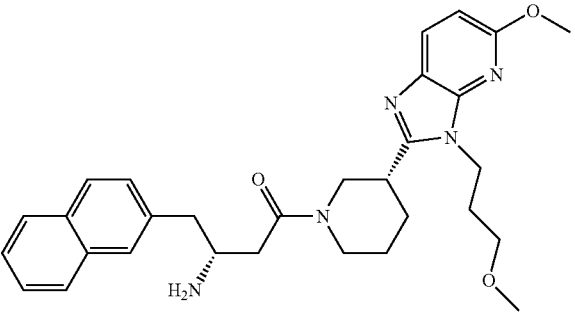 (3R)-3-amino-1-(3-(5-methoxy-3-(3-methoxypropyl)-3H-imidazo[4,5-b]pyridin-2-yl)piperidin-1-yl)-4-(naphthalen-2-yl)butan-1-one | 515.65 |

TABLE X-continued

| Compound | Structure/Name | ESI-MS: m/z (M + H+) |
|---|---|---|
| 504 | 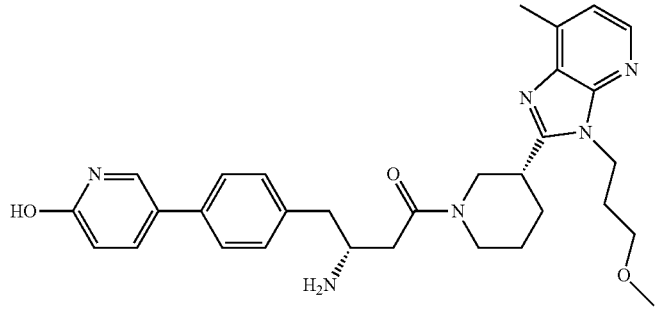(R)-3-amino-4-(4-(6-hydroxypyridin-3-yl)phenyl)-1-((R)-3-(3-(3-methoxypropyl)-7-methyl-3H-imidazo[4,5-b]pyridin-2-yl)piperidin-1-yl)butan-1-one | 542.68 |
| 505 | 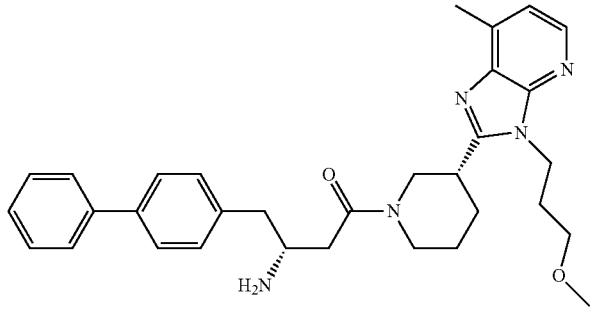(R)-3-amino-4-(biphenyl-4-yl)-1-((R)-3-(3-(3-methoxypropyl)-7-methyl-3H-imidazo[4,5-b]pyridin-2-yl)piperidin-1-yl)butan-1-one | 525.69 |

Table XI below lists another pyrrolidine compound prepared according to the schemes described above.

TABLE XI

| Compound | Structure/Name | ESI-MS: m/z (M + H+) |
|---|---|---|
| 506 | 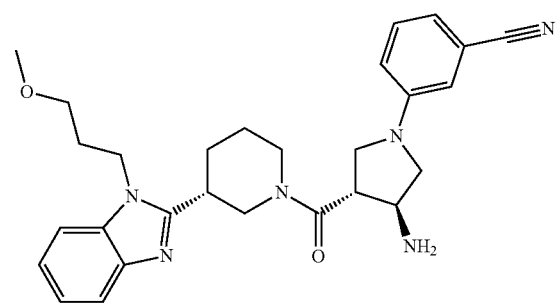3-((3S,4R)-3-amino-4-((R)-3-(1-(3-methoxypropyl)-1H-benzo[d]imidazol-2-yl)piperidine-1-carbonyl)pyrrolidin-1-yl)benzonitrile | 474.65 |

Example 141

SFC Separation of Racemic Mixtures

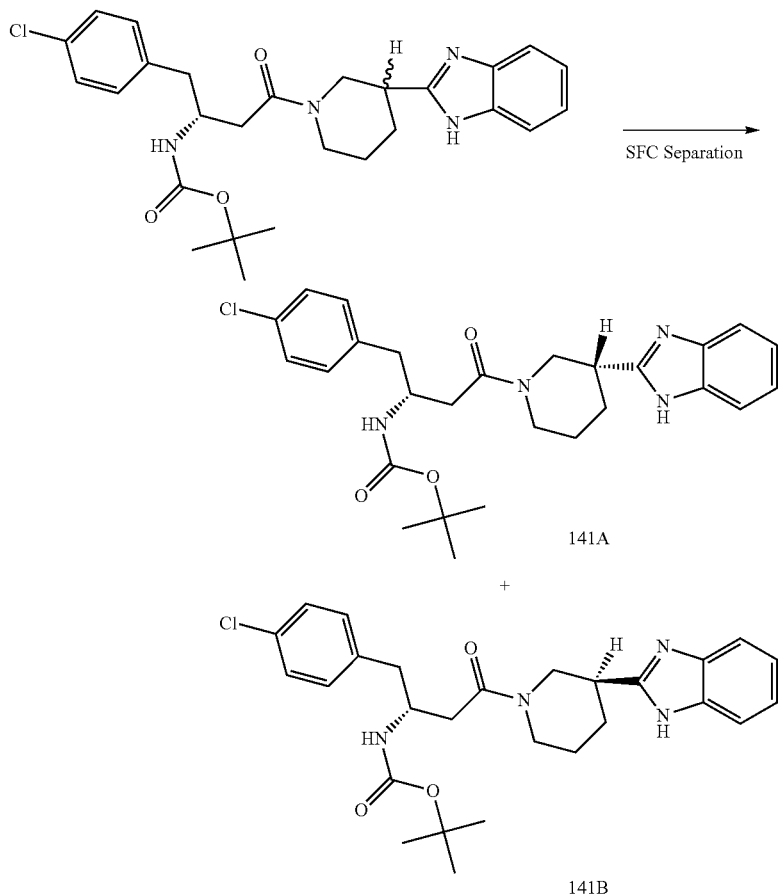

Racemic mixture of tert-butyl (2R)-4-(3-(1H-benzo[d]imidazol-2-yl)piperidin-1-yl)-1-(4-chlorophenyl)-4-oxobutan-2-ylcarbamate were separated into steroisomeric components of tert-butyl (R)-4-((R)-3-(1H-benzo[d]imidazol-2-yl)piperidin-1-yl)-1-(4-chlorophenyl)-4-oxobutan-2-ylcarbamate (140A) and tert-butyl (R)-44(S)-3-(1H-benzo[d]imidazol-2-yl)piperidin-1-yl)-1-(4-chlorophenyl)-4-oxobutan-2-ylcarbamate (14013) by supercritical fluid chromatography under the following conditions:

Column: ChiralPak AD-H (5 um, 21×250 mm)
Mobile Phase:
  A: liquid CO,
  B: IPOH
Flow Rate: 45 mLJmin
Gradient: 20% IPA
Prep injection volume: 1000 μL
Total injections: 12
Anal injection volume: 100 μL
Run Time: 20 min.

The ee ratio of each of the fractions is >99%. ESI-MS: m/z 469.3 (M+H)$^+$.

Example 142

Regioisomer LC/MS Separation

A mixture of (R)-tert-butyl 3-(4-chloro-1-(3-methoxypropyl)-1H-benzo[d]imidazol-2-yl)piperidine-1-carboxylate and (R)-tert-butyl 3-(7-chloro-1-(3-methoxypropyl)-1H-benzo[d]imidazol-2-yl)piperidine-1-carboxylate (18.39 mmole, 7.50 g) was separated by LC/MS under the following conditions:

Instrument: Waters ZQ LC/MS Prep System
  ZQ 2000 single quadrupole mass detector
  2767 sample manager for injection and collection
  2525 binary gradient pump and 515 isocratic pump
  2487 UV detector and AllTech 2000 ELSD detector
  Controlled by MassLynx 4.1 software with FractionLynx program
MS Method: (PrepScan200-800Pos or AnalScan200-800Pos)
  Mass Range: 200-800
  Ion mode: positive
Column: Gemini 5 um 75×30 mm. Mobile phase: A-10 mM $NH_4HCO_3$ in $H_2O$; B-10 mM $NH_4HCO_3$ in 20/80 $H_2O$/CAN. Flow rate: 50 mLJmin. Total run time: 8 min.
Gradient: 75-85% B in 6 min Prep injection: batch 1-250 uL, batch2-210 uL
Total injections: 75
Product purified:
(R)-tert-butyl 3-(4-chloro-1-(3-methoxypropyl)-1H-benzo[d]imidazol-2-yl)piperidine-1-carboxylate (142A) (3.02 g).

(R)-tert-butyl 3-(7-chloro-1-(3-methoxypropyl)-1H-benzo[d]imidazol-2-yl)piperidine-1-carboxylate (142B) (1.00 g).

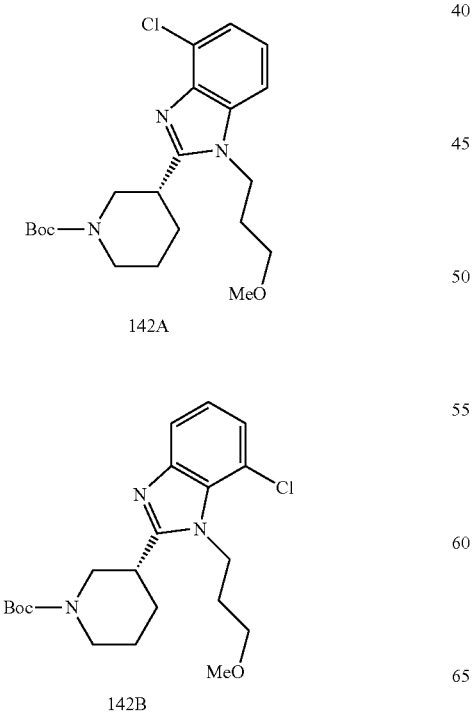

Example 143

Synthesis of 34(3S,4R)-3-amino-4-((R)-3-(1-(3-methoxypropyl)-1H-benzo[d]imidazol-2-yl)piperidine-1-carbonyl)pyrrolidin-1-yl)benzonitrile (507)

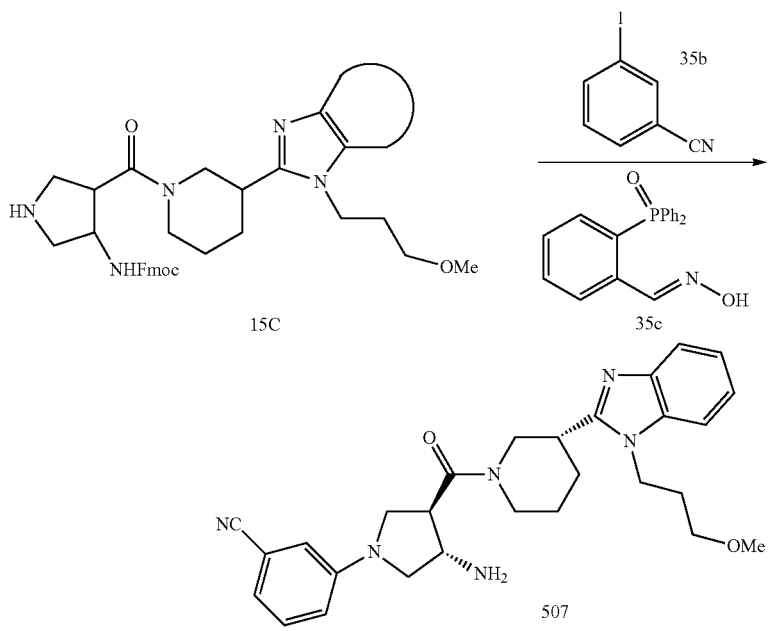

The compound was synthesized according general scheme 35. To a mixture of the intermediate, (9H-fluoren-9-yl)methyl 4-(3-(1-(3-methoxypropyl)-4,5-dimethyl-1H-imidazol-2-yl)piperidine-1-carbonyl)pyrrolidin-3-ylcarbamate (15c, general scheme 15, 49.0 mg, 0.081 mmol) and 3-iodobenzonitrile (25.3 mg, 1.5 eq) in 2 ml acetonitril was added (E)-2-(diphenylphosphoryl)benzaldehyde oxime (5.2 mg, 20% mol), cesim carbonate (55.4 mg, 2.1 eq) and copper (1) oxide (0.6 mg, 5% mol). The reaction mixture was heated at 80° C. for 18 hrs. The mixture was filtered and filtrate was concentrated and purified on preparative HPLC to give the product as light brown solid (10.4 mg, 26%); MS: MH+=487.4 (RT=1.90 min STDTFA-2 method).

Example 144

Synthesis of ((3R,4S)-4-amino-1-(4-nitrophenyl)pyrrolidin-3-yl)((R)-3-(1-(3-methoxypropyl)-1H-benzo[d]imidazol-2-yl)piperidin-1-yl)methanone (508)

719

-continued

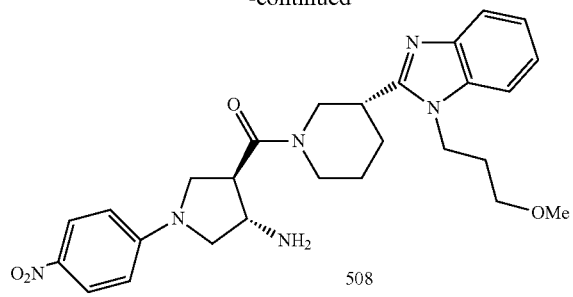

508

To a solution of the intermediate 15c (9H-fluoren-9-yl) methyl 4-(3-(1-(3-methoxypropyl)-4,5-dimethyl-1H-imida-

720 zol-2-yl)piperidine-1-carbonyl)pyrrolidin-3-ylcarbamate (also see Example 139, 50.0 mg, 0.082 mmol) in 2 mL DMF was added 1-fluoro-4-nitrobenzene (12 uL, 0.112 mmol) and potassium carbonate (200 mg). The mixture was heated at 100° C. for 4 hrs. The reaction mixture was filtered and purified by preparative HPLC (5 to 50% CH3CN/water) to give 10.0 mg product, MS: MH+=507.2, RT=4.44 min.

Example 145

Synthesis of (R)-3-amino-4-(4-(2-aminopyrimidin-5-yl)phenyl)-1-((R)-3-(1-(2-fluoroethyl)-1H-benzo[d]imidazol-2-yl)piperidin-1-yl)butan-1-one (509)

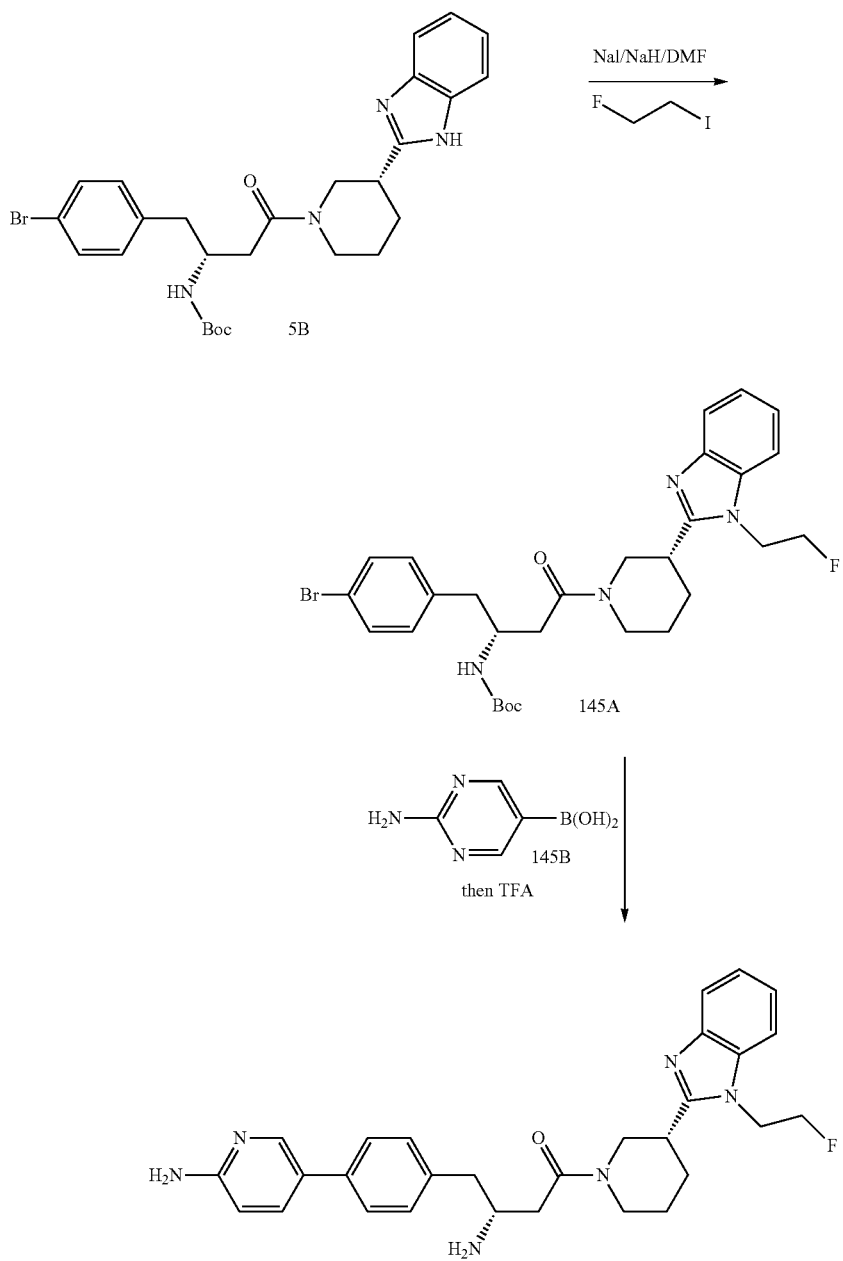

To a solution of Compound 513 (Example 5, 300 mg, 0.555 mmol) in 5 mL of DMF at 0° C. was added NaI (92 mg, 0.61 mmol), NaH (60%, 29 mg, 0.72 mmol). The mixture was stirred at 0° C. for 30 mins. 1-Fluoro-2-iodoethane (97 mg, 0.72 mmol) was added, the reaction was warmed to room temperature and stirred overnight. It was poured into 20 mL crushed ice and extracted with DCM (3×25 mL), the combined organic layer was dried over $MgS_2O_4$ and concentrated. The resulting residue was purified by preparative HPLC using 15-45% $CH_3CN$/water). tert-Butyl (R)-1-(4-bromophenyl)-4-((R)-3-(1-(2-fluoroethyl)-1H-benzo[d]imidazol-2-yl)piperidin-1-yl)-4-oxobutan-2-ylcarbamate (145A) was obtained after lyophilizing as white solid w=146 mg (45%).

Suzuki coupling of 145A with 2-aminopyrimidin-5-ylboronic acid (145E) was carried out analogously to the synthesis of Compound 613 (Example 6, Step B). The crude Boc-protected intermediate was de-protected with TFA using procedure similar to that for the synthesis of Compound 72 from Compound 6B (Example 6, Step C). The crude product was purified by preparative HPLC using 15% $CH_3CN$/water as mobile phase. Compound 509 was obtained in 14.4% yield over two steps (17.8 mg), MS: $MH^+$=502.4.

Example A

Expression of Preprorenin and Purification of Prorenin

The sequence of human wild-type renin is known in the art; see, Imai, T. et al., Proc. Natl. Acad. Sci. USA 1983, 80, 7105-7409. It is noted that the fragment of the renin protein useful for the assay comprises amino acid residues 67-406 of human renin (active renin). To prepare active renin, a fragment longer than active renin, a preprorenin (e.g., comprising residues 1-406), may be expressed and from which a prorenin (e.g., comprising residues 23-406) may be recovered. The prorenin may later be cleaved to obtain active renin.

Expression of human preprorenin (residues 1-406) can be conducted using a FreeStyle 293 Expression System (Invitrogen Corp.), wherein the plasmid DNA for human prorenin expression (pcDNA3.1(+)/hREN) is used to conduct transient expression in FreeStyle 293-F cells. After transfection of the plasmid DNA, the cells are subjected to shaking at 37° C., 8% $CO_2$ and 125 rpm for 3 days.

The prorenin protein is then accumulated and purified by salting out. Powdered ammonium sulfate is added to the culture medium and dissolved to make a 40% saturation of the salt. The resulting precipitate can be collected by centrifugation and discarded. Ammonium sulfate is added to the remaining solution and dissolved to make an 80% saturation of salt. The resulting precipitate can be collected by, for example, centrifugation. The prorenin protein is recovered by dissolving the precipitate in buffer.

The concentrated liquid is subjected to gel filtration chromatography using, for example, HiLoad 16/60 Superdex 200 pg (Amersham Biosciences, Inc.) equilibrated with 20 mM Tris-hydrochloric acid (pH 8.0) containing 0.15 M sodium chloride, at a flow rate of 1.4 mL/min, to obtain 3.6 mg of purified prorenin (residues 24-406).

Example B

Purification of Active Renin

To 3.6 mg of prorenin (residues 24-406, as prepared in Example A) dissolved in 5.2 mL of 0.1 M Tris-hydrochloric acid (pH 8.0), is added 12 µg of trypsin (Roche Diagnostics Corp.), and the mixture is allowed to react at 28° C. for 55 minutes to carry out activation of renin. After the reaction, 0.4 mL of immobilized trypsin inhibitor (Pierce Biotechnology, Inc.) is added to remove the trypsin used in the activation, by adsorption. The reaction liquid containing the active renin is concentrated using Vivaspin 20 (molecular weight of the fraction 10,000; Vivascience, Inc.), and diluted with 20 mM Tris-hydrochloric acid (pH 8.0). The diluted liquid is fed to a TSKgel DEAE-5 PW column (7.5 mm I.D.×75 mm, Tosoh Corp.) equilibrated with 20 mM Tris-hydrochloric acid (pH 8.0) at a flow rate of 1 mL/min to adsorb the active renin (residues 67 406). The column is washed with the buffer solution used for the equilibration, and then elution is carried out by means of a linear concentration gradient of sodium chloride from 0 M to 0.3 M, to obtain 1.5 mg of purified active renin (residues 67-406).

Example C

Establishment of Renin Expressing Vector

A plasmid DNA to express human renin in HEIC293 cells can be prepared as follows. PCR is carried out using human renal cDNA (Clontech Laboratories, Inc., Marathon Ready cDNA) as the template and using two synthetic DNAs (5'-AAGCTTATGGATGGATGGAGA-3' (SEQ ID NO: 1) and 5'-GGATCCTCAGCGGGCCAAGGC-3' (SEQ ID NO: 2)), and the obtained fragment is cloned using TOPO TA Cloning Kit (Invitrogen Corp.). The obtained fragment is subcloned into pcDNA3.1(+) that has been cleaved by HindIII and BamHI, to obtain a plasmid DNA for human preprorenin expression (pcDNA3.1(+)/hREN).

Example D

Assaying the In Vitro Enzymatic Activity of Renin Inhibitors

Solutions of test compounds in varying concentrations mM final concentration) are prepared in dimethyl sulfoxide (DMSO) and then diluted into assay buffer comprising 50 mM Hepes, 1 mM EDTA, 1 mM DTT, 0.1 mg/mL BSA, 0.01% Brij35, pH 7.4. Alternatively, the assay can be performed with a high BSA concentration, wherein the buffer contains an additional 2% BSA.

Recombinant human renin (3 nM final concentration) is added to the dilutions and pre-incubated with the compounds for 10 minutes at 37° C. As described in Examples A-C above, human renin can be obtained by expressing preprorenin (residue 1-406) in mammalian cells, treating the prorenin (residues 24-406) contained in the culture supernatant with trypsin, and isolate the active form (residues 67-406). After pre-incubation, the reaction is initiated with of substrate QXL520-γ-Abu-Ile-His-Pro-Phe-His-Leu-Val-Ile-His-Thr-Lys (HiLyteFluo488)-Arg-OH (Anaspec, San Jose, Calif.). The final DMSO in the assay is 5%. The total volume of the reaction mixture is 20 µL, which can be placed on Greiner 384-well small volume plates.

Renin activity may be determined via fluorescence (excitation λ=485 nm; emission X=538 nm), e.g., on a Molecular Devices SPECTROmax GEMINI XPS. The fluorescence intensity is determined upon the addition of substrate and determined again after incubation at 37° C. for one hour. The fluorescence intensity of a blank (no inhibition) using vehicle alone is also determined. Renin activity is linearly proportional to the change in fluorescence observed (final-initial).

The percent inhibition of renin at a given compound concentration is defined as:

$$100\% \times [1-(F_{compound}/F_{blank})]$$

where $F_{compound}$ is the observed fluorescence at a given concentration of test compound and $F_{blank}$ is the observed fluorescence in the presence of vehicle alone.

The $pIC_{50}$ value (negative log of the molar concentration of the compound that produces 50% inhibition) of a test compound is calculated by non-linear least squares curve fitting of the equation:

$$\text{Percent Inhibition} = 100\%/(1+(10^{-pIC50}/10 \log [I]))$$

to percent inhibition versus compound concentration. The 50% inhibitory concentration ($IC_{50}$) of a test compound is calculated by raising 10 to the negative $pIC_{50}$ ($10^{-pIC50}$).

$IC_{50}$ values for selected compounds of the present invention are given in Table XII.

TABLE XII

| IC$_{50}$ of Exemplified Compounds Against Renin | |
|---|---|
| Compound No. | IC$_{50}$ (nM) |
| 1 | >1,000 |
| 3 | >1,000 |
| 4 | >1,000 |
| 5 | >1,000 |
| 6 | >1,000 |
| 7 | >1,000 |
| 8 | >1,000 |
| 9 | >1,000 |
| 10 | >1,000 |
| 11 | >1,000 |
| 12 | >1,000 |
| 13 | >1,000 |
| 14 | >1,000 |
| 15 | >1,000 |
| 16 | >1,000 |
| 17 | >1,000 |
| 18 | >1,000 |
| 19 | >1,000 |
| 20 | >1,000 |
| 21 | >1,000 |
| 23 | >1,000 |
| 24 | 100-1,000 |
| 25 | >1,000 |
| 26 | >1,000 |
| 27 | >1,000 |
| 28 | >1,000 |
| 29 | >1,000 |
| 30 | >1,000 |
| 31 | >1,000 |
| 32 | >1,000 |
| 33 | >1,000 |
| 34 | >1,000 |
| 35 | >1,000 |
| 36 | >1,000 |
| 37 | >1,000 |
| 38 | >1,000 |
| 39 | >1,000 |
| 40 | >1,000 |
| 41 | >1,000 |
| 42 | >1,000 |
| 43 | >1,000 |
| 44 | >1,000 |
| 45 | >1,000 |
| 46 | >1,000 |
| 47 | >1,000 |
| 48 | >1,000 |
| 49 | >1,000 |
| 50 | >1,000 |
| 51 | >1,000 |
| 52 | >1,000 |
| 53 | >1,000 |
| 54 | >1,000 |
| 55 | >1,000 |

TABLE XII-continued

| IC$_{50}$ of Exemplified Compounds Against Renin | |
|---|---|
| Compound No. | IC$_{50}$ (nM) |
| 56 | >1,000 |
| 57 | >1,000 |
| 58 | >1,000 |
| 59 | >1,000 |
| 60 | >1,000 |
| 61 | >1,000 |
| 62 | >1,000 |
| 63 | >1,000 |
| 64 | >1,000 |
| 65 | >1,000 |
| 66 | >1,000 |
| 67 | >1,000 |
| 68 | >1,000 |
| 69 | >1,000 |
| 70 | >1,000 |
| 71 | >1,000 |
| 72 | <100 |
| 73 | 100-1,000 |
| 74 | <100 |
| 75 | 100-1,000 |
| 76 | 100-1,000 |
| 77 | 100-1,000 |
| 78 | >1,000 |
| 79 | 100-1,000 |
| 80 | 100-1,000 |
| 81 | 100-1,000 |
| 82 | >1,000 |
| 83 | >1,000 |
| 84 | 100-1,000 |
| 85 | >1,000 |
| 86 | 100-1,000 |
| 87 | 100-1,000 |
| 88 | >1,000 |
| 89 | >1,000 |
| 90 | <100 |
| 91 | 100-1,000 |
| 92 | 100-1,000 |
| 93 | >1,000 |
| 94 | >1,000 |
| 95 | 100-1,000 |
| 96 | 100-1,000 |
| 97 | <100 |
| 98 | <100 |
| 99 | 100-1,000 |
| 100 | 100-1,000 |
| 101 | >1,000 |
| 102 | >1,000 |
| 103 | >1,000 |
| 104 | 100-1,000 |
| 105 | <100 |
| 106 | <100 |
| 107 | >1,000 |
| 108 | 100-1,000 |
| 109 | 100-1,000 |
| 110 | 100-1,000 |
| 111 | 100-1,000 |
| 112 | >1,000 |
| 113 | 100-1,000 |
| 114 | >1,000 |
| 115 | 100-1,000 |
| 116 | 100-1,000 |
| 118 | <100 |
| 119 | 100-1,000 |
| 120 | >1,000 |
| 121 | >1,000 |
| 122 | <100 |
| 123 | <100 |
| 124 | <100 |
| 125 | <100 |
| 126 | <100 |
| 127 | <100 |
| 128 | <100 |
| 129 | <100 |
| 130 | <100 |
| 131 | <100 |
| 132 | <100 |

TABLE XII-continued

IC$_{50}$ of Exemplified Compounds Against Renin

| Compound No. | IC$_{50}$ (nM) |
|---|---|
| 133 | <100 |
| 134 | <100 |
| 135 | <100 |
| 136 | <100 |
| 137 | <100 |
| 138 | <100 |
| 139 | <100 |
| 140 | <100 |
| 141 | 100-1,000 |
| 142 | <100 |
| 143 | <100 |
| 144 | <100 |
| 145 | <100 |
| 146 | <100 |
| 147 | <100 |
| 148 | <100 |
| 149 | <100 |
| 150 | <100 |
| 151 | <100 |
| 152 | <100 |
| 153 | <100 |
| 154 | <100 |
| 155 | <100 |
| 156 | <100 |
| 157 | <100 |
| 158 | <100 |
| 159 | <100 |
| 160 | <100 |
| 161 | <100 |
| 162 | <100 |
| 163 | <100 |
| 164 | <100 |
| 165 | <100 |
| 166 | 100-1,000 |
| 167 | <100 |
| 168 | <100 |
| 169 | <100 |
| 170 | <100 |
| 171 | <100 |
| 172 | <100 |
| 173 | <100 |
| 174 | <100 |
| 175 | <100 |
| 176 | <100 |
| 177 | <100 |
| 178 | <100 |
| 179 | <100 |
| 180 | <100 |
| 181 | <100 |
| 182 | <100 |
| 183 | <100 |
| 184 | <100 |
| 185 | <100 |
| 186 | <100 |
| 187 | <100 |
| 188 | <100 |
| 189 | <100 |
| 190 | <100 |
| 191 | <100 |
| 192 | <100 |
| 193 | <100 |
| 194 | <100 |
| 195 | <100 |
| 197 | <100 |
| 198 | <100 |
| 199 | <100 |
| 200 | <100 |
| 201 | <100 |
| 202 | <100 |
| 203 | 100-1,000 |
| 204 | 100-1,000 |
| 205 | <100 |
| 206 | <100 |
| 207 | 100-1,000 |
| 208 | <100 |
| 209 | 100-1,000 |
| 210 | 100-1,000 |
| 211 | <100 |
| 212 | <100 |
| 213 | 100-1,000 |
| 214 | <100 |
| mixture of 215 & 216 | <100 |
| mixture of 217 & 218 | <100 |
| 219 | <100 |
| 220 | <100 |
| 221 | <100 |
| 222 | <100 |
| mixture of 223 & 224 | <100 |
| 226 mixture of 225 & 226 | <100 |
| mixture of 227 & 228 | <100 |
| 229 | <100 |
| 231 | 100-1,000 |
| 232 | 100-1,000 |
| 233 | 100-1,000 |
| 234 | >1,000 |
| 235 | 100-1,000 |
| 236 | <100 |
| 237 | 100-1,000 |
| 238 | <100 |
| 239 | 100-1,000 |
| 240 | >1,000 |
| 241 | 100-1,000 |
| 242 | >1,000 |
| 243 | >1,000 |
| 244 | >1,000 |
| 245 | >1,000 |
| 246 | >1,000 |
| 247 | >1,000 |
| 248 | >1,000 |
| 249 | <100 |
| 250 | <100 |
| 251 | <100 |
| 252 | <100 |
| 253 | <100 |
| 254 | <100 |
| 255 | <100 |
| 256 | <100 |
| 257 | <100 |
| 258 | <100 |
| 259 | <100 |
| 260 | <100 |
| 261 | <100 |
| 262 | 100-1,000 |
| 263 | 100-1,000 |
| 264 | 100-1,000 |
| 265 | 100-1,000 |
| 266 | 100-1,000 |
| 267 | 100-1,000 |
| 268 | 100-1,000 |
| 269 | 100-1,000 |
| 270 | 100-1,000 |
| 271 | 100-1,000 |
| 272 | 100-1,000 |
| 273 | 100-1,000 |
| 274 | 100-1,000 |
| 275 | 100-1,000 |
| 276 | 100-1,000 |
| 277 | 100-1,000 |
| 278 | 100-1,000 |
| 279 | 100-1,000 |
| 280 | 100-1,000 |
| 281 | 100-1,000 |
| 282 | 100-1,000 |
| 283 | 100-1,000 |
| 284 | 100-1,000 |
| 285 | 100-1,000 |
| 286 | 100-1,000 |
| 287 | 100-1,000 |
| 288 | 100-1,000 |
| 289 | 100-1,000 |
| 290 | 100-1,000 |
| 291 | 100-1,000 |

TABLE XII-continued

IC$_{50}$ of Exemplified Compounds Against Renin

| Compound No. | IC$_{50}$ (nM) |
|---|---|
| 292 | 100-1,000 |
| 293 | 100-1,000 |
| 294 | 100-1,000 |
| 295 | 100-1,000 |
| 296 | 100-1,000 |
| 297 | 100-1,000 |
| 298 | 100-1,000 |
| 299 | 100-1,000 |
| 300 | 100-1,000 |
| 301 | 100-1,000 |
| 302 | 100-1,000 |
| 303 | 100-1,000 |
| 304 | 100-1,000 |
| 305 | 100-1,000 |
| 306 | 100-1,000 |
| 307 | 100-1,000 |
| 308 | 100-1,000 |
| 309 | 100-1,000 |
| 310 | 100-1,000 |
| 311 | 100-1,000 |
| 312 | 100-1,000 |
| 313 | 100-1,000 |
| 314 | 100-1,000 |
| 315 | 100-1,000 |
| 316 | 100-1,000 |
| 317 | 100-1,000 |
| 318 | 100-1,000 |
| 319 | 100-1,000 |
| 320 | 100-1,000 |
| 321 | 100-1,000 |
| 322 | 100-1,000 |
| 323 | >1,000 |
| 324 | >1,000 |
| 325 | >1,000 |
| 326 | >1,000 |
| 327 | >1,000 |
| 328 | >1,000 |
| 329 | >1,000 |
| 330 | >1,000 |
| 331 | >1,000 |
| 332 | >1,000 |
| 333 | >1,000 |
| 334 | >1,000 |
| 335 | 100-1,000 |
| 337 | >1,000 |
| 338 | <100 |
| 339 | 100-1,000 |
| 340 | 100-1,000 |
| 341 | 100-1,000 |
| 342 | 100-1,000 |
| 343 | 100-1,000 |
| 344 | 100-1,000 |
| 345 | 100-1,000 |
| 346 | 100-1,000 |
| 347 | 100-1,000 |
| 348 | 100-1,000 |
| 349 | 100-1,000 |
| 350 | 100-1,000 |
| 351 | 100-1,000 |
| 352 | 100-1,000 |
| 353 | 100-1,000 |
| 354 | 100-1,000 |
| 355 | 100-1,000 |
| 356 | 100-1,000 |
| 357 | 100-1,000 |
| 358 | 100-1,000 |
| 359 | 100-1,000 |
| 360 | 100-1,000 |
| 361 | 100-1,000 |
| 362 | 100-1,000 |
| 363 | 100-1,000 |
| 364 | 100-1,000 |
| 365 | 100-1,000 |
| 366 | 100-1,000 |
| 367 | 100-1,000 |
| 368 | 100-1,000 |
| 369 | 100-1,000 |
| 370 | 100-1,000 |
| 371 | 100-1,000 |
| 372 | 100-1,000 |
| 373 | 100-1,000 |
| 374 | 100-1,000 |
| 375 | 100-1,000 |
| 376 | 100-1,000 |
| 377 | 100-1,000 |
| 378 | 100-1,000 |
| 379 | 100-1,000 |
| 380 | 100-1,000 |
| 381 | 100-1,000 |
| 382 | 100-1,000 |
| 383 | 100-1,000 |
| 384 | >1,000 |
| 385 | >1,000 |
| 386 | >1,000 |
| 387 | >1,000 |
| 388 | >1,000 |
| 389 | >1,000 |
| 390 | >1,000 |
| 391 | >1,000 |
| 392 | >1,000 |
| 393 | >1,000 |
| 394 | >1,000 |
| 395 | >1,000 |
| 396 | >1,000 |
| 397 | >1,000 |
| 398 | >1,000 |
| 399 | >1,000 |
| 400 | >1,000 |
| 401 | >1,000 |
| 402 | >1,000 |
| 403 | >1,000 |
| 404 | >1,000 |
| 405 | >1,000 |
| 406 | >1,000 |
| 407 | >1,000 |
| 408 | >1,000 |
| 409 | >1,000 |
| 410 | >1,000 |
| 411 | >1,000 |
| 412 | >1,000 |
| 413 | >1,000 |
| 414 | >1,000 |
| 415 | >1,000 |
| 416 | >1,000 |
| 417 | >1,000 |
| 418 | >1,000 |
| 419 | >1,000 |
| 420 | >1,000 |
| 421 | >1,000 |
| 422 | >1,000 |
| 423 | >1,000 |
| 424 | >1,000 |
| 425 | 100-1,000 |
| 426 | 100-1,000 |
| 427 | >1,000 |
| 428 | 100-1,000 |
| 429 | <100 |
| 430 | 100-1,000 |
| 431 | >1,000 |
| 432 | >1,000 |
| 433 | >1,000 |
| 434 | 100-1,000 |
| 435 | <100 |
| 436 | <100 |
| 437 | <100 |
| 438 | <100 |
| 439 | <100 |
| 441 | <100 |
| 442 | <100 |
| 443 | <100 |
| 444 | <100 |
| 445 | 100-1,000 |

TABLE XII-continued

IC$_{50}$ of Exemplified Compounds Against Renin

| Compound No. | IC$_{50}$ (nM) |
|---|---|
| 446 | 100-1,000 |
| 447 | 100-1,000 |
| 448 | 100-1,000 |
| 449 | 100-1,000 |
| 450 | 100-1,000 |
| 451 | <100 |
| 452 | <100 |
| 453 | <100 |
| 454 | <100 |
| 455 | <100 |
| 456 | <100 |
| 457 | <100 |
| 458 | <100 |
| 459 | <100 |
| 460 | <100 |
| 461 | 100-1,000 |
| 462 | 100-1,000 |
| 463 | <100 |
| 464 | <100 |
| 465 | <100 |
| 466 | 100-1,000 |
| 467 | 100-1,000 |
| 468 | 100-1,000 |
| 469 | 100-1,000 |
| 470 | 100-1,000 |
| 471 | 100-1,000 |
| 472 | 100-1,000 |
| 473 | 100-1,000 |
| 474 | 100-1,000 |
| 475 | 100-1,000 |
| 476 | 100-1,000 |
| 477 | 100-1,000 |
| 478 | 100-1,000 |
| 479 | <100 |
| 480 | 100-1,000 |
| 481 | 100-1,000 |
| 482 | 100-1,000 |
| 483 | 100-1,000 |
| 484 | >1,000 |
| 485 | >1,000 |
| 486 | 100-1,000 |
| 487 | 100-1,000 |
| 488 | 100-1,000 |
| 489 | >1,000 |
| 490 | <100 |
| 491 | <100 |
| 492 | <100 |
| 493 | <100 |
| 494 | <100 |
| 495 | <100 |
| 496 | <100 |
| 497 | <100 |
| 498 | <100 |
| 499 | <100 |
| 500 | <100 |
| 501 | 100-1,000 |
| 502 | >1,000 |
| 503 | 100-1,000 |
| 504 | 100-1,000 |
| 505 | <100 |
| 506 | 100-1,000 |
| 507 | 100-1,000 |
| 508 | 100-1,000 |
| 509 | 100-1,000 |

What is claimed is:

1. A compound of the formula

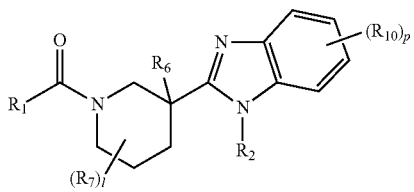

or a pharmaceutically acceptable salt thereof, wherein
- l is 0, 1, 2, or 3;
- p is 0, 1, 2, 3, or 4;
- $R_1$ is selected from the group consisting of $(C_{4-12})$aryloxy, hetero$(C_{1-10})$aryloxy, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, amino$(C_{1-10})$alkyl, $(C_{3-12})$cycloalkyl$(C_{1-10})$alkyl, $(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{9-12})$bicycloaryl and hetero$(C_{4-12})$bicycloaryl, each unsubstituted or substituted;
- $R_2$ is selected from the group consisting of $(C_{1-10})$alkoxy, $(C_{4-12})$aryloxy, hetero$(C_{1-10})$aryloxy, carbonyloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;
- $R_6$ is selected from the group consisting of hydrogen, hydroxyl, unsubstituted and substituted $(C_{1-6})$alkyl, —COOR$_9$, and —CH$_2$OR$_9$, where R$_9$ is selected from the group consisting of hydrogen, $(C_{1-6})$alkyl, $(C_6)$aryl, $(C_{5-6})$heteroaryl, $(C_{3-6})$cycloalkyl, and hetero$(C_{2-5})$cycloalkyl, each unsubstituted or substituted;
- $R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and
- each $R_{10}$ is independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted, or $R_{10}'$ is absent when the carbon to which it is bound forms part of a double bond.

2. The compound or pharmaceutically acceptable salt according to claim 1, having the formula

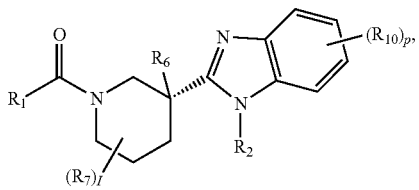

wherein l, p, $R_1$, $R_2$, $R_6$, $R_7$, and $R_{10}$ are as defined for the formula in claim 1.

3. The compound or pharmaceutically acceptable salt according to claim 1, wherein $R_1$ is selected from the group consisting of amino, $(C_{1-10})$alkylamino, $(C_{1-10})$alkyl, hetero$(C_{1-10})$alkyl, amino$(C_{1-10})$alkyl, $(C_{3-12})$cycloalkyl, and hetero$(C_{3-12})$cycloalkyl, each unsubstituted or substituted.

4. The compound or pharmaceutically acceptable salt according to claim 3, wherein $R_1$ is a substituted $(C_{1-10})$alkyl of the formula

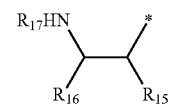

wherein
- $R_{15}$ is selected from the group consisting of hydrogen, hydroxyl, $(C_{1-6})$alkyl, hydroxy$(C_{1-6})$alkyl, $(C_{1-6})$alkoxy, aryl$(C_{1-6})$alkyl, heteroaryl$(C_{1-6})$alkyl, cycloalkyl$(C_{1-6})$alkyl, and $(C_{1-6})$heterocycloalkyl$(C_{1-6})$alkyl;
- $R_{16}$ is a $(C_{1-6})$alkyl or a cyclic moiety selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, wherein said $(C_{1-6})$alkyl and cyclic moiety are each independently unsubstituted or substituted with 1-3 $R_{16a}$ substituents, or $R_{15}$ and $R_{16}$ are taken together, along with the carbon atoms to which they are attached, to form a 5, 6, or 7 membered saturated, unsaturated or aromatic ring, which is unsubstituted or substituted with 1-3 $R_{16a}$ substituents, wherein each $R_{16a}$ is independently selected from the group consisting of halo, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonyl, $(C_{1-10})$alkyl, halo$(C_{1-10})$alkyl, perhalo$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, each unsubstituted or substituted; and $R_{17}$ is selected from the group consisting of hydrogen, $(C_{1-10})$alkyl, halo$(C_{1-10})$alkyl, hydroxy$(C_{1-10})$alkyl, carbonyl$(C_{1-10})$alkyl, sulfonyl$(C_{1-10})$alkyl, sulfinyl$(C_{1-10})$alkyl, $(C_{1-10})$azaalkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryk$C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

5. The compound or pharmaceutically acceptable salt according to claim 4, wherein $R_{15}$ and $R_{16}$ are taken together, along with the carbon atoms to which they are attached, to form a ring selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

6. The compound or pharmaceutically acceptable salt according to claim 5, wherein $R_{15}$ and $R_{16}$ are taken together, along with the carbon atoms to which they are attached, to form a pyrrolidinyl of the formula

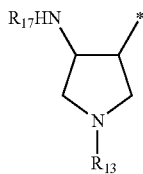

wherein $R_{13}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amido, carboxamido, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

7. The compound or pharmaceutically acceptable salt according to claim 6, wherein $R_{13}$ is selected from the group consisting of hydrogen, unsubstituted $(C_{1-6})$alkyl, $R_{18}$ substituted $(C_{1-6})$alkyl, and

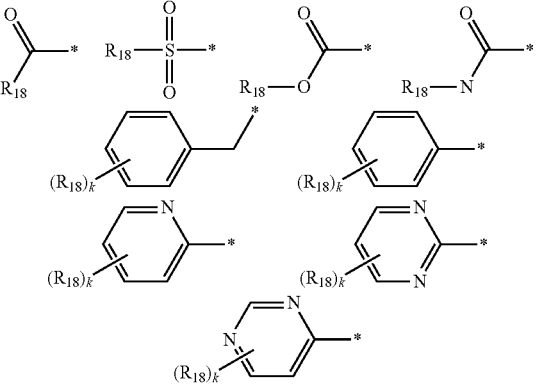

where k is 0, 1, or 2;

each $R_{18}$ is independently selected from the group consisting of hydrogen, oxy, cyano, nitro, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or is substituted with 1-3 $R_{18a}$ substituents, wherein each $R_{18a}$ is independently selected from the group consisting of halo, nitro, cyano, thio, oxy, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or further substituted.

8. The compound or pharmaceutically acceptable salt according to claim 7, wherein $R_{18}$ is selected from the group consisting of nitro, cyano, and

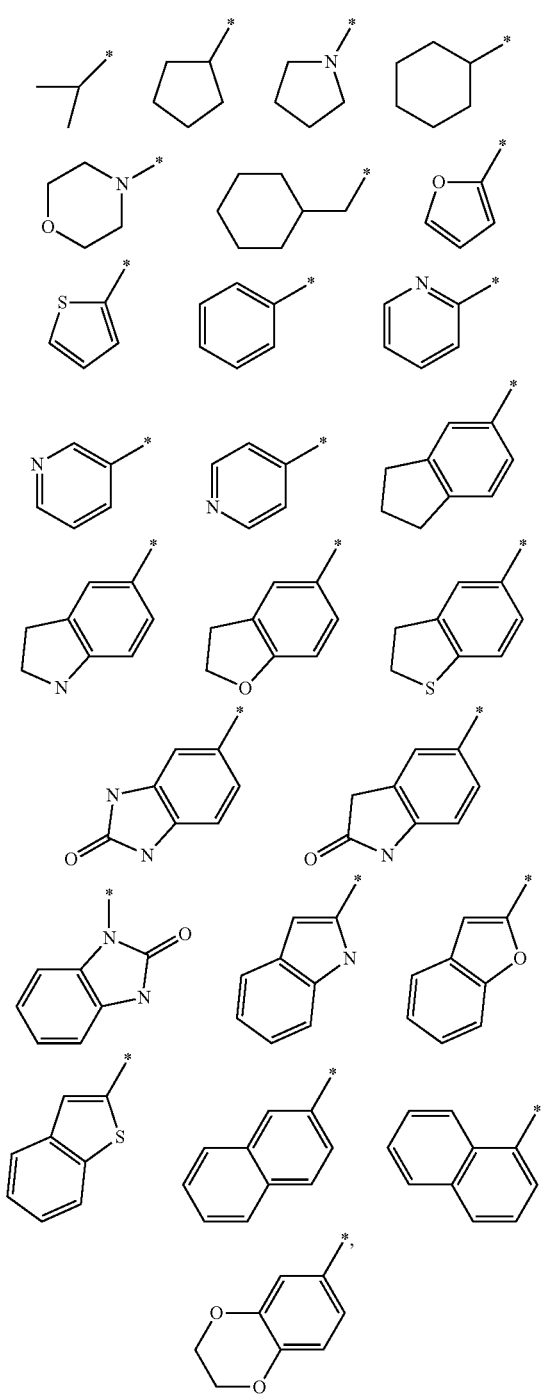

each unsubstituted or substituted with 1-3 $R_{18a}$ substituents.

9. The compound or pharmaceutically acceptable salt according to claim 7, wherein $R_{18}$ is selected from the group consisting of

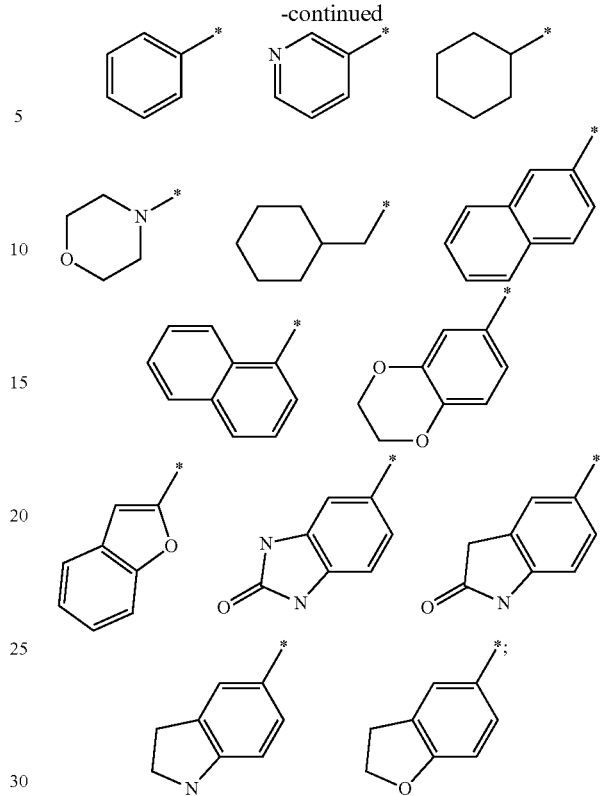

each unsubstituted or substituted with 1-3 $R_{18a}$ substituents.

10. The compound or pharmaceutically acceptable salt according to claim 8, wherein $R_{18}$ is selected from the group consisting of

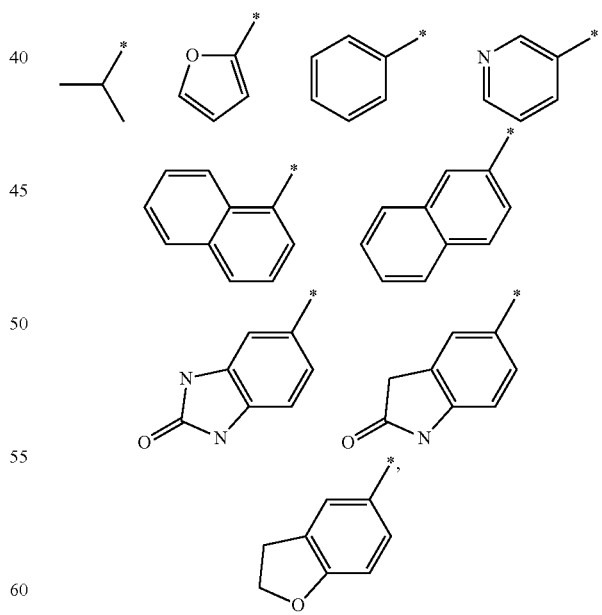

each unsubstituted or substituted with 1-3 $R_{18a}$ substituents.

11. The compound or pharmaceutically acceptable salt according to claim 7, wherein each $R_{18a}$ is independently selected from the group consisting of halo, cyano, oxo, $(C_{1-6})$alkyl, halo$(C_{1-6})$alkyl, perhalo$(C_{1-6})$alkyl, $(C_6)$aryl, ($C_{1-6}$)heteroaryl, ($C_{1-6}$)alkoxy, aryloxy, heteroaryloxy, and ($C_{1-6}$)alkylthio, each unsubstituted or further substituted.

12. The compound or pharmaceutically acceptable salt according to claim 11, wherein each $R_{18a}$ is independently selected from the group consisting of methyl, ethyl, propyl, isopropyl, trifluoromethyl, butyl, isobutyl, t-butyl, phenyl, pyridinyl, methoxy, phenoxy, pyroylthio, methoxycarbonyl, difluoromethoxy, and

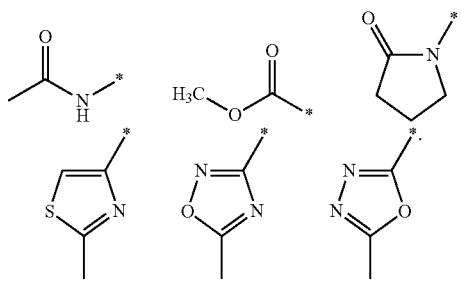

13. The compound or pharmaceutically acceptable salt according to claim 4, wherein $R_{16}$ is a cyclic moiety selected from the group consisting of ($C_{3-12}$)cycloalkyl, hetero ($C_{3-12}$) cyclo alkyl, ($C_{9-12}$)bicyclo alkyl, hetero ($C_{3-12}$)bicyclo alkyl, ($C_{4-12}$)aryl, hetero($C_{1-10}$)aryl, ($C_{9-12}$)bicycloaryl and hetero ($C_{4-12}$)bicycloaryl, each unsubstituted or substituted with 1-3 $R_{16a}$ substituents.

14. The compound or pharmaceutically acceptable salt according to claim 13, wherein $R_{16}$ is selected from the group consisting of

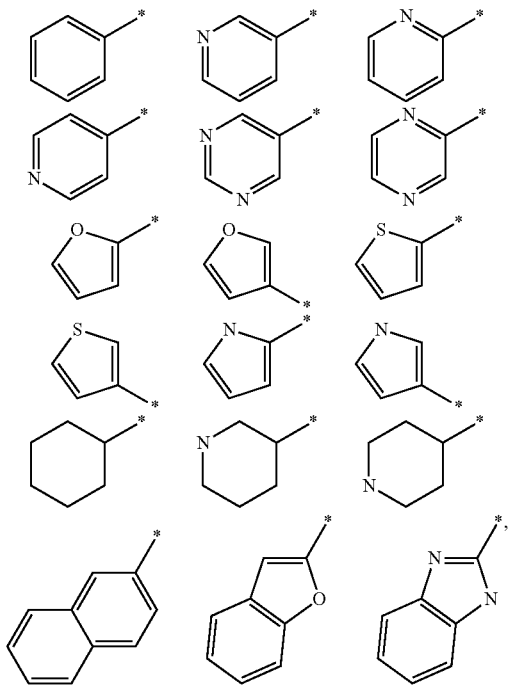

each unsubstituted or substituted with 1-3 $R_{16a}$ substituents.

15. The compound or pharmaceutically acceptable salt according to claim 14, wherein $R_{16}$ is selected from the group consisting of

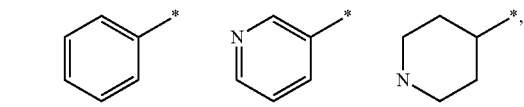

each unsubstituted or substituted with 1-3 $R_{16a}$ substituents.

16. The compound or pharmaceutically acceptable salt according to claim 13, wherein each $R_{16a}$ is independently selected from the group consisting of halo, hydroxy, ($C_{1-10}$) alkoxy, ($C_{4-12}$)aryloxy, ($C_{1-6}$)alkyl, hydroxy($C_{1-6}$)alkyl, alkoxy($C_{1-6}$)alkyl, ($C_{4-12}$)aryl, hetero($C_{1-10}$)aryl, ($C_{3-12}$)cycloalkyl, hetero($C_{3-12}$)cycloalkyl, hydroxycyclo($C_{3-6}$)alkyl, alkoxycyclo($C_{3-6}$)alkyl, amido, carboxamido, sulfonamide, carbamate, urea, each unsubstituted or further substituted with 1-3 substituents.

17. The compound or pharmaceutically acceptable salt according to claim 16, wherein each $R_{16a}$ is independently selected from the group consisting of halo, hydroxyl, unsubstituted or substituted ($C_{1-6}$)alkyl, and unsubstituted or substituted ($C_{1-10}$)alkoxy.

18. The compound or pharmaceutically acceptable salt according to claim 4, wherein $R_{16}$ is a substituted methyl of the formula

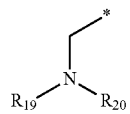

wherein
$R_{19}$ is selected from the group consisting of hydrogen, hydroxy, carbonyloxy, ($C_{1-10}$)alkoxy, ($C_{4-12}$)aryloxy, hetero($C_{1-10}$)aryloxy, carbonyl, oxycarbonyl, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$) alkyl, ($C_{3-12}$)cycloalkyl($C_{1-10}$)alkyl, hetero($C_{3-12}$)cycloalkyl($C_{1-10}$)alkyl, ($C_{4-12}$)aryl($C_{1-10}$)alkyl, hetero ($C_{1-10}$)aryl($C_{1-10}$)alkyl, ($C_{9-12}$)bicycloaryl($C_{1-10}$) alkyl, hetero($C_{8-12}$)bicycloaryl($C_{1-10}$)alkyl, hetero ($C_{1-10}$)alkyl, ($C_{3-12}$)cycloalkyl, hetero($C_{3-12}$) cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each unsubstituted or substituted; $R_{20}$ is selected from the group consisting of hydrogen, hydroxy, carbonyloxy, ($C_{1-10}$)alkoxy, ($C_{4-12}$)aryloxy, hetero($C_{1-10}$)aryloxy, carbonyl, oxycarbonyl, sulfonamido, imino, sulfonyl, sulfinyl, ($C_{1-10}$)alkyl, halo($C_{1-10}$)alkyl, hydroxy ($C_{1-10}$)alkyl, carbonyl($C_{1-10}$)alkyl, thiocarbonyl ($C_{1-10}$)alkyl, sulfonyl($C_{1-10}$)alkyl, sulfinyl($C_{1-10}$) alkyl, ($C_{1-10}$)azaalkyl, imino($C_{1-10}$)alkyl, ($C_{3-12}$)cycloalkyl($C_{1-10}$)alkyl, hetero($C_{3-12}$)cycloalkyl($C_{1-10}$) alkyl, ($C_{4-12}$)aryl($C_{1-10}$)alkyl, hetero($C_{1-10}$)aryl ($C_{1-10}$)alkyl, ($C_{9-12}$)bicycloaryl($C_{1-10}$)alkyl, hetero ($C_{8-12}$)bicycloaryl($C_{1-10}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero ($C_{4-12}$)bicycloaryl, each unsubstituted or substituted; or
$R_{19}$ and $R_{20}$ are taken together, along with the nitrogen atom to which they are attached, to form a 5, 6, or 7 membered, unsubstituted or substituted, saturated, unsaturated or heteroaromatic ring.

19. The compound or pharmaceutically acceptable salt according to claim 18, wherein $R_{19}$ is selected from the group consisting of hydrogen, unsubstituted $(C_{1-6})$alkyl, and substituted $(C_{1-6})$alkyl;

$R_{20}$ is selected from the group consisting of hydrogen, $(C_{1-6})$alkyl,

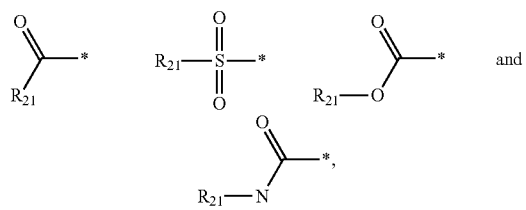

wherein each $R_{21}$ is independently selected from the group consisting of hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 $R_{21a}$ substituents, wherein each $R_{21a}$ is independently selected from the group consisting of halo, nitro, cyano, thio, oxy, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

20. The compound or pharmaceutically acceptable salt according to claim 19, wherein each $R_{21}$ is independently selected from the group consisting of $(C_{1-6})$alkyl, isopropyl, and

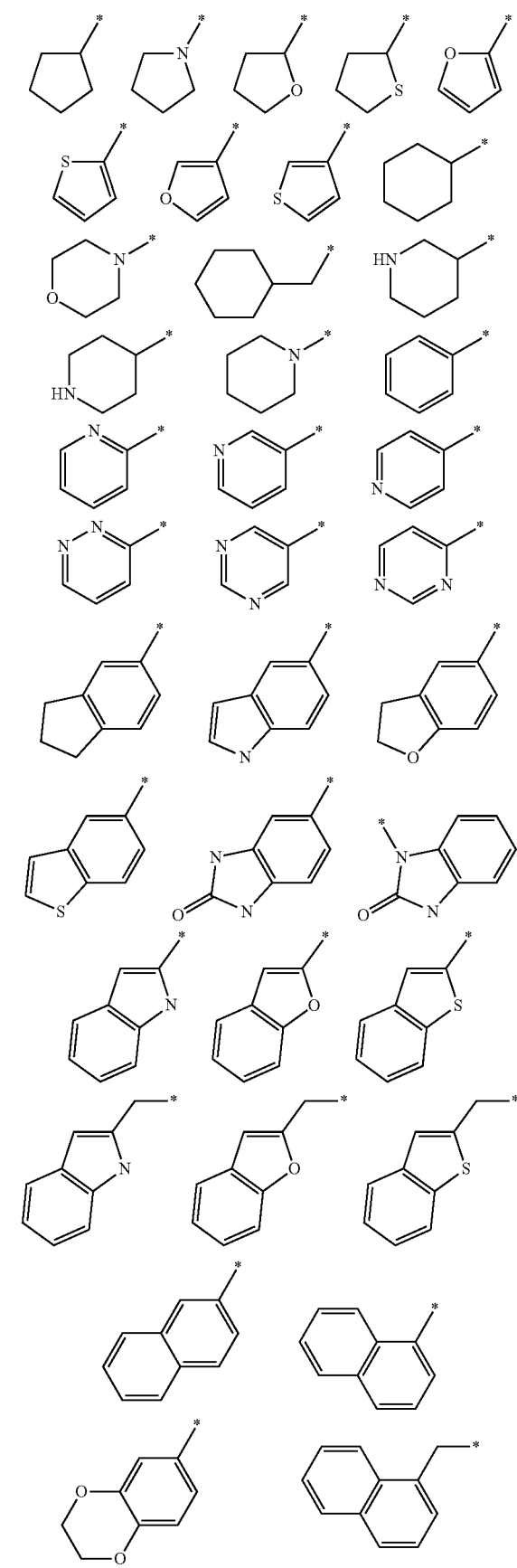

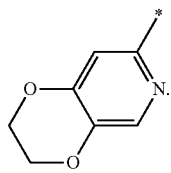

each unsubstituted or substituted with 1-3 $R_{21a}$ substituents.

21. The compound or pharmaceutically acceptable salt according to claim 20, wherein each $R_{21}$ is independently selected from the group consisting of $(C_{1-6})$alkyl, isopropyl,

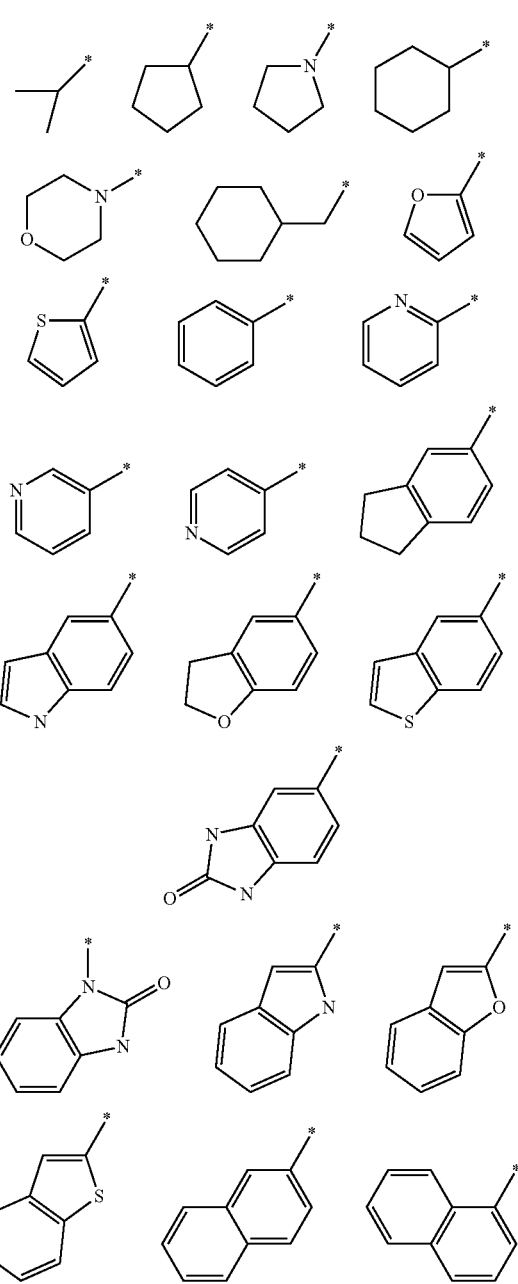

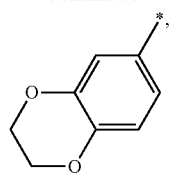

each unsubstituted or substituted with 1-3 $R_{21a}$ substituents.

22. The compound or pharmaceutically acceptable salt according to claim 21, wherein each $R_{21}$ is independently selected from the group consisting of

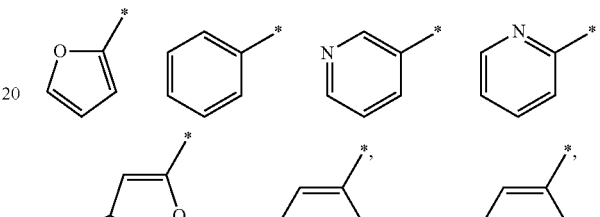

each unsubstituted or substituted with 1-3 $R_{21a}$ substituents.

23. The compound or pharmaceutically acceptable salt according to claim 19, wherein each $R_{21a}$ is independently selected from the group consisting of halo, nitro, cyano, oxo, $(C_{1-6})$alkyl, halo$(C_{1-6})$alkyl, perhalo$(C_{1-6})$alkyl, amido, alkoxycarbonyl, $(C_6)$aryl, $(C_{1-5})$hetero aryl, $(C_{1-6})$cyclo alkyl, $(C_{1-5})$hetero cyclo alkyl, $(C_{1-6})$alkoxy, aryloxy, heteroaryloxy, and $(C_{1-6})$alkylthio, each unsubstituted or further substituted.

24. The compound or pharmaceutically acceptable salt according to claim 23, wherein each $R_{21a}$ is independently selected from the group consisting of chloro, fluoro, cyano, oxo, nitro, methyl, ethyl, propyl, isopropyl, tertbutyl, phenyl, substituted phenyl, halo substituted phenyl, piperidinyl, thiophene, methoxy, difluoromethoxy, trifluoromethoxy, ethoxy, phenoxy, methoxycarbonyl, ethoxycarbonyl, $(C_{1-6})$alkylthio,

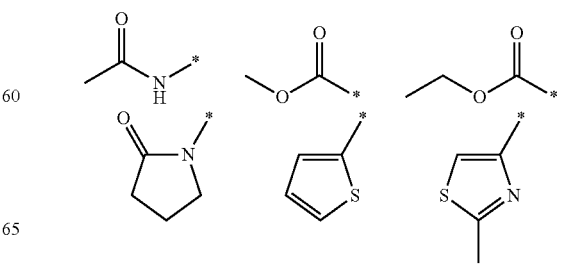

743

-continued

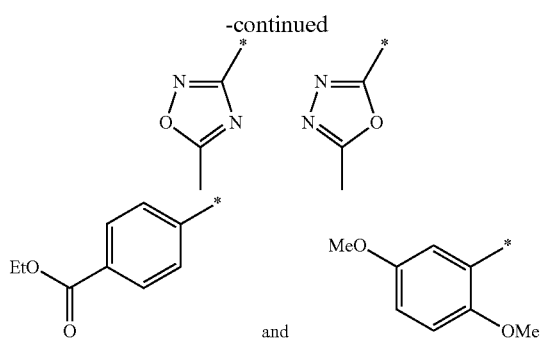

and each unsubstituted or further substituted.

25. The compound or pharmaceutically acceptable salt according to claim 23, wherein each $R_{21a}$ is selected from the group consisting of methoxy, phenyl, chloro, and

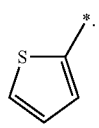

26. The compound or pharmaceutically acceptable salt according to claim 18, wherein $R_{19}$ and $R_{20}$ are taken together to form a ring of the formula

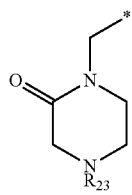

wherein
  $R_{23}$ is selected from the group consisting of hydrogen, unsubstituted $(C_{1-6})$alkyl, substituted $(C_{1-6})$alkyl,

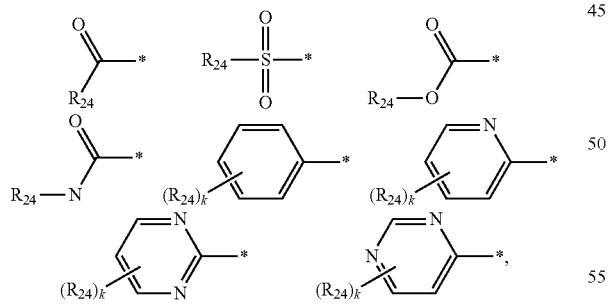

wherein
  k is 0, 1, or 2;
  each $R_{24}$ is independently selected from the group consisting of oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$ox-

744 aalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 $R_{24a}$ substituents, wherein
  each $R_{24a}$ is independently selected from the group consisting of halo, nitro, cyano, thio, oxy, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

27. The compound or pharmaceutically acceptable salt according to claim 26, wherein $R_{24}$ is selected from the group consisting of $(C_{1-6})$alkyl,

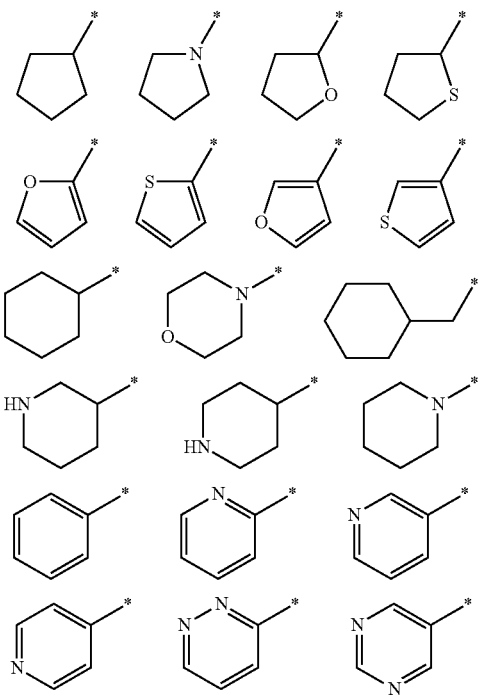

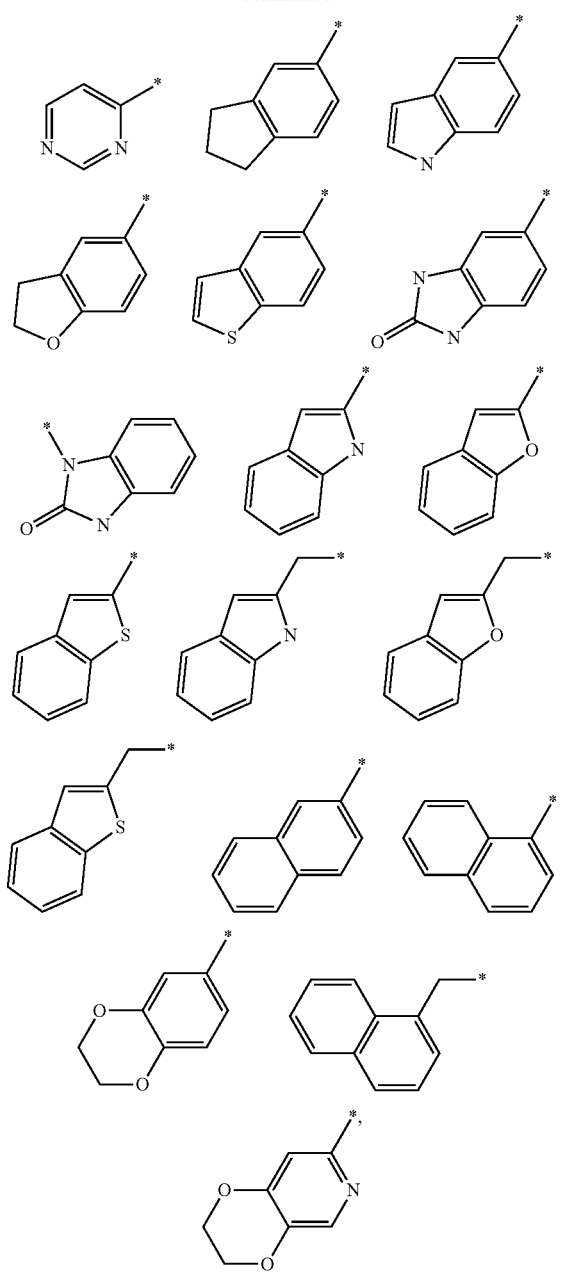

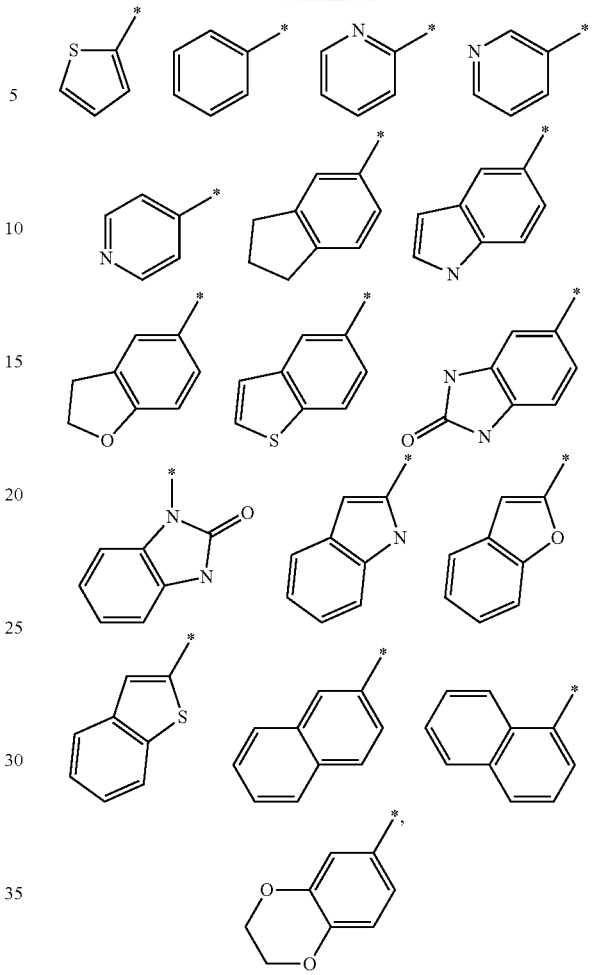

each unsubstituted or substituted with 1-3 $R_{24a}$ substituents.

28. The compound or pharmaceutically acceptable salt according to claim 27, wherein $R_{24}$ is selected from the group consisting of $(C_{1-6})$alkyl,

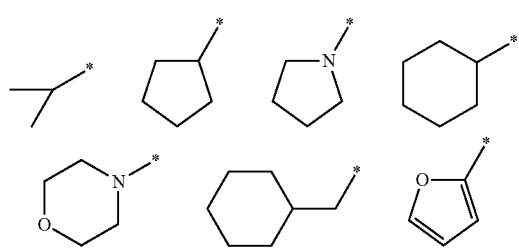

each unsubstituted or substituted with 1-3 $R_{24a}$ substituents.

29. The compound or pharmaceutically acceptable salt according to claim 28, wherein $R_{24}$ is selected from the group consisting of

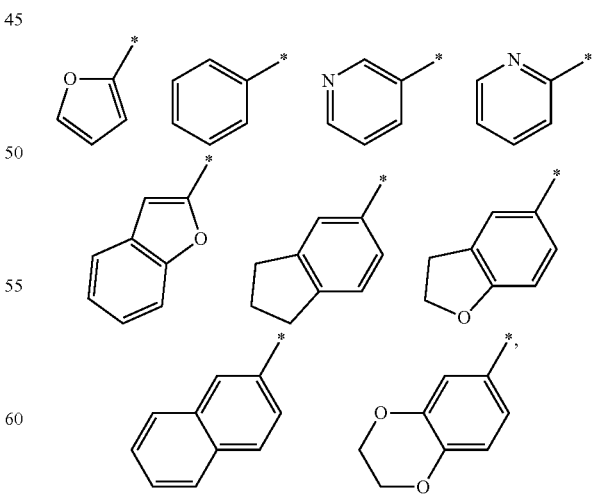

each unsubstituted or substituted with 1-3 $R_{24a}$ substituents.

30. The compound or pharmaceutically acceptable salt according to claim 26, wherein each $R_{24a}$ is independently selected from the group consisting of halo, cyano, oxo, $(C_{1-6})$alkyl, halo$(C_{1-6})$alkyl, perhalo$(C_{1-6})$alkyl, $(C_6)$aryl, $(C_{1-6})$heteroaryl, $(C_{1-6})$alkoxy, aryloxy, heteroaryloxy, and $(C_{1-6})$alkylthio, each unsubstituted or further substituted.

31. The compound or pharmaceutically acceptable salt according to claim 30, wherein each $R_{24a}$ is independently selected from the group consisting of methyl, ethyl, propyl, isopropyl, tertbutyl, phenyl, substituted phenyl, halosubstituted phenyl, piperidinyl, thiophene, methoxy, difluoromethoxy, trifluoromethoxy, ethoxy, phenoxy, methoxycarbonyl, ethoxycarbonyl, $(C_{1-6})$alkylthio, and

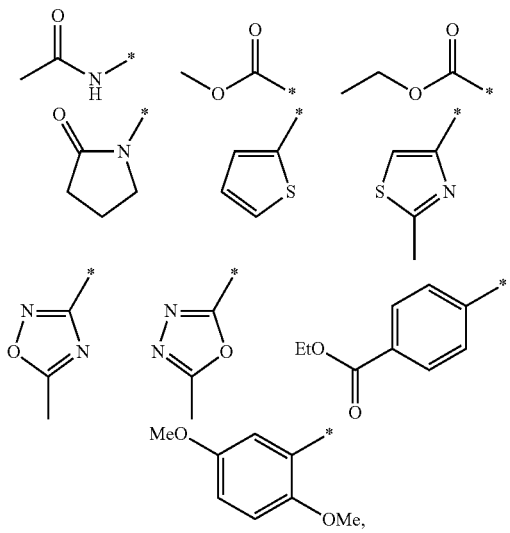

each unsubstituted or substituted.

32. The compound or pharmaceutically acceptable salt according to claim 4, wherein $R_{16}$ is a substituted methyl of the formula

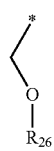

wherein
$R_{26}$ is selected from the group consisting of hydrogen, carbonyl, oxycarbonyl, aminocarbonyl, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$alkyl, $(C_{9-12})$bicycloaryl$(C_{1-10})$alkyl, hetero$(C_{8-12})$bicycloaryl$(C_{1-10})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 $R_{26a}$ substituents;
wherein
each $R_{26a}$ is independently selected from the group consisting of hydrogen, halo, nitro, cyano, thio, oxy, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl $(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl $(C_{1-10})$alkyl, $(C_{4-12})$aryl$(C_{1-10})$alkyl, hetero $(C_{1-10})$aryl$(C_{1-10})$alkyl, $(C_{9-12})$bicycloaryl $(C_{1-10})$alkyl, hetero$(C_{8-12})$bicycloaryl$(C_{1-10})$ alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$ bicycloaryl, each unsubstituted or further substituted.

33. The compound or pharmaceutically acceptable salt according to claim 32, wherein $R_{26}$ is selected from the group consisting of hydrogen, $(C_{1-6})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 $R_{26a}$ substituents.

34. The compound or pharmaceutically acceptable salt according to claim 33, wherein $R_{26}$ is selected from the group consisting of hydrogen, $(C_{1-6})$alkyl,

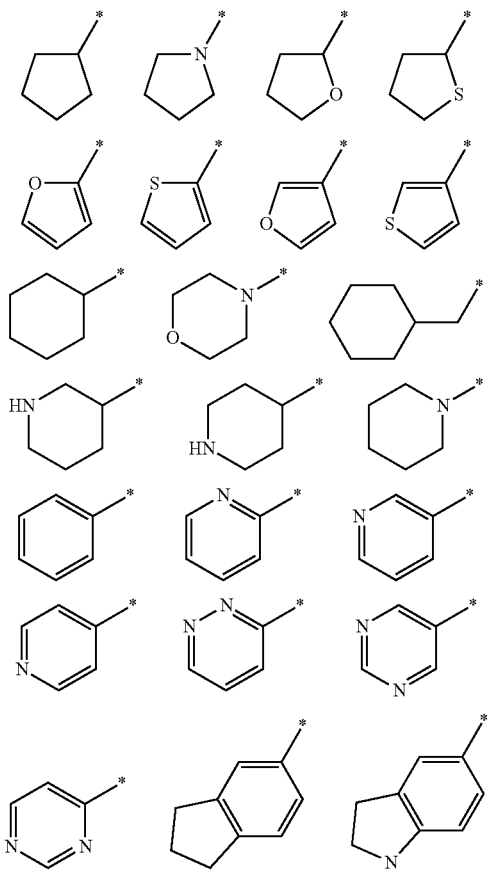

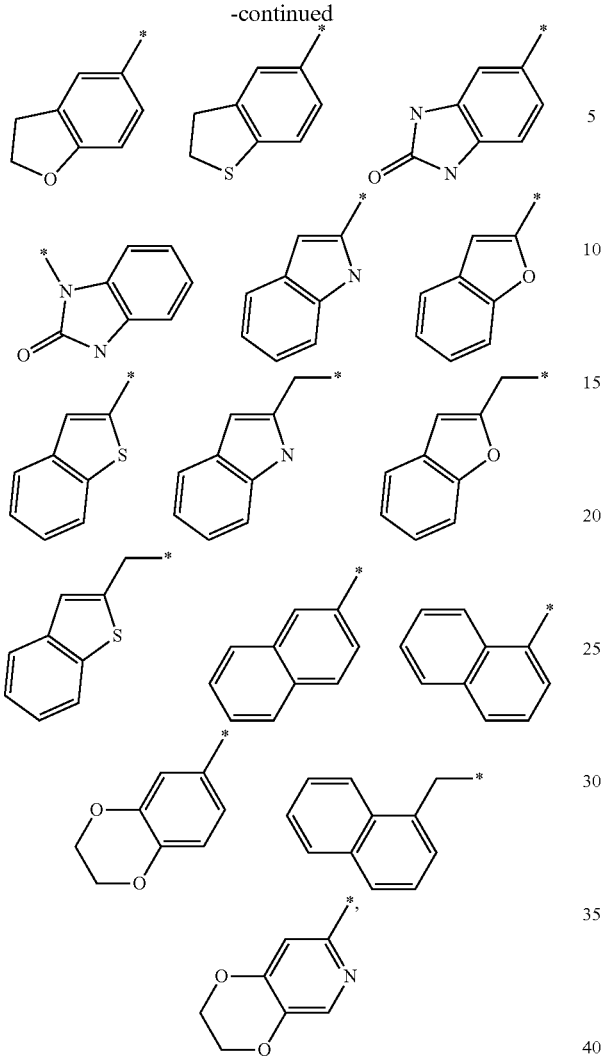

each unsubstituted or substituted with 1-3 $R_{26a}$ substituents.

35. The compound or pharmaceutically acceptable salt according to claim 33, wherein $R_{26}$ is selected from the group consisting of

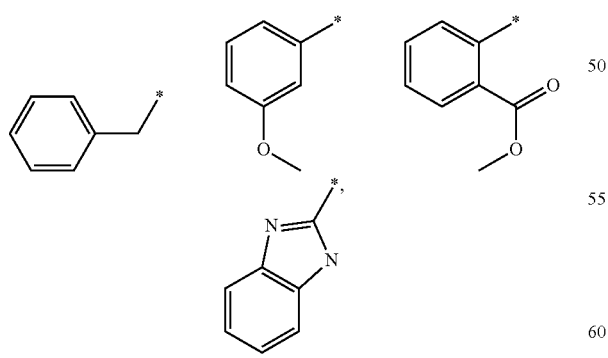

each unsubstituted or substituted with 1-3 $R_{26a}$ substituents.

36. The compound or pharmaceutically acceptable salt according to claim 32, wherein each $R_{26a}$ is independently selected from the group consisting of $(C_{1-6})$alkyl, alkylthio, $(C_{1-6})$alkoxy, oxo, haloalkyl, perhaloalkyl, $(C_{1-6})$alkoxy, ary- loxy, $(C_{1-6})$alkoxycarbonyl, aryl, heteroaryl, cycloalkyl, and heterocycloalkyl, each unsubstituted or further substituted.

37. The compound or pharmaceutically acceptable salt according to claim 4, wherein $R_{16}$ is a substituted methyl of the formula

wherein
$R_{28}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$ alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl $(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$aryl$(C_{1-10})$ alkyl, $(C_{9-12})$bicycloaryl$(C_{1-10})$alkyl, hetero$(C_{8-12})$ bicycloaryl$(C_{1-10})$alkyl, hetero$(C_{1-10})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero $(C_{4-12})$bicycloaryl, each unsubstituted or substituted with 1-3 $R_{28a}$ substituents,
wherein
each $R_{28a}$ is independently selected from the group consisting of halo, nitro, cyano, thio, oxy, hydroxy, oxo, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$ alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl $(C_{1-10})$alkyl, sulfonyl$(C_{1-10})$alkyl, sulfinyl $(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-10})$alkyl, hetero$(C_{3-12})$cycloalkyl $(C_{1-10})$alkyl, $(C_{4-12})$aryl$(C_{1-10})$alkyl, hetero $(C_{1-10})$aryl$(C_{1-10})$alkyl, $(C_{9-12})$bicycloaryl $(C_{1-10})$alkyl, hetero$(C_{8-12})$bicycloaryl$(C_{1-10})$ alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$ bicycloaryl, each unsubstituted or further substituted.

38. The compound or pharmaceutically acceptable salt according to claim 37, wherein $R_{28}$ is selected from the group consisting of $(C_{1-6})$alkyl, aryl, heteroaryl, cycloalkyl and heterocycloalkyl, aryl$(C_{1-6})$alkyl, heteroaryl$(C_{1-6})$alkyl, cycloalkyl$(C_{1-6})$alkyl, and heterocycloalkyl$(C_{1-6})$alkyl, each unsubstituted or substituted with 1-3 $R_{28a}$ substituents.

39. The compound or pharmaceutically acceptable salt according to claim 38, wherein $R_{28}$ is selected from the group consisting of aryl and heteroaryl, each unsubstituted or substituted with 1-3 $R_{28a}$ substituents.

40. The compound or pharmaceutically acceptable salt according to claim 39, wherein $R_{28}$ is selected from the group consisting of

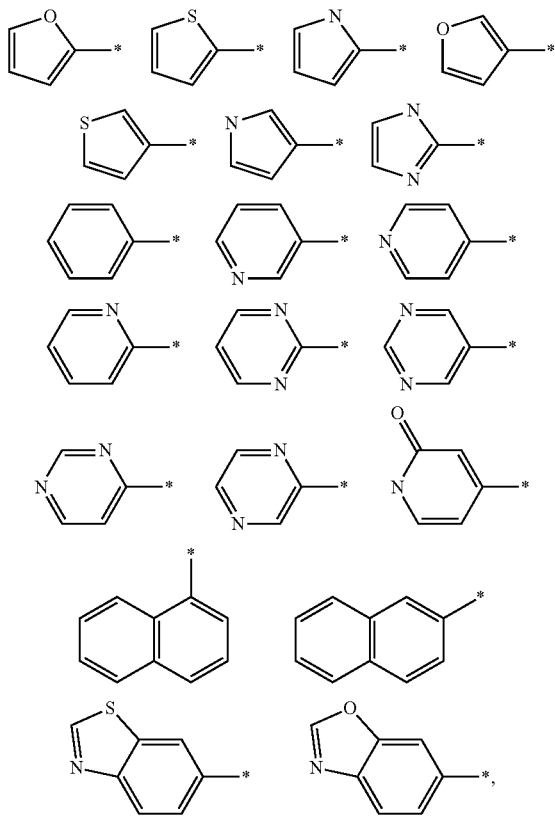

each unsubstituted or substituted with 1-3 $R_{28a}$ substituents.

41. The compound or pharmaceutically acceptable salt according to claim 40, wherein $R_{28}$ is selected from the group consisting of

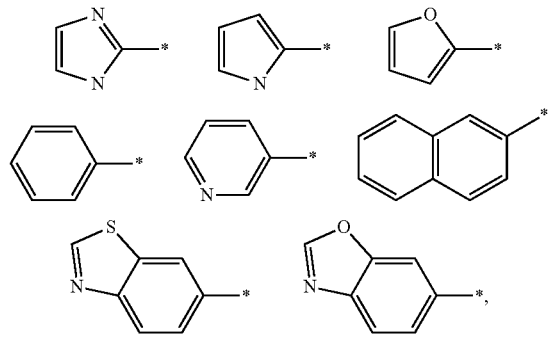

each unsubstituted or substituted with 1-3 $R_{28a}$ substituents.

42. The compound or pharmaceutically acceptable salt according to claim 41, wherein $R_{28}$ is an unsubstituted or a substituted phenyl.

43. The compound or pharmaceutically acceptable salt according to claim 41, wherein $R_{28}$ is a unsubstituted or substituted naphthyl of the formula

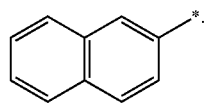

44. The compound or pharmaceutically acceptable salt according to claim 39, wherein $R_{28}$ is selected from the group consisting of substituted six-membered aryls and heteroaryls, each substituted with 1-3 $R_{28a}$ substituents, and one of $R_{28a}$ is bonded to the ring atom at the para-position relative to the point where $R_{28}$ is attached to the remainder of $R_{16}$.

45. The compound or pharmaceutically acceptable salt according to claim 37, wherein each $R_{28a}$ is independently selected from the group consisting of halo, alkoxy, aryloxy, $(C_{1-6})$alkyl, hydroxyalkyl, alkoxyalkyl, aryl, heteroaryl, cycloalkyl, heterocycloalkyl, hydroxycyclo$(C_{3-6})$alkyl, alkoxycyclo$(C_{3-6})$alkyl, amido, carboxamido, sulfonamide, carbamate, urea, each unsubstituted or further substituted.

46. The compound or pharmaceutically acceptable salt according to claim 45, wherein each $R_{28a}$ is independently selected from the group consisting of fluoro, chloro, bromo, tertbutyl, amino,

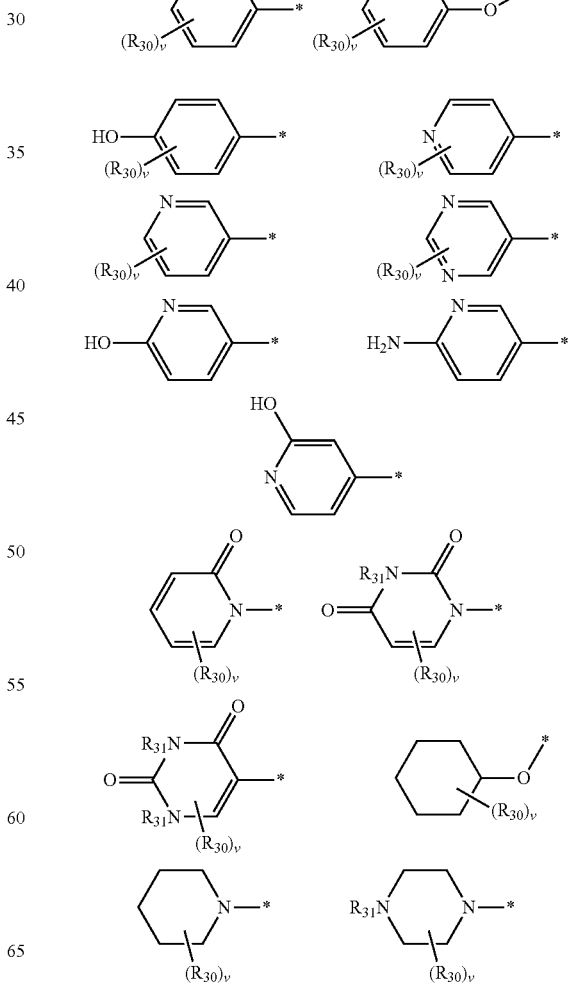

753
-continued
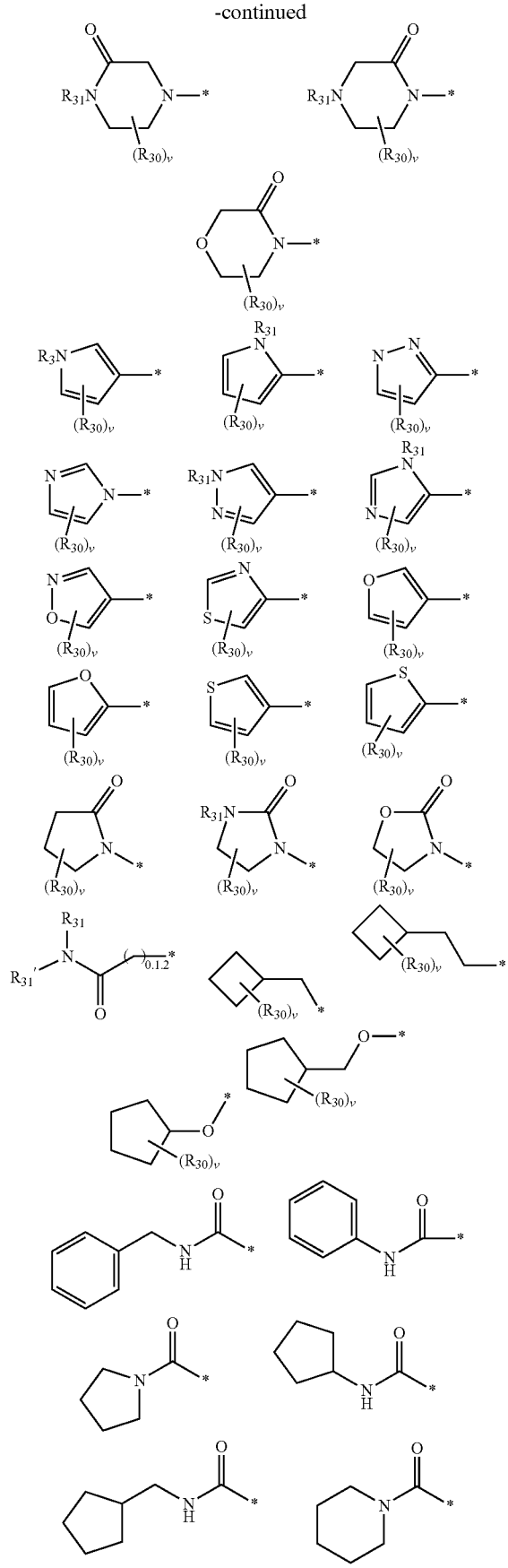
754
-continued
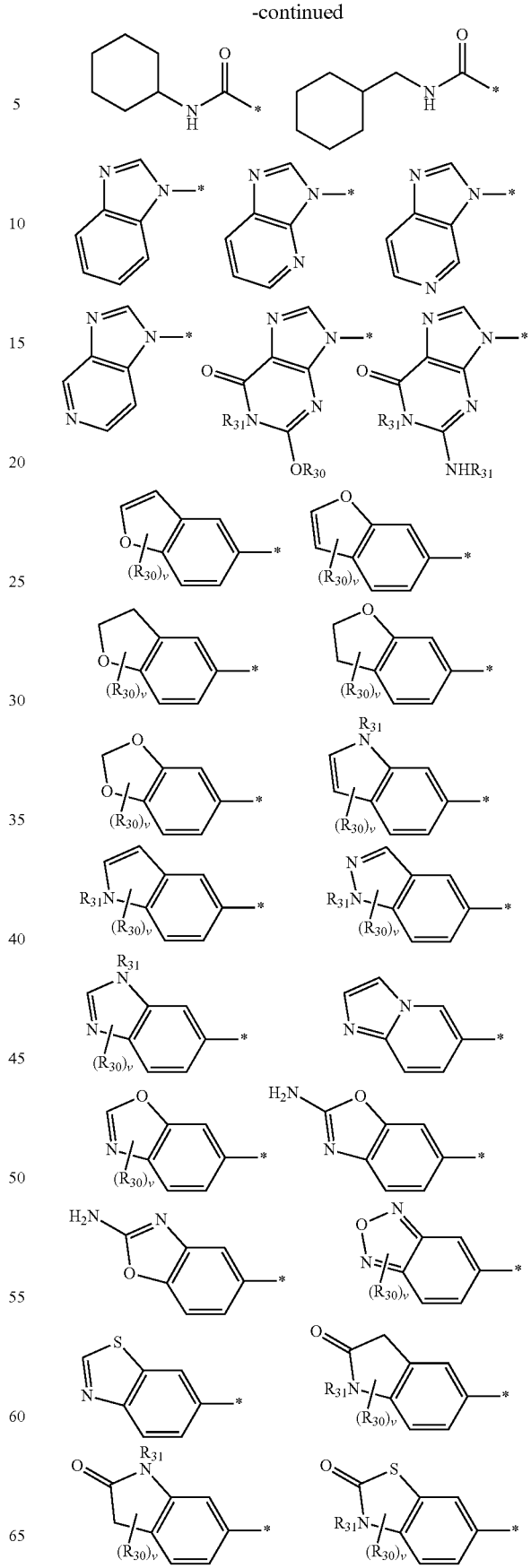

-continued

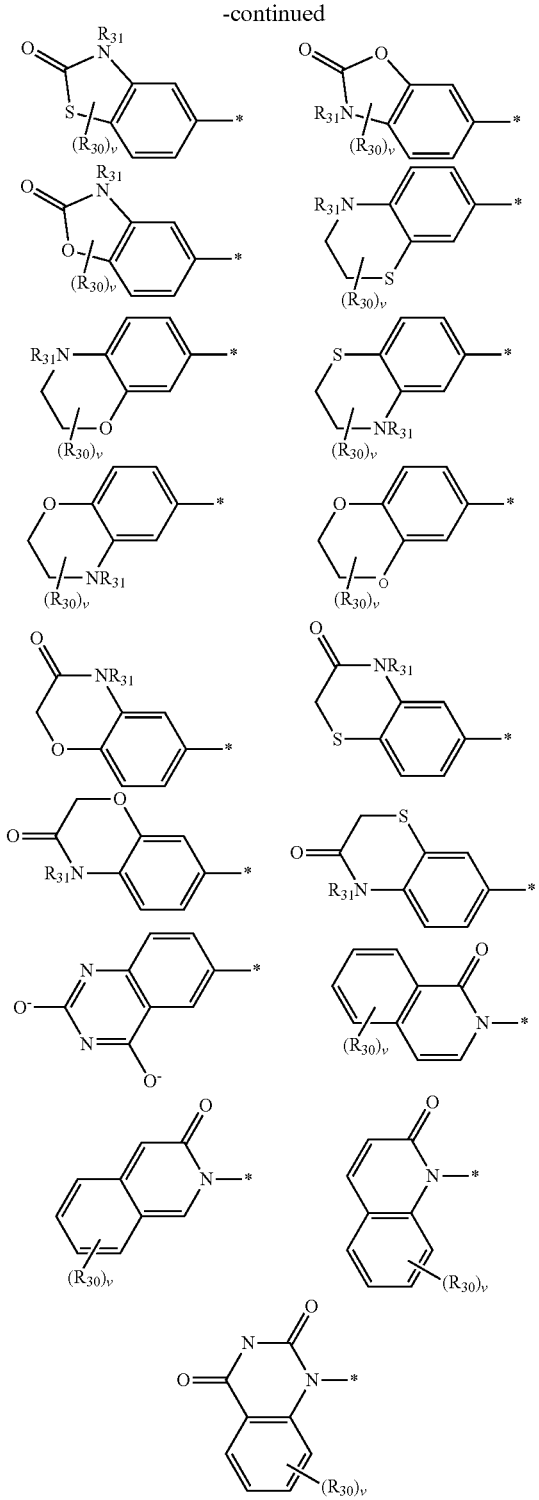

wherein
v is 0, 1, 2 or 3;
each $R_{30}$ is independently selected from the group consisting of hydrogen, halo, hydroxyl, cyano, oxo, amino, $(C_{1-6})$alkyl, alkylamino, alkylaminooxy, aminocarbonyl, alkoxycarbonyl, $(C_{1-6})$alkoxy, alkoxyalkyl, heterocycloalkyl, aryl, heteroaryl, alkylsulfonyl, amidosulfonyl, aminosulfonyl, sulfonyl, amino, amido, carboxamido, carbamate, and urea, each unsubstituted or substituted; and each $R_{31}$ or $R_{31}'$ is independently selected from the group consisting of hydrogen, $(C_{1-6})$alkyl, hydroxyalkyl, alkoxyalkyl, cycloalkyl, hydroxycyclo$(C_{3-6})$alkyl, and alkoxycyclo$(C_{3-6})$alkyl, each unsubstituted or substituted, and any two of $R_{31}$ and $R_{31}'$ may be taken together with the nitrogen atom to which they are both attached to form a 5, 6 or 7 membered, unsubstituted or substituted, saturated, unsaturated or heteroaromatic ring.

47. The compound or pharmaceutically acceptable salt according to claim 45, wherein each $R_{28a}$ is independently selected from the group consisting of tertbutyl,

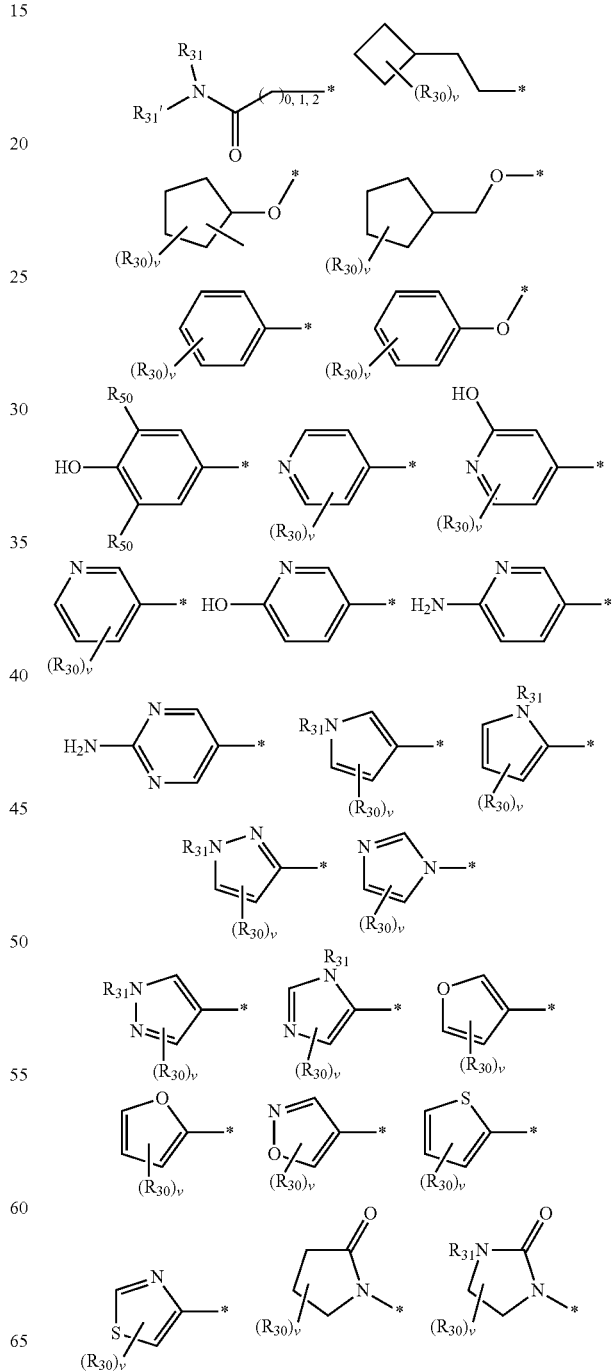

-continued

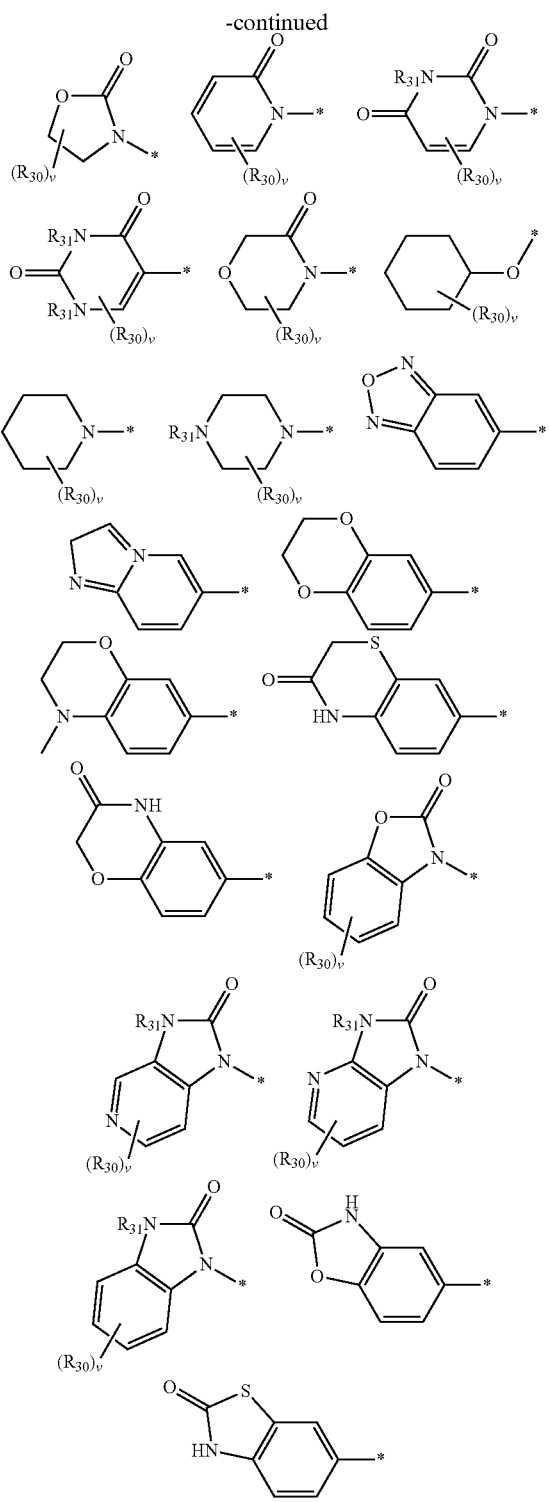

where
v is 0, 1, 2 or 3;
each $R_{30}$ is independently selected from the group consisting of hydrogen, halo, hydroxyl, cyano, oxo, amino, $(C_{1-6})$alkyl, alkylamino, alkylaminooxy, aminocarbonyl, alkoxycarbonyl, $(C_{1-6})$alkoxy, alkoxyalkyl, heterocycloalkyl, aryl, heteroaryl, alkylsulfonyl, amidosulfonyl, aminosulfonyl, sulfonyl, amino, amido, carboxamido, carbamate, and urea, each unsubstituted or substituted, and any two $R_{30}$ bonded to adjacent ring atoms may be taken together to form a 5 or 6 membered, unsubstituted or substituted, saturated, unsaturated or aromatic ring;

each $R_{31}$ or $R_{31}'$ is independently selected from the group consisting of hydrogen, $(C_{1-6})$alkyl, hydroxyalkyl, alkoxyalkyl, cycloalkyl, hydroxycyclo$(C_{3-6})$alkyl, alkoxycyclo$(C_{3-6})$alkyl, each unsubstituted or substituted, and any two of $R_{31}$ and $R_{31}'$ may be taken together with the nitrogen atom to which they are both attached to form a 5, 6 or 7 membered, unsubstituted or substituted, saturated, unsaturated or heteroaromatic ring; and each $R_{50}$ is independently selected from the group consisting of H, methyl, methoxy, chloro, and fluoro.

48. The compound or pharmaceutically acceptable salt according to claim 45, wherein each $R_{28a}$ is independently selected from the group consisting of tertbutyl,

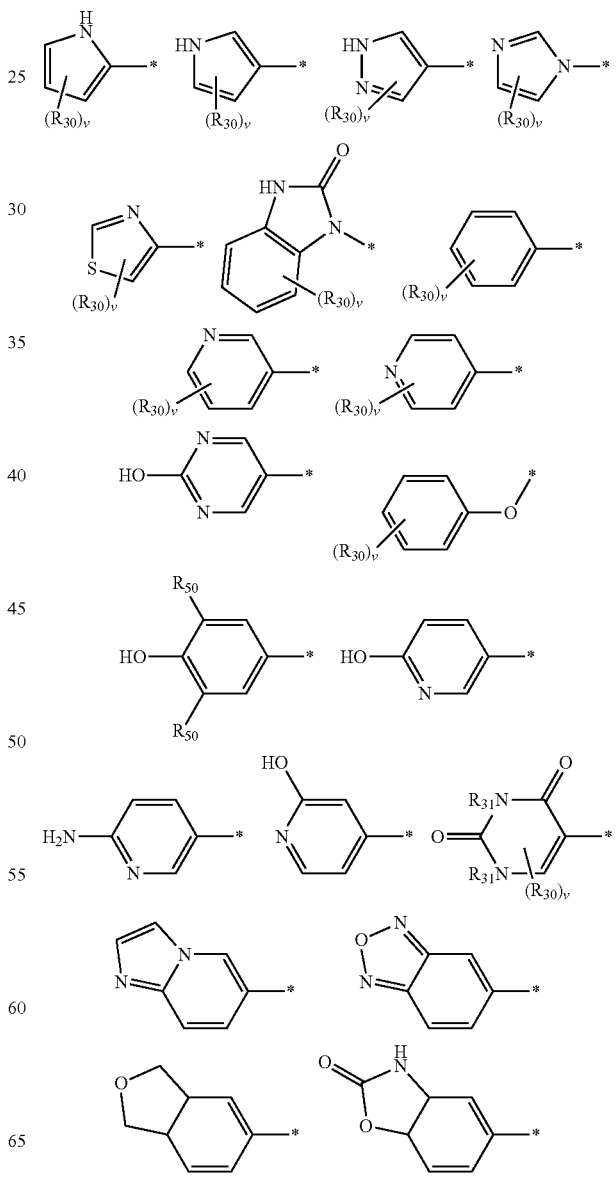

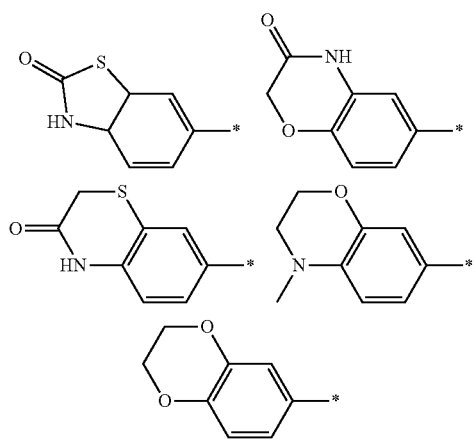

wherein v is 0, 1, 2 or 3;

each $R_{30}$ is independently selected from the group consisting of hydrogen, halo, cyano, amino, oxo, $(C_{1-6})$ alkyl, alkylamino, alkylaminooxy, aminocarbonyl, alkoxycarbonyl, $(C_{1-6})$alkoxy, alkoxyalkyl, heterocycloalkyl, aryl, heteroaryl, alkylsulfonyl, amidosulfonyl, aminosulfonyl, sulfonyl, amino, amido, carboxamido, carbamate, and urea, each unsubstituted or substituted;

each $R_{31}$ is independently selected from the group consisting of hydrogen, $(C_{1-6})$alkyl, hydroxyalkyl, alkoxyalkyl, cycloalkyl, hydroxycyclo$(C_{3-6})$alkyl, and alkoxycyclo$(C_{3-6})$alkyl, each unsubstituted or substituted; and each $R_{50}$ is independently selected from the group consisting of H, methyl, methoxy, chloro, and fluoro.

49. The compound or pharmaceutically acceptable salt according to claim 45, wherein $R_{30}$ is selected from the group consisting of hydrogen, halo, hydroxyl, cyano, oxo, $(C_{1-6})$ alkyl, —NHC(O)CH$_3$, alkylsulfonyl, amino, —C(O)NH—$(C_{1-6})$alkyl, —C(O)NH—$(C_{1-6})$alkyl$(C_{1-6})$alkoxy, $(C_{1-6})$ alkoxy, hydroxy$(C_{1-6})$alkylamino, $(C_{1-6})$alkoxy$(C_{1-6})$alkyl, —NH—$(C_{1-6})$alkyl, heterocycloalkylacyl, amido, carboxamido, phenyl, and $(C_{1-4})$heteroaryl.

50. The compound or pharmaceutically acceptable salt according to claim 45, wherein $R_{30}$ is selected from the group consisting of hydrogen, hydroxyl, halo, cyano, oxo, $(C_{1-6})$ alkyl, hydroxy$(C_{1-6})$alkyl, phenyl, $(C_{1-6})$alkoxy$(C_{1-6})$alkyl, amino, sulfonyl, $(C_{1-6})$alkoxy, $(C_{1-6})$alkylsulfonyl, morpholinyl,

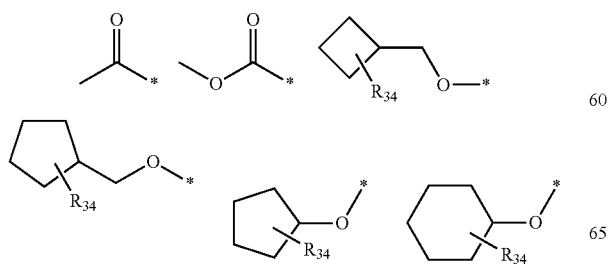

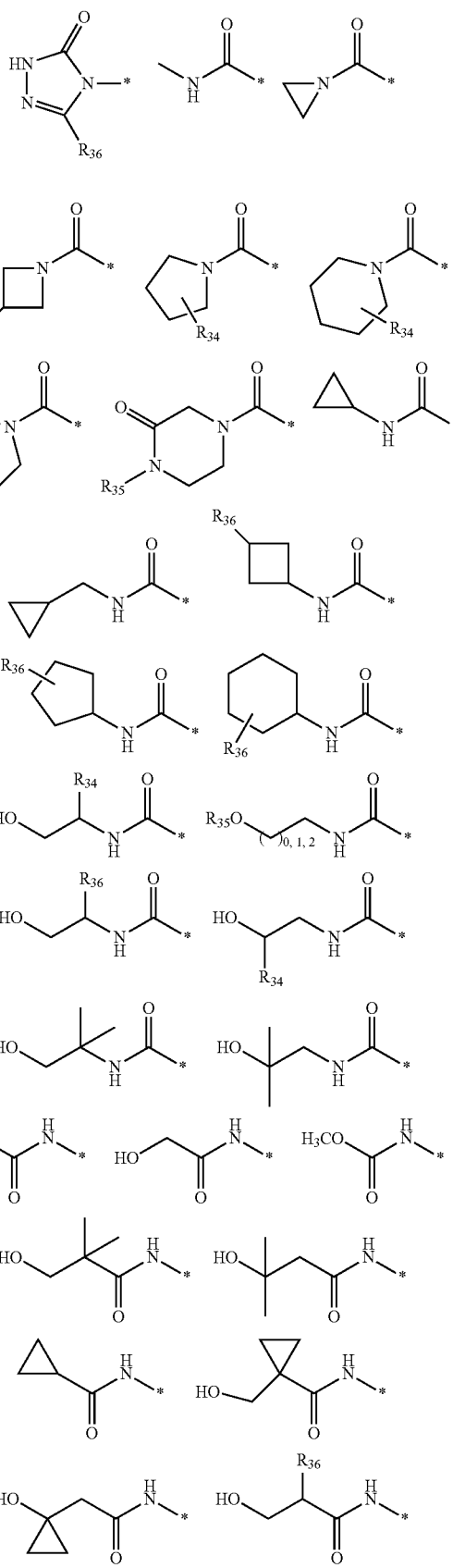

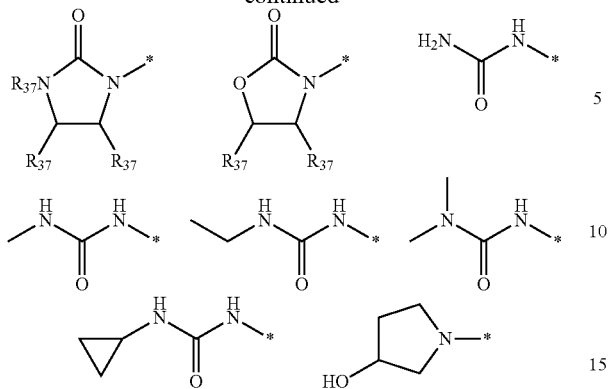

wherein
R$_{34}$ is selected from the group consisting of hydrogen, hydroxyl, halo, and hydroxymethyl;
R$_{35}$ is selected from the group consisting of hydrogen and unsubstituted or substituted (C$_{1-6}$)alkyl;
R$_{36}$ is selected from the group consisting of hydroxyl, unsubstituted or substituted (C$_{1-6}$)alkyl; and
R$_{37}$ is selected from the group consisting of hydrogen, (C$_{1-6}$)alkyl, cycloalkyl, hydroxy(C$_{1-6}$)alkyl, alkoxy (C$_{1-6}$)alkyl, hydroxycyloalkyl, alkoxycycloalkyl, halo(C$_{1-6}$)alkyl, and halocycloalkyl, each unsubstituted or substituted.

51. The compound or pharmaceutically acceptable salt according to claim 45, wherein R$_{30}$ is selected from the group consisting hydrogen, hydroxyl, fluoro, chloro, cyano, oxo, methyl, propyl, isopropyl, tertbutyl, phenyl, hydroxyethyl, methoxymethyl, methoxyethyl, ethoxypropyl, —NH$_2$, —N(CH$_3$)$_2$, —NH(CH$_3$), cyclopropylamino, methoxy, ethoxy, isopropyloxy, cyclopropylmethyloxy, methylsulfonyl, morpholinyl,

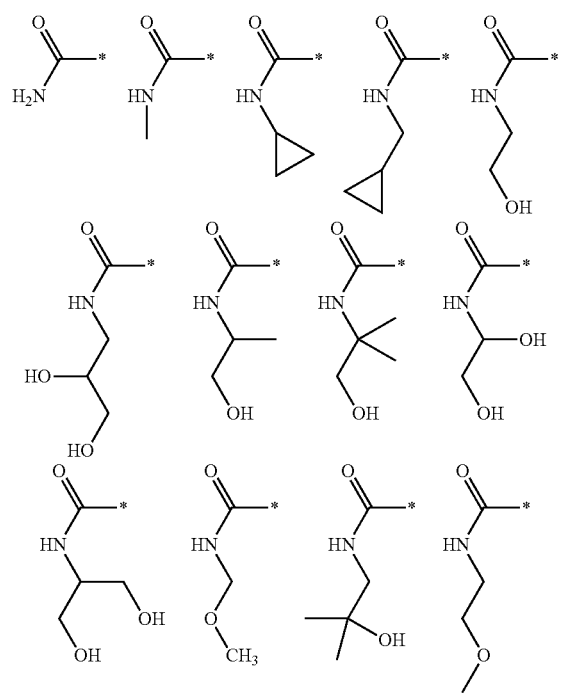

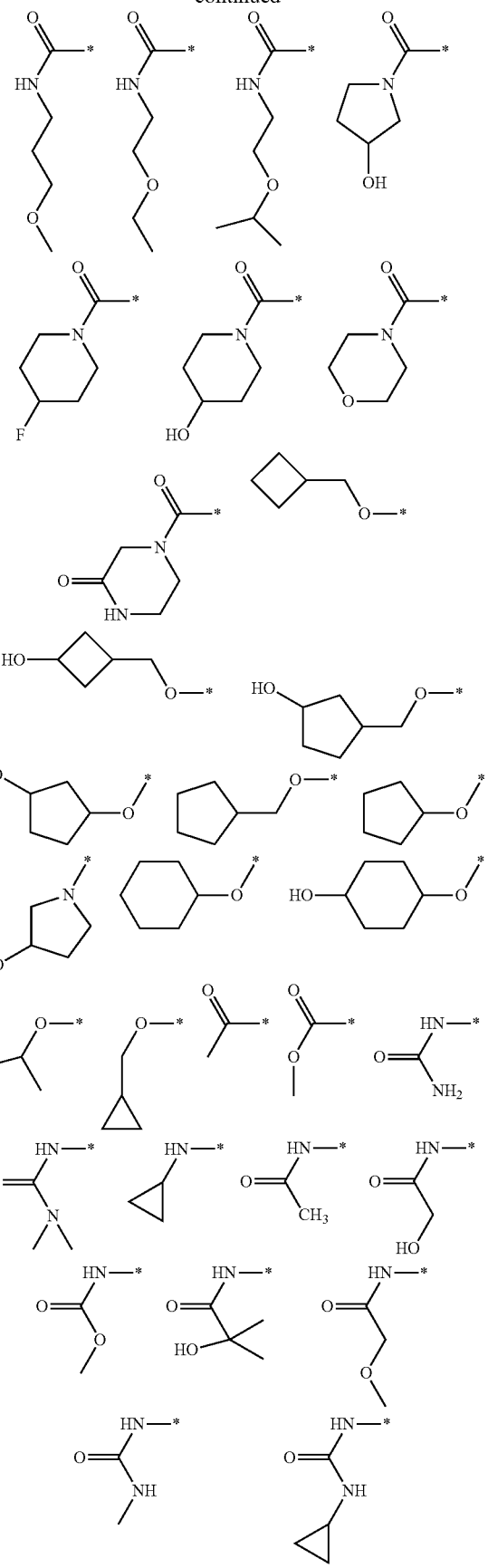

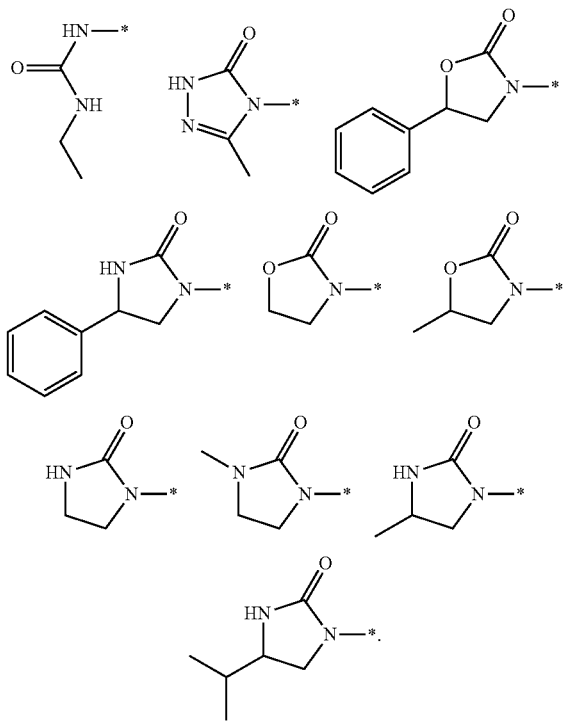

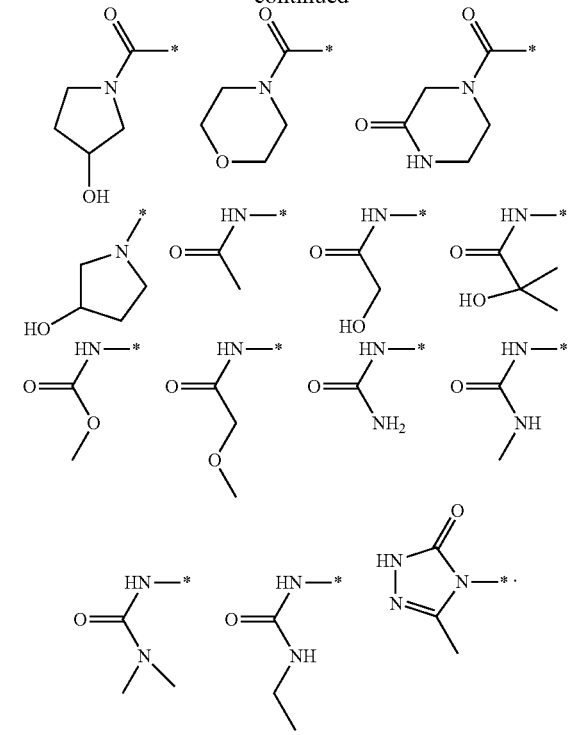

52. The compound or pharmaceutically acceptable salt according to claim 45, wherein $R_{30}$ is selected from the group consisting hydrogen, hydroxyl, fluoro, chloro, cyano, methyl, n-propyl, isopropyl, tertbutyl, hydroxyethyl, methoxymethyl, methoxyethyl, —$NH_2$, —$N(CH_3)_2$, methoxy, ethoxy, isopropyloxy, methylsulfonyl, morpholinyl, 53. The compound or pharmaceutically acceptable salt according to claim 46, wherein $R_{31}$ is selected from the group consisting of hydrogen, hydroxyl, and unsubstituted or substituted ($C_{1-6}$)alkyl.

54. The compound or pharmaceutically acceptable salt according to claim 4, wherein $R_1$ is of the formula

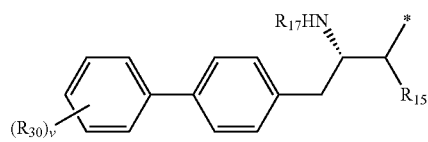

wherein v is 0, 1, 2, or 3; and $R_{30}$ is selected from the group consisting of hydroxyl, chloro,

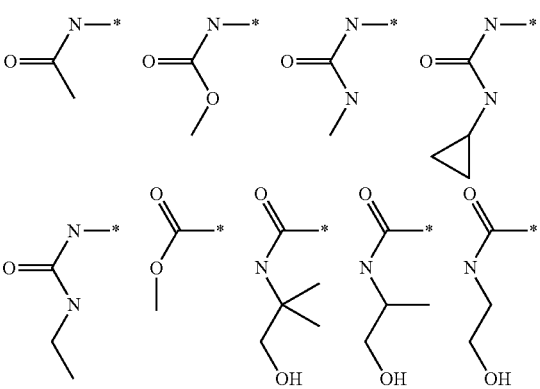

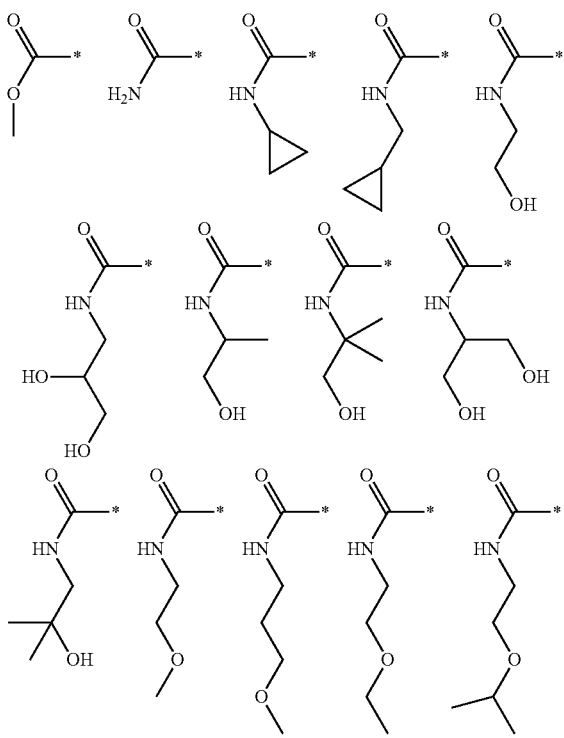

-continued

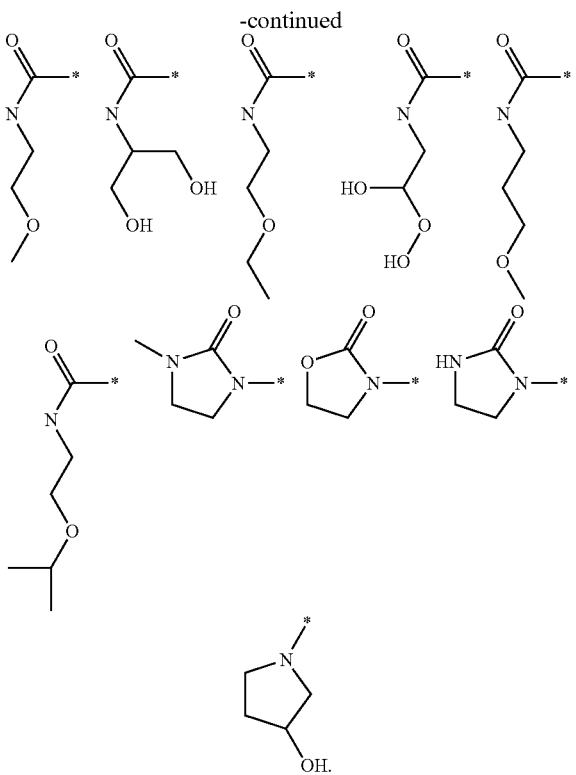

55. The compound or pharmaceutically acceptable according to claim 54, wherein $R_{15}$ is selected from the group consisting of hydrogen, hydroxyl, $(C_{1-6})$alkyl, hydroxyl$(C_{1-6})$alkyl, aryl$(C_{1-6})$alkyl, and heteroaryl$(C_{1-6})$alkyl, and $R_{17}$ is selected from the group consisting of hydrogen, $(C_{1-6})$alkyl, hydroxyl$(C_{1-6})$alkyl, alkoxy$(C_{1-6})$alkyl, halo$(C_{1-6})$alkyl, and amino$(C_{1-6})$alkyl, each unsubstituted or substituted.

56. The compound or pharmaceutically acceptable salt according to claim 55, wherein $R_{15}$ and $R_{17}$ are both hydrogen.

57. The compound or pharmaceutically acceptable salt according to claim 4, wherein $R_1$ is of the formula

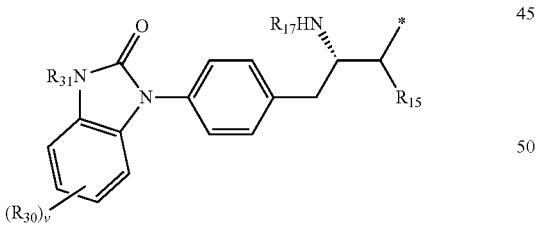

wherein
v is 0, 1, 2, or 3;
$R_{15}$ is selected from the group consisting of hydrogen, hydroxyl, $(C_{1-4})$alkyl, hydroxy$(C_{1-4})$alkyl, $(C_{1-4})$alkoxy, aryl$(C_{1-4})$alkyl, heteroaryl$(C_{1-4}$alkyl, cycloalkyl$(C_{1-4}$alkyl, and $(C_{1-4})$heterocycloalkyl $(C_{1-4})$alkyl, each unsubstituted or substituted;
$R_{17}$ is selected from the group consisting of hydrogen, $(C_{1-6})$alkyl, halo$(C_{1-6})$alkyl, hydroxy$(C_{1-6})$alkyl, carbonyl$(C_{1-6})$alkyl, sulfonyl$(C_{1-6})$alkyl, sulfinyl$(C_{1-6})$alkyl, $(C_{1-6})$azaalkyl, $(C_{3-12})$cycloalkyl$(C_{1-6})$alkyl, hetero$(C_{3-12})$cycloalkyl$(C_{1-6})$alkyl, $(C_{4-12})$aryl$(C_{1-6})$alkyl, hetero$(C_{1-10})$aryl$(C_{1-6})$alkyl, $(C_{9-12})$bicycloaryl$(C_{1-6})$alkyl, hetero$(C_{8-12})$bicycloaryl$(C_{1-6})$alkyl, hetero$(C_{1-6})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;
$R_{30}$ is selected from the group consisting of hydrogen, fluoro, methyl, propyl, hydroxyethyl, and methoxyethyl; and
$R_{31}$ is selected from the group consisting of hydrogen and $(C_{1-6})$alkyl.

58. The compound or pharmaceutically acceptable salt according to claim 57, wherein $R_{15}$ is selected from the group consisting of hydrogen, hydroxyl, $(C_{1-6})$alkyl, hydroxyl $(C_{1-6})$alkyl, aryl$(C_{1-6})$alkyl, and heteroaryl$(C_{1-6})$alkyl, and $R_{17}$ is selected from the group consisting of hydrogen, $(C_{1-6})$alkyl, hydroxyl$(C_{1-6})$alkyl, alkoxy$(C_{1-6})$alkyl, halo$(C_{1-6})$alkyl, and amino$(C_{1-6})$alkyl, each unsubstituted or substituted.

59. The compound or pharmaceutically acceptable salt according to claim 57, wherein $R_{15}$ and $R_{17}$ are both hydrogen.

60. The compound or pharmaceutically acceptable salt according to claim 4, wherein $R_1$ is of the formula

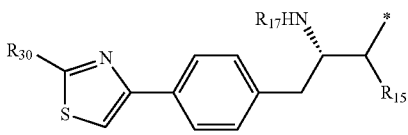

wherein
$R_{15}$ is selected from the group consisting of hydrogen, hydroxyl, $(C_{1-4})$alkyl, hydroxy$(C_{1-4})$alkyl, $(C_{1-4})$alkoxy, aryl$(C_{1-4})$alkyl, heteroaryl$(C_{1-4})$alkyl, cycloalkyl$(C_{1-4})$alkyl, and $(C_{1-4})$heterocycloalkyl $(C_{1-4})$alkyl, each unsubstituted or substituted;
$R_{17}$ is selected from the group consisting of hydrogen, $(C_{1-6})$alkyl, halo$(C_{1-6})$alkyl, hydroxy$(C_{1-6})$alkyl, carbonyl$(C_{1-6})$alkyl, sulfonyl$(C_{1-6})$alkyl, sulfinyl$(C_{1-6})$alkyl, $(C_{1-6})$azaalkyl, $(C_{3-12})$cycloalkyl$(C_{1-6})$alkyl, hetero$(C_{3-12})$cycloalkyl$(C_{1-6})$alkyl, $(C_{4-12})$aryl$(C_{1-6})$alkyl, hetero$(C_{1-10})$aryl$(C_{1-6})$alkyl, $(C_{9-12})$bicycloaryl$(C_{1-6})$alkyl, hetero$(C_{8-12})$bicycloaryl$(C_{1-6})$alkyl, hetero$(C_{1-6})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and
$R_{30}$ is selected from the group consisting of hydrogen, hydroxyl,

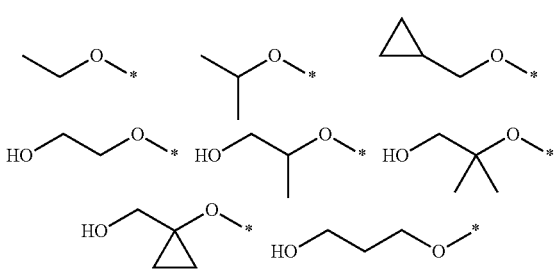

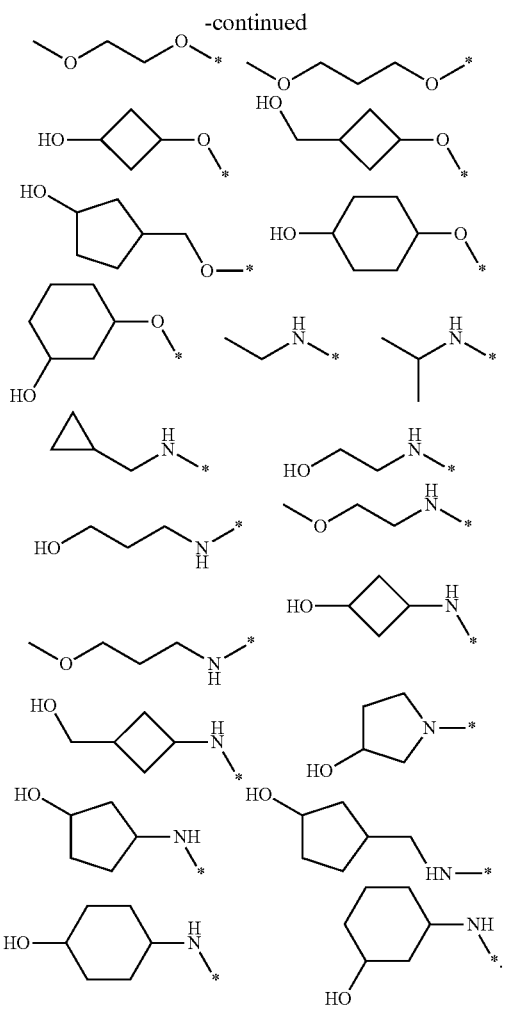

61. The compound or pharmaceutically acceptable salt according to claim 60, wherein $R_{15}$ is selected from the group consisting of hydrogen, hydroxyl, $(C_{1-6})$alkyl, hydroxyl $(C_{1-6})$alkyl, aryl$(C_{1-6})$alkyl, and heteroaryl$(C_{1-6})$alkyl, and $R_{17}$ is selected from the group consisting of hydrogen, $(C_{1-6})$ alkyl, hydroxyl$(C_{1-6})$alkyl, alkoxy$(C_{1-6})$alkyl, halo$(C_{1-6})$ alkyl, and amino$(C_{1-6})$alkyl, each unsubstituted or substituted.

62. The compound or pharmaceutically acceptable salt according to claim 61, wherein $R_{15}$ and $R_{17}$ are both hydrogen.

63. The compound or pharmaceutically acceptable salt according to claim 1, wherein $R_2$ is selected from the group consisting of $(C_{1-4})$alkyl, halo$(C_{1-10})$alkyl, hydroxy$(C_{1-10})$ alkyl, $(C_{1-6})$alkoxy$(C_{1-10})$alkyl carbonyl$(C_{1-4})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino $(C_{1-10})$alkyl, $(C_{3-12})$cycloalkyl$(C_{1-10})$alkyl, hetero$(C_{3-12})$cycloalkyl$(C_{1-10})$alkyl, $(C_{4-12})$aryl$(C_{1-10})$alkyl, hetero$(C_{1-10})$ aryl$(C_{1-10})$alkyl, $(C_{9-12})$bicycloaryl$(C_{1-10})$alkyl, hetero $(C_{8-12})$bicycloaryl$(C_{1-10})$alkyl, hetero$(C_{1-10})$alkyl, $(C_{3-12})$ cycloalkyl, hetero$(C_{3-12})$cycloalkyl, $(C_{9-12})$bicycloalkyl, and hetero$(C_{3-12})$bicycloalkyl, each unsubstituted or substituted.

64. The compound or pharmaceutically acceptable salt according to claim 1, wherein $R_2$ is -L-$R_{25}$, wherein L is a linker providing 1, 2, 3, 4, 5 or 6 atom separation between the ring atom and $R_{25}$ to which L is attached, wherein the atoms of the linker providing the separation are selected from the group consisting of carbon, oxygen, nitrogen, and sulfur; and $R_{25}$ is selected from the group consisting of cyano, halo, hydroxyl, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, amido, carboxamido, sulfonamido, imino, sulfonyl, sulfinyl, $(C_{1-10})$alkyl, $(C_{1-10})$haloalkyl, $(C_{1-10})$perhaloalkyl, $(C_{1-10})$azaalkyl, $(C_{1-10})$oxaalkyl, $(C_{1-10})$oxoalkyl, imino$(C_{1-10})$alkyl, aryl, and heteroaryl, each unsubstituted or substituted.

65. The compound or pharmaceutically acceptable salt according to claim 64, wherein L is $(C_{1-4})$alkyl, unsubstituted or substituted.

66. The compound or pharmaceutically acceptable salt according to claim 65, wherein L is —$(CH_2)_3$—.

67. The compound or pharmaceutically acceptable salt according to claim 65, wherein L is —$(CH_2)_2$—.

68. The compound or pharmaceutically acceptable salt according to claim 65, wherein L is —$(CH_2)$—.

69. The compound or pharmaceutically acceptable salt according to claim 64, wherein $R_{25}$ is selected from the group consisting of cyano, halo, haloalkyl, perhaloalkyl, hydroxyl, carbonyloxy, $(C_{1-10})$alkoxy, $(C_{4-12})$aryloxy, hetero$(C_{1-10})$ aryloxy, carbonyl, carboxamido, amido, oxycarbonyl, aminocarbonyl, amino, $(C_{1-10})$alkylamino, sulfonamido, imino, sulfonyl, sulfinyl, aryl and heteroaryl, each unsubstituted or substituted.

70. The compound or pharmaceutically acceptable salt according to claim 69, wherein $R_{25}$ is selected from the group consisting of —F, —Cl, —CN, —$CF_3$, —$OR_{27}$, —C(O) $NR_{27}R_{27}'$, —OC(O)$NR_{27}R_{27}'$, —O$(CH_2)_nOR_{27}$, —$NR_{27}R_{27}'$, —NHC(O)$OR_{27}$, —NHC(O)$R_{27}$, —NHS(O)$_2$ $R_{27}$, $(C_{4-14})$aryl, and $(C_{1-13})$heteroaryl, wherein n is 1 or 2, and $R_{27}$ and $R_{27}'$ are each independently selected from the group consisting of H, perhalo$(C_{1-7})$alkyl, $(C_{1-7})$alkyl, hydroxyl$(C_{1-7})$alkyl, $(C_6)$aryl and $(C_{1-5})$heteroaryl, each unsubstituted or substituted.

71. The compound or pharmaceutically acceptable salt according to claim 70, wherein $R_{25}$ is selected from the group consisting of —OH, —F, —$CF_3$, —CN, —$OCH_3$, —$OCH_2CH_3$, —$OCF_3$, —OC(O)$NHCH_3$, —OC(O) $NHCH_3$, —(O)$NHCH_3$, —C(O)$NHCH_2CH_3$, —NHS(O)$_2$ $CH_3$, —NHC(O)$CH_2OH$, —NHC(O)$CH_3$, —$OCH_2OCH_3$, —$OCH_2OCH_2CH_3$, —O$(CH_2)_2OH$, —O$(CH_2)_2OCH_3$, —O$(CH_2)_2OCH_2CH_3$, —$OCH_2CH(OH)CH_2OCH_3$, —$OCH_2CH(OH)CH_2OH$, —$(C_{1-5})$heteroaryl, —$(CH_2)_2$ $(C_{1-5})$heteroaryl, —$(CH_2)_2(C_{1-5})$heteroaryl,

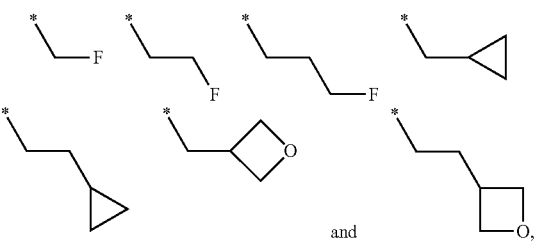

each unsubstituted or substituted.

72. The compound or pharmaceutically acceptable salt according to claim 71, wherein $R_{25}$ is selected from the group consisting of —$CF_3$, —F, —CN, —OH, and —$OCH_3$.

73. The compound or pharmaceutically acceptable salt according to claim 1, wherein $R_2$ is selected from the group consisting of —(CH$_2$)$_2$F, —(CH$_2$)$_3$OCH$_3$, (CH$_2$)$_3$OH, —(CH$_2$)$_3$OEt, —(CH$_2$)$_3$OCF$_3$, —(CH$_2$)$_3$CF$_3$, —(CH$_2$)$_3$CN, —(CH$_2$)$_3$OC(O)NHCH$_3$, —(CH$_2$)$_3$NHC(O)OCH$_3$, —(CH$_2$)$_2$NHC(O)CH$_3$, —(CH$_2$)$_2$CN, —(CH$_2$)$_2$CF$_3$, —(CH$_2$)$_3$NHC(O)OCH$_3$, —(CH$_2$)$_2$OCONHCH$_3$, —(CH$_2$)$_2$C(O)NHCH$_3$, —(CH$_2$)$_2$OCF$_3$, —(CH$_2$)$_2$NHS(O)$_2$CH$_3$, —(CH$_2$)$_2$CONHCH$_2$CH$_3$, —(CH$_2$)$_2$C(O)NHCH$_2$OH, —(CH$_2$)$_2$(C$_{1-4}$)heteroaryl, —CH$_2$CONHCH$_3$, —CH$_2$CONHCH$_2$CH$_3$, and —(CH$_2$)$_2$(C$_{1-4}$)heteroaryl, each unsubstituted or substituted.

74. The compound or pharmaceutically acceptable salt according to claim 1, wherein R$_2$ is selected from the group consisting of —(CH$_2$)$_2$F, —(CH$_2$)$_3$CF$_3$, —(CH$_2$)$_3$OCH$_3$, —(CH$_2$)$_3$OH, —(CH$_2$)$_3$CN,

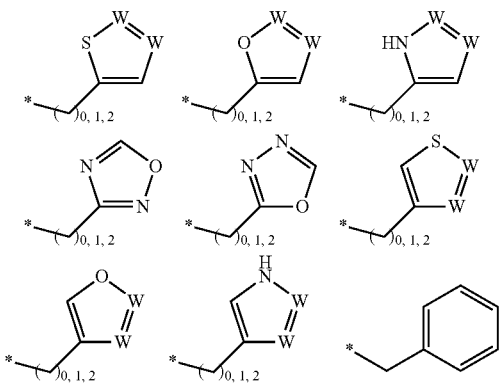

wherein W$_1$ and W$_2$ are each independently —CH— or N.

75. The compound or pharmaceutically acceptable salt according to claim 1, wherein R$_2$ is —(CH$_2$)$_3$OCH$_3$.

76. The compound or pharmaceutically acceptable salt according to claim 1, wherein R$_6$ is selected from the group consisting of hydrogen, hydroxyl, (C$_{1-3}$)alkyl, (C$_{1-3}$)alkoxy, (C$_{1-3}$)alkoxy(C$_{1-3}$)alkyl, and —COOR, wherein R is alkyl, cycloalkyl, cycloheteroalkyl, aryl and heteroaryl, each unsubstituted or substituted.

77. The compound or pharmaceutically acceptable salt according to claim 76, wherein R$_6$ is selected from the group consisting of hydrogen and hydroxyl.

78. The compound or pharmaceutically acceptable salt according to claim 1, wherein R$_7$ is selected from the group consisting of hydrogen, halo, cyano, thio, oxy, hydroxy, carbonyloxy, alkoxy, aryloxy, heteroaryloxy, carbonyl, aminocarbonyl, amino, (C$_{1-10}$)alkylamino, (C$_{1-10}$)alkyl, carbonyl(C$_{1-3}$)alkyl, sulfonyl(C$_{1-3}$)alkyl, amino(C$_{1-10}$)alkyl, (C$_{3-7}$)cycloalkyl(C$_{1-10}$)alkyl, hetero(C$_{3-7}$)cycloalkyl(C$_{1-10}$)alkyl, (C$_{4-12}$)aryl(C$_{1-10}$)alkyl, heteroaryl(C$_{1-10}$)alkyl, and aminocarbonyloxy, each unsubstituted or substituted.

79. The compound or pharmaceutically acceptable salt according to claim 78, wherein R$_7$ is selected from the group consisting of hydrogen, methyl, ethyl, and methoxy.

80. The compound or pharmaceutically acceptable salt according to claim 1, wherein each R$_{10}$ is independently selected from the group consisting of hydrogen, cyano, nitro, oxo, halo, hydroxyl, carbonyloxy, (C$_{1-10}$)alkoxy, carbonyl, amino, (C$_{1-10}$)alkylamino, sulfonamido, (C$_{1-10}$)alkyl, halo(C$_{1-10}$)alkyl, hydroxy(C$_{1-10}$)alkyl, carbonyl(C$_{1-10}$)alkyl, sulfonyl(C$_{1-10}$)alkyl, (C$_{1-10}$)azaalkyl, (C$_{1-10}$)oxaalkyl, (C$_{1-10}$)oxoalkyl, and hetero(C$_{1-10}$)alkyl, each unsubstituted or substituted.

81. The compound or pharmaceutically acceptable salt according to claim 80, wherein each R$_{10}$ is independently selected from the group consisting of hydrogen, (C$_{1-4}$)alkyl, cyano, oxo, and halo.

82. The compound or pharmaceutically acceptable salt according to claim 80, wherein each R$_{10}$ is independently selected from the group consisting of hydrogen, methyl, isopropyl, chloro, fluoro, oxo, nitro, and methoxy.

83. The compound or pharmaceutically acceptable salt according to claim 1, wherein when bound to a benzimidazole of the formula

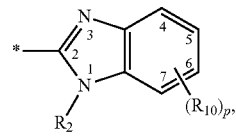

R$_{10}$ is selected from the group consisting of hydrogen, 4-methyl, 5-methyl, 6-methyl, 6-isopropyl, 4-fluoro, 5-fluoro, 6-fluoro, 7-fluoro, 4-chloro, 5-chloro, 6-chloro, 7-chloro, 4-cyano, 6-cyano, 7-cyano, 5-nitro, 6-nitro, 4-methoxy, 6-methoxy, and 7-methoxy.

84. The compound or pharmaceutically acceptable salt according to claim 83, wherein R$_{10}$ is selected from the group consisting of hydrogen, 4-methyl, 5-methyl, 6-methyl, 6-fluoro, 4-chloro, 6-chloro, and 7-chloro.

85. The compound or pharmaceutically acceptable salt according to claim 84, wherein R$_{10}$ is selected from the group consisting of hydrogen and 4-chloro.

86. The compound or pharmaceutically acceptable salt according to claim 84, wherein R$_{10}$ is selected from the group consisting of hydrogen and 4-methyl.

87. The compound or pharmaceutically acceptable salt according to claim 84, wherein R$_{10}$ is selected from the group consisting of hydrogen and 7-chloro.

88. A compound according to claim 1 which is selected from the group consisting of:
  (3R)-1-(3-(1H-benzo[d]imidazol-2-yl)piperidin-1-yl)-3-amino-4-(4-chlorophenyl)butan-1-one;
  (3R)-3-amino-4-(4-chlorophenyl)-1-(3-(1-(3-methoxypropyl)-1H-benzo[d]imidazol-2-yl)piperidin-1-yl)butan-1-one;
  (3S)-1-(3-(1H-benzo[d]imidazol-2-yl)piperidin-1-yl)-3-amino-3-(4-(trifluoromethyl)phenyl)propan-1-one;
  (3S)-1-(3-(1H-benzo[d]imidazol-2-yl)piperidin-1-yl)-3-amino-3-(2-nitrophenyl)propan-1-one;
  (3R)-1-(3-(1H-benzo[d]imidazol-2-yl)piperidin-1-yl)-3-amino-4-(2-chlorophenyl)butan-1-one;
  (3S)-1-(3-(1H-benzo[d]imidazol-2-yl)piperidin-1-yl)-3-amino-3-(2,3-dimethoxyphenyl)propan-1-one;
  (3R)-1-(3-(1H-benzo[d]imidazol-2-yl)piperidin-1-yl)-3-amino-4-(benzo[b]thiophen-3-yl)butan-1-one;
  (3S)-1-(3-(1H-benzo[d]imidazol-2-yl)piperidin-1-yl)-3-amino-3-(3-chlorophenyl)propan-1-one;
  (3S)-1-(3-(1H-benzo[d]imidazol-2-yl)piperidin-1-yl)-3-amino-3-(3,5-dimethoxyphenyl)propan-1-one;
  (3R)-1-(3-(1H-benzo[d]imidazol-2-yl)piperidin-1-yl)-3-amino-5-phenylpentan-1-one;
  (3S)-1-(3-(1H-benzo[d]imidazol-2-yl)piperidin-1-yl)-3-amino-3-(4-nitrophenyl)propan-1-one;
  (3R)-1-(3-(1H-benzo[d]imidazol-2-yl)piperidin-1-yl)-3-amino-4-(4-bromophenyl)butan-1-one;
  (3S)-1-(3-(1H-benzo[d]imidazol-2-yl)piperidin-1-yl)-3-amino-3-(2,4-dichlorophenyl)propan-1-one;
  (3R)-1-(3-(1H-benzo[d]imidazol-2-yl)piperidin-1-yl)-3-amino-4-(3,4-dichlorophenyl)butan-1-one;
  (3S)-1-(3-(1H-benzo[d]imidazol-2-yl)piperidin-1-yl)-3-amino-3-(2,3-dichlorophenyl)propan-1-one;

(3R)-1-(3-(1H-benzo[d]imidazol-2-yl)piperidin-1-yl)-3-amino-4-(naphthalen-1-yl)butan-1-one;
(3R)-1-(3-(1H-benzo[d]imidazol-2-yl)piperidin-1-yl)-3-amino-4-(4-nitrophenyl)butan-1-one;
(3S)-1-(3-(1H-benzo[d]imidazol-2-yl)piperidin-1-yl)-3-amino-3-(3-nitrophenyl)propan-1-one;
(3S)-1-(3-(1H-benzo[d]imidazol-2-yl)piperidin-1-yl)-3-amino-3-(3-bromophenyl)propan-1-one;
(3R)-1-(3-(1H-benzo[d]imidazol-2-yl)piperidin-1-yl)-3-amino-4-o-tolylbutan-1-one;
(3R)-1-(3-(1H-benzo[d]imidazol-2-yl)piperidin-1-yl)-3-amino-4-m-tolylbutan-1-one;
(3R)-1-(3-(1H-benzo[d]imidazol-2-yl)piperidin-1-yl)-3-amino-4-(naphthalen-2-yl)butan-1-one;
(3-(1H-benzo[d]imidazol-2-yl)piperidin-1-yl)(piperidin-3-yl)methanone;
(3R)-3-amino-1-(3-(1-(3-methoxypropyl)-1H-benzo[d]imidazol-2-yl)piperidin-1-yl)-3-phenylpropan-1-one;
(3S)-3-amino-1-(3-(1-(3-methoxypropyl)-1H-benzo[d]imidazol-2-yl)piperidin-1-yl)-3-phenylpropan-1-one;
(3S)-3-amino-4-(4-chlorophenyl)-1-(3-(1-(3-methoxypropyl)-1H-benzo[d]imidazol-2-yl)piperidin-1-yl)butan-1-one;
(R)-3-amino-4-(4-chlorophenyl)-1-((S)-3-(1-(3-methoxypropyl)-1H-benzo[d]imidazol-2-yl)piperidin-1-yl)butan-1-one;
(S)-3-amino-4-(4-chlorophenyl)-1-((R)-3-(1-(3-methoxypropyl)-1H-benzo[d]imidazol-2-yl)piperidin-1-yl)butan-1-one;
(S)-3-amino-4-(4-chlorophenyl)-1-((S)-3-(1-(3-methoxypropyl)-1H-benzo[d]imidazol-2-yl)piperidin-1-yl)butan-1-one;
(R)-1-((R)-3-(1H-benzo[d]imidazol-2-yl)piperidin-1-yl)-3-amino-4-(biphenyl-4-yl)butan-1-one;
(R)-3-Amino-4-(biphenyl-4-yl)-1-((R)-3-(1-(3-methoxypropyl)-1H-benzo[d]imidazol-2-yl)piperidin-1-yl)butan-1-one;
4-(biphenyl-4-yl)-3-hydroxy-1-((R)-3-(1-(3-methoxypropyl)-1H-benzo[d]imidazol-2-yl)piperidin-1-yl)butan-1-one;
(R)-3-amino-1-((R)-3-(1-(3-methoxypropyl)-1H-benzo[d]imidazol-2-yl)piperidin-1-yl)-4-(naphthalen-2-yl)butan-1-one;
(R)-3-amino-4-(4-chlorophenyl)-1-((R)-3-(1-(3-methoxypropyl)-1H-benzo[d]imidazol-2-yl)piperidin-1-yl)butan-1-one;
(R)-3-amino-4-(3,4-difluorophenyl)-1-((R)-3-(1-(3-methoxypropyl)-1H-benzo[d]imidazol-2-yl)piperidin-1-yl)butan-1-one;
(R)-3-amino-4-(3,4-dichlorophenyl)-1-((R)-3-(1-(3-methoxypropyl)-1H-benzo[d]imidazol-2-yl)piperidin-1-yl)butan-1-one;
(R)-3-amino-1-((R)-3-(1-(3-methoxypropyl)-1H-benzo[d]imidazol-2-yl)piperidin-1-yl)-4-(pyridin-4-yl)butan-1-one
(R)-3-amino-4-(3-chlorophenyl)-1-((R)-3-(1-(3-methoxypropyl)-1H-benzo[d]imidazol-2-yl)piperidin-1-yl)butan-1-one;
(S)-3-amino-3-(3-bromophenyl)-1-((R)-3-(1-(3-methoxypropyl)-1H-benzo[d]imidazol-2-yl)piperidin-1-yl)propan-1-one;
(R)-3-amino-1-((R)-3-(5,6-dichloro-1-(3-methoxypropyl)-1H-benzo[d]imidazol-2-yl)piperidin-1-yl)-4-(naphthalen-2-yl)butan-1-one;
(R)-3-amino-1-((R)-3-(1-(3-methoxypropyl)-1H-benzo[d]imidazol-2-yl)piperidin-1-yl)-4-(pyridin-3-yl)butan-1-one;
(S)-3-amino-3-(3-chlorophenyl)-1-((R)-3-(1-(3-methoxypropyl)-1H-benzo[d]imidazol-2-yl)piperidin-1-yl)propan-1-one;
(S)-3-amino-1-((R)-3-(1-(3-methoxypropyl)-1H-benzo[d]imidazol-2-yl)piperidin-1-yl)-3-(3-(trifluoromethyl)phenyl)propan-1-one;
3-((S)-1-amino-3-((R)-3-(1-(3-methoxypropyl)-1H-benzo[d]imidazol-2-yl)piperidin-1-yl)-3-oxopropyl)benzonitrile;
(R)-3-amino-1-((R)-3-(1-(3-methoxypropyl)-1H-benzo[d]imidazol-2-yl)piperidin-1-yl)-4-(2,4,5-trifluorophenyl)butan-1-one;
(R)-3-amino-1-((R)-3-(1-(3-methoxypropyl)-1H-benzo[d]imidazol-2-yl)piperidin-1-yl)-4-phenylbutan-1-one;
(S)-3-amino-4-(benzyloxy)-1-((R)-3-(1-(3-methoxypropyl)-1H-benzo[d]imidazol-2-yl)piperidin-1-yl)butan-1-one;
(S)-3-amino-1-((R)-3-(1-(3-methoxypropyl)-1H-benzo[d]imidazol-2-yl)piperidin-1-yl)-3-phenylpropan-1-one;
(R)-3-amino-4-(4-tert-butylphenyl)-1-((R)-3-(1-(3-methoxypropyl)-1H-benzo[d]imidazol-2-yl)piperidin-1-yl)butan-1-one;
(R)-3-amino-4-(4-bromophenyl)-1-((R)-3-(1-(3-methoxypropyl)-1H-benzo[d]imidazol-2-yl)piperidin-1-yl)butan-1-one;
2R,3R)-3-amino-2-hydroxy-1-((R)-3-(1-(3-methoxypropyl)-1H-benzo[d]imidazol-2-yl)piperidin-1-yl)-3-phenylpropan-1-one;
4-amino-3-(4-chlorophenyl)-1-((R)-3-(1-(3-methoxypropyl)-1H-benzo[d]imidazol-2-yl)piperidin-1-yl)butan-1-one;
3-amino-1-((R)-3-(1-(3-methoxypropyl)-1H-benzo[d]imidazol-2-yl)piperidin-1-yl)-3-(piperidin-4-yl)propan-1-one;
(R)-3-amino-1-((R)-3-(6-fluoro-1-(3-methoxypropyl)-1H-benzo[d]imidazol-2-yl)piperidin-1-yl)-4-(naphthalen-2-yl)butan-1-one;
(R)-3-amino-1-((R)-3-(5-fluoro-1-(3-methoxypropyl)-1H-benzo[d]imidazol-2-yl)piperidin-1-yl)-4-(naphthalen-2-yl)butan-1-one;
(R)-3-Amino-1-((R)-3-(7-chloro-1-(3-methoxypropyl)-1H-benzo[d]imidazol-2-yl)piperidin-1-yl)-4-(naphthalen-2-yl)butan-1-one;
(R)-3-amino-4-(biphenyl-4-yl)-1-((R)-3-(7-chloro-1-(3-methoxypropyl)-1H-benzo[d]imidazol-2-yl)piperidin-1-yl)butan-1-one;
(R)-3-amino-1-((R)-3-(6-chloro-1-(3-methoxypropyl)-1H-benzo[d]imidazol-2-yl)piperidin-1-yl)-4-(naphthalen-2-yl)butan-1-one;
(R)-3-amino-1-(3-(5-methoxy-3-(3-methoxypropyl)-3H-imidazo[4,5-b]pyridin-2-yl)piperidin-1-yl)-4-(naphthalen-2-yl)butan-1-one;
(R)-2-(1-(3-amino-4-(naphthalen-2-yl)butanoyl)piperidin-3-yl)-3-(3-methoxypropyl)-3H-imidazo[4,5-b]pyridin-5(4H)-one;
(R)-3-amino-1-(3-(5-chloro-3-(3-methoxypropyl)-3H-imidazo[4,5-b]pyridin-2-yl)piperidin-1-yl)-4-(naphthalen-2-yl)butan-1-one;
(R)-3-amino-4-(biphenyl-4-yl)-1((R)-3-(3-(3-methoxypropyl)-3H-imidazo[4,5-c]pyridin-2-yl)piperidin-1-yl)butan-1-one;
(R)-3-amino-1-((R)-3-(4-methoxy-1-(3-methoxypropyl)-1H-benzo[d]imidazol-2-yl)piperidin-1-yl)-4-(naphthalen-2-yl)butan-1-one;

(R)-3-amino-1-((R)-3-(1-(3-methoxypropyl)-5-methyl-1H-benzo[d]imidazol-2-yl)piperidin-1-yl)-4-(naphthalen-2-yl)butan-1-one;

(R)-3-amino-1-((R)-3-(1-(3-methoxypropyl)-4-methyl-1H-benzo[d]imidazol-2-yl)piperidin-1-yl)-4-(naphthalen-2-yl)butan-1-one;

(R)-3-amino-1-((R)-3-(4-methoxy-1-(3-methoxypropyl)-1H-benzo[d]imidazol-2-yl)piperidin-1-yl)-4-(naphthalen-2-yl)butan-1-one;

(R)-3-amino-1-((R)-3-(7-methoxy-1-(3-methoxypropyl)-1H-benzo[d]imidazol-2-yl)piperidin-1-yl)-4-(naphthalen-2-yl)butan-1-one;

2-((R)-1((R)-3-amino-4-(naphthalen-2-yl)butanoyl)piperidin-3-yl)-1-(3-methoxypropyl)-1H-benzo[d]imidazole-6-carbonitrile;

(R)-3-amino-1-((R)-3-(6-methoxy-1-(3-methoxypropyl)-1H-benzo[c/]imidazol-2-yl)piperidin-1-yl)-4-(naphthalen-2-yl)butan-1-one;

methyl 2-(1-((R)-3-amino-4-(naphthalen-2-yl)butanoyl)piperidin-3-yl)-1-(3-methoxypropyl)-1H-benzo[d]imidazole-6-carboxylate;

methyl 2-(1-((R)-3-amino-4-(naphthalen-2-yl)butanoyl)piperidin-3-yl)-1-(3-methoxypropyl)-1H-benzo[d]imidazole-7-carboxylate;

(R)-3-amino-1-(3-(6-(hydroxymethyl)-1-(3-methoxypropyl)-1H-benzo[c/]imidazol-2-yl)piperidin-1-yl)-4-(naphthalen-2-yl)butan-1-one;

(R)-3-amino-1-((R)-3-(1-(3-methoxypropyl)-6-nitro-1H-benzo[d]imidazol-2-yl)piperidin-1-yl)-4-(naphthalen-2-yl)butan-1-one;

(R)-3-amino-1-((R)-3-(1-(3-methoxypropyl)-7-nitro-1H-benzo[d]imidazol-2-yl)piperidin-1-yl)-4-(naphthalen-2-yl)butan-1-one;

(R)-3-amino-1-((R)-3-(6-isopropyl-1-(3-methoxypropyl)-1H-benzo[d]imidazol-2-yl)piperidin-1-yl)-4-(naphthalen-2-yl)butan-1-one;

(R)-3-amino-1-((R)-3-(5-isopropyl-1-(3-methoxypropyl)-1H-benzo[d]imidazol-2-yl)piperidin-1-yl)-4-(naphthalen-2-yl)butan-1-one;

(R)-3-amino-4-(biphenyl-4-yl)-1-((R)-3-(4-chloro-1-(3-methoxypropyl)-1H-benzo[d]imidazol-2-yl)piperidin-1-yl)butan-1-one;

(S)-3-amino-1-((R)-3-(1-(3-methoxypropyl)-1H-benzo[d]imidazol-2-yl)piperidin-1-yl)-3-(pyridin-3-yl)propan-1-one;

(S)-3-amino-1-((R)-3-(1-(3-methoxypropyl)-1H-benzo[d]imidazol-2-yl)piperidin-1-yl)-3-(4-methoxypyridin-3-yl)propan-1-one;

(S)-3-amino-3-(3-methoxyphenyl)-1-(R)-3-(1-(3-methoxypropyl)-1H-benzo[d]imidazol-2-yl)piperidine-1-yl)propan-1-one;

(R)-3-amino-4-(biphenyl-3-yl)-1-((R)-3-(1-(3-methoxypropyl)-1H-benzo[d]imidazol-2-yl)piperidin-1-yl)butan-1-one;

Methyl 4'-((R)-2-amino-4-((R)-3-(1-(3-methoxypropyl)-1H-benzo[d]imidazol-2-yl)piperidin-1-yl)-4-oxobutyl)biphenyl-4-carboxylate;

(R)-3-amino-4-(biphenyl-4-yl)-1-((R)-3-(1-(3-methoxypropyl)-1H-benzo[d]imidazol-2-yl)piperidin-1-yl)butan-1-one;

(R)-3-amino-1-((R)-3-(1-(3-methoxypropyl)-1H-benzo[d]imidazol-2-yl)piperidin-1-yl)-4-(4-(pyridin-3-yl)phenyl)butan-1-one;

(R)-3-amino-1-((R)-3-(1-(3-methoxypropyl)-1H-benzo[d]imidazol-2-yl)piperidin-1-yl)-4-(4-(pyridin-4-yl)phenyl)butan-1-one;

(R)-3-amino-1-((R)-3-(1-(3-methoxypropyl)-1H-benzo[d]imidazol-2-yl)piperidin-1-yl)-4-(4'-(morpholine-4-carbonyl)biphenyl-4-yl)butan-1-one;

(R)-3-amino-1-((R)-3-(1-(3-methoxypropyl)-1H-benzo[d]imidazol-2-yl)piperidin-1-yl)-4-(4'-morpholinobiphenyl-4-yl)butan-1-one;

N-(4'-((R)-2-amino-4-((R)-3-(1-(3-methoxypropyl)-1H-benzo[d]imidazol-2-yl)piperidin-1-yl)-4-oxobutyl)biphenyl-4-yl)acetamide;

(R)-3-amino-4-(2'-(methoxymethyl)biphenyl-4-yl)-1-((R)-3-(1-(3-methoxypropyl)-1H-benzo[d]imidazol-2-yl)piperidin-1-yl)butan-1-one;

(R)-3-amino-4-(4-(3-chloropyridin-4-yl)phenyl)-1-((R)-3-(1-(3-methoxypropyl)-1H-benzo[d]imidazol-2-yl)piperidin-1-yl)butan-1-one;

(R)-3-amino-4-(4-(2,6-dimethoxypyridin-3-yl)phenyl)-1-((R)-3-(1-(3-methoxypropyl)-1H-benzo[d]imidazol-2-yl)piperidin-1-yl)butan-1-one;

(R)-3-amino-4-(4-(2-chloropyridin-4-yl)phenyl)-1-((R)-3-(1-(3-methoxypropyl)-1H-benzo[d]imidazol-2-yl)piperidin-1-yl)butan-1-one;

4'-((R)-2-amino-4-((R)-3-(1-(3-methoxypropyl)-1H-benzo[d]imidazol-2-yl)piperidin-1-yl)-4-oxobutyl)-N-cyclopropyl)biphenyl-4-carboxamide;

(R)-3-amino-1-((R)-3-(1-(3-methoxypropyl)-1H-benzo[d]imidazol-2-yl)piperidin-1-yl)-4-(4-(6-morpholinopyridin-3-yl)phenyl)butan-1-one;

(R)-3-amino-4-(4-(6-aminopyridin-3-yl)phenyl)-1-((R)-3-(1-(3-methoxypropyl)-1H-benzo[d]imidazol-2-yl)piperidin-1-yl)butan-1-one;

(R)-3-amino-4-(4-(3,5-dimethyl-1H-pyrazol-4-yl)phenyl)-1-((R)-3-(1-(3-methoxypropyl)-1H-benzo[d]imidazol-2-yl)piperidin-1-yl)butan-1-one;

(R)-3-amino-4-(4-(6-ethoxypyridin-3-yl)phenyl)-1-((R)-3-(1-(3-methoxypropyl)-1H-benzo[d]imidazol-2-yl)piperidin-1-yl)butan-1-one;

(R)-3-amino-4-(4-(imidazo[1,2-a]pyridin-6-yl)phenyl)-1-((R)-3-(1-(3-methoxypropyl)-1H-benzo[d]imidazol-2-yl)piperidin-1-yl)butan-1-one;

(R)-3-amino-4-(4-(benzo[d][1,2,5]oxadiazol-5-yl)phenyl)-1-((R)-3-(1-(3-methoxypropyl)-1H-benzo[d]imidazol-2-yl)piperidin-1-yl)butan-1-one;

(R)-4-(4-(1H-pyrazol-5-yl)phenyl)-3-amino-1-((R)-3-(1-(3-methoxypropyl)-1H-benzo[d]imidazol-2-yl)piperidin-1-yl)butan-1-one;

(R)-3-amino-4-(4-(6-isopropoxypyridin-3-yl)phenyl)-1-((R)-3-(1-(3-methoxypropyl)-1H-benzo[d]imidazol-2-yl)piperidin-1-yl)butan-1-one;

(R)-3-amino-4-(4-(6-(cyclopropylmethoxy)pyridin-3-yl)phenyl)-1-((R)-3-(1-(3-methoxypropyl)-1H-benzo[d]imidazol-2-yl)piperidin-1-yl)butan-1-one;

(R)-3-amino-1-((R)-3-(1-(3-methoxypropyl)-1H-benzo[d]imidazol-2-yl)piperidin-1-yl)-4-(4-(3-methoxypyridin-4-yl)phenyl)butan-1-one;

(R)-3-amino-4-(4-(furan-3-yl)phenyl)-1-((R)-3-(1-(3-methoxypropyl)-1H-benzo[d]imidazol-2-yl)piperidin-1-yl)butan-1-one;

(R)-3-amino-4-(4-(furan-2-yl)phenyl)-1-((R)-3-(1-(3-methoxypropyl)-1H-benzo[d]imidazol-2-yl)piperidin-1-yl)butan-1-one;

(R)-3-amino-4-(4-(6-(dimethylamino)pyridin-3-yl)phenyl)-1-((R)-3-(1-(3-methoxypropyl)-1H-benzo[d]imidazol-2-yl)piperidin-1-yl)butan-1-one;

(R)-3-amino-1-((R)-3-(1-(3-methoxypropyl)-1H-benzo[d]imidazol-2-yl)piperidin-1-yl)-4-(4-(2-methoxypyridin-4-yl)phenyl)butan-1-one;

(R)-3-amino-1-((R)-3-(1-(3-methoxypropyl)-1H-benzo
  [d]imidazol-2-yl)piperidin-1-yl)-4-(4-(pyrimidin-5-yl)
  phenyl)butan-1-one;
(R)-3-amino-4-(4-(2-fluoropyridin-4-yl)phenyl)-1-((R)-
  3-(1-(3-methoxypropyl)-1H-benzo[d]imidazol-2-yl)pi-
  peridin-1-yl)butan-1-one;
(R)-3-amino-4-(4-(2-fluoropyridin-3-yl)phenyl)-1-((R)-
  3-(1-(3-methoxypropyl)-1H-benzo[d]imidazol-2-yl)pi-
  peridin-1-yl)butan-1-one;
(R)-4-(4-(1H-pyrrol-3-yl)phenyl)-3-amino-1-((R)-3-(1-
  (3-methoxypropyl)-1H-benzo[d]imidazol-2-yl)piperi-
  din-1-yl)butan-1-one;
(R)-4-(4-(1H-pyrrol-2-yl)phenyl)-3-amino-1-((R)-3-(1-
  (3-methoxypropyl)-1H-benzo[d]imidazol-2-yl)piperi-
  din-1-yl)butan-1-one;
(R)-3-amino-4-(4-(2-aminopyrimidin-5-yl)phenyl)-1-
  ((R)-3-(1-(3-methoxypropyl)-1H-benzo[d]imidazol-2-
  yl)piperidin-1-yl)butan-1-one;
(R)-3-amino-4-(2'-chlorobiphenyl-4-yl)-1-((R)-3-(1-(3-
  methoxypropyl)-1H-benzo[d]imidazol-2-yl)piperidin-
  1-yl)butan-1-one;
(R)-3-amino-4-(4'-methoxybiphenyl-4-yl)-1-((R)-3-(1-
  (3-methoxypropyl)-1H-benzo[d]imidazol-2-yl)piperi-
  din-1-yl)butan-1-one;
(R)-3-amino-1-((R)-3-(1-(3-methoxypropyl)-1H-benzo
  [d]imidazol-2-yl)piperidin-1-yl)-4-(2'-methylbiphenyl-
  4-yl)butan-1-one;
(R)-3-amino-4-(3'-methoxybiphenyl-4-yl)-1-((R)-3-(1-
  (3-methoxypropyl)-1H-benzo[d]imidazol-2-yl)piperi-
  din-1-yl)butan-1-one;
(R)-3-amino-4-(2'-methoxybiphenyl-4-yl)-1-((R)-3-(1-
  (3-methoxypropyl)-1H-benzo[d]imidazol-2-yl)piperi-
  din-1-yl)butan-1-one;
(R)-3-amino-4-(2'-fluorobiphenyl-4-yl)-1-((R)-3-(1-(3-
  methoxypropyl)-1H-benzo[d]imidazol-2-yl)piperidin-
  1-yl)butan-1-one;
(R)-3-amino-4-(4'-(dimethylamino)biphenyl-4-yl)-1-
  ((R)-3-(1-(3-methoxypropyl)-1H-benzo[d]imidazol-2-
  yl)piperidin-1-yl)butan-1-one;
(R)-3-amino-1-((R)-3-(1-(3-methoxypropyl)-1H-benzo
  [d]imidazol-2-yl)piperidin-1-yl)-4-(4-(4-methoxypyri-
  din-3-yl)phenyl)butan-1-one;
(R)-3-amino-1-((R)-3-(1-(3-methoxypropyl)-1H-benzo
  [d]imidazol-2-yl)piperidin-1-yl)-4-(4-(2-methoxypyri-
  din-3-yl)phenyl)butan-1-one;
4'-((R)-2-amino-4-((R)-3-(1-(3-methoxypropyl)-1H-
  benzo[d]imidazol-2-yl)piperidin-1-yl)-4-oxobutyl)bi-
  phenyl-4-carbonitrile;
(R)-3-amino-1-((R)-3-(1-(3-methoxypropyl)-1H-benzo
  [d]imidazol-2-yl)piperidin-1-yl)-4-(4'-(methylsulfo-
  nyl)biphenyl-4-yl)butan-1-one;
(R)-3-amino-4-(4-(3,5-dimethylisoxazol-4-yl)phenyl)-1-
  ((R)-3-(1-(3-methoxypropyl)-1H-benzo[d]imidazol-2-
  yl)piperidin-1-yl)butan-1-one;
(R)-3-amino-4-(4-(2-chloropyridin-3-yl)phenyl)-1-((R)-
  3-(1-(3-methoxypropyl)-1H-benzo[d]imidazol-2-yl)pi-
  peridin-1-yl)butan-1-one;
4'-((R)-2-amino-4-((R)-3-(1-(3-methoxypropyl)-1H-
  benzo[d]imidazol-2-yl)piperidin-1-yl)-4-oxobutyl)bi-
  phenyl-4-carboxamide;
5-(4-((R)-2-amino-4-((R)-3-(1-(3-methoxypropyl)-1H-
  benzo[d]imidazol-2-yl)piperidin-1-yl)-4-oxobutyl)
  phenyl)pyrimidine-2,4(1H,3H)— dione;
(R)-3-amino-4-(4'-aminobiphenyl-4-yl)-1-((R)-3-(1-(3-
  methoxypropyl)-1H-benzo[d]imidazol-2-yl)piperidin-
  1-yl)butan-1-one;
1-(4'-((R)-2-amino-4-((R)-3-(1-(3-methoxypropyl)-1H-
  benzo[d]imidazol-2-yl)piperidin-1-yl)-4-oxobutyl)bi-
  phenyl-4-yl)-3-cyclopropylurea;
1-(4'-((R)-2-amino-4-((R)-3-(1-(3-methoxypropyl)-1H-
  benzo[d]imidazol-2-yl)piperidin-1-yl)-4-oxobutyl)bi-
  phenyl-4-yl)urea;
1-(4'-((R)-2-amino-4-((R)-3-(1-(3-methoxypropyl)-1H-
  benzo[d]imidazol-2-yl)piperidin-1-yl)-4-oxobutyl)bi-
  phenyl-4-yl)-3-ethylurea;
3-(4'-((R)-2-amino-4-((R)-3-(1-(3-methoxypropyl)-1H-
  benzo[d]imidazol-2-yl)piperidin-1-yl)-4-oxobutyl)bi-
  phenyl-4-yl)-1,1-dimethylurea;
1-(4'-((R)-2-amino-4-((R)-3-(1-(3-methoxypropyl)-1H-
  benzo[d]imidazol-2-yl)piperidin-1-yl)-4-oxobutyl)bi-
  phenyl-4-yl)-3-methylurea;
methyl 4'-((R)-2-amino-4-((R)-3-(1-(3-methoxypropyl)-
  1H-benzo[d]imidazol-2-yl)piperidin-1-yl)-4-oxobutyl)
  biphenyl-4-ylcarbamate;
4'-((R)-2-amino-4-((R)-3-(1-(3-methoxypropyl)-1H-
  benzo[d]imidazol-2-yl)piperidin-1-yl)-4-oxobutyl)-N-
  (2-methoxyethyl)biphenyl-4-carboxamide;
4'-((R)-2-amino-4-((R)-3-(1-(3-methoxypropyl)-1H-
  benzo[d]imidazol-2-yl)piperidin-1-yl)-4-oxobutyl)-N-
  (2-ethoxyethyl)biphenyl-4-carboxamide;
4'-((R)-2-amino-4-((R)-3-(1-(3-methoxypropyl)-1H-
  benzo[d]imidazol-2-yl)piperidin-1-yl)-4-oxobutyl)-N-
  (2-isopropoxyethyl)biphenyl-4-carboxamide;
4'-((R)-2-amino-4-((R)-3-(1-(3-methoxypropyl)-1H-
  benzo[d]imidazol-2-yl)piperidin-1-yl)-4-oxobutyl)-N-
  (3-methoxypropyl)biphenyl-4-carboxamide;
4'-((R)-2-amino-4-((R)-3-(1-(3-methoxypropyl)-1H-
  benzo[d]imidazol-2-yl)piperidin-1-yl)-4-oxobutyl)-N-
  (2,3-dihydroxypropyl)biphenyl-4-carboxamide;
4'-((R)-2-amino-4-((R)-3-(1-(3-methoxypropyl)-1H-
  benzo[d]imidazol-2-yl)piperidin-1-yl)-4-oxobutyl)-N-
  (2-hydroxyethyl)biphenyl-4-carboxamide;
4'-((R)-2-amino-4-((R)-3-(1-(3-methoxypropyl)-1H-
  benzo[d]imidazol-2-yl)piperidin-1-yl)-4-oxobutyl)-N-
  (1-hydroxy-2-methylpropan-2-yl)biphenyl-4-carboxa-
  mide;
4'-((R)-2-amino-4-((R)-3-(1-(3-methoxypropyl)-1H-
  benzo[d]imidazol-2-yl)piperidin-1-yl)-4-oxobutyl)-N-
  (1,3-dihydroxypropan-2-yl)biphenyl-4-carboxamide;
(R)-3-amino-4-(4'-((R)-3-hydroxypyrrolidine-1-carbo-
  nyl)biphenyl-4-yl)-1-((R)-3-(1-(3-methoxypropyl)-
  1H-benzo[d]imidazol-2-yl)piperidin-1-yl)butan-1-one;
4'-((R)-2-amino-4-((R)-3-(1-(3-methoxypropyl)-1H-
  benzo[d]imidazol-2-yl)piperidin-1-yl)-4-oxobutyl)-
  N—((R)-1-hydroxypropan-2-yl)biphenyl-4-carboxam-
  ide;
4'-((R)-2-amino-4-((R)-3-(1-(3-methoxypropyl)-1H-
  benzo[d]imidazol-2-yl)piperidin-1-yl)-4-oxobutyl)-
  N—((S)-1-hydroxypropan-2-yl)biphenyl-4-carboxam-
  ide;
4'-((R)-2-amino-4-((R)-3-(1-(3-methoxypropyl)-1H-
  benzo[d]imidazol-2-yl)piperidin-1-yl)-4-oxobutyl)-N-
  (2-hydroxy-2-methylpropyl)biphenyl-4-carboxamide;
4-(4'-((R)-2-amino-4-((R)-3-(1-(3-methoxypropyl)-1H-
  benzo[d]imidazol-2-yl)piperidin-1-yl)-4-oxobutyl)bi-
  phenylcarbonyl)piperazin-2-one;
4'-((R)-2-amino-4-((R)-3-(1-(3-methoxypropyl)-1H-
  benzo[d]imidazol-2-yl)piperidin-1-yl)-4-oxobutyl)-3-
  fluoro-N-(2-hydroxyethyl) biphenyl-4-carboxamide;
4'-((R)-2-amino-4-((R)-3-(1-(3-methoxypropyl)-1H-
  benzo[d]imidazol-2-yl)piperidin-1-yl)-4-oxobutyl)-3-
  fluoro-N-(2-methoxyethyl)biphenyl-4-carboxamide;

4'-((R)-2-amino-4-((R)-3-(1-(3-methoxypropyl)-1H-benzo[d]imidazol-2-yl)piperidin-1-yl)-4-oxobutyl)-2-chloro-N-(2-hydroxyethyl)biphenyl-4-carboxamide;
4'-((R)-2-amino-4-((R)-3-(1-(3-methoxypropyl)-1H-benzo[d]imidazol-2-yl)piperidin-1-yl)-4-oxobutyl)-2-chloro-N-(2-methoxyethyl)biphenyl-4-carboxamide;
5-(4-((R)-2-amino-4-((R)-3-(1-(3-methoxypropyl)-1H-benzo[d]imidazol-2-yl)piperidin-1-yl)-4-oxobutyl) phenyl)-N-(2-hydroxyethyl)picolinamide;
5-(4-((R)-2-amino-4-((R)-3-(1-(3-methoxypropyl)-1H-benzo[d]imidazol-2-yl)piperidin-1-yl)-4-oxobutyl) phenyl)-N-(2-methoxyethyl)picolinamide;
5-(4-((R)-2-amino-4-((R)-3-(1-(3-methoxypropyl)-1H-benzo[d]imidazol-2-yl)piperidin-1-yl)-4-oxobutyl) phenyl)-N-(1-hydroxy-2-methylpropan-2-yl) thiophene-2-carboxamide;
N-(4'-((R)-2-amino-4-((R)-3-(1-(3-methoxypropyl)-1H-benzo[d]imidazol-2-yl)piperidin-1-yl)-4-oxobutyl)biphenyl-4-yl)-2-methoxyacetamide;
N-(4'-((R)-2-amino-4-((R)-3-(1-(3-methoxypropyl)-1H-benzo[d]imidazol-2-yl)piperidin-1-yl)-4-oxobutyl)biphenyl-4-yl)-2-hydroxy-2-methylpropanamide;
N-(4'-((R)-2-amino-4-((R)-3-(1-(3-methoxypropyl)-1H-benzo[d]imidazol-2-yl)piperidin-1-yl)-4-oxobutyl)biphenyl-4-yl)-2-hydroxyacetamide;
(R)-3-amino-4-(4-(2-ethoxythiazol-4-yl)phenyl)-1-((R)-3-(1-(3-methoxypropyl)-1H-benzo[d]imidazol-2-yl)piperidin-1-yl)butan-1-one;
(R)-3-amino-1-((R)-3-(1-(3-methoxypropyl)-1H-benzo[d]imidazol-2-yl)piperidin-1-yl)-4-(4-(2-methoxythiazol-4-yl)phenyl)butan-1-one;
(R)-3-amino-4-(4-(2-isopropylthiazol-4-yl)phenyl)-1-((R)-3-(1-(3-methoxypropyl)-1H-benzo[d]imidazol-2-yl)piperidin-1-yl)butan-1-one;
4-((R)-2-amino-4-((R)-3-(1-(3-methoxypropyl)-1H-benzo[d]imidazol-2-yl)piperidin-1-yl)-4-oxobutyl)-N-cyclohexylbenzamide;
(R)-3-amino-4-(4-(1,2-dimethyl-1H-imidazol-5-yl)phenyl)-1-((R)-3-(1-(3-methoxypropyl)-1H-benzo[d]imidazol-2-yl)piperidin-1-yl)butan-1-one;
5-(4-((R)-2-amino-4-((R)-3-(1-(3-methoxypropyl)-1H-benzo[d]imidazol-2-yl)piperidin-1-yl)-4-oxobutyl) phenyl)-1,3-dimethylpyrimidine-2,4(1H,3H)-dione;
4-(4'-((R)-2-amino-4-((R)-3-(1-(3-methoxypropyl)-1H-benzo[d]imidazol-2-yl)piperidin-1-yl)-4-oxobutyl)biphenyl-4-yl)-3-methyl-1H-1,2,4-triazol-5(4H)-one;
1-(4-((R)-2-amino-4-((R)-3-(1-(3-methoxypropyl)-1H-benzo[d]imidazol-2-yl)piperidin-1-yl)-4-oxobutyl) phenyl)pyridin-2(1H)-one;
(R)-4-(4-(1H-imidazol-1-yl)phenyl)-3-amino-1-((R)-3-(1-(3-methoxypropyl)-1H-benzo[d]imidazol-2-yl)piperidin-1-yl)butan-1-one;
1-(4-((R)-2-amino-4-((R)-3-(1-(3-methoxypropyl)-1H-benzo[d]imidazol-2-yl)piperidin-1-yl)-4-oxobutyl) phenyl)pyrrolidin-2-one;
1-(4-((R)-2-amino-4-((R)-3-(1-(3-methoxypropyl)-1H-benzo[d]imidazol-2-yl)piperidin-1-yl)-4-oxobutyl) phenyl)-3-methylpyrimidine-2,4(1H,3H)-dione;
1-(4-((R)-2-amino-4-((R)-3-(1-(3-methoxypropyl)-1H-benzo[d]imidazol-2-yl)piperidin-1-yl)-4-oxobutyl) phenyl)-3-methylpyrimidine-2,4(1H,3H)-dione;
1-(4-((R)-2-amino-4-((R)-3-(1-(3-methoxypropyl)-1H-benzo[d]imidazol-2-yl)piperidin-1-yl)-4-oxobutyl) phenyl)-3-methylpyrimidine-2,4(1H,3H)-dione;
1-(4-((R)-2-Amino-4-((R)-3-(1-(3-methoxypropyl)-1H-benzo[d]imidazol-2-yl)piperidin-1-yl)-4-oxobutyl) phenyl)-3-methylpyrimidine-2,4(1H,3H)-dione;
1-(4-((R)-2-amino-4-((R)-3-(1-(3-methoxypropyl)-1H-benzo[d]imidazol-2-yl)piperidin-1-yl)-4-oxobutyl) phenyl)-3-(2-methoxyethyl)-1H-benzo[d]imidazol-2 (3H)-one;
1-(4-((R)-2-amino-4-((R)-3-(1-(3-methoxypropyl)-1H-benzo[d]imidazol-2-yl)piperidin-1-yl)-4-oxobutyl) phenyl)-5-methyl-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-6-methyl-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-4-fluoro-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-7-fluoro-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-5,6-dimethyl-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-3-methyl-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-3-propyl-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-3-(2-hydroxyethyl)-1H-benzo[d]imidazol-2 (3H)-one;
1-(4-((R)-2-amino-4-((R)-3-(1-(3-methoxypropyl)-1H-benzo[d]imidazol-2-yl)piperidin-1-yl)-4-oxobutyl) phenyl)-5-fluoro-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-6-fluoro-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-4-methyl-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-7-methyl-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-5-methoxy-1H-benzo[d]imidazol-2(3H)-one;
1-(4-((R)-2-amino-4-((R)-3-(1-(3-methoxypropyl)-1H-benzo[d]imidazol-2-yl)piperidin-1-yl)-4-oxobutyl) phenyl)-6-methoxy-1H-benzo[d]imidazol-2(3H)-one
2-(4-((R)-2-amino-4-((R)-3-(1-(3-methoxypropyl)-1H-benzo[d]imidazol-2-yl)piperidin-1-yl)-4-oxobutyl) phenyl)isoquinolin-1(2H)-one;
2-(4-((R)-2-amino-4-((R)-3-(1-(3-methoxypropyl)-1H-benzo[d]imidazol-2-yl)piperidin-1-yl)-4-oxobutyl) phenyl)isoquinolin-1(2H)-one;
(R)-3-amino-1-((R)-3-(1-(3-methoxypropyl)-1H-benzo[d]imidazol-2-yl)piperidin-1-yl)-4-(4-(4-phenylpiperazin-1-yl)phenyl)butan-1-one;
(R)-4-(4-(4-acetylpiperazin-1-yl)phenyl)-3-amino-1-((R)-3-(1-(3-methoxypropyl)-1H-benzo[d]imidazol-2-yl)piperidin-1-yl)butan-1-one;
4-(4-((R)-2-amino-4-((R)-3-(1-(3-methoxypropyl)-1H-benzo[d]imidazol-2-yl)piperidin-1-yl)-4-oxobutyl) phenyl)-1-phenylpiperazin-2-one;
(R)-3-amino-4-(4-(4-hydroxypiperidin-1-yl)phenyl)-1-((R)-3-(1-(3-methoxypropyl)-1H-benzo[d]imidazol-2-yl)piperidin-1-yl)butan-1-one;

(R)-3-amino-4-(4-(4-(hydroxymethyl)piperidin-1-yl)phenyl)-1-((R)-3-(1-(3-methoxypropyl)-1H-benzo[d]imidazol-2-yl)piperidin-1-yl)butan-1-one;

(R)-3-amino-4-(4-(4-(hydroxymethyl)piperidin-1-yl)phenyl)-1-((R)-3-(1-(3-methoxypropyl)-1H-benzo[d]imidazol-2-yl)piperidin-1-yl)butan-1-one;

methyl 1-(4-((R)-2-amino-4-((R)-3-(1-(3-methoxypropyl)-1H-benzo[d]imidazol-2-yl)piperidin-1-yl)-4-oxobutyl)phenyl)piperidine-4-carboxylate;

(R)-3-amino-1-((R)-3-(1-(3-methoxypropyl)-1H-benzo[d]imidazol-2-yl)piperidin-1-yl)-4-(4-phenoxyphenyl)butan-1-one;

N-(2-(2-((R)-1((R)-3-amino-4-(naphthalen-2-yl)butanoyl)piperidin-3-yl)-1H-benzo[d]imidazol-1-yl)ethyl)acetamide;

(R)-3-amino-2-benzyl-4-(4-chlorophenyl)-1-((R)-3-(1-(3-methoxypropyl)-1H-benzo[d]imidazol-2-yl)piperidin-1-yl)butan-1-one;

(R)-3-amino-1-((R)-3-(1-(3-methoxypropyl)-4,5,6,7-tetrahydro-1H-benzo[d]imidazol-2-yl)piperidin-1-yl)-4-(naphthalen-2-yl)butan-1-one;

methyl 4'42R)-2-amino-4-(3-(5-tert-butyl-1-(3-methoxypropyl)-1H-imidazol-2-yl)-3-hydroxypiperidin-1-yl)-4-oxobutyl)biphenyl-4-carboxylate;

(R)-3-amino-1-((R)-3-(2-(3-methoxypropyl)-1H-benzo[d]imidazol-1-yl)piperidin-1-yl)-4-(naphthalen-2-yl)butan-1-one;

(R)-3-amino-1-((S)-3-(2-methyl-1H-benzo[d]imidazol-1-yl)piperidin-1-yl)-4-(naphthalen-2-yl)butan-1-one;

(R)-3-amino-1-((R)-3-(2-methyl-1H-benzo[d]imidazol-1-yl)piperidin-1-yl)-4-(naphthalen-2-yl)butan-1-one;

(R)-3-amino-1-(3-(1-(3-methoxypropyl)-1H-benzo[d]imidazol-2-yl)-5-methylpiperidin-1-yl)-4-(naphthalen-2-yl)butan-1-one;

(R)-3-amino-4-(4-chlorophenyl)-1-((S)-3-hydroxy-3-(1-(3-methoxypropyl)-1H-benzo[d]imidazol-2-yl)piperidin-1-yl)butan-1-one;

(R)-3-amino-4-(4-chlorophenyl)-1-((R)-3-hydroxy-3-(1-(3-methoxypropyl)-1H-benzo[d]imidazol-2-yl)piperidin-1-yl)butan-1-one;

N—((S)-2-amino-4-((R)-3-(1-(3-methoxypropyl)-1H-benzo[d]imidazol-2-yl)piperidin-1-yl)-4-oxobutyl)-2-naphthamide;

1-((S)-2-amino-4-((R)-3-(1-(3-methoxypropyl)-1H-benzo[d]imidazol-2-yl)piperidin-1-yl)-4-oxobutyl)-3-(2-methoxyphenyl)urea;

N—((S)-2-amino-4-((R)-3-(1-(3-methoxypropyl)-1H-benzo[d]imidazol-2-yl)piperidin-1-yl)-4-oxobutyl)-5-phenylfuran-2-carboxamide;

N—((S)-2-amino-4-((R)-3-(1-(3-methoxypropyl)-1H-benzo[d]imidazol-2-yl)piperidin-1-yl)-4-oxobutyl)-5-phenylthiophene-2-carboxamide;

1-((S)-2-amino-4-((R)-3-(1-(3-methoxypropyl)-1H-benzo[d]imidazol-2-yl)piperidin-1-yl)-4-oxobutyl)-3-(4-methoxyphenyl)urea;

1-((S)-2-amino-4-((R)-3-(1-(3-methoxypropyl)-1H-benzo[d]imidazol-2-yl)piperidin-1-yl)-4-oxobutyl)-3-(3-methoxyphenyl)urea;

1-((S)-2-amino-4-((R)-3-(1-(3-methoxypropyl)-1H-benzo[d]imidazol-2-yl)piperidin-1-yl)-4-oxobutyl)-3-(3,4-dichlorophenyl)urea;

1-((S)-2-amino-4-((R)-3-(1-(3-methoxypropyl)-1H-benzo[d]imidazol-2-yl)piperidin-1-yl)-4-oxobutyl)-3-(3-chlorophenyl)urea;

1-((S)-2-amino-4-((R)-3-(1-(3-methoxypropyl)-1H-benzo[d]imidazol-2-yl)piperidin-1-yl)-4-oxobutyl)-3-(2-chlorophenyl)urea;

1-((S)-2-amino-4-((R)-3-(1-(3-methoxypropyl)-1H-benzo[d]imidazol-2-yl)piperidin-1-yl)-4-oxobutyl)-3-(2,3-dihydrobenzo[b][1,4]dioxin-6-yl)urea;

N—((S)-2-amino-4-((R)-3-(1-(3-methoxypropyl)-1H-benzo[d]imidazol-2-yl)piperidin-1-yl)-4-oxobutyl)-4-(thiophen-2-yl)benzamide;

N—((S)-2-amino-4-((R)-3-(1-(3-methoxypropyl)-1H-benzo[d]imidazol-2-yl)piperidin-1-yl)-4-oxobutyl)-5-(2-fluorophenyl)furan-2-carboxamide;

N—((S)-2-amino-4-((R)-3-(1-(3-methoxypropyl)-1H-benzo[d]imidazol-2-yl)piperidin-1-yl)-4-oxobutyl)-4-(thiophen-3-yl)benzamide;

N—((S)-2-amino-4-((R)-3-(1-(3-methoxypropyl)-1H-benzo[d]imidazol-2-yl)piperidin-1-yl)-4-oxobutyl)-3,4-dichlorobenzamide;

N—((S)-2-amino-4-((R)-3-(1-(3-methoxypropyl)-1H-benzo[d]imidazol-2-yl)piperidin-1-yl)-4-oxobutyl)benzofuran-2-carboxamide;

N—((S)-2-amino-4-((R)-3-(1-(3-methoxypropyl)-1H-benzo[d]imidazol-2-yl)piperidin-1-yl)-4-oxobutyl)biphenyl-4-carboxamide;

1-((S)-2-amino-4-((R)-3-(1-(3-methoxypropyl)-1H-benzo[d]imidazol-2-yl)piperidin-1-yl)-4-oxobutyl)-3-(2-(trifluoromethoxy)phenyl)urea;

1-((S)-2-amino-4-((R)-3-(1-(3-methoxypropyl)-1H-benzo[d]imidazol-2-yl)piperidin-1-yl)-4-oxobutyl)-3-(2,3-dihydro-1H-inden-5-yl)urea;

N—((S)-2-amino-4-((R)-3-(1-(3-methoxypropyl)-1H-benzo[d]imidazol-2-yl)piperidin-1-yl)-4-oxobutyl)-5-(2,4-dichlorophenyl)furan-2-carboxamide;

1-((S)-2-amino-4-((R)-3-(1-(3-methoxypropyl)-1H-benzo[d]imidazol-2-yl)piperidin-1-yl)-4-oxobutyl)-3-(5-tert-butyl-2-methoxyphenyl)urea;

1-((S)-2-amino-4-((R)-3-(1-(3-methoxypropyl)-1H-benzo[d]imidazol-2-yl)piperidin-1-yl)-4-oxobutyl)-3-phenylure a;

N—((S)-2-amino-4-((R)-3-(1-(3-methoxypropyl)-1H-benzo[d]imidazol-2-yl)piperidin-1-yl)-4-oxobutyl)-3-phenoxybenzamide;

N—((S)-2-amino-4-((R)-3-(1-(3-methoxypropyl)-1H-benzo[d]imidazol-2-yl)piperidin-1-yl)-4-oxobutyl)-2,3-dihydrobenzofuran-5-carboxamide;

1-((S)-2-amino-4-((R)-3-(1-(3-methoxypropyl)-1H-benzo[d]imidazol-2-yl)piperidin-1-yl)-4-oxobutyl)-3-(2-phenoxyphenyl)ure a;

1-((S)-2-amino-4-((R)-3-(1-(3-methoxypropyl)-1H-benzo[d]imidazol-2-yl)piperidin-1-yl)-4-oxobutyl)-3-(2,5-dimethoxyphenyl)urea;

1-((S)-2-amino-4-((R)-3-(1-(3-methoxypropyl)-1H-benzo[d]imidazol-2-yl)piperidin-1-yl)-4-oxobutyl)-3-(2-(difluoromethoxy)phenyl)ure a;

N—((S)-2-amino-4-((R)-3-(1-(3-methoxypropyl)-1H-benzo[d]imidazol-2-yl)piperidin-1-yl)-4-oxobutyl)-5-(2-nitrophenyl)furan-2-carboxamide;

N—((S)-2-amino-4-((R)-3-(1-(3-methoxypropyl)-1H-benzo[d]imidazol-2-yl)piperidin-1-yl)-4-oxobutyl)-5-(2,5-dichlorophenyl) furan-2-carboxamide;

N—((S)-2-amino-4-((R)-3-(1-(3-methoxypropyl)-1H-benzo[d]imidazol-2-yl)piperidin-1-yl)-4-oxobutyl)-5-(2,3-dichlorophenyl) furan-2-carboxamide;

N—((S)-2-amino-4-((R)-3-(1-(3-methoxypropyl)-1H-benzo[d]imidazol-2-yl)piperidin-1-yl)-4-oxobutyl)-4-phenoxybenzamide;

1-((S)-2-amino-4-((R)-3-(1-(3-methoxypropyl)-1H-benzo[d]imidazol-2-yl)piperidin-lyl)-4-oxobutyl)-3-(2,4-dimethoxyphenyl)ure a;

N—((S)-2-amino-4-((R)-3-(1-(3-methoxypropyl)-1H-benzo[d]imidazol-2-yl)piperidin-1-yl)-4-oxobutyl)-4-methoxybenzamide;
N—((S)-2-amino-4-((R)-3-(1-(3-methoxypropyl)-1H-benzo[d]imidazol-2-yl)piperidin-1-yl)-4-oxobutyl)-4-chlorobenzenesulfonamide;
methyl 3-((S)-2-amino-4-((R)-3-(1-(3-methoxypropyl)-1H-benzo[d]imidazol-2-yl)piperidin-1-yl)-4-oxobutyl-carbamoyl)benzo ate;
1-((S)-2-amino-4-((R)-3-(1-(3-methoxypropyl)-1H-benzo[d]imidazol-2-yl)piperidin-1-yl)-4-oxobutyl)-3-(4-chlorophenyl)urea;
1-((S)-2-amino-4-((R)-3-(1-(3-methoxypropyl)-1H-benzo[d]imidazol-2-yl)piperidin-1-yl)-4-oxobutyl)-3-(2-(methylthio)phenyl)urea;
1-((S)-2-amino-4-((R)-3-(1-(3-methoxypropyl)-1H-benzo[d]imidazol-2-yl)piperidin-1-yl)-4-oxobutyl)-3-(2-ethoxyphenyl)urea;
1-((S)-2-amino-4-((R)-3-(1-(3-methoxypropyl)-1H-benzo[d]imidazol-2-yl)piperidin-1-yl)-4-oxobutyl)-3-(2-propylphenyl)urea;
1-((S)-2-amino-4-((R)-3-(1-(3-methoxypropyl)-1H-benzo[d]imidazol-2-yl)piperidin-1-yl)-4-oxobutyl)-3-(2-methoxy-5-methylphenyl)urea;
1-((S)-2-amino-4-((R)-3-(1-(3-methoxypropyl)-1H-benzo[d]imidazol-2-yl)piperidin-1-yl)-4-oxobutyl)-3-(3-phenoxyphenyl)urea;
N—((S)-2-amino-4-((R)-3-(1-(3-methoxypropyl)-1H-benzo[d]imidazol-2-yl)piperidin-1-yl)-4-oxobutyl)-2,6-dichlorobenzamide;
N—((S)-2-amino-4-((R)-3-(1-(3-methoxypropyl)-1H-benzo[d]imidazol-2-yl)piperidin-1-yl)-4-oxobutyl)-2,6-dichlorobenzenesulfonamide;
1-((S)-2-amino-4-((R)-3-(1-(3-methoxypropyl)-1H-benzo[d]imidazol-2-yl)piperidin-1-yl)-4-oxobutyl)-3-(biphenyl-2-yOurea;
1-((S)-2-amino-4-((R)-3-(1-(3-methoxypropyl)-1H-benzo[d]imidazol-2-yl)piperidin-1-yl)-4-oxobutyl)-3-(4-methoxy-2-methylphenyl)urea;
N—((S)-2-amino-4-((R)-3-(1-(3-methoxypropyl)-1H-benzo[d]imidazol-2-yl)piperidin-1-yl)-4-oxobutyl)-3,4-dimethylbenzamide;
ethyl 4-(5-((S)-2-amino-4-((R)-3-(1-(3-methoxypropyl)-1H-benzo[d]imidazol-2-yl)piperidin-1-yl)-4-oxobutyl-carbamoyl)furan-2-yl)benzo ate;
N—((S)-2-amino-4-((R)-3-(1-(3-methoxypropyl)-1H-benzo[d]imidazol-2-yl)piperidin-1-yl)-4-oxobutyl)-5-(3,5-dichlorophenyl)furan-2-carboxamide;
N—((S)-2-amino-4-((R)-3-(1-(3-methoxypropyl)-1H-benzo[d]imidazol-2-yl)piperidin-1-yl)-4-oxobutyl)-5-(3-chlorophenyl)furan-2-carboxamide;
N—((S)-2-amino-4-((R)-3-(1-(3-methoxypropyl)-1H-benzo[d]imidazol-2-yl)piperidin-1-yl)-4-oxobutyl)-5-(3-nitrophenyl)furan-2-carboxamide;
N—((S)-2-amino-4-((R)-3-(1-(3-methoxypropyl)-1H-benzo[d]imidazol-2-yl)piperidin-1-yl)-4-oxobutyl)-3-chlorobenzamide;
N—((S)-2-amino-4-((R)-3-(1-(3-methoxypropyl)-1H-benzo[d]imidazol-2-yl)piperidin-1-yl)-4-oxobutyl)-2-phenoxynicotinamide;
N—((S)-2-amino-4-((R)-3-(1-(3-methoxypropyl)-1H-benzo[d]imidazol-2-yl)piperidin-1-yl)-4-oxobutyl)-3-chlorobenzenesulfonamide;
1-((S)-2-amino-4-((R)-3-(1-(3-methoxypropyl)-1H-benzo[d]imidazol-2-yl)piperidin-1-yl)-4-oxobutyl)-3-(2-isopropylphenyl)urea;
1-((S)-2-amino-4-((R)-3-(1-(3-methoxypropyl)-1H-benzo[d]imidazol-2-yl)piperidin-1-yl)-4-oxobutyl)-3-(2-tert-butylphenyl)urea;
N—((S)-2-amino-4-((R)-3-(1-(3-methoxypropyl)-1H-benzo[d]imidazol-2-yl)piperidin-1-yl)-4-oxobutyl)-3-(5-methyl-1,2,4-oxadiazol-3-yl)benzamide;
N—((S)-2-amino-4-((R)-3-(1-(3-methoxypropyl)-1H-benzo[d]imidazol-2-yl)piperidin-1-yl)-4-oxobutyl)-5-(4-fluorophenyl)furan-2-carboxamide;
N—((S)-2-amino-4-((R)-3-(1-(3-methoxypropyl)-1H-benzo[d]imidazol-2-yl)piperidin-1-yl)-4-oxobutyl)-3,4-dichlorobenzenesulfonamide;
N—((S)-2-amino-4-((R)-3-(1-(3-methoxypropyl)-1H-benzo[d]imidazol-2-yl)piperidin-1-yl)-4-oxobutyl)-2-chlorobenzenesulfonamide;
N—((S)-2-amino-4-((R)-3-(1-(3-methoxypropyl)-1H-benzo[d]imidazol-2-yl)piperidin-1-yl)-4-oxobutyl)-2-(propylthio)nicotinamide;
N—((S)-2-amino-4-((R)-3-(1-(3-methoxypropyl)-1H-benzo[d]imidazol-2-yl)piperidin-1-yl)-4-oxobutyl)-2,3-dihydrobenzo[b][1,4]dioxine-6-carboxamide;
N—((S)-2-amino-4-((R)-3-(1-(3-methoxypropyl)-1H-benzo[d]imidazol-2-yl)piperidin-1-yl)-4-oxobutyl)-4-chlorobenzamide;
N—((S)-2-amino-4-((R)-3-(1-(3-methoxypropyl)-1H-benzo[d]imidazol-2-yl)piperidin-1-yl)-4-oxobutyl)-3-methoxybenzamide;
N—((S)-2-amino-4-((R)-3-(1-(3-methoxypropyl)-1H-benzo[d]imidazol-2-yl)piperidin-1-yl)-4-oxobutyl)-1-naphthamide;
N—((S)-2-amino-4-((R)-3-(1-(3-methoxypropyl)-1H-benzo[d]imidazol-2-yl)piperidin-1-yl)-4-oxobutyl)propane-2-sulfonamide;
N—((S)-2-amino-4-((R)-3-(1-(3-methoxypropyl)-1H-benzo[d]imidazol-2-yl)piperidin-1-yl)-4-oxobutyl)-6-(piperidin-1-yl)picolinamide;
methyl 4-((S)-2-amino-4-((R)-3-(1-(3-methoxypropyl)-1H-benzo[d]imidazol-2-yl)piperidin-1-yl)-4-oxobutyl-carbamoyl)benzo ate;
N—((S)-2-amino-4-((R)-3-(1-(3-methoxypropyl)-1H-benzo[d]imidazol-2-yl)piperidin-1-yl)-4-oxobutyl)-3-methoxybenzenesulfonamide;
N—((S)-2-amino-4-((R)-3-(1-(3-methoxypropyl)-1H-benzo[d]imidazol-2-yl)piperidin-1-yl)-4-oxobutyl)benzenesulfonamide;
N—((S)-2-amino-4-((R)-3-(1-(3-methoxypropyl)-1H-benzo[d]imidazol-2-yl)piperidin-1-yl)-4-oxobutyl)benzamide;
N—((S)-2-amino-4-((R)-3-(1-(3-methoxypropyl)-1H-benzo[d]imidazol-2-yl)piperidin-1-yl)-4-oxobutyl)-3-fluorobenzamide;
N—((S)-2-amino-4-((R)-3-(1-(3-methoxypropyl)-1H-benzo[d]imidazol-2-yl)piperidin-1-yl)-4-oxobutyl)-2-cyclohexylacetamide;
N—((S)-2-amino-4-((R)-3-(1-(3-methoxypropyl)-1H-benzo[d]imidazol-2-yl)piperidin-1-yl)-4-oxobutyl)-2-chlorobenzamide;
N—((S)-2-amino-4-((R)-3-(1-(3-methoxypropyl)-1H-benzo[d]imidazol-2-yl)piperidin-1-yl)-4-oxobutyl)-4-methoxybenzenesulfonamide;
1-((S)-2-amino-4-((R)-3-(1-(3-methoxypropyl)-1H-benzo[d]imidazol-2-yl)piperidin-1-yl)-4-oxobutyl)-3-(2,5-dimethoxyphenethypurea;
1-((S)-2-amino-4-((R)-3-(1-(3-methoxypropyl)-1H-benzo[d]imidazol-2-yl)piperidin-1-yl)-4-oxobutyl)-3-cyclohexylurea;

N—((S)-2-amino-4-((R)-3-(1-(3-methoxypropyl)-1H-benzo[d]imidazol-2-yl)piperidin-1-yl)-4-oxobutyl)-2-methoxybenzenesulfonamide;
N—((S)-2-amino-4-((R)-3-(1-(3-methoxypropyl)-1H-benzo[d]imidazol-2-yl)piperidin-1-yl)-4-oxobutyl)furan-2-carboxamide;
N—((S)-2-amino-4-((R)-3-(1-(3-methoxypropyl)-1H-benzo[d]imidazol-2-yl)piperidin-1-yl)-4-oxobutyl)cyclohexanecarboxamide;
N—((S)-2-amino-4-((R)-3-(1-(3-methoxypropyl)-1H-benzo[d]imidazol-2-yl)piperidin-1-yl)-4-oxobutyl)-2-methoxybenzamide;
N—((S)-2-amino-4-((R)-3-(1-(3-methoxypropyl)-1H-benzo[d]imidazol-2-yl)piperidin-1-yl)-4-oxobutyl)morpholine-4-carboxamide;
methyl 2-(3-((S)-2-amino-4-((R)-3-(1-(3-methoxypropyl)-1H-benzo[d]imidazol-2-yl)piperidin-1-yl)-4-oxobutyl)ureido)benzo ate;
ethyl 2-(3-((S)-2-amino-4-((R)-3-(1-(3-methoxypropyl)-1H-benzo[d]imidazol-2-yl)piperidin-1-yl)-4-oxobutyl)ureido)benzo ate;
N—((S)-2-amino-4-((R)-3-(1-(3-methoxypropyl)-1H-benzo[d]imidazol-2-yl)piperidin-1-yl)-4-oxobutyl)cyclop entanecarboxamide;
1-((S)-2-amino-4-((R)-3-(1-(3-methoxypropyl)-1H-benzo[d]imidazol-2-yl)piperidin-1-yl)-4-oxobutyl)-3-cyclopentylurea;
N—((S)-2-amino-4-((R)-3-(1-(3-methoxypropyl)-1H-benzo[d]imidazol-2-yl)piperidin-1-yl)-4-oxobutyl)isobutyramide;
N—((S)-2-amino-4-((R)-3-(1-(3-methoxypropyl)-1H-benzo[d]imidazol-2-yl)piperidin-1-yl)-4-oxobutyl)pyrrolidine-1-carboxamide;
N—((S)-2-amino-4-((R)-3-(1-(3-methoxypropyl)-1H-benzo[d]imidazol-2-yl)piperidin-1-yl)-4-oxobutyl)propane-2-sulfonamide;
1-((S)-2-amino-4-((R)-3-(1-(3-methoxypropyl)-1H-benzo[d]imidazol-2-yl)piperidin-1-yl)-4-oxobutyl)-3-(2-cyanophenyl)urea;
((3R,4 S)-4-amino-1-(2,3-dihydrobenzo[b][1,4]dioxin-6-ylsulfonyl)pyrrolidin-3-yl)((R)-3-(1-(3-methoxypropyl)-1H-benzo[d]imidazol-2-yl)piperidin-1-yl)methanone;
5-((3S,4R)-3-amino-4-((R)-3-(1-(3-methoxypropyl)-1H-benzo[d]imidazol-2-yl)piperidine-1-carbonyl)pyrrolidin-1-ylsulfonyl)-1H-benzo[d]imidazol-2(3H)-one;
((3R,4 S)-4-amino-1-(4-bromo-2,6-dichlorophenylsulfonyl)pyrrolidin-3-yl)((R)-3-(1-(3-methoxypropyl)-1H-benzo[d]imidazol-2-yl)piperidin-1-yl)methanone;
((3R,4 S)-4-amino-1-(2,4,6-trichlorophenylsulfonyl)pyrrolidin-3-yl)((R)-3-(1-(3-methoxypropyl)-1H-benzo[d]imidazol-2-yl)piperidin-1-yl)methanone;
((3R,4 S)-4-amino-1-(naphthalen-2-ylsulfonyl)pyrrolidin-3-yl)((R)-3-(1-(3-methoxypropyl)-1H-benzo[d]imidazol-2-yl)piperidin-1-yl)methanone;
((3R,4 S)-4-amino-1-(4-bromo-2-chlorophenyl sulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(2,5-dichlorophenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(4-chloro-2,5-dimethylphenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(2,4,5-trichlorophenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(2-chlorophenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(2,6-dichlorophenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(biphenyl-4-ylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(2-chloro-4-fluorophenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(2,4-dichlorophenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(3-chlorophenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(5-phenylfuran-2-carbonyl)pyrrolidin-3-yl)((R)-3-(1-(3-methoxypropyl)-1H-benzo[d]imidazol-2-yl)piperidin-1-yl)methanone;
((3R,4S)-4-amino-1-(3-chloro-2-methylphenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(naphthalen-1-ylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(2,3-dihydrobenzofuran-5-ylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(2-chloro-5-(trifluoromethyl)phenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(3-methoxyphenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(3-phenoxybenzoyl)pyrrolidin-3-yl)((R)-3-(1-(3-methoxypropyl)-1H-benzo[d]imidazol-2-yl)piperidin-1-yl)methanone;
((3R,4S)-4-amino-1-(2-chloro-6-methylphenylsulfonyl)pyrrolidin-3-yl)((R)-3-(1-(3-methoxypropyl)-1H-benzo[d]imidazol-2-yl)piperidin-1-yl)methanone;
((3R,4 S)-4-amino-1-(1-methyl-1H-indol-5-ylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(3,4-dichlorophenylsulfonyl)pyrrolidin-3-yl)((R)-3-(1-(3-methoxypropyl)-1H-benzo[d]imidazol-2-yl)piperidin-1-yl)methanone;
((3R,4S)-1-(2-naphthoyl)-4-aminopyrrolidin-3-yl)((R)-3-(1-(3-methoxypropyl)-1H-benzo[d]imidazol-2-yl)piperidin-1-yl)methanone;
((3R,4S)-4-amino-1-(2,3-dichlorophenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(3-(2-methylthiazol-4-yl)phenylsulfonyl)pyrrolidin-3-yl)((R)-3-(1-(3-methoxypropyl)-1H-benzo[d]imidazol-2-yl)piperidin-1-yl)methanone;
((3R,4S)-4-amino-1-(3,4-dichlorobenzoyl)pyrrolidin-3-yl)((R)-3-(1-(3-methoxypropyl)-1H-benzo[d]imidazol-2-yl)piperidin-1-yl)methanone;
((3R,4S)-4-amino-1-(2-phenoxynicotinoyl)pyrrolidin-3-yl)((R)-3-(1-(3-methoxypropyl)-1H-benzo[d]imidazol-2-yl)piperidin-1-yl)methanone;
4R)-3-amino-N-(3-methoxyphenyl)-4-((R)-3-(1-(3-methoxypropyl)-1H-benzo[d]imidazol-2-yl)piperidine-1-carbonyl)pyrrolidine-1-carboxamide;

((3R,4S)-4-amino-1-(3-phenoxyphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(4-methoxyphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(4-chlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(isopropylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3,4-dimethoxyphenylsulfonyl)pyrrolidin-3-yl)((R)-3-(1-(3-methoxypropyl)-1H-benzo[d]imidazol-2-yl)piperidin-1-yl)methanone;

methyl 2-((3S,4R)-3-amino-4-((R)-3-(1-(3-methoxypropyl)-1H-benzo[d]imidazol-2-yl)piperidine-1-carbonyl)pyrrolidin-1-ylsulfonyl)benzoate;

((3R,4S)-4-amino-1-(4-tert-butylphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-chlorobenzoyl)pyrrolidin-3-yl)((R)-3-(1-(3-methoxypropyl)-1H-benzo[d]imidazol-2-yl)piperidin-1-yl)methanone;

((3R,4S)-1-(1-naphthoyl)-4-aminopyrrolidin-3-yl)((R)-3-(1-(3-methoxypropyl)-1H-benzo[d]imidazol-2-yl)piperidin-1-yl)methanone;

methyl 3-((3S,4R)-3-amino-4-((R)-3-(1-(3-methoxypropyl)-1H-benzo[d]imidazol-2-yl)piperidine-1-carbonyl)pyrrolidine-1-carbonyl)benzoate;

4R)-3-amino-N-(3-chlorophenyl)-4-((R)-3-(1-(3-methoxypropyl)-1H-benzo[d]imidazol-2-yl)piperidine-1-carbonyl)pyrrolidine-1-carboxamide;

((3R,4S)-4-amino-1-(2-methoxyphenylsulfonyl)pyrrolidin-3-yl)((R)-3-(1-(3-methoxypropyl)-1H-benzo[d]imidazol-2-yl)piperidin-1-yl)methanone;

N-(4-((3S,4R)-3-amino-4-((R)-3-(1-(3-methoxypropyl)-1H-benzo[d]imidazol-2-yl)piperidine-1-carbonyl)pyrrolidin-1-ylsulfonyl)phenyl)acetamide;

((3R,4S)-4-amino-1-(4-methoxy-2-nitrophenylsulfonyl)pyrrolidin-3-yl)((R)-3-(1-(3-methoxypropyl)-1H-benzo[d]imidazol-2-yl)piperidin-1-yl)methanone;

1-(4-((3S,4R)-3-amino-4-((R)-3-(1-(3-methoxypropyl)-1H-benzo[d]imidazol-2-yl)piperidine-1-carbonyl)pyrrolidin-1-ylsulfonyl)phenyl)pyrrolidin-2-one;

((3R,4S)-4-amino-1-(2,4-dimethylphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(phenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-benzoylpyrrolidin-3-yl)((R)-3-(1-(3-methoxypropyl)-1H-benzo[d]imidazol-2-yl)piperidin-1-yl)methanone;

4R)-3-amino-N-cyclohexyl-4-((R)-3-(1-(3-methoxypropyl)-1H-benzo[d]imidazol-2-yl)piperidine-1-carbonyl)pyrrolidine-1-carboxamide;

((3R,4S)-4-amino-1-(2-methoxybenzoyl)pyrrolidin-3-yl)((R)-3-(1-(3-methoxypropyl)-1H-benzo[d]imidazol-2-yl)piperidin-1-yl)methanone;

(3S,4R)-3-amino-N-(4-chlorophenyl)-4-((R)-3-(1-(3-methoxypropyl)-1H-benzo[d]imidazol-2-yl)piperidine-1-carbonyl)pyrrolidine-1-carboxamide; 4R)-3-amino-N-(2-chlorophenyl)-4-((R)-3-(1-(3-methoxypropyl)-1H-benzo[d]imidazol-2-yl)piperidine-1-carbonyl)pyrrolidine-1-carboxamide;

4R)-2-chlorophenyl 3-amino-4-((R)-3-(1-(3-methoxypropyl)-1H-benzo[d]imidazol-2-yl)piperidine-1-carbonyl)pyrrolidine-1-carboxylate;

4-((3S,4R)-3-amino-4-((R)-3-(1-(3-methoxypropyl)-1H-benzo[d]imidazol-2-yl)piperidine-1-carbonyl)pyrrolidin-1-ylsulfonyl)-3-chlorobenzonitrile;

((3R,4 S)-4-amino-1-(1-methyl-1H-indol-4-ylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-fluorobenzoyl)pyrrolidin-3-yl)((R)-3-(1-(3-methoxypropyl)-1H-benzo[d]imidazol-2-yl)piperidin-1-yl)methanone;

((3R,4S)-4-amino-1-(4-methoxybenzoyl)pyrrolidin-3-yl)((R)-3-(1-(3-methoxypropyl)-1H-benzo[d]imidazol-2-yl)piperidin-1-yl)methanone;

((3R,4S)-4-amino-1-(cyclopentanecarbonyl)pyrrolidin-3-yl)((R)-3-(1-(3-methoxypropyl)-1H-benzo[d]imidazol-2-yl)piperidin-1-yl)methanone;

1-((3S,4R)-3-amino-4-((R)-3-(1-(3-methoxypropyl)-1H-benzo[d]imidazol-2-yl)piperidine-1-carbonyl)pyrrolidin-1-yl)-2-methylpropan-1-one;

1-((3S,4R)-3-amino-4-((R)-3-(1-(3-methoxypropyl)-1H-benzo[d]imidazol-2-yl)piperidine-1-carbonyl)pyrrolidin-1-yl)-2-cyclohexylethanone;

((3R,4S)-4-amino-1-(2-chlorobenzoyl)pyrrolidin-3-yl)((R)-3-(1-(3-methoxypropyl)-1H-benzo[d]imidazol-2-yl)piperidin-1-yl)methanone;

4R)-3-amino-N-cyclopentyl-4-((R)-3-(1-(3-methoxypropyl)-1H-benzo[d]imidazol-2-yl)piperidine-1-carbonyl)pyrrolidine-1-carboxamide;

4R)-3-amino-N-(2-methoxyphenyl)-4-((R)-3-(1-(3-methoxypropyl)-1H-benzo[d]imidazol-2-yl)piperidine-1-carbonyl)pyrrolidine-1-carboxamide;

((3R,4S)-4-amino-1-(5-bromo-2-methoxyphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2-(trifluoromethyl)phenylsulfonyl)pyrrolidin-3-yl)((R)-3-(1-(3-methoxypropyl)-1H-benzo[d]imidazol-2-yl)piperidin-1-yl)methanone;

2-((3S,4R)-3-amino-4-((R)-3-(1-(3-methoxypropyl)-1H-benzo[d]imidazol-2-yl)piperidine-1-carbonyl)pyrrolidin-1-ylsulfonyl)-4-methylbenzonitrile; 4R)-3-amino-4-((R)-3-(1-(3-methoxypropyl)-1H-benzo[d]imidazol-2-yl)piperidine-1-carbonyl)-N-phenylpyrrolidine-1-carboxamide;

((3R,4S)-4-amino-1-(cyclohexanecarbonyl)pyrrolidin-3-yl)((R)-3-(1-(3-methoxypropyl)-1H-benzo[d]imidazol-2-yl)piperidin-1-yl)methanone;

((3R,4S)-4-amino-1-(benzofuran-2-carbonyl)pyrrolidin-3-yl)((R)-3-(1-(3-methoxypropyl)-1H-benzo[d]imidazol-2-yl)piperidin-1-yl)methanone;

((3S,4R)-4-chlorophenyl 3-amino-4-((R)-3-(1-(3-methoxypropyl)-1H-benzo[d]imidazol-2-yl)piperidine-1-carbonyl)pyrrolidine-1-carboxylate;

((3S,4R)-3-(trifluoromethyl)phenyl 3-amino-4-((R)-3-(1-(3-methoxypropyl)-1H-benzo[d]imidazol-2-yl)piperidine-1-carbonyl)pyrrolidine-1-carboxylate;

((3R,4 S)-4-amino-1-(3-(5-methyl-1,2,4-oxadiazol-3-yl)phenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2-methoxy-5-methylphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2-methoxy-4-nitrophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(5-chloro-2-methoxyphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,5-dimethoxyphenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,6-dichlorobenzoyl)pyrrolidin-3-yl)((R)-3-(1-(3-methoxypropyl)-1H-benzo[d]imidazol-2-yl)piperidin-1-yl)methanone;

4R)-3-amino-N-(4-methoxyphenyl)-4-((R)-3-(1-(3-methoxypropyl)-1H-benzo[d]imidazol-2-yl)piperidine-1-carbonyl)pyrrolidine-1-carboxamide;

((3R,4S)-4-amino-1-(4-chlorobenzoyl)pyrrolidin-3-yl)((R)-3-(1-(3-methoxypropyl)-1H-benzo[d]imidazol-2-yl)piperidin-1-yl)methanone;

((3R,4S)-4-amino-1-(pyrrolidine-1-carbonyl)pyrrolidin-3-yl)((R)-3-(1-(3-methoxypropyl)-1H-benzo[d]imidazol-2-yl)piperidin-1-yl)methanone;

((3R,4S)-4-amino-1-(2-(propylthio)nicotinoyl)pyrrolidin-3-yl)((R)-3-(1-(3-methoxypropyl)-1H-benzo[d]imidazol-2-yl)piperidin-1-yl)methanone;

((3R,4S)-4-amino-1-(3-(difluoromethoxy)phenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(furan-2-carbonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-methoxybenzoyl)pyrrolidin-3-yl)((R)-3-(1-(3-methoxypropyl)-1H-benzo[d]imidazol-2-yl)piperidin-1-yl)methanone;

methyl 4-((3S,4R)-3-amino-4-((R)-3-(1-(3-methoxypropyl)-1H-benzo[d]imidazol-2-yl)piperidine-1-carbonyl)pyrrolidine-1-carbonyl)benzoate;

((3R,4S)-4-amino-1-(morpholine-4-carbonyl)pyrrolidin-3-yl)((R)-3-(1-(3-methoxypropyl)-1H-benzo[d]imidazol-2-yl)piperidin-1-yl)methanone;

methyl 2-((3S,4R)-3-amino-4-((R)-3-(1-(3-methoxypropyl)-1H-benzo[d]imidazol-2-yl)piperidine-1-carbonyl)pyrrolidine-1-carbonyl)benzoate;

((3R,4S)-4-amino-1-(2,6-dichlorophenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(2,6-difluorophenylsulfonyl)pyrrolidin-3-yl)((R)-3-(1-(3-methoxypropyl)-1H-benzo[d]imidazol-2-yl)piperidin-1-yl)methanone;

2-((3S,4R)-3-amino-4-((R)-3-(1-(3-methoxypropyl)-1H-benzo[d]imidazol-2-yl)piperidine-1-carbonyl)pyrrolidin-1-ylsulfonyl)benzonitrile;

((3R,4S)-4-amino-1-(3-fluorophenylsulfonyl)pyrrolidin-3-yl)((R)-3-(1-(3-methoxypropyl)-1H-benzo[d]imidazol-2-yl)piperidin-1-yl)methanone;

N-(3-((3S,4R)-3-amino-4-((R)-3-(1-(3-methoxypropyl)-1H-benzo[d]imidazol-2-yl)piperidine-1-carbonyl)pyrrolidin-1-ylsulfonyl)phenyl)acetamide;

((3R,4S)-4-amino-1-(3-(2-methylpyrimidin-4-yl)phenylsulfonyl)pyrrolidin-3-yl)((R)-3-(1-(3-methoxypropyl)-1H-benzo[d]imidazol-2-yl)piperidin-1-yl)methanone;

((3R,4S)-4-amino-1-(3-(5-methyl-1,3,4-oxadiazol-2-yl)phenylsulfonyl)pyrrolidin-3-yl)((R)-3-(1-(3-methoxypropyl)-1H-benzo[d]imidazol-2-yl)piperidin-1-yl)methanone;

methyl 2-((R)-2-amino-4-((R)-3-(1-(3-methoxypropyl)-1H-benzo[d]imidazol-2-yl)piperidin-1-yl)-4-oxobutoxy)benzoate;

(R)-3-amino-4-(3-methoxyphenoxy)-1-((R)-3-(1-(3-methoxypropyl)-1H-benzo[d]imidazol-2-yl)piperidin-1-yl)butan-1-one;

(R)-4-(1H-benzo[d]imidazol-2-yloxy)-3-amino-1-((R)-3-(1-(3-methoxypropyl)-1H-benzo[d]imidazol-2-yl)piperidin-1-yl)butan-1-one;

(R)-3-amino-4-(4-(2-((S)-3-hydroxypyrrolidin-1-yl)thiazol-4-yl)phenyl)-1-((R)-3-(1-(3-methoxypropyl)-1H-benzo[d]imidazol-2-yl)piperidin-1-yl)butan-1-one;

1-(4'-((R)-2-amino-4-((R)-3-(1-(3-methoxypropyl)-1H-benzo[d]imidazol-2-yl)piperidin-1-yl)-4-oxobutyl)biphenyl-4-yl)imidazolidin-2-one;

(R)-3-amino-4-(4-(2-hydroxypyridin-4-yl)phenyl)-1-((R)-3-(1-(3-methoxypropyl)-1H-benzo[d]imidazol-2-yl)piperidin-1-yl)butan-1-one;

6-(4-((R)-2-amino-4-((R)-3-(1-(3-methoxypropyl)-1H-benzo[d]imidazol-2-yl)piperidin-1-yl)-4-oxobutyl)phenyl)-2H-benzo[b][1,4]oxazin-3(4H)-one;

6-(4-((R)-2-amino-4-((R)-3-(1-(3-methoxypropyl)-1H-benzo[d]imidazol-2-yl)piperidin-1-yl)-4-oxobutyl)phenyl)-2H-benzo[b][1,4]oxazin-3(4H)-one;

(R)-3-amino-1-((R)-3-(1-(3-methoxypropyl)-1H-benzo[d]imidazol-2-yl)piperidin-1-yl)-4-(4-(4-methyl-3,4-dihydro-2H-benzo[b][1,4]oxazin-7-yl)phenyl)butan-1-one;

1-(4-((R)-2-amino-4-((R)-3-(1-(3-methoxypropyl)-1H-benzo[d]imidazol-2-yl)piperidin-1-yl)-4-oxobutyl)phenyl)-6-fluoro-1H-benzo[d]imidazol-2(3H)-one;

1-(4'-((R)-2-amino-4-((R)-3-(4-fluoro-1-(3-methoxypropyl)-1H-benzo[d]imidazol-2-yl)piperidin-1-yl)-4-oxobutyl)biphenyl-4-yl)imidazolidin-2-one 7-(4-((R)-2-amino-4-((R)-3-(4-fluoro-1-(3-methoxypropyl)-1H-benzo[d]imidazol-2-yl)piperidin-1-yl)-4-oxobutyl)phenyl)-2H-benzo[b][1,4]thiazin-3(4H)-one 7-(4-((R)-2-amino-4-((R)-3-(4-fluoro-1-(3-methoxypropyl)-1H-benzo[d]imidazol-2-yl)piperidin-1-yl)-4-oxobutyl)phenyl)-2H-benzo[b][1,4]oxazin-3(4H)-one (R)-3-amino-1-((R)-3-(4-fluoro-1-(3-methoxypropyl)-1H-benzo[d]imidazol-2-yl)piperidin-1-yl)-4-(4-(2-hydroxypyridin-4-yl)phenyl)butan-1-one N-(2-(2-((R)-1-((R)-3-amino-4-(4-(6-hydroxypyridin-3-yl)phenyl)butanoyl)piperidin-3-yl)-1H-benzo[d]imidazol-1-yl)ethyl)acetamide N-(2-(2-((R)-1-((R)-3-amino-4-(4-(6-aminopyridin-3-yl)phenyl)butanoyl)piperidin-3-yl)-1H-benzo[d]imidazol-1-yl)ethyl)acetamide 3-(2-((R)-1-((R)-3-amino-4-(4-(4-methyl-3,4-dihydro-2H-benzo[b][1,4]oxazin-7-yl)phenyl)butanoyl)piperidin-3-yl)-1H-benzo[d]imidazol-1-yl)propanamide N-(2-(2-((R)-1-((R)-3-amino-4-(4-(2,2-difluorobenzo[d][1,3]dioxol-5-yl)phenyl)butanoyl)piperidin-3-yl)-1H-benzo[d]imidazol-1-yl)ethyl)acetamide N-(2-(2-((R)-1-((R)-3-amino-4-(4-(2,3-dihydrobenzo[b][1,4]dioxin-6-yl)phenyl)butanoyl)piperidin-3-yl)-1H-benzo[d]imidazol-1-yl)ethyl)acetamide N-(2-(2-((R)-1-((R)-3-amino-4-(4-(2-aminopyrimidin-5-yl)phenyl)butanoyl)piperidin-3-yl)-1H-benzo[d]imidazol-1-yl)ethyl)acetamide (R)-3-amino-1-((R)-3-(4-fluoro-1-(3-methoxypropyl)-1H-benzo[d]imidazol-2-yl)piperidin-1-yl)-4-(4-(6-hydroxypyridin-3-yl)phenyl)butan-1-one (R)-3-amino-4-(4-(6-aminopyridin-3-yl)phenyl)-1-((R)-3-(4-fluoro-1-(3-methoxypropyl)-1H-benzo[d]imidazol-2-yl)piperidin-1-yl)butan-1-one (R)-3-amino-1-((R)-3-(4-fluoro-1-(3-methoxypropyl)-1H-benzo[d]imidazol-2-yl)piperidin-1-yl)-4-(4-(4-methyl-3,4-dihydro-2H-benzo[b][1,4]oxazin-7-yl)phenyl)butan-1-one (R)-3-amino-4-(4-(2,2-difluorobenzo[d][1,3]dioxol-5-yl)phenyl)-1-((R)-3-(4-fluoro-1-(3-methoxypropyl)-1H-benzo[d]imidazol-2-yl)piperidin-1-yl)butan-1-one (R)-3-amino-4-(4-(2,3-dihydrobenzo[b][1,4]dioxin-6-yl)phenyl)-1-((R)-3-(4-fluoro-1-(3-methoxypropyl)-1H-benzo[d]imidazol-2-yl)piperidin-1-yl)butan-1-one (R)-3-amino-4-(4-(2-aminopyrimidin-5-yl)phenyl)-1-((R)-3-(4-fluoro-1-(3-methoxypropyl)-1H-benzo[d]imidazol-2-yl)piperidin-1-yl)butan-1-one methyl 4'-((R)-4-((R)-3-(1-(2-acetamidoethyl)-1H-benzo[d]imidazol-2-yl)piperidin-1-yl)-2-amino-4-oxobutyl)biphenyl-4-ylcarb amate 5-(4-((R)-2-amino-4-((R)-3-(4-fluoro-1-(3-methoxypropyl)-1H-benzo[d]imidazol-2-yl)piperidin-1-yl)-4-oxobutyl)phenyl)indolin-2-one 6-(4-((R)-2-amino-4-((R)-3-(4-fluoro-1-(3-methoxypropyl)-1H-benzo[d]imidazol-2-yl)piperidin-1-yl)-4-oxobutyl)phenyl)indolin-2-one 5-(4-((R)-2-amino-4-((R)-3-(4-fluoro-1-(3-methoxypropyl)-1H-benzo[d]imidazol-2-yl)piperidin-1-yl)-4-oxobutyl)phenyl)benzo[d]oxazol-2(3H)-one N-(2-(2-((R)-1-((R)-3-amino-4-(4-(2-hydroxypyridin-4-yl)phenyl)butanoyl)piperidin-3-yl)-1H-benzo[d]imidazol-1-yl)ethyl)acetamide N-(2-(2-((R)-1-((R)-3-amino-4-(4'-(2-oxoimidazolidin-1-yl)biphenyl-4-yl)butanoyl)piperidin-3-yl)-1H-benzo[d]imidazol-1-yl)ethyl)acetamide (R)-3-amino-4-(4-(2-aminobenzo[d]oxazol-5-yl)phenyl)-1-((R)-3-(4-fluoro-1-(3-methoxypropyl)-1H-benzo[d]imidazol-2-yl)piperidin-1-yl)butan-1-one N-(2-(2-((R)-1-((R)-3-amino-4-(4-(2-oxo-2,3-dihydrobenzo[b][1,4]oxathiin-6-yl)phenyl)butanoyl)piperidin-3-yl)-1H-benzo[d]imidazol-1-yl)ethyl)acetamide N-(2-(2-((R)-1-((R)-3-amino-4-(4-(2-oxoindolin-5-yl)phenyl)butanoyl)piperidin-3-yl)-1H-benzo[d]imidazol-1-yl)ethyl)acetamide N-(2-(2-((R)-1-((R)-3-amino-4-(4-(2-oxoindolin-6-yl)phenyl)butanoyl)piperidin-3-yl)-1H-benzo[d]imidazol-1-yl)ethyl)acetamide N-(2-(2-((R)-1-((R)-3-amino-4-(4-(2-oxo-2,3-dihydrobenzo[d]oxazol-5-yl)phenyl)butanoyl)piperidin-3-yl)-1H-benzo[d]imidazol-1-yl)ethyl)acetamide 5-(4-((R)-2-amino-4-((R)-3-(4-fluoro-1-(3-methoxypropyl)-1H-benzo[d]imidazol-2-yl)piperidin-1-yl)-4-oxobutyl)phenyl)benzo[d]oxazol-2(3H)-one (R)-3-amino-4-(4-(2-aminobenzo[d]oxazol-5-yl)phenyl)-1-((R)-3-(4-fluoro-1-(3-methoxypropyl)-1H-benzo[d]imidazol-2-yl)piperidin-1-yl)butan-1-one N-(2-(2-((R)-1-((R)-3-amino-4-(4-(2-aminopyrimidin-5-yl)phenyl)butanoyl)piperidin-3-yl)-4-chloro-1H-benzo[d]imidazol-1-yl)ethyl)acetamide N-(2-(2-((R)-1-((R)-3-amino-4-(4-(6-aminopyridin-3-yl)phenyl)butanoyl)piperidin-3-yl)-4-methyl-1H-benzo[d]imidazol-1-yl)ethyl)acetamide N-(2-(2-((R)-1-((R)-3-amino-4-(4-(2-aminopyrimidin-5-yl)phenyl)butanoyl)piperidin-3-yl)-4-methyl-1H-benzo[d]imidazol-1-yl)ethyl)acetamide N-(2-(2-((R)-1-((R)-3-amino-4-(4-(6-hydroxypyridin-3-yl)phenyl)butanoyl)piperidin-3-yl)-4-methyl-1H-benzo[d]imidazol-1-yl)ethyl)acetamide N-(2-(2-((R)-1-((R)-3-amino-4-(4-(2,2-difluorobenzo[d][1,3]dioxol-5-yl)phenyl)butanoyl)piperidin-3-yl)-4-methyl-1H-benzo[d]imidazol-1-yl)ethyl)acetamide N-(2-(2-((R)-1-((R)-3-amino-4-(4-(4-methyl-3,4-dihydro-2H-benzo[b][1,4]oxazin-7-yl)phenyl)butanoyl)piperidin-3-yl)-4-methyl-1H-benzo[d]imidazol-1-yl)ethyl)acetamide N-(2-(2-((R)-1-((R)-3-amino-4-(4-(6-hydroxypyridin-3-yl)phenyl)butanoyl)piperidin-3-yl)-1H-benzo[d]imidazol-1-yl)ethyl)acetamide N-(2-(2-((R)-1-((R)-3-amino-4-(4-(2,3-dihydrobenzo[b][1,4]dioxin-6-yl)phenyl)butanoyl)piperidin-3-yl)-4-methyl-1H-benzo[d]imidazol-1-yl)ethyl)acetamide N-(2-(2-((R)-1-((R)-3-amino-4-(4-(6-hydroxypyridin-3-yl)phenyl)butanoyl)piperidin-3-yl)-4-chloro-1H-benzo[d]imidazol-1-yl)ethyl)acetamide N-(2-(2-((R)-1-((R)-3-amino-4-(4-(6-aminopyridin-3-yl)phenyl)butanoyl)piperidin-3-yl)-4-chloro-1H-benzo[d]imidazol-1-yl)ethyl)acetamide 3-(2-((R)-1-((R)-3-amino-4-(4-(6-aminopyridin-3-yl)phenyl)butanoyl)piperidin-3-yl)-1H-benzo[d]imidazol-1-yl)propanamide;

3-(2-((R)-1-((R)-3-amino-4-(4-(2-aminopyrimidin-5-yl)phenyl)butanoyl)piperidin-3-yl)-1H-benzo[d]imidazol-1-yl)propanamide;

3-(2-((R)-1-((R)-3-amino-4-(4-(4-methyl-3,4-dihydro-2H-benzo[b][1,4]oxazin-7-yl)phenyl)butanoyl)piperidin-3-yl)-1H-benzo[d]imidazol-1-yl)propanamide;

3-(2-((R)-1-((R)-3-amino-4-(4-(4-methyl-3,4-dihydro-2H-benzo[b][1,4]oxazin-7-yl)phenyl)butanoyl)piperidin-3-yl)-1H-benzo[d]imidazol-1-yl)propanamide;

3-(2-((R)-1-((R)-3-amino-4-(4-(2,3-dihydrobenzo[b][1,4]dioxin-6-yl)phenyl)butanoyl)piperidin-3-yl)-1H-benzo[d]imidazol-1-yl)propanamide;

3-(2-((R)-1-((R)-3-amino-4-(biphenyl-4-yl)butanoyl)piperidin-3-yl)-1H-benzo[d]imidazol-1-yl)propanamide;

3-(2-((R)-1-((R)-4-(4'-acetamidobiphenyl-4-yl)-3-aminobutanoyl)piperidin-3-yl)-1H-benzo[d]imidazol-1-yl)propanamide;

3-(2-((R)-1-((R)-3-amino-4-(4'-methoxybiphenyl-4-yl)butanoyl)piperidin-3-yl)-1H-benzo[d]imidazol-1-yl)propanamide;

3-(2-((R)-1-((R)-3-amino-4-(4-(pyridin-4-yl)phenyl)butanoyl)piperidin-3-yl)-1H-benzo[d]imidazol-1-yl)propanamide;

3-(2-((R)-1-((R)-3-amino-4-(4'-chlorobiphenyl-4-yl)butanoyl)piperidin-3-yl)-1H-benzo[d]imidazol-1-yl)propanamide;

(R)-3-amino-4-(4-(2,3-dihydrobenzofuran-5-yl)phenyl)-1-((R)-3-(4-fluoro-1-(3-methoxypropyl)-1H-benzo[d]imidazol-2-yl)piperidin-1-yl)butan-1-one N-(4'-((R)-2-amino-4-((R)-3-(4-fluoro-1-(3-methoxypropyl)-1H-benzo[d]imidazol-2-yl)piperidin-1-yl)-4-oxobutyl)biphenyl-4-yl)acetamide;

(R)-3-amino-1-((R)-3-(4-fluoro-1-(3-methoxypropyl)-1H-benzo[d]imidazol-2-yl)piperidin-1-yl)-4-(4'-methoxybiphenyl-4-yl)butan-1-one;

(R)-3-amino-4-(4-(2,3-dihydrobenzofuran-5-yl)phenyl)-1-((R)-3-(1-(3-methoxypropyl)-4-methyl-1H-benzo[d]imidazol-2-yl)piperidin-1-yl)butan-1-one (R)-3-amino-4-(4-(benzofuran-5-yl)phenyl)-1-((R)-3-(1-(3-methoxypropyl)-4-methyl-1H-benzo[d]imidazol-2-yl)piperidin-1-yl)butan-1-one 5-(4-((R)-2-amino-4-((R)-3-(1-(3-methoxypropyl)-4-methyl-1H-benzo[d]imidazol-2-yl)piperidin-1-yl)-4-oxobutyl)phenyl)indolin-2-one 7-(4-((R)-2-amino-4-((R)-3-(1-(3-methoxypropyl)-4-methyl-1H-benzo[d]imidazol-2-yl)piperidin-1-yl)-4-oxobutyl)phenyl)-2H-benzo[b][1,4]thiazin-3(4H)-one 7-(4-((R)-2-amino-4-((R)-3-(1-(3-methoxypropyl)-4-methyl-1H-benzo[d]imidazol-2-yl)piperidin-1-yl)-4-oxobutyl)phenyl)-2H-benzo[b][1,4]oxazin-3(4H)-one 5-(4-((R)-2-amino-4-((R)-3-(1-(3-methoxypropyl)-4-methyl-1H-benzo[d]imidazol-2-yl)piperidin-1-yl)-4-oxobutyl)phenyl)-1-methylindolin-2-one (R)-4-(4-(1H-indazol-5-yl)phenyl)-3-amino-1-((R)-3-(1-(3-methoxypropyl)-4-methyl-1H-benzo[d]imidazol-2-yl)piperidin-1-yl)butan-1-one (R)-3-amino-4-(4-(3-amino-1H-indazol-5-yl)phenyl)-1-((R)-3-(1-(3-methoxypropyl)-4-methyl-1H-benzo[d]imidazol-2-yl)piperidin-1-yl)butan-1-one 3-(2-((R)-1((R)-3-amino-4-(4-(2,3-dihydrobenzofuran-5-yl)phenyl)butanoyl)piperidin-3-yl)-4-methyl-1H-benzo[d]imidazol-1-yl)-N-methylpropanamide (3R)-3-amino-1-(3-(5-chloro-3-(3-methoxypropyl)-3H-imidazo[4,5-b]pyridin-2-yl)piperidin-1-yl)-4-(naphthalen-2-yl)butan-1-one;

(3R)-3-amino-1-(3-(5-methoxy-3-(3-methoxypropyl)-3H-imidazo[4,5-b]pyridin-2-yl)piperidin-1-yl)-4-(naphthalen-2-yl)butan-1-one;

(R)-3-amino-4-(4-(6-hydroxypyridin-3-yl)phenyl)-1-4R)-3-(3-(3-methoxypropyl)-7-methyl-3H-imidazo[4,5-b]pyridin-2-yl)piperidin-1-yl)butan-1-one;

(R)-3-amino-4-(biphenyl-4-yl)-1((R)-3-(3-(3-methoxypropyl)-7-methyl-3H-imidazo[4,5-b]pyridin-2-yl)piperidin-1-yl)butan-1-one;

3-((3S,4R)-3-amino-4-((R)-3-(1-(3-methoxypropyl)-1H-benzo[d]imidazol-2-yl)piperidine-1-carbonyl)pyrrolidin-1-yl)benzonitrile;

3-((3S,4R)-3-amino-4-((R)-3-(1-(3-methoxypropyl)-1H-benzo[d]imidazol-2-yl)piperidine-1-carbonyl)pyrrolidin-1-yl)benzonitrile; ((3R,4S)-4-amino-1-(4-nitrophenyl)pyrrolidin-3-yl)((R)-3-(1-(3-methoxypropyl)-1H-benzo[d]imidazol-2-yl)piperidin-1-yl)methanone;

(R)-3-amino-4-(4-(2-aminopyrimidin-5-yl)phenyl)-1-((R)-3-(1-(2-fluoroethyl)-1H-benzo[d]imidazol-2-yl)piperidin-1-yl)butan-1-one;

stereoisomers of the aforementioned compounds; and a pharmaceutically acceptable salt of the aforementioned compounds or stereoisomers.

89. A pharmaceutical composition comprising a compound according to any one of claims 1-88 and at least one pharmaceutical excipient.

90. The pharmaceutical composition according to claim 89, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, and intrathecally.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Synthetic Primers

<400> SEQUENCE: 1
aagcttatgg atggatggag a                    21

<210> SEQ ID NO 2
<211> LENGTH: 21
<212> TYPE: DNA
<213> ORGANISM: Artificial
<220> FEATURE:
<223> OTHER INFORMATION: Synthetic Primers

<400> SEQUENCE: 2
ggatcctcag cgggccaagg c                    21